(12) United States Patent
Chung et al.

(10) Patent No.: US 11,339,143 B2
(45) Date of Patent: May 24, 2022

(54) CONDENSED CYCLIC COMPOUND AND ORGANIC LIGHT-EMITTING DEVICE INCLUDING THE SAME

(71) Applicant: Samsung Electronics Co., Ltd., Suwon-si (KR)

(72) Inventors: Yeonsook Chung, Seoul (KR); Soonok Jeon, Suwon-si (KR); Masaki Numata, Hwaseong-si (KR); Myungsun Sim, Suwon-si (KR); Hasup Lee, Seoul (KR); Sooghang Ihn, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 471 days.

(21) Appl. No.: 16/244,431

(22) Filed: Jan. 10, 2019

(65) Prior Publication Data

US 2020/0002315 A1    Jan. 2, 2020

(30) Foreign Application Priority Data

Jun. 26, 2018    (KR) .................. 10-2018-0073457
Nov. 28, 2018    (KR) .................. 10-2018-0150081

(51) Int. Cl.
*C07D 403/10*    (2006.01)
*C07D 487/04*    (2006.01)
(Continued)

(52) U.S. Cl.
CPC ......... *C07D 403/10* (2013.01); *C07D 401/14* (2013.01); *C07D 403/14* (2013.01);
(Continued)

(58) Field of Classification Search
None
See application file for complete search history.

(56) References Cited

U.S. PATENT DOCUMENTS

2018/0166634 A1    6/2018  Numata et al.
2018/0170914 A1*   6/2018  Miyata ............... C07D 209/86
(Continued)

FOREIGN PATENT DOCUMENTS

CN    107880027 A    4/2018
CN    108707136 A    10/2018
(Continued)

OTHER PUBLICATIONS

Machine English translation of Xu et al. (CN 107880027 A). Apr. 1, 2021.*

(Continued)

*Primary Examiner* — Jay Yang
(74) *Attorney, Agent, or Firm* — Cantor Colburn LLP

(57) ABSTRACT

A condensed cyclic compound represented by Formula 1:

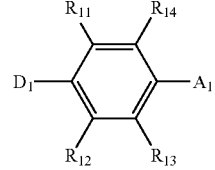

Formula 1 wherein, in Formula 1, $A_1$, $D_1$, and $R_{11}$ to $R_{14}$ are the same as described in the specification.

20 Claims, 1 Drawing Sheet

(51) Int. Cl.
*C07D 403/14* (2006.01)
*C07D 405/14* (2006.01)
*C07D 409/14* (2006.01)
*C07D 401/14* (2006.01)
*C07D 495/04* (2006.01)
*C07D 495/14* (2006.01)
*C07D 491/048* (2006.01)
*C07D 491/147* (2006.01)
*C07D 491/153* (2006.01)
*C07D 519/00* (2006.01)
*H01L 51/00* (2006.01)
*H01L 51/50* (2006.01)

(52) U.S. Cl.
CPC ......... *C07D 405/14* (2013.01); *C07D 409/14* (2013.01); *C07D 487/04* (2013.01); *C07D 491/048* (2013.01); *C07D 491/147* (2013.01); *C07D 491/153* (2013.01); *C07D 495/04* (2013.01); *C07D 495/14* (2013.01); *C07D 519/00* (2013.01); *H01L 51/0067* (2013.01); *H01L 51/0072* (2013.01); *H01L 51/0073* (2013.01); *H01L 51/0074* (2013.01); *H01L 51/5012* (2013.01)

(56) References Cited

U.S. PATENT DOCUMENTS

2018/0248127 A1    8/2018  Lee et al.
2020/0407343 A1*  12/2020  Arjona Esteban ... C07D 495/04

FOREIGN PATENT DOCUMENTS

| JP | 4741028 B1 | 8/2011 |
| KR | 10-1396171 B1 | 5/2014 |
| WO | 2012-150826 A1 | 11/2012 |
| WO | 2015-175678 A1 | 11/2015 |
| WO | 2016-181846 A1 | 11/2016 |
| WO | WO-2016/181846 * | 11/2016 |
| WO | WO-2019/166666 A1 * | 9/2019 |

OTHER PUBLICATIONS

Extended European Search Report issued by the European Patent Office dated Apr. 17, 2019 in the examination of the European Patent Application No. 19153701.8-1116.

* cited by examiner

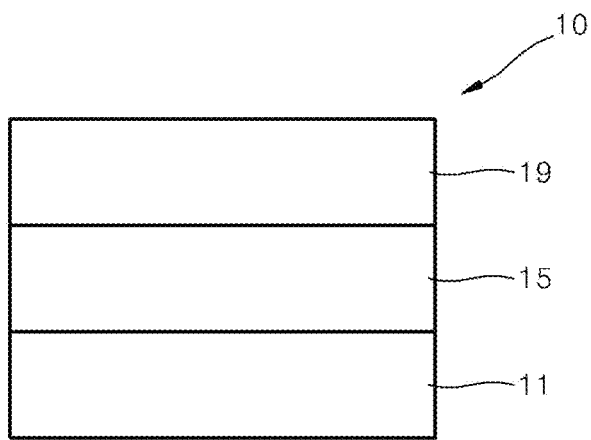

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Applications No. 10-2018-0073457, filed on Jun. 26, 2018 and No. 10-2018-0150081, filed on Nov. 28, 2018, in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound and an organic light-emitting device including the same.

2. Description of the Related Art

Organic light-emitting devices (OLEDs) are self-emission devices that produce full-color images, and that also have wide viewing angles, high contrast ratios, short response times, and excellent characteristics in terms of brightness, driving voltage, and response speed, compared to devices in the art.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide a condensed cyclic compound having excellent delayed fluorescence emission characteristics and an organic light-emitting device including the same and thus having high efficiency and/or a long lifespan.

Additional aspects will be set forth in part in the description which follows and, in part, will be apparent from the description, or may be learned by practice of the presented embodiments.

An aspect provides a condensed cyclic compound represented by Formula 1:

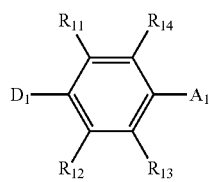

Formula 1

-continued

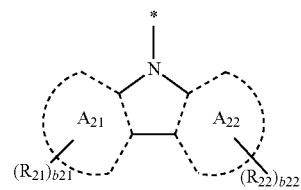

Formula 2

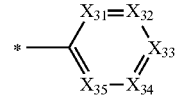

Formula 3-1

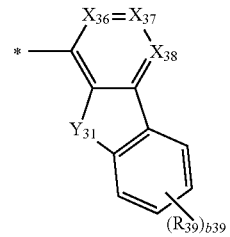

Formula 3-2

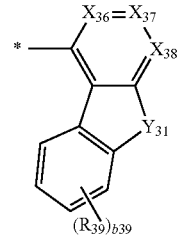

Formula 3-3

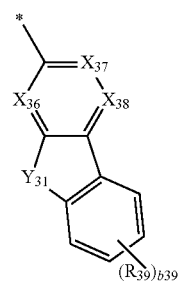

Formula 3-4

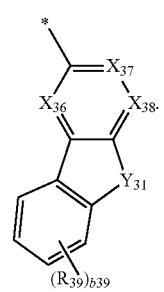

Formula 3-5

In Formulae 1, 2, and 3-1 to 3-5, $D_1$ may be a group represented by Formula 2, $A_1$ may be a group represented by one selected from Formulae 3-1 to 3-5, $R_{11}$ and $R_{12}$ may each independently be a substituted or unsubstituted $C_6$-$C_{30}$ aryl group, $A_{21}$ and $A_{22}$ may each independently be selected from a benzene group, a fluorene group, a carbazole group, a dibenzofuran group, a dibenzothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group, $X_{31}$ may be N or $C(R_{31})$; $X_{32}$ may be N or $C(R_{32})$; $X_{33}$ may be N or $C(R_{33})$; $X_{34}$ may be N or $C(R_{34})$; $X_{35}$ may be N or $C(R_{35})$; $X_{36}$ may be N or $C(R_{36})$; $X_{37}$ may be N or $C(R_{37})$; and $X_{38}$ may be N or $C(R_{38})$, wherein at least one selected from $X_{31}$ to $X_{35}$ in Formula 3-1 may be N, and at least one selected from $X_{36}$ to $X_{38}$ in Formulae 3-2 to 3-5 may be N, $Y_{31}$ may be selected from O and S, $R_{13}$, $R_{14}$, $R_{21}$, $R_{22}$, and $R_{31}$ to $R_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ aryl alkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroaryl alkyl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$, two neighboring groups selected from $R_{31}$ to $R_{39}$ may optionally be linked to form a condensed ring, b21 and b22 may each independently be selected from 1, 2, 3, 4, 5, 6, 7, and 8, b39 may be selected from 1, 2, 3, and 4, $Q_1$ to $Q_7$ may each independently be selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and

* indicates a binding site to a neighboring atom.

Another aspect provides an organic light-emitting device including:

a first electrode;

a second electrode; and an organic layer disposed between the first electrode and the second electrode, wherein the organic layer includes an emission layer, and wherein the organic layer includes at least one condensed cyclic compound described above.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An aspect of the present disclosure provides a condensed cyclic compound represented by Formula 1, wherein $D_1$ in Formula 1 may be a group represented by Formula 2, and $A_1$ in Formula 1 may be a group represented by one selected from Formulae 3-1 to 3-5:

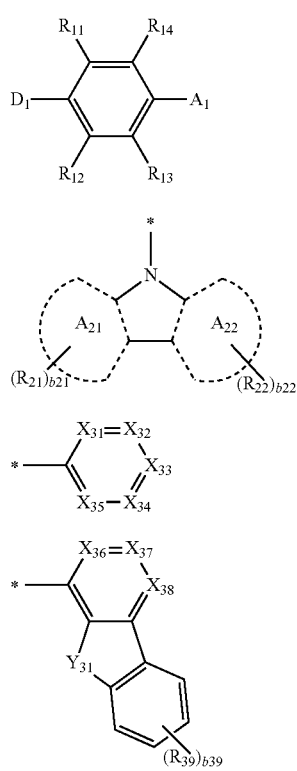

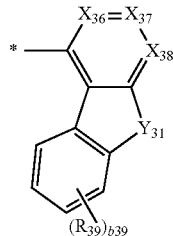

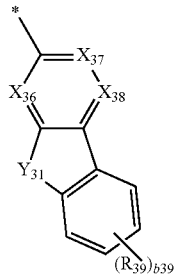

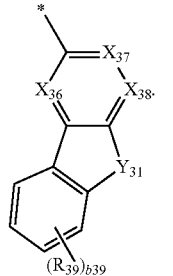

Formulae 1, 2, and 3-1 to 3-5 will be described below.

$R_{11}$ and $R_{12}$ in Formula 1 may each independently be a substituted or unsubstituted $C_6$-$C_{30}$ aryl group.

In an embodiment, $R_{11}$ and $R_{12}$ in Formula 1 may each independently be selected from:

a phenyl group, a biphenyl group, a terphenyl group, a naphthyl group, a phenanthrenyl group, an anthracenyl group, a triphenylenyl group, a pyrenyl group, and a chrysenyl group; and a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, —F, —Cl, —Br, —I, a cyano group, a $C_1$-$C_{20}$ alkyl group, a $C_1$-$C_{20}$ alkoxy group, and a phenyl group, but embodiments of the present disclosure are not limited thereto.

In one or more embodiments, $R_{11}$ and $R_{12}$ in Formula 1 may each independently be selected from:

a phenyl group, a biphenyl group, a terphenyl group, and a naphthyl group; and a phenyl group, a biphenyl group, a terphenyl group, and a naphthyl group, each substituted with at least one selected from deuterium, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, a methoxy group, an ethoxy group, a propoxy group, a butoxy group, a pentoxy group, and a phenyl group, but embodiments of the present disclosure are not limited thereto.

In one or more embodiments, $R_{11}$ and $R_{12}$ in Formula 1 may each independently be selected from:
a phenyl group; and
a phenyl group substituted with at least one selected from a methyl group, an ethyl group, an n-propyl group, an iso-propyl group, an n-butyl group, an iso-butyl group, a sec-butyl group, a tert-butyl group, and a phenyl group, but embodiments of the present disclosure are not limited thereto.

$A_{21}$ and $A_{22}$ in Formula 1 may each independently be selected from a benzene group, a fluorene group, a carbazole group, a dibenzofuran group, a dibenzothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group.

In an embodiment, in Formula 1,
$A_{21}$ may be a benzene group,
$A_{22}$ may be selected from a benzene group, a fluorene group, a carbazole group, a dibenzofuran group, a dibenzothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group, but embodiments of the present disclosure are not limited thereto.

In Formulae 3-1 to 3-5, $X_{31}$ may be N or $C(R_{31})$; $X_{32}$ may be N or $C(R_{32})$; $X_{33}$ may be N or $C(R_{33})$; $X_{34}$ may be N or $C(R_{34})$; $X_{35}$ may be N or $C(R_{35})$; $X_{36}$ may be N or $C(R_{36})$; $X_{37}$ may be N or $C(R_{37})$; and $X_{38}$ may be N or $C(R_{38})$, wherein at least one selected from $X_{31}$ to $X_{35}$ in Formula 3-1 may each independently be N, and at least one selected from $X_{36}$ to $X_{38}$ in Formulae 3-2 to 3-5 may each independently be N.

In an embodiment, two or three selected from $X_{31}$ to $X_{35}$ in Formula 3-1 may each independently be N, and two selected from $X_{36}$ to $X_{38}$ in Formulae 3-2 to 3-5 may each independently be N, but embodiments of the present disclosure are not limited thereto.

In Formulae 3-2 to 3-5, $Y_{31}$ may be selected from O and S.

In Formulae 1, 2, and 3-1 to 3-5, $R_{13}$, $R_{14}$, $R_{21}$, $R_{22}$, and $R_{31}$ to $R_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{69}$ alkenyl group, a substituted or unsubstituted $C_2$-$C_{69}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{69}$ aryl group, a substituted or unsubstituted $C_6$-$C_{69}$ aryloxy group, a substituted or unsubstituted $C_6$-$C_{69}$ arylthio group, a substituted or unsubstituted $C_7$-$C_{60}$ aryl alkyl group, a substituted or unsubstituted $C_1$-$C_{60}$ heteroaryl group, a substituted or unsubstituted $C_1$-$C_{69}$ heteroaryloxy group, a substituted or unsubstituted $C_1$-$C_{60}$ heteroarylthio group, a substituted or unsubstituted $C_2$-$C_{69}$ heteroaryl alkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), two neighboring groups selected from $R_{31}$ to $R_{30}$ may optionally be linked each other to form a condensed ring, and $Q_1$ to $Q_7$ may each independently be selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In an embodiment, in Formula 1, $R_{13}$ and $R_{14}$ may each independently be selected from:
hydrogen, deuterium, —F, —Cl, —Br, —I, a cyano group, a phenyl group, a biphenyl group, a terphenyl group, a naphthyl group, a phenanthrenyl group, an anthracenyl group, a triphenylenyl group, a pyrenyl group, and a chrysenyl group; and
a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, —F, —Cl, —Br, —I, a cyano group, a $C_1$-$C_{20}$ alkyl group, a $C_1$-$C_{20}$ alkoxy group, and a phenyl group, but embodiments of the present disclosure are not limited thereto.

In one or more embodiments, $R_{13}$ and $R_{11}$ in Formula 1 may each independently be selected from:
hydrogen, deuterium, —F, —Cl, —Br, —I, a cyano group, a phenyl group, a biphenyl group, a terphenyl group, and a naphthyl group; and
a phenyl group, a biphenyl group, a terphenyl group, and a naphthyl group, each substituted with at least one selected from deuterium, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, a methoxy group, an ethoxy group, a propoxy group, a butoxy group, a pentoxy group, and a phenyl group, but embodiments of the present disclosure are not limited thereto.

In one or more embodiments, $R_{13}$ and $R_{14}$ in Formula 1 may be hydrogen, but embodiments of the present disclosure are not limited thereto.

In an embodiment, $R_{21}$ and $R_{22}$ in Formula 2 may each independently be selected from hydrogen, deuterium, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group; and a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, a naphthyl group, a fluorenyl group, a dimethylfluorenyl group, a diphenylfluorenyl group, a carbazolyl group, a phenylcarbazolyl group, a biphenylcarbazolyl group, a dibenzofuranyl group, and a dibenzothiophenyl group, but embodiments of the present disclosure are not limited thereto.

In one or more embodiments, $R_{21}$ and $R_{22}$ in Formula 2 may each independently be selected from:

hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a dimethylfluorenyl group, a diphenylfluorenyl group, a carbazolyl group, a phenylcarbazolyl group, a biphenylcarbazolyl group, a dibenzofuranyl group, and a dibenzothiophenyl group; and a phenyl group and a carbazolyl group, each substituted with at least one selected from a cyano group, a $C_1$-$C_{20}$ alkyl group, and a phenyl group, but embodiments of the present disclosure are not limited thereto.

In an embodiment, $R_{31}$ to $R_{39}$ in Formula 3 may each independently be selected from:

hydrogen, a phenyl group, a biphenyl group, a terphenyl group, a naphthyl group, a dibenzofuranyl group, a dibenzothiophenyl group, a pyridyl group, a pyrimidyl group, a pyrazinyl group, a triazinyl group, an azadibenzofuranyl group, an azadibenzothiophenyl group, a diazadibenzofuranyl group, and a diazadibenzothiophenyl group; and a phenyl group, a biphenyl group, a terphenyl group, a naphthyl group, a dibenzofuranyl group, a dibenzothiophenyl group, a pyridyl group, a pyrimidyl group, a pyrazinyl group, a triazinyl group, an azadibenzofuranyl group, an azadibenzothiophenyl group, a diazadibenzofuranyl group, and a diazadibenzothiophenyl group, each substituted with at least one selected from deuterium, —F, —Cl, —Br, —I, a cyano group, a $C_1$-$C_{20}$ alkyl group, a $C_1$-$C_{20}$ alkoxy group, and a phenyl group, but embodiments of the present disclosure are not limited thereto.

In one or more embodiments, $R_{31}$ to $R_{39}$ in Formula 3 may each independently be selected from:

hydrogen, a phenyl group, a biphenyl group, a terphenyl group, a dibenzofuranyl group, a dibenzothiophenyl group, a pyridyl group, an azadibenzofuranyl group, an azadibenzothiophenyl group, a diazadibenzofuranyl group, and a diazadibenzothiophenyl group; and a phenyl group, a biphenyl group, a terphenyl group, a dibenzofuranyl group, a dibenzothiophenyl group, an azadibenzofuranyl group, an azadibenzothiophenyl group, a diazadibenzofuranyl group, and a diazadibenzothiophenyl group, each substituted with a phenyl group, but embodiments of the present disclosure are not limited thereto.

For example, $D_1$ in Formula 1 may be represented by one selected from Formulae 2-1 and 2-2, but embodiments of the present disclosure are not limited thereto:

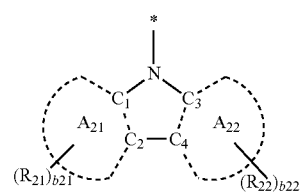

2-1

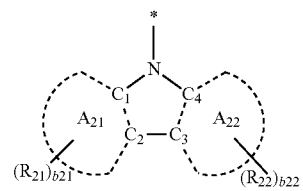

2-2

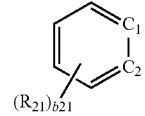

9-11

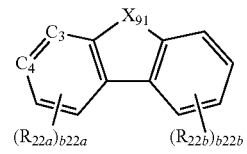

9-21

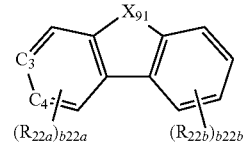

9-22

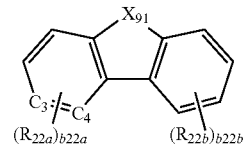

9-23

9-31 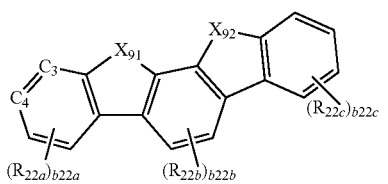
9-32 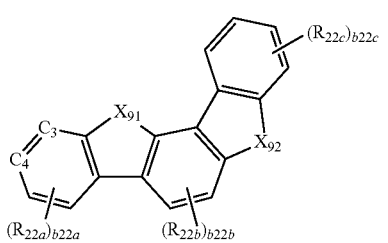
9-33 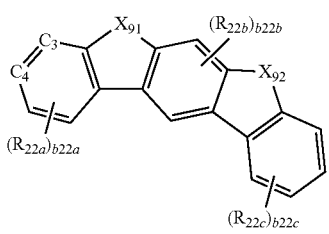
9-34 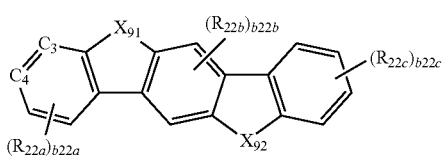
9-35 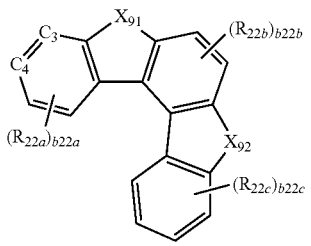
9-36 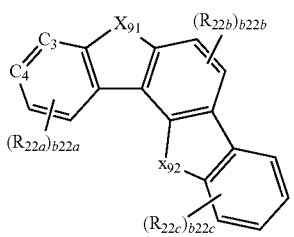
9-37 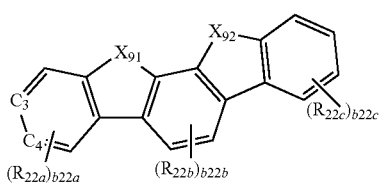
9-38 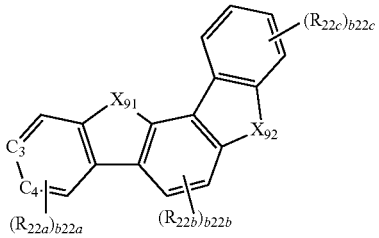
9-39 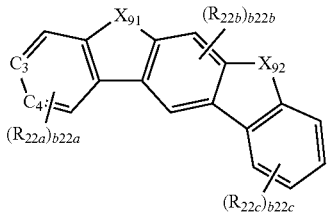
9-40 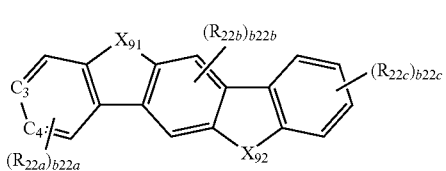
9-41 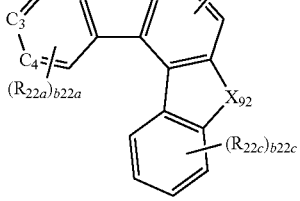
9-42 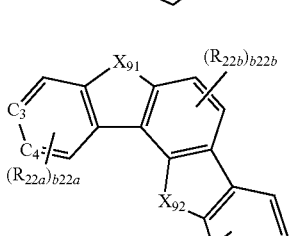
9-43 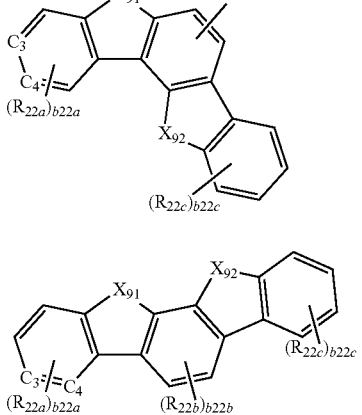
9-44 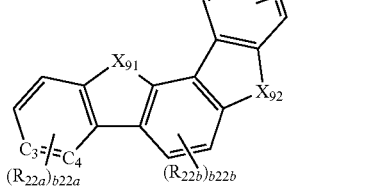

-continued 9-45
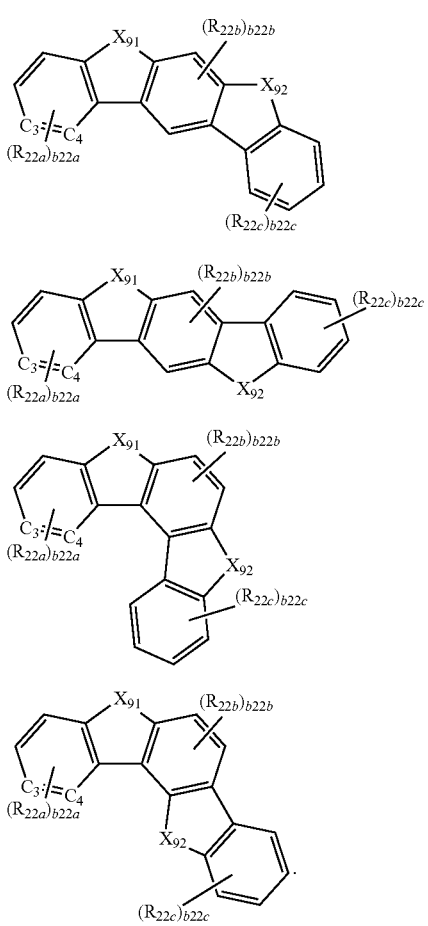

9-46

9-47

9-48

In Formulae 2-1, 2-2, 9-11, 9-21 to 9-23, and 9-31 to 9-48, $A_{21}$ may be a group represented by Formula 9-11, $A_{22}$ may be a group represented by one selected from Formulae 9-11, 9-21 to 9-23, and 9-31 to 9-48, $C_1$ to $C_4$ may each independently be a carbon atom, $X_{91}$ may be selected from O, S, $N(R_{22d})$, and $C(R_{22d})(R_{22e})$, $X_{92}$ may be selected from O, S, $N(R_{22f})$, and $C(R_{22f})(R_{22g})$, $R_{22a}$ to $R_{22g}$ may each independently have the same definition as that of $R_{22}$ in Formula 2, and b22a to b22c may each independently have the same definition as that b22 in Formula 2.

For example, $A_1$ in Formula 1 may be represented by one selected from Formulae 3-11 to 3-35, but embodiments of the present disclosure are not limited thereto:

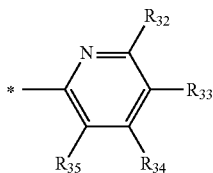
3-11

-continued

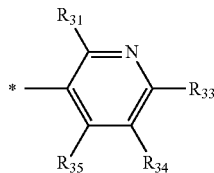
3-12

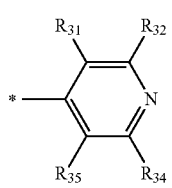
3-13

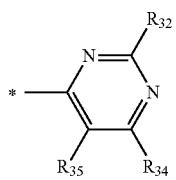
3-14

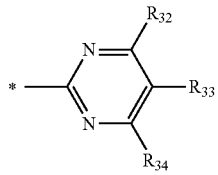
3-15

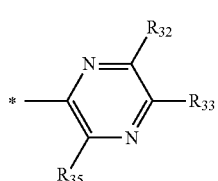
3-16

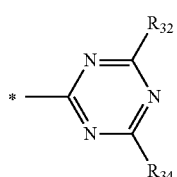
3-17

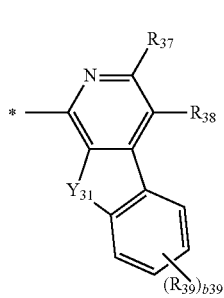
3-18

-continued
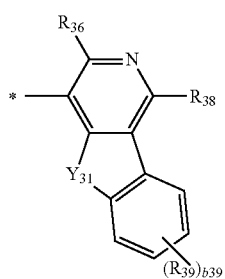
3-19
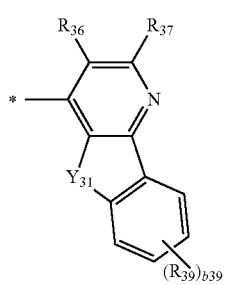
3-20
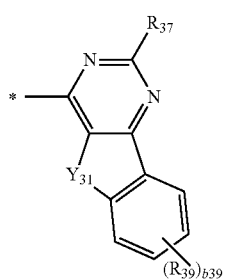
3-21
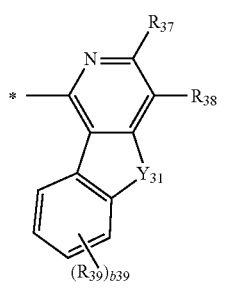
3-22
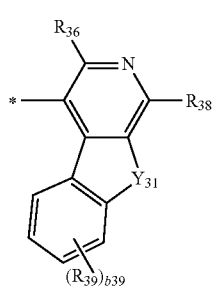
3-23
-continued
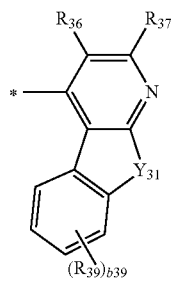
3-24
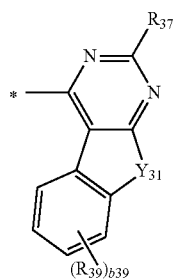
3-25
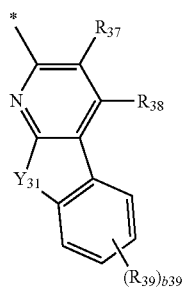
3-26
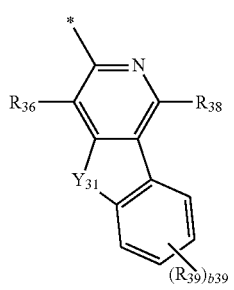
3-37
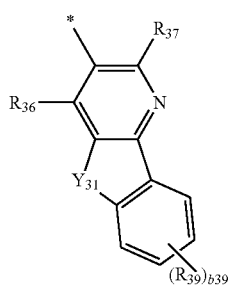
3-28

3-29 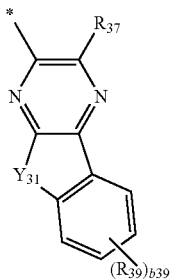

3-30 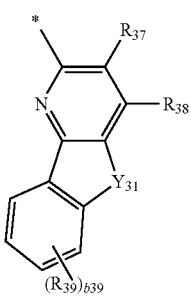

3-31 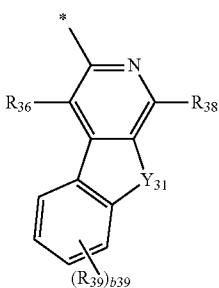

3-32 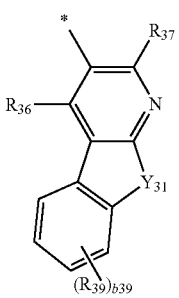

3-33 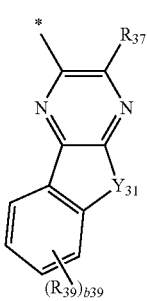

3-34 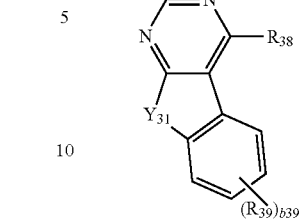

3-35 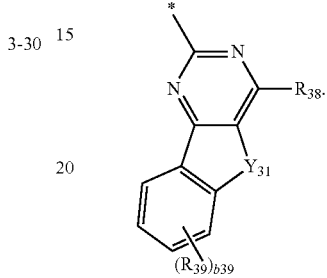

In Formulae 3-11 to 3-35, $Y_{31}$, $R_{36}$ to $R_{39}$, and b39 may each independently have the same definition as those of Formula 3-1 to 3-5, and

* indicates a binding site to a neighboring atom.

In an embodiment, $A_1$ in Formula 1 may be represented by one selected from Formulae 3-14, 3-15, 3-17, 3-21, 3-25, 3-29, 3-33, 3-34, and 3-35, but embodiments of the present disclosure are not limited thereto.

For example, the condensed cyclic compound represented by Formula 1 may be represented by Formula 1-1, but embodiments of the present disclosure are not limited thereto:

Formula 1-1

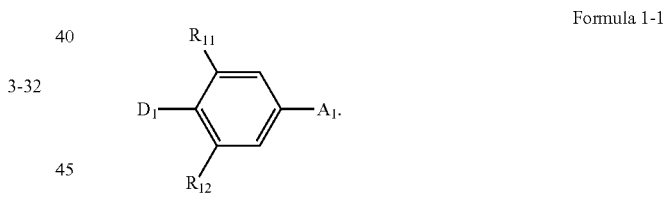

In Formula 1-1, $D_1$, $A_1$, $R_{11}$, and $R_{12}$ may each independently have the same definition as those in Formula 1.

In an embodiment, in Formula 1, $D_1$ 1 may be represented by one selected from Formulae 2-1 and 2-2, $A_1$ may be represented by one selected from Formulae 3-11 to 3-35, and $R_{11}$ and $R_{12}$ may each independently have the same definition as those in Formula 1:

2-1

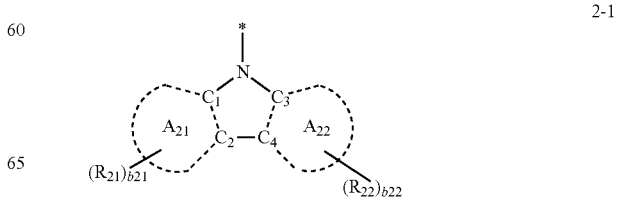

-continued
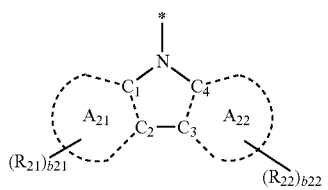
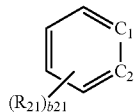
2-2
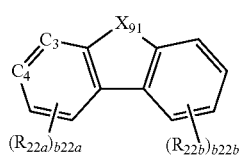
9-11
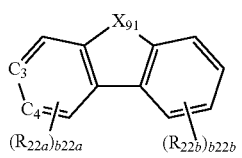
9-21

9-22
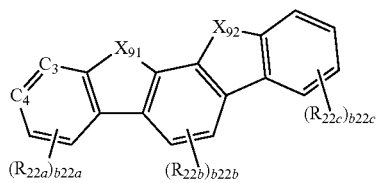
9-23
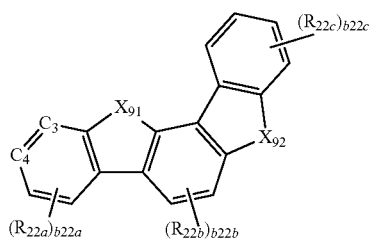
9-31
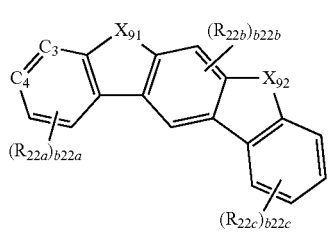
9-32
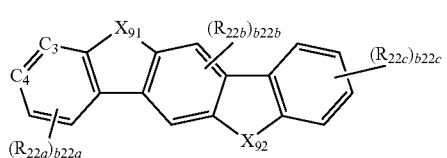
9-33
-continued
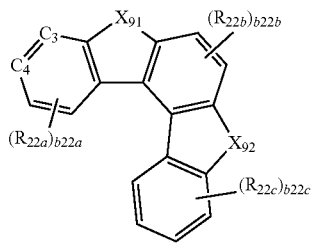
9-35
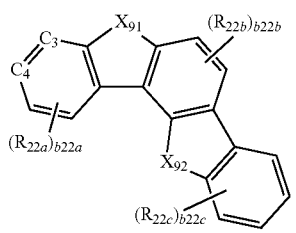
9-36
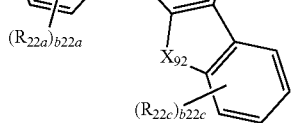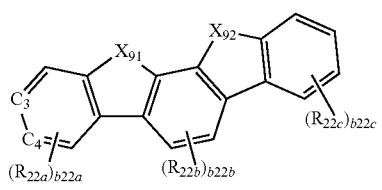
9-37
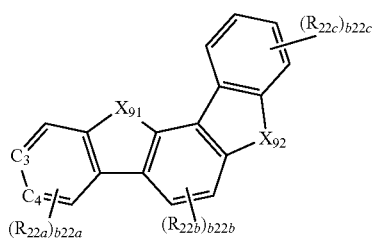
9-38
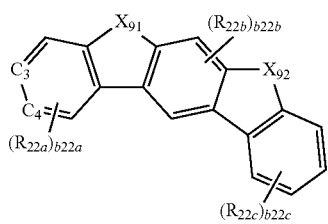
9-39
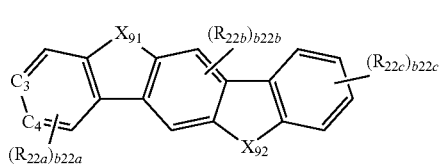
9-40
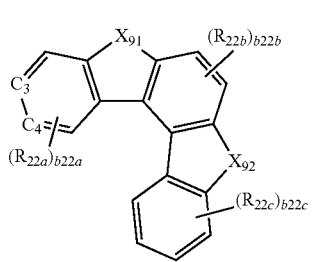
9-41
9-34

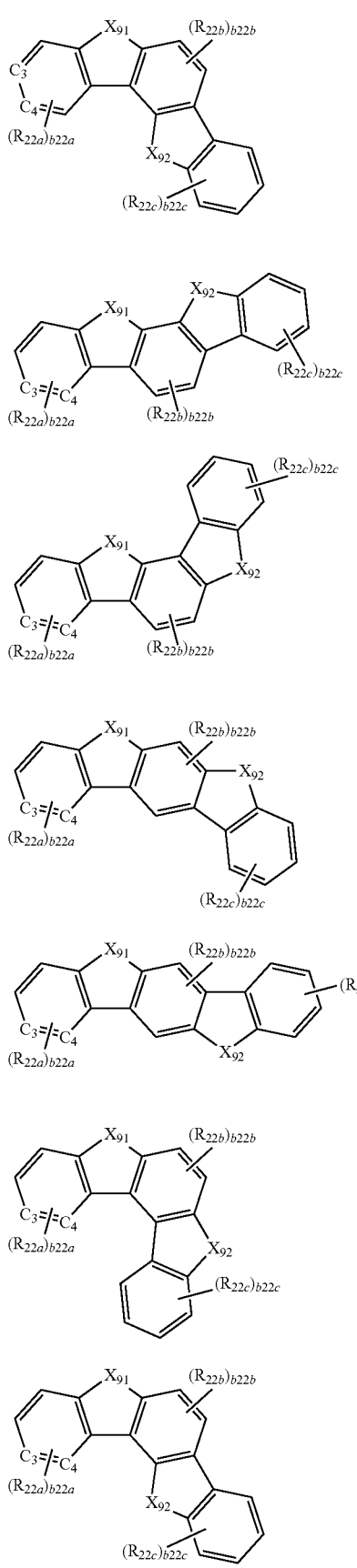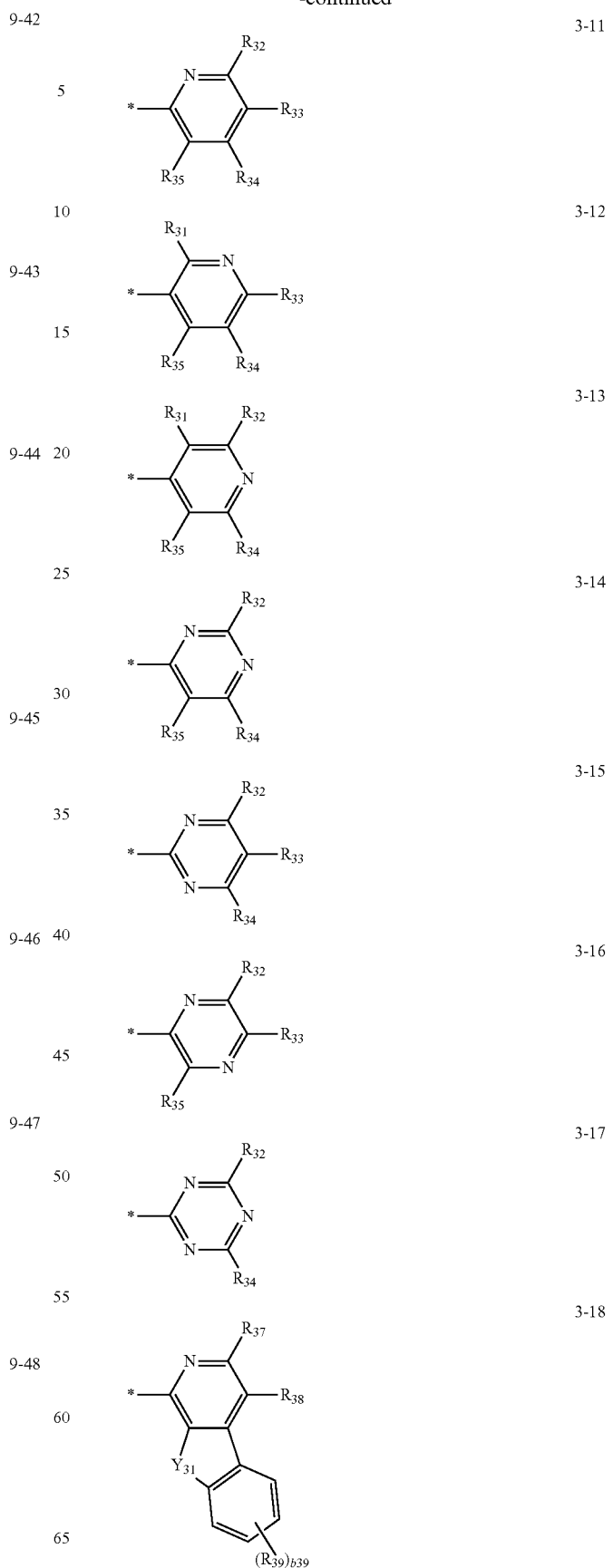

3-19 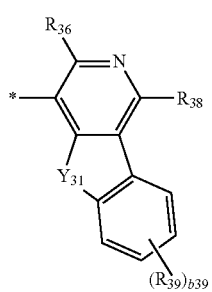
3-20 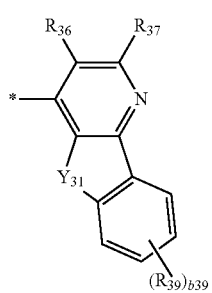
3-21 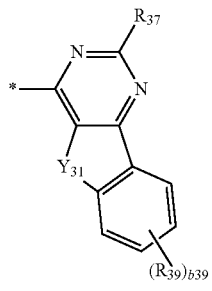
3-22 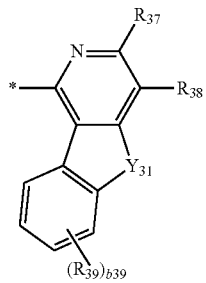
3-23 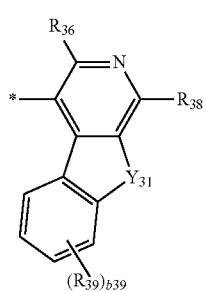
3-24 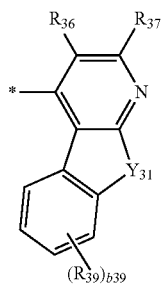
3-25 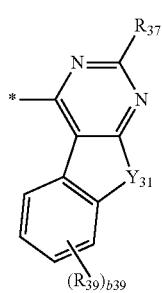
3-26 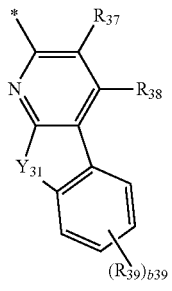
3-37 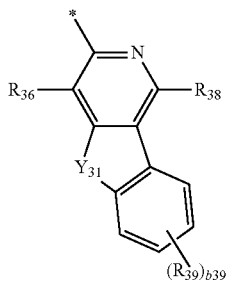
3-28 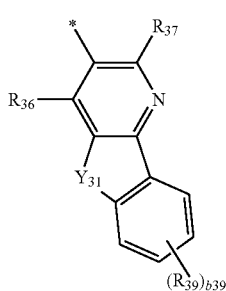

3-29

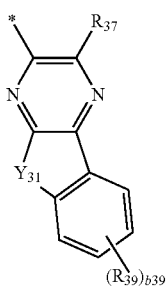

3-30

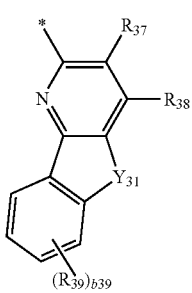

3-31

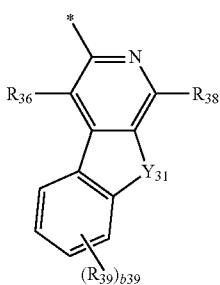

3-32

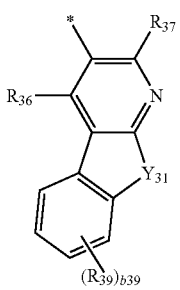

3-33

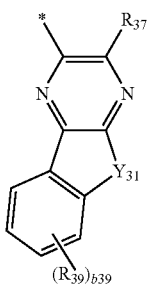

3-34

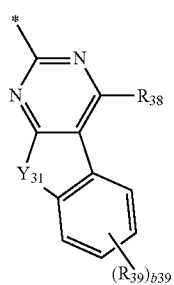

3-35

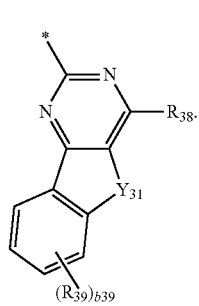

In Formulae 2-1, 2-2, 9-11, 9-21 to 9-23, 9-31 to 9-48, and 3-11 to 3-35, $A_{21}$ may be a group represented by Formula 9-11, $A_{22}$ may be a group represented by one selected from Formulae 9-11, 9-21 to 9-23, and 9-31 to 9-48, $C_1$ to $C_4$ may each independently be a carbon atom, $X_{91}$ may be selected from O, S, N($R_{22d}$), and C($R_{22d}$)($R_{22e}$), $X_{92}$ may be selected from O, S, N($R_{22f}$), and C($R_{22f}$)($R_{22g}$), $R_{22a}$ to $R_{22g}$ may each independently have the same definition as that of $R_{22}$ in Formula 2, b22a to b22c may each independently have the same definition as that of b22 in Formula 2, $Y_{31}$, $R_{36}$ to $R_{39}$, and b39 may each independently have the same definition as those described in Formulae 3-1 to 3-5, and

* indicates a binding site to a neighboring atom.

In an embodiment, the condensed cyclic compound represented by Formula 1 may be selected from Compounds 1 to 1030, but embodiments of the present disclosure are not limited thereto:

1

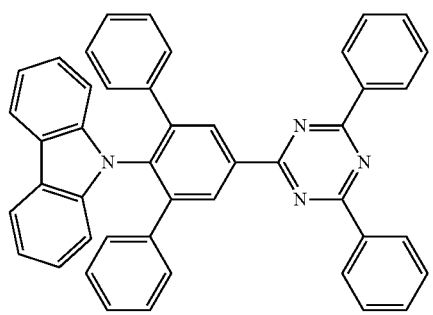

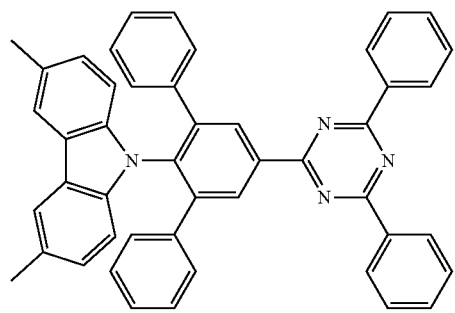
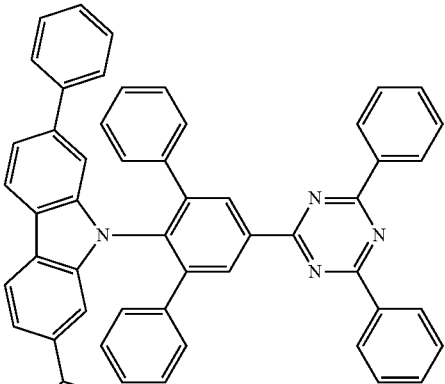
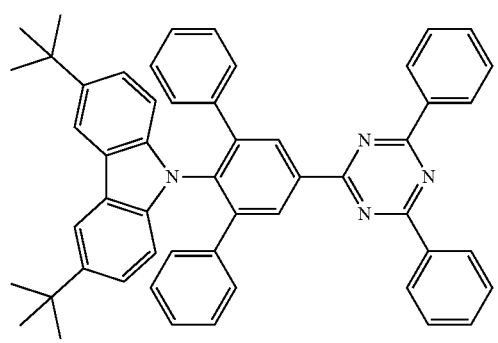
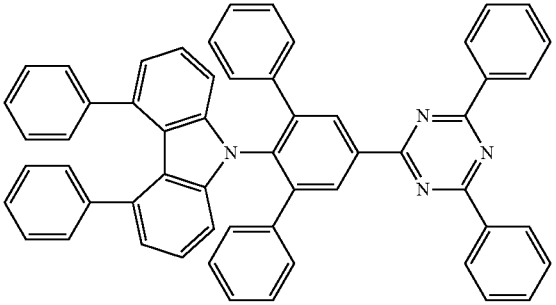
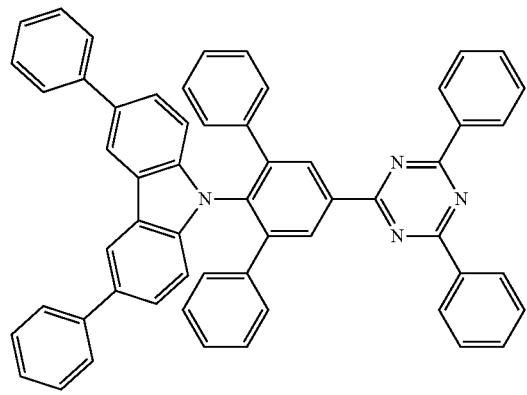
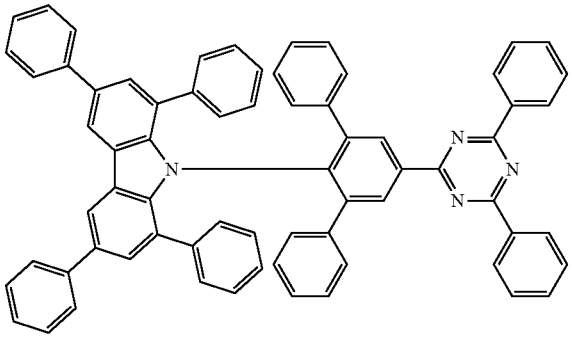
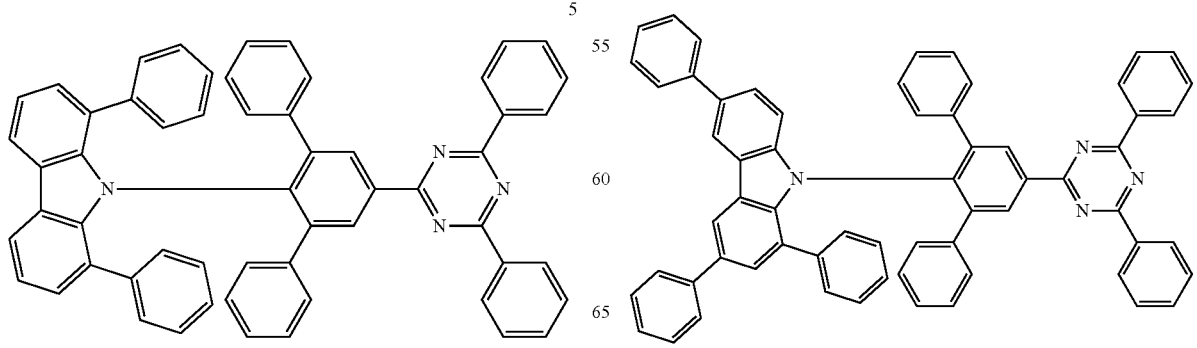

10
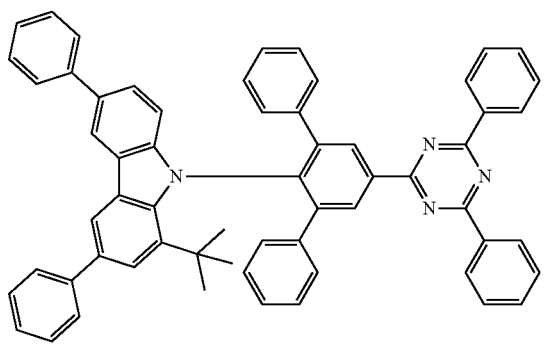
11
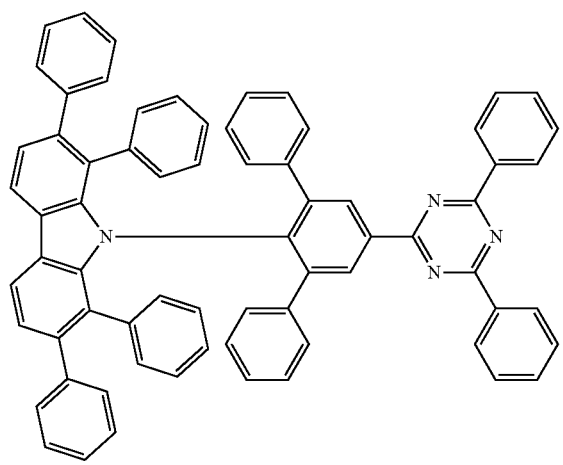
12
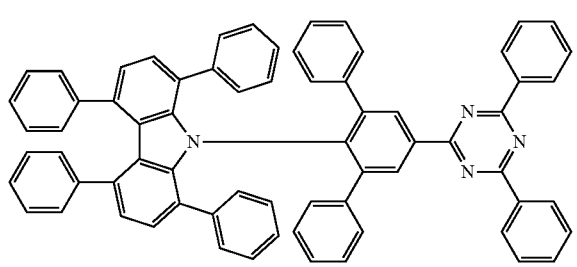
13
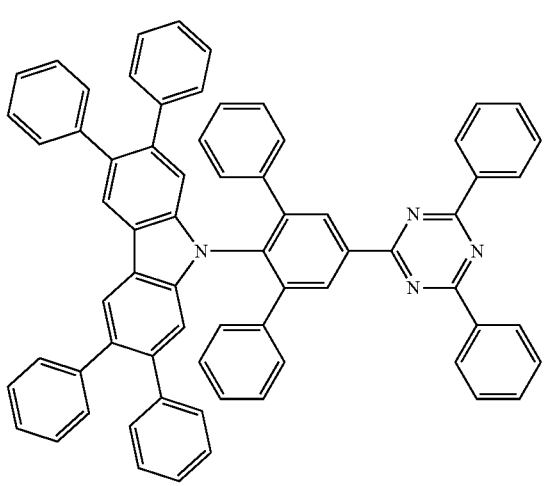
14
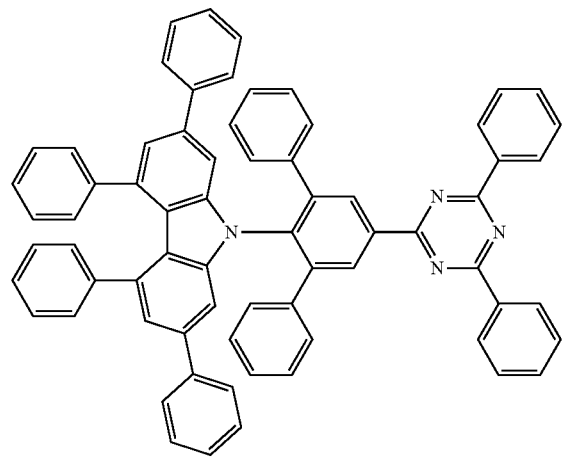
15
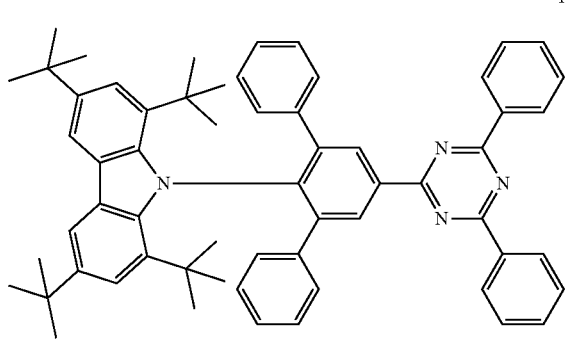
16
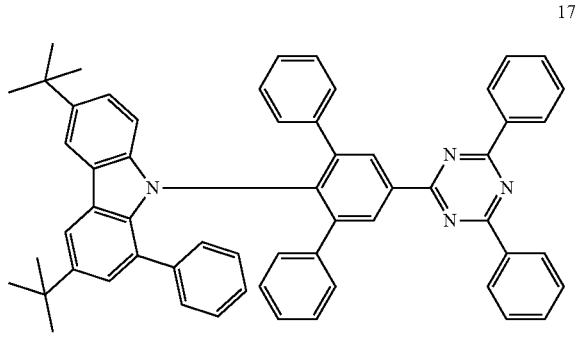
17

18
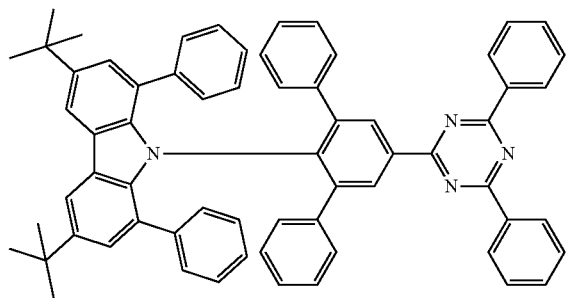
19
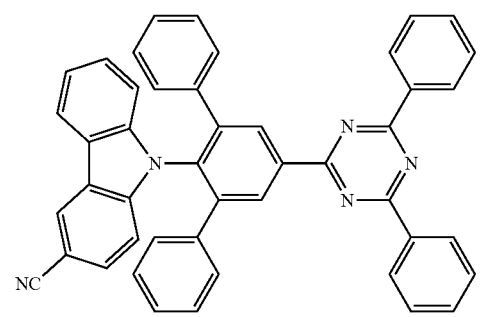
20
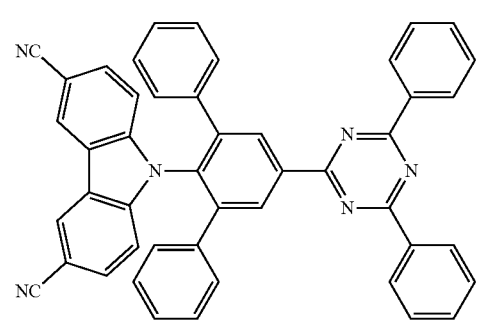
21
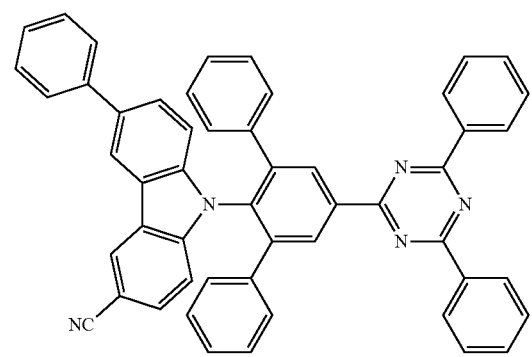
22
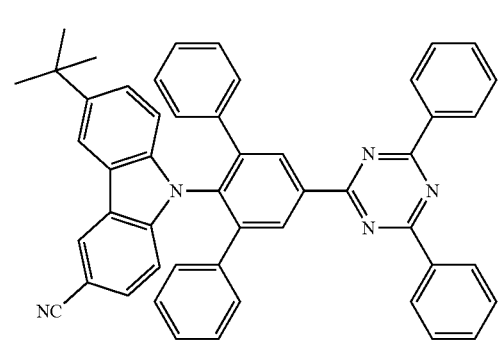
23
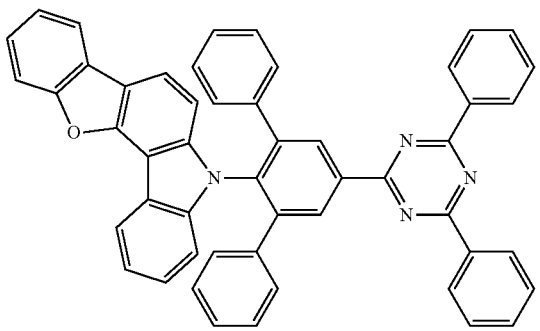
24
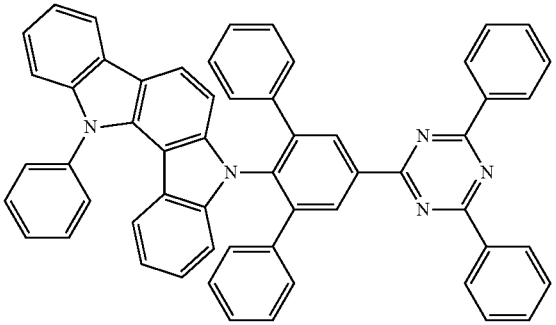
25
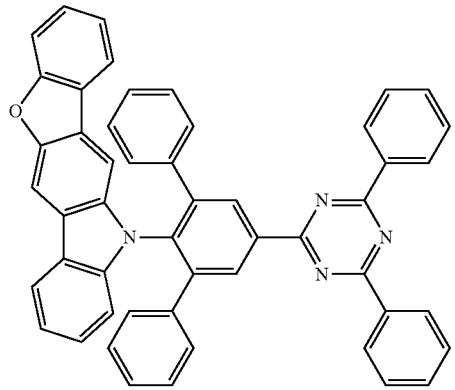
26
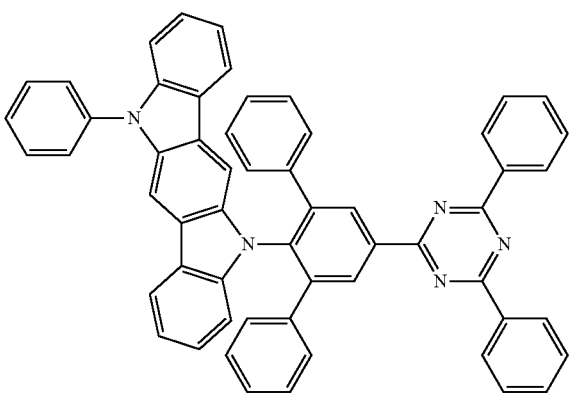

27
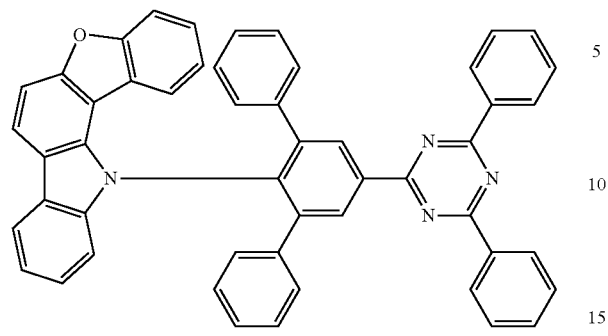
28
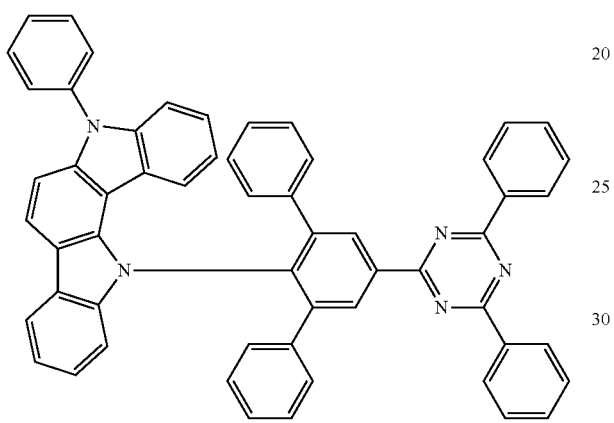
29
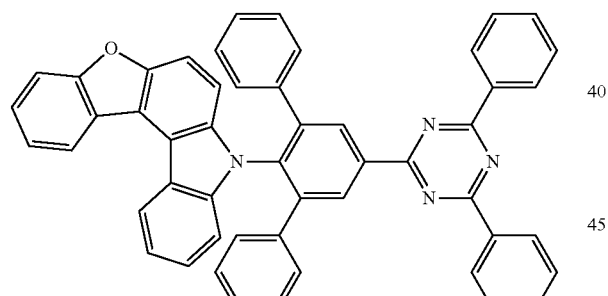
30
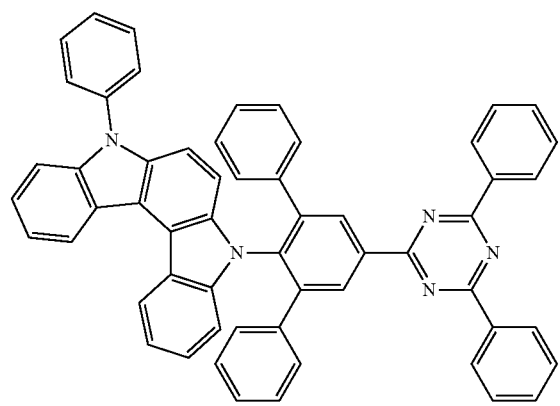
31
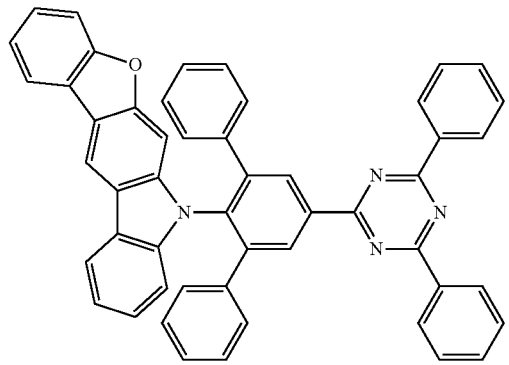
32
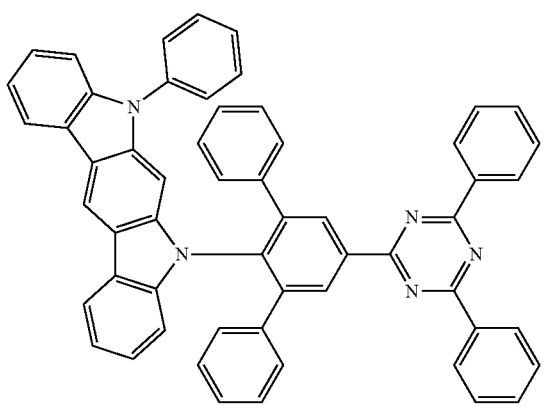
33
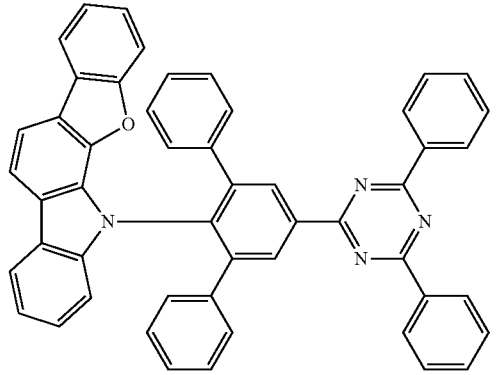
34
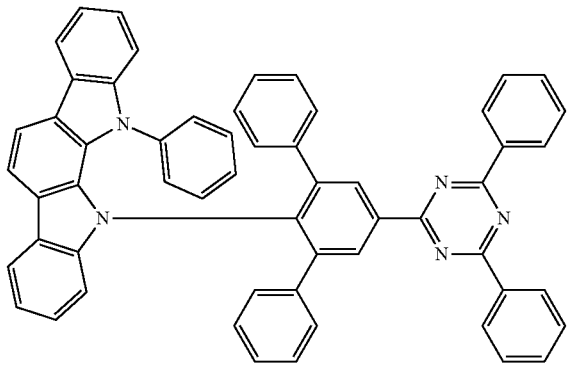

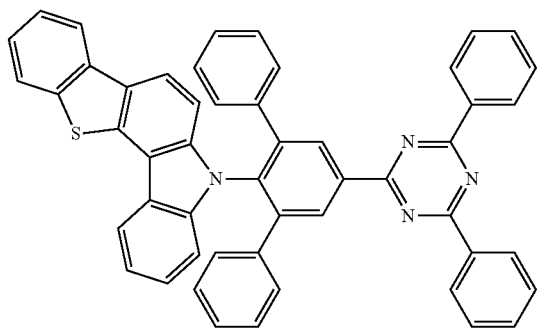
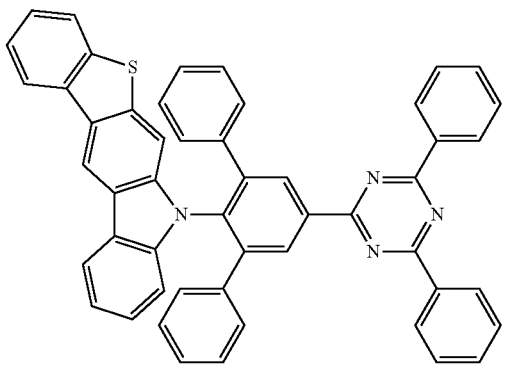
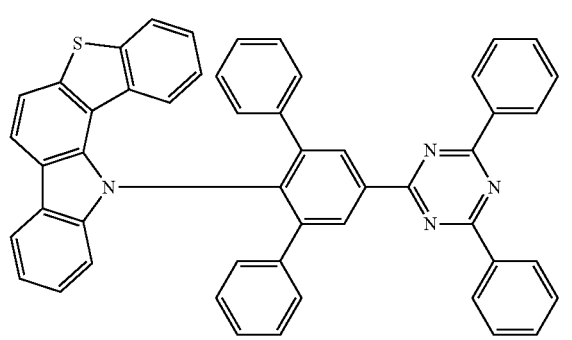
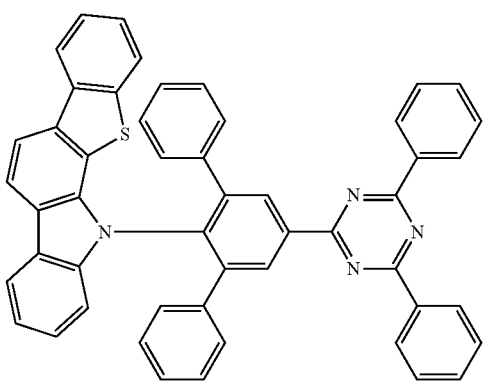
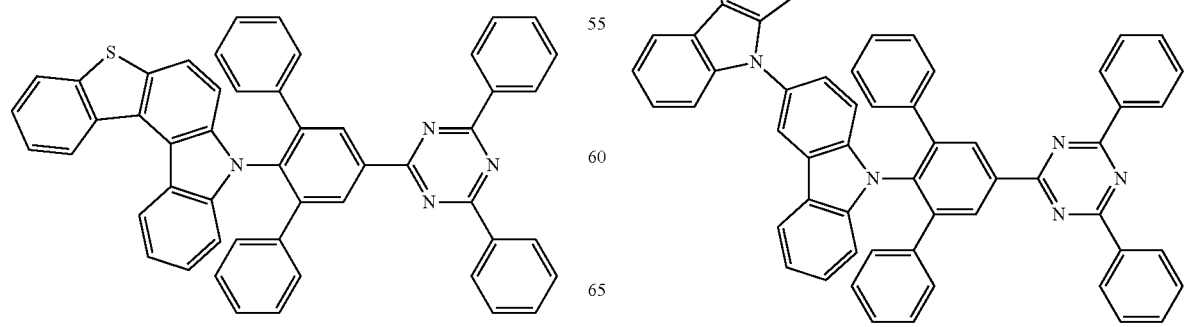

42
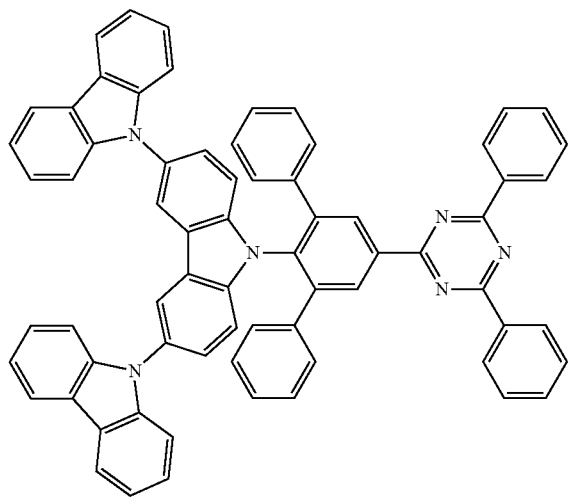
43
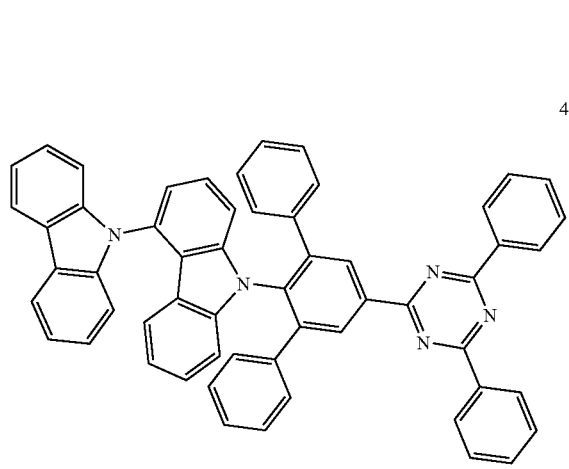
44
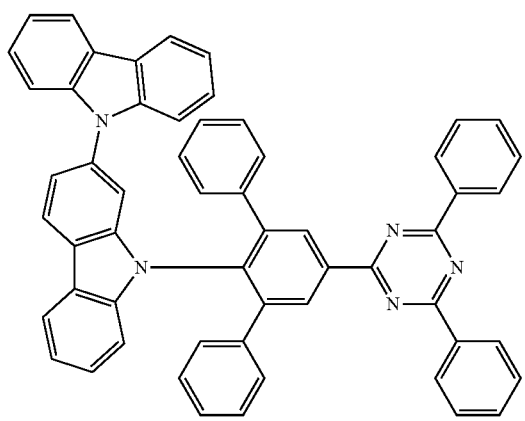
45
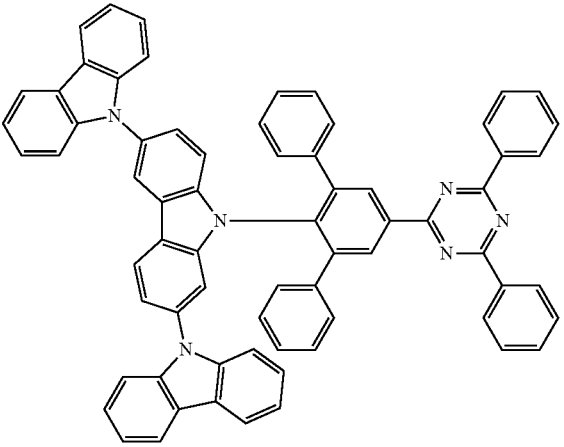
46
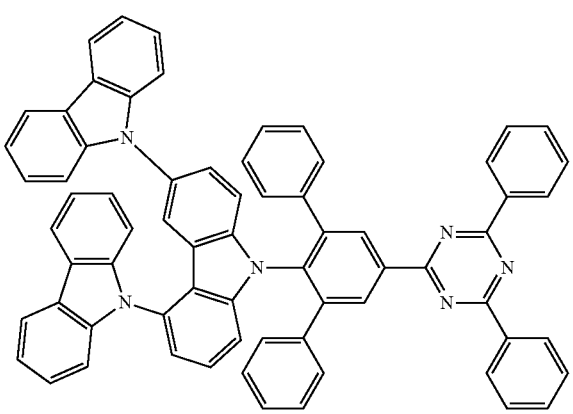
47
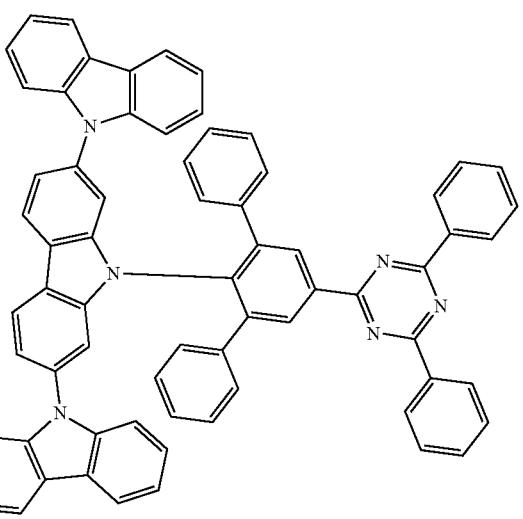

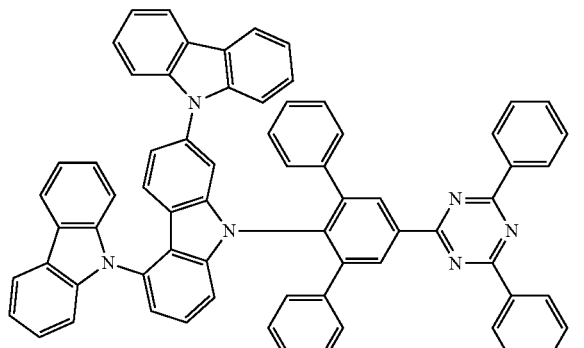
48
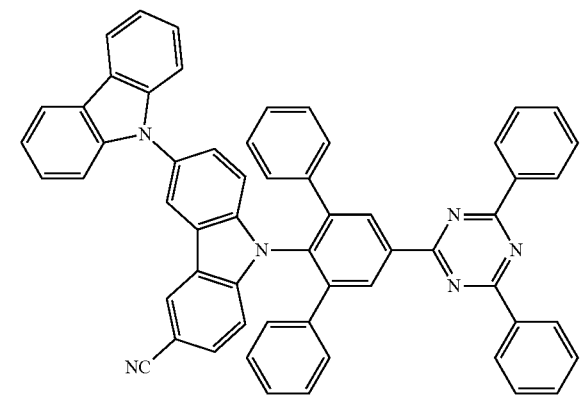
51
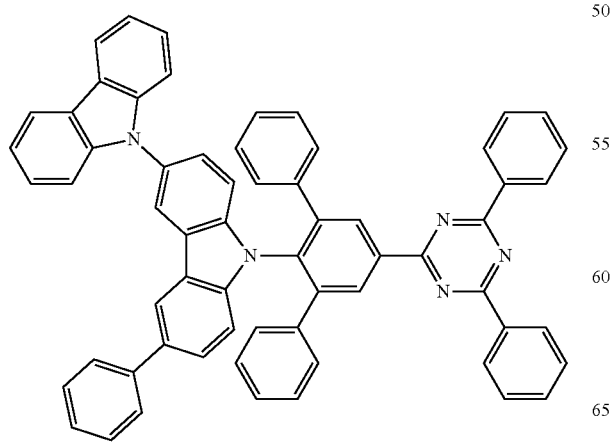
49
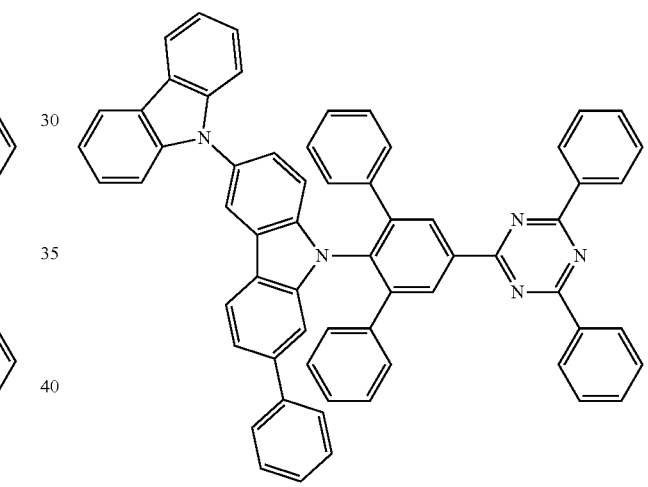
52
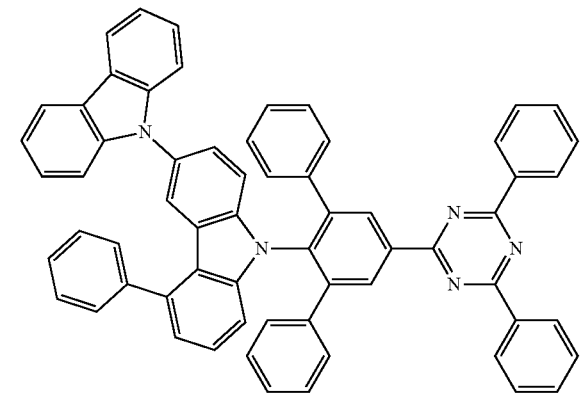
53

54
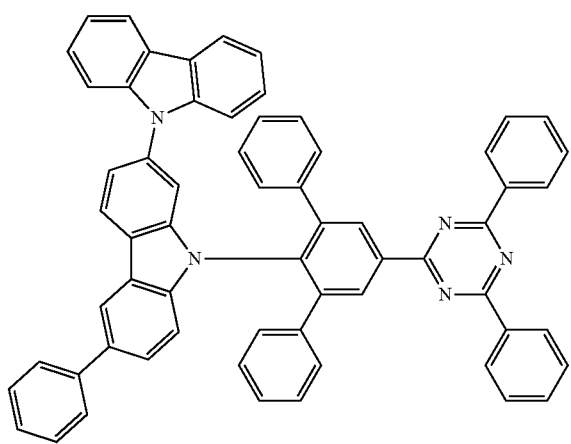
55
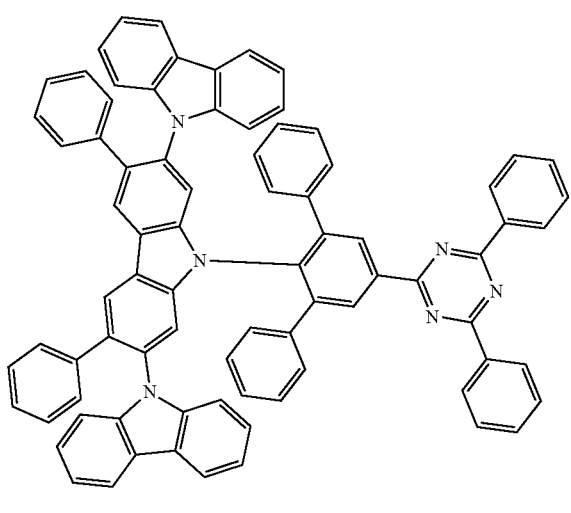
56
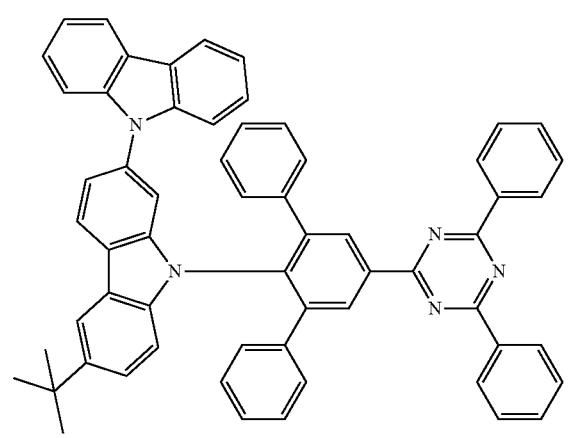
57
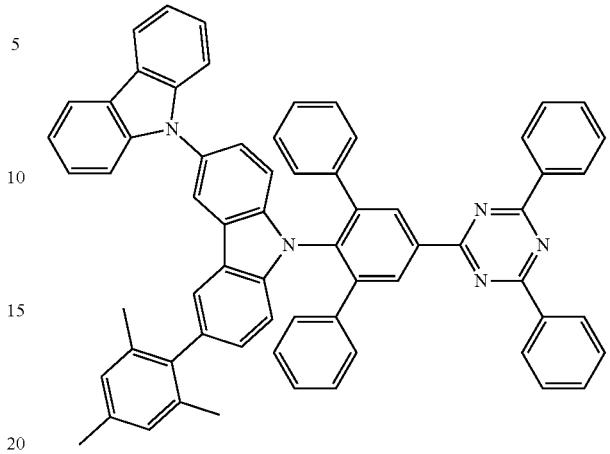
58
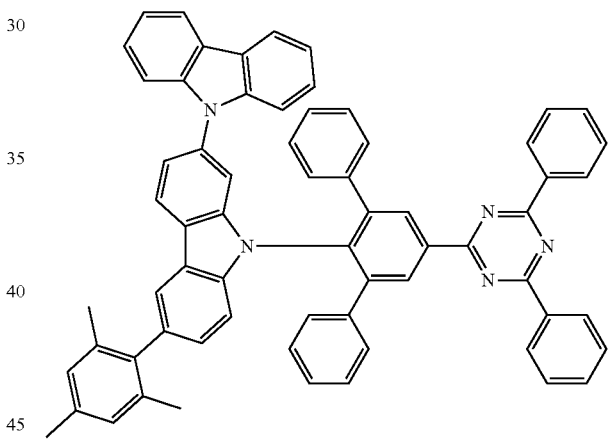
59
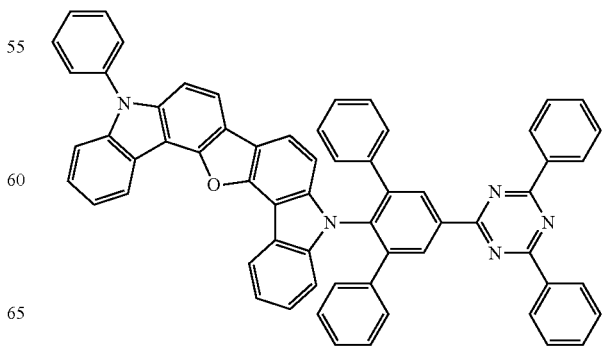

60
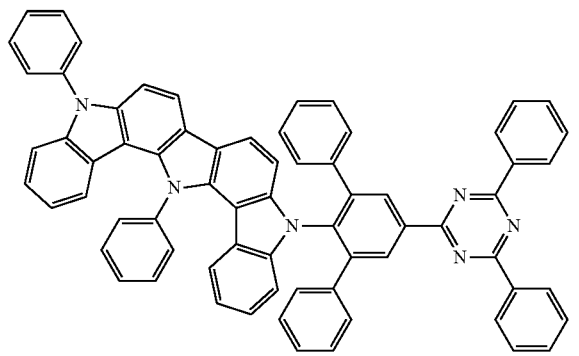
61
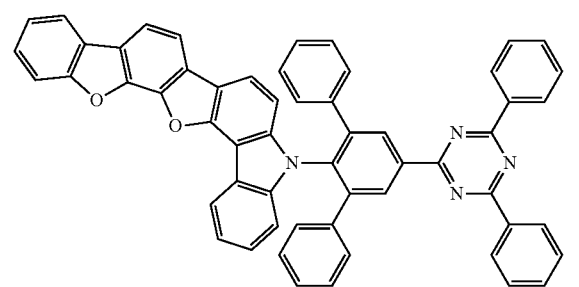
62
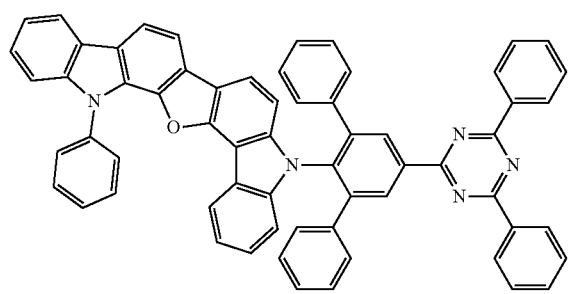
63
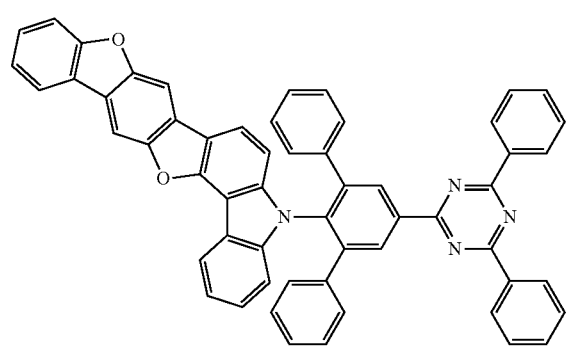
64
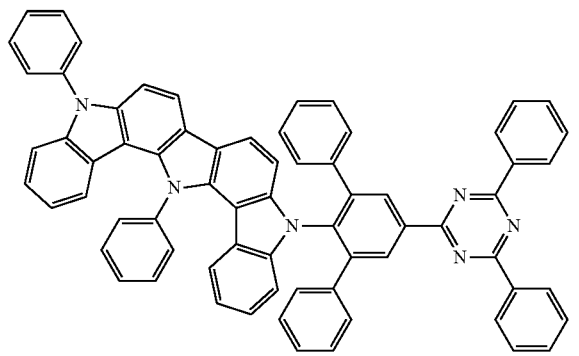
65
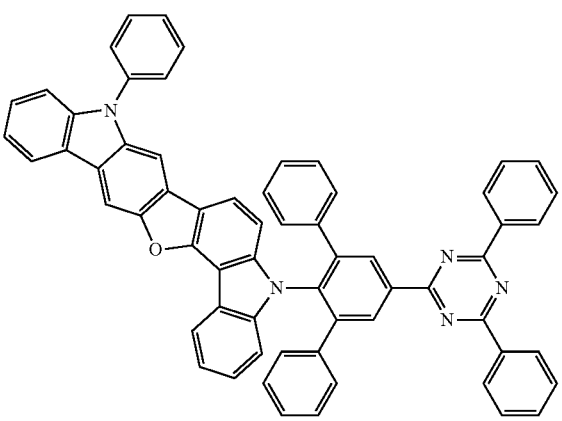
66
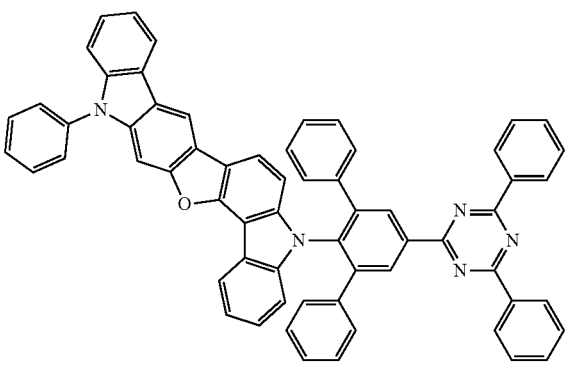

67
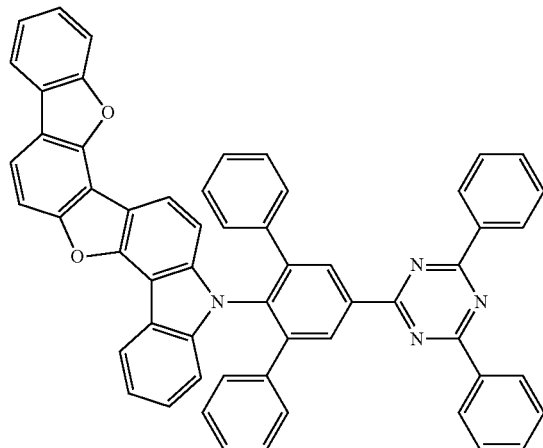
68
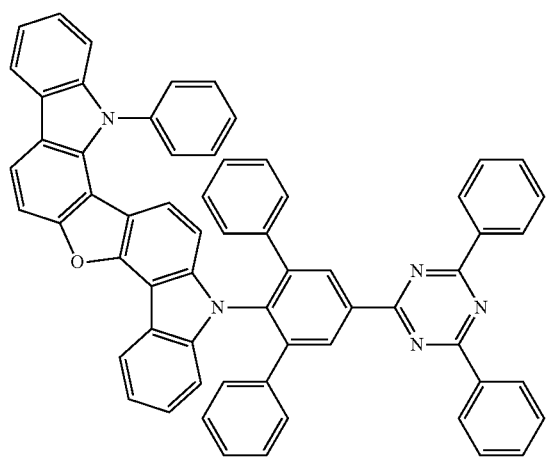
69
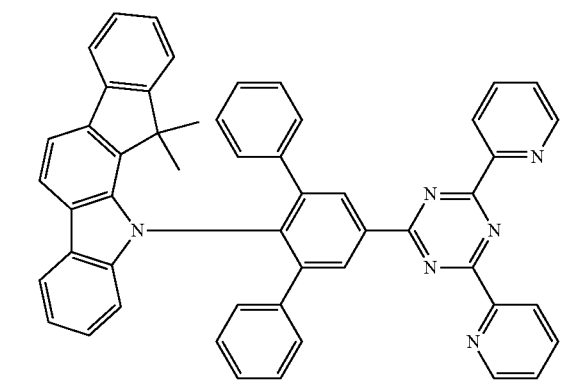
70
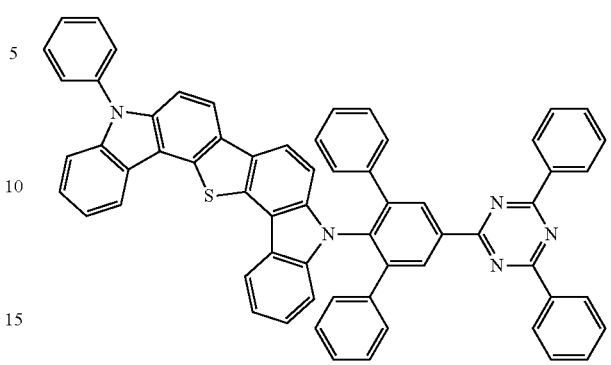
71
72
73
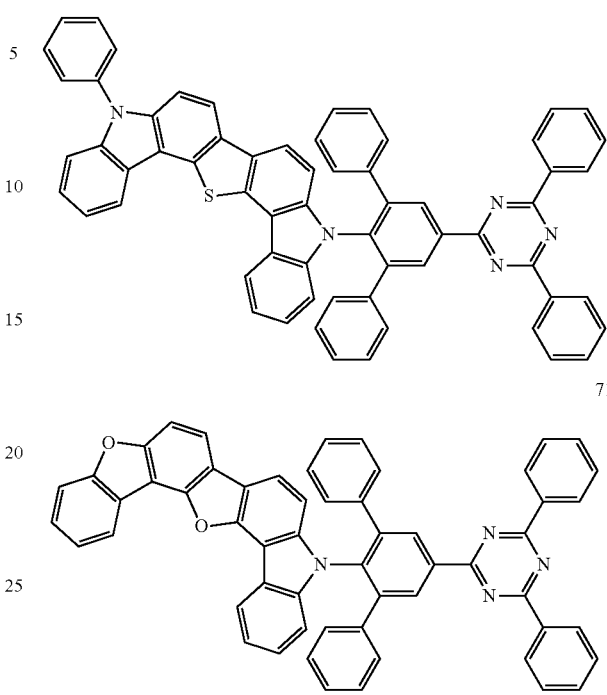
74
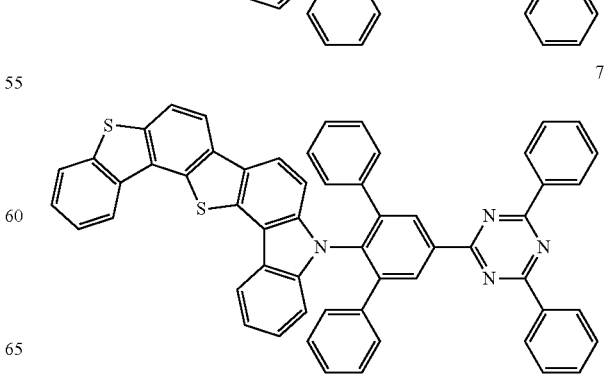

75
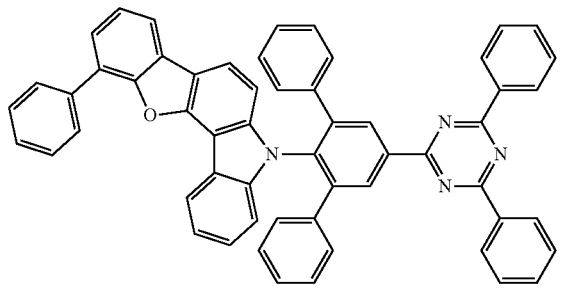
76
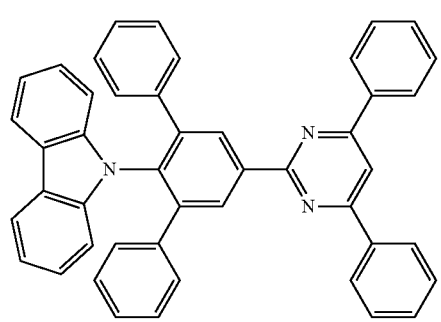
77
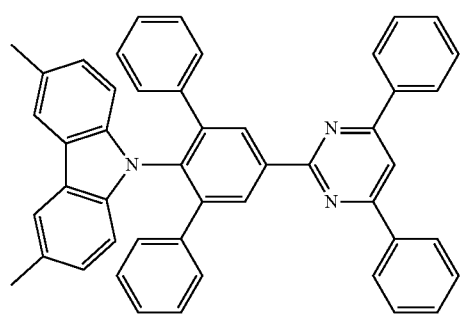
78
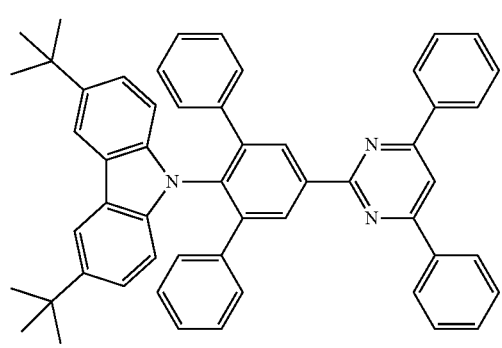
79
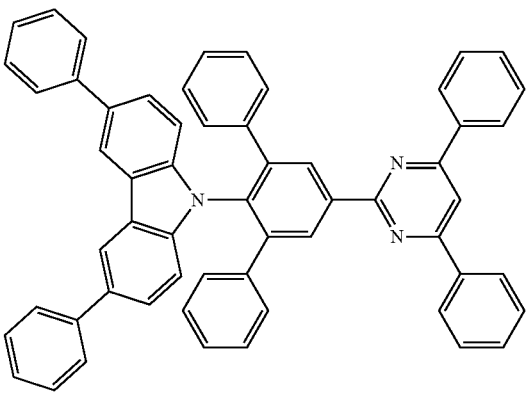
80
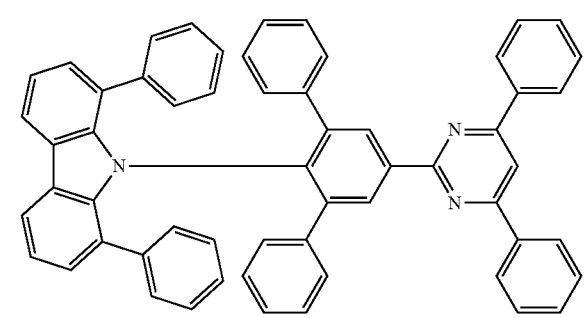
81
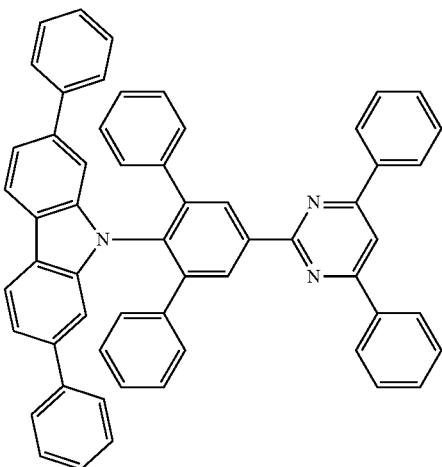
82
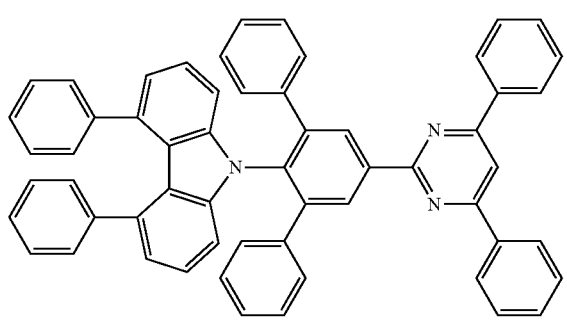

83
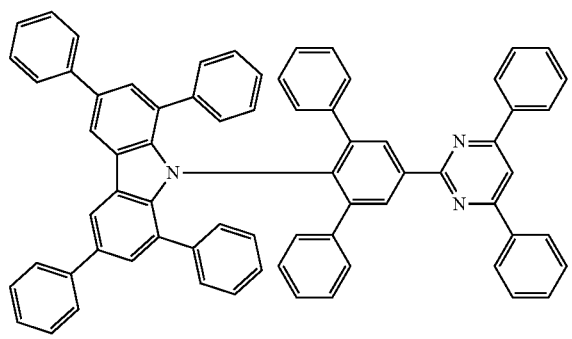
84
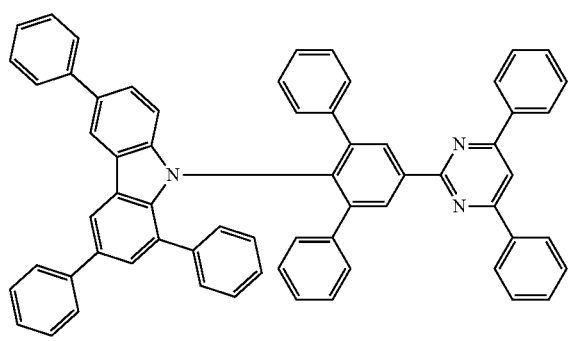
85
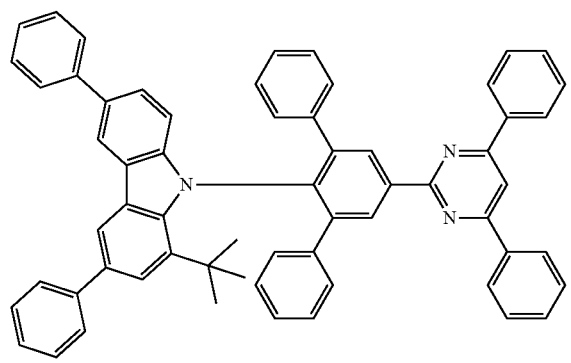
86
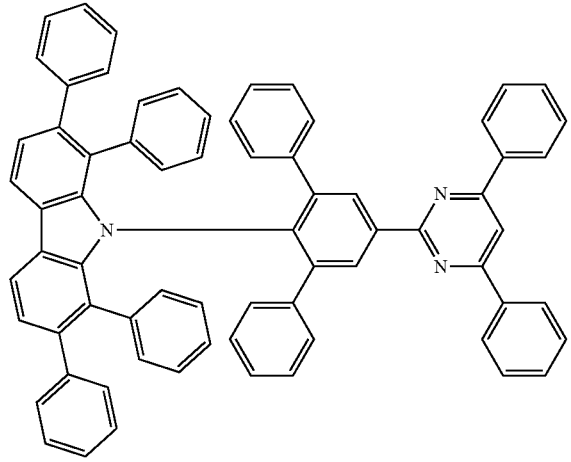
87
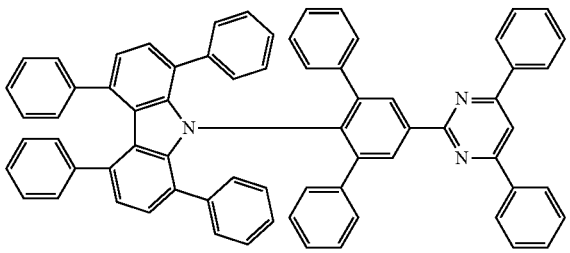
88
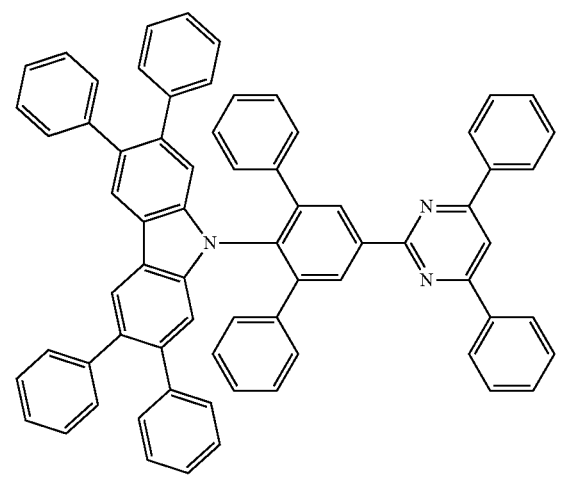
89
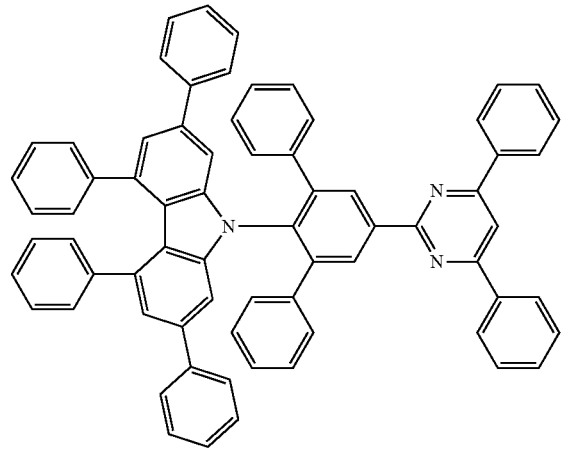
90
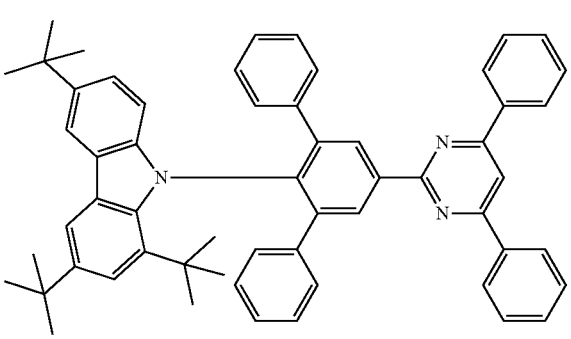

US 11,339,143 B2
51
-continued
91
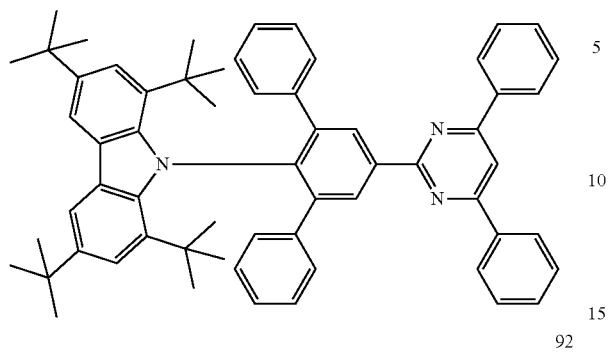
92
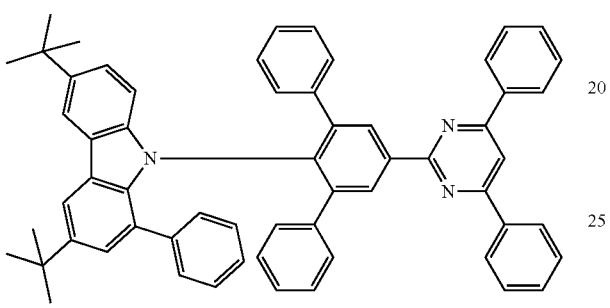
93
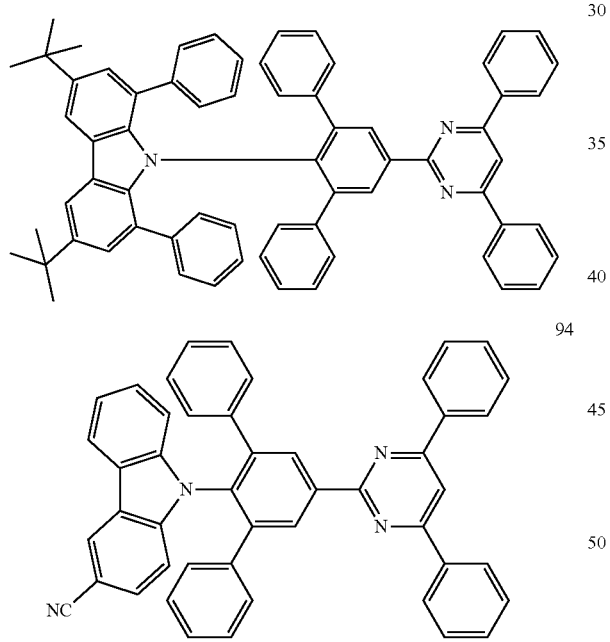
94
95
52
-continued
96
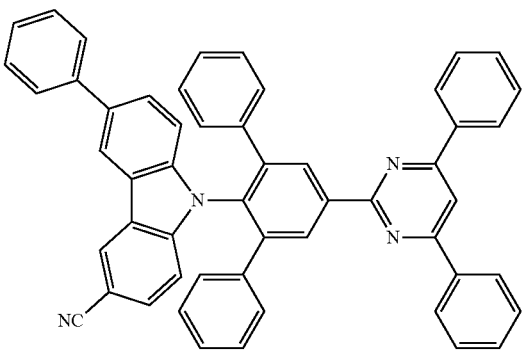
97
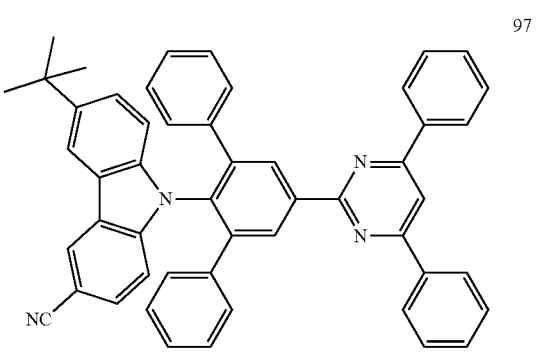
98
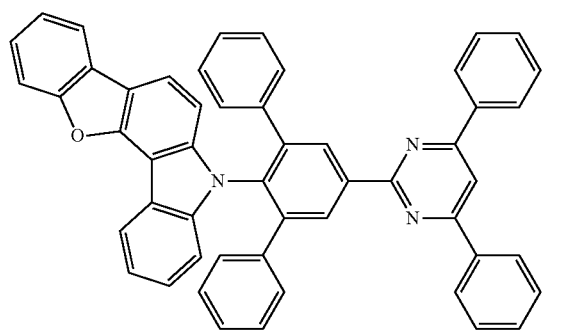
99
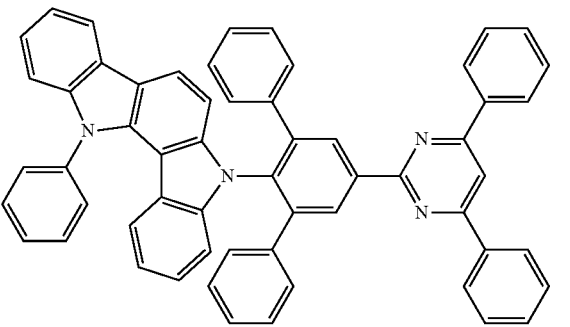

100
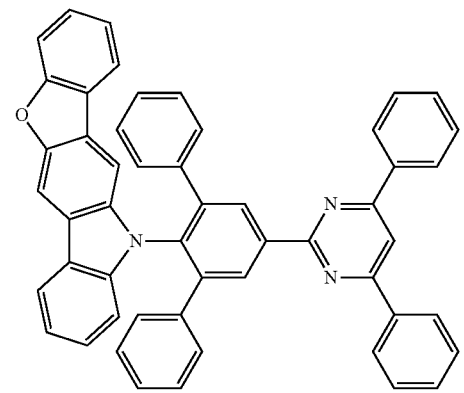
101
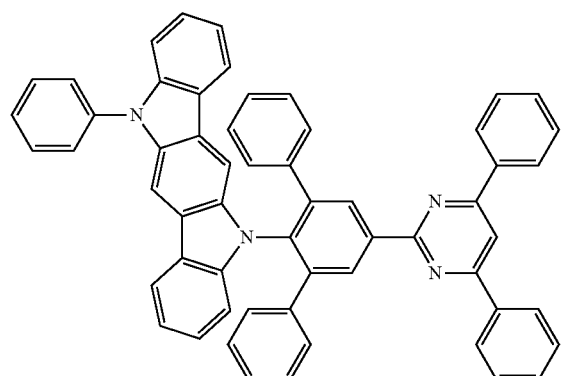
102
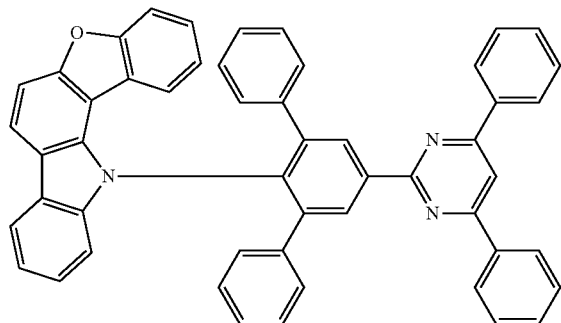
103
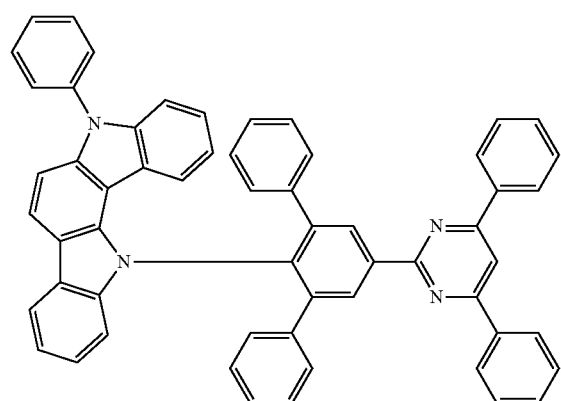
104
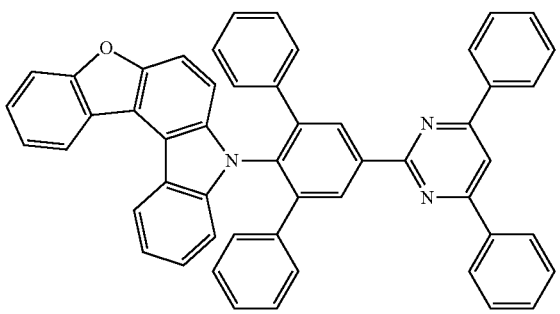
105
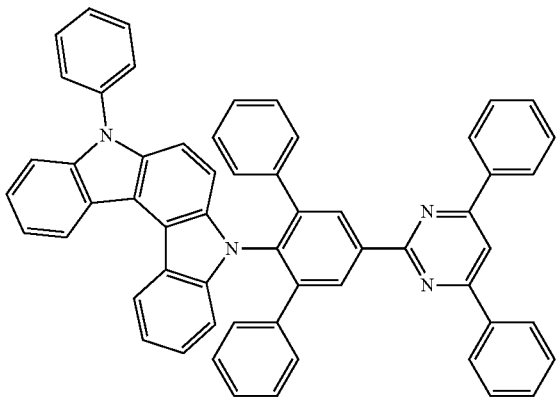
106
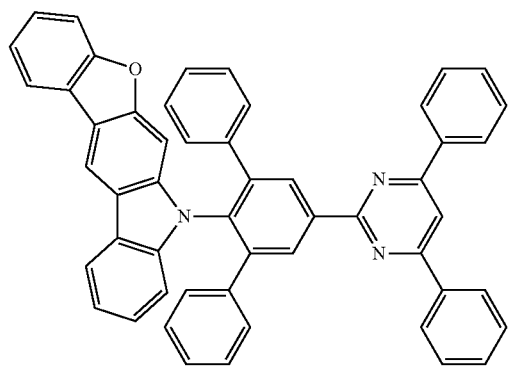
107
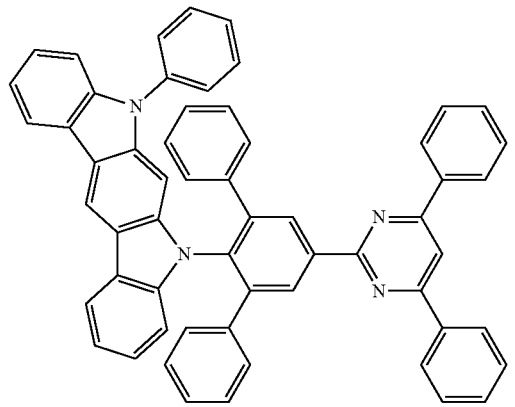

108
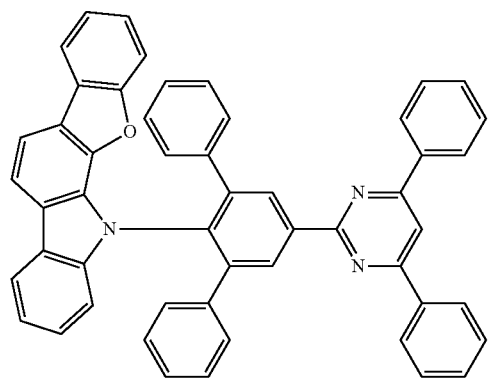
109

110
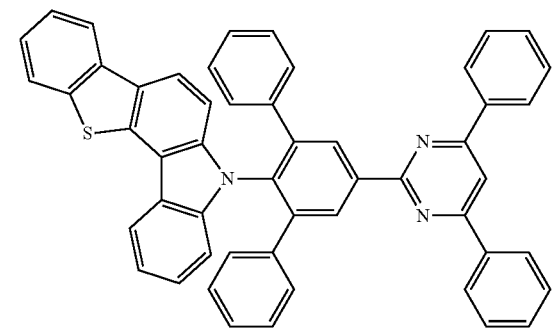
111
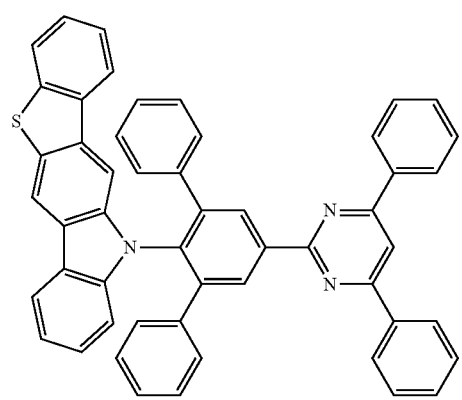
112
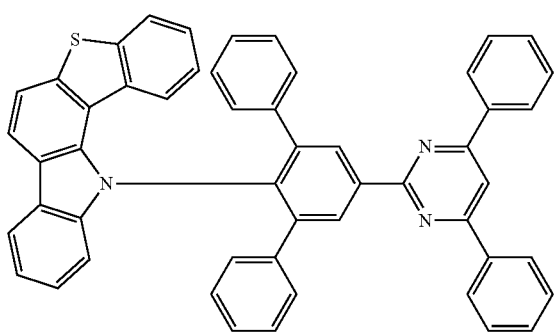
113
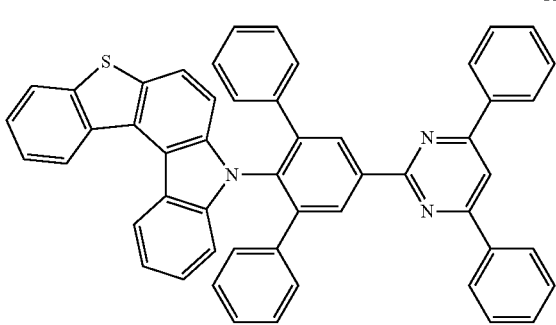
114
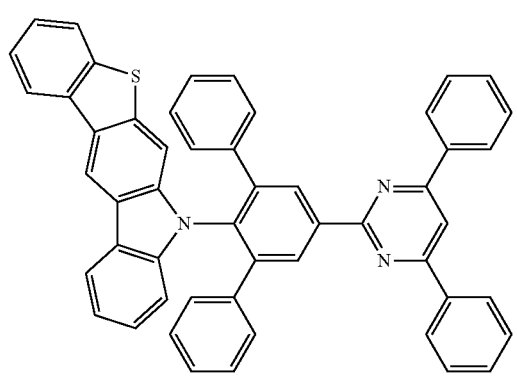
115
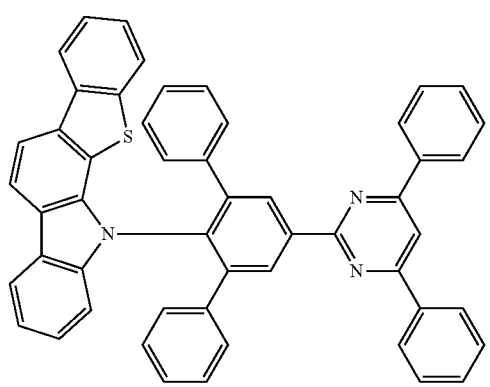

116
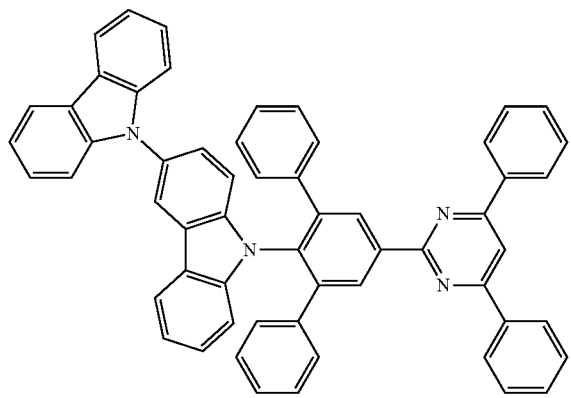
117
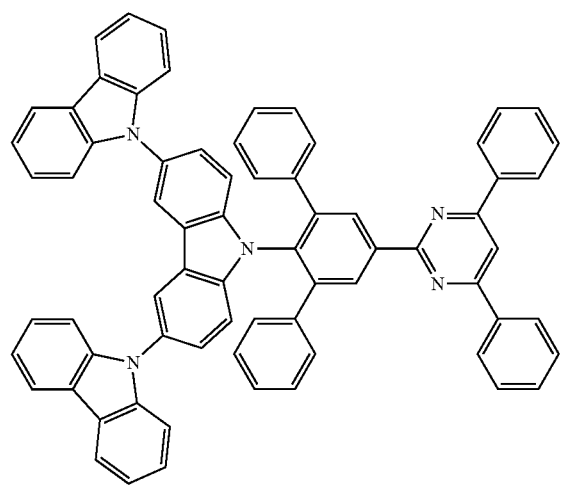
118
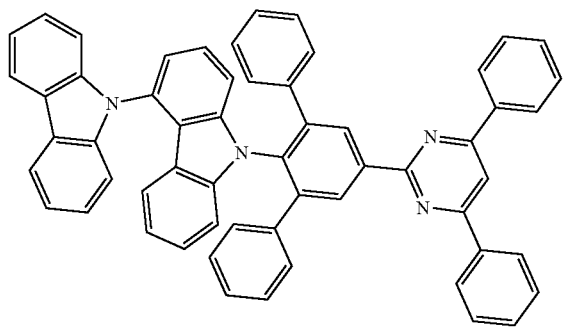
119
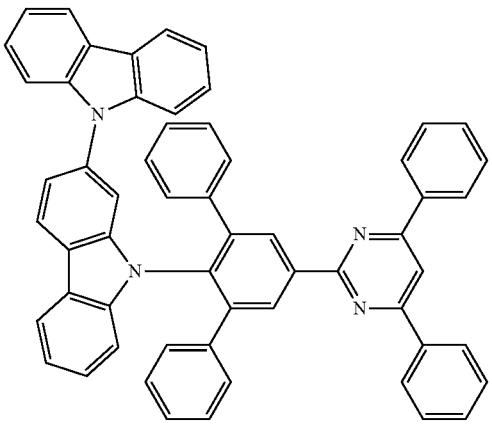
120
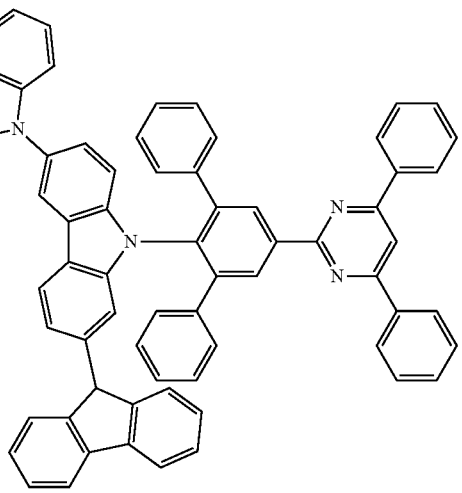
121
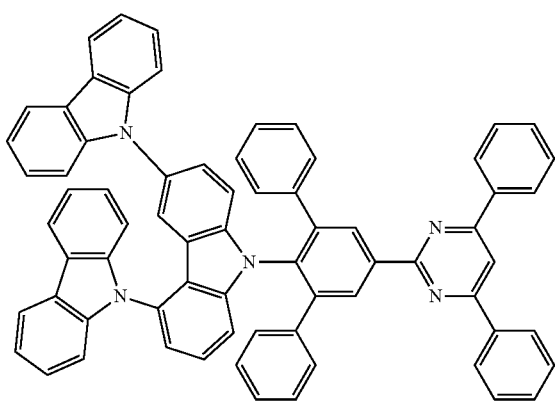

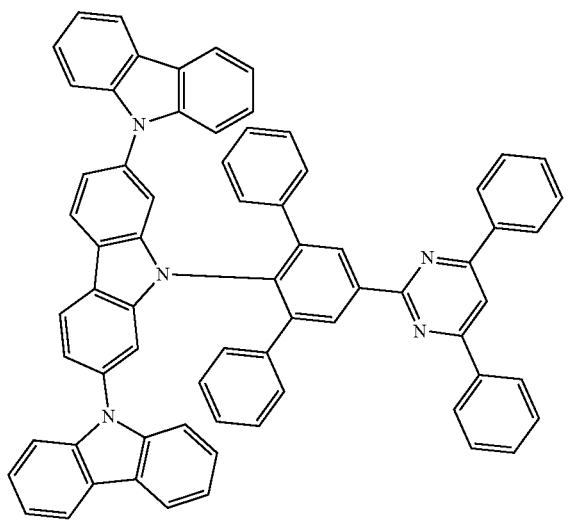
122
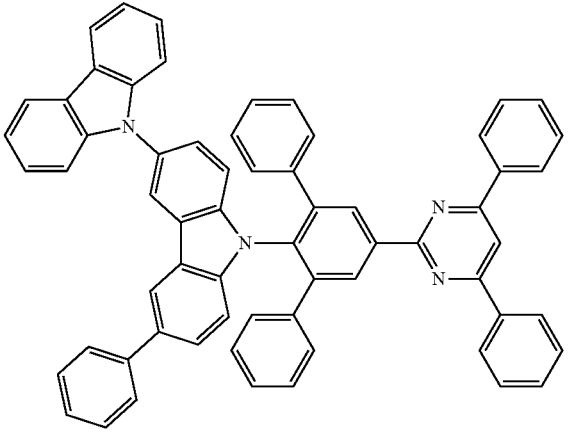
125
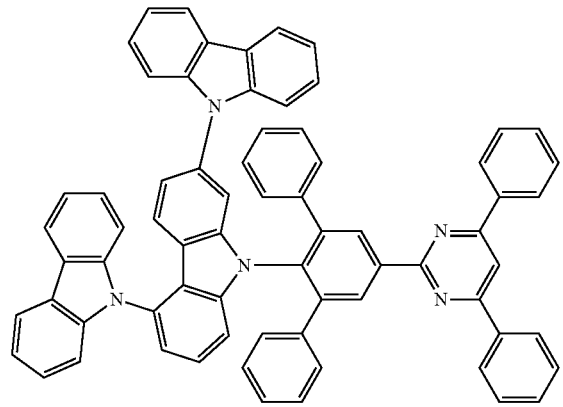
123
126
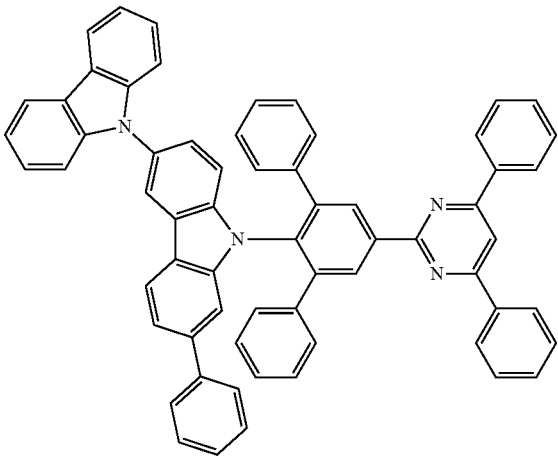
124
127

-continued
128
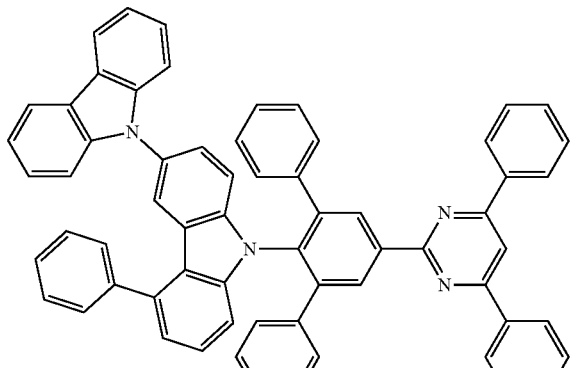
129
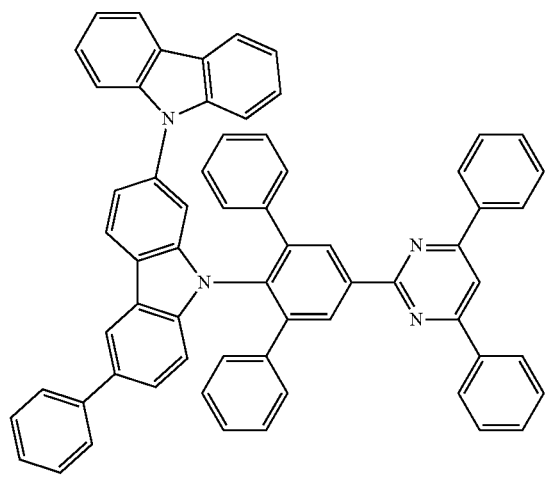
130
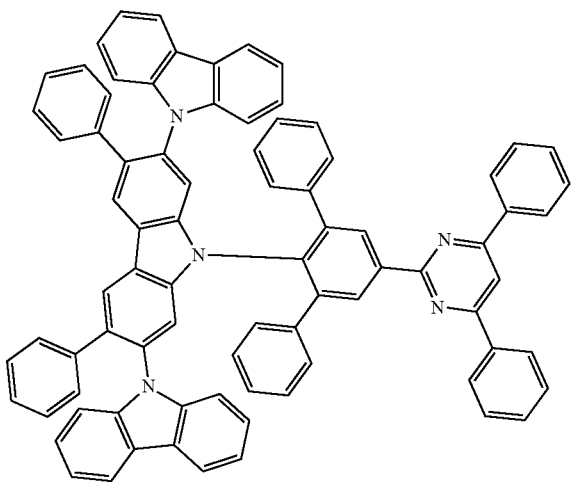
-continued
131
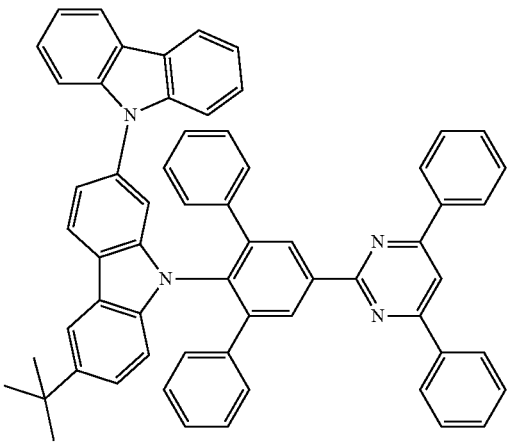
132
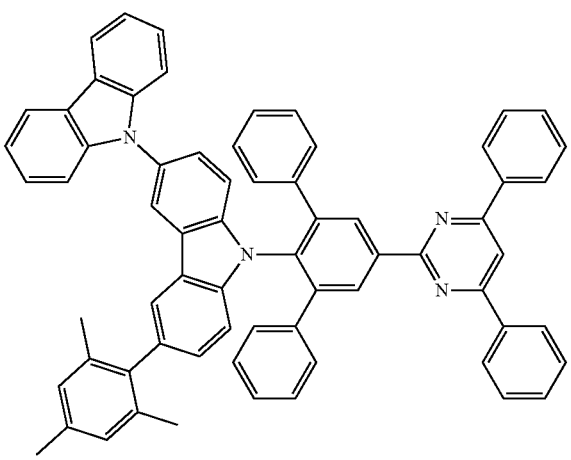
133
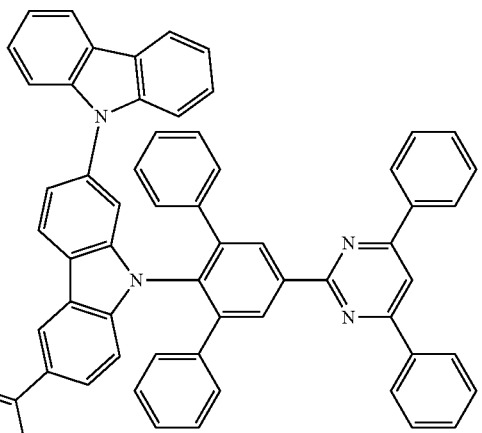

134
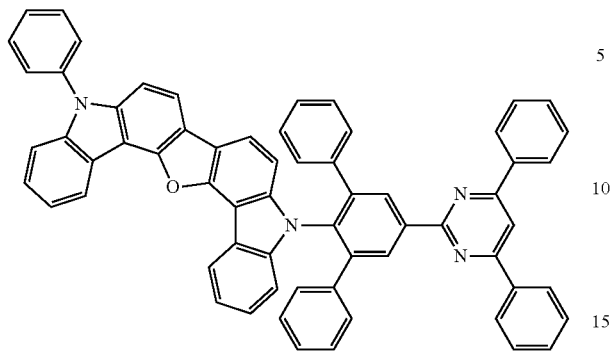
135
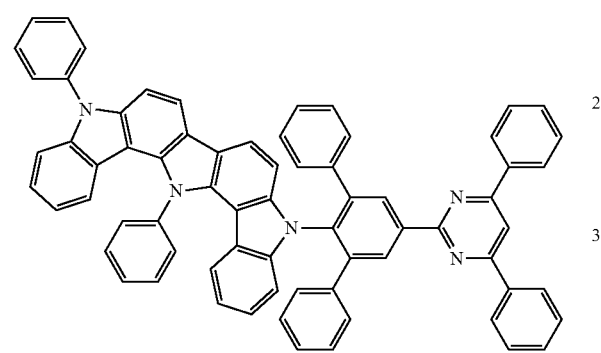
136
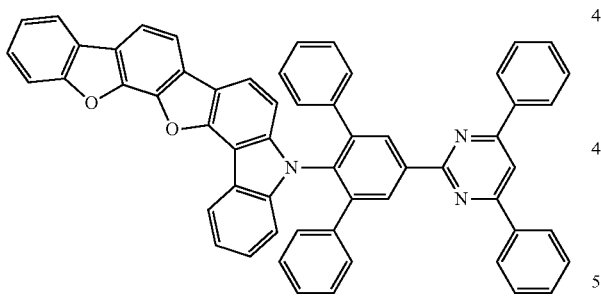
137
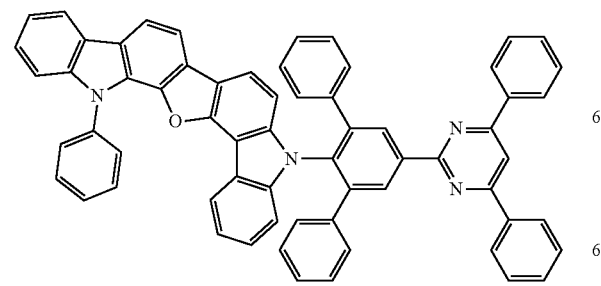
138
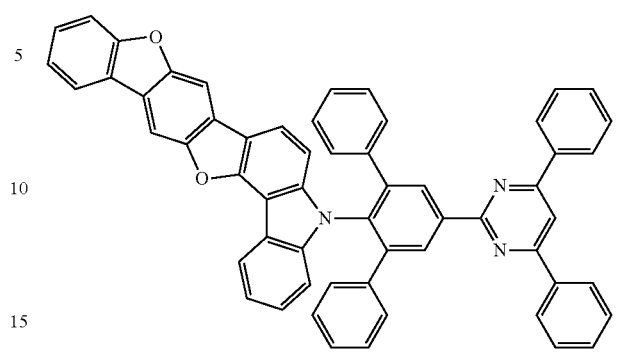
139
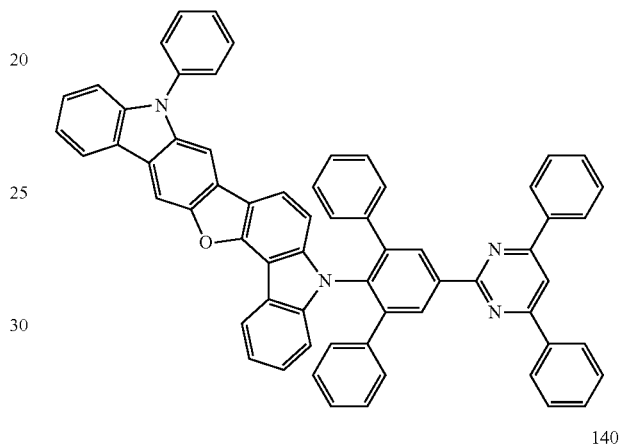
140
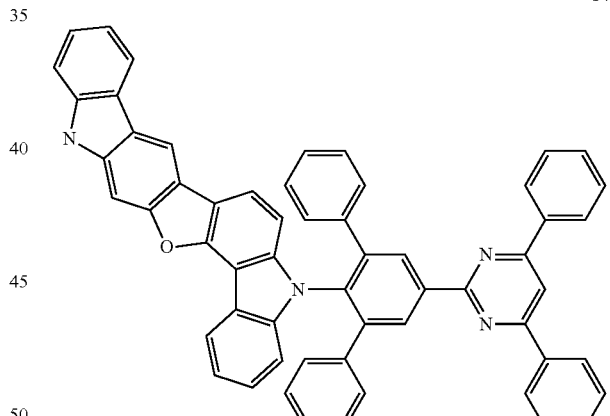
141
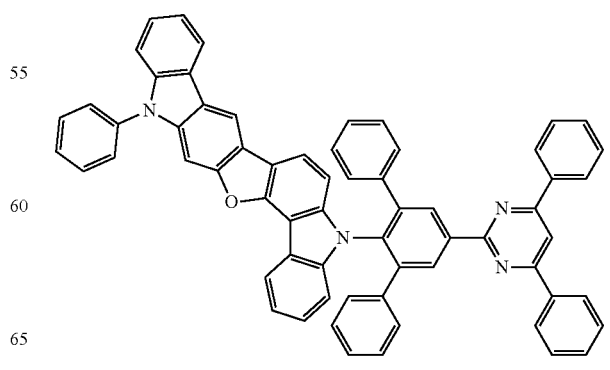

142
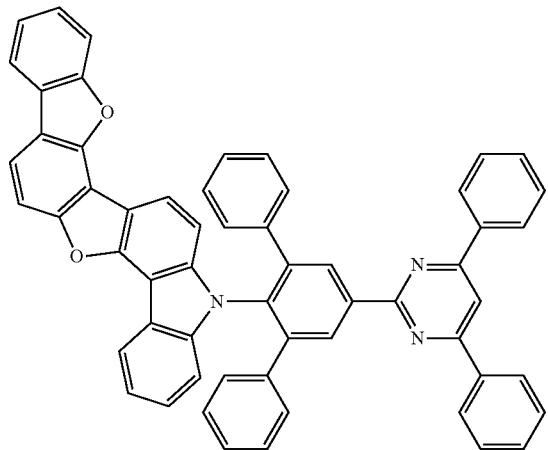
143
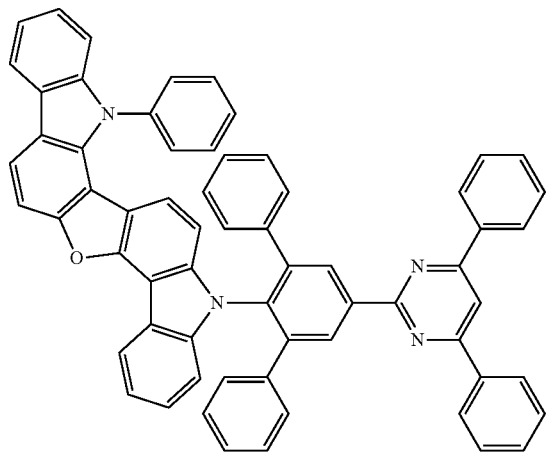
144
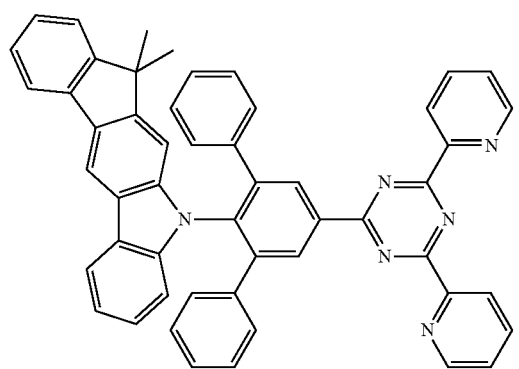
145
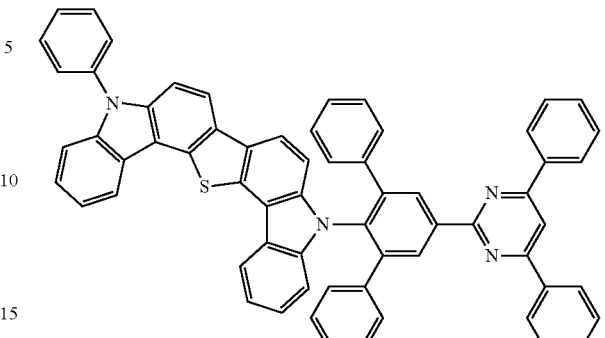
146
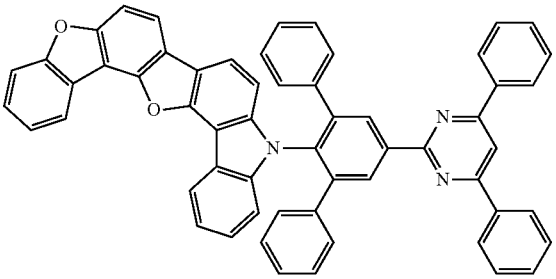
147
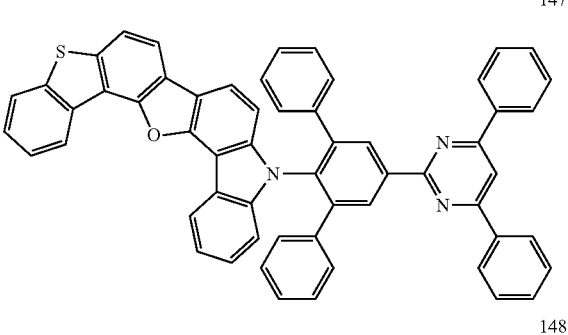
148
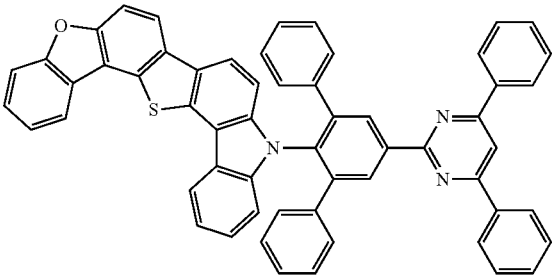
149

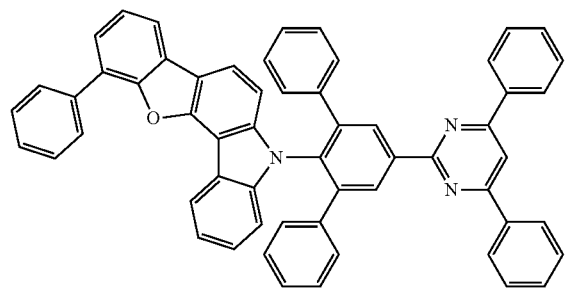
150
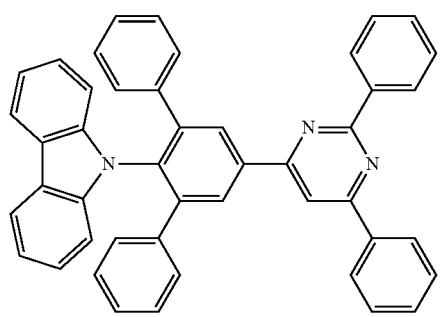
151
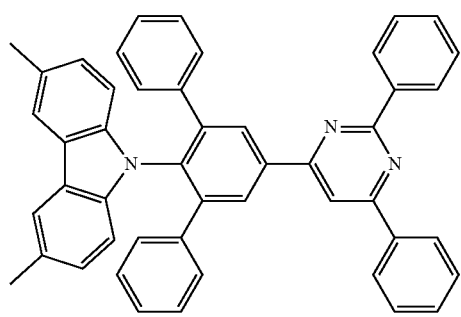
152
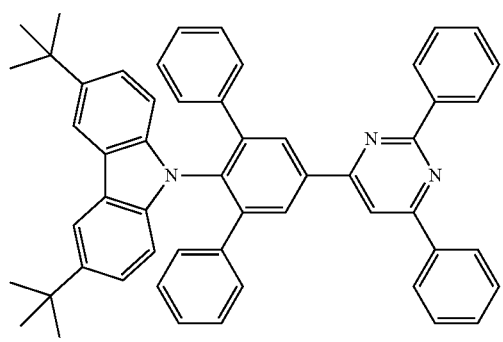
153
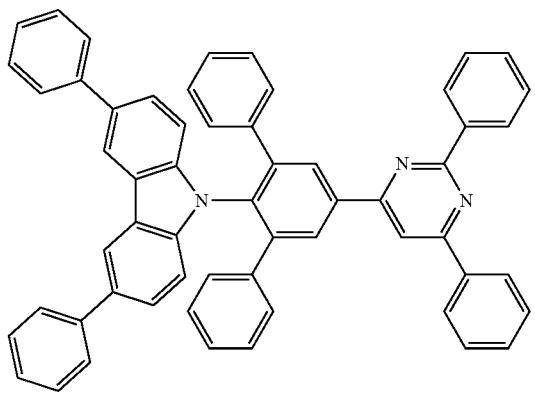
154
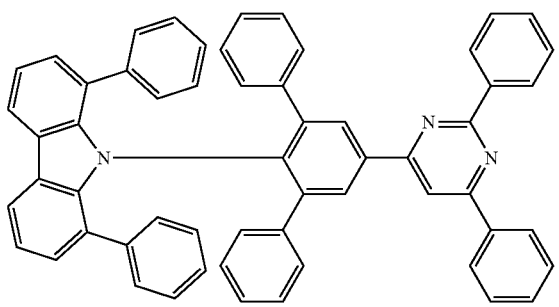
155
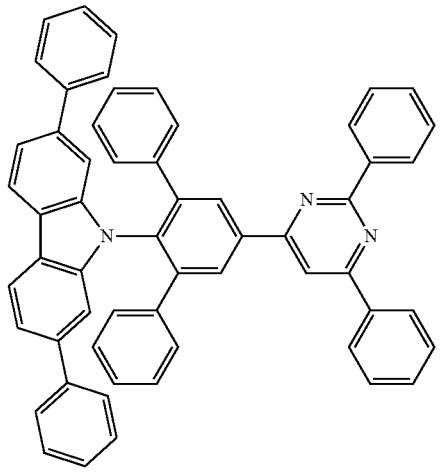
156
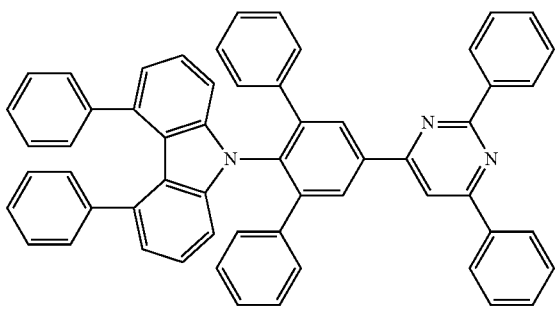
157

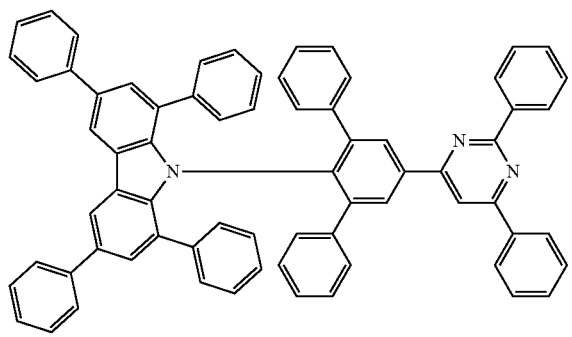
158
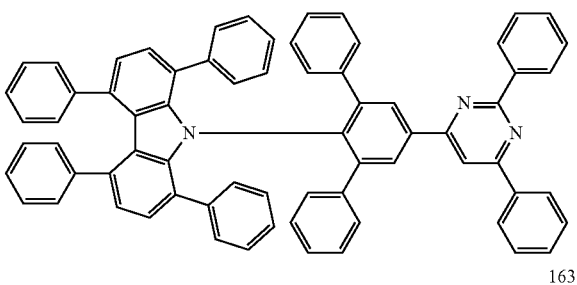
162
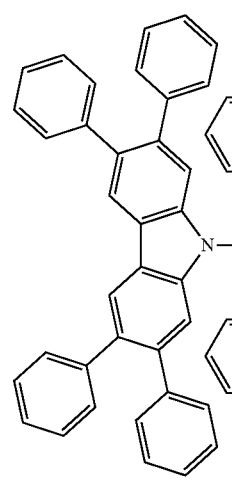
159
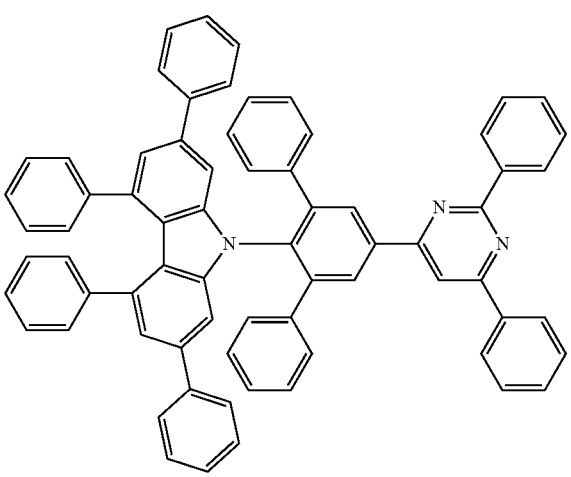
163
160
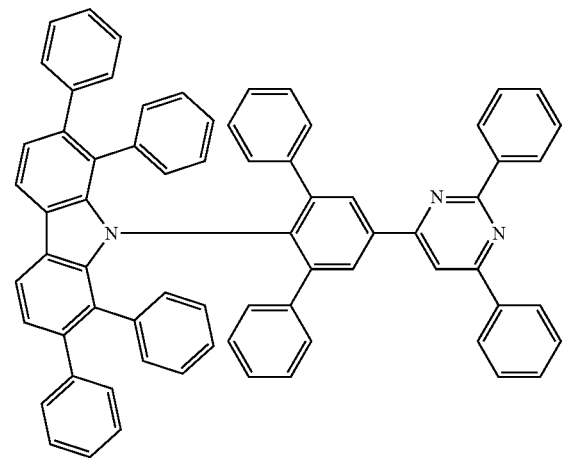
164
161
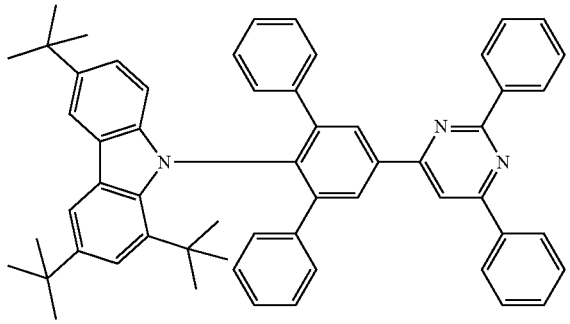
165

166
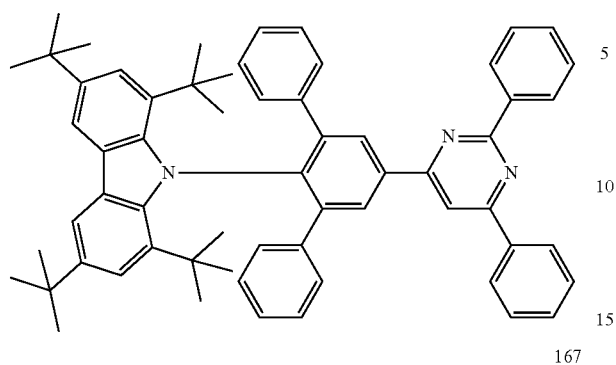
167
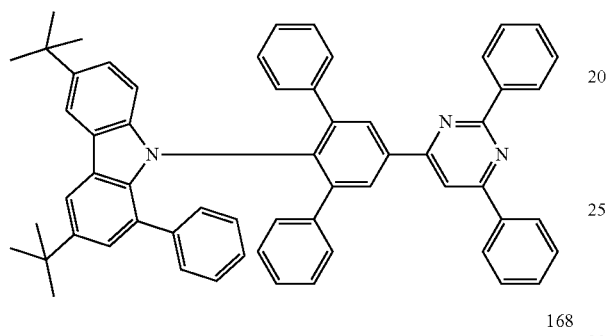
168
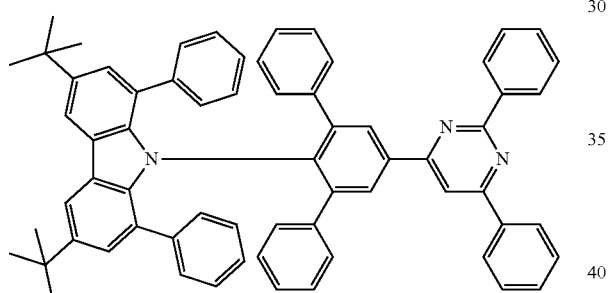
169
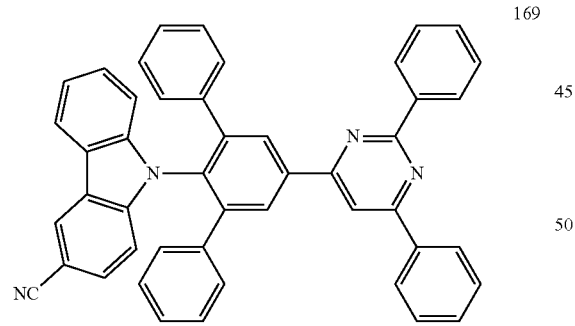
170
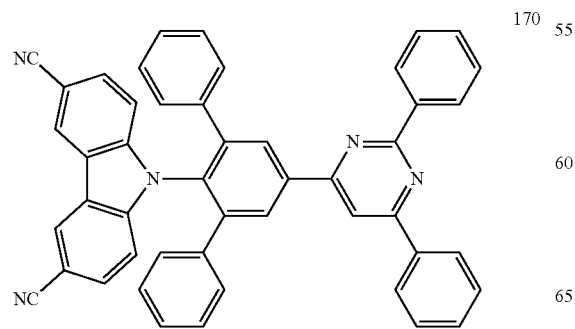
171
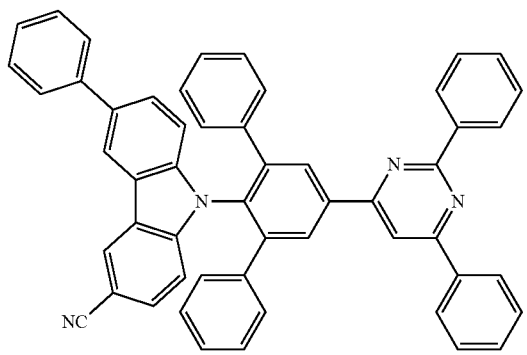
172
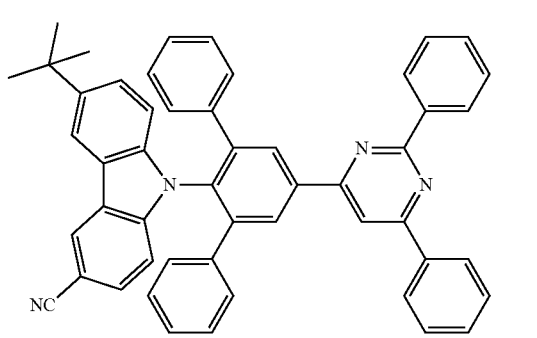
173
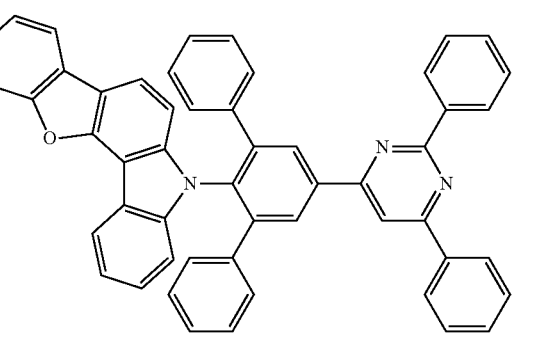
174
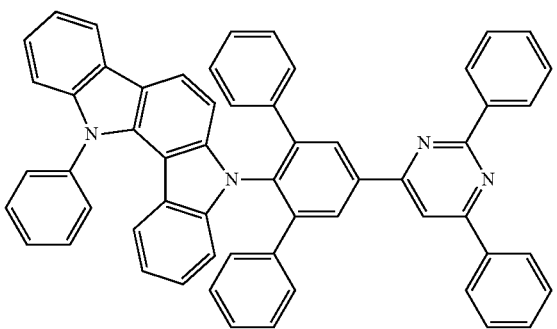

175
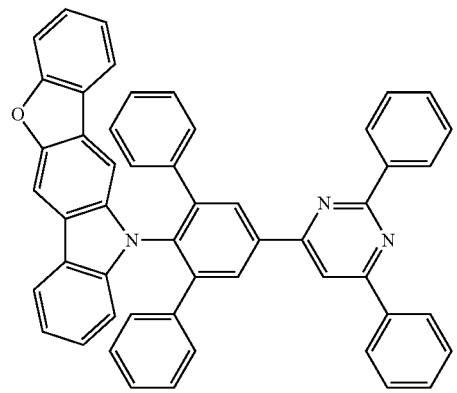
176
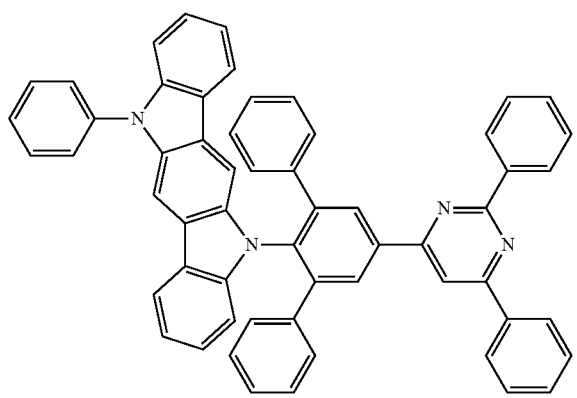
177
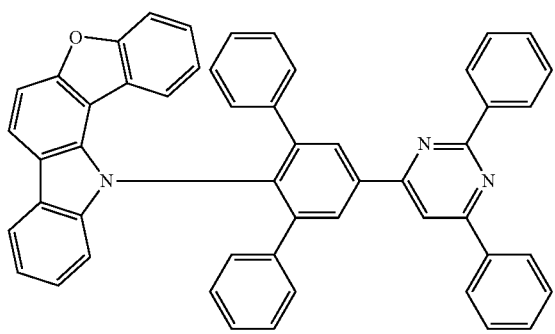
178
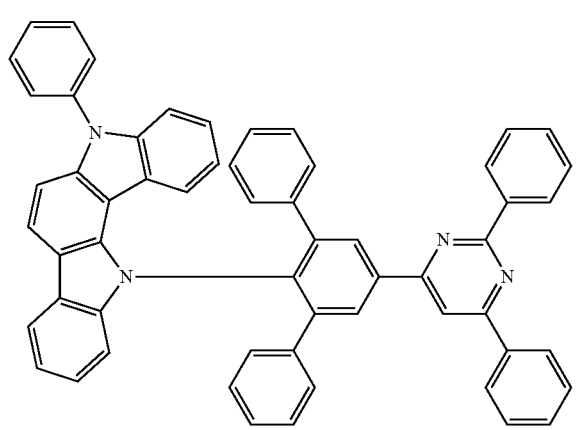
179
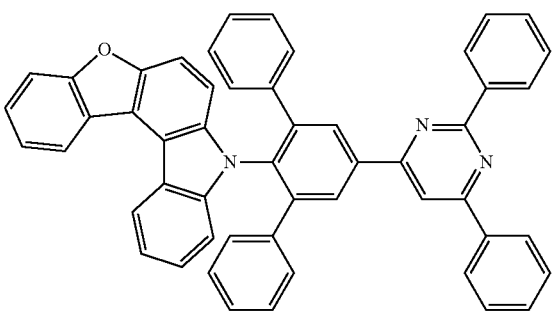
180
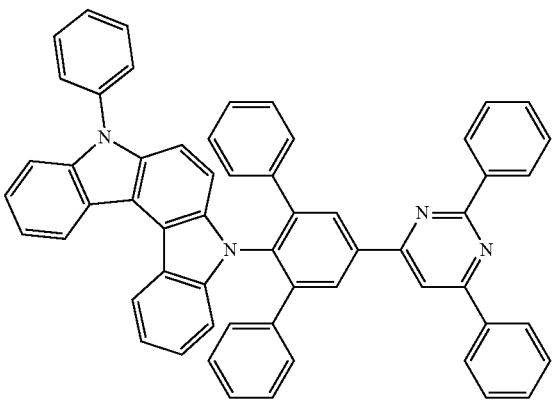
181
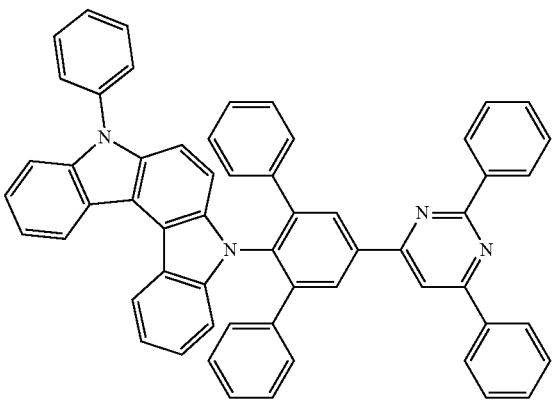
182
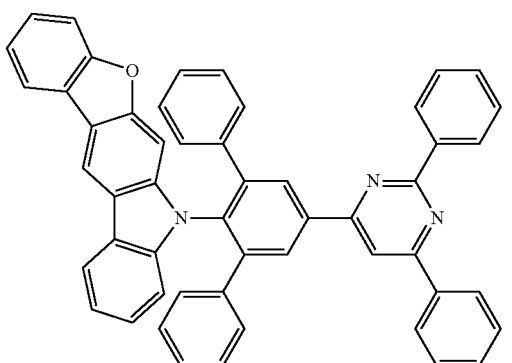

183
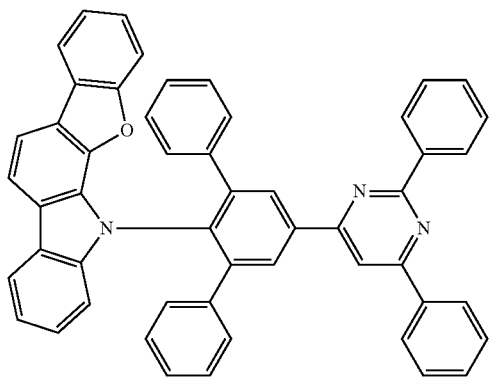
184
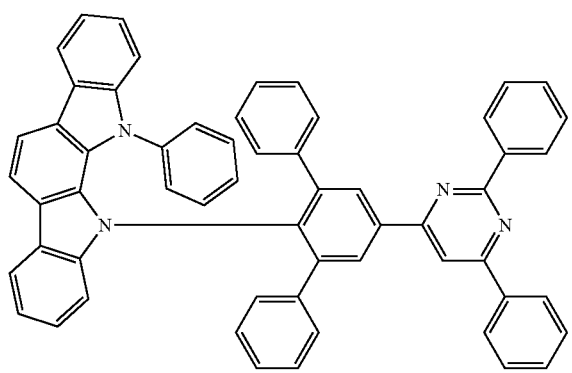
185
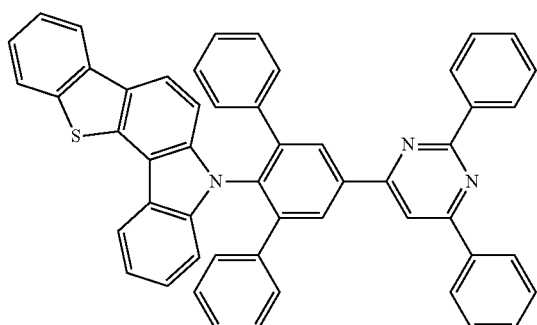
186
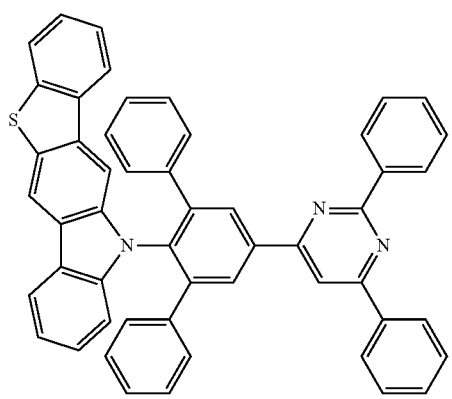
187
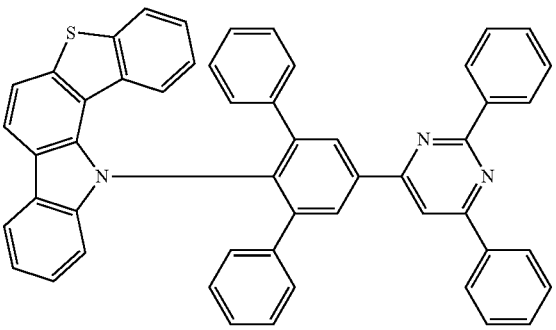
188
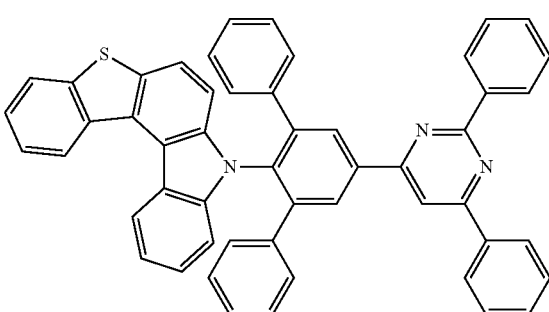
189
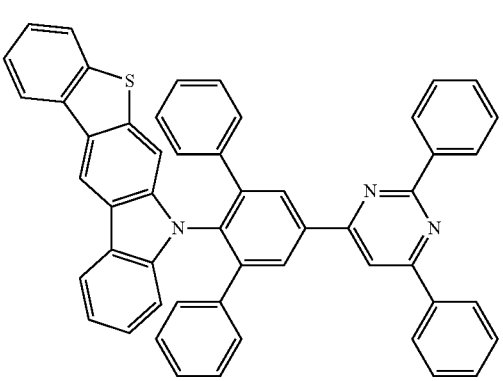
190
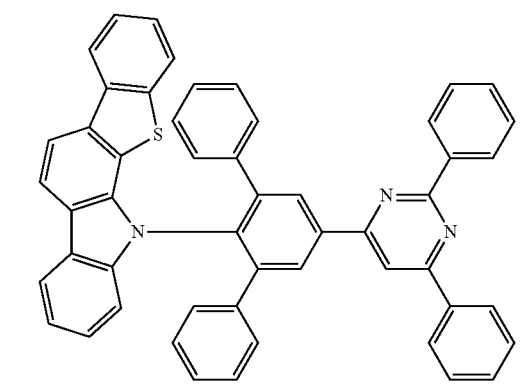

191
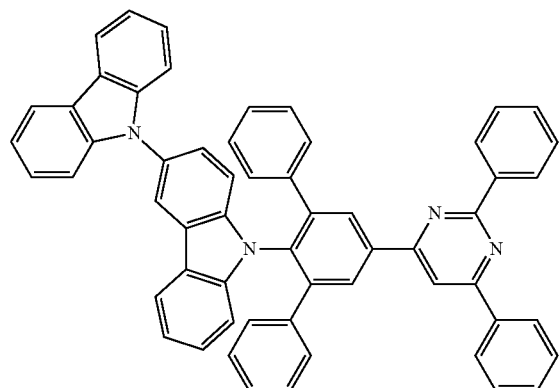
194
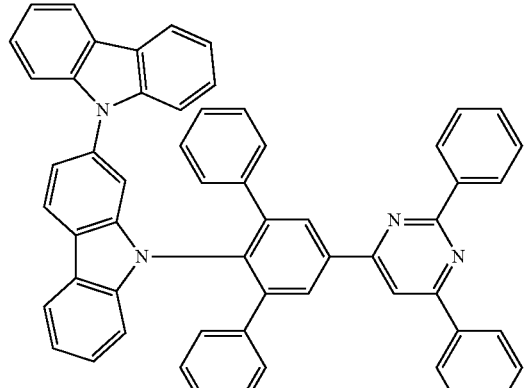
192
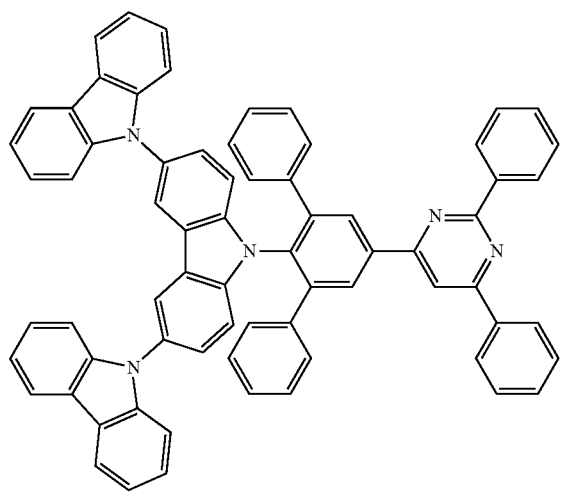
195
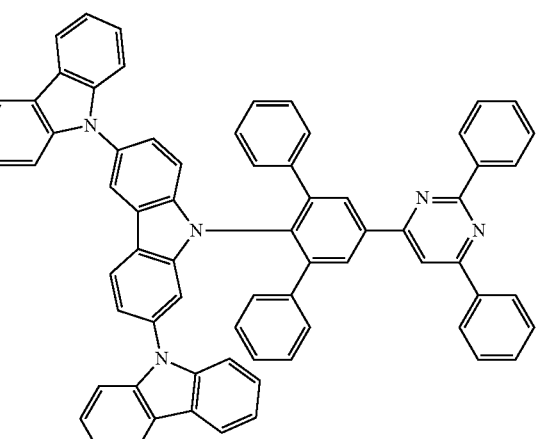
193
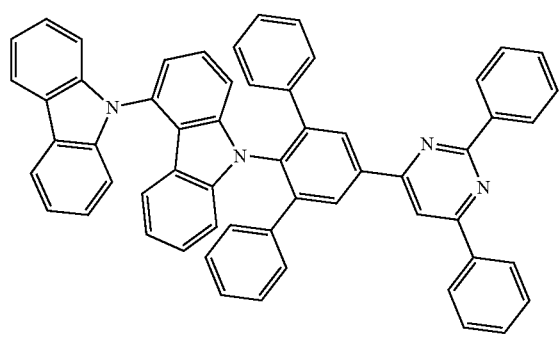
196
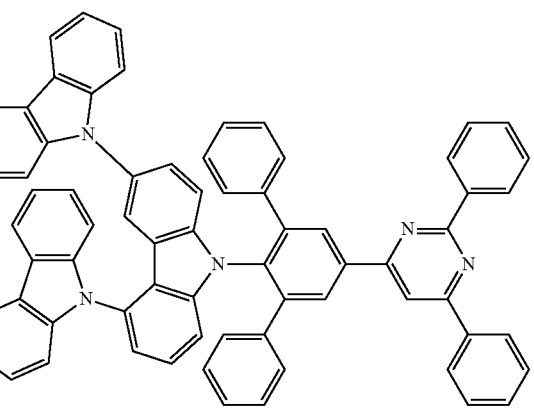

197
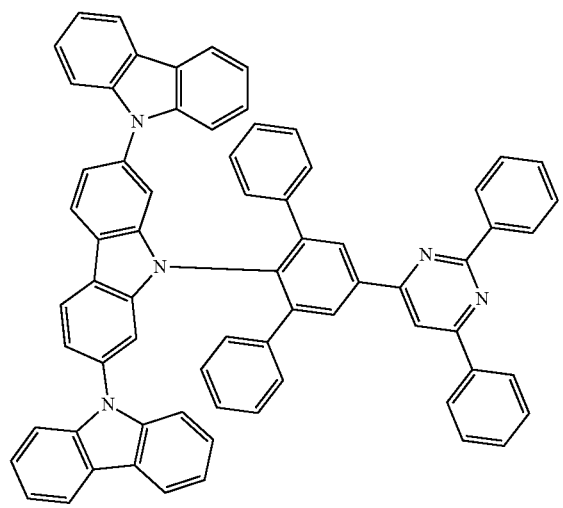
200
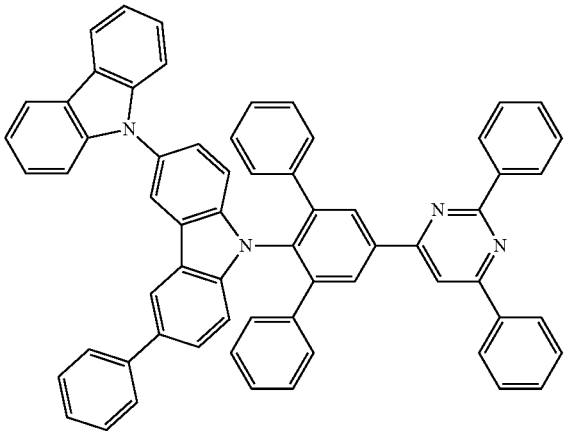
198
199
201
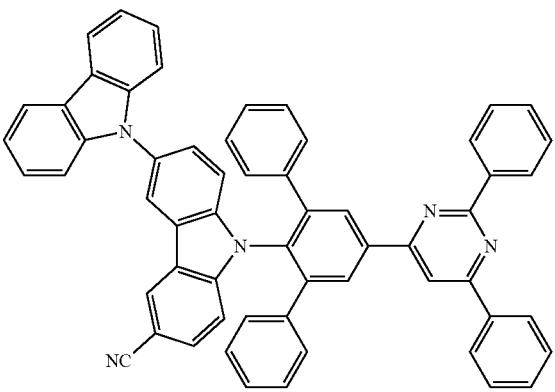
202
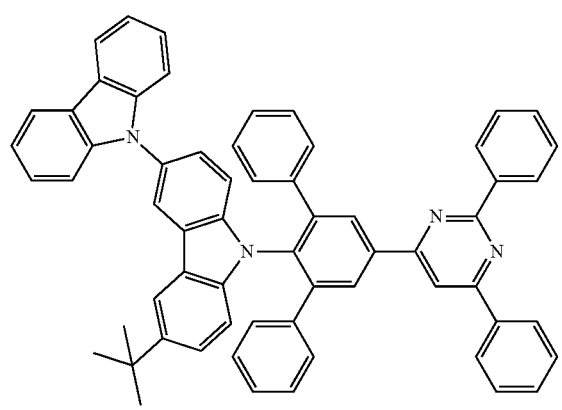
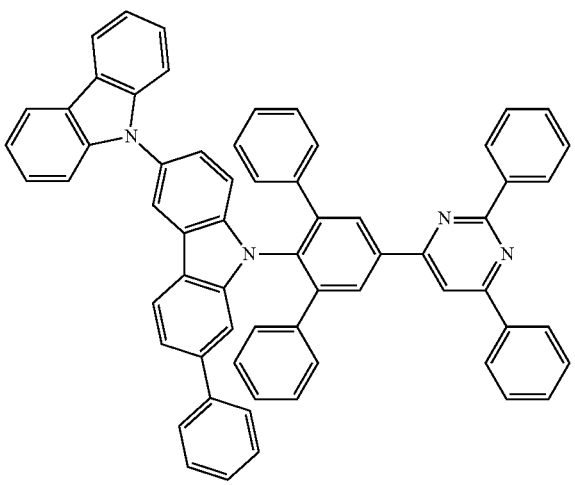

203
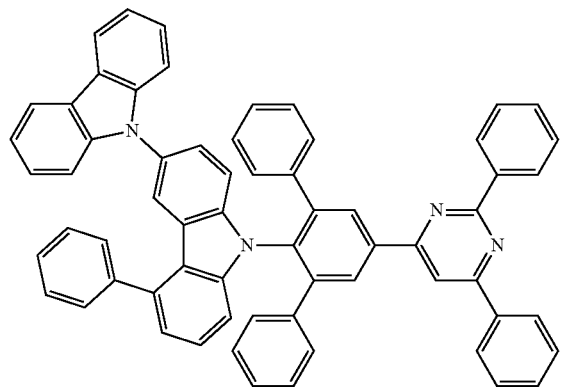
206
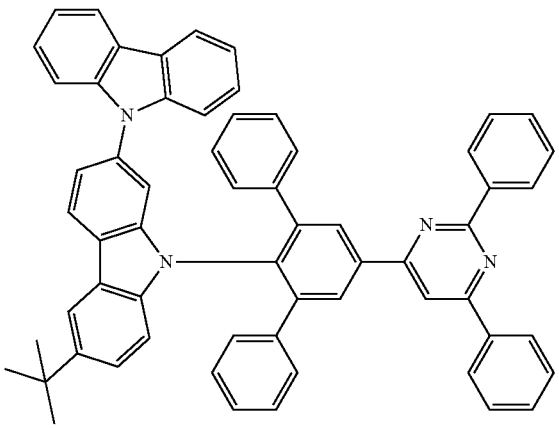
204
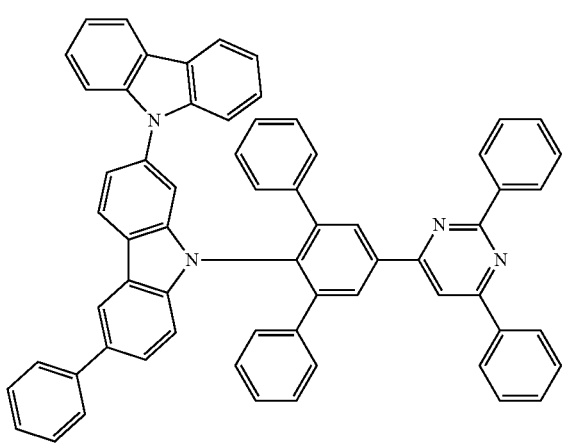
207
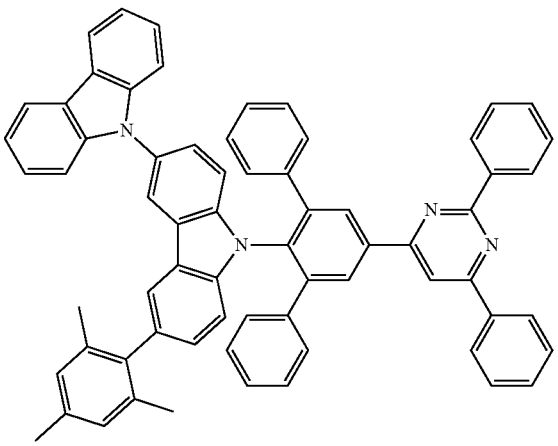
205
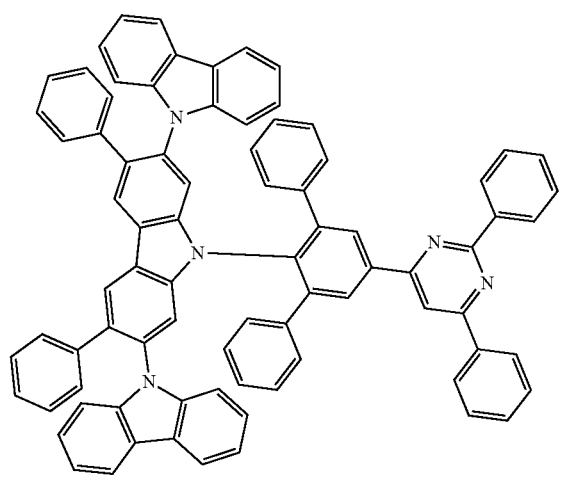
208
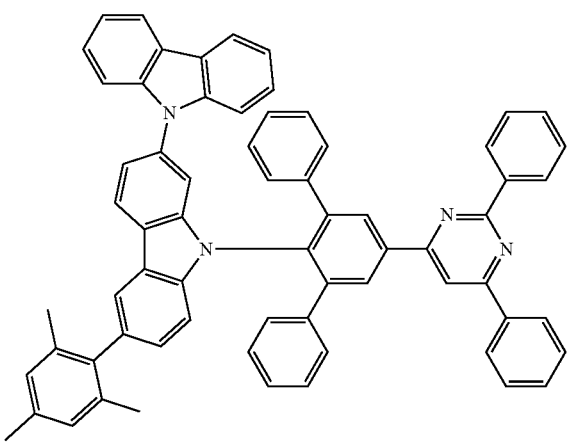

209
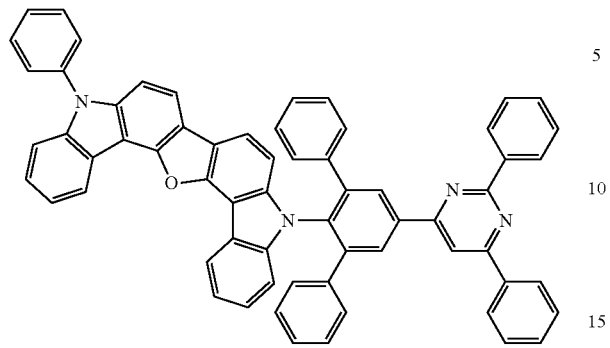
213
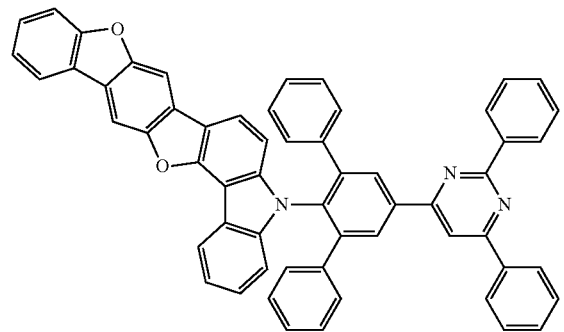
210
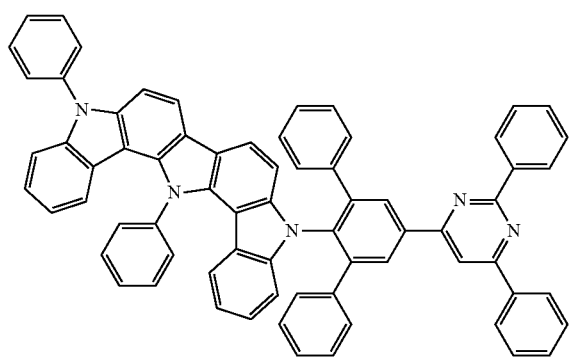
214
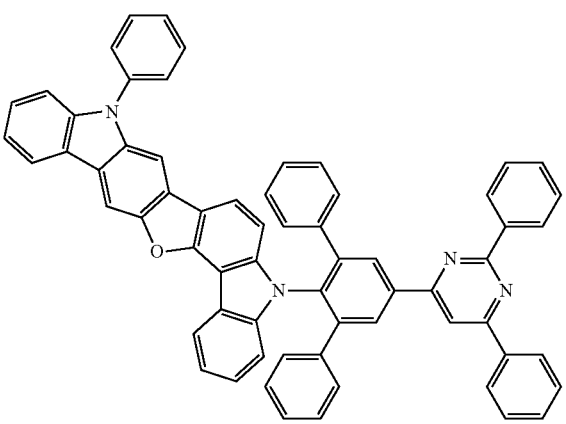
211
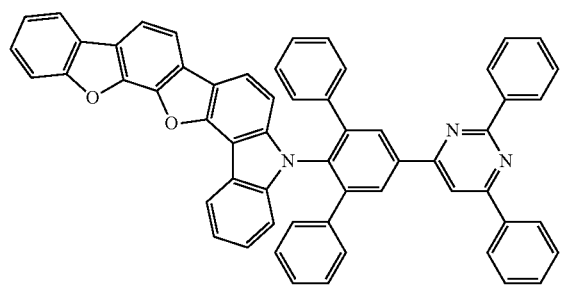
215
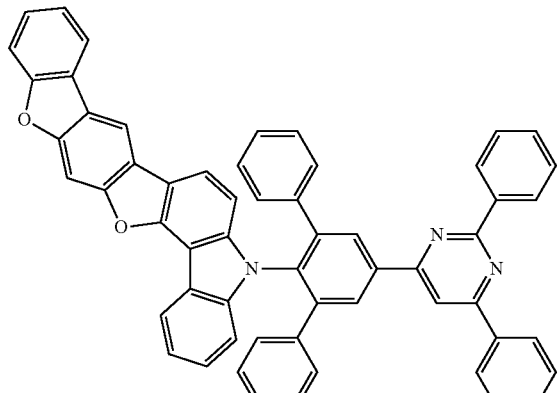
212
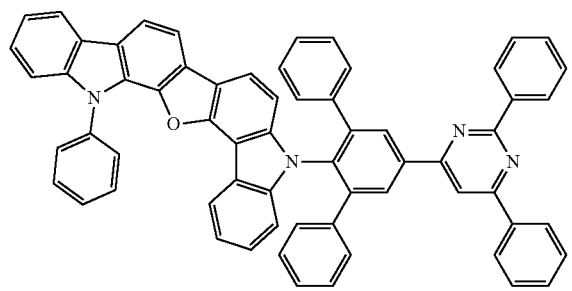
216
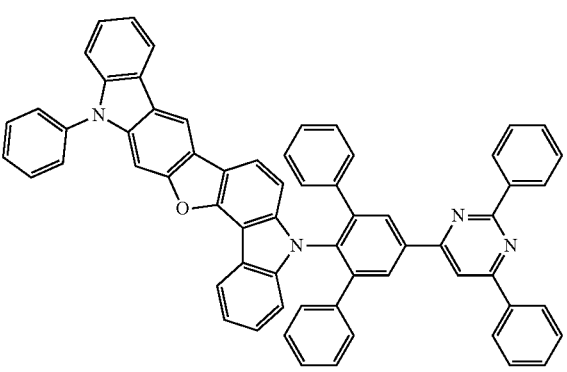

217
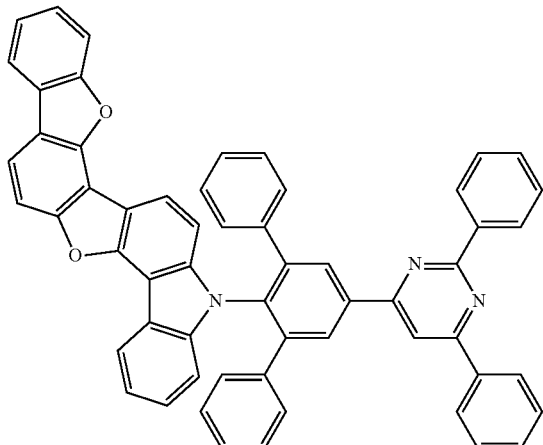
218
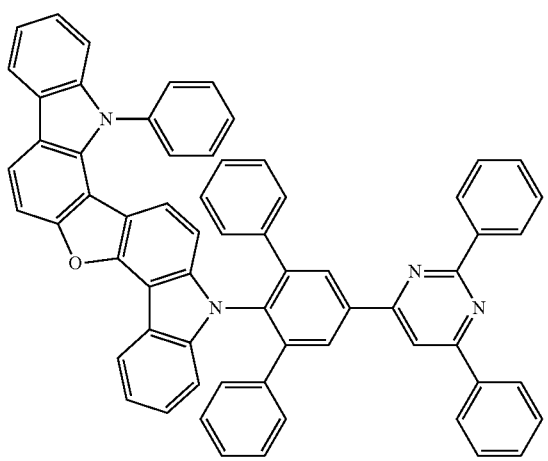
219
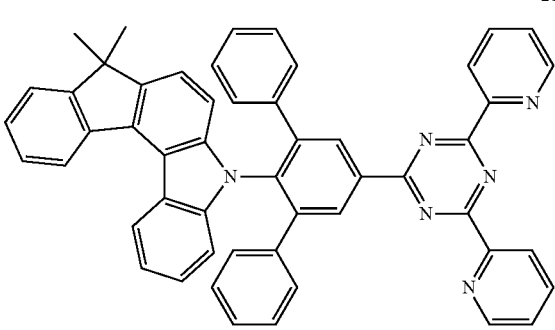
220
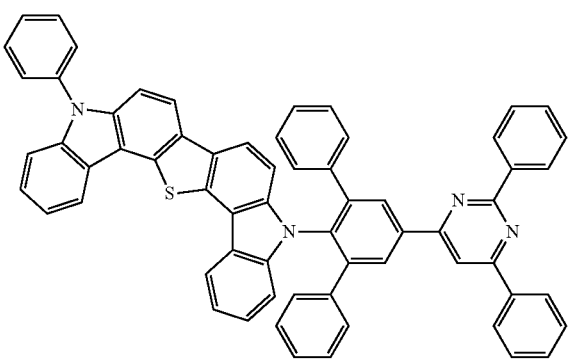
221
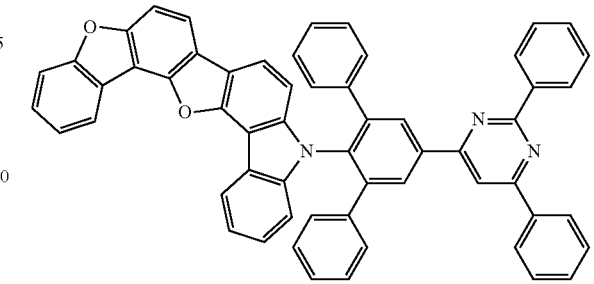
222
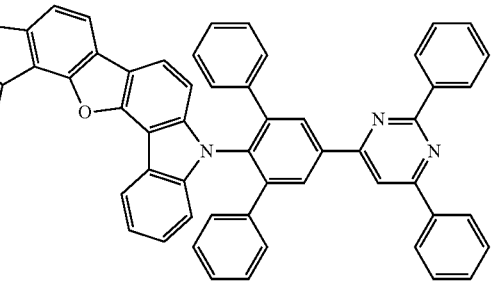
223
224
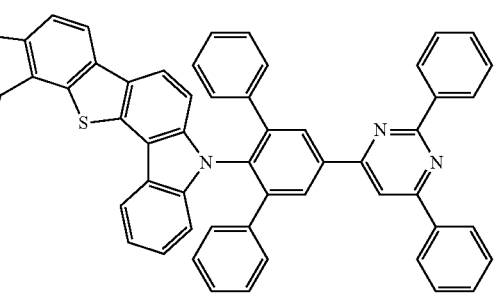

225
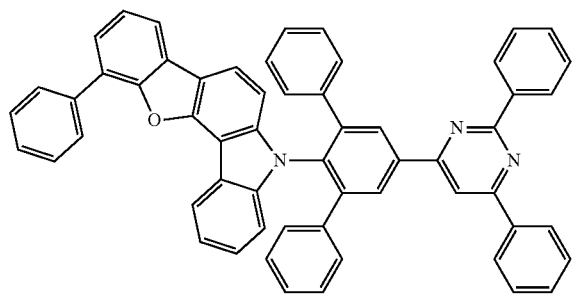
226
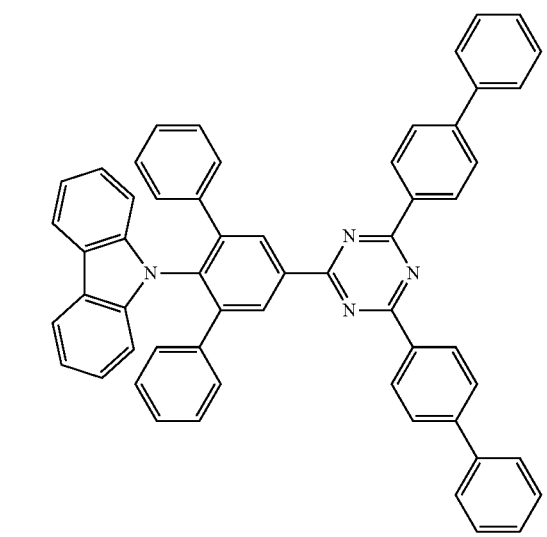
227
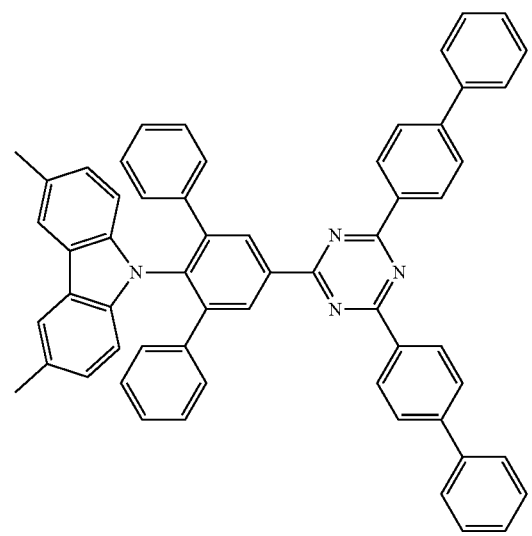
228
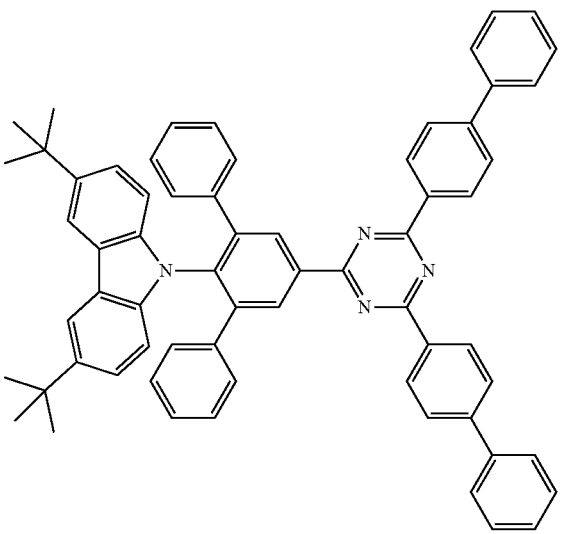
229
230
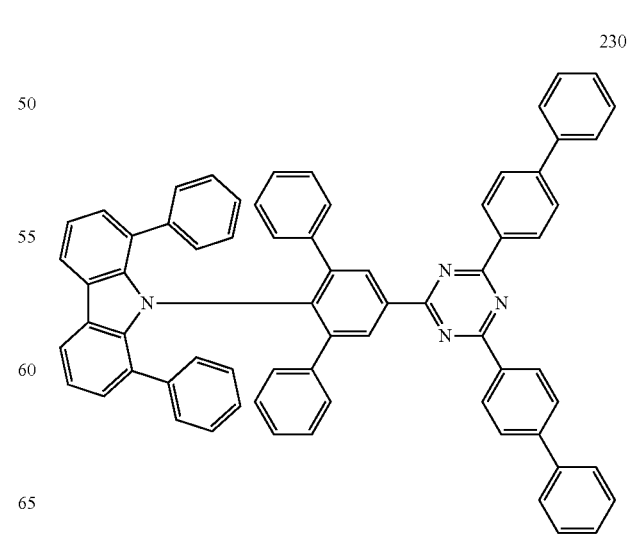

89
-continued
90
-continued
231
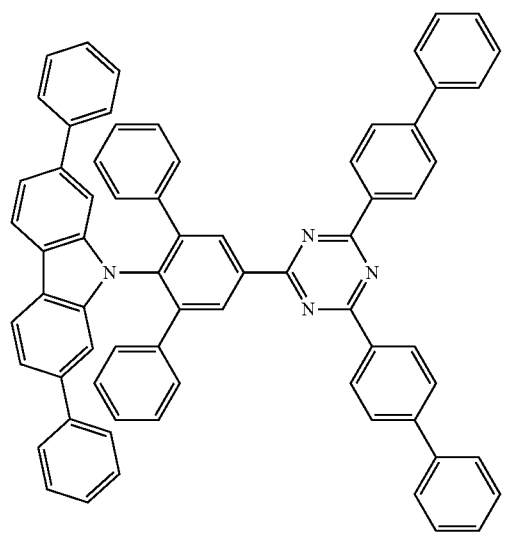
234
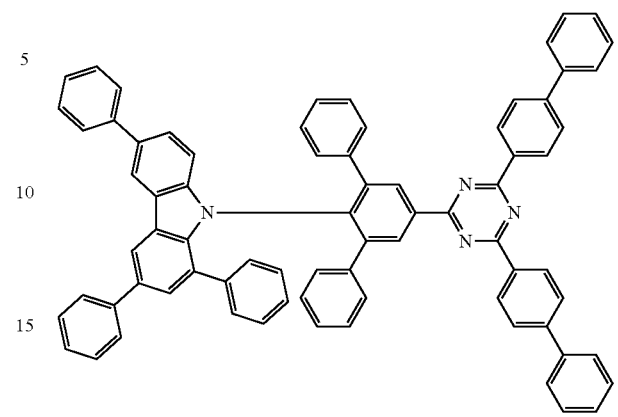
232
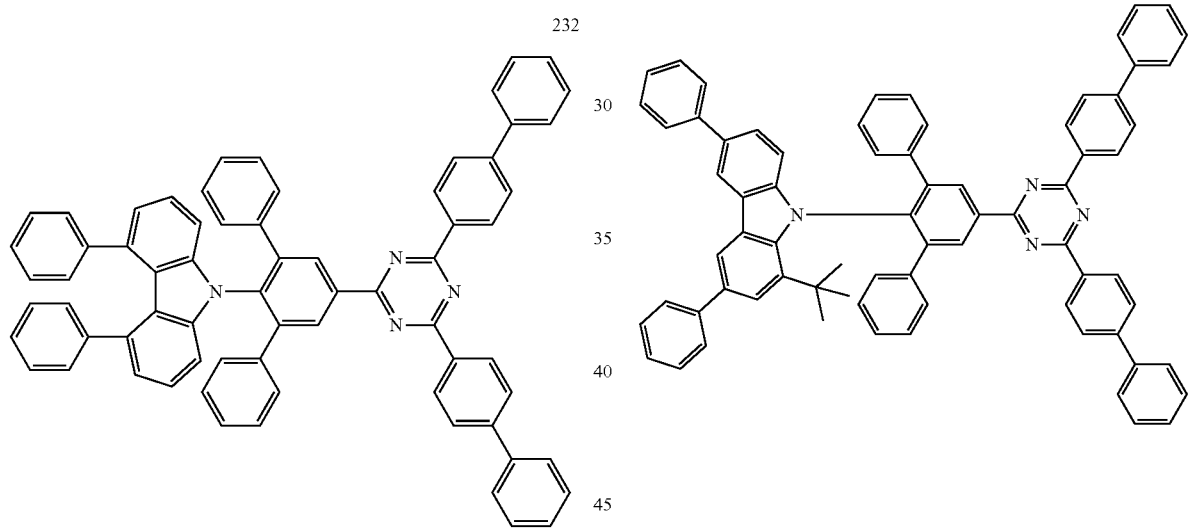
235
233
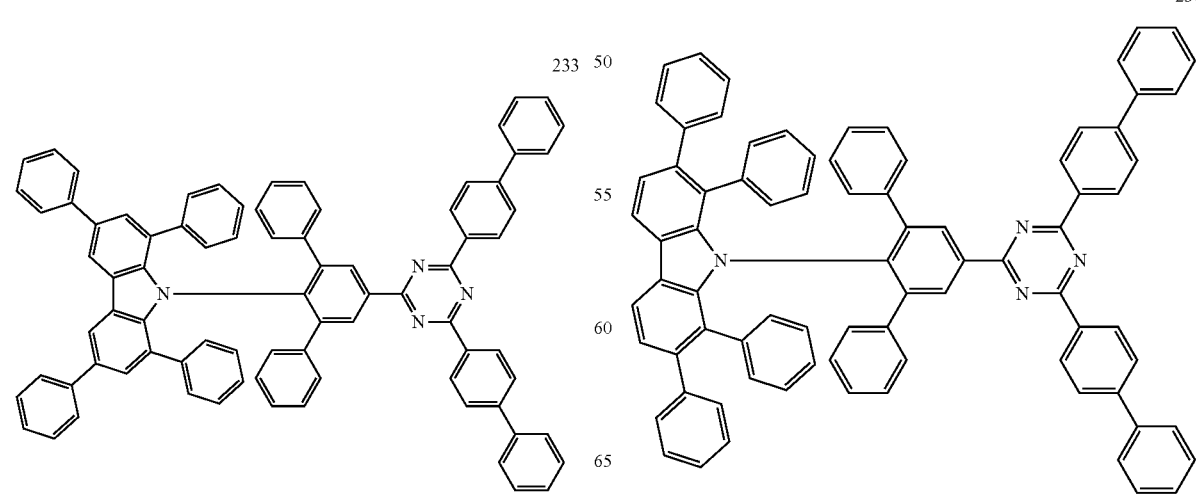
236

237
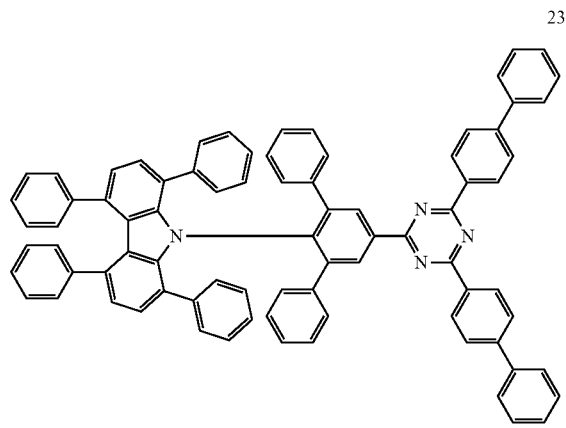
238
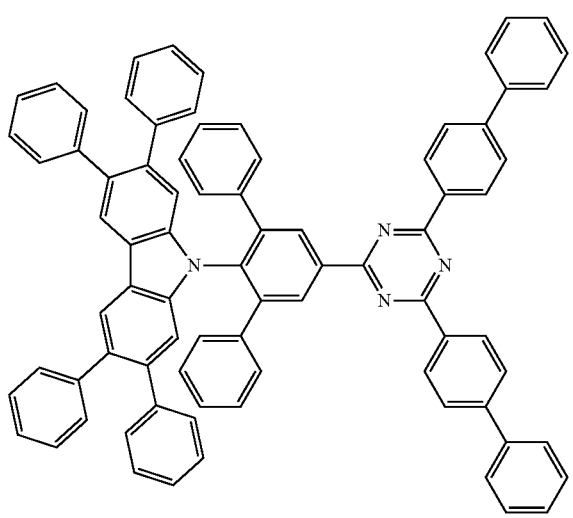
239
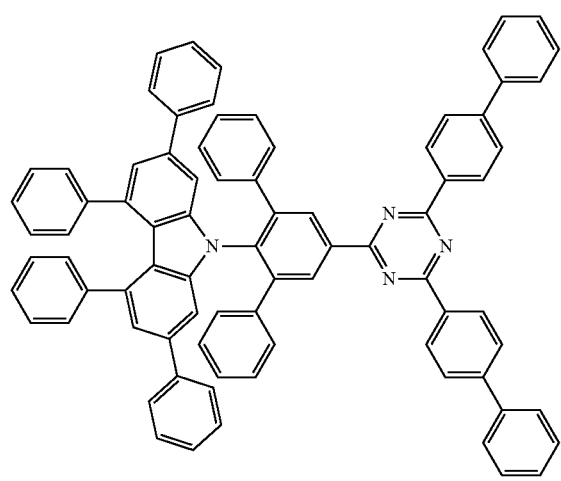
240
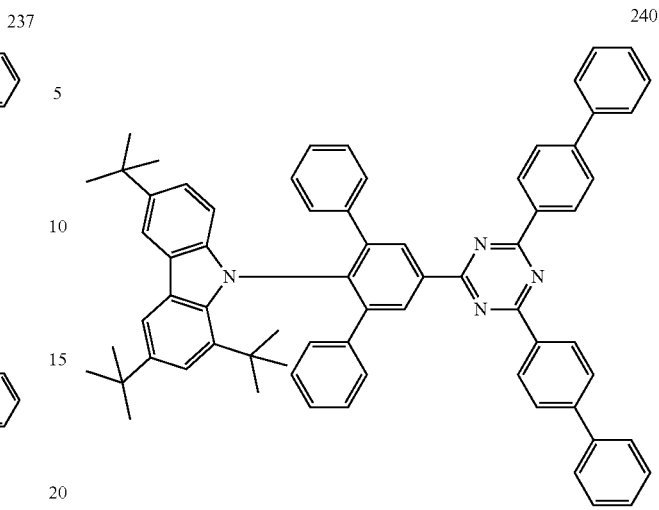
241
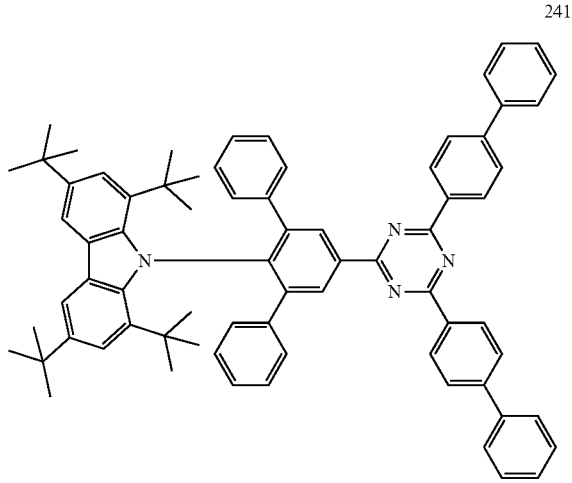
242
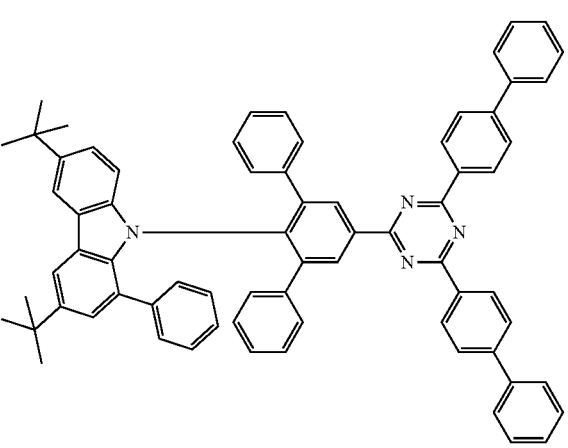

243
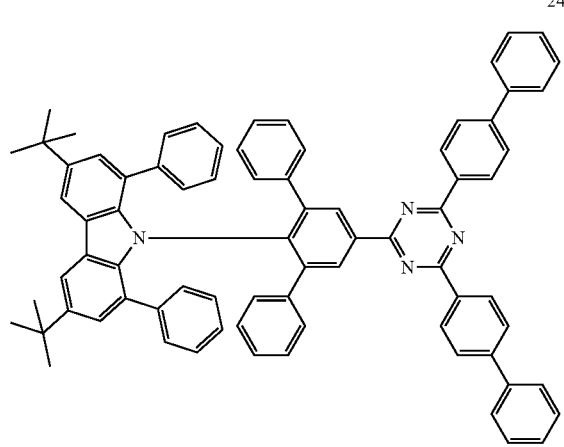
244
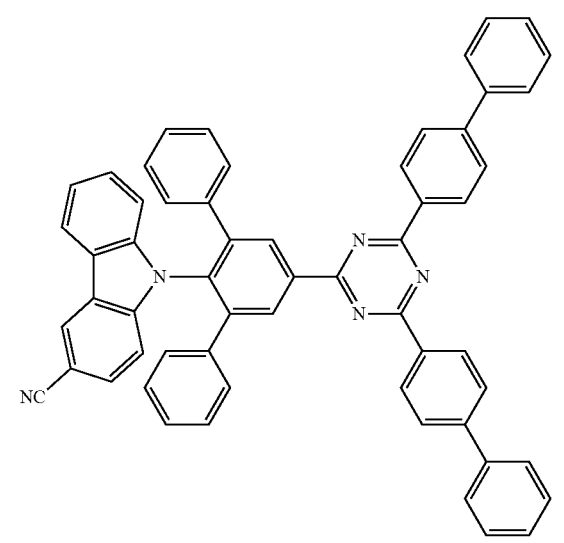
245
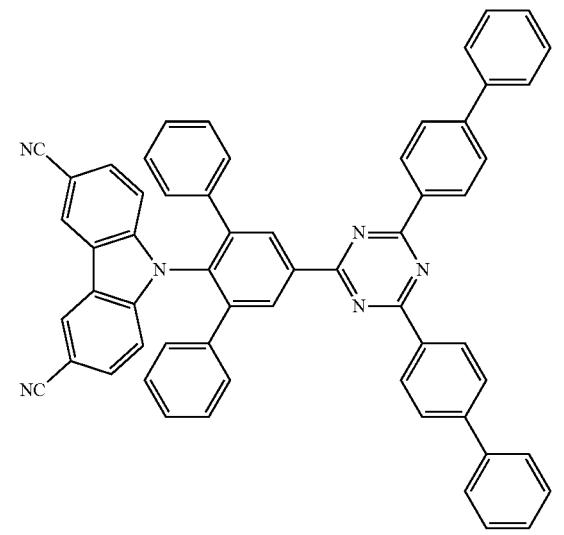
246
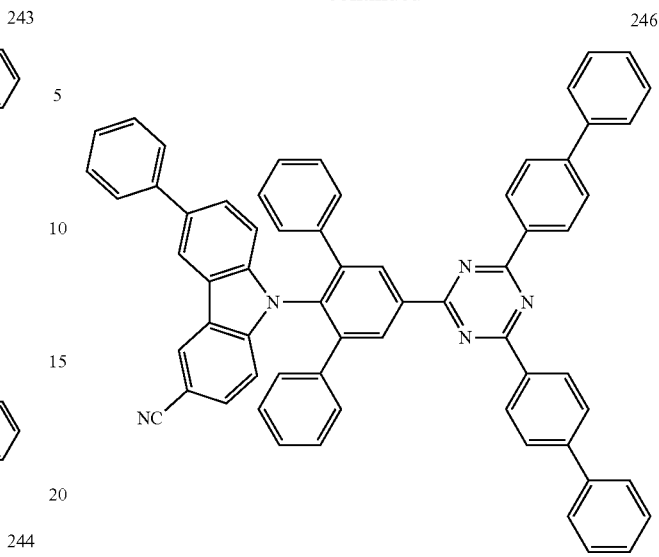
247
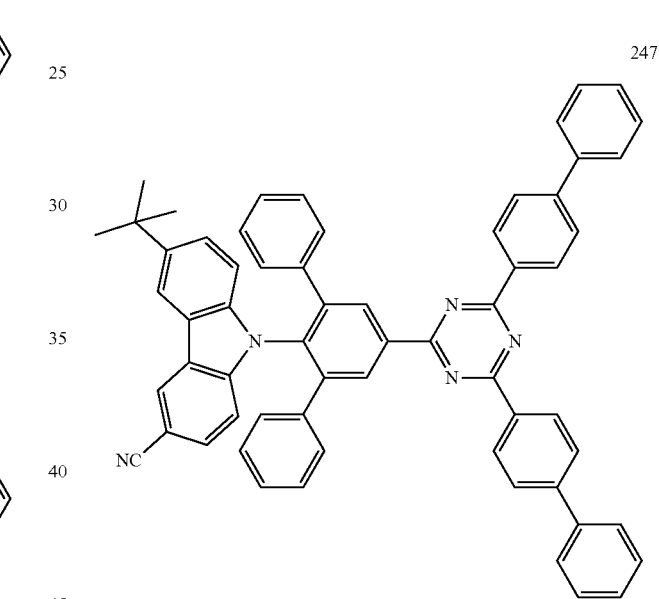
248
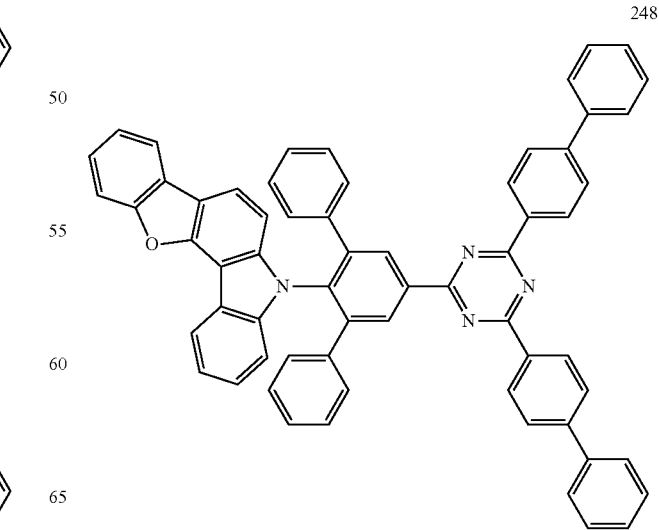

249
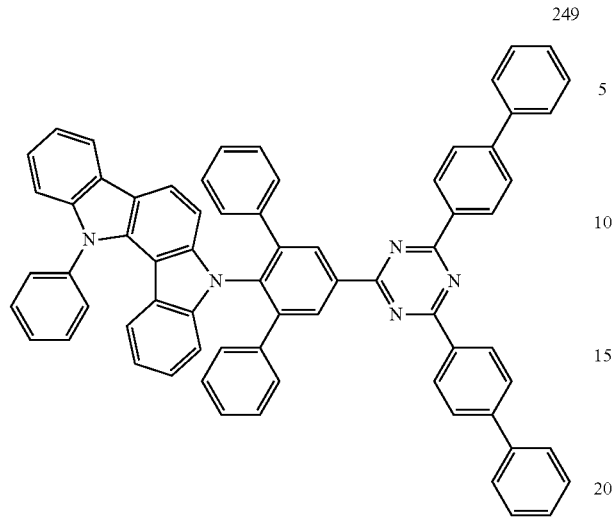
250
252
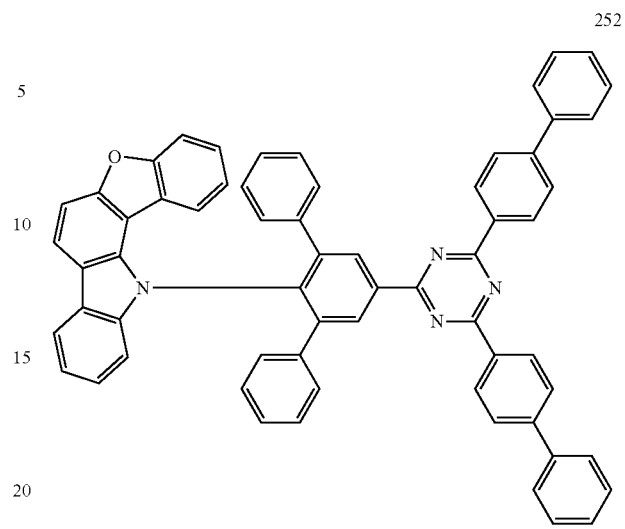
253
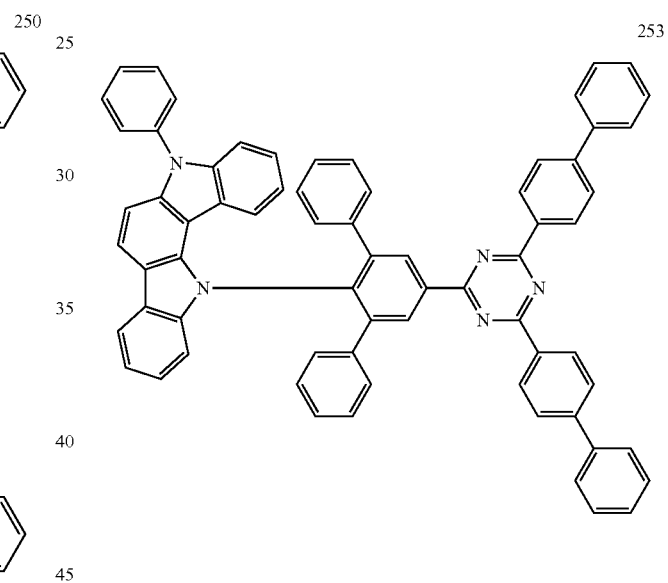
251
254
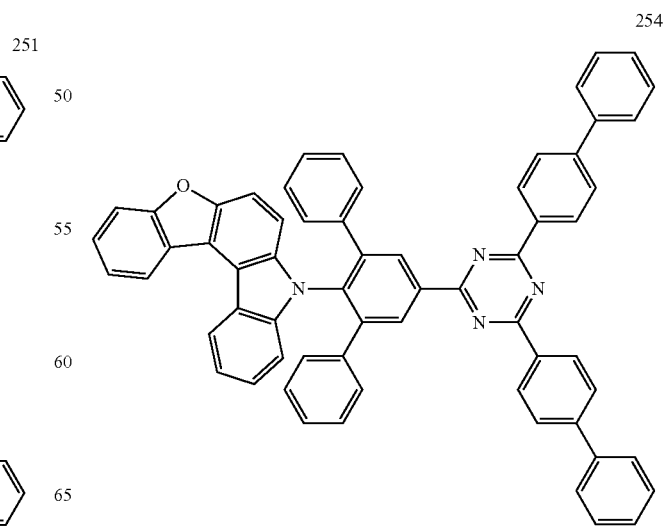

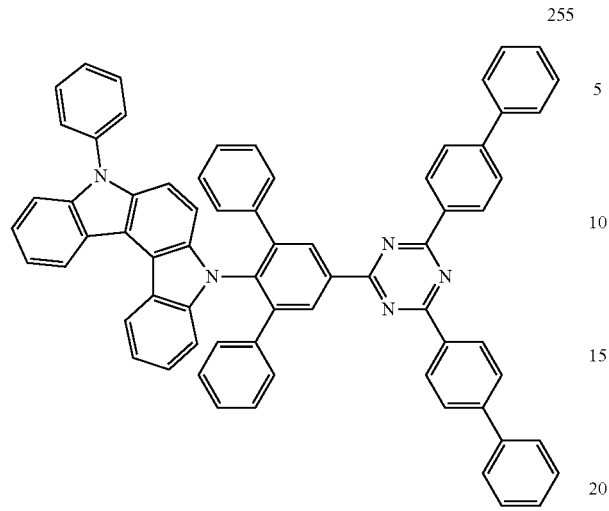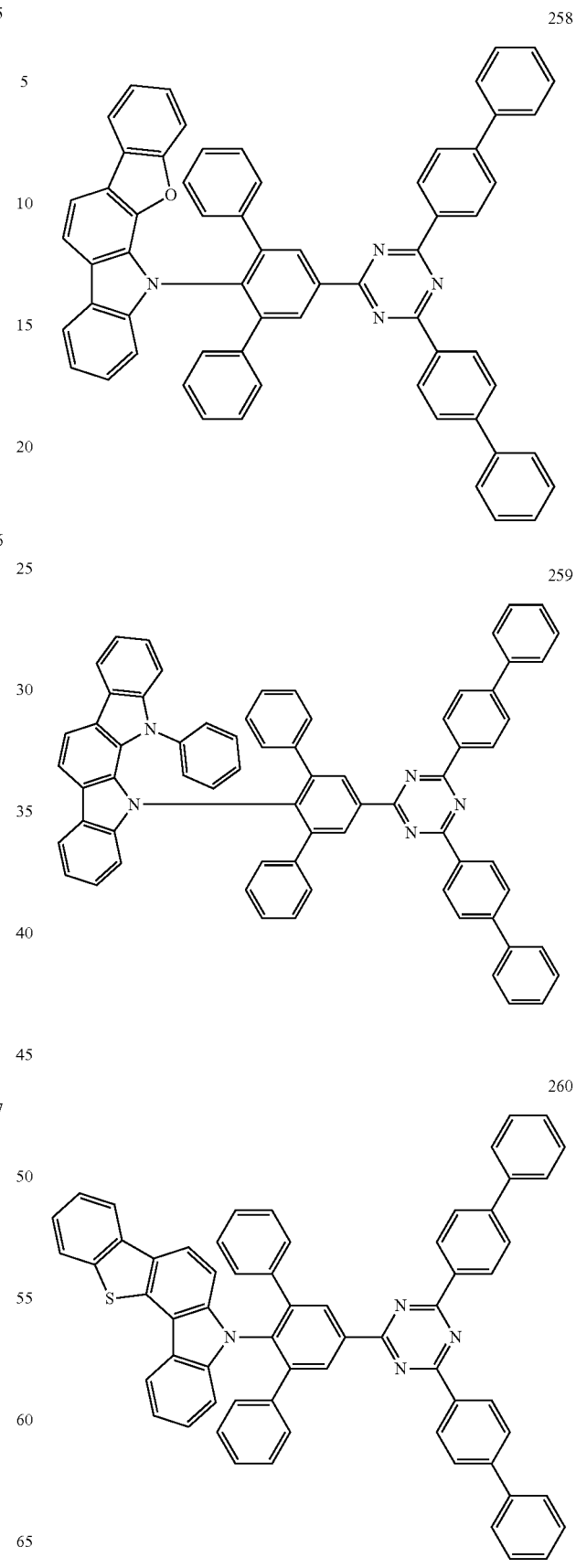

261
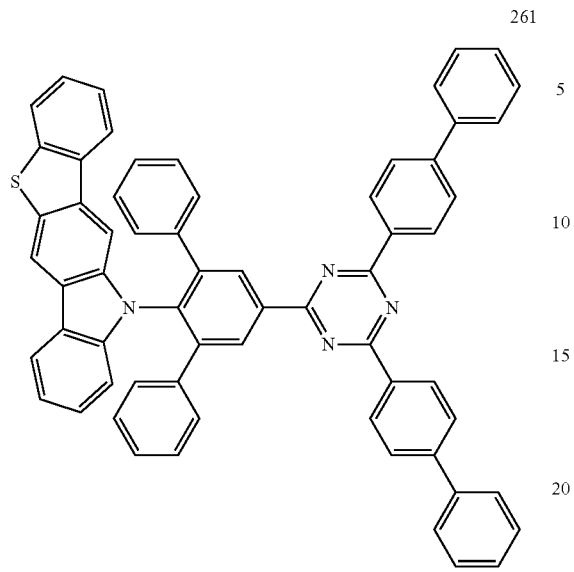
262
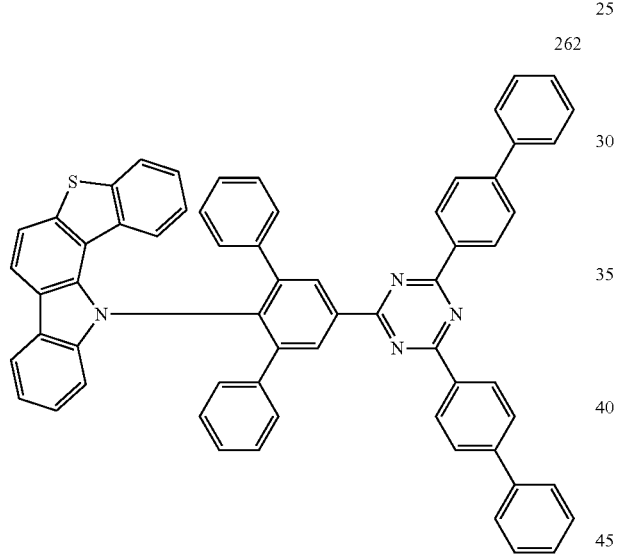
263
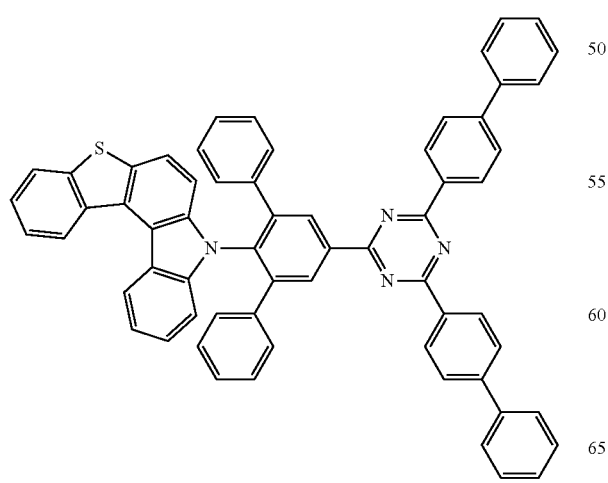
264
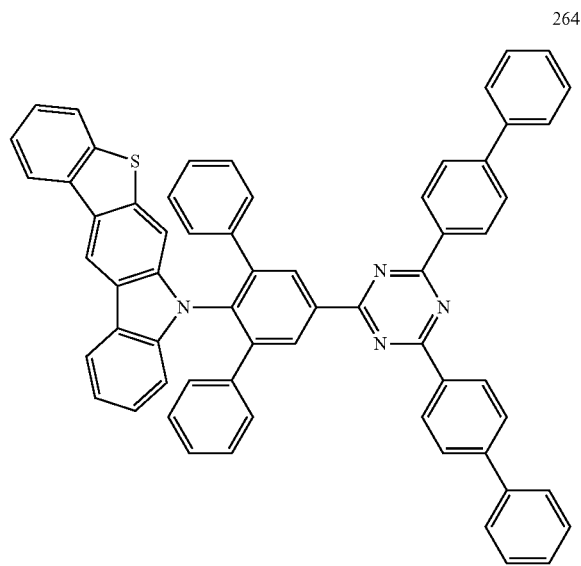
265
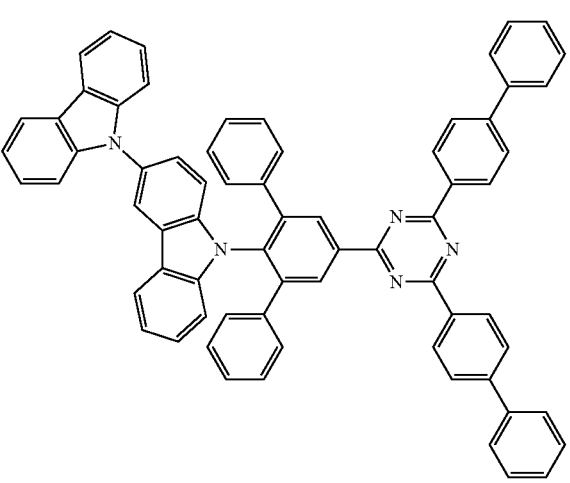
266

-continued
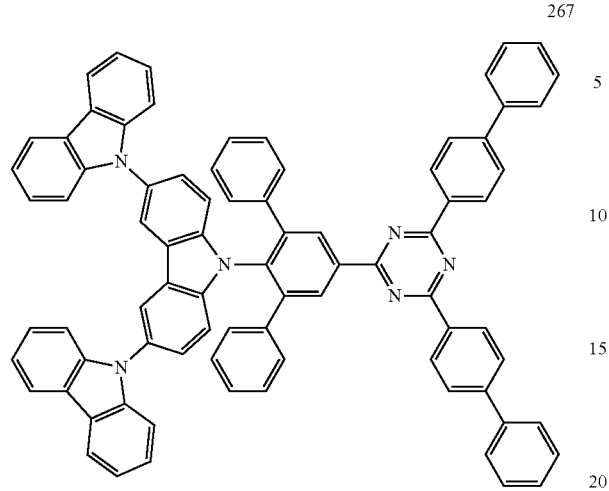
267
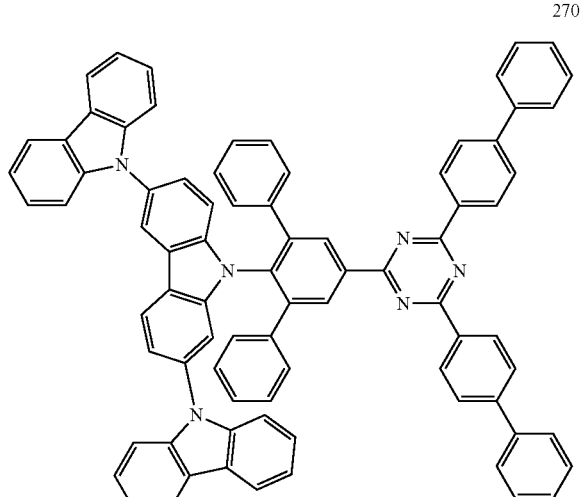
270
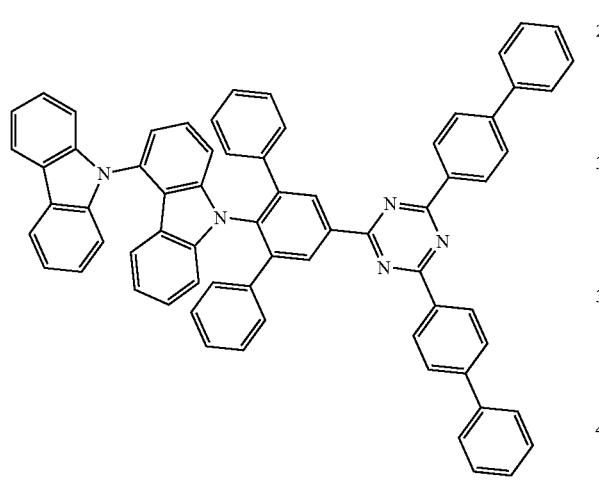
268
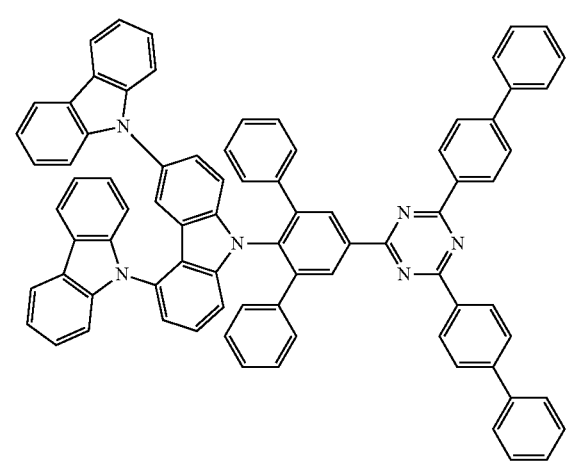
271
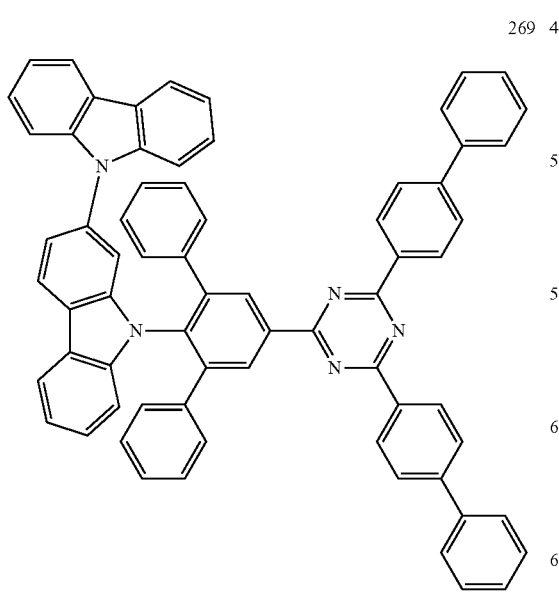
269
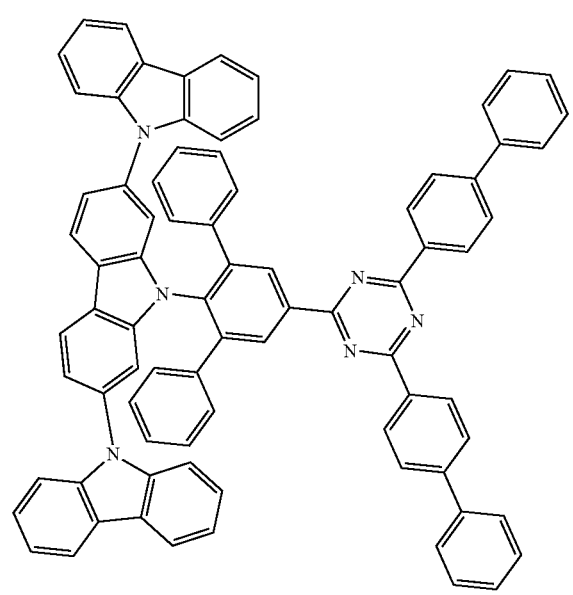
272

103
-continued
273
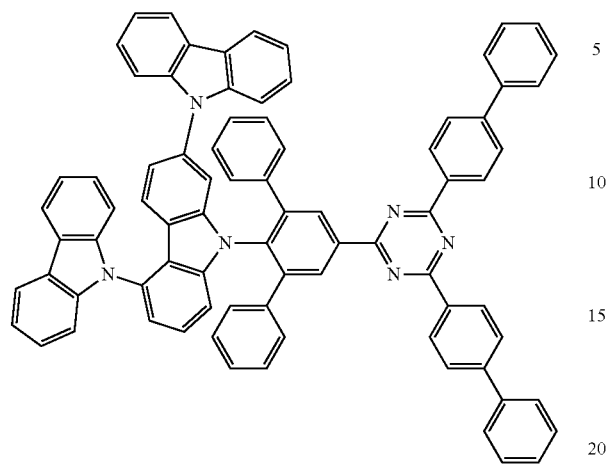
274
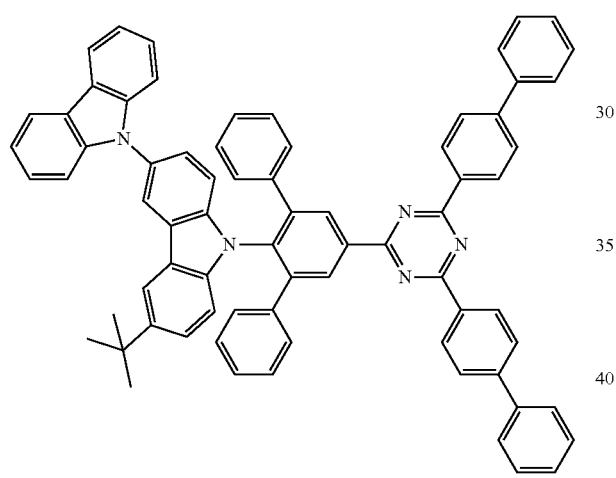
275
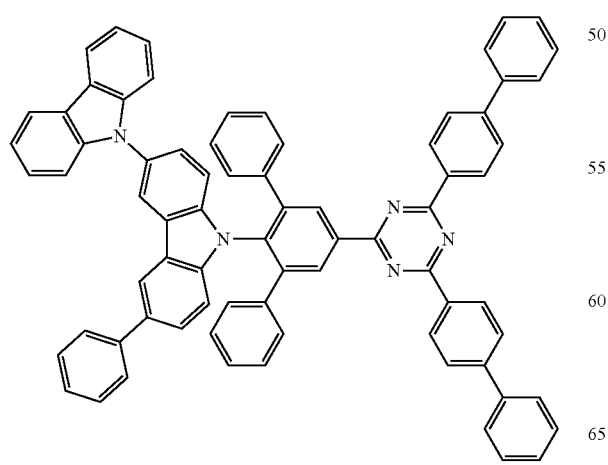
104
-continued
276
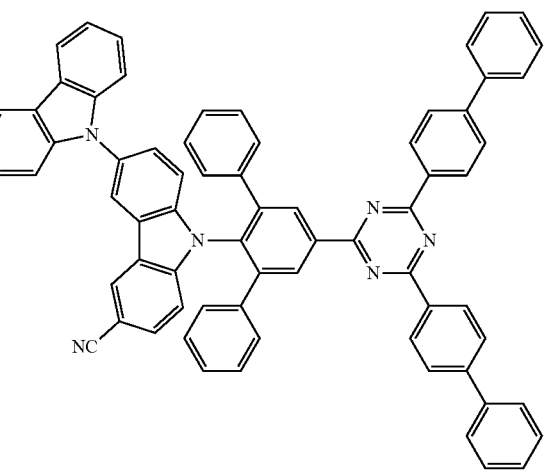
277
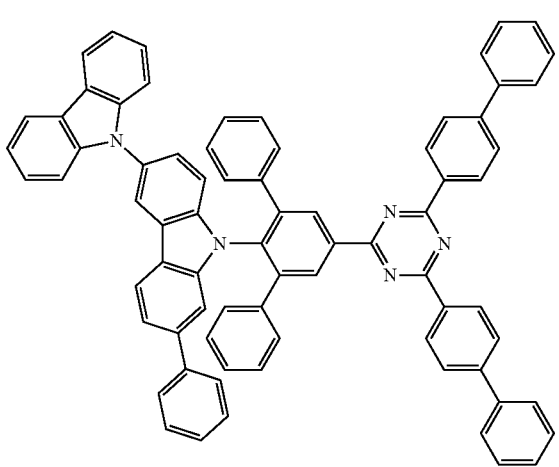
278
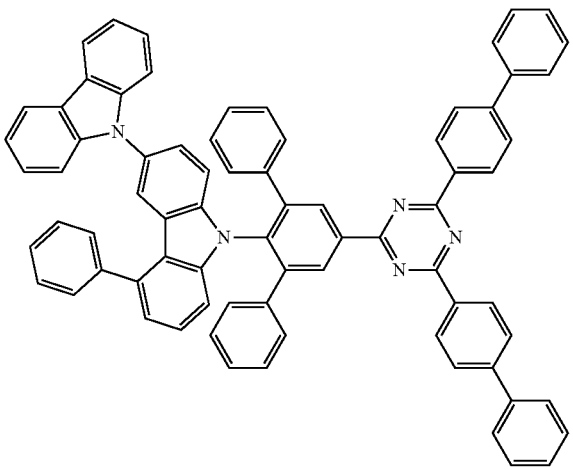

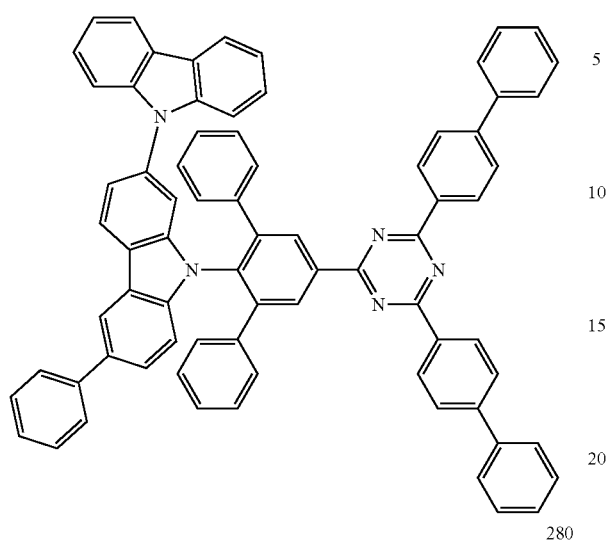
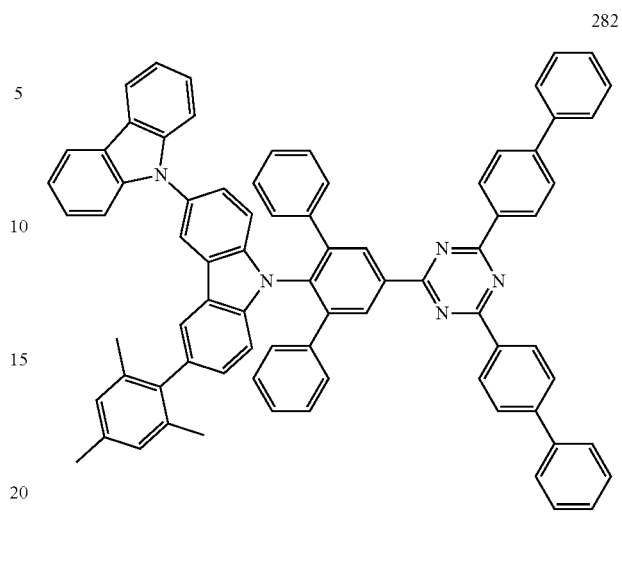
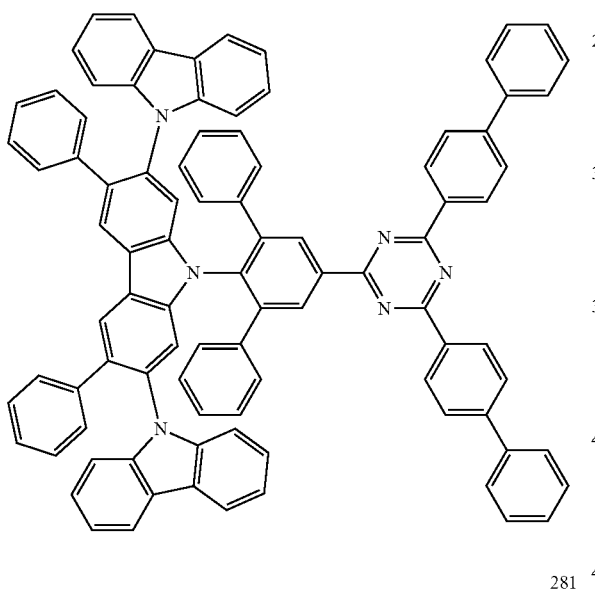
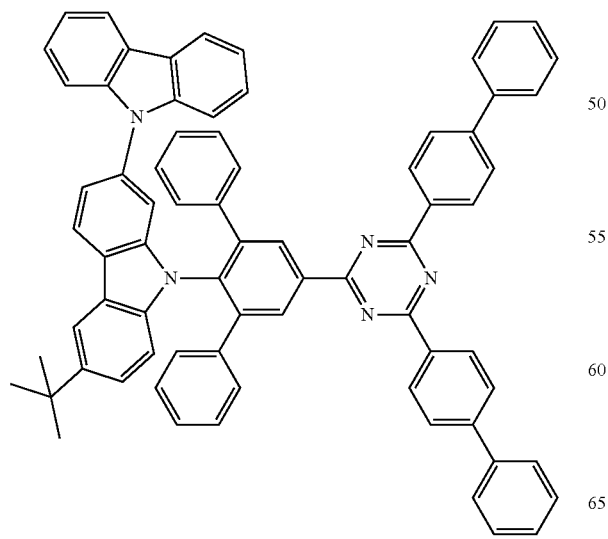

285
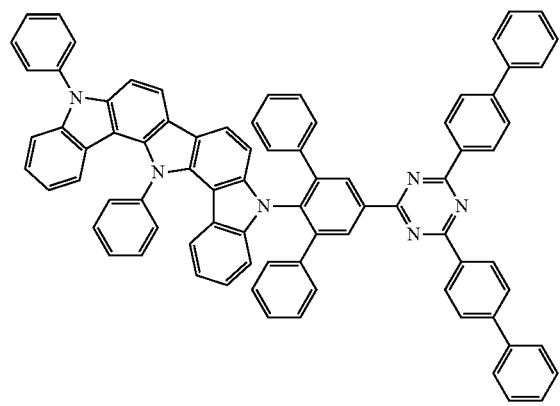
286
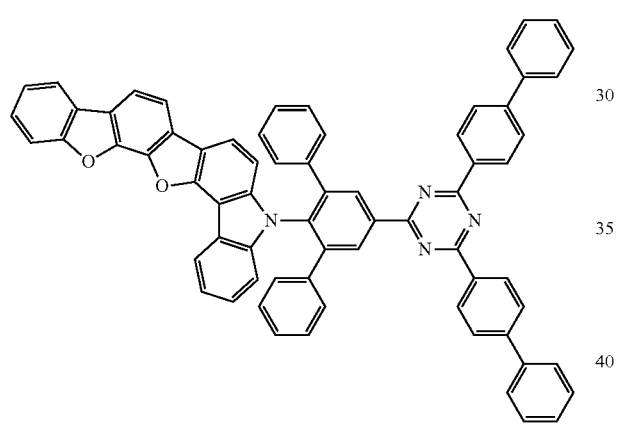
287
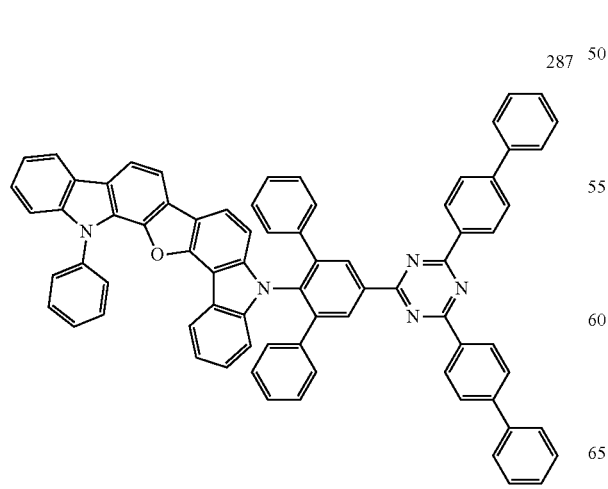
288
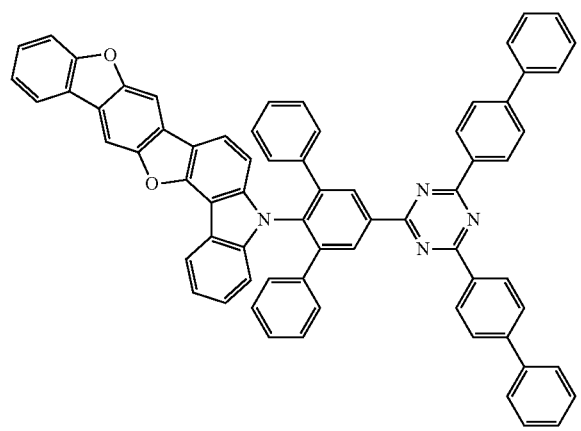
289
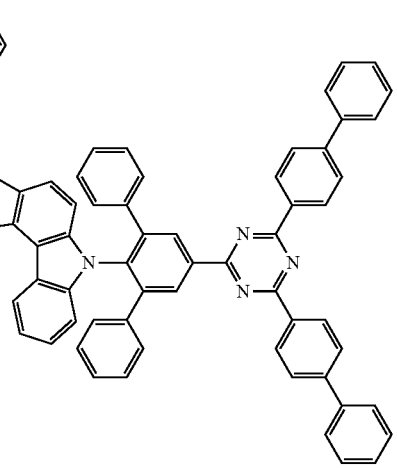
290
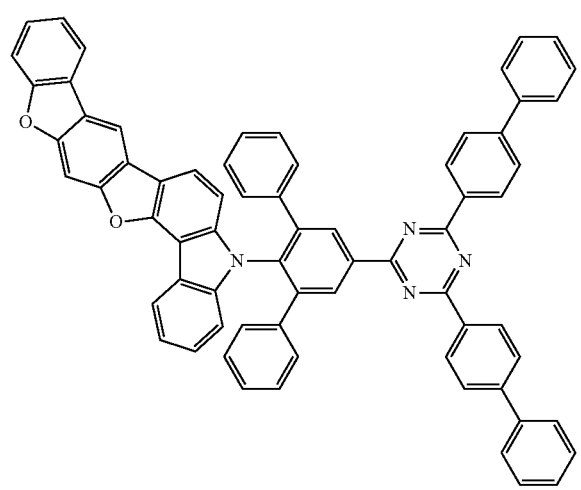

-continued
291
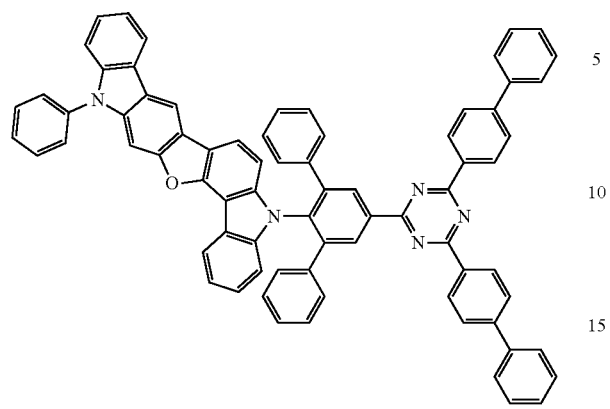
292
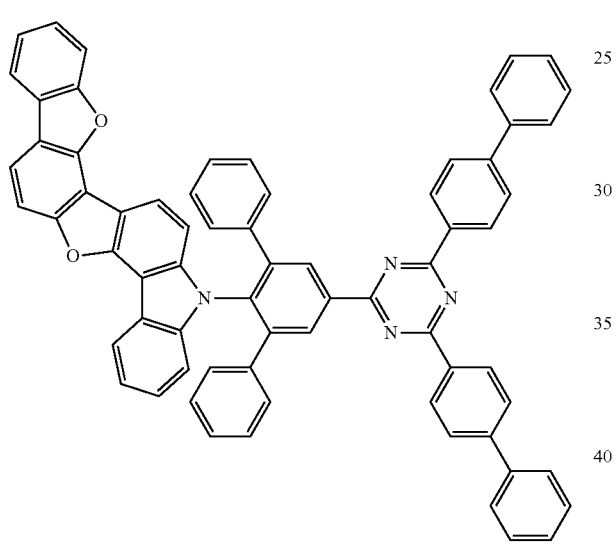
293
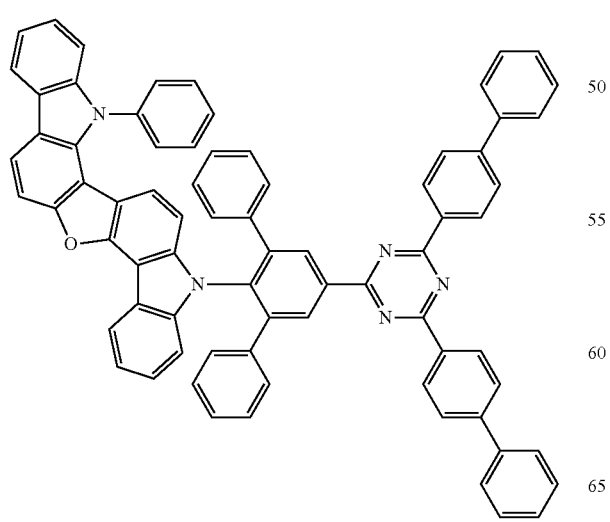
-continued
294
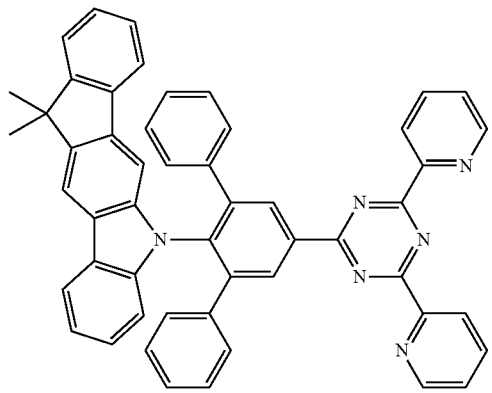
295
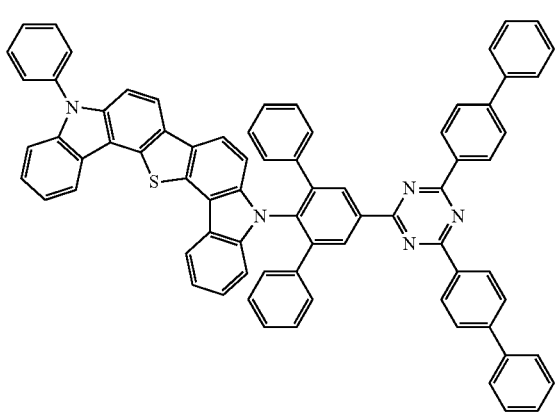
296
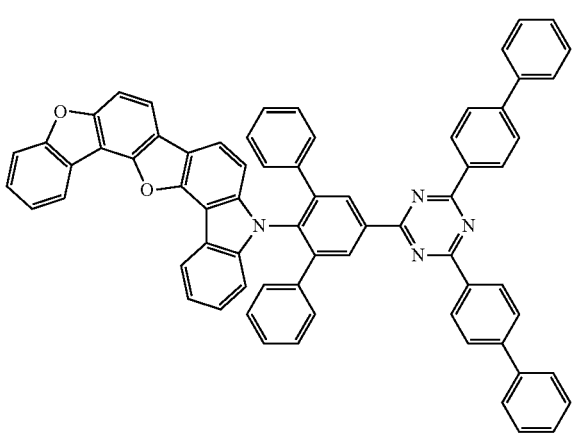

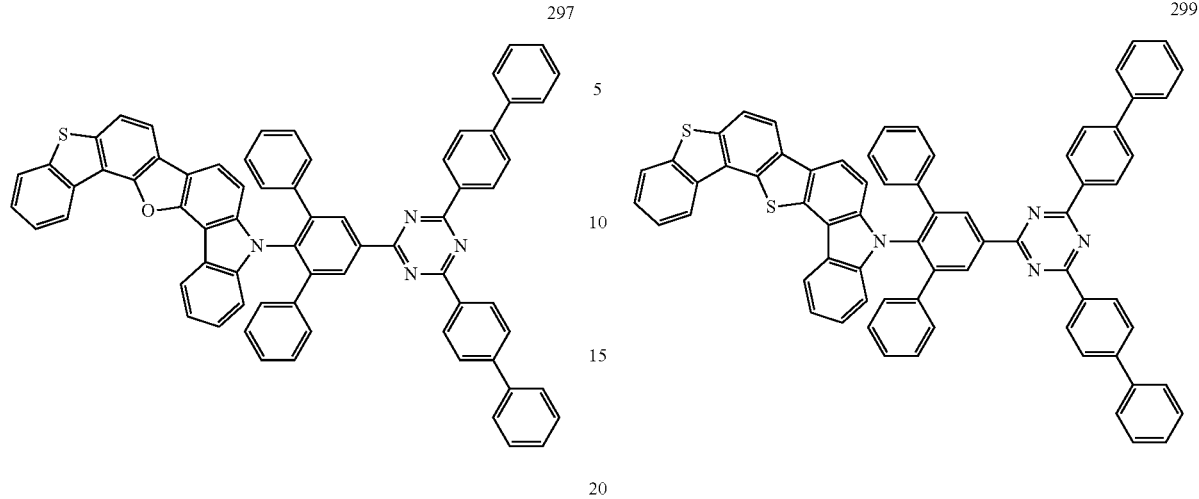
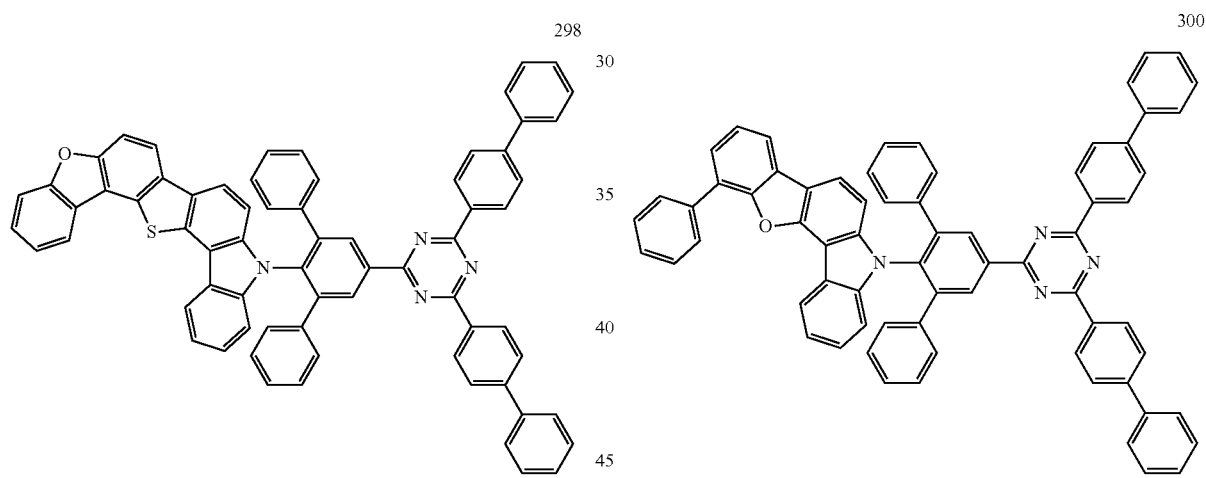
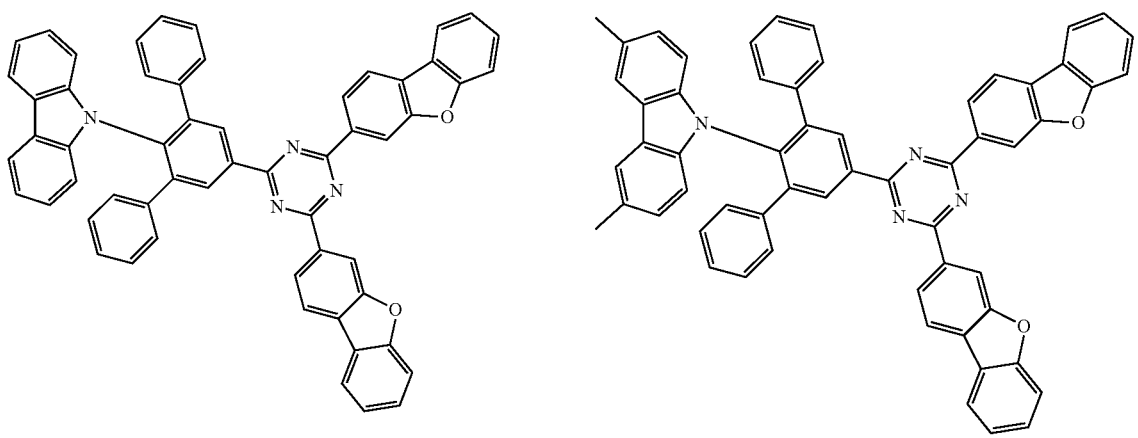

-continued
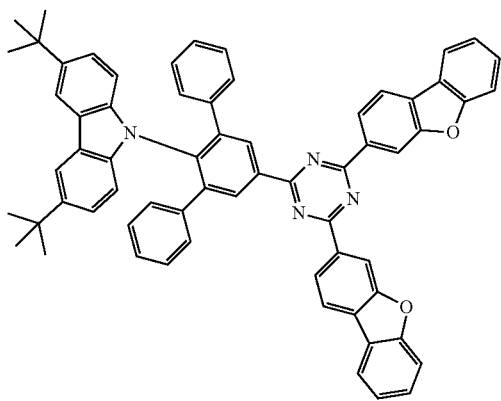
303
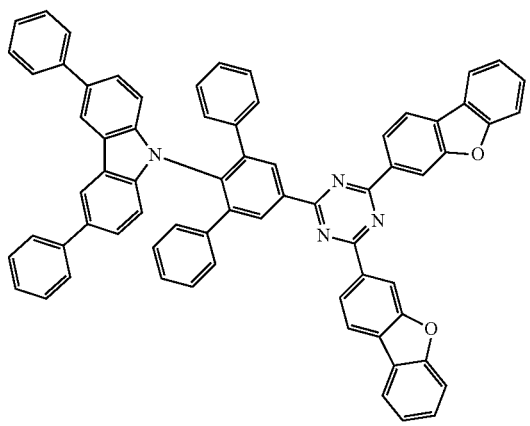
304
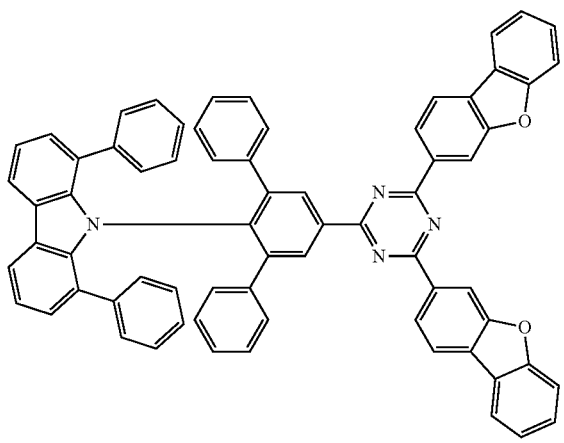
305
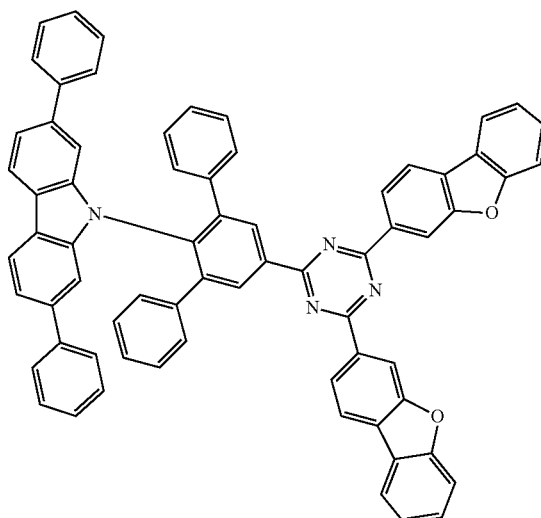
306
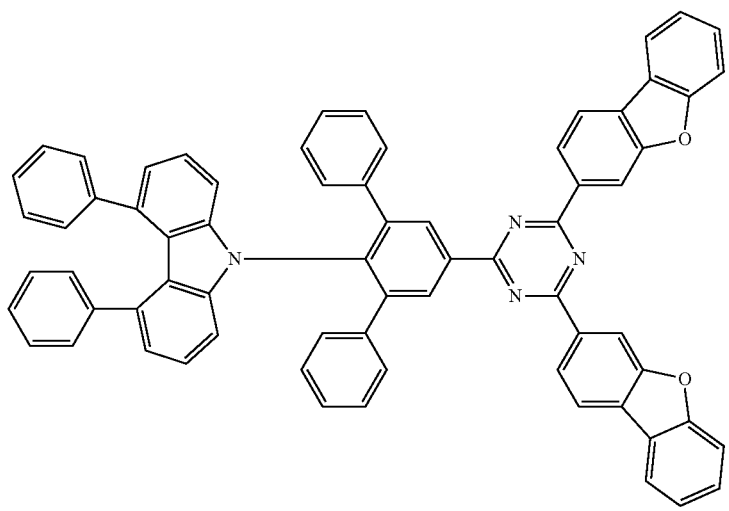
307

308
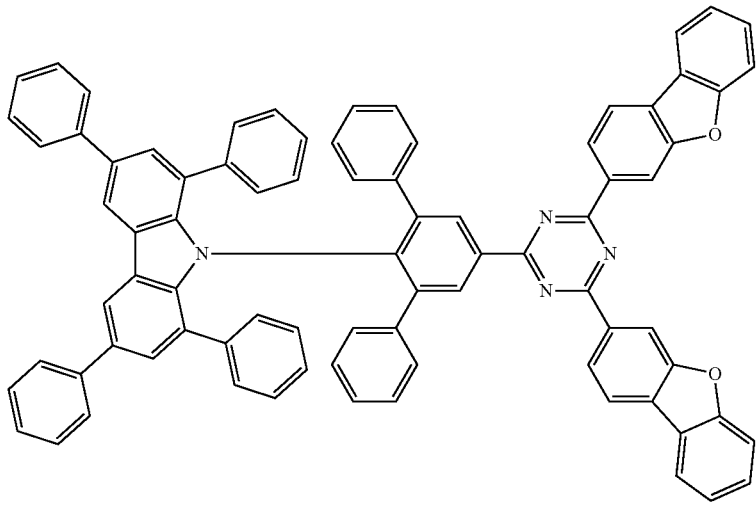
309
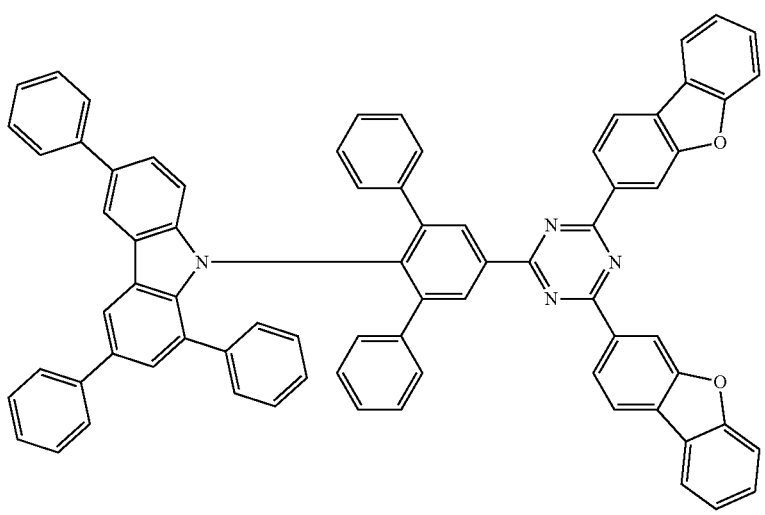
310
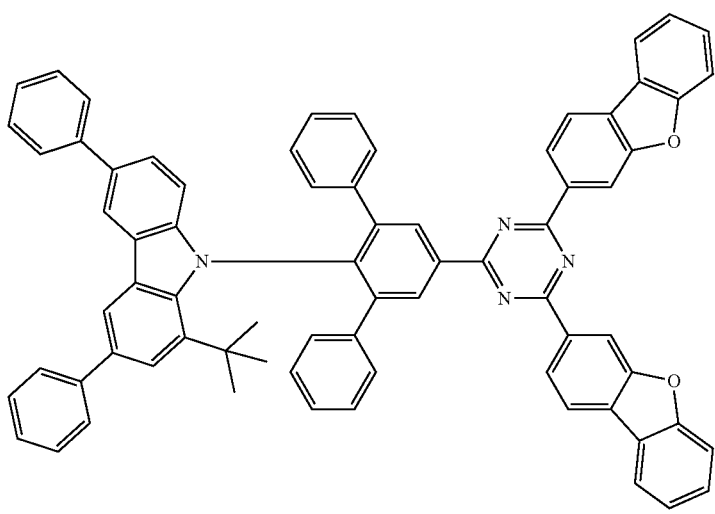

311
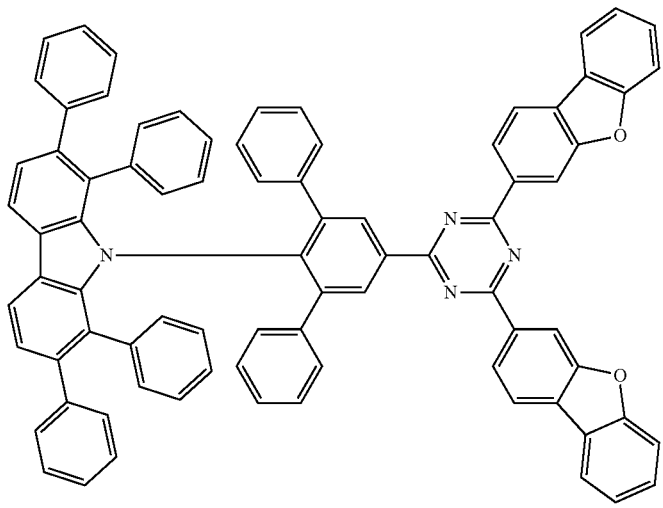
312
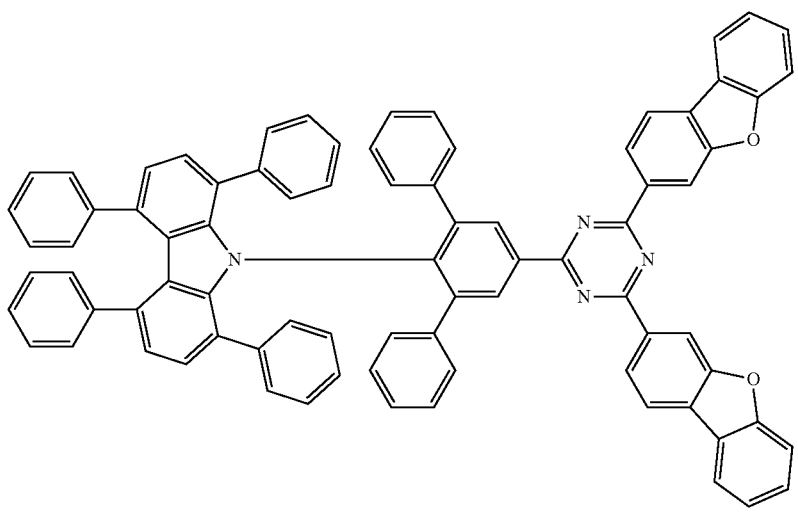
313
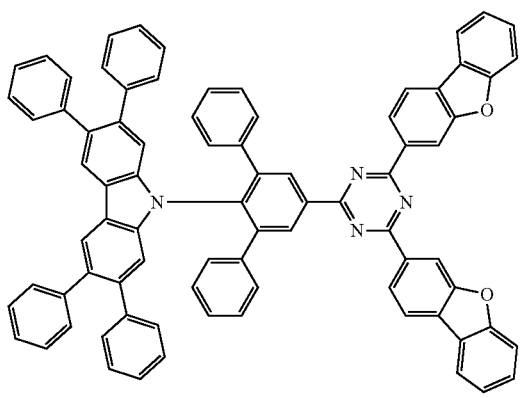
314
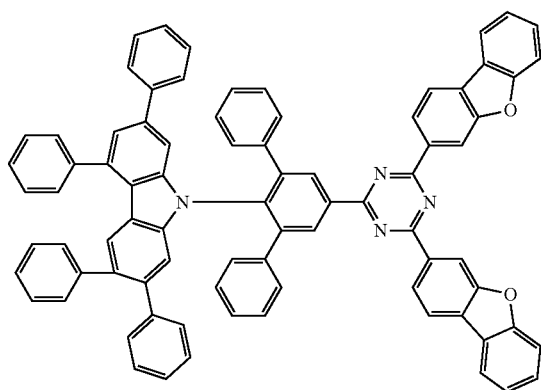

-continued
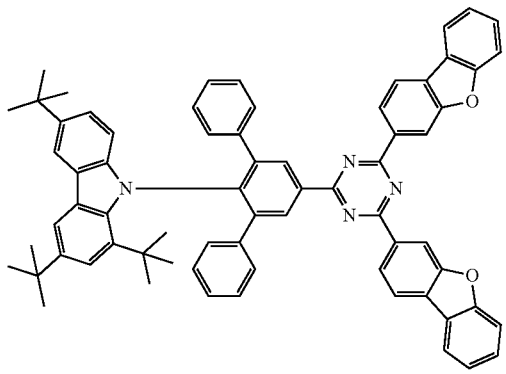
315
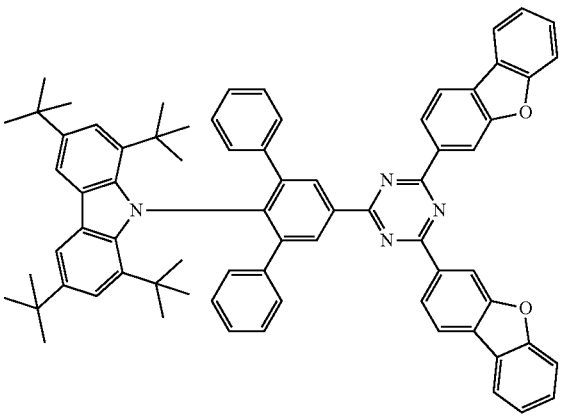
316
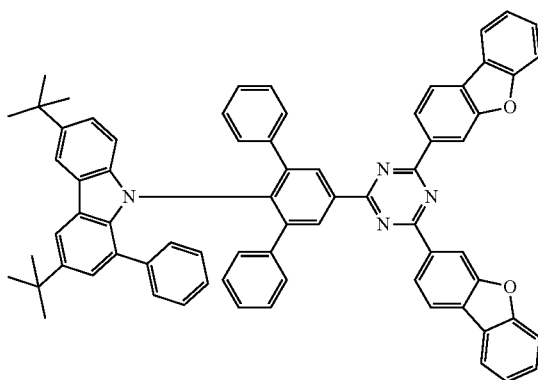
317
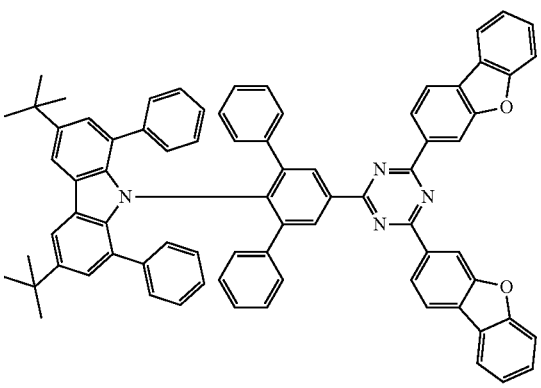
318
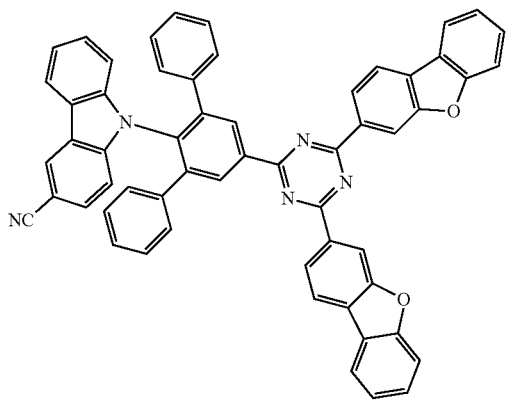
319
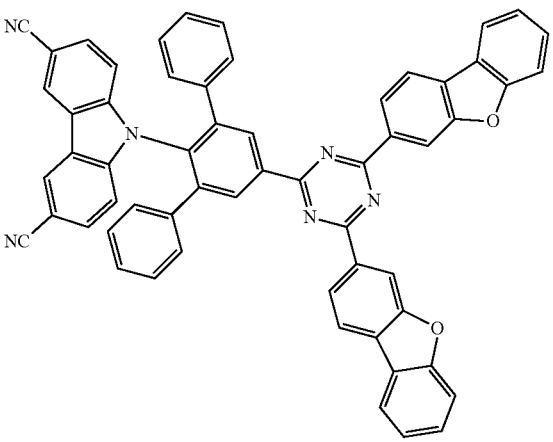
320

-continued
121
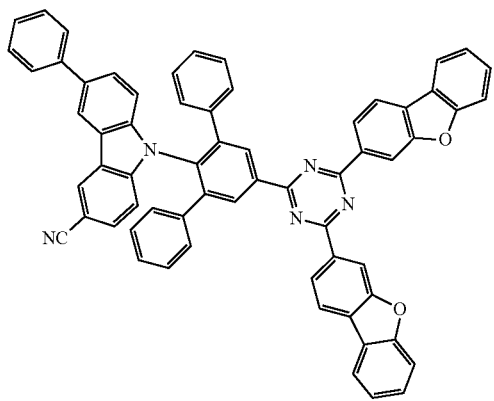
321
122
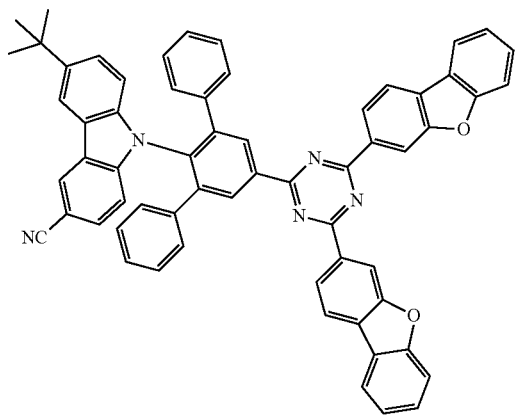
322
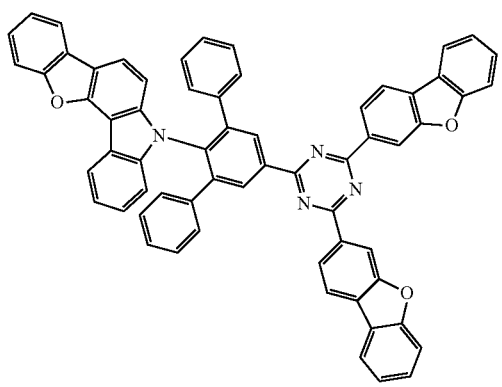
323
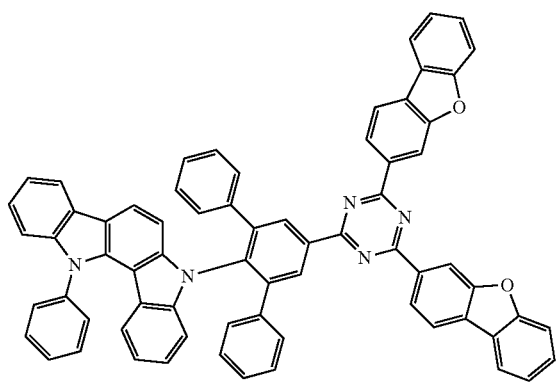
324
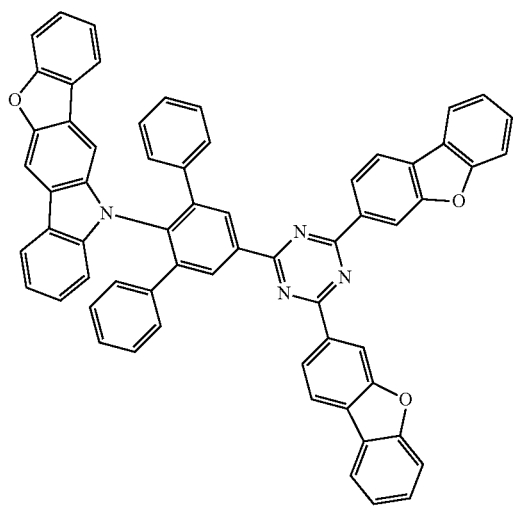
325
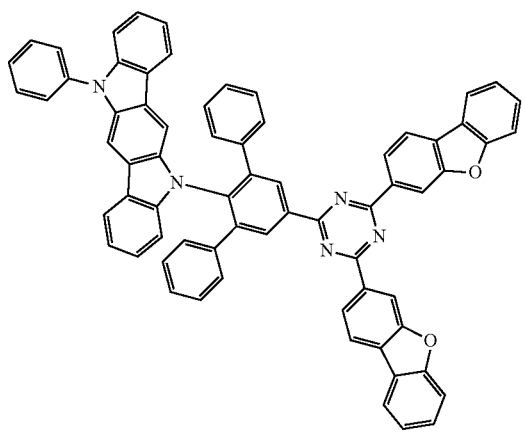
326

327
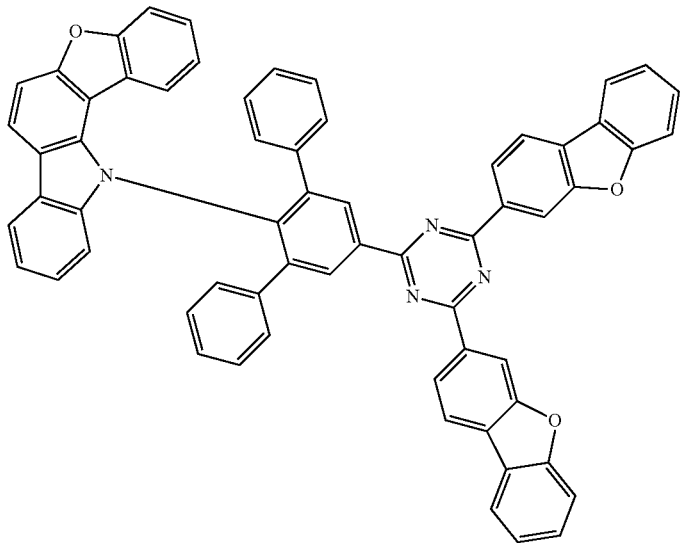
328
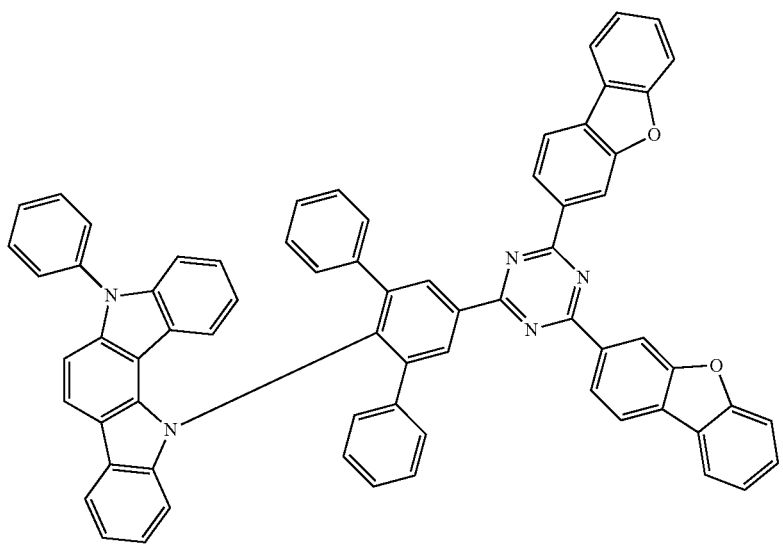
329
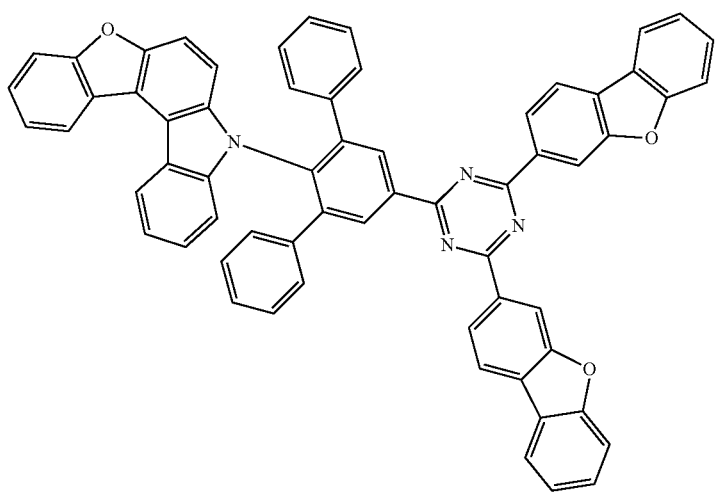

-continued
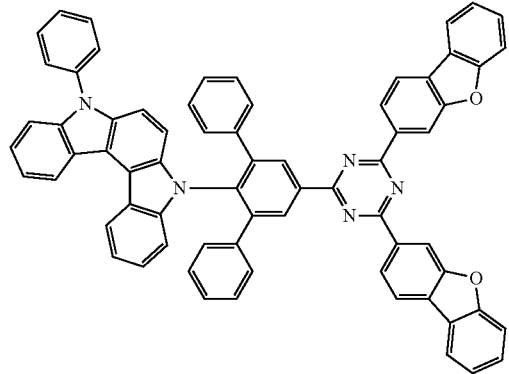
330
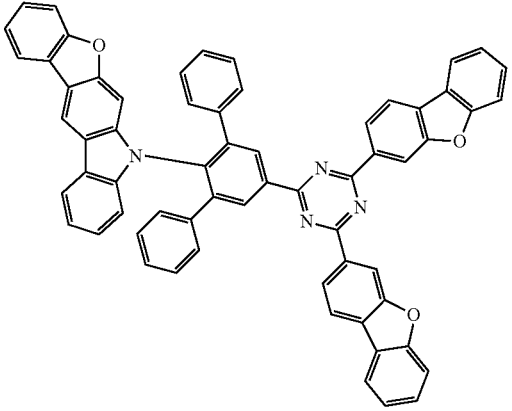
331
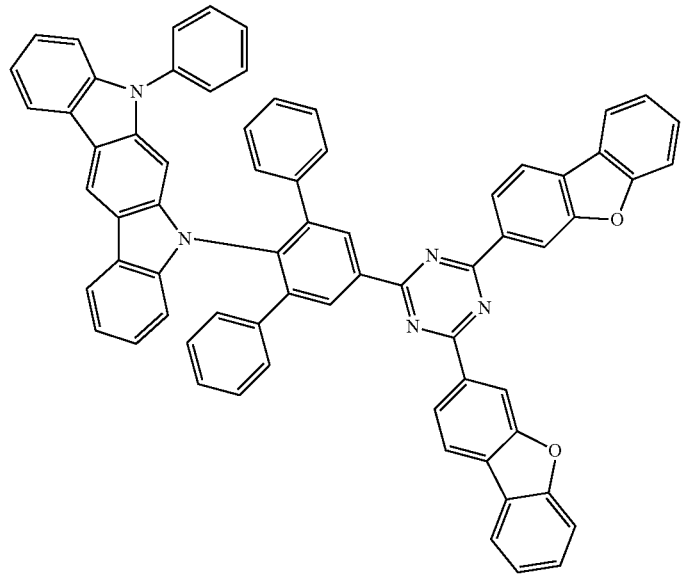
332
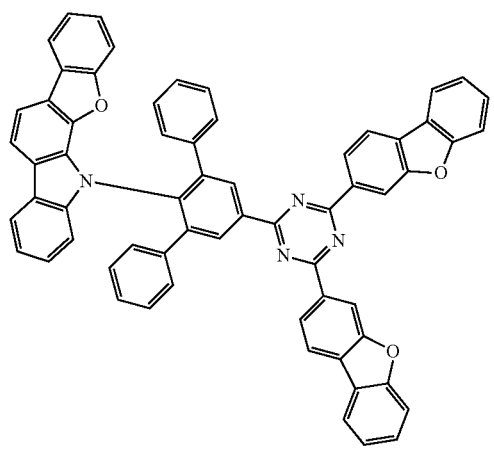
333
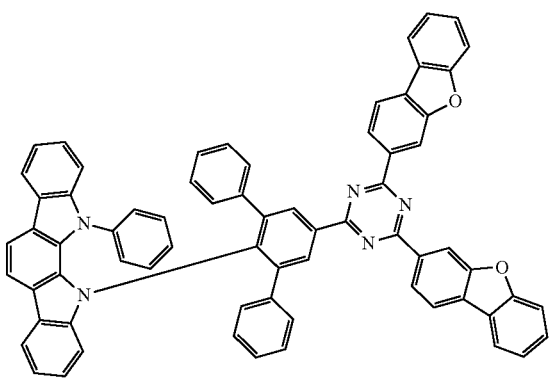
334

-continued
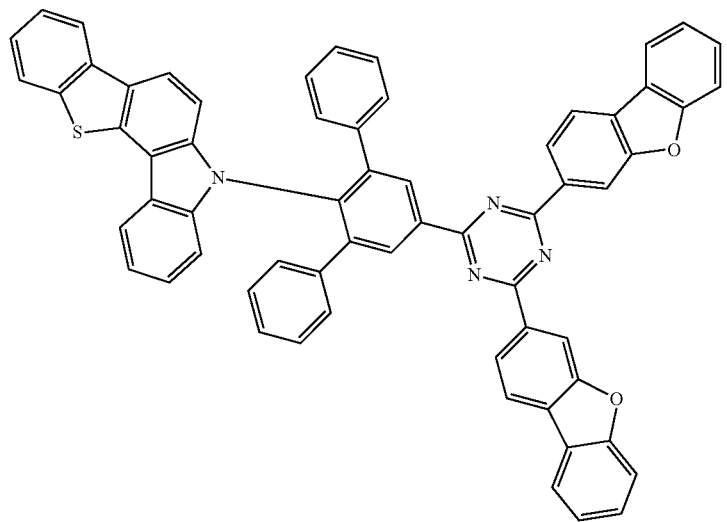
335
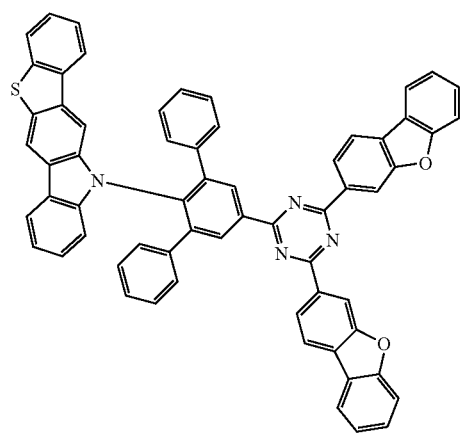
336
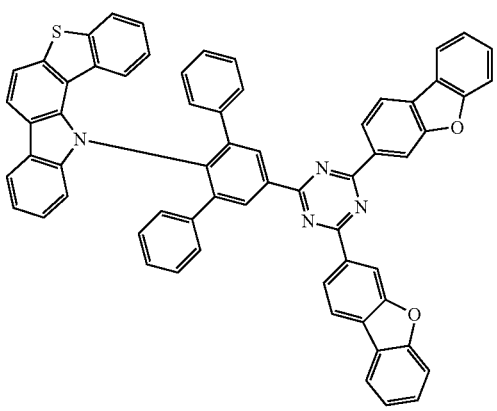
337
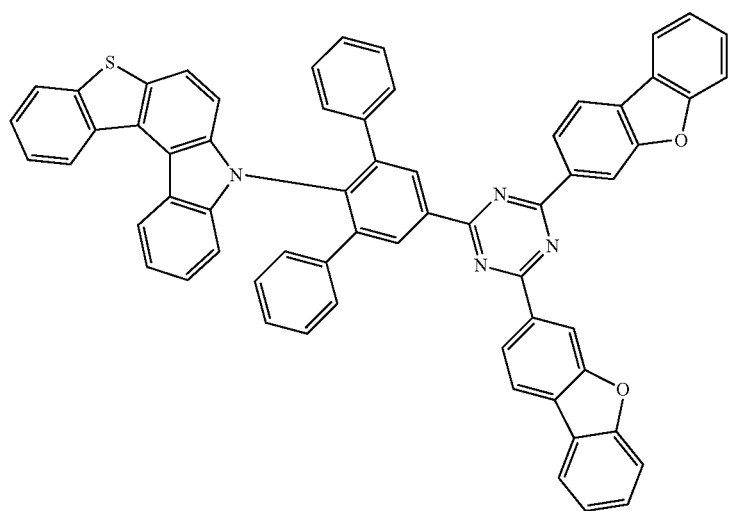
338

-continued
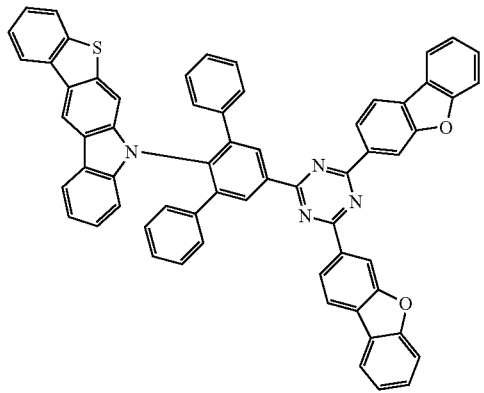
339
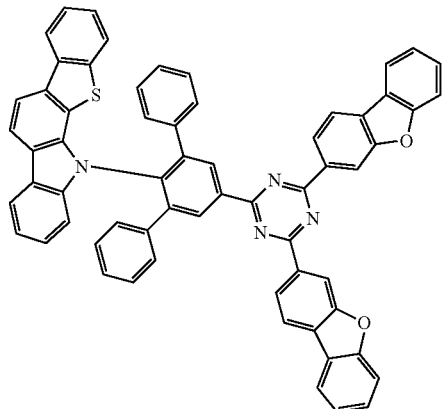
340
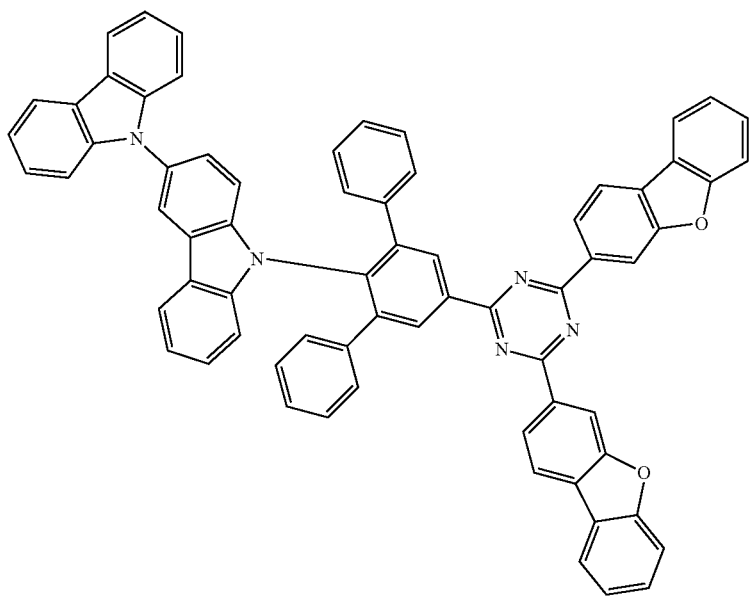
341
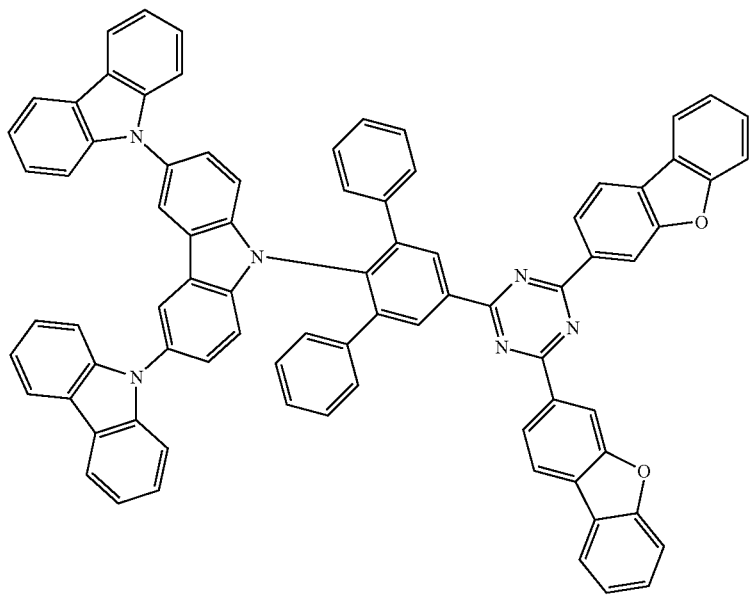
342

-continued
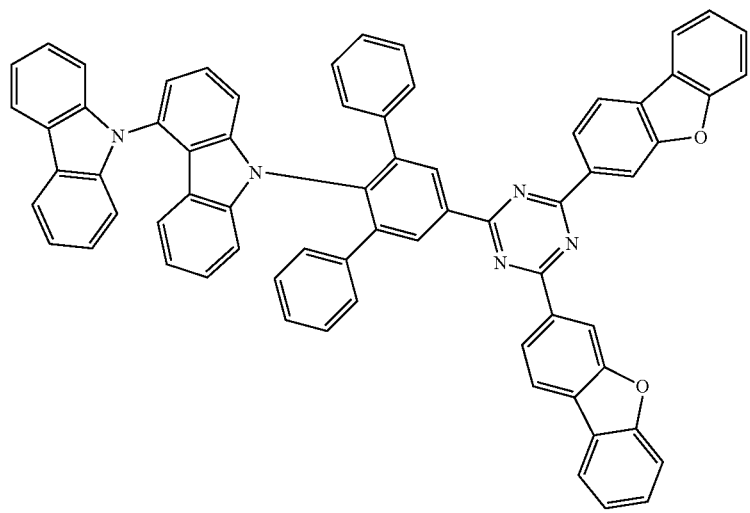
343
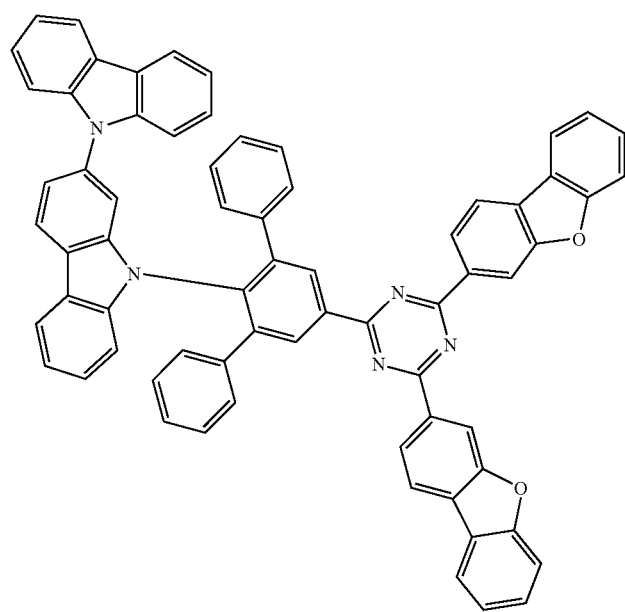
344

345
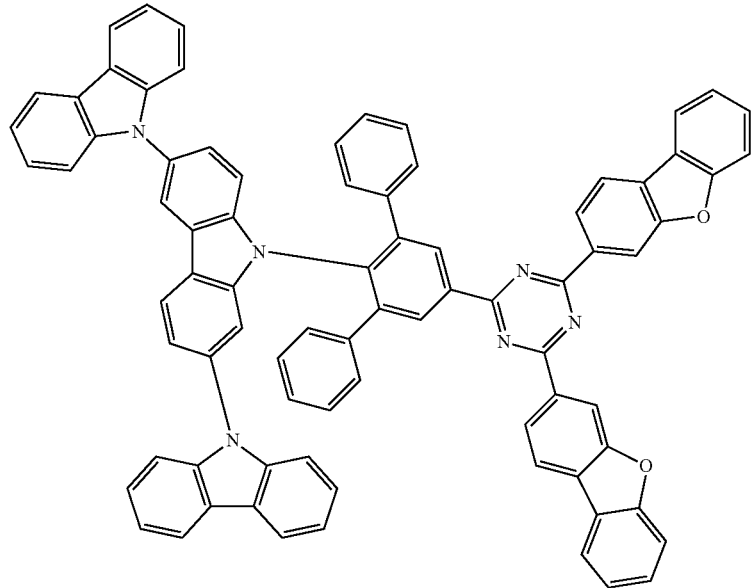
346
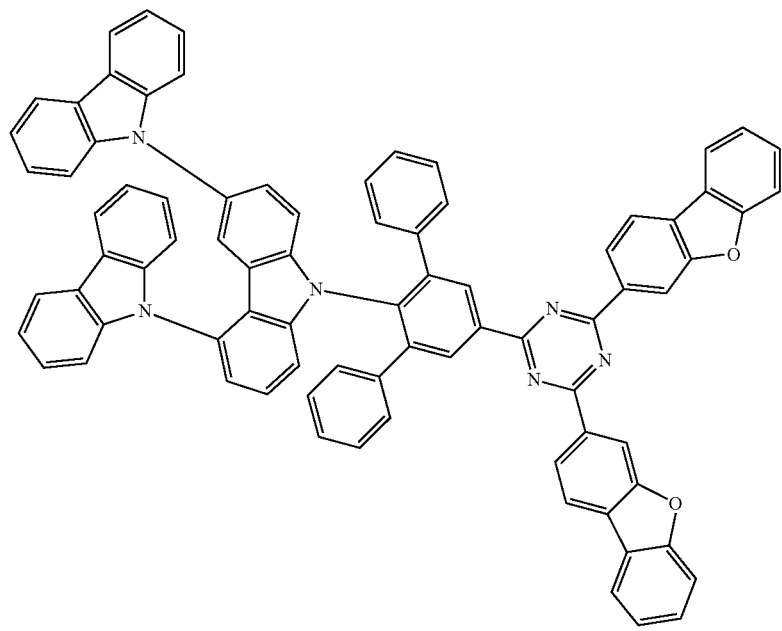

347
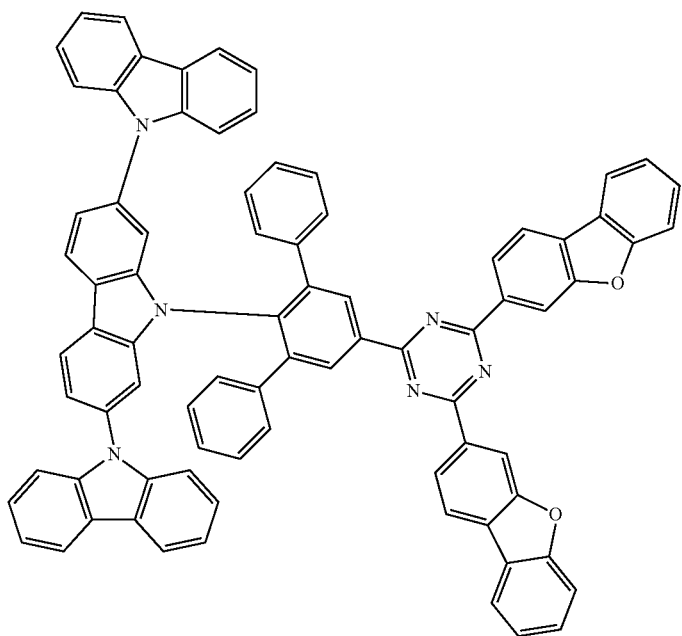
348
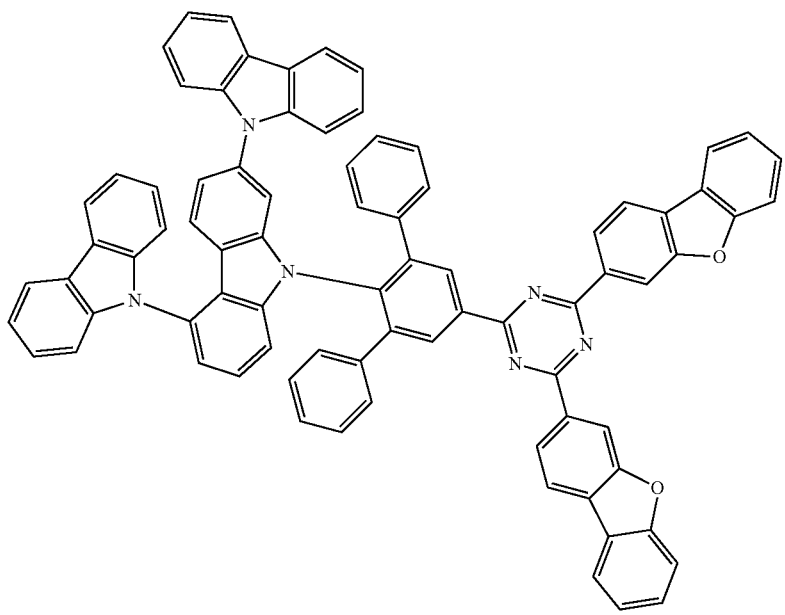

349
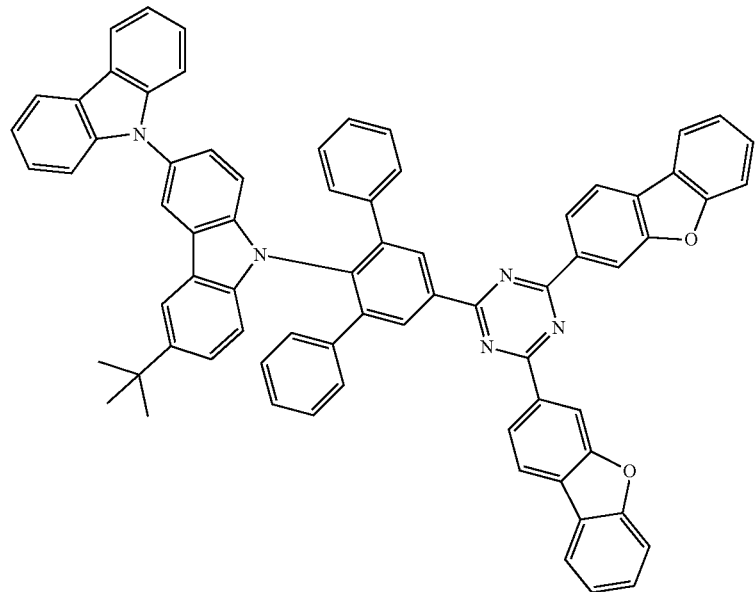
350
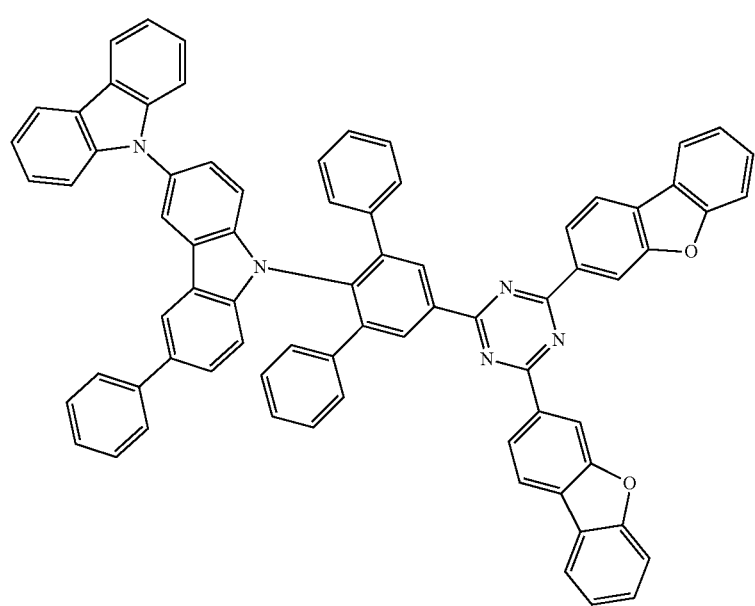

-continued
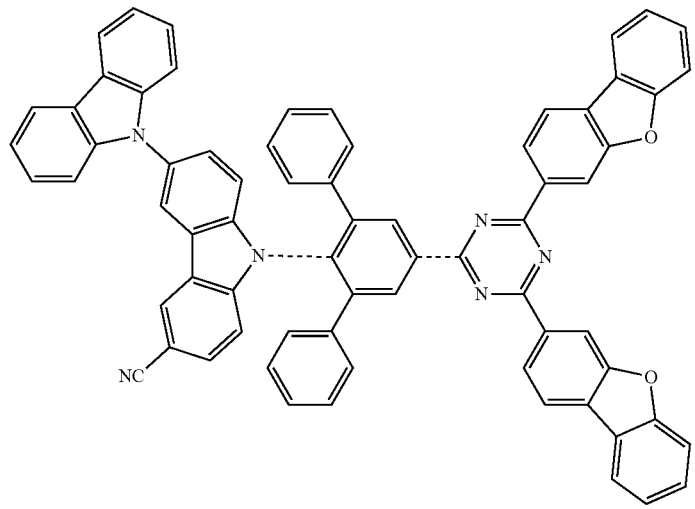
351
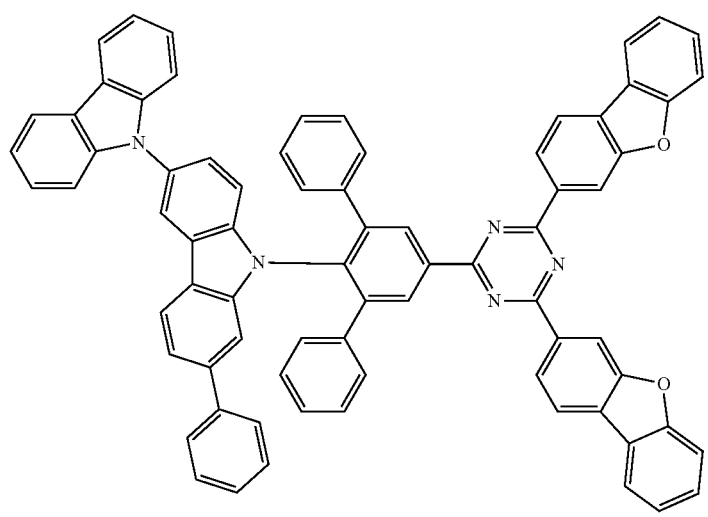
352
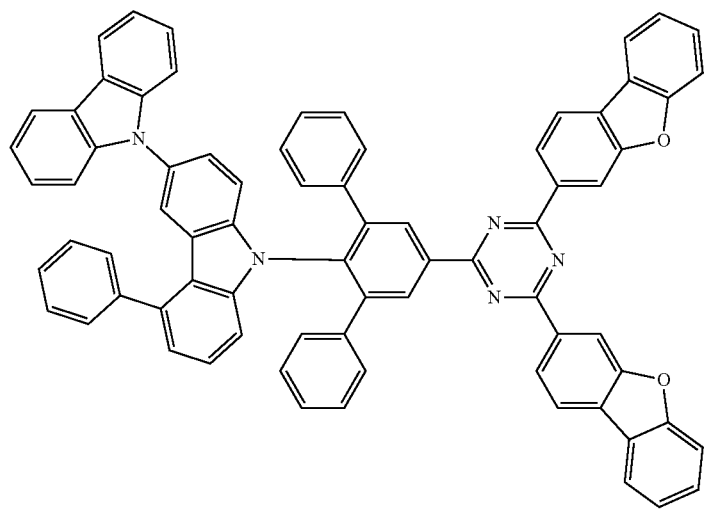
353

-continued
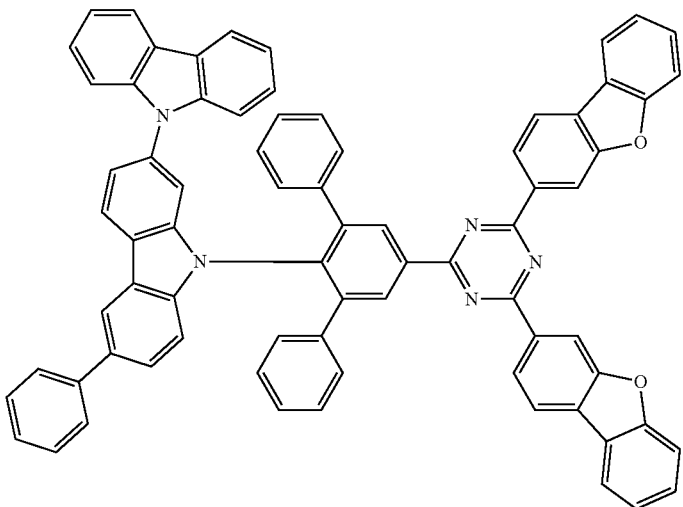
354
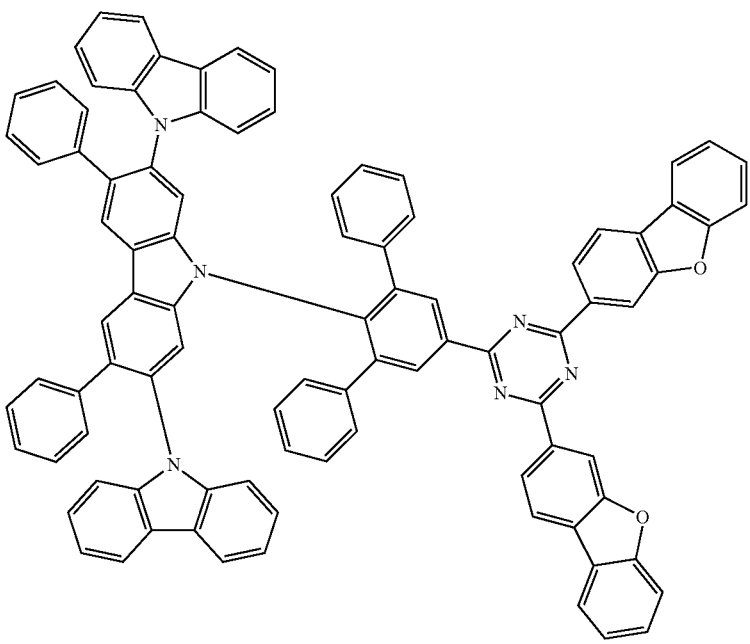
355
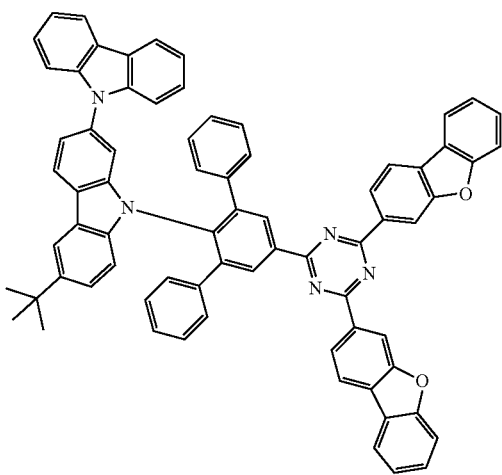
356
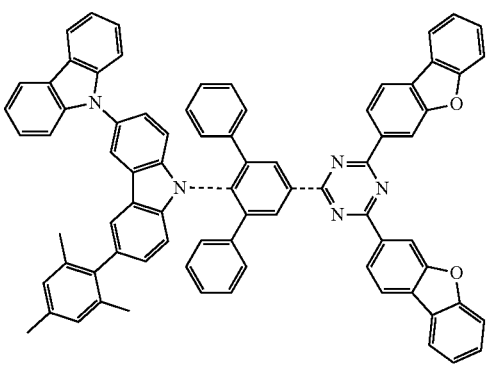
357

-continued
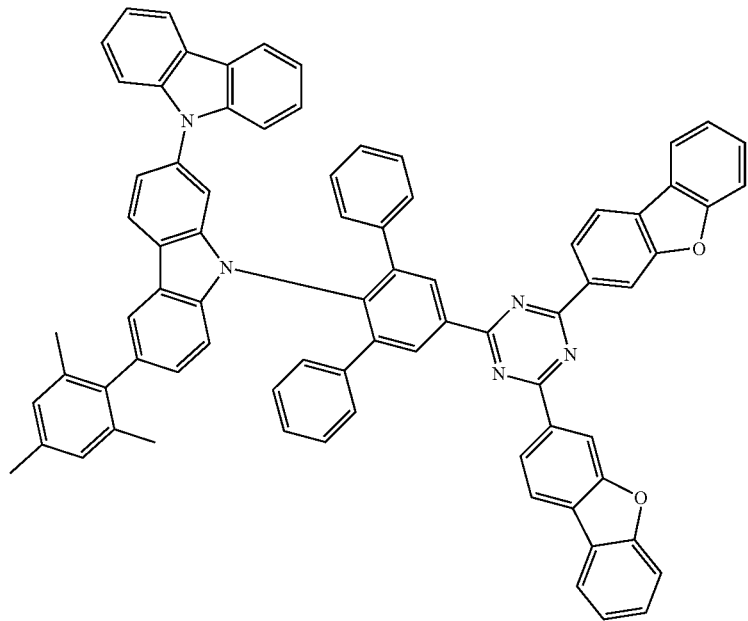
358
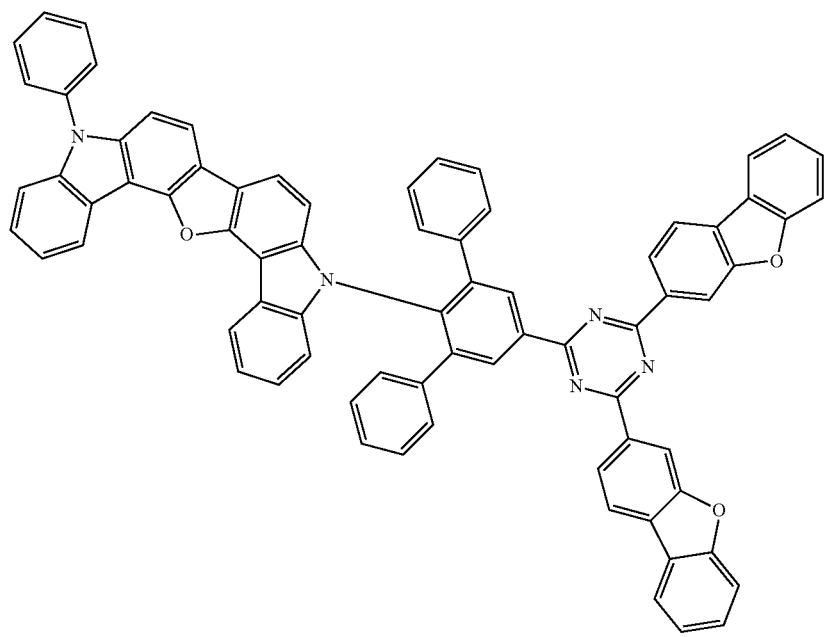
359

-continued
360
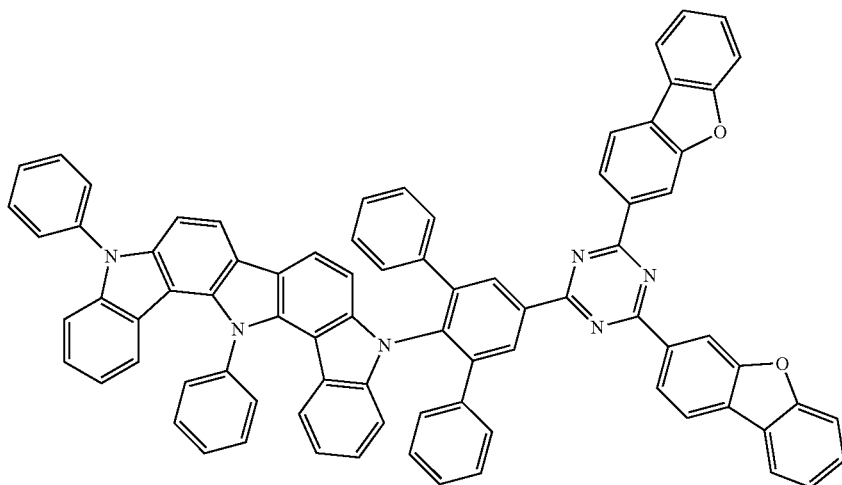
361
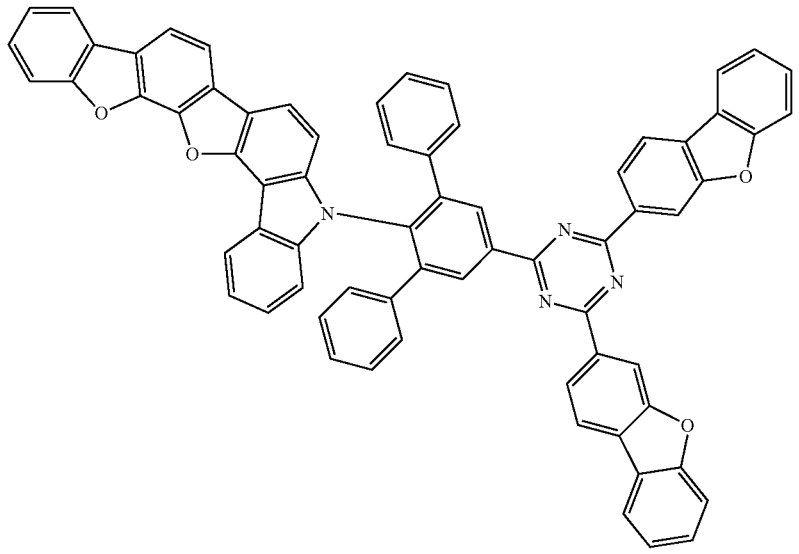
362
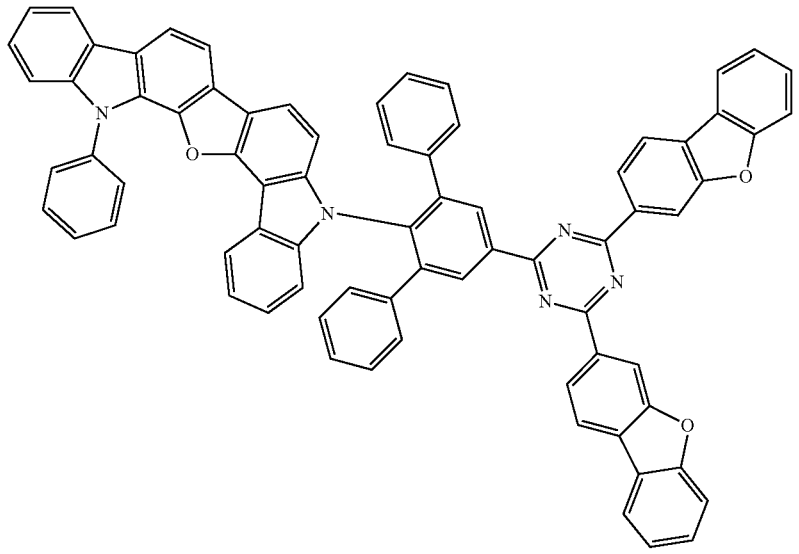

363
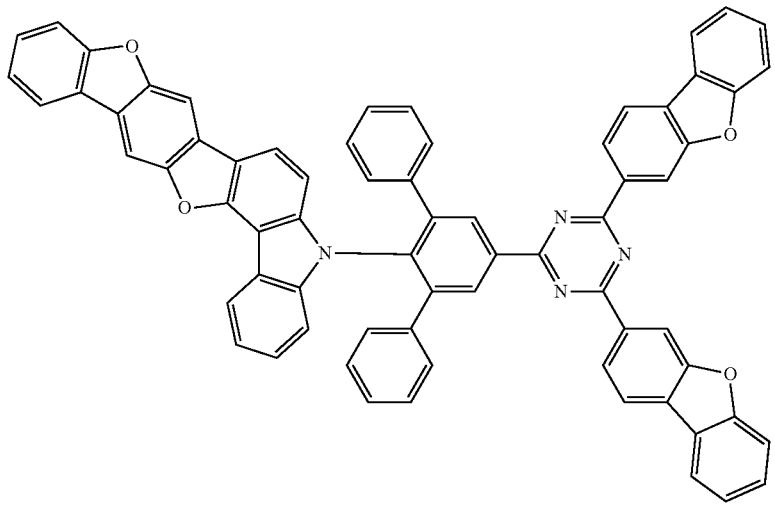
364
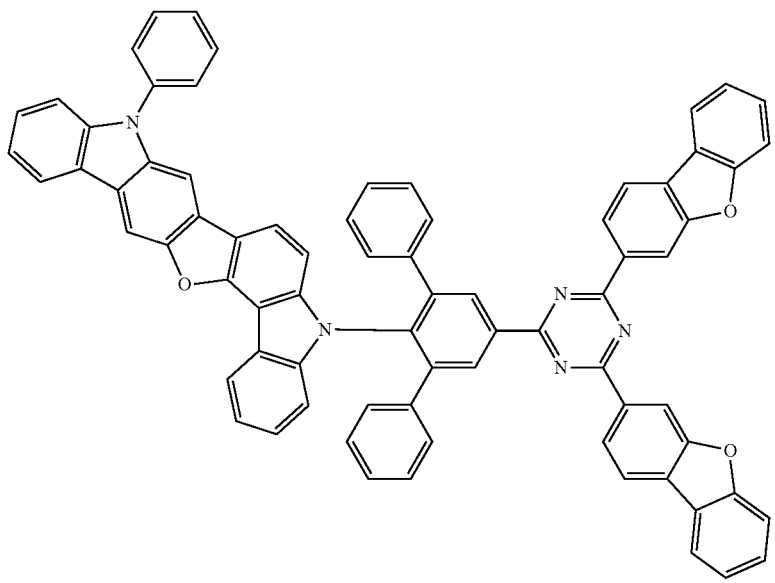
365
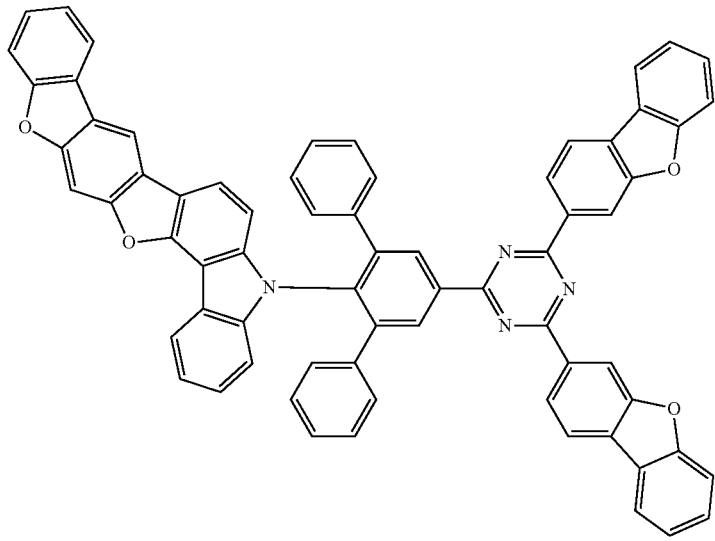

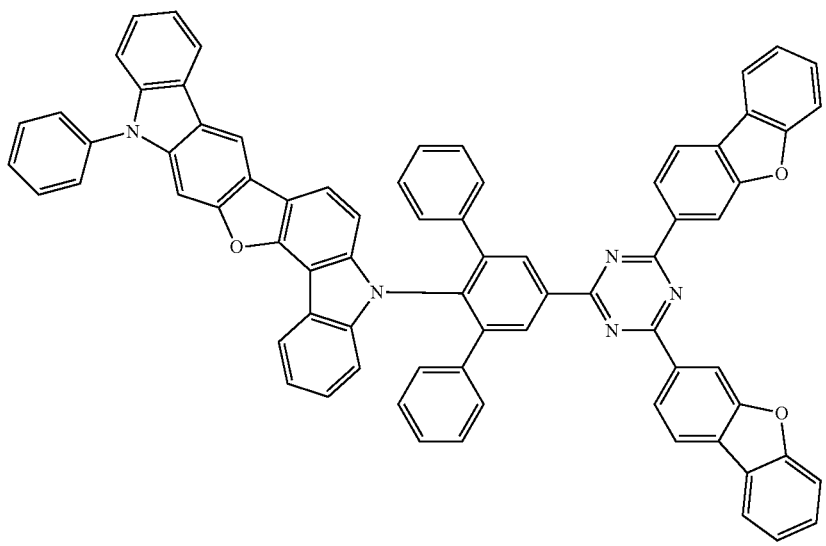
366
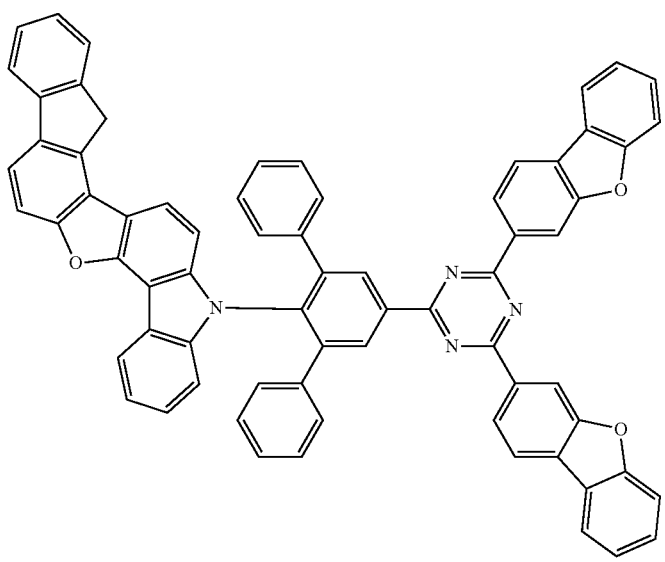
367
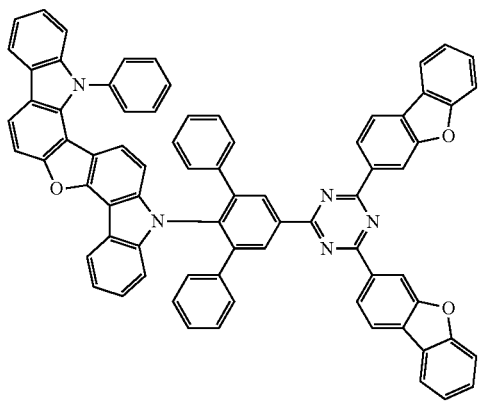
368
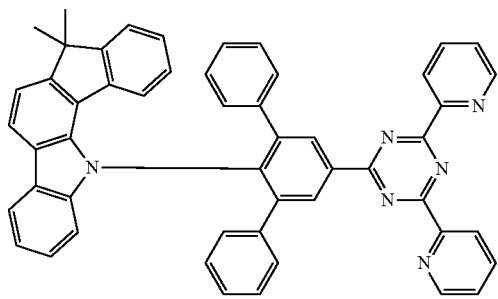
369

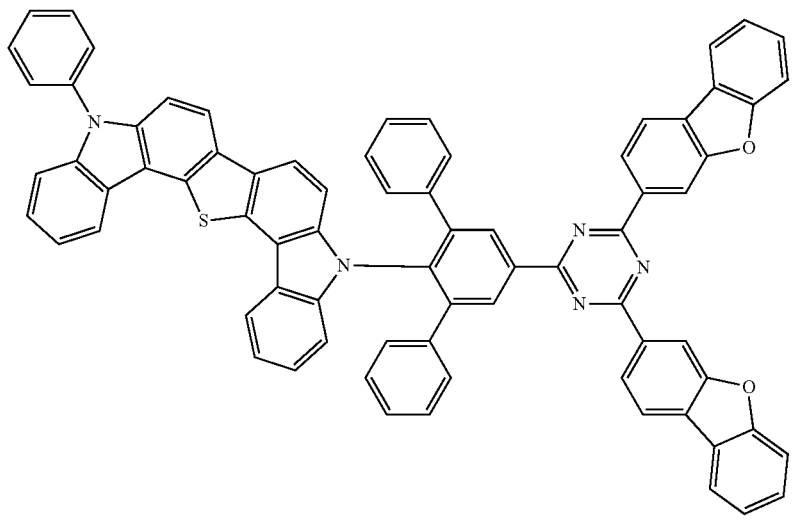
370
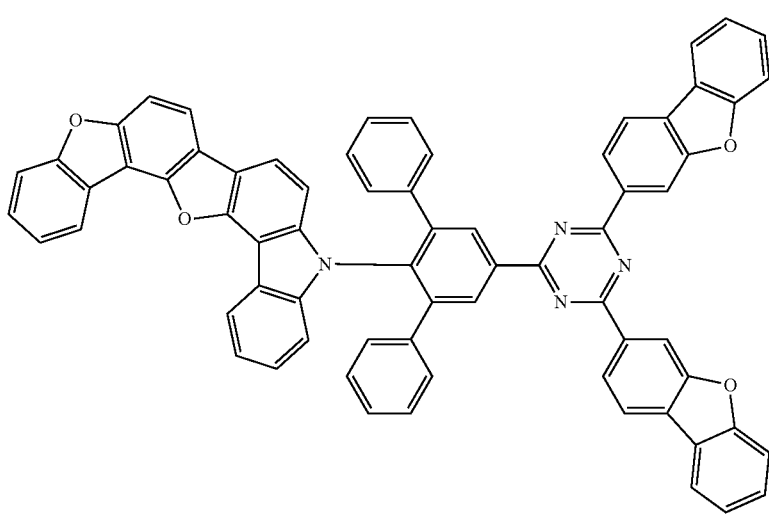
371
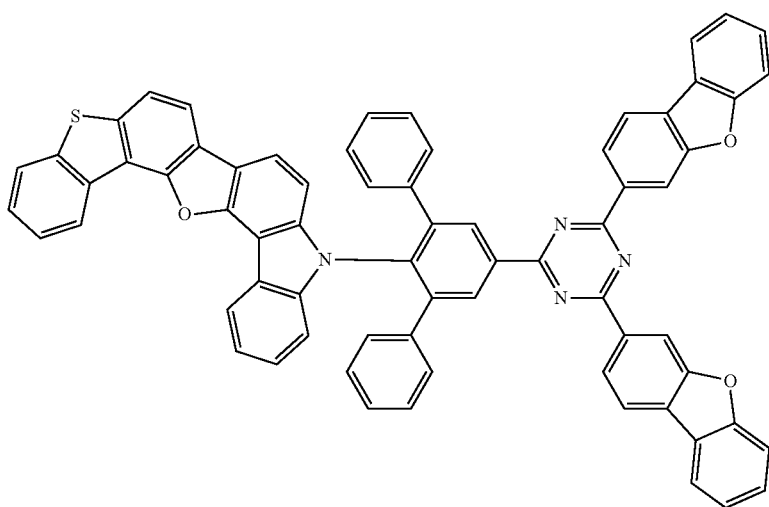
372

-continued
373
374
375
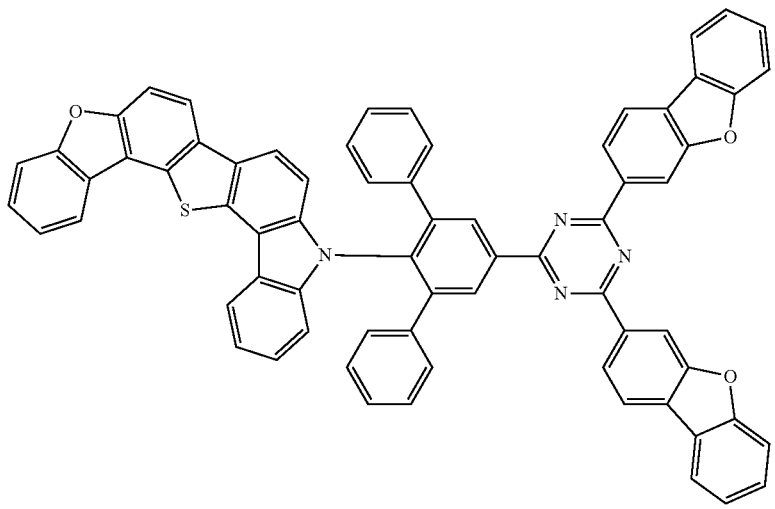

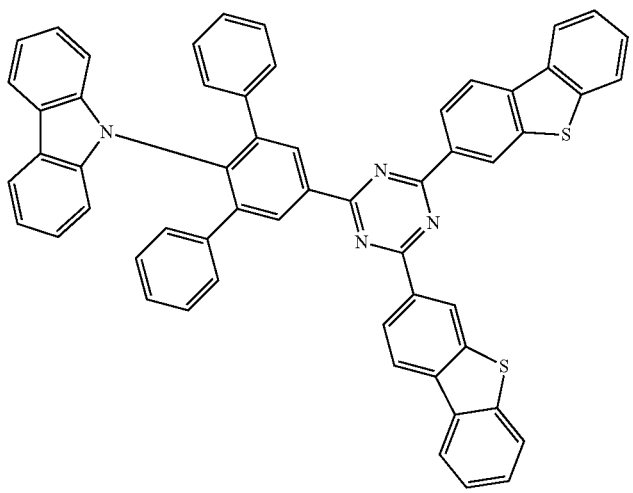
376
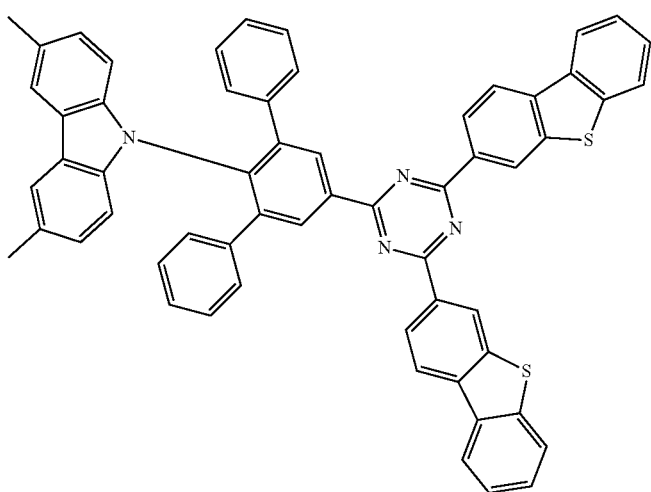
377
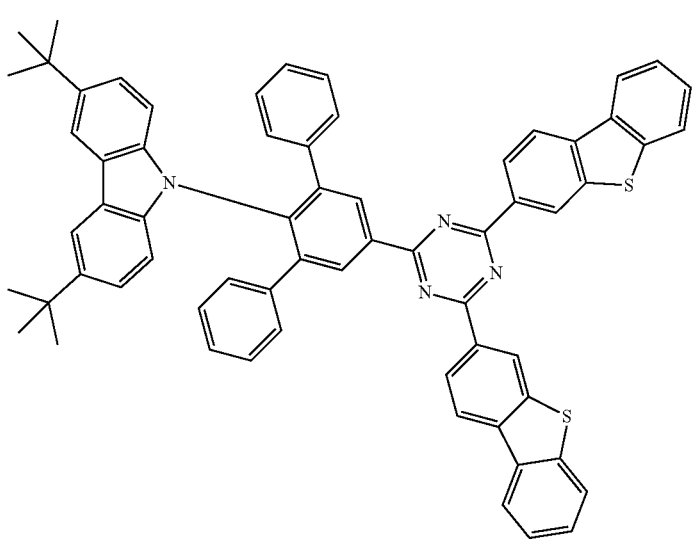
378

379
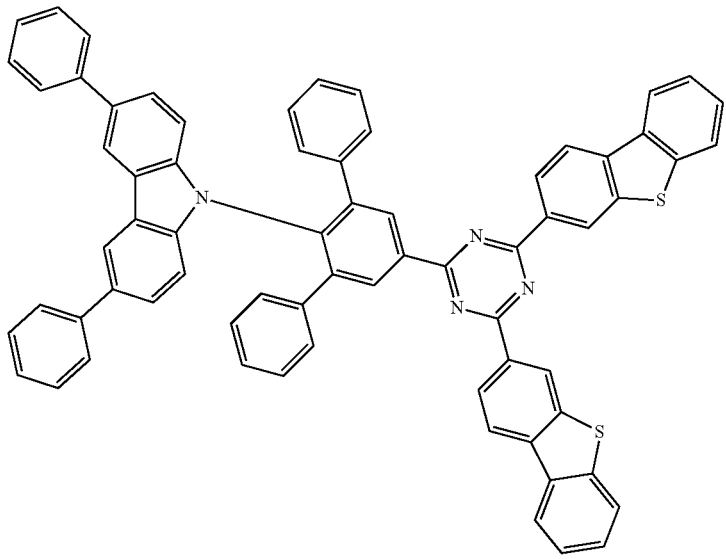
380
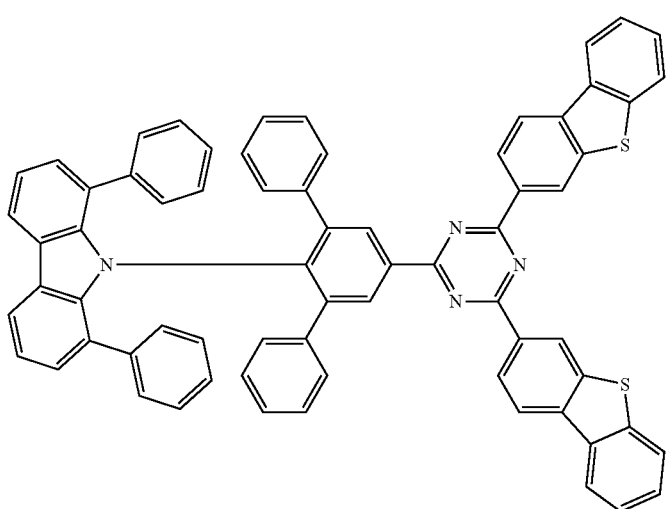
381
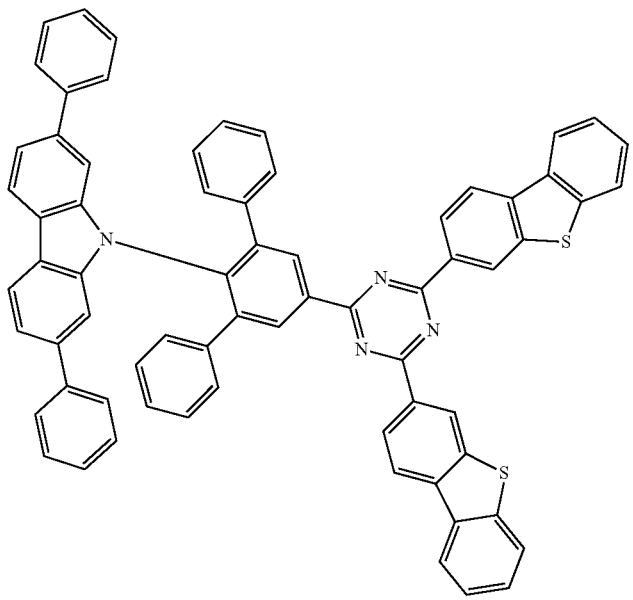

382
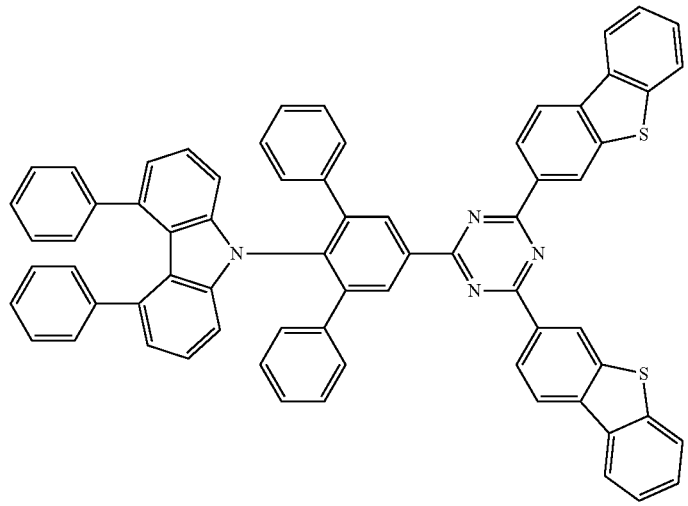
383
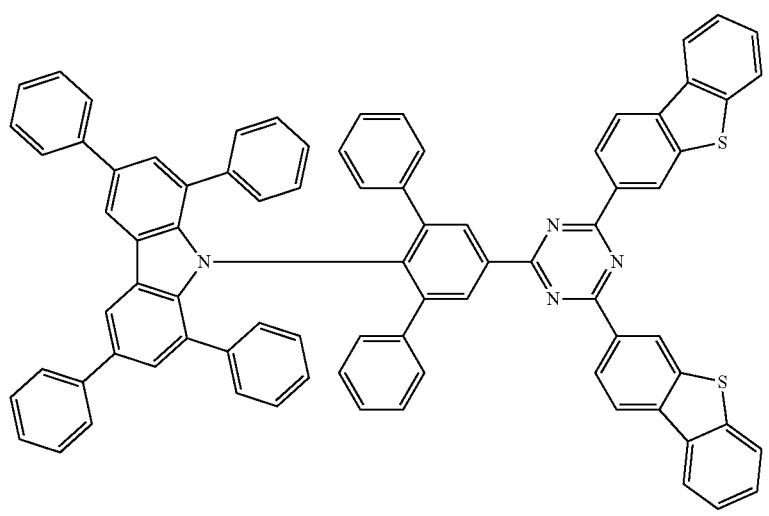
384
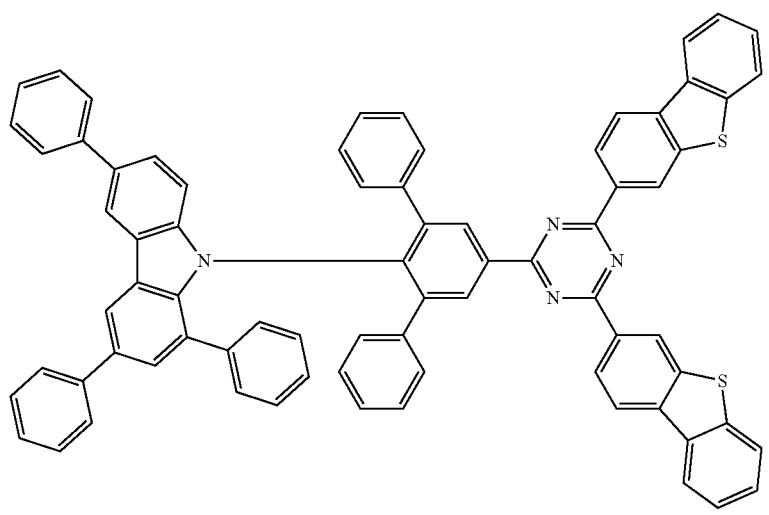

385
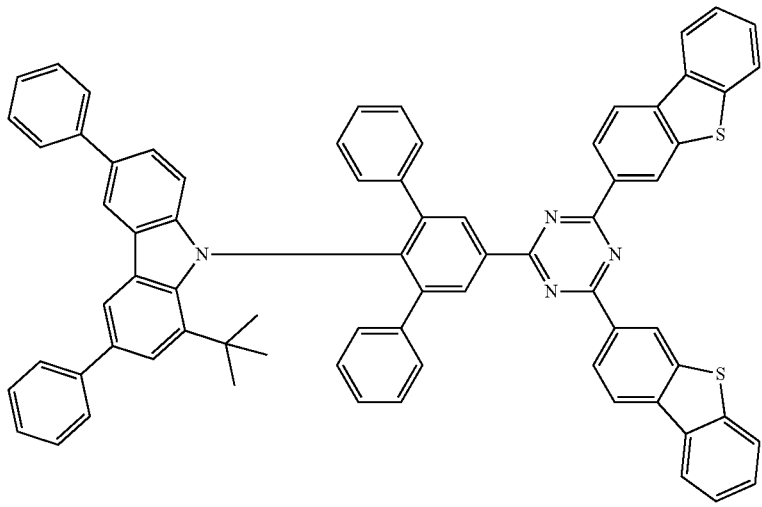
386
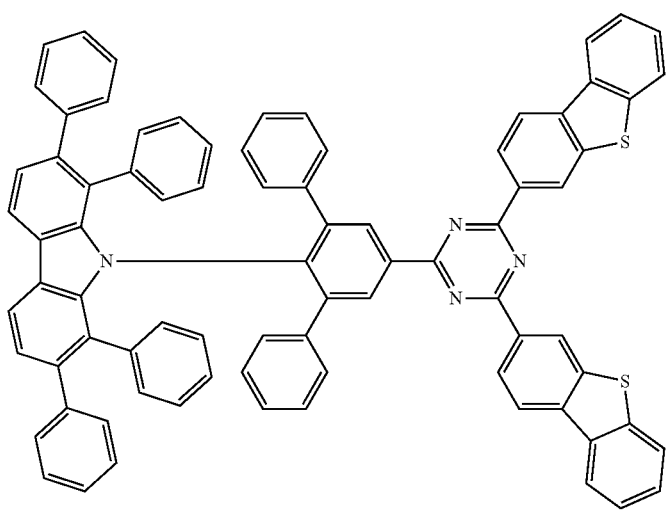
387
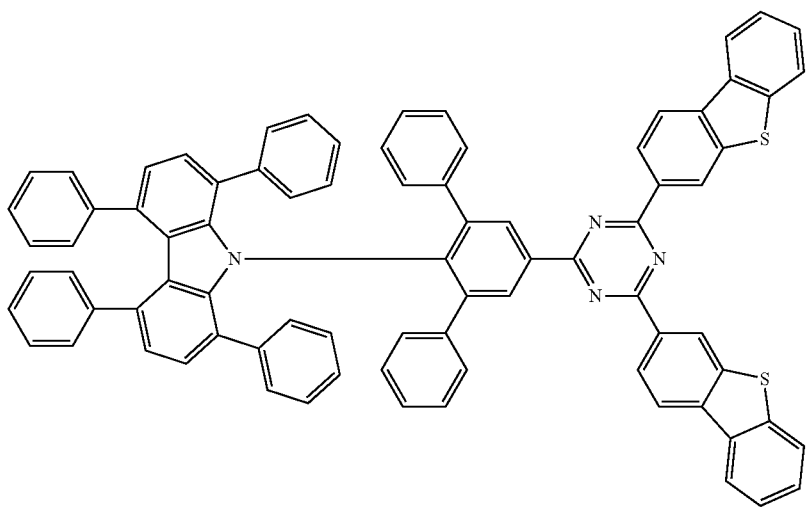

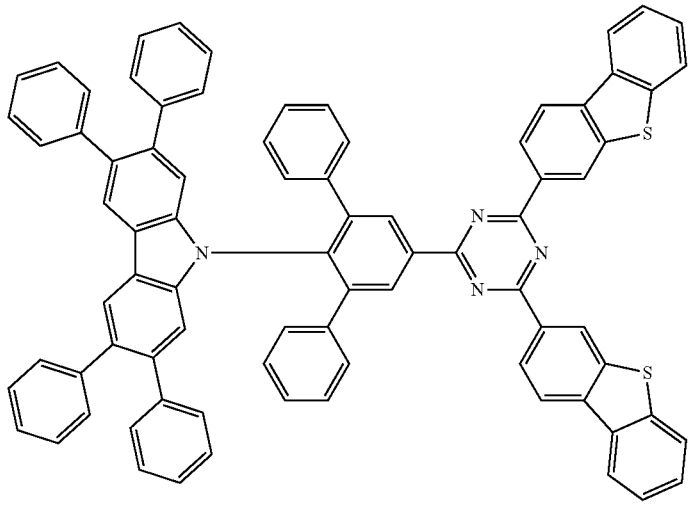
388
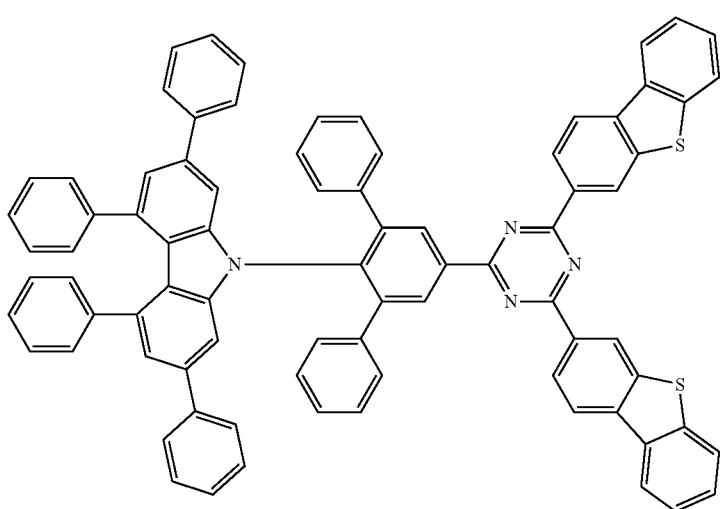
389
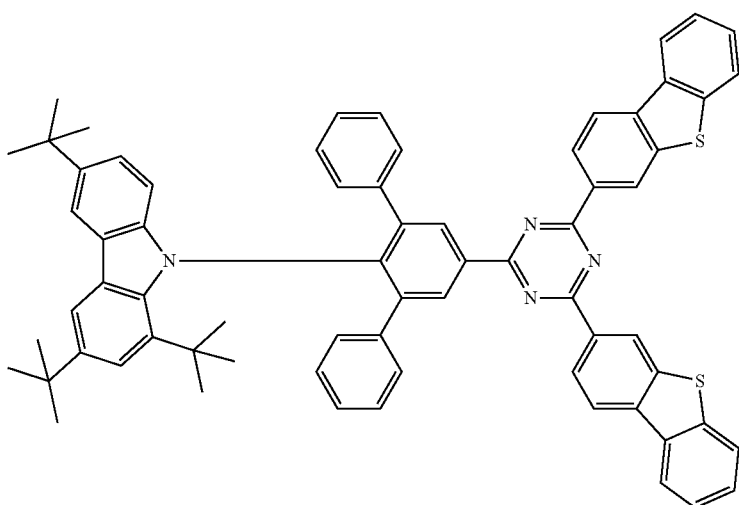
390

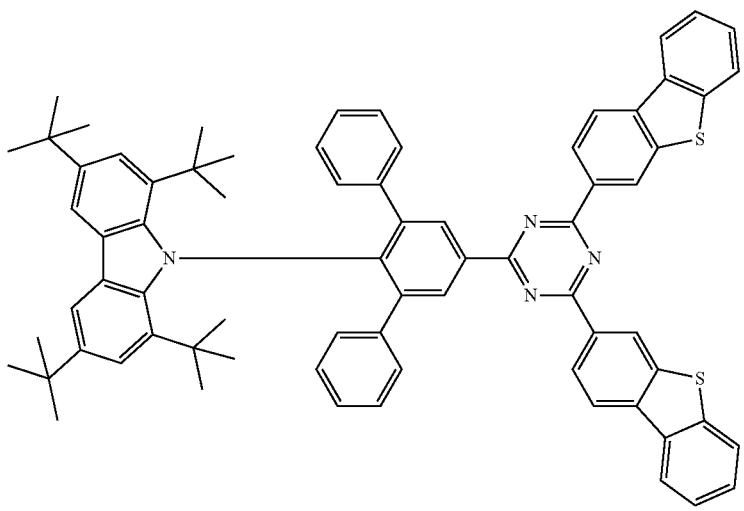
391
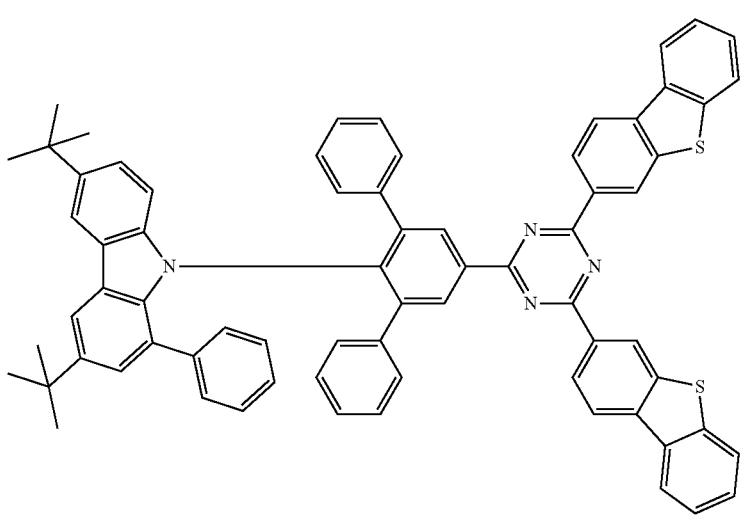
392
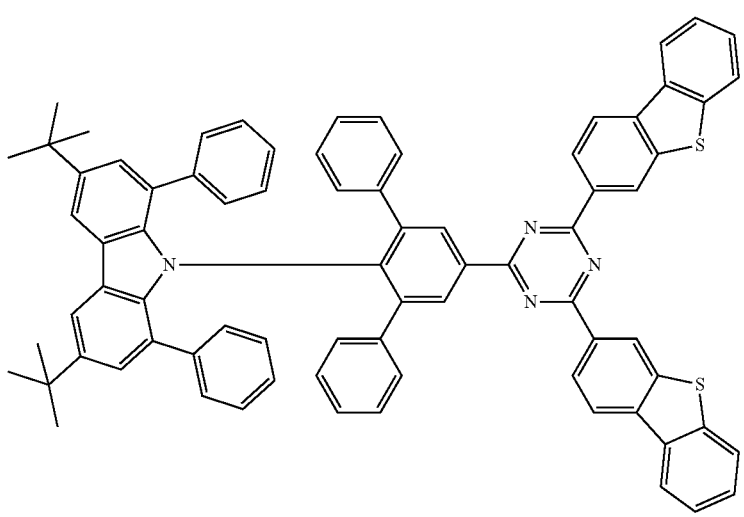
393

394
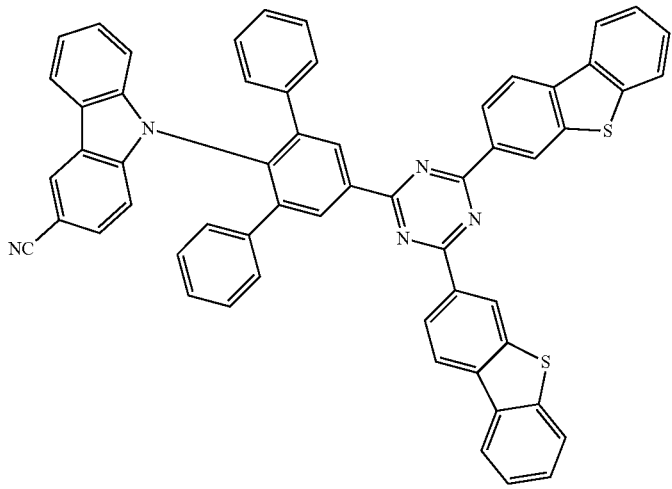
395
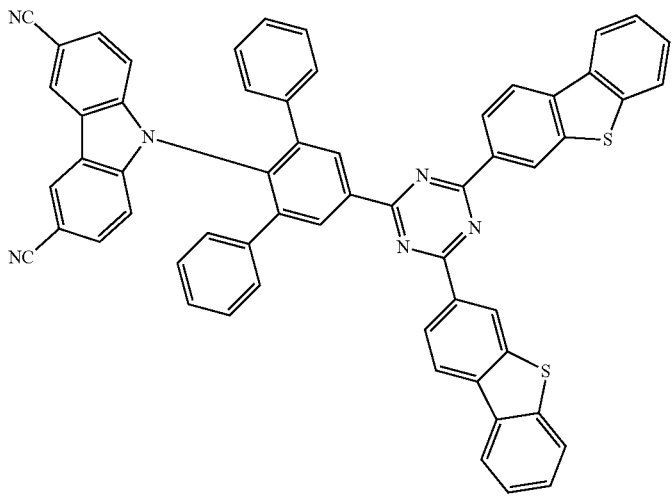
396
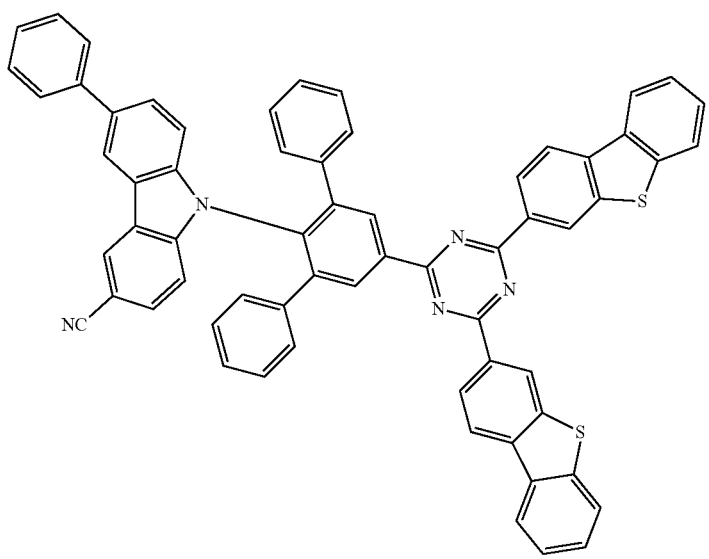

-continued
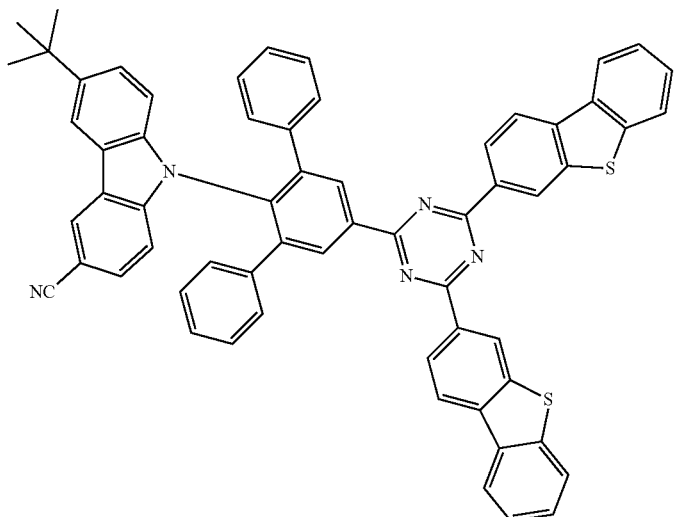
397
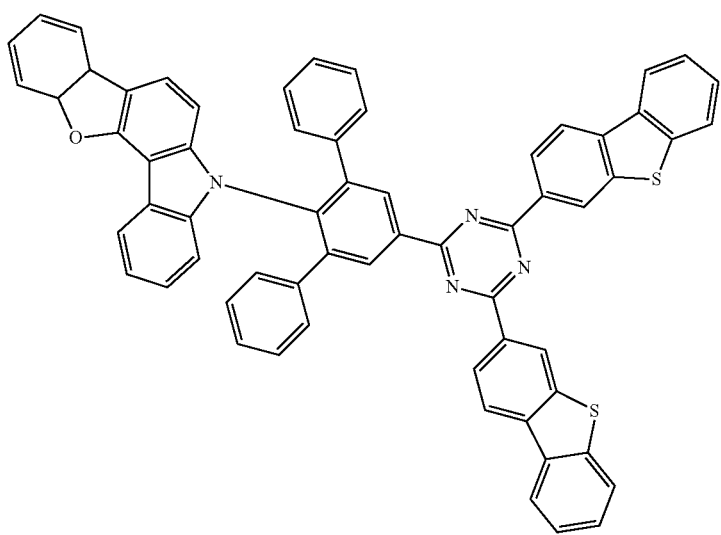
398
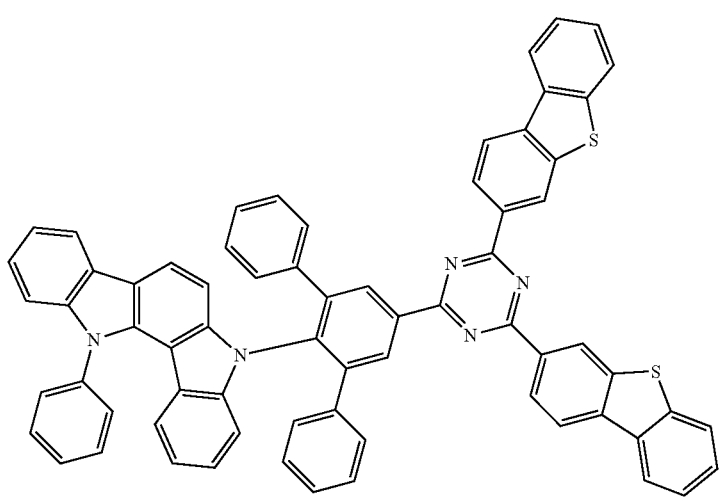
399

-continued
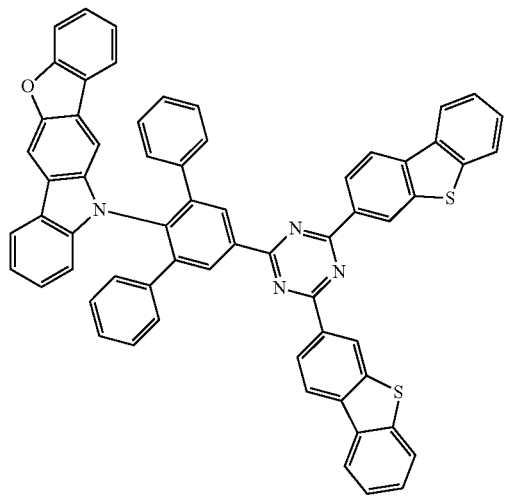
400
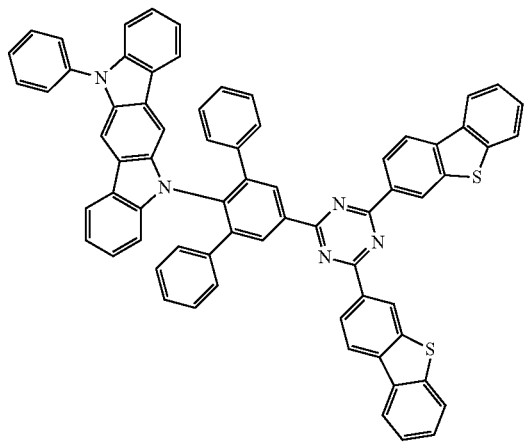
401
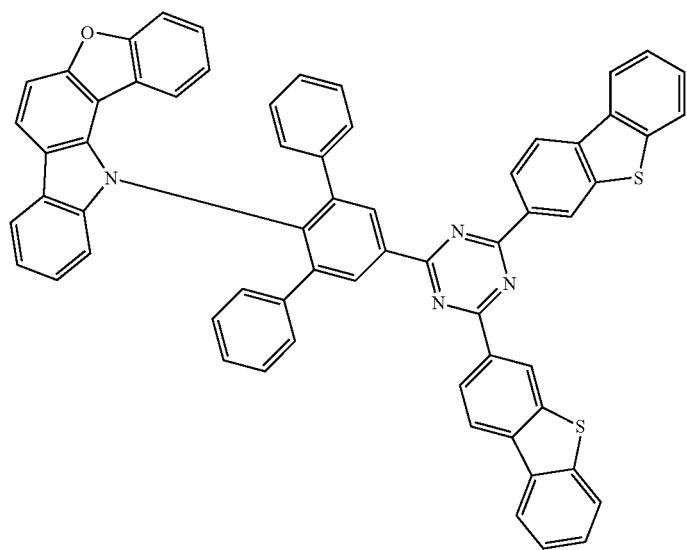
402
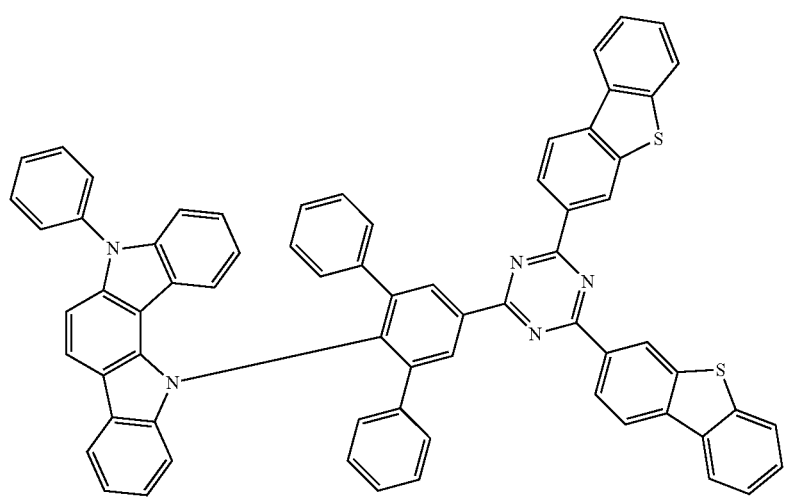
403

404
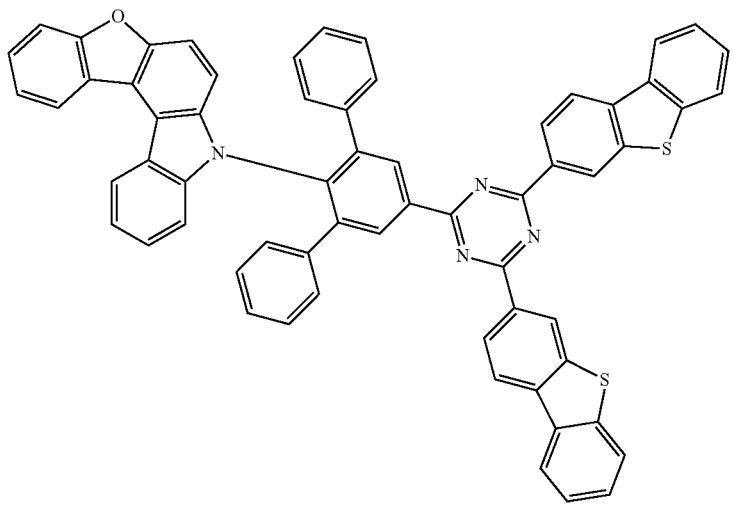
405
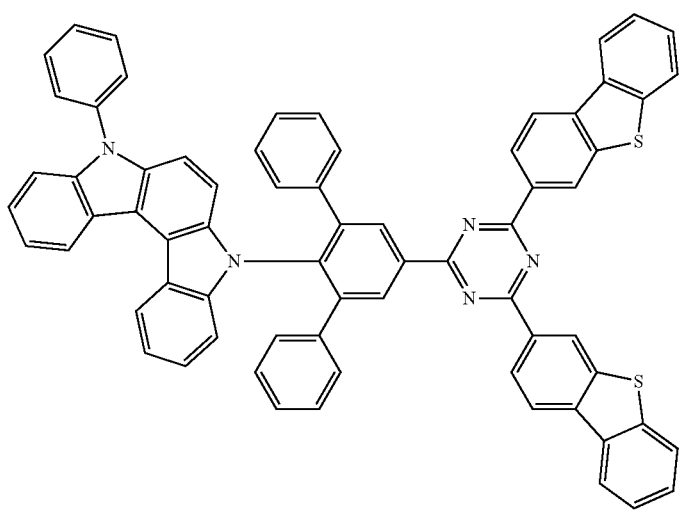
406
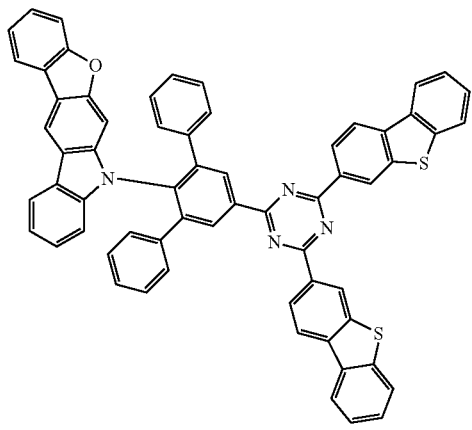
407
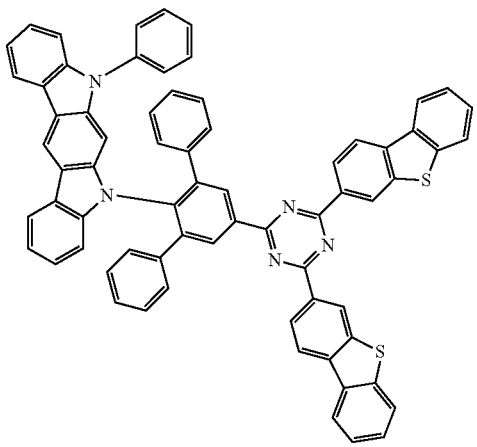

408
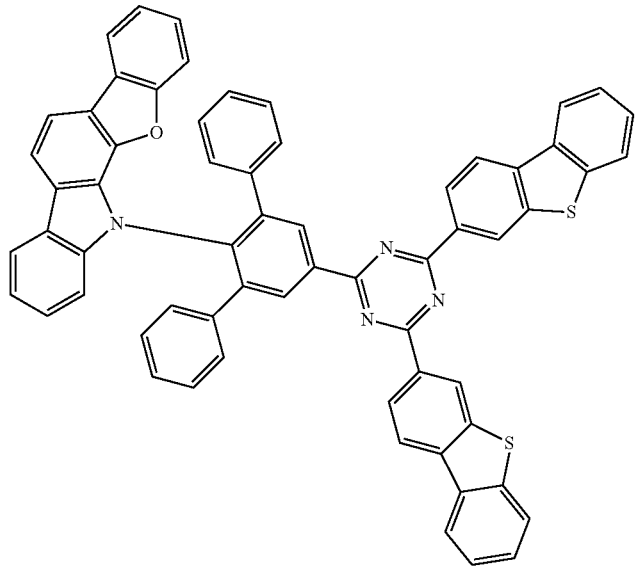
409
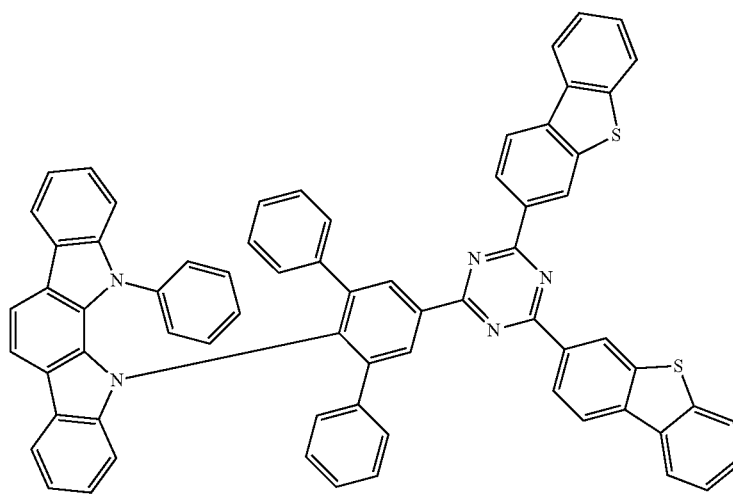
410
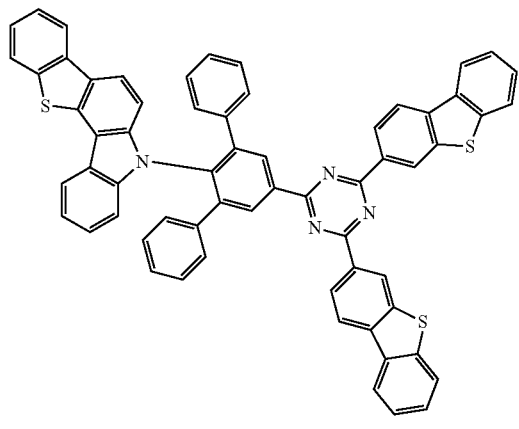
411
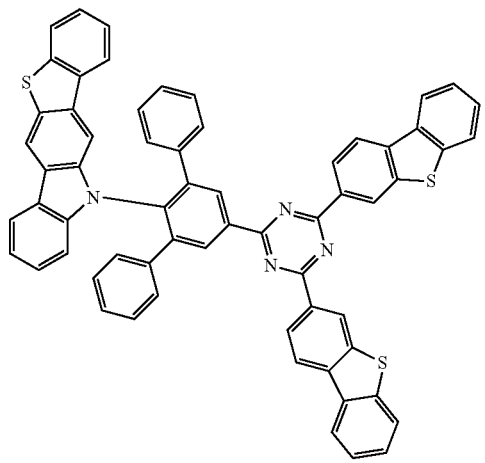

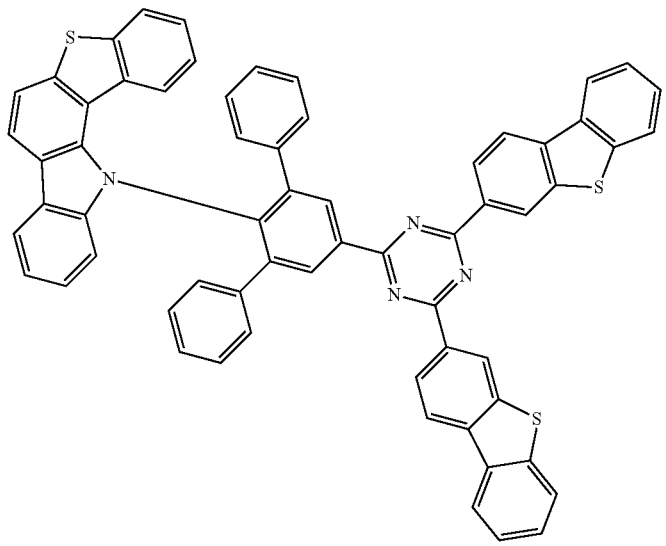
412
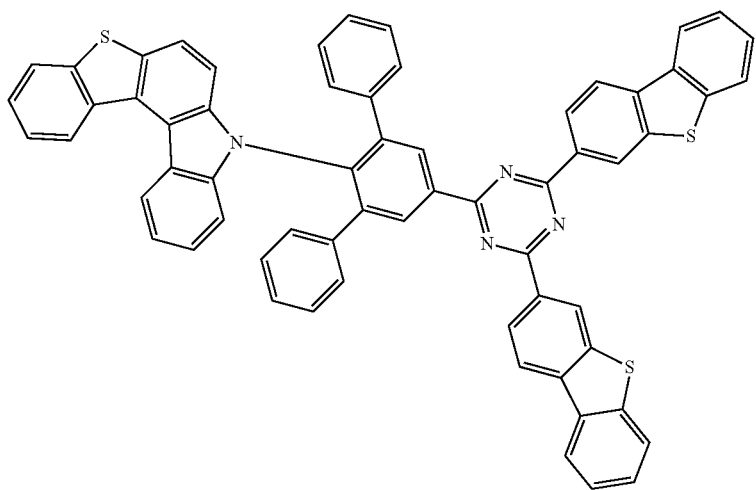
413
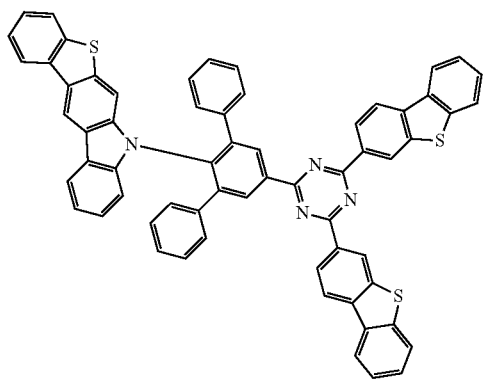
414
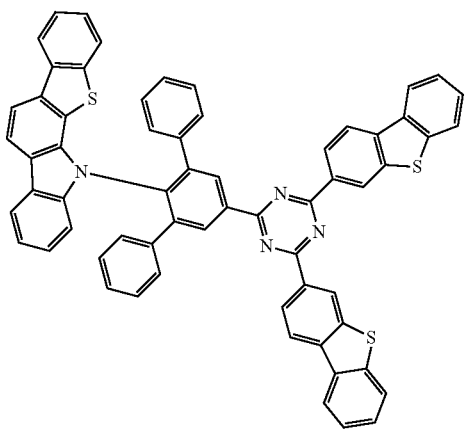
415

-continued
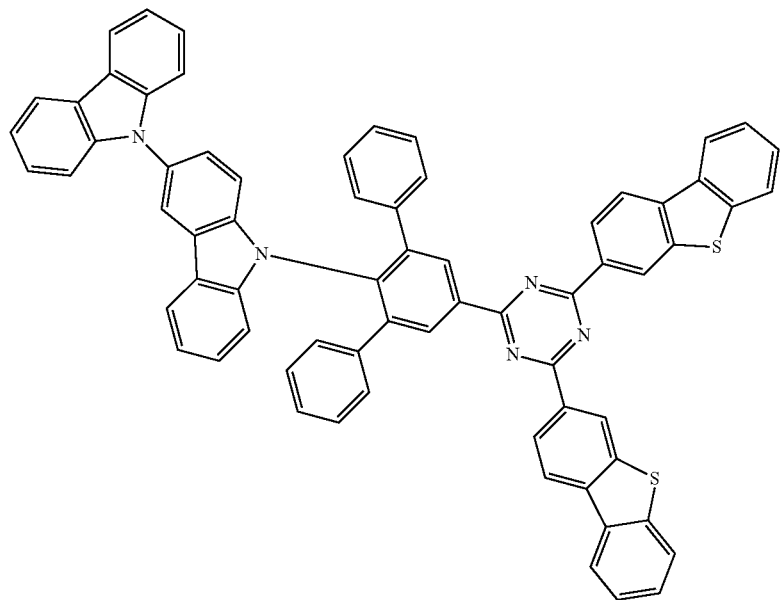
416
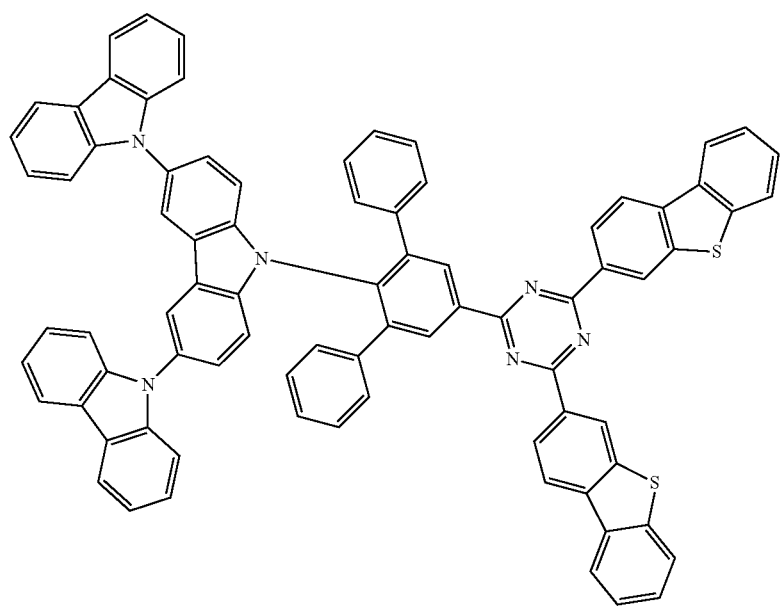
417

-continued
418
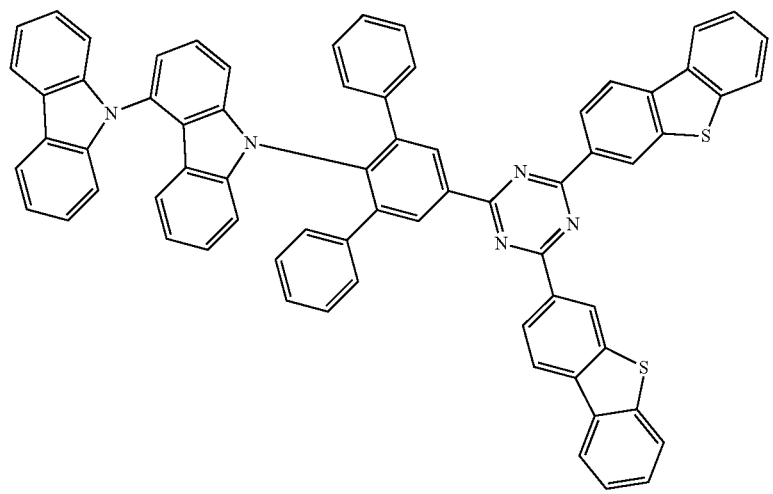
419
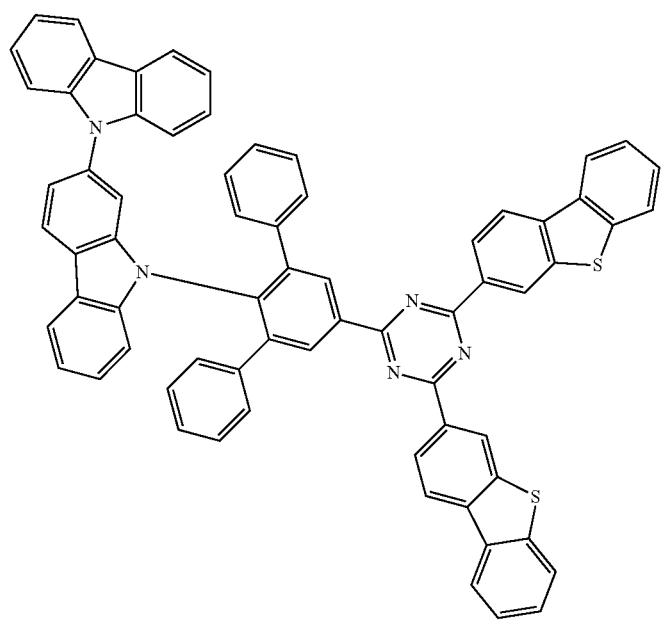

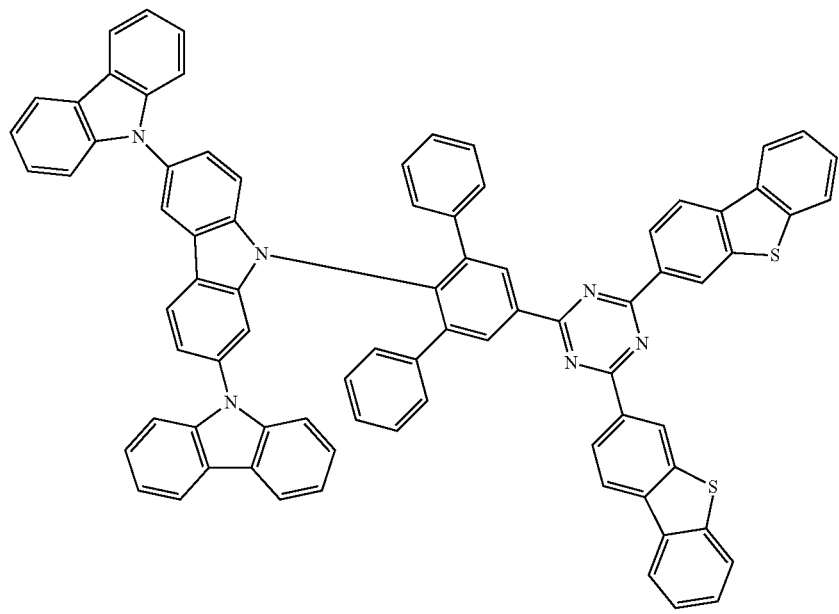
420
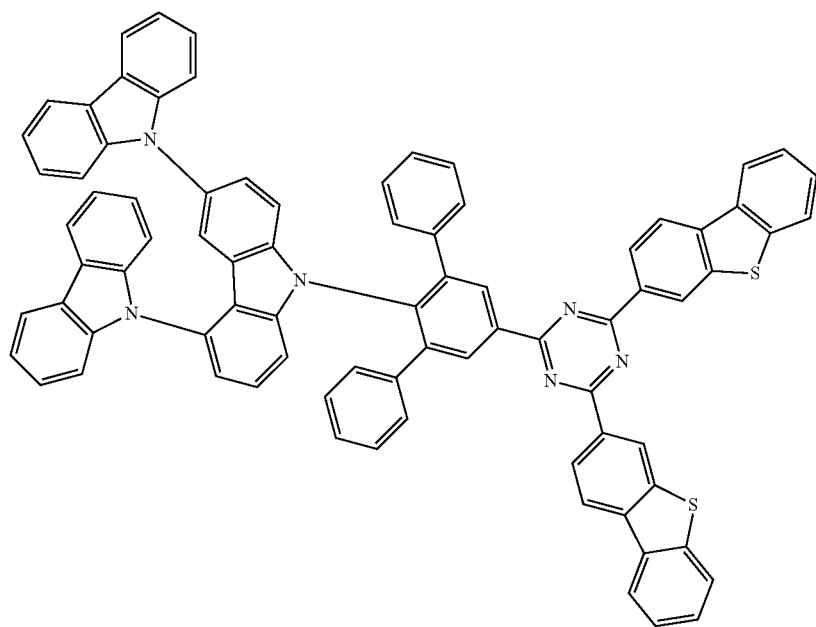
421

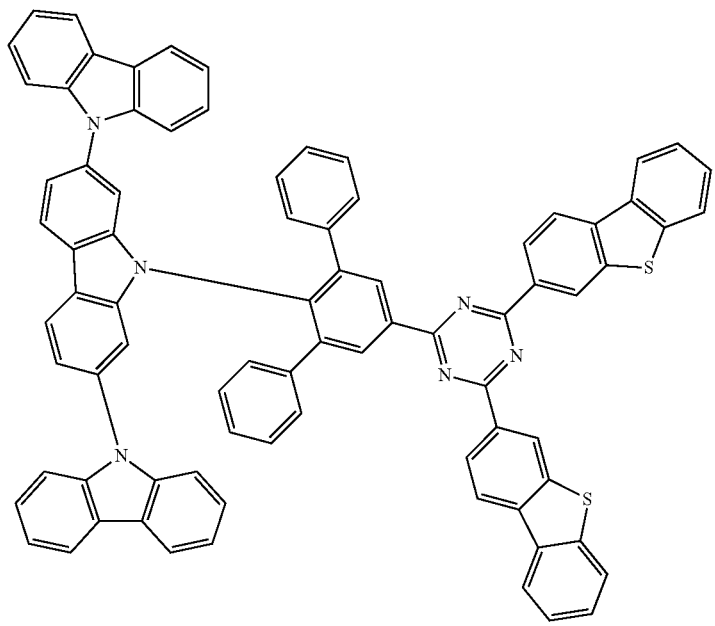
422
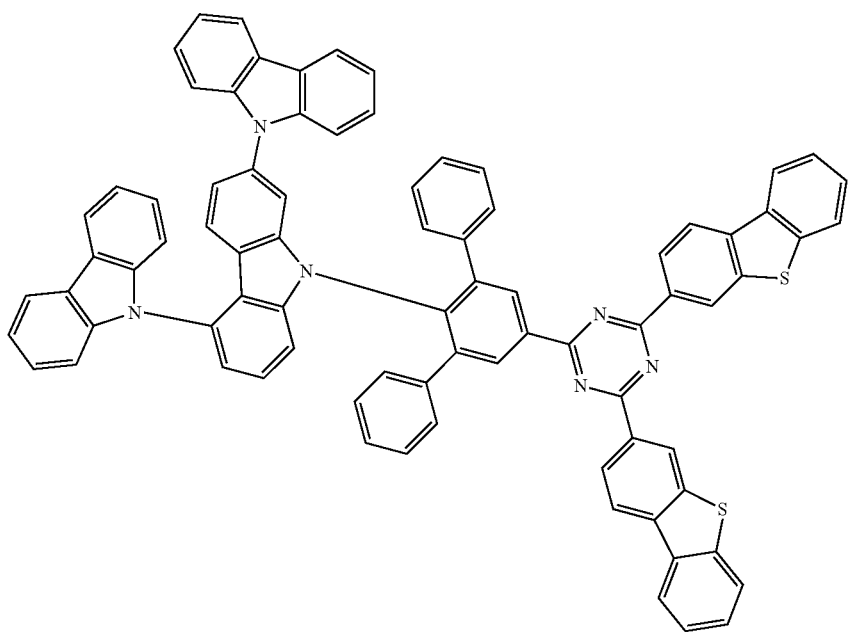
423

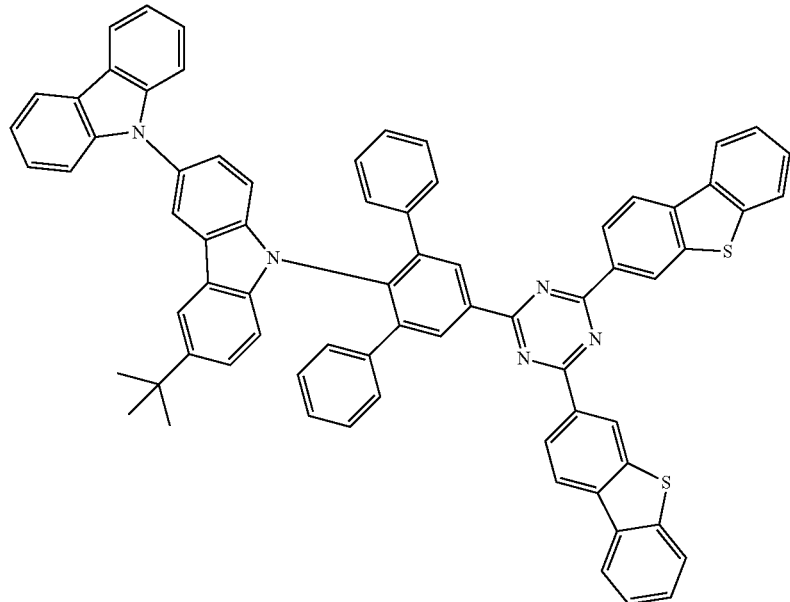
424
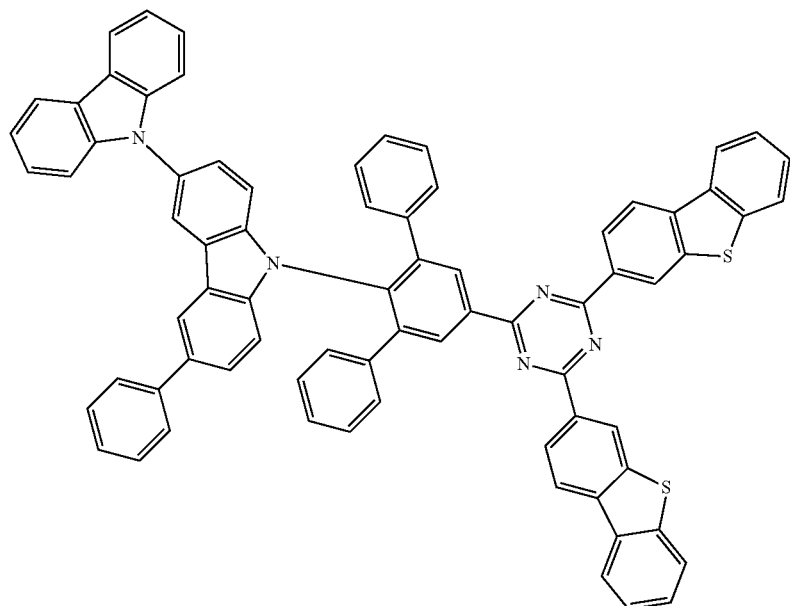
425

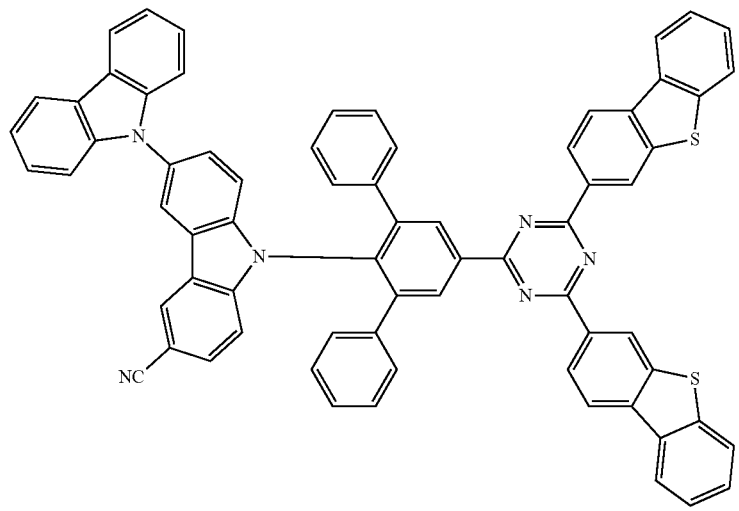
426
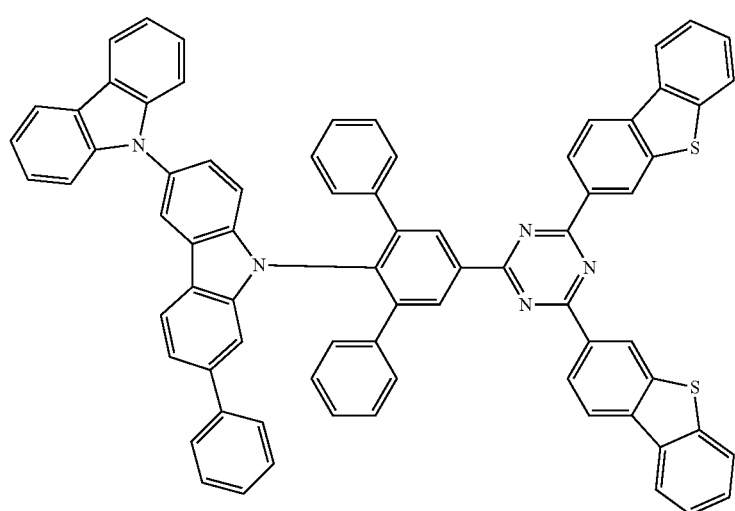
427
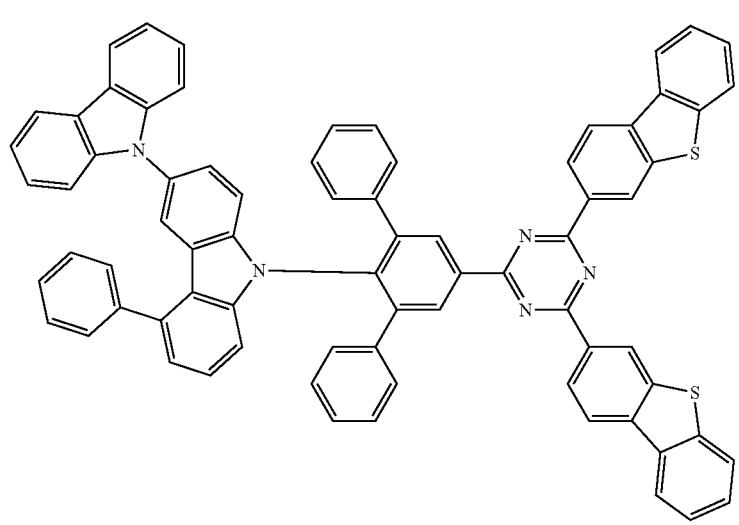
428

-continued
429
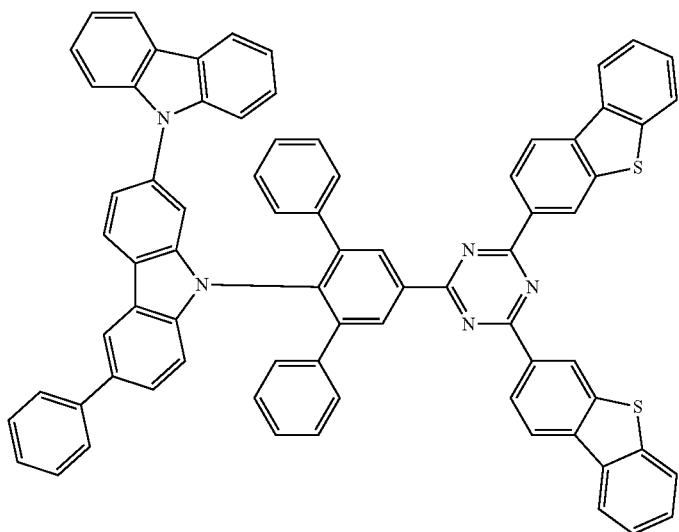
430
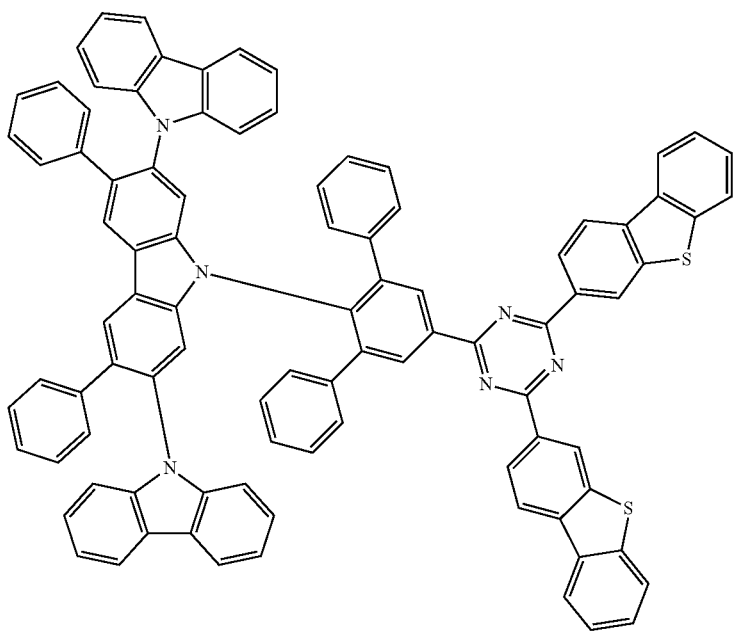

431
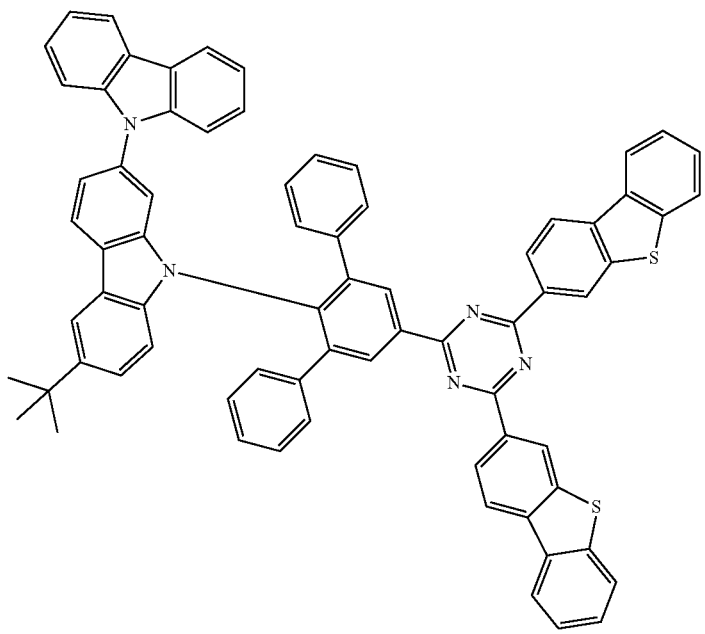
432
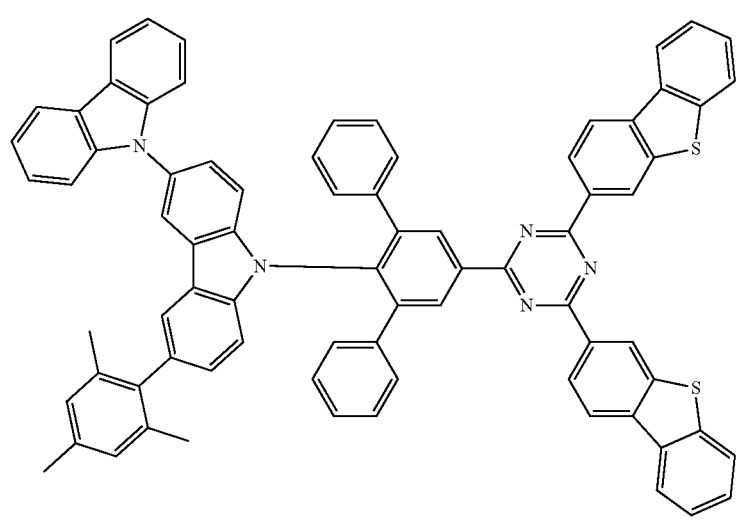

-continued
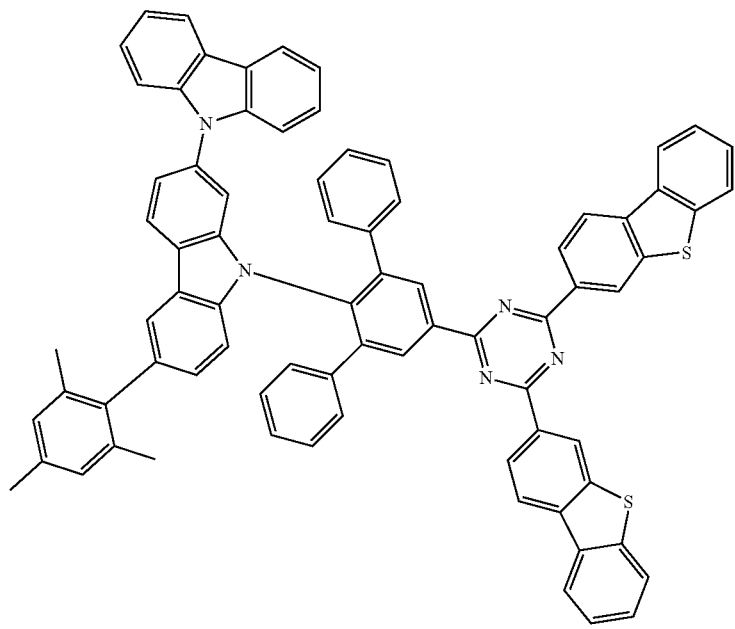
433
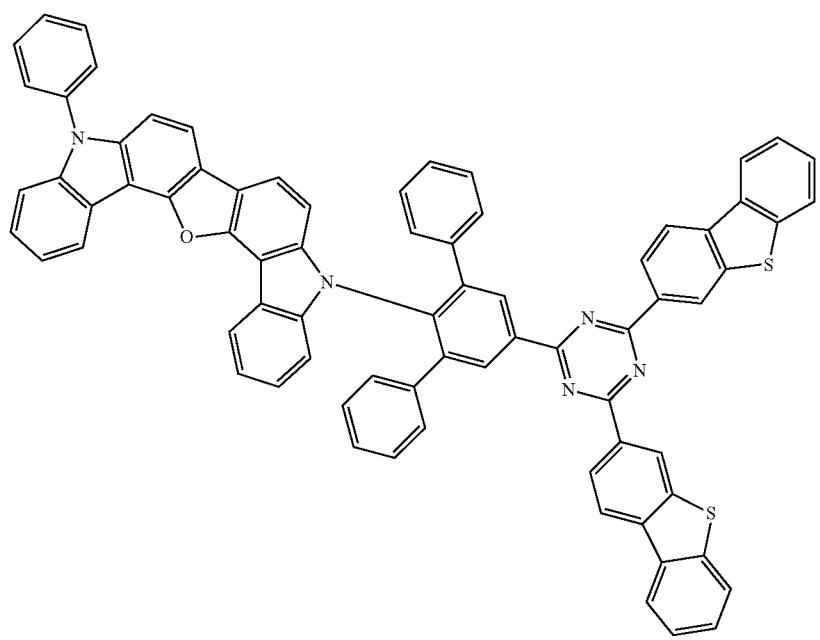
434

-continued
435
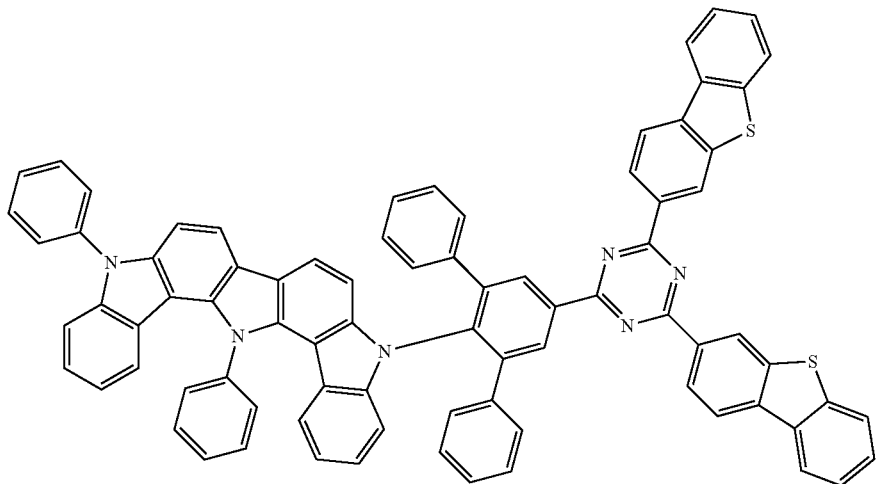
436
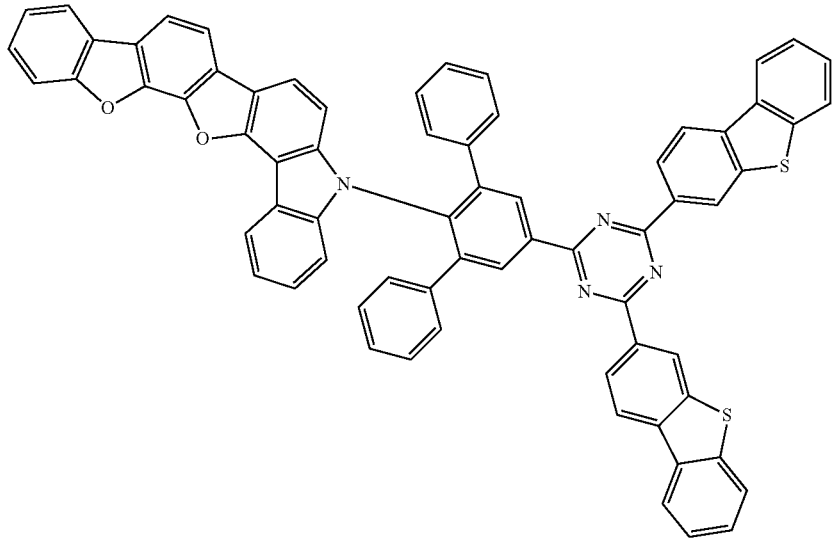
437
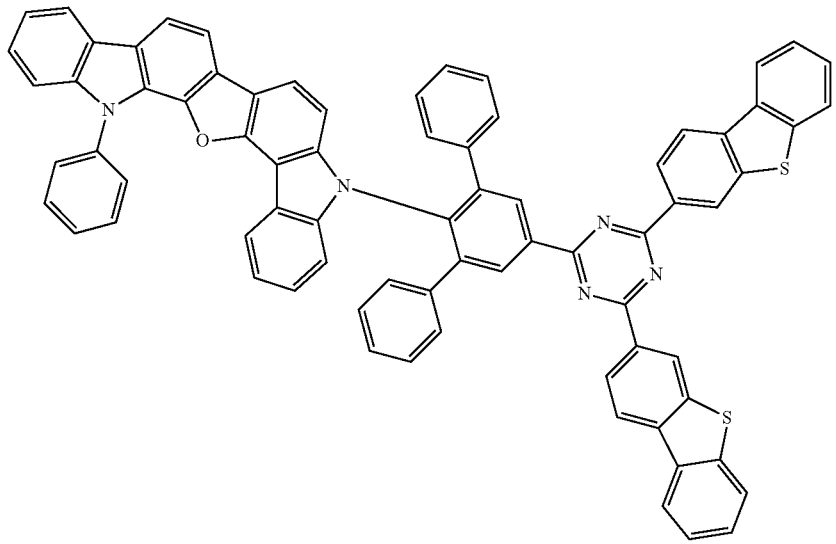

-continued
438
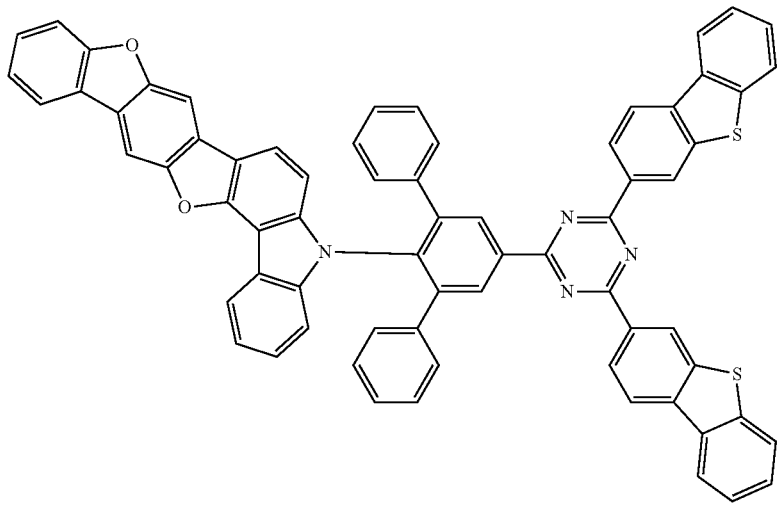
439
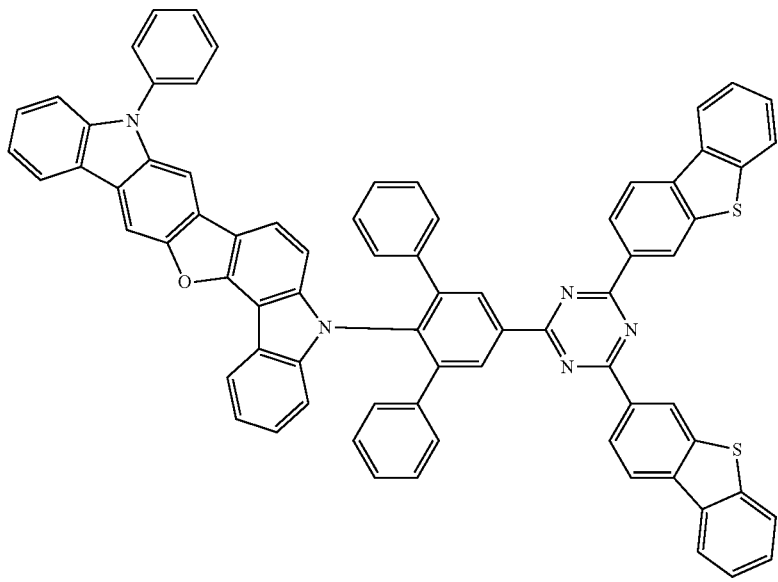
440
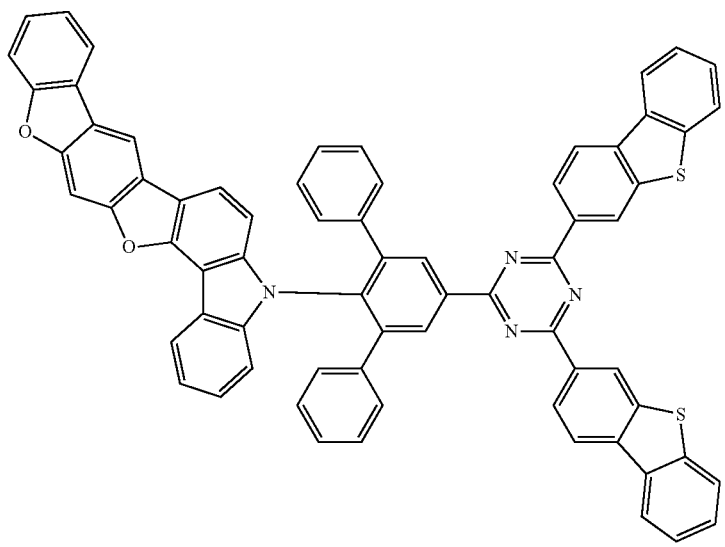

441
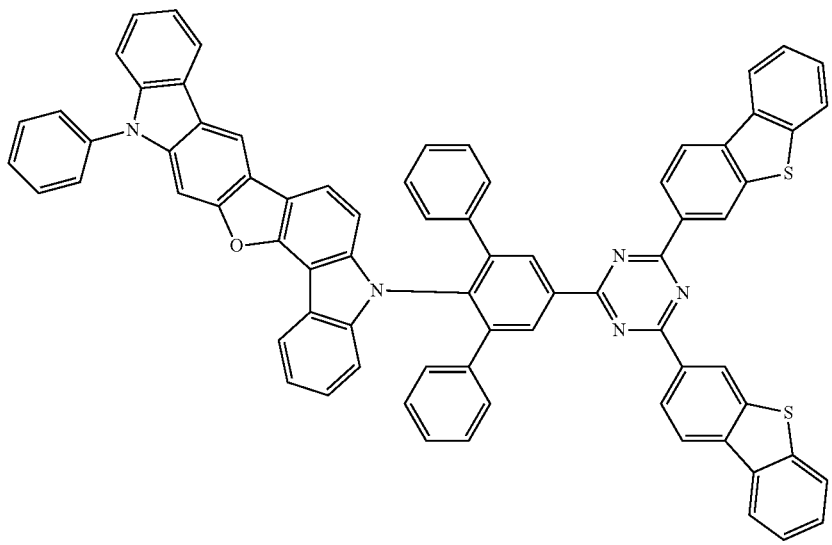
442
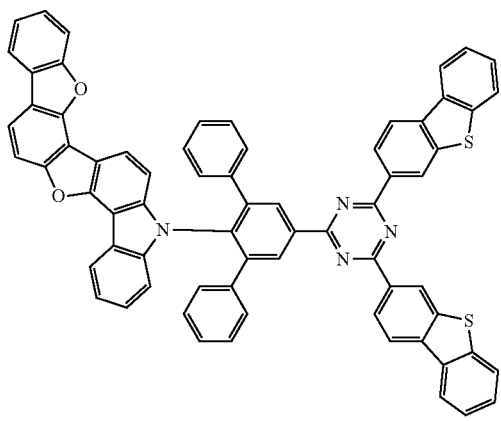
443
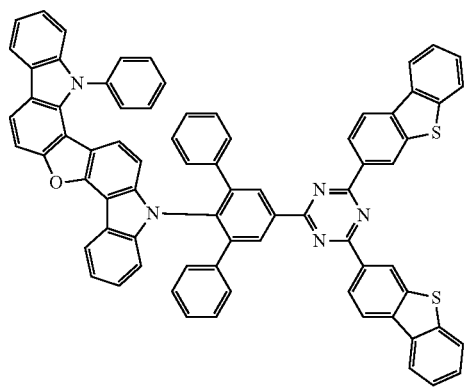
444
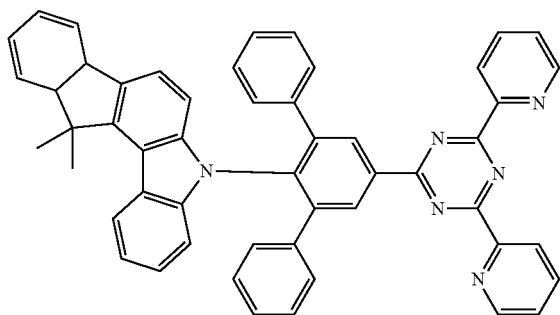

-continued
445
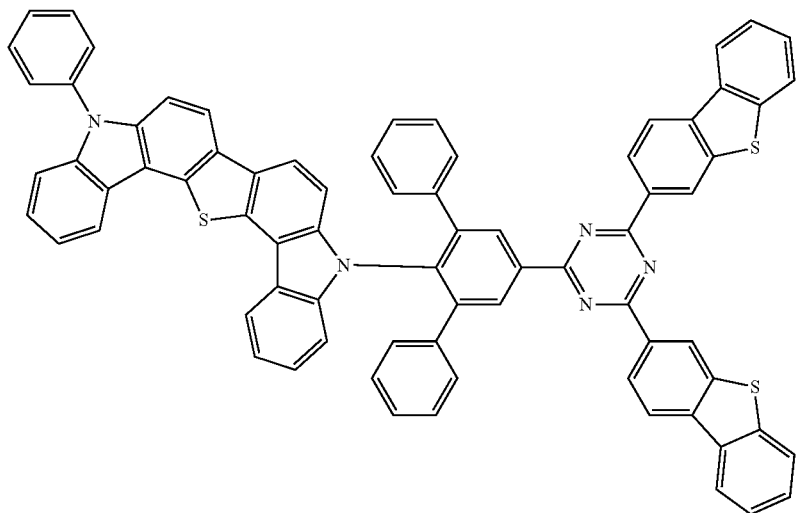
446
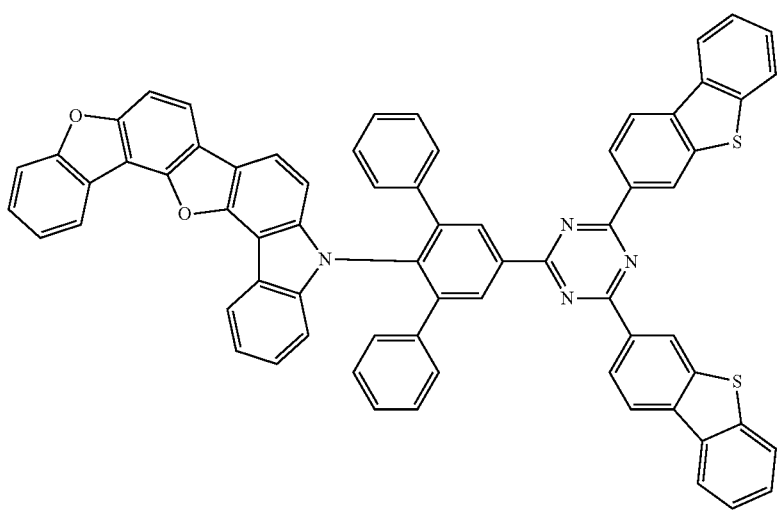
447
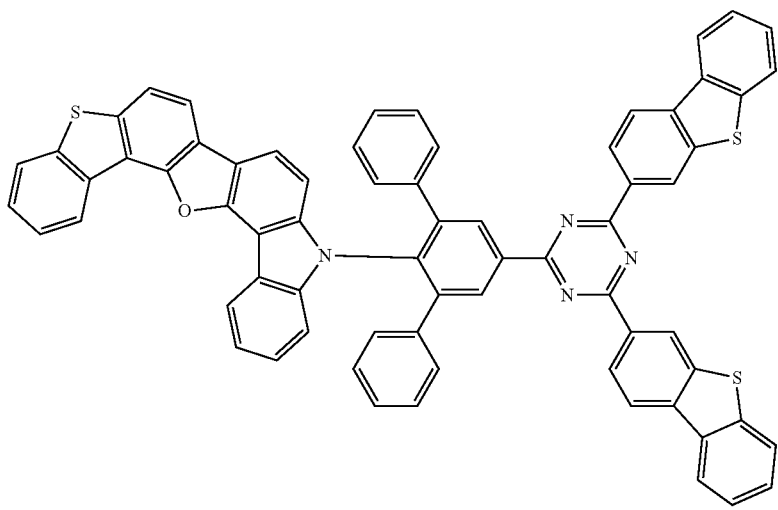

448
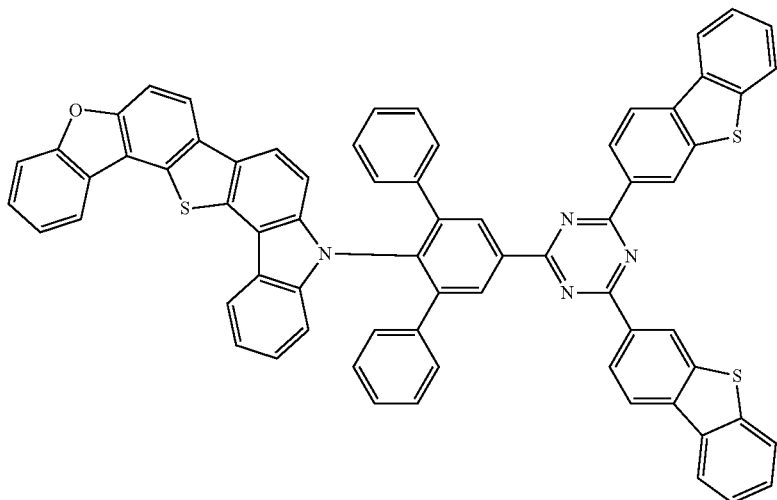
449
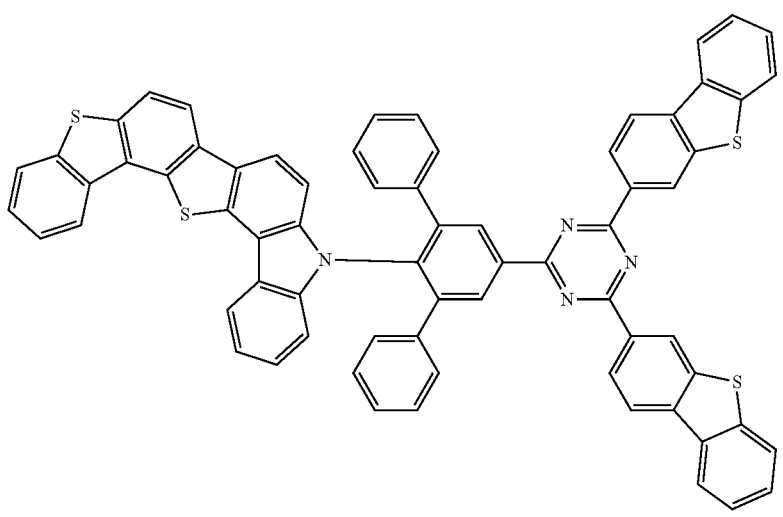
450
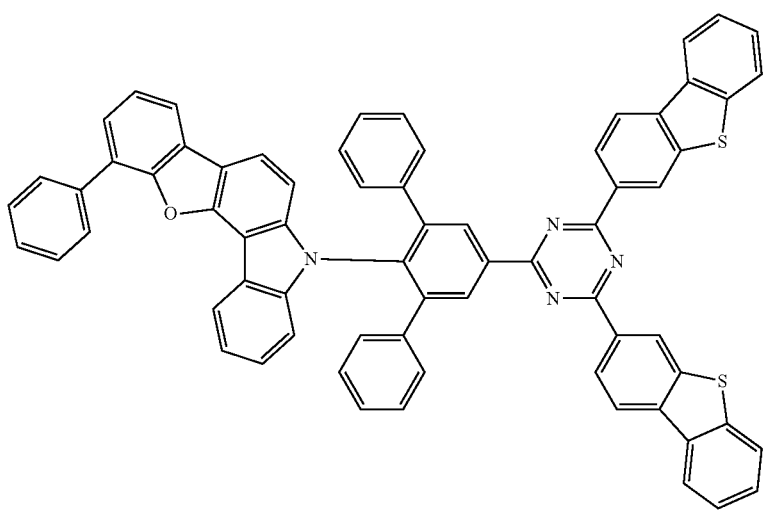

-continued
| 451 | 452 |
|---|---|
| 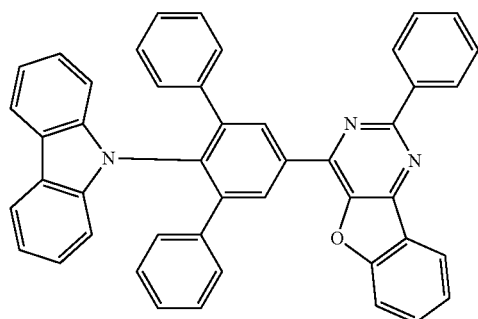 | 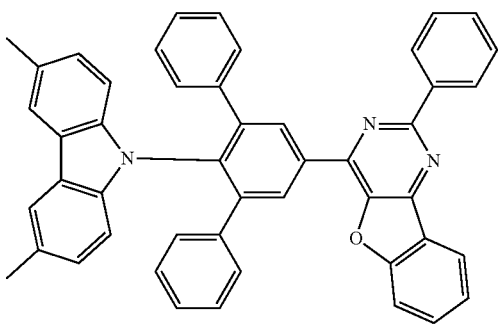 |
| 453 | 454 |
| 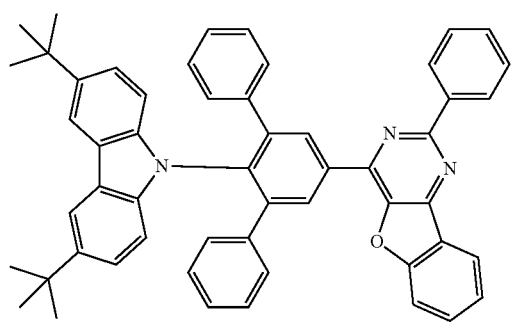 | 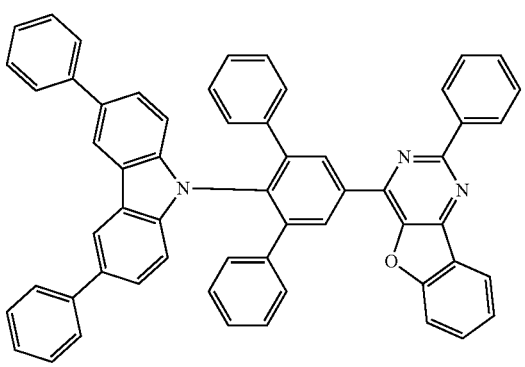 |
| 455 | 456 |
| 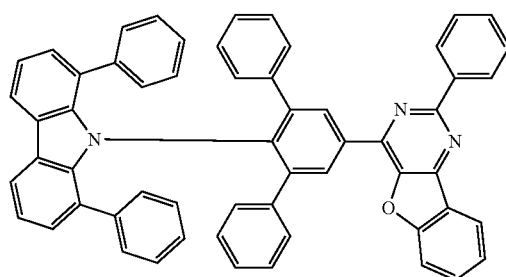 | 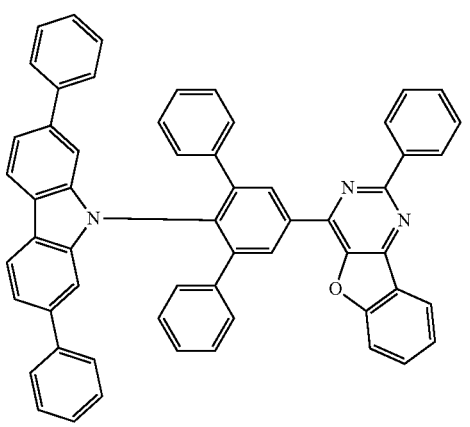 |
| 457 | 458 |
| 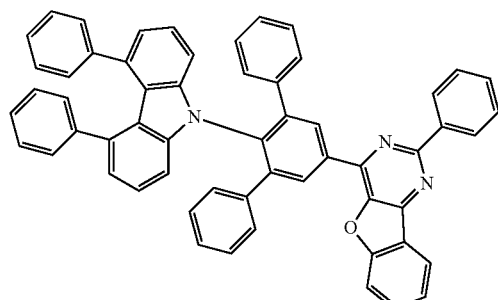 | 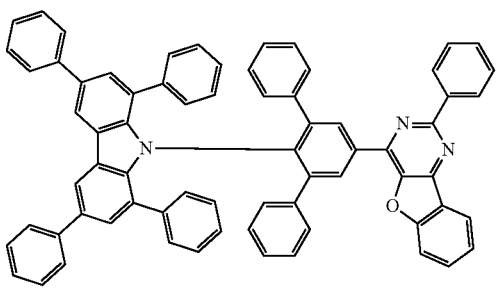 |

-continued
459
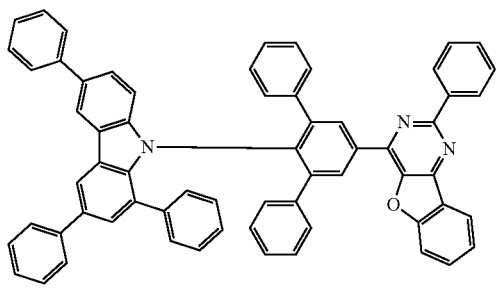
460
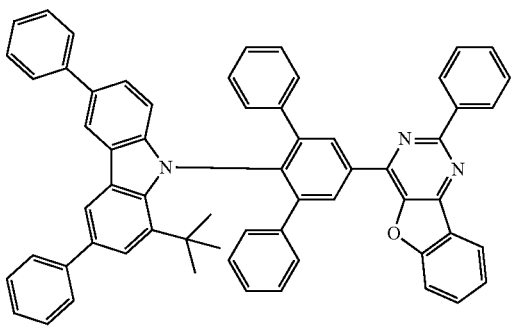
461
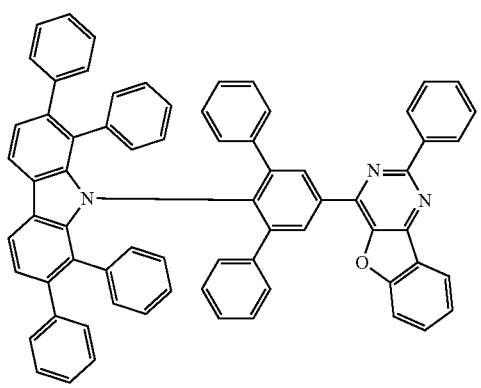
462
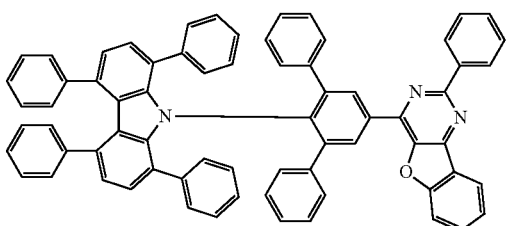
463
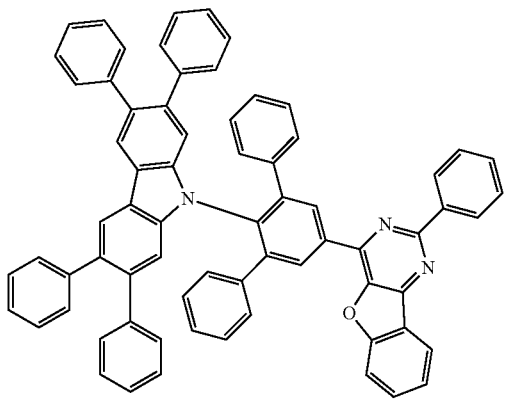
464
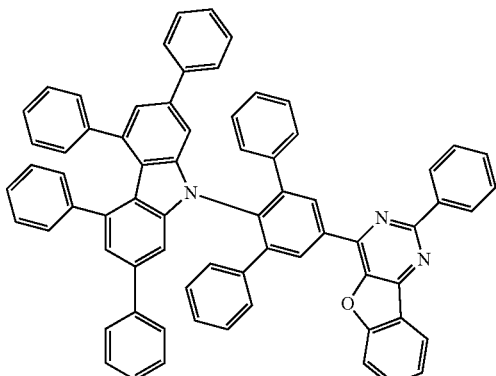
465
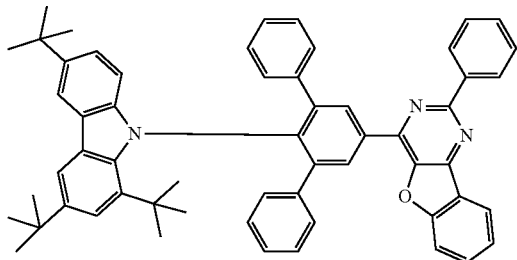
466
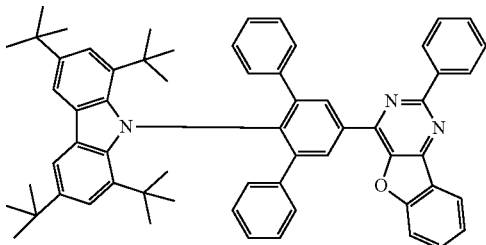

-continued
211 | 212
467 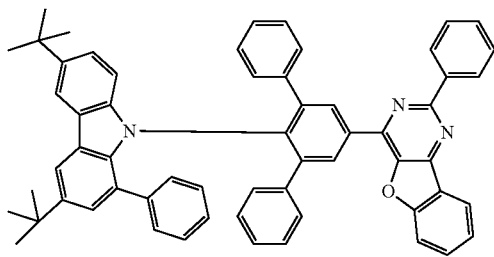 | 468 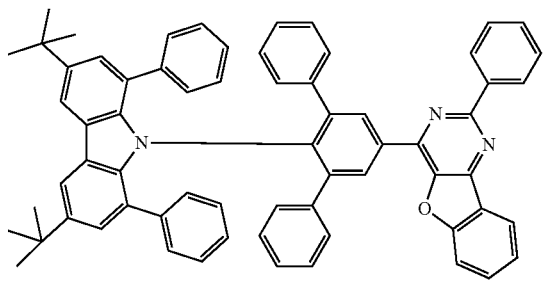
469 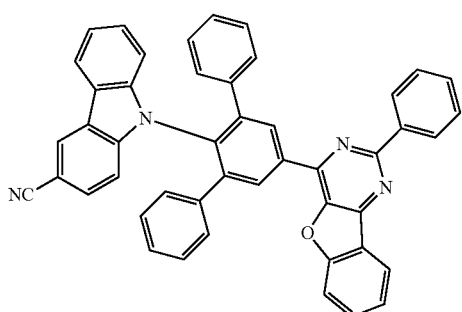 | 470 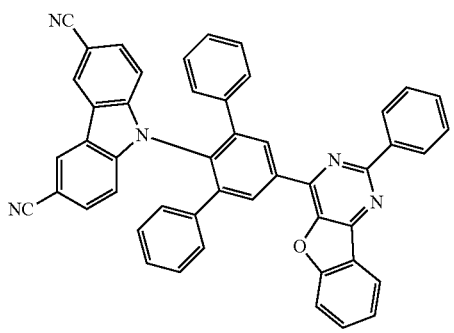
471 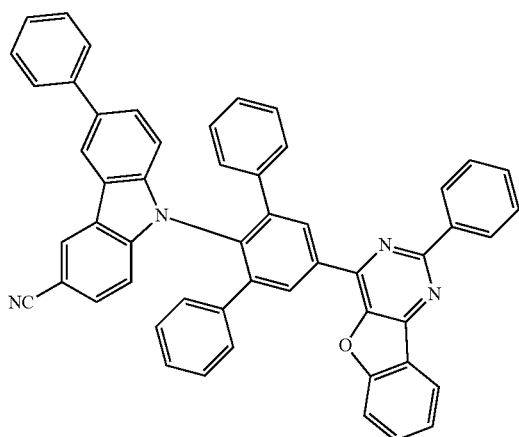 | 472 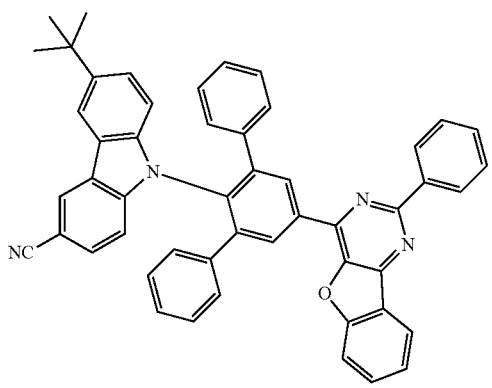
473 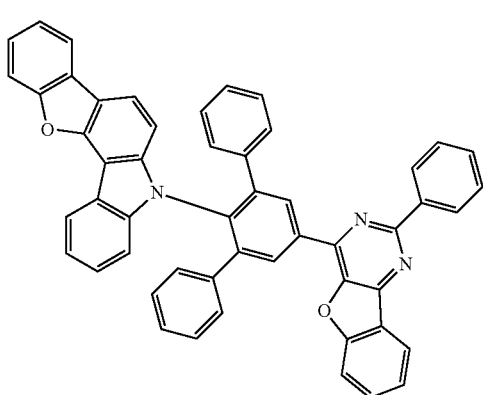 | 474 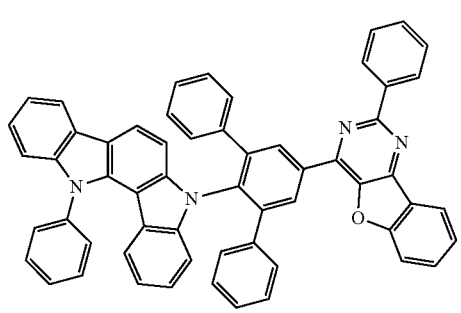

-continued
213     214
475
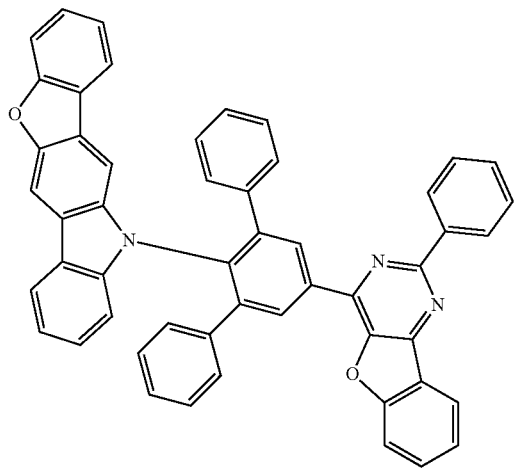
476
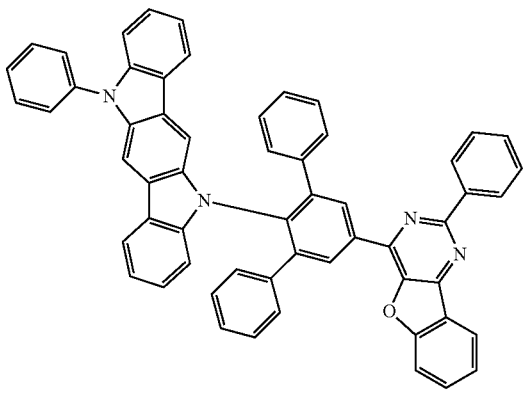
477
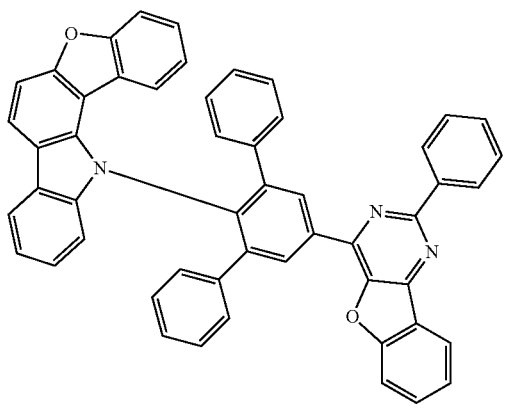
478
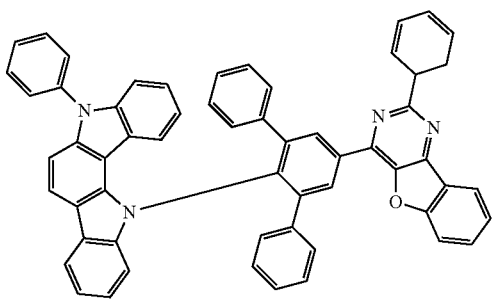
479
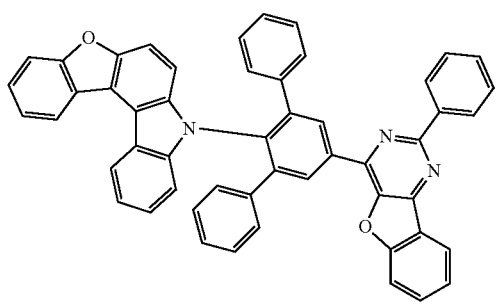
480
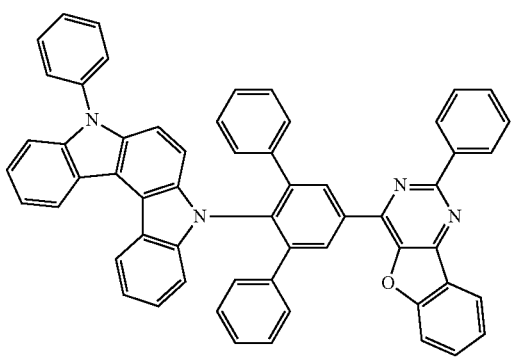

-continued
481
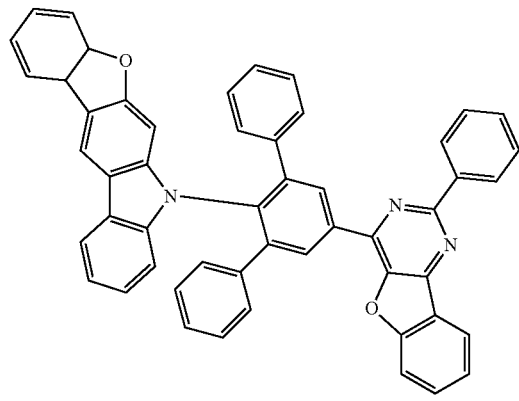
482
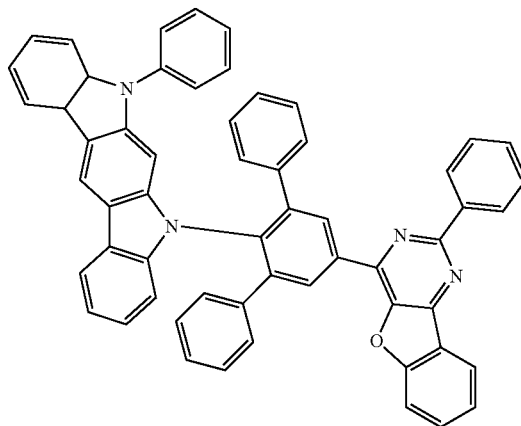
483
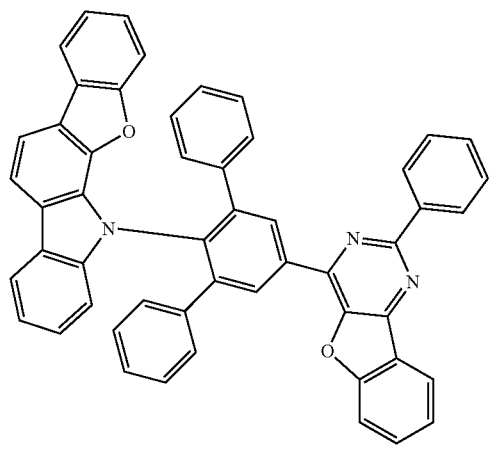
484
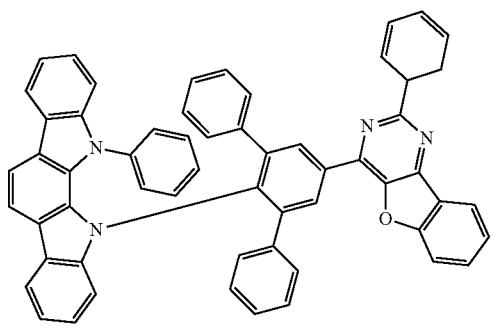
485
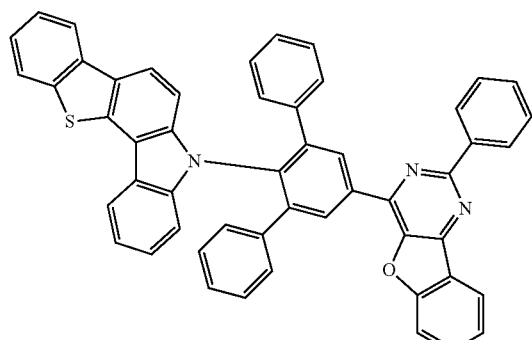
486
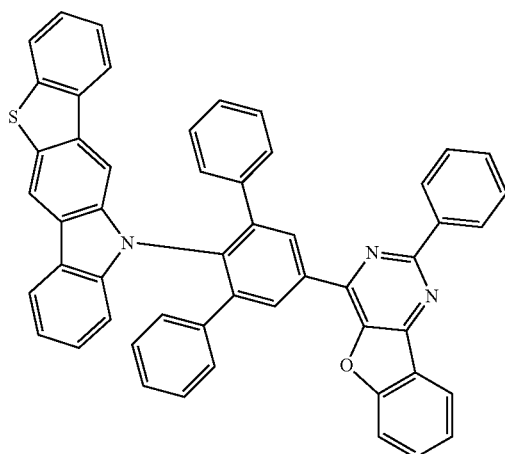

-continued
487
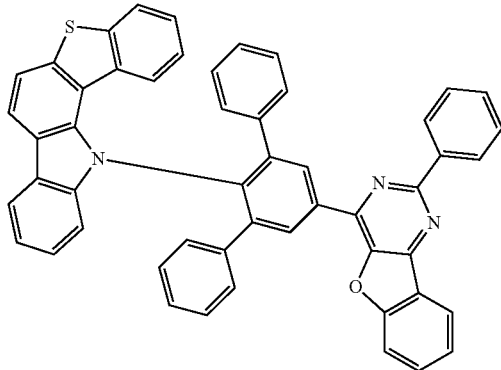
488
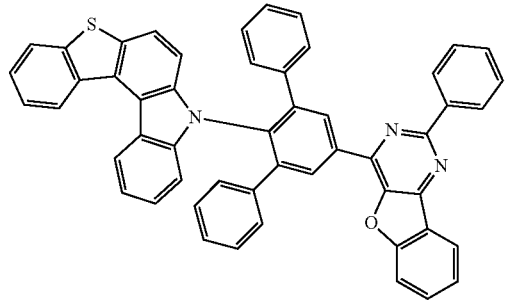
489
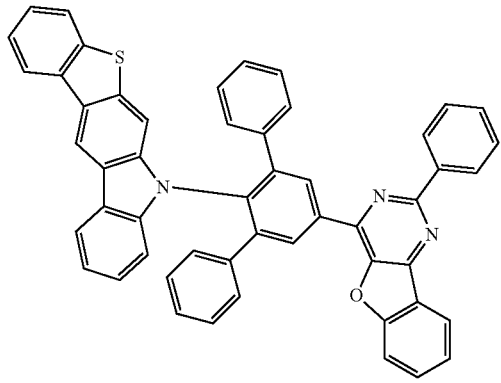
490
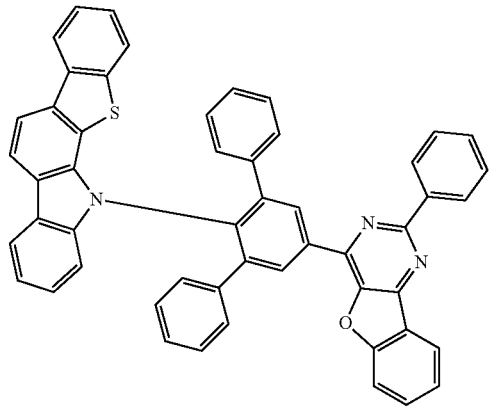
491
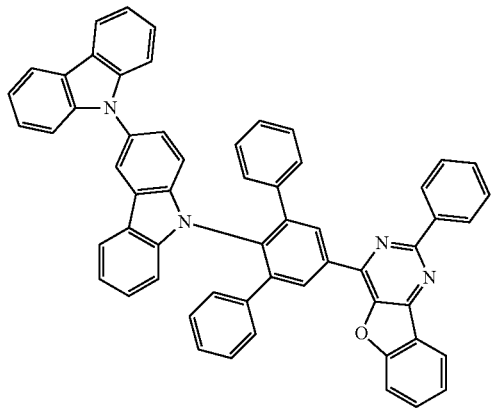
492
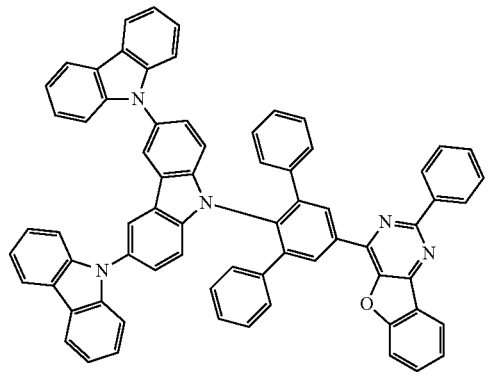

-continued
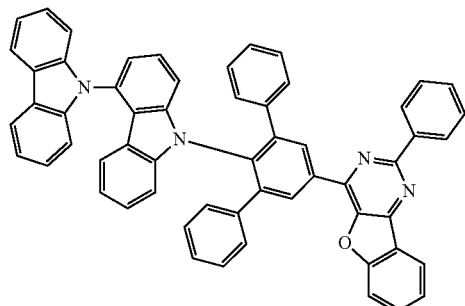
493
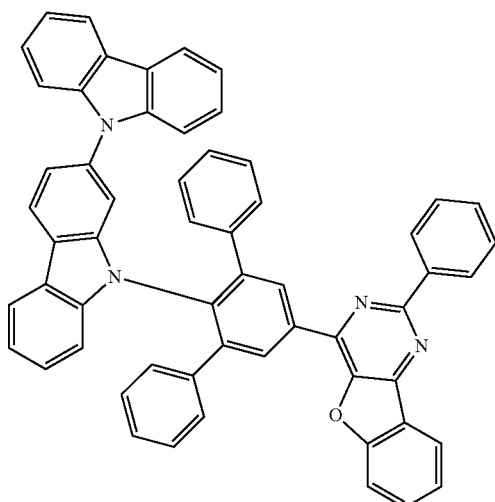
494
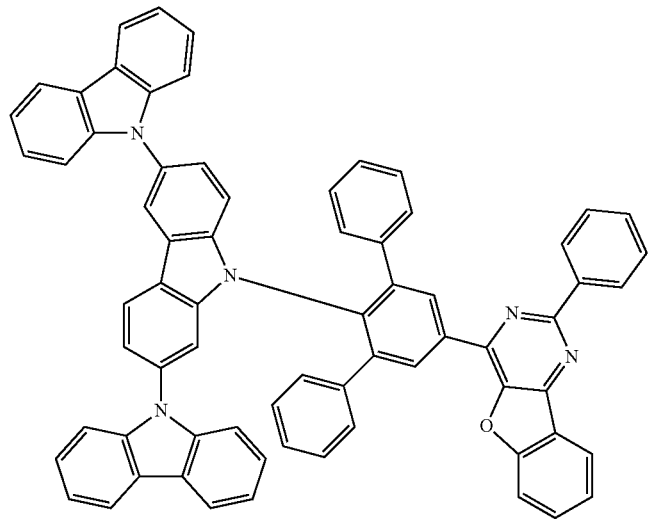
495
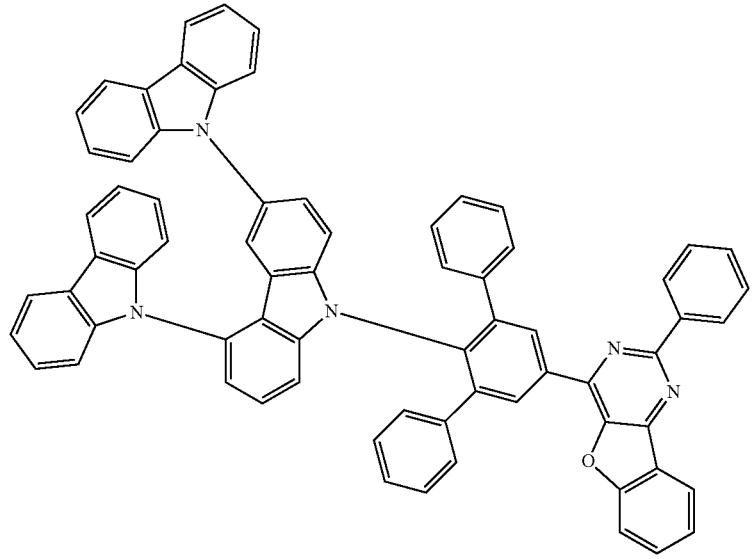
496

-continued
497
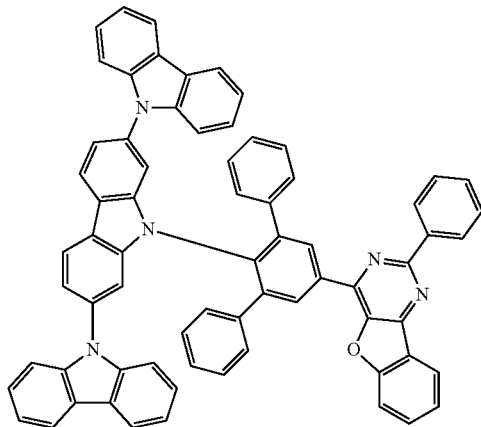
498
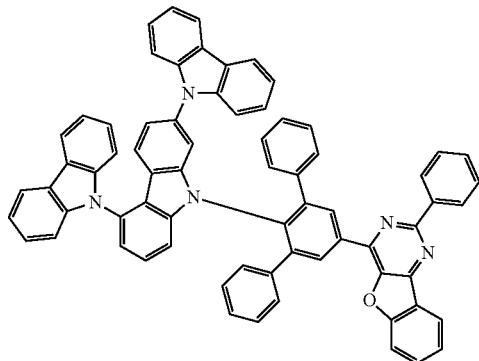
499
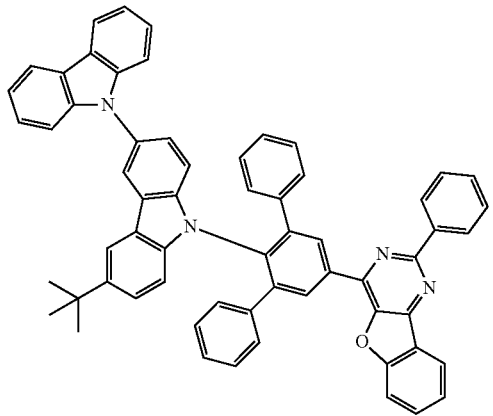
500
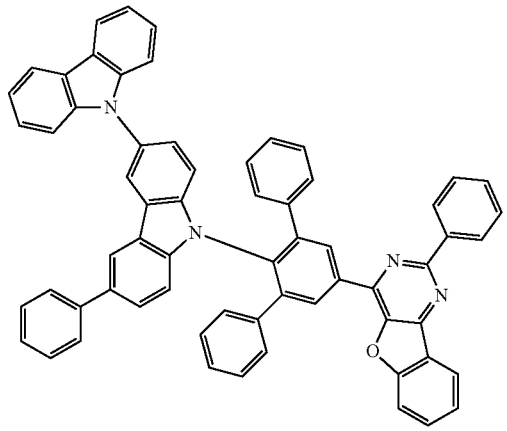
501
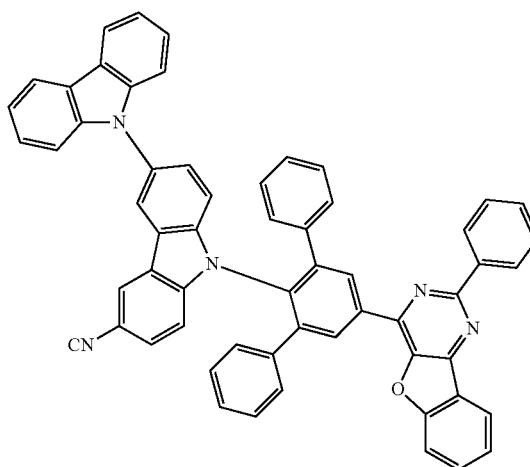
502
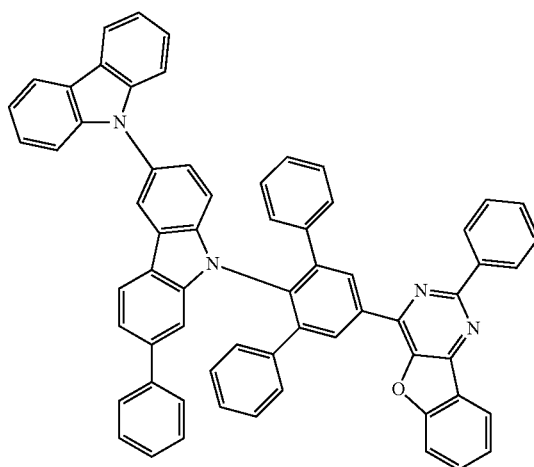

-continued
503
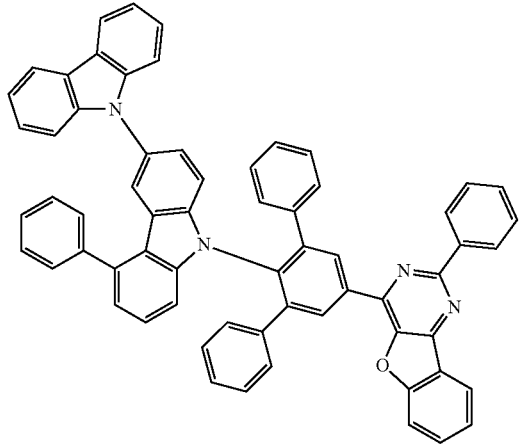
504
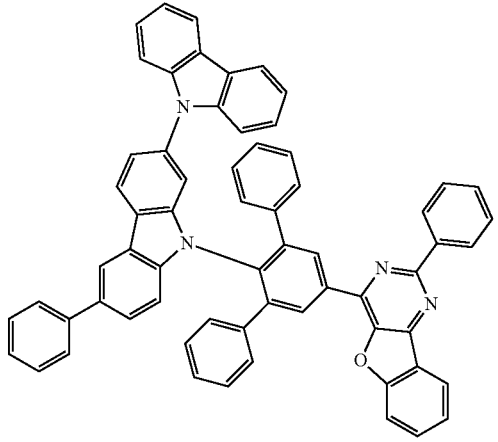
505
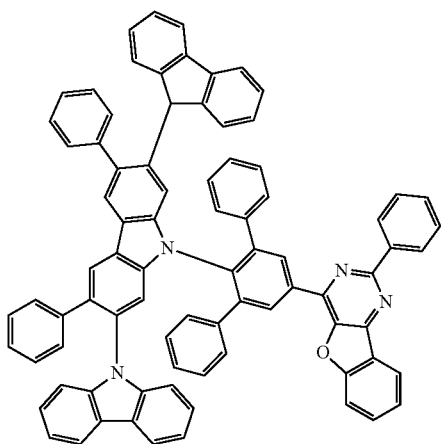
506
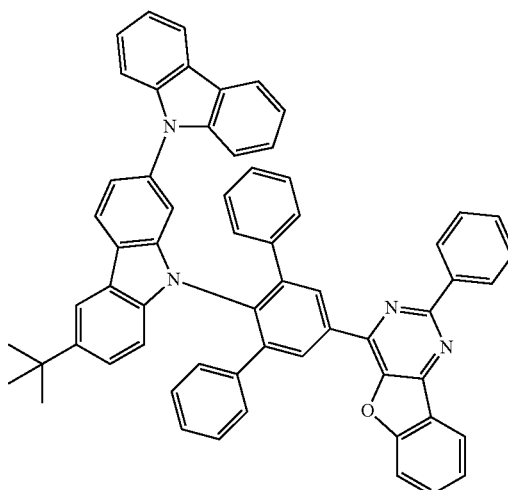
507
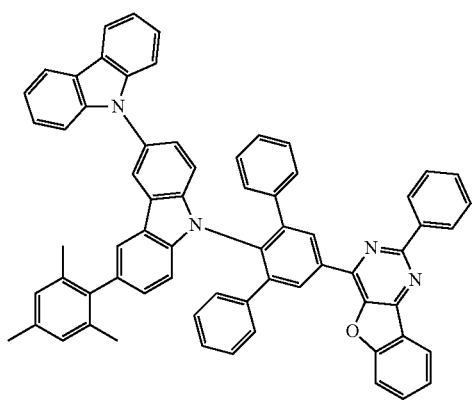
508
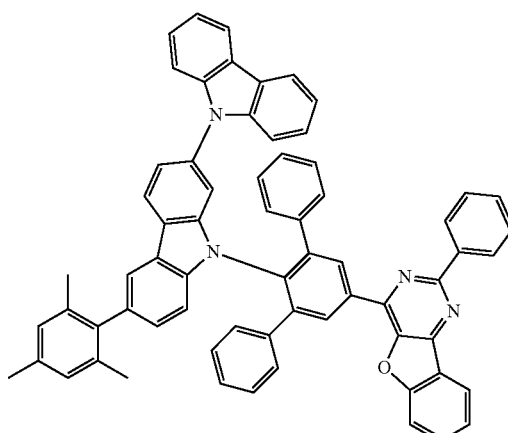

-continued
509
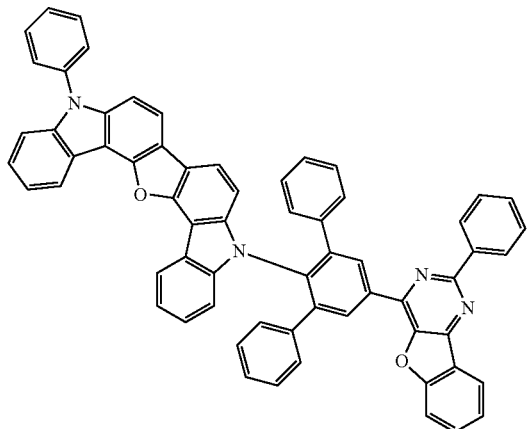
510
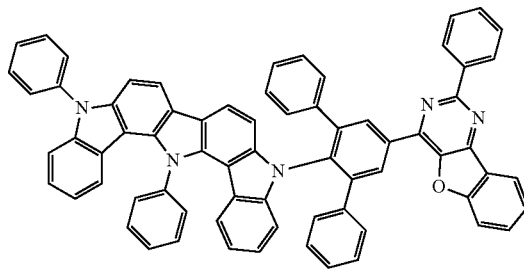
511
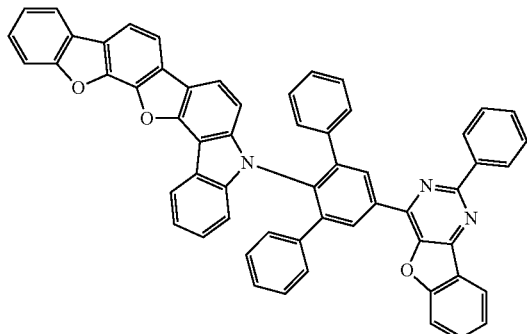
512
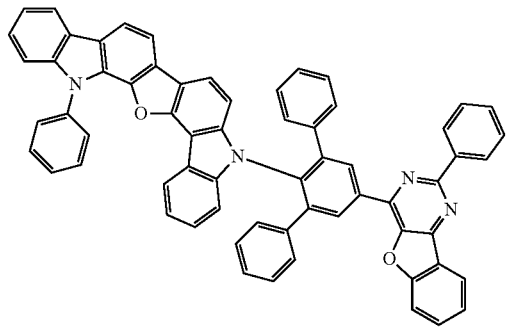
513
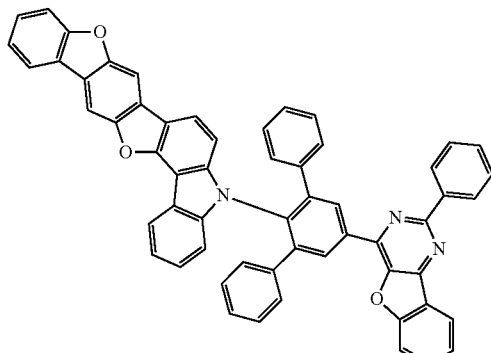
514
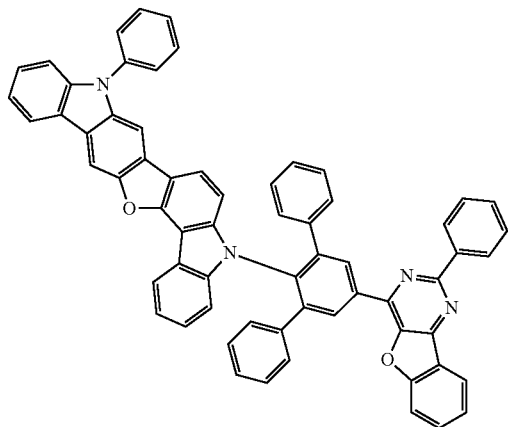

-continued
515
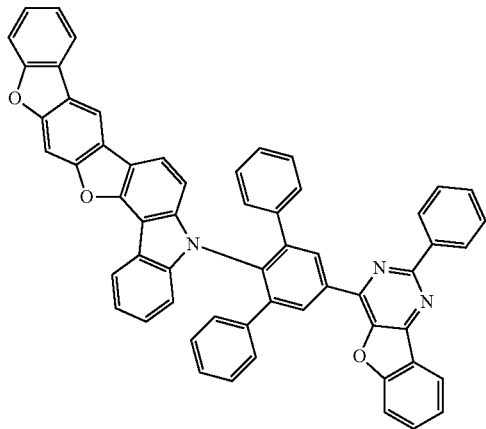
516
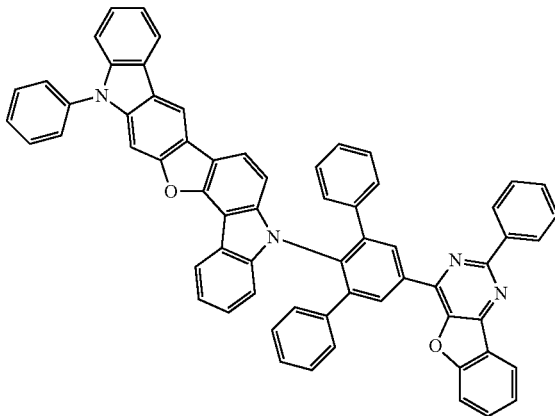
517
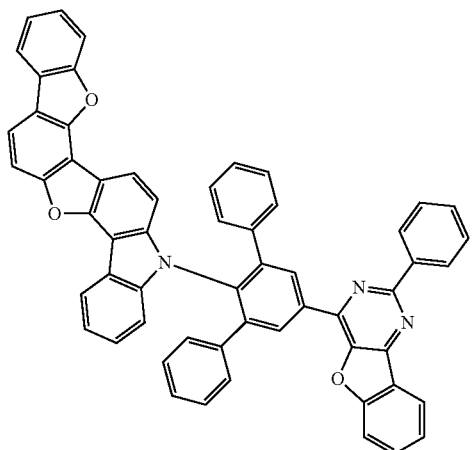
518
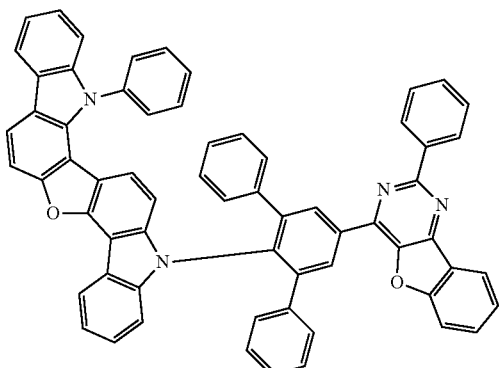
519
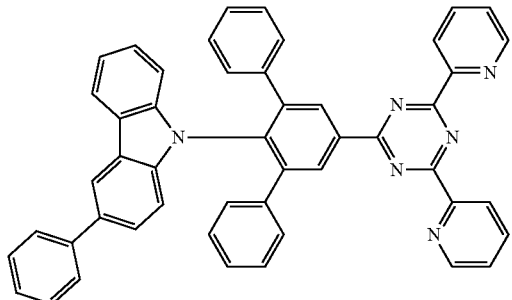
520
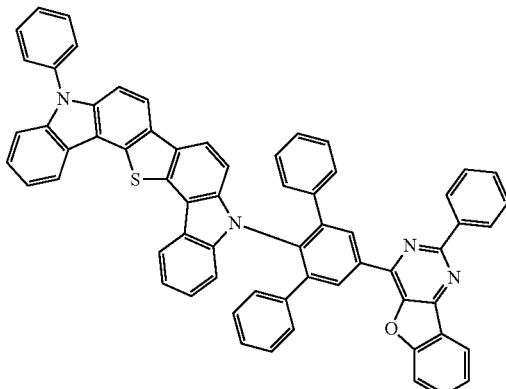
521
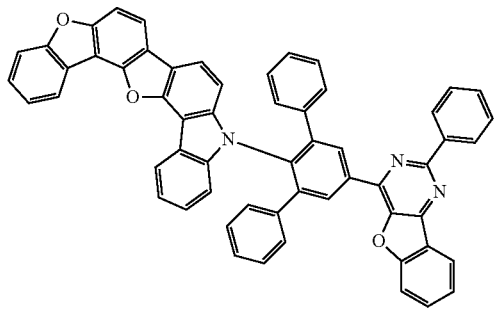
522
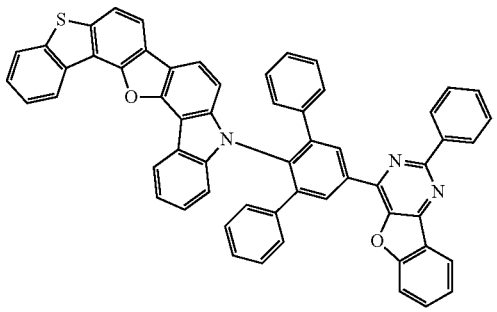

-continued
| 523 | 524 |
|---|---|
| 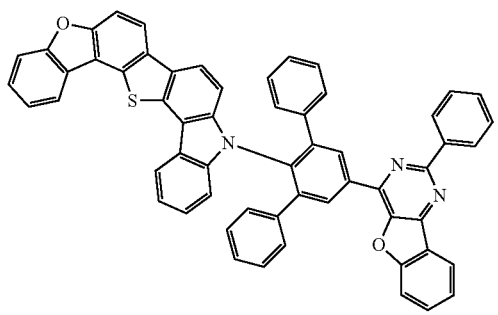 | 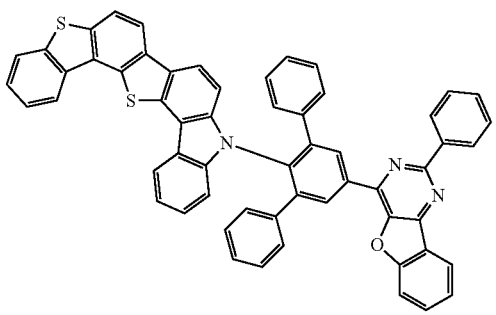 |
| 525 | 526 |
| 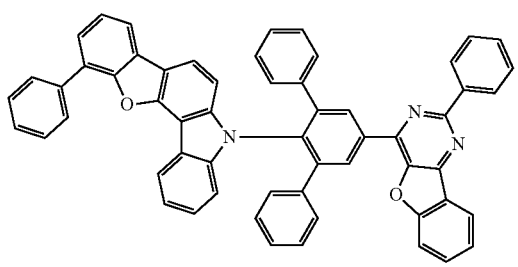 | 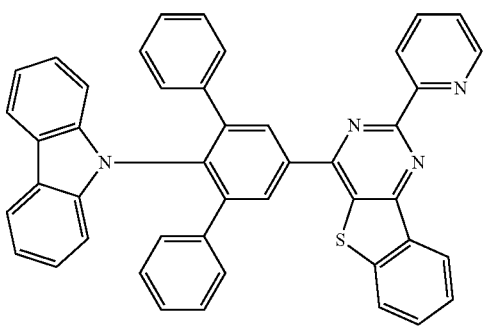 |
| 527 | 528 |
| 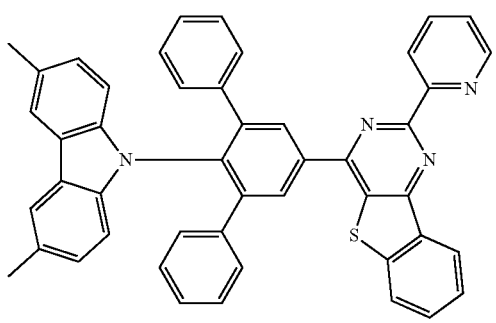 | 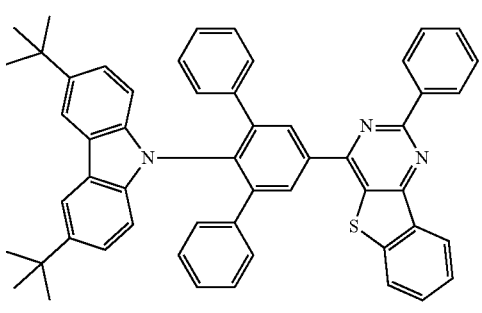 |
| 529 | 530 |
| 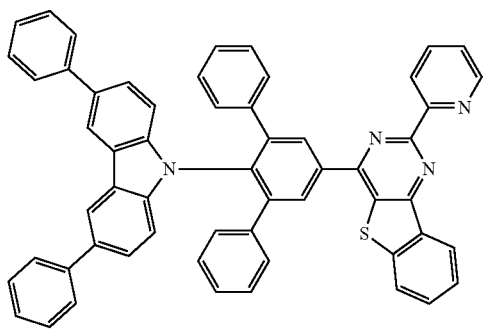 | 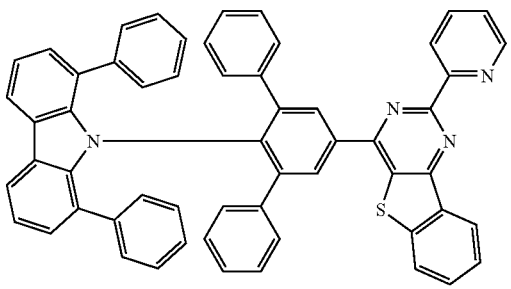 |

-continued
531
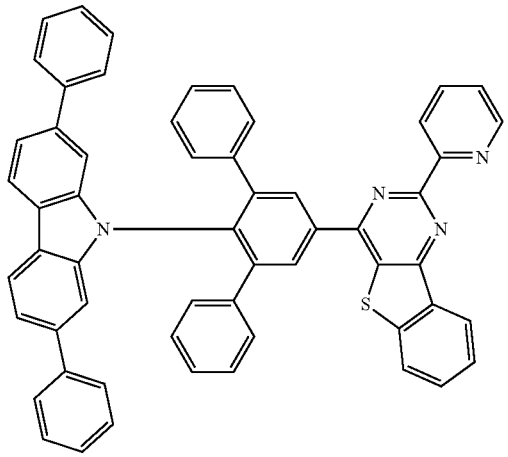
532
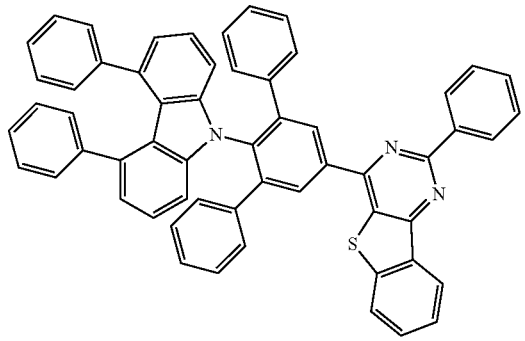
533
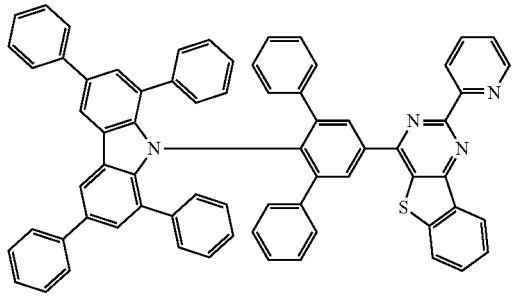
534
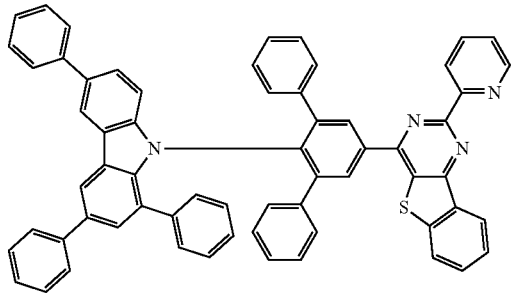
535
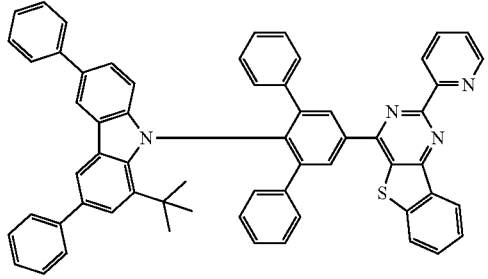
536
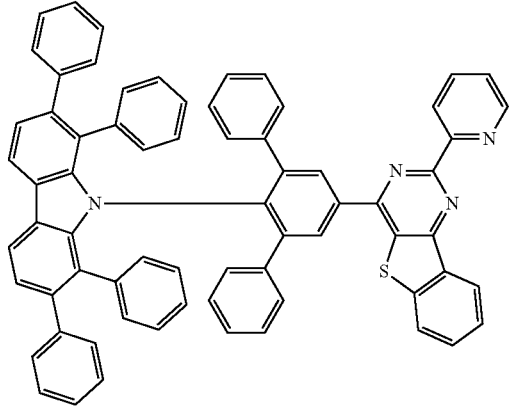
537
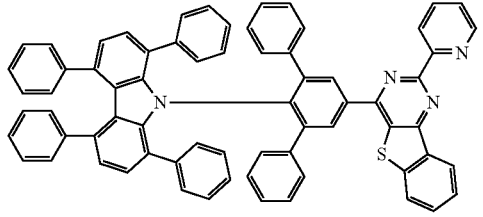
538
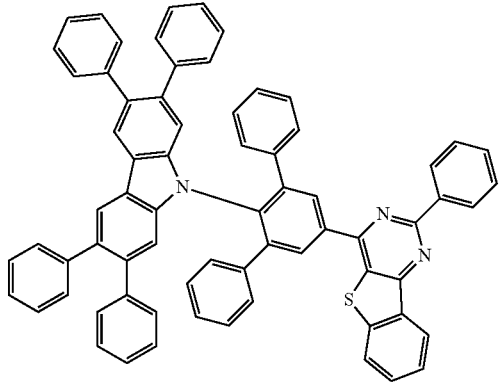

-continued
539
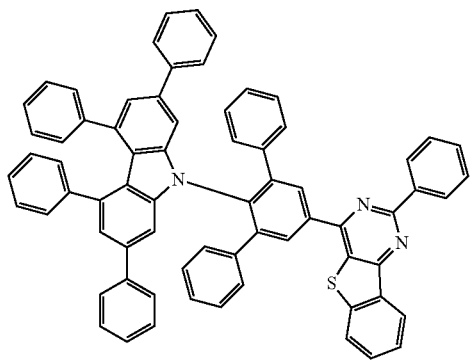
540
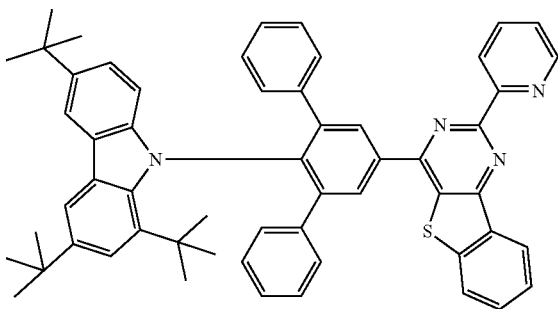
541
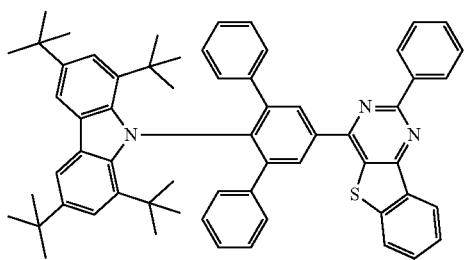
542
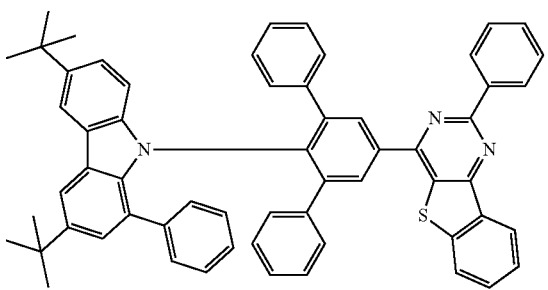
543
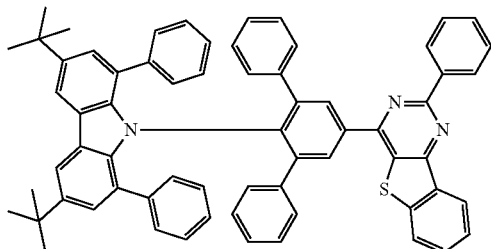
544
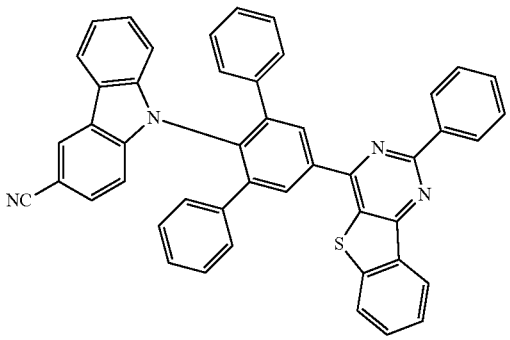
545
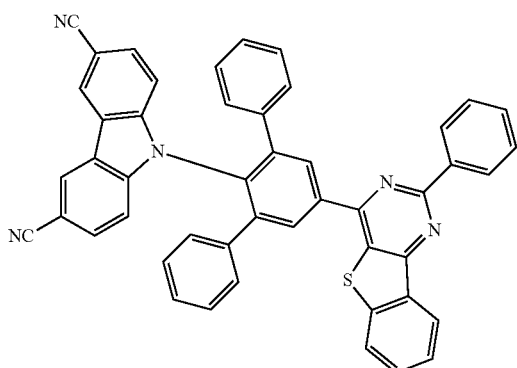
546
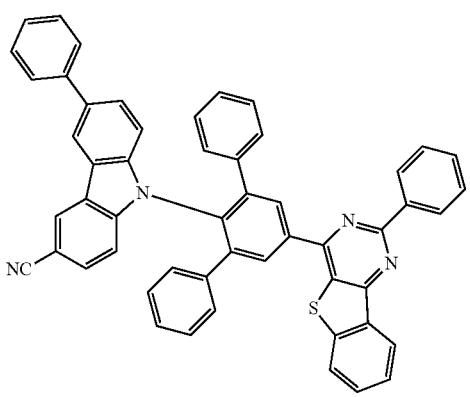

-continued
235
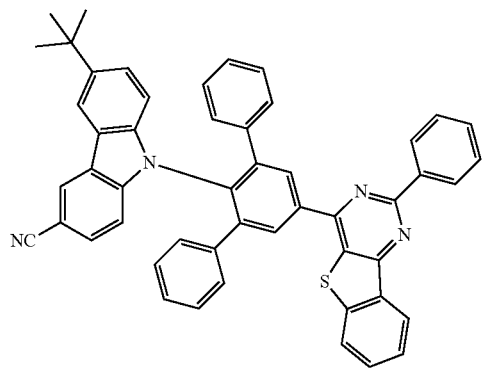
547
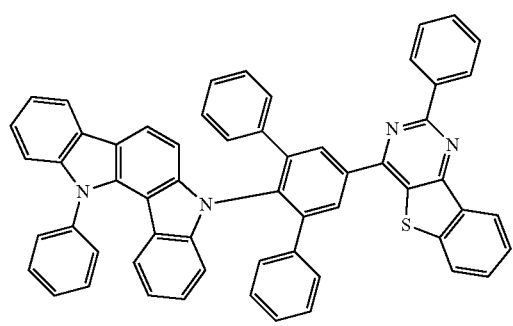
549
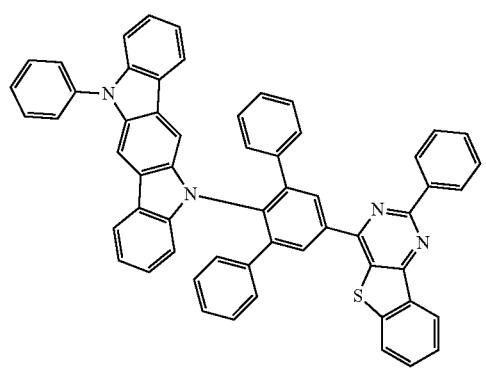
551
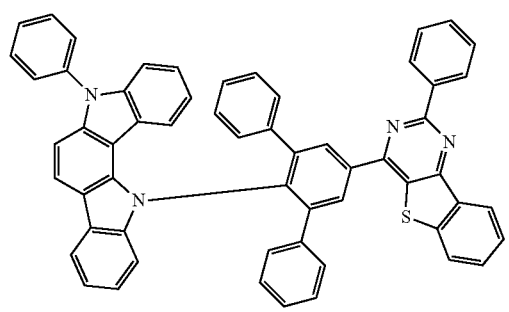
553
236
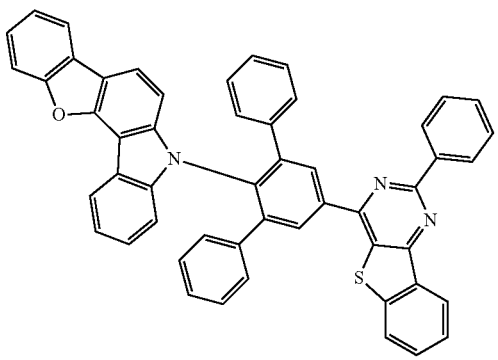
548
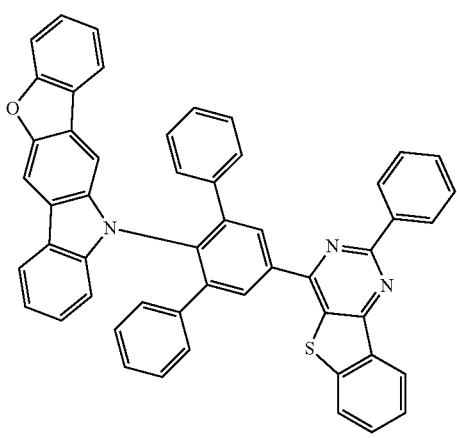
550
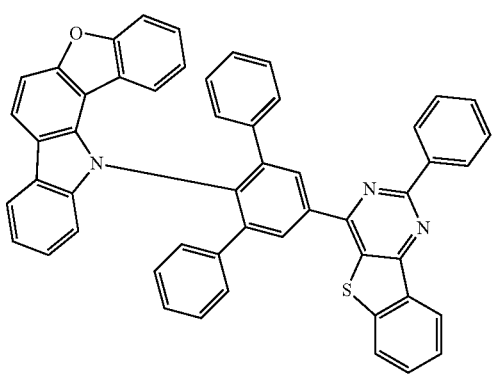
552
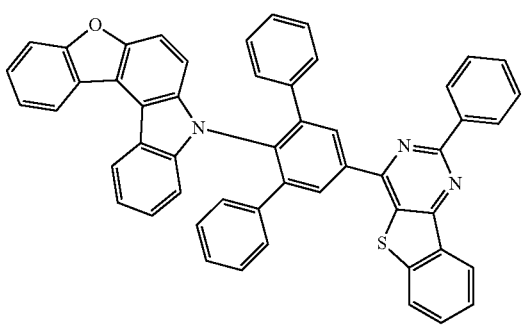
554

-continued
555
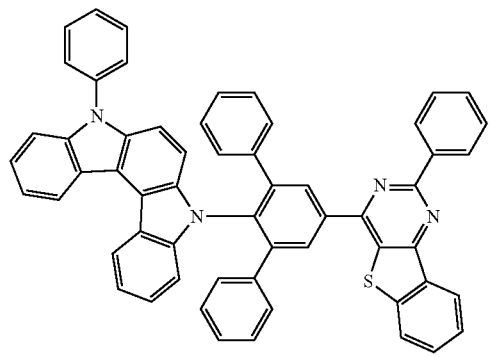
556
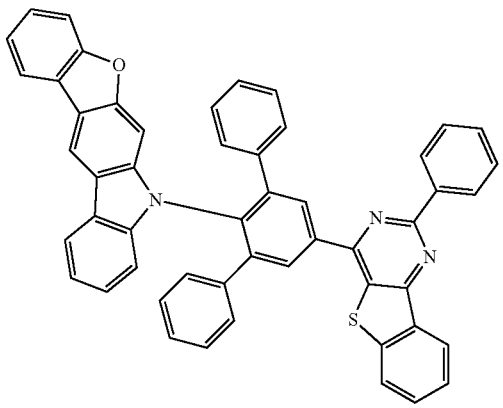
557
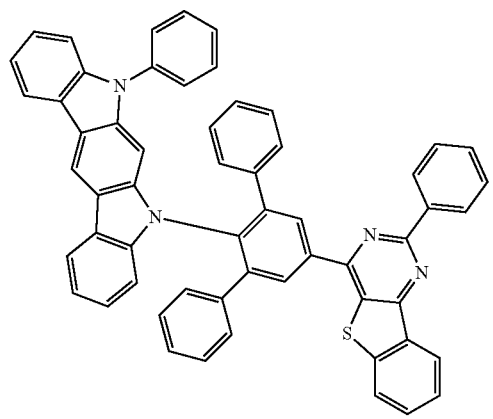
558
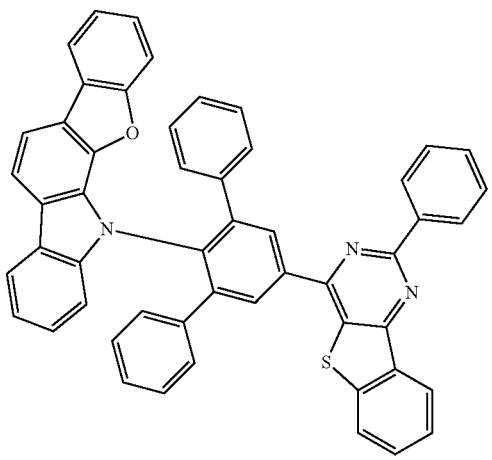
559
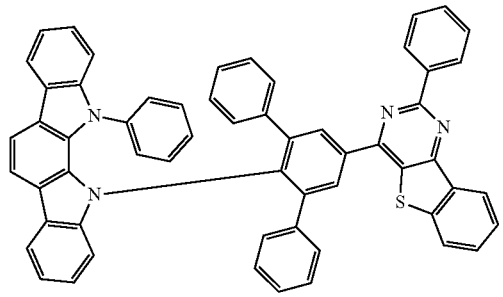
560
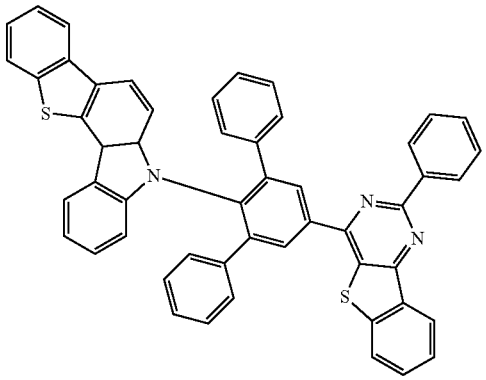

-continued
561 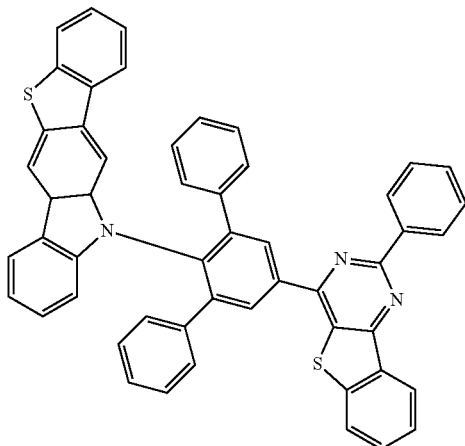
562 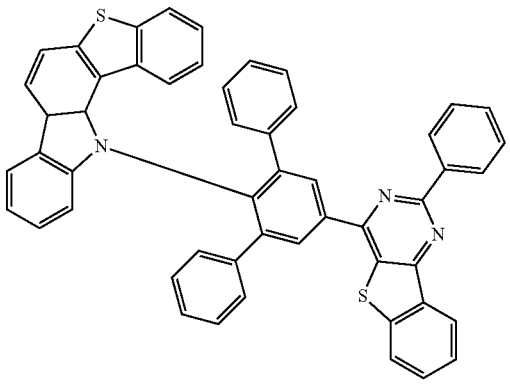
563 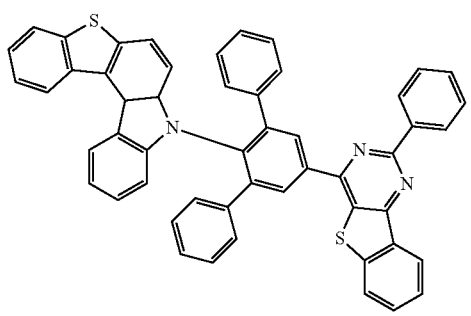
564 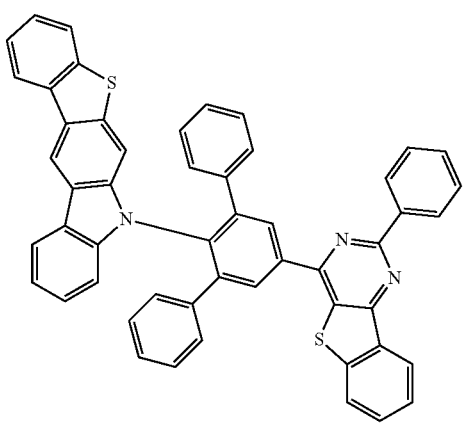
565 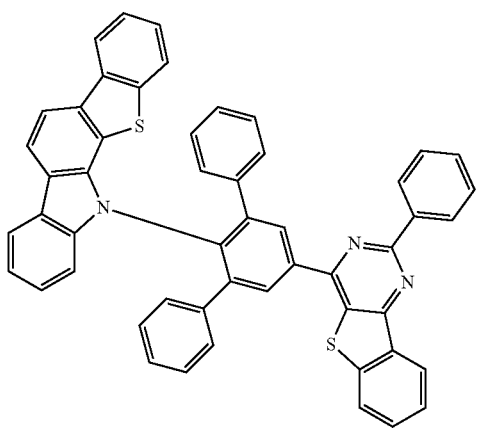
566 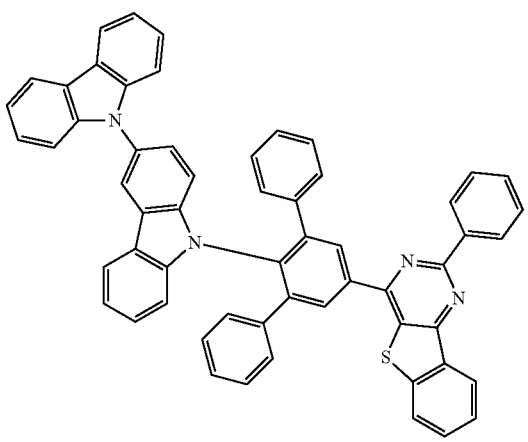

-continued
567
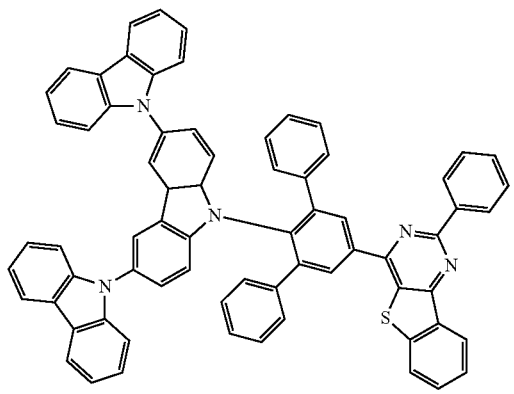
568
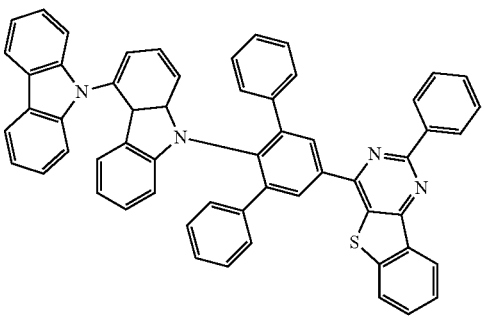
569
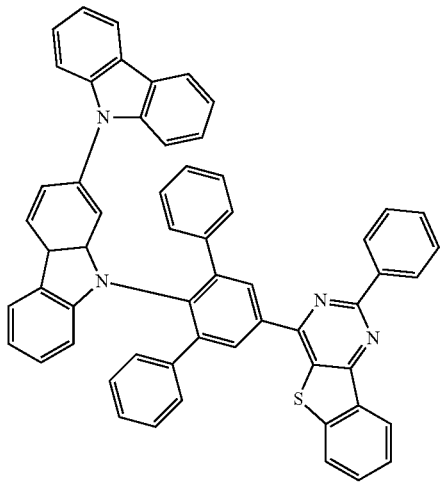
570
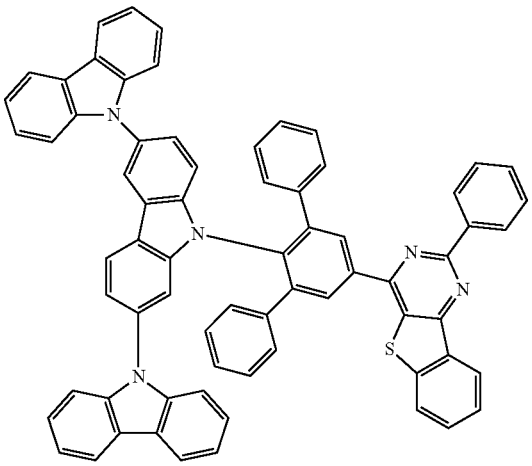
571
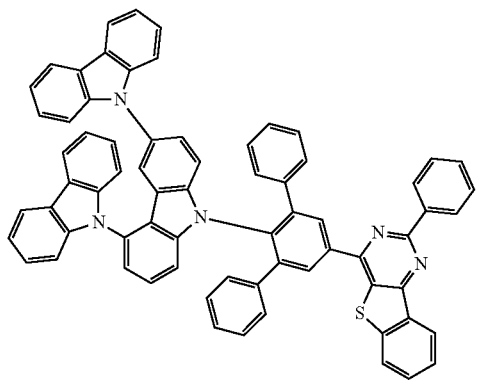
572
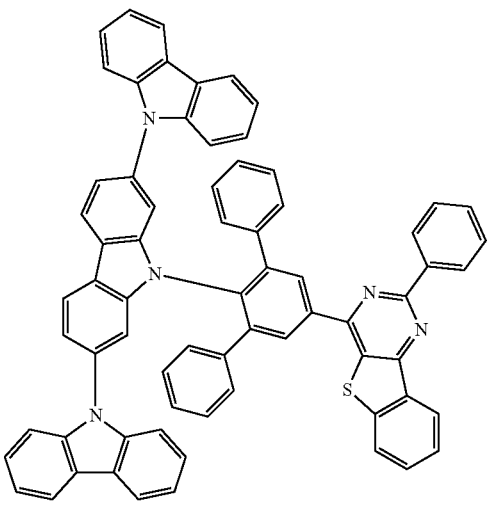

573 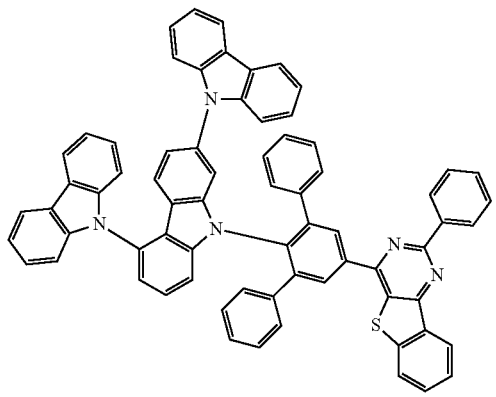
574 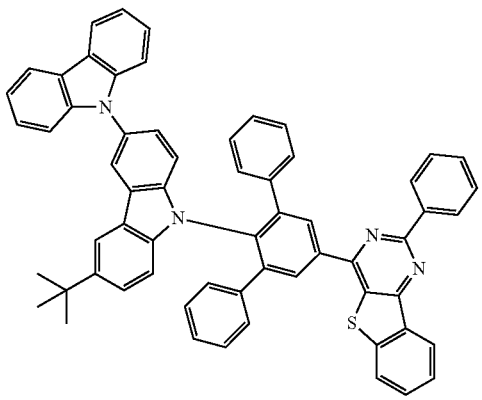
575 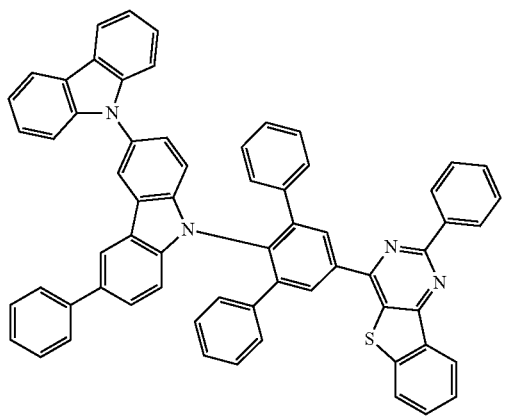
576 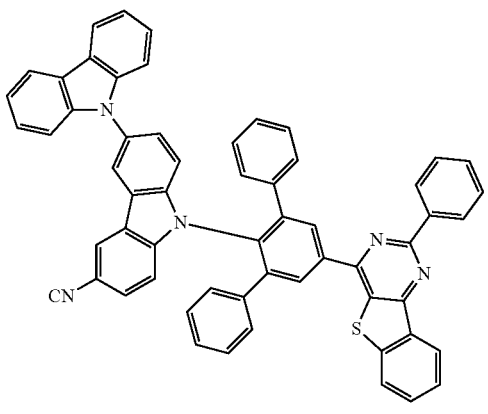
577 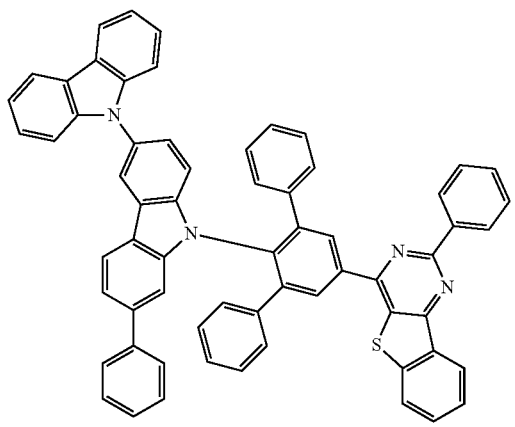
578 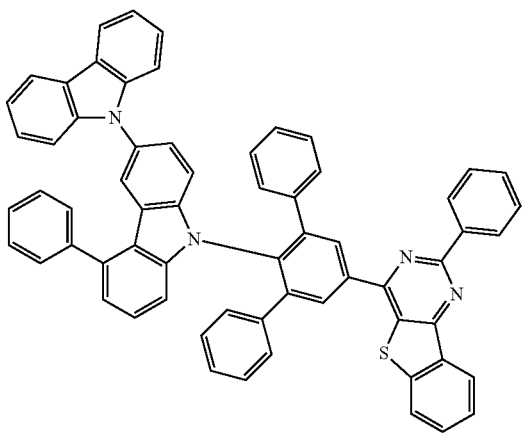

-continued
579
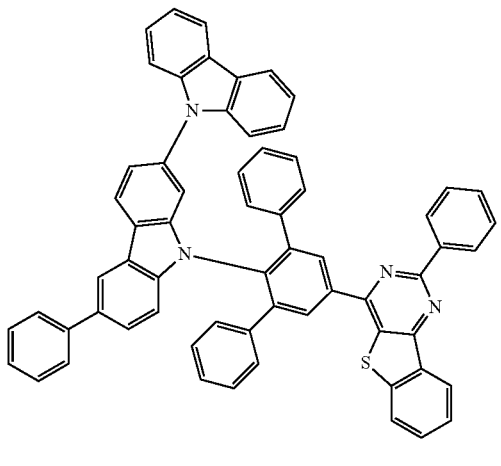
580
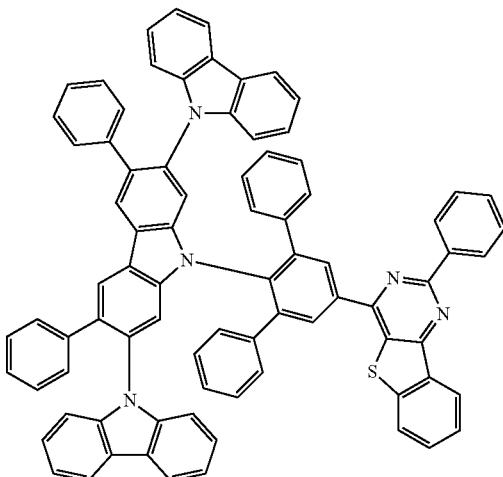
581
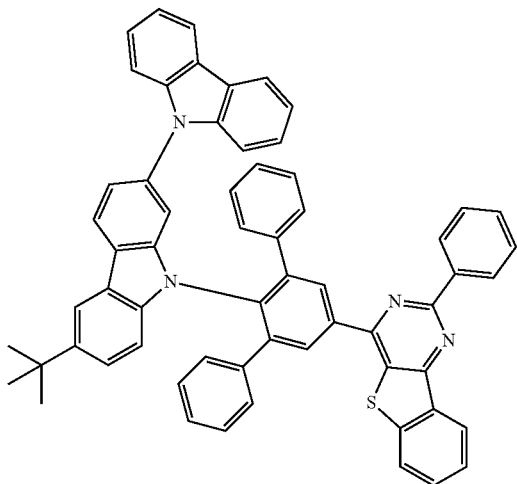
582
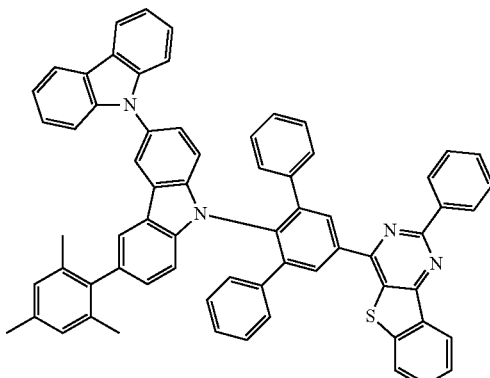
583
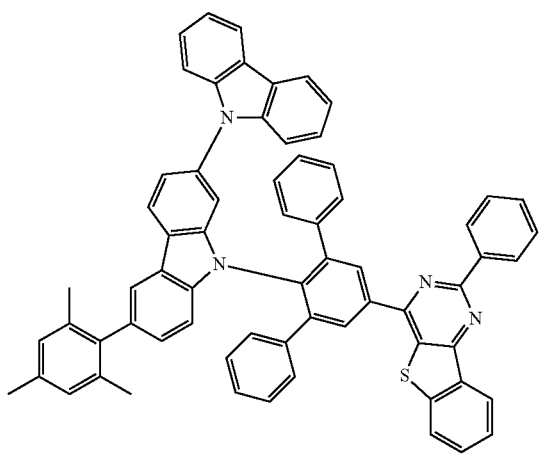
584
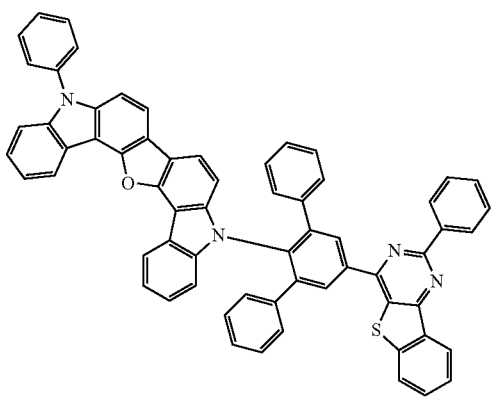

585
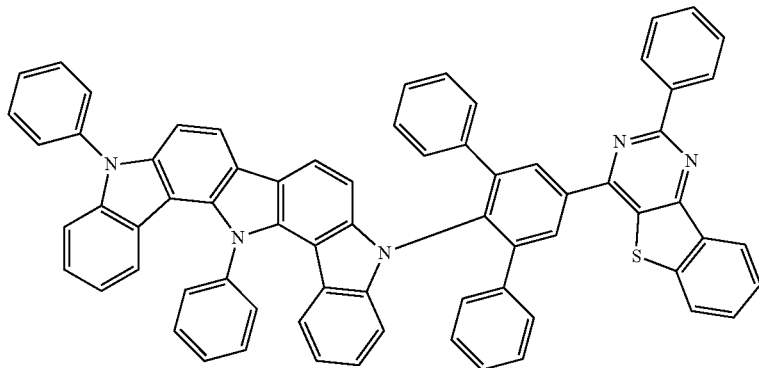
586
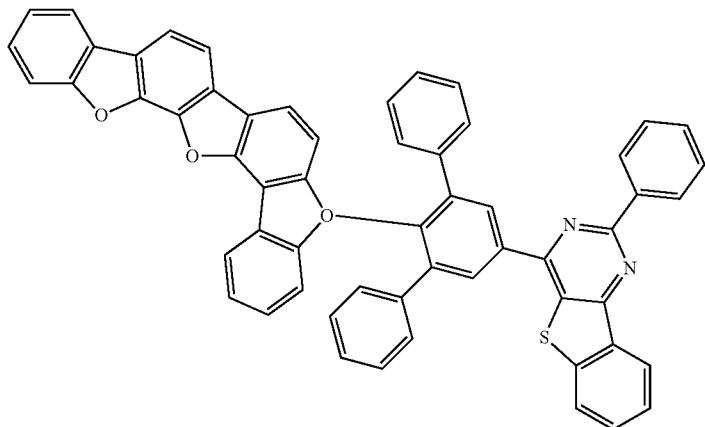
587
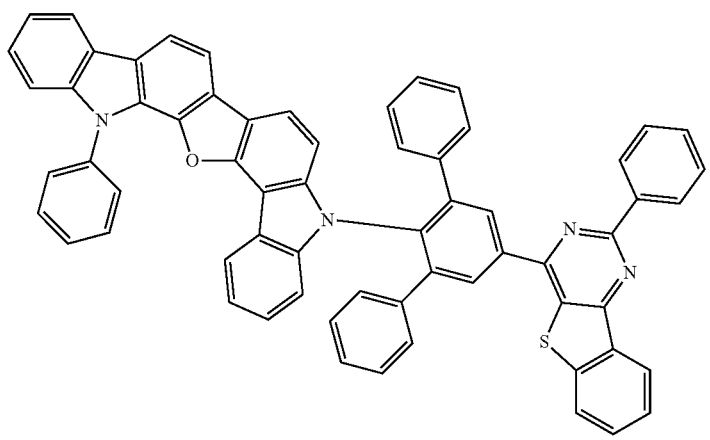

588
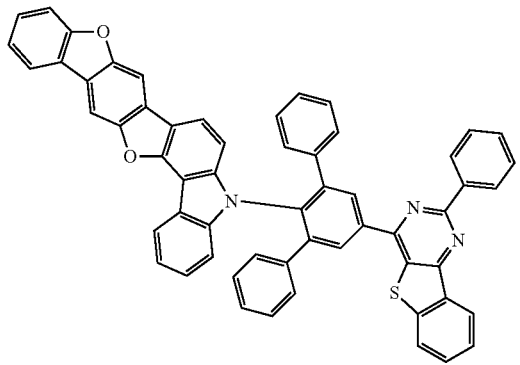
589
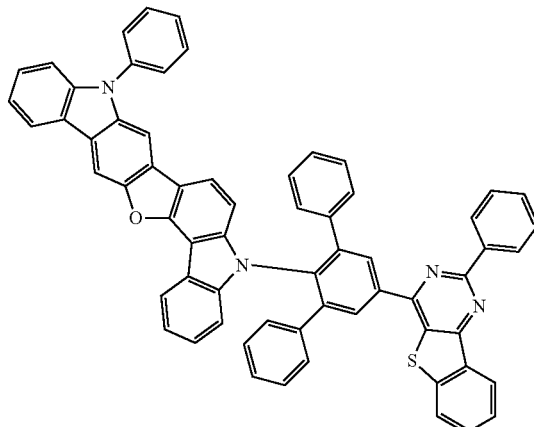
590
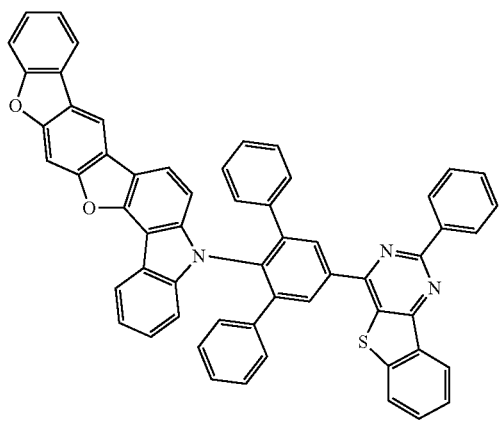
591
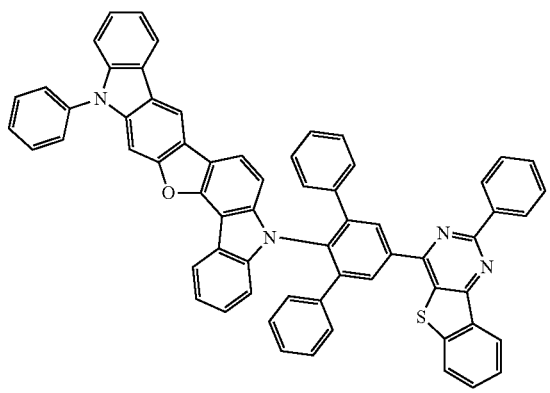
592
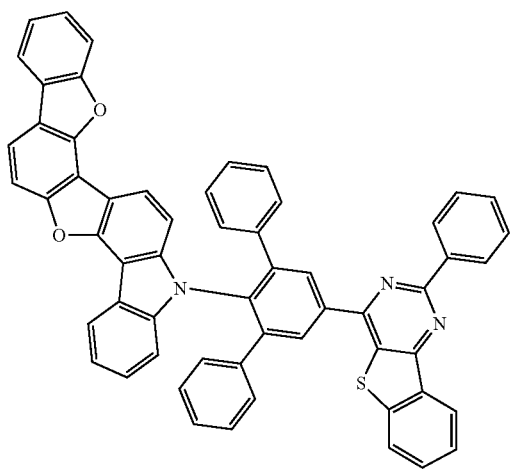
593
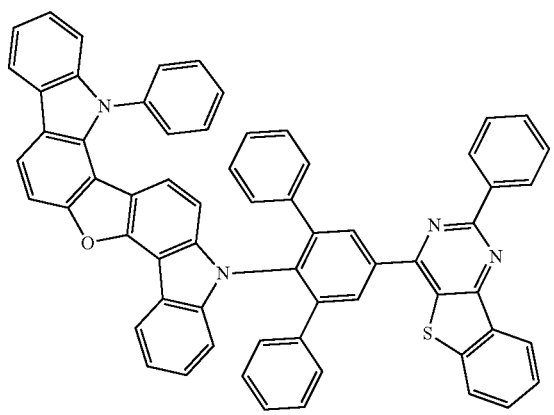

594
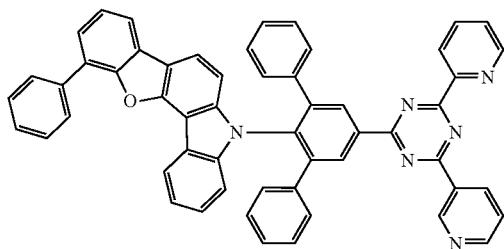
595
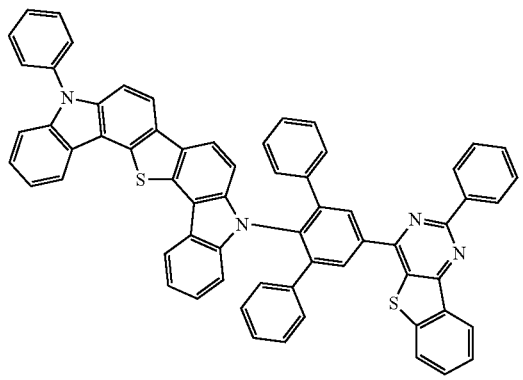
596
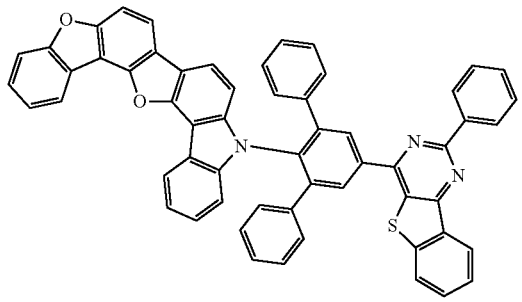
597
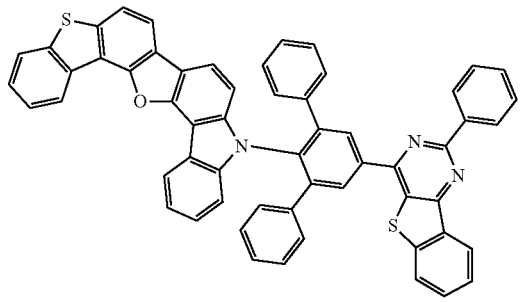
598
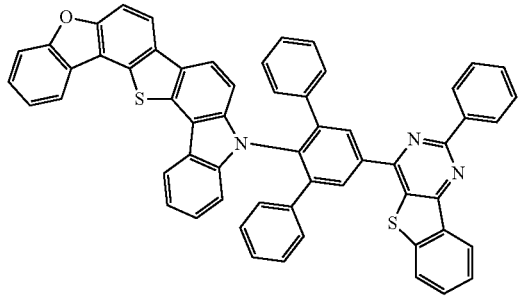
599
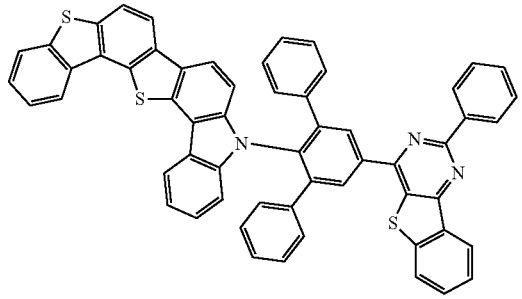
600
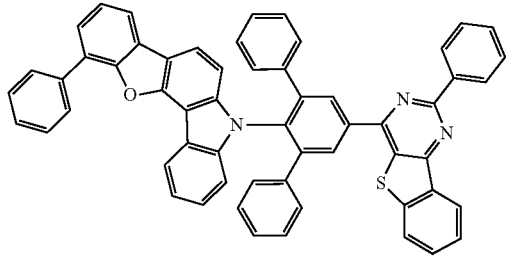
601
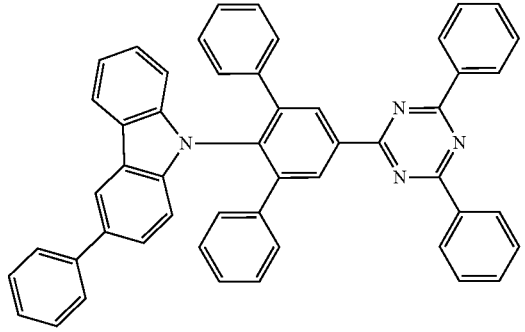
602
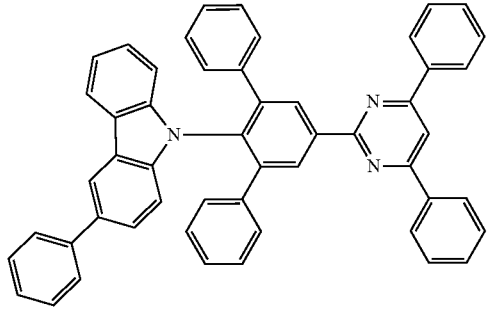
603
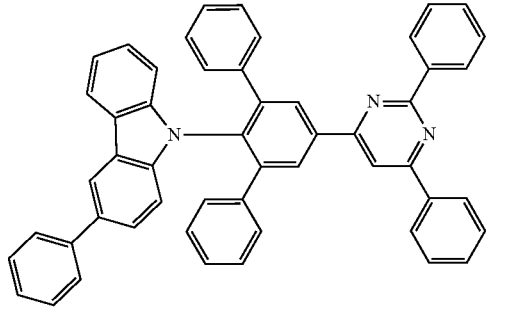

-continued
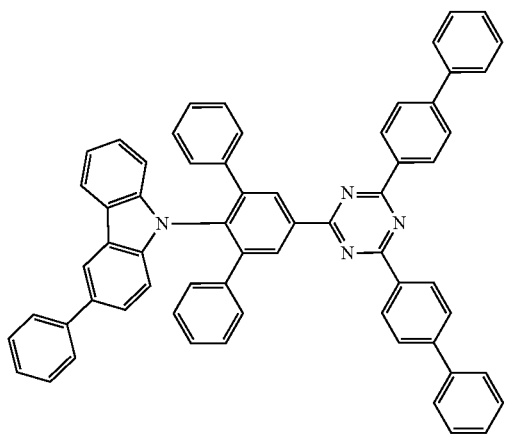
604
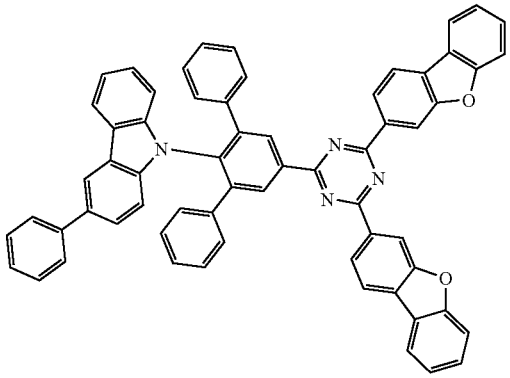
605
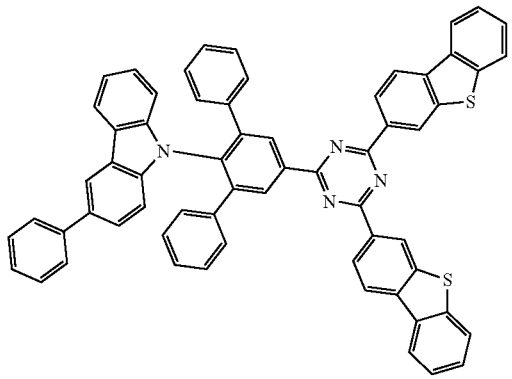
606
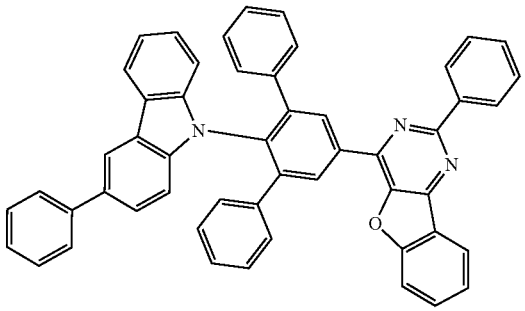
607
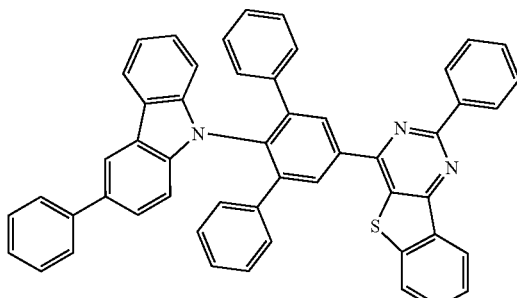
608
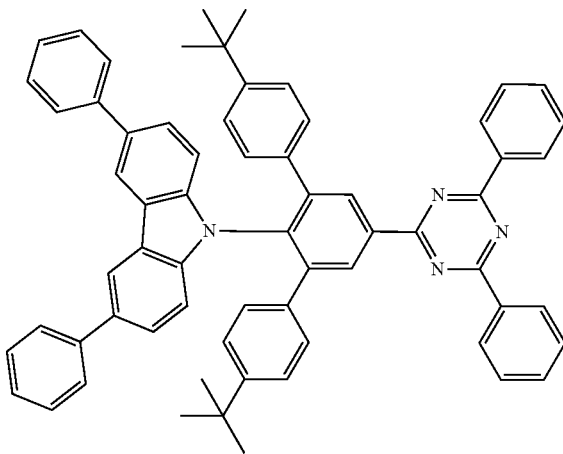
609

-continued
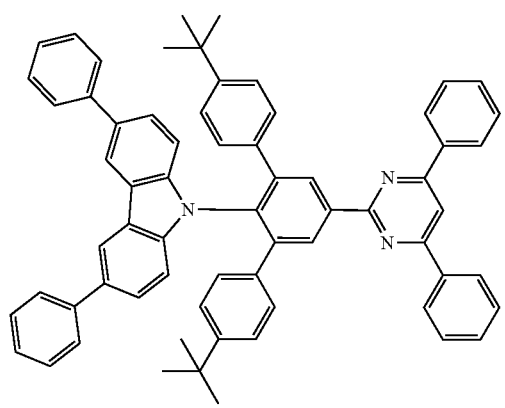
610
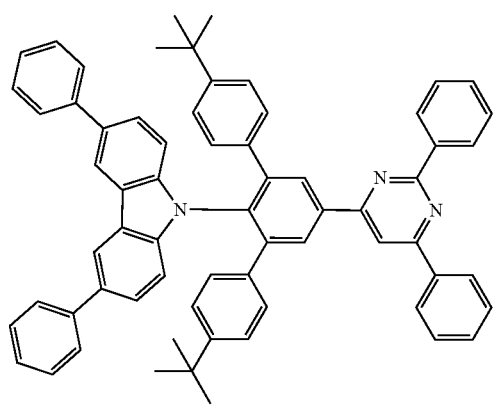
611
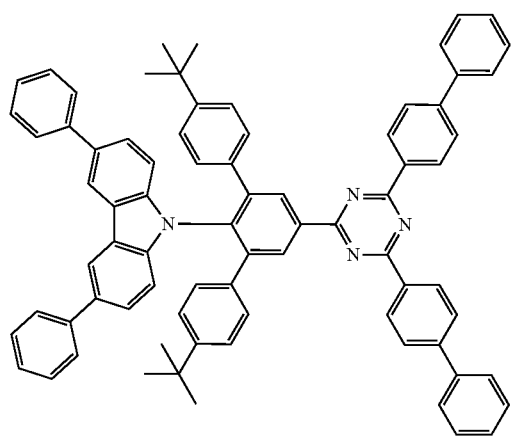
612
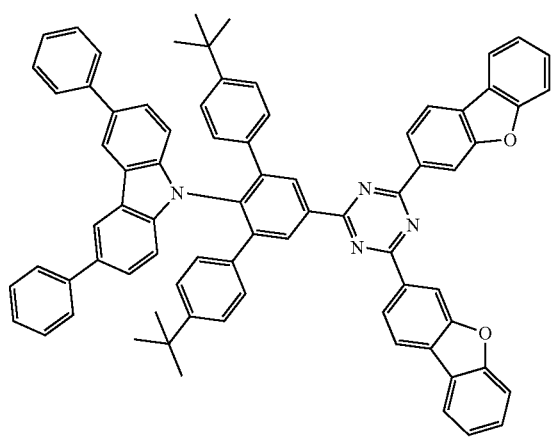
613
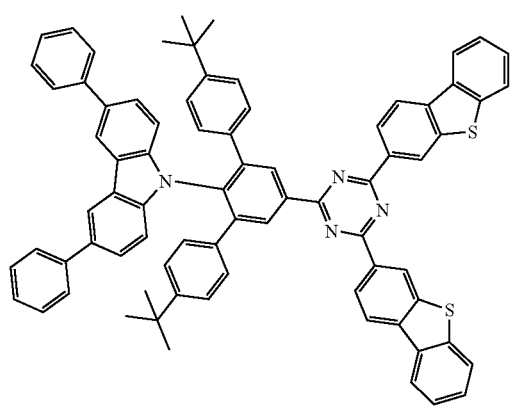
614
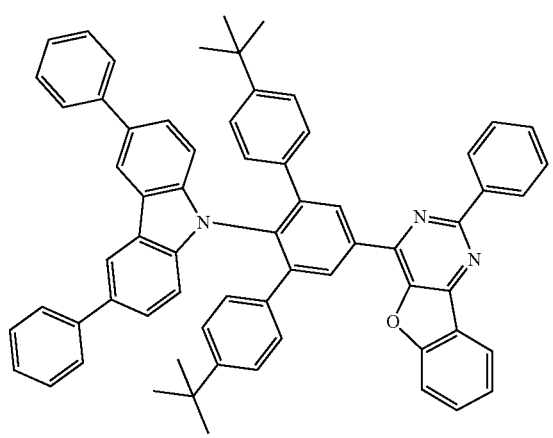
615

-continued
616
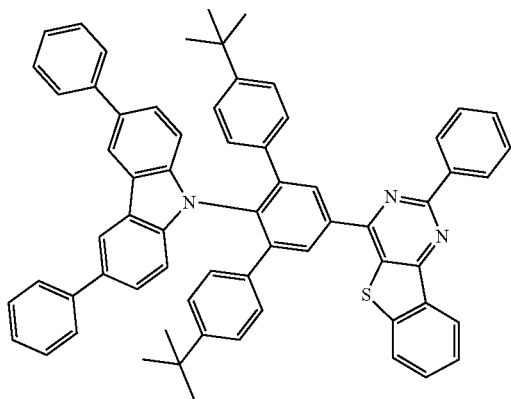
617
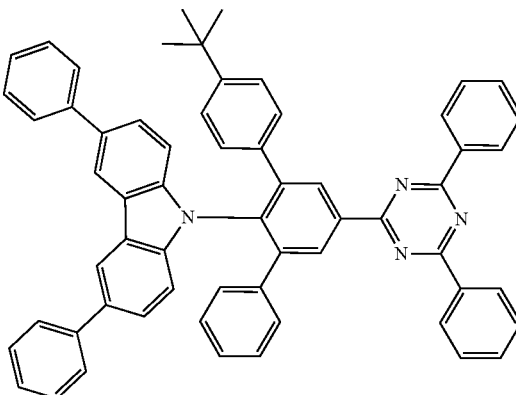
618
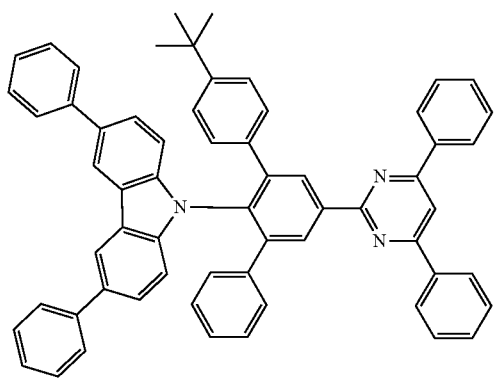
619
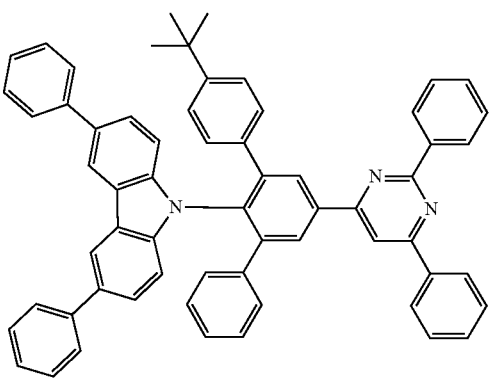
620
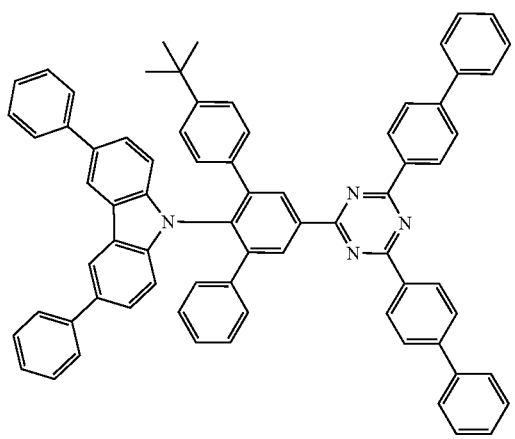
621
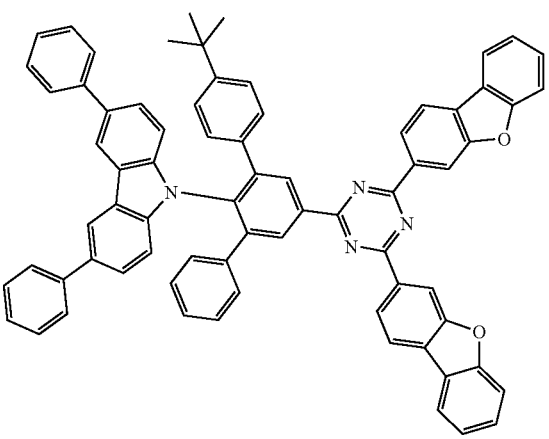

-continued
| 622 | 623 |
|---|---|
| 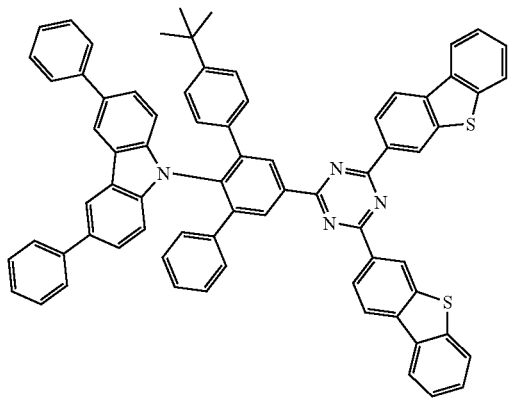 | 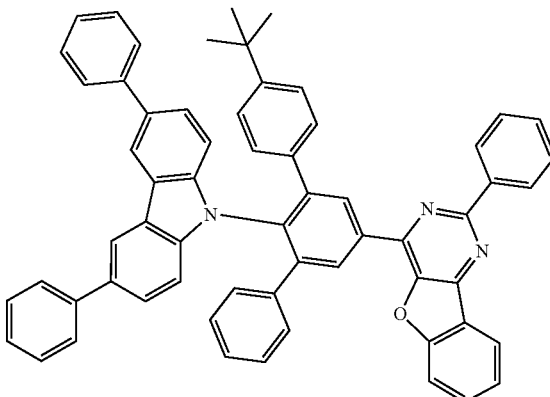 |
| 624 | 625 |
| 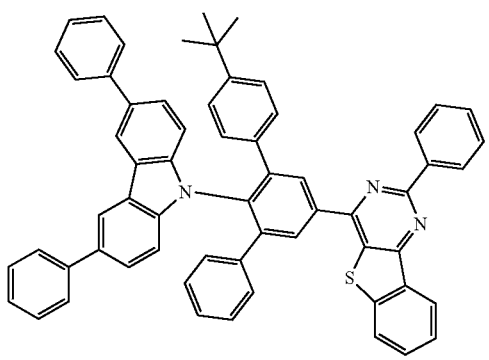 | 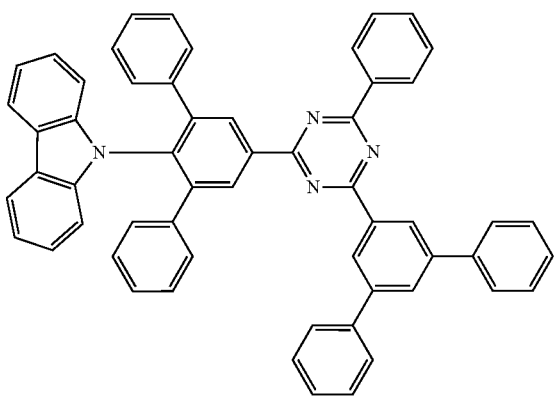 |
| 626 | 627 |
| 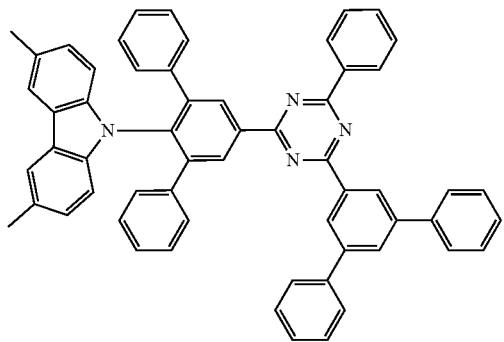 | 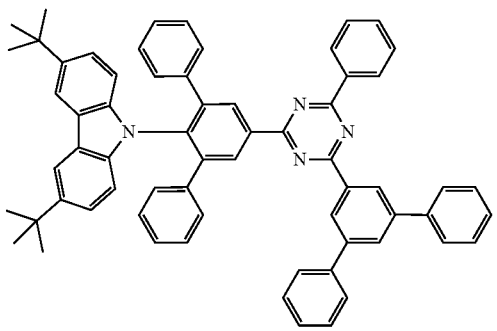 |
| 628 | 629 |
| 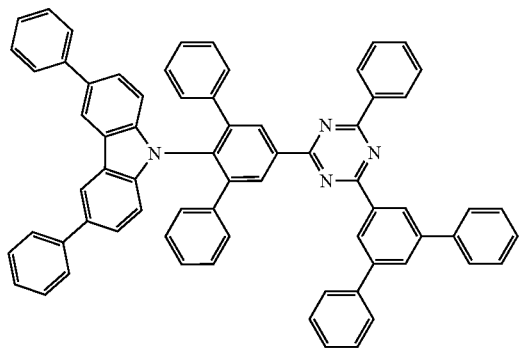 | 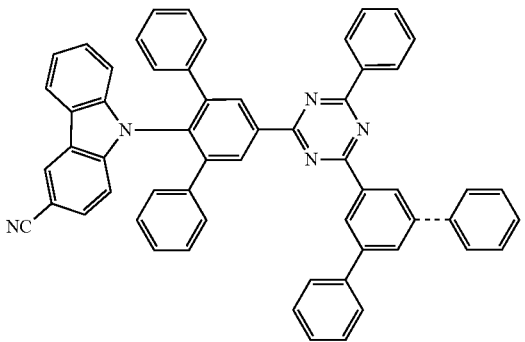 |

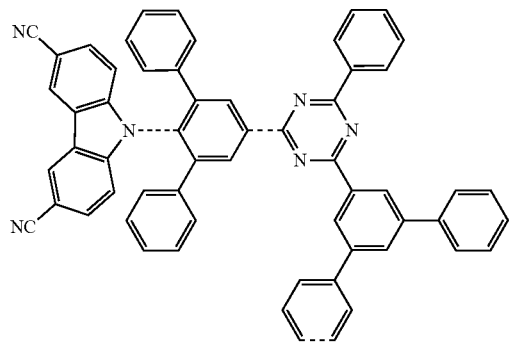
630
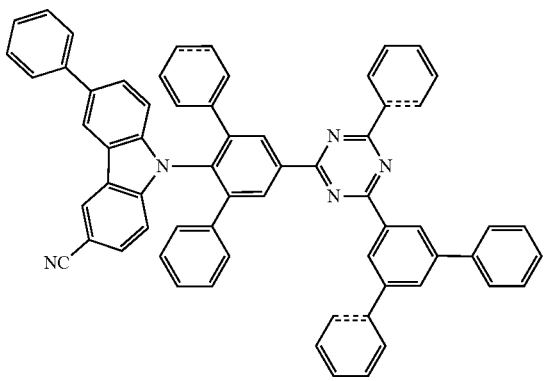
631
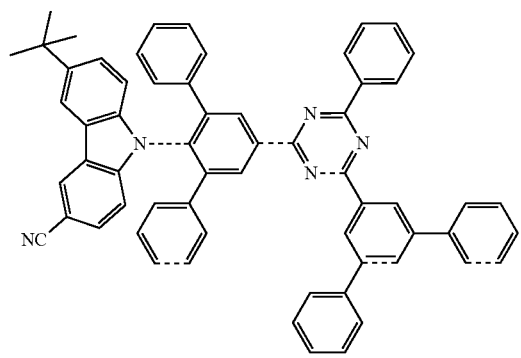
632
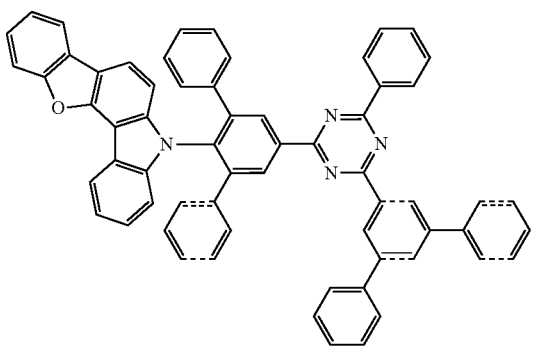
633
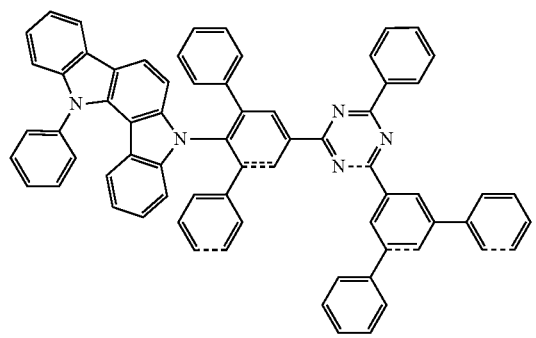
634
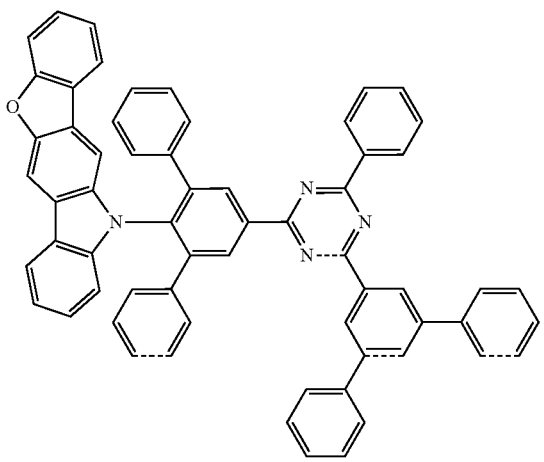
635

636
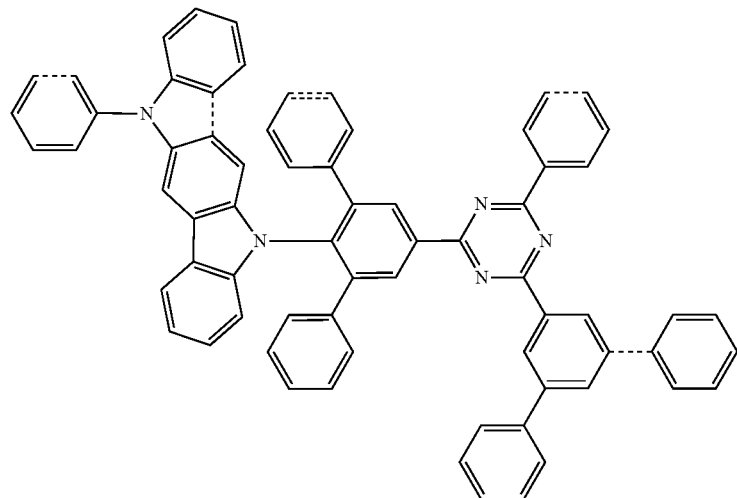
637
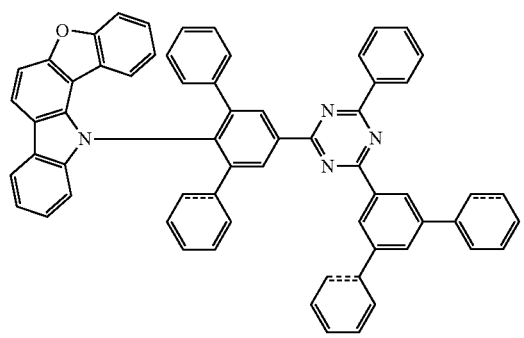
638
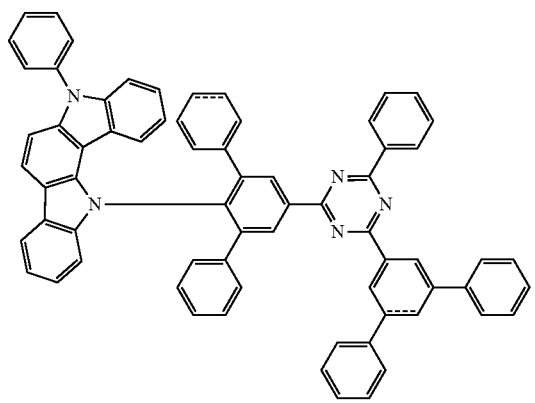
639
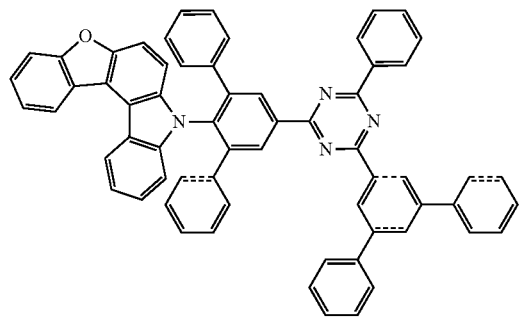
640
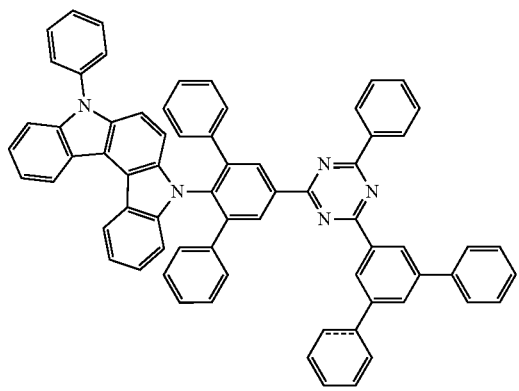

-continued
641
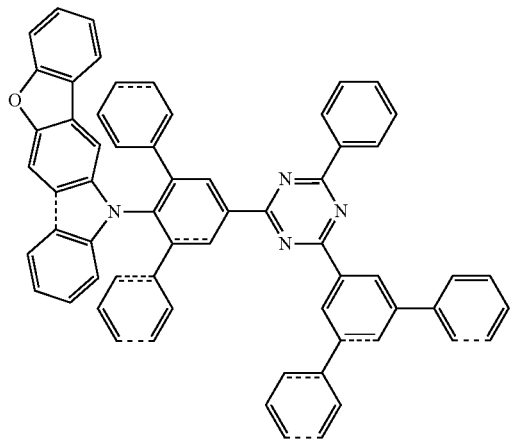
642
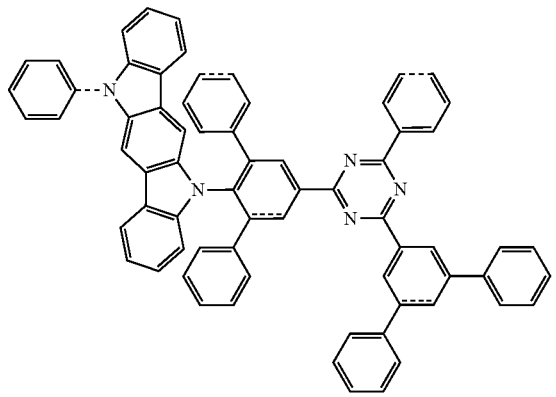
643
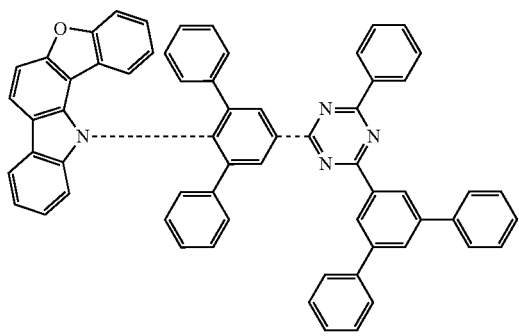
644
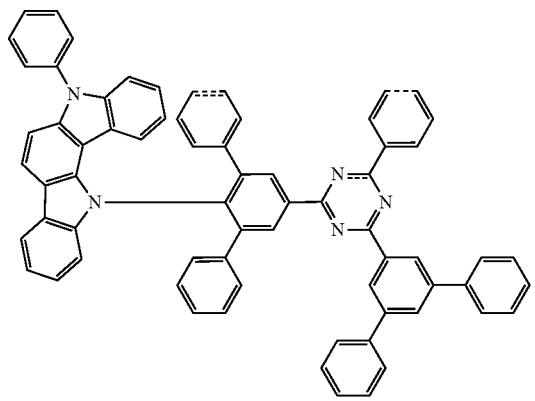
645
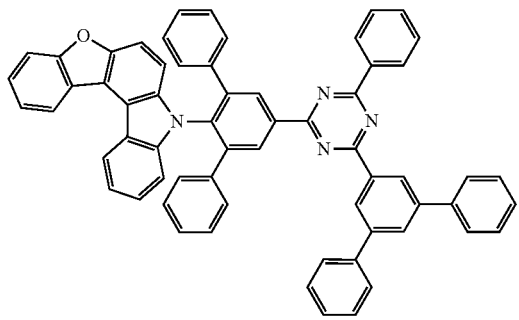
646
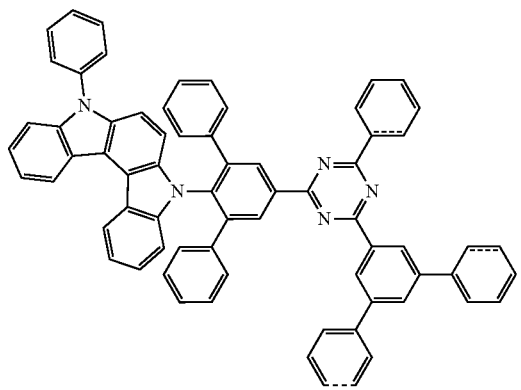
647
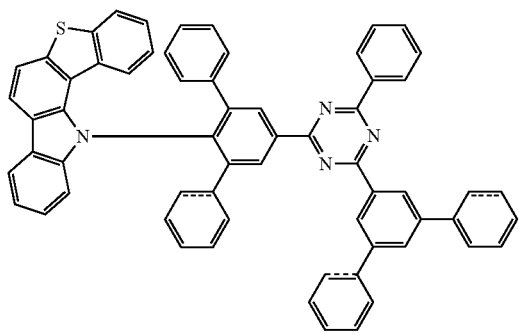
648
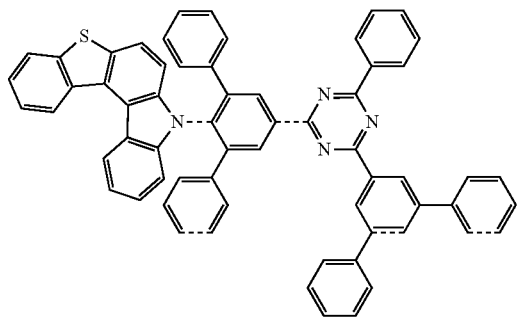

-continued
649
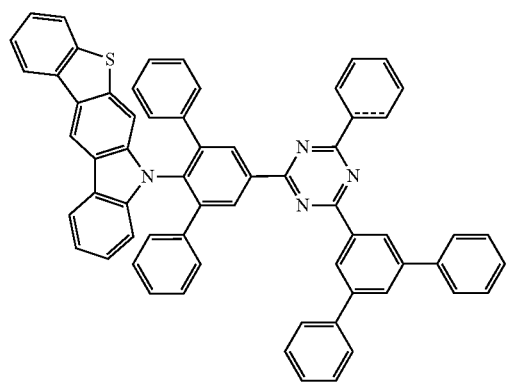
650
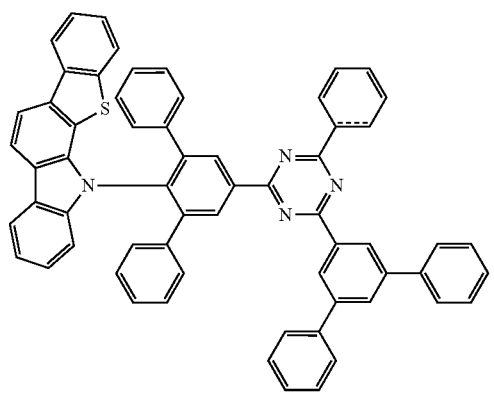
651
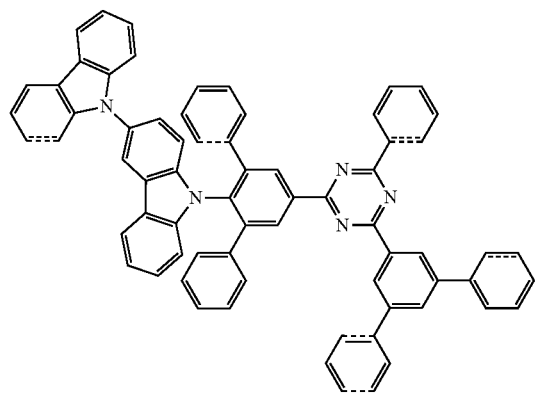
652
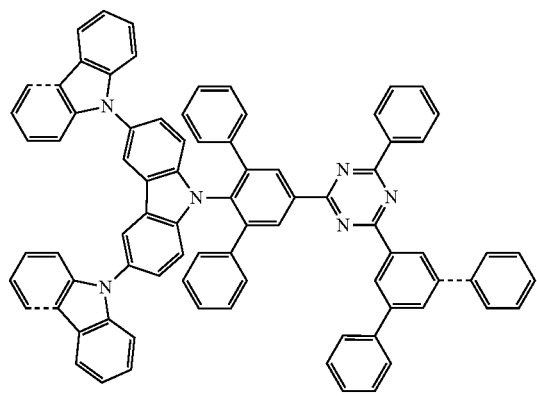
653
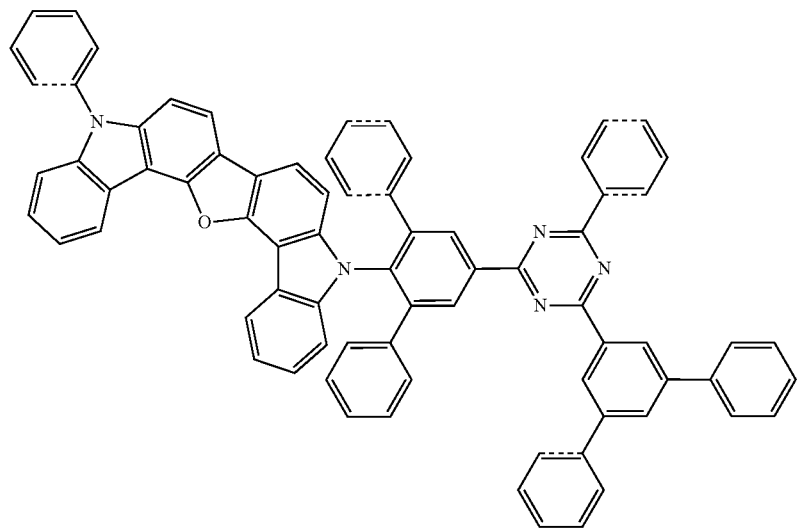

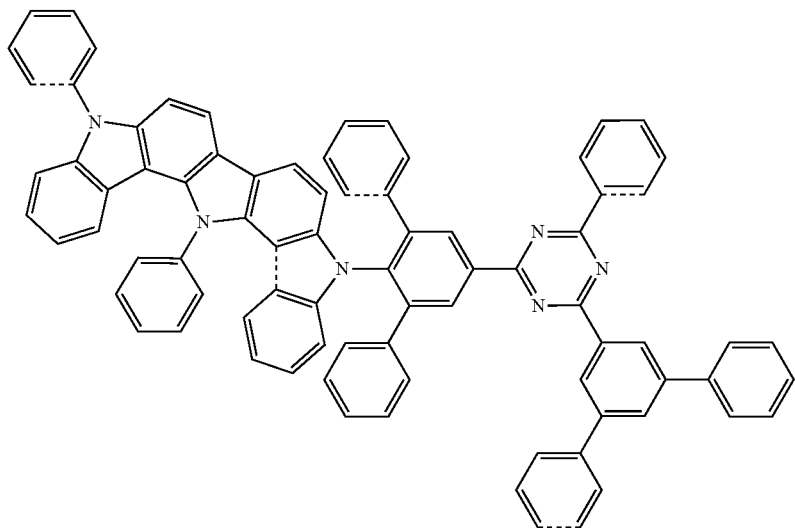
654
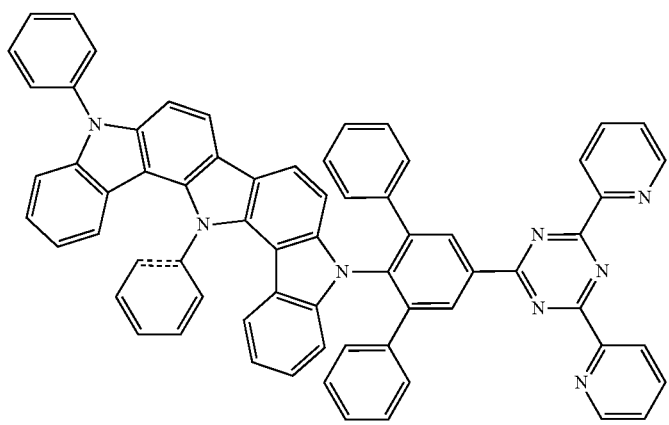
655
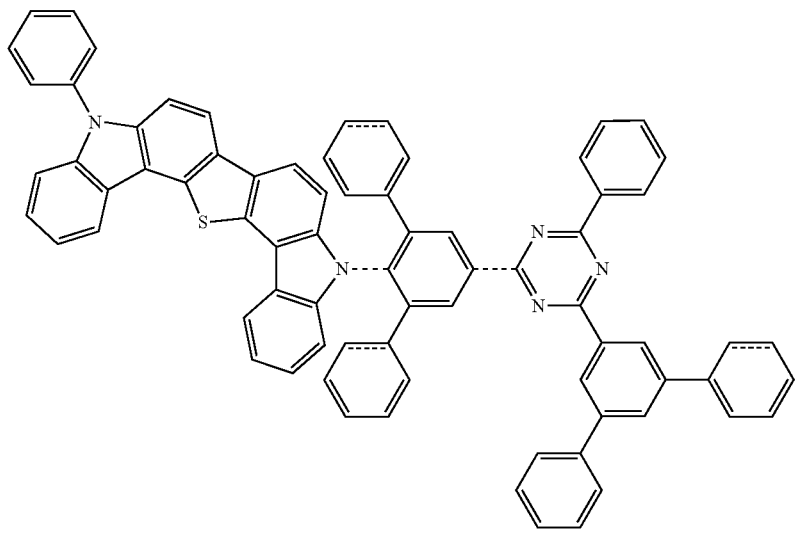
656

657
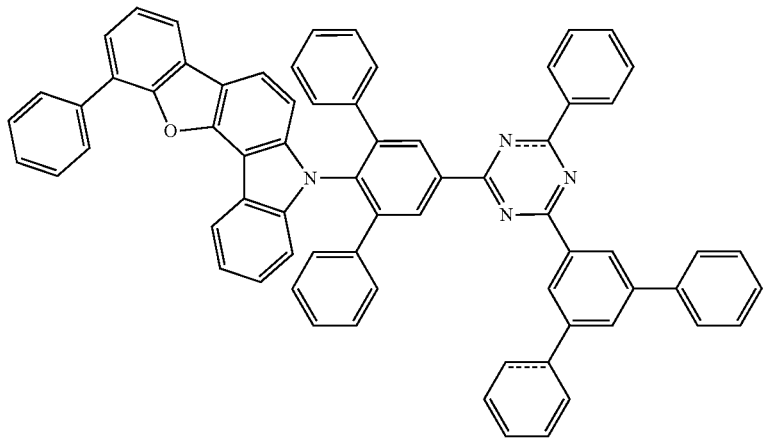
658 659
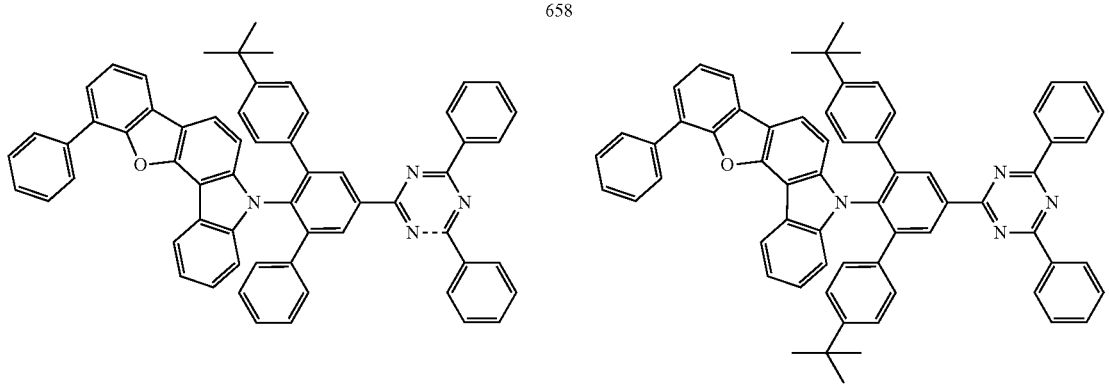
660 661
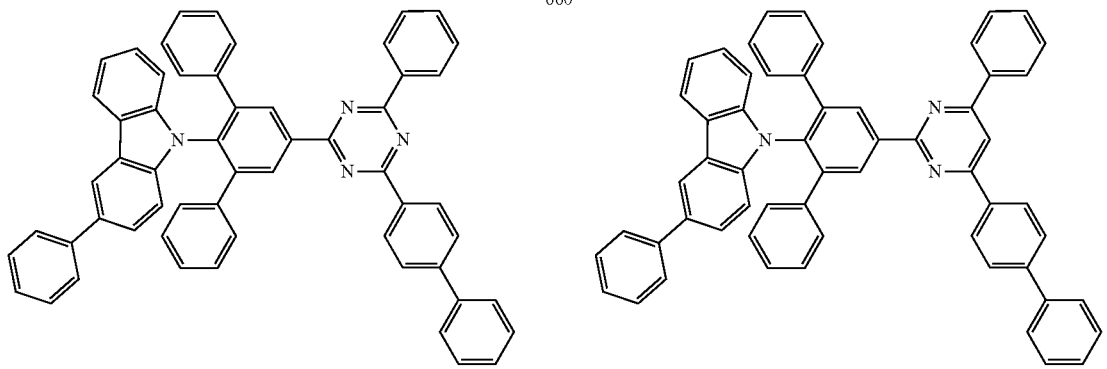
662 663
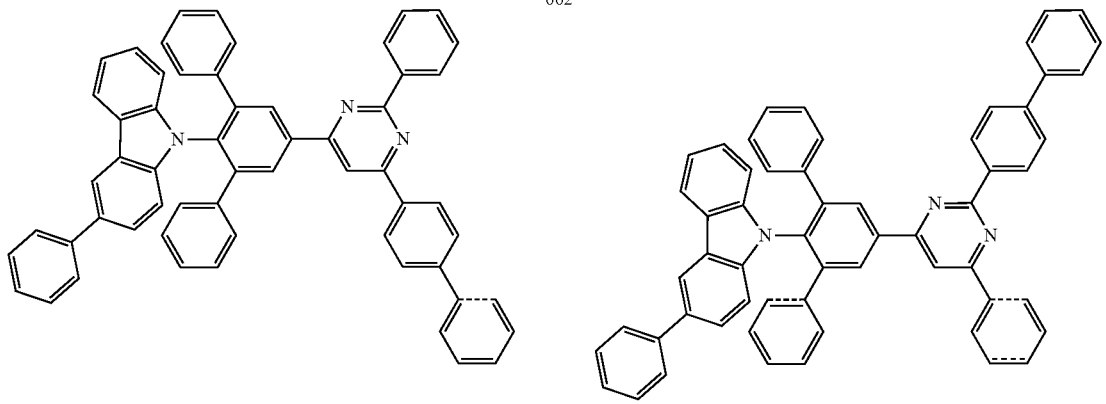

-continued
| 664 | 665 |
|---|---|
| 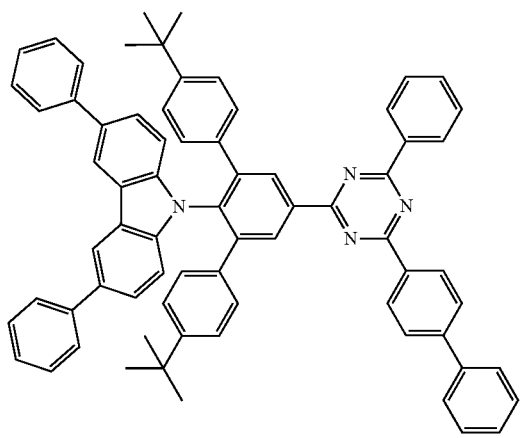 | 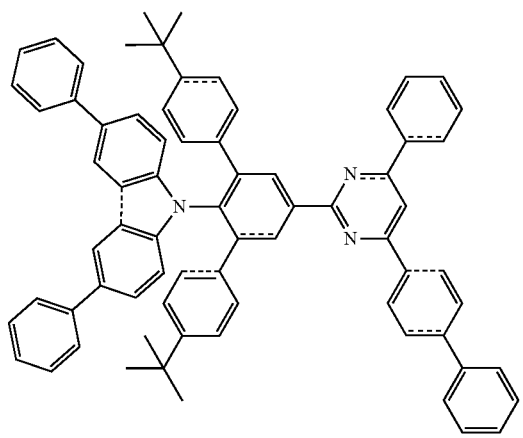 |
| 666 | 667 |
| 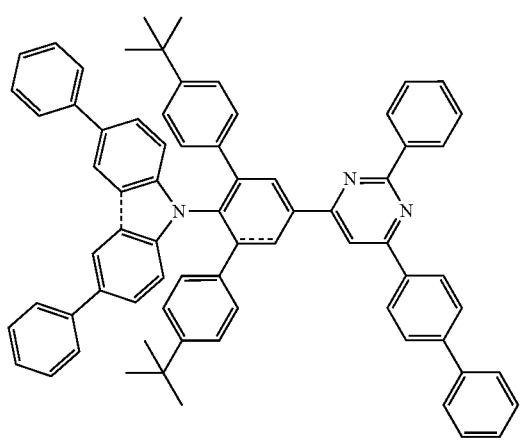 | 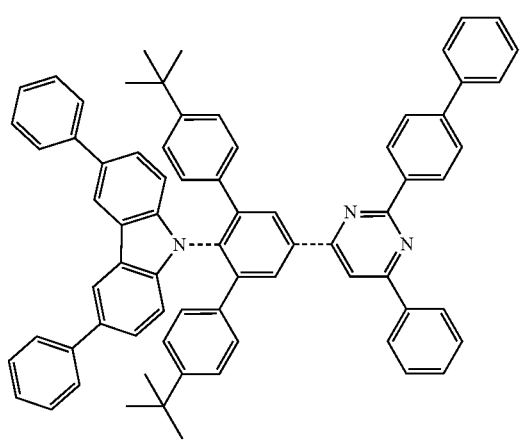 |
| 668 | 669 |
| 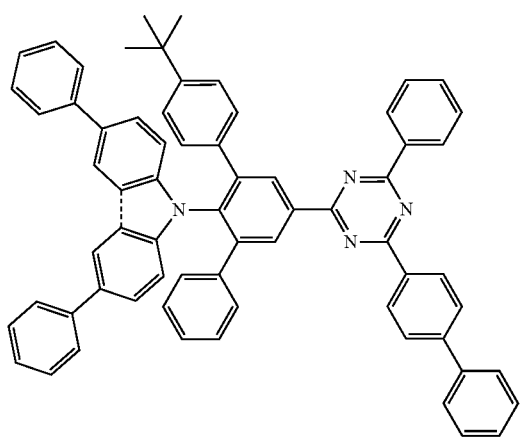 | 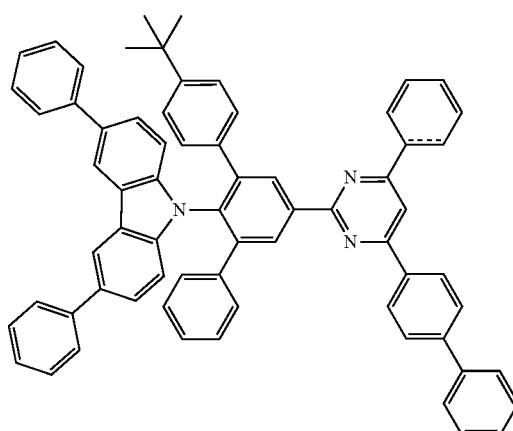 |

| 670 | 671 |
|---|---|
| 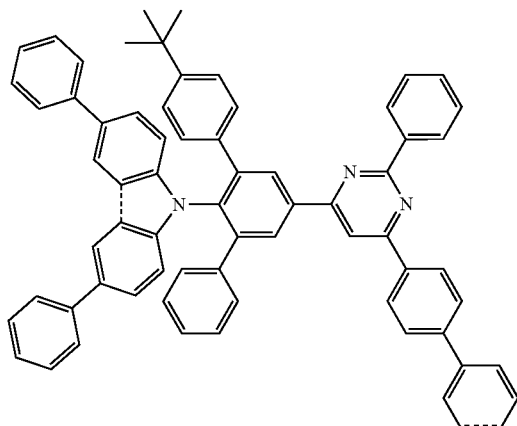 | 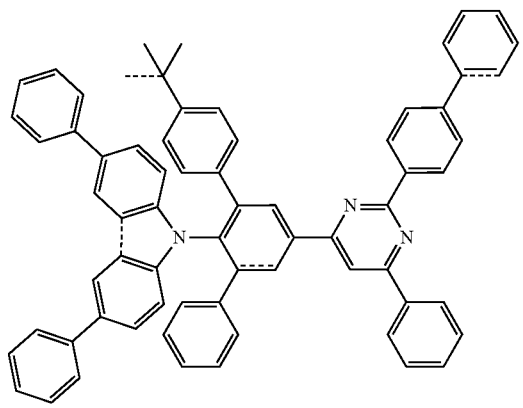 |
| 672 | 673 |
| 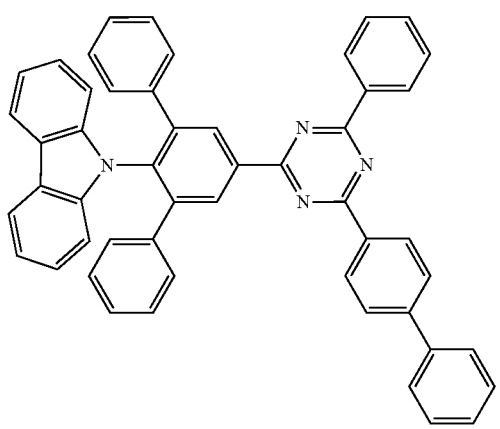 | 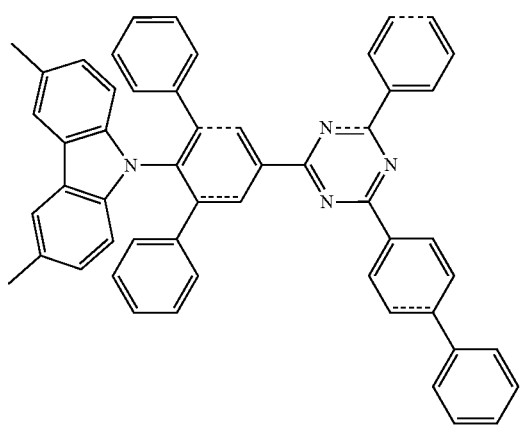 |
| 674 | 675 |
| 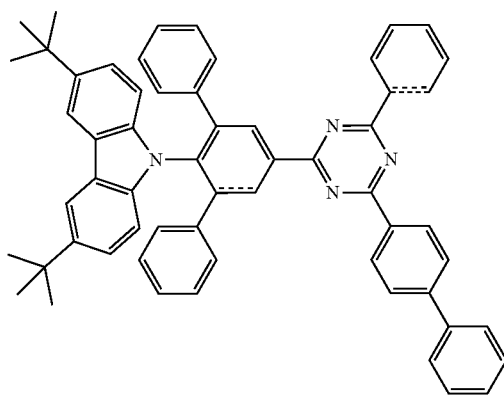 | 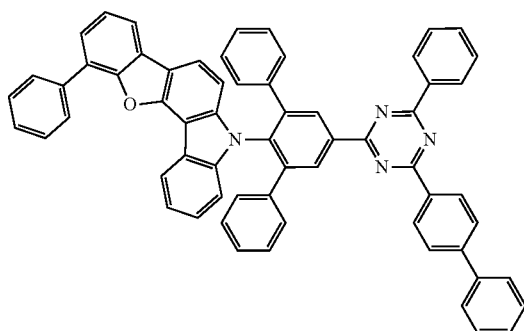 |
| 676 | 677 |
| 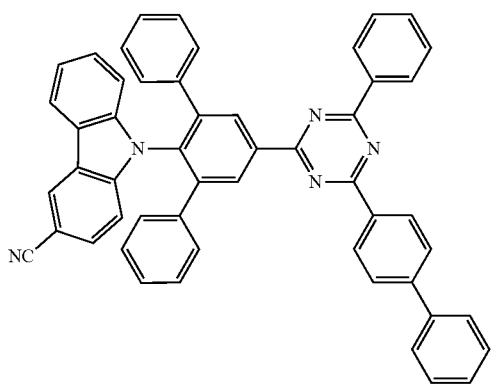 | 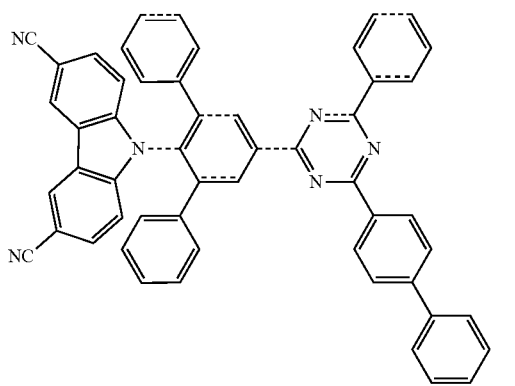 |

-continued
678
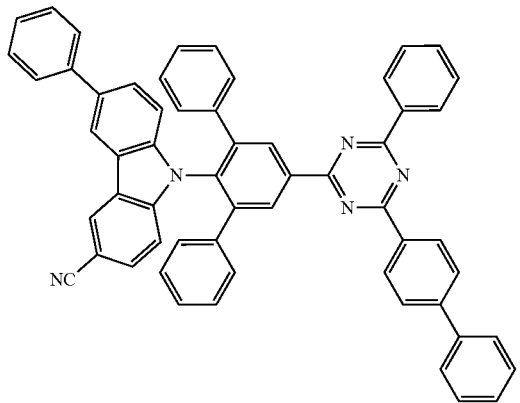
679
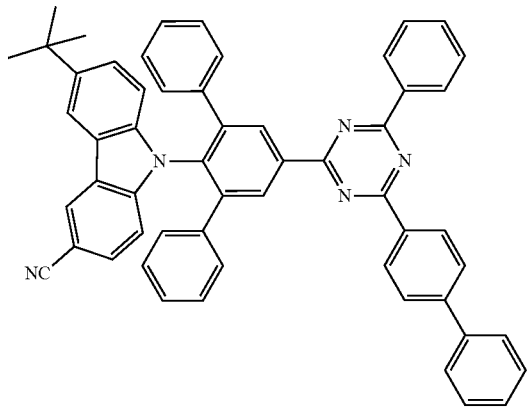
680
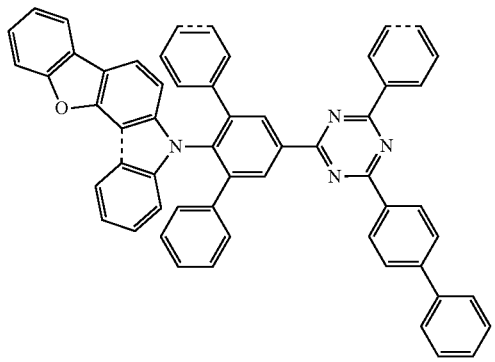
681
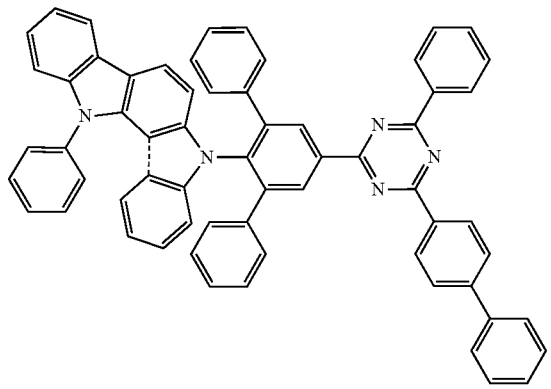
682
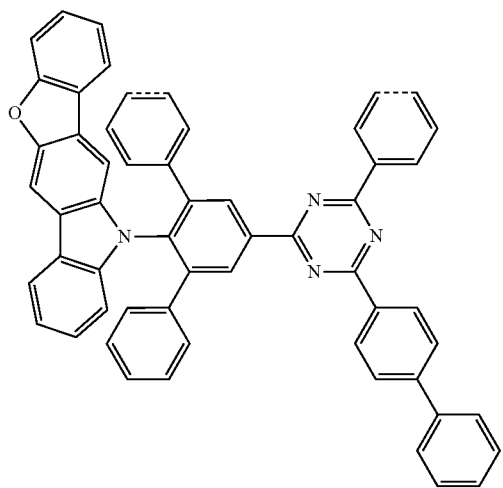
683
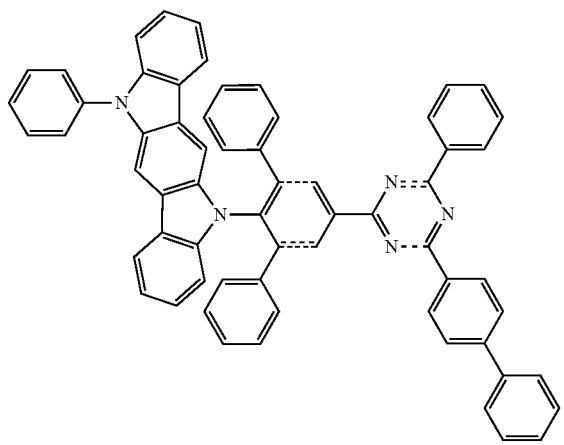

| 684 | 685 |
|---|---|
| 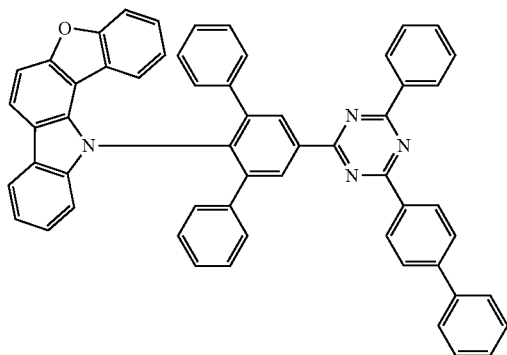 | 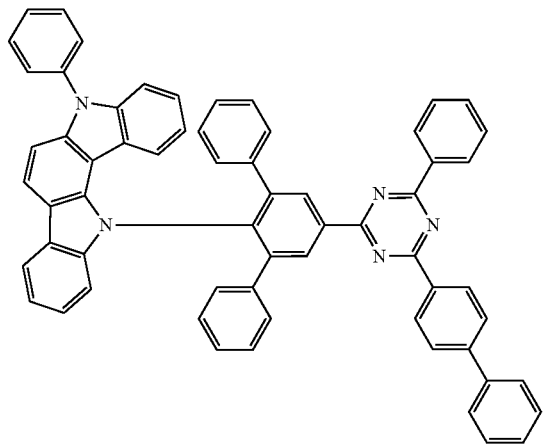 |
| 686 | 687 |
| 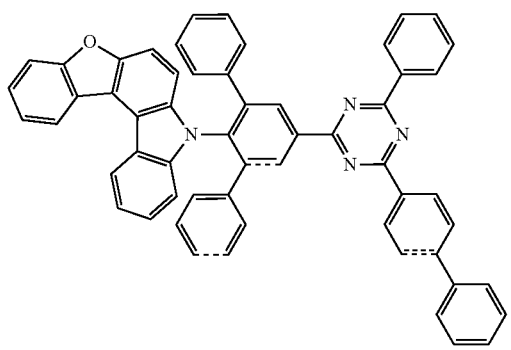 | 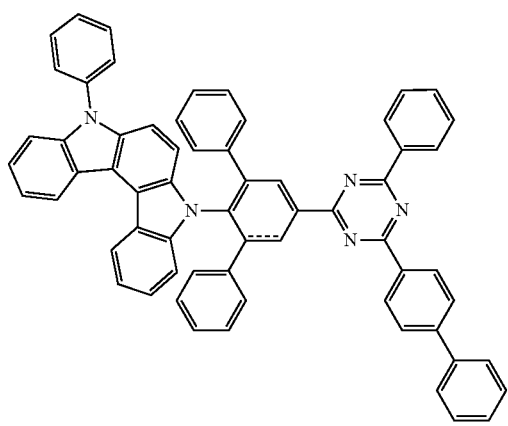 |
| 688 | 689 |
| 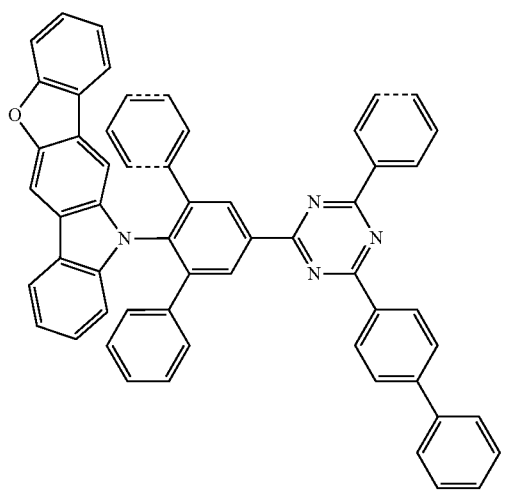 | 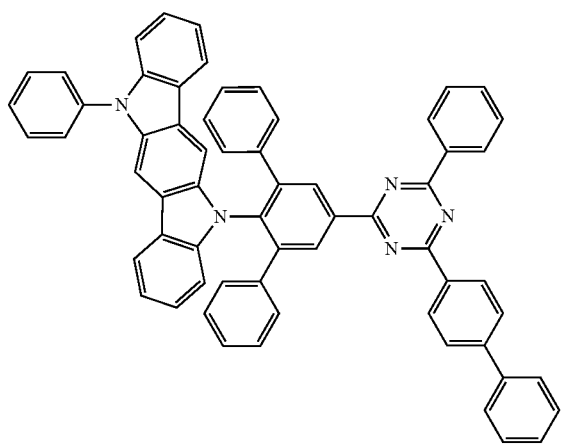 |

-continued
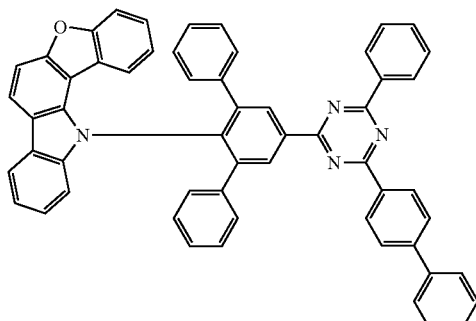
690
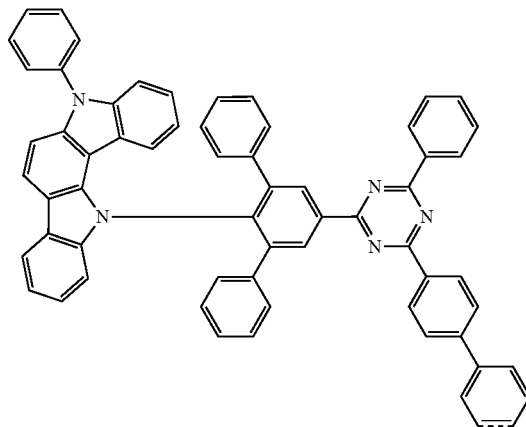
691
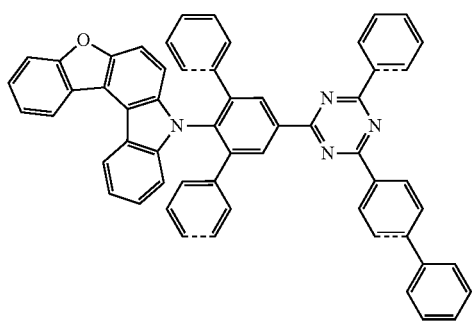
692
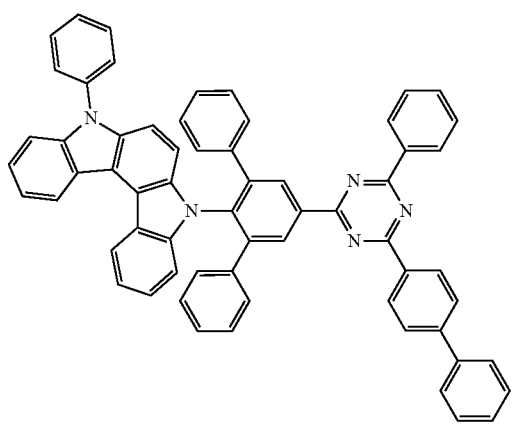
693
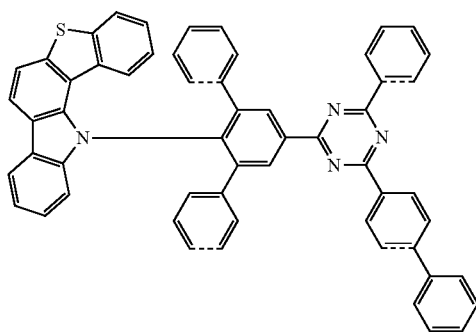
694
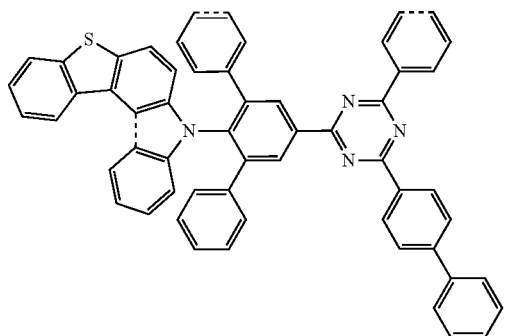
695

696
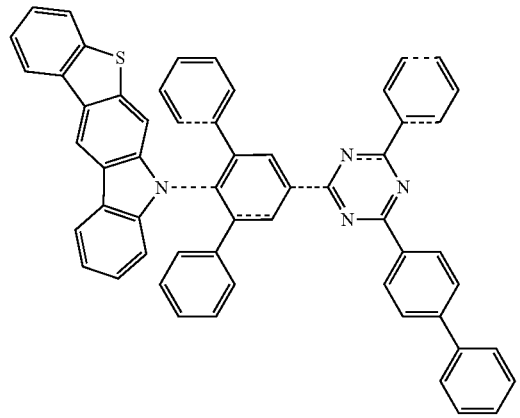
697
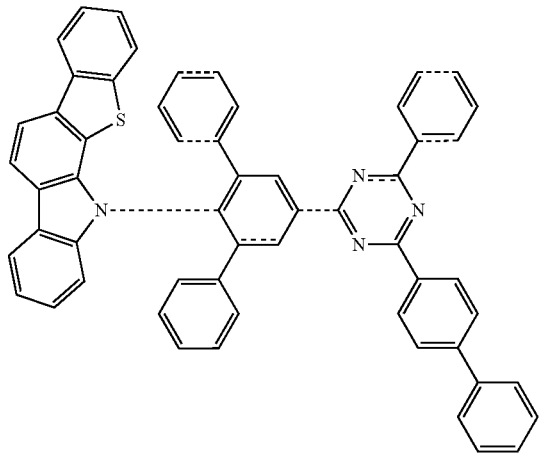
698
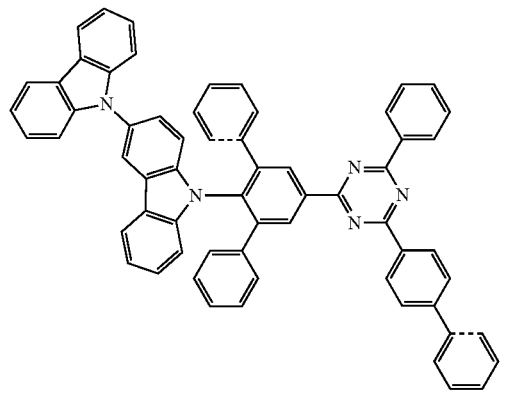
699

700
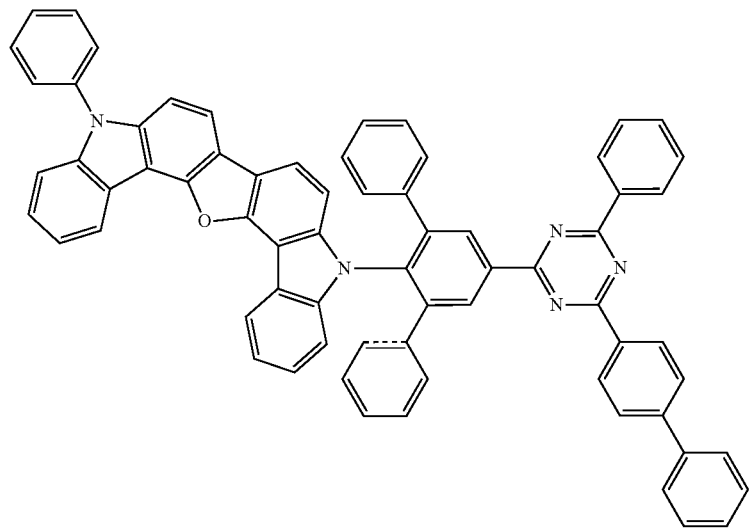

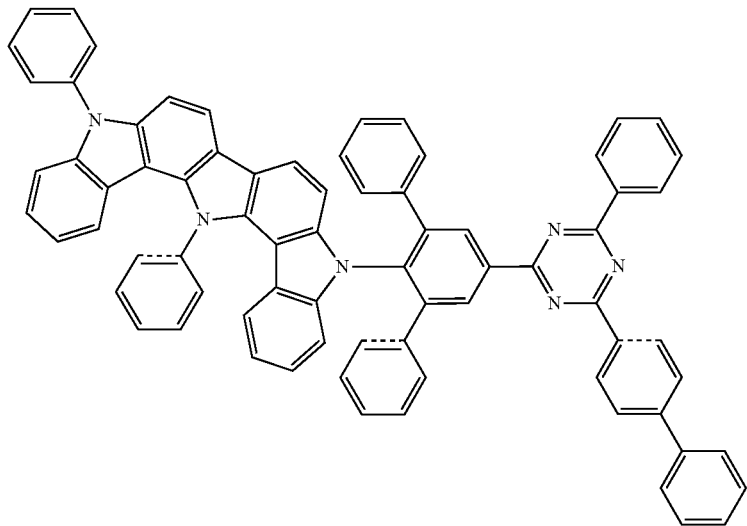
701
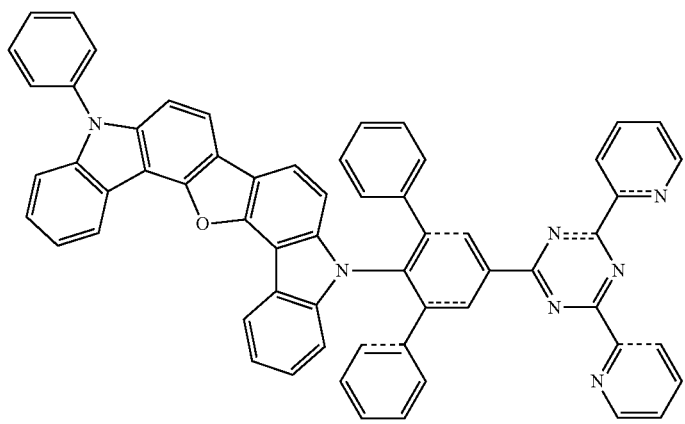
702
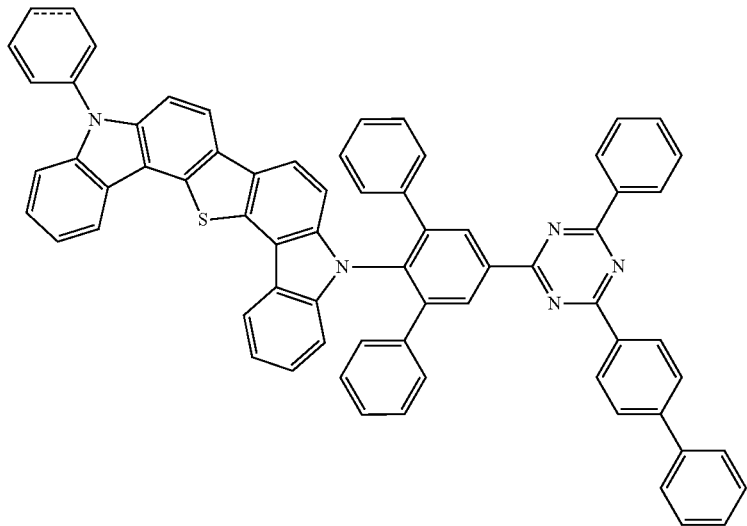
703

-continued
704
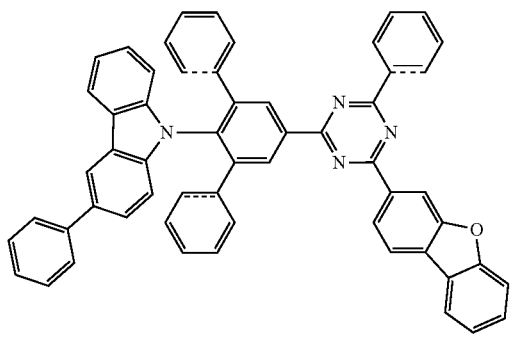
705
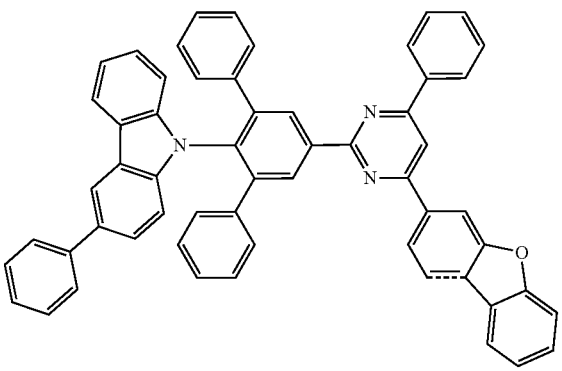
706
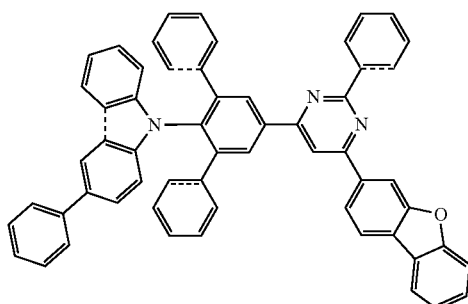
707
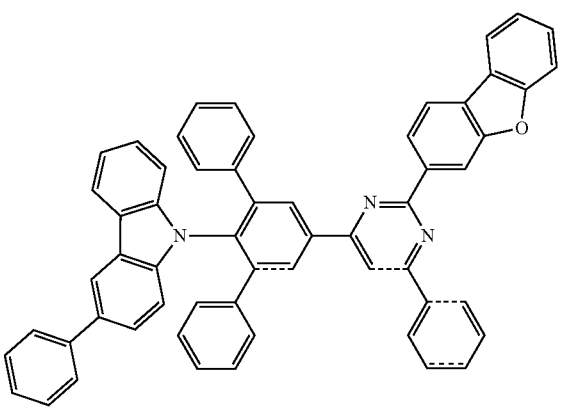
708
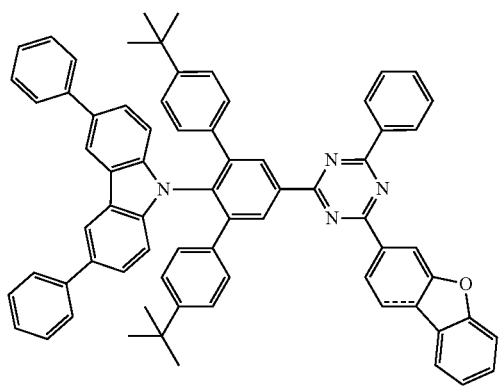
709
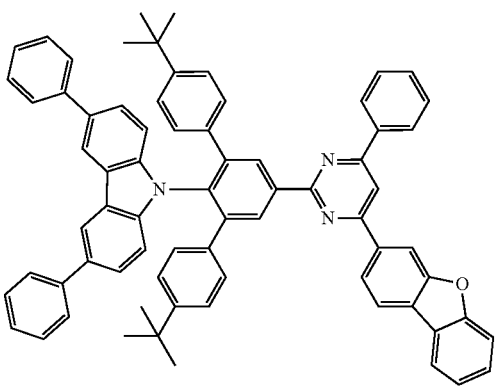
710
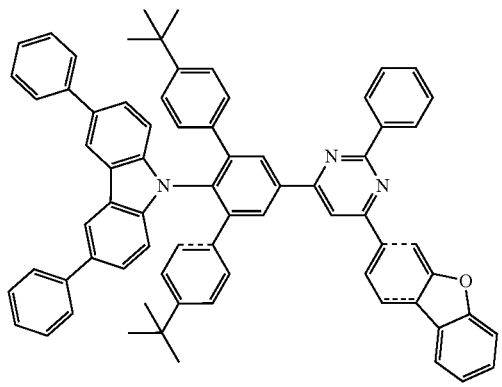
711
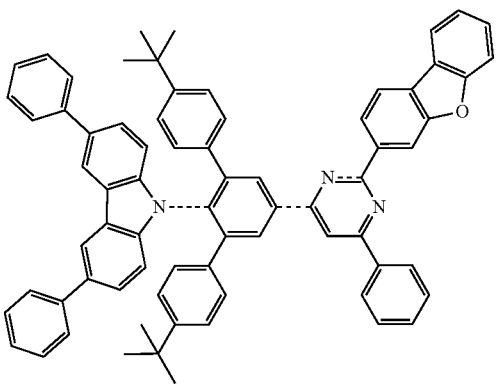

-continued
712
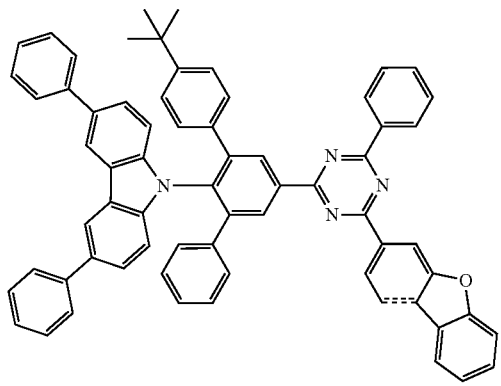
713
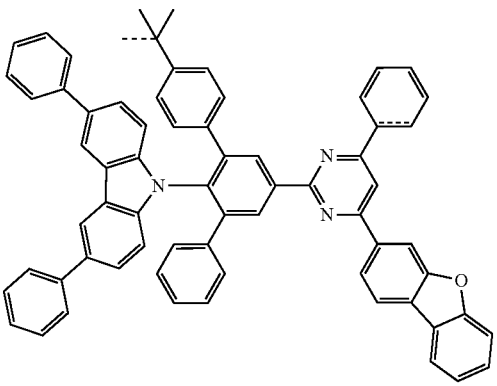
714
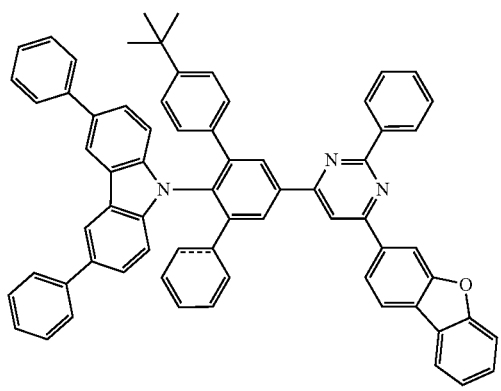
715
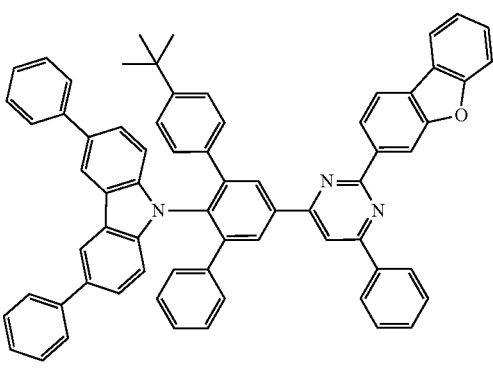
716
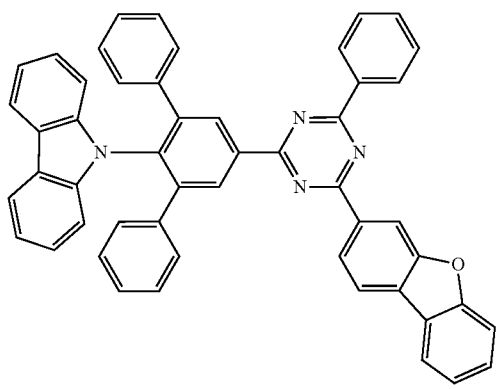
717
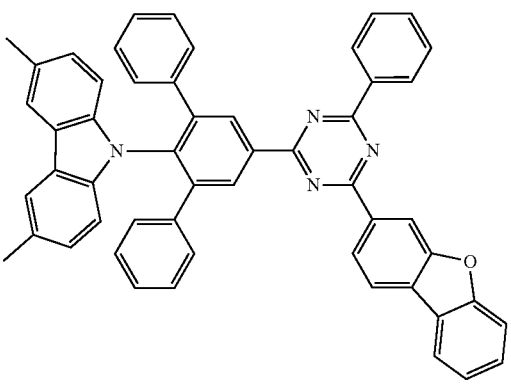
718
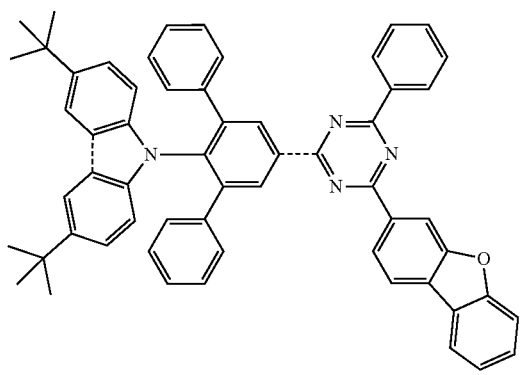
719
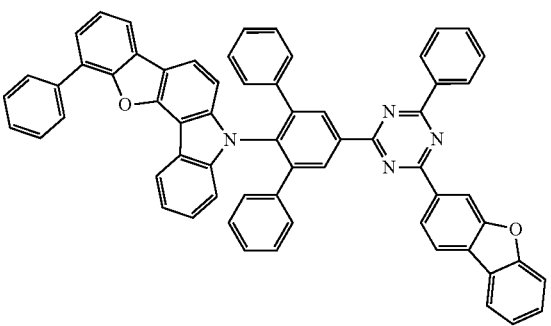

-continued
720
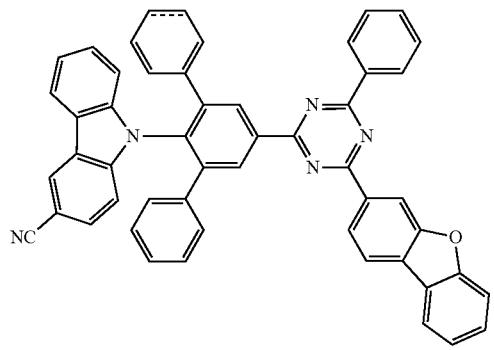
721
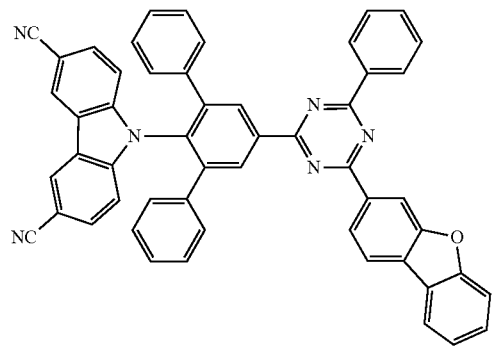
722
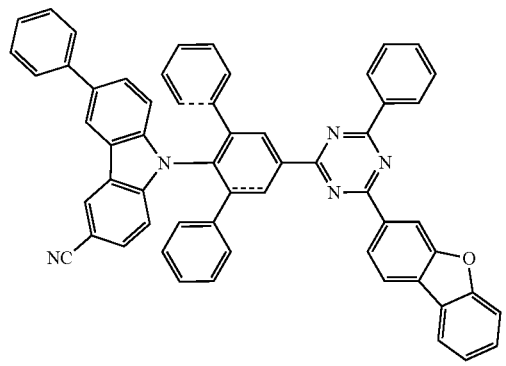
723
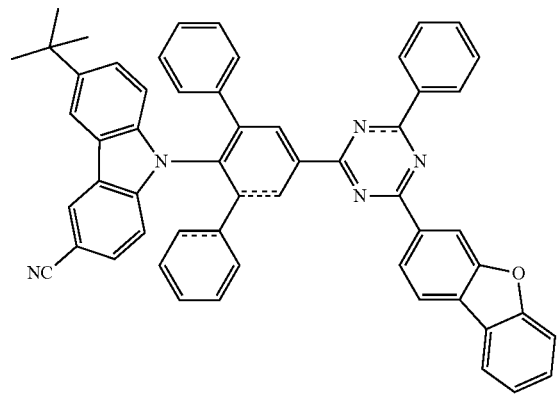
724
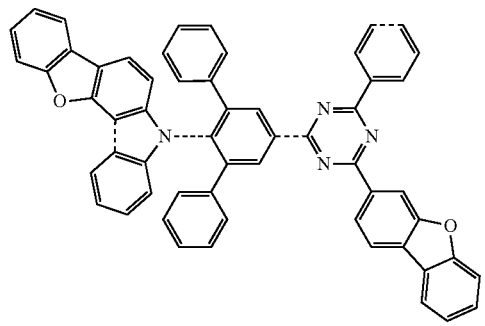
725
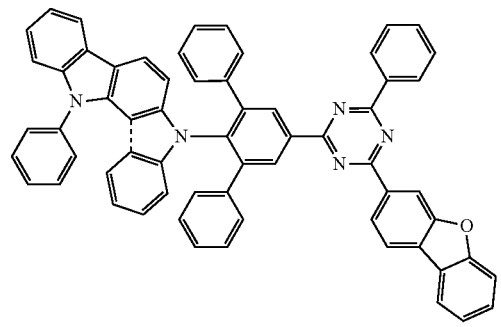
726
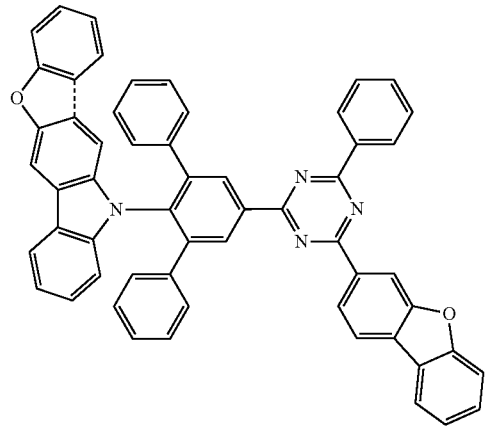
727
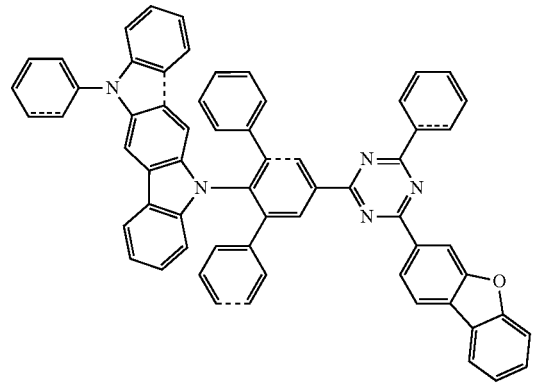

-continued
728
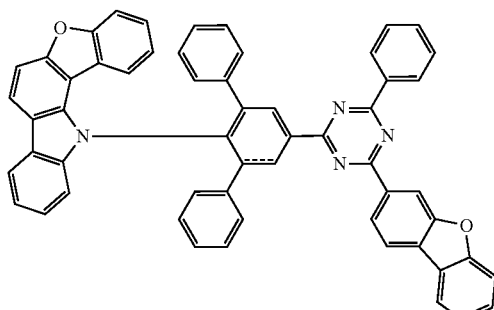
729
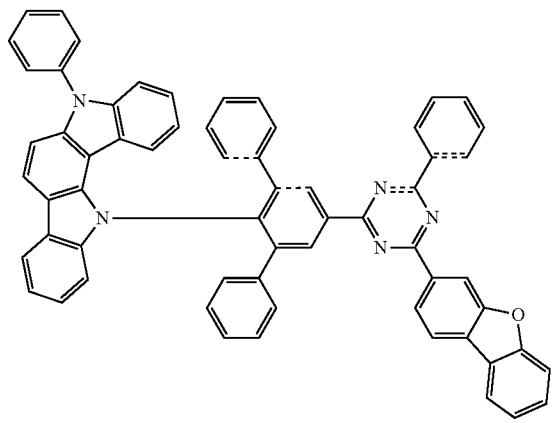
730
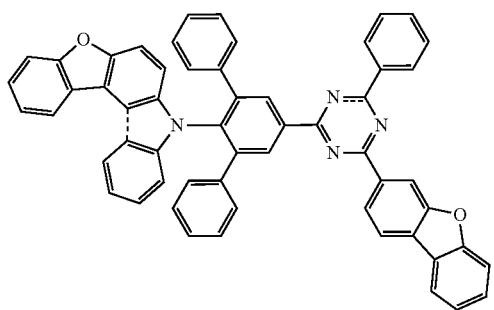
731
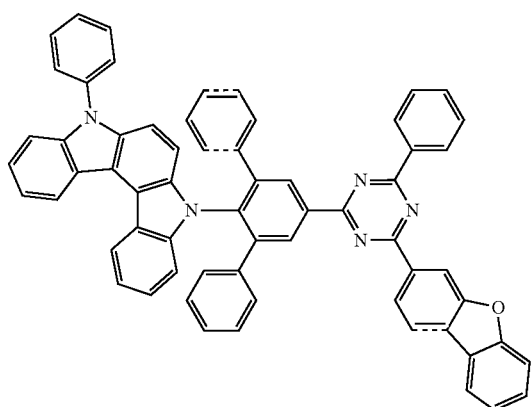
732
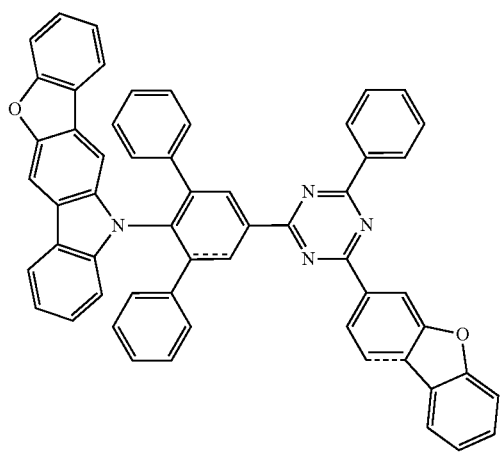
733
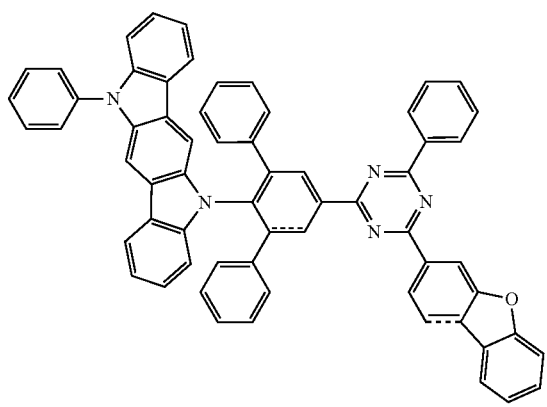

-continued
734
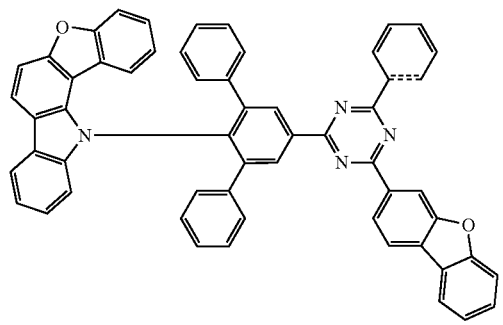
735
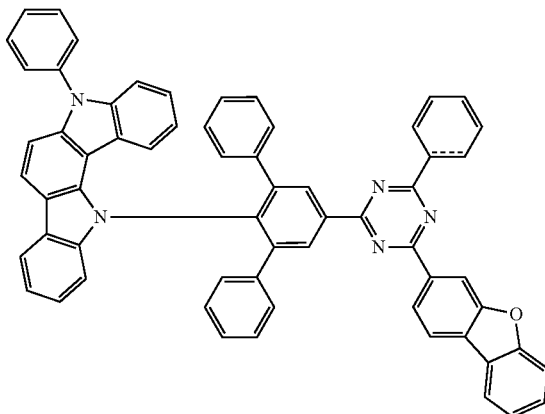
736
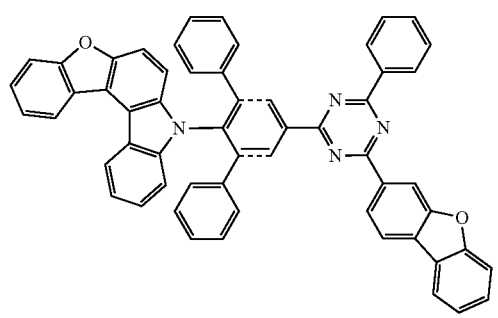
737
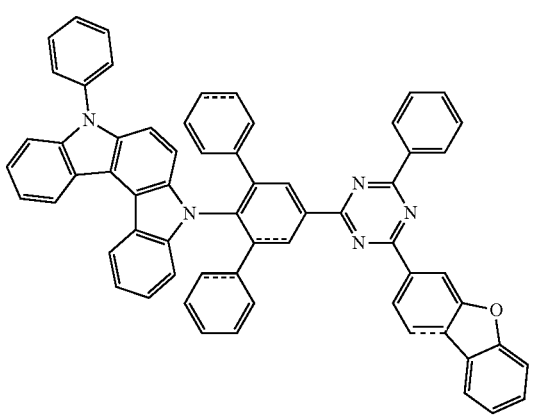
738
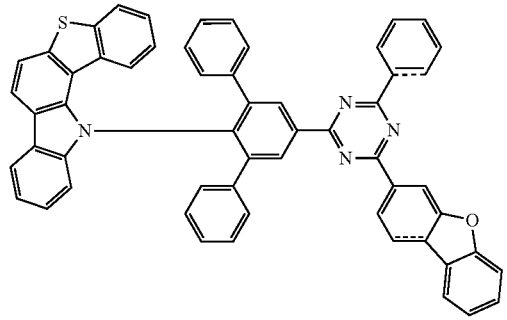
739
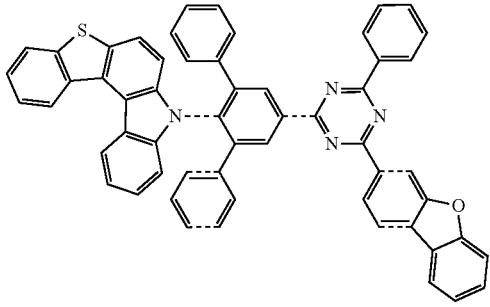
740
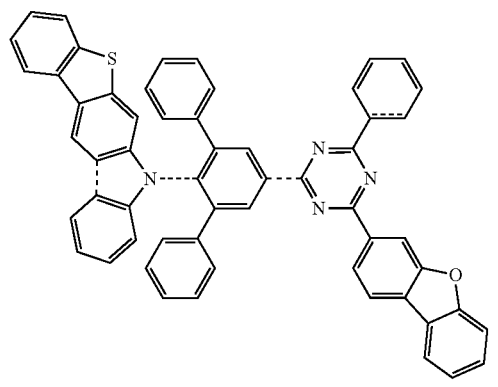
741
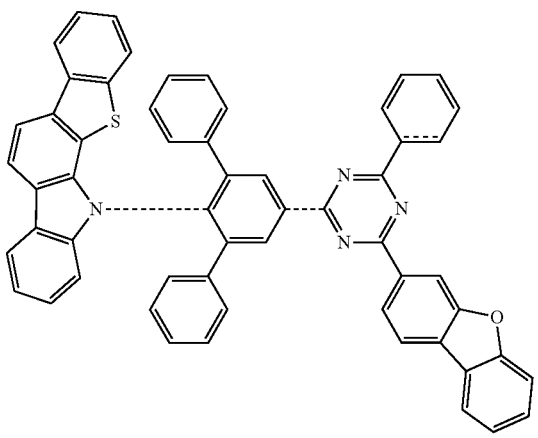

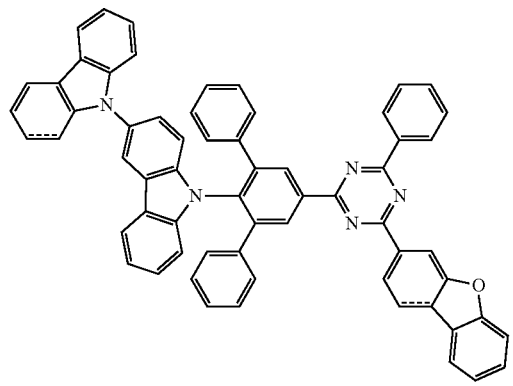
742
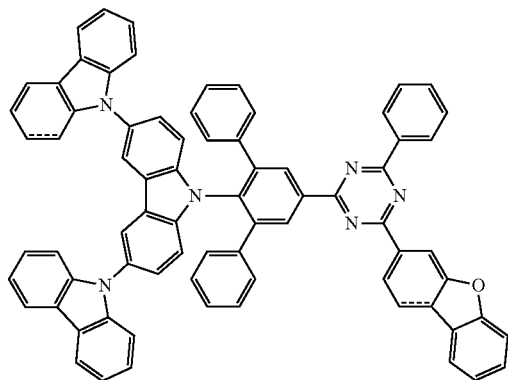
743
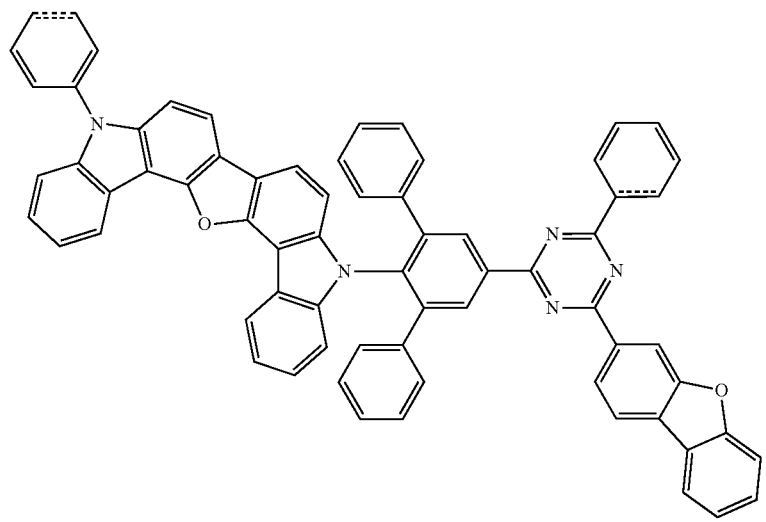
744
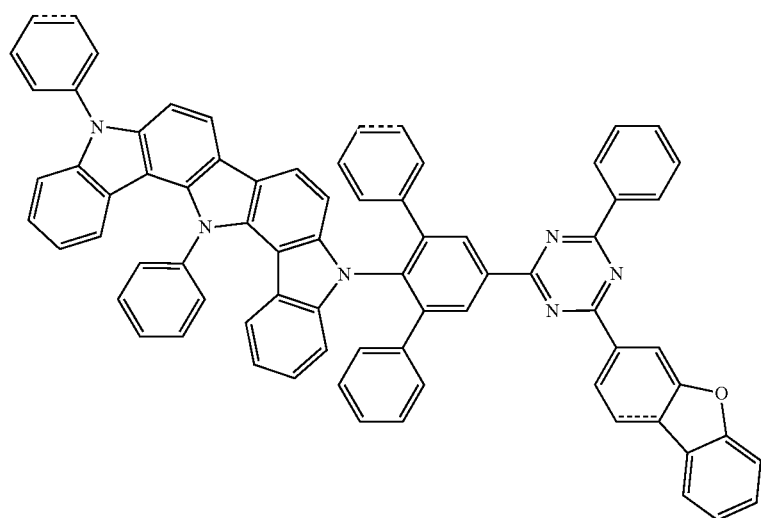
745

-continued
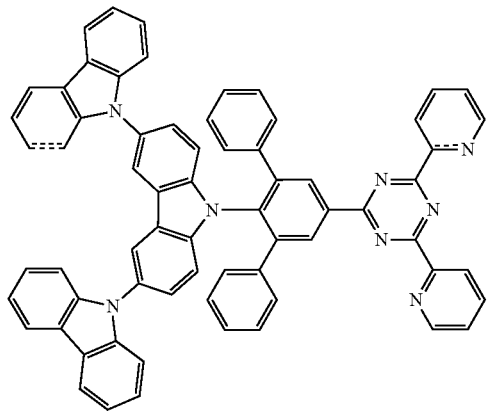
746
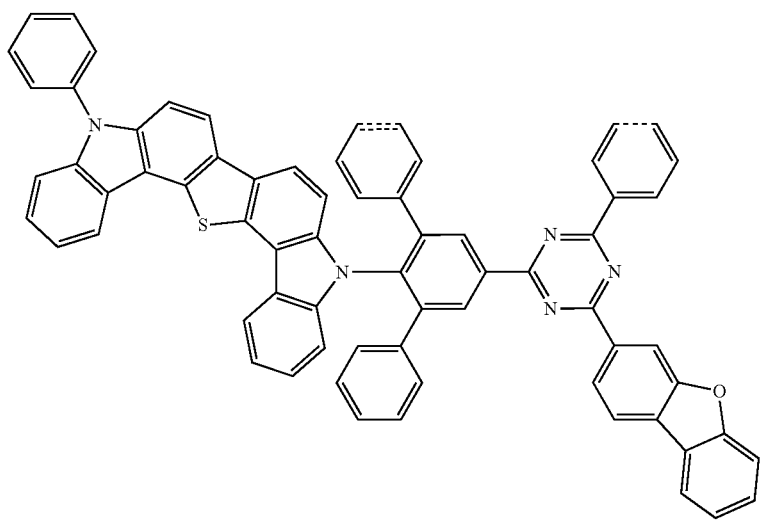
747
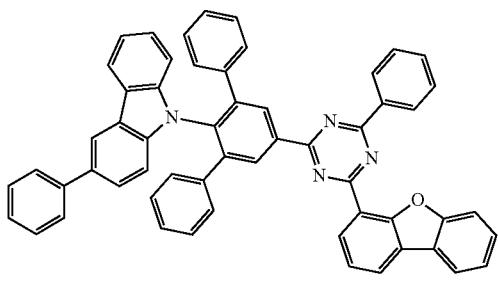
748
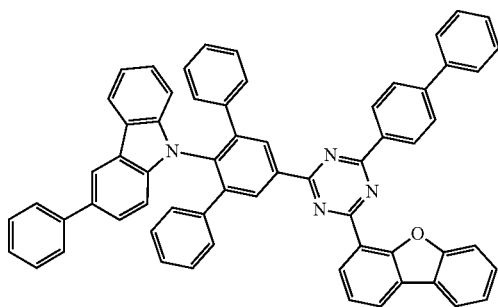
749
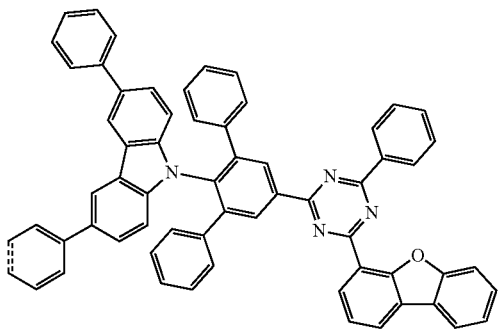
750
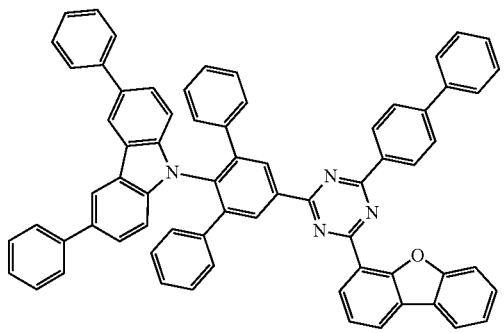
751

-continued
| 752 | 753 |
|---|---|
| 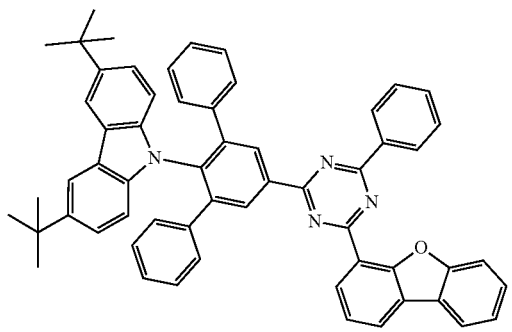 | 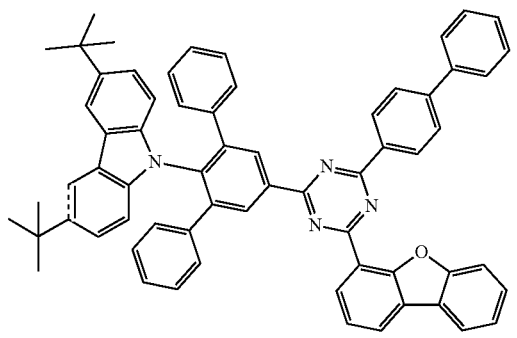 |
| 754 | 755 |
| 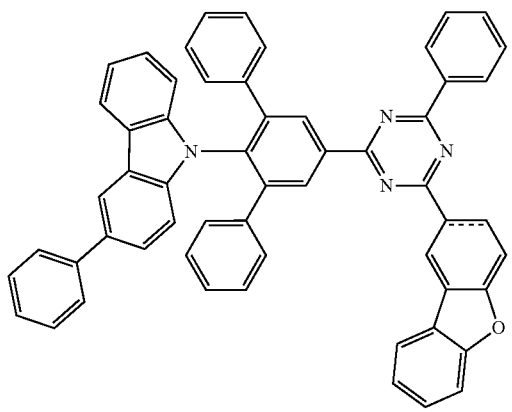 | 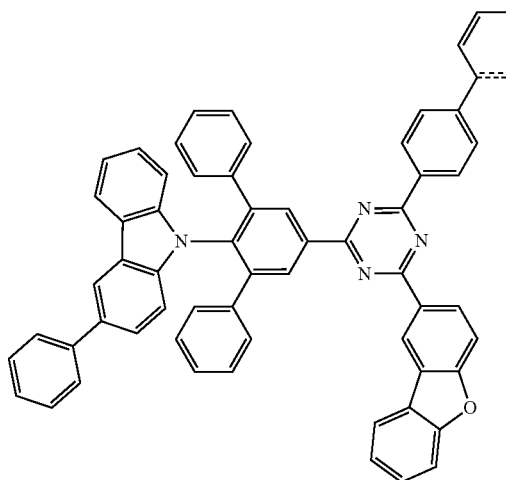 |
| 756 | 757 |
| 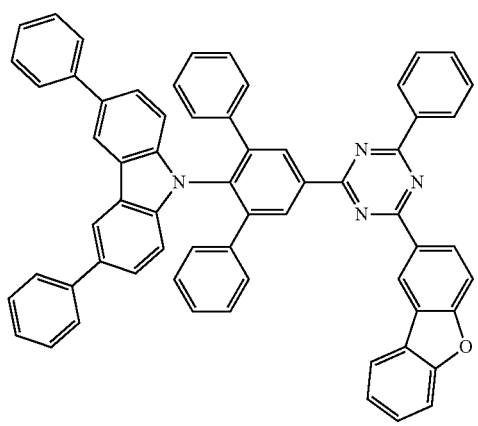 | 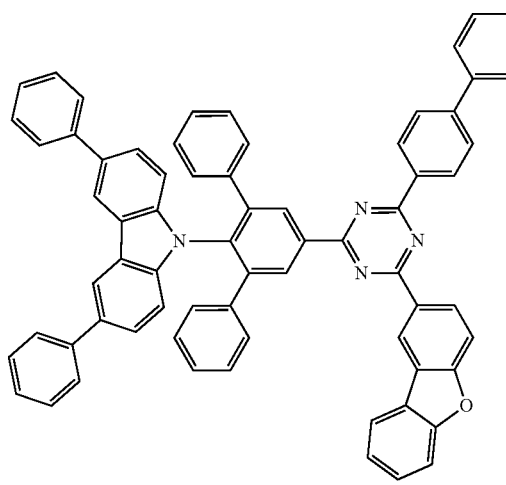 |

-continued
758
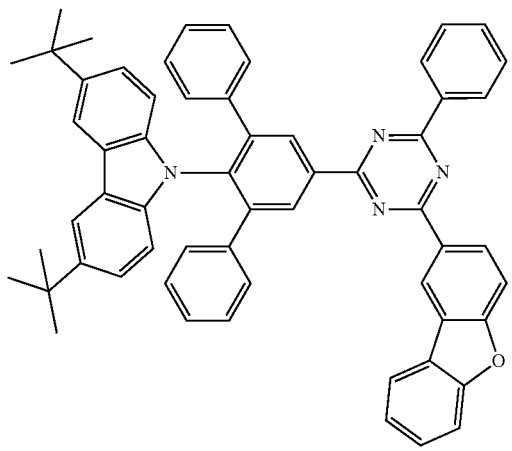
759
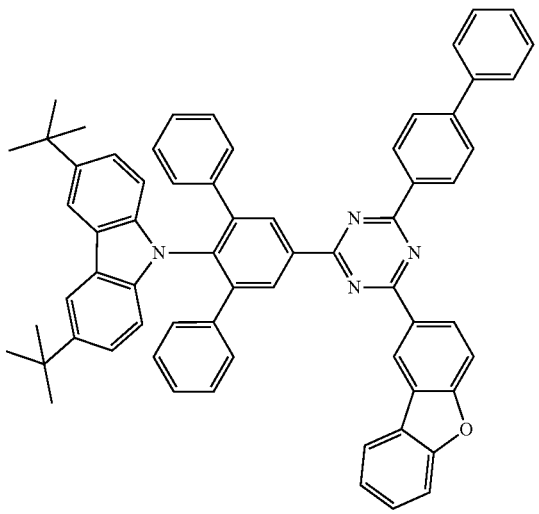
760
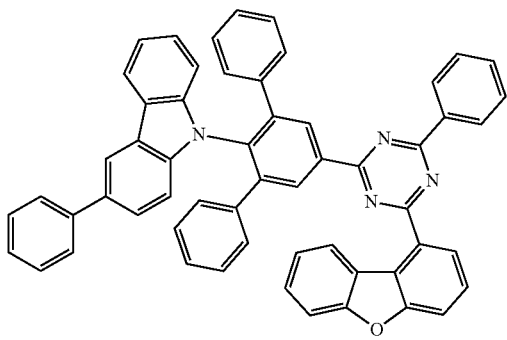
761
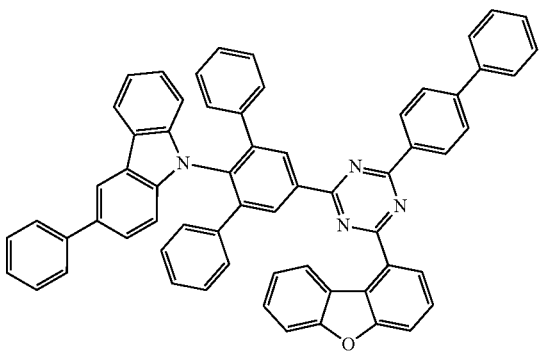
762
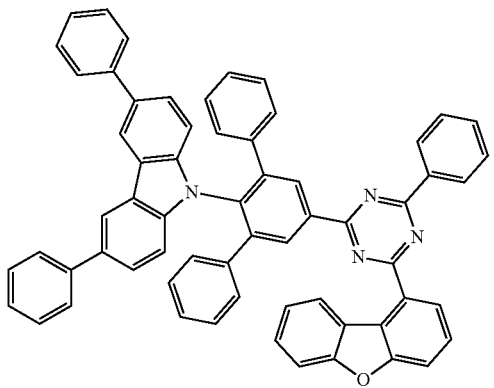
763
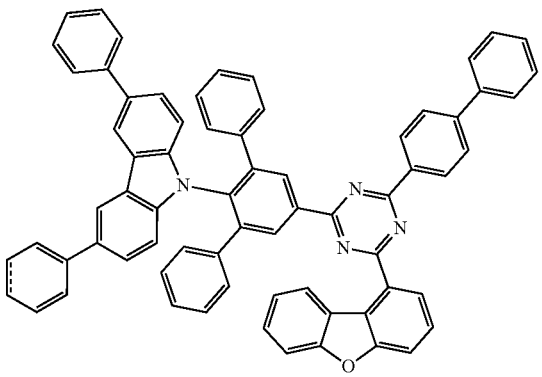

764
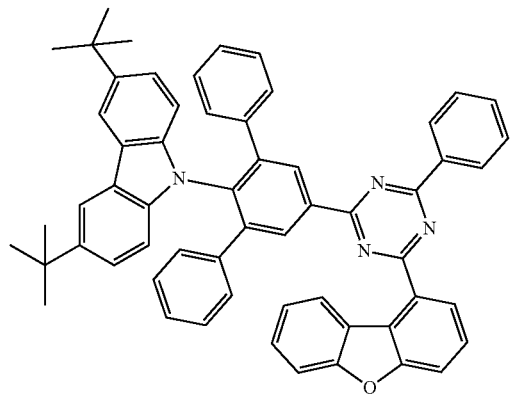
765
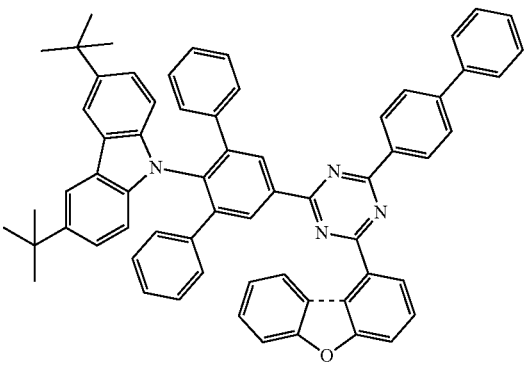
766
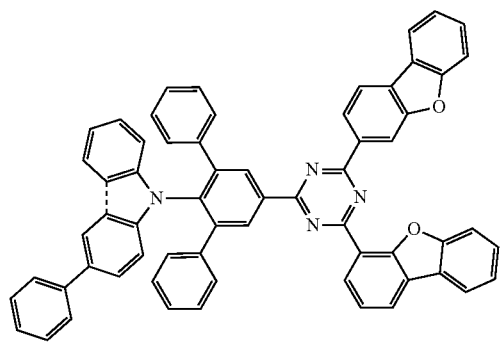
767
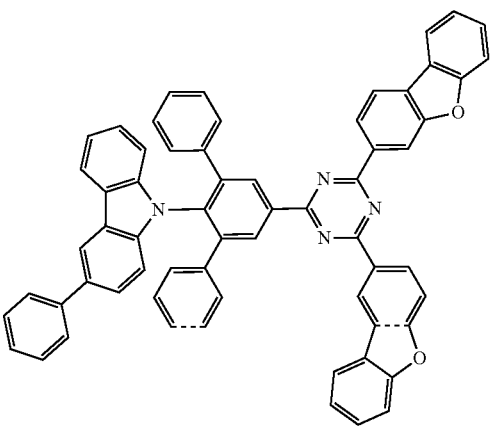
768
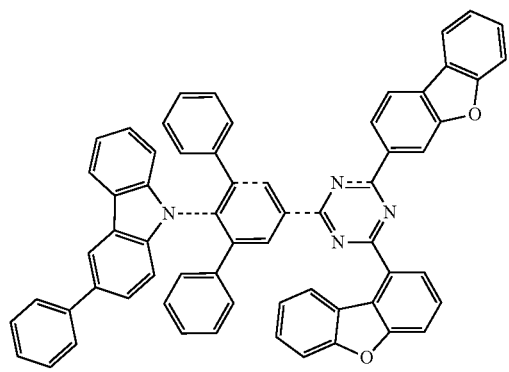
769
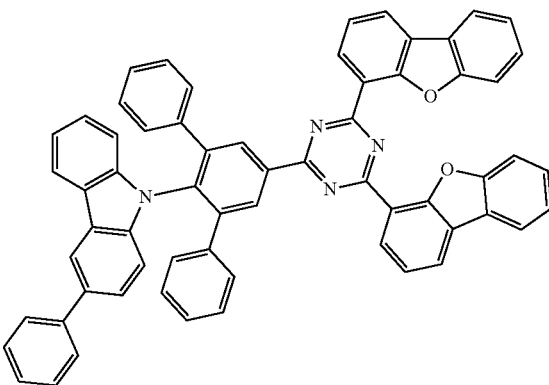
770
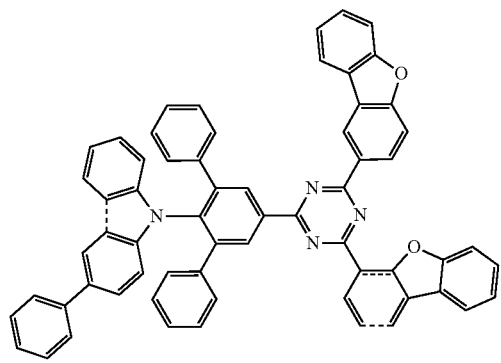
771

-continued
772
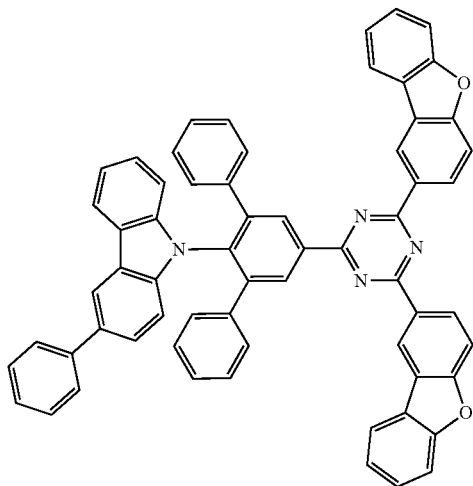
773
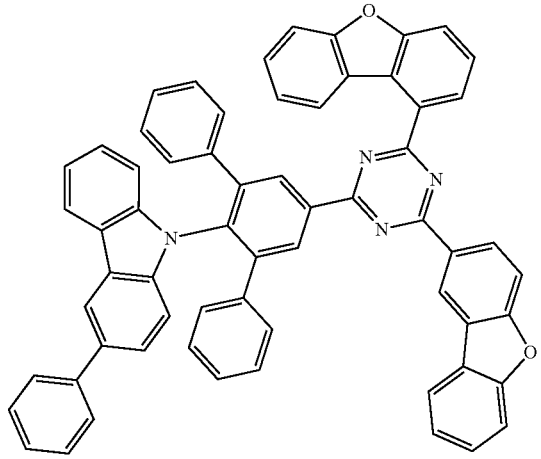
774
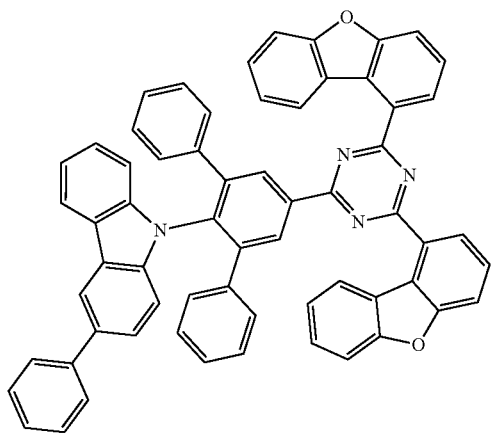
775
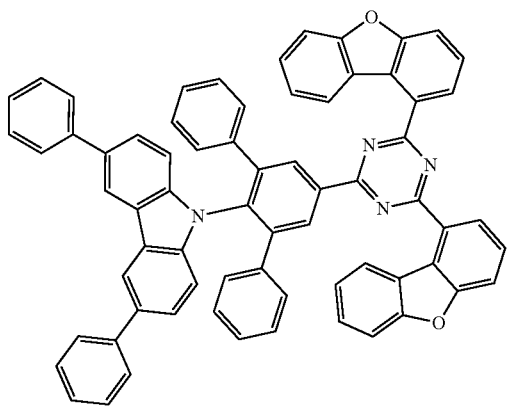
776
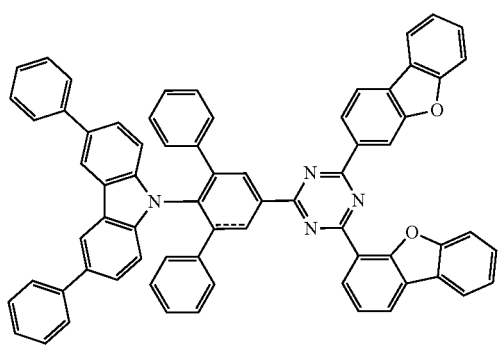
777
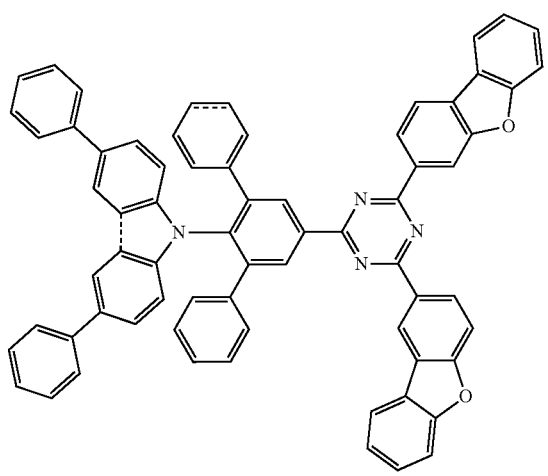

-continued
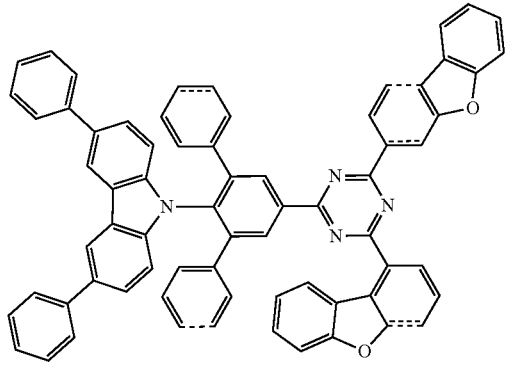
778
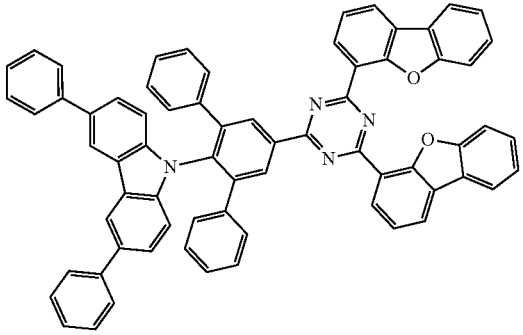
779
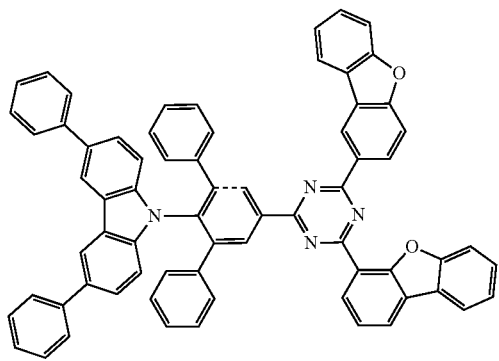
780
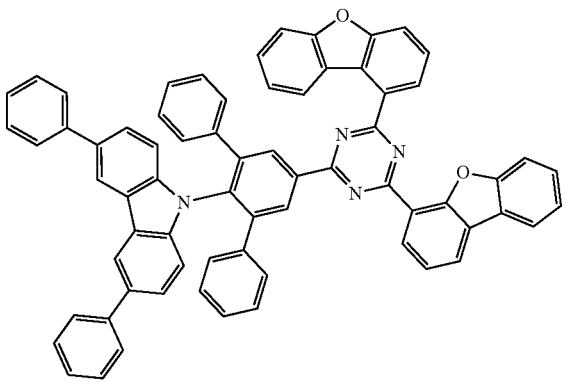
781
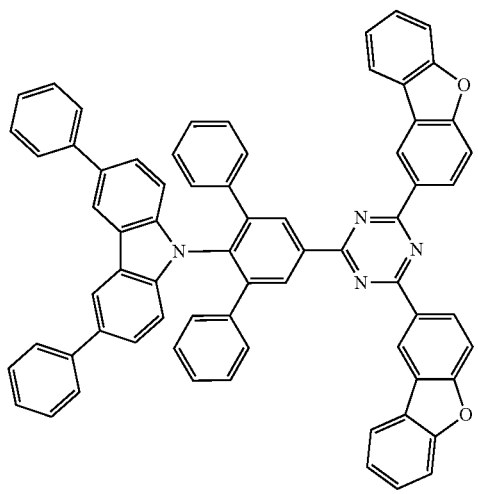
782
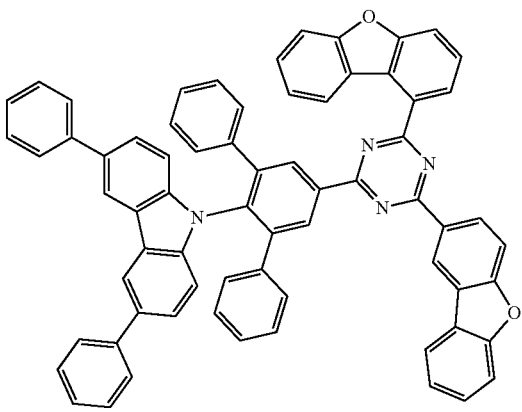
783

-continued
784
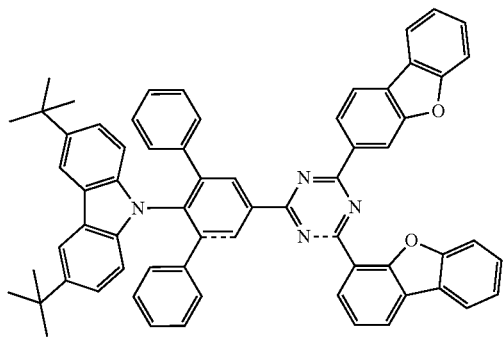
785
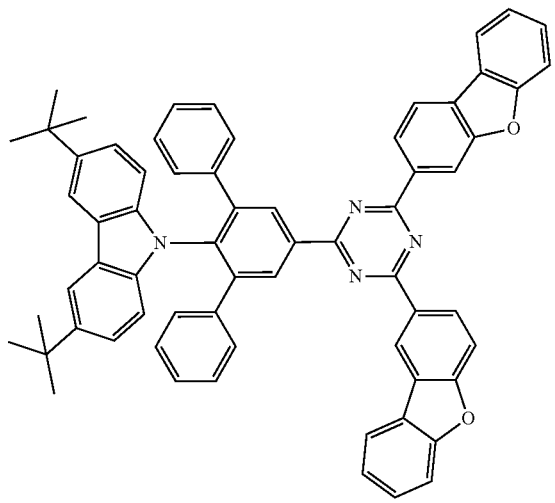
786
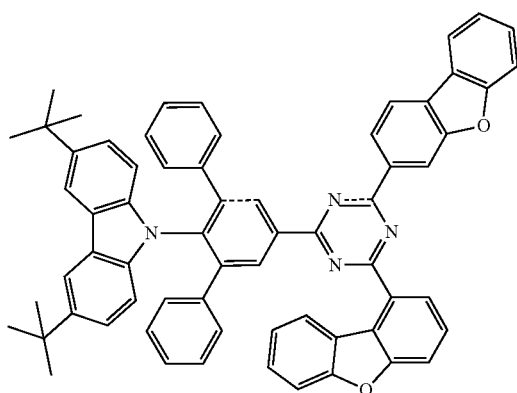
787
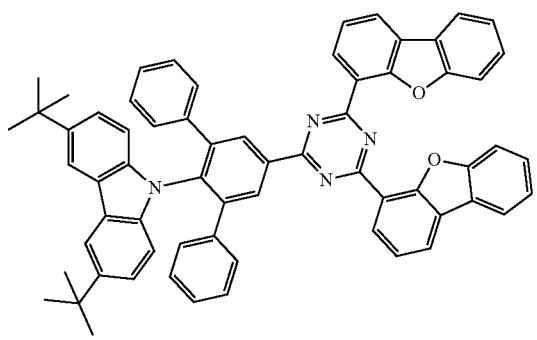
788
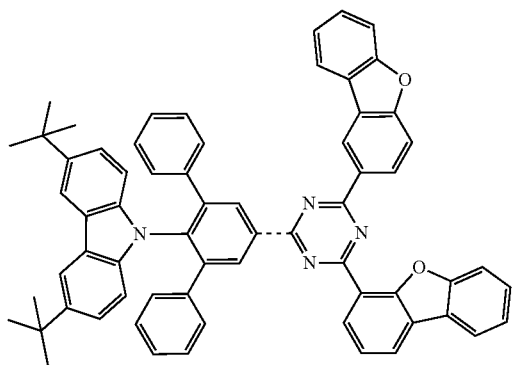
789
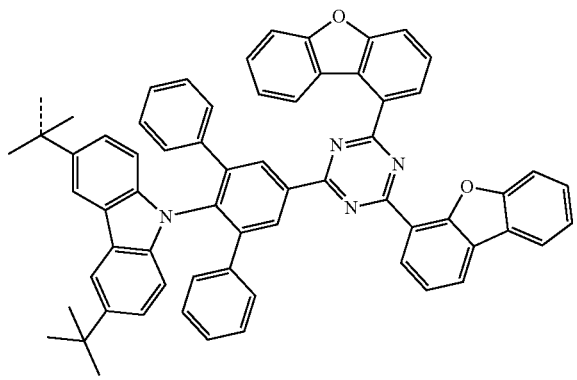

-continued
790
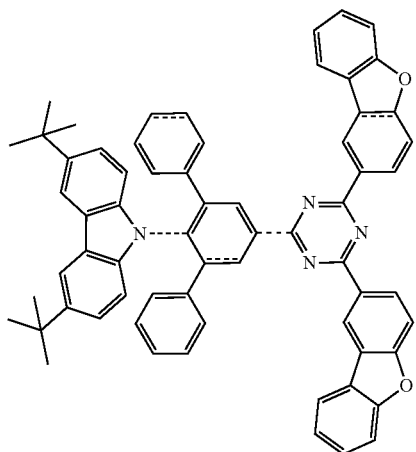
791
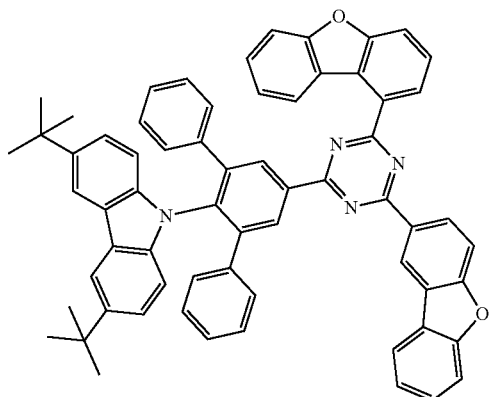
792
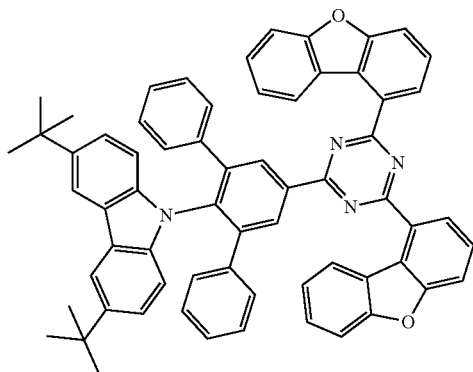
793
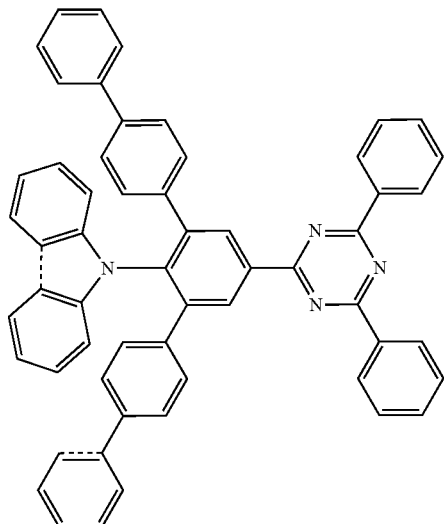
794
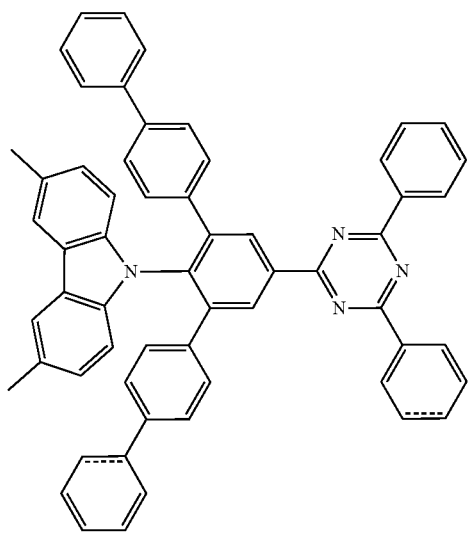
795
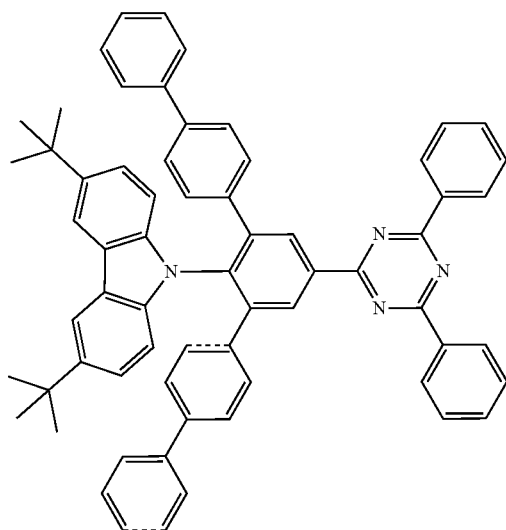

-continued
796
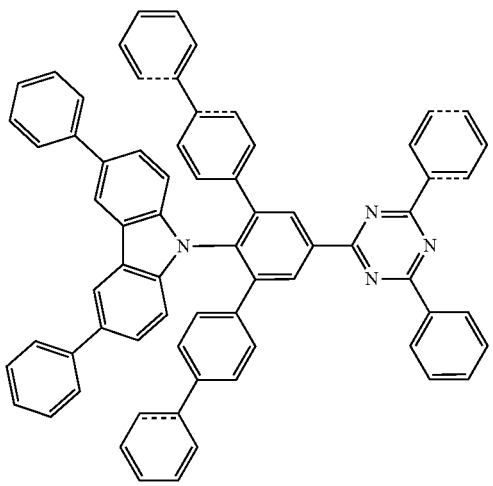
797
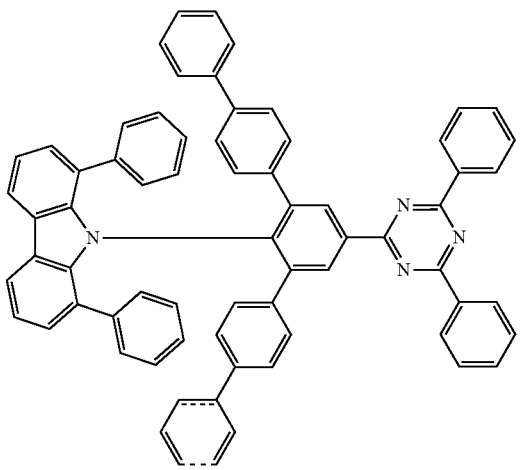
798
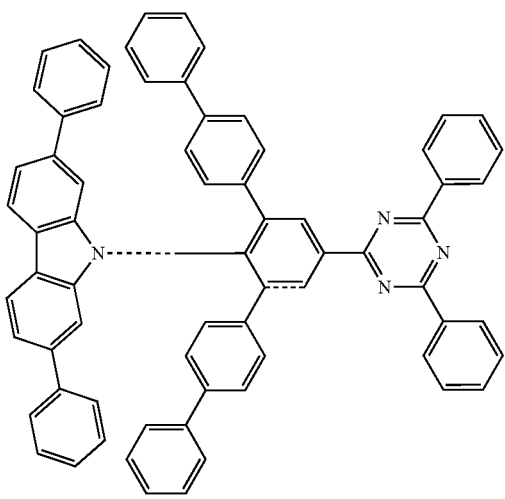
799
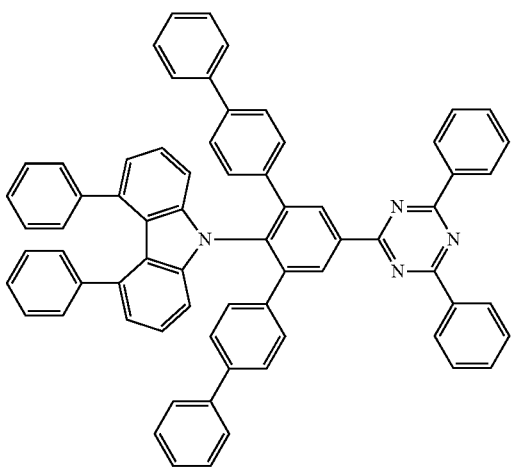
800
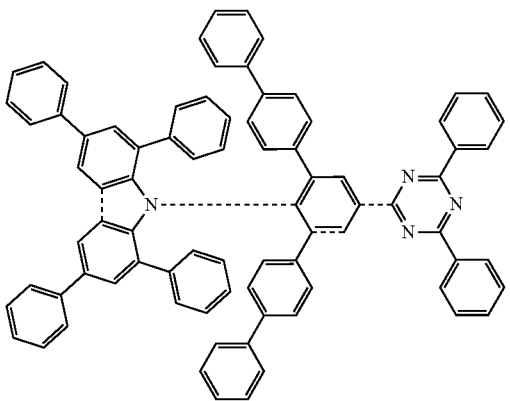
801
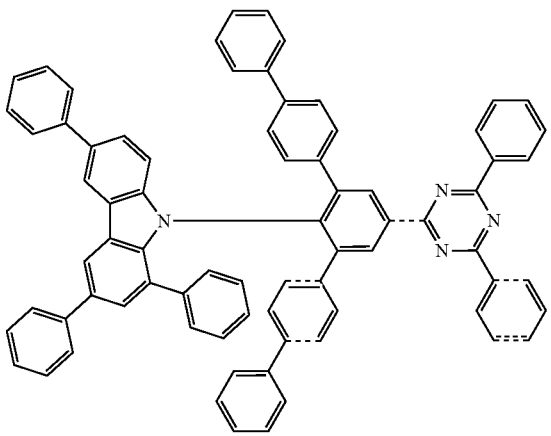

-continued
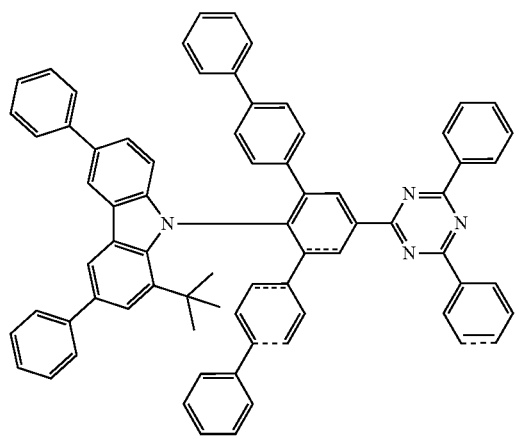
802
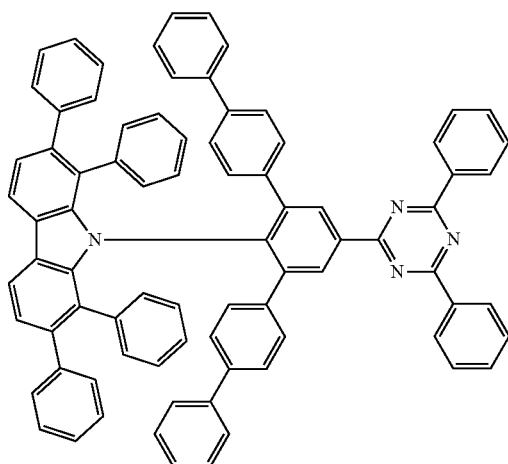
803
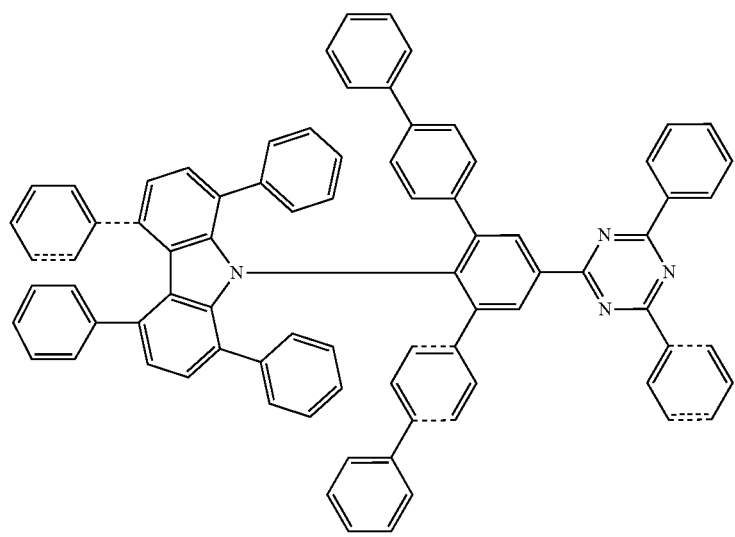
804
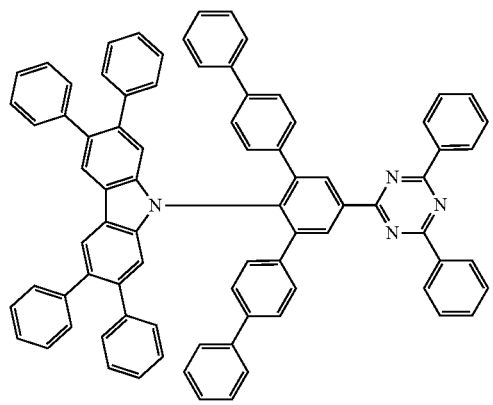
805
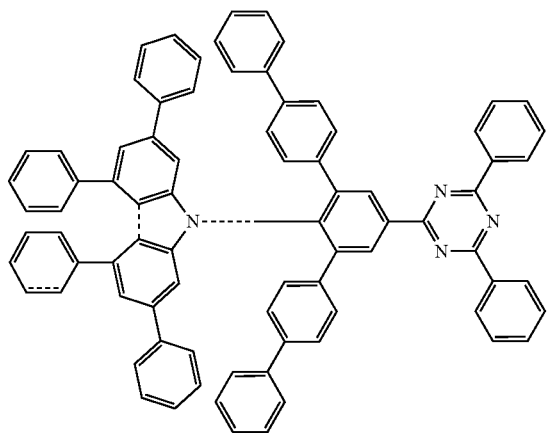
806

807 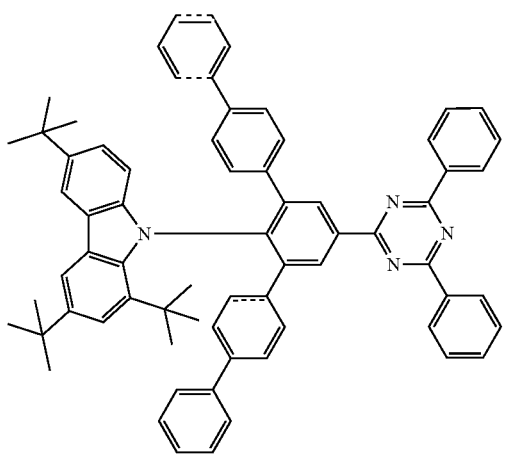
808 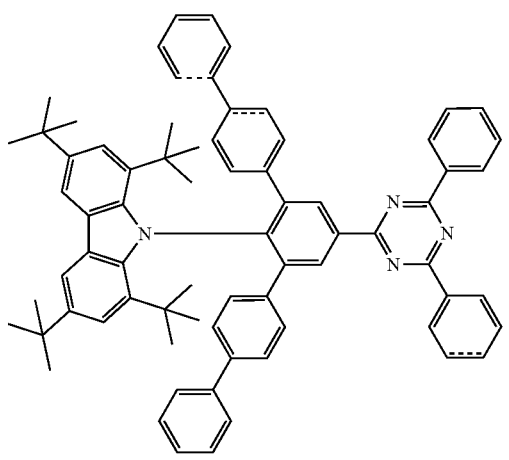
809 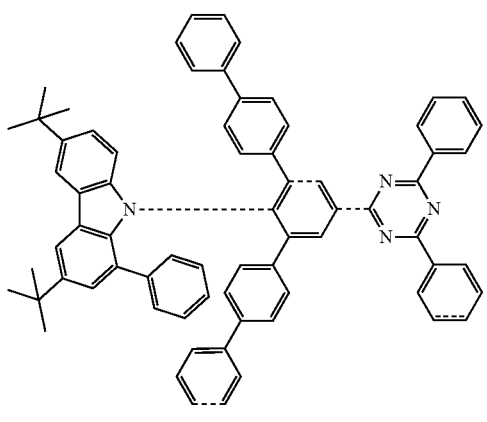
810 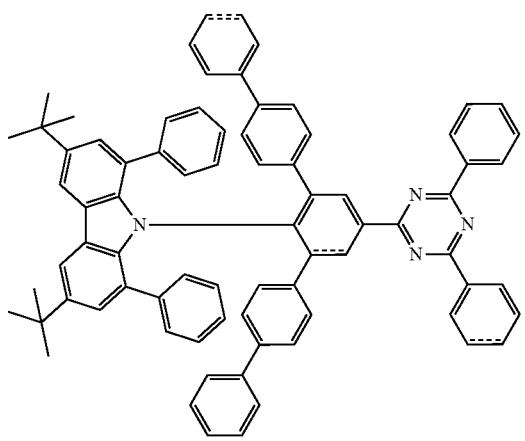
811 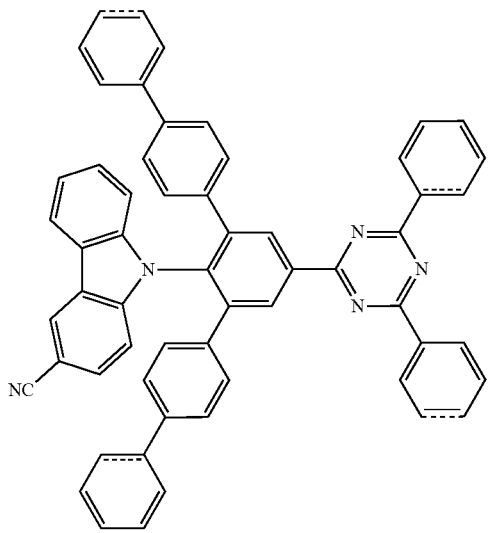
812 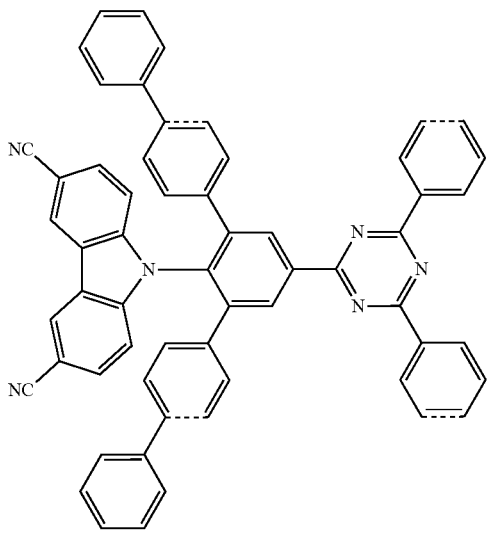

-continued
| 331 | 332 |
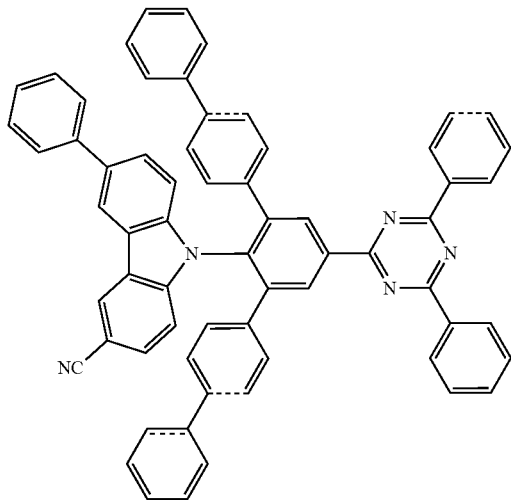
813
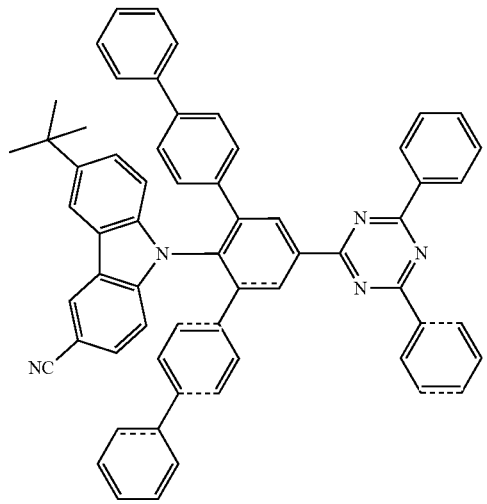
814
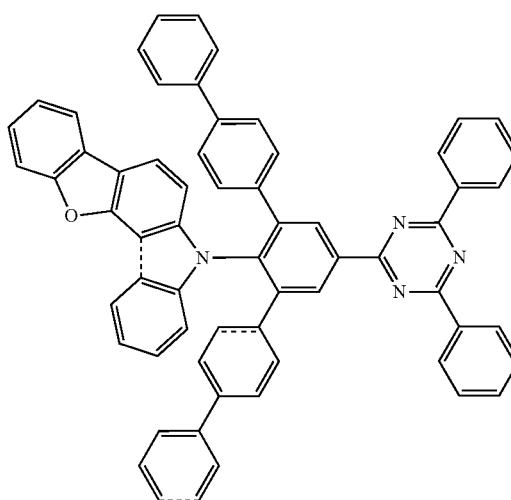
815
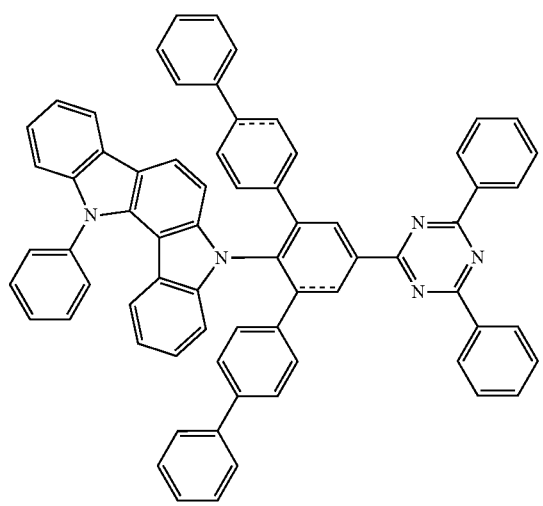
816
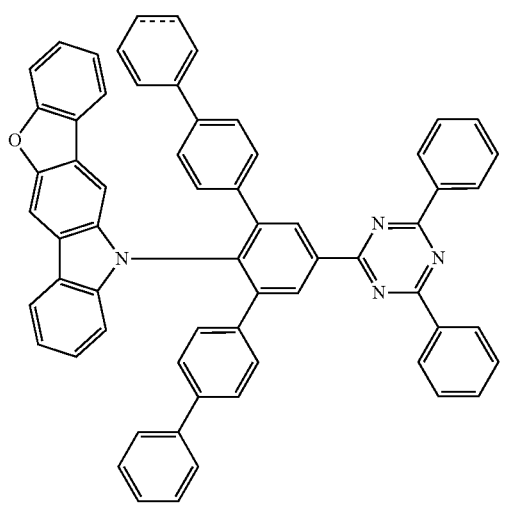
817
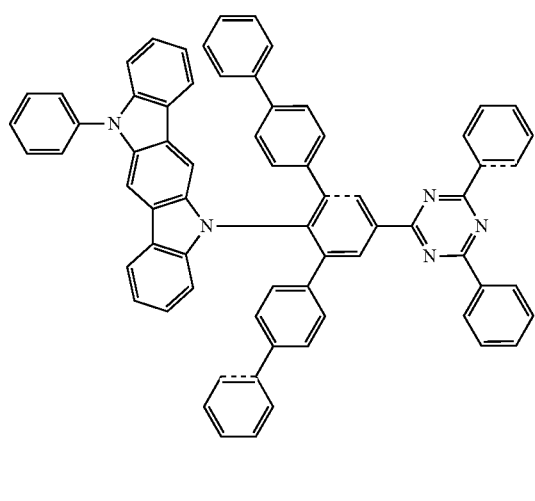
818

-continued
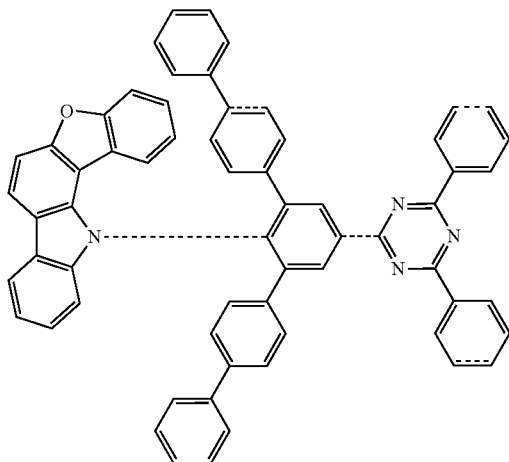
819
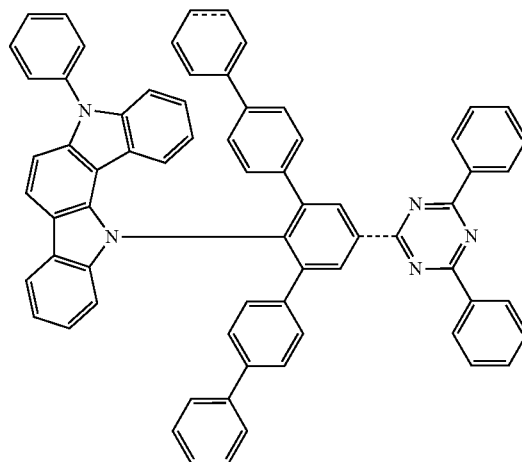
820
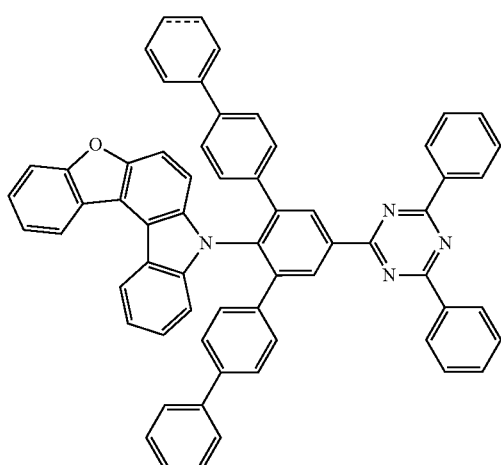
821
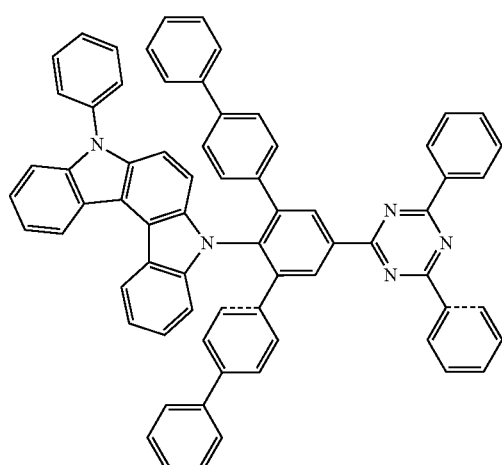
822
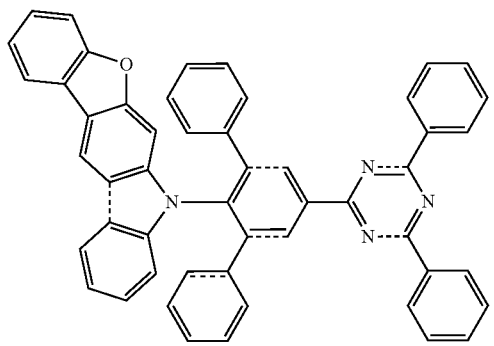
823
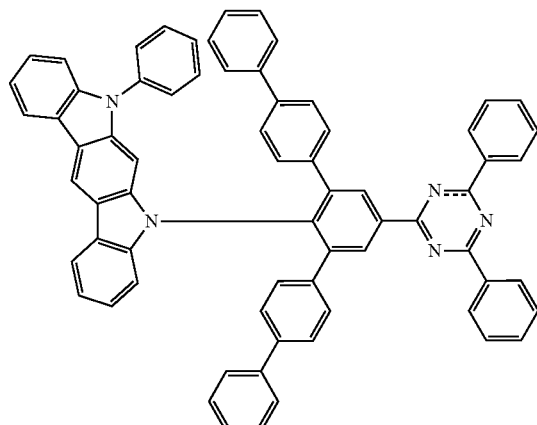
824

| 825 | 826 |
|---|---|
| 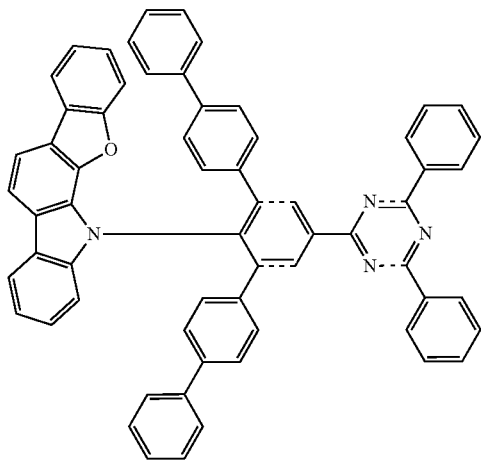 | 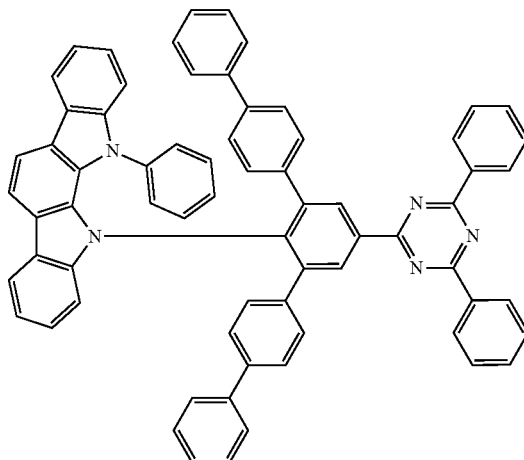 |
| 827 | 828 |
| 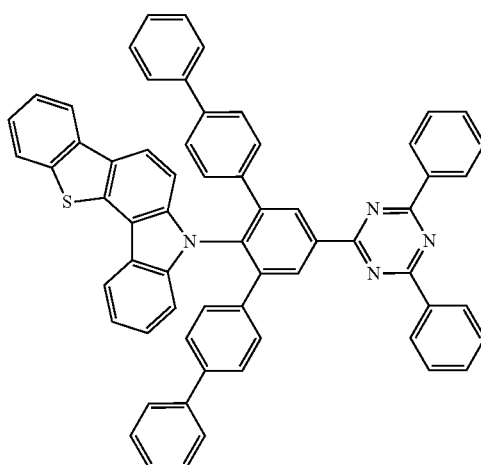 | 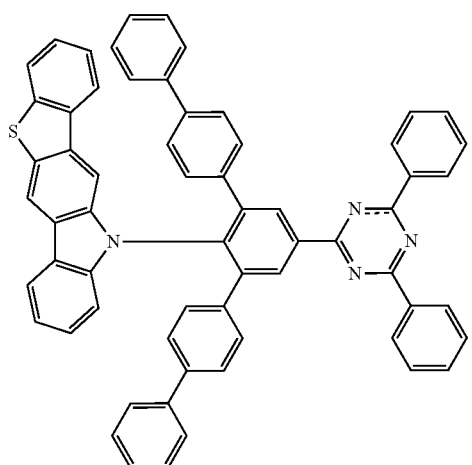 |
| 829 | 830 |
| 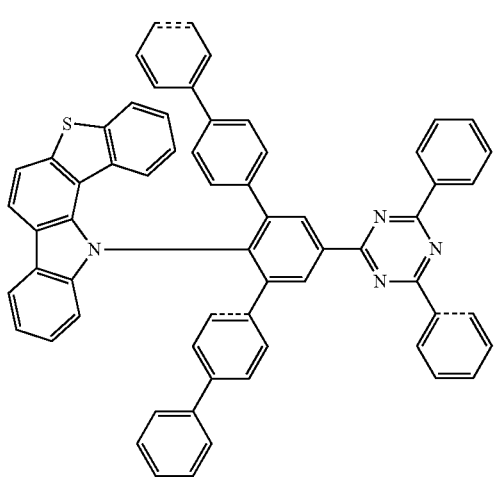 | 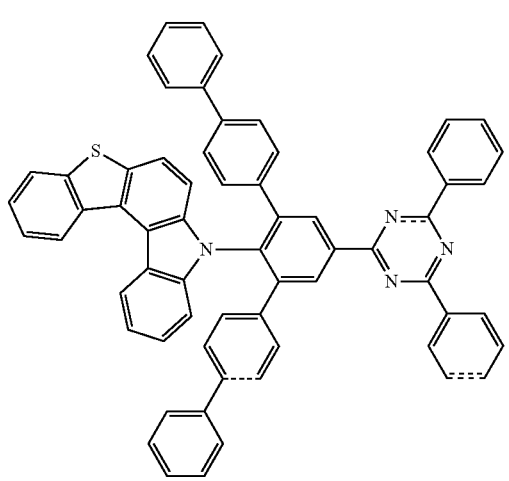 |

-continued
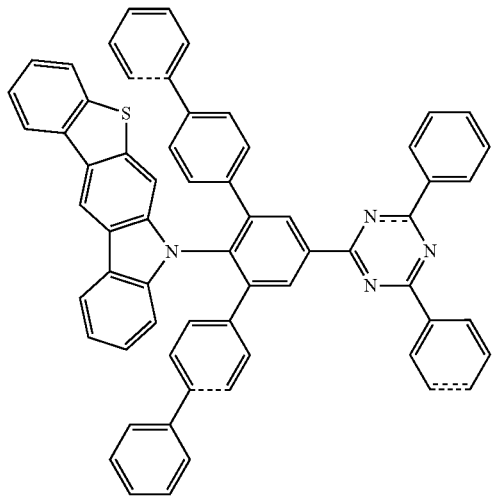
831
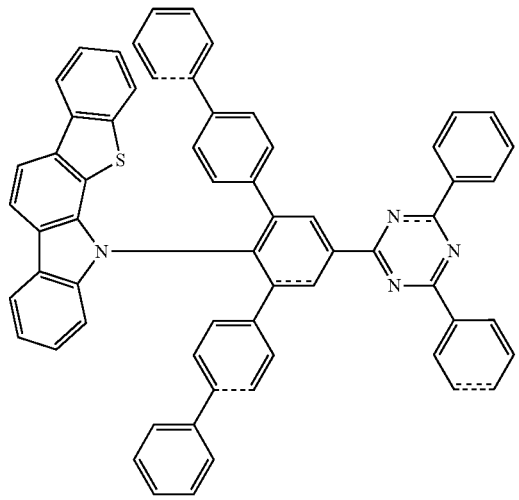
832
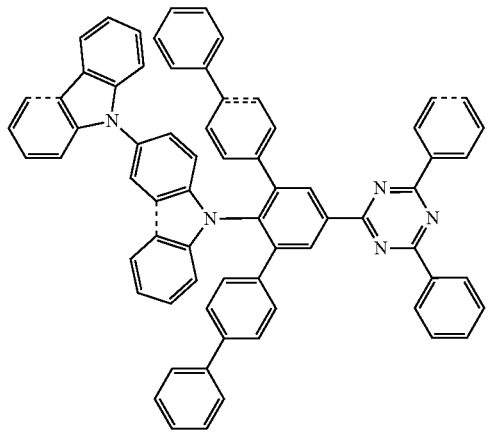
833
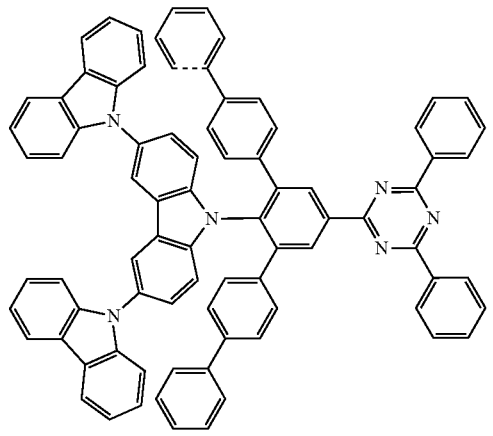
834
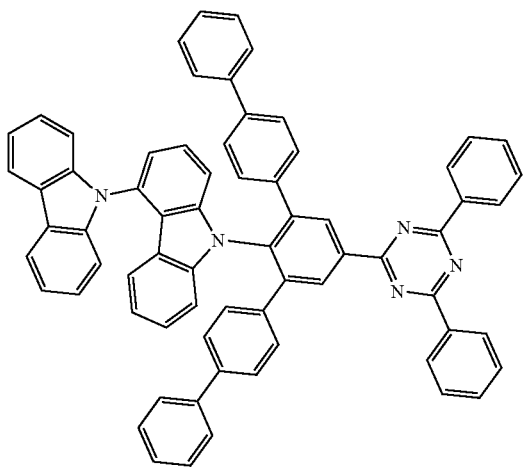
835
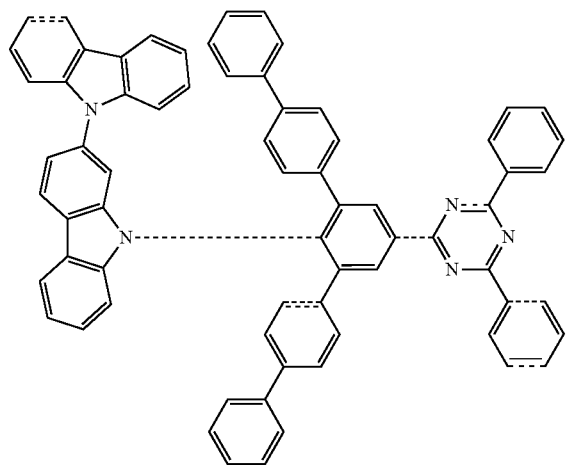
836

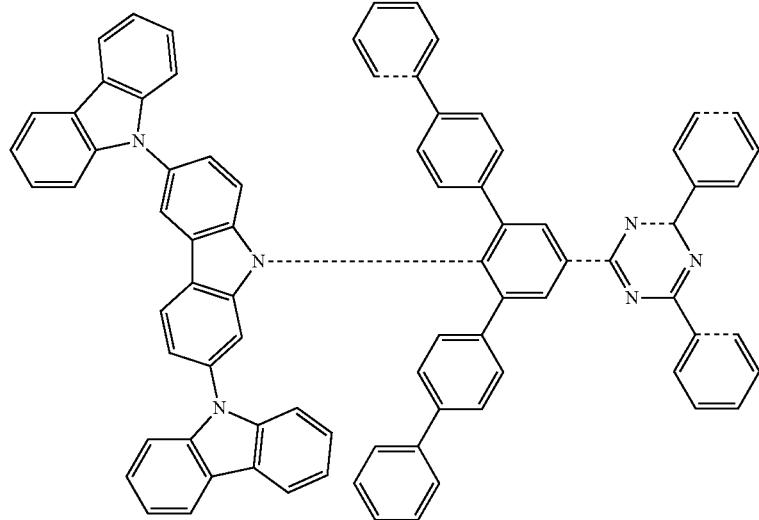
837
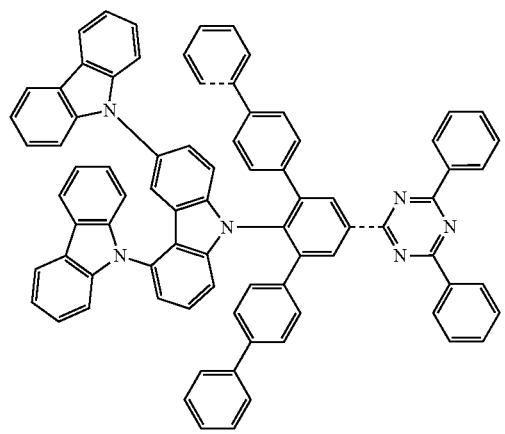
838
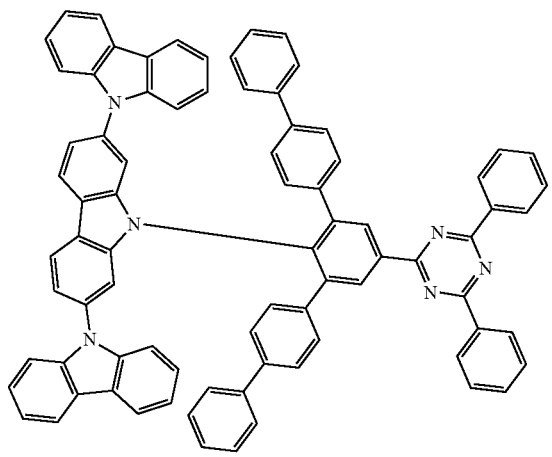
839
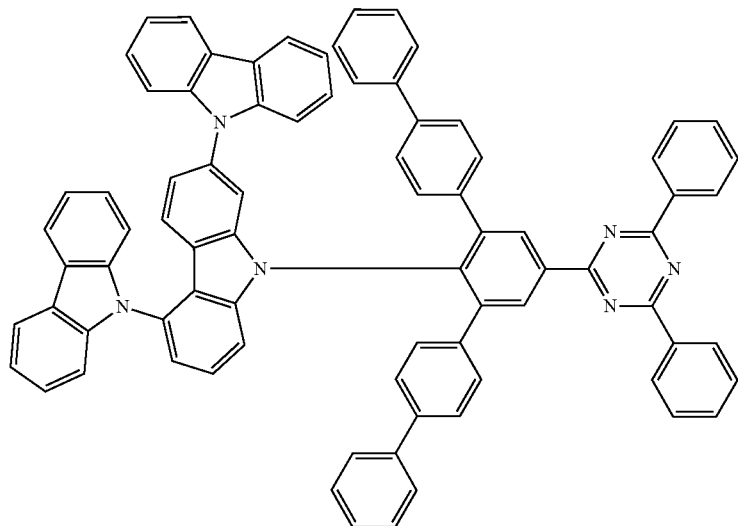
840

341 342
-continued
841
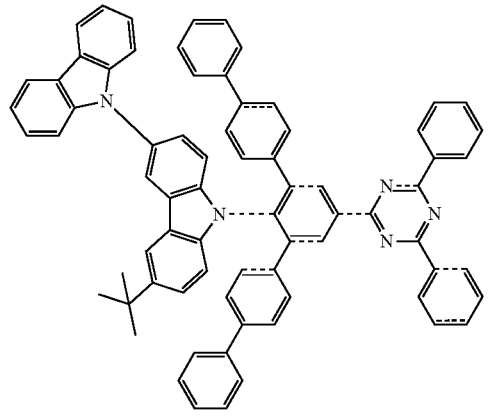
842
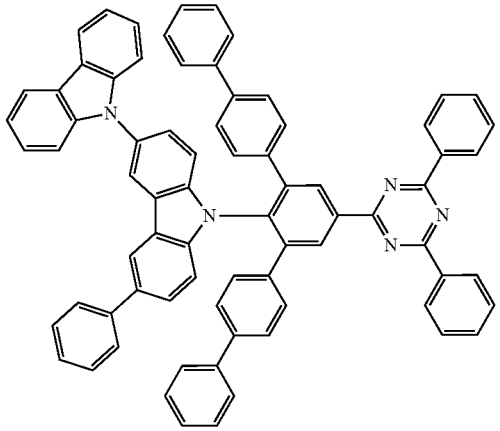
843
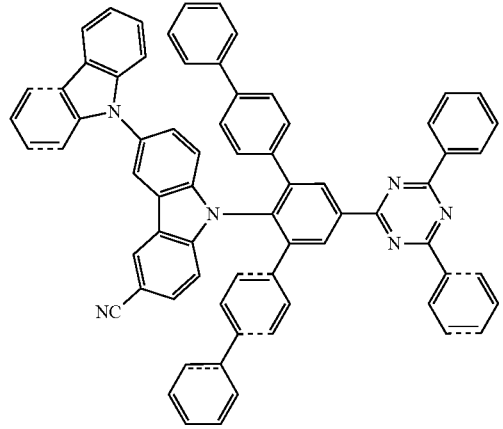
844
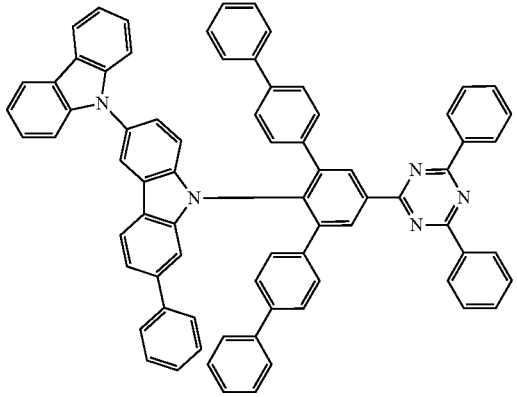
845
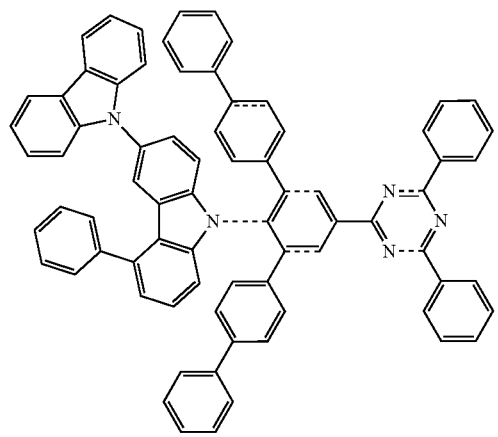
846
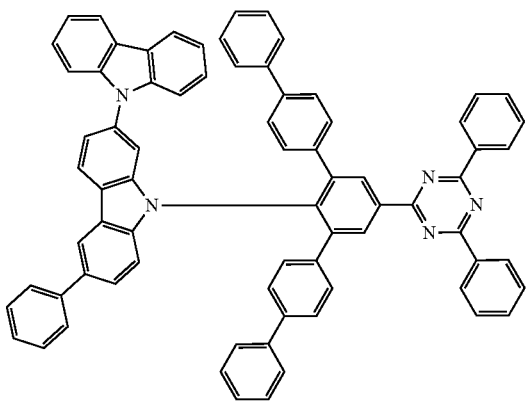

847
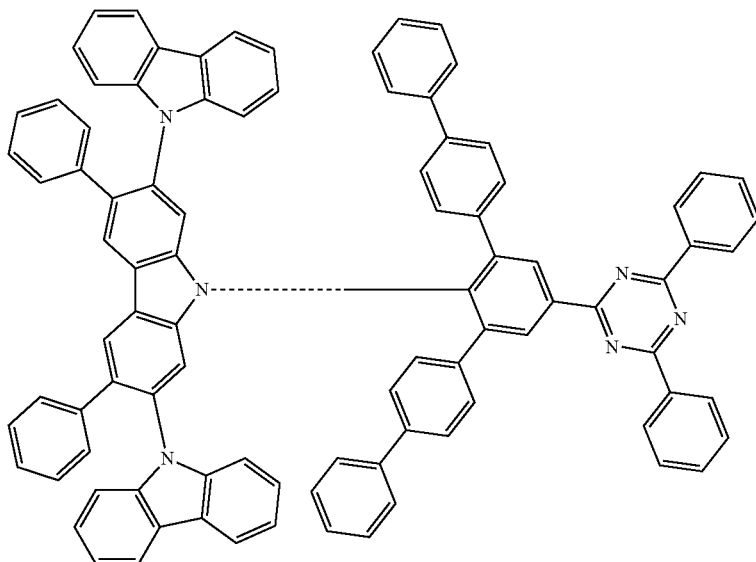
848
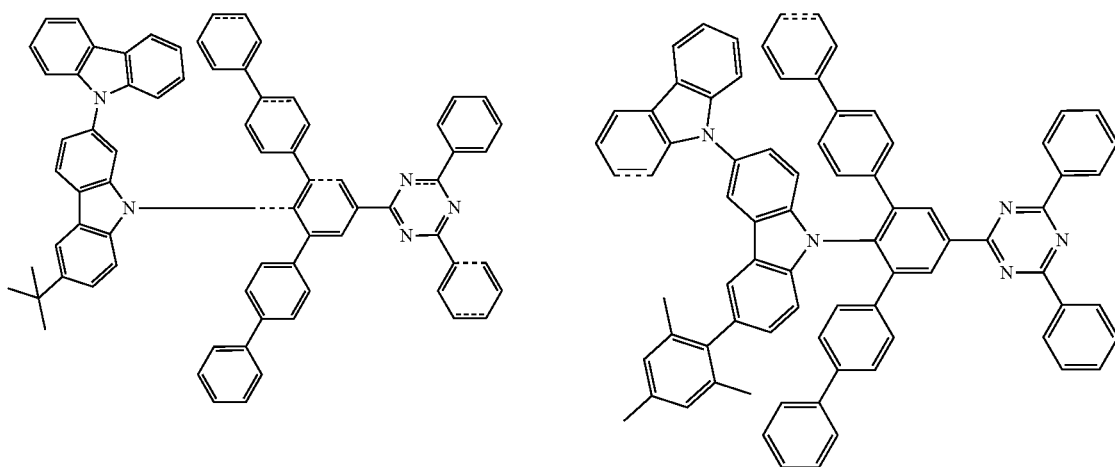
849
850
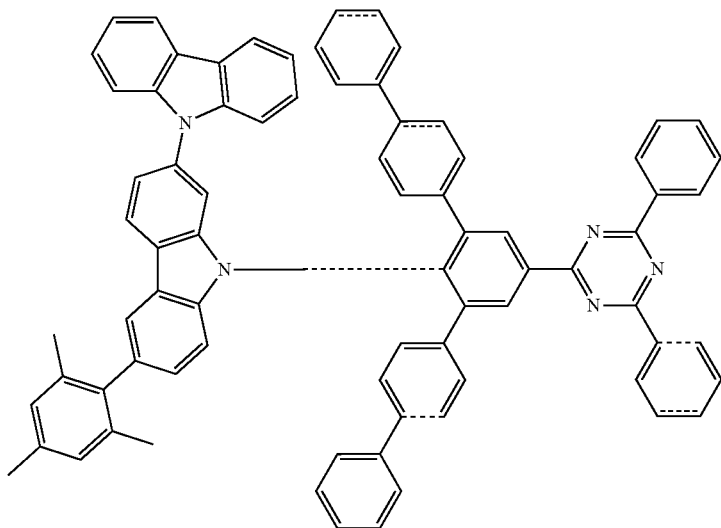

851
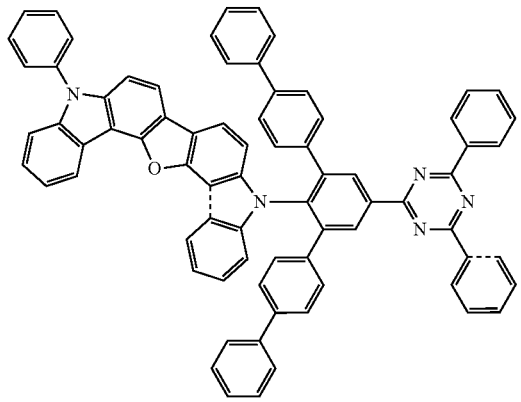
852
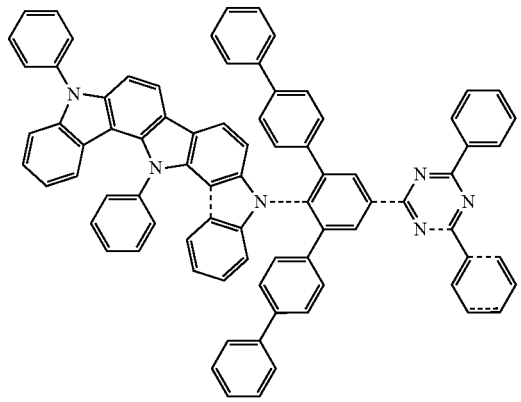
853
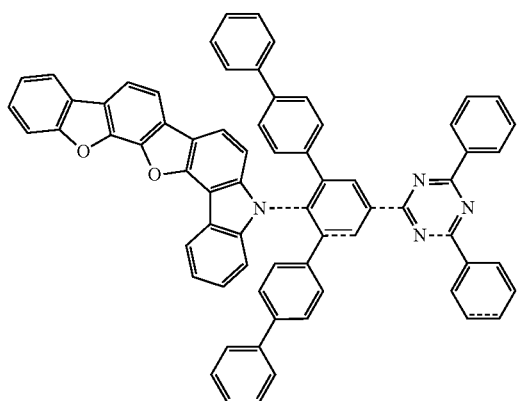
854
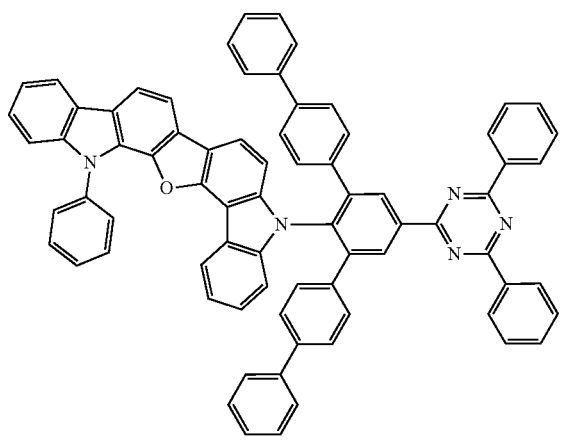
855
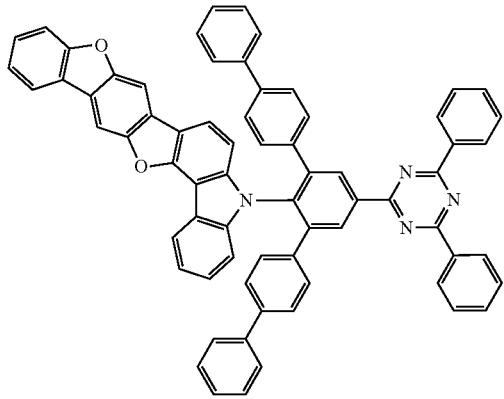
856
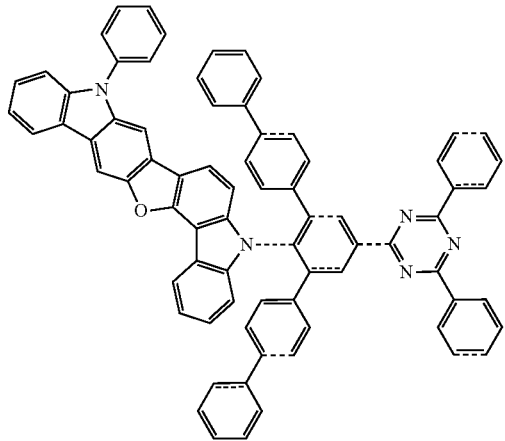

-continued
857
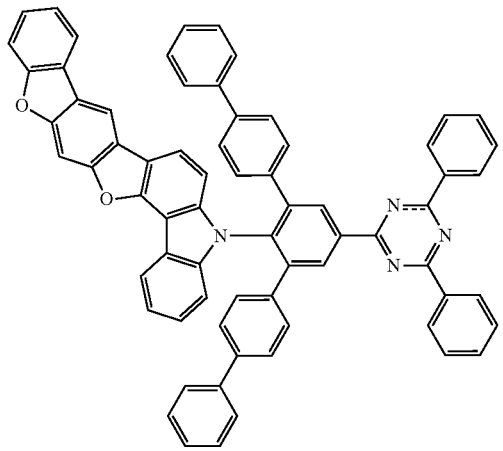
858
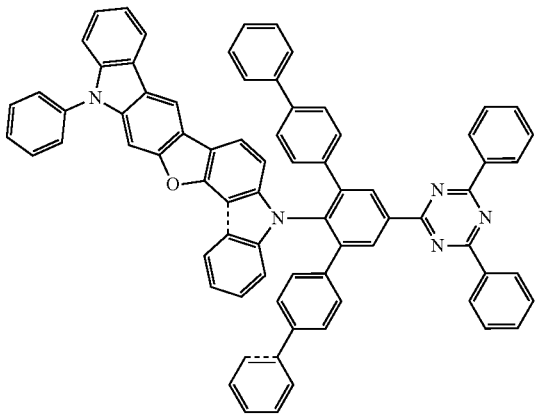
859
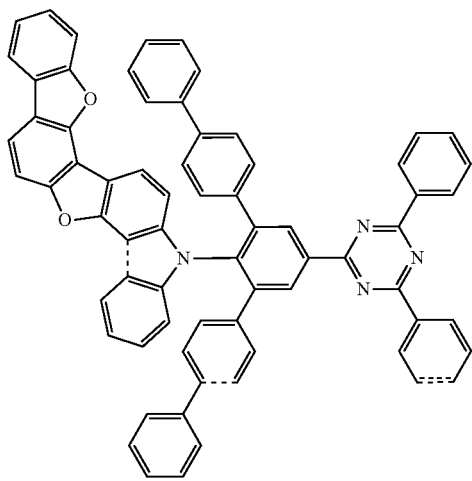
860
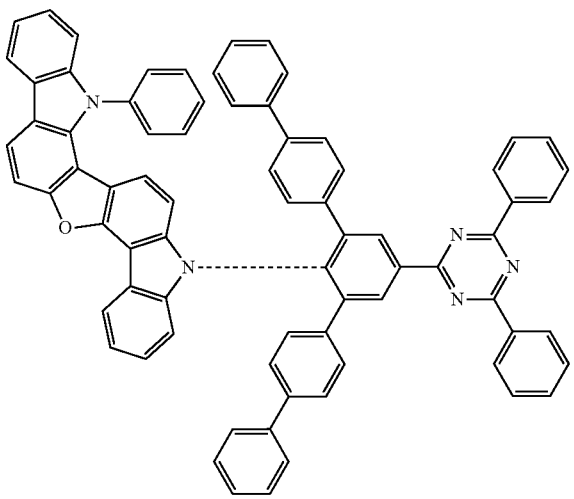
861
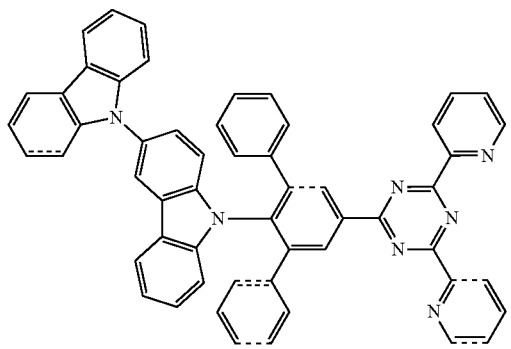
862
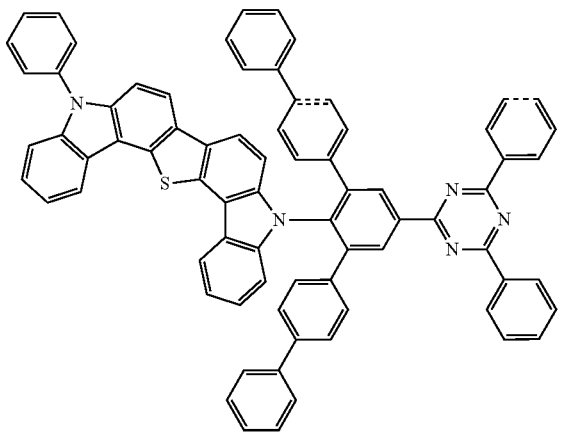

-continued
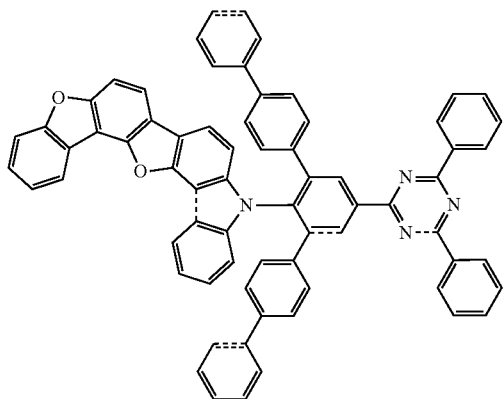
863
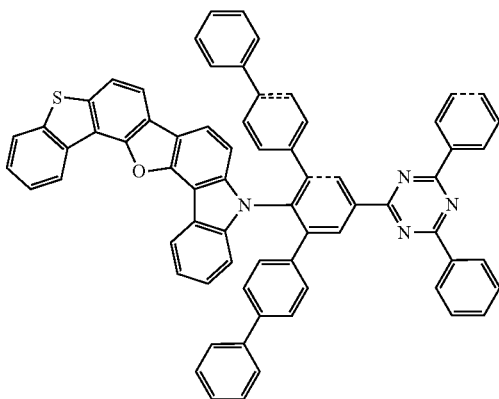
864
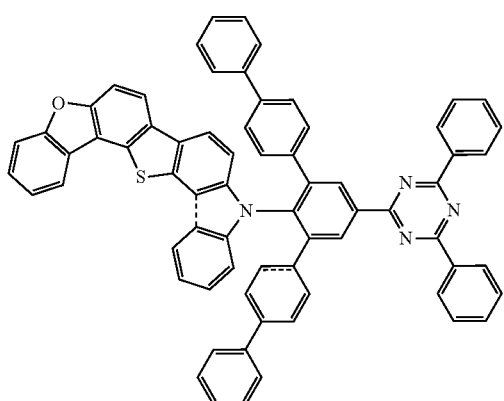
865
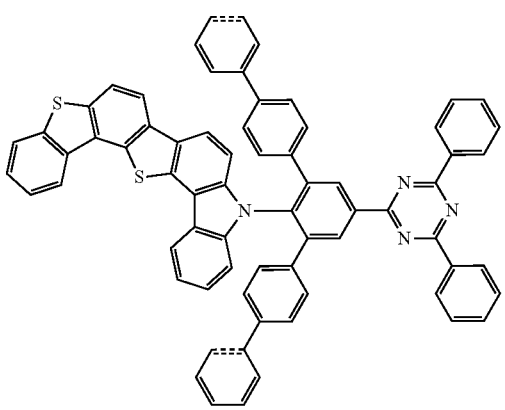
866
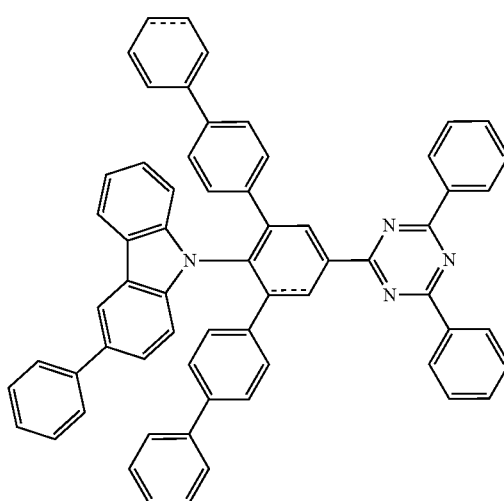
867
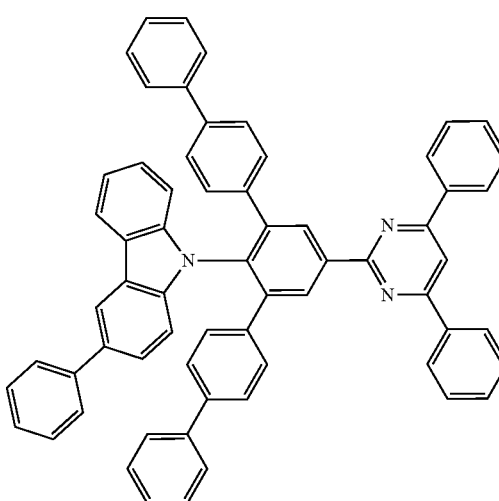
868

-continued
869
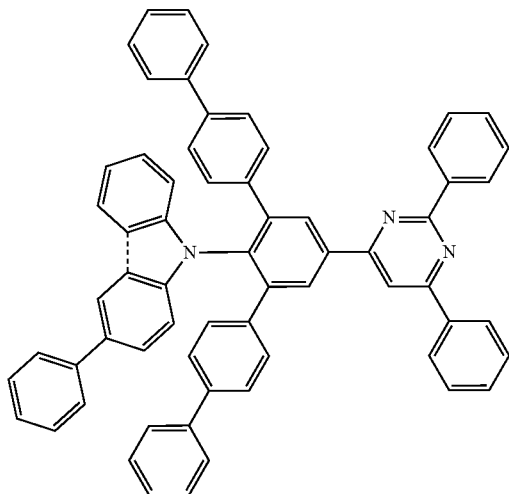
870
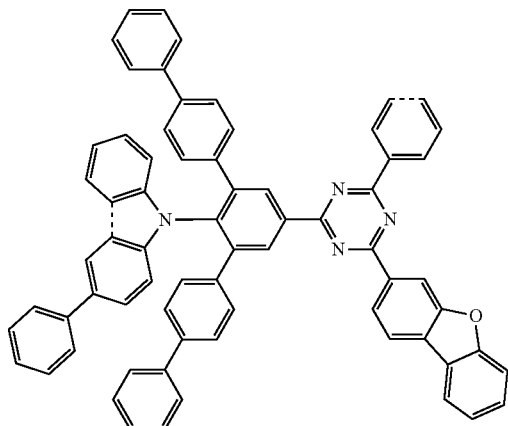
871
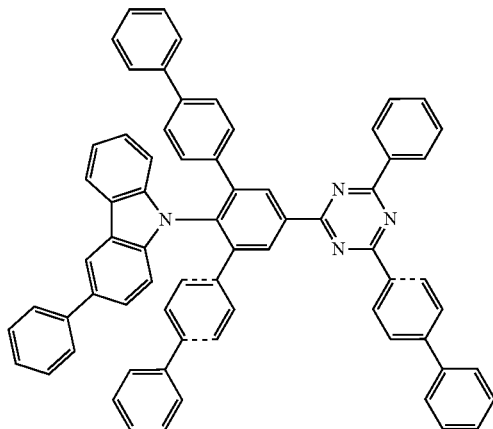
872
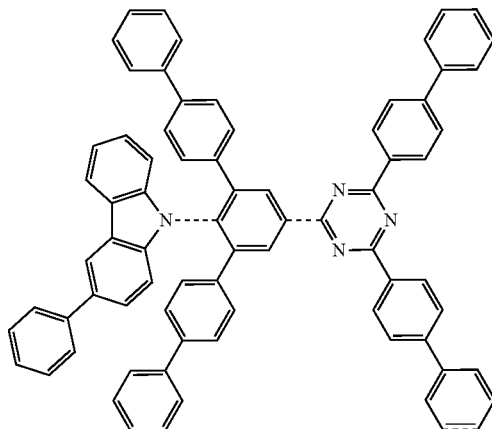
873
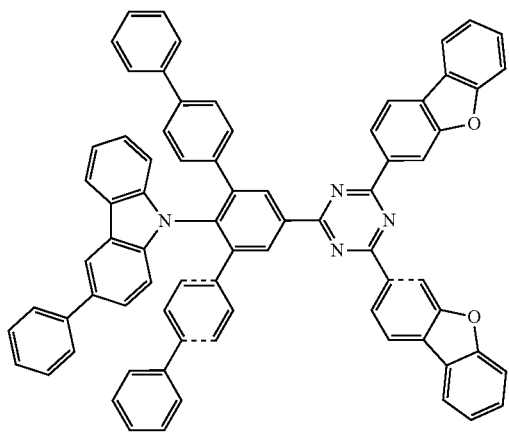
874
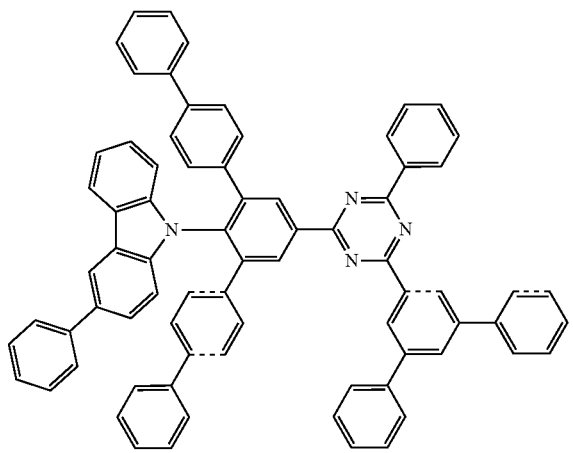

875 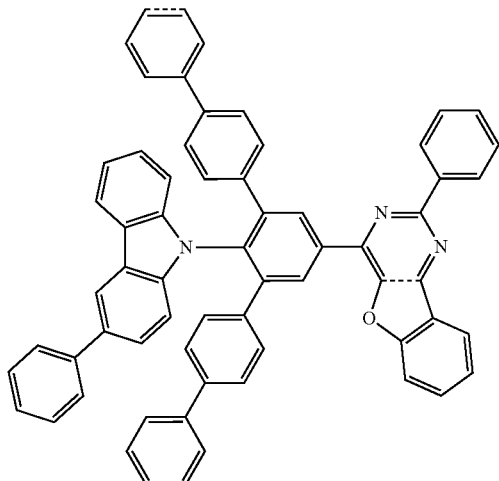
876 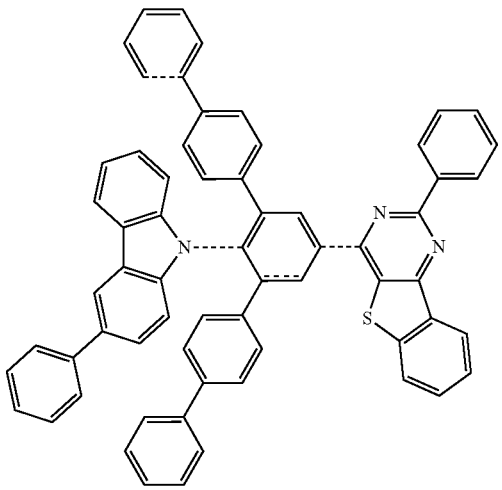
877 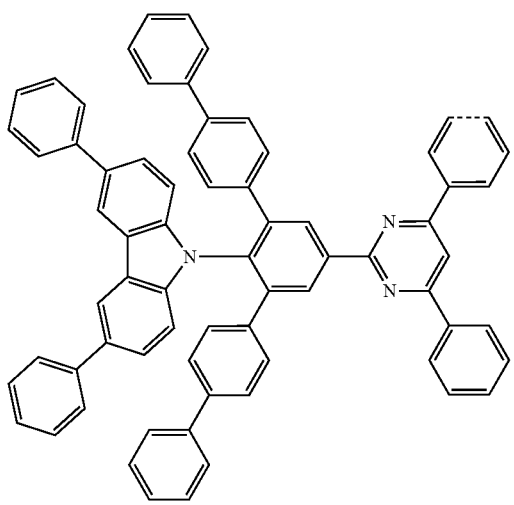
878 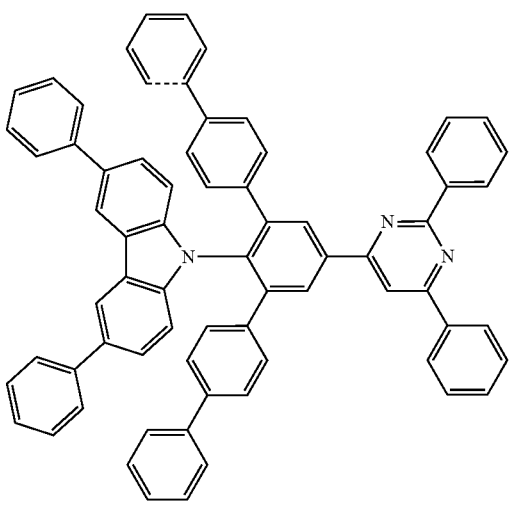
879 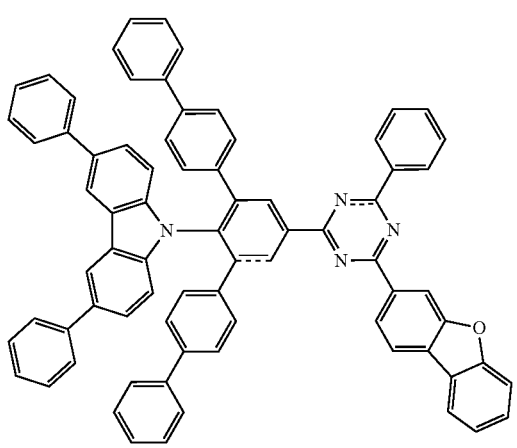

355 356
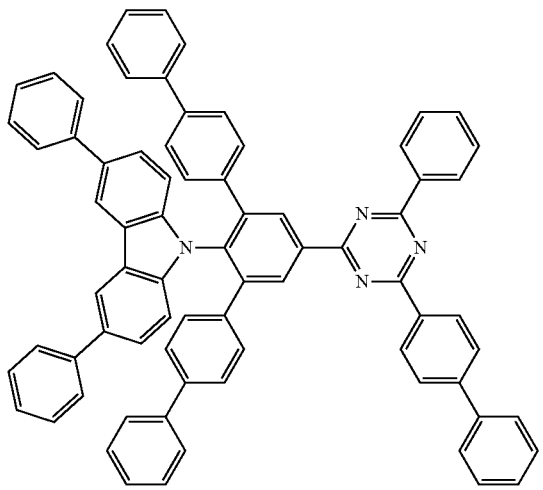
880
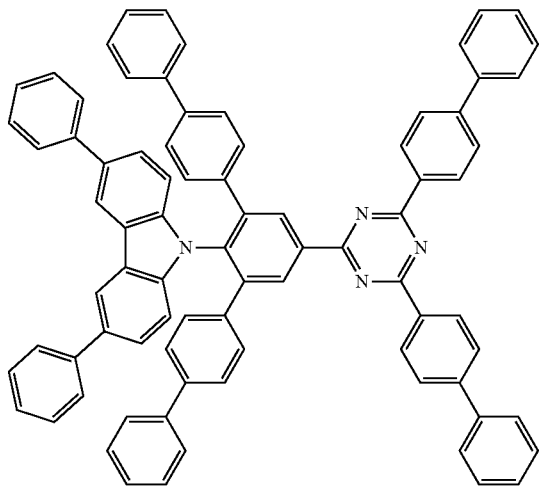
881
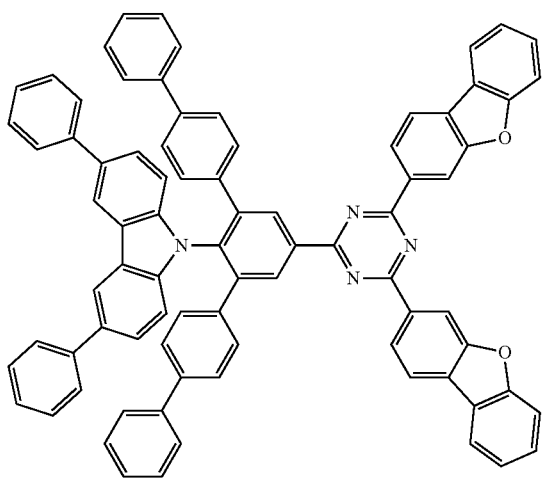
882
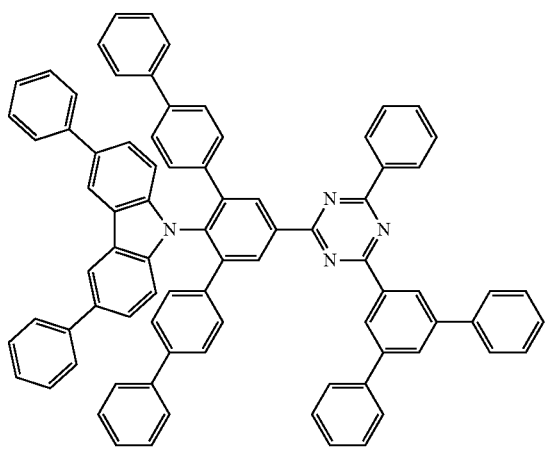
883
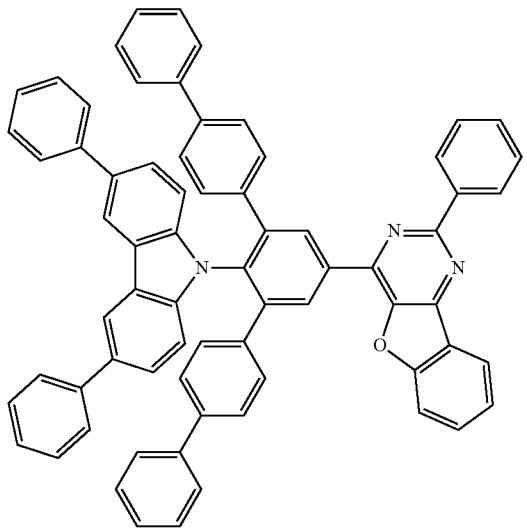
884
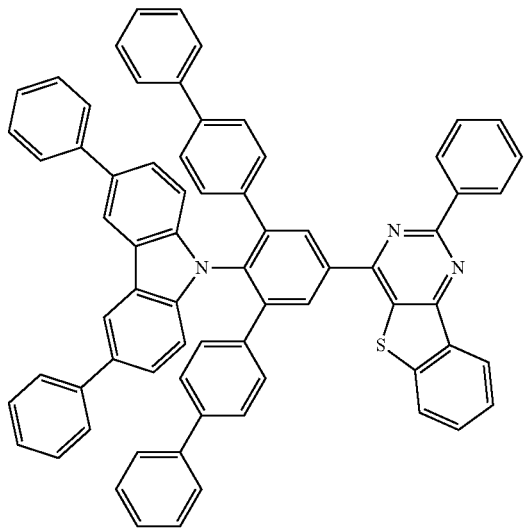
885

-continued
886
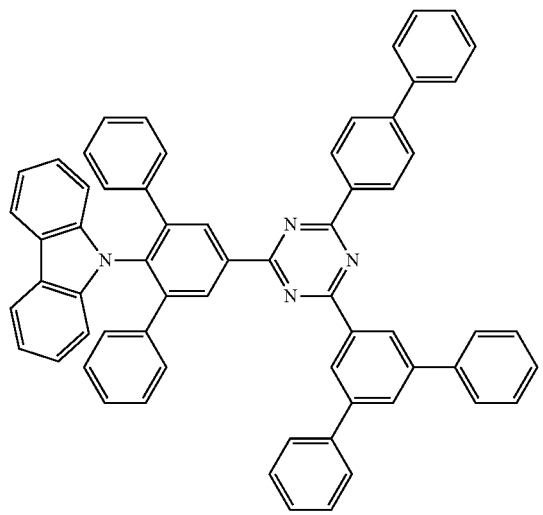
887
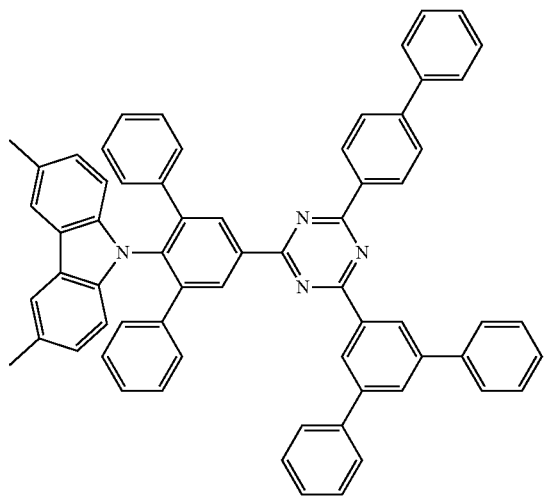
888
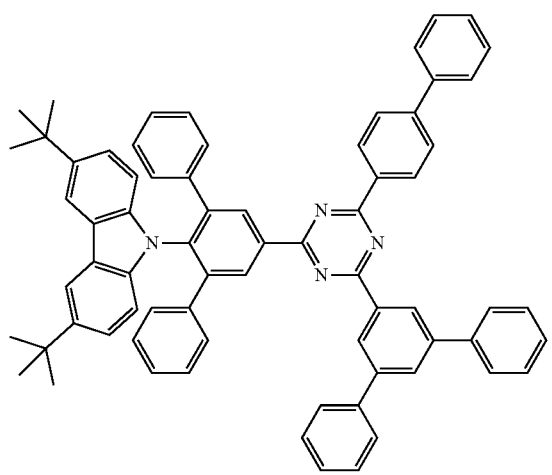
889
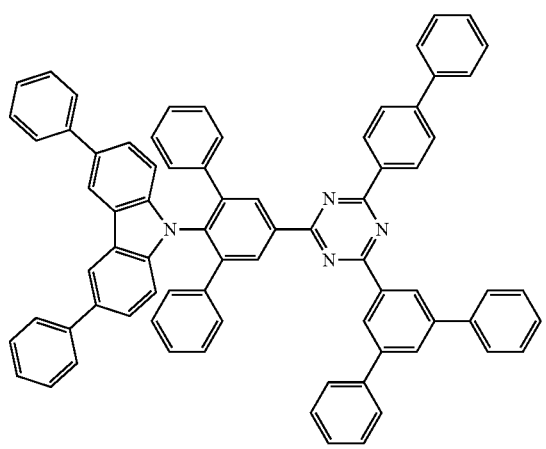
890
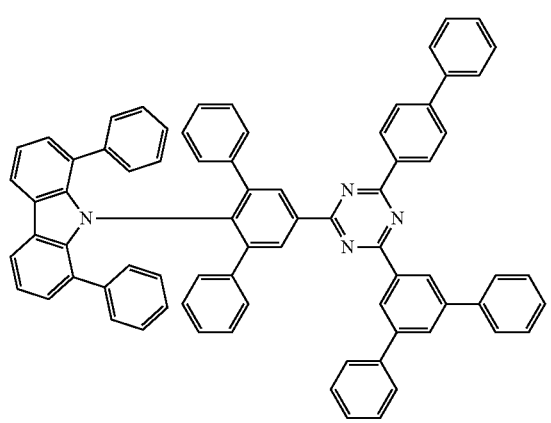
891
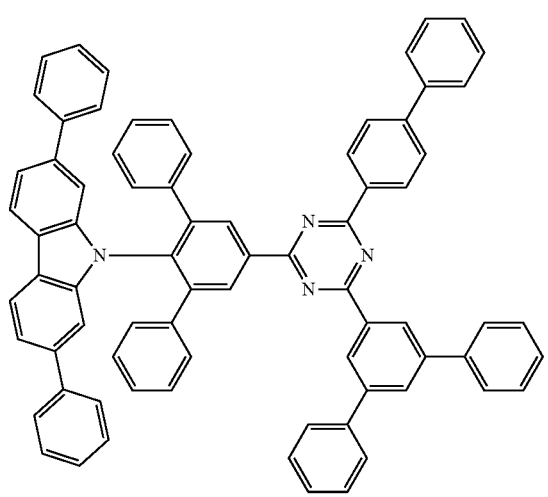

-continued
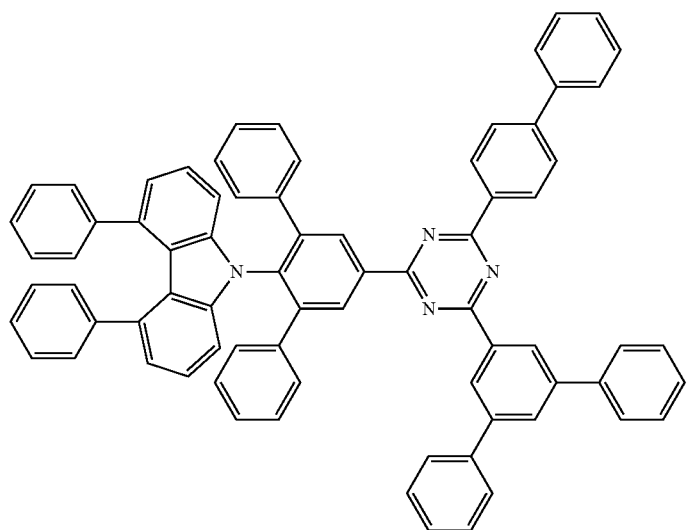
892
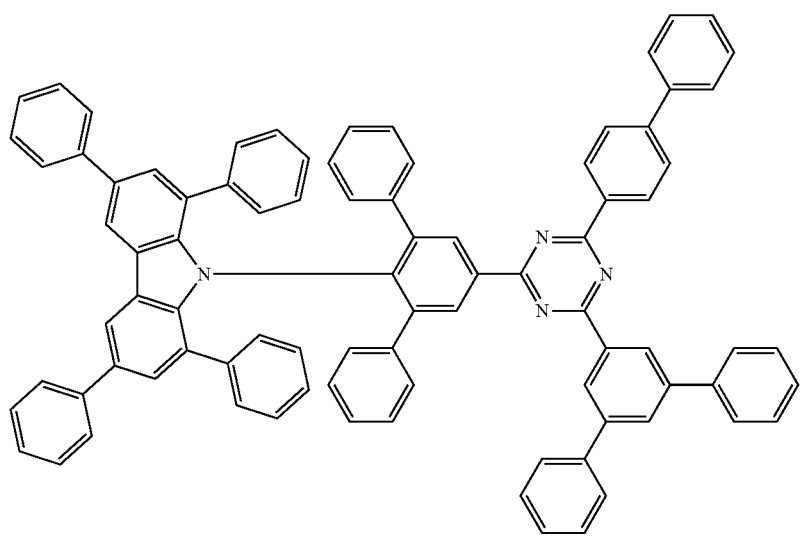
893
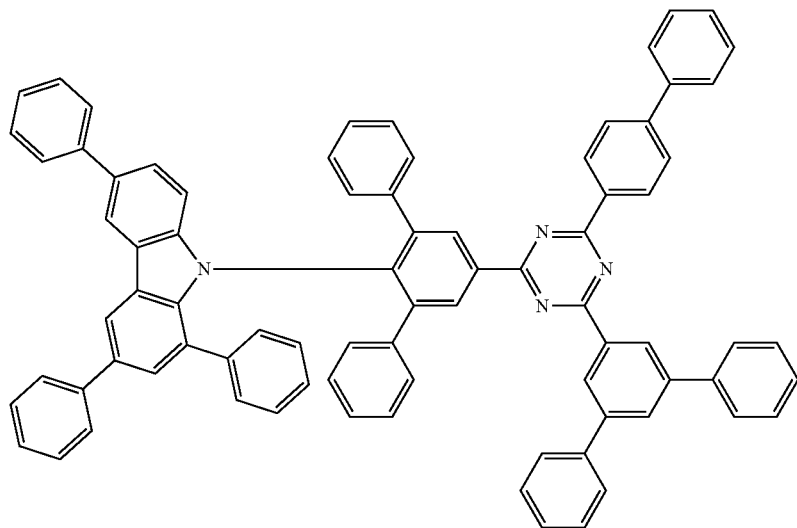
894

895
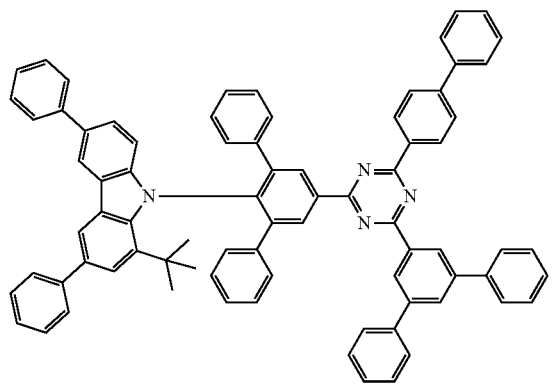
896
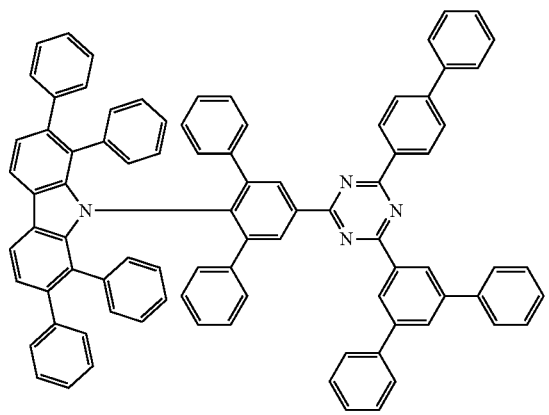
897
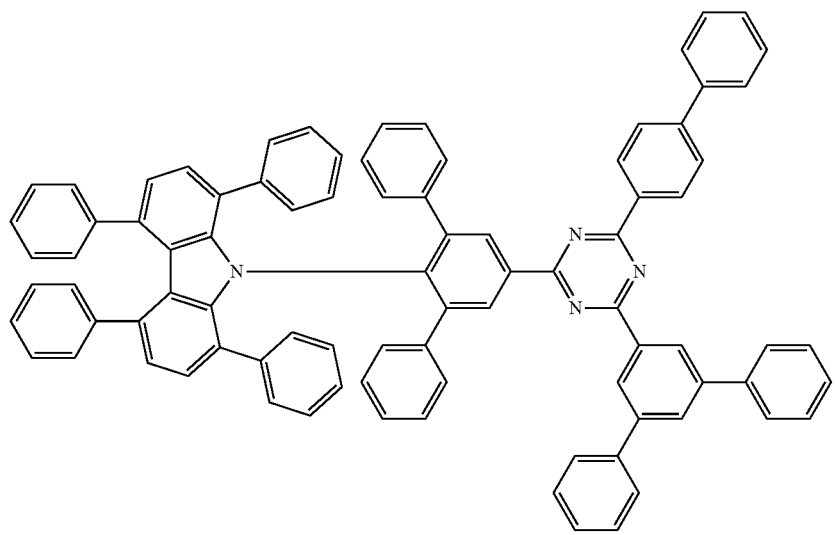
898
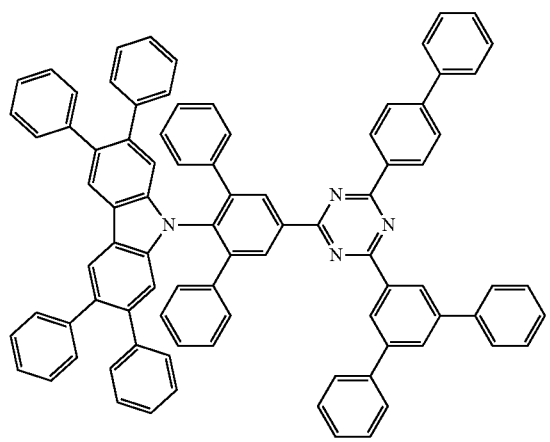
899
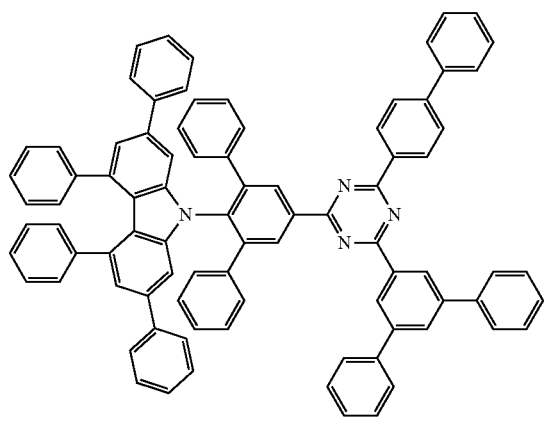

| 900 | 901 |
|---|---|
| 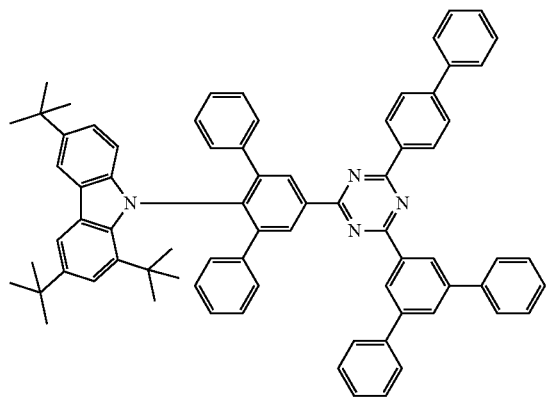 | 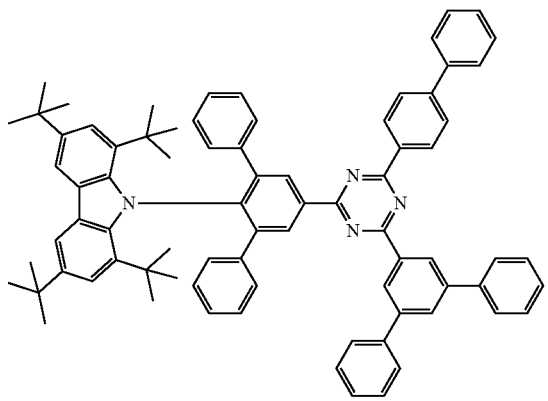 |
| 902 | 903 |
| 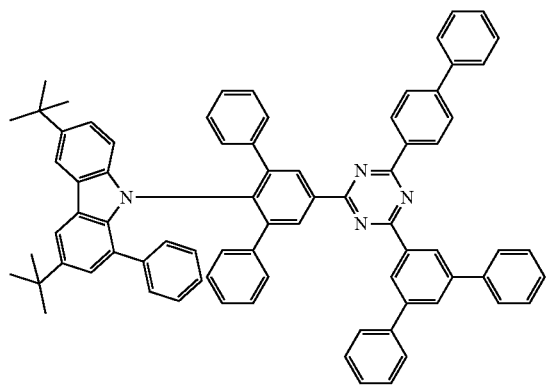 | 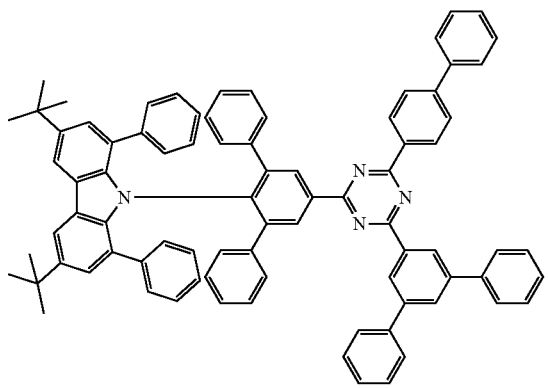 |
| 904 | 905 |
| 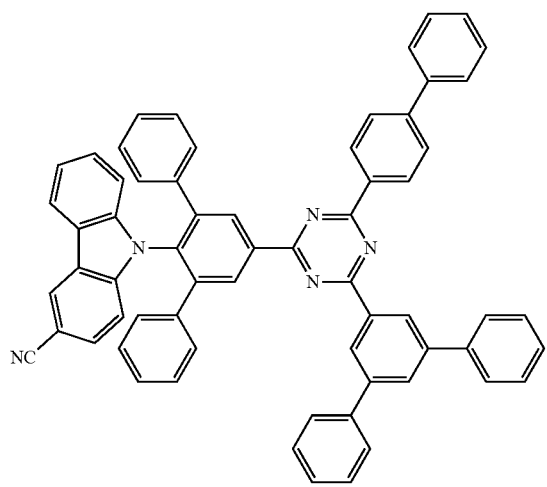 | 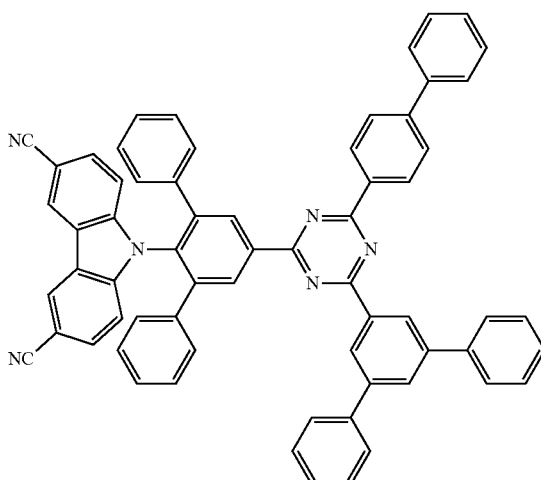 |

906
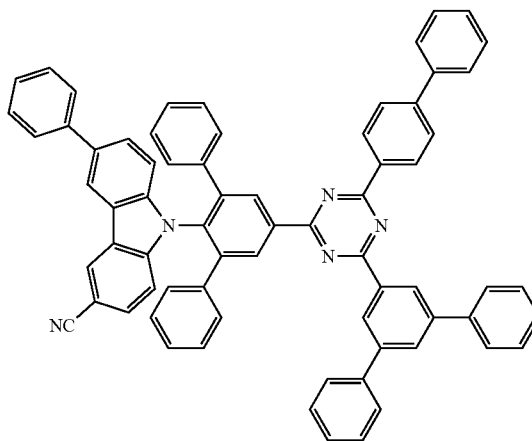
907
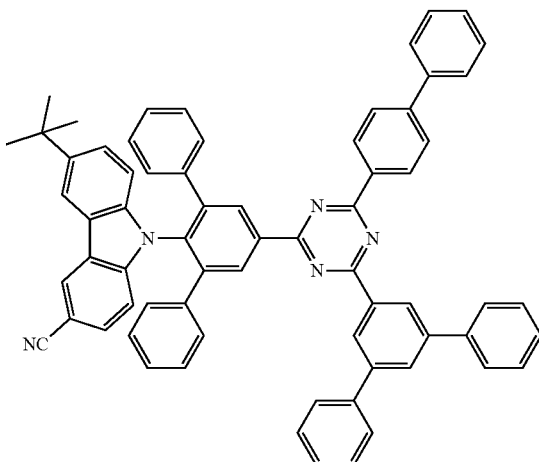
908
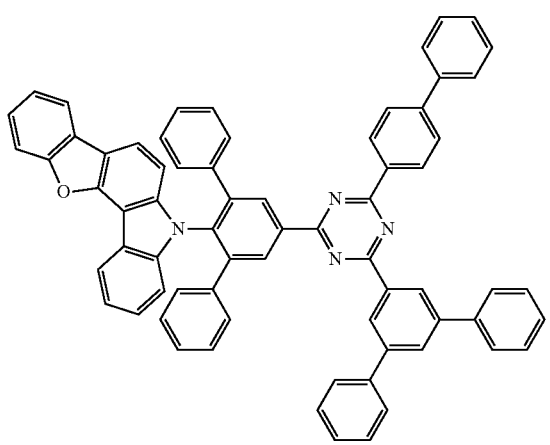
909
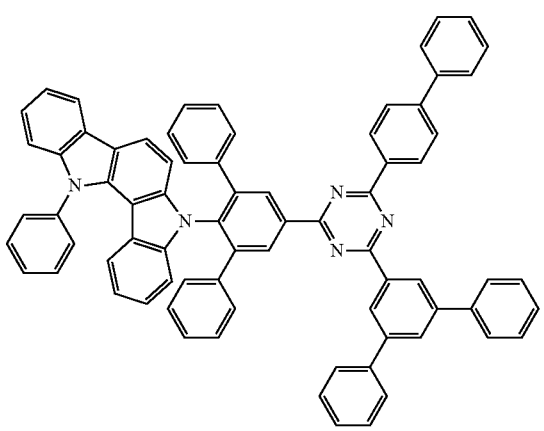
910
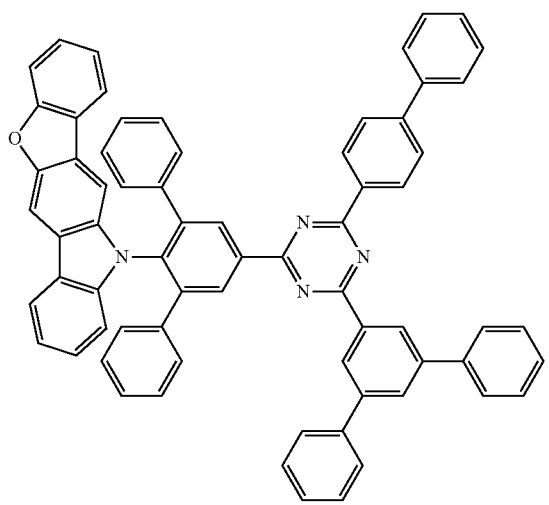
911
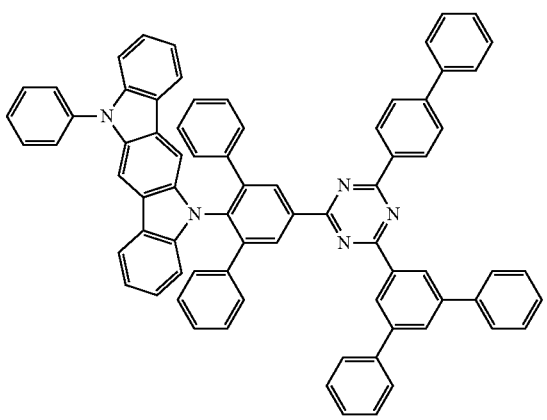

-continued
912
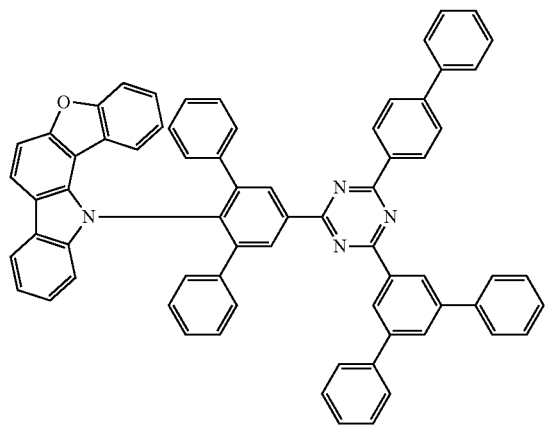
913
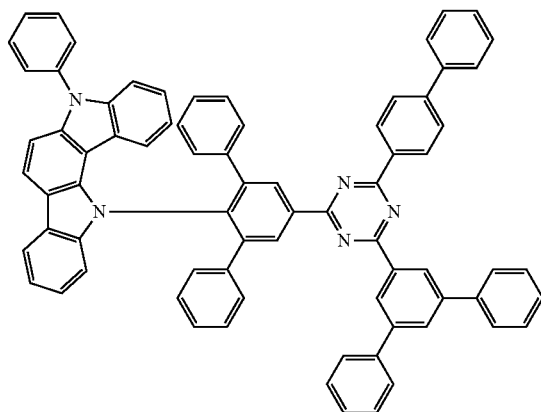
914
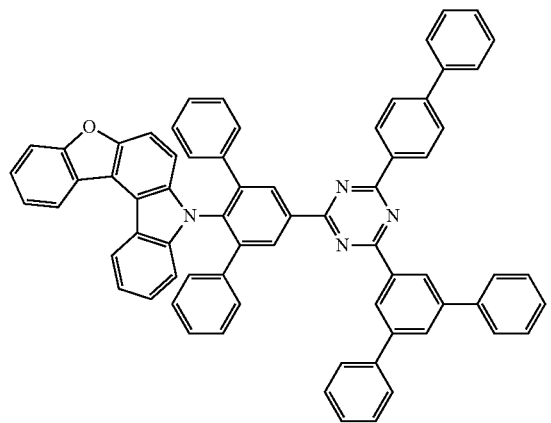
915
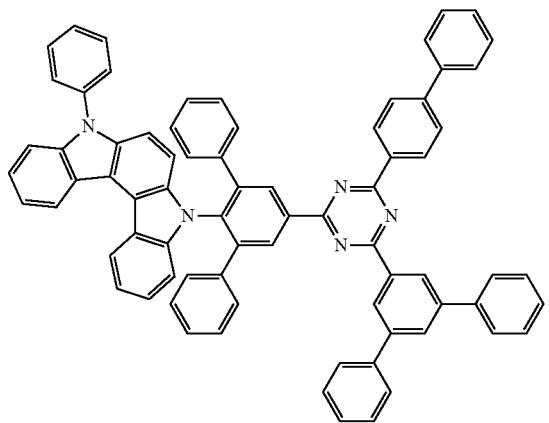
916
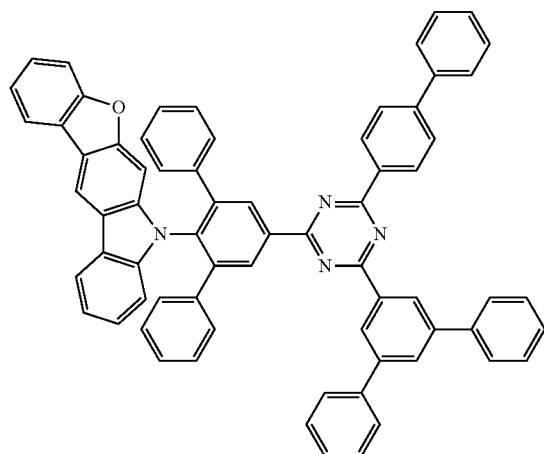
917
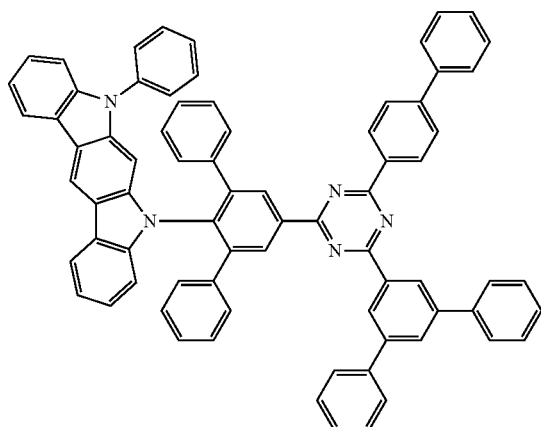

-continued
918
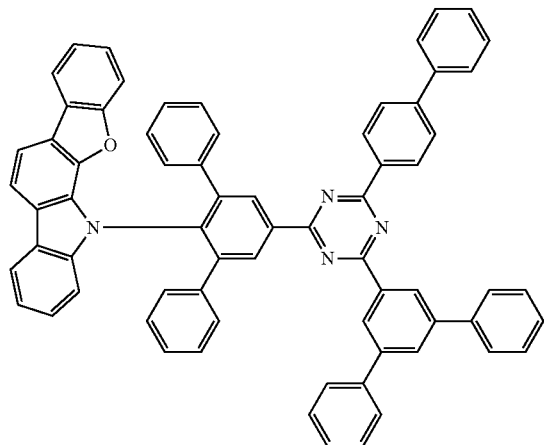
919
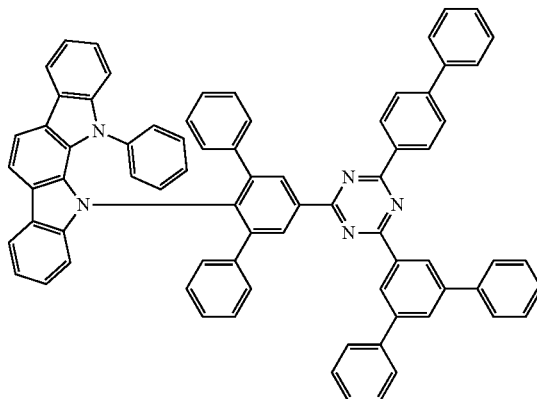
920
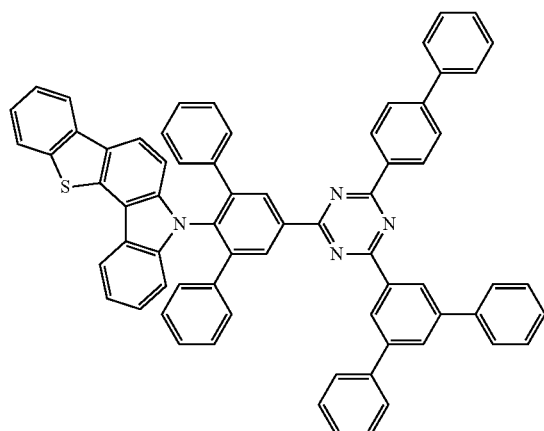
921
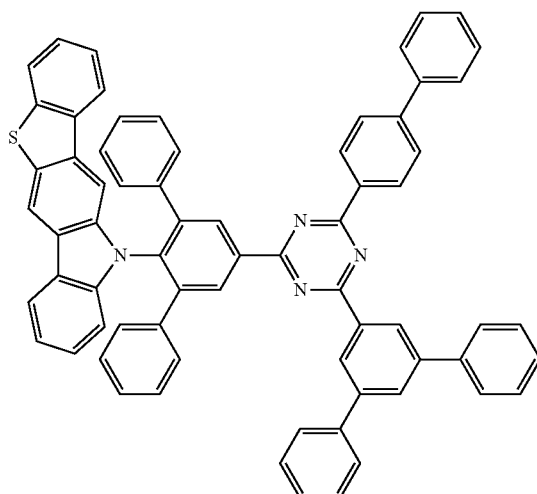
922
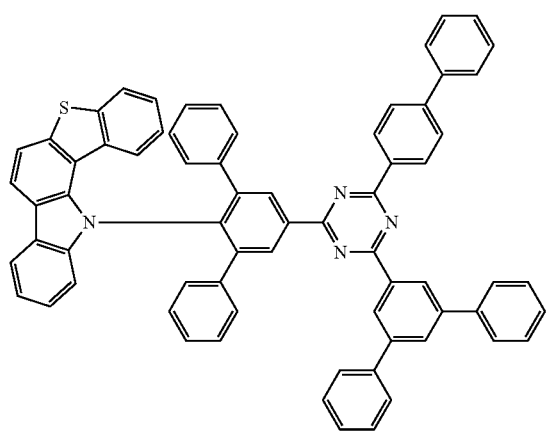
923
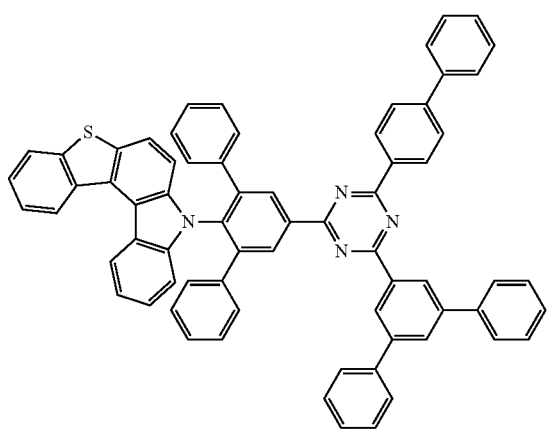

-continued
924
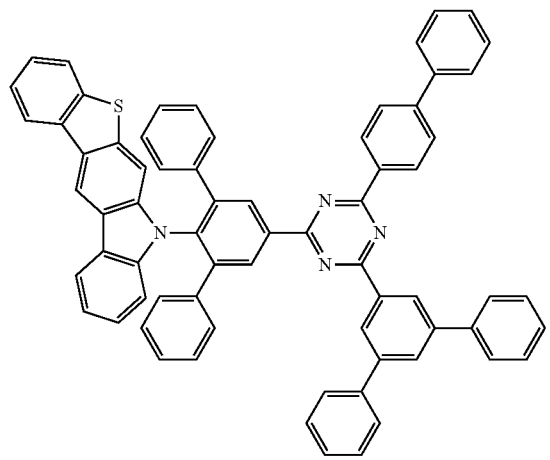
925
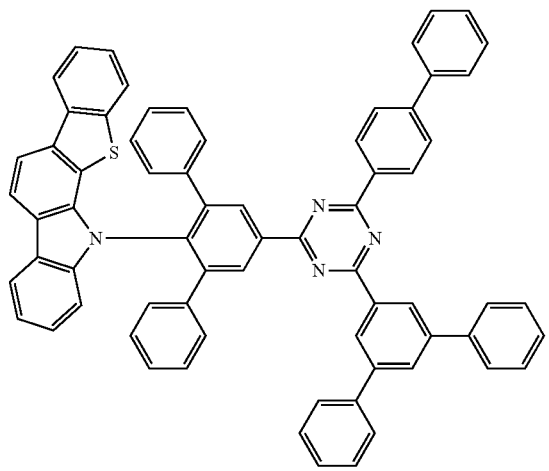
926
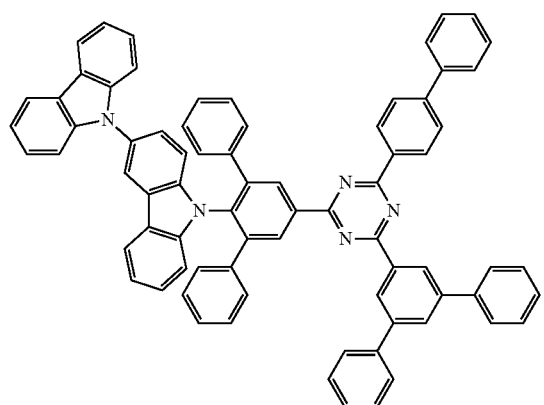
927
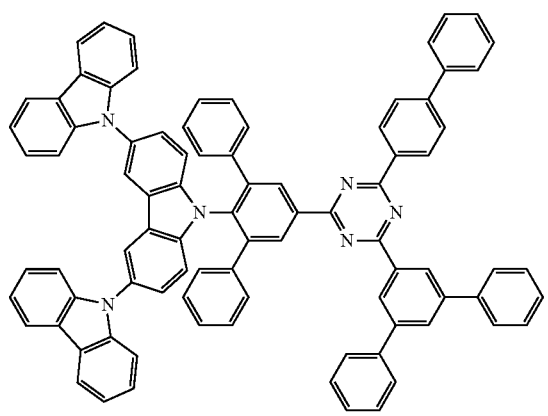
928
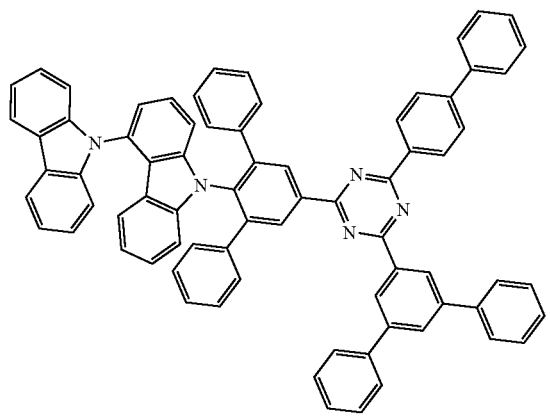
929
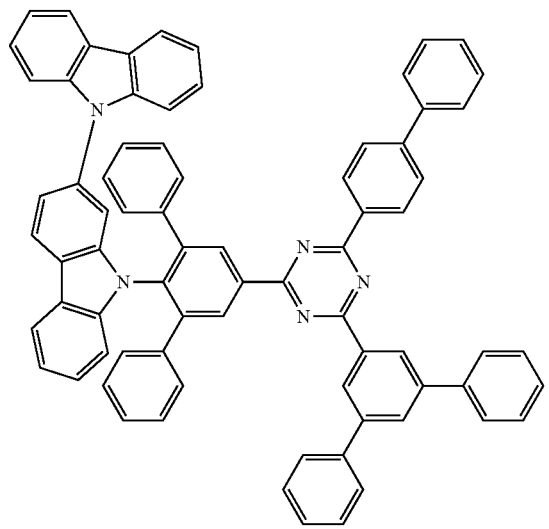

-continued
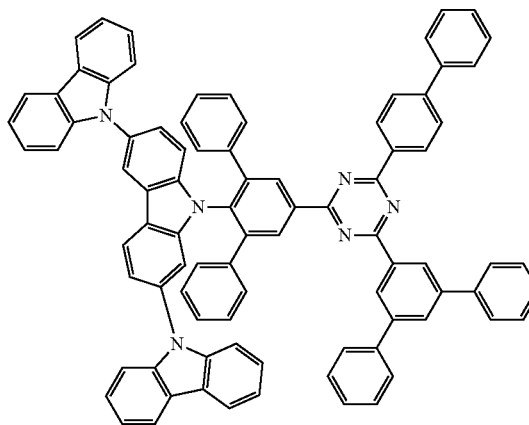
930
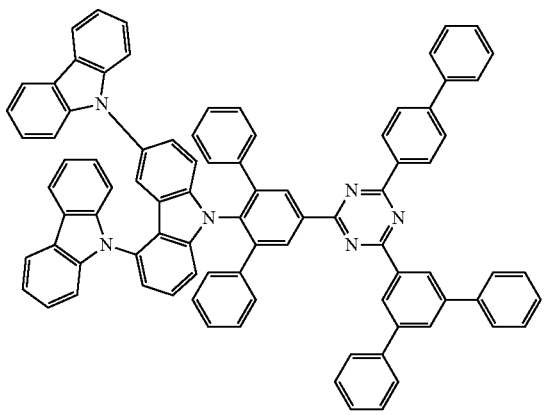
931
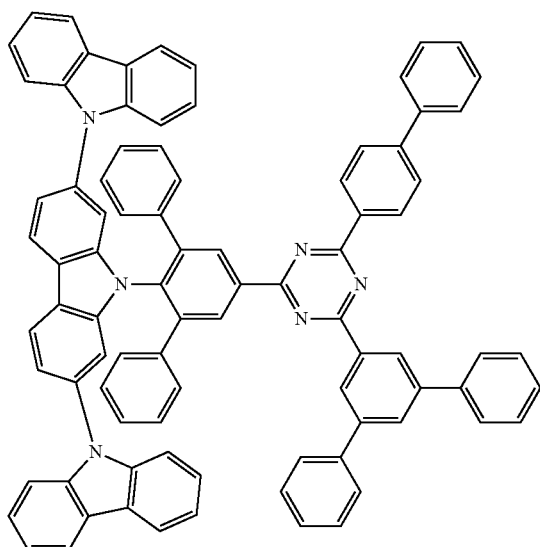
932
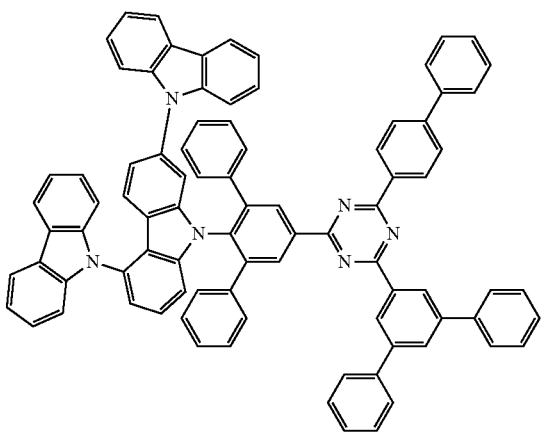
933
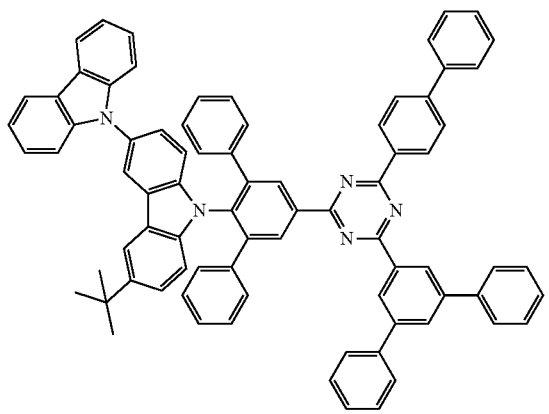
934
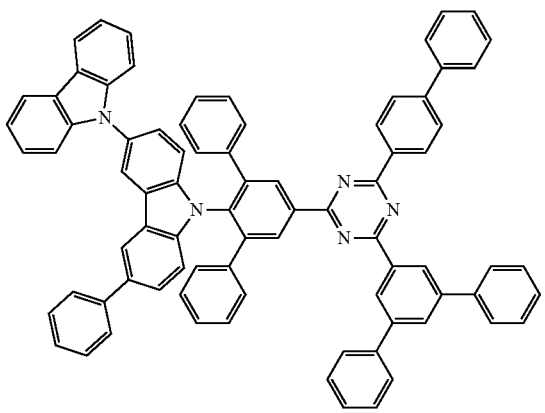
935

936
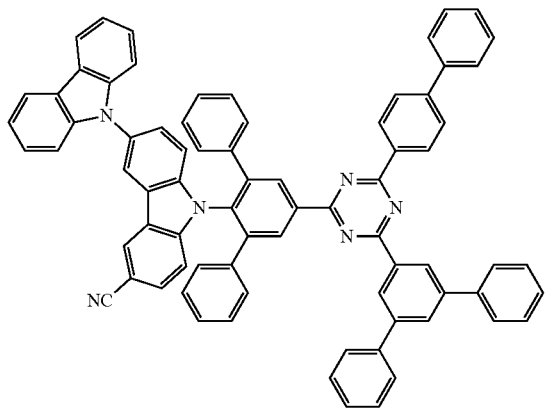
937
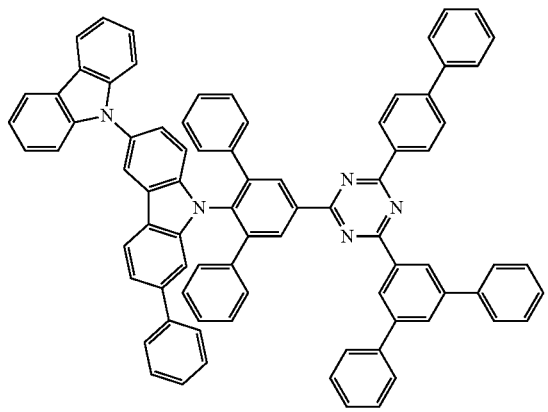
938
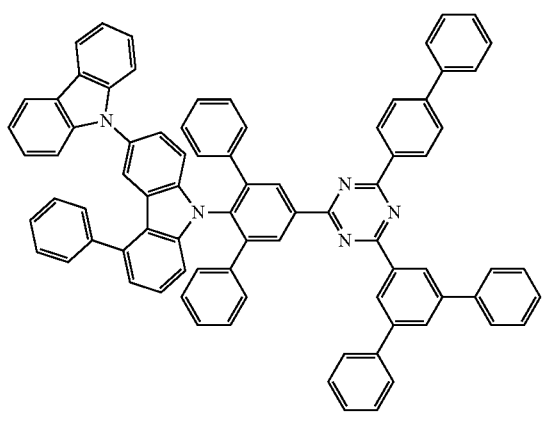
939
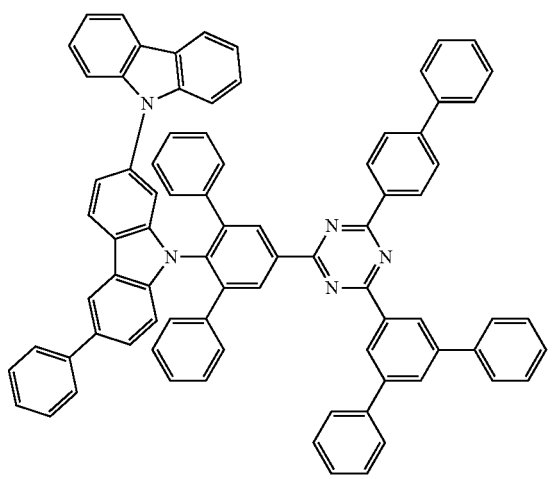
940
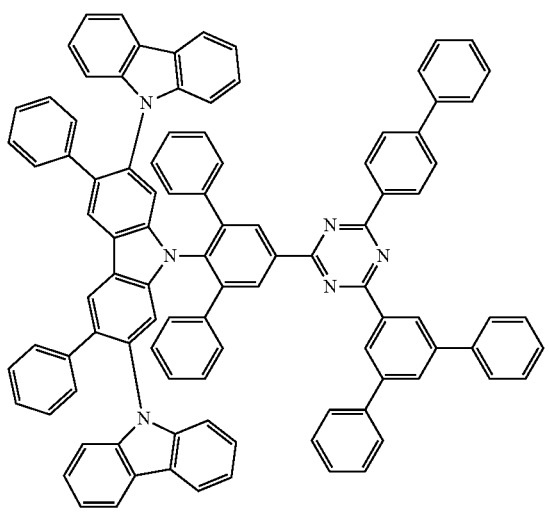
941
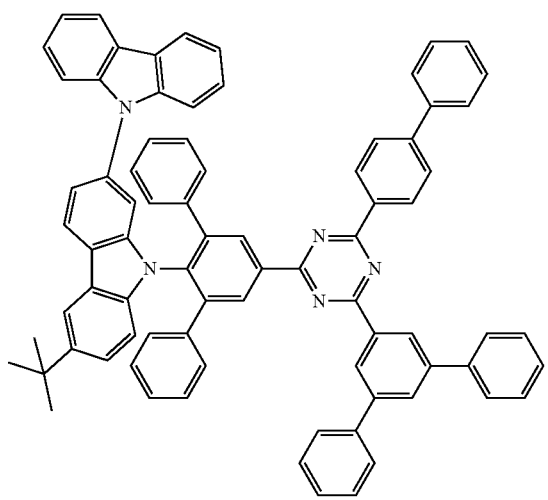

942
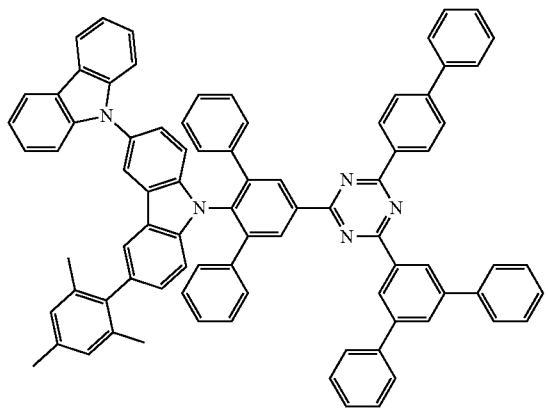
943
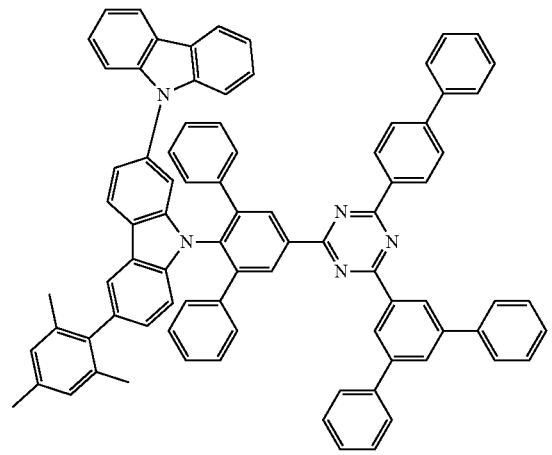
944
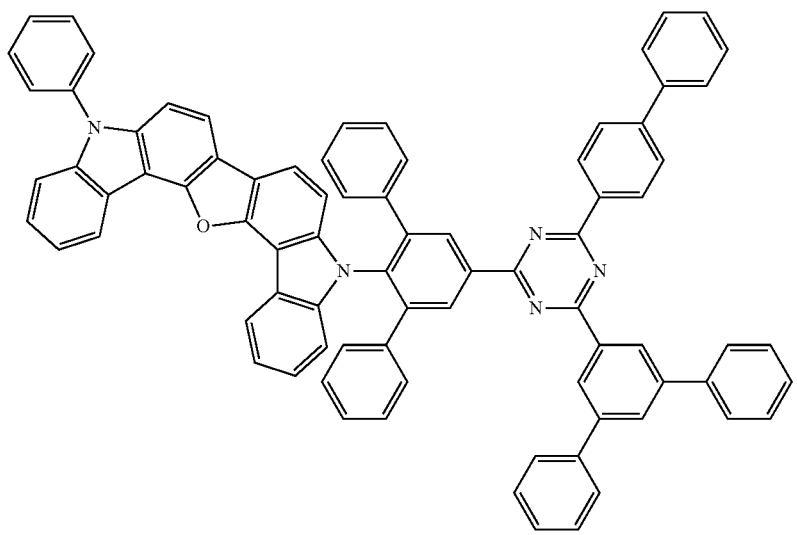
945
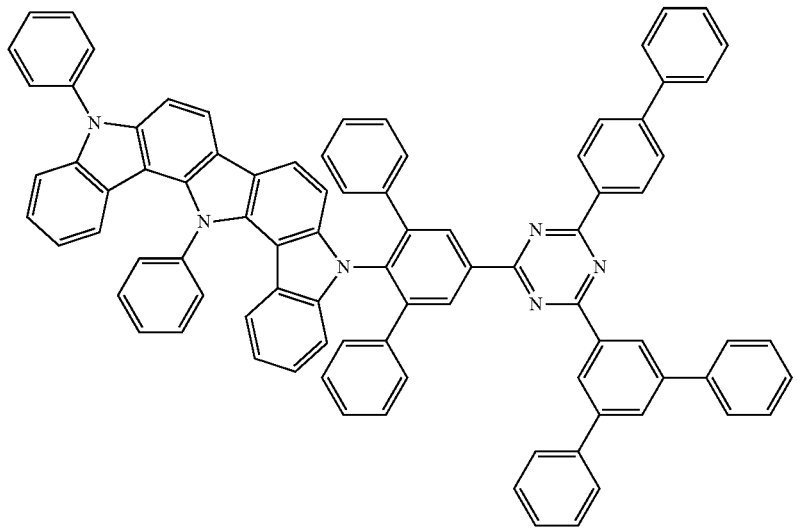

-continued
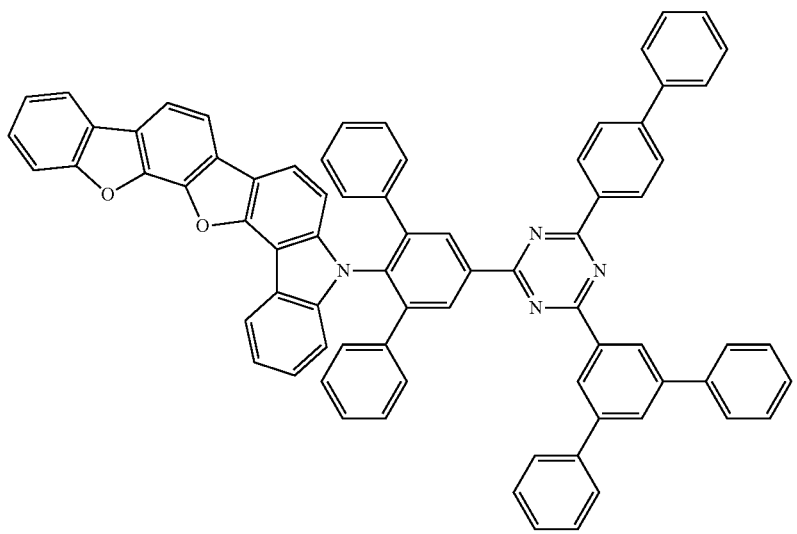
946
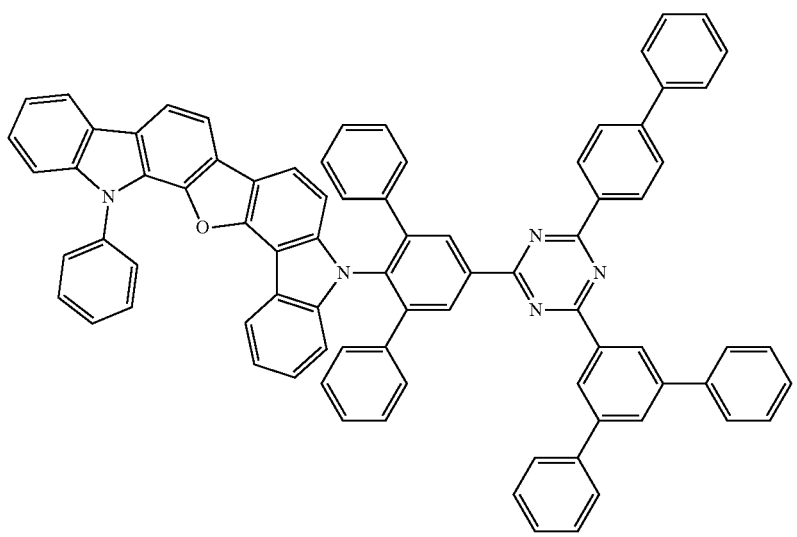
947
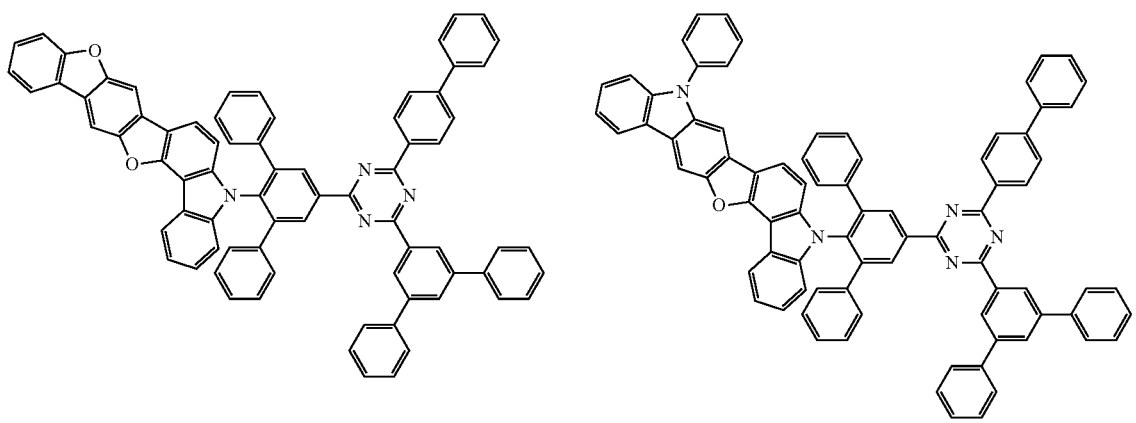
948 949

-continued
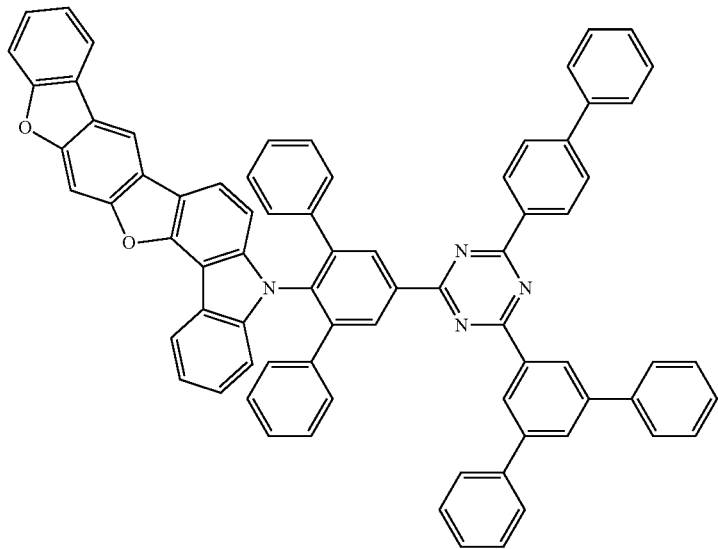
950
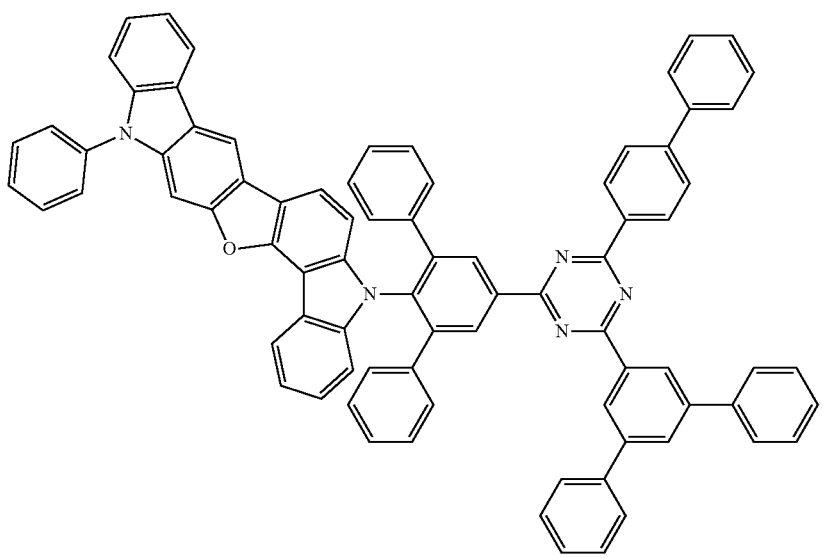
951
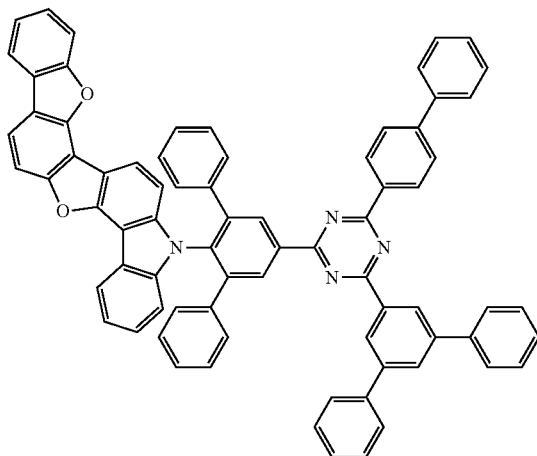
952
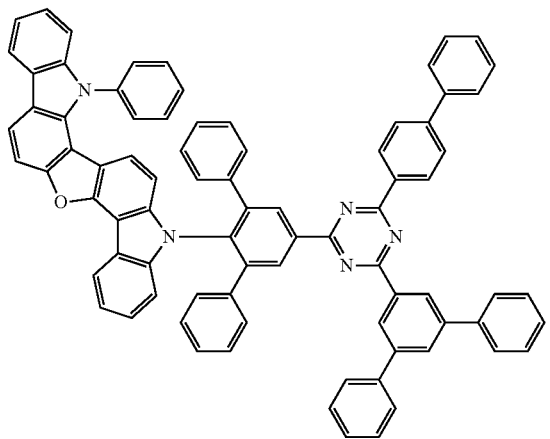
953

954
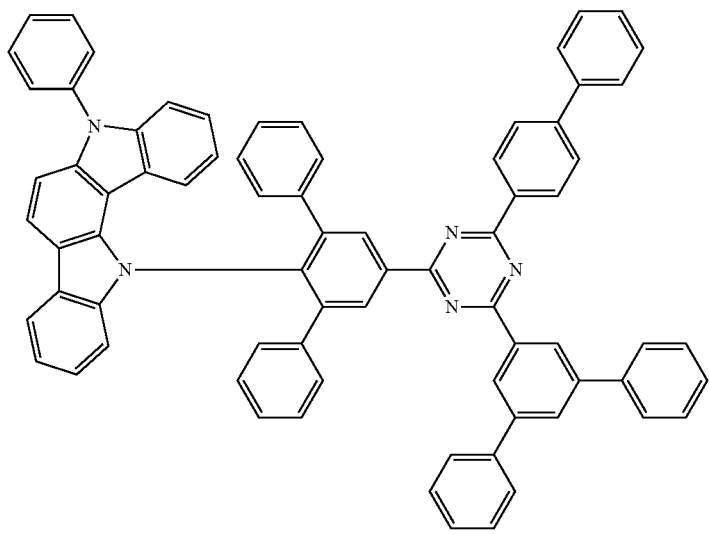
955
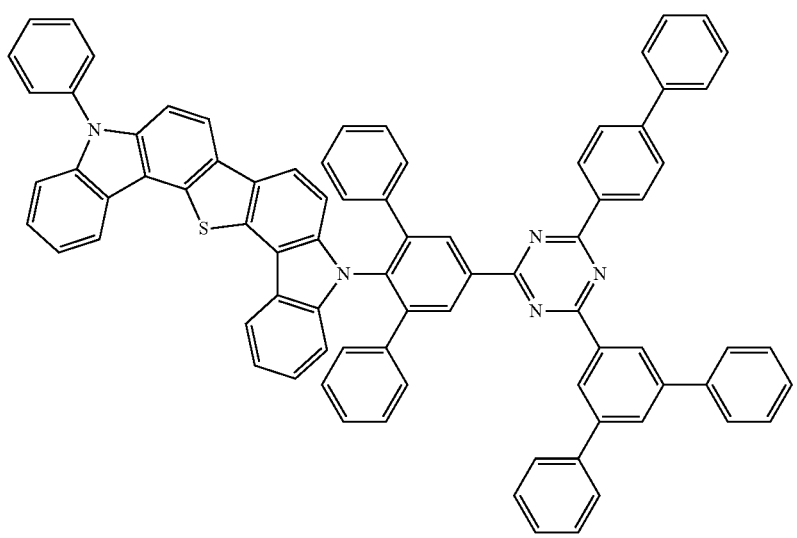
956
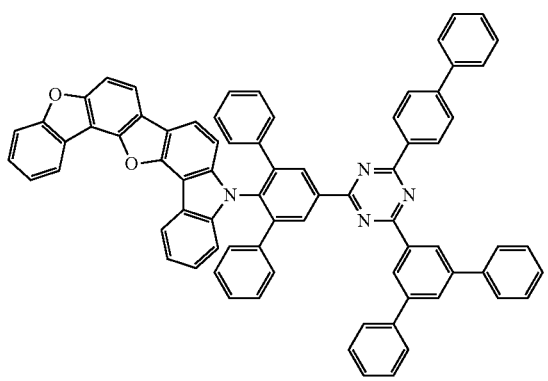
957
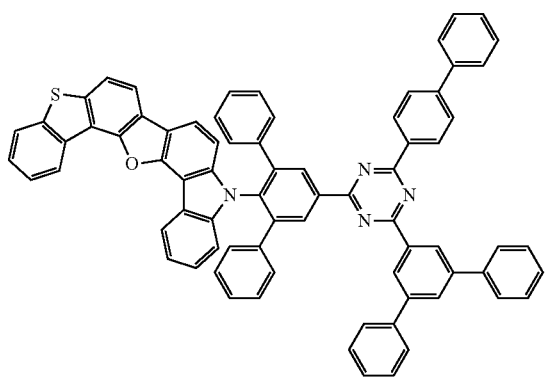

-continued
958
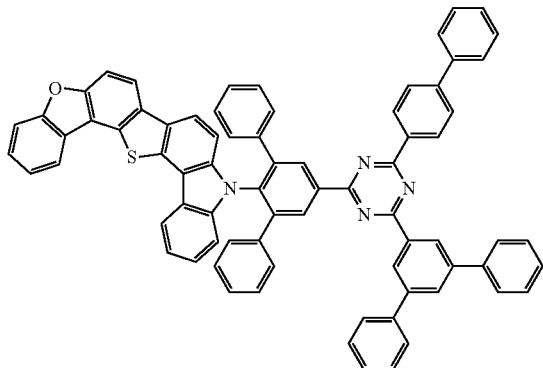
959
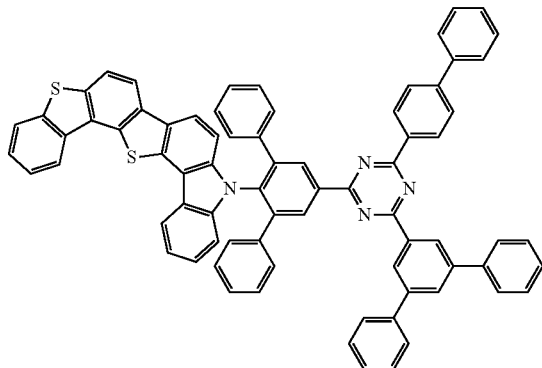
960
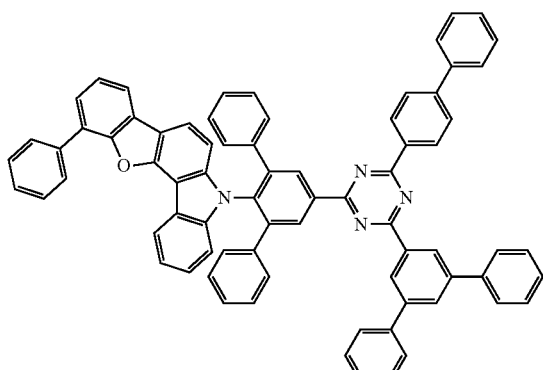
961
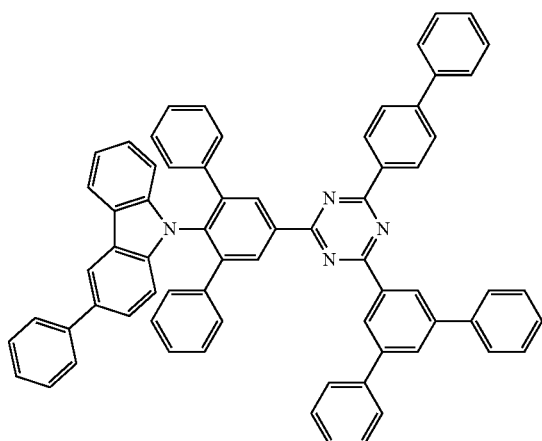
962
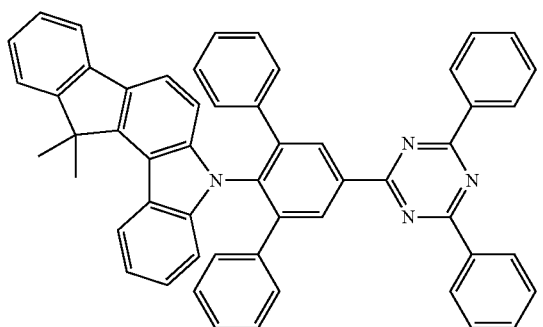
963
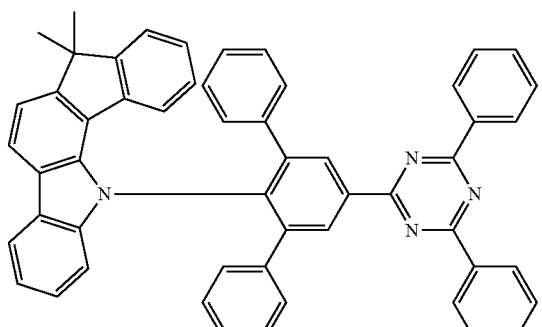
964
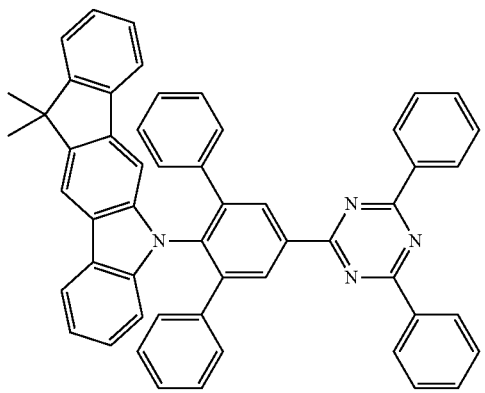
965
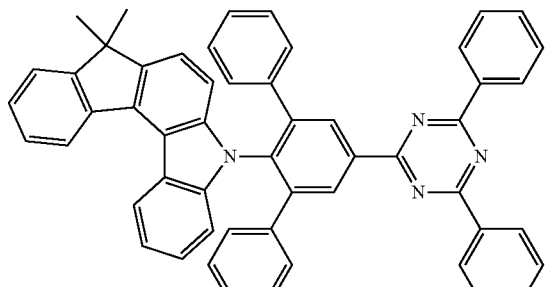

-continued
966
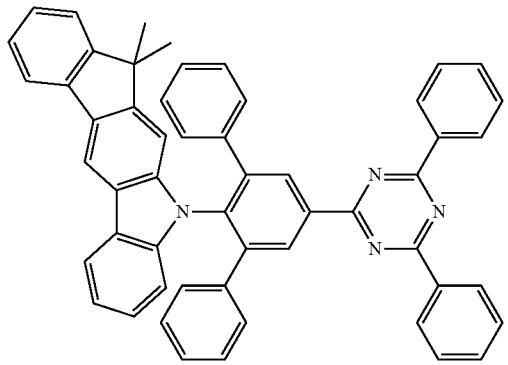
967
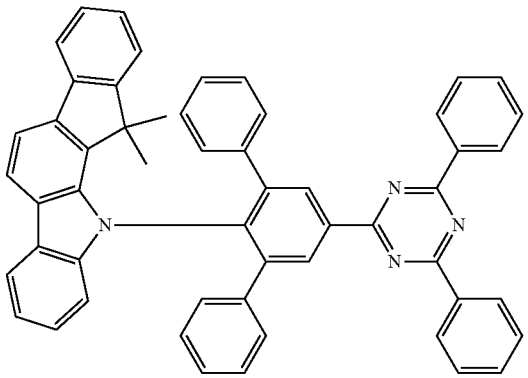
968
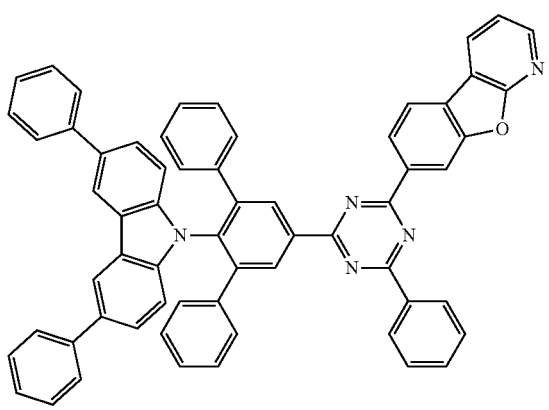
969
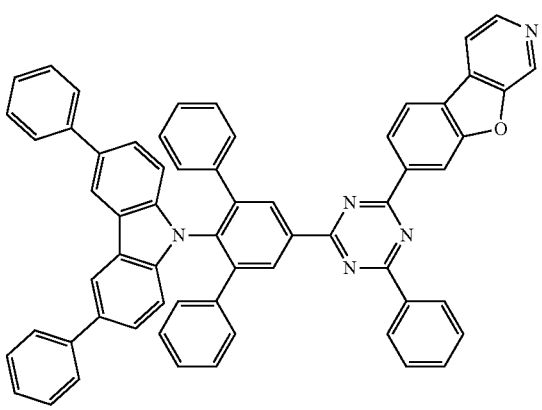
970
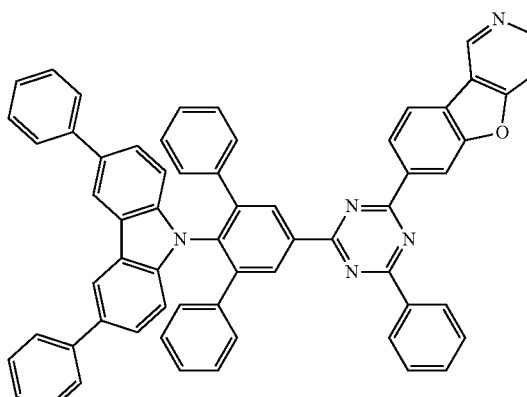
971
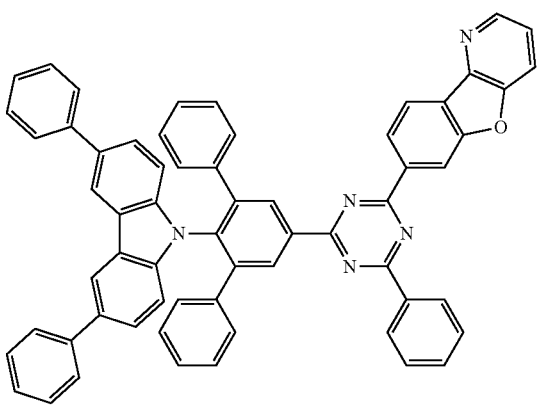
972
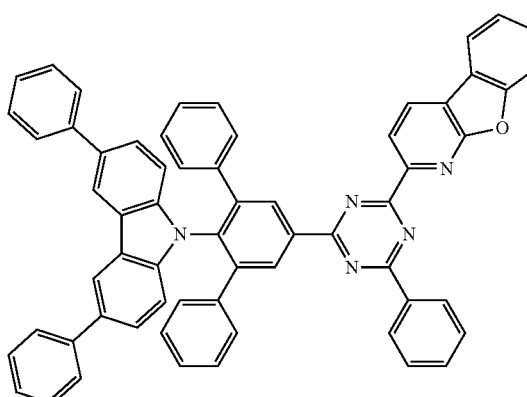
973
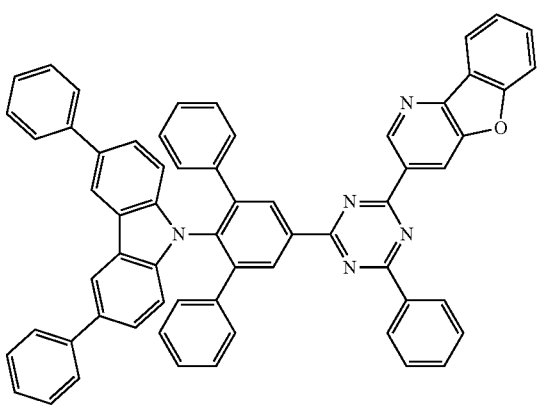

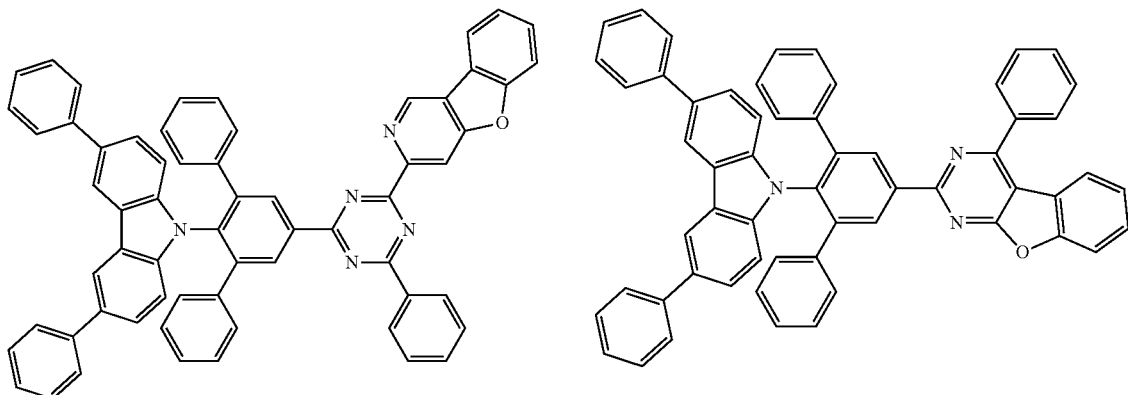
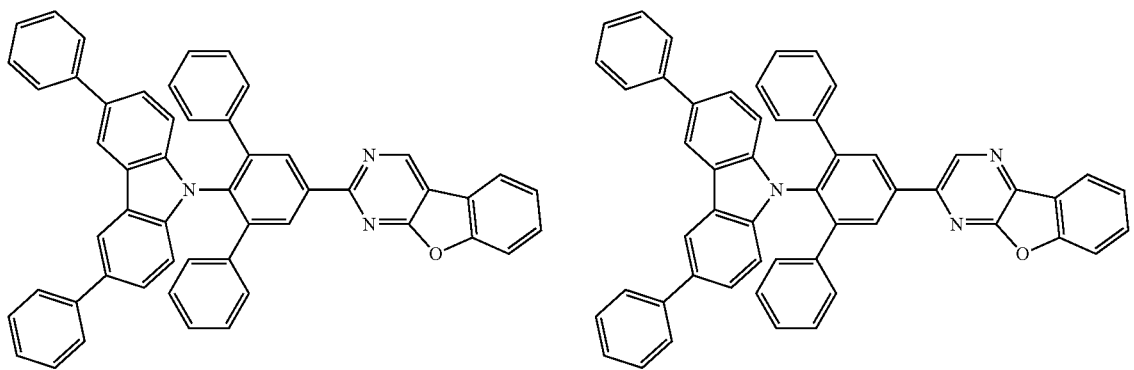
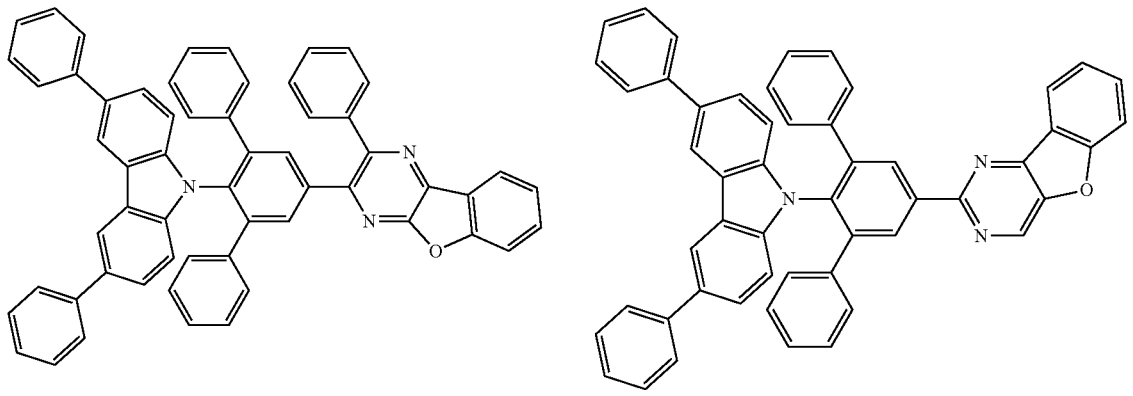
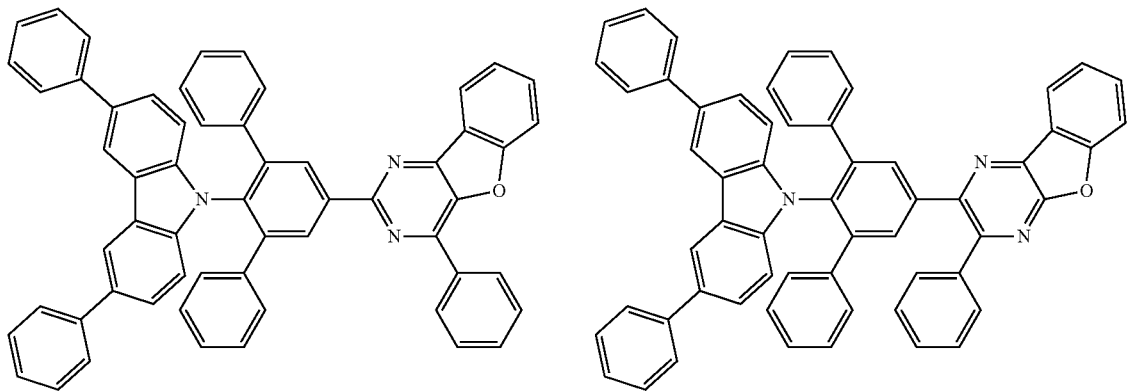

-continued
982
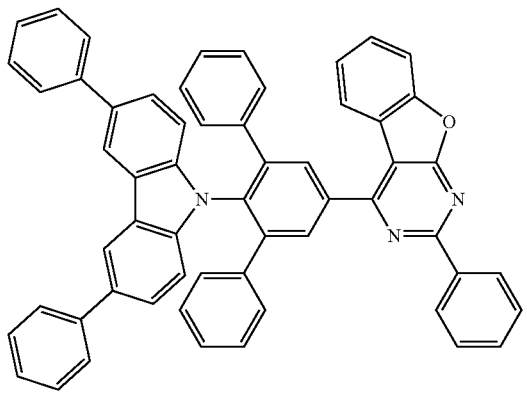
983
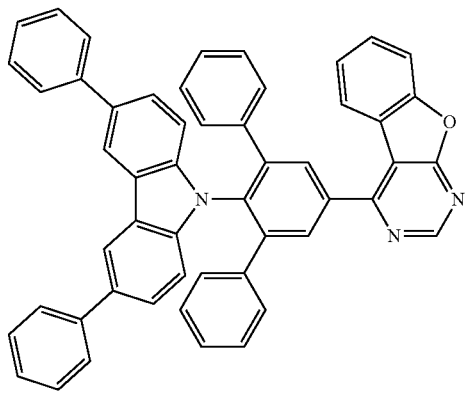
984
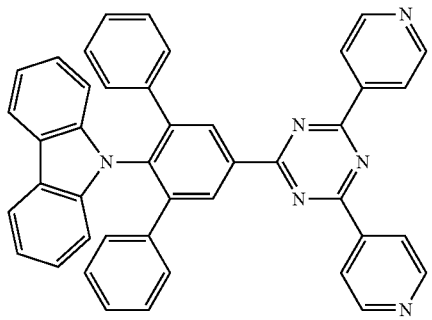
985
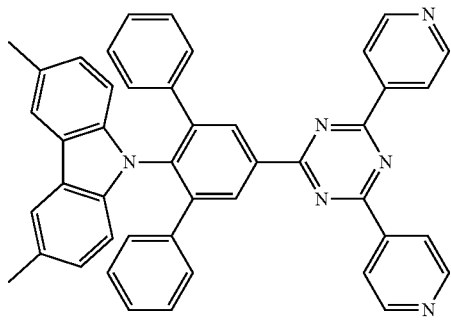
986
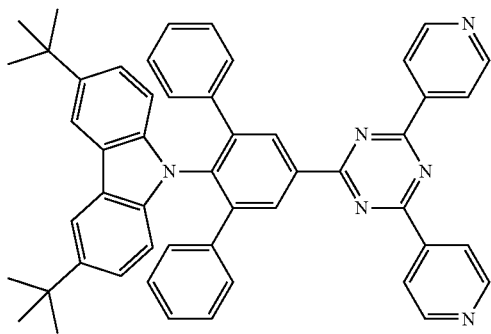
987
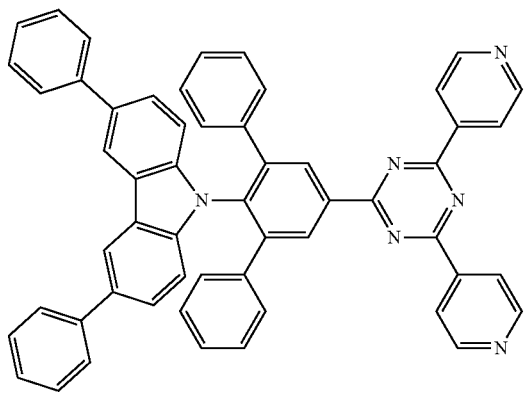
988
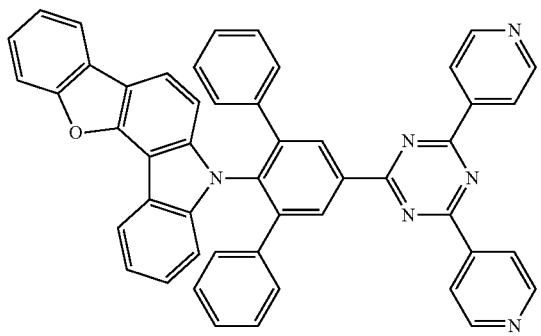
989
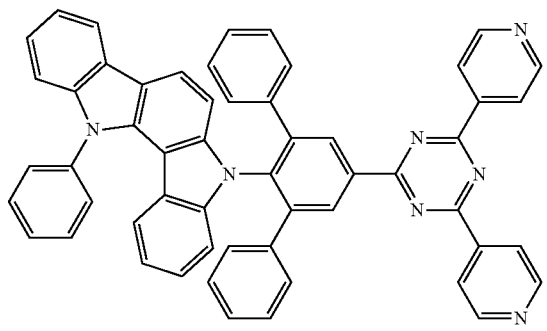

-continued
990
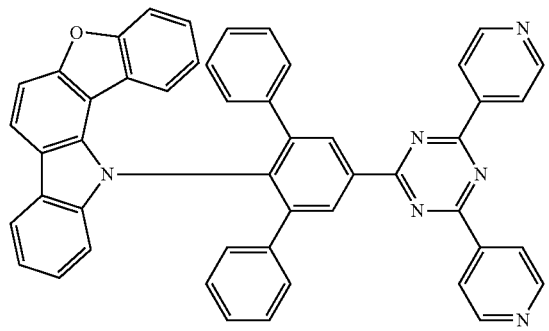
991
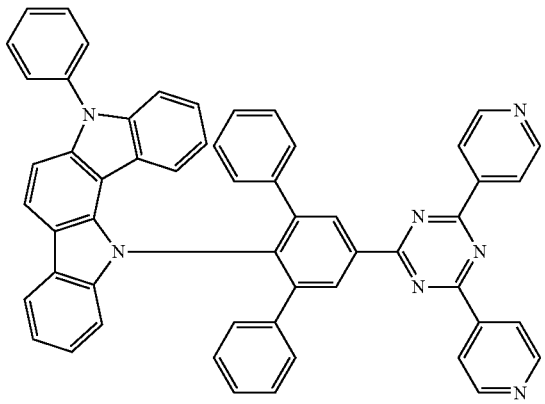
992
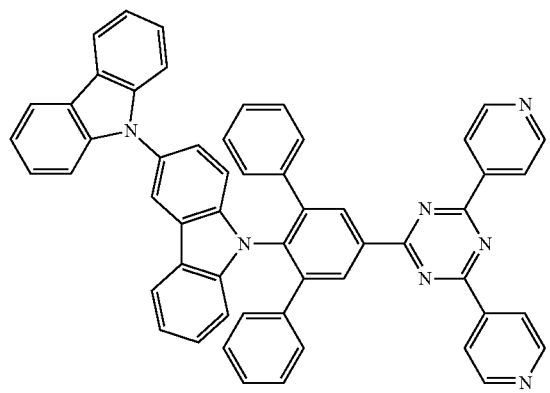
993
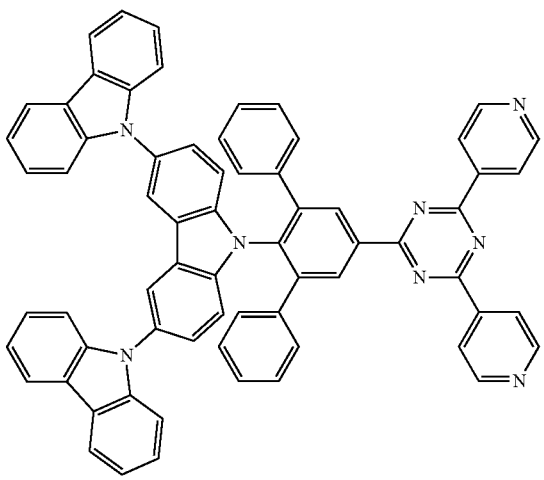
994
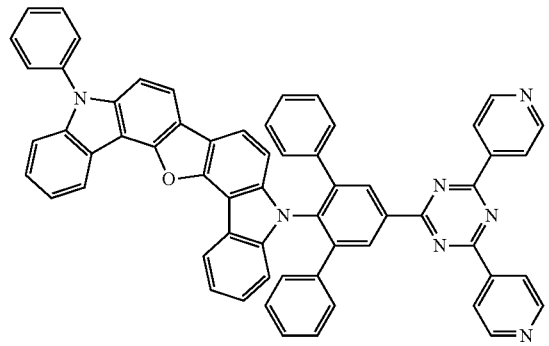
995
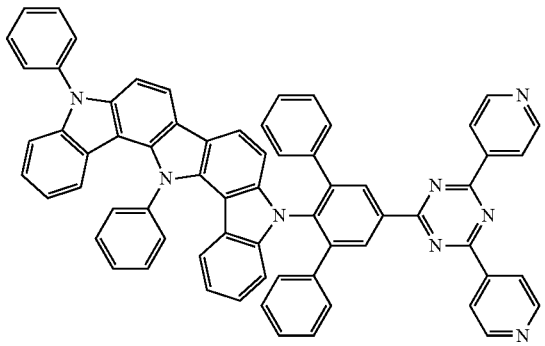

-continued
996
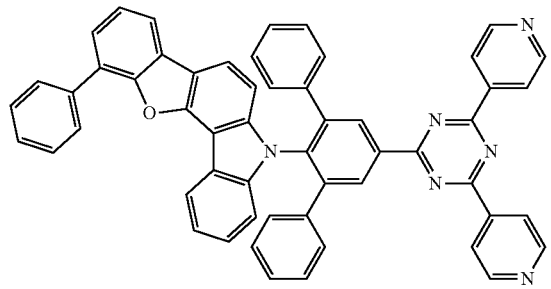
997
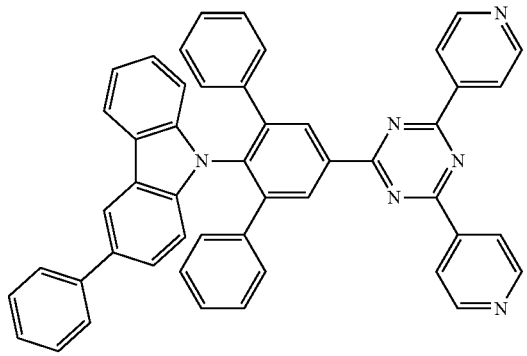
998
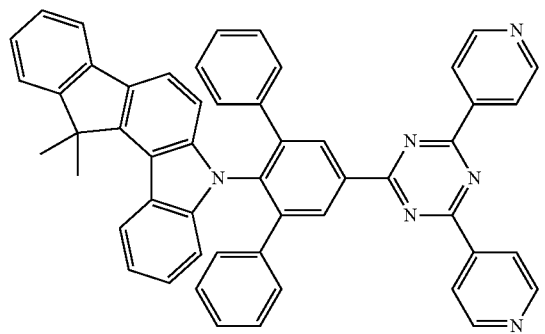
999
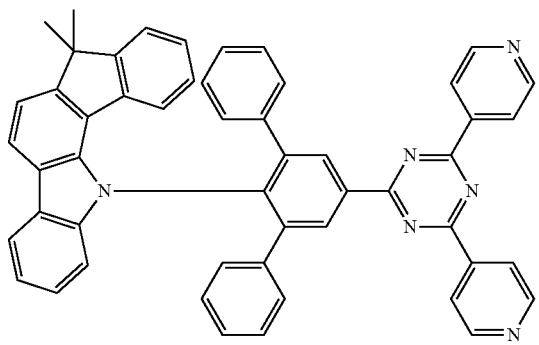
1000
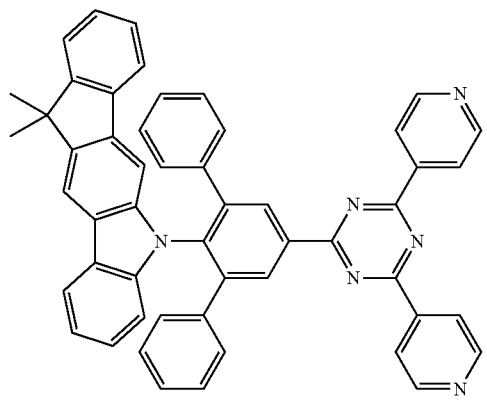
1001
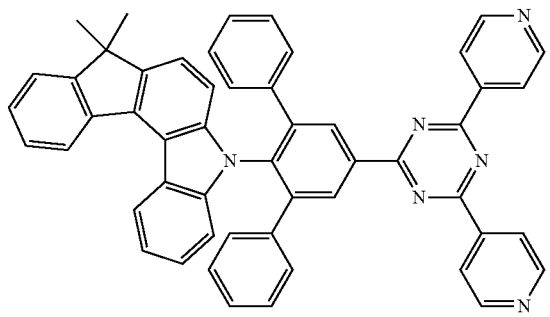
1002
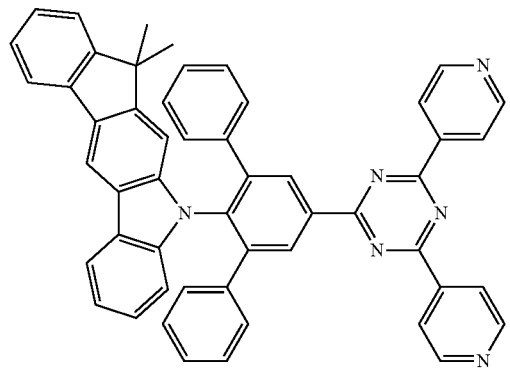
1003
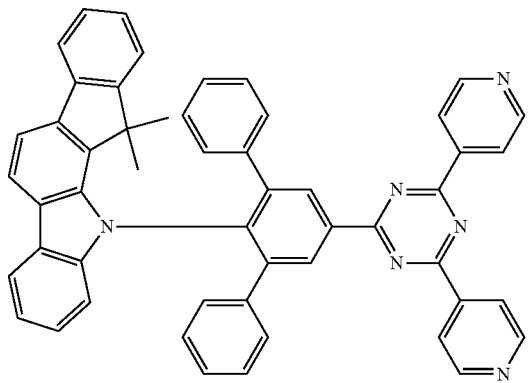

-continued
| 1004 | 1005 |
|---|---|
| 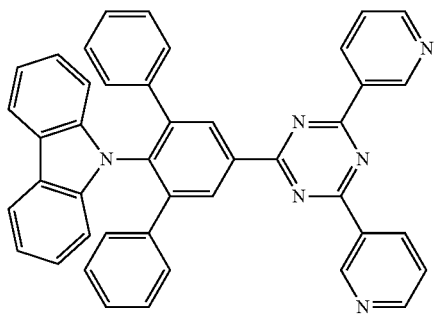 | 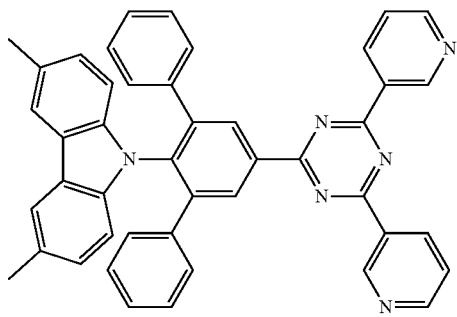 |
| 1006 | 1007 |
| 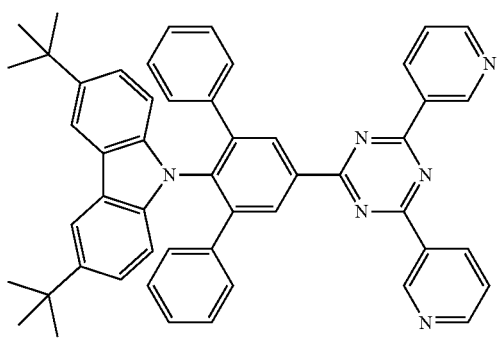 | 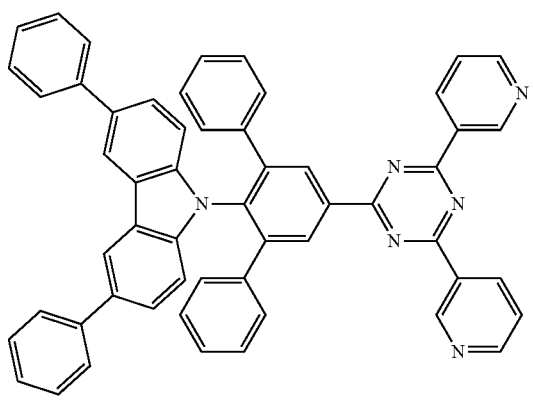 |
| 1008 | 1009 |
| 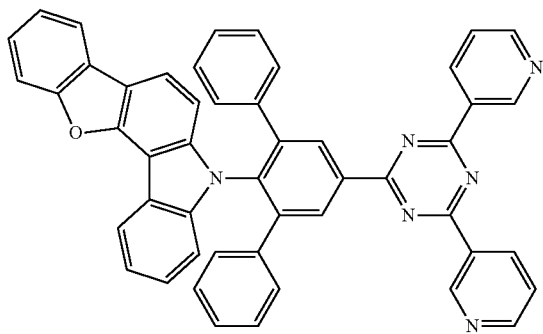 | 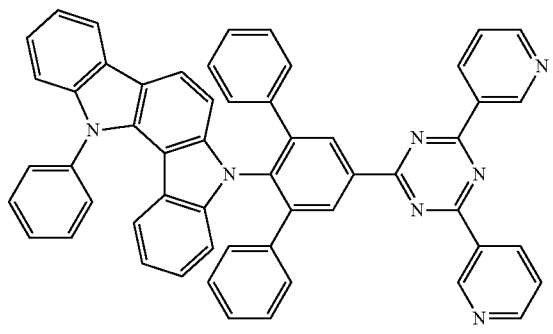 |
| 1010 | 1011 |
| 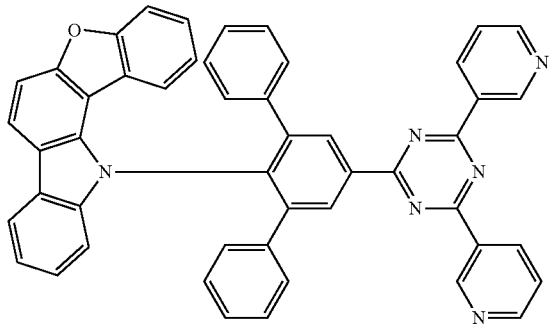 | 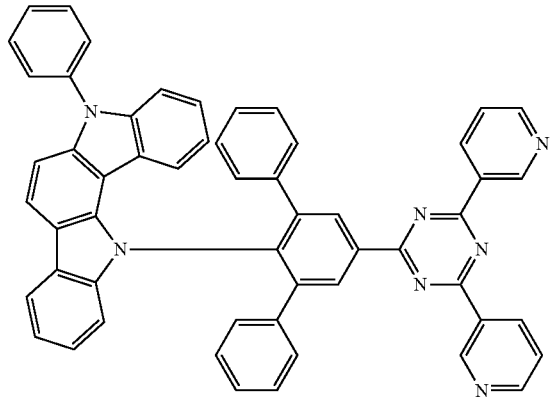 |

-continued
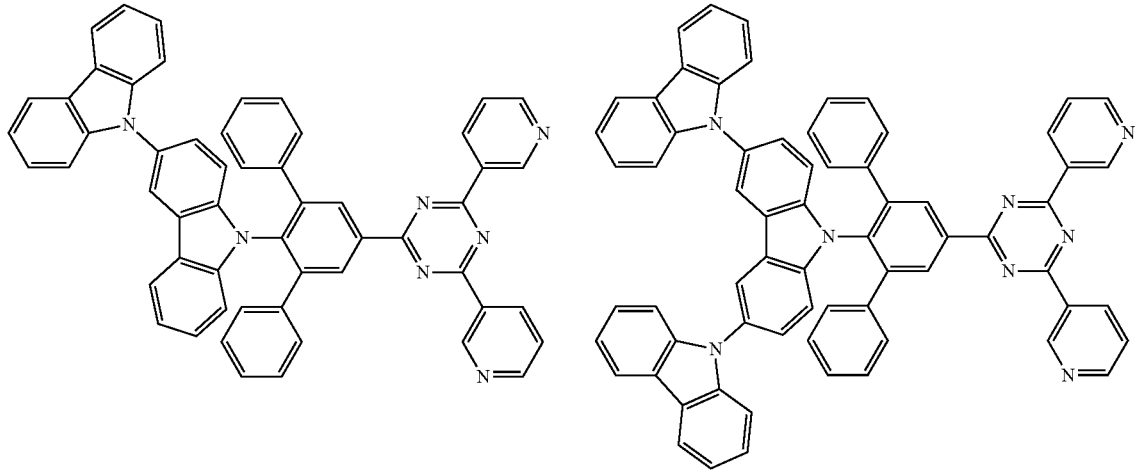
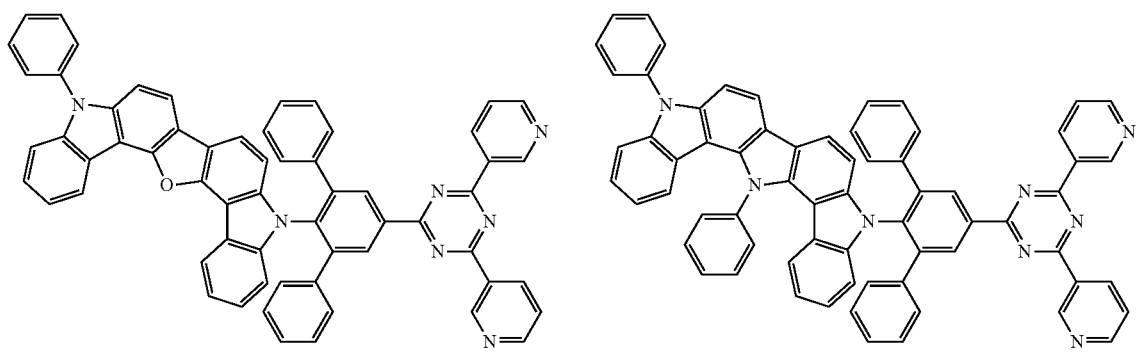
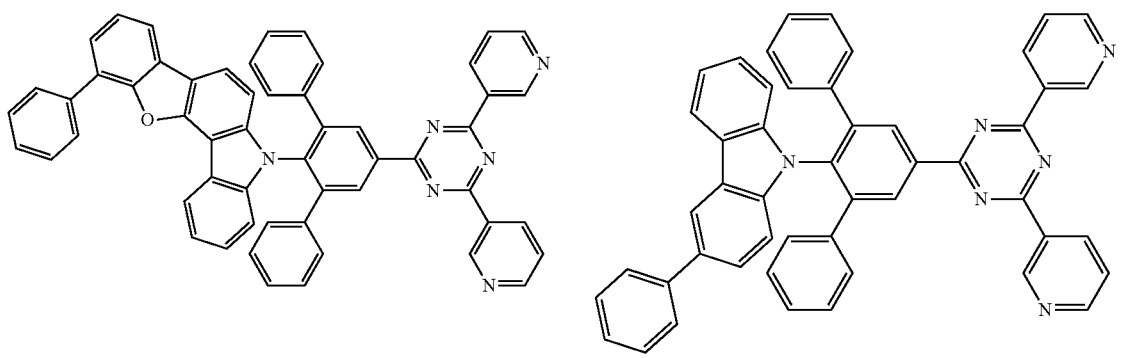
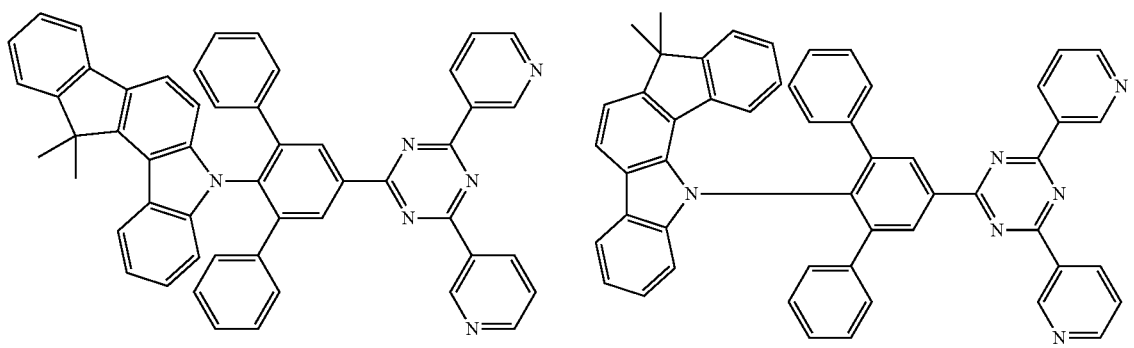

-continued
1020
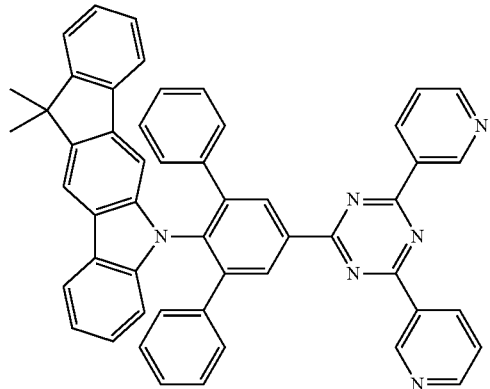
1021
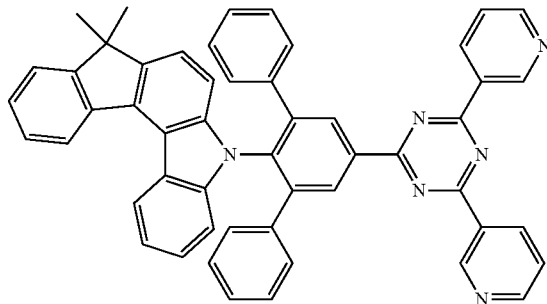
1022
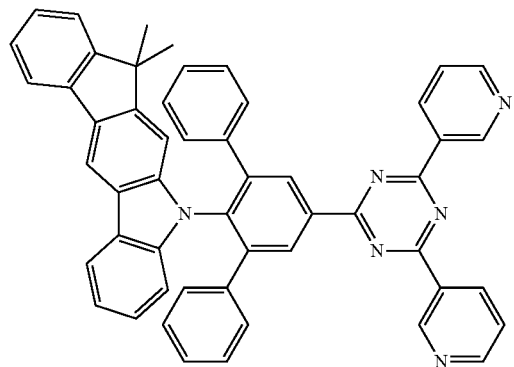
1023
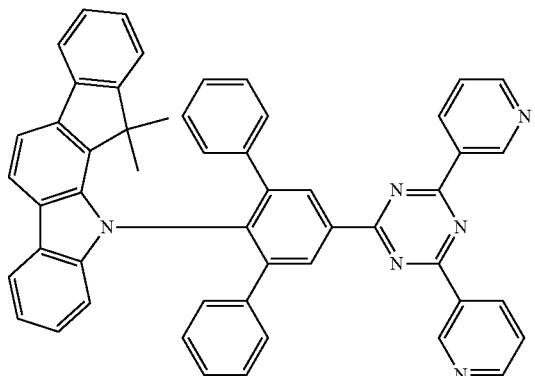
1024
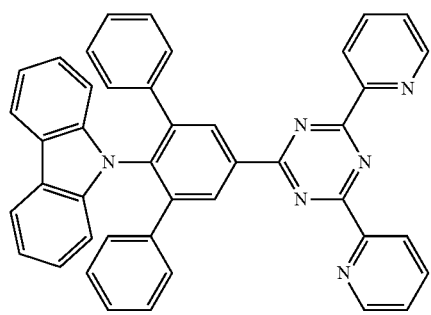
1025
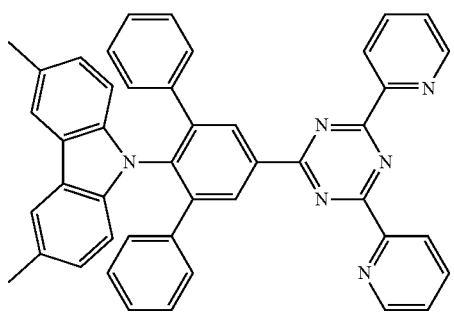
1026
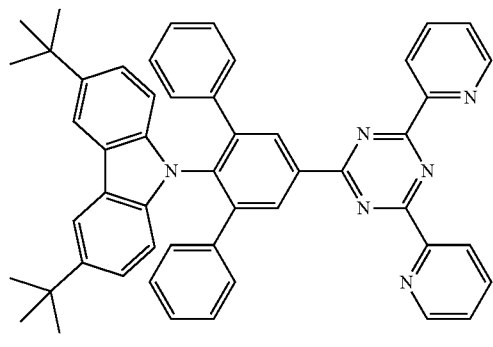
1027
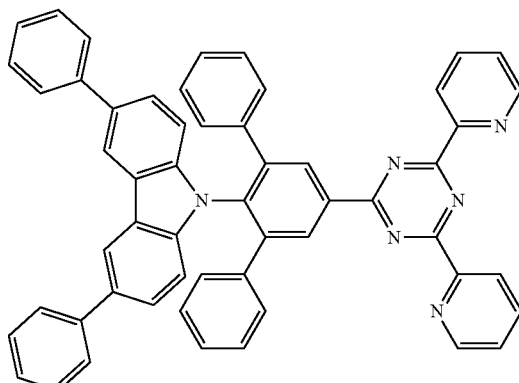

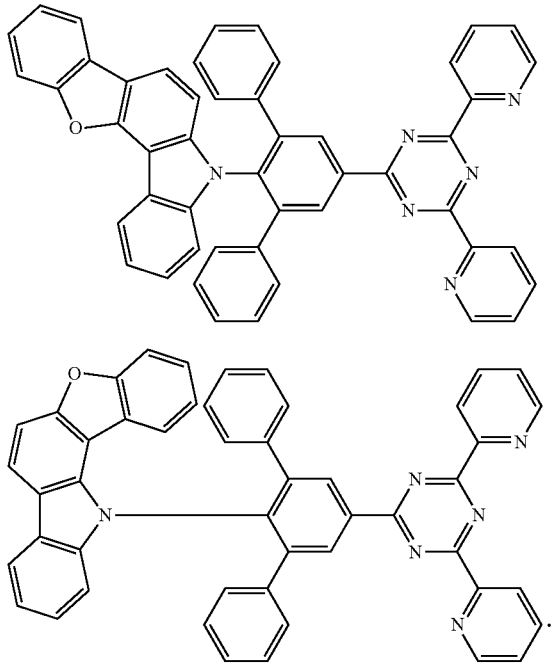

The condensed cyclic compound represented by Formula 1 may include a group ($A_1$) represented by one selected from Formulae 3-1 to 3-5 and capable of acting as an electron acceptor group and a group ($D_1$) represented by Formula 2 and capable of acting as an electron donator group. Therefore, in the condensed cyclic compound represented by Formula 1, HOMO and LUMO may be spatially separated from each other, and thus $\Delta E_{ST}$ (a difference between the lowest excitation singlet energy level ($E_{S1}$) and the lowest excitation energy level ($E_{T1}$)) may be reduced. Therefore, the condensed cyclic compound represented by Formula 1 may cause reverse intersystem crossing (RISC) even at a low temperature (for example, room temperature).

$R_{11}$ and $R_{12}$ in Formula 1 is a substituted or unsubstituted $C_6$-$C_{30}$ aryl group. Therefore, since an angle formed by a plane including $D_1$ and a plane including $A_1$ in Formula 1 increases (that, the plane including $D_1$ and the plane including $A_1$ are twisted), a difference between a lowest excitation singlet energy level and a lowest excitation triplet energy level of the condensed cyclic compound represented by Formula 1 may be reduced. Since the condensed cyclic compound represented by Formula 1 may have high RISC efficiency, an electronic device, for example, an organic light-emitting device, which includes the condensed cyclic compound, may have high efficiency and/or a long lifespan.

The condensed cyclic compound represented by Formula 1 may satisfy Equation 1 below:

$$0 \text{ eV} < \Delta E_{ST} \leq 0.5 \text{ eV}. \qquad \text{Equation 1}$$

In Equation 1, $\Delta E_{ST}$ is a difference between a lowest excitation singlet energy level ($E_{S1}$) of the condensed cyclic compound represented by Formula 1 and a lowest excitation triplet energy level ($E_{T1}$) of the condensed cyclic compound represented by Formula 1. $E_{T1}$ and $E_{S1}$ are evaluated by using a DFT method of Gaussian program structurally optimized at a level of B3LYP/6-31G(d,p).

In an embodiment, the condensed cyclic compound represented by Formula 1 may satisfy Equation 1-1, but embodiments of the present disclosure are not limited thereto:

$$0.01 \text{ eV} < \Delta E_{ST} 0.3 \text{ eV}. \qquad \text{Equation 1-1}$$

The lowest excitation singlet energy level of the condensed cyclic compound represented by Formula 1 may be in a range of about 2.5 electron volts (eV) to about 3.0 eV, but embodiments of the present disclosure are not limited thereto.

In addition, $D_1$ and $A_1$ in the condensed cyclic compound represented by Formula 1 may be linked at a "para position" with respect to a phenylene group. Therefore, the condensed cyclic compound represented by Formula 1 has high oscillator strength, and an electronic device, for example, an organic light-emitting device, which includes the condensed cyclic compound, may have high luminescent efficiency.

For example, HOMO, LUMO, $T_1$ energy level, $S_1$ energy level, and oscillator strength of some of Compounds were evaluated by using a DFT method of Gaussian program (structurally optimized at a level of B3LYP, 6-31G(d,p)), and results thereof are shown in Table 1.

TABLE 1

| Compound No. | HOMO (eV) | LUMO (eV) | $T_1$ (eV) | $S_1$ (eV) | $S_1 - T_1$ (eV) | Oscillator strength (f) |
|---|---|---|---|---|---|---|
| Compound 3 | −5.184 | −1.970 | 2.627 | 2.740 | 0.113 | 0.080 |
| Compound 4 | −5.205 | −2.029 | 2.646 | 2.731 | 0.084 | 0.073 |
| Compound 41 | −5.112 | −2.079 | 2.665 | 2.707 | 0.042 | 0.029 |
| Compound 23 | −5.232 | −2.029 | 2.671 | 2.756 | 0.085 | 0.066 |
| Compound 69 | −5.147 | −2.041 | 2.648 | 2.691 | 0.043 | 0.042 |
| Compound 174 | −5.021 | −1.819 | 2.708 | 2.772 | 0.068 | 0.050 |
| Compound 209 | −4.900 | −1.825 | 2.663 | 2.713 | 0.050 | 0.053 |
| Compound 229 | −5.196 | −2.032 | 2.641 | 2.732 | 0.090 | 0.089 |
| Compound 481 | −5.235 | −2.081 | 2.640 | 2.736 | 0.096 | 0.053 |
| Compound 617 | −5.191 | −2.006 | 2.646 | 2.742 | 0.096 | 0.079 |

TABLE 1-continued

| Compound No. | HOMO (eV) | LUMO (eV) | $T_1$ (eV) | $S_1$ (eV) | $S_1 - T_1$ (eV) | Oscillator strength (f) |
|---|---|---|---|---|---|---|
| Compound 796 | −5.205 | −2.032 | 2.629 | 2.726 | 0.098 | 0.076 |
| Compound 889 | −5.202 | −2.057 | 2.632 | 2.720 | 0.088 | 0.085 |
| Compound 57 | −5.119 | −2.088 | 2.663 | 2.704 | 0.041 | 0.030 |
| Compound 75 | −5.242 | −2.033 | 2.677 | 2.765 | 0.088 | 0.071 |

Referring to Table 1, it is confirmed that the compounds represented by Formula 1 have a small difference between the singlet energy level and the triplet energy level and large oscillator strength. Therefore, an electronic device, for example, an organic light-emitting device, which includes the compound represented by Formula 1 may have high luminescent efficiency.

Synthesis methods of the condensed cyclic compound represented by Formula 1 may be recognizable by one of ordinary skill in the art by referring to Synthesis Examples provided below.

The condensed cyclic compound of Formula 1 may be used as a material for an electronic device, such as an organic light-emitting device. According to another aspect of an exemplary embodiment, an organic light-emitting device includes: a first electrode, a second electrode, and an organic layer disposed between the first electrode and the second electrode, wherein the organic layer includes an emission layer and at least one condensed cyclic compound represented by Formula 1 described above.

The organic light-emitting device may have, due to the inclusion of an organic layer including the condensed cyclic compound represented by Formula 1, low driving voltage, high efficiency, high brightness, high quantum emission efficiency, and a long lifespan.

The condensed cyclic compound of Formula 1 may be used between a pair of electrodes of an organic light-emitting device. For example, the condensed cyclic compound may be included in at least one selected from an emission layer, a hole transport region (including, for example, at least one of a hole injection layer, a hole transport layer, a buffer layer, and an electron blocking layer) that is disposed between the first electrode and the emission layer, and an electron transport region (including, for example, at least one selected from a hole blocking layer, an electron transport layer, and an electron injection layer) that is disposed between the emission layer and the second electrode.

The emission layer of the organic light-emitting device may be implemented according to Embodiment 1, 2, or 3, depending on use of the condensed cyclic compound represented by Formula 1.

Embodiment 1

Embodiment 1 is an embodiment in which the condensed cyclic compound included in the emission layer is used as a fluorescence emitter, that is, the condensed cyclic compound is a fluorescence emitter.

According to Embodiment 1, the emission layer consists of the condensed cyclic compound; or the emission layer may further include a host (hereinafter, referred to as "host A", the host A is not identical to the condensed cyclic compound).

Therefore, according to Embodiment 1, a ratio of an emission component emitted from the condensed cyclic compound to a total emission component emitted from the emission layer may be 80% or more, for example, 90% or more. For example, the ratio of the emission component emitted from the condensed cyclic component to the total emission component emitted from the emission layer may be 95% or more. The condensed cyclic compound may emit fluorescence and/or delayed fluorescence, and the emission component of the condensed cyclic compound is the sum of prompt emission component of the condensed cyclic compound and the delayed fluorescence component by the reverse intersystem crossing of the condensed cyclic compound.

In Embodiment 1, when the emission layer includes, in addition to the condensed cyclic compound, the host A, an amount of the condensed cyclic compound may be about 50 parts by weight or less, for example, about 30 parts by weight or less, based on 100 parts by weight of the emission layer, and an amount of the host A in the emission layer may be about 50 parts by weight or more, for example, about 70 parts by weight or more, based on 100 parts by weight of the emission layer, but embodiments of the present disclosure are not limited thereto.

In Embodiment 1, when the emission layer includes, in addition to the condensed cyclic compound, the host A, the host A and the condensed cyclic compound represented by Formula 1 may satisfy Equation 2:

$$E(H_A)_{S1} > E_{S1}. \qquad \text{Equation 2}$$

In Equation 2, $E(H_A)_{S1}$ is a lowest excitation singlet energy level of the host A, and $E_{S1}$ is a lowest excitation singlet energy level of the condensed cyclic compound represented by Formula 1. $E(H_A)_{S1}$ and $E_{S1}$ are evaluated by using a DFT method of Gaussian program structurally optimized at a level of B3LYP/6-31G(d,p).

When the condensed cyclic compound represented by Formula 1 satisfies Equation 1 and the condensed cyclic compound represented by Formula 1 and the host A satisfy Equation 2, the condensed cyclic compound represented by Formula 1 may emit fluorescence and/or delayed fluorescence. Therefore, the luminescent efficiency of the organic light-emitting device including the condensed cyclic compound represented by Formula 1 and the host A may be improved.

For example, the host A may be a host material described below, but embodiments of the present disclosure are not limited thereto.

Embodiment 2

Embodiment 2 is an embodiment in which the condensed cyclic compound included in the emission layer is used as a host.

According to Embodiment 2, the emission layer may include a host and a dopant, and the host may include the condensed cyclic compound represented by Formula 1. That is, the host consists of the condensed cyclic compound represented by Formula 1, or may further include another known host. The dopant may be, for example, a fluorescent dopant, a phosphorescent dopant, or a thermally activated delayed fluorescent dopant.

Therefore, according to Embodiment 2, a ratio of an emission component of the dopant to a total emission component emitted from the emission layer may be about 80% or more, for example, about 90% or more (in an embodiment, about 95% or more).

In Embodiment 2, an amount of the dopant in the emission layer may be about 50 parts by weight or less, for example, about 30 parts by weight or less, based on 100 parts by weight of the emission layer, and an amount of the host in the emission layer may be about 50 parts by weight or more, for example, about 70 parts by weight or more, based on 100 parts by weight of the emission layer, but embodiments of the present disclosure are not limited thereto.

For example, in Embodiment 2, when the dopant includes a fluorescent dopant (hereinafter, referred to as "fluorescent dopant A"), the condensed cyclic compound represented by Formula 1 and the fluorescent dopant A may satisfy Equation 3:

$$E_{S1} > E(F_A)_{S1}.\qquad\text{Equation 3}$$

In Equation 3, $E_{S1}$ is a lowest excitation singlet energy level of the condensed cyclic compound represented by Formula 1, and $E(F_A)_{S1}$ is a lowest excitation singlet energy level of the fluorescent dopant A.

$E_{S1}$ and $E(F_A)_{S1}$ are evaluated by using a DFT method of Gaussian program structurally optimized at a level of B3LYP/6-31G(d,p).

When the condensed cyclic compound represented by Formula 1 and the fluorescent dopant A satisfy Equation 3, Forster energy transfer from the condensed cyclic compound represented by Formula 1 to the fluorescent dopant A may be accelerated. Therefore, the luminescent efficiency of the organic light-emitting device including the condensed cyclic compound represented by Formula 1 and the fluorescent dopant A may be improved.

For example, the dopant may be a dopant material described below, but embodiments of the present disclosure are not limited thereto.

When the host further includes another known host, the known host may be a host material described below, but embodiments of the present disclosure are not limited thereto.

Embodiment 3

Embodiment 3 is an embodiment in which the condensed cyclic compound included in the emission layer is used as an auxiliary dopant.

According to Embodiment 3, the emission layer may include a host, an auxiliary dopant, and a dopant, and the auxiliary dopant may include the condensed cyclic compound. The dopant may be, for example, a fluorescent dopant, a phosphorescent dopant, or a thermally activated delayed fluorescent dopant.

Therefore, according to Embodiment 3, a ratio of an emission component of the dopant to a total emission component emitted from the emission layer may be about 80% or more, for example, about 90% or more (in an embodiment, about 95% or more).

In Embodiment 3, an amount of the dopant in the emission layer may be about 50 parts by weight or less, for example, about 30 parts by weight or less, based on 100 parts by weight of the emission layer, and an amount of the host in the emission layer may be about 50 parts by weight or more, for example, about 70 parts by weight or more, based on 100 parts by weight of the emission layer, and an amount of the auxiliary dopant may be about 30 parts by weight or less, for example, about 20 parts by weight or less, based on 100 parts by weight of the emission layer, but embodiments of the present disclosure are not limited thereto.

For example, in Embodiment 3, when the dopant is a fluorescent dopant (hereinafter, referred to as "fluorescent dopant B"), the host (hereinafter, referred to as "host B"), the condensed cyclic compound represented by Formula 1, and the fluorescent dopant B may satisfy Equation 4:

$$E(H_B)_{S1} > E_{S1} > E(F_B)_{S1}.\qquad\text{Equation 4}$$

In Equation 4, $E(H_B)_{S1}$ is a lowest excitation singlet energy level of the host B, $E_{S1}$ is a lowest excitation singlet energy level of the condensed cyclic compound represented by Formula 1, and $E(F_B)_{S1}$ is a lowest excitation singlet energy level of the fluorescent dopant B.

$E(H_B)_{S1}$, $E_{S1}$, and $E(F_B)_{S1}$ are evaluated by using a DFT method of Gaussian program structurally optimized at a level of B3LYP/6-31G(d,p).

When the host B, the condensed cyclic compound represented by Formula 1, and the fluorescent dopant B satisfy Equation 4, Forster energy transfer from the condensed cyclic compound represented by Formula 1 to the fluorescent dopant B may be accelerated. Therefore, the luminescent efficiency of the organic light-emitting device including the host B, the condensed cyclic compound represented by Formula 1, and the fluorescent dopant B may be improved.

The host B and the condensed cyclic compound represented by Formula 1 may further satisfy Equation 5:

$$E(H_B)_{T1} - E_{T1} > 0.05\text{ eV}.\qquad\text{Equation 5}$$

In Equation 5, $E(H_B)_{T1}$ is a lowest excitation triplet energy level of the host B, and $E_{T1}$ is a lowest excitation triplet energy level of the condensed cyclic compound represented by Formula 1.

$E(H_B)_{T1}$ and $E_{T1}$ are evaluated by using a DFT method of Gaussian program structurally optimized at a level of B3LYP/6-31G(d,p).

In Embodiment 3, since Equation 5 is satisfied (for example, $E(H_B)_{T1} - E_{T1}$ is in a range of about 0.10 eV about 0.65 eV), the energy of triplet excitons generated in the auxiliary dopant in the emission layer cannot move to the host B in the emission layer, and the probability that the triplet excitons will be lost in paths other than the light emission is reduced. Therefore, the organic light-emitting device may have high efficiency.

The condensed cyclic compound represented by Formula 1 and the fluorescent dopant B may further satisfy Equation 6:

$$E(F_B)_{S1} - E_{S1} < 0\text{ eV}.\qquad\text{Equation 6}$$

In Equation 6, $E(F_B)_{S1}$ is a lowest excitation singlet energy level of the fluorescent dopant, and $E_{S1}$ is a lowest excitation triplet energy level of the condensed cyclic compound represented by Formula 1.

$E(F_B)_{S1}$ and $E_{S1}$ are evaluated by using a DFT method of Gaussian program structurally optimized at a level of B3LYP/6-31G(d,p).

In Embodiment 3, when Equation 6 is satisfied (for example, $E_{S1(FD)} - E_{S1(AD)}$ is in a range of about −0.4 eV to about −0.05 eV), the energy of singlet excitons generated in the auxiliary dopant in the emission layer may quickly move to the fluorescent dopant B. Therefore, the light emission is substantially performed only in the fluorescent dopant B in the emission layer of the organic light-emitting device, and the fluorescence emission spectrum having excellent color purity based on the fluorescent dopant B may be implemented. In addition, since the fluorescence emission having a relatively short exciton lifespan is achieved, it is possible to suppress an efficiency droop phenomenon under high luminance (so-called roll-off phenomenon) caused by exciton-exciton interaction or exciton-charge (hole or electron) interaction (exciton-polaron interaction), thereby implementing an organic light-emitting device having high efficiency. Furthermore, since the auxiliary dopant has a short exciton lifespan, the probability of chemical or physical deteriorations that may occur in the exciton state of the auxiliary dopant may be reduced, and thus, the organic light-emitting device satisfying Equation 6 may have improved durability.

The host in Embodiment 3 may be a host material described below, but embodiments of the present disclosure are not limited thereto.

The dopant in Embodiment 3 may be a dopant material described below, but embodiments of the present disclosure are not limited thereto.

For example, the host may have a triplet energy level of about 2.9 eV or more, for example, a triplet energy level of about 2.9 eV to about 4.5 eV. Therefore, since the energy transfer from the host to the fluorescent dopant, the phosphorescent dopant, and/or the delayed fluorescent dopant is effectively achieved, the organic light-emitting device may have high efficiency.

For example, the host may include at least one compound selected from a fluorene-containing compound, a carbazole-containing compound, a dibenzofuran-containing compound, a dibenzothiophene-containing compound, an indenocarbazole-containing compound, an indolocarbazole-containing compound, a benzofurocarbazole-containing compound, a benzothienocarbazole-containing compound, an acridine-containing compound, dihyroacridine-containing compound, a triindolobenzene-containing compound, a pyridine-containing compound, a pyrimidine-containing compound, a triazine-containing compound, a silicon-containing compound, a cyano group-containing compound, a phosphine oxide-containing compound, and a sulfoxide-containing compound, but embodiments of the present disclosure are not limited thereto.

In an embodiment, the host may include a compound including at least one carbazole ring and at least one cyano group.

For example, the host may be a group represented by one selected from Formulae 11-1 to 11-3, but embodiments of the present disclosure are not limited thereto:

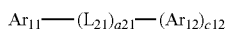

Formula 11-1

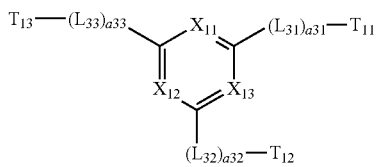

Formula 11-2

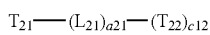

Formula 11-3

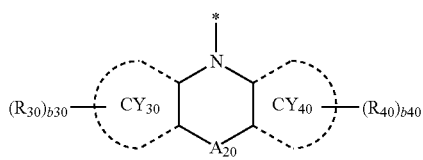

Formula 13

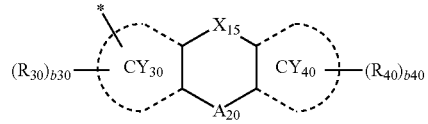

Formula 14

In Formulae 11-1 to 11-3, 13, and 14, $Ar_{11}$ and $Ar_{12}$ may each independently be a group represented one selected from by Formulae 13 and 14, $X_{15}$ may be $N(R_{200})$, O, or S, $X_{11}$ may be N or $C(T_{14})$, $X_{12}$ may be N or $C(T_{15})$, and $X_{13}$ may be N or $C(T_{16})$, wherein at least one selected from $X_{11}$ to $X_{13}$ may each independently be N, $T_{21}$ and $T_{22}$ may each independently be selected from *-$(L_{21})_{a21}$-$Si(Q_{41})(Q_{42})(Q_{43})$ and *-$(L_{21})_{a21}$-$P(=O)(Q_{51})(Q_{52})$, $L_{21}$ and $L_{31}$ to $L_{33}$ may each independently be selected from:

a single bond, O, S, $Si(Q_{61})(Q_{62})$, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{71})(Q_{72})(Q_{73})$, a21 and a31 to a33 may each independently be an integer from 0 to 5, wherein, when all is two or more, two or more of groups $L_{11}$ may be identical to or different from each other, when a21 is two or more, two or more of groups $L_{21}$ may be identical to or different from each other, when a31 is two or more, two or more of groups $L_{31}$ may be identical to or different from each other, when a32 is two or more, two or more of groups $L_{32}$ may be identical to or different from each other, and when a33 is two or more, two or more of groups $L_{33}$ may be identical to or different from each other, $CY_{30}$ and $CY_{40}$ may each independently be selected from a benzene group, a naphthalene group, a fluorene group, a carbazole group, a benzocarbazole group, an indolocarbazole group, a dibenzofuran group, and a dibenzothiophene group, $A_{20}$ may be selected from:

a single bond, a $C_1$-$C_4$ alkylene group, and a $C_2$-$C_4$ alkenylene group; and a $C_1$-$C_4$ alkylene group, and a $C_2$-$C_4$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($C_{281}$)($Q_{82}$)($Q_{83}$), and $T_{11}$ to $T_{16}$, $R_{200}$, $R_{30}$, and $R_{40}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ aryl alkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroaryl alkyl group, a substituted or unsubstituted monovalent non-aromatic condensed polycyclic group, a substituted or unsubstituted monovalent non-aromatic condensed heteropolycyclic group, and —Si($Q_{91}$)($Q_{92}$)($Q_{93}$), b30 and b40 may each independently be an integer from 0 to 10, c12 may be 0, 1, 2, or 3,

* indicates a binding site to a neighboring atom, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ aryl alkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroaryl alkyl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, a monovalent non-aromatic condensed heteropolycyclic group, and —Si($Q_{101}$)($Q_{102}$)($Q_{103}$), and $Q_{41}$ to $Q_{43}$, $Q_{51}$ to $Q_{52}$, $Q_{61}$ to $Q_{62}$, $Q_{71}$ to $Q_{73}$, $Q_{81}$ to $Q_{83}$, $Q_{91}$ to $Q_{93}$, and $Q_{101}$ to $Q_{103}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, the host may include at least one selected from Compounds H-1 to H-27, but embodiments of the present disclosure are not limited thereto:

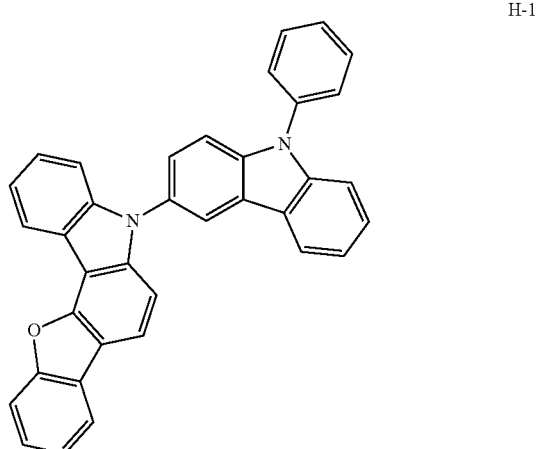

H-1

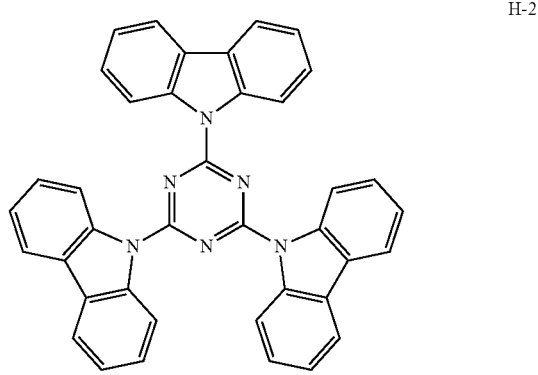

H-2

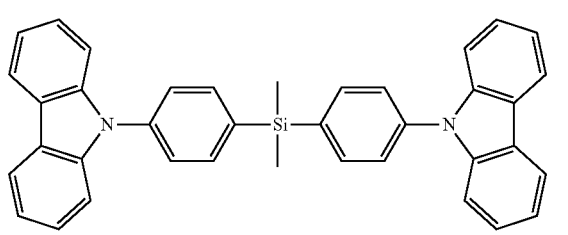

H-3

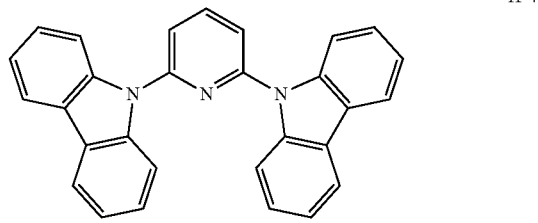

H-4

H-5
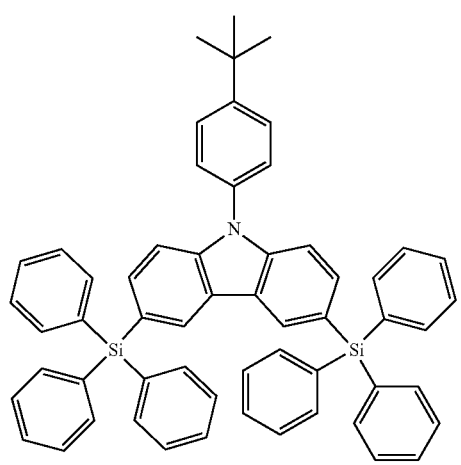
H-6
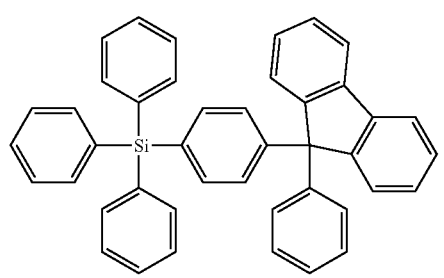
H-7
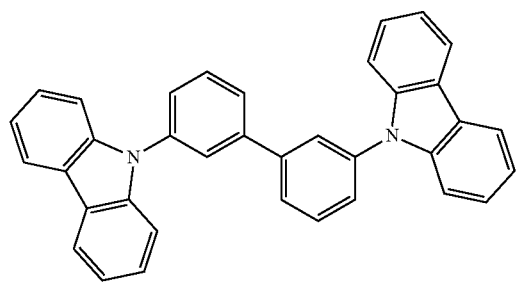
H-8
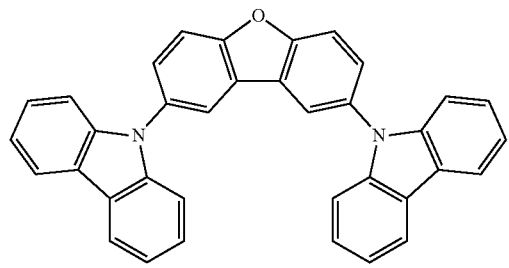
H-9
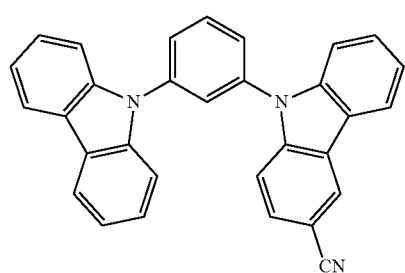
H-10
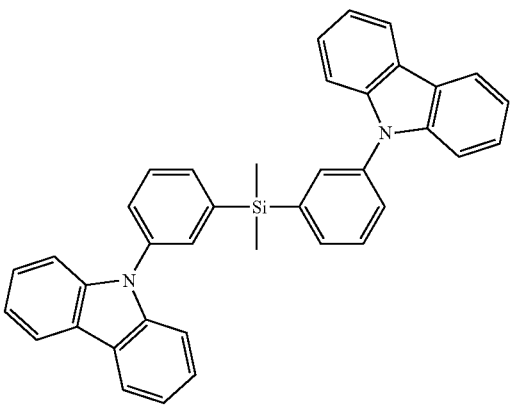
H-11
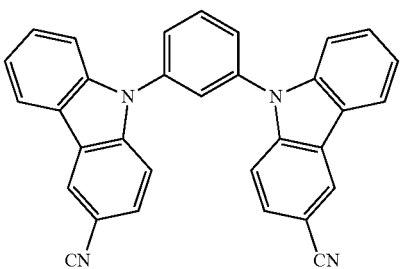
H-12
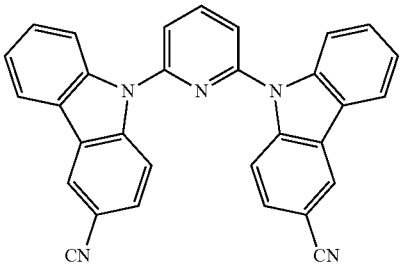
H-13
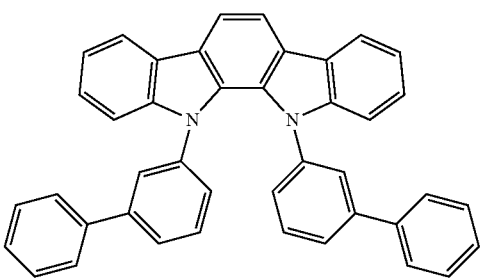
H-14
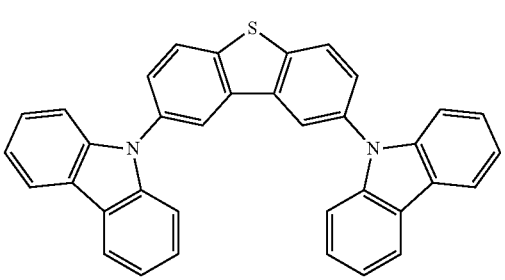

H-15
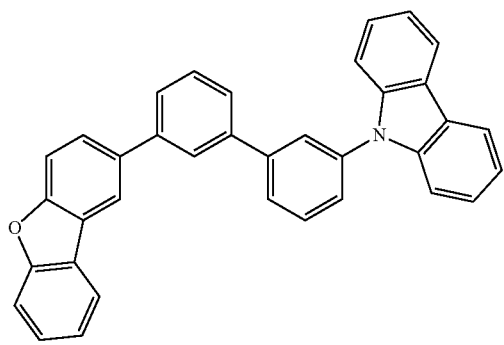
H-16
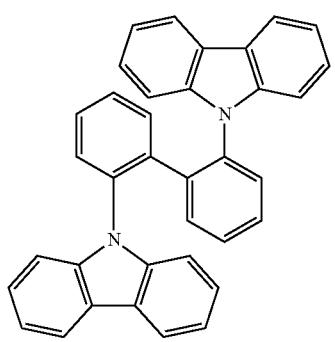
H-17
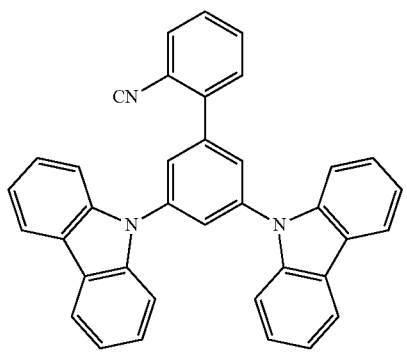
H-18
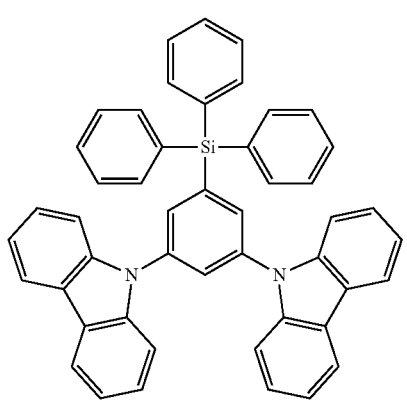
H-19
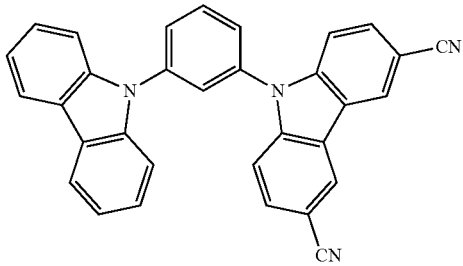
H-20
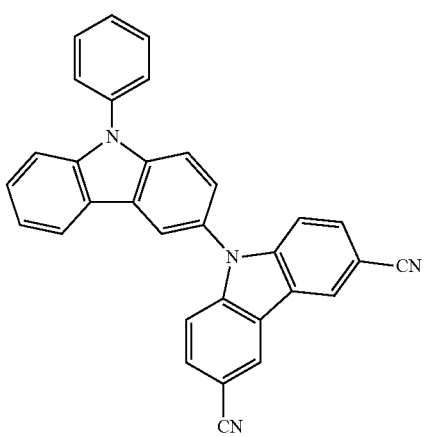
H-21
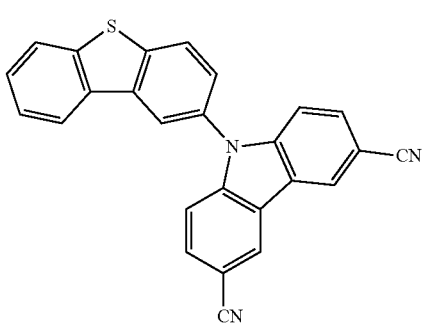
H-22
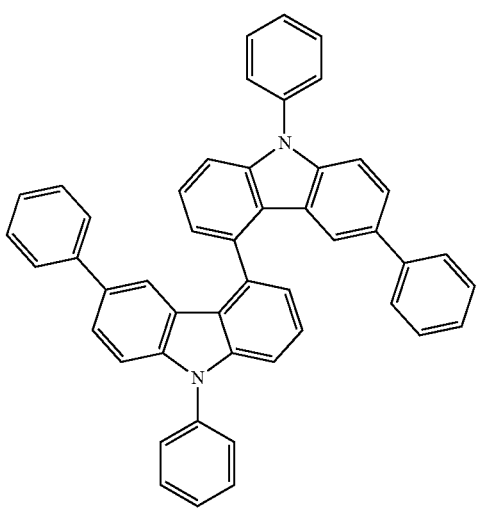

H-23

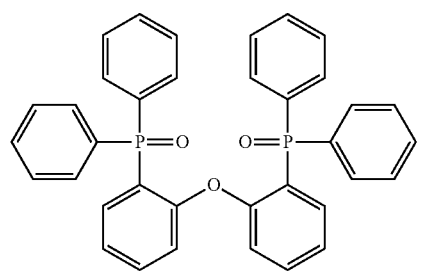

H-24

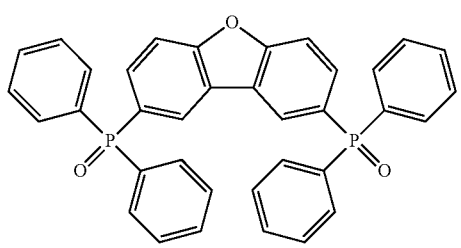

H-25

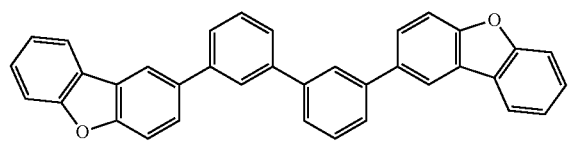

H-26

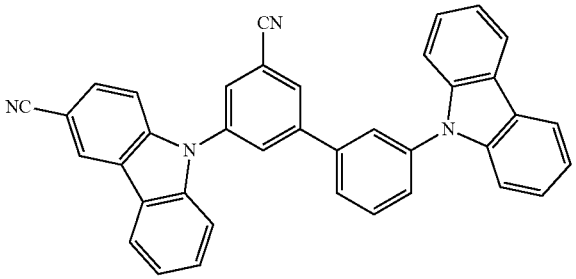

H-27

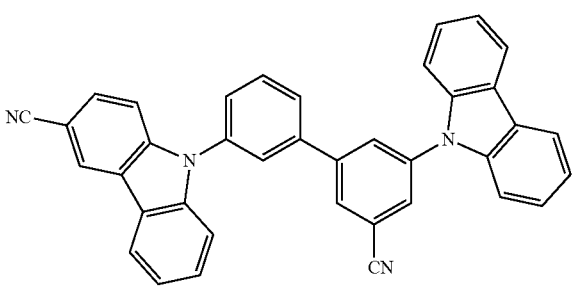

The fluorescent dopant may be selected from a condensed polycyclic compound and a styryl based compound.

In an embodiment, the fluorescent dopant may include at least one selected from a naphthalene-containing core, a fluorene-containing core, a spiro-bifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, and a core represented by one selected from Formulae 501-1 to 501-18, but embodiments of the present disclosure are not limited thereto:

501-1

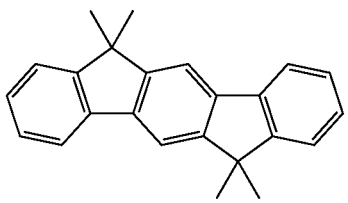

501-2

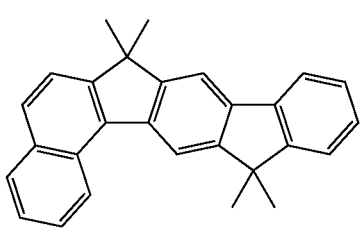

501-3

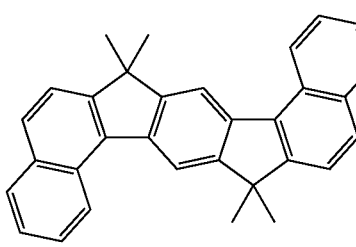

501-4

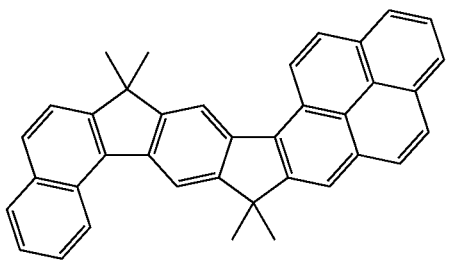

501-5

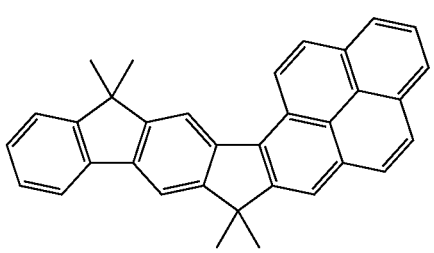

501-6

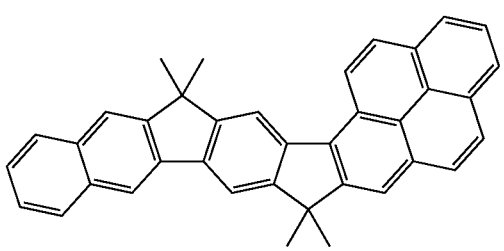

501-7
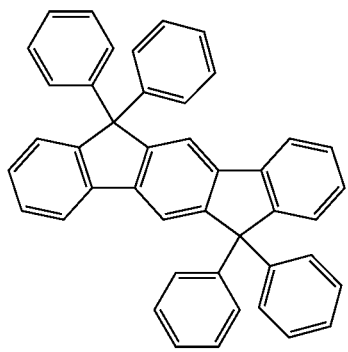
501-8
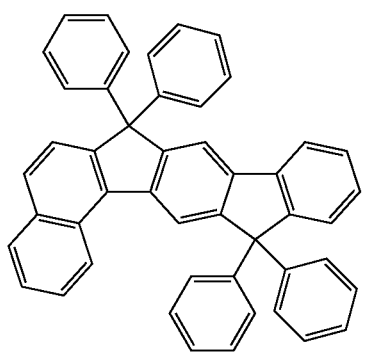
501-9
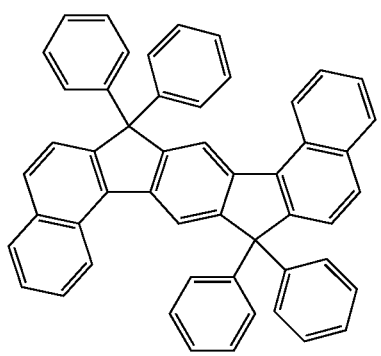
501-10
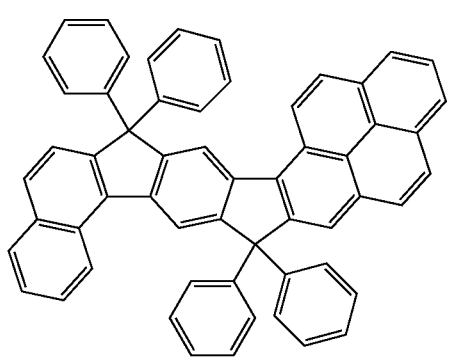
501-11
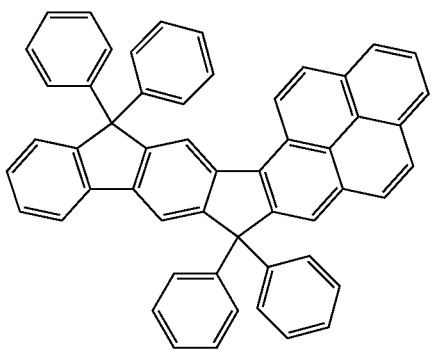
501-12
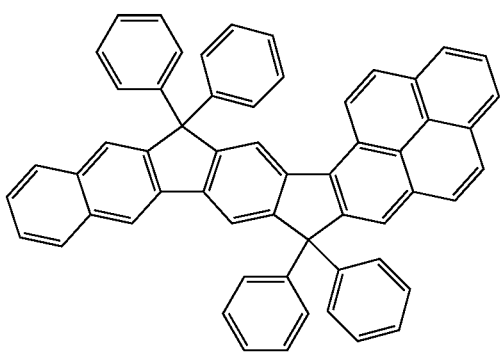
501-13
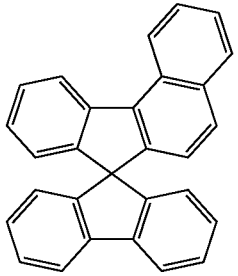
501-14
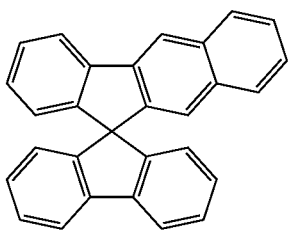
501-15
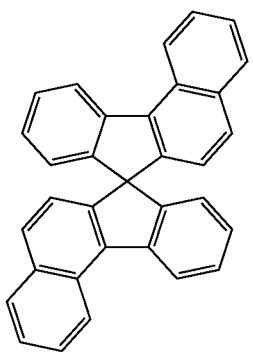

-continued

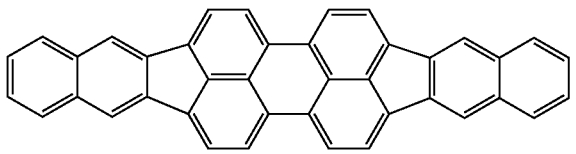
501-16

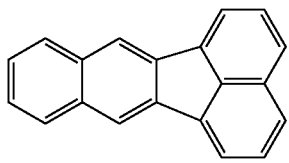
501-17

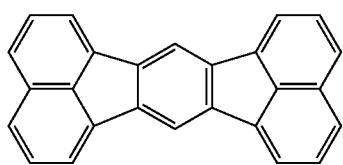
501-18

In one or more embodiments, the fluorescent dopant may be selected from a styryl-amine-based compound and a styryl-carbazole-based compound, but embodiments of the present disclosure are not limited thereto.

In one or more embodiments, the fluorescent dopant may be a compound represented by Formula 501:

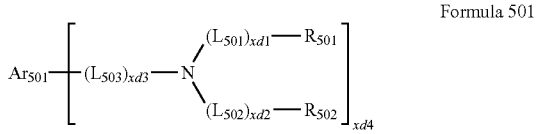
Formula 501

In Formula 50, $Ar_{501}$ may be selected from:

a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene, an indenoanthracene, a tetracene, a bisanthracene, and a group represented by one selected from Formulae 501-1 to 501-18; and a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene an indenoanthracene, a tetracene, a bisanthracene, and a group represented by one selected from Formulae 501-1 to 501-18, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a alkoxy group, a $C_3$-$C_{10}$ cycloalkyl group, a $C_1$-$C_{10}$ heterocycloalkyl group, a $C_3$-$C_{10}$-cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may each independently be selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group), $L_{501}$ to $L_{503}$ may each independently be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3; and xd4 may be selected from 0, 1, 2, 3, 4, 5, and 6.

For example, in Formula 50, $Ar_{501}$ may be selected from:

a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene, an indenoanthracene, a tetracene, a bisanthracene, and a group represented by one selected from Formulae 501-1 to 501-18; and a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene, an indenoanthracene, a tetracene, a bisanthracene, and a group represented by one selected from Formulae 501-1 to 501-18, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, and —Si($Q_{501}$)($Q_{502}$)($Q_{503}$) (wherein $Q_{501}$ to $Q_{503}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group), $L_{501}$ to $L_{503}$ may each independently have the same definition as that of $L_{21}$, xd1 to xd3 may each independently be selected from 0, 1, and 2, xd4 may be selected from 0, 1, 2, and 3, but embodiments of the present disclosure are not limited thereto.

In one or more embodiments, the fluorescent dopant may include a compound represented by one selected from Formulae 502-1 to 502-5:

xd1 to xd8 may each independently have the same definition as that of xd1 in Formula 501, $R_{501}$ to $R_{508}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, Formula 502-1

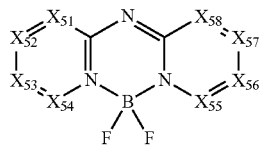

Formula 502-2

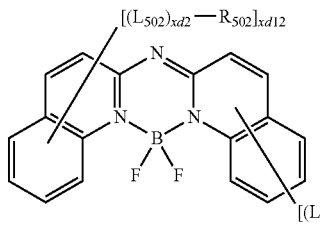

Formula 502-3

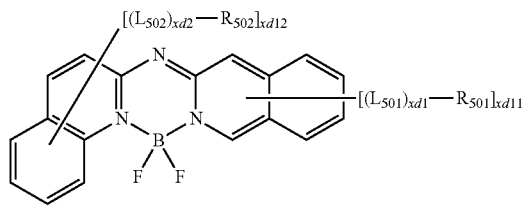

Formula 502-4

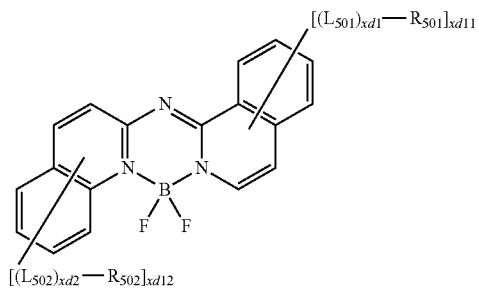

Formula 502-5

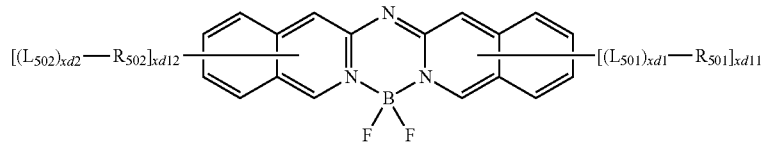

In Formulae 502-1 to 502-5, $X_{51}$ may be N or C-[($L_{501}$)$_{xd1}$-$R_{501}$], $X_{52}$ may be N or C-[($L_{502}$)$_{xd2}$-$R_{502}$], $X_{53}$ may be N or C-[($L_{503}$)$_{xd3}$-$R_{503}$], $X_{54}$ may be N or C-[($L_{504}$)$_{xd4}$-$R_{504}$], $X_{55}$ may be N or C-[($L_{505}$)$_{xd5}$-$R_{505}$], $X_{56}$ may be N or C-[($L_{506}$)$_{xd6}$-$R_{506}$], $X_{57}$ may be N or C-[($L_{507}$)$_{xd7}$-$R_{507}$], and $X_{58}$ may be N or C-[($L_{508}$)$_{xd8}$-$R_{508}$], $L_{501}$ to $L_{508}$ may each independently have the same definition as that of $L_{501}$ in Formula 501, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, and xd11 and xd12 may each independently be an integer from 0 to 5, two groups selected from $R_{501}$ to $R_{504}$ may optionally be linked each other to form a saturated or unsaturated ring, and two groups selected from $R_{505}$ to $R_{508}$ may optionally be linked each other to form a saturated or unsaturated ring.

The fluorescent dopant may include, for example, at least one selected from Compounds FD(1) to FD(16) and FD1 to FD13:

FD(1)

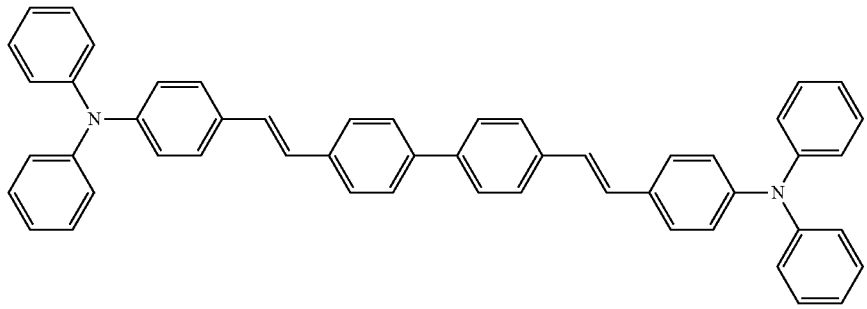

FD(2)

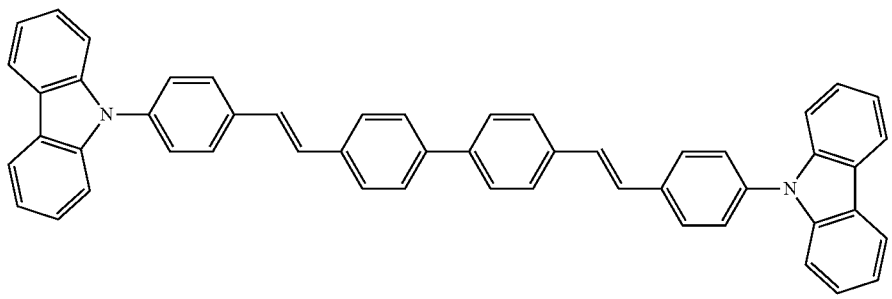

FD(3)

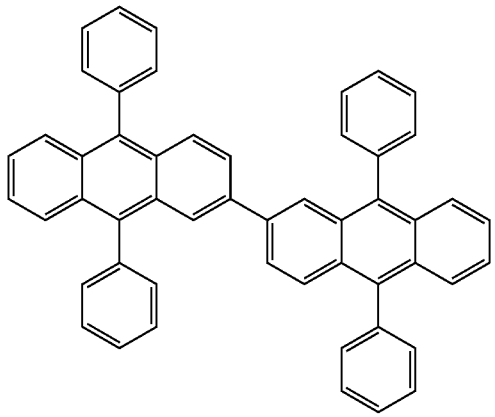

FD(4)

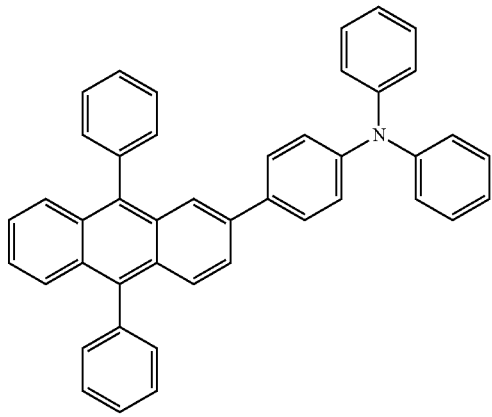

FD(5)

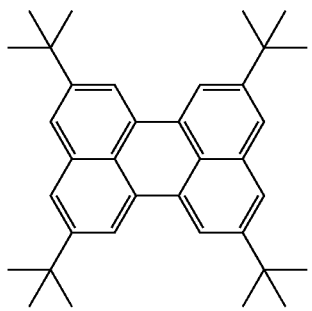

-continued
FD(6)
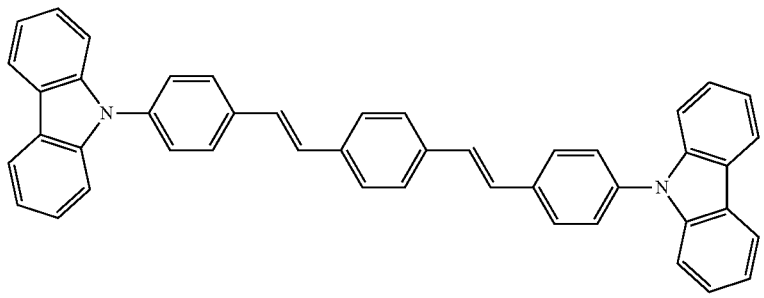
FD(7)
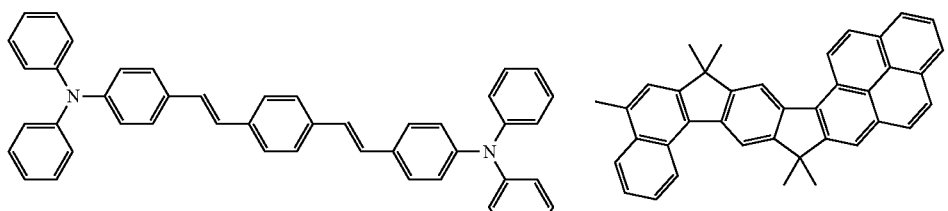
FD(8)
FD(9)
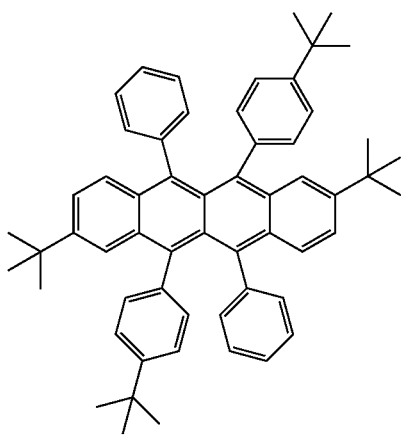
FD(10)
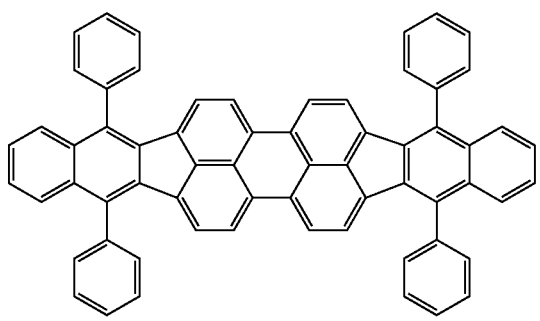
FD(11)
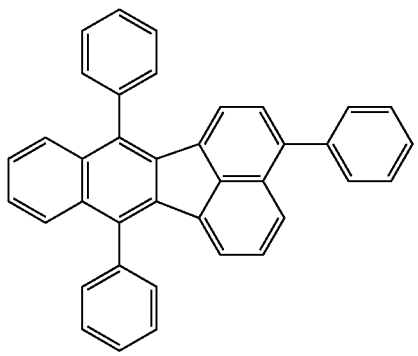
FD(12)
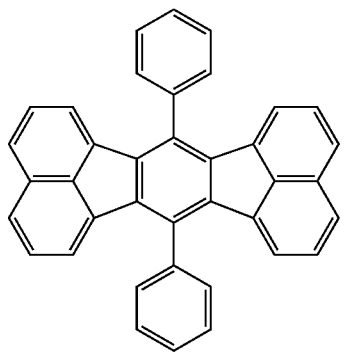
FD(13)
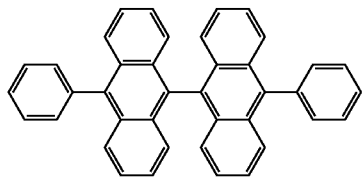
FD(14)
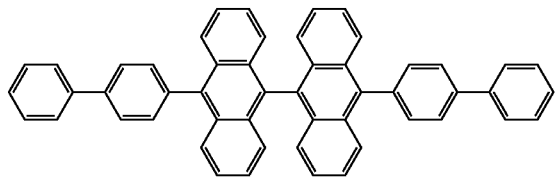

-continued
| FD(15) | FD(16) |
|---|---|
| 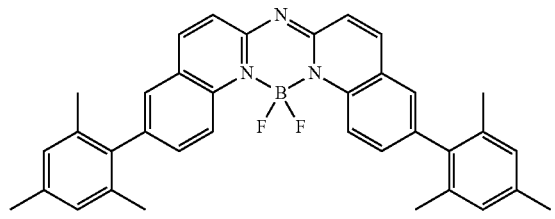 | 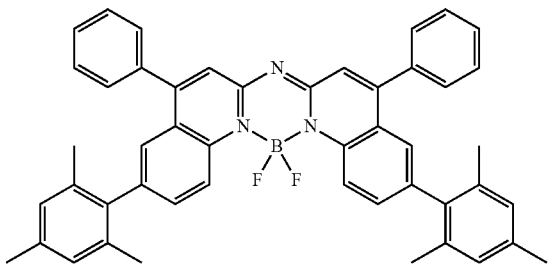 |
| FD1 | FD2 |
|---|---|
| 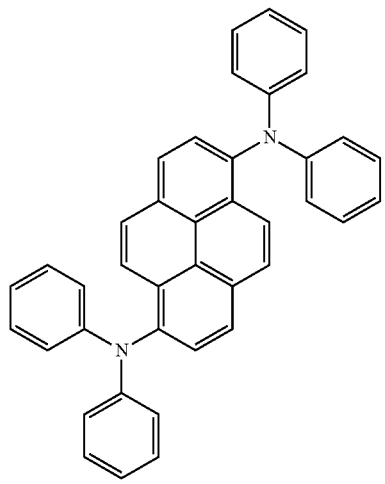 | 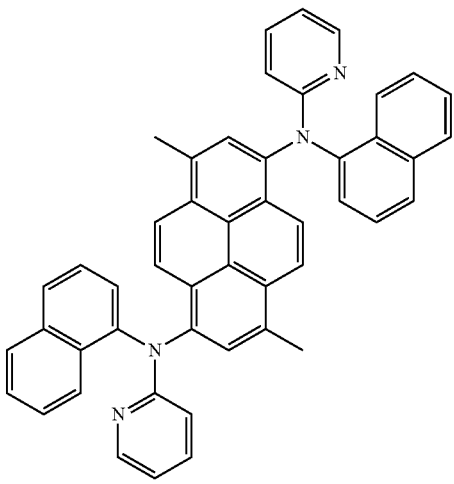 |
| FD3 | FD4 |
|---|---|
| 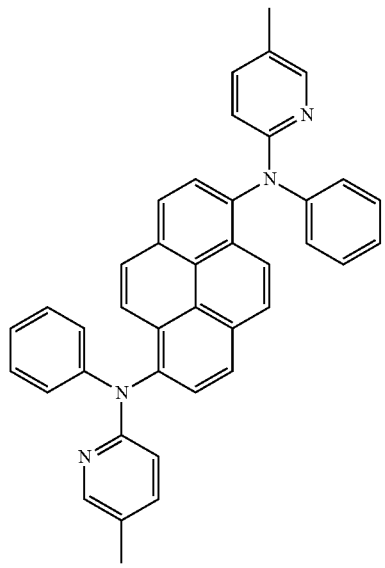 | 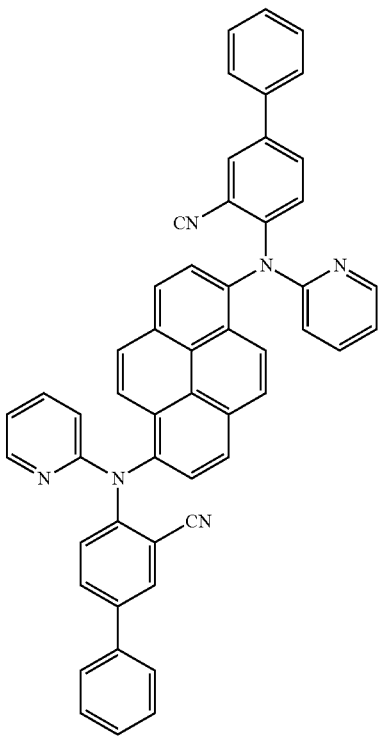 |

-continued
FD5
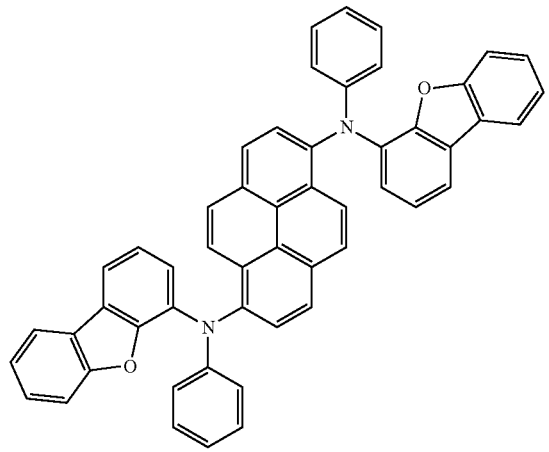
FD6
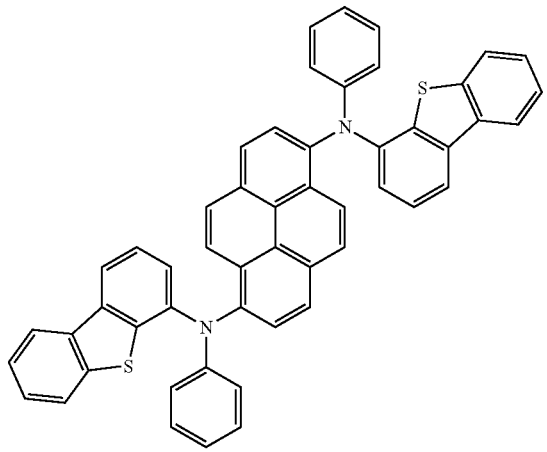
FD7
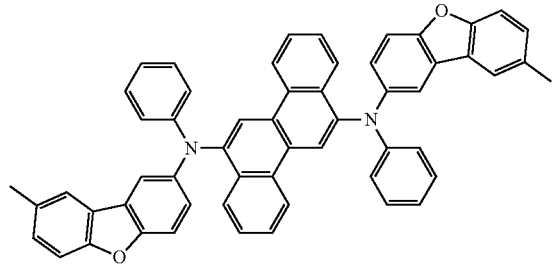
FD8
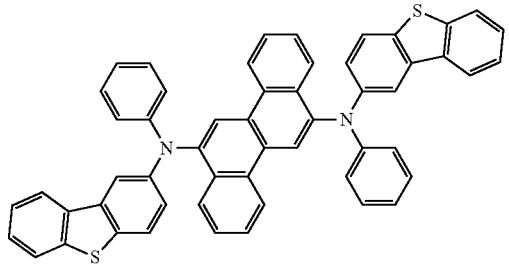
FD9
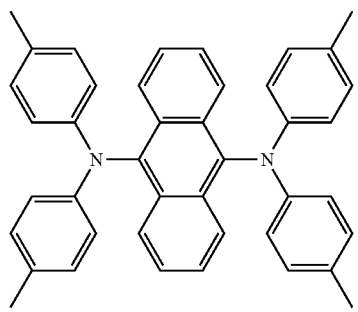
FD10
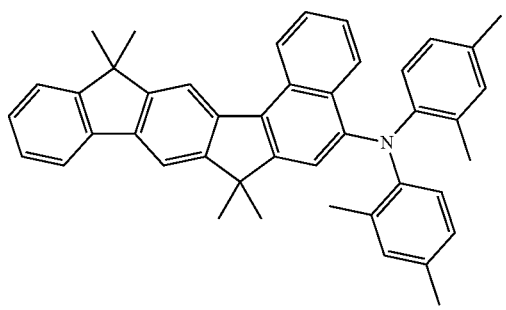
FD11
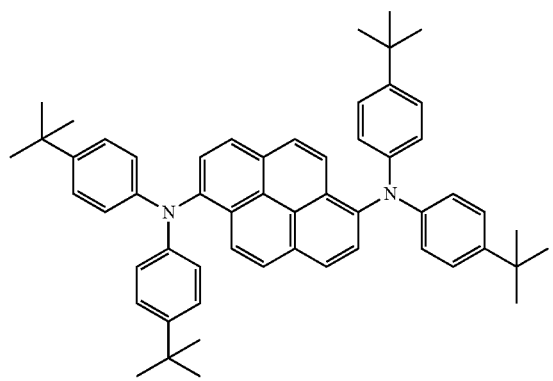
FD12
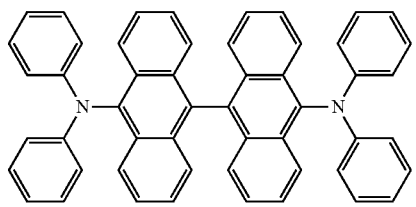

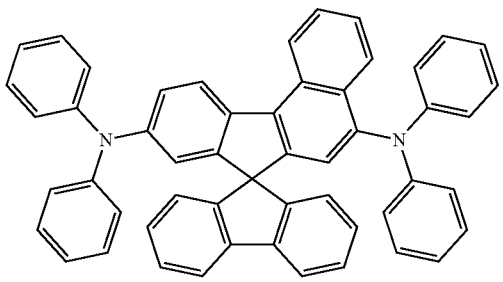

-continued

FD13

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202:

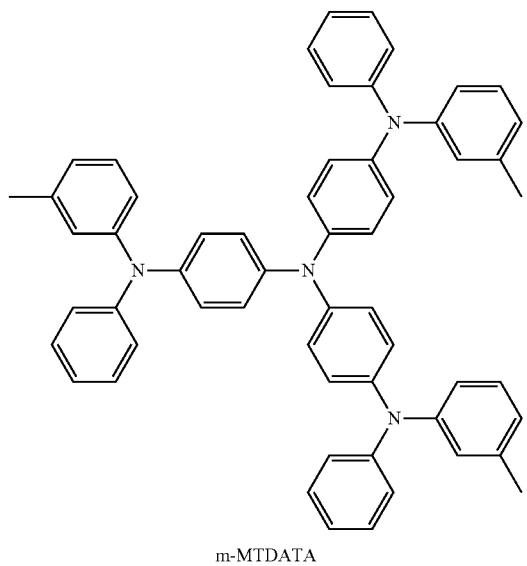

m-MTDATA

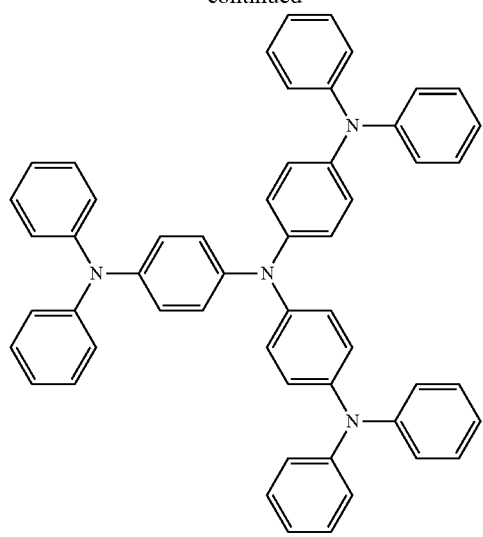
TDATA
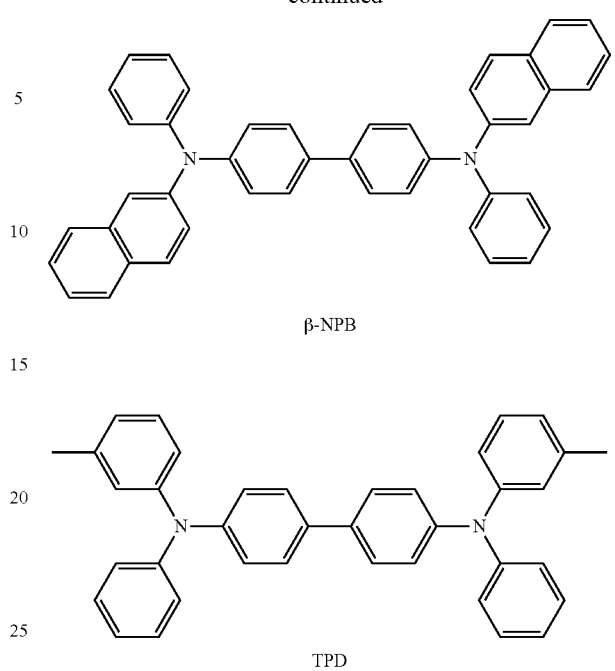
β-NPB
TPD
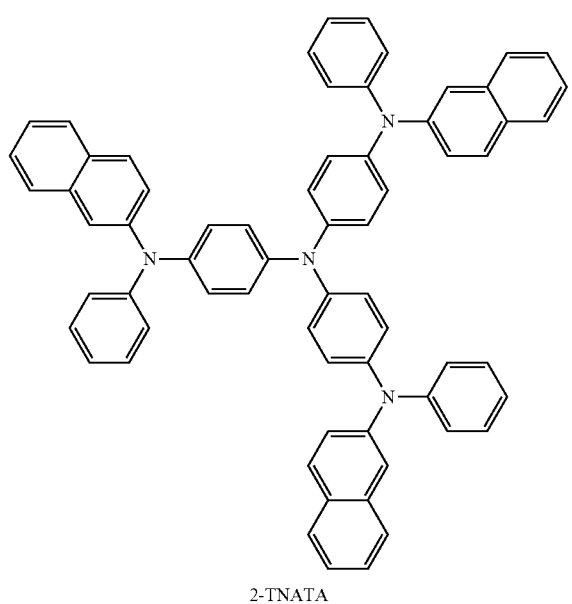
2-TNATA
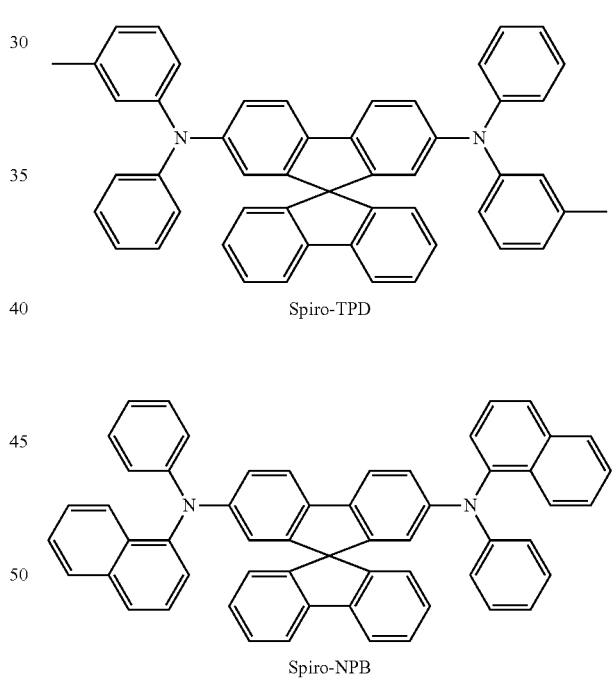
Spiro-TPD
Spiro-NPB
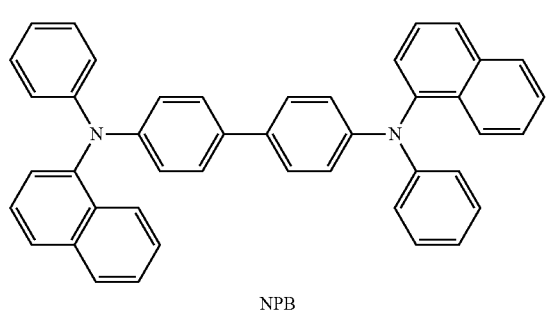
NPB
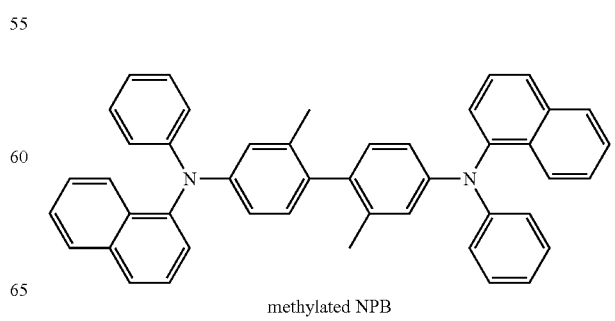
methylated NPB -continued

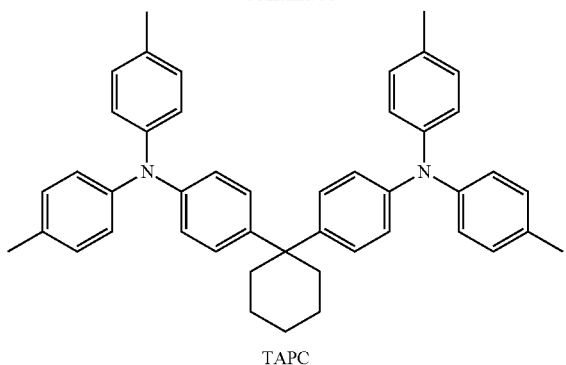

TAPC

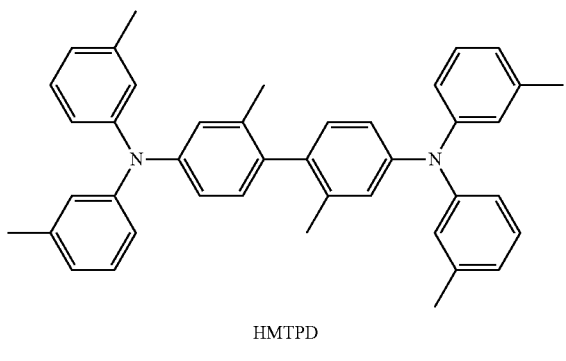

HMTPD

Formula 201

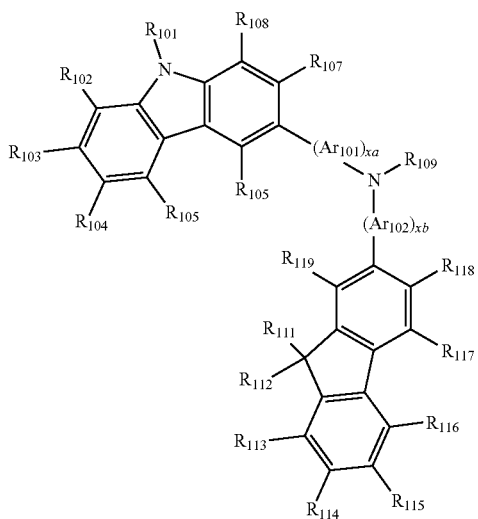

Formula 202

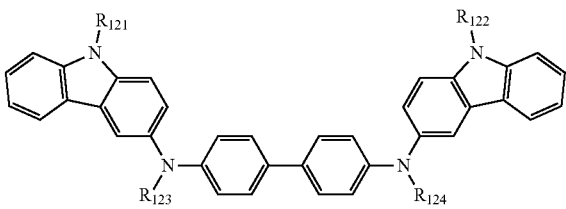

In Formula 201,

Ar$_{101}$ and Ar$_{102}$ may each independently be selected from:
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, and a monovalent non-aromatic condensed heteropolycyclic group, and xa and xb may each independently be an integer from 0 to 5, or 0, 1 or 2, wherein xa may be 1 and xb may be 0, but xa and xb are not limited thereto.

In Formulae 201 and 202, R$_{101}$ to R$_{108}$, R$_{111}$ to R$_{119}$, and R$_{121}$ to R$_{124}$ may each independently be selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and the like), and a $C_1$-$C_{10}$ alkoxy group (for example, a methoxy group, an ethoxy group, a propoxy group, a butoxy group, a pentoxy group, and the like);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a alkoxy group, a phenyl group, a naphthyl group, an anthracenyl group, and a pyridinyl group.

In an embodiment, the compound represented by Formula 201 may be represented by Formula 201A, but embodiments of the present disclosure are not limited thereto:

Formula 201A

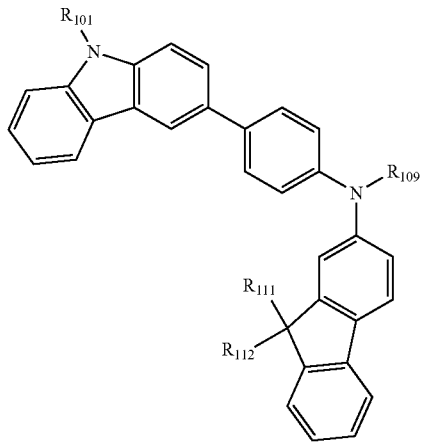

In Formula 201A, $R_{101}$, $R_{111}$, $R_{112}$, and $R_{109}$ may each independently have the same definition as described above.

For example, the compound represented by Formula 201, and the compound represented by Formula 202 may include compounds HT1 to HT20, but are not limited thereto:

HT1

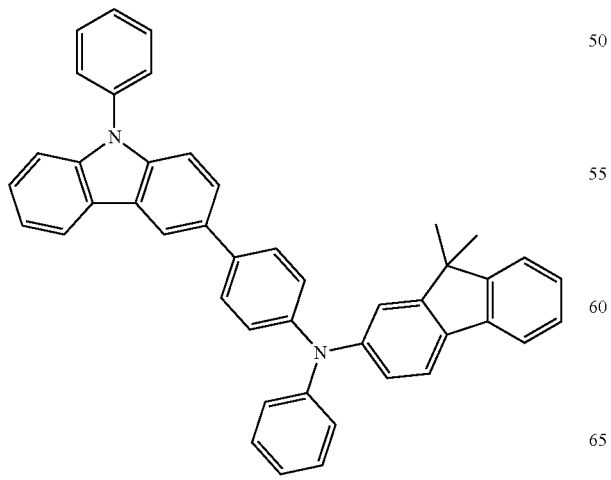

HT2

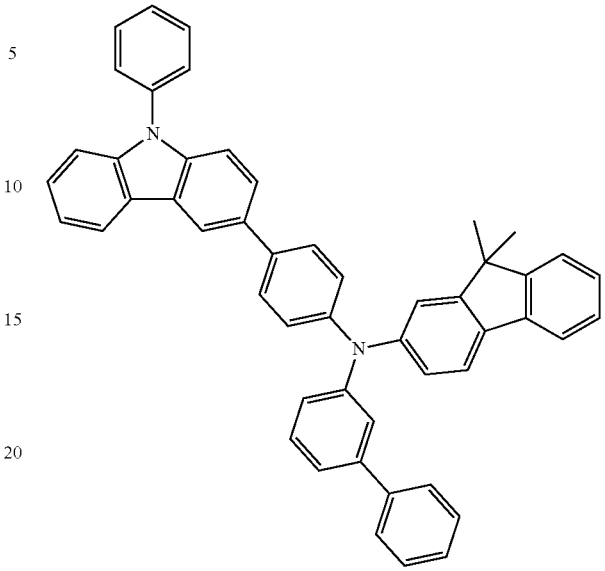

HT3

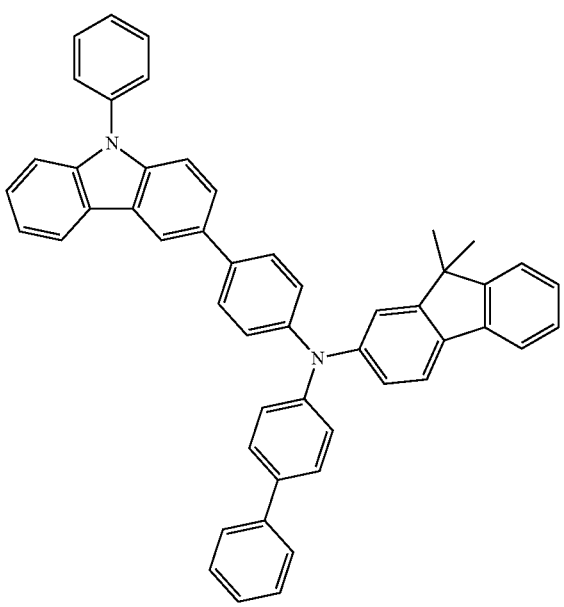

-continued
HT4
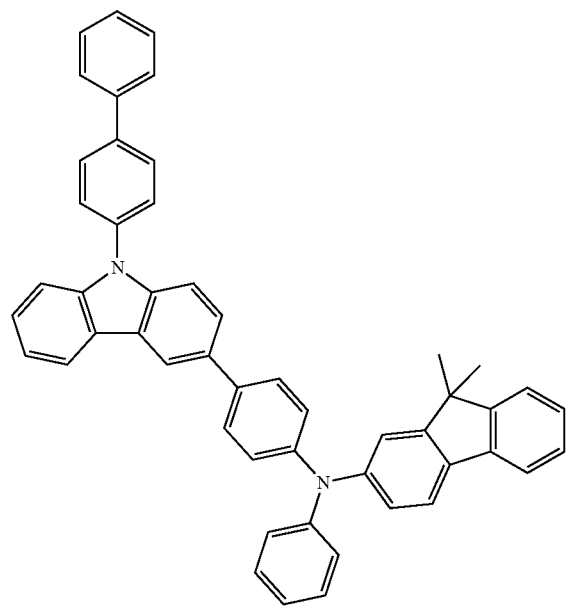
HT5
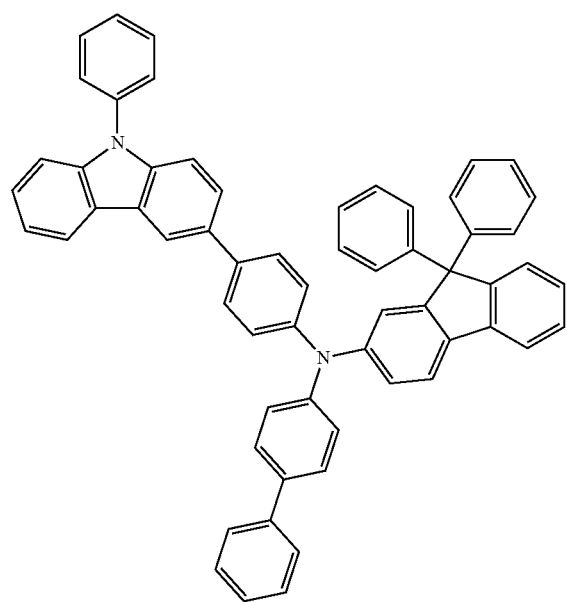
-continued
HT6
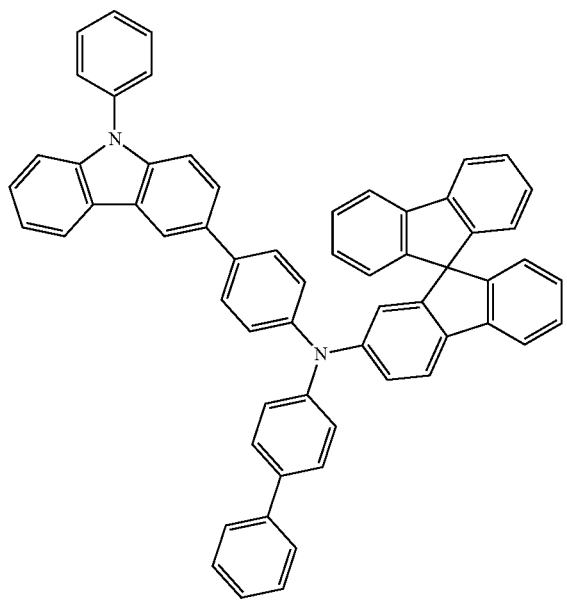
HT7

HT8
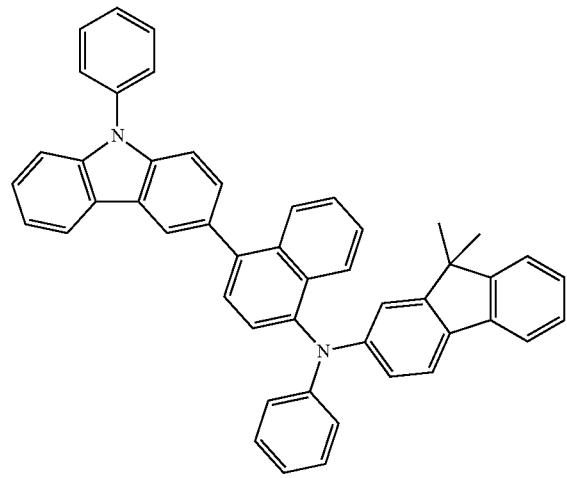
HT9
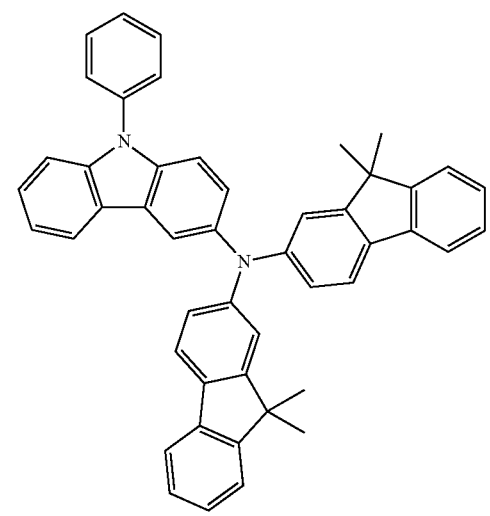
HT10
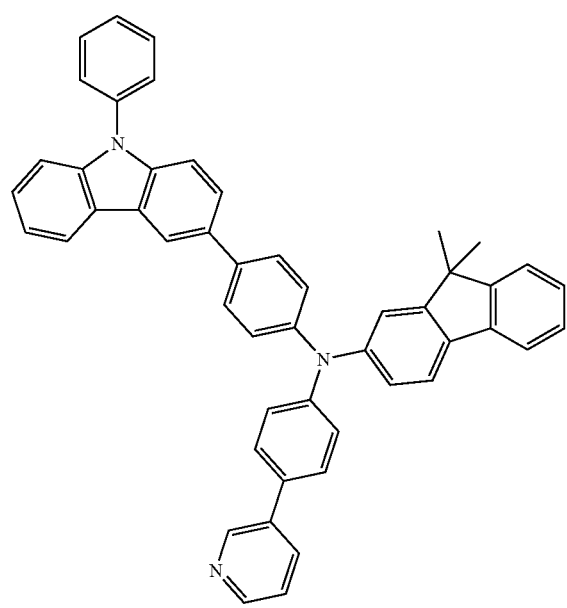
HT11
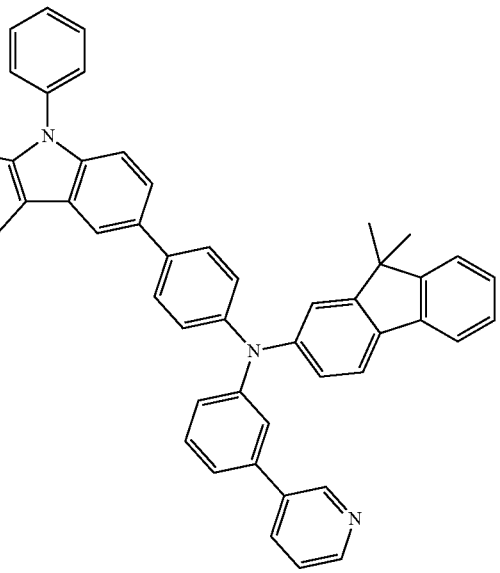
HT12
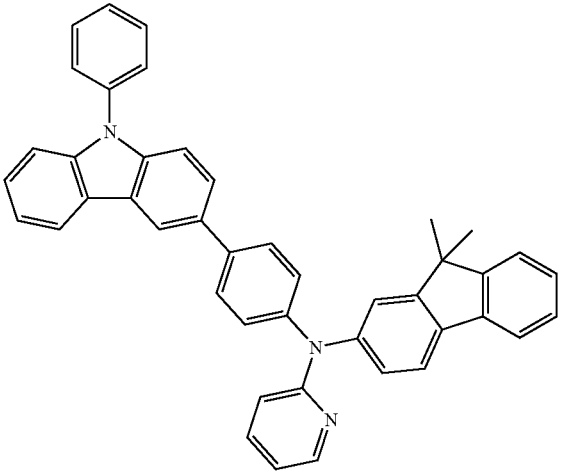
HT13
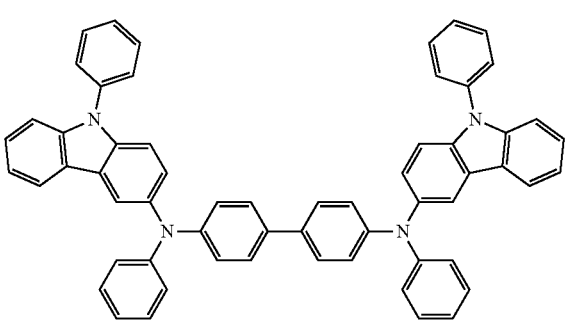

-continued

HT14
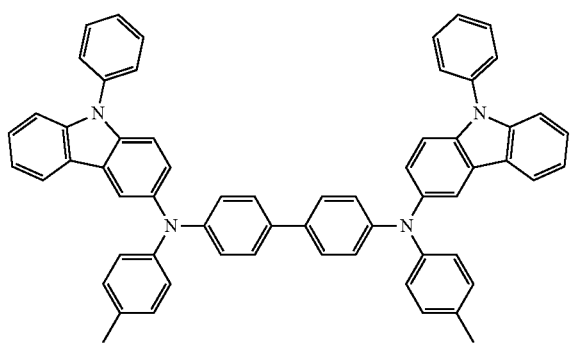

HT15
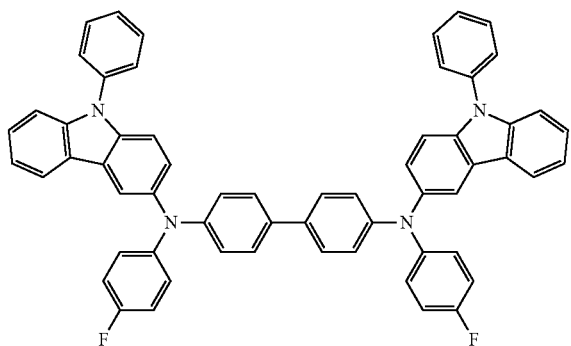

HT16
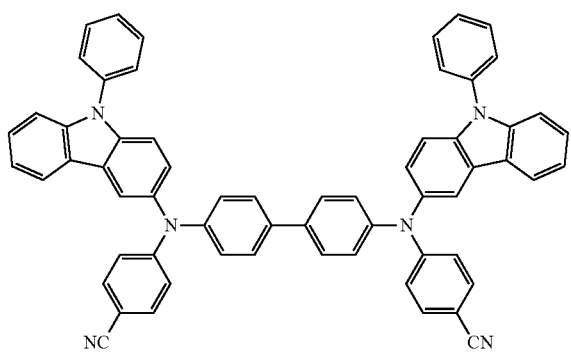

HT17
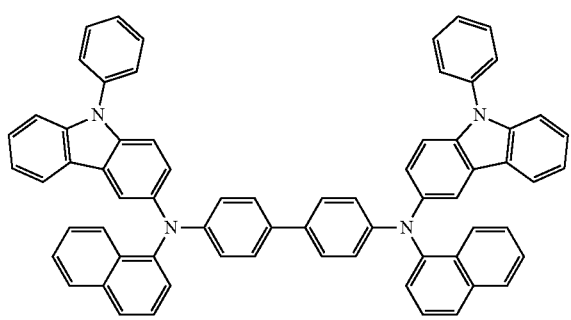

-continued

HT18
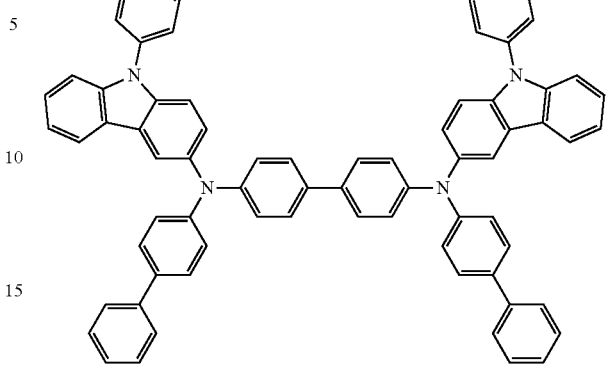

HT19
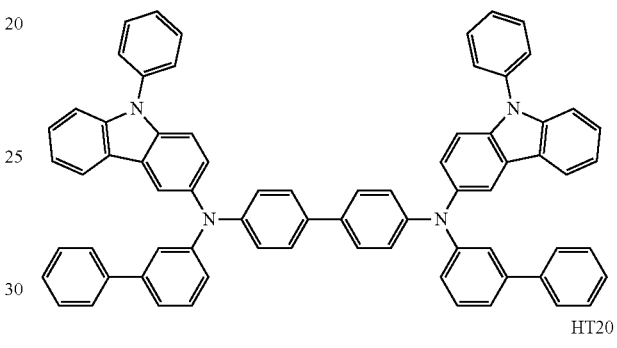

HT20
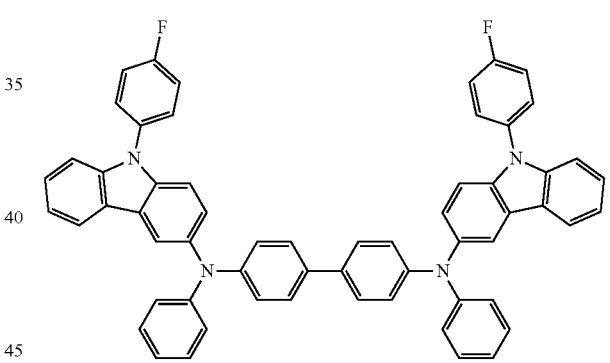

A thickness of the hole transport region may be in a range of about 100 Angstroms (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or HP-1, but are not limited thereto.

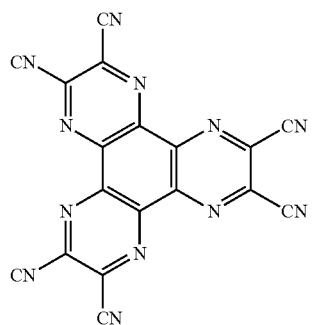

HT-D1

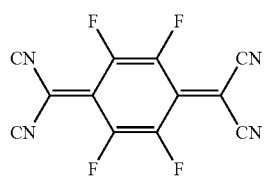

F4-TCNQ

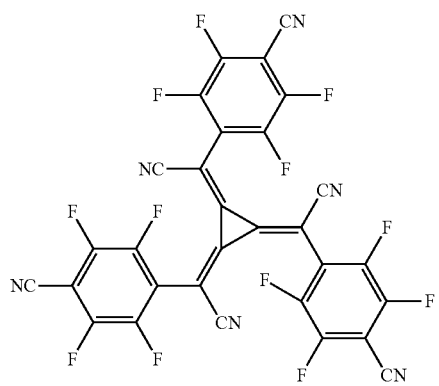

HP-1

The hole transport region may include a buffer layer.

Also, the buffer layer may compensate for an optical resonance distance according to a wavelength of light emitted from the emission layer, and thus, efficiency of a formed organic light-emitting device may be improved.

The electron transport region may further include an electron blocking layer. The electron blocking layer may include, for example, mCP, but a material therefor is not limited thereto.

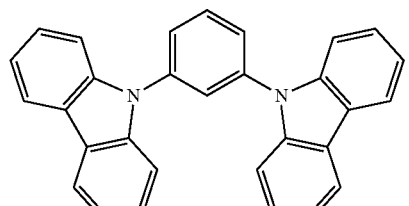

mCP

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The emission layer is the same as described above.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials.

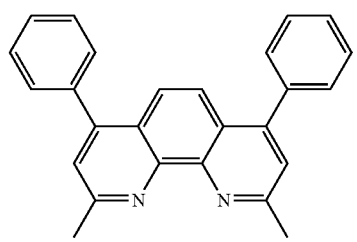

BCP

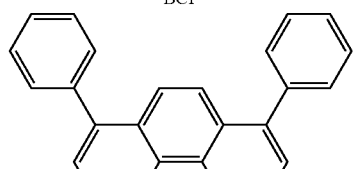

Bphen

The hole blocking layer may include a compound selected from the hosts described above. For example, the hole blocking layer may include Compound H19, but may also include other compounds.

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include at least one selected from BCP, Bphen, Alq₃, BAlq, TAZ, and NTAZ.

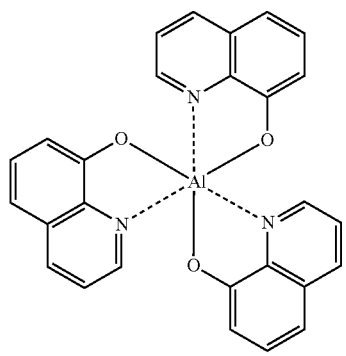

Alq₃

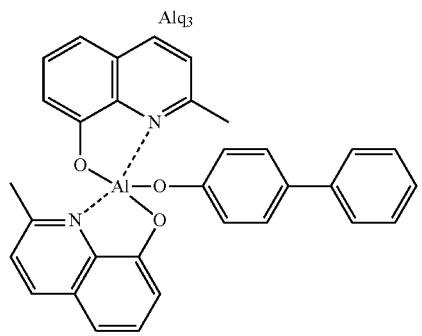

BAlq

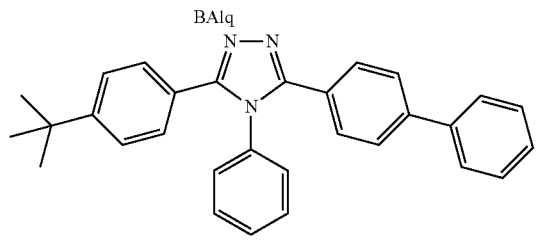

TAZ

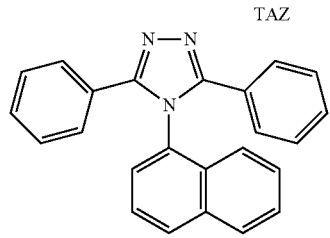

NTAZ

In one or more embodiments, the electron transport layer may include at least one selected from Compounds ET1, ET2, and ET3, but embodiments of the present disclosure are not limited thereto:

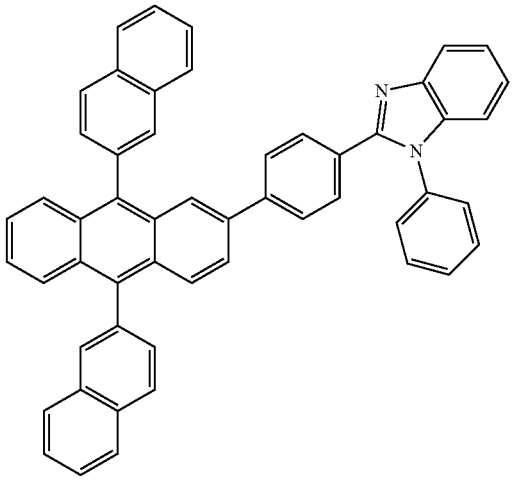

ET1

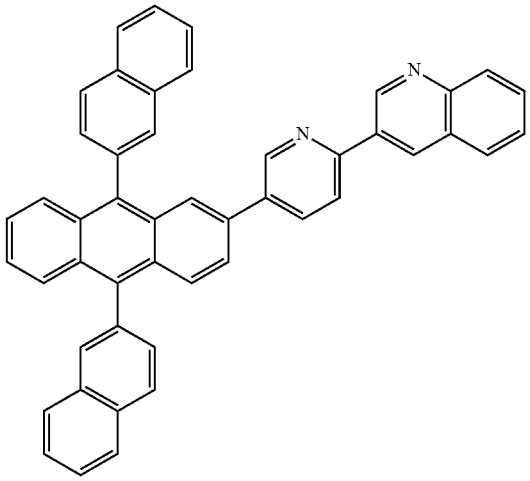

ET2

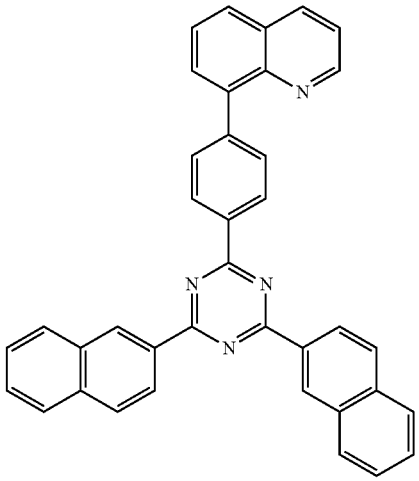

ET3

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D$_1$ (lithium 8-hydroxyquinolate, LiQ) or ET-D2.

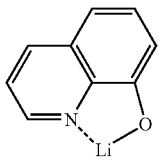

ET-D1

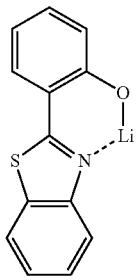

ET-D2

The electron transport region may include an electron injection layer (EIL) that promotes flow of electrons from the second electrode 19 thereinto.

The electron injection layer may include at least one selected from LiF, NaCl, CsF, Li$_2$O, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

Hereinbefore, the organic light-emitting device has been described with reference to the FIGURE, but embodiments of the present disclosure are not limited thereto.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —OA$_{101}$ (wherein A$_{101}$ is the $C_1$-$C_{60}$ alkyl group), and examples thereof include a methoxy group, an ethoxy group, and an iso-propyloxy group.

The term "$C_2$-$C_{60}$ alkenyl group" as used herein refers to a hydrocarbon group having at least one double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group having at least one heteroatom selected from N, O, P, Si and S as a ring-forming atom and 2 to 10 carbon atoms, and non-limiting examples thereof include a tetrahydrofuranyl group, and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, Si, and S as a ring-forming atom, 2 to 10 carbon atoms, and at least one double bond in its ring. Examples of the $C_2$-$C_{10}$ heterocycloalkenyl group are a 2,3-dihydrofuranyl group, and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group" as used herein refers to a monovalent group having a heterocyclic aromatic system that has at least one heteroatom selected from N, O, P, and S as a ring-forming atom, and 2 to 60 carbon atoms. The term $C_2$-$C_{60}$ heteroarylene group" as used herein refers to a divalent group having a heterocyclic aromatic system that has at least one heteroatom selected from N, O, P, and S as a ring-forming atom, and 2 to 60 carbon atoms. Non-limiting examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), a $C_6$-$C_{60}$ arylthio group as used herein indicates —$SA_{103}$ (wherein $A_{103}$ is the $C_6$-$C_{60}$ aryl group), and the term "$C_7$-$C_{60}$ arylalkyl group" as used herein indicates -$A_{104}A_{105}$ (wherein $A_{105}$ is the $C_6$-$C_{59}$ aryl group and $A_{104}$ is the $C_1$-$C_{53}$ alkylene group).

The term "$C_1$-$C_{60}$ heteroaryloxy group" as used herein refers to —$OA_{106}$ (wherein $A_{106}$ is the $C_2$-$C_{60}$ heteroaryl group), the term "$C_1$-$C_{60}$ heteroarylthio group" as used herein indicates —$SA_{107}$ (wherein $A_{107}$ is the $C_1$-$C_{60}$ heteroaryl group), and the term "$C_2$-$C_{60}$ heteroarylalkyl group" as used herein refers to -$A_{108}A_{109}$ ($A_{109}$ is a $C_1$-$C_{59}$ heteroaryl group, and $A_{108}$ is a $C_1$-$C_{59}$ alkylene group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having, as a ring-forming atom, 5 to 60 carbon atoms only. The term "$C_5$-$C_{60}$ carbocyclic group" as used herein refers to a monocyclic group or a polycyclic group, and, according to its chemical structure, a monovalent, divalent, trivalent, tetravalent, pentavalent, or hexavalent group.

The term "$C_2$-$C_{60}$ heterocyclic group" as used herein refers to a saturated or unsaturated cyclic group having, as a ring-forming atom, at least one heteroatom selected from N, O, Si, P, and S other than 2 to 60 carbon atoms. The term "$C_2$-$C_{60}$ heterocyclic group" as used herein refers to a monocyclic group or a polycyclic group, and, according to its chemical structure, a monovalent, divalent, trivalent, tetravalent, pentavalent, or hexavalent group.

At least one substituent of the substituted $C_5$-$C_{60}$ carbocyclic group, the substituted $C_2$-$C_{60}$ heterocyclic group, the substituted π electron-depleted nitrogen-containing $C_2$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ aryl alkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroaryl alkyl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —F, —Cl, —Br, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, and a monovalent non-aromatic condensed heteropolycyclic group, each substituted with at least one selected from deuterium, —F, —Br, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$), and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group, and a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroaryl alkyl group, a monovalent non-aromatic condensed polycyclic group, and a monovalent non-aromatic condensed heteropolycyclic group.

The term "room temperature" as used herein refers to about 25° C.

Hereinafter, a compound and an organic light-emitting device according to embodiments are described in detail with reference to Synthesis Example and Examples. However, the organic light-emitting device is not limited thereto. The wording "'B' was used instead of 'A'" used in describing Synthesis Examples means that a molar equivalent of 'A' was identical to a molar equivalent of 'B'.

EXAMPLES

Synthesis Example 1: Synthesis of Compound 3

Compound 3 was synthesized according to the Reaction Scheme below:

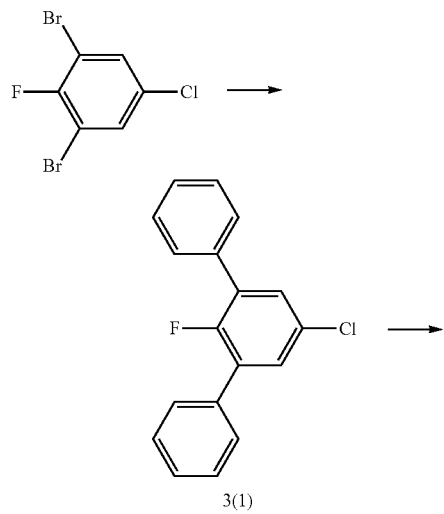

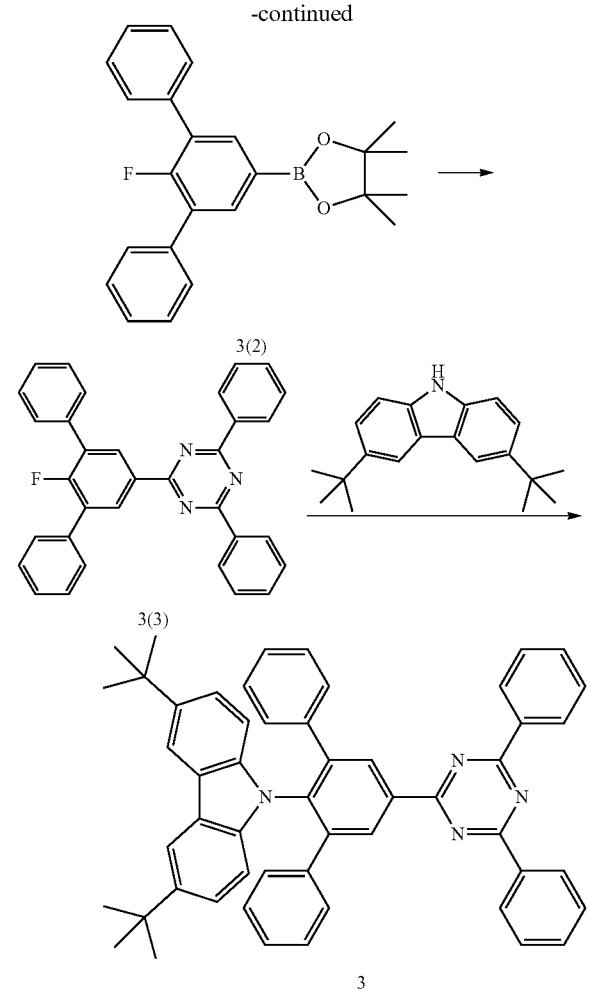

Synthesis of Intermediate 3(1)

Phenylboronic acid (63.43 grams (g), 520.22 millimoles, mmol), 1,3-dibromo-5-chloro-2-fluorobenzene (50 g, 173.41 mmol), palladium tetrakis(triphenylphosphine (Pd (PPh$_3$)$_4$) (20.04 g, 17.34 mmol), potassium carbonate (K$_2$CO$_3$) (95.87 g, 693.63 mmol), and S-phos (14.24 g, 34.68 mmol) were added to 300 milliliters (ml) of tetrahydrofuran and 300 ml of distilled water, and the resulting mixture was heated under reflux. After the reaction was completed, the reaction product was cooled to room temperature, and the organic layer was extracted therefrom by using ethyl acetate, dried by anhydrous sodium sulfate (Na$_2$SO$_4$), concentrated, and then separated by silica gel column chromatography (dichloromethane/hexane). A solid obtained therefrom was recrystallized by using hexane to obtain Intermediate 3(1) (40.7 g, 143.81 mmol, yield of 83%) that was a white solid.

Synthesis of Intermediate 3(2)

Intermediate 3(1) (40.7 g, 143.81 mmol), bis(pinacolato) diboron (54.78 g, 215.71 mmol), potassium acetate (35.29 g, 359.52 mmol), tris(dibenzylideneacetone)dipalladium(0) (Pd$_2$(dba)$_3$)) (13.17 g, 14.38 mmol), and tricyclohexylphosphine (4.03 g, 14.38 mmol) were added to 290 ml of dioxane, and the resulting mixture was heated under reflux. After the reaction was completed, the reaction product was cooled to room temperature, dissolved in a large amount of toluene, and filtered through silica gel. An organic layer obtained therefrom was concentrated, precipitated by pouring hexane thereto, and filtered to obtain Intermediate 3(2) (47.0 g, 125.58 mmol, yield of 87%) that was a white solid.

Synthesis of Intermediate 3(3)

2-chloro-4,6-diphenyl-1,3,5-triazine (18 g, 67.23 mmol), Intermediate 3(2) (30.2 g, 80.68 mmol), palladium tetrakis (triphenylphosphine) (Pd(PPh$_3$)$_4$) (3.89 g, 3.36 mmol), potassium carbonate (K$_2$CO$_3$) (18.59 g, 134.47 mmol), and S-phos (5.52 g, 13.45 mmol) were added to 120 ml of tetrahydrofuran and 120 ml of distilled water, and the resulting mixture was heated under reflux. After the reaction was completed, the reaction product was cooled to room temperature, and methanol was added thereto. The reaction product was filtered through silica gel. The organic layer obtained therefrom was concentrated and precipitated by pouring methanol thereto to synchronize Intermediate 3(3) (30.0 g, 62.56 mmol, yield of 93%) that was a white solid.

Synthesis of Compound 3

Intermediate 3(3) (4.80 g, 10 mmol), 3,6-di-tert-butyl-9H-carbazole (4.19 g, 15 mmol), and cesium carbonate (Cs$_2$CO$_3$) (6.52 g, 20 mmol) were added to 20 ml of N,N-dimethylformamide, and the resulting mixture was stirred at a temperature of 165° C. for 20 hours. After the reaction was completed, the reaction product was cooled to room temperature, and methanol was added thereto. The reaction product was filtered through silica gel. The organic layer obtained therefrom was concentrated, dissolved again in toluene, filtered through silica gel, and concentrated. The resulting product was recrystallized (ethyl acetate/ethanol) to synchronize Compound 3 (7.89 g, 10.68 mmol, yield of 97%) that was a yellow solid.

LC-Mass (Calcd.: 738.37 g/mol, Found: 739.35 g/mol (M+1)).

Synthesis Example 2: Synthesis of Compound 4

Compound 4 (yield of 68%) was synthesized in the same manner as in Synthesis of Compound 3, except that 3,6-diphenyl-9H-carbazole was used instead of 3,6-di-tert-butyl-9H-carbazole.

LC-Mass (Calcd.: 778.31 g/mol, Found: 779.32 g/mol (M+1)).

Synthesis Example 3: Synthesis of Compound 23

Compound 23 (yield of 58%) was synthesized in the same manner as in Synthesis of Compound 3 of Synthesis Example 1, except that 5H-benzofuro[3,2-c]carbazole was used instead of 3,6-dibutyl-9H-carbazole.

LC-Mass (Calcd.: 716.26 g/mol, Found: 717.26 g/mol (M+1)).

Synthesis Example 4: Synthesis of Compound 41

Compound 41 (yield of 52%) was synthesized in the same manner as in Synthesis Example 1, except that 9H-3,9'-bicarbazole was used instead of 3,6-di-tert-butyl-9H-carbazole in synthesizing Compound 3.

LC-Mass (Calcd.: 791.30 g/mol, Found: 792.31 g/mol (M+1)).

Synthesis Example 5: Synthesis of Compound 174

Synthesis of Intermediate 174(3)

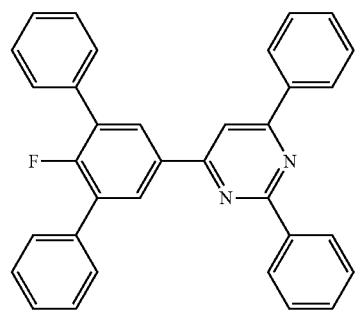

174(3)

Intermediate 174(3) (yield of 83%) was synthesized in the same manner as in Synthesis of Intermediate 3(3) of Synthesis Example 1, except that 4-bromo-2,6-diphenylpyrimidine was used instead of 2-chloro-4,6-diphenyl-1,3,5-triazine in synthesizing Intermediate 3(3).

Synthesis of Intermediate 174(4)

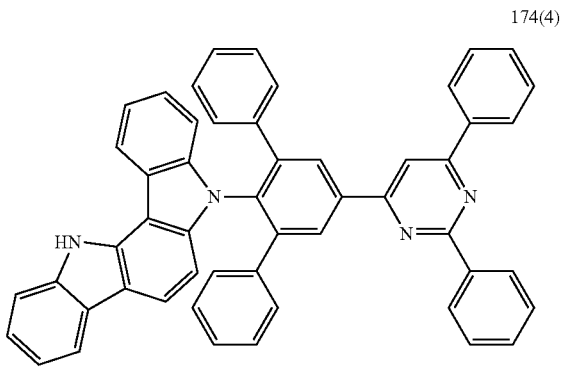 [SMILES: c1ccc(-c2cc(-c3cc(-c4ccccc4)c(-n4c5ccccc5c5c6[nH]c7ccccc7c6ccc54)c(-c4ccccc4)c3)nc(-c3ccccc3)n2)cc1]

174(4)

Intermediate 174(4) (yield of 94%) was synthesized in the same manner as in Synthesis of Compound 3 of Synthesis Example 1, except that Intermediate 174(3) was used instead of Intermediate 3(3) and 5,12-dihydroindolo[3,2-a]carbazole was used instead of 3,6-di-tert-butyl-9H-carbazole in synthesizing Compound 3.

Synthesis of Compound 174

Intermediate 174(4) (6.8 g, 9.51 mmol), bromobenzene (8.96 g, 57.1 mmol), tris(dibenzylideneacetone)dipalladium (0) (Pd$_2$(dba)$_3$) (3.48 g, 3.8 mmol), sodium tert-butoxide (3.66 g, 38.05 mmol), and tri-tert-butylphosphine (1.54 g, 7.61 mmol) were added to 50 ml of toluene, and the resulting mixture was stirred at a temperature of 130° C. for 12 hours. After the reaction was completed, the reaction product was cooled to room temperature, and methanol was added thereto. The reaction product was filtered and dried. A solid generated by separation through silica gel column chromatography (dichloromethane/hexane) and recrystallized (methanol) to synchronize Compound 174 (4.26 g, 5.39 mmol, yield of 57%) that was a yellow solid LC-Mass (Calcd.: 790.31 g/mol, Found: 791.28 g/mol (M+1)).

Synthesis Example 6: Synthesis of Compound 209

Compound 209 (yield of 81%) was synthesized in the same manner as in Synthesis Example 1, except that Intermediate 174(3) was used instead of Intermediate 3(3), and 5-phenyl-5,10-dihydrofuro[3,2-c:4,5-c']dicarbazole was used instead of 3,6-di-tert-butyl-9H-carbazole.

LC-Mass (Calcd.: 880.32 g/mol, Found: 881.36 g/mol (M+1)).

Synthesis Example 7: Synthesis of Compound 229

Synthesis of Intermediate 229(3)

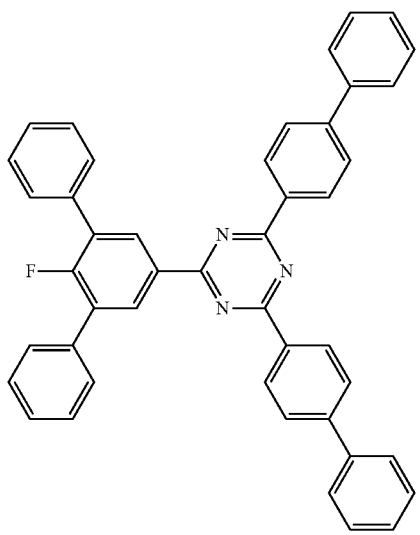

229(3)

Intermediate 229(3) (yield of 79%) was synthesized in the same manner as in Synthesis of Intermediate 3(3) of Synthesis Example 1, except that 2,4-di([1,1-biphenyl]-4-yl)-6-chloro-1,3,5-triazine was used instead of 2-chloro-4,6-diphenyl-1,3,5-triazine.

Synthesis of Compound 229

Compound 229 (yield of 65%) was synthesized in the same manner as in Synthesis of Compound 3 of Synthesis Example 1, except that Intermediate 229(3) was used instead of Intermediate 3(3), and 3,6-diphenyl-9H-carbazole was used instead of 3,6-di-tert-butyl-9H-carbazole.

LC-Mass (Calcd.: 930.37 g/mol, Found: 931.37 g/mol (M+1)).

Synthesis Example 8: Synthesis of Compound 481

Synthesis of Intermediate 481(3)

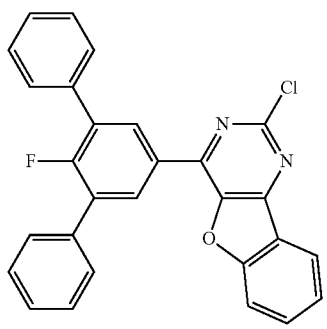

481(3)

Intermediate 481(3) (yield of 84%) was synthesized in the same manner as in Synthesis of Intermediate 3(3) of Synthesis Example 1, except that 2,4-dichlorobenzofuro[3,2-d]pyrimidine was used instead of 2-chloro-4,6-diphenyl-1,3,5-triazine in synthesizing Intermediate (3) and the temperature was 55° C.

Synthesis of Intermediate 481(4)

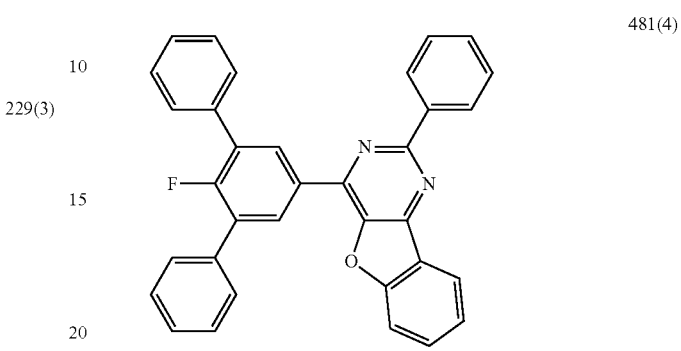

481(4)

Intermediate 481(3) (6.2 g, 13.75 mmol), phenylboronic acid (2.52 g, 20.63 mmol), palladium acetate (Pd(OAc)$_2$) (0.062 g, 0.28 mmol), sodium carbonate (Na$_2$CO$_3$) (2.92 g, 27.5 mmol), and S-Phos (0.23 g, 0.55 mmol) were added to 130 ml of toluene, 65 ml of ethanol, and 50 ml of water, and the resulting mixture was stirred at a temperature of 60° C. for 4 hours. After the reaction was completed, extraction was performed by using toluene, and filtering was performed thereon. Then, a solvent was removed therefrom. Recrystallization (dichloromethane/methanol) was performed to obtain Intermediate 481(4) (yield of 96%) that was a white solid.

Synthesis of Compound 481

Compound 481 (yield of 32%) was synthesized in the same manner as in Synthesis of Compound 3 of Synthesis Example 1, except that Intermediate 481(4) was used instead of Intermediate 3(3), and 7H-benzofuro[2,3-b]carbazole was used instead of 3,6-di-tert-butyl-9H-carbazole in synthesizing Compound 3.

LC-Mass (Calcd.: 729.24 g/mol, Found: 730.23 g/mol (M+1)).

Synthesis Example 9: Synthesis of Compound 617

Compound 617 was synthesized according to the Reaction Scheme below.

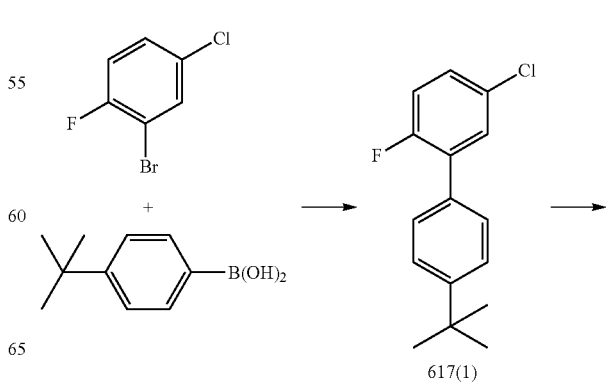

617(1)

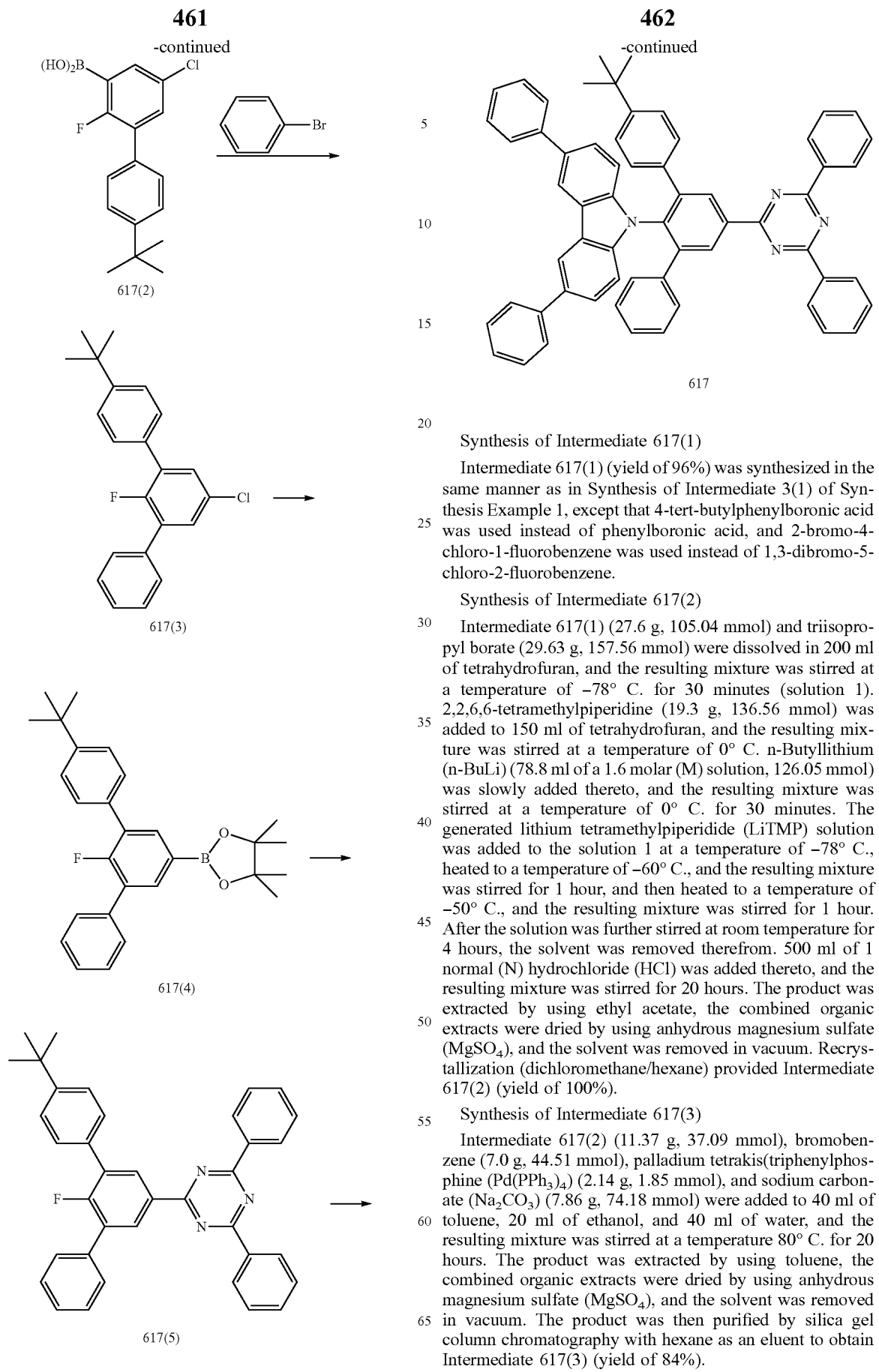

Synthesis of Intermediate 617(1)

Intermediate 617(1) (yield of 96%) was synthesized in the same manner as in Synthesis of Intermediate 3(1) of Synthesis Example 1, except that 4-tert-butylphenylboronic acid was used instead of phenylboronic acid, and 2-bromo-4-chloro-1-fluorobenzene was used instead of 1,3-dibromo-5-chloro-2-fluorobenzene.

Synthesis of Intermediate 617(2)

Intermediate 617(1) (27.6 g, 105.04 mmol) and triisopropyl borate (29.63 g, 157.56 mmol) were dissolved in 200 ml of tetrahydrofuran, and the resulting mixture was stirred at a temperature of −78° C. for 30 minutes (solution 1). 2,2,6,6-tetramethylpiperidine (19.3 g, 136.56 mmol) was added to 150 ml of tetrahydrofuran, and the resulting mixture was stirred at a temperature of 0° C. n-Butyllithium (n-BuLi) (78.8 ml of a 1.6 molar (M) solution, 126.05 mmol) was slowly added thereto, and the resulting mixture was stirred at a temperature of 0° C. for 30 minutes. The generated lithium tetramethylpiperidide (LiTMP) solution was added to the solution 1 at a temperature of −78° C., heated to a temperature of −60° C., and the resulting mixture was stirred for 1 hour, and then heated to a temperature of −50° C., and the resulting mixture was stirred for 1 hour. After the solution was further stirred at room temperature for 4 hours, the solvent was removed therefrom. 500 ml of 1 normal (N) hydrochloride (HCl) was added thereto, and the resulting mixture was stirred for 20 hours. The product was extracted by using ethyl acetate, the combined organic extracts were dried by using anhydrous magnesium sulfate (MgSO$_4$), and the solvent was removed in vacuum. Recrystallization (dichloromethane/hexane) provided Intermediate 617(2) (yield of 100%).

Synthesis of Intermediate 617(3)

Intermediate 617(2) (11.37 g, 37.09 mmol), bromobenzene (7.0 g, 44.51 mmol), palladium tetrakis(triphenylphosphine) (Pd(PPh$_3$)$_4$) (2.14 g, 1.85 mmol), and sodium carbonate (Na$_2$CO$_3$) (7.86 g, 74.18 mmol) were added to 40 ml of toluene, 20 ml of ethanol, and 40 ml of water, and the resulting mixture was stirred at a temperature 80° C. for 20 hours. The product was extracted by using toluene, the combined organic extracts were dried by using anhydrous magnesium sulfate (MgSO$_4$), and the solvent was removed in vacuum. The product was then purified by silica gel column chromatography with hexane as an eluent to obtain Intermediate 617(3) (yield of 84%).

Synthesis of Intermediate 617(4)

Intermediate 617(4) (yield of 48%) was synthesized in the same manner as in Synthesis of Intermediate 3(2) of Synthesis Example 1, except that Intermediate 617(3) was used instead of Intermediate 3(1).

Synthesis of Intermediate 617(5)

Intermediate 617(5) (yield of 91%) was synthesized in the same manner as in Synthesis of Intermediate 3(3) of Synthesis Example 1, except that Intermediate 617(4) was used instead of Intermediate 3(2).

Synthesis of Compound 617

Compound 617 (yield of 73%) was synthesized in the same manner as in Synthesis of Compound 3 of Synthesis Example 1, except that Intermediate 617(5) was used instead of Intermediate 3(3), and 3,6-diphenyl-9H-carbazole was used instead of 3,6-di-tert-butyl-9H-carbazole.

LC-Mass (Calcd.: 834.37 g/mol, Found: 835.37 g/mol (M+1)).

Synthesis Example 10: Synthesis of Compound 796

Compound 796 (yield of 49%) was synthesized in the same manner as in Synthesis of Compound 3 of Synthesis Example 1, except that biphenylboronic acid ([1,1'-biphenyl]-4-ylboronic acid) was used instead of phenylboronic acid, and 3,6-diphenyl-9H-carbazole was used instead of 3,6-di-tert-butyl-9H-carbazole.

LC-Mass (Calcd.: 930.37 g/mol, Found: 931.37 g/mol (M+1)).

Synthesis Example 11: Synthesis of Compound 889

Synthesis of Intermediate 889(1)

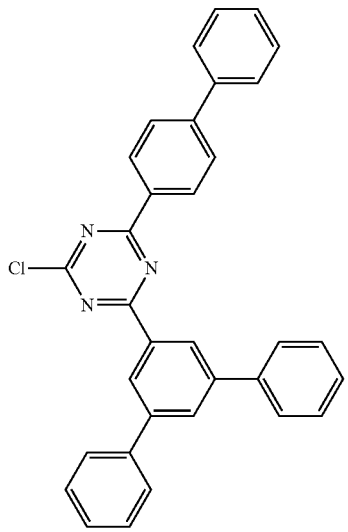

889(1)

2-biphenyl-4,6-dichloro-1,3,5-triazine (7 g, 23.17 mmol), [1,1': 3',1"-terphenyl]-5-yl boronic acid (6.35 g, 23.17 mmol), palladium tetrakis(triphenylphosphine) (Pd(PPh$_3$)$_4$) (0.535 g, 0.46 mmol), and sodium carbonate (Na$_2$CO$_3$) (4.911 g, 46.33 mmol) were added to 25 ml of toluene, 25 ml of dioxane, and 25 ml of water, and the resulting mixture was stirred at a temperature of 80° C. for 20 hours. After toluene was added thereto, the product obtained therefrom was filtered through silica gel and recrystallized by using toluene to obtain Intermediate 889(1) (yield of 52%).

Synthesis of Compound 889

Compound 889 (yield of 68%) was synthesized in the same manner as in Synthesis of Compound 3 of Synthesis Example 1, except that Intermediate 889(1) was used instead of 2-chloro-4,6-diphenyl-1,3,5-triazine, and 3,6-diphenyl-9H-carbazole was used instead of 3,6-di-tert-butyl-9H-carbazole.

LC-Mass (Calcd.: 1006.40 g/mol, Found: 1007.36 g/mol (M+1)).

Synthesis Example 12: Synthesis of Compound 57

Compound 57 (yield of 67%) was synthesized in the same manner as in Synthesis Example 1, except that 6-mesityl-9H-3,9'-bicarbazole was used instead of 3,6-di-tert-butyl-9H-carbazole.

LC-Mass (Calcd.: 909.38 g/mol, Found: 910.37 g/mol (M+1)).

Synthesis Example 13: Synthesis of Compound 75

Compound 75 (yield of 96%) was synthesized in the same manner as in Synthesis Example 1, except that 11-phenyl-5H-benzofuro[3,2-c]carbazole was used instead of 3,6-di-tert-butyl-9H-carbazole.

LC-Mass (Calcd.: 792.29 g/mol, Found: 793.29 g/mol (M+1)).

Evaluation Example 1

The photoluminescence (PL) spectrum, HOMO, LUMO, lowest excited singlet (Si) energy level, lowest excited triplet (T$_1$) energy level, and $\Delta E_{ST}$ of Compounds 3, 4, 23, 41, 174, 209, 229, 481, 617, 796, 889, 57, 75 and A were evaluated according to methods shown in Table 2, and results thereof are shown in Table 3.

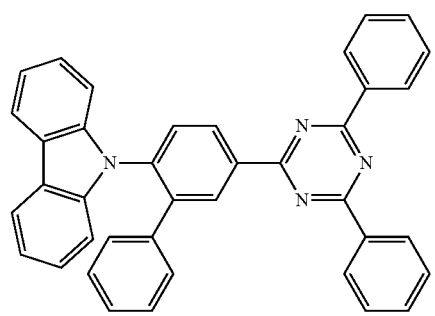

A

-continued

B
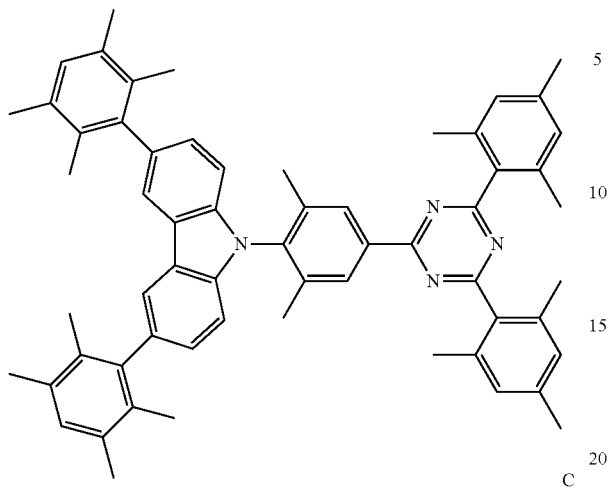

C
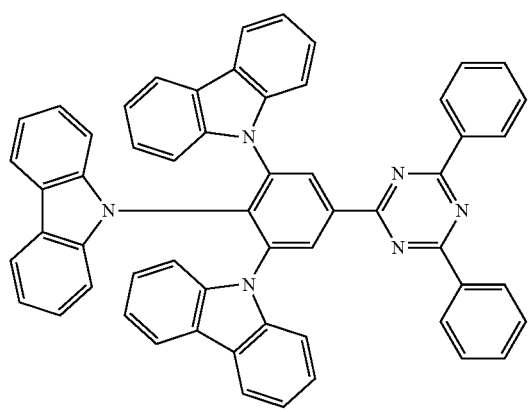

TABLE 2

| | |
|---|---|
| PL spectrum | Each Compound was diluted at a concentration of $10^{-5}$M in toluene, and a PL spectrum was measured (@ 298 Kelvins, K) by using F7000 Spectrofluorometer (manufactured by Hitachi) equipped with a xenon lamp. |
| $S_1$ energy level evaluation method | A PL spectrum of a mixture of toluene and each Compound (diluted in a concentration of $1 \times 10^{-4}$M) was measured at room temperature by using a photoluminescence measurement device, and an observed peak was analyzed to calculate "on set $S_1$ energy level". |
| $T_1$ energy level evaluation method | A mixture of toluene and each Compound (diluted in a concentration of $1 \times 10^{-4}$M) was added to a quartz cell and added to a liquid nitrogen (77 K), and a PL spectrum was measured by using a photoluminescence measurement device. The PL spectrum was compared with a general room-temperature photoluminescence spectrum, and only a peak observed only at a low temperature was analyzed to calculate "on set $T_1$ energy level". |
| $\Delta E_{ST}$ | A difference between the $S_1$ energy level and the $T_1$ energy level was calculated. |

TABLE 3

| Compound No. | HOMO (eV) | LUMO (eV) | $S_1$ energy level (eV) | $T_1$ energy level (eV) | $\Delta E_{ST}$ (eV) | Maximum emission wavelength in PL spectrum (nm) |
|---|---|---|---|---|---|---|
| 3 | −5.58 | −2.68 | 3.03 | 2.86 | 0.17 | 443 |
| 4 | −5.58 | −2.64 | 3.00 | 2.84 | 0.16 | 444 |
| 23 | −6.07 | −3.01 | 3.02 | 2.85 | 0.17 | 444 |
| 41 | −5.50 | −2.45 | 2.97 | 2.86 | 0.11 | 462 |
| 174 | −5.41 | −2.44 | 3.00 | 2.91 | 0.08 | 448 |
| 209 | −5.33 | −2.38 | 2.95 | 2.92 | 0.03 | 459 |
| 229 | −5.62 | −2.68 | 2.96 | 2.69 | 0.27 | 448 |
| 481 | −5.66 | −2.64 | 3.03 | 2.79 | 0.24 | 446 |
| 617 | −5.59 | −2.68 | 3.00 | 2.83 | 0.17 | 438 |
| 796 | −5.60 | −2.67 | 3.00 | 2.79 | 0.21 | 446 |
| 889 | −5.61 | −2.69 | 2.97 | 2.71 | 0.26 | 447 |
| 57 | −5.51 | −2.51 | 2.95 | 2.84 | 0.11 | 471 |
| 75 | −5.66 | −2.68 | 3.01 | 2.88 | 0.13 | 446 |
| A | −5.79 | −2.20 | 3.19 | 2.90 | 0.29 | 423 |

Referring to Table 3, it is confirmed that Compounds 3, 4, 23, 41, 174, 209, 229, 481, 617, 796, 889, 57, and 75 may emit deep blue light and may have small $\Delta E_{ST}$ and emit thermally activated delayed fluorescence light.

Evaluation Example 2

Compound H19 and Compound 3 (15 percent by weight, weight %) were co-deposited on a quartz cell to manufacture a film having a thickness of 100 Å. Films 2 to 13, A, and B were manufactured in the same manner as described above, except that Compounds 4, 23, 41, 174, 209, 229, 481, 617, 796, 889, 57, 75, A, and B were used instead of Compound 3. Then, C9920-02 and PMA-11 (manufactured by Hamamatsu photonics) were used to excite the films 1 to 13, A, and B by excited light having a wavelength of 340 nanometers (nm) in a nitrogen atmosphere and measure a PL quantum yield of each film. Results thereof are shown in Table 4.

TABLE 4

| Film No. | Film component | PL quantum efficiency (%) |
|---|---|---|
| 1 | Compound 3 + H19 | 70 |
| 2 | Compound 4 + H19 | 66 |
| 3 | Compound 23 + H19 | 57 |
| 4 | Compound 41 + H19 | 65 |
| 5 | Compound 174 + H19 | 48 |
| 6 | Compound 209 + H19 | 66 |
| 7 | Compound 229 + H19 | 54 |
| 8 | Compound 481 + H19 | 51 |
| 9 | Compound 617 + H19 | 52 |
| 10 | Compound 796 + H19 | 48 |
| 11 | Compound 889 + H19 | 54 |
| 12 | Compound 57 + H19 | 65 |
| 13 | Compound 75 + H19 | 58 |
| A | Compound A + H19 | 45 |
| B | Compound B + H19 | 29 |

Referring to Table 4, it is confirmed that the films 1 to 13 have high PL quantum efficiency, as compared with the films A and B.

Example 1

A glass substrate, on which a 1,500 Å ITO electrode (first electrode, anode), was formed, was washed with distilled water ultrasonic wave. When the washing with distilled water was completed, sonification washing was performed by sequentially using iso-propyl alcohol, acetone, and methanol. The resultant was dried and then transferred to a plasma washer, and the resultant substrate was washed with plasma for 5 minutes and then transferred to a vacuum depositing device.

Compound HT3 was vacuum-deposited on the ITO electrode of the glass substrate to form a first hole injection layer having a thickness of 100 Å, Compound HT-D$_1$ was vacuum-deposited on the first hole injection layer to form a second hole injection layer having a thickness of 100 Å, and mCP was deposited on the second hole injection layer to form an electron blocking layer having a thickness of 150 Å, thereby forming a hole transport region.

Compound H19 (host) and Compound 3 (dopant) were co-deposited on the hole transport region at a volume ratio of 85:15 to form an emission layer having a thickness of 300 Å.

Compound ET3 was vacuum-deposited on the emission layer to form an electron transport layer having a thickness of 300 Å, ET-D1 (LiQ) was deposited on the electron transport layer to form an electron injection layer having a thickness of 10 Å, and Al was deposited on the electron injection layer to form an Al second electrode (cathode) having a thickness of 1,200 Å, thereby completing the manufacture of an organic light-emitting device.

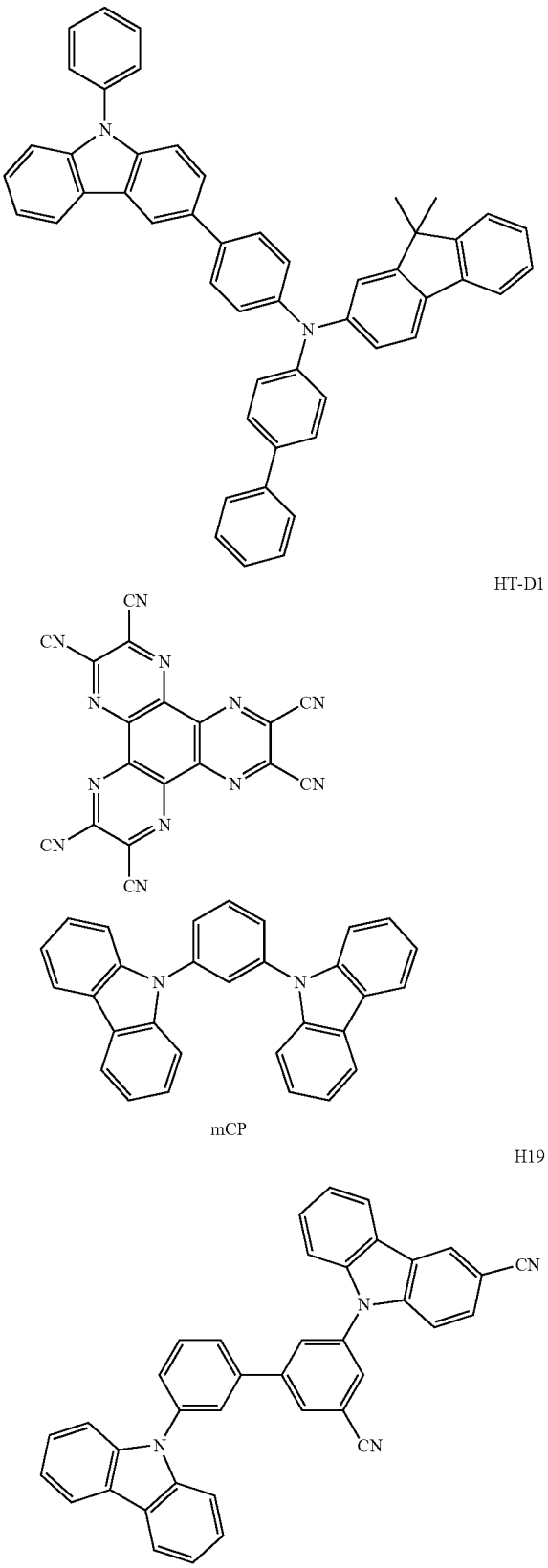

ET3

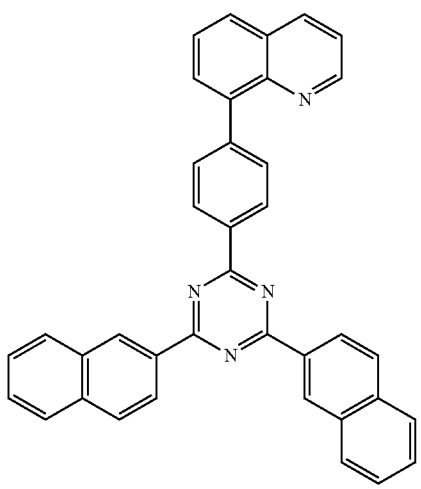

Examples 2 to 13 and Comparative Examples A to C

Organic light-emitting devices were manufactured in the same manner as in Example 1, except that Compounds shown in Table 5 were each used instead of Compound 1 as a dopant in forming an emission layer.

Evaluation Example 3

The driving voltage, external quantum efficiency, and lifespan of the organic light-emitting devices manufactured according to Examples 1 to 13 and Comparative Examples A to C were measured (at 500 candelas per square meter, $cd/m^2$) by using a current-voltage meter (Keithley 2400) and a luminance meter (Minolta Cs-1000A), and results thereof are shown in Table 5. The lifespan ($T_{95}$) (at 500 $cd/m^2$) (relative value) data in Table 5 indicates a relative value of an amount of time (hours, hr) that lapsed when luminance was 95% of initial luminance (100%).

TABLE 5

| Example No. | Host | Dopant | Driving voltage (V) | External quantum efficiency (relative value (%)) | $LT_{95}$@500 $cd/m^2$ (relative value (%)) |
|---|---|---|---|---|---|
| Example 1 | Compound H19 | Compound 3 | 4.56 | 156 | 3611 |
| Example 2 | Compound H19 | Compound 4 | 4.50 | 170 | 5707 |
| Example 3 | Compound H19 | Compound 23 | 4.99 | 105 | 4537 |
| Example 4 | Compound H19 | Compound 41 | 4.85 | 156 | 8817 |
| Example 5 | Compound H19 | Compound 174 | 4.37 | 130 | 4769 |
| Example 6 | Compound H19 | Compound 209 | 4.27 | 200 | 12153 |
| Example 7 | Compound H19 | Compound 229 | 5.21 | 83 | 9637 |
| Example 8 | Compound H19 | Compound 481 | 4.79 | 128 | 1934 |
| Example 9 | Compound H19 | Compound 617 | 4.40 | 180 | 4489 |
| Example 10 | Compound H19 | Compound 796 | 4.88 | 113 | 3370 |
| Example 11 | Compound H19 | Compound 889 | 5.03 | 96 | 8258 |
| Example 12 | Compound H19 | Compound 57 | 4.16 | 179 | 3030 |
| Example 13 | Compound H19 | Compound 75 | 4.09 | 125 | 1687 |
| Comparative Example A | Compound H19 | Compound A | 5.61 | 102 | 162 |
| Comparative Example B | Compound H19 | Compound B | 4.63 | 100 | 100 |
| Comparative Example C | Compound H19 | Compound C | 4.28 | 107 | 2477 |

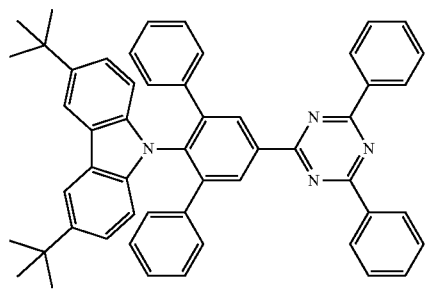

TABLE 5-continued
| Example No. | Host | Dopant | Driving voltage (V) | External quantum efficiency (relative value (%)) | LT$_{95}$@500 cd/m$^2$ (relative value (%)) |
|---|---|---|---|---|---|
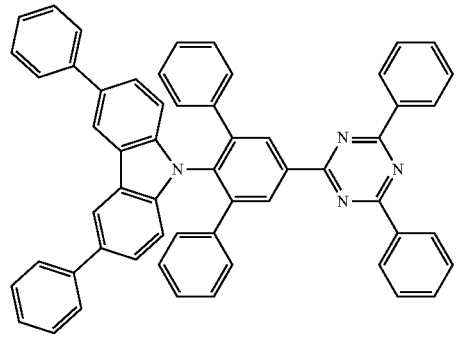
4
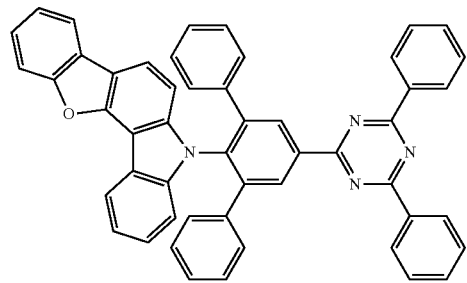
23
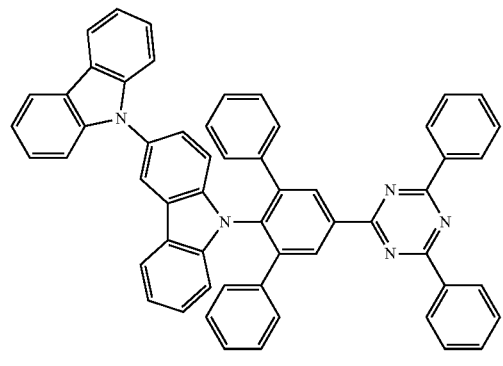
41
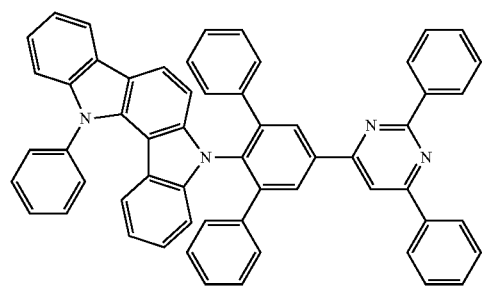
174

TABLE 5-continued
| Example No. | Host | Dopant | Driving voltage (V) | External quantum efficiency (relative value (%)) | LT$_{95}$@500 cd/m$^2$ (relative value (%)) |
| --- | --- | --- | --- | --- | --- |
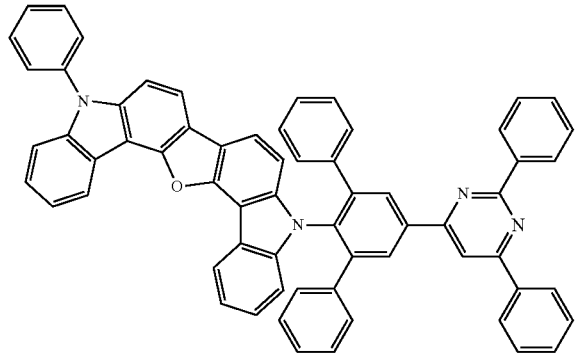
209
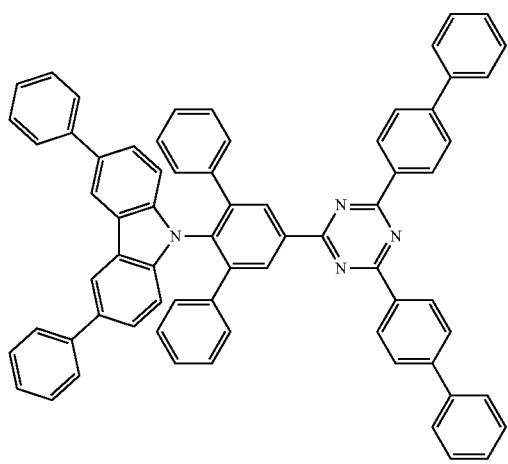
229
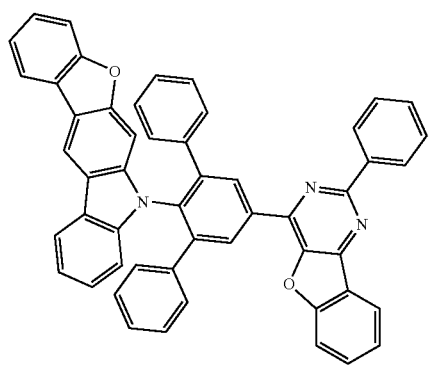
481

TABLE 5-continued
| Example No. | Host | Dopant | Driving voltage (V) | External quantum efficiency (relative value (%)) | LT$_{95}$@500 cd/m$^2$ (relative value (%)) |
|---|---|---|---|---|---|
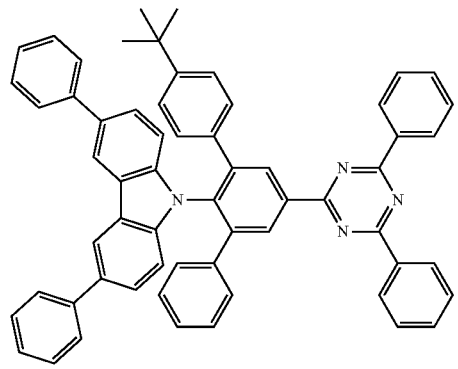
617
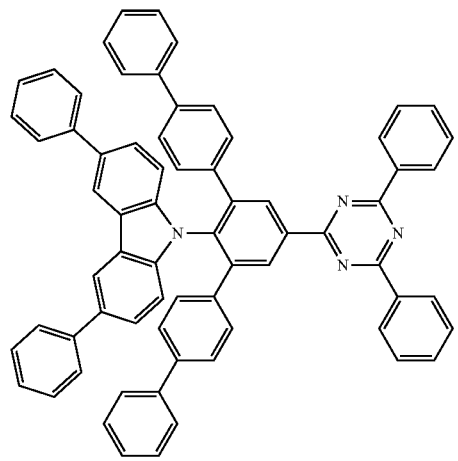
796
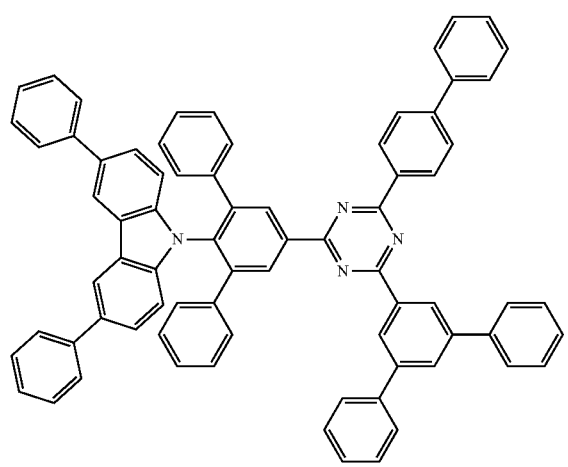
889

TABLE 5-continued
| Example No. | Host | Dopant | Driving voltage (V) | External quantum efficiency (relative value (%)) | LT$_{95}$@500 cd/m$^2$ (relative value (%)) |
| --- | --- | --- | --- | --- | --- |
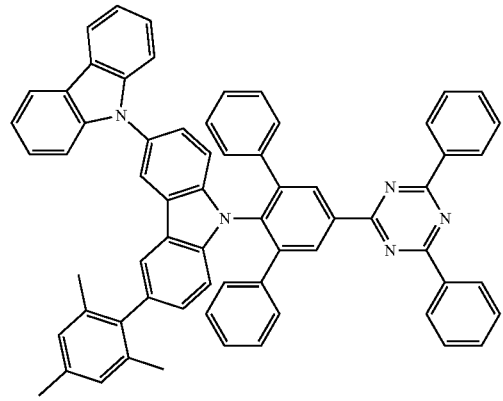
57
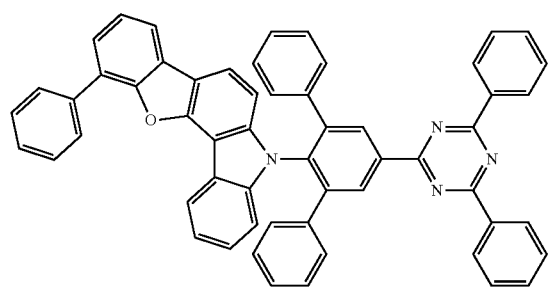
75
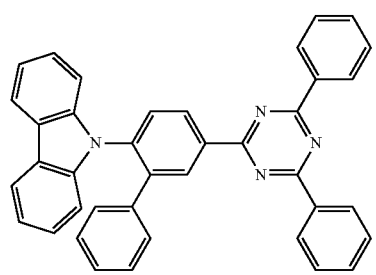
A
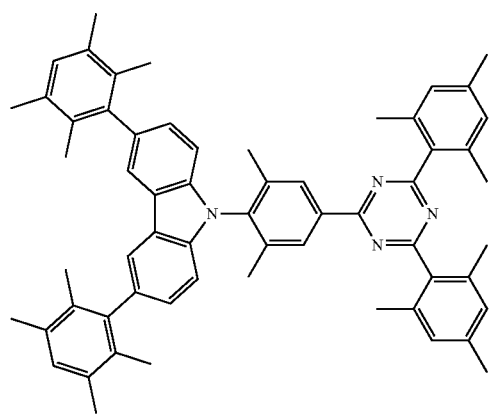
B TABLE 5-continued

| Example No. | Host | Dopant | Driving voltage (V) | External quantum efficiency (relative value (%)) | LT$_{95}$@500 cd/m$^2$ (relative value (%)) |
|---|---|---|---|---|---|

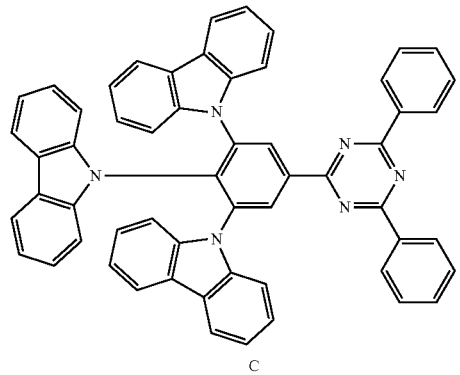

C

Referring to Table 5, it is confirmed that the organic light-emitting devices of Examples 1 to 13 have excellent driving voltage, external quantum efficiency, and/or lifespan characteristics, as compared with those of the organic light-emitting devices of Comparative Examples A to C.

The condensed cyclic compound may have excellent delayed fluorescence emission characteristics, and the organic light-emitting device including the condensed cyclic compound may have high efficiency and/or a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present description as defined by the following claims.

What is claimed is:

1. A condensed cyclic compound represented by Formula 1:

Formula 1

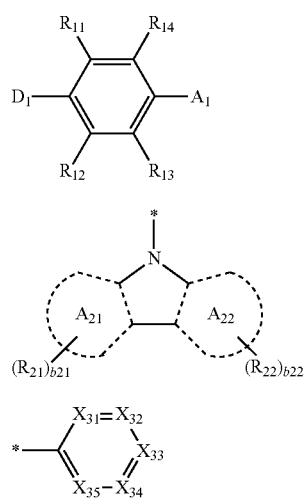

Formula 2

Formula 3-1

-continued

Formula 3-2

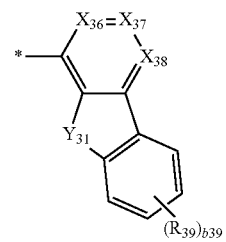

Formula 3-3

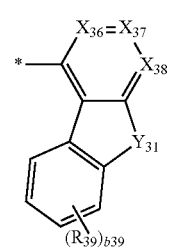

Formula 3-4

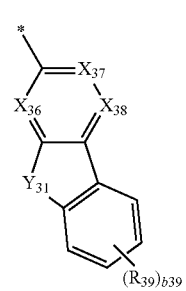

Formula 3-5

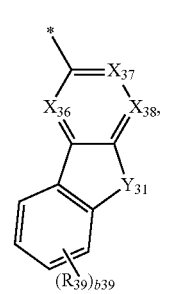

wherein, in Formulae 1, 2, and 3-1 to 3-5,
$D_1$ is a group represented by Formula 2,
$A_1$ is a group represented by one selected from Formulae 3-1 to 3-5, $R_{11}$ and $R_{12}$ are each independently a substituted or unsubstituted $C_6$-$C_{30}$ aryl group, $A_{21}$ and $A_{22}$ are each independently selected from a benzene group, a fluorene group, a carbazole group, a dibenzofuran group, a dibenzothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group, $X_{31}$ is N or $C(R_{31})$; $X_{32}$ is N or $C(R_{32})$; $X_{33}$ is N or $C(R_{33})$; $X_{34}$ is N or $C(R_{34})$; $X_{35}$ is N or $C(R_{35})$; $X_{36}$ is N or $C(R_{36})$; $X_{37}$ is N or $C(R_{37})$; and $X_{38}$ is N or $C(R_{38})$, wherein at least one selected from $X_{31}$ to $X_{35}$ in Formula 3-1 is N, and at least one selected from $X_{36}$ to $X_{38}$ in Formulae 3-2 to 3-5 is N, $Y_{31}$ is selected from O and S, $R_{13}$, $R_{14}$, $R_{21}$, $R_{22}$, and $R_{31}$ to $R_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ aryl alkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroaryl alkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), two neighboring groups selected from $R_{31}$ to $R_{39}$ are optionally linked to form a condensed ring, b21 and b22 are each independently selected from 1, 2, 3, 4, 5, 6, 7, and 8, b39 is selected from 1, 2, 3, and 4, $Q_1$ to $Q_7$ are each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, provided that when $A_1$ is a group represented by Formula 3-1 and $R_{21}$ or $R_{22}$ is N($Q_4$)($Q_5$), then $Q_4$ and $Q_5$ are each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_1$-$C_{60}$ heteroaryl group, a monovalent non-aromatic condensed polycyclic group, and a monovalent non-aromatic condensed heteropolycyclic group, provided that when $A_1$ is a group represented by Formula 3-1, then $R_{11}$ and $R_{12}$ are each independently selected from:

a phenyl group, a biphenyl group, a terphenyl group, a naphthyl group, a phenanthrenyl group, an anthracenyl group, a triphenylenyl group, a pyrenyl group, and a chrysenyl group; and a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, —F, —Cl, —Br, —I, a $C_1$-$C_{20}$ alkyl group, a $C_1$-$C_{20}$ alkoxy group, and a phenyl group, and ii) $R_{13}$ and $R_{14}$ are each independently selected from:

hydrogen, deuterium, —F, —Cl, —Br, —I, a cyano group, a phenyl group, a biphenyl group, a terphenyl group, a naphthyl group, a phenanthrenyl group, an anthracenyl group, a triphenylenyl group, a pyrenyl group, and a chrysenyl group; and a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, —F, —Cl, —Br, —I, a cyano group, a $C_1$-$C_{20}$ alkyl group, a $C_1$-$C_{20}$ alkoxy group, and a phenyl group, and

* indicates a binding site to a neighboring atom.

2. The condensed cyclic compound of claim 1, wherein $R_{11}$ and $R_{12}$ are each independently selected from:

a phenyl group, a biphenyl group, a terphenyl group, a naphthyl group, a phenanthrenyl group, an anthracenyl group, a triphenylenyl group, a pyrenyl group, and a chrysenyl group; and a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, —F, —Cl, —Br, —I, a cyano group, a $C_1$-$C_{20}$ alkyl group, a $C_1$-$C_{20}$ alkoxy group, and a phenyl group.

3. The condensed cyclic compound of claim 1, wherein $R_{11}$ and $R_{12}$ are each independently selected from:

a phenyl group, a biphenyl group, a terphenyl group, and a naphthyl group; and a phenyl group, a biphenyl group, a terphenyl group, and a naphthyl group, each substituted with at least one selected from deuterium, a methyl group, an ethyl group, an n-propyl group, an isopropyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, a methoxy group, an ethoxy group, a propoxy group, a butoxy group, a pentoxy group, and a phenyl group.

4. The condensed cyclic compound of claim 1, wherein $A_{21}$ is a benzene group, and $A_{22}$ is selected from a benzene group, a fluorene group, a carbazole group, a dibenzofuran group, a dibenzothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group.

5. The condensed cyclic compound of claim 1, wherein two or three selected from $X_{31}$ to $X_{35}$ in Formula 3-1 are each independently N, and two selected from $X_{36}$ to $X_{38}$ in Formulae 3-2 to 3-5 are each independently N.

6. The condensed cyclic compound of claim 1, wherein $R_{13}$ and $R_{14}$ are each independently selected from:
hydrogen, deuterium, —F, —Cl, —Br, —I, a cyano group, a phenyl group, a biphenyl group, a terphenyl group, a naphthyl group, a phenanthrenyl group, an anthracenyl group, a triphenylenyl group, a pyrenyl group, and a chrysenyl group; and
a phenyl group, a biphenyl group, a terphenyl group, a naphthyl group, a phenanthrenyl group, an anthracenyl group, a triphenylenyl group, a pyrenyl group, and a chrysenyl group, each substituted with at least one selected from deuterium, —F, —Cl, —Br, —I, a cyano group, a $C_1$-$C_{20}$ alkyl group, a $C_1$-$C_{20}$ alkoxy group, and a phenyl group.

7. The condensed cyclic compound of claim 1, wherein $R_{21}$ and $R_{22}$ are each independently selected from:
hydrogen, deuterium, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group; and
a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, a naphthyl group, a fluorenyl group, a dimethylfluorenyl group, a diphenylfluorenyl group, a carbazolyl group, a phenylcarbazolyl group, a biphenylcarbazolyl group, a dibenzofuranyl group, and a dibenzothiophenyl group.

8. The condensed cyclic compound of claim 1, wherein $D_1$ is represented by one selected from Formulae 2-1 and 2-2:

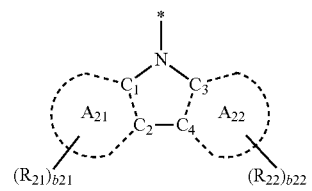

2-1

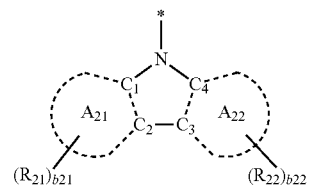

2-2

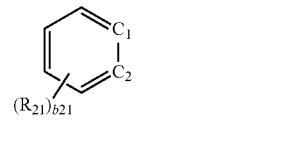

9-11

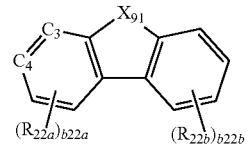

9-21

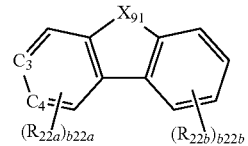

9-22

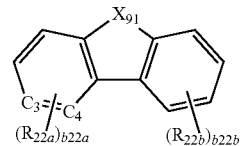

9-23

9-31 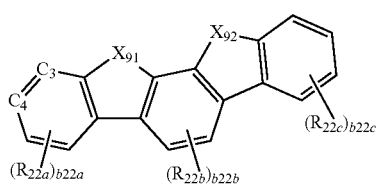
9-32 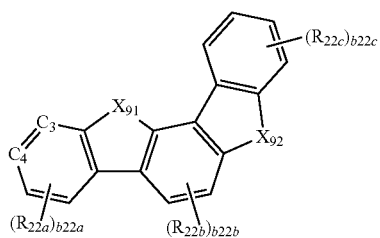
9-33 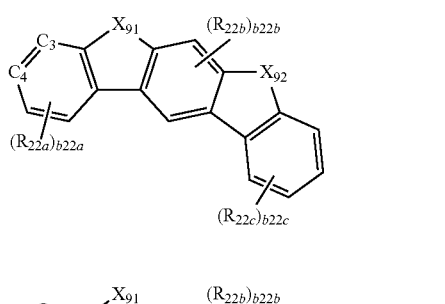
9-34 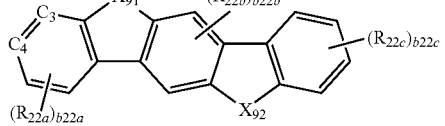
9-35 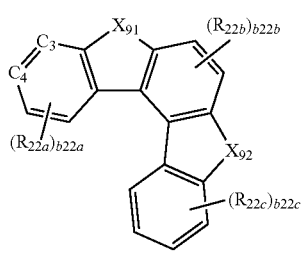
9-36 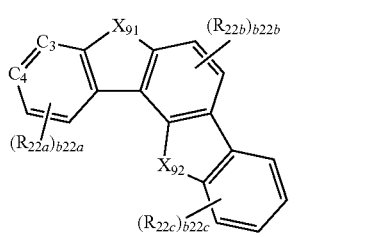
9-37 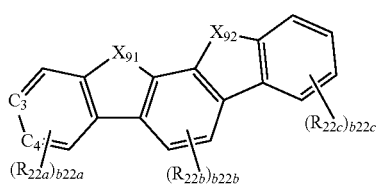
9-38 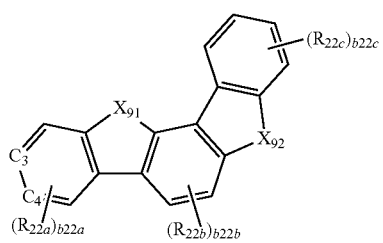
9-39 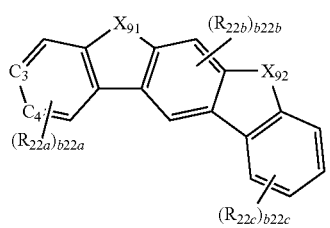
9-40 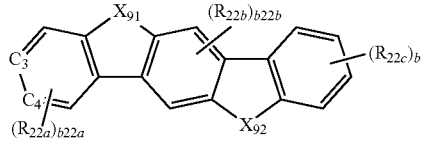
9-41 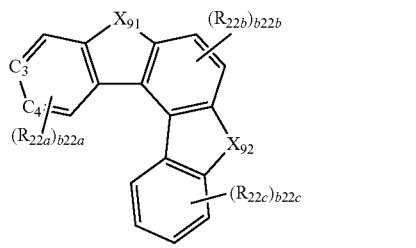
9-42 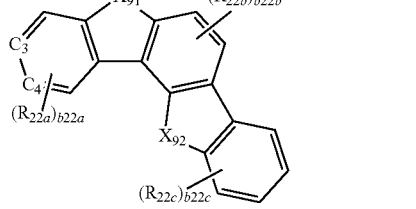
9-43 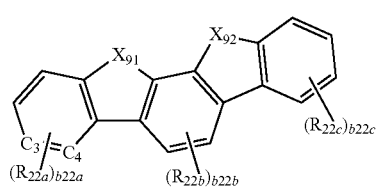
9-44 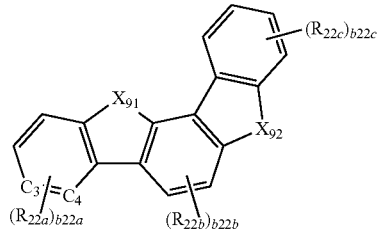

-continued 9-45
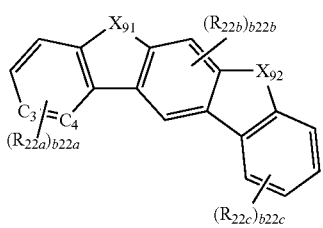

9-46
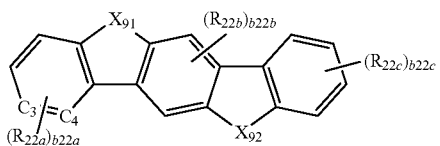

9-47
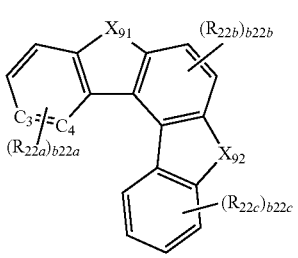

9-48
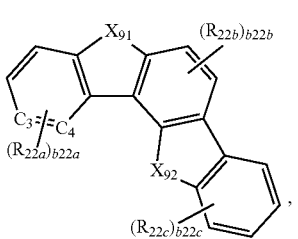

wherein, in Formulae 2-1, 2-2, 9-11, 9-21 to 9-23, and 9-31 to 9-48, $A_{21}$ is a group represented by Formula 9-11, $A_{22}$ selected from groups represented by Formulae 9-11, 9-21 to 9-23, and 9-31 to 9-48, $C_1$ to $C_4$ are each independently a carbon atom, $X_{91}$ is selected from O, S, $N(R_{22d})$, and $C(R_{22d})(R_{22e})$, $X_{92}$ is selected from O, S, $N(R_{22f})$, and $C(R_{22f})(R_{22g})$, $R_{22a}$ to $R_{22g}$ are each independently the same as described in connection with $R_{22}$ in Formula 2, and b22a to b22c are each independently the same as described in connection with b22 in Formula 2.

9. The condensed cyclic compound of claim 1, wherein $A_1$ is represented by one selected from Formulae 3-11 to 3-35:

3-11
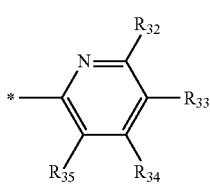

-continued 3-12
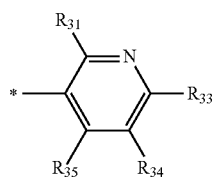

3-13
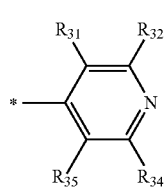

3-14
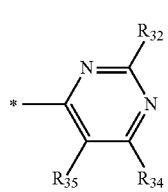

3-15
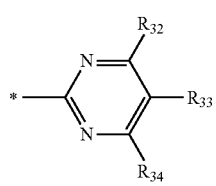

3-16
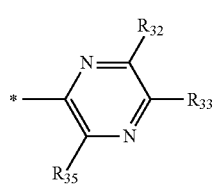

3-17
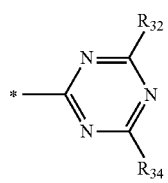

3-18
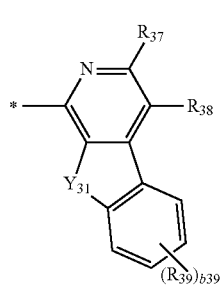

| | |
|---|---|
| 3-19 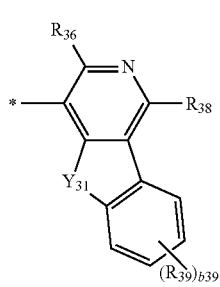 | 3-24 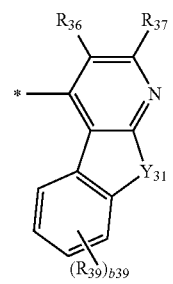 |
| 3-20 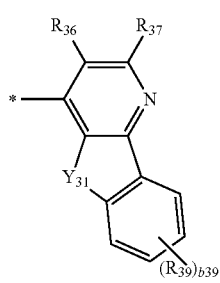 | 3-25 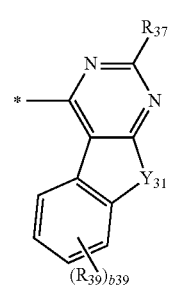 |
| 3-21 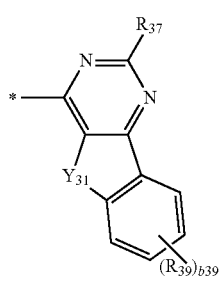 | 3-26 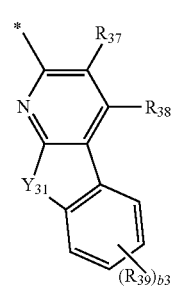 |
| 3-22 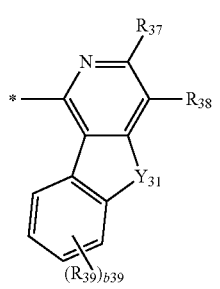 | 3-37 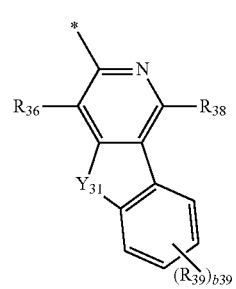 |
| 3-23 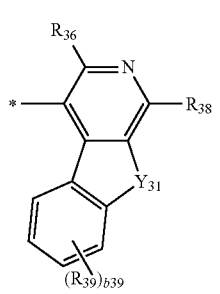 | 3-28 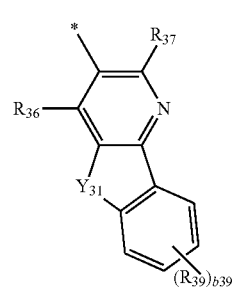 |

491
-continued 3-29

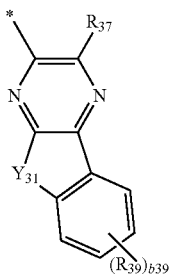

3-30

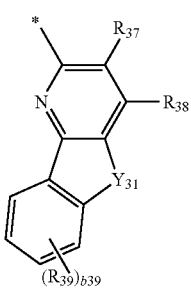

3-31

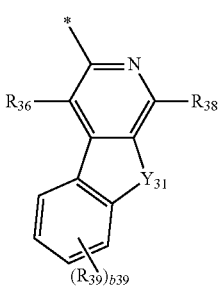

3-32

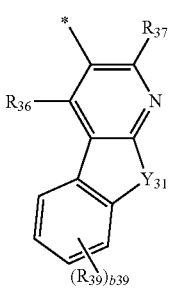

3-33

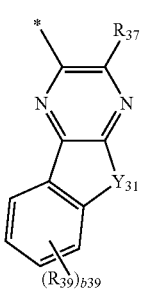

492
-continued 3-34

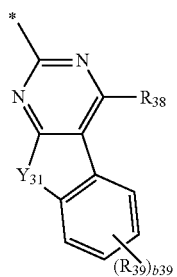

3-35

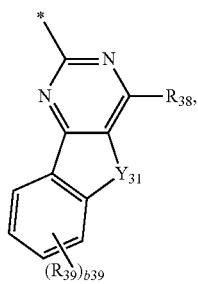

wherein, in Formulae 3-11 to 3-35, $Y_{31}$, $R_{36}$ to $R_{39}$, and b39 are each independently the same as in Formulae 3-1 to 3-5, and \* indicates a binding site to a neighboring atom.

10. The condensed cyclic compound of claim 1, wherein the condensed cyclic compound represented by Formula 1 is represented by Formula 1-1:

Formula 1-1

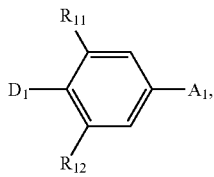

wherein, in Formula 1-1, $D_1$, $A_1$, $R_{11}$, and $R_{12}$ are each independently the same as in Formula 1.

11. The condensed cyclic compound of claim 10, wherein $D_1$ is represented by one selected from Formulae 2-1 and 2-2, and $A_1$ is represented by one selected from Formulae 3-11 to 3-35:

2-1

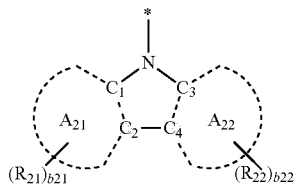

493
-continued
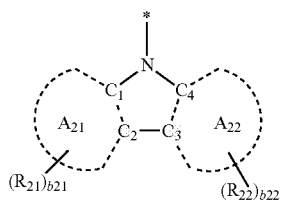
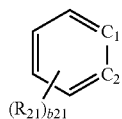
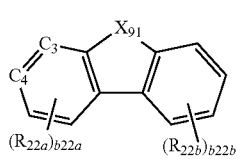
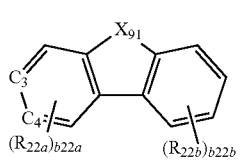
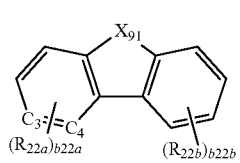
9-31
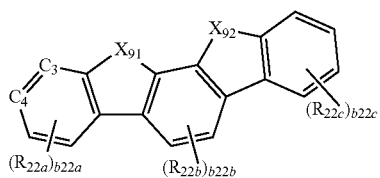
9-32
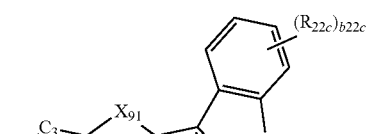
9-33
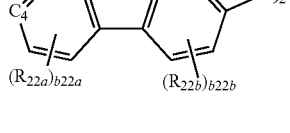
494
-continued
2-2
9-11
9-21
9-22
9-23
9-34
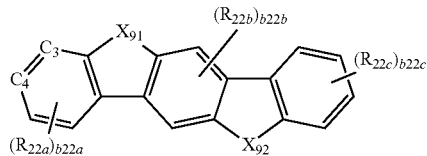
9-35
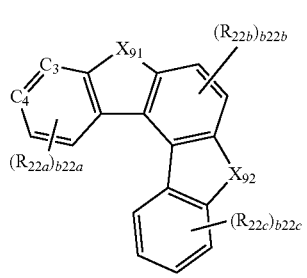
9-36
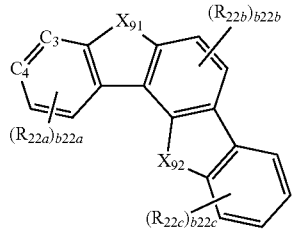
9-37
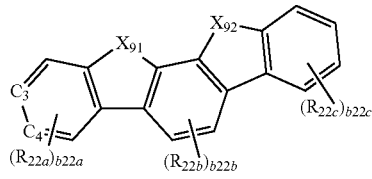
9-38
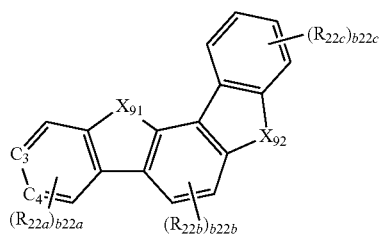
9-39
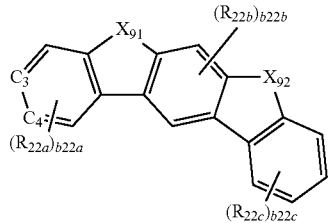
9-40
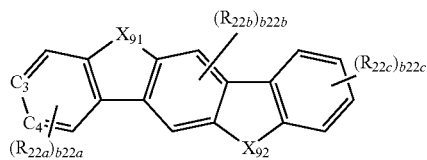

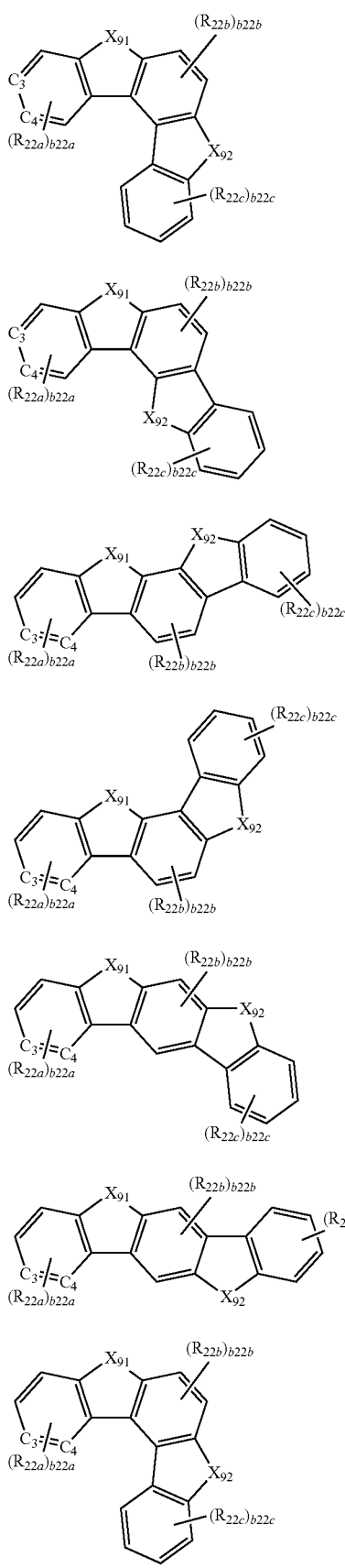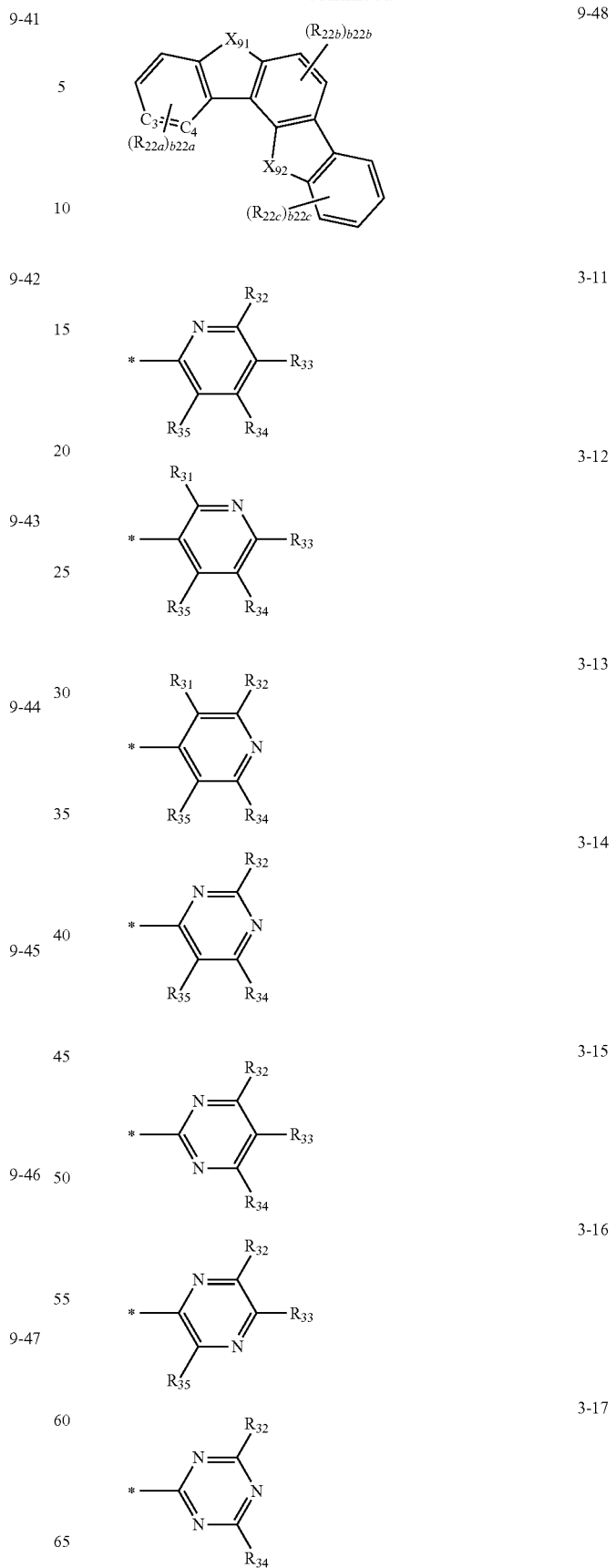

-continued
3-18
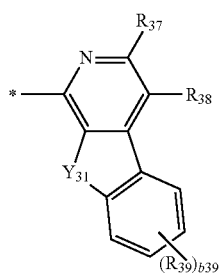
3-19
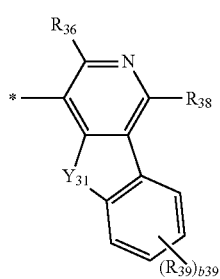
3-20
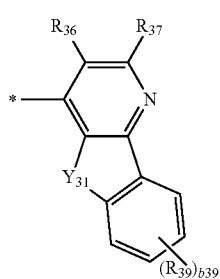
3-21
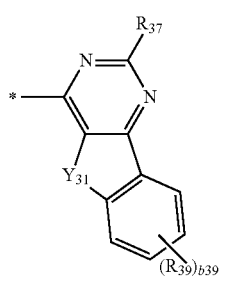
3-22
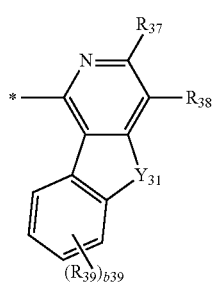
-continued
3-23
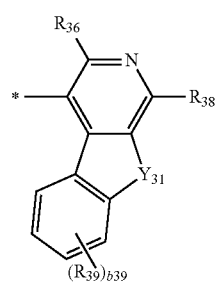
3-24
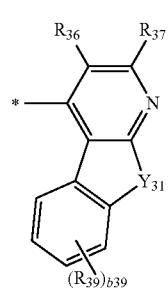
3-25
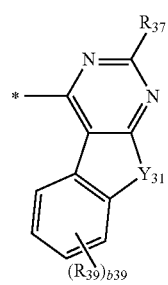
3-26
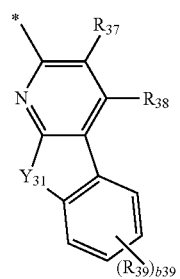
3-37
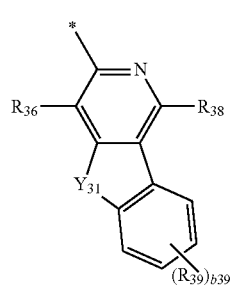

3-28 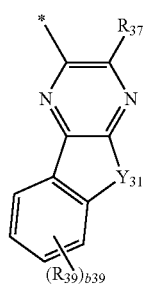

3-29 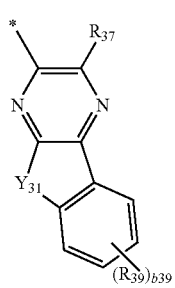

3-30 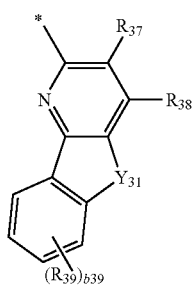

3-31 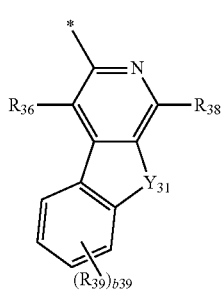

3-32 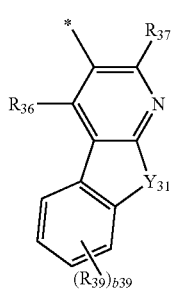

3-33 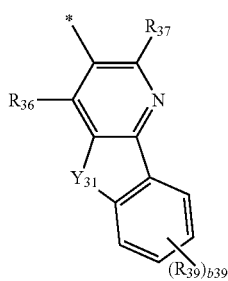

3-34 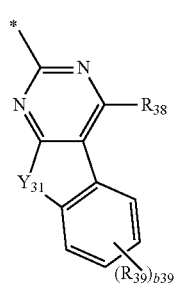

3-35 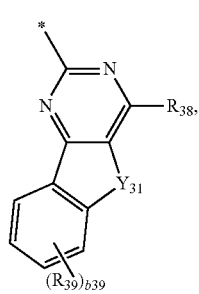

wherein, in Formulae 2-1, 2-2, 9-11, 9-21 to 9-23, 9-31 to 9-48, and 3-11 to 3-35, $A_{21}$ is a group represented by Formula 9-11, $A_{22}$ is selected from groups represented by Formulae 9-11, 9-21 to 9-23, and 9-31 to 9-48, $C_1$ to $C_4$ are each independently a carbon atom, $X_{91}$ is selected from O, S, $N(R_{22d})$, and $C(R_{22d})(R_{22e})$, $X_{92}$ is selected from O, S, $N(R_{22f})$, and $C(R_{22f})(R_{22g})$, $R_{22a}$ to $R_{22g}$ are each independently the same as described in connection with $R_{22}$ in Formula 2, b22a to b22c are each independently the same as described in connection with b22 in Formula 2, $Y_{31}$, $R_{36}$ to $R_{39}$, and b39 are each independently the same as described in connection with Formulae 3-1 to 3-5, and

* indicates a binding site to a neighboring atom.

12. The condensed cyclic compound of claim 1, wherein the condensed cyclic compound represented by Formula 1 is selected from Compounds 1 to 1030:

1
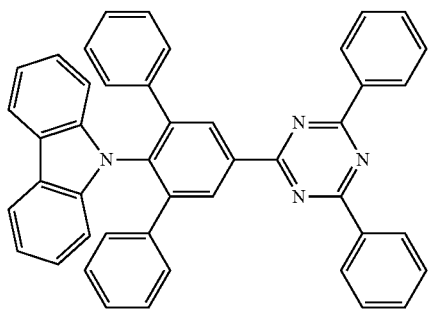
2
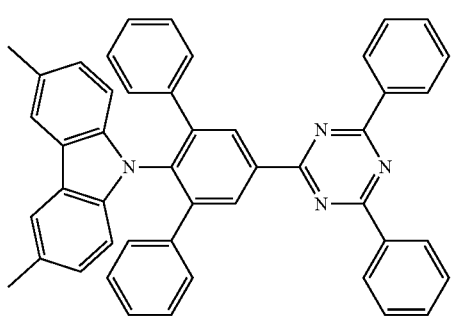
3
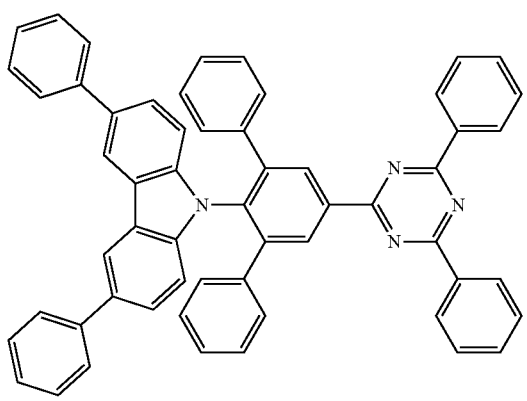
4
5
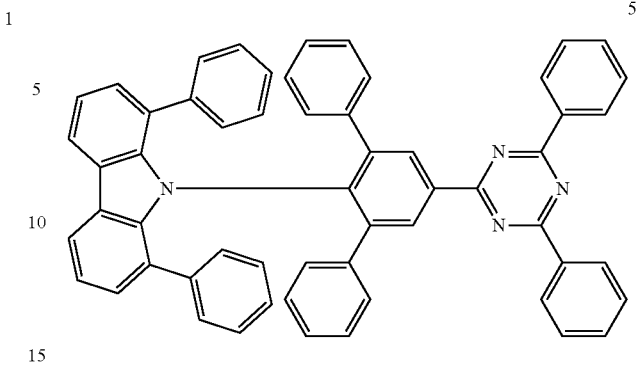
6
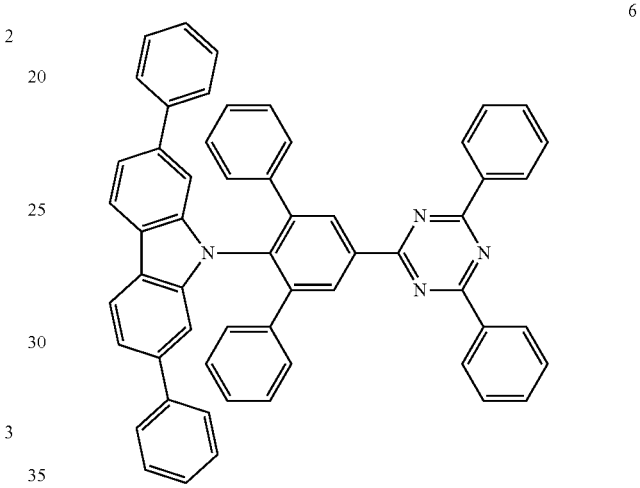
7
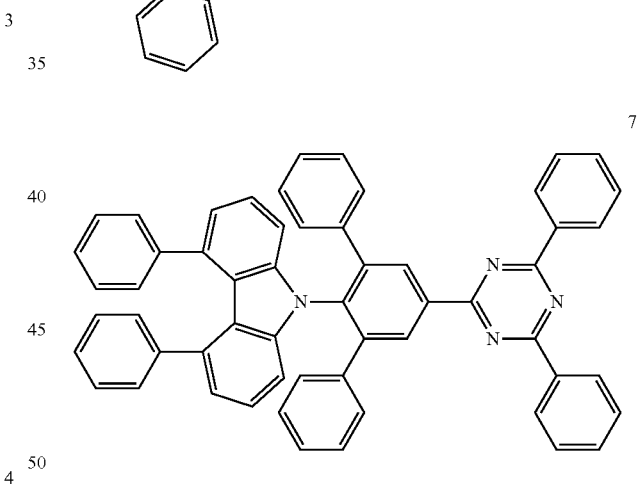
8
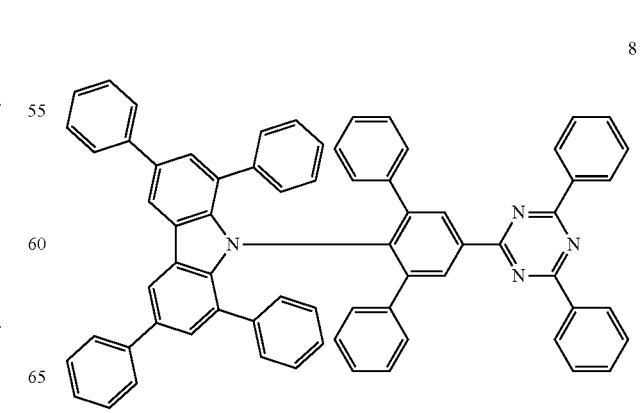

-continued
9
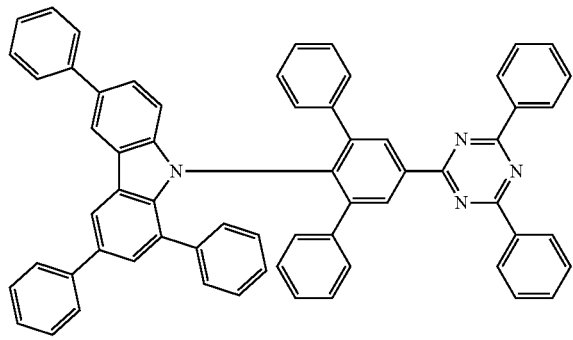
10
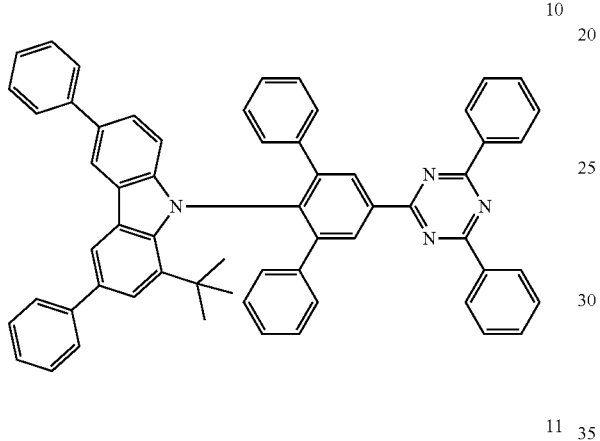
11
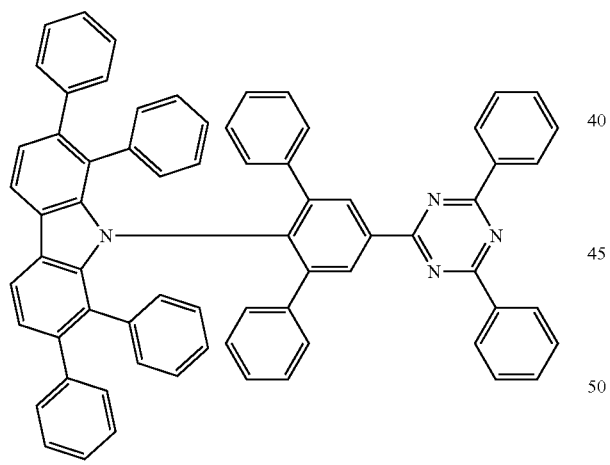
12
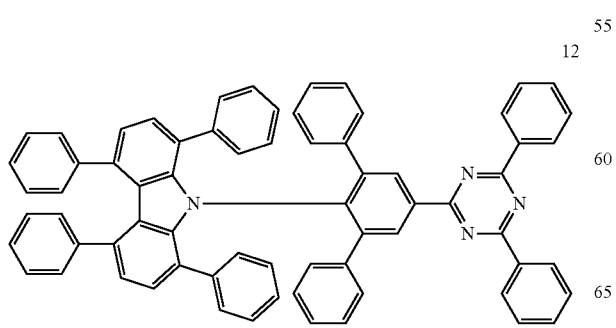
-continued
13
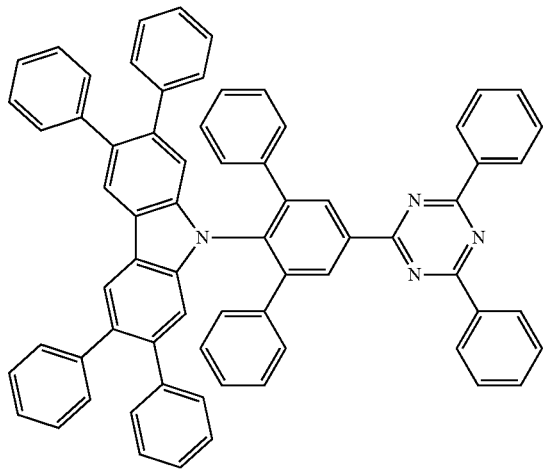
14
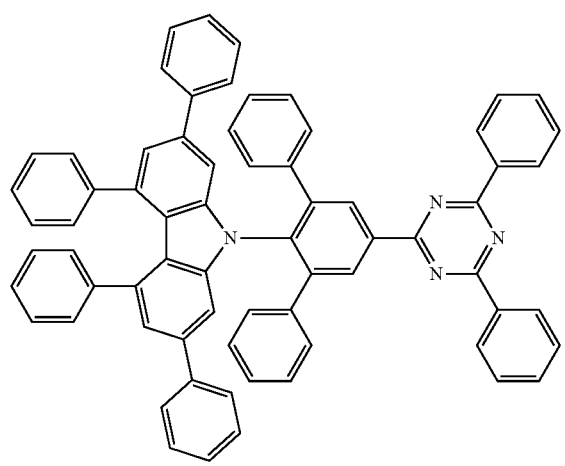
15
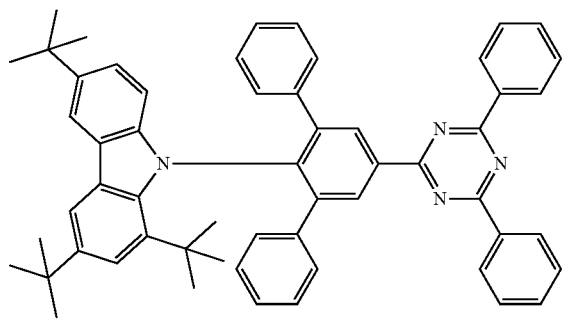
16
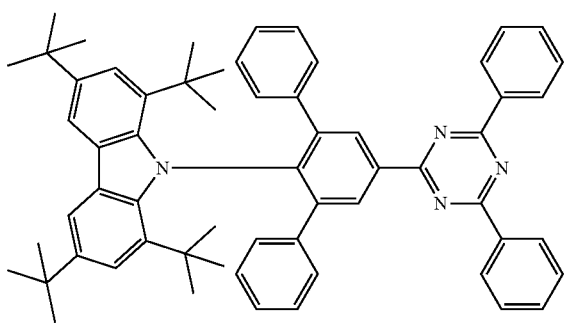

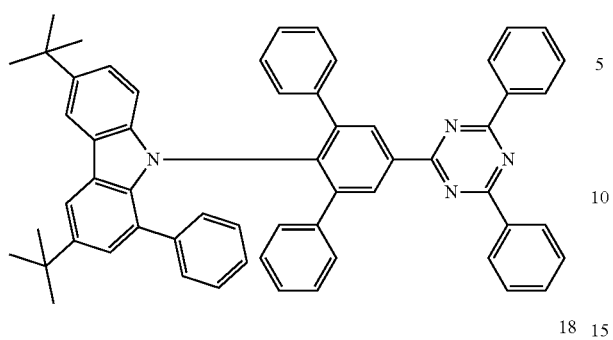
17
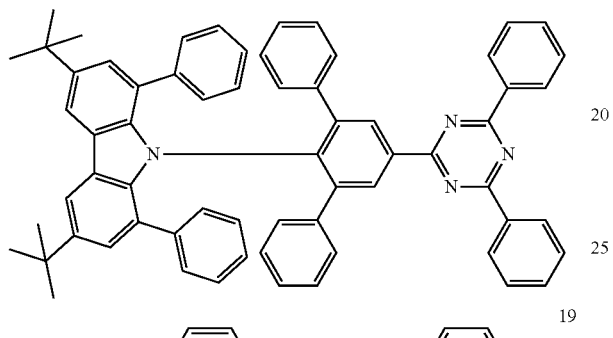
18
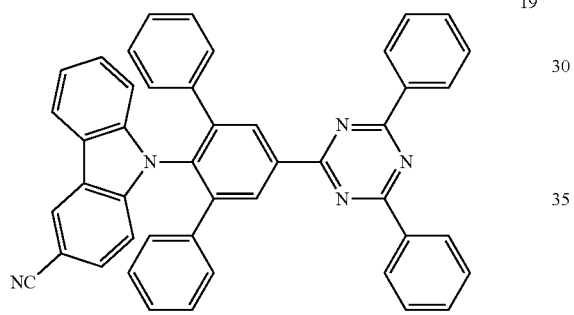
19
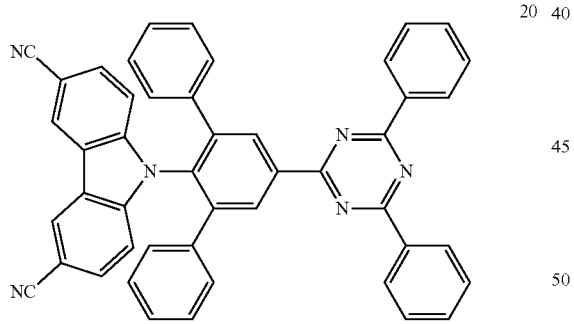
20
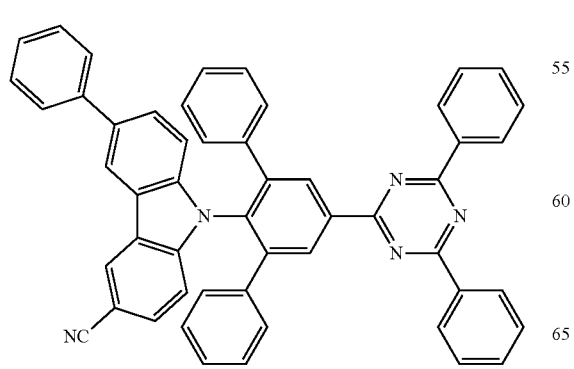
21
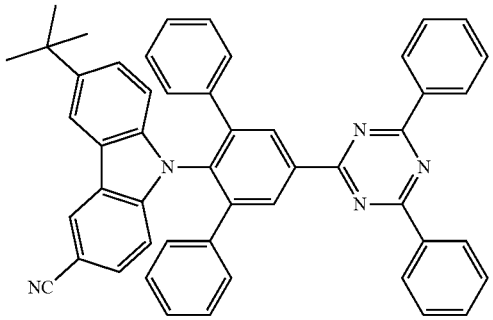
22
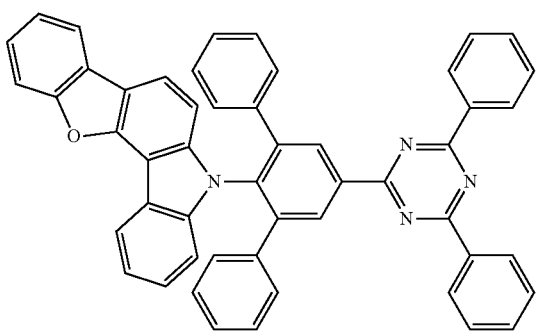
23
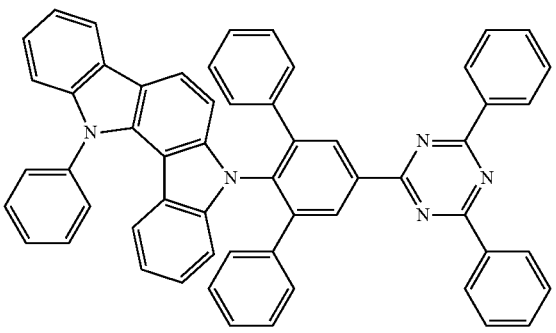
24
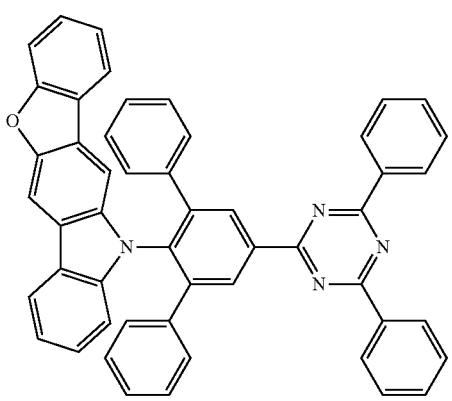
25

26
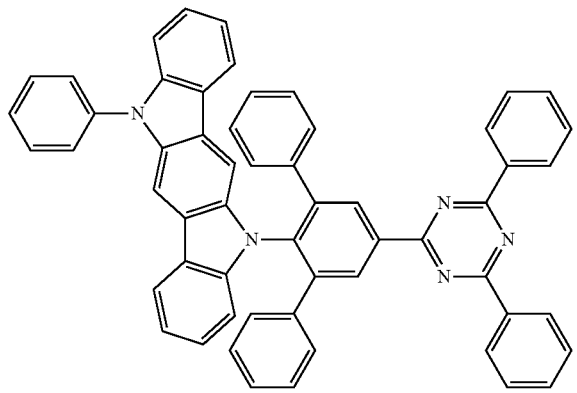
27
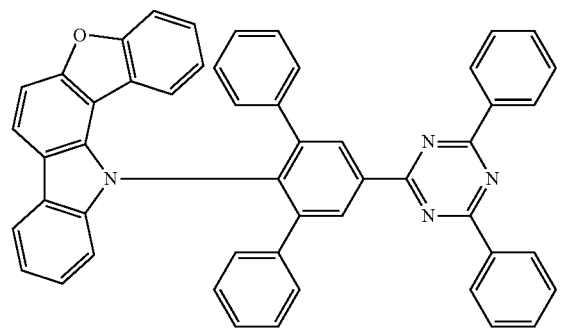
28
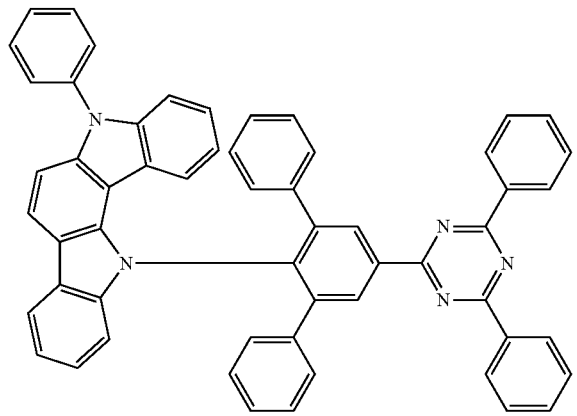
29
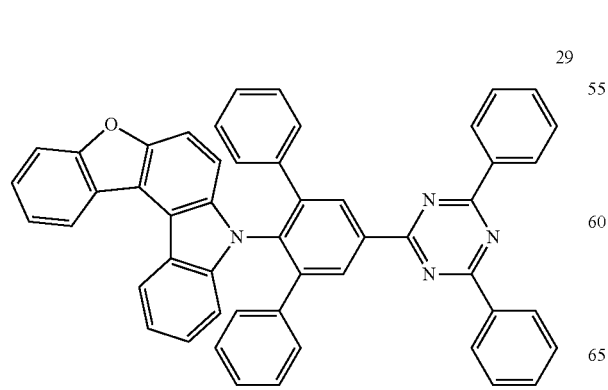
30
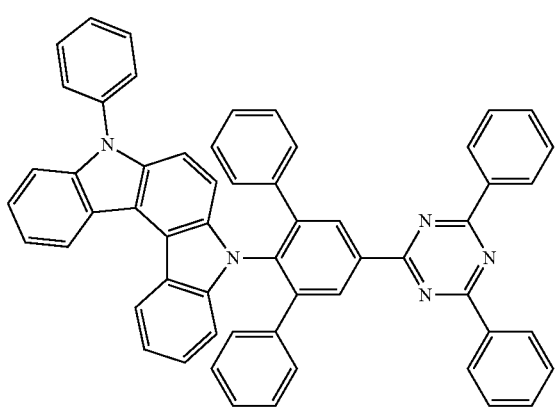
31
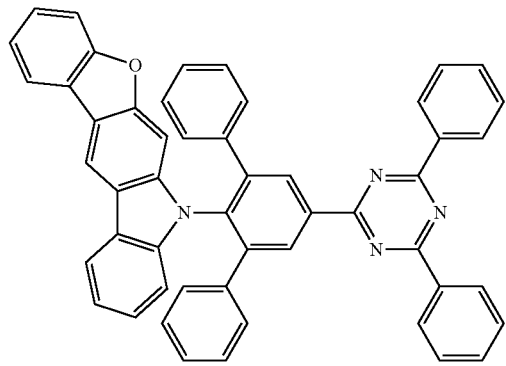
32
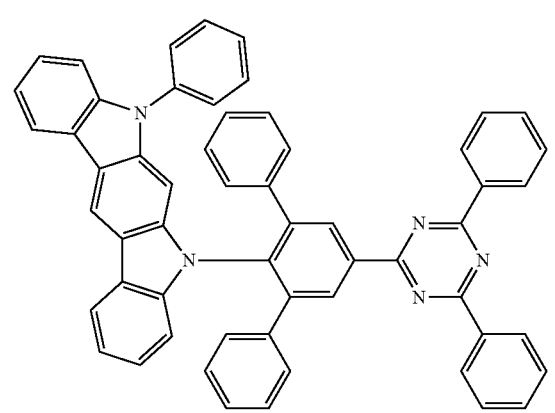
33
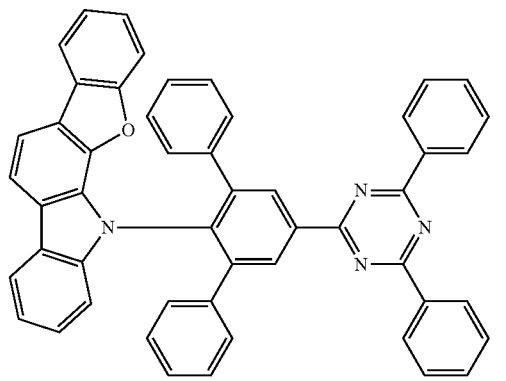

34
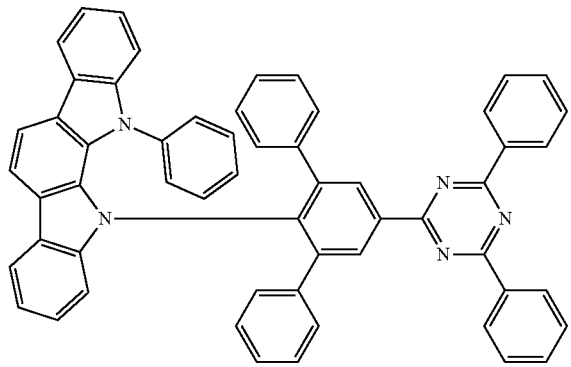
35
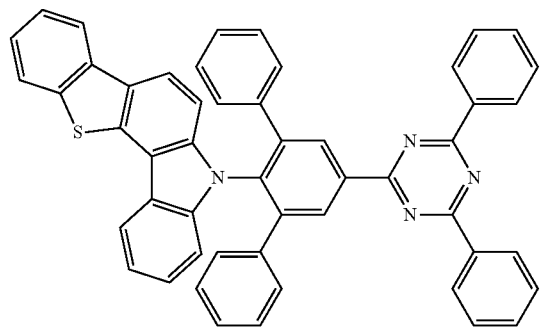
36
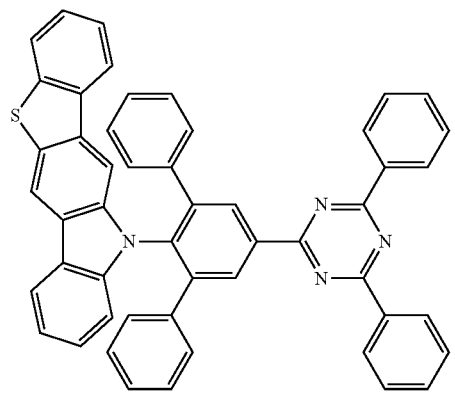
37
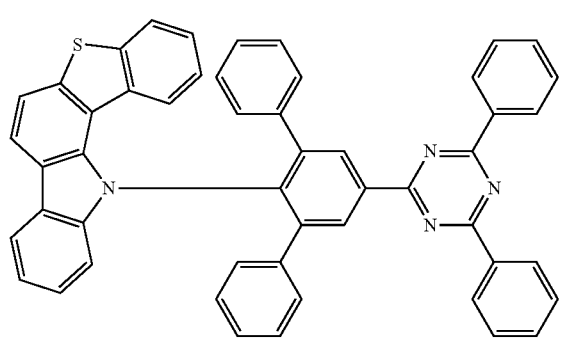
38
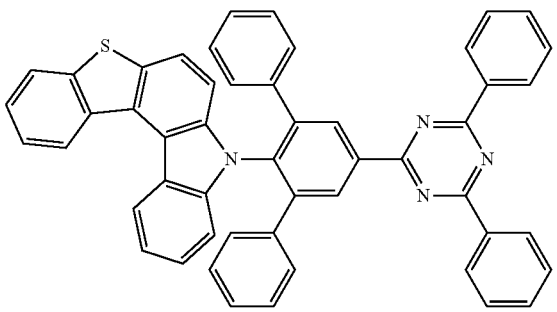
39
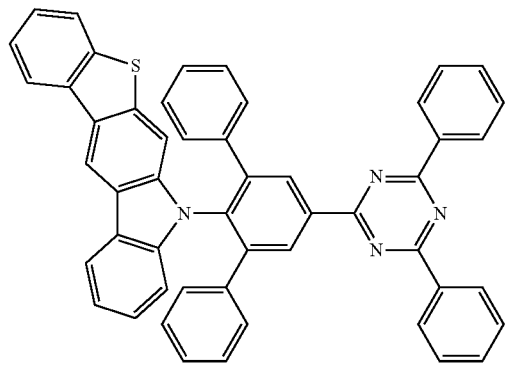
40
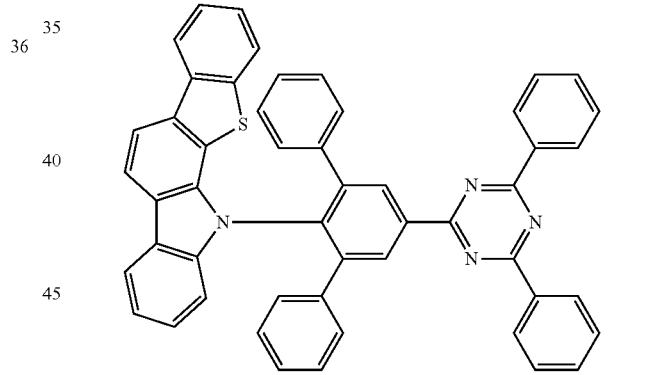
41
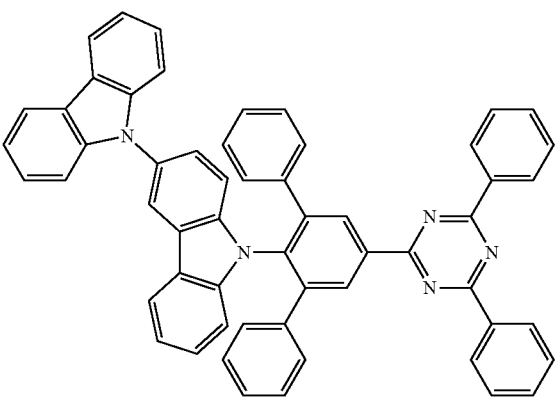

511
-continued
42
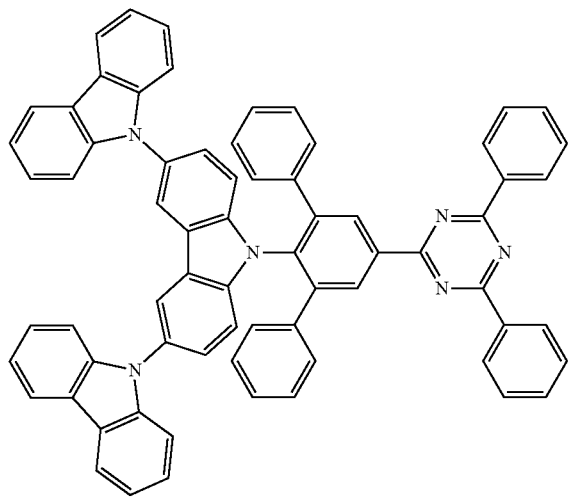
43
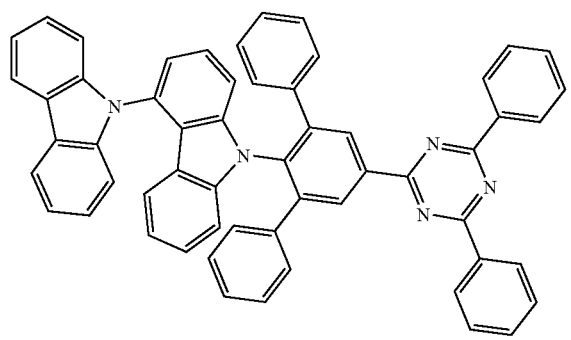
44
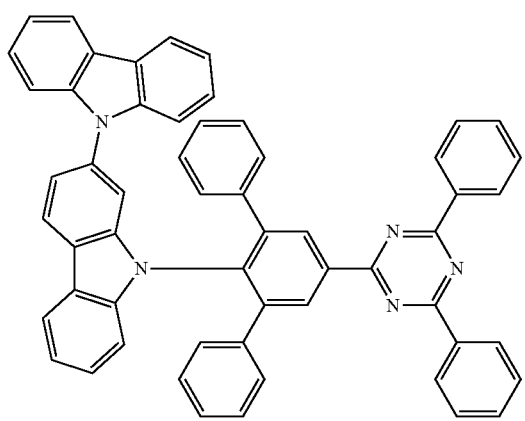
512
-continued
45
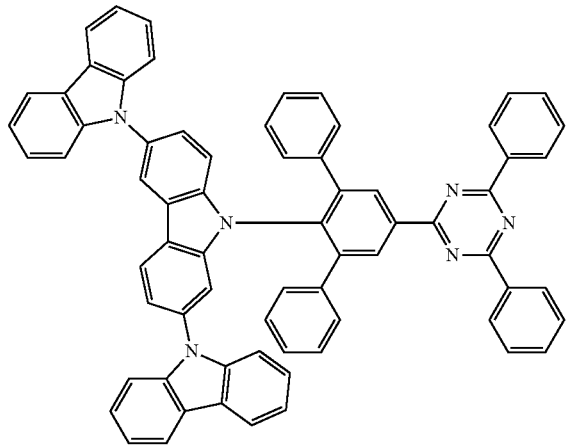
46
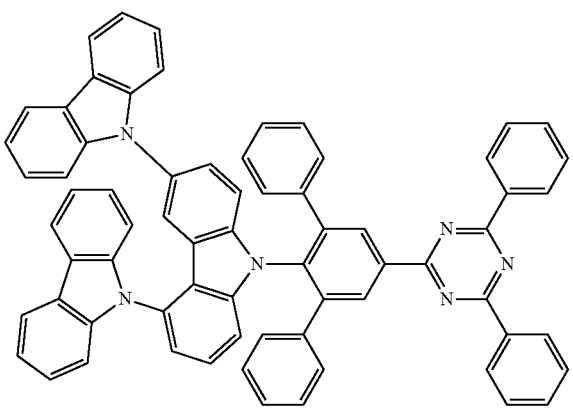
47
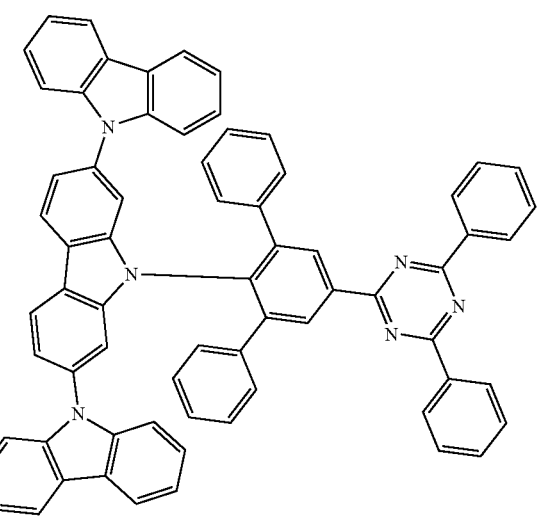

513
-continued
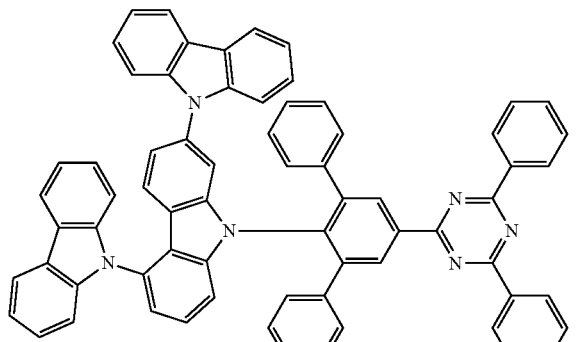
48
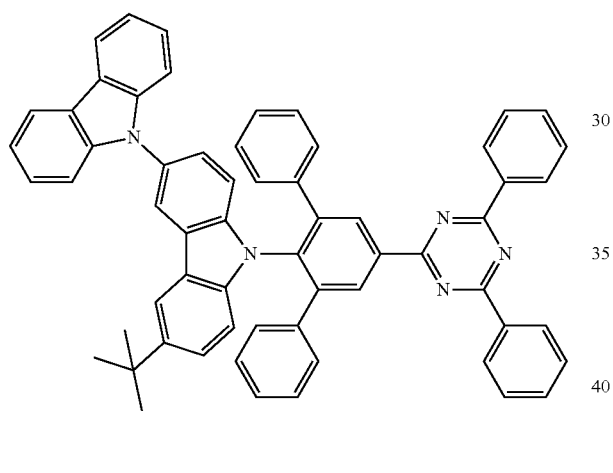
49
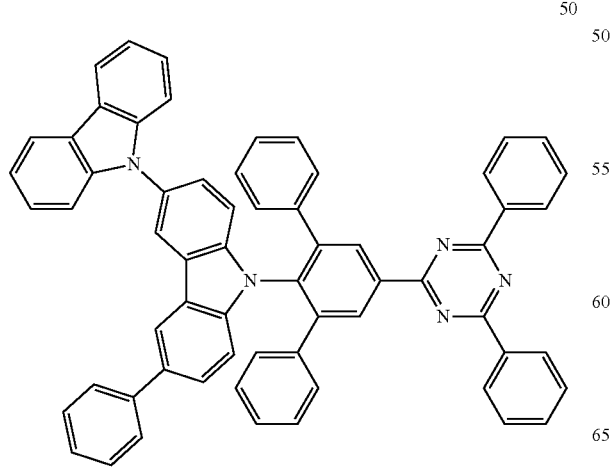
50
514
-continued
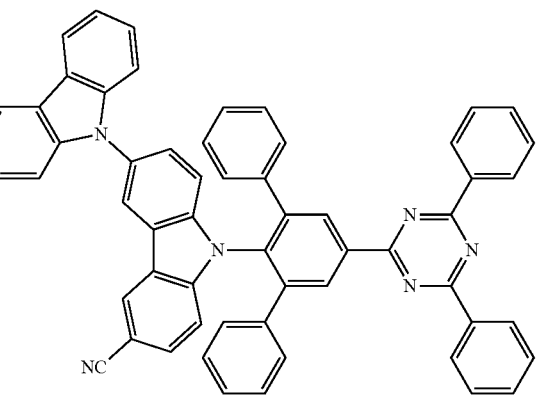
51
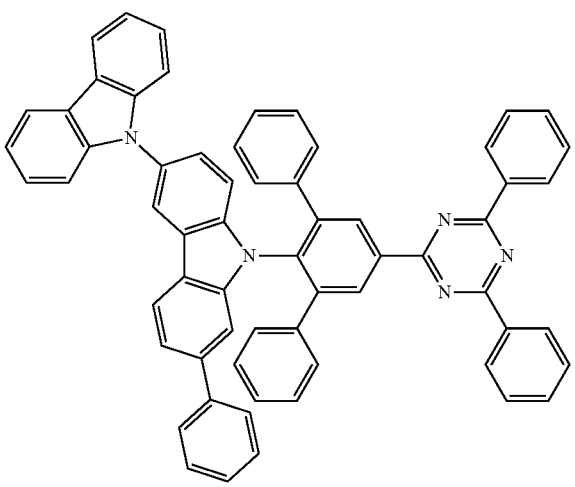
52
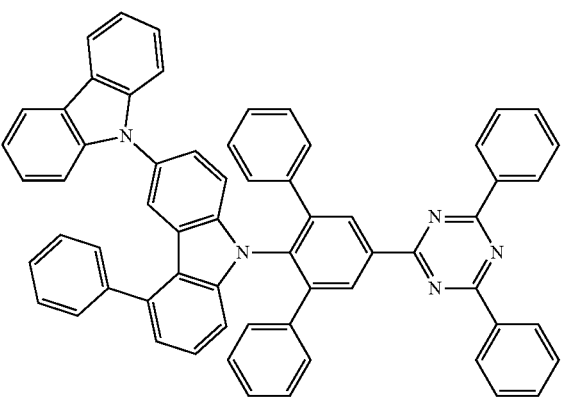
53

515
-continued
54
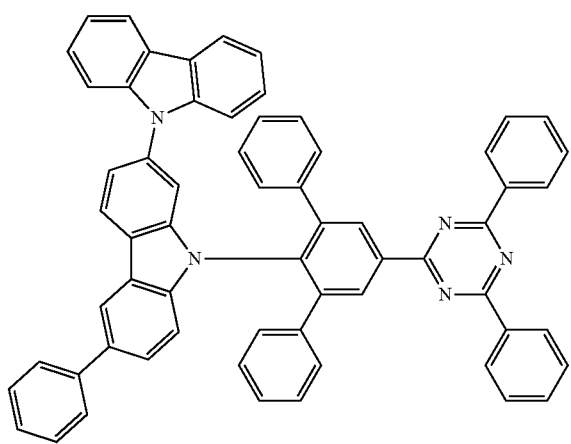
55
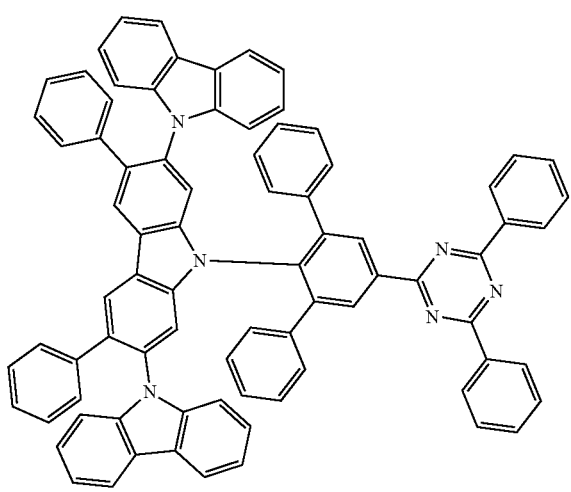
56
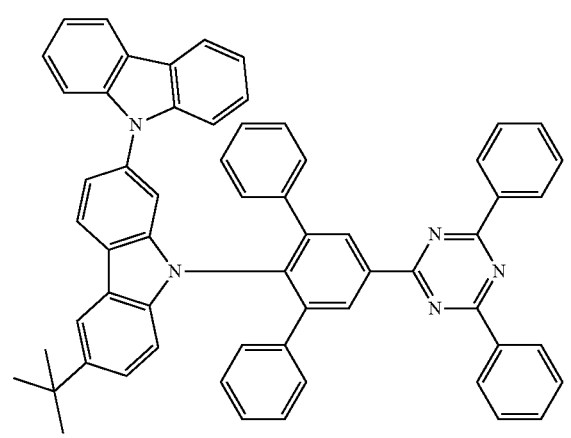
516
-continued
57
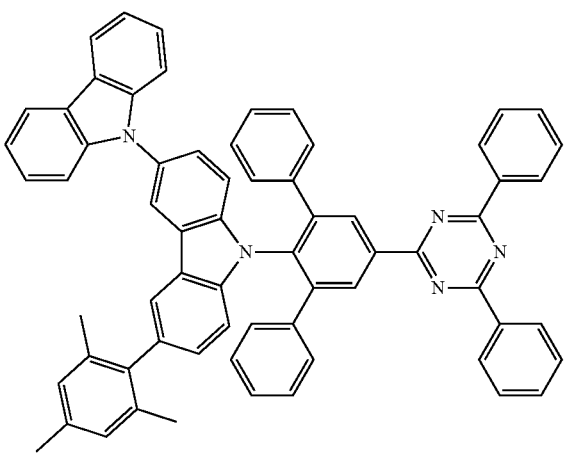
58
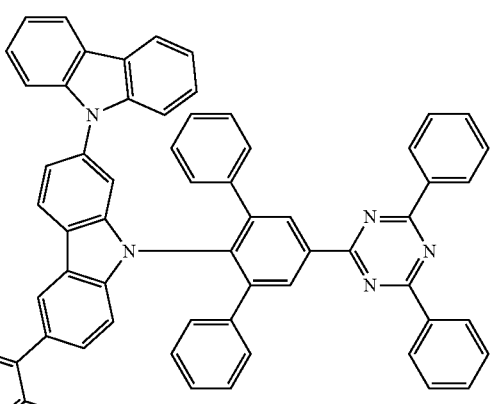
59
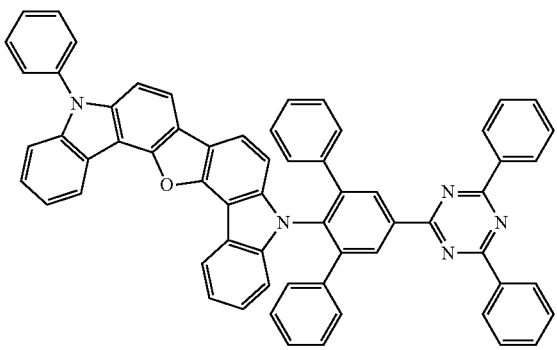

517
-continued
60
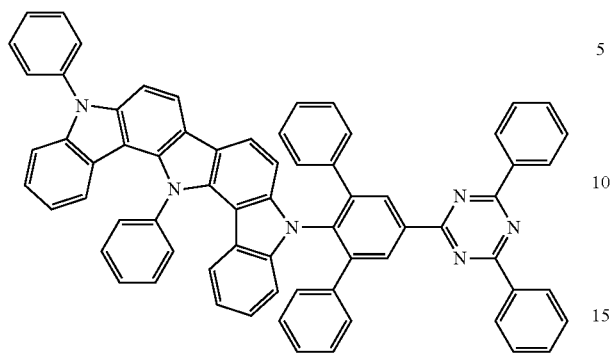
61
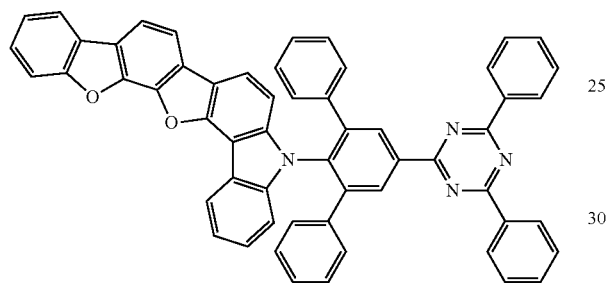
62
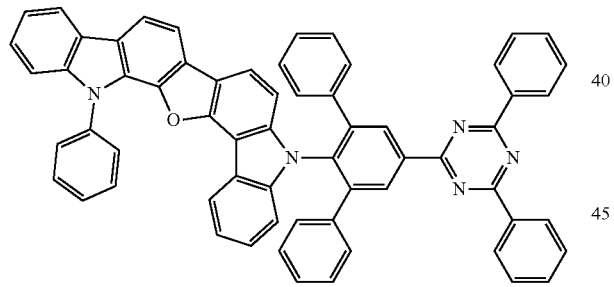
63
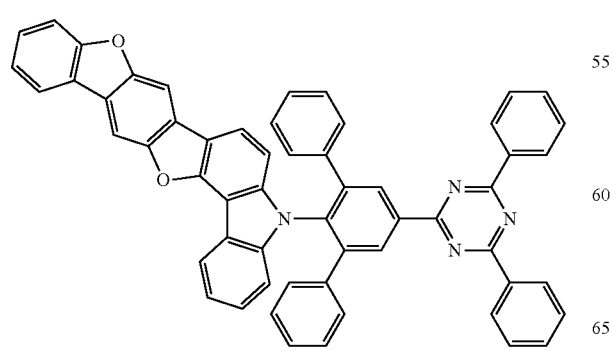
518
-continued
64
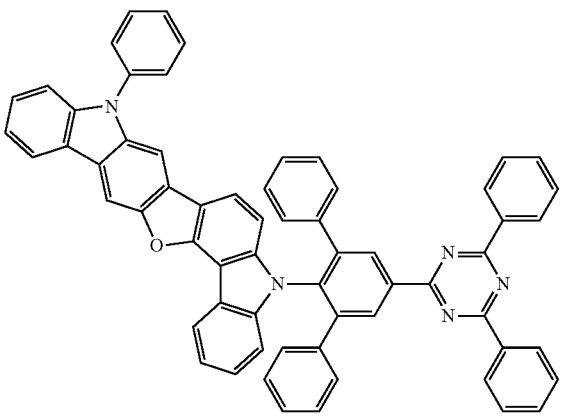
65
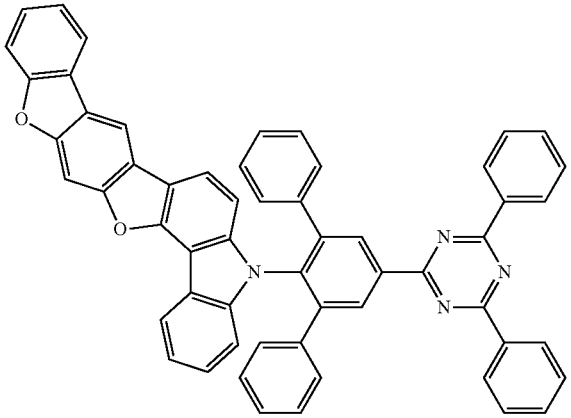
66
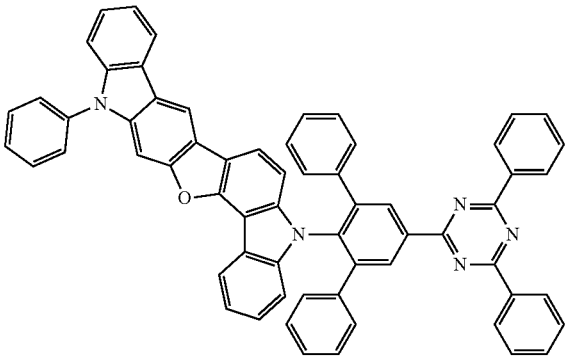

519
-continued
67
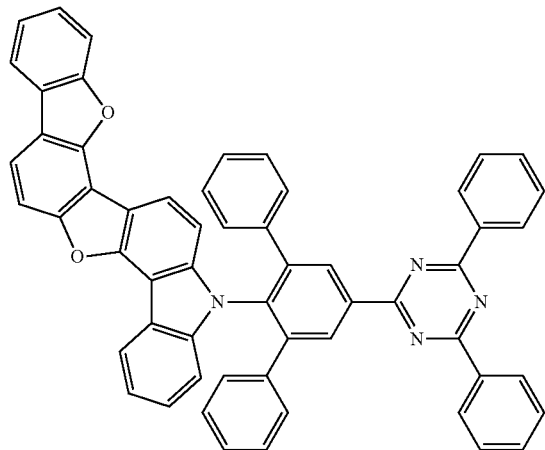
68
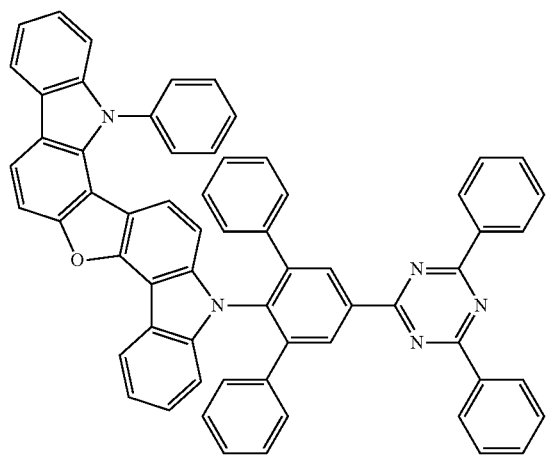
69
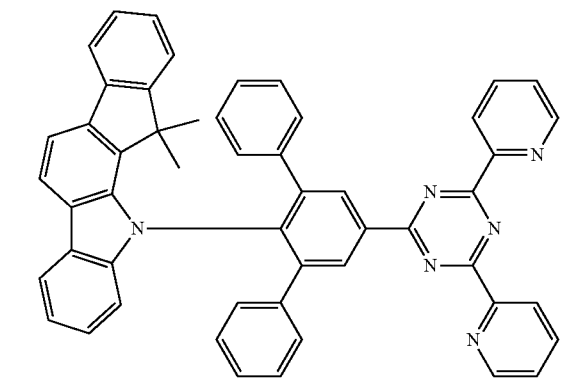
520
-continued
70
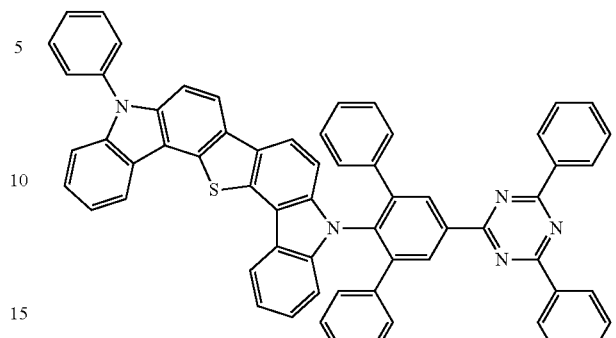
71
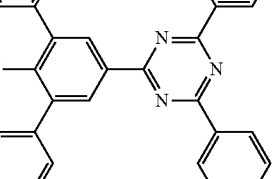
72
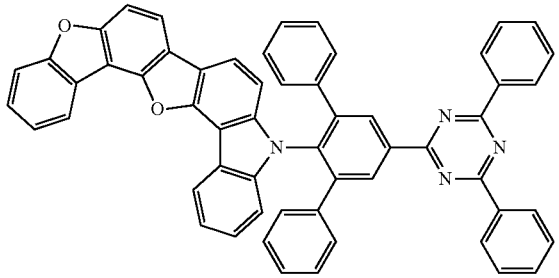
73
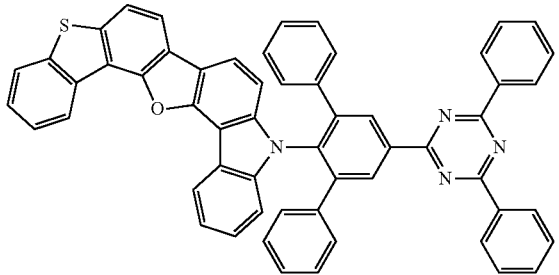
74
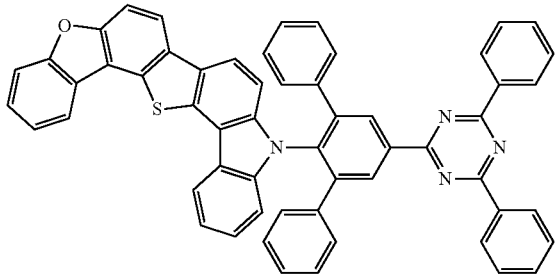
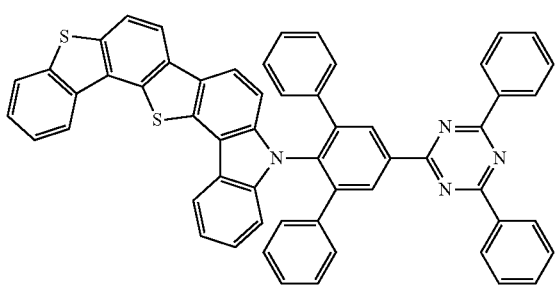

521
-continued
75
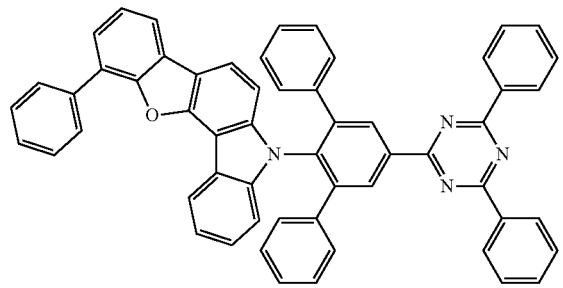
76
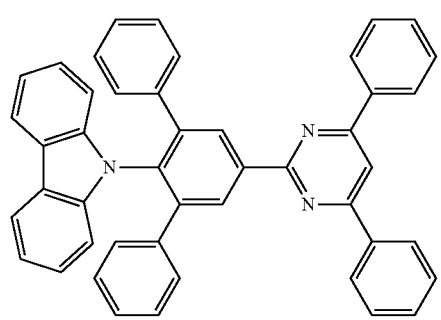
77
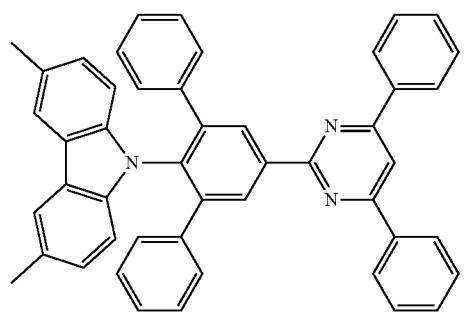
78
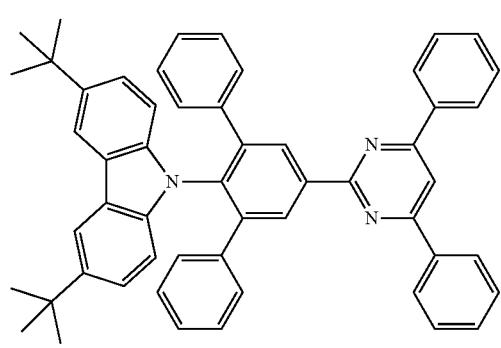
522
-continued
79
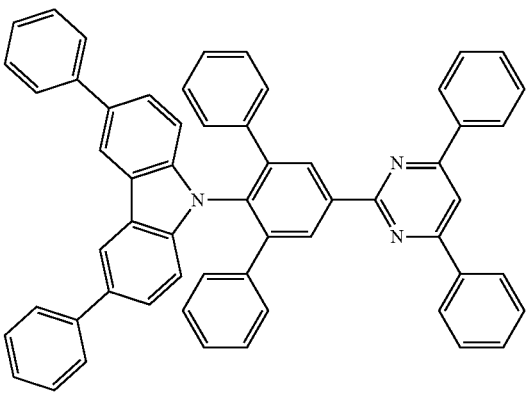
80
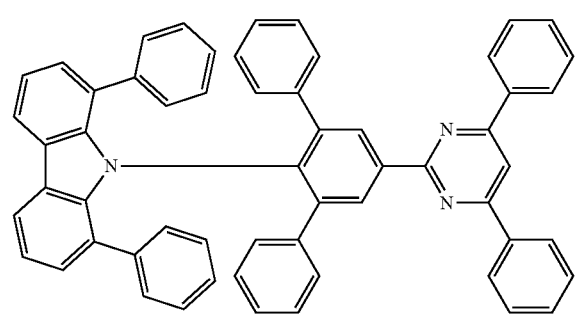
81
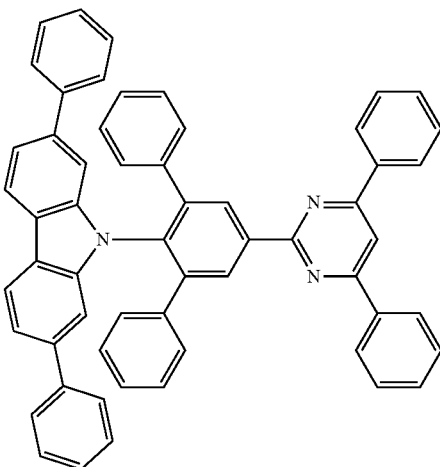
82
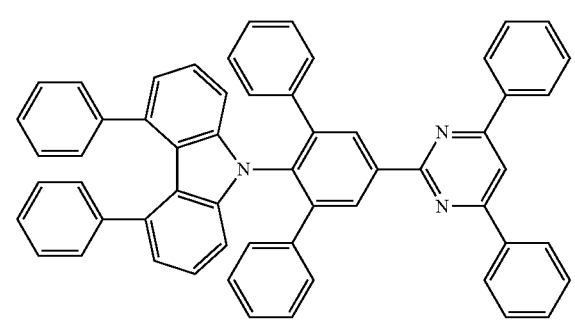

523
-continued
83
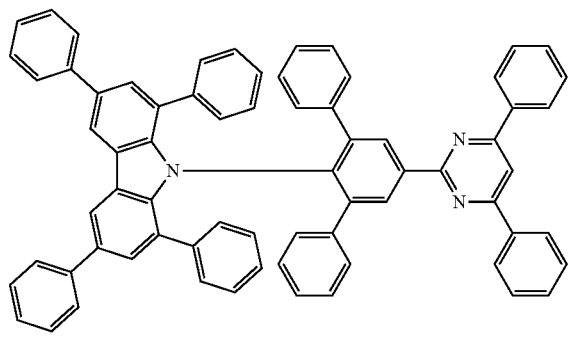
84
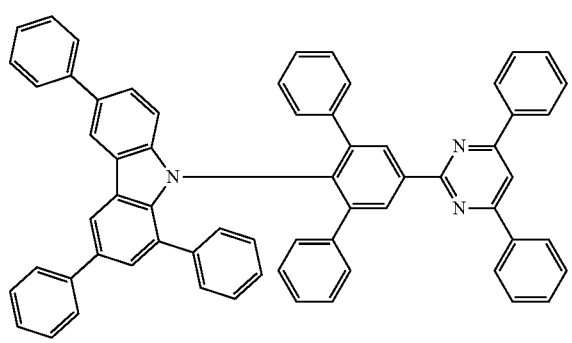
85
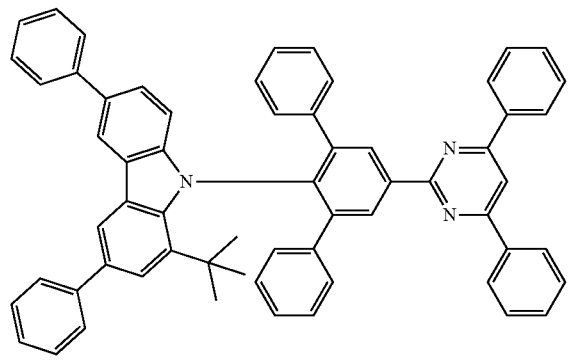
86
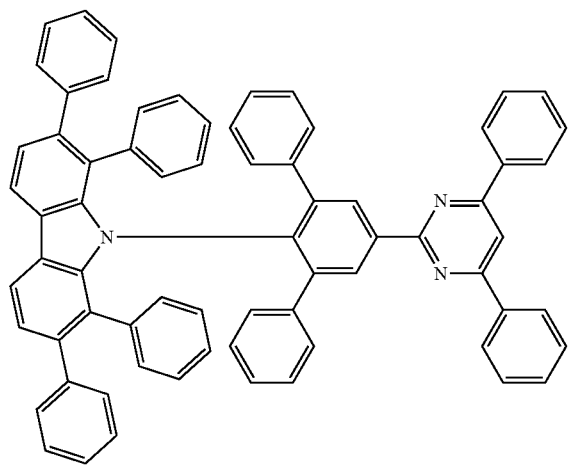
524
-continued
87
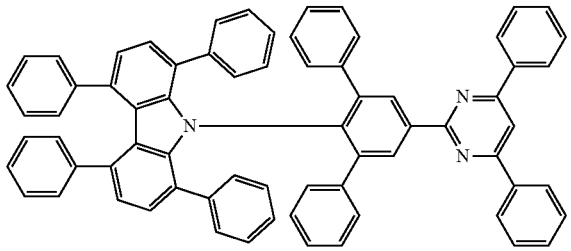
88
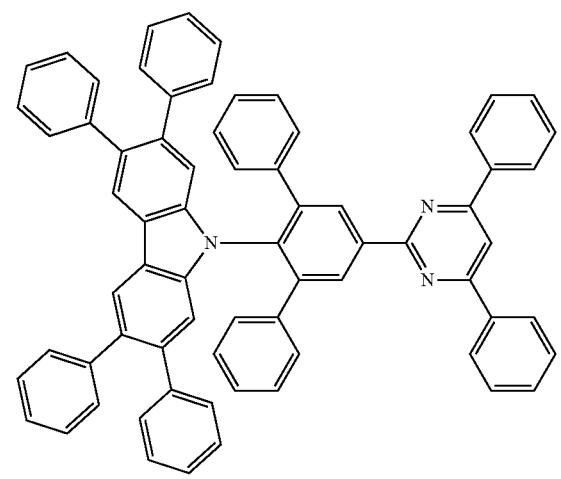
89
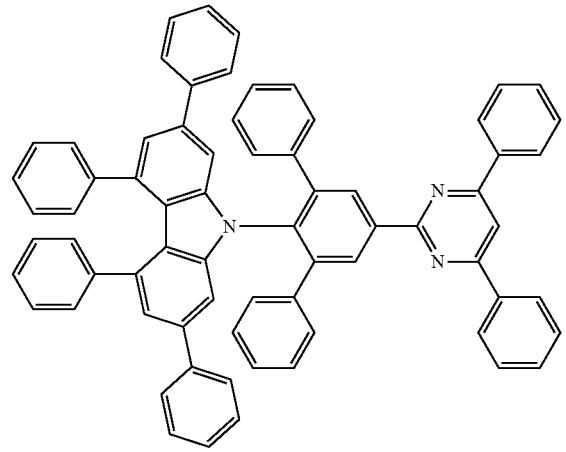
90
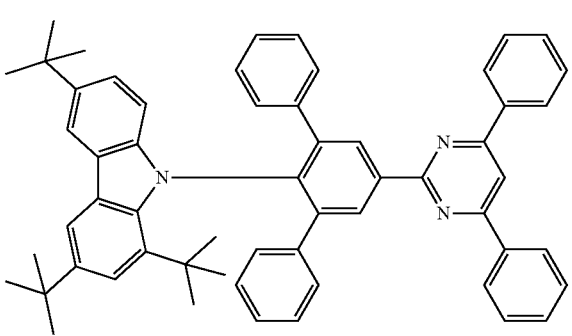

525
-continued
91
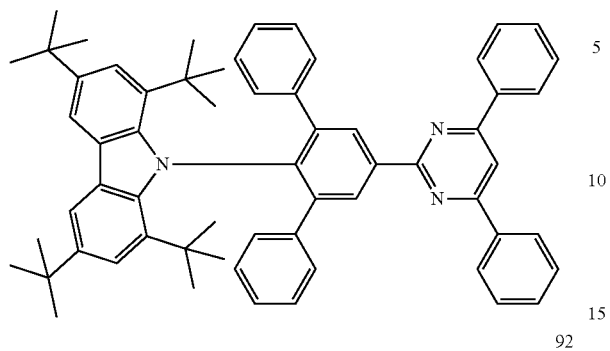
92
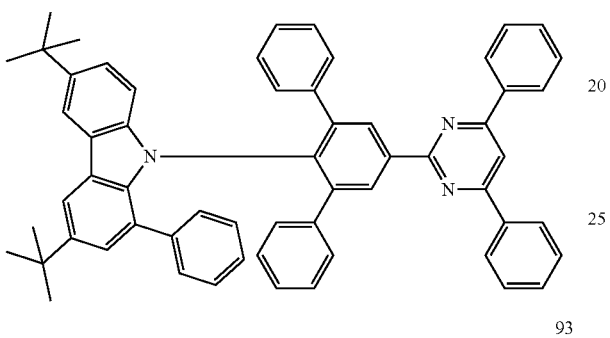
93
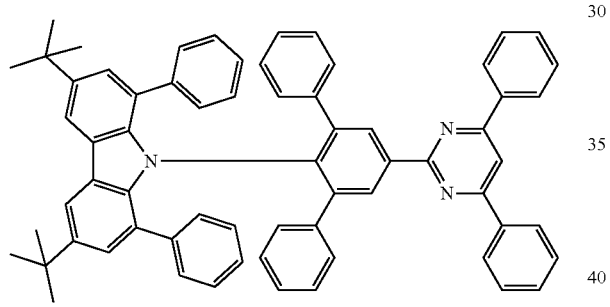
94
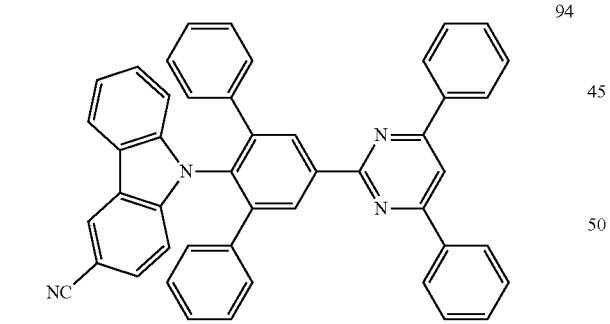
95
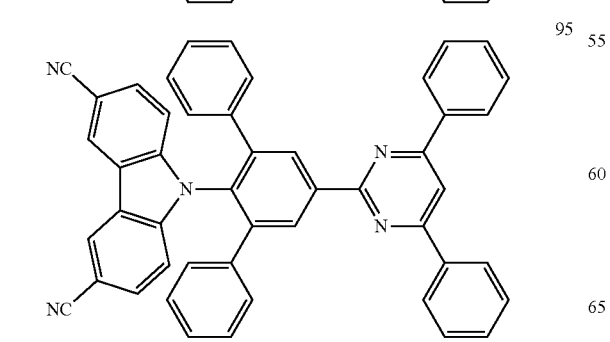
526
-continued
96
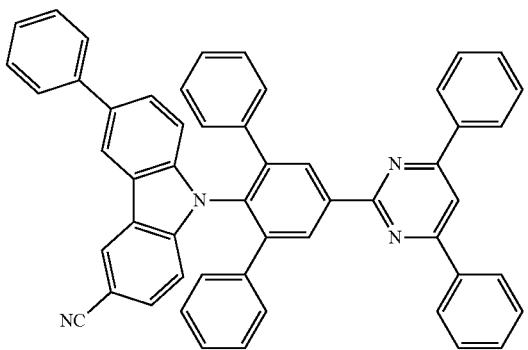
97
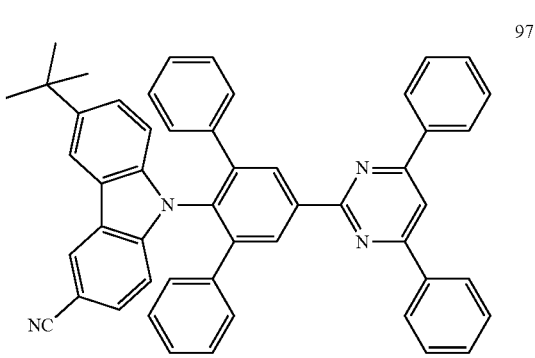
98
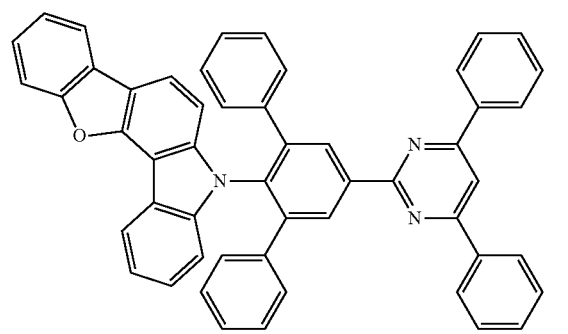
99
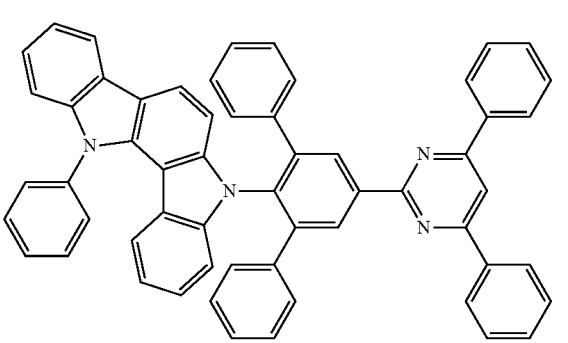

100
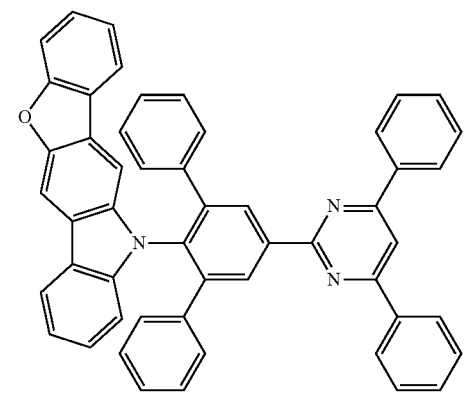
101
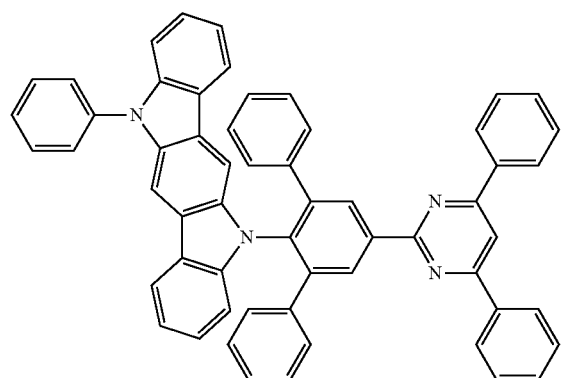
102
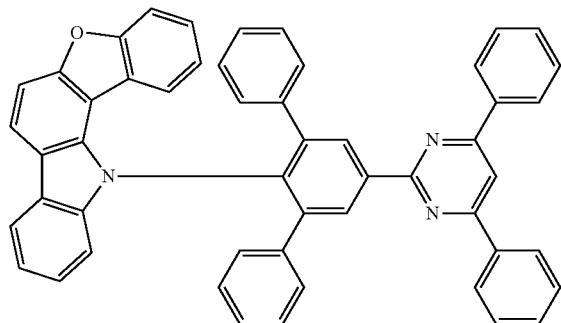
103
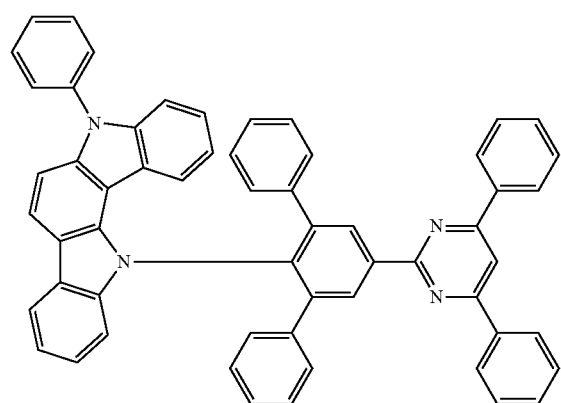
104
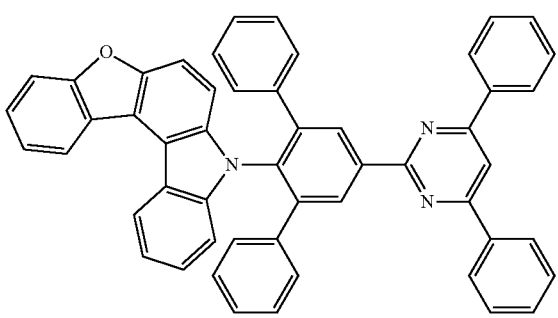
105
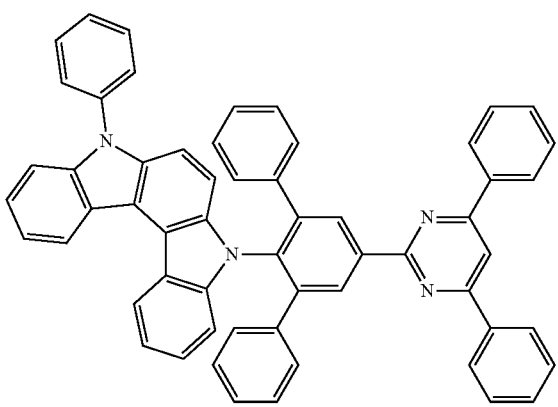
106
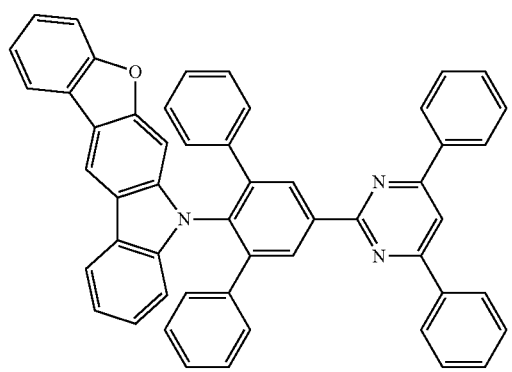
107
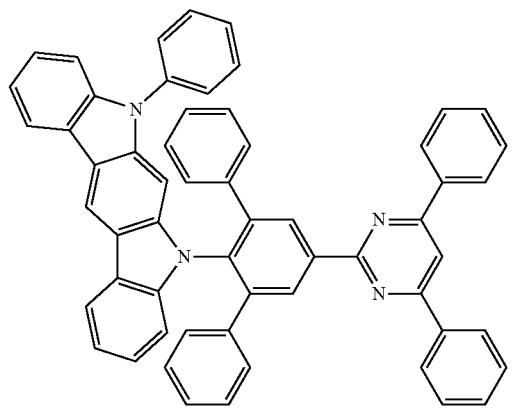

529
-continued
108
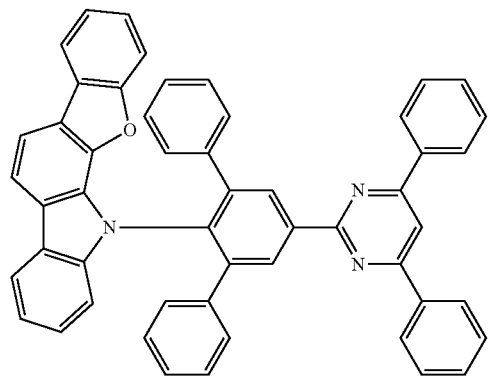
109
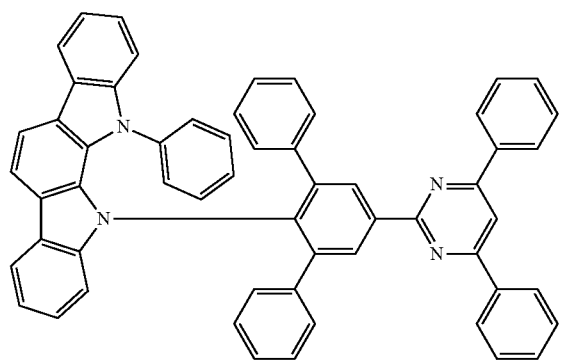
110
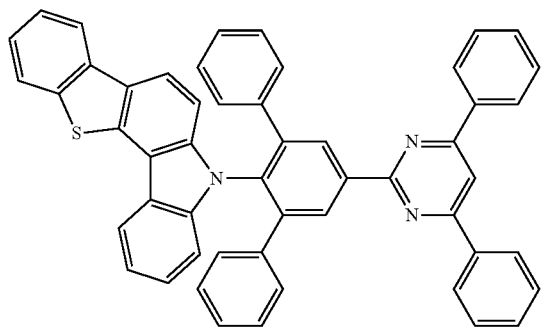
111
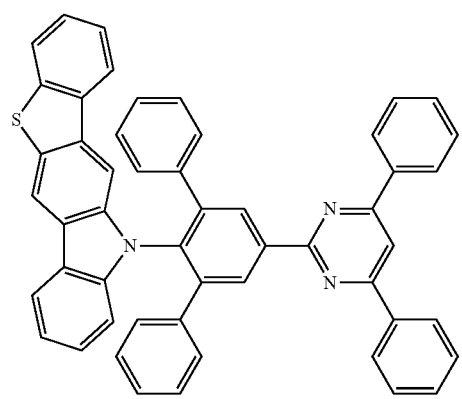
530
-continued
112
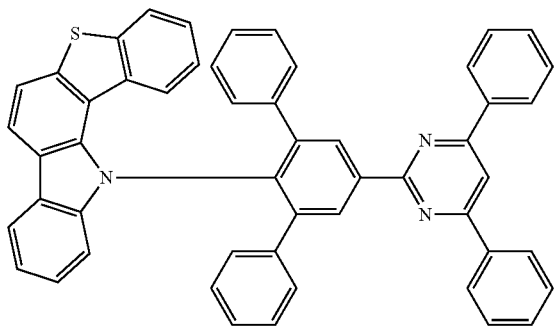
113
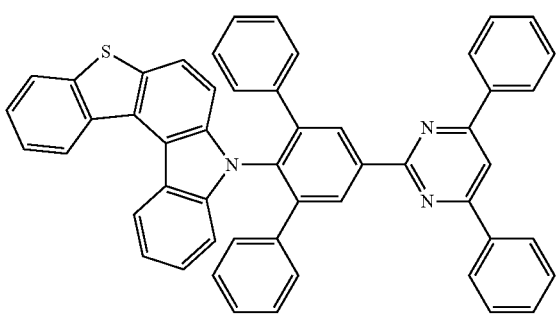
114
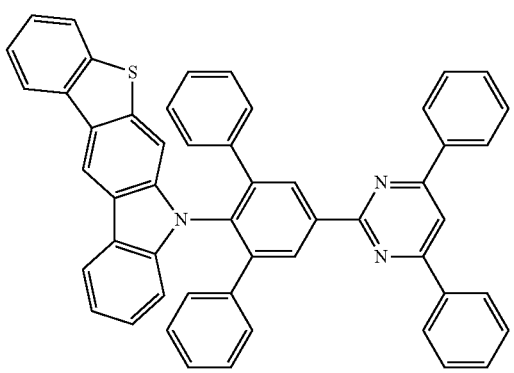
115
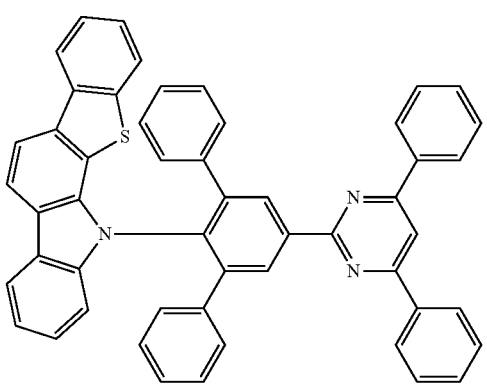

531
-continued
116
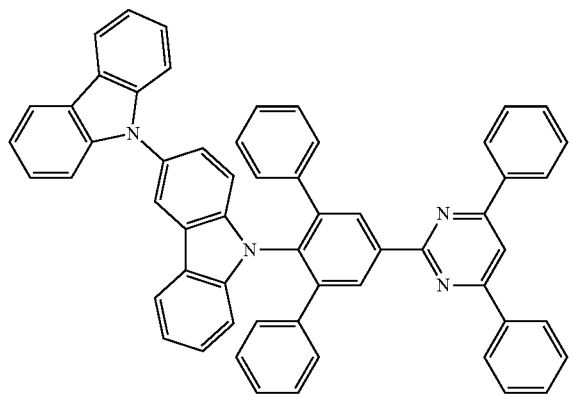
117
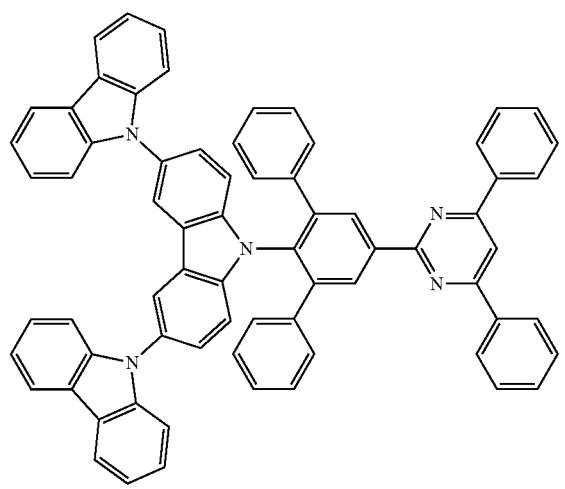
118
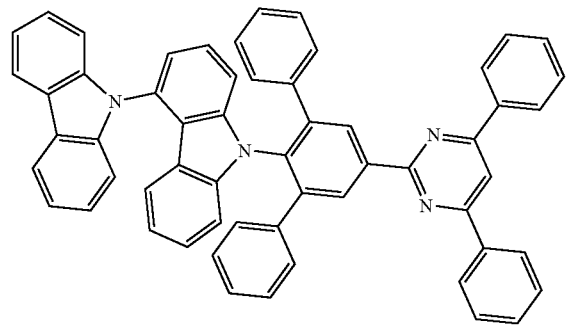
532
-continued
119
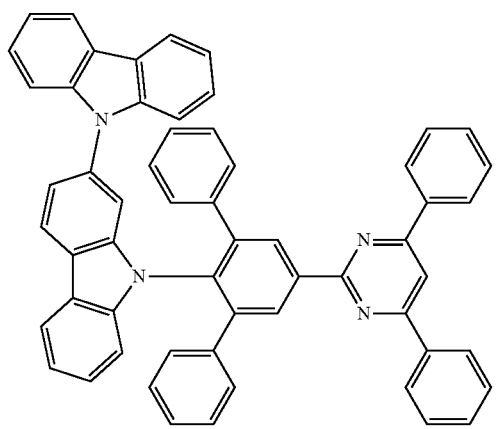
120
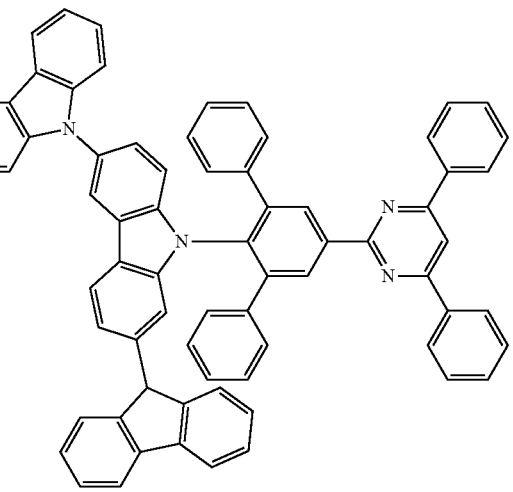
121
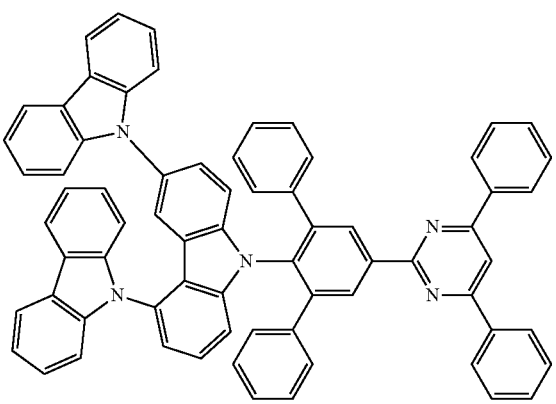

122
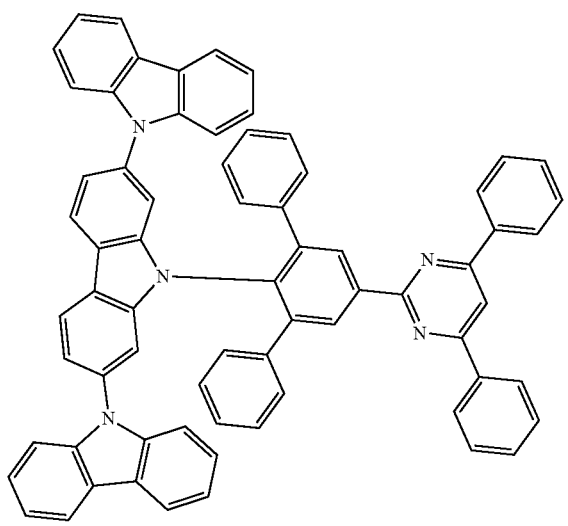
123
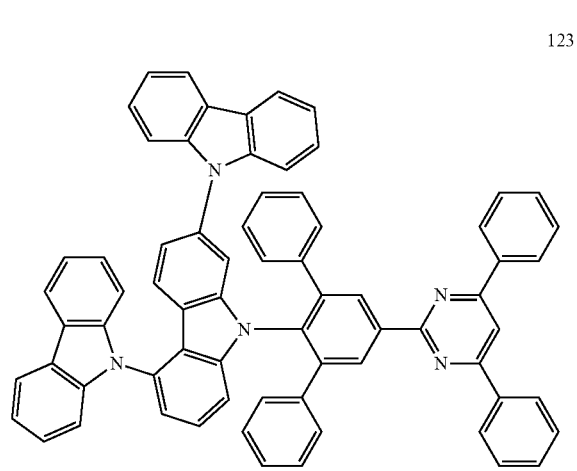
124
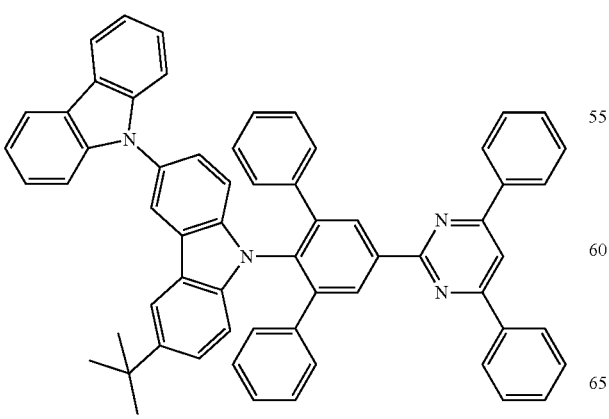
125
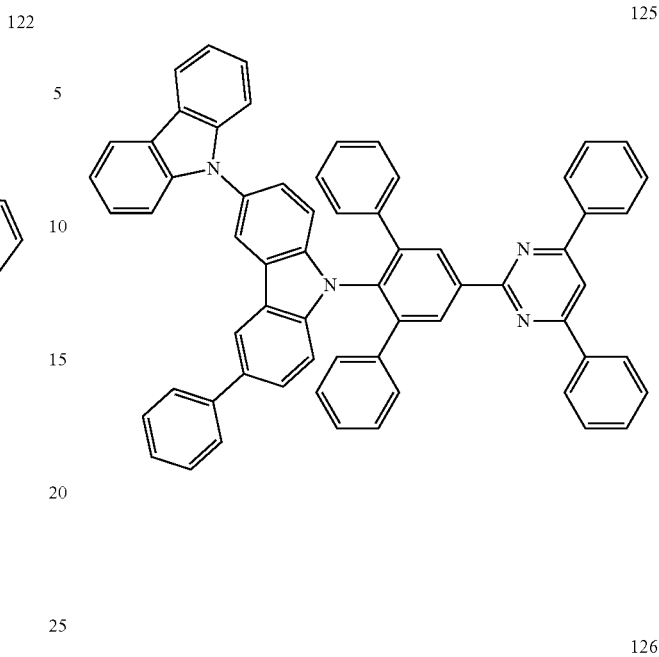
126
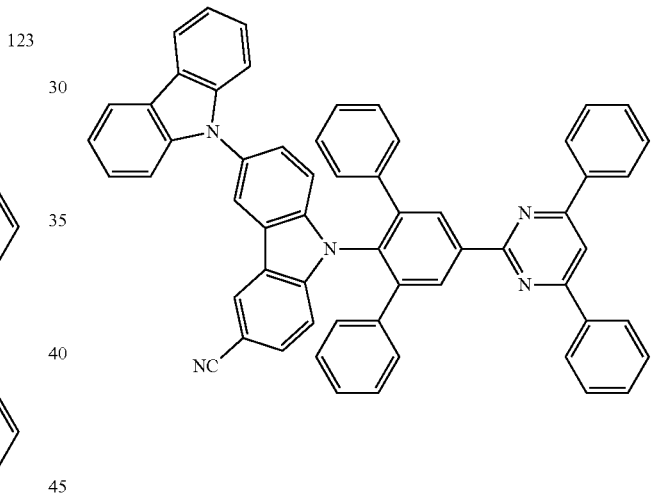
127
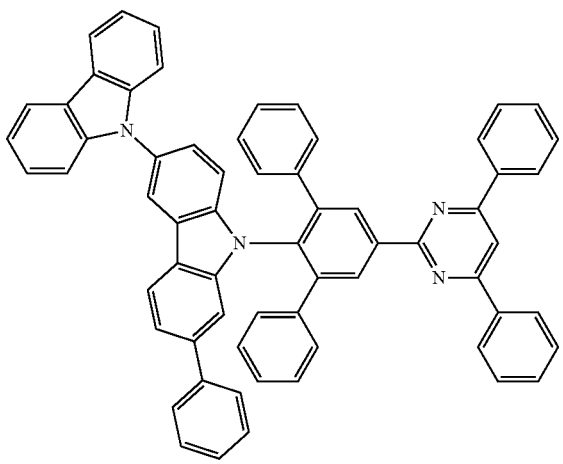

128
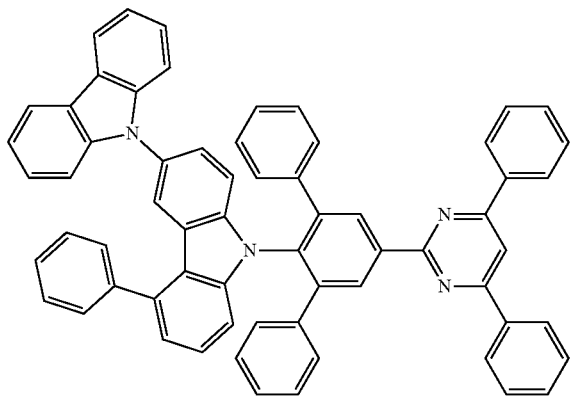
131
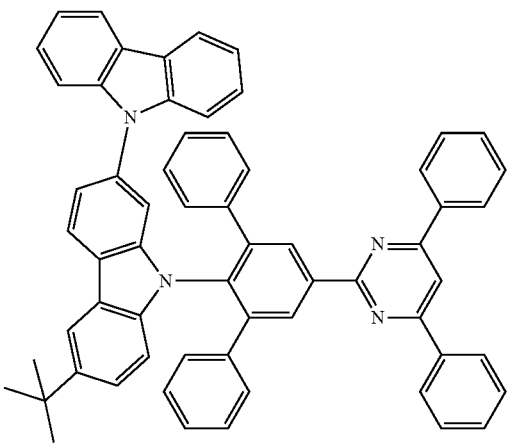
129
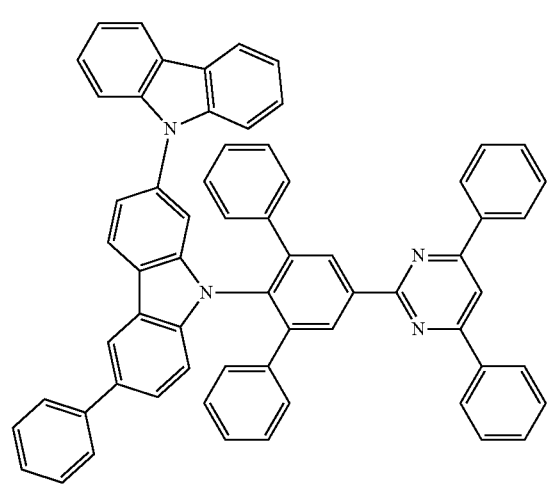
132
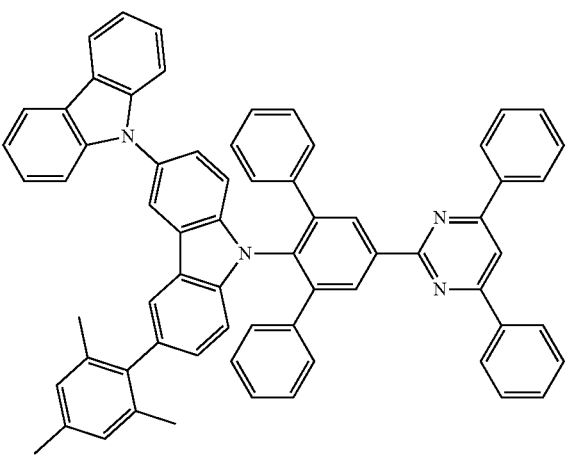
130
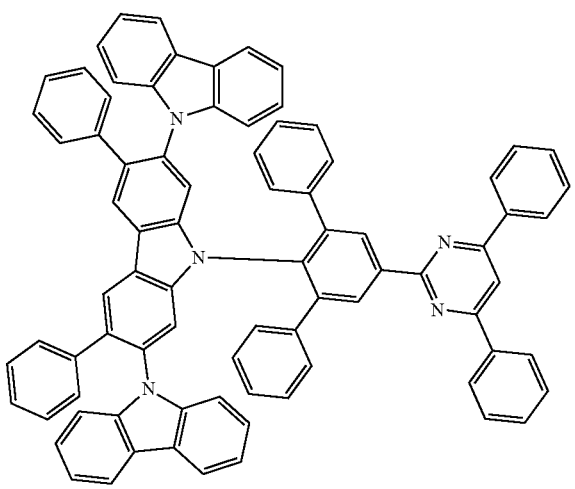
133
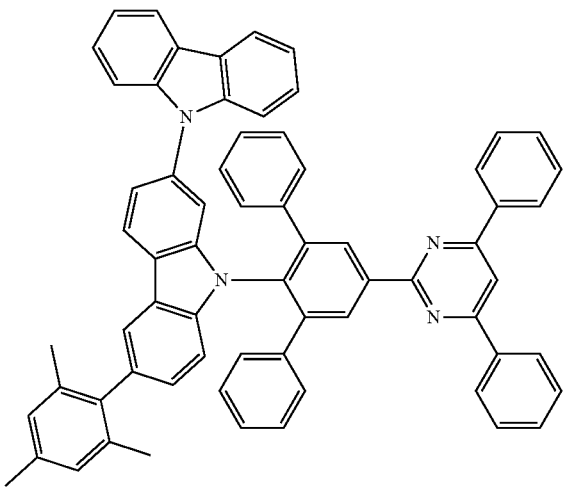

537
-continued
134
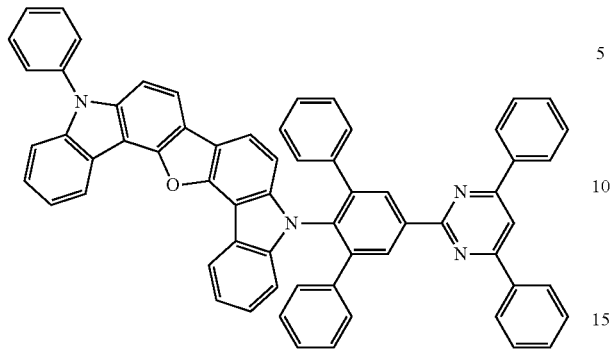
135
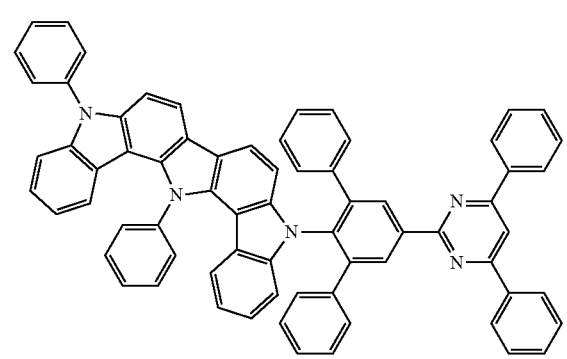
136
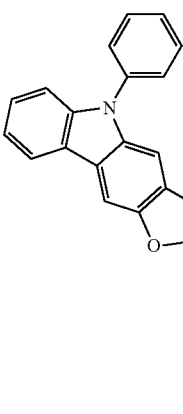
137
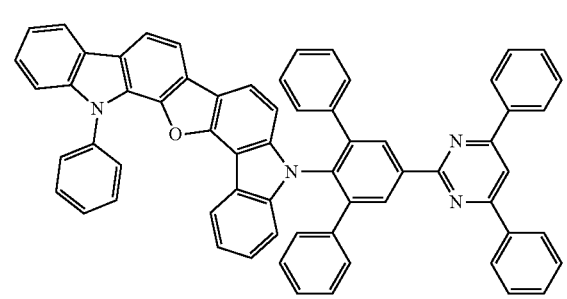
538
-continued
138
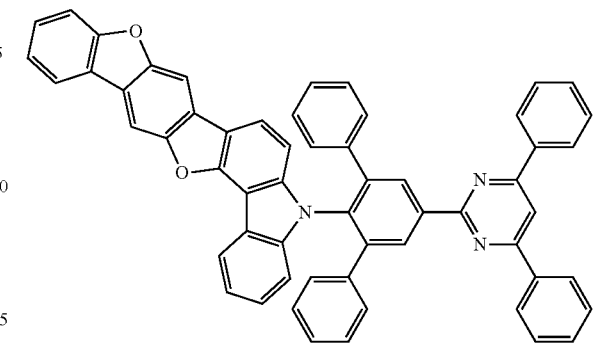
139
140
141
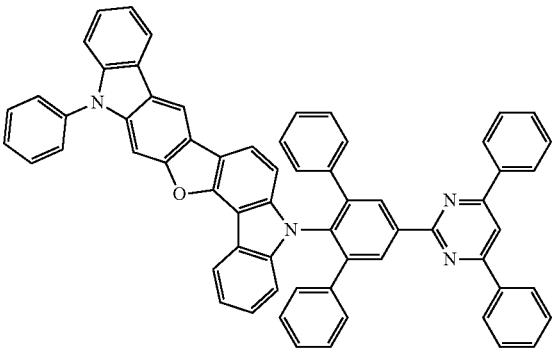

539
-continued
142
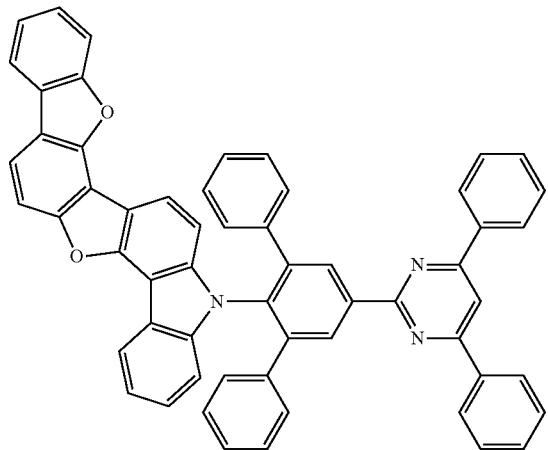
143
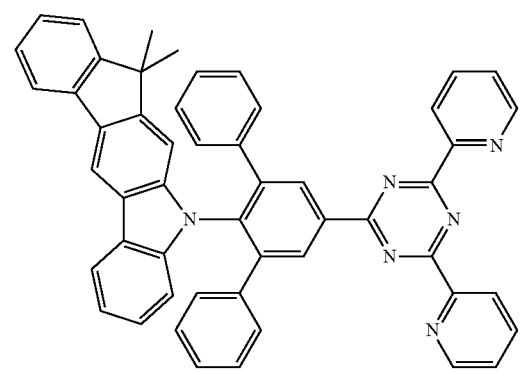
144
540
-continued
145
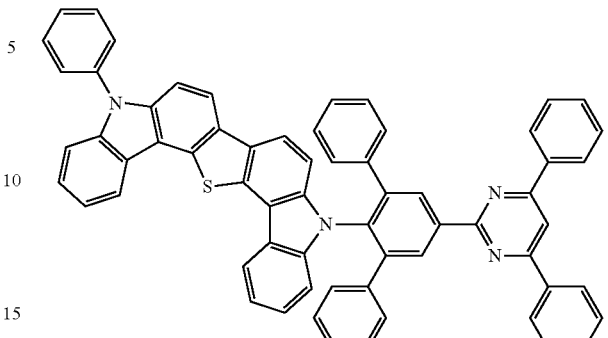
146

147

148
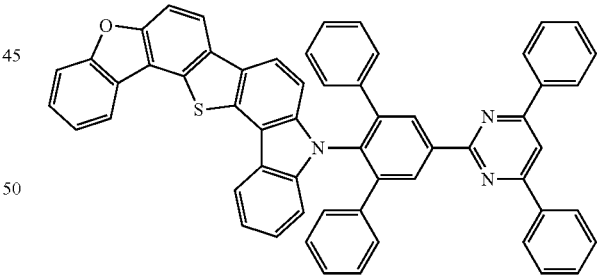
149
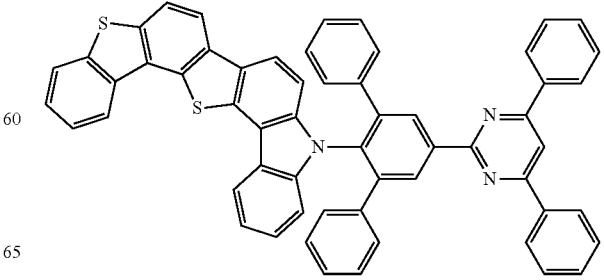

150 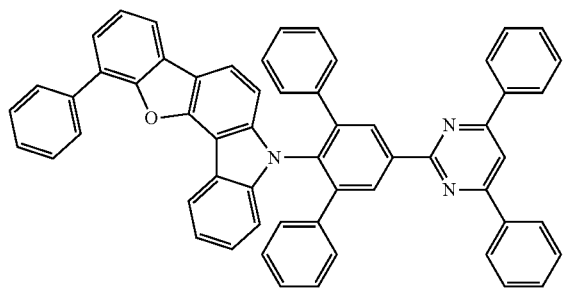
154 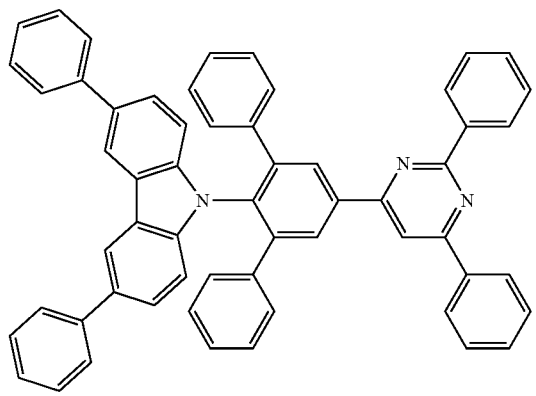
151 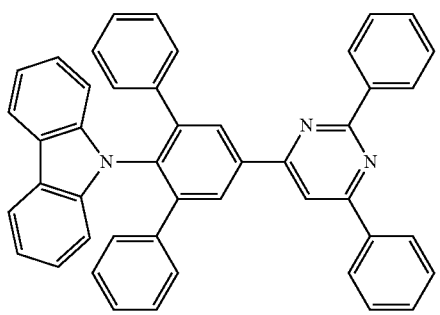
155 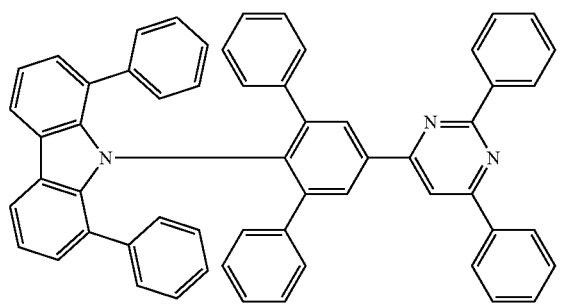
152 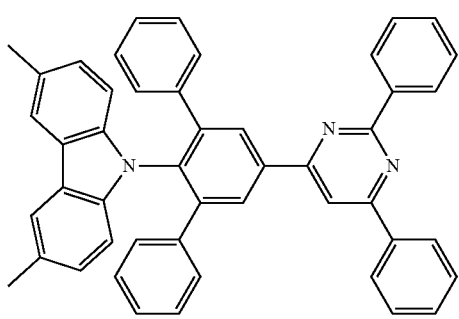
156 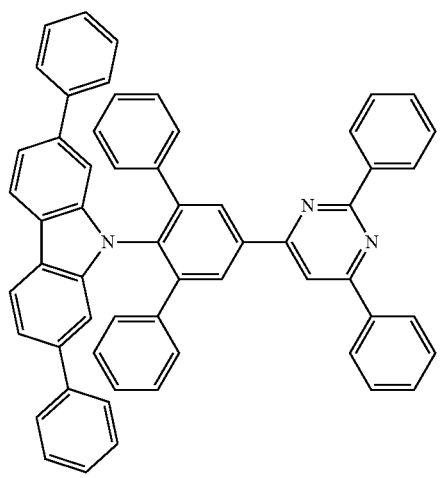
153 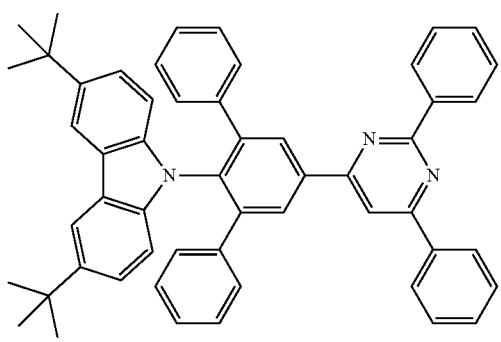
157 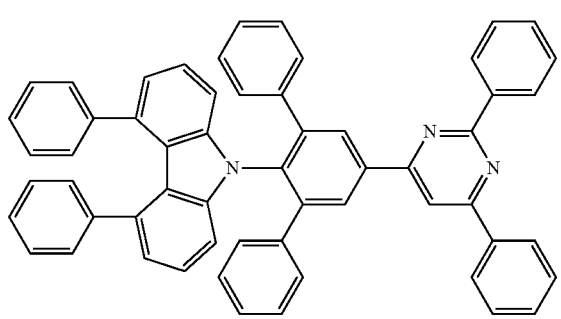

543
-continued
158
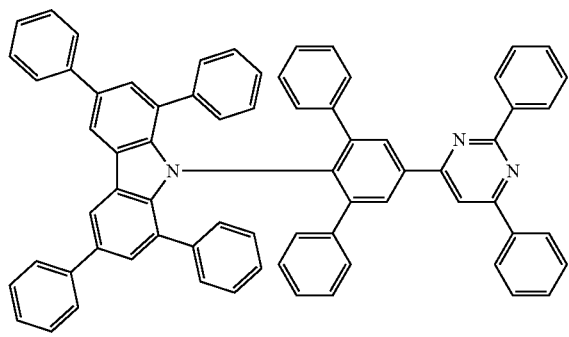
159
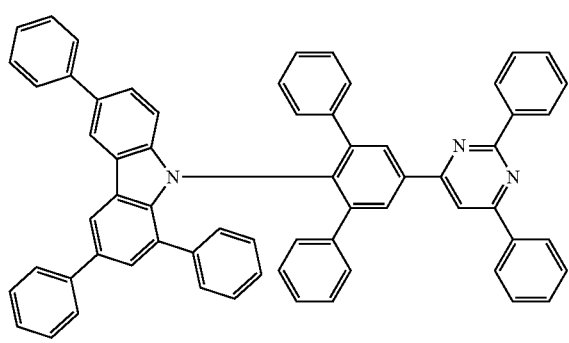
160
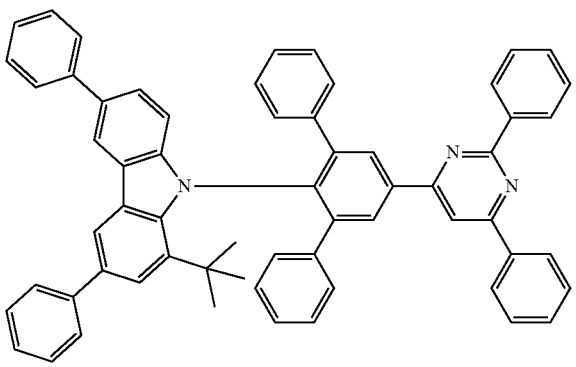
161
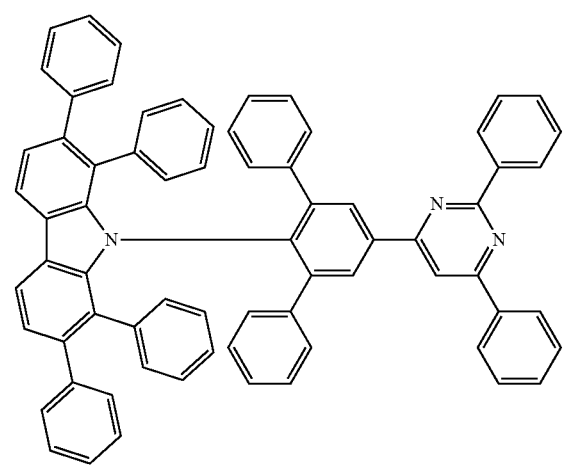
544
-continued
162
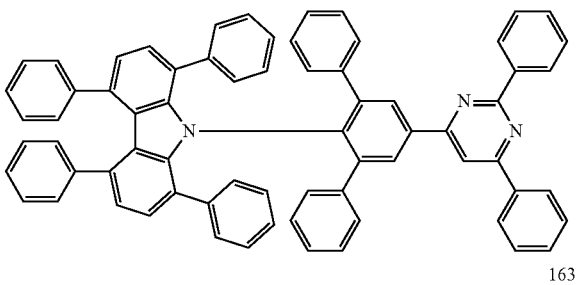
163
164
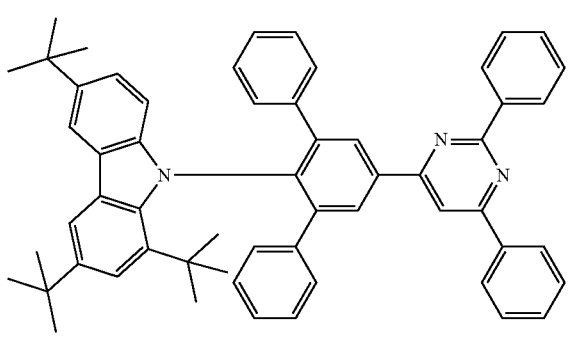
165

166
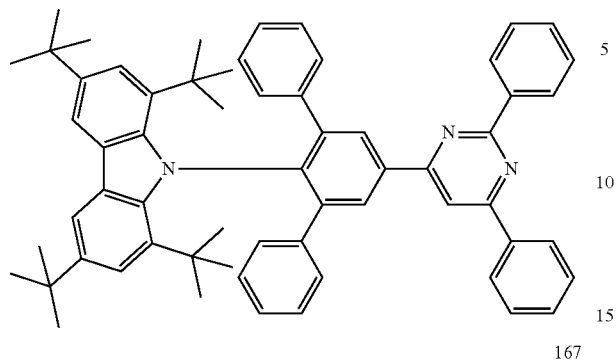
167
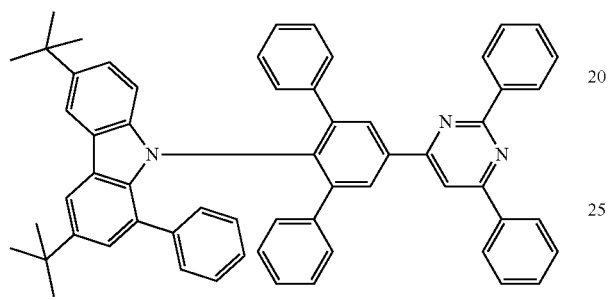
168
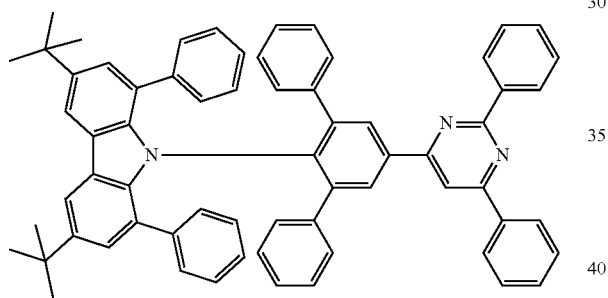
169
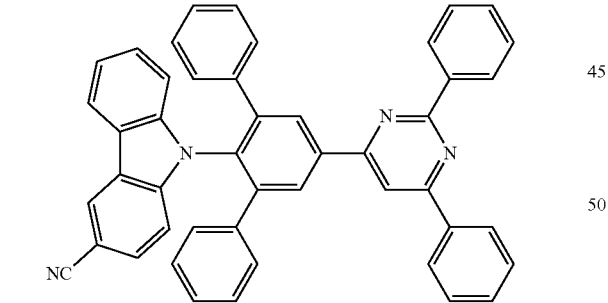
170
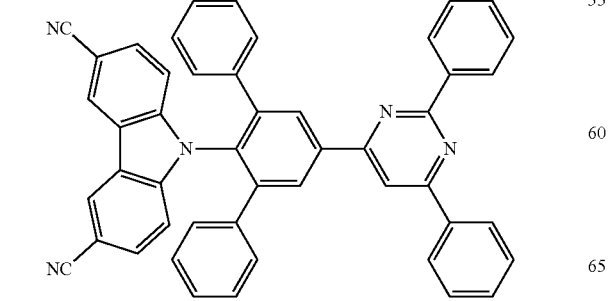
171
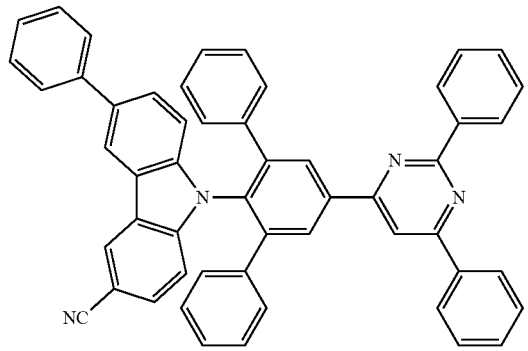
172
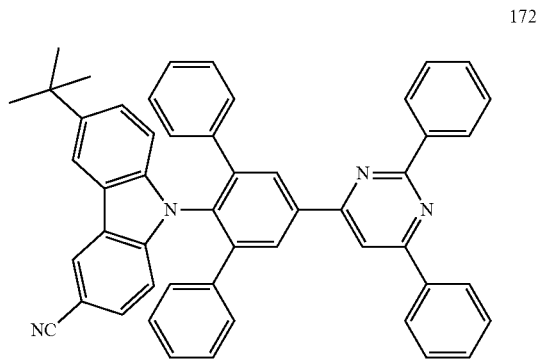
173
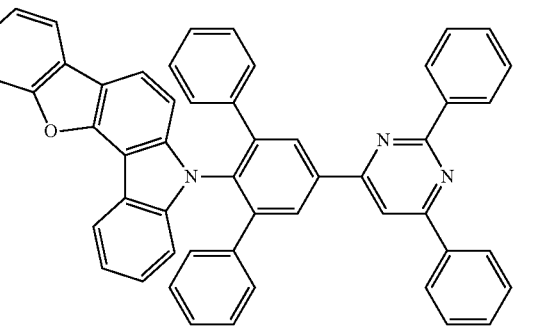
174
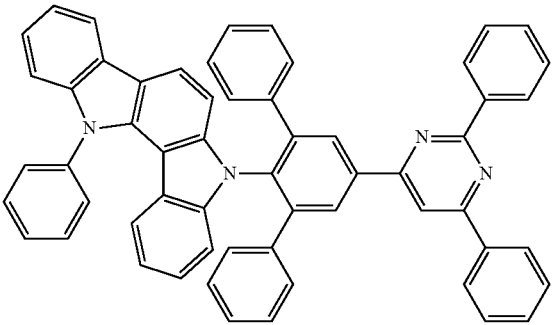

547
-continued
175
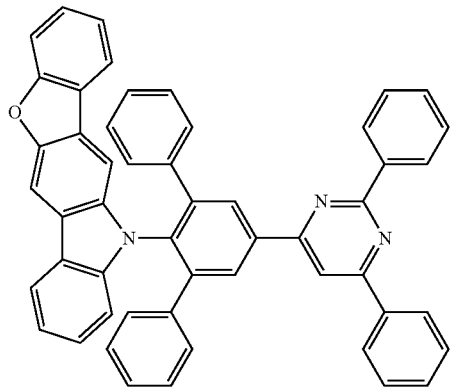
176
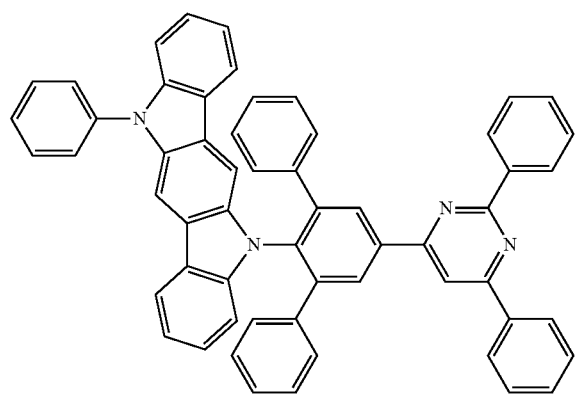
177
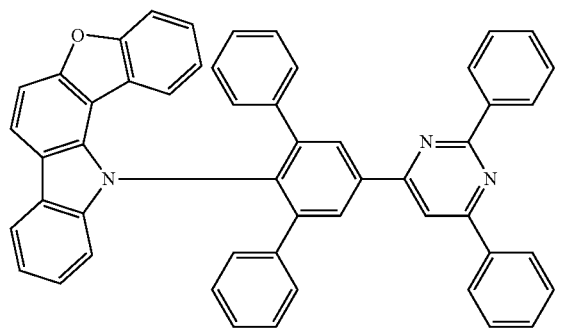
178
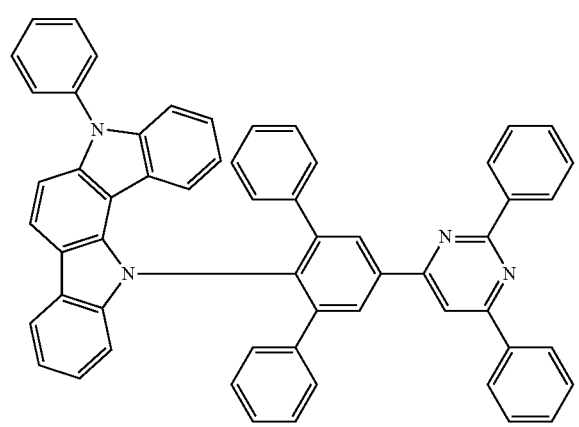
548
-continued
179
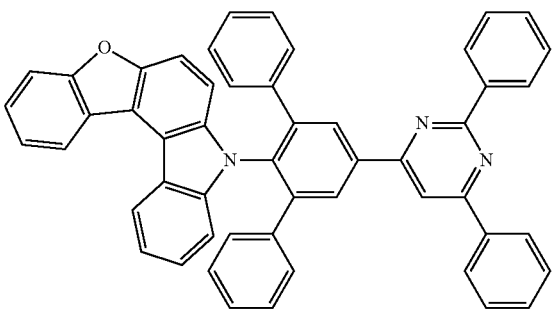
180
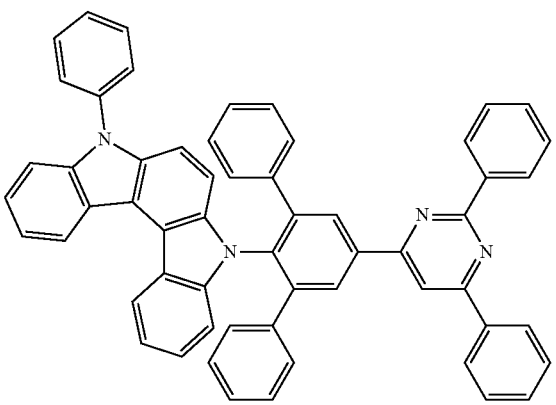
181
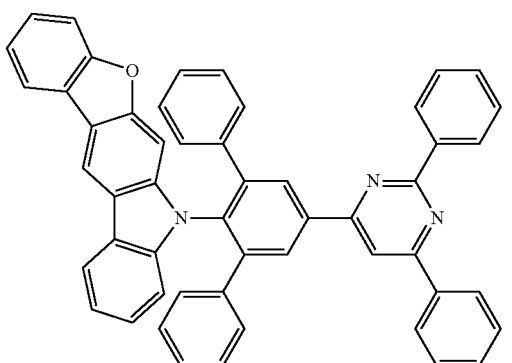
182
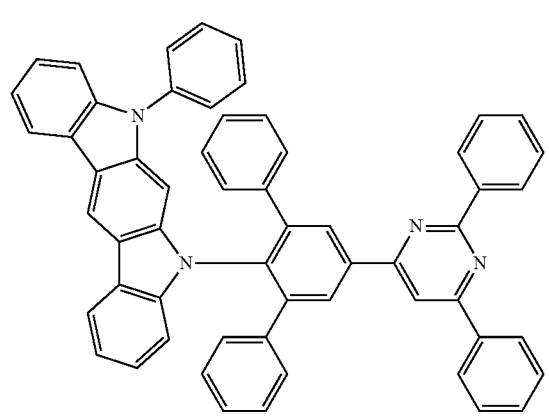

183 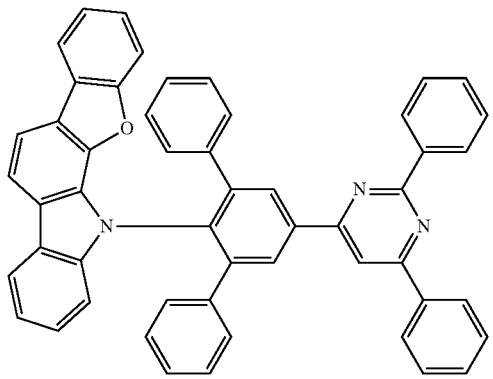
184 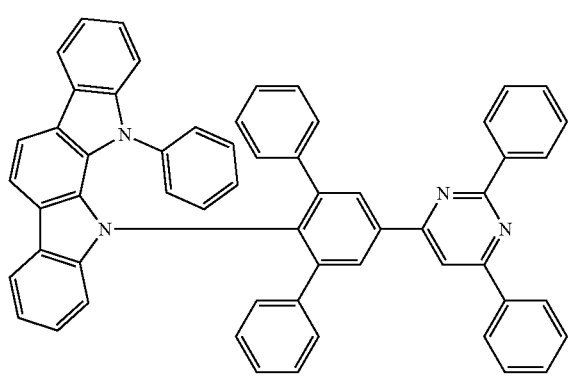
185 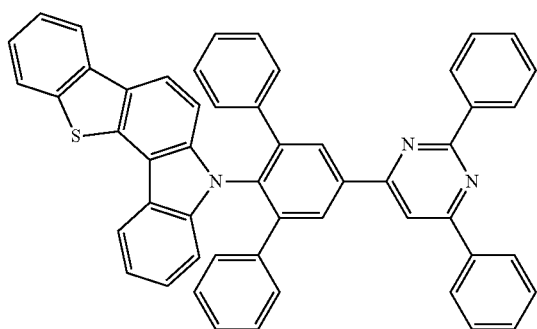
186 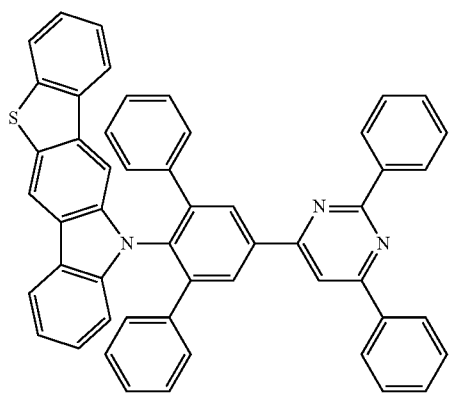
187 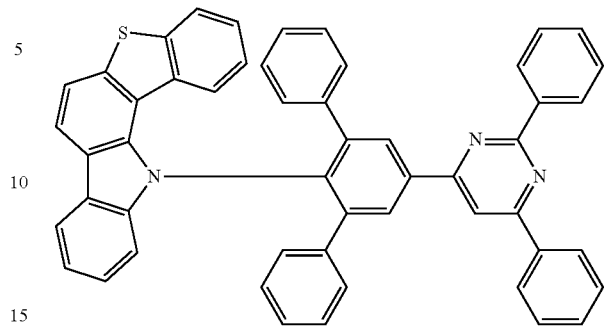
188 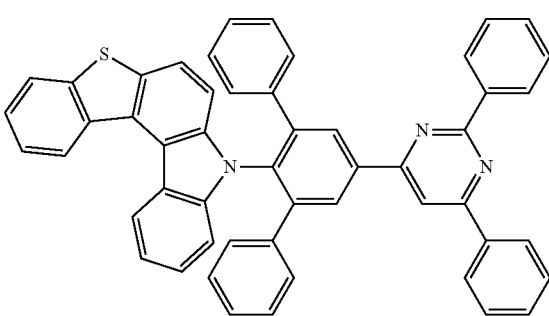
189 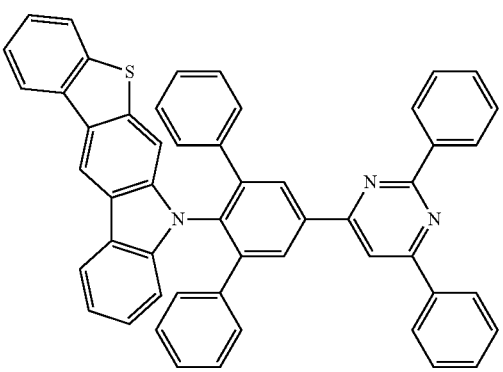
190 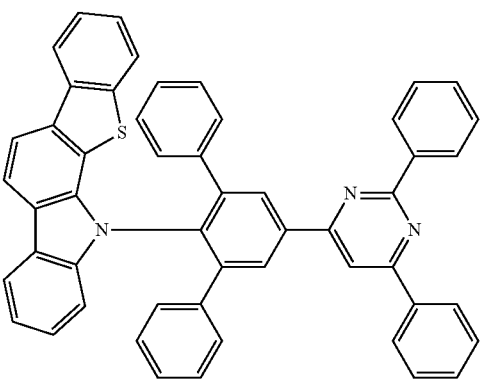

551
-continued
191
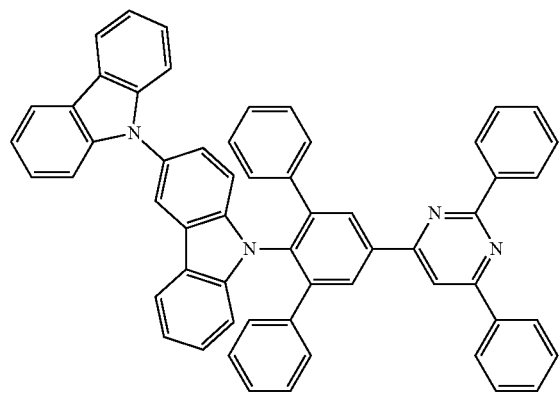
192
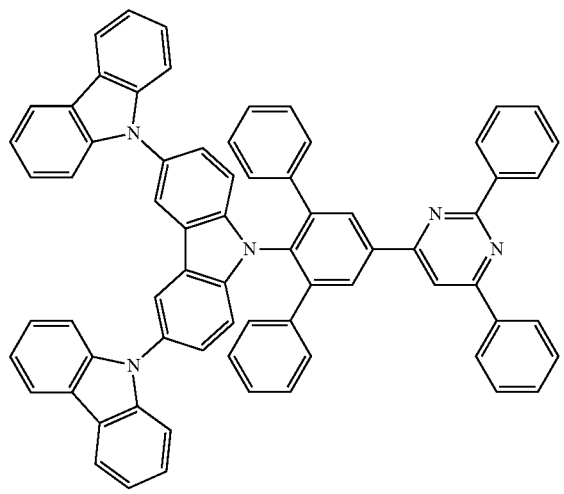
193
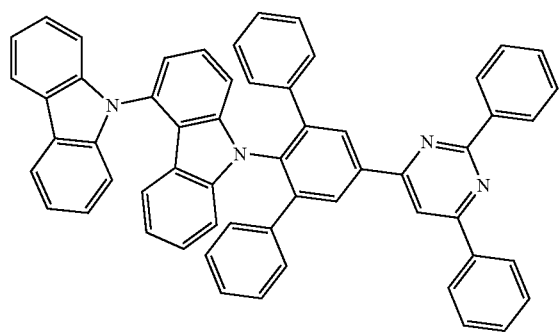
552
-continued
194
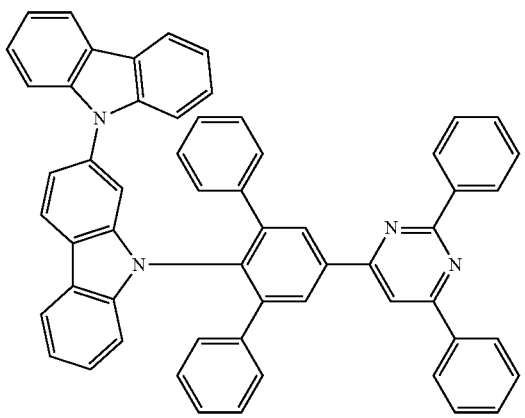
195
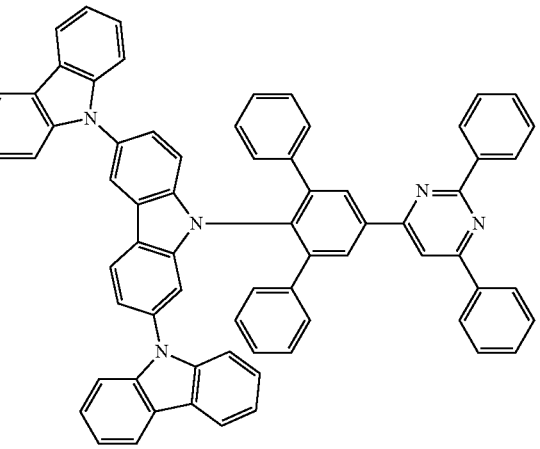
196
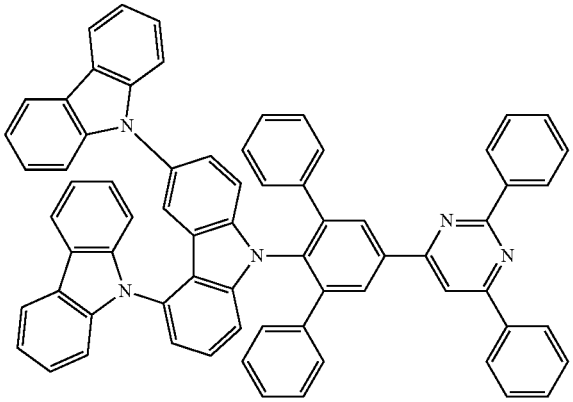

197
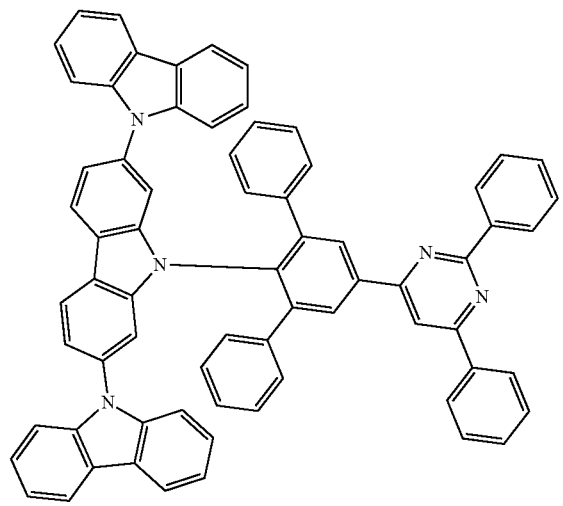
198
199
200
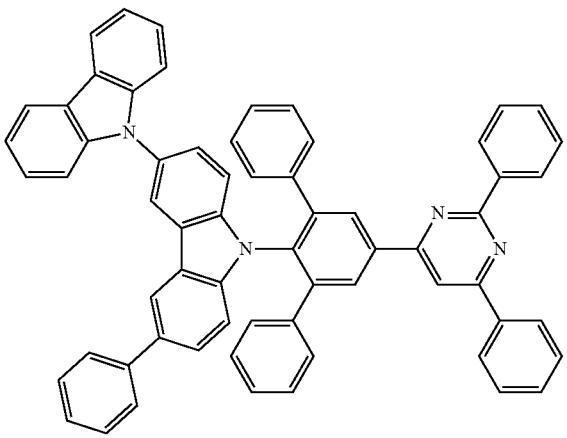
201
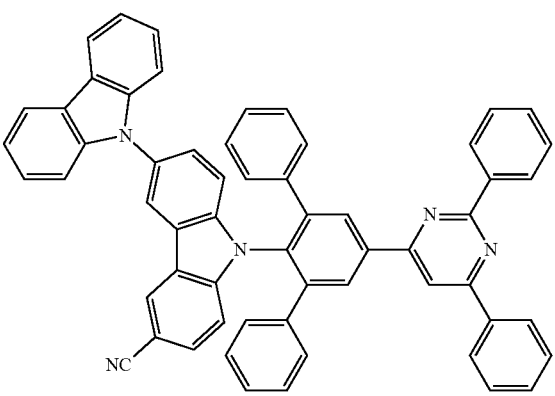
202
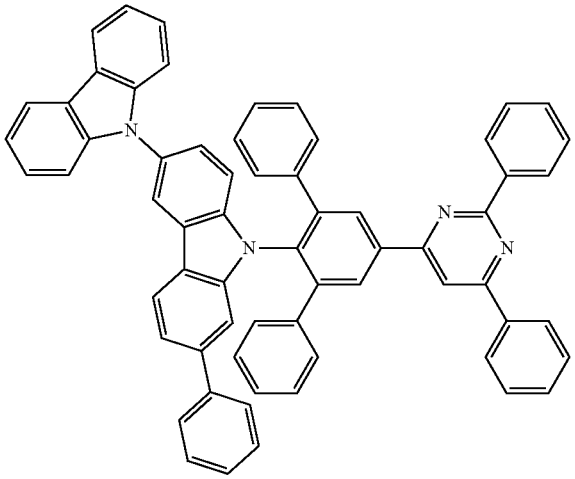

203
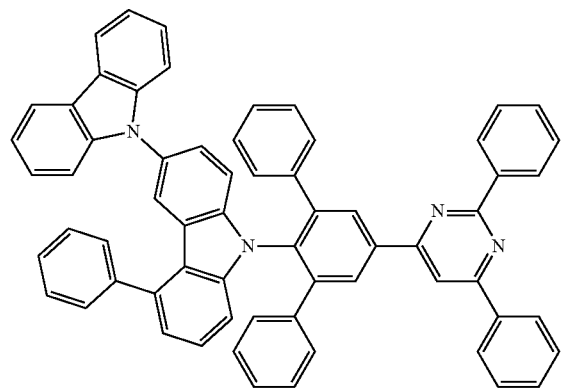
204
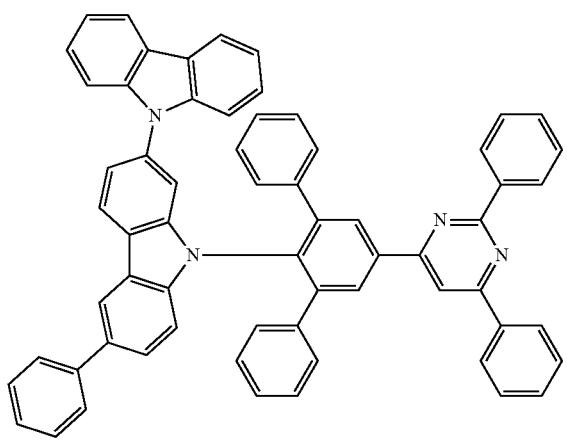
205
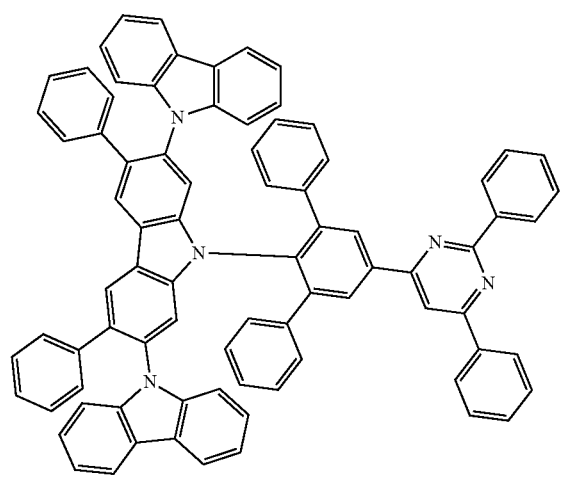
206
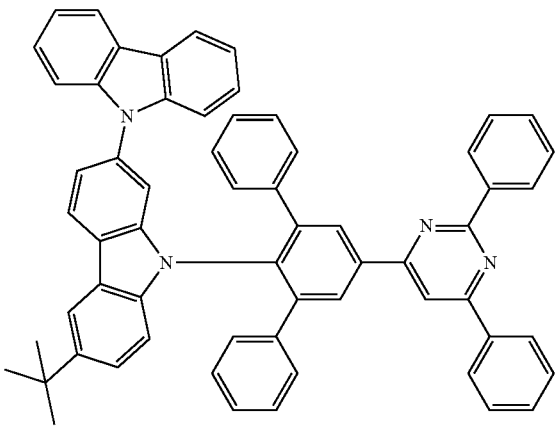
207
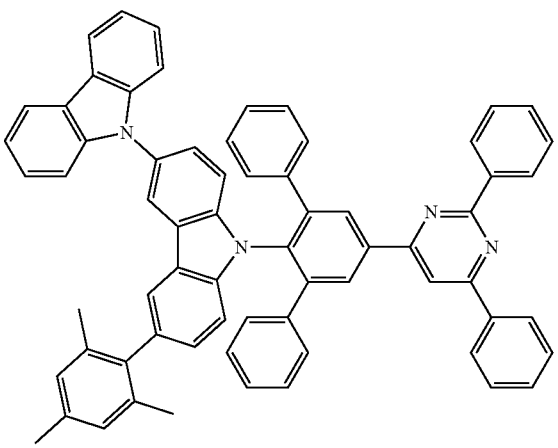
208
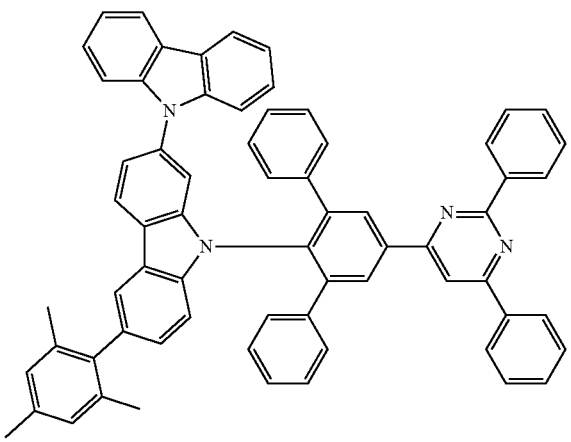

209
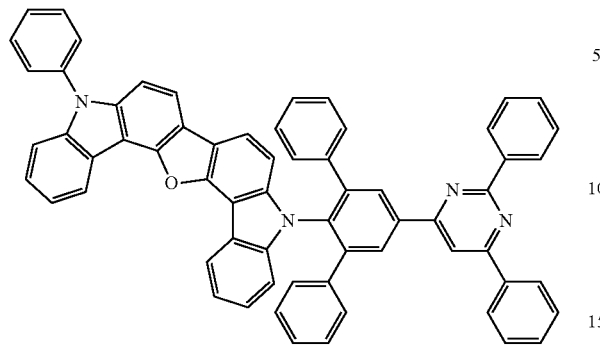
213
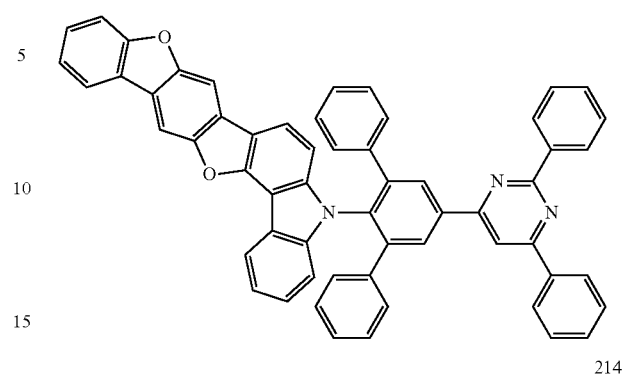
210
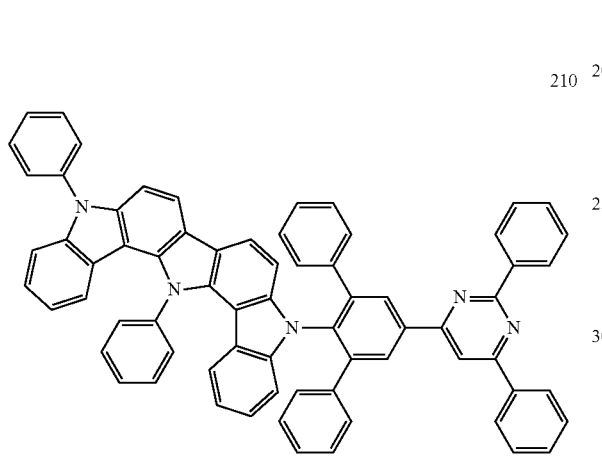
214
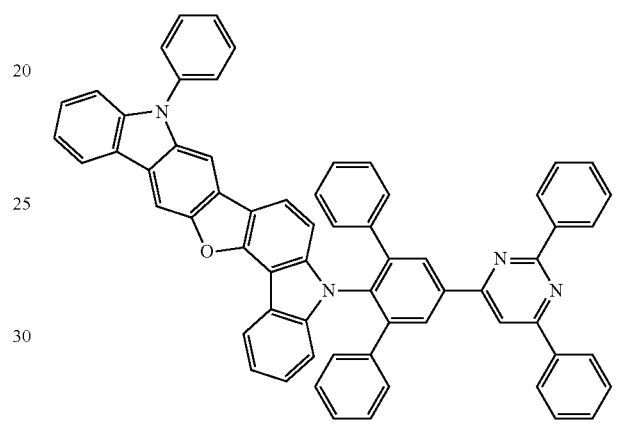
211
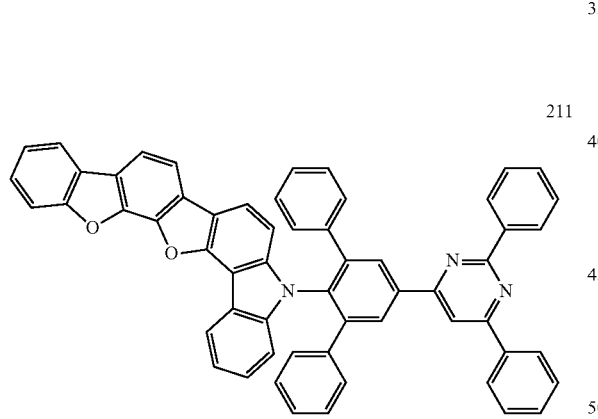
215
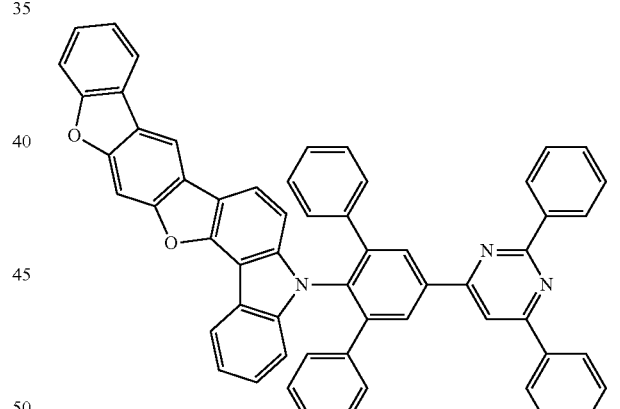
212
216
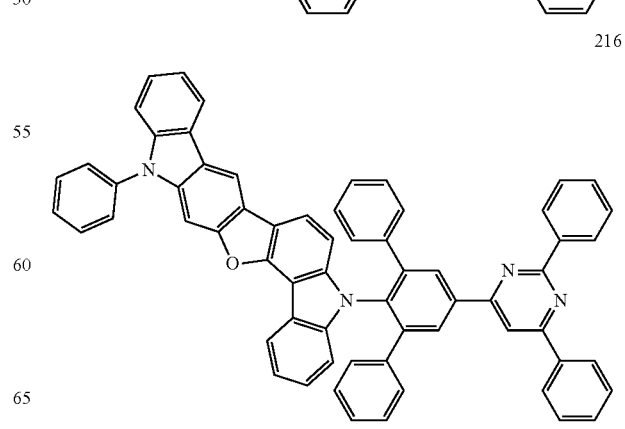

-continued
217
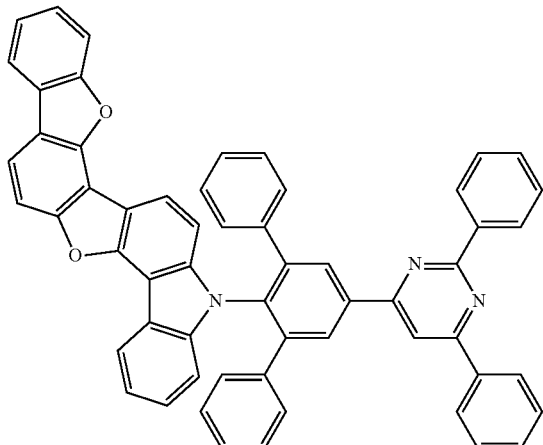
218
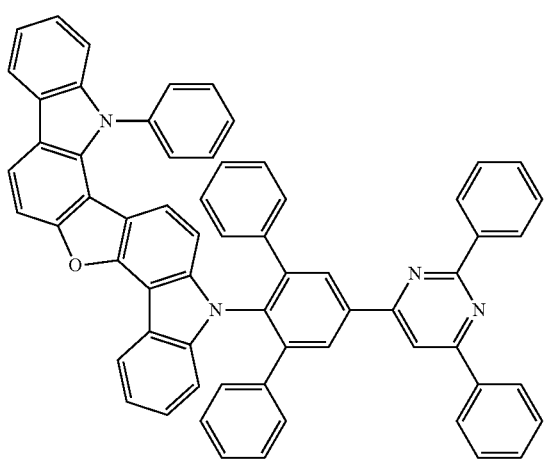
219
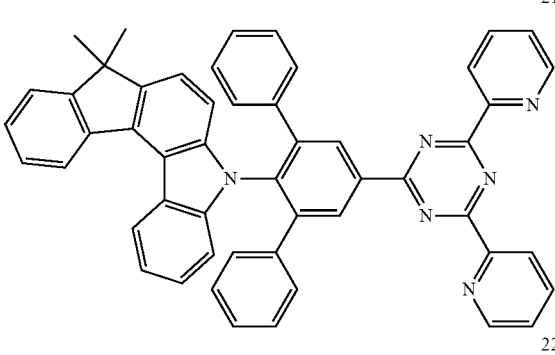
220
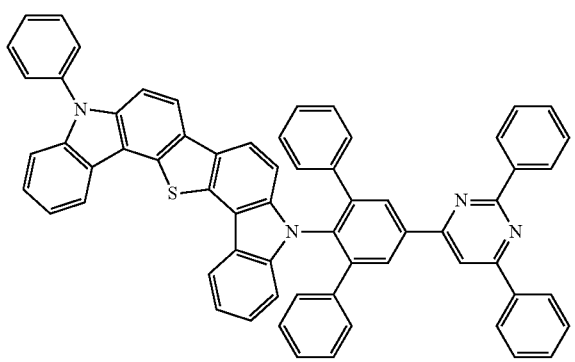
-continued
221
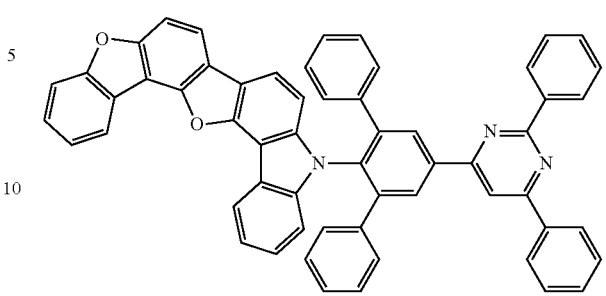
222
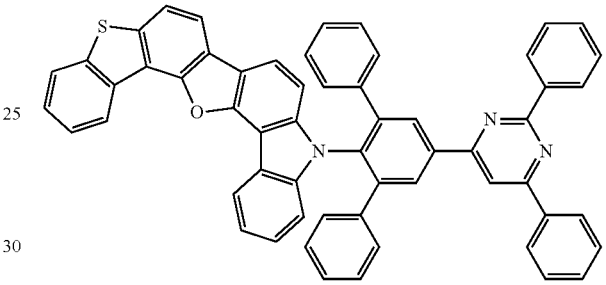
223
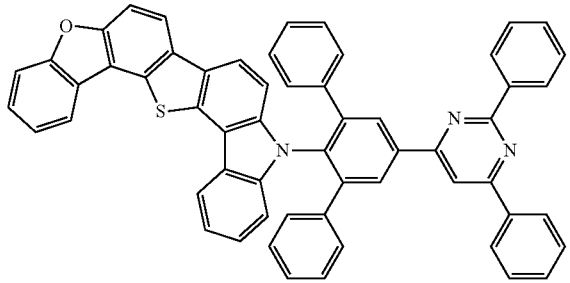
224
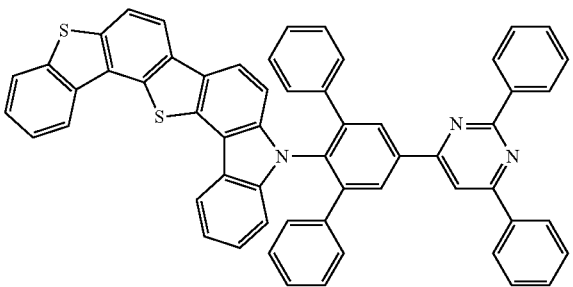

561
-continued
225
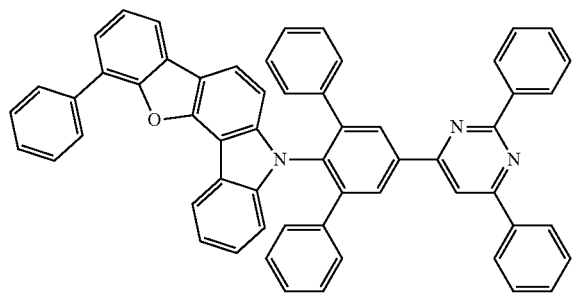
226
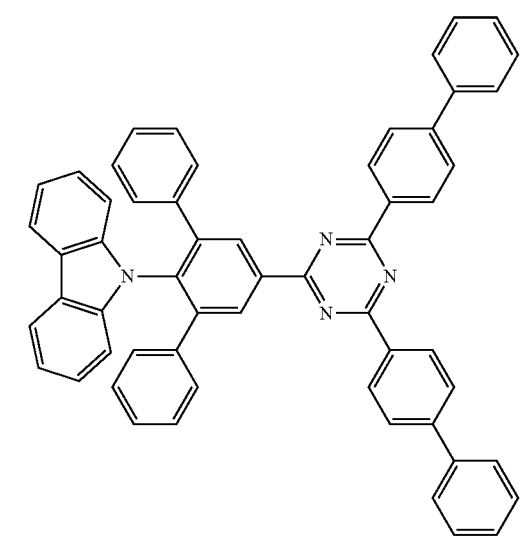
227
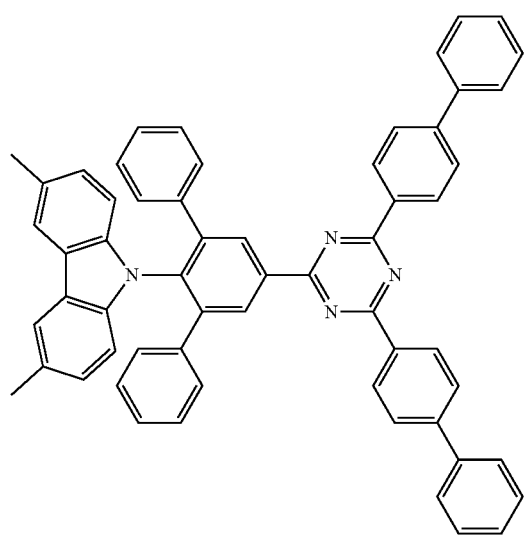
562
-continued
228
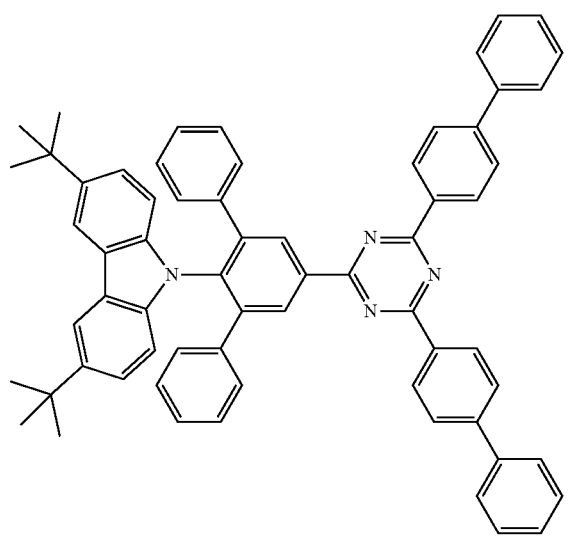
229
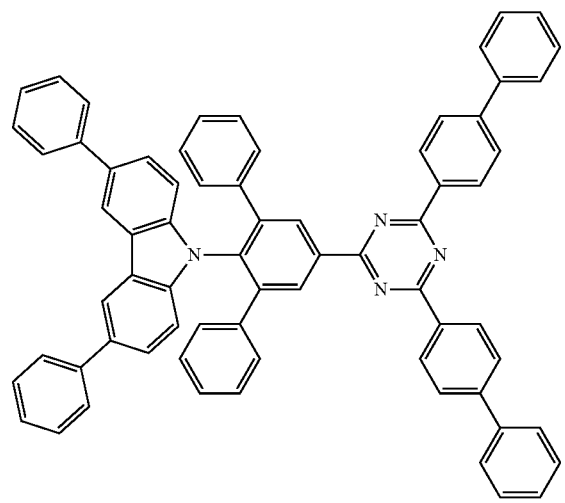
230
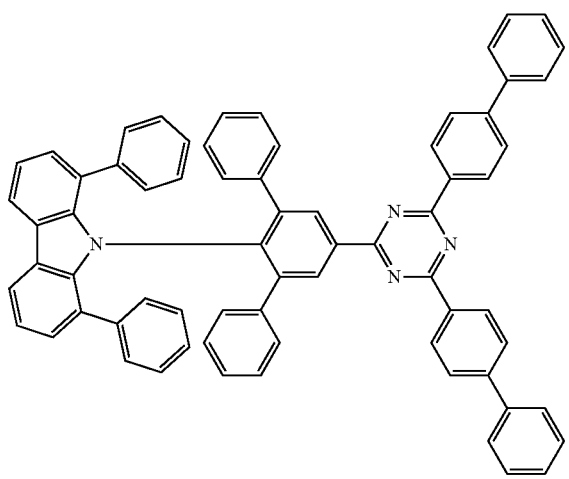

231
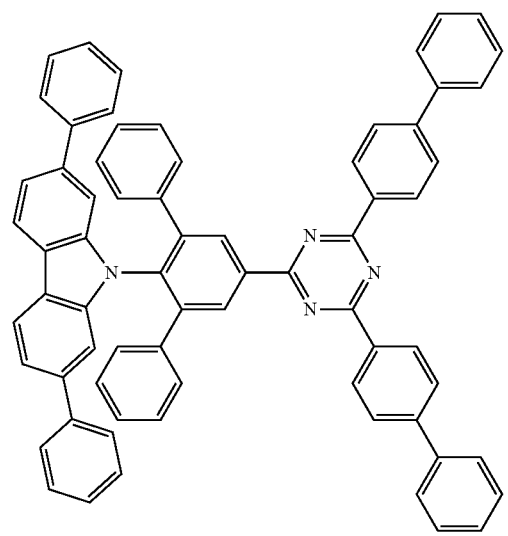
232
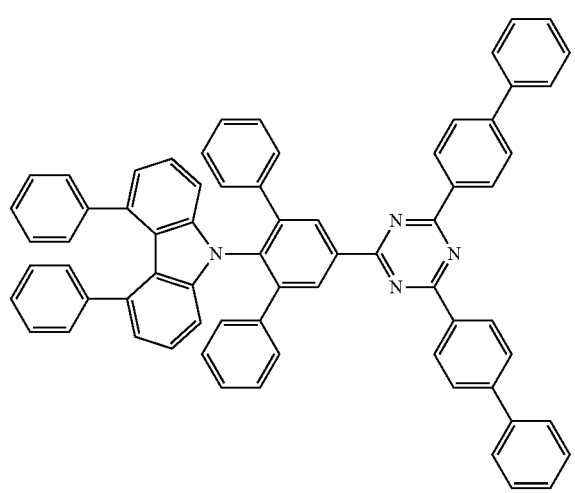
233
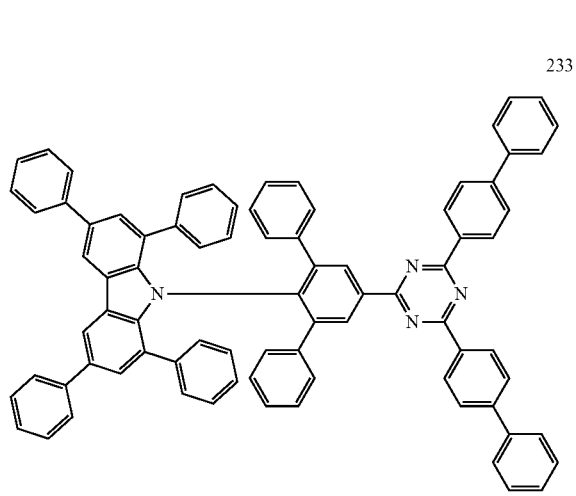
234
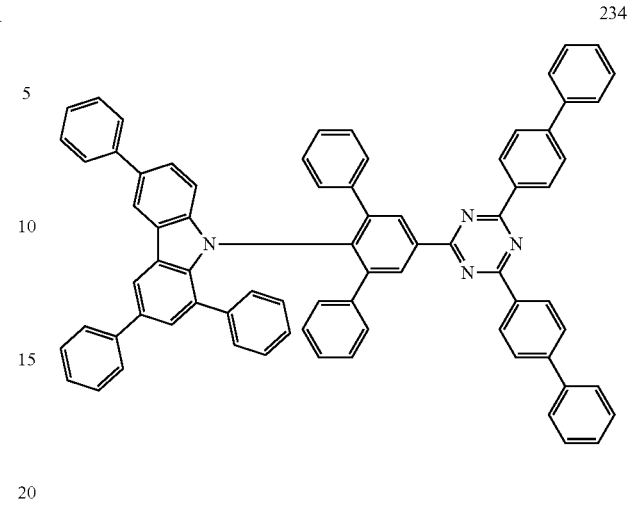
235
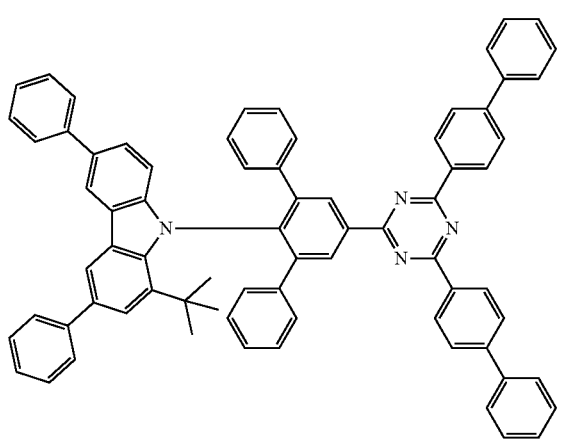
236
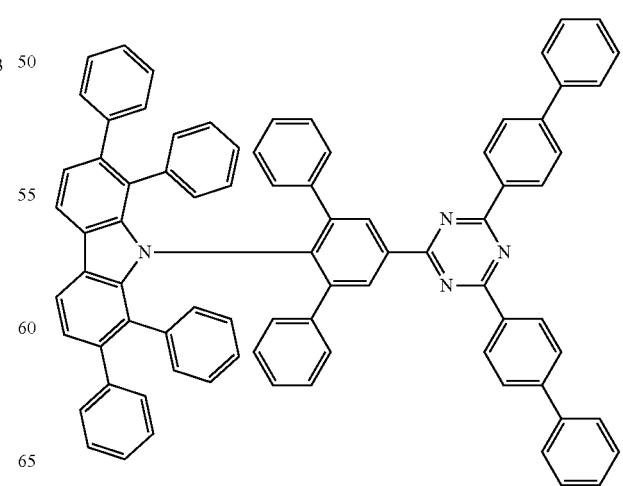

565
238
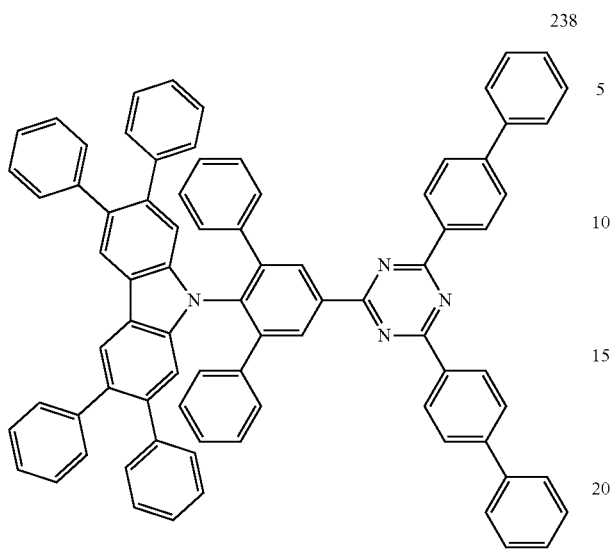
239
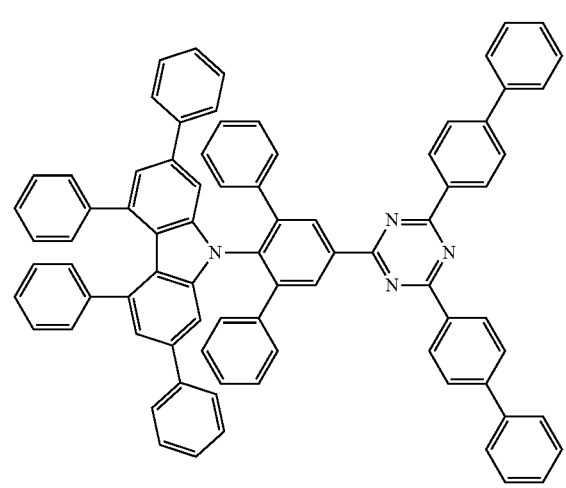
240
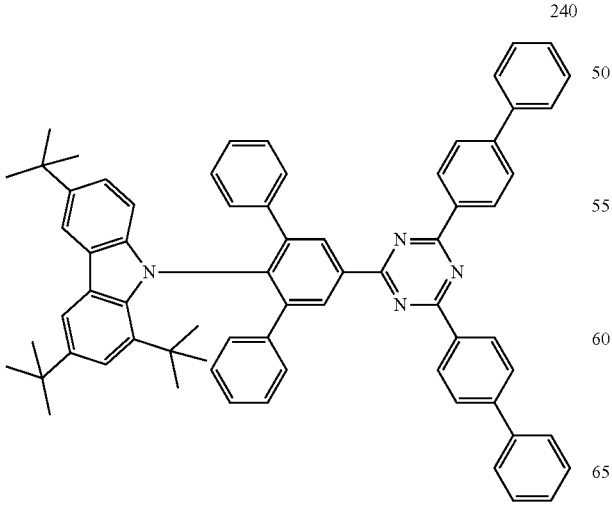
566
241
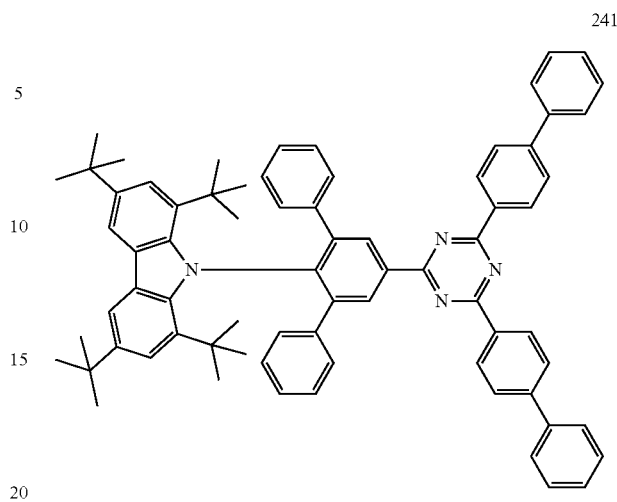
242
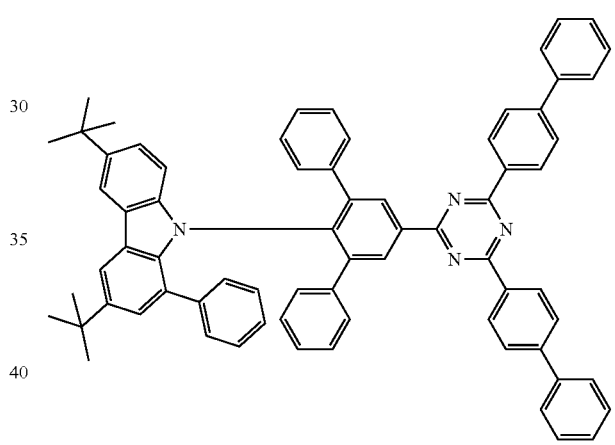
243
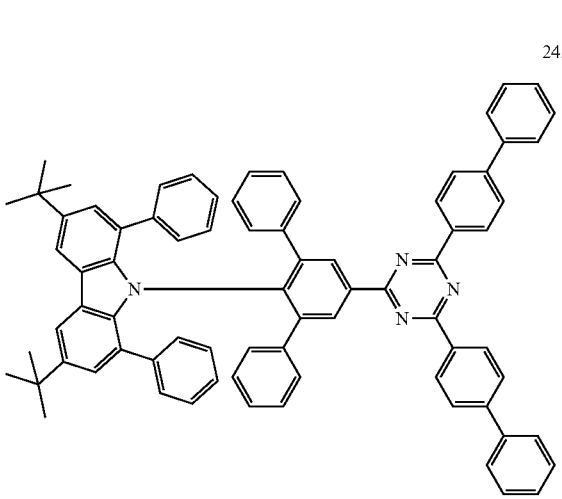

244
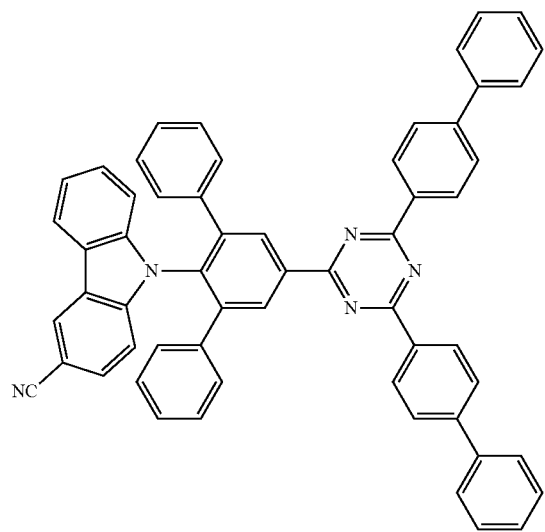
245
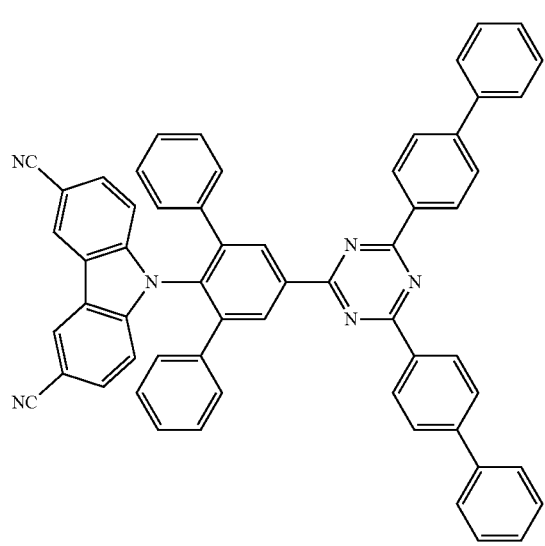
246
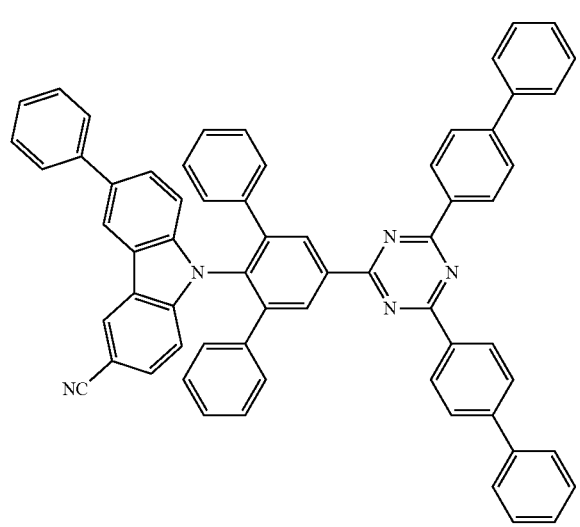
247
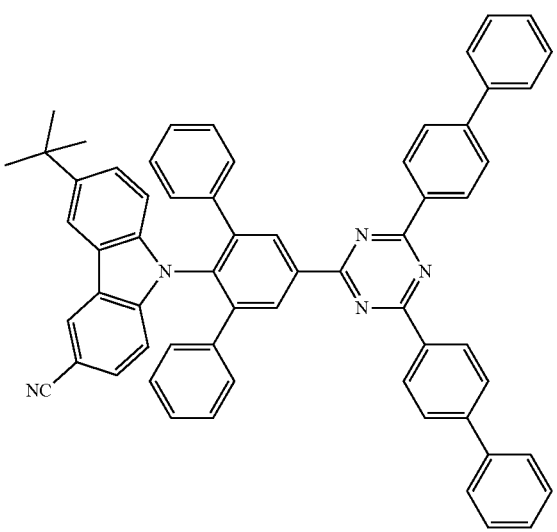
248
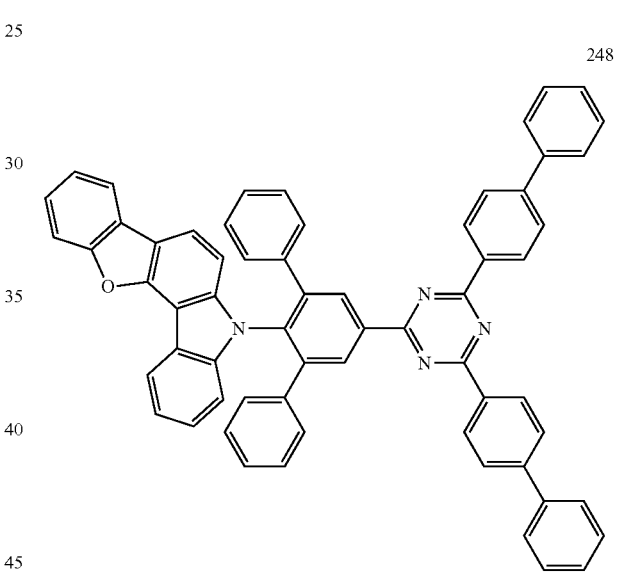
249
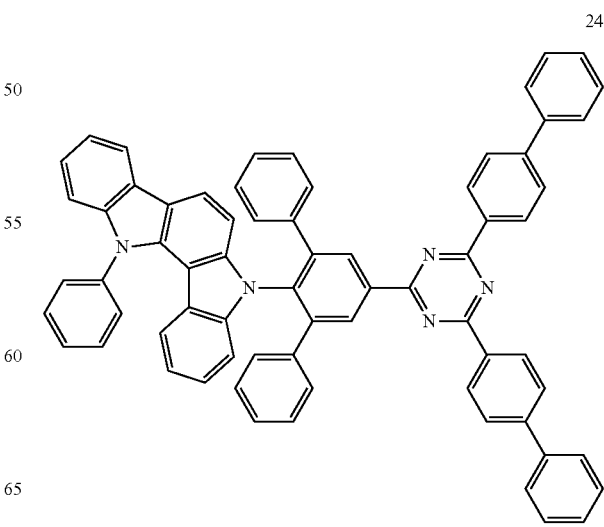

250
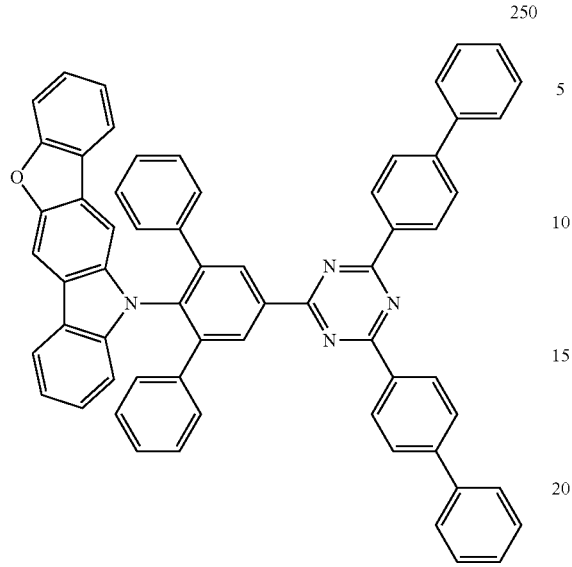
251
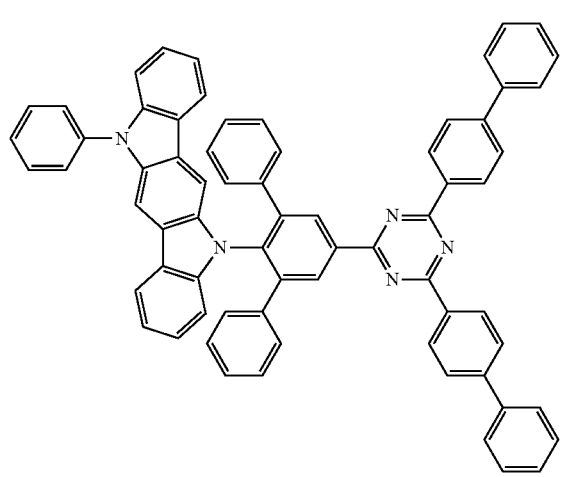
252
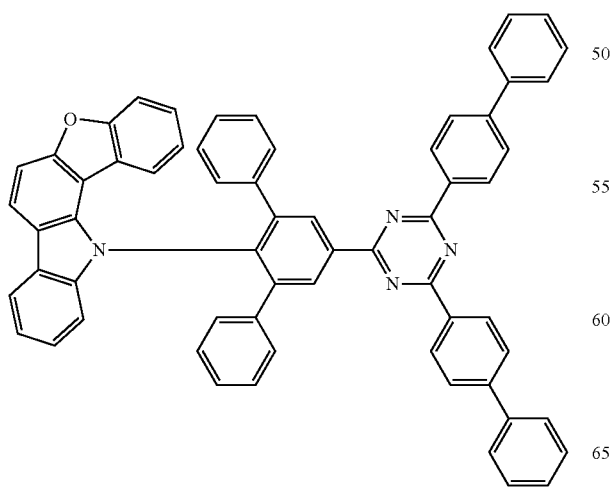
253
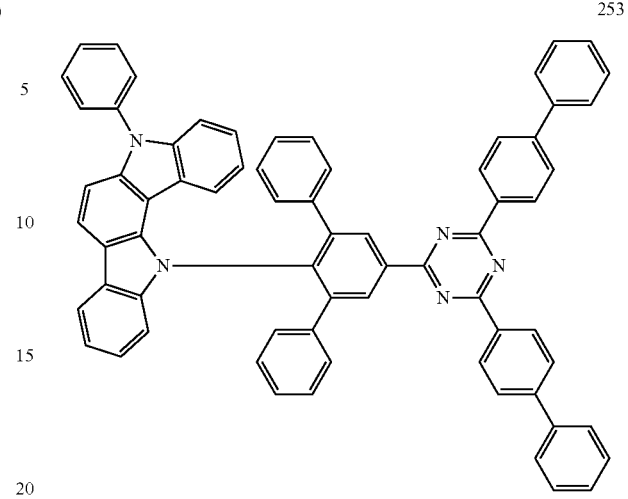
254
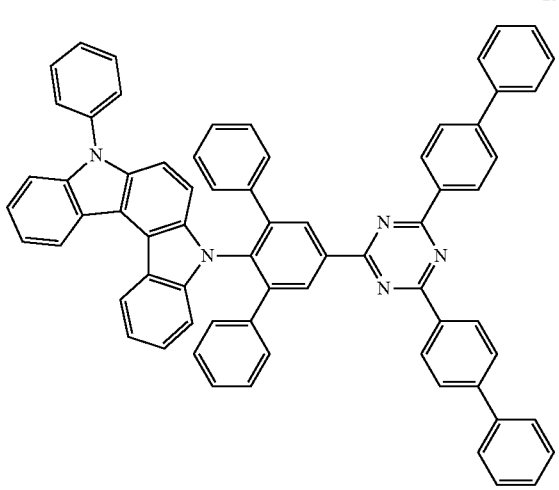
255

256
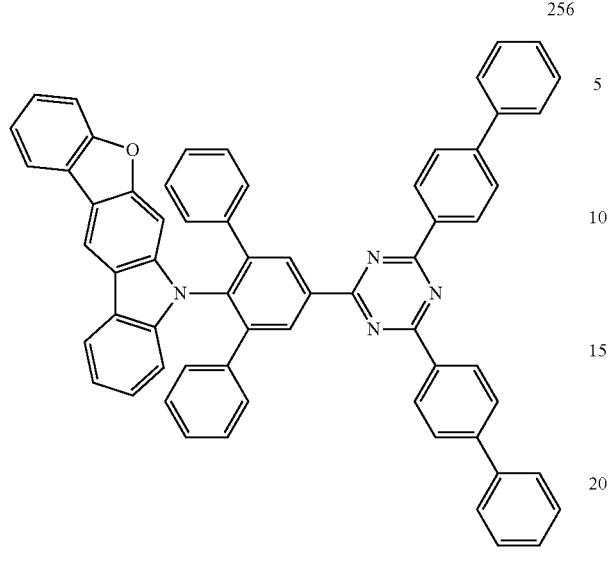
257
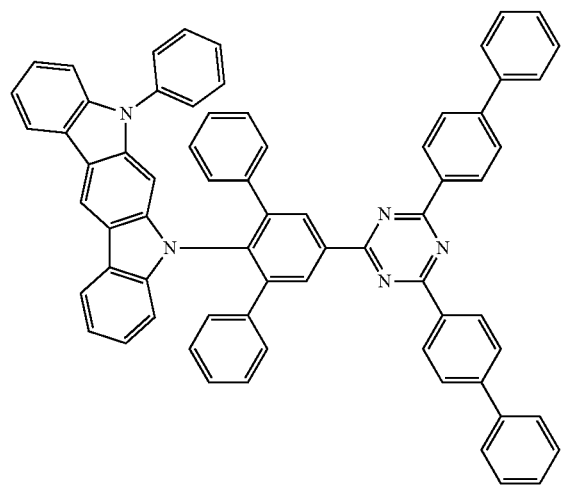
258
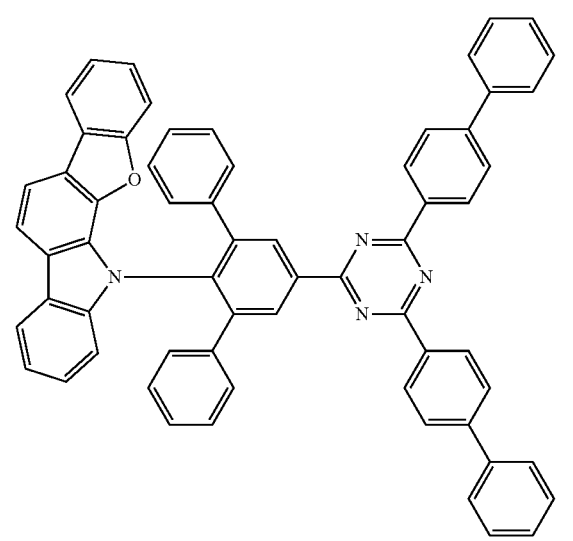
259
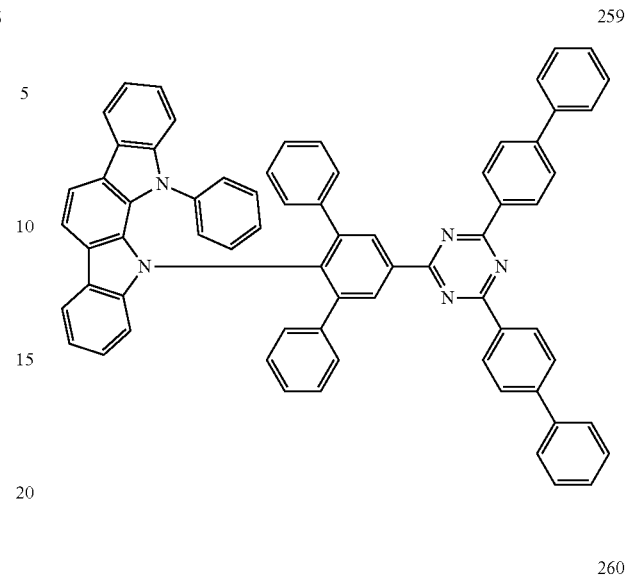
260
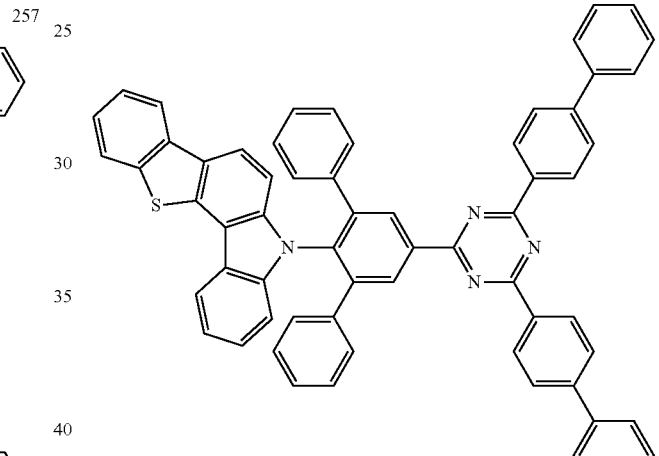
261
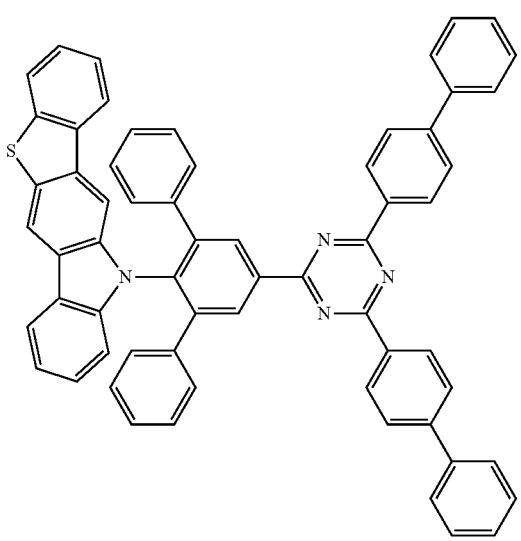

262
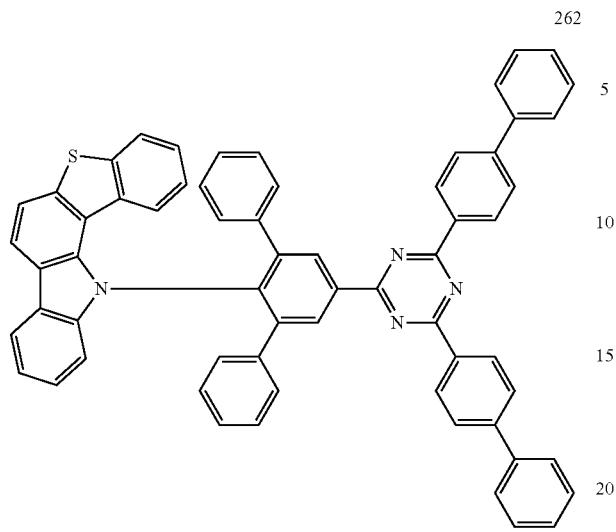
263
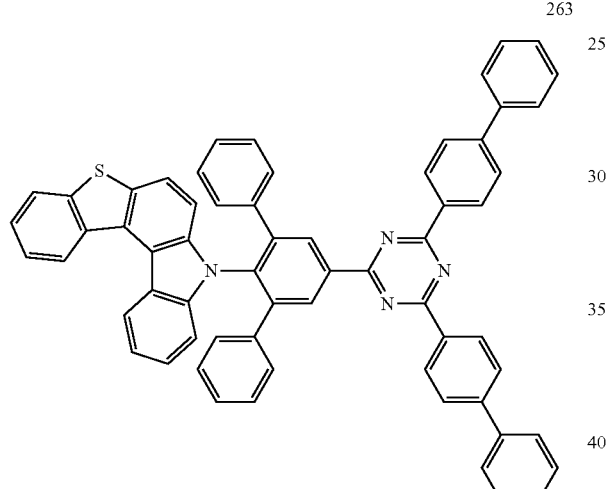
264
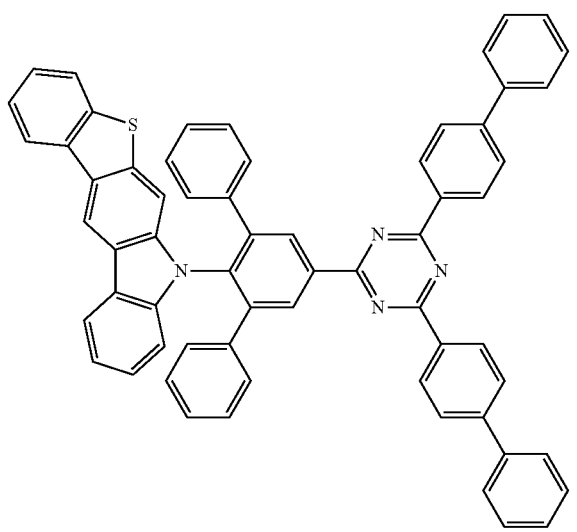
265
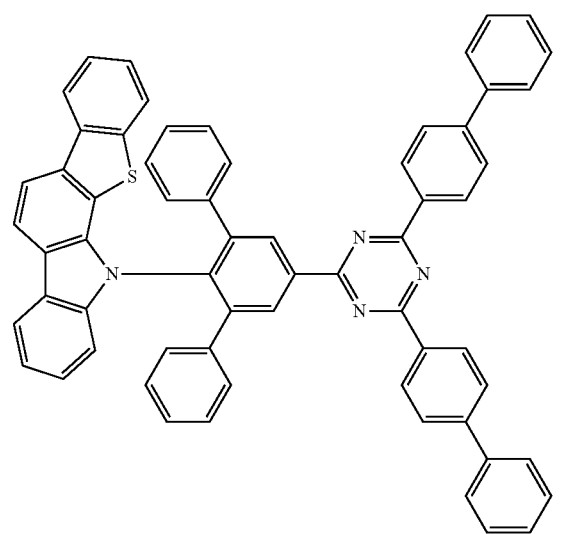
266
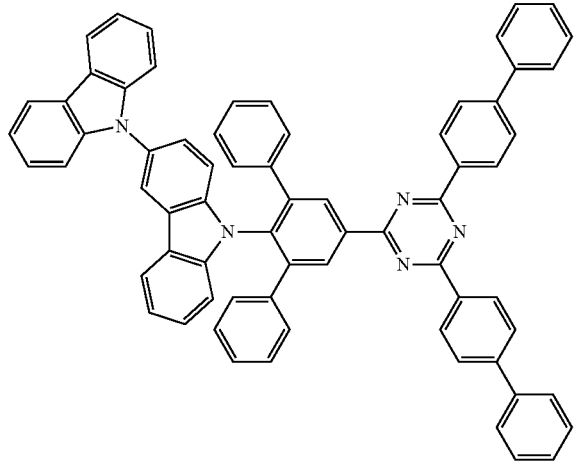
267
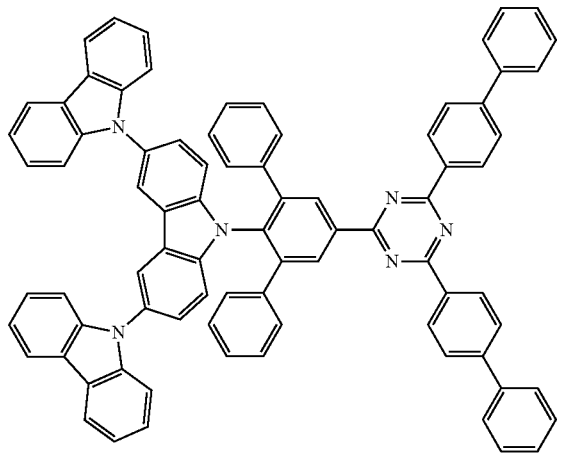

268
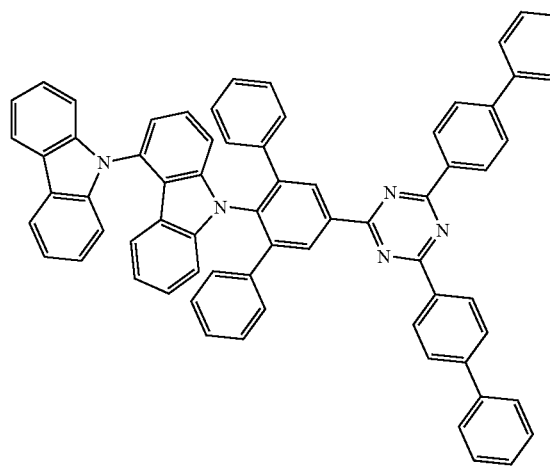
269
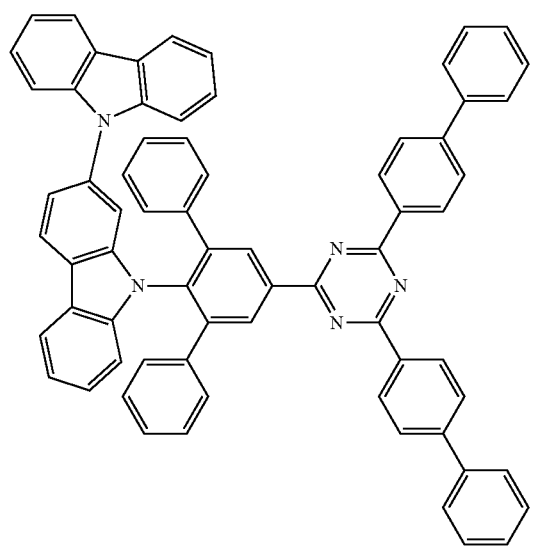
270
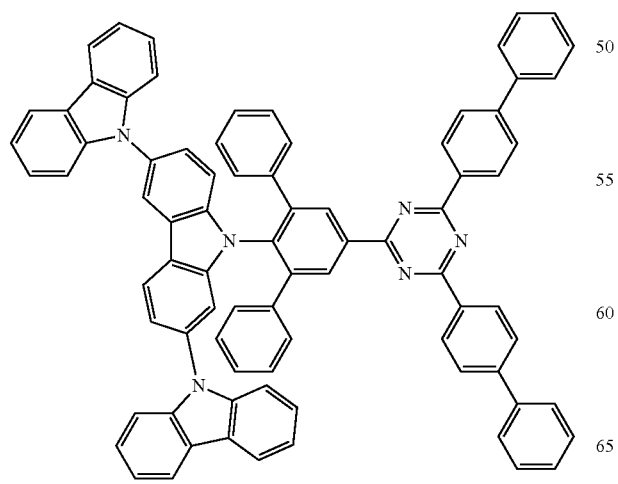
271
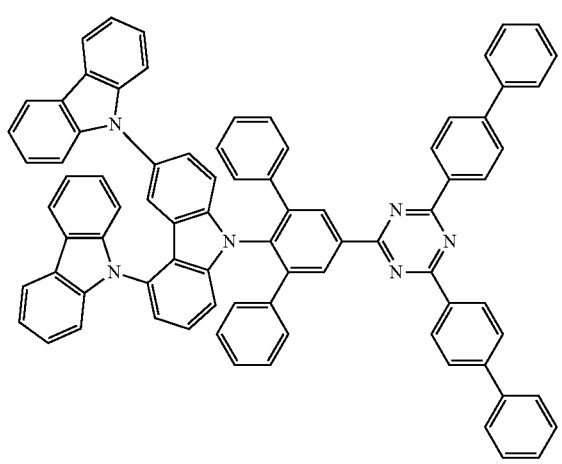
272
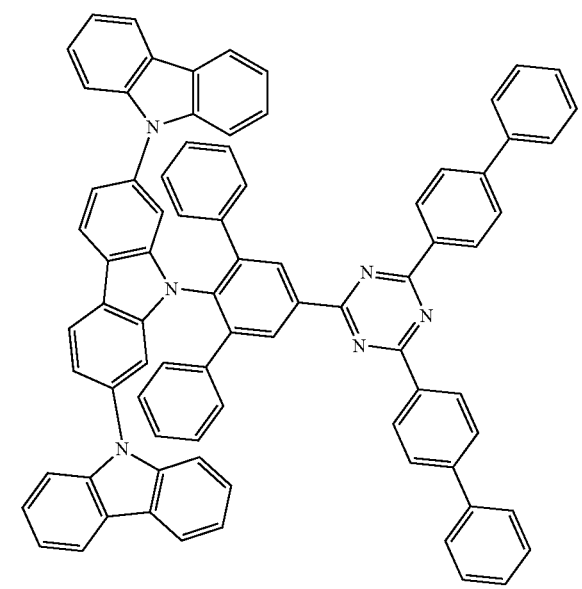
273
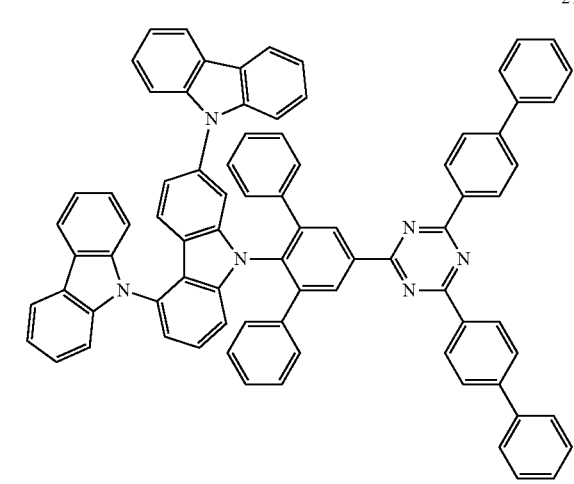

274
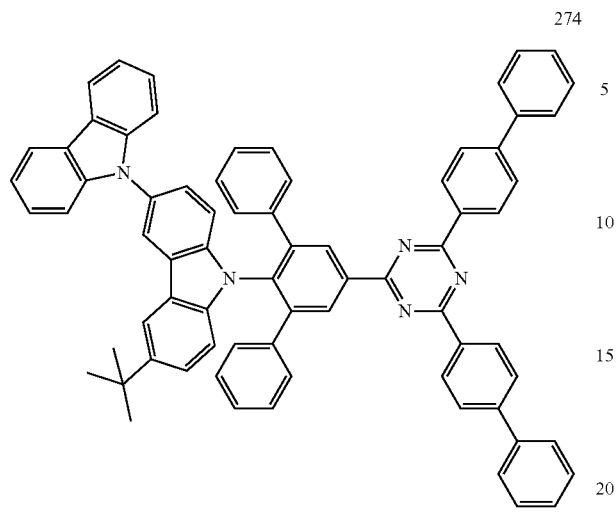
277
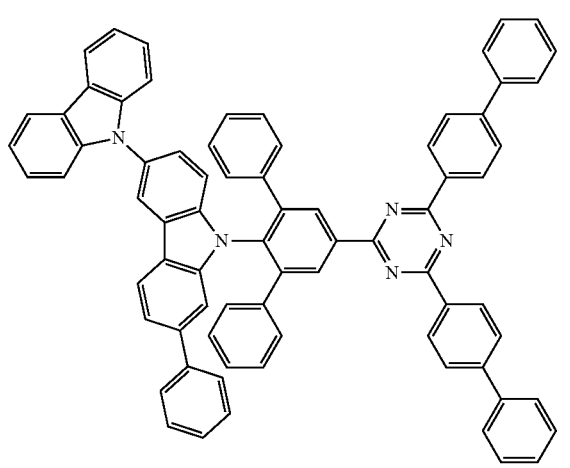
275
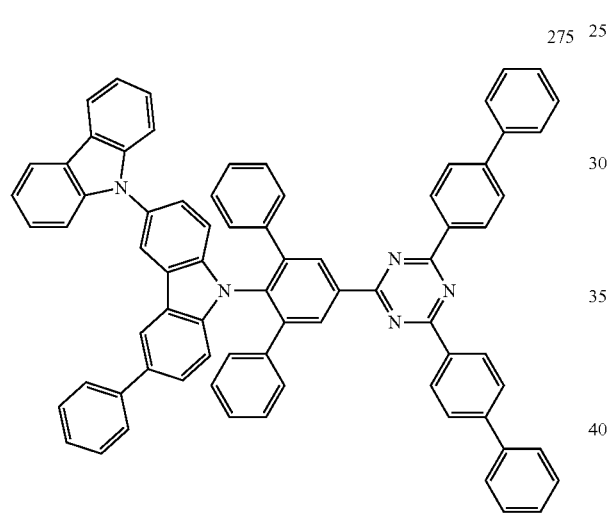
278
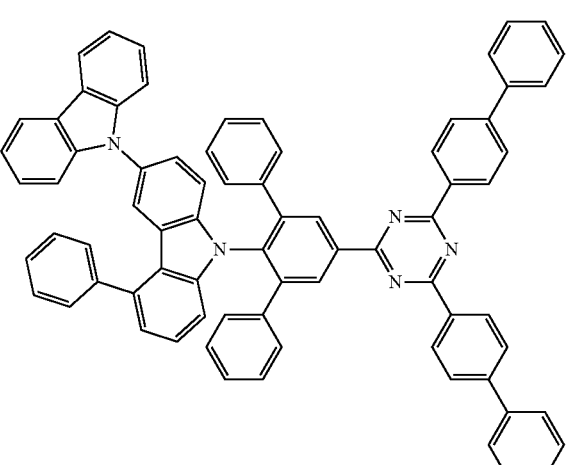
276
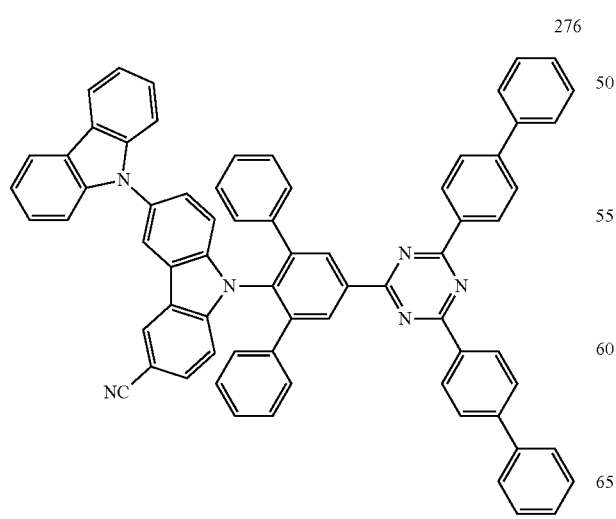
279
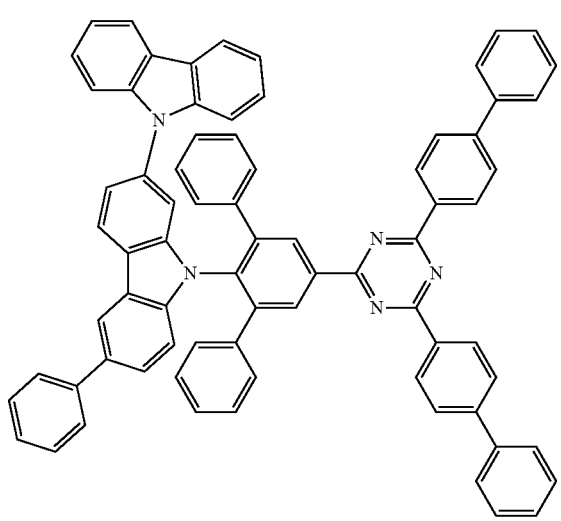

579 -continued
280
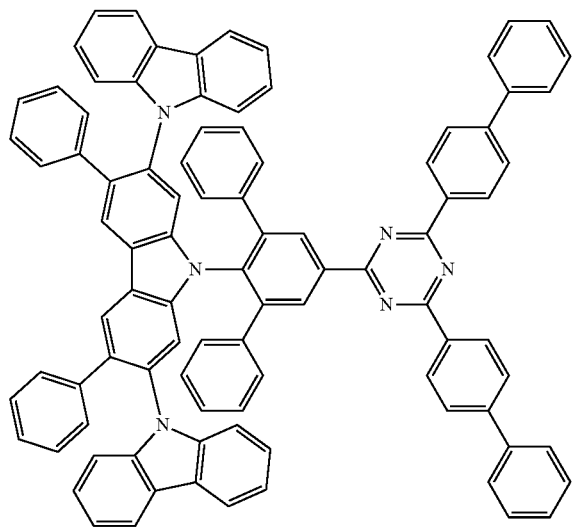
281
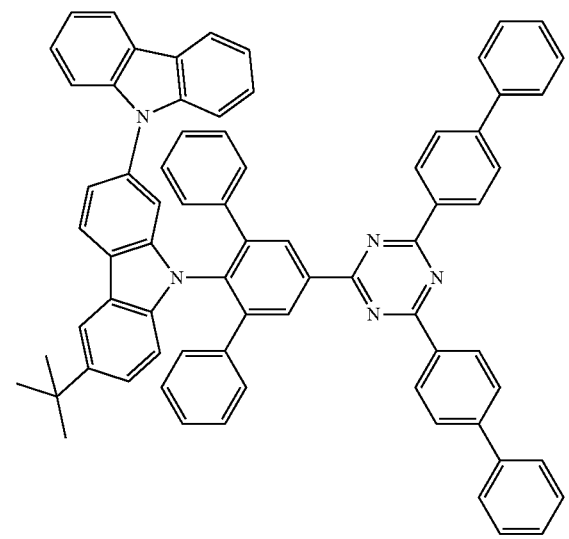
282
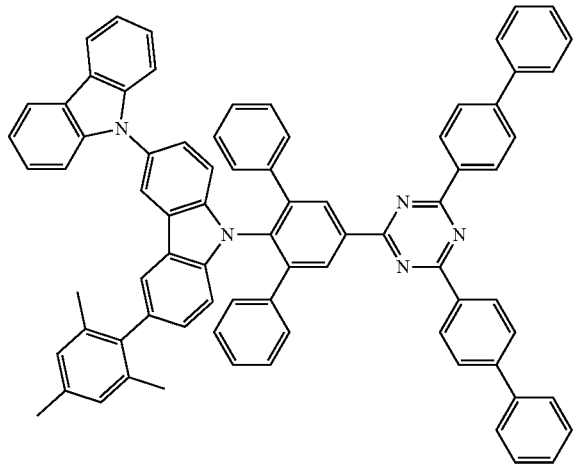
580 -continued
283
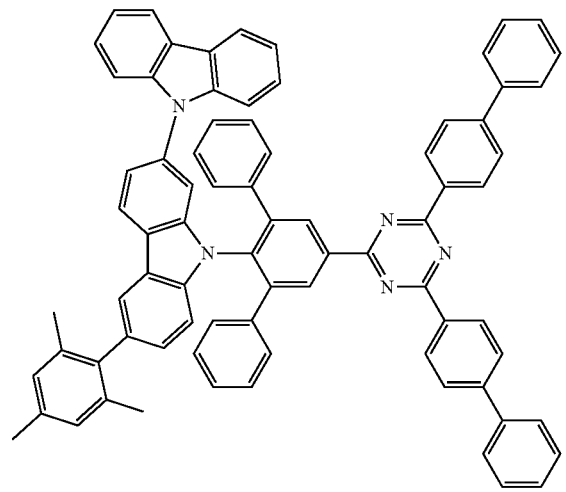
284
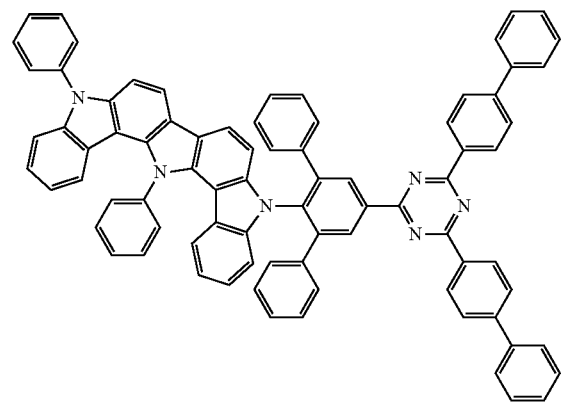
285

286
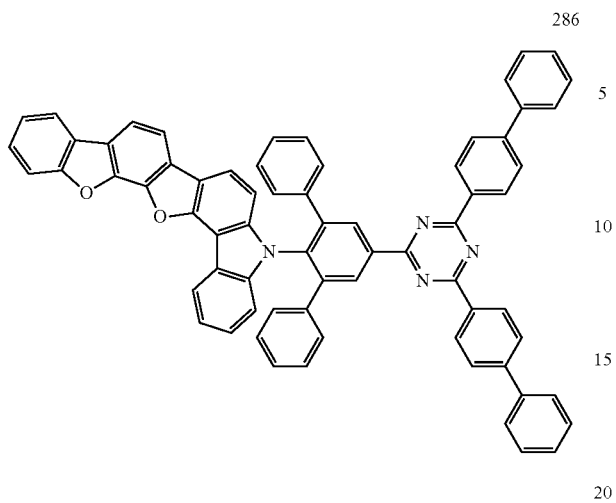
287
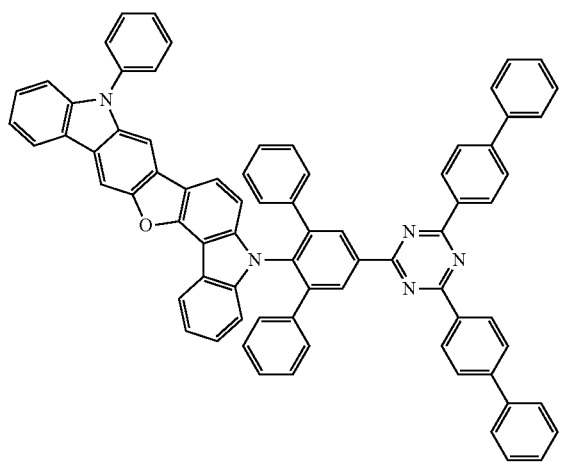
288
289
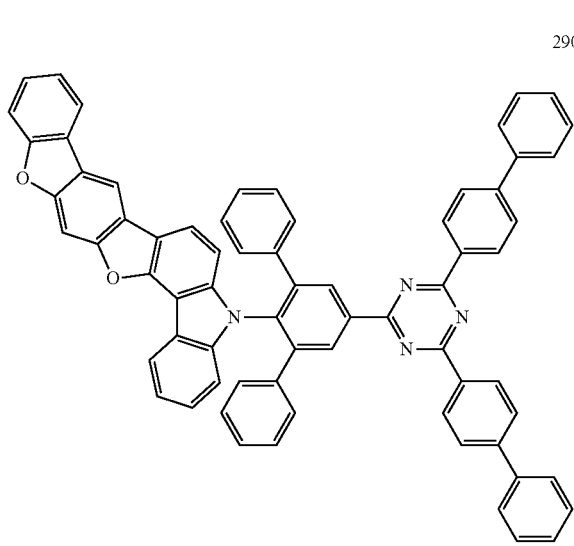
290
291
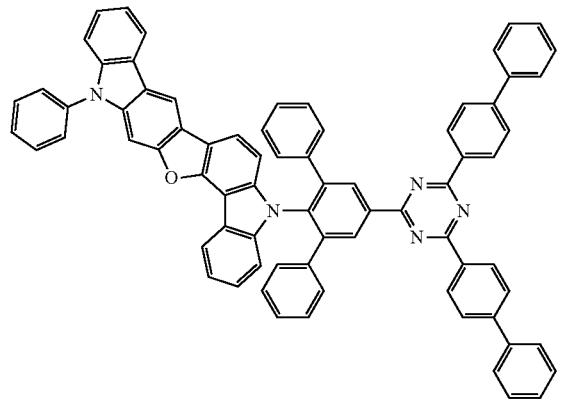

583
-continued
292
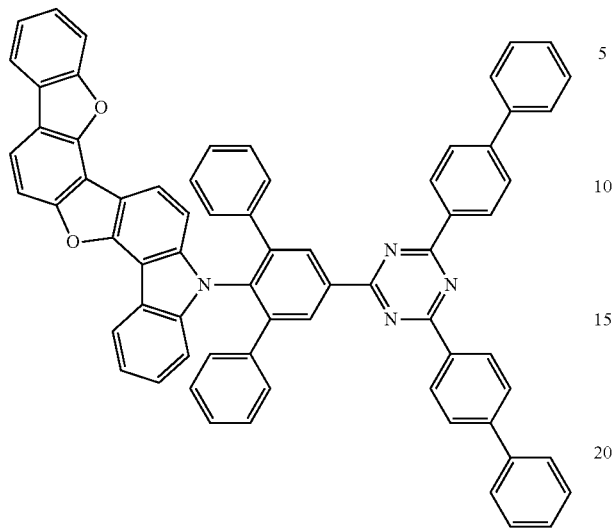
293
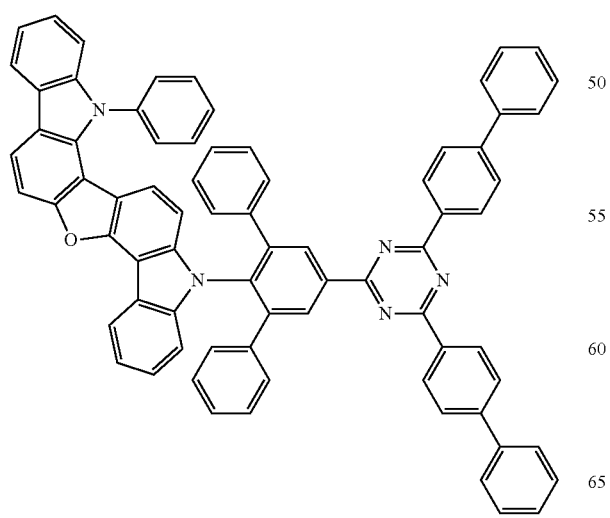
584
-continued
294
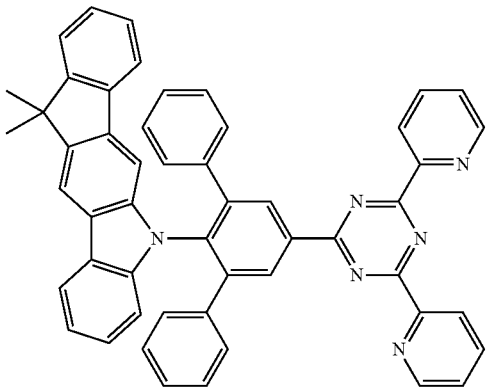
295
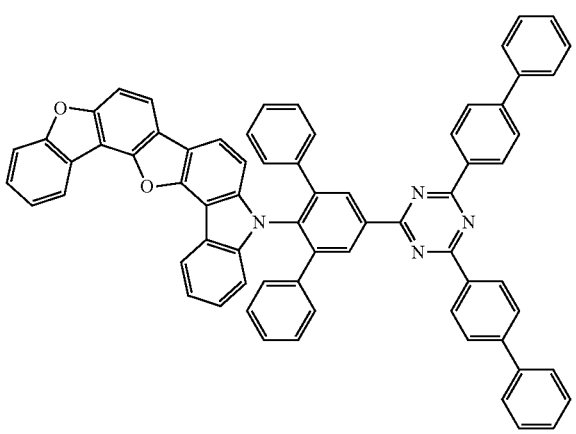
296

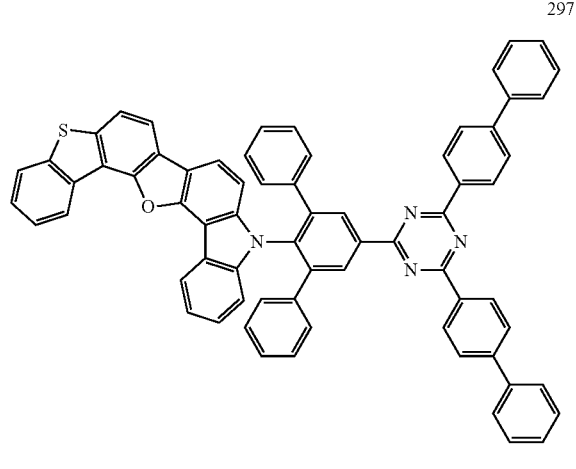
297
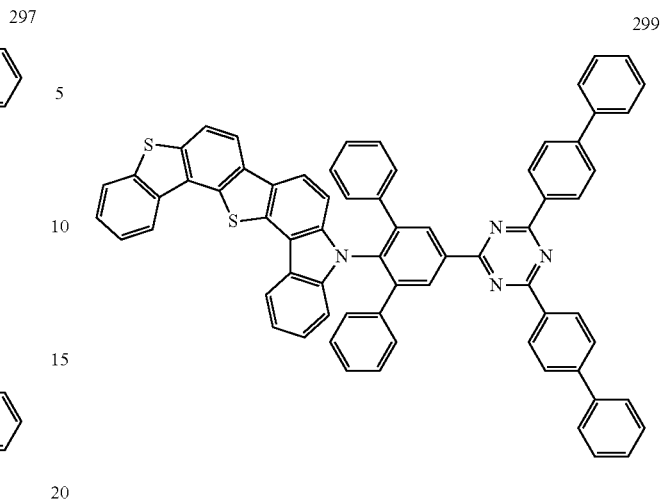
299
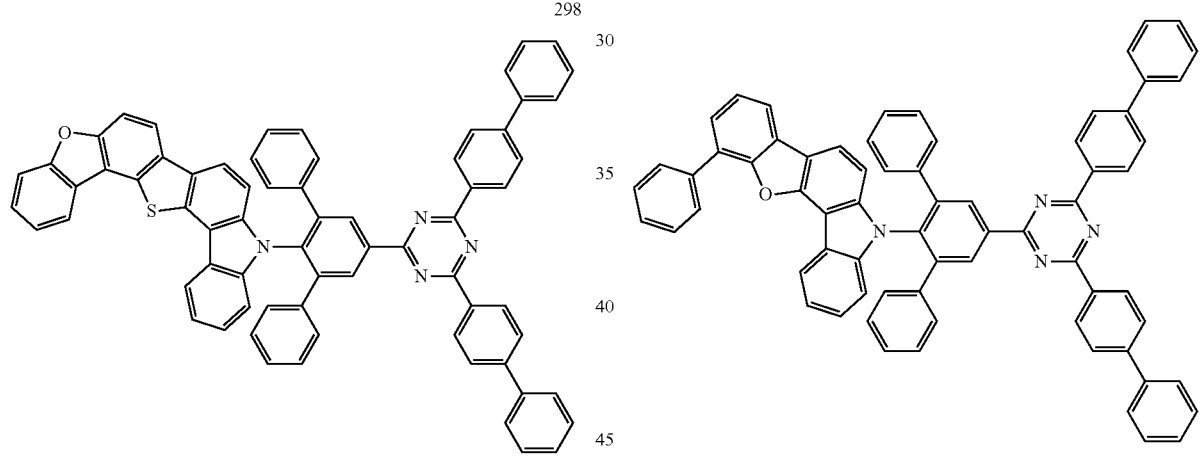
298
300
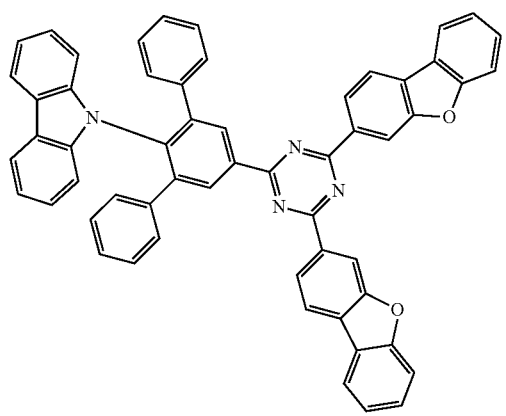
301
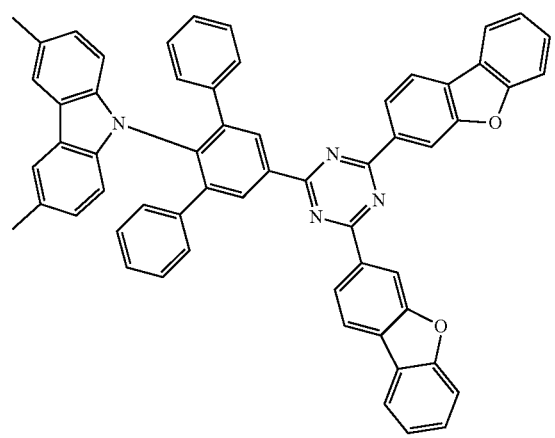
302

-continued
303
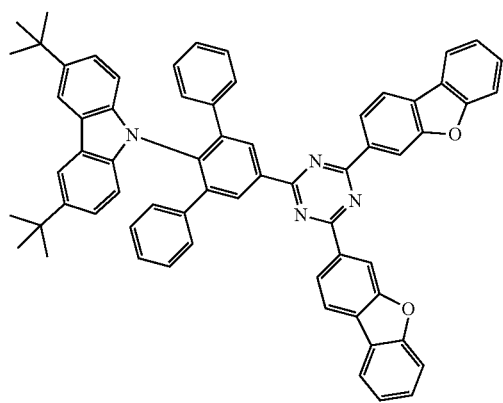
304
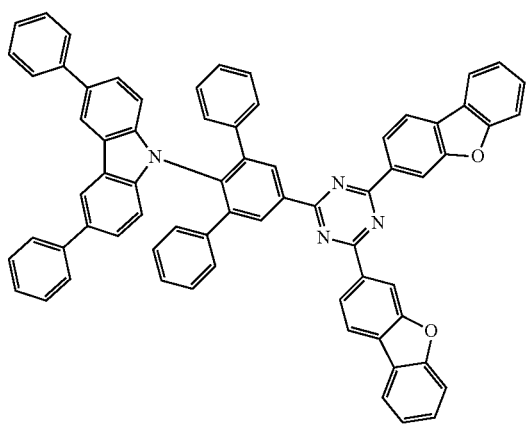
305
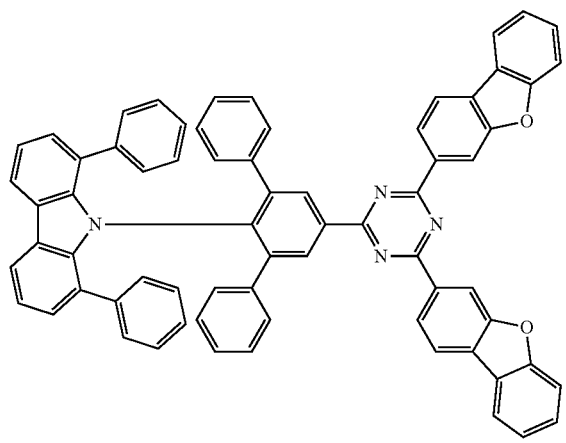
306
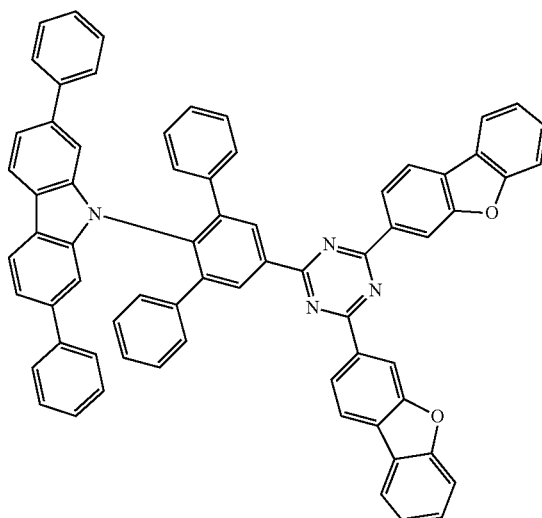
307
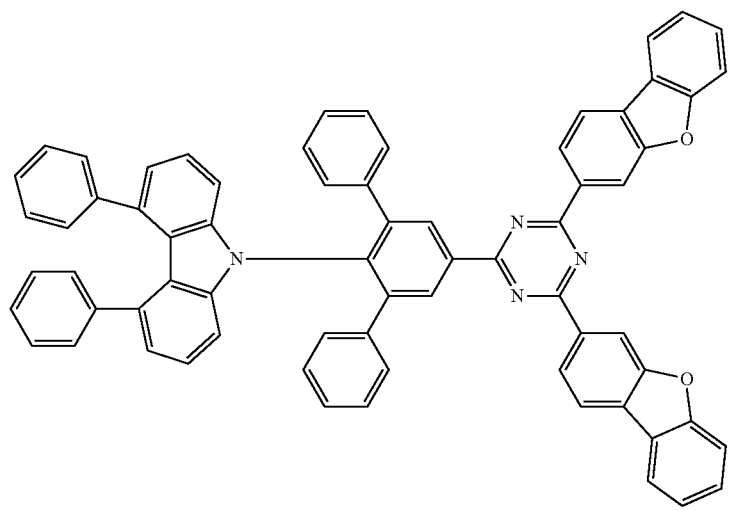

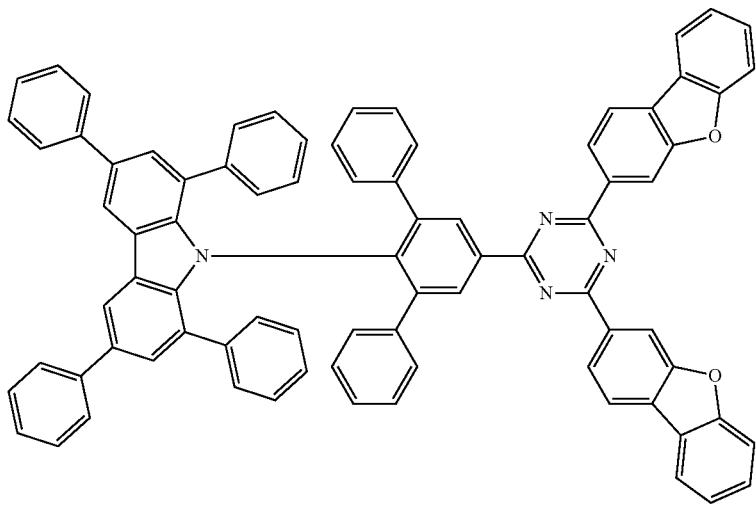
308
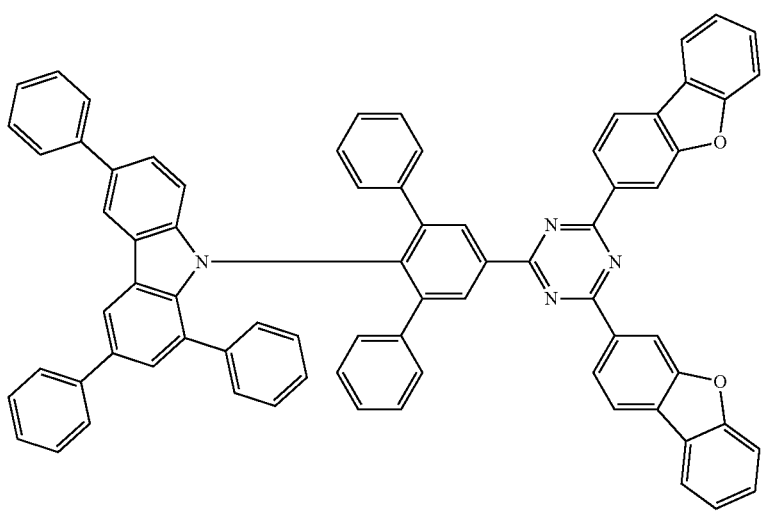
309
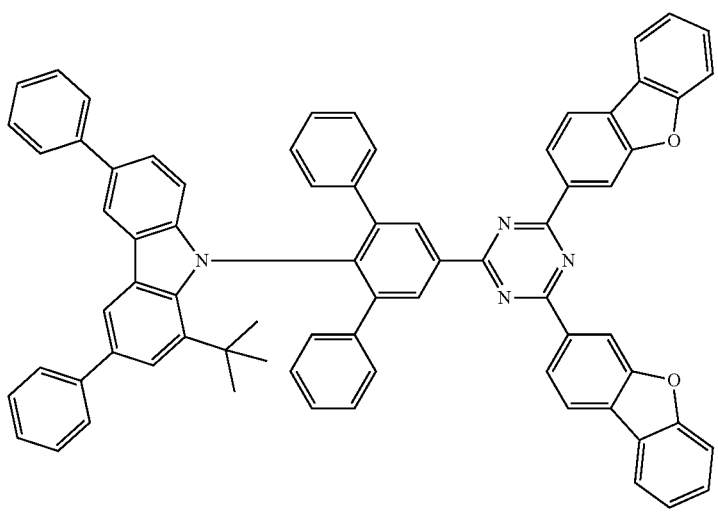
310

-continued
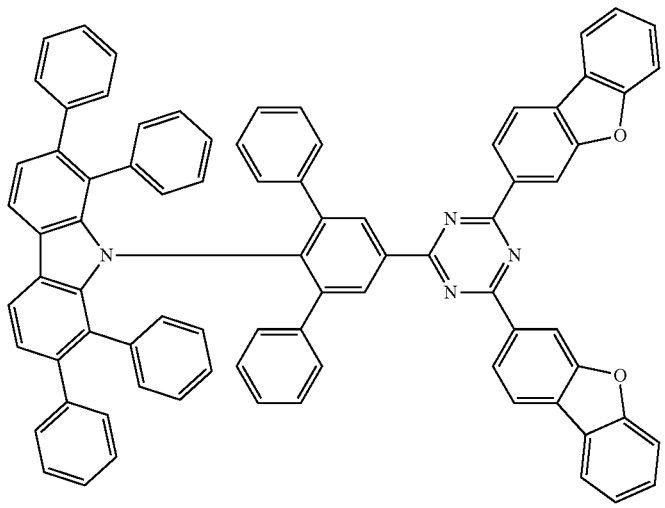
311
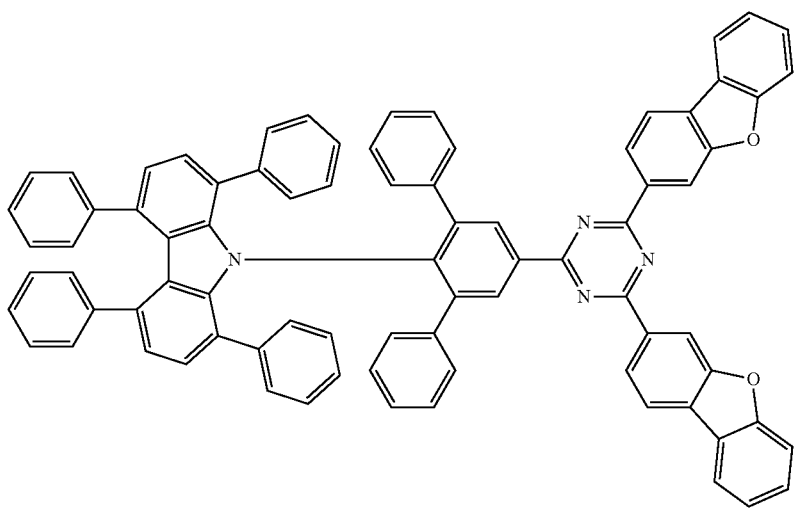
312
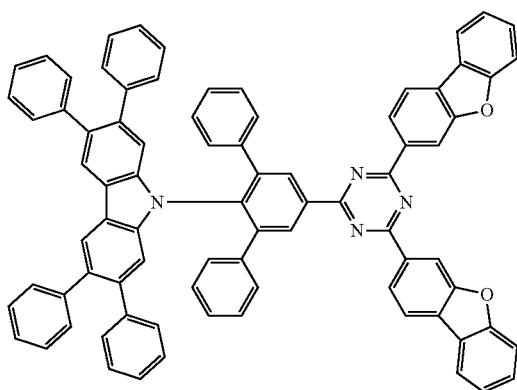
313
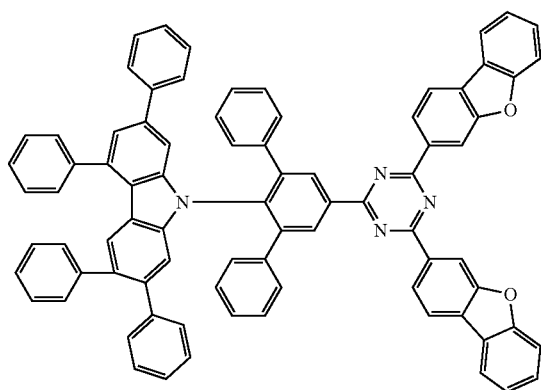
314

-continued
315
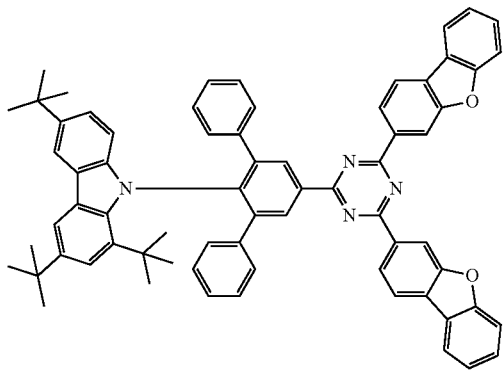
316
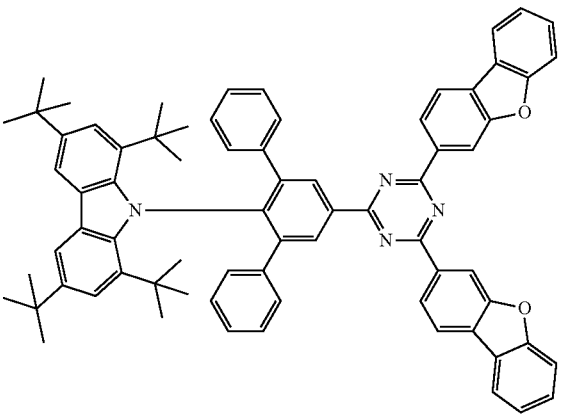
317
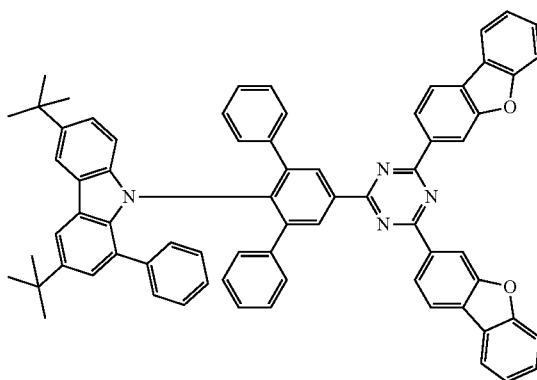
318
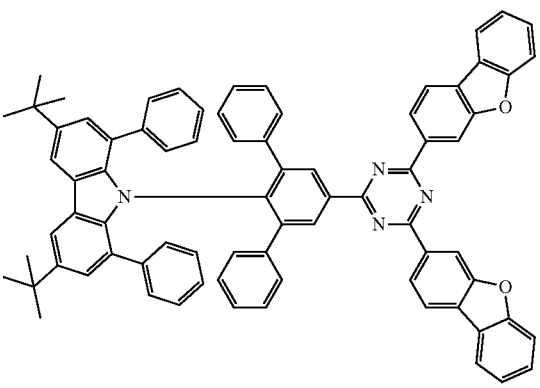
319
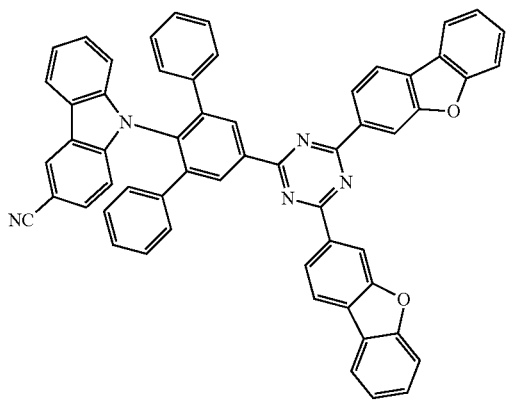
320
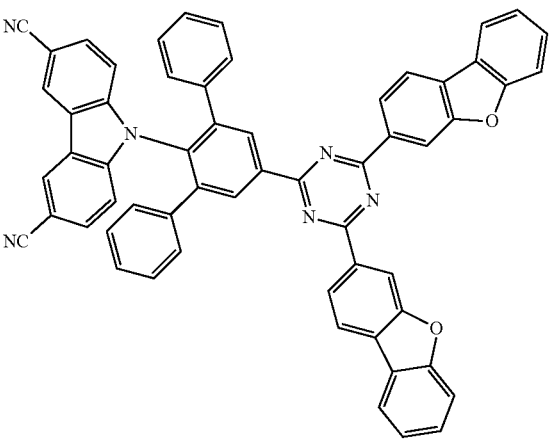

-continued
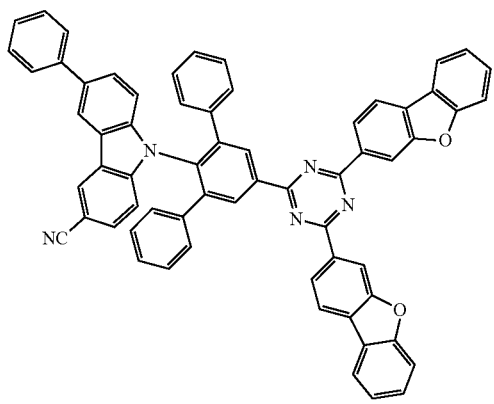
321
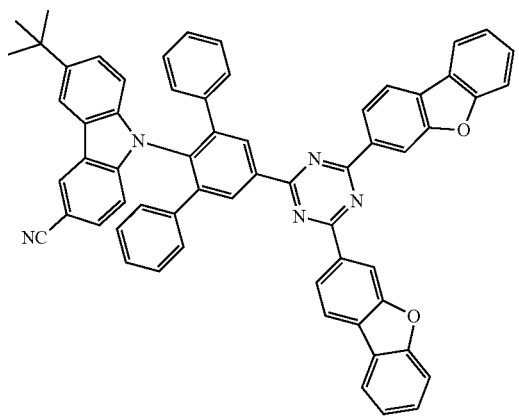
322
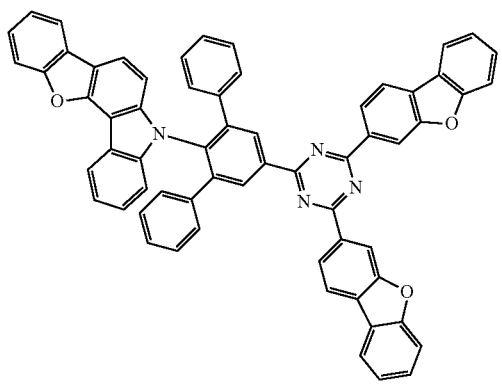
323
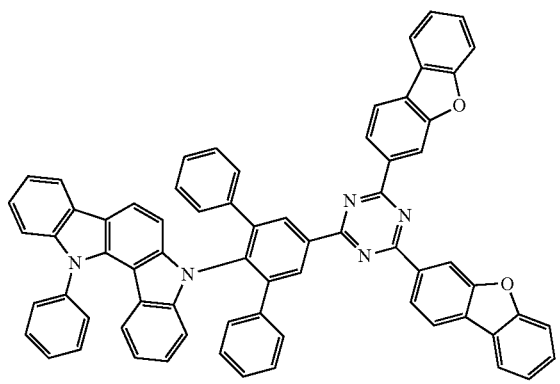
324
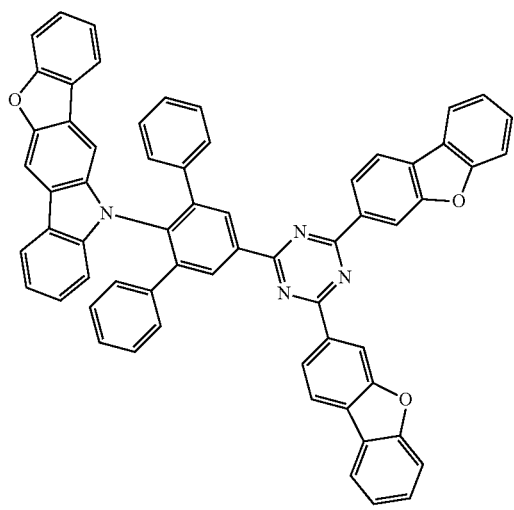
325
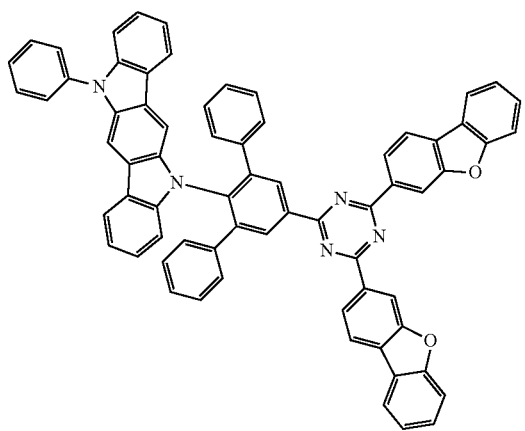
326

327
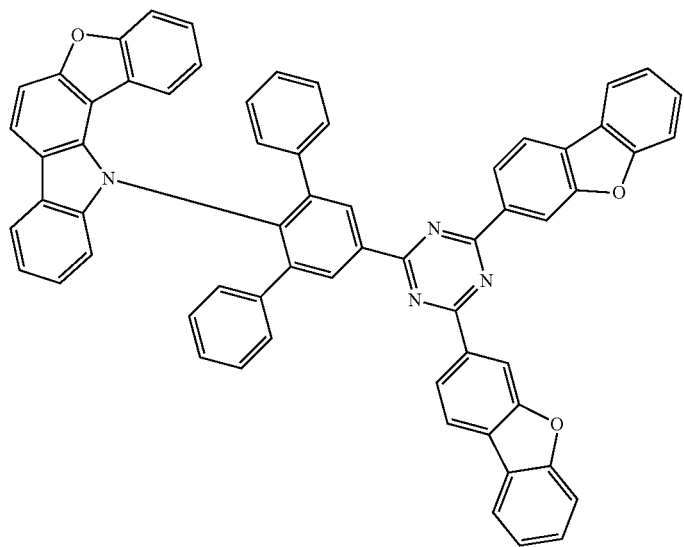
328
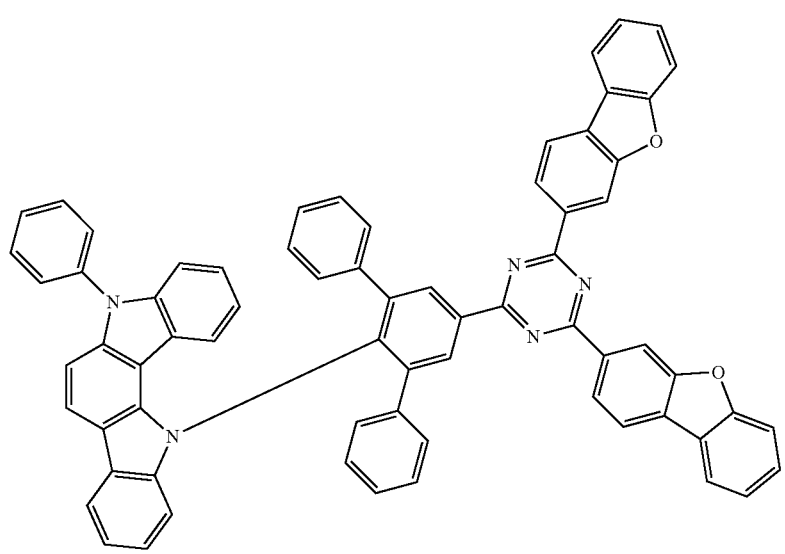
329
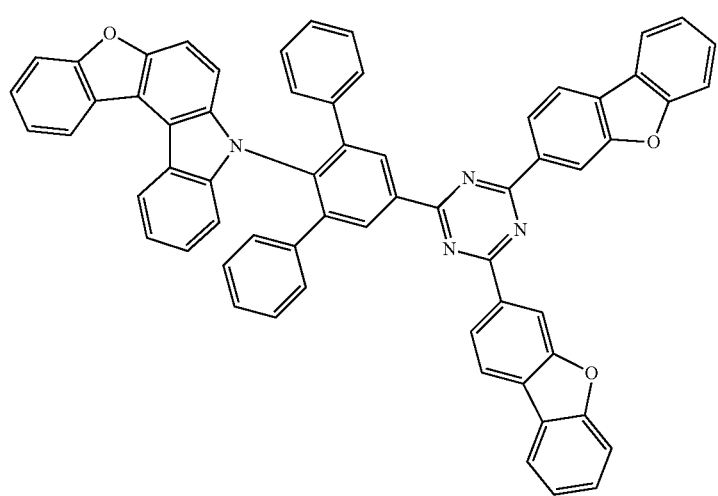

-continued
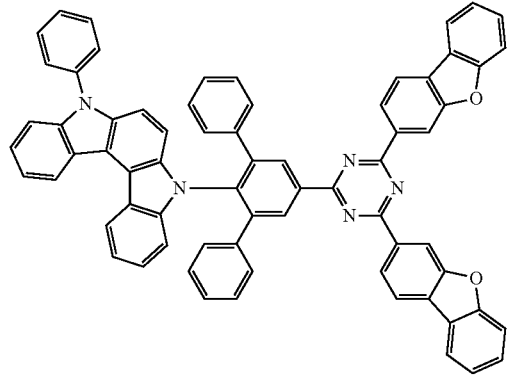
330
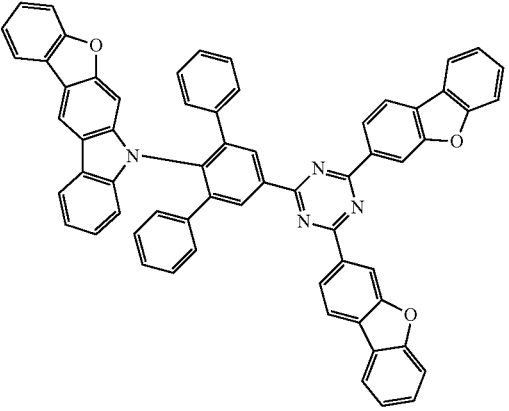
331
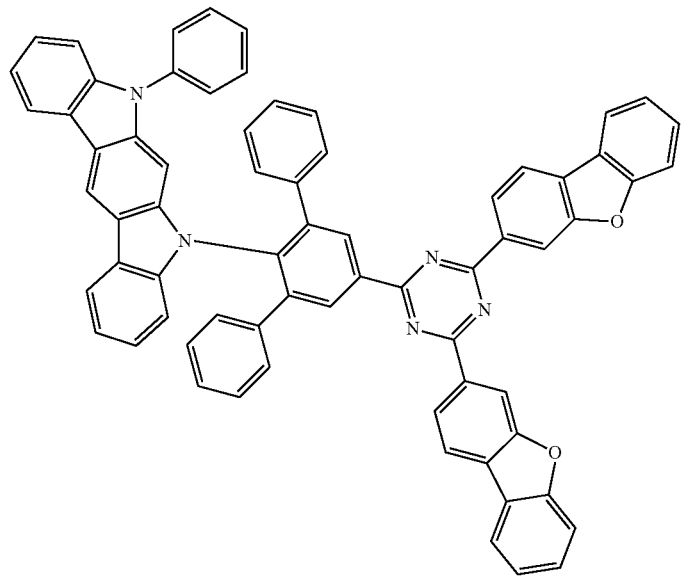
332
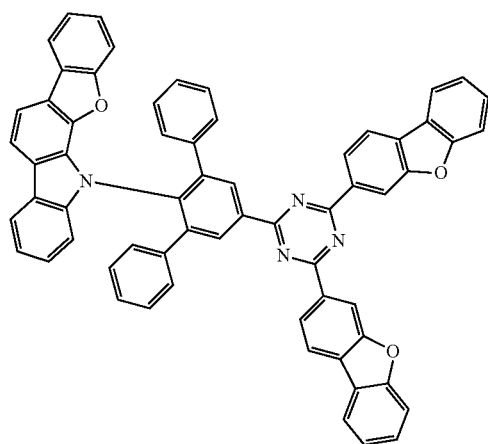
333
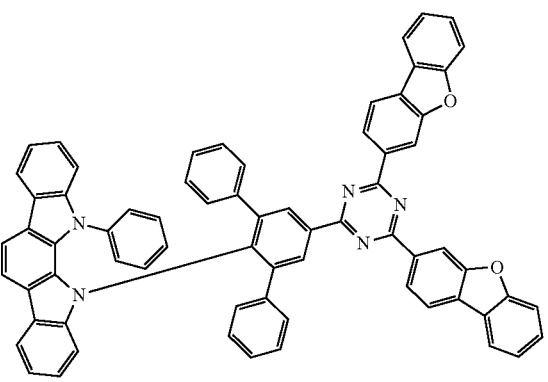
334

-continued
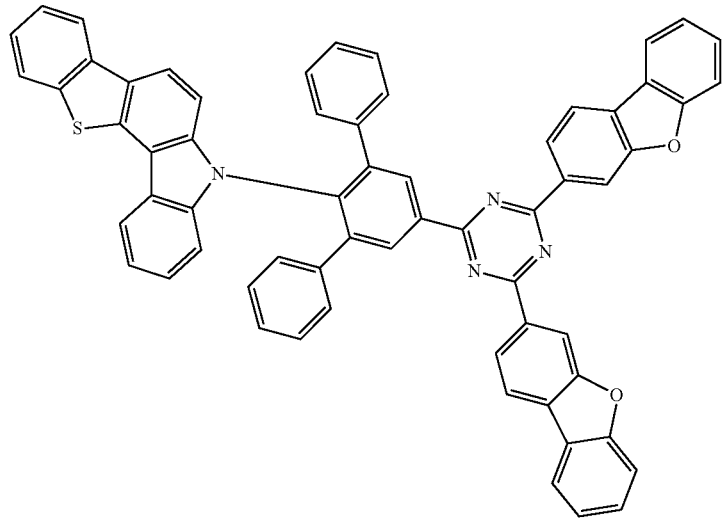
335
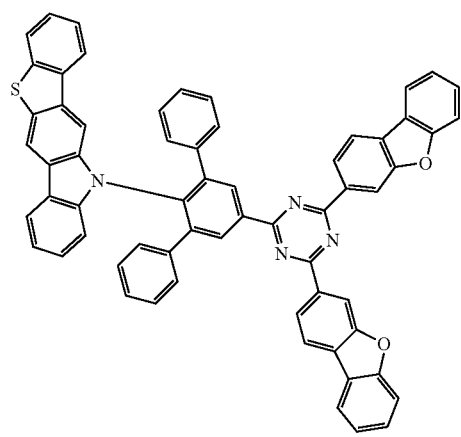
336
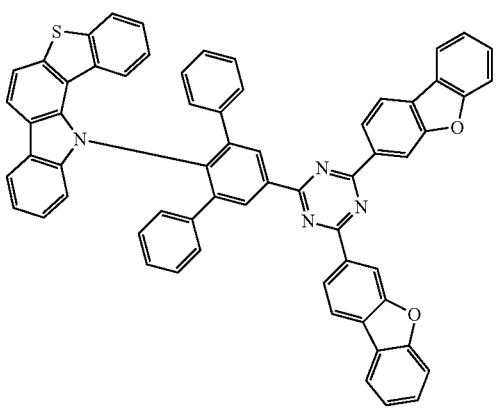
337
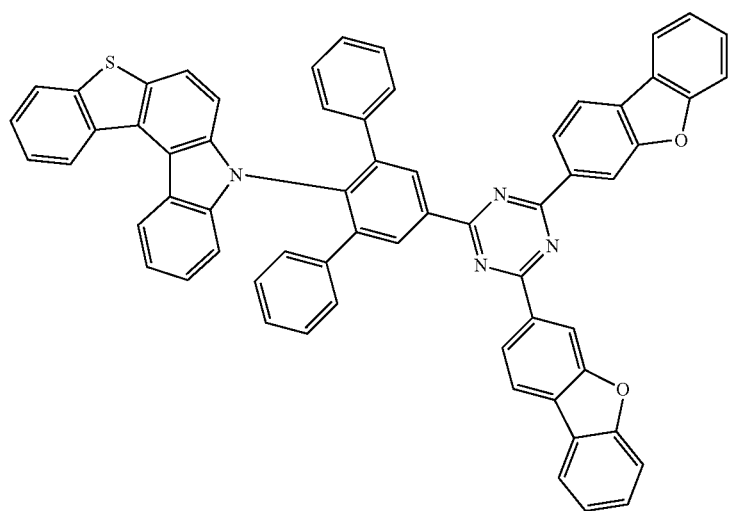
338

-continued
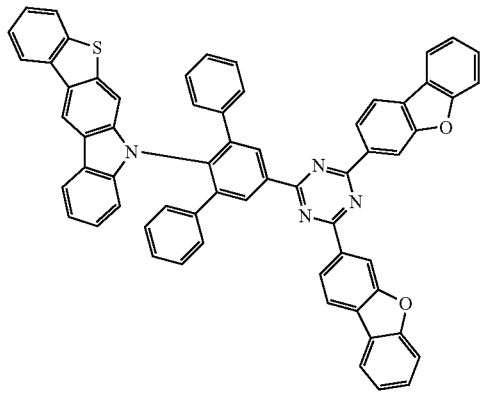
339
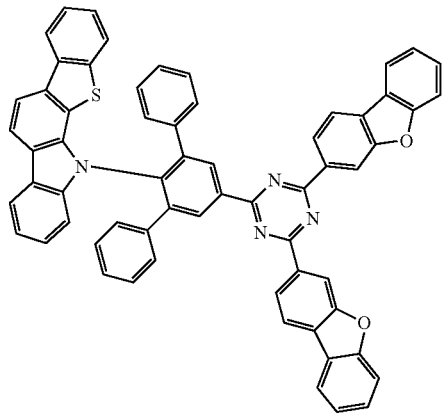
340
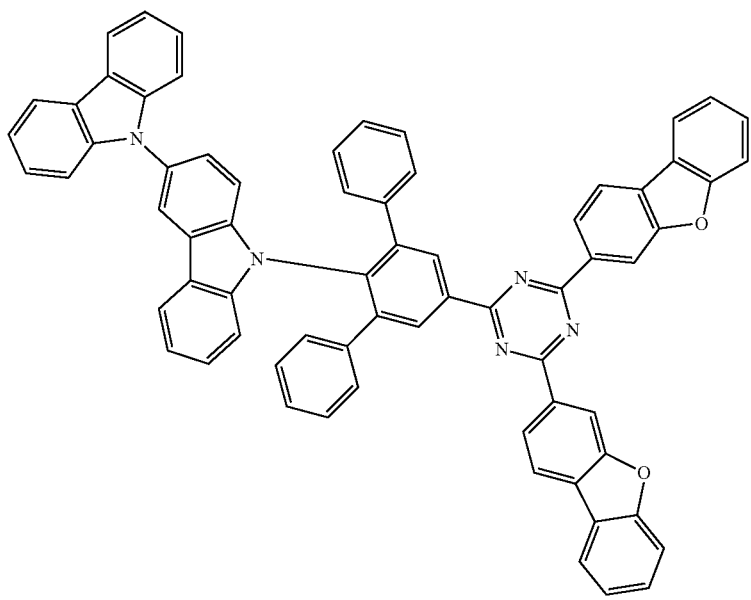
341
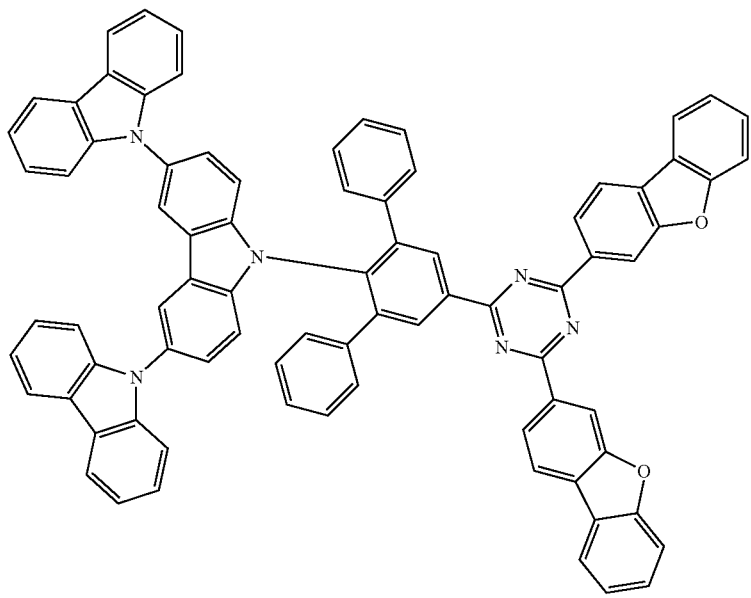
342

343
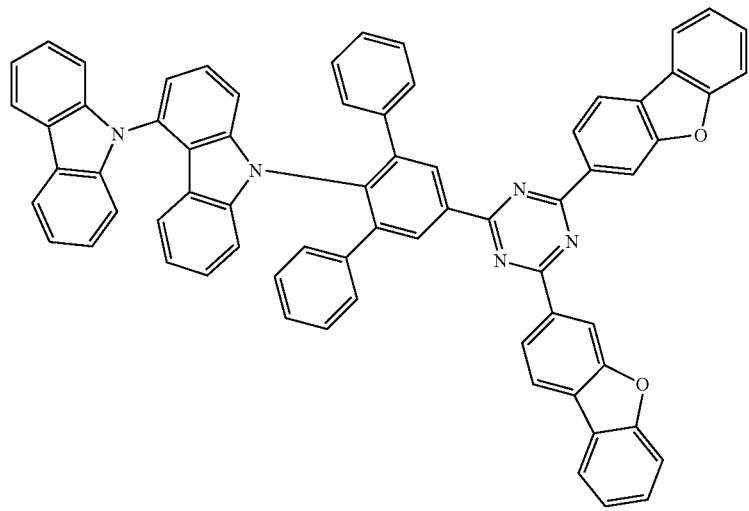
344
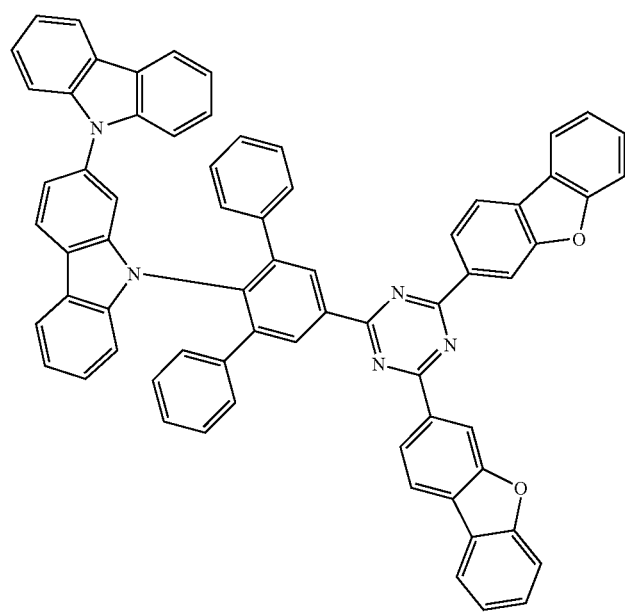

345
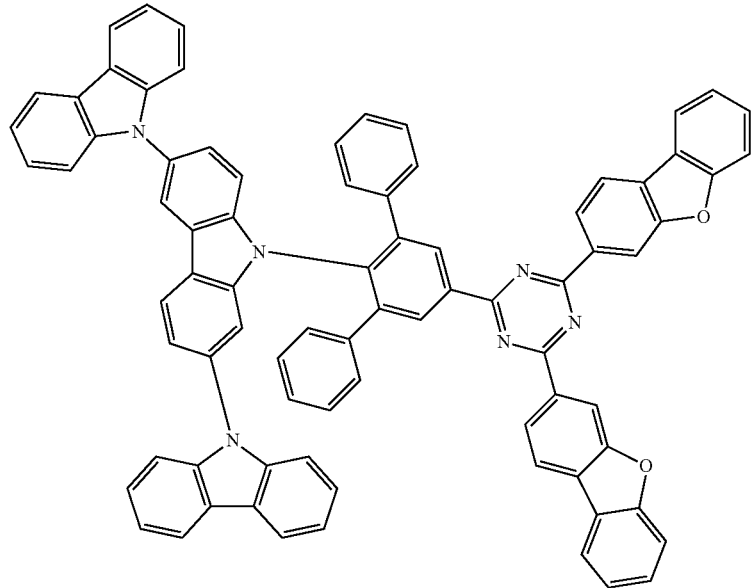
346
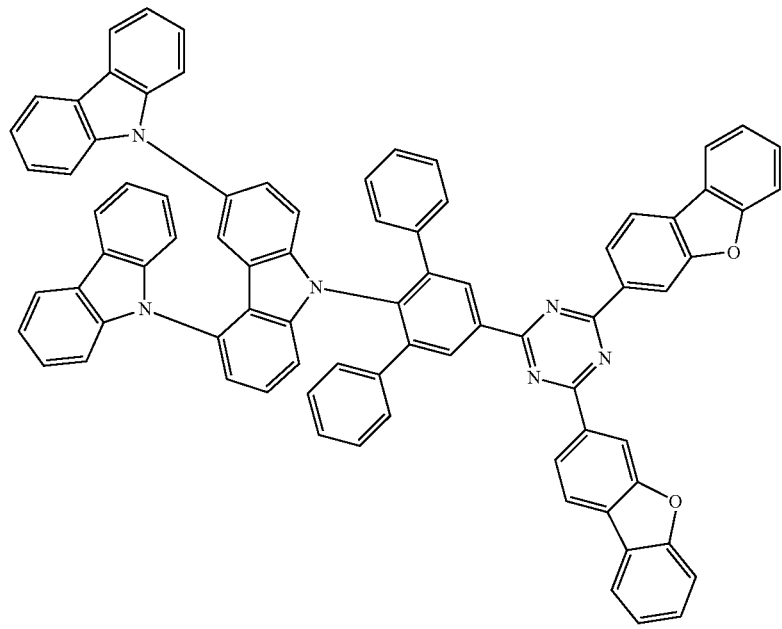

347
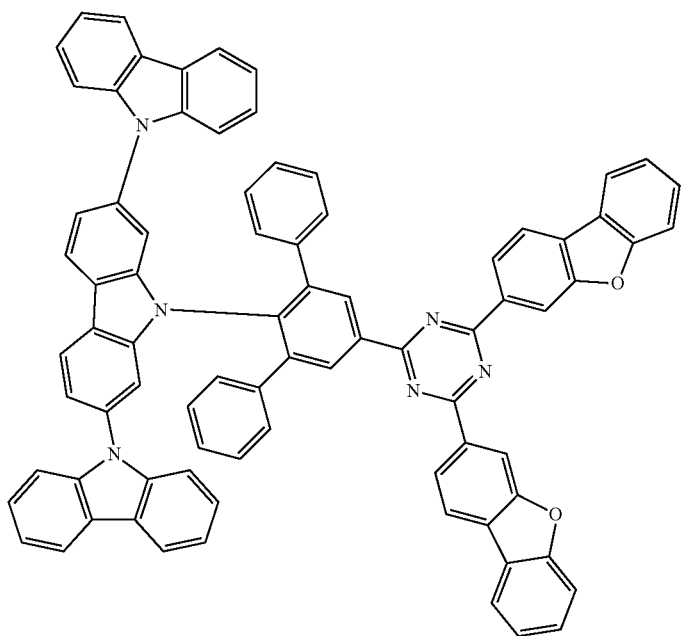
348
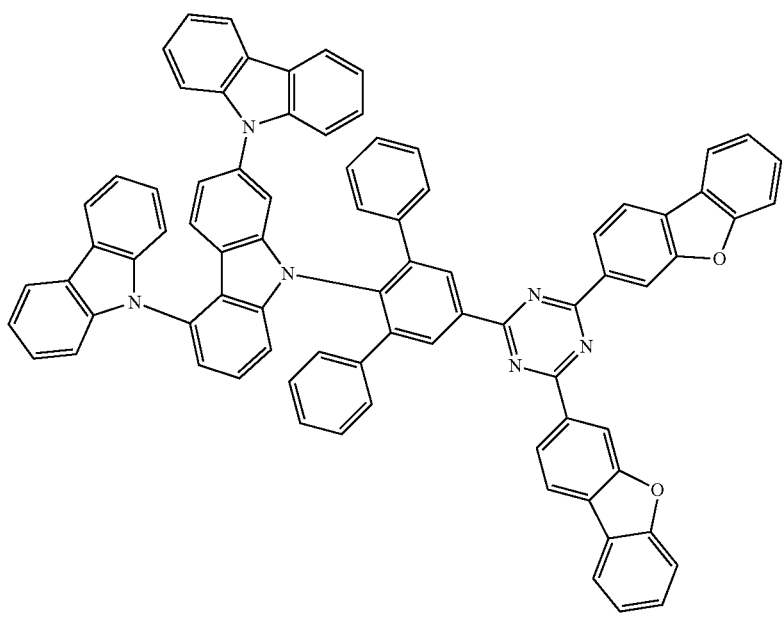

-continued
349
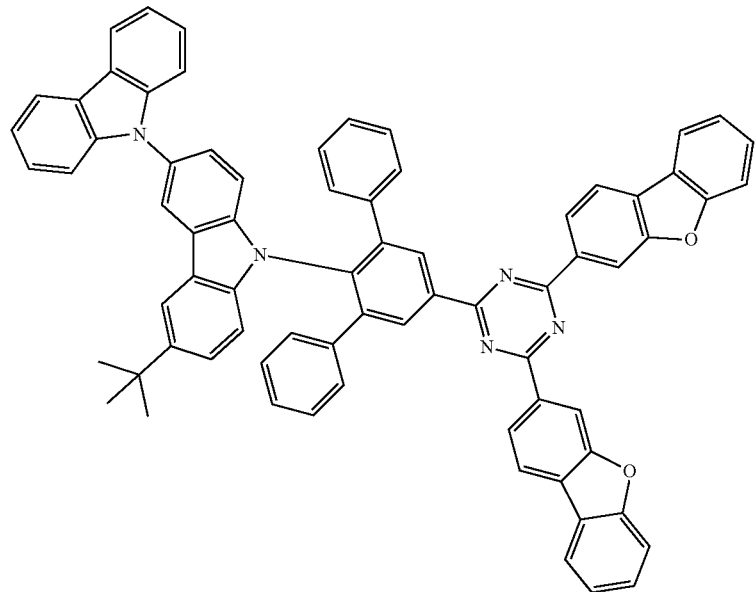
350
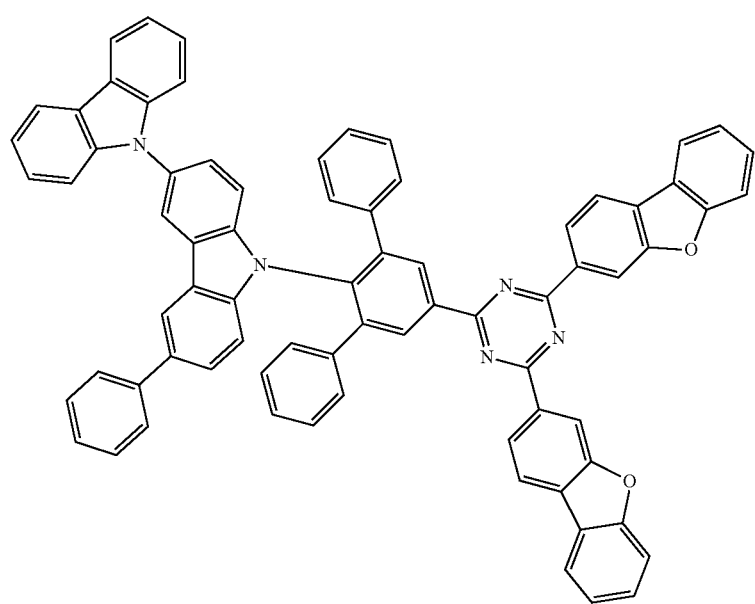

351
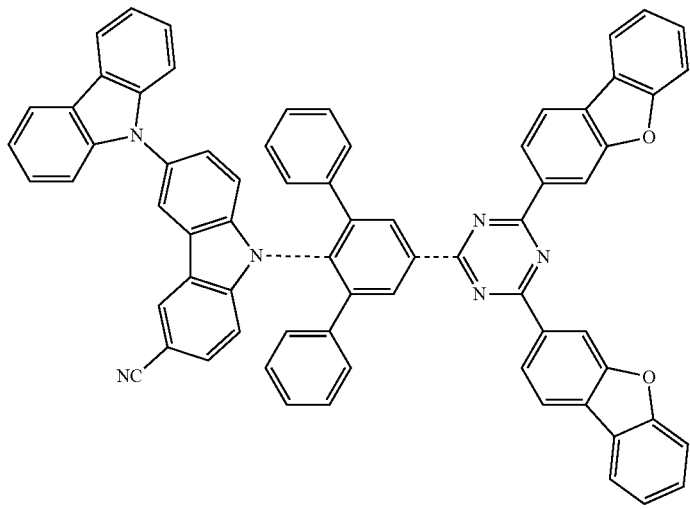
352
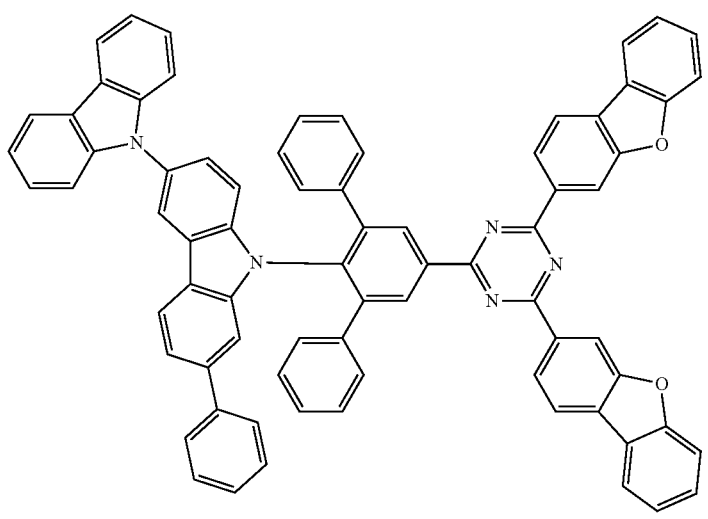
353
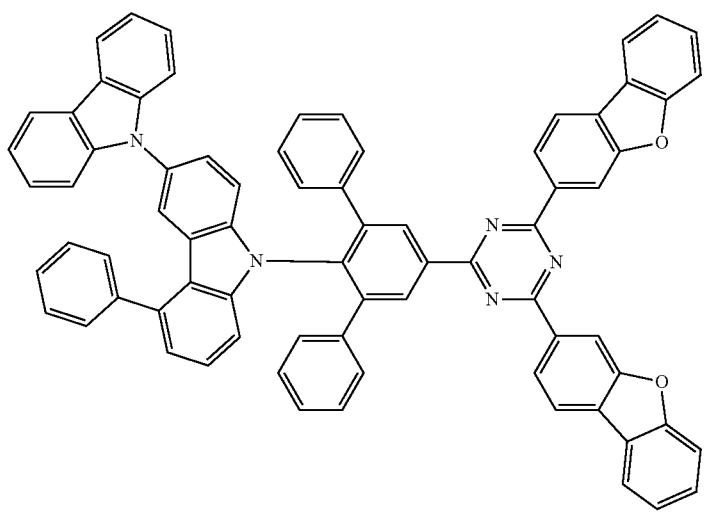

354
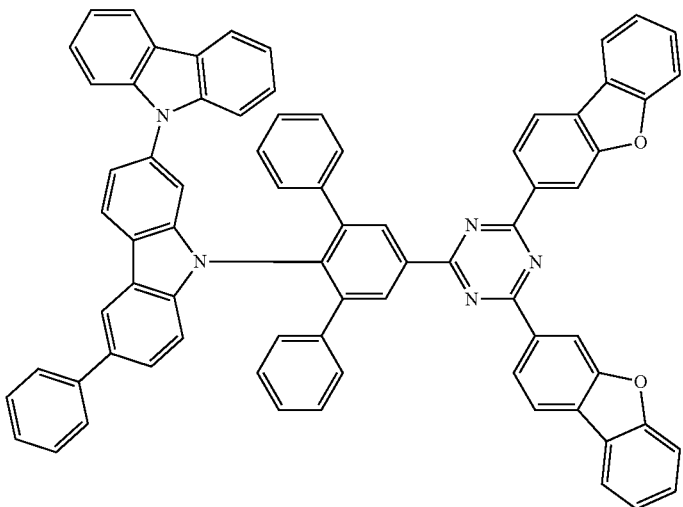
355
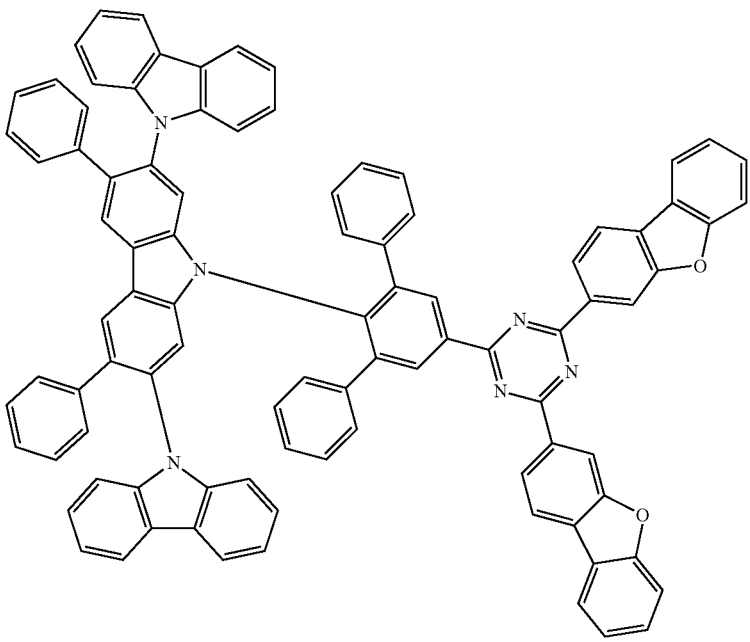
356
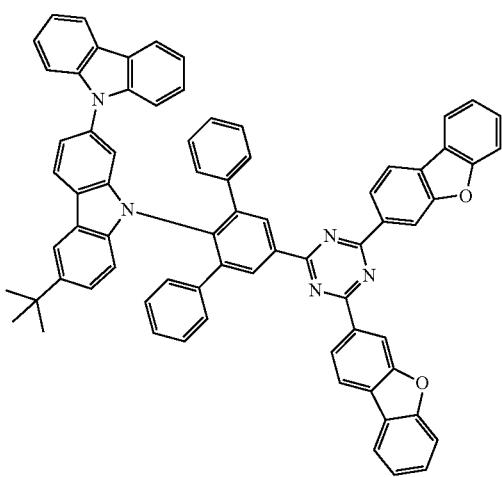
357
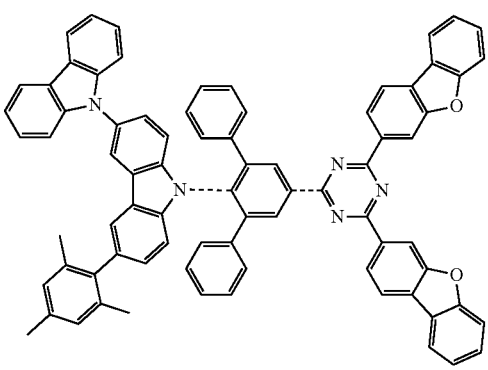

-continued
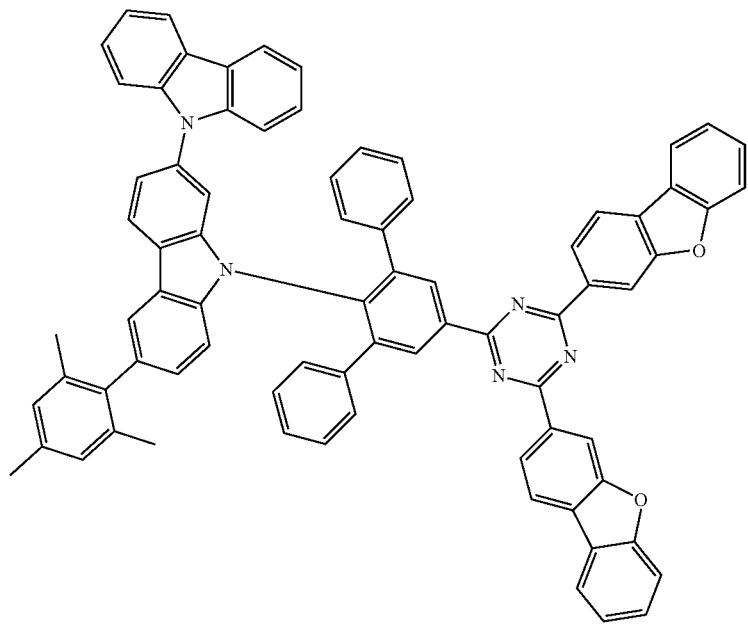
358
359

-continued
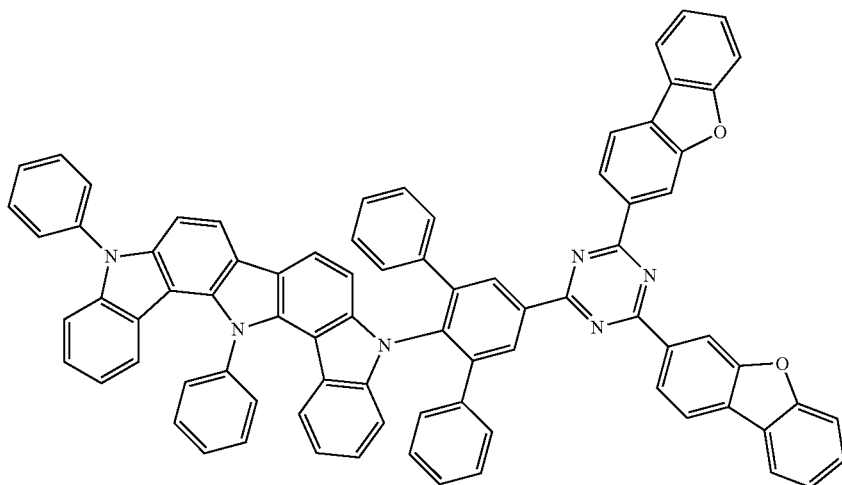
360
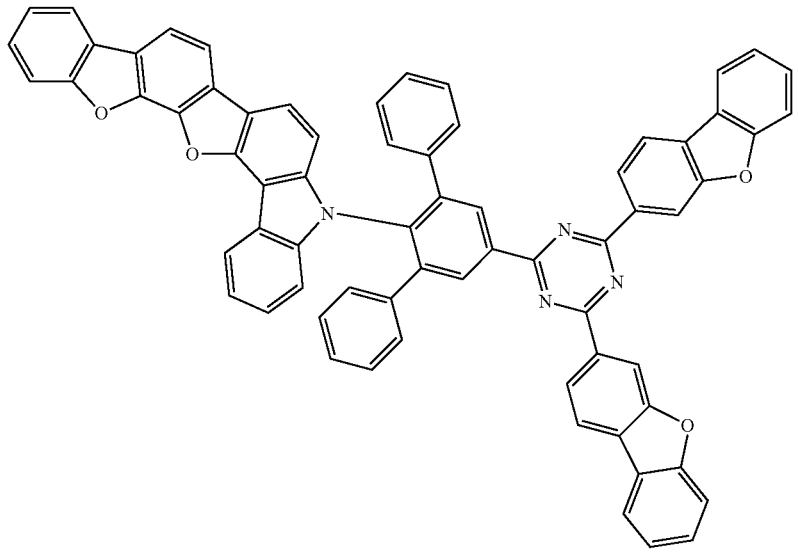
361
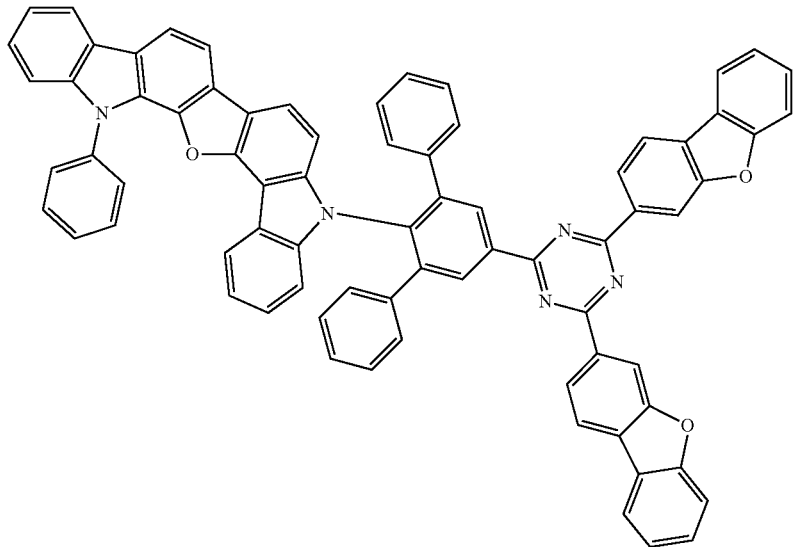
362

363
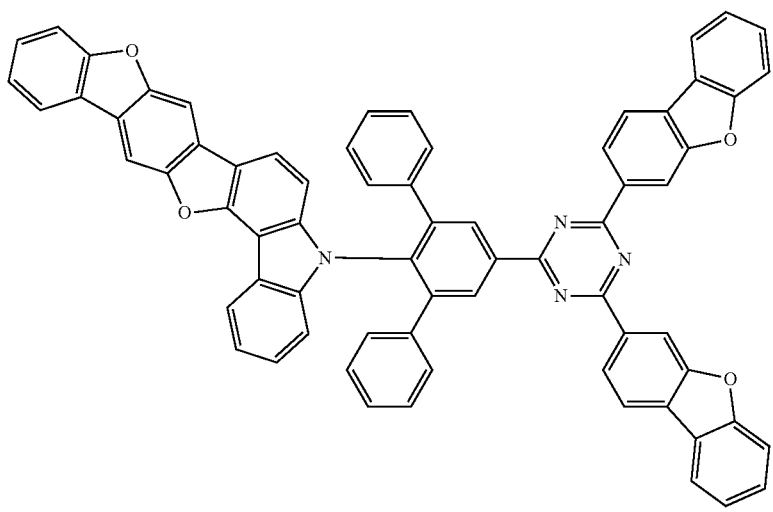
364
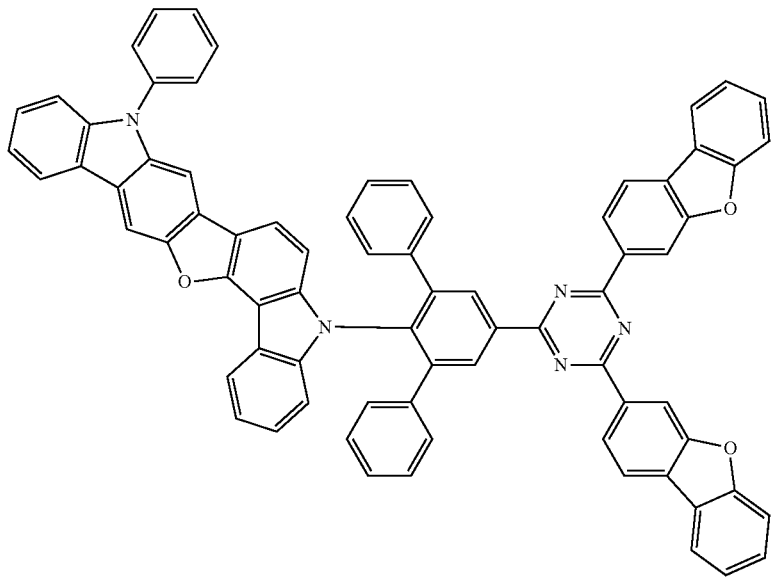
365
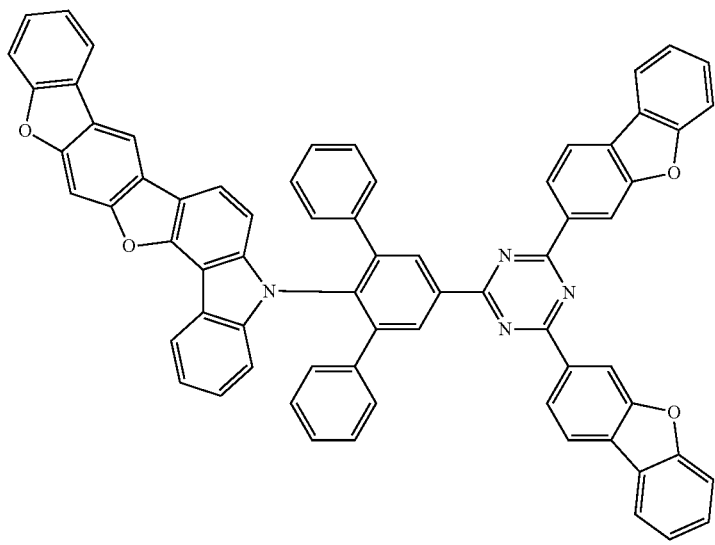

366
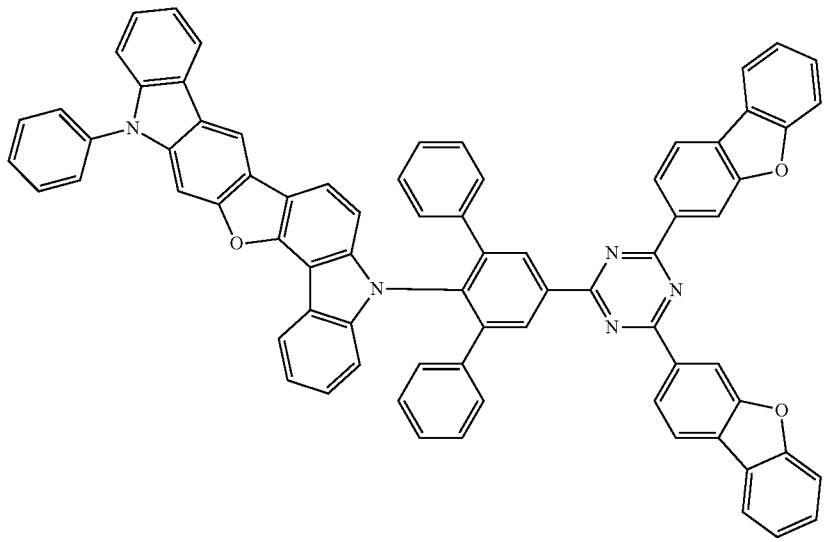
367
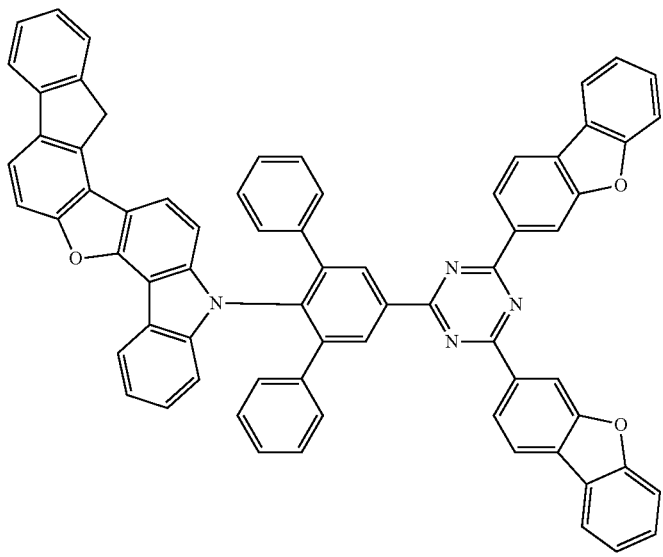
368
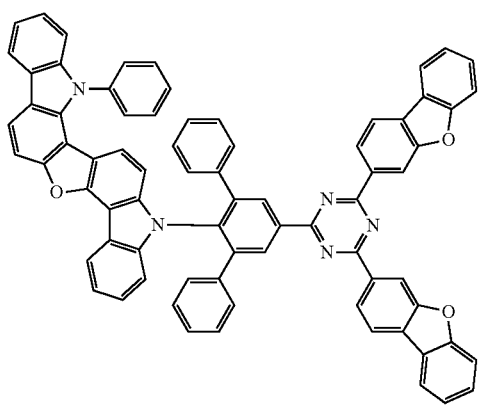
369
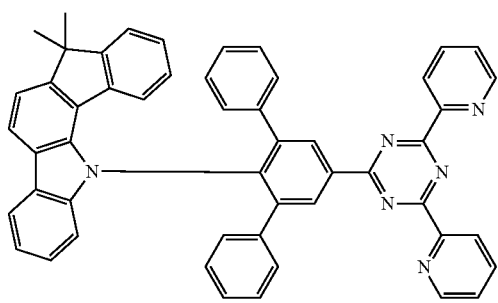

-continued
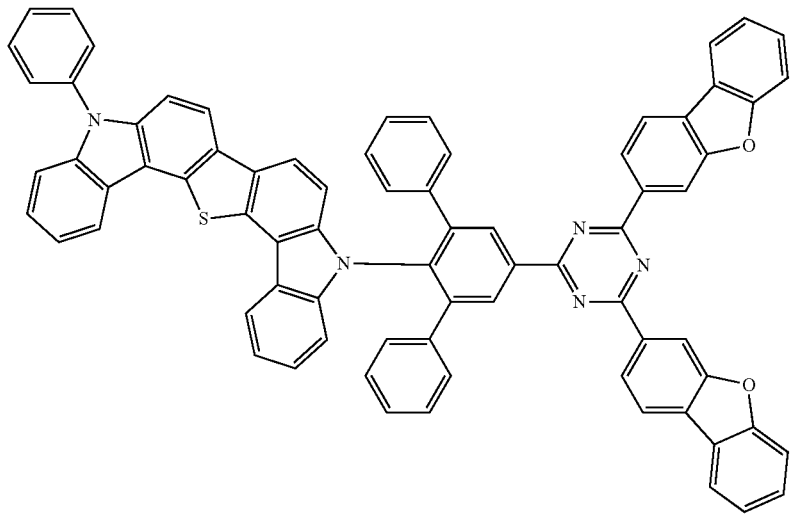
370
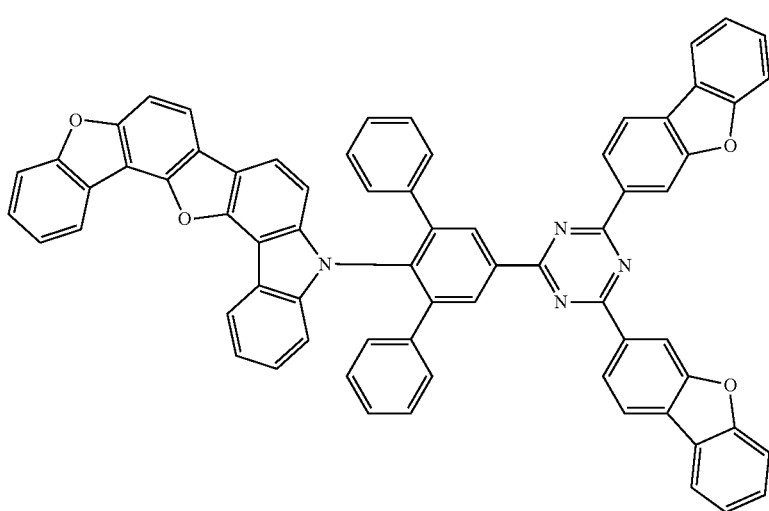
371
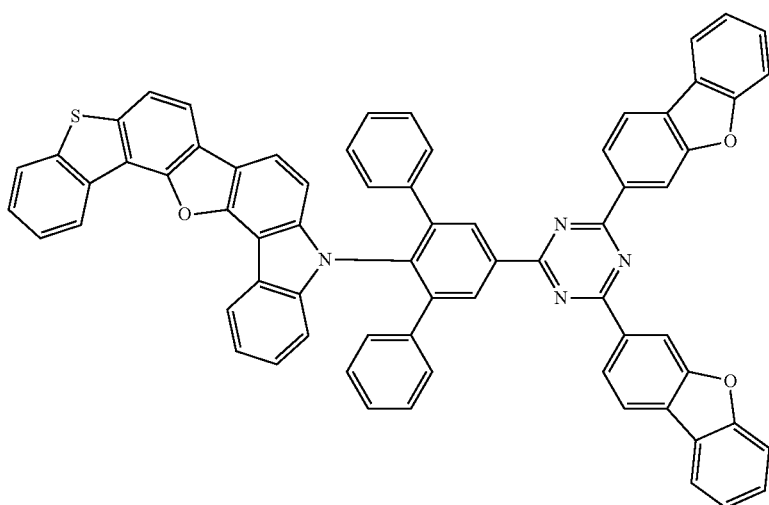
372

373
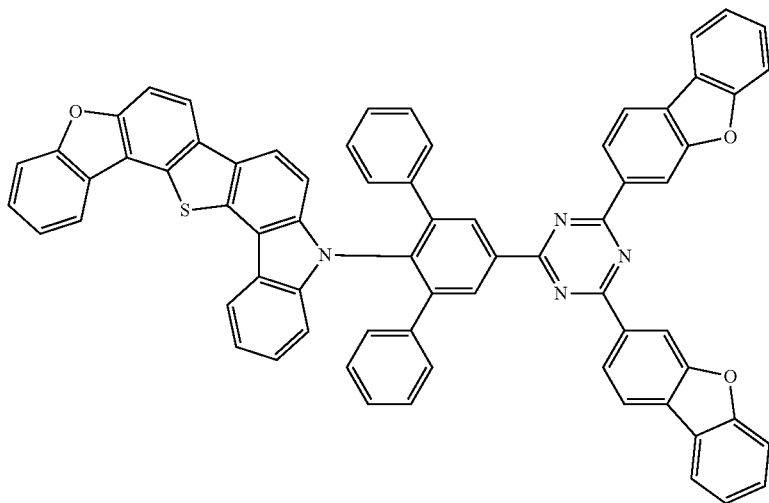
374
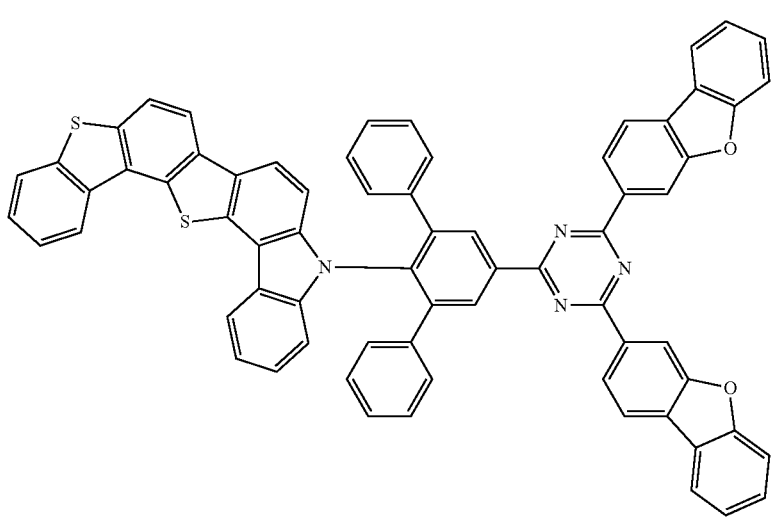
375
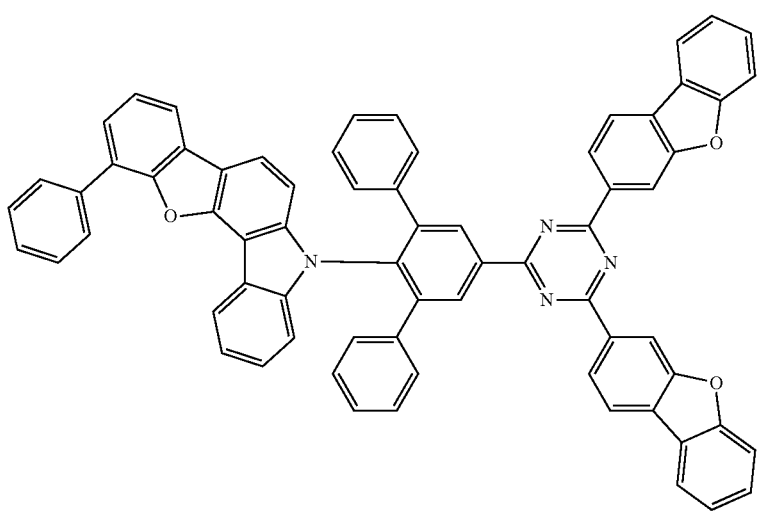

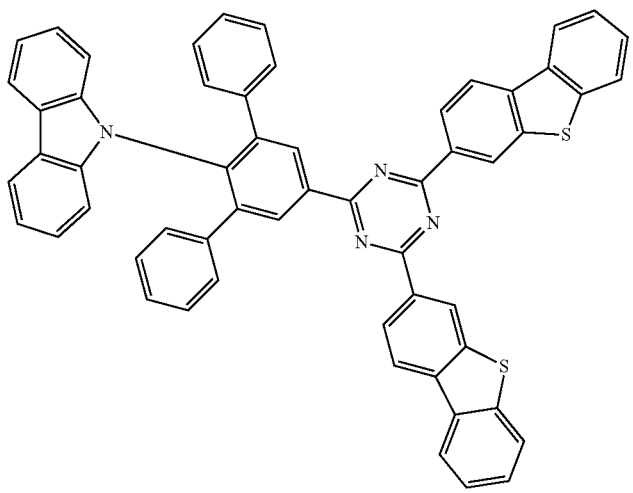
376
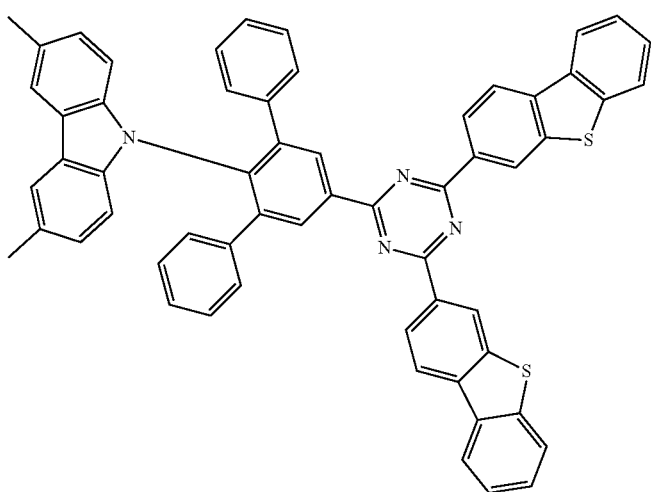
377
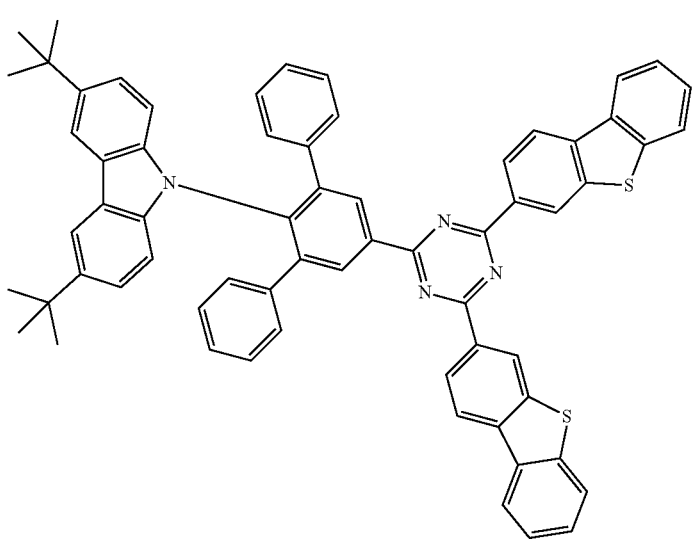
378

379
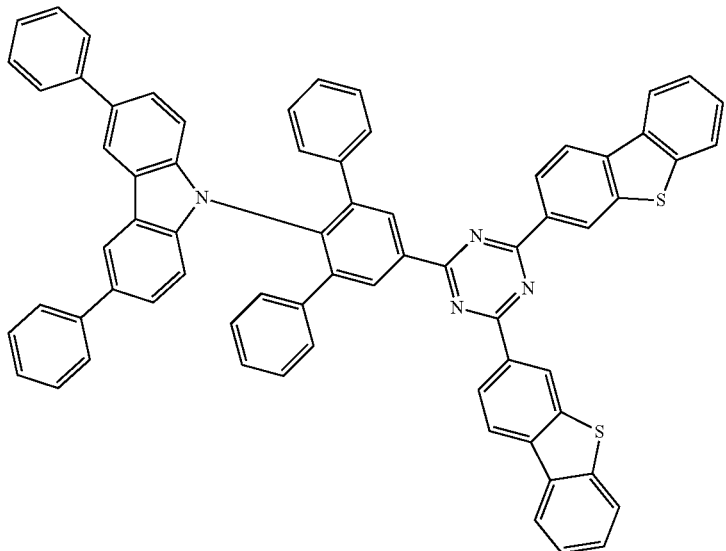
380
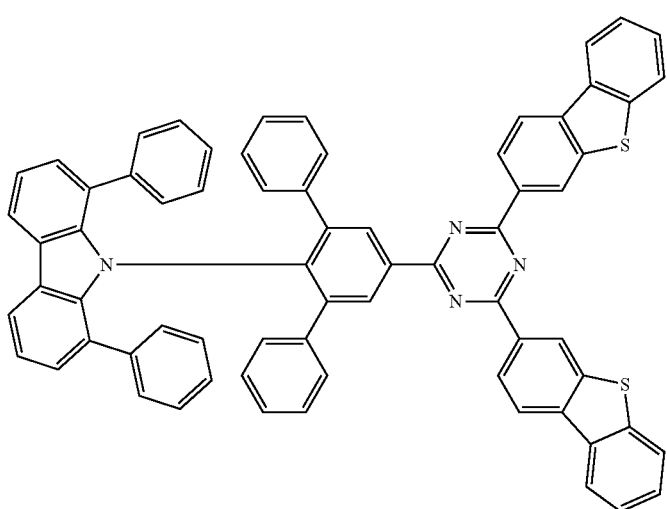
381
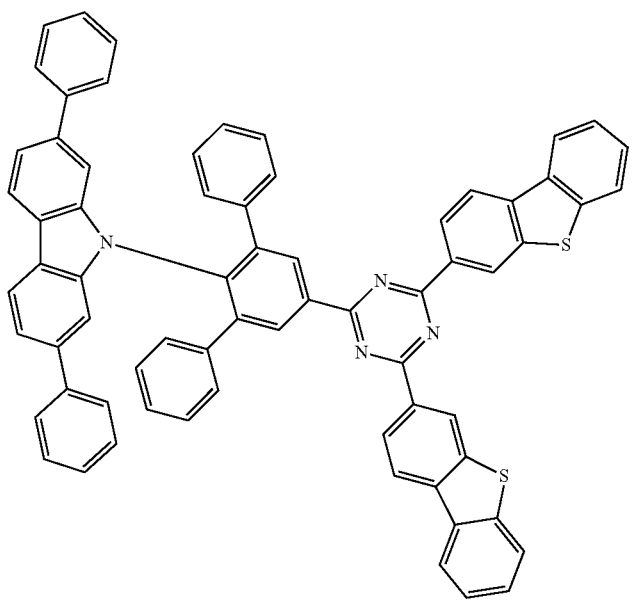

382
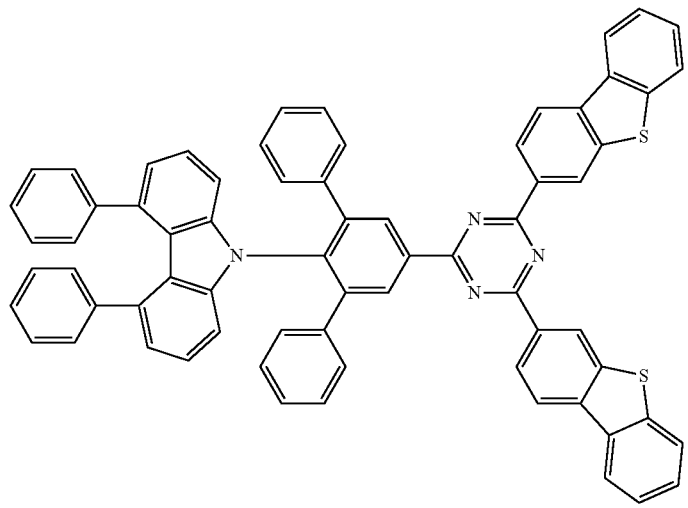
383
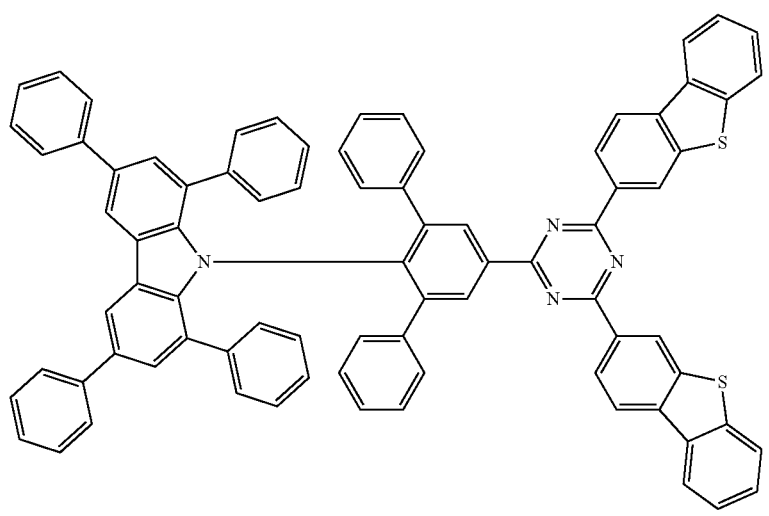
384
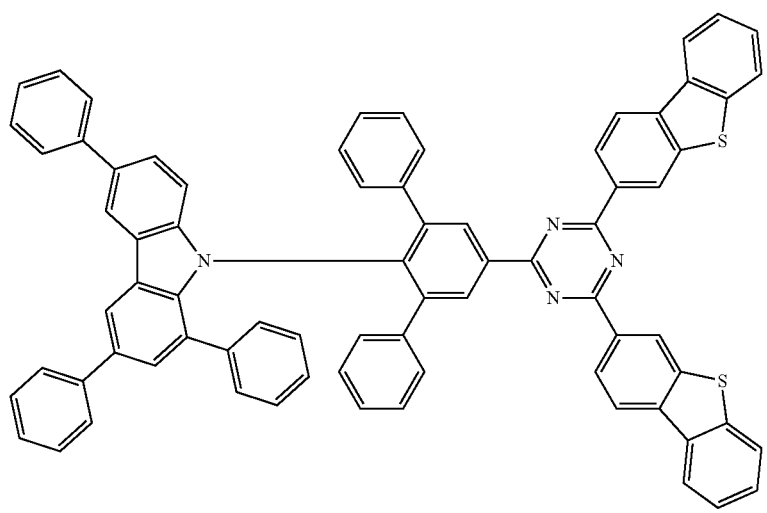

385
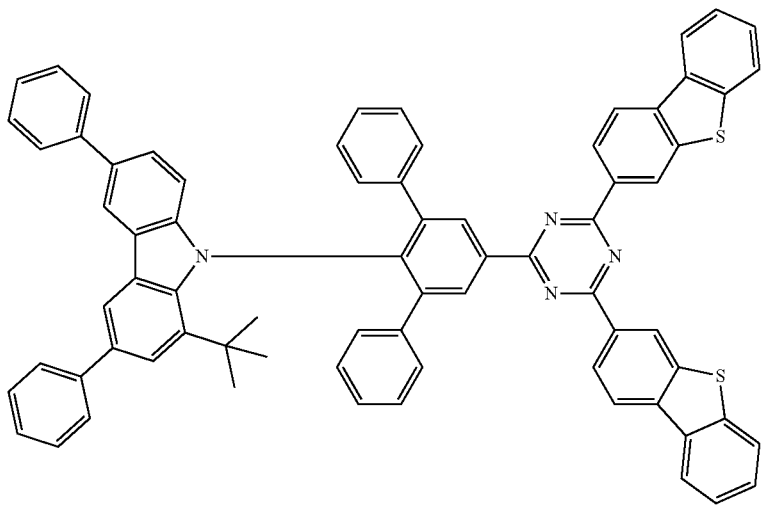
386
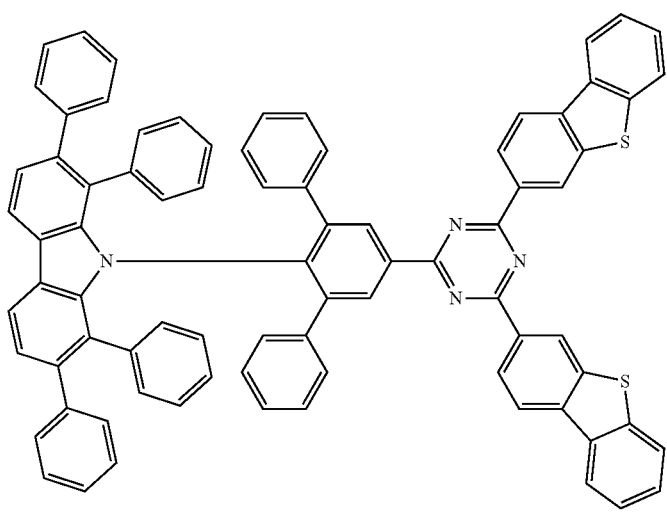
387
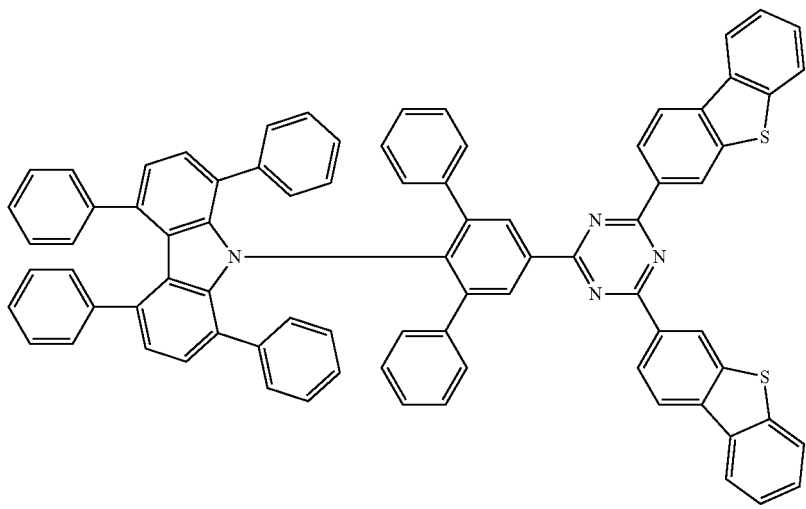

388
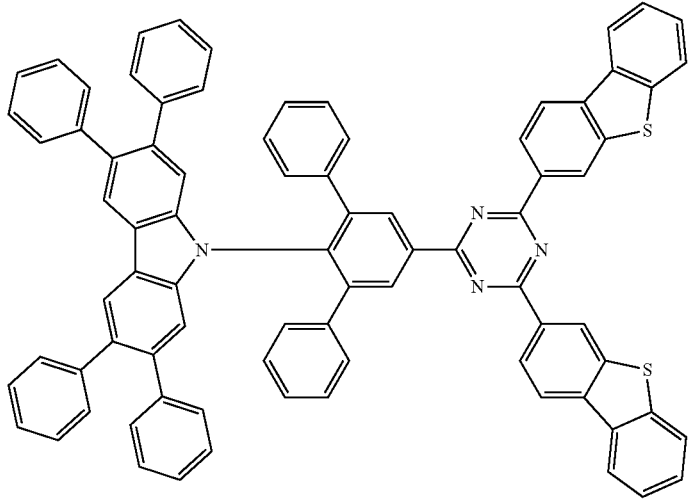
389
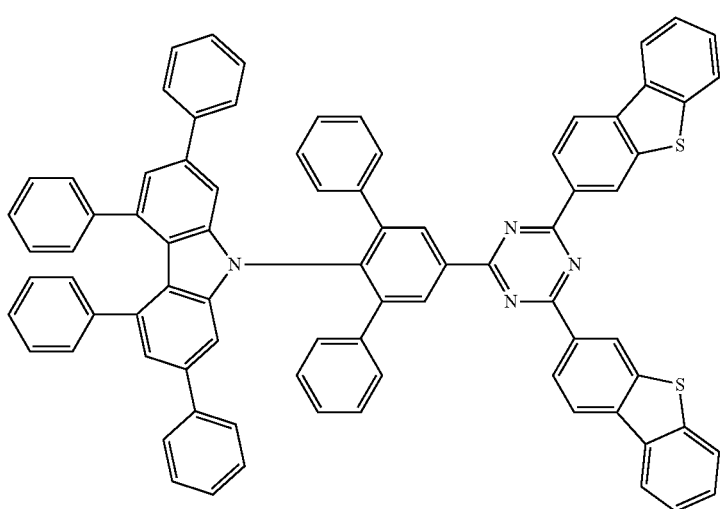
390
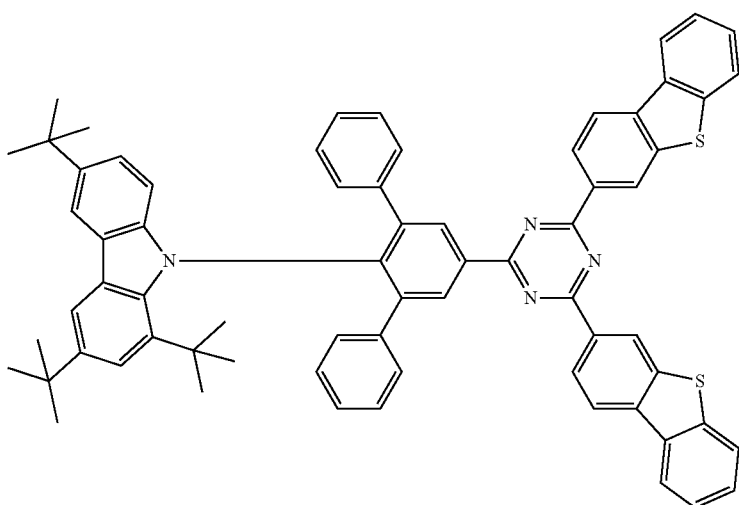

-continued
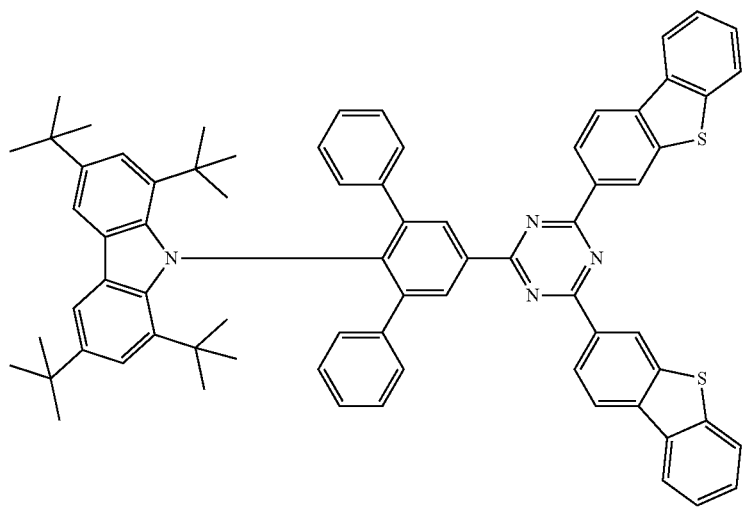
391
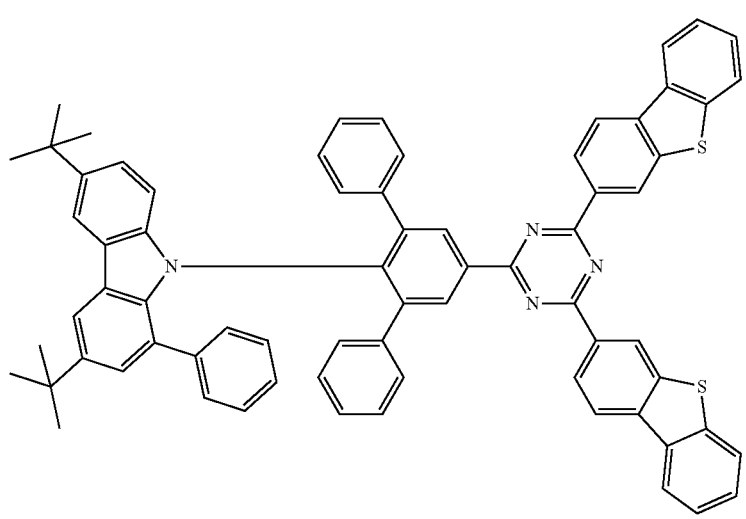
392
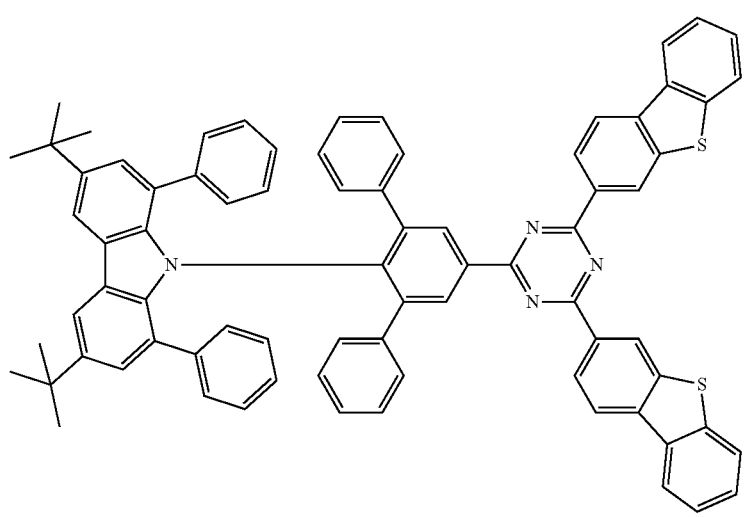
393

394
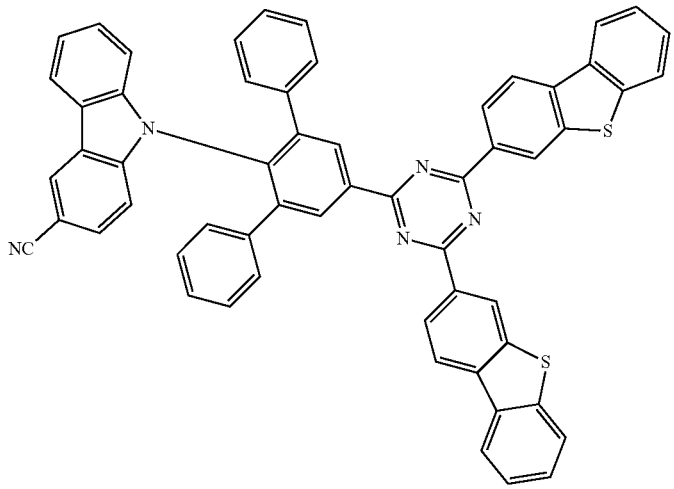
395
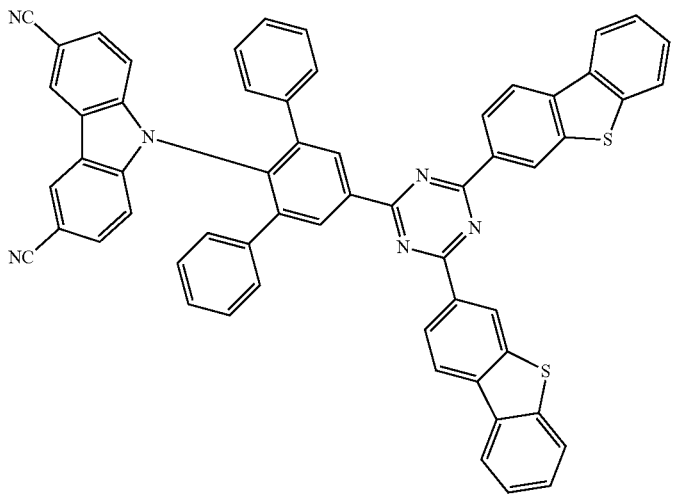
396
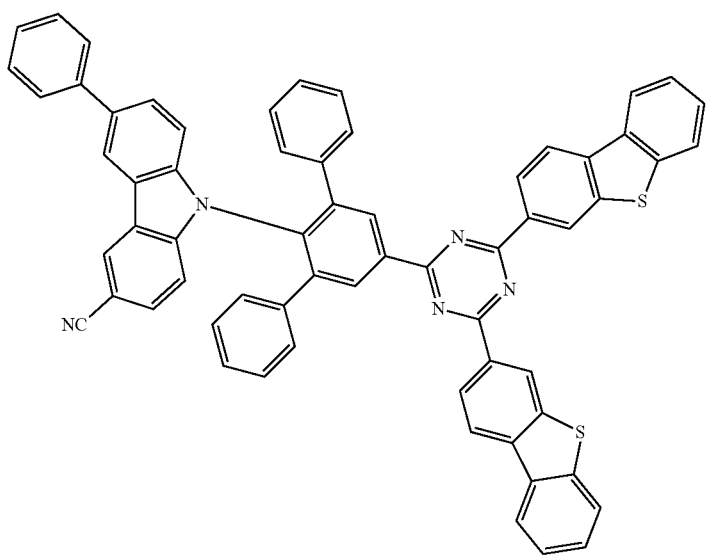

397
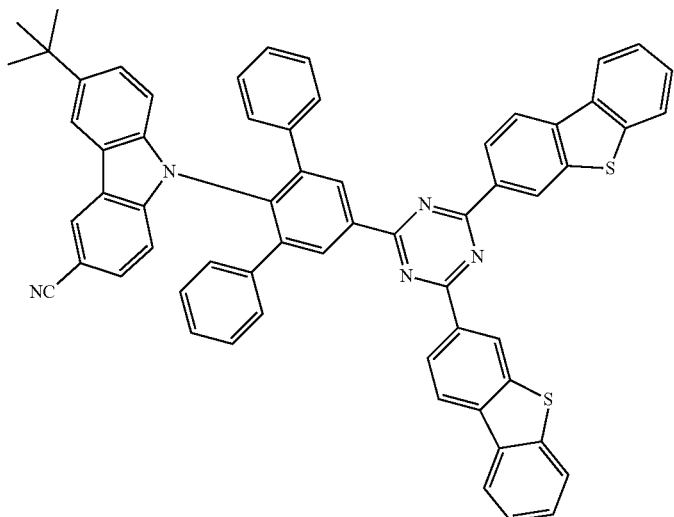
398
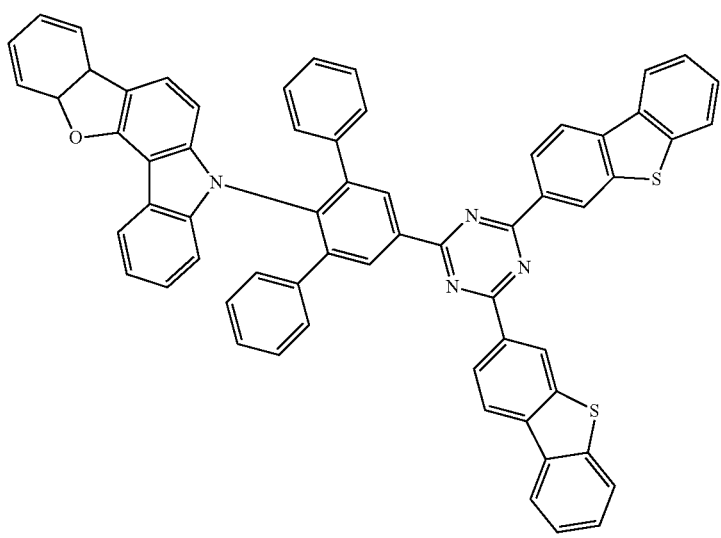
399
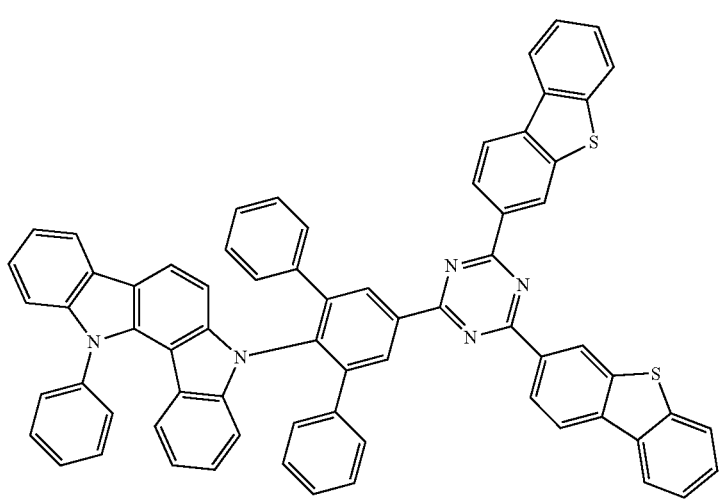

-continued
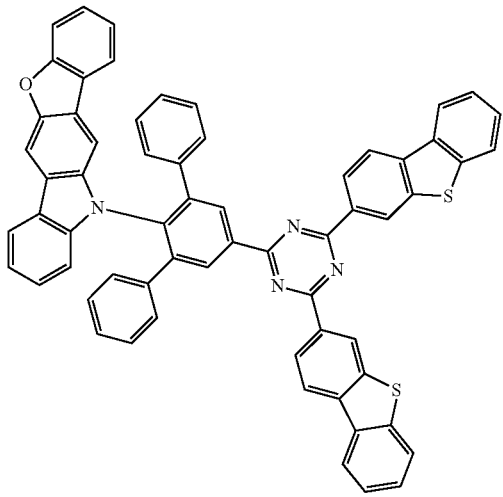
400
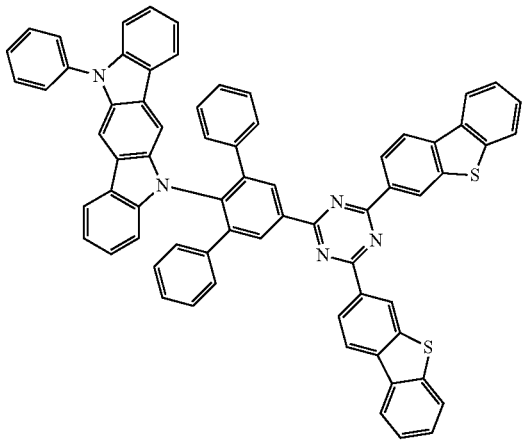
401
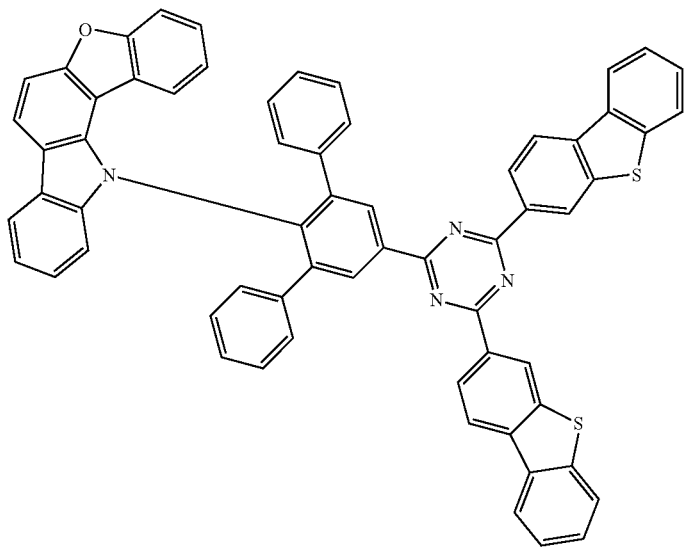
402
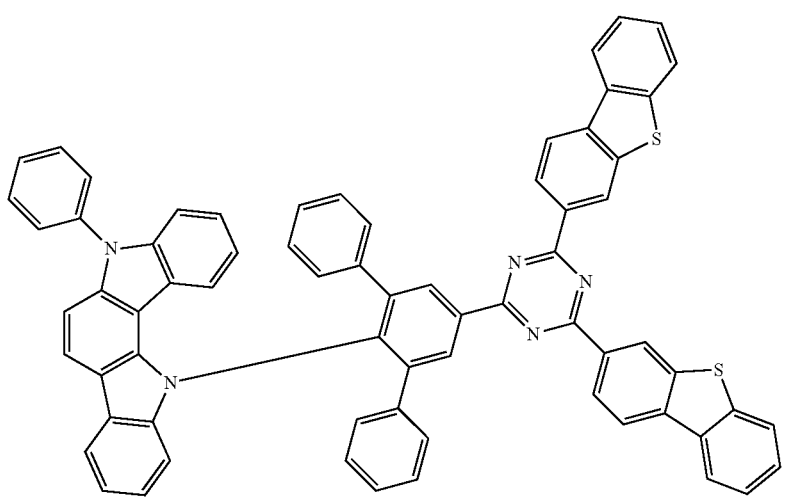
403

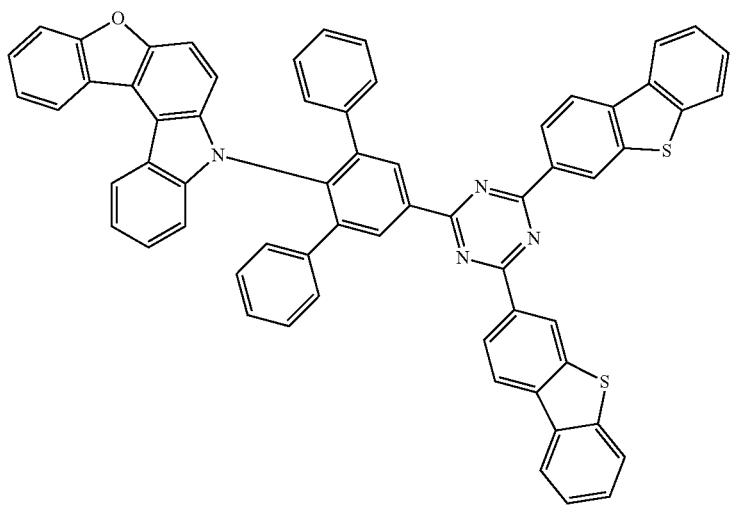
404
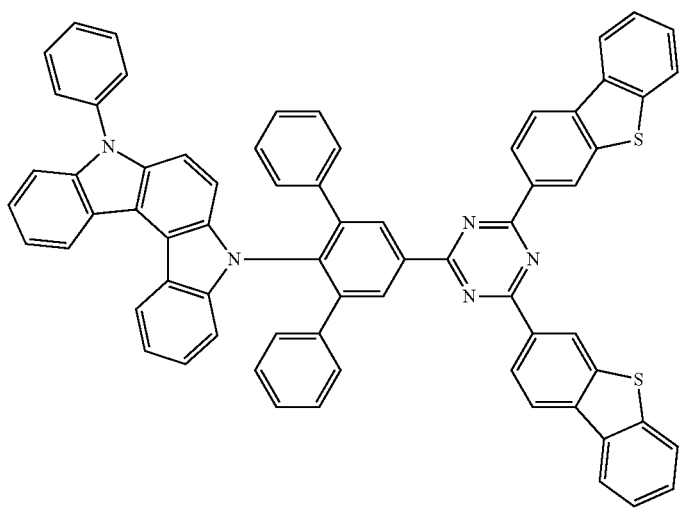
405
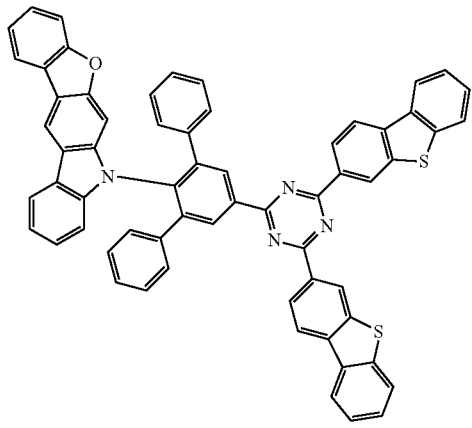
406
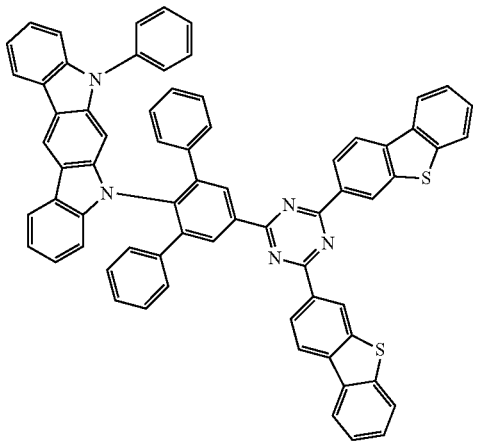
407

408
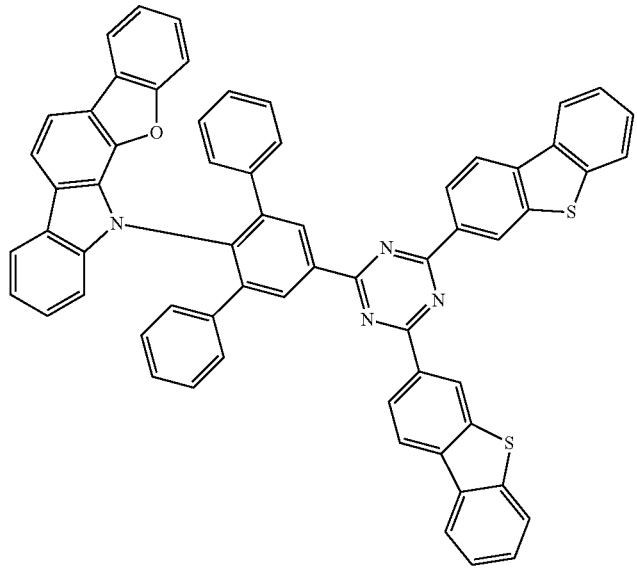
409
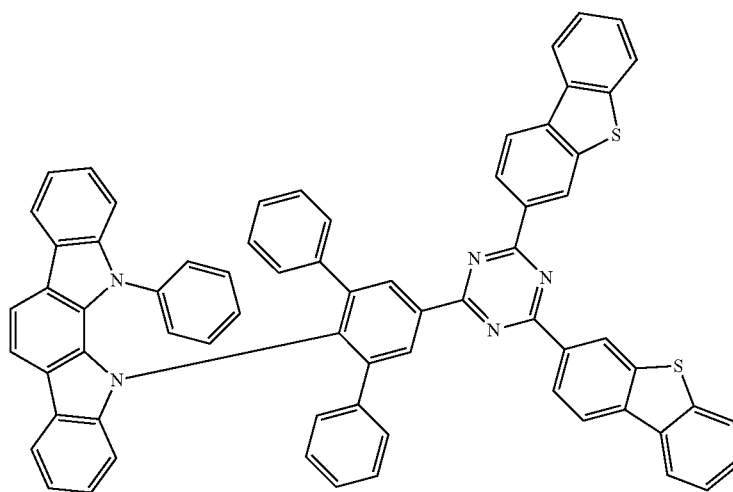
410
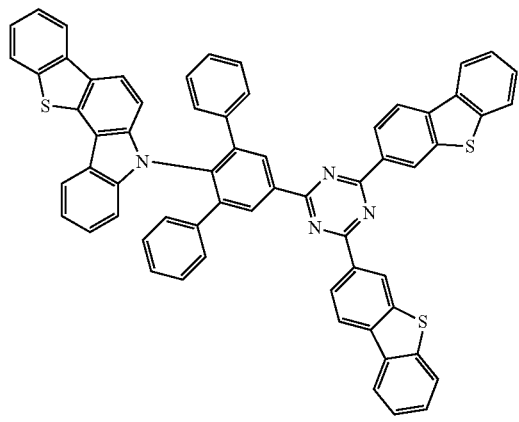
411
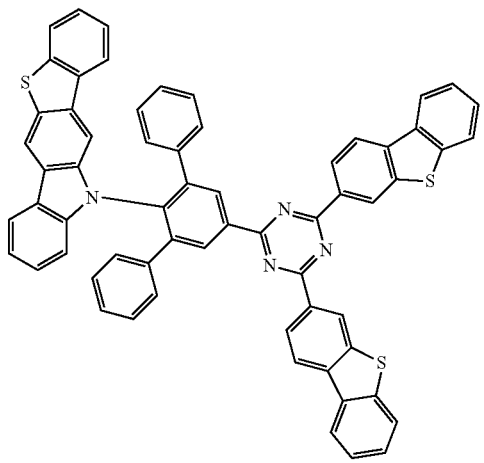

412
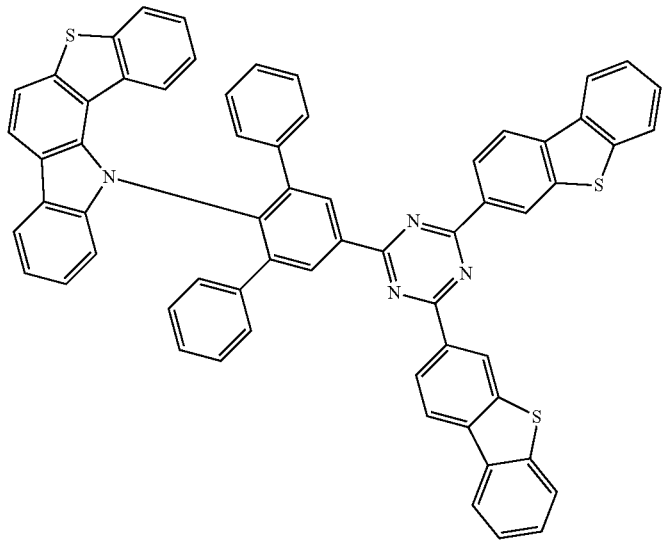
413
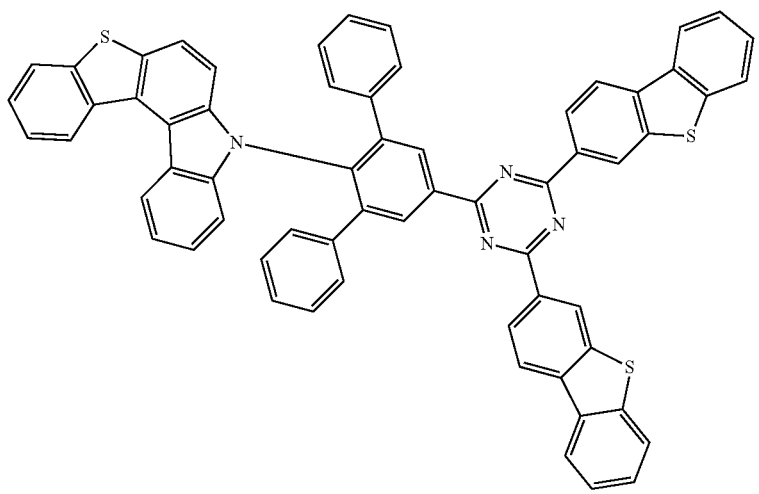
414
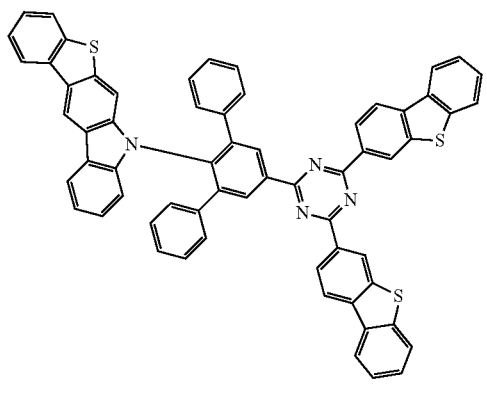
415
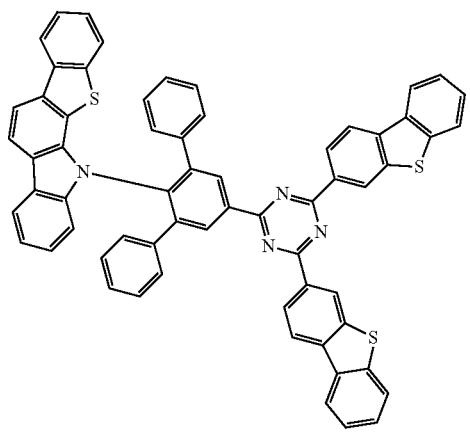

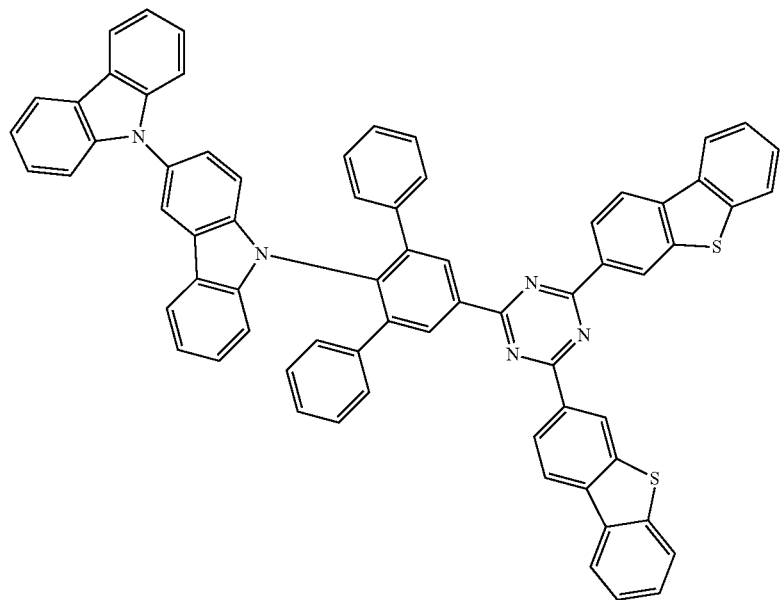
416
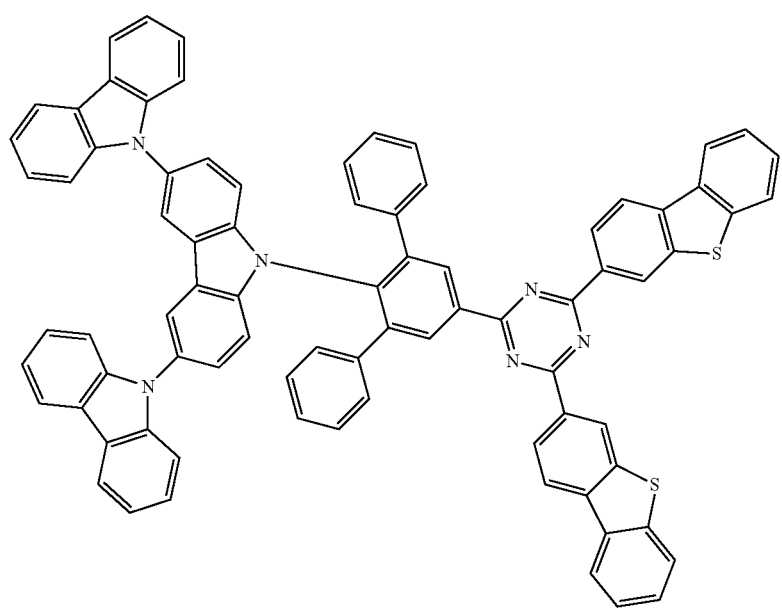
417

-continued
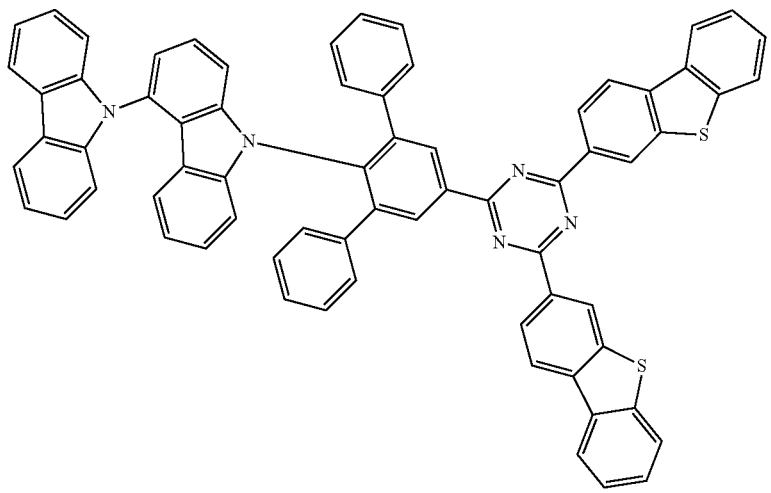
418
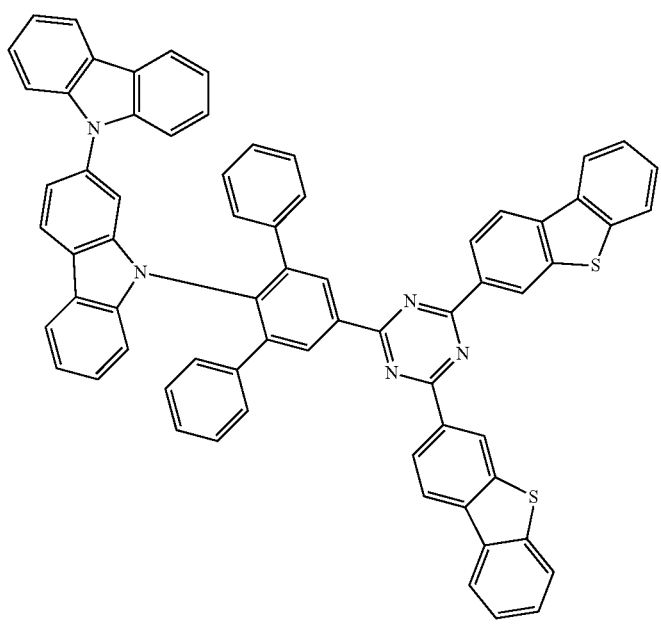
419

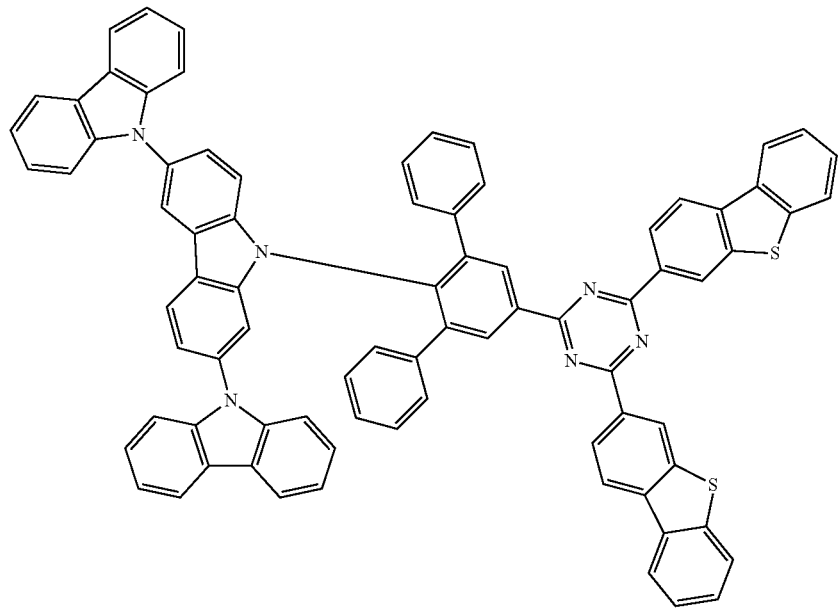
420
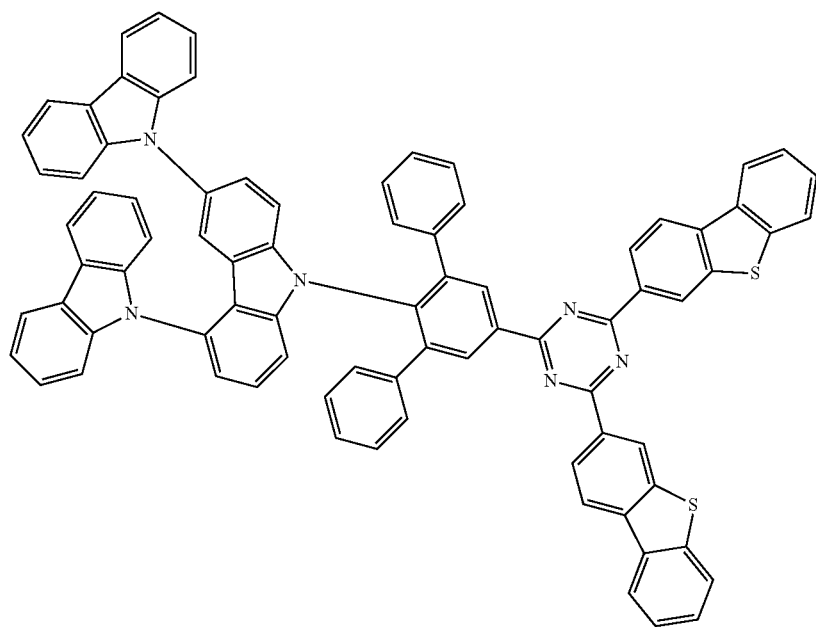
421

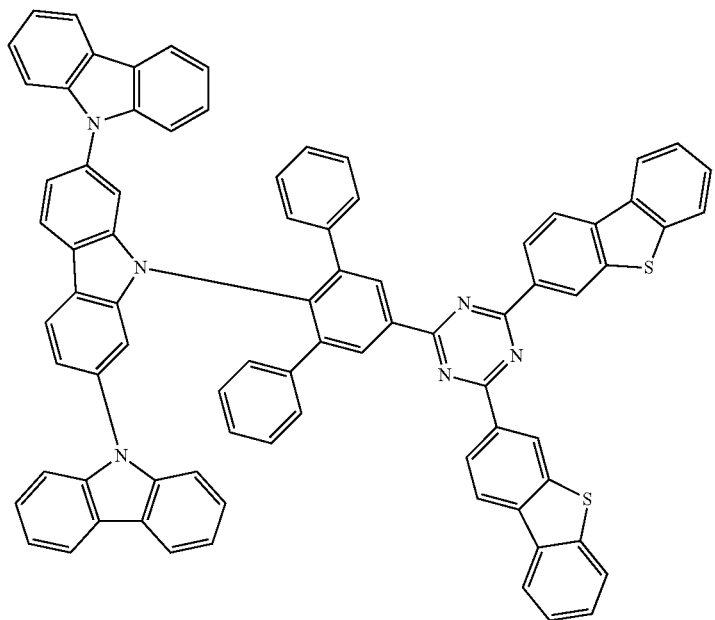
422
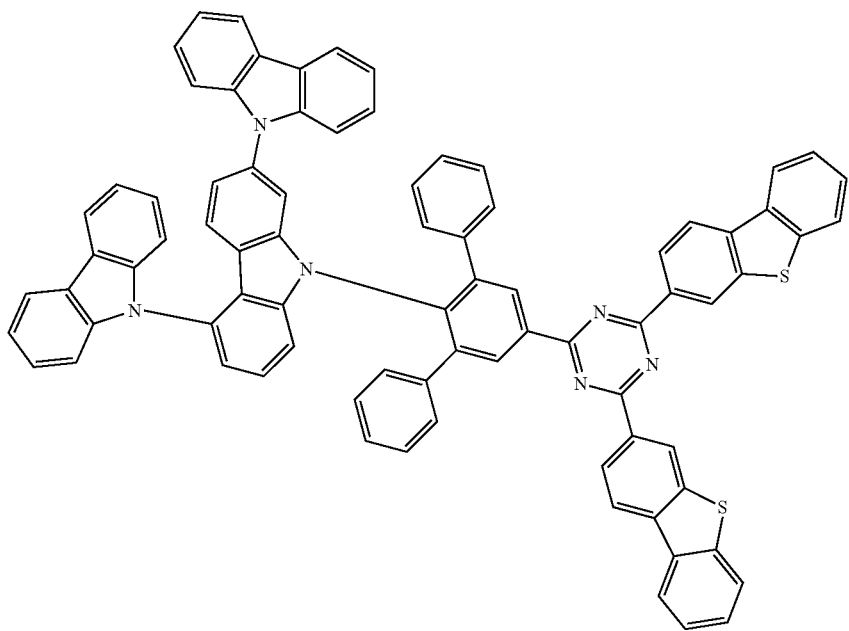
423

-continued
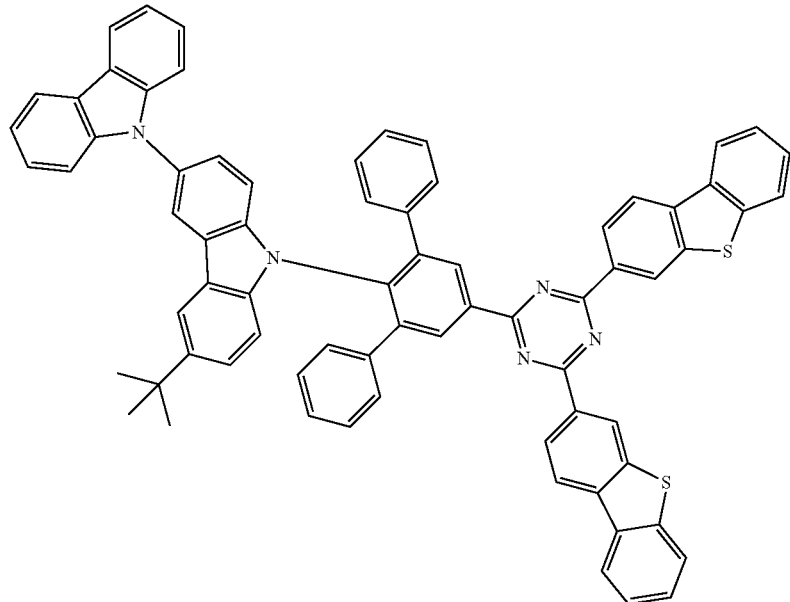
424
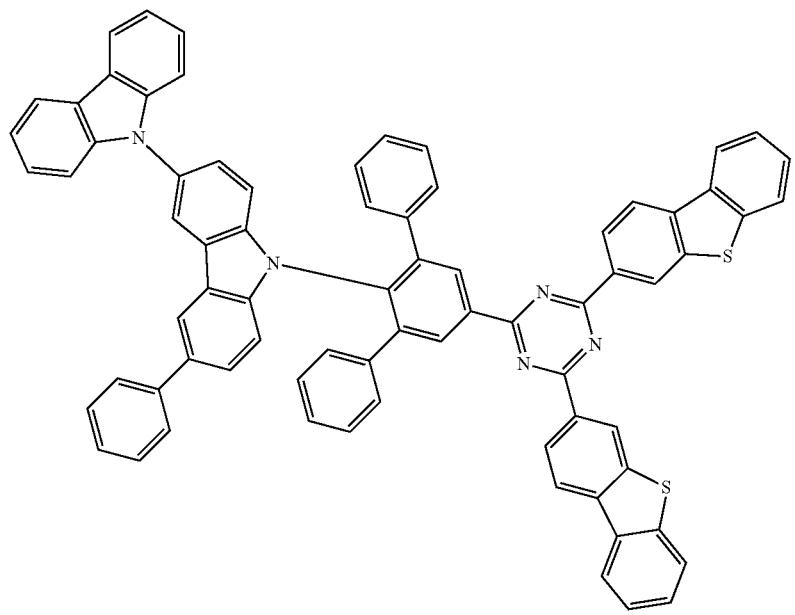
425

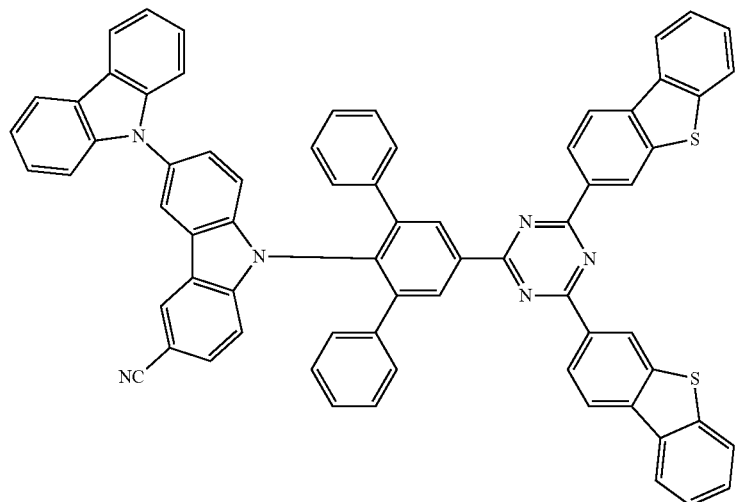
426
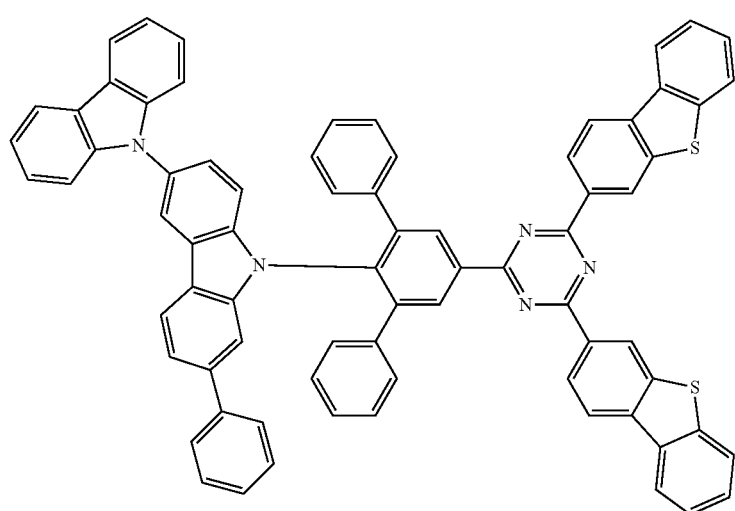
427
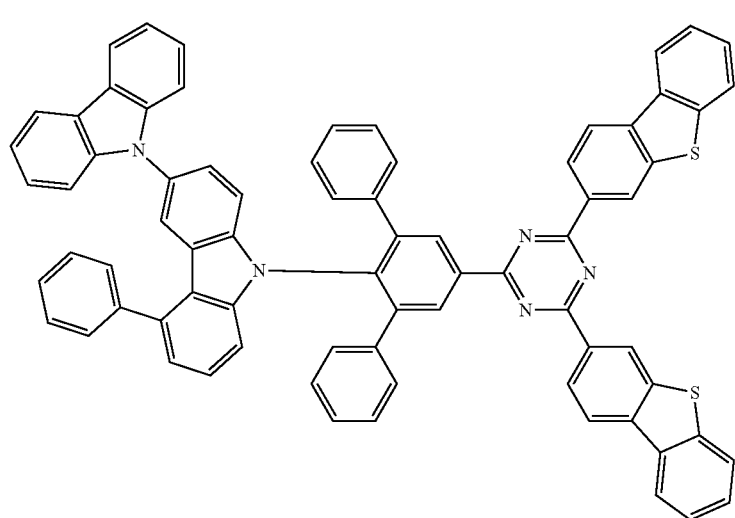
428

-continued
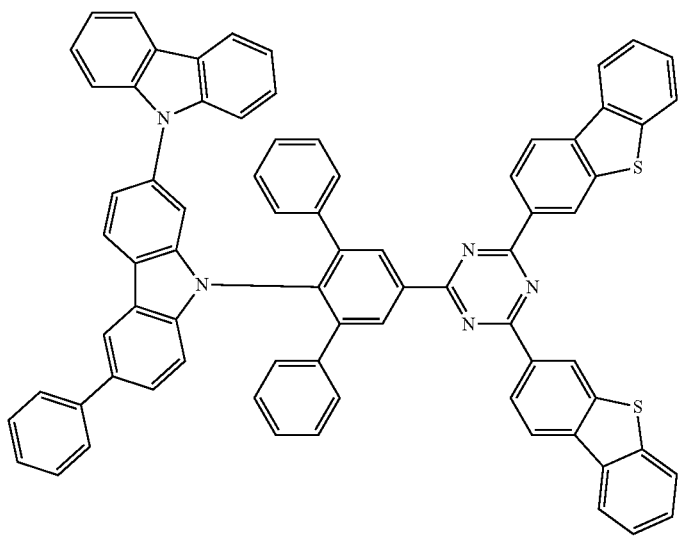
429
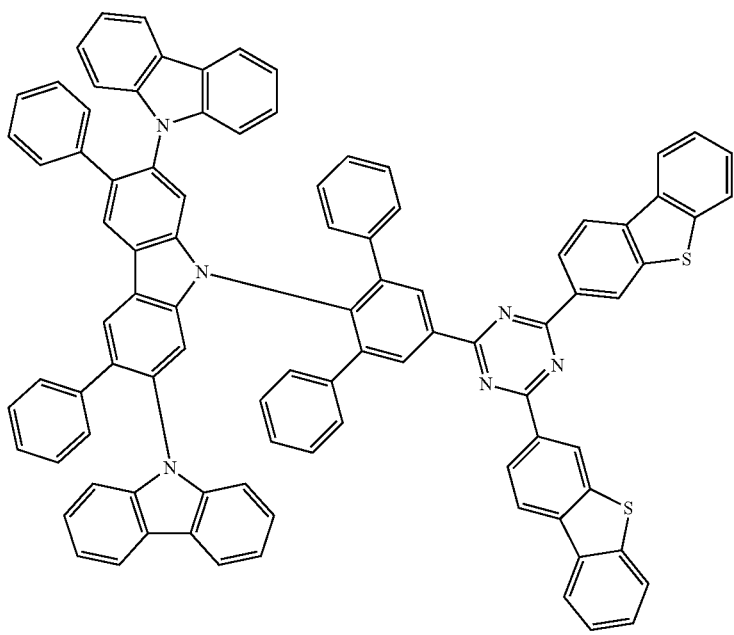
430

431
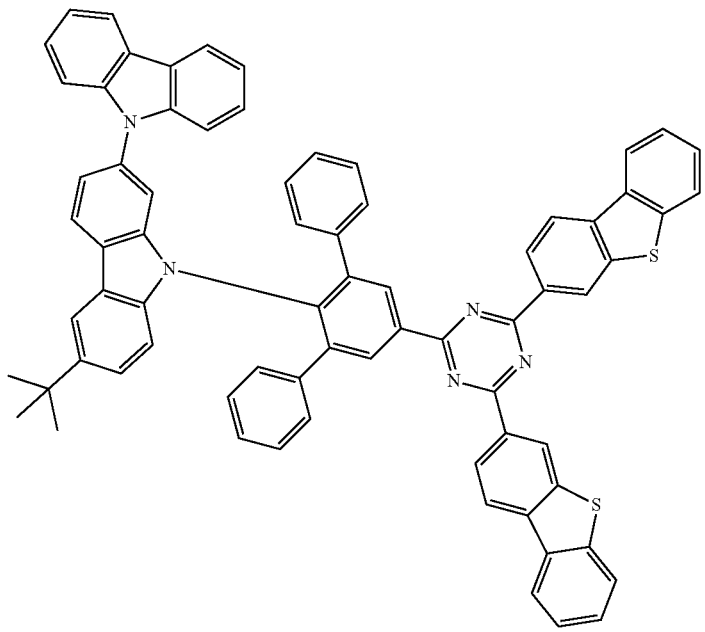
432
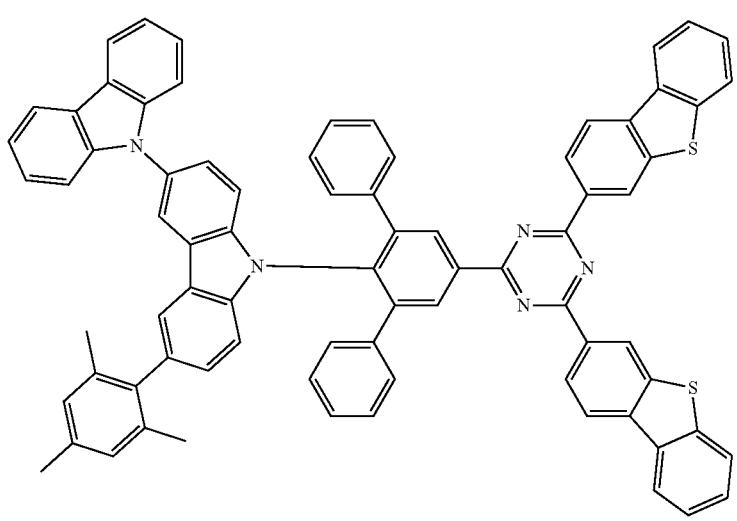

433
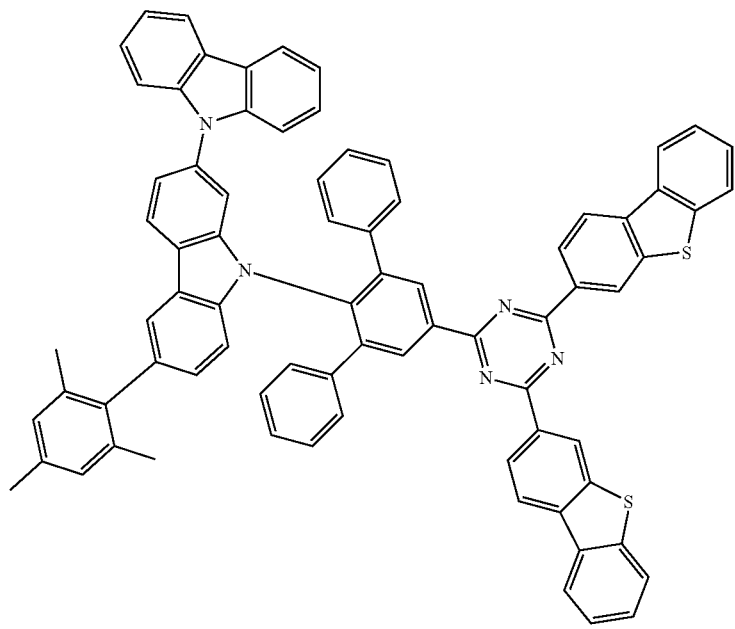
434
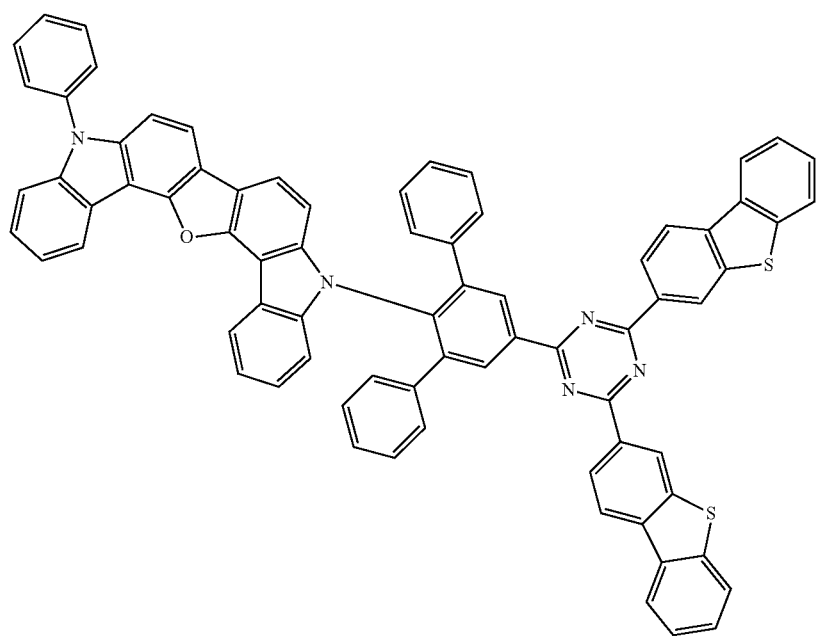

435
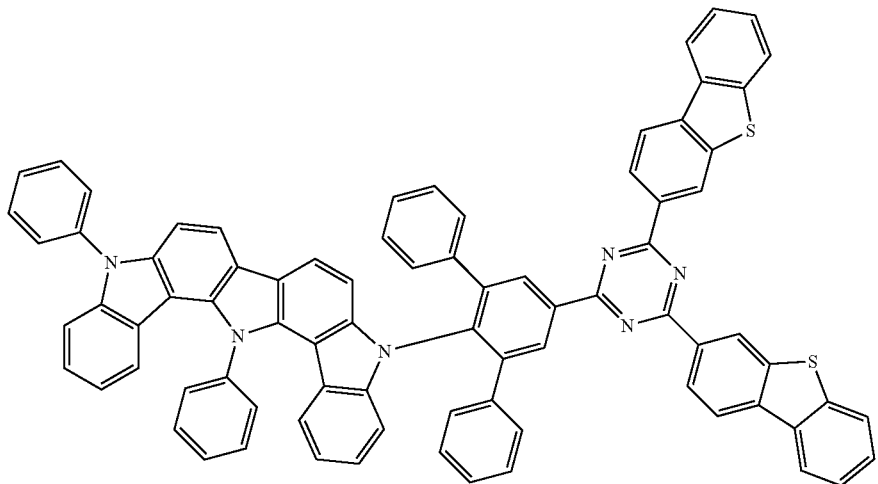
436
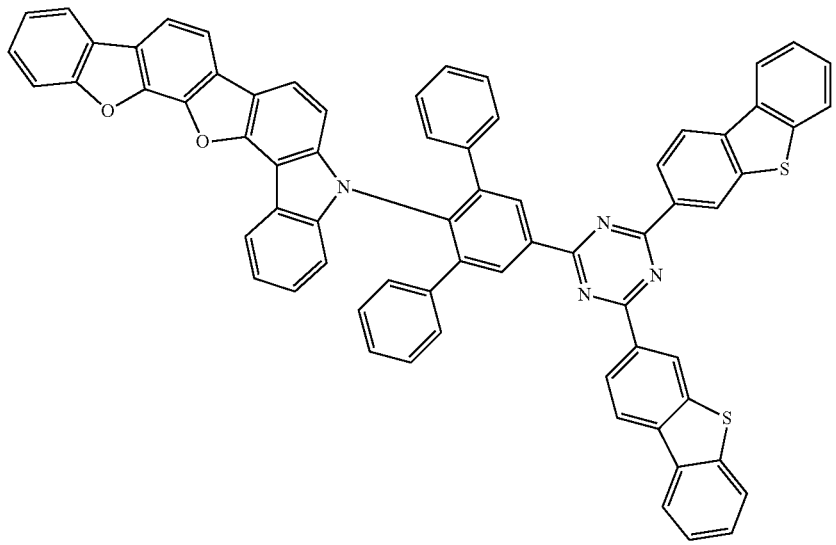
437
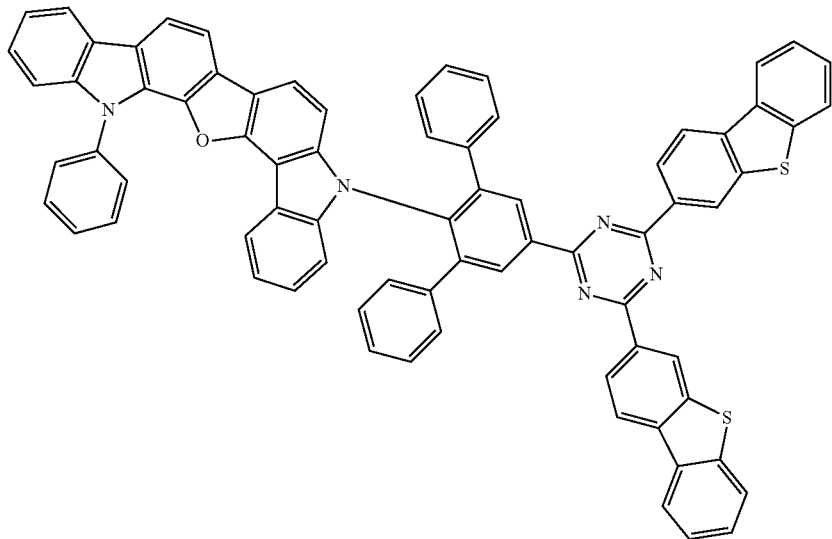

438
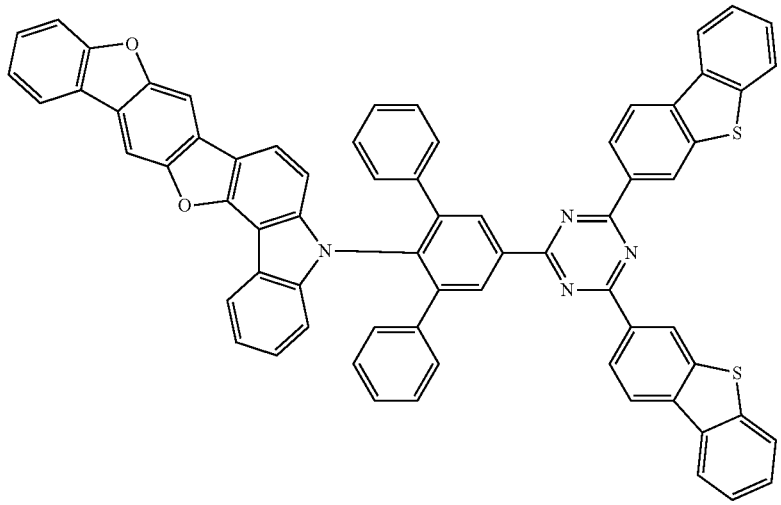
439
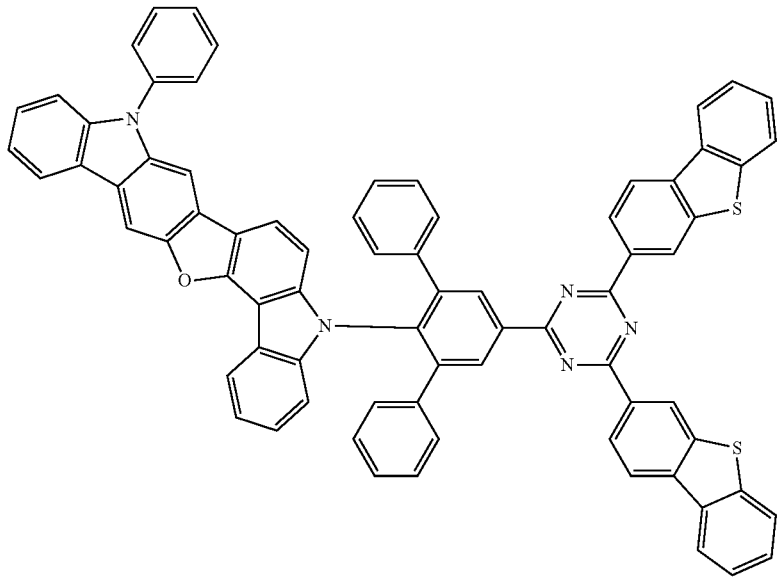
440
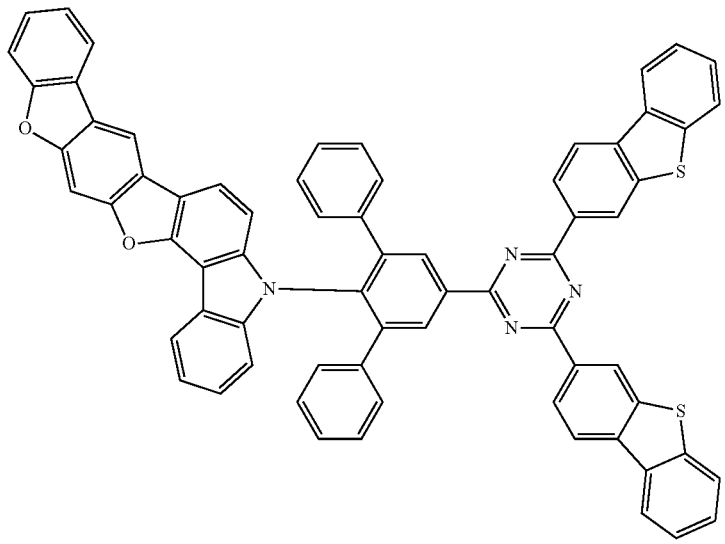

-continued
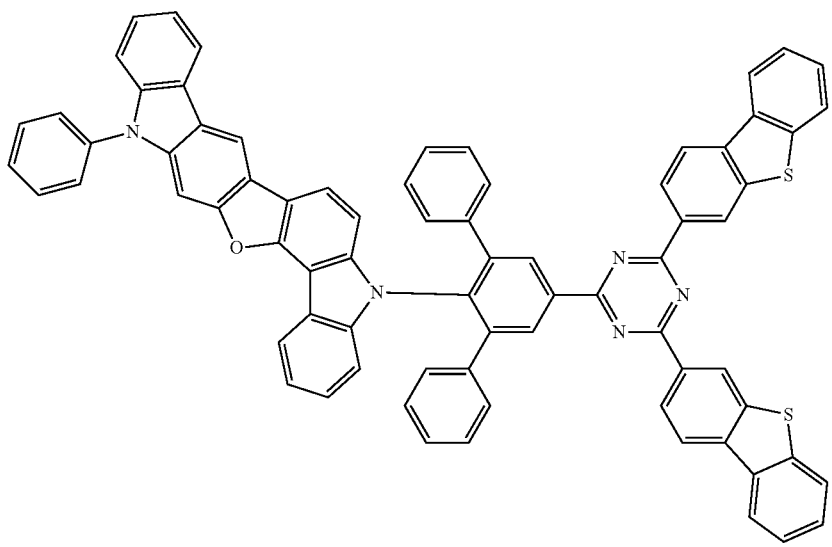
441
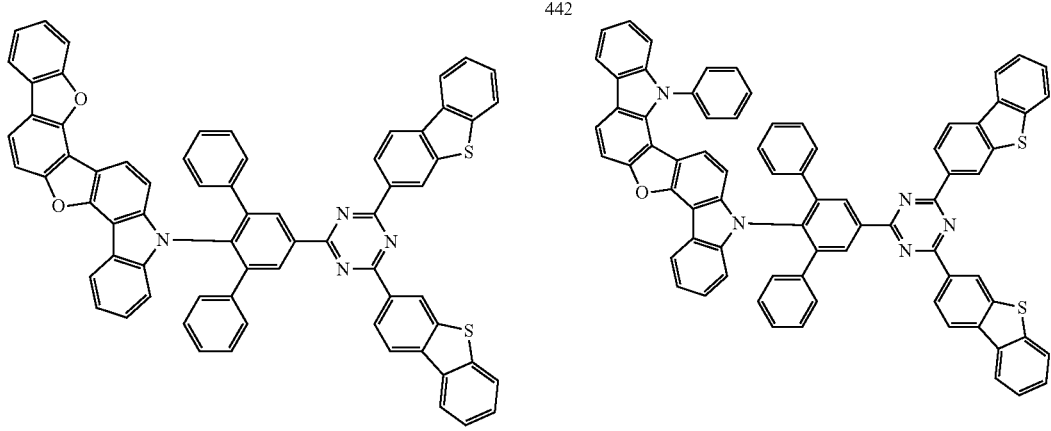
442 443
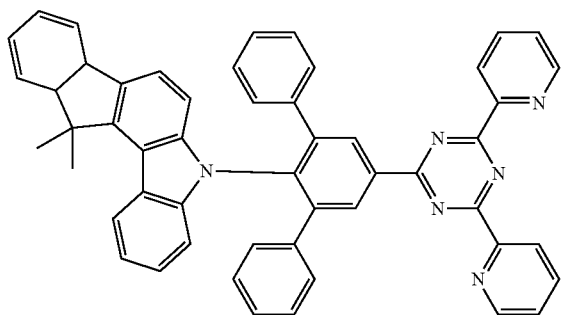
444

445
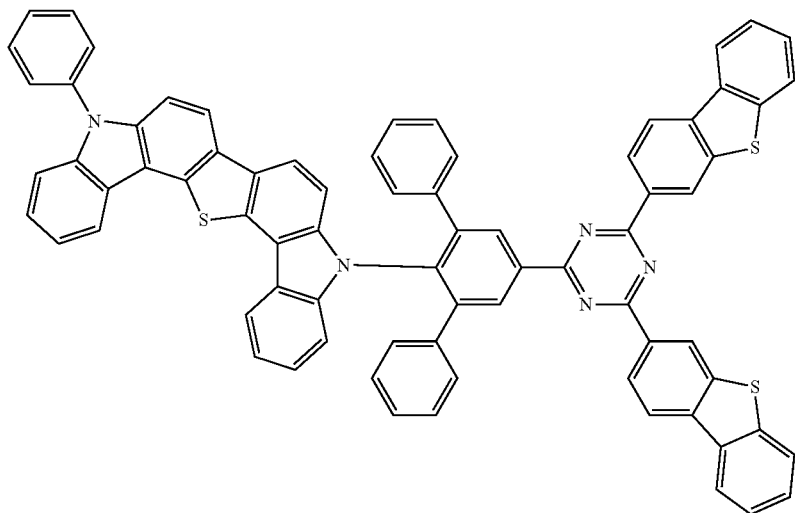
446
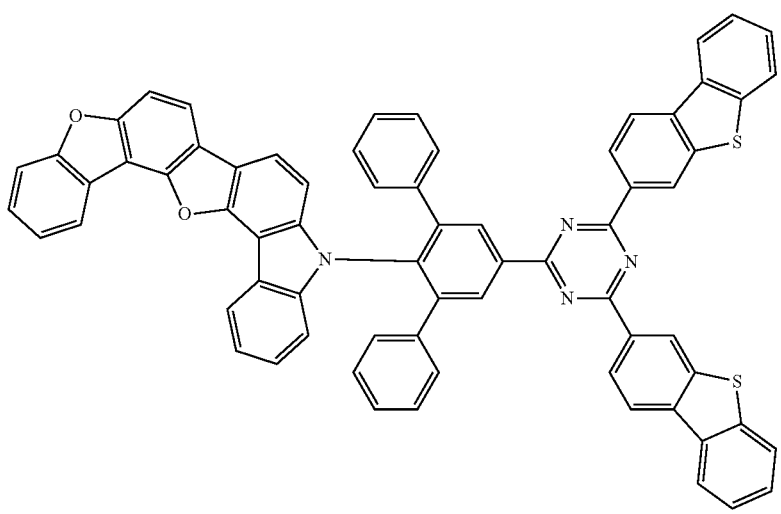
447
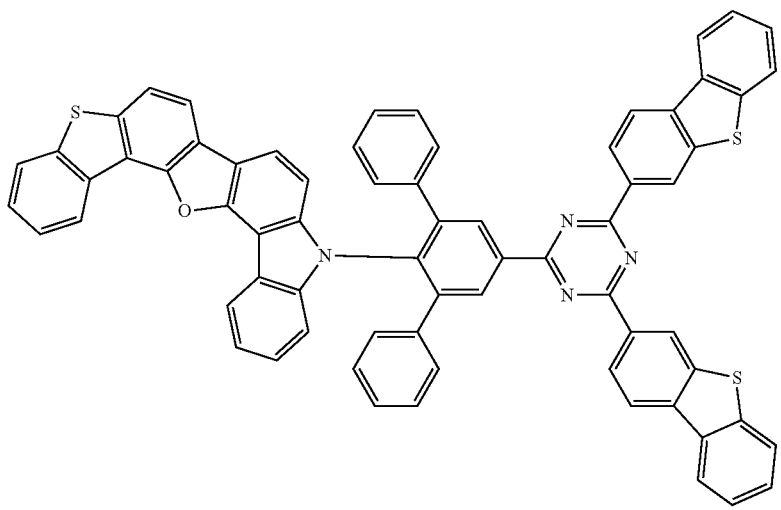

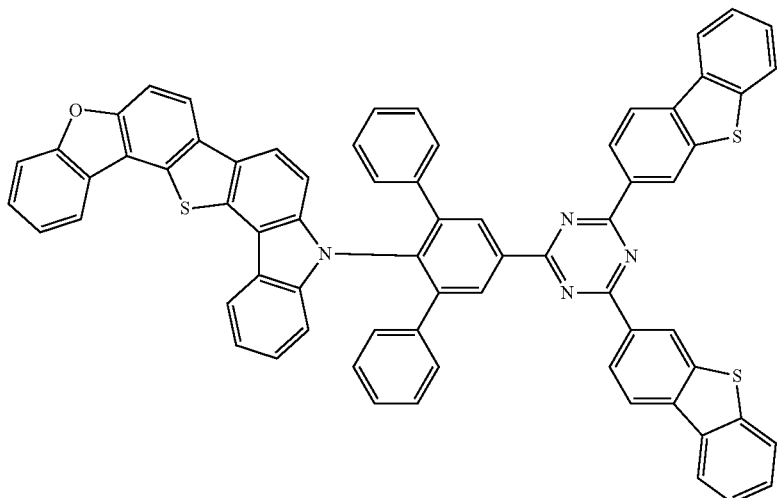
448
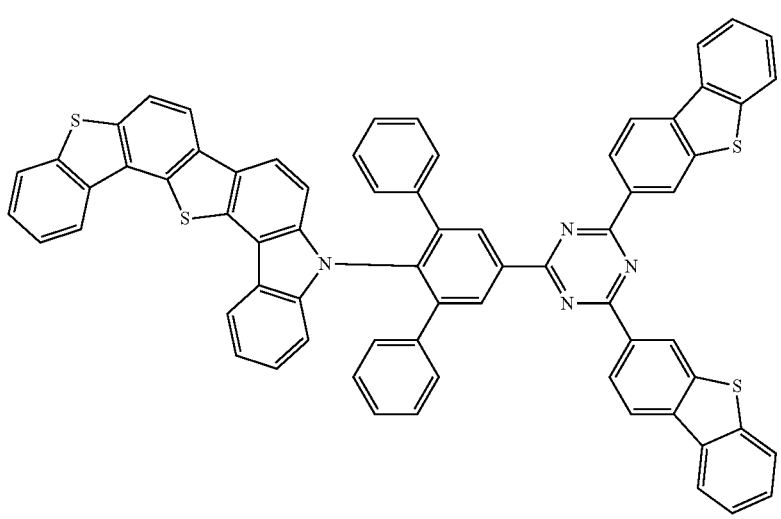
449
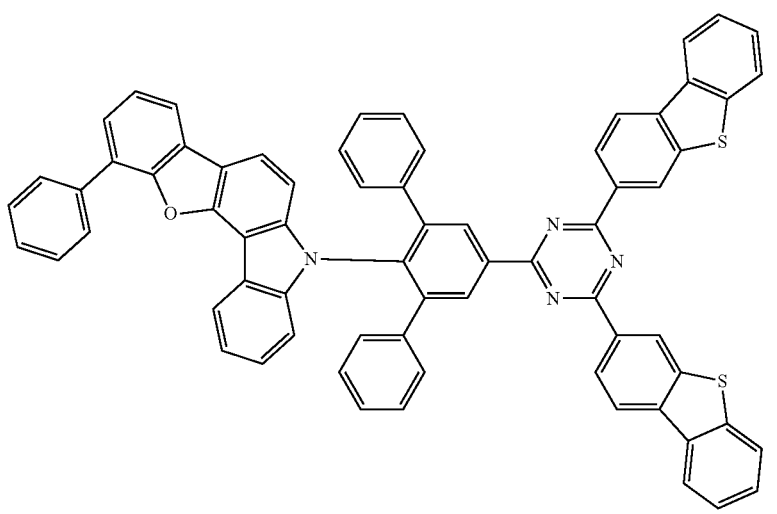
450

-continued
451 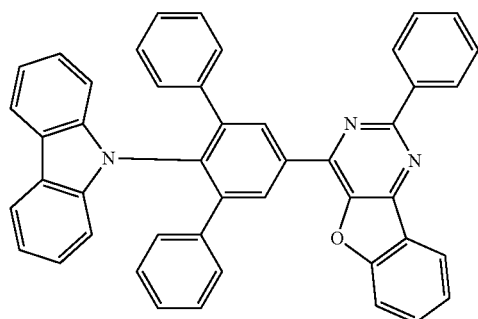
452 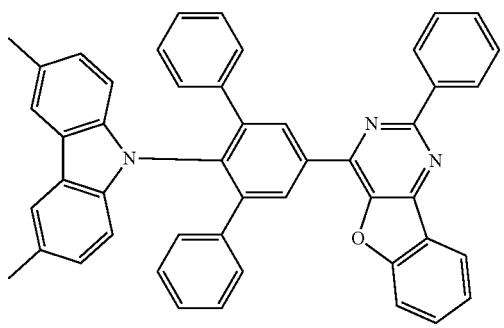
453 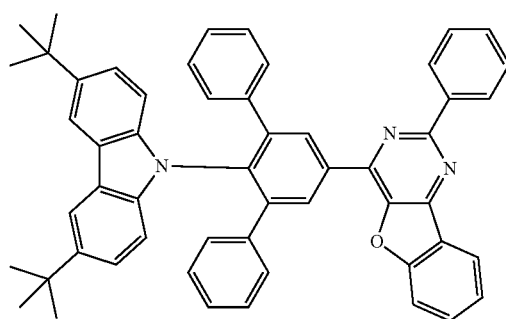
454 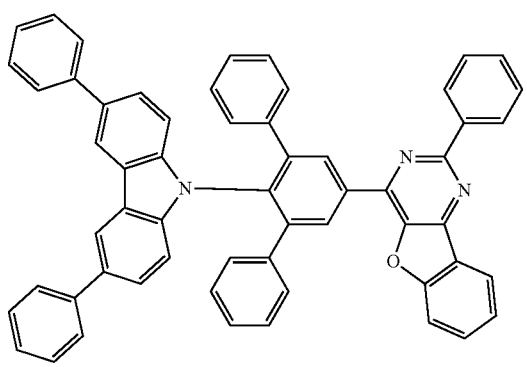
455 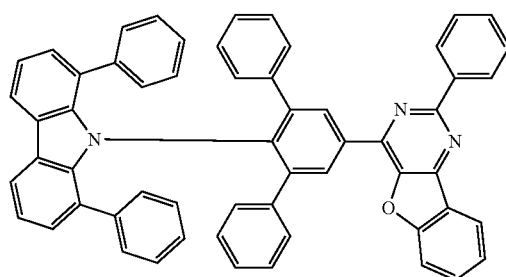
456 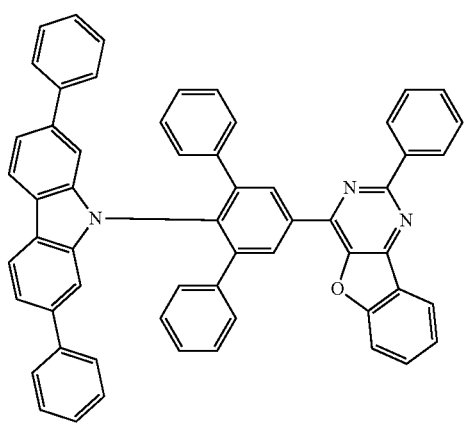
457 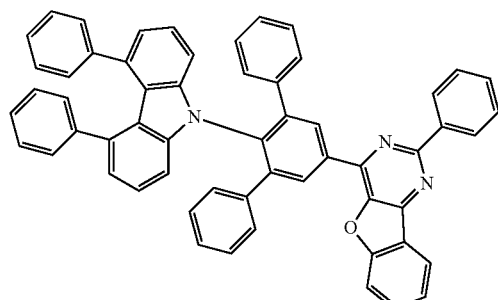
458 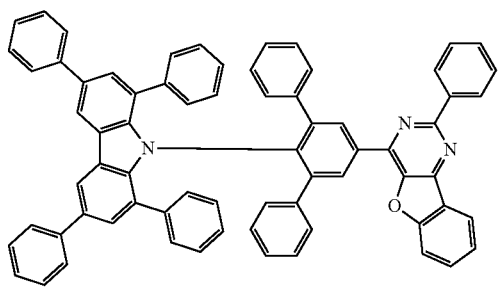

459
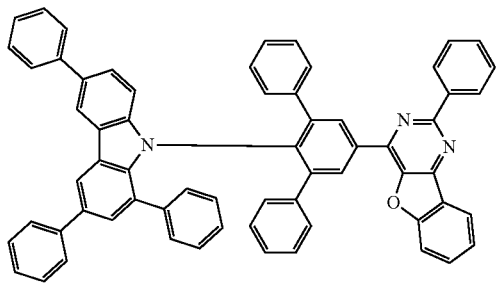
460
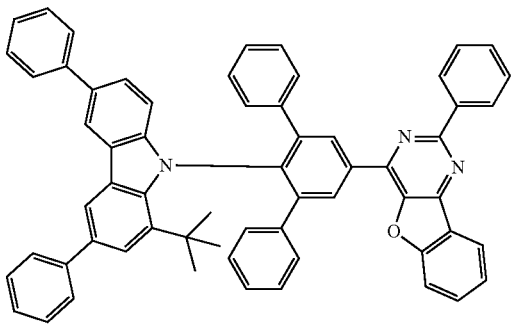
461
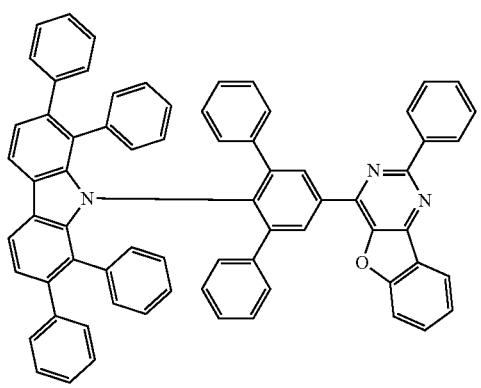
462
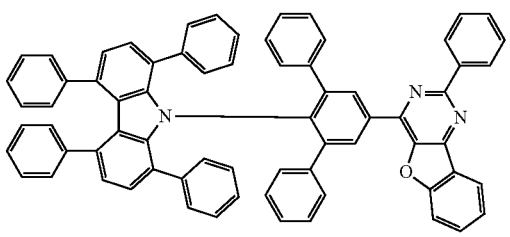
463
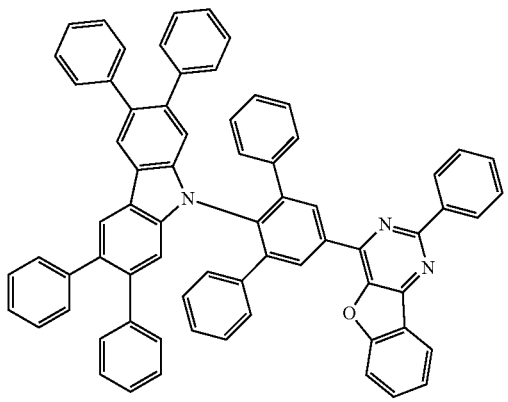
464
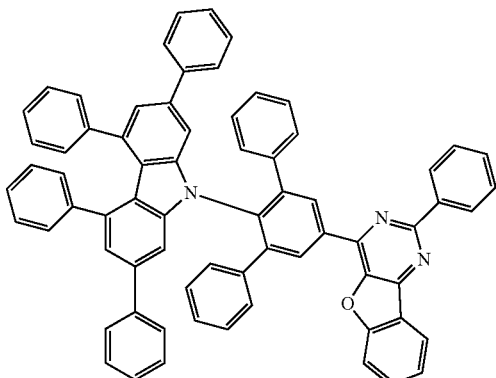
465
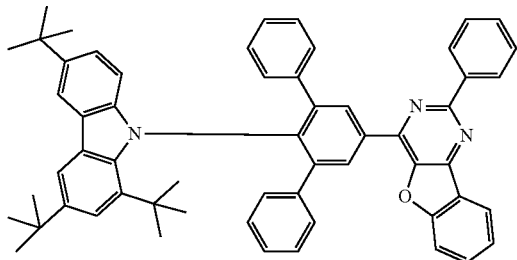
466
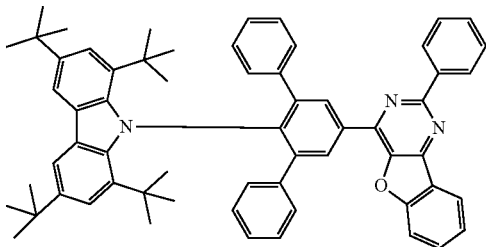

-continued
467
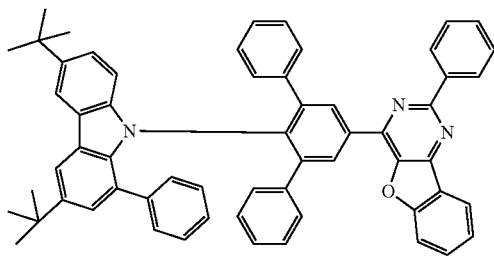
468
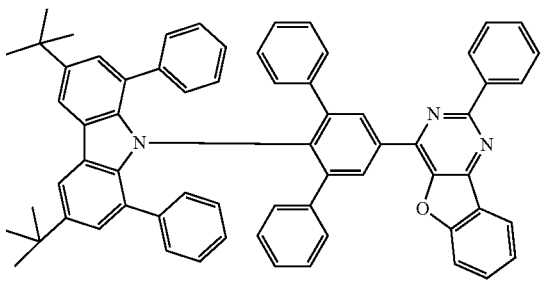
469
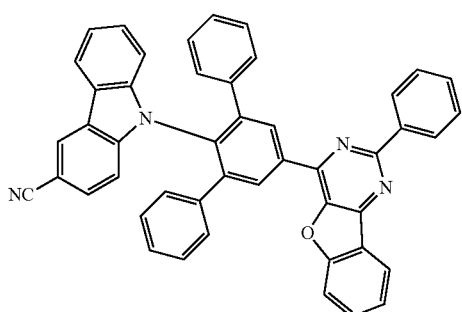
470
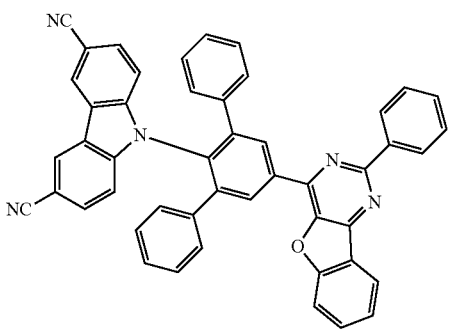
471
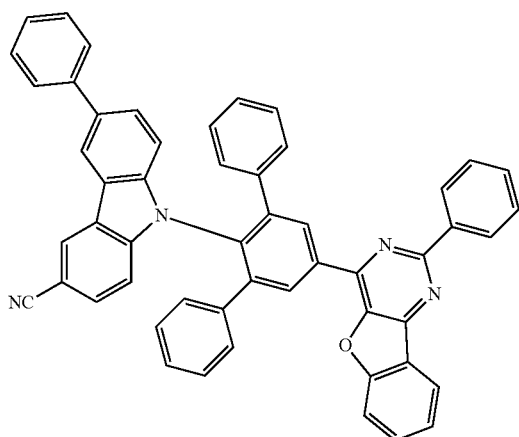
472
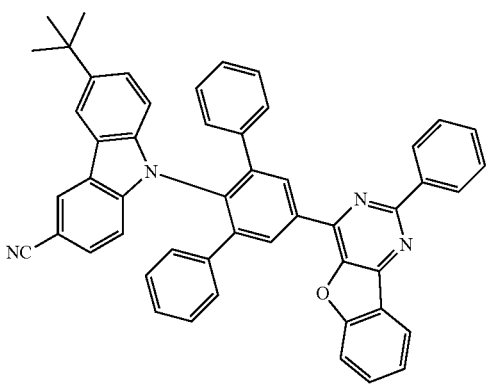
473
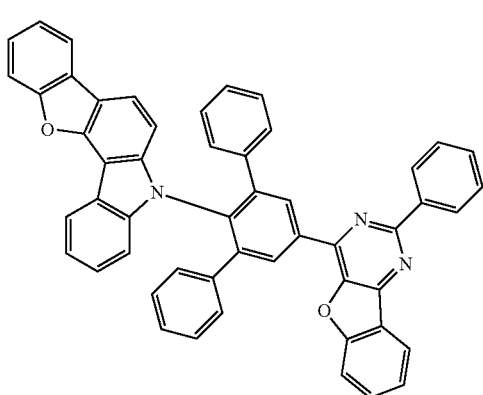
474
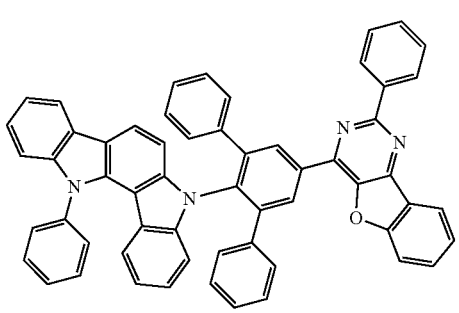

| 475 | 476 |
|---|---|
| 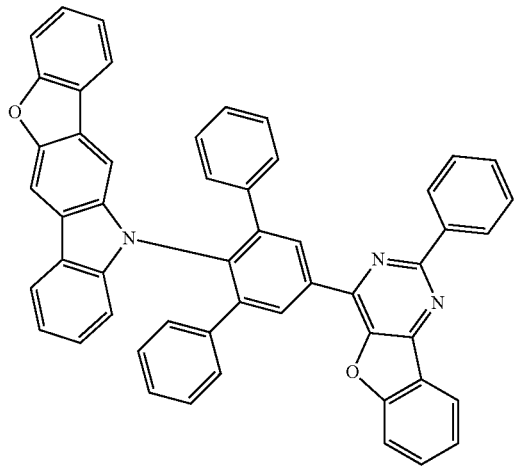 | 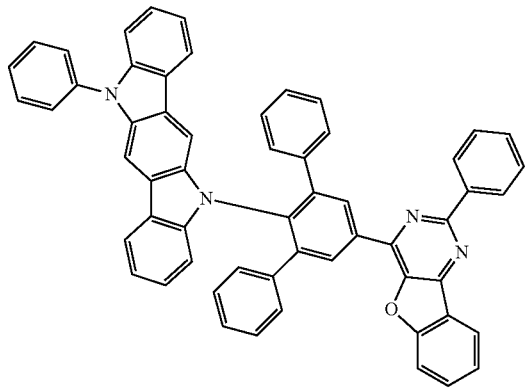 |
| 477 | 478 |
| 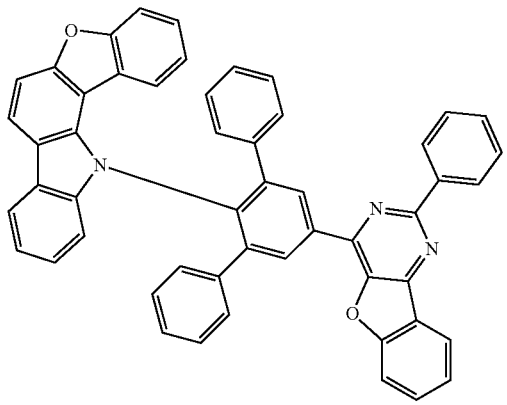 | 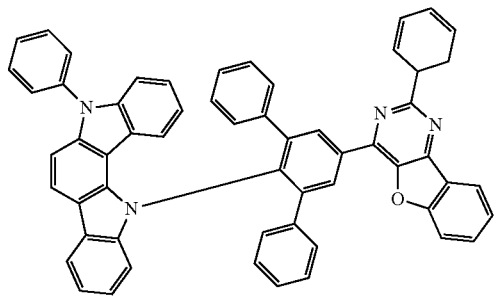 |
| 479 | 480 |
| 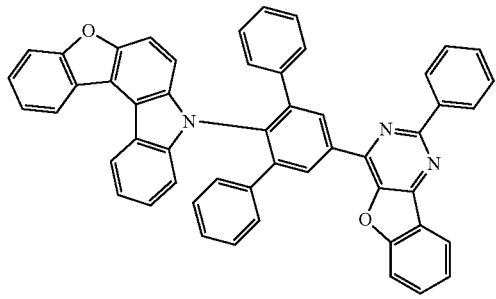 | 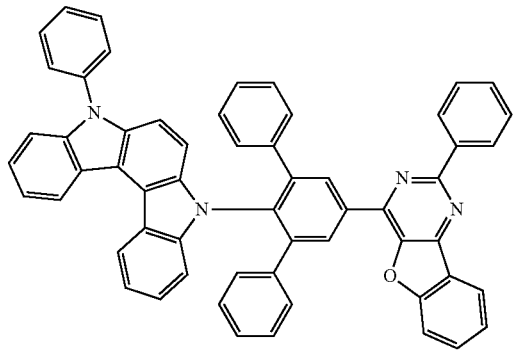 |

689
481
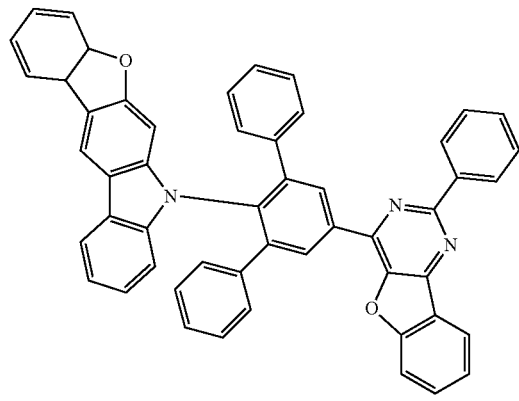
690
482
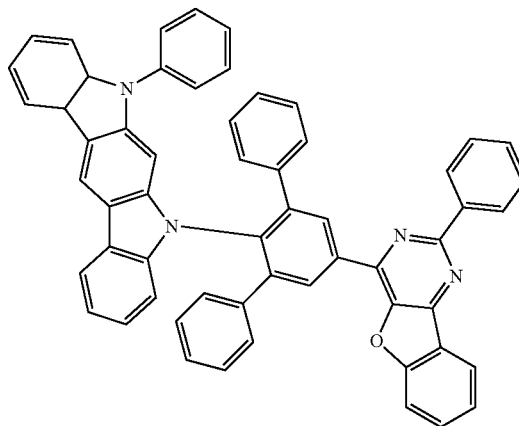
483
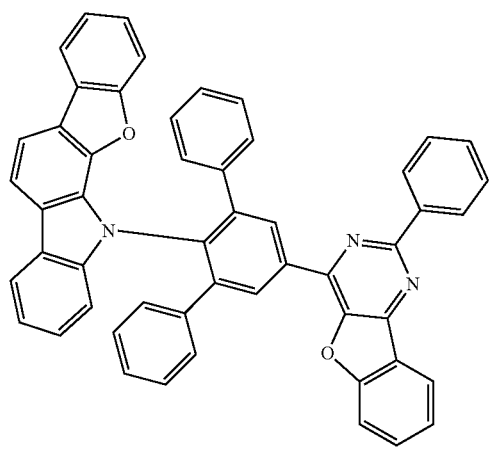
484
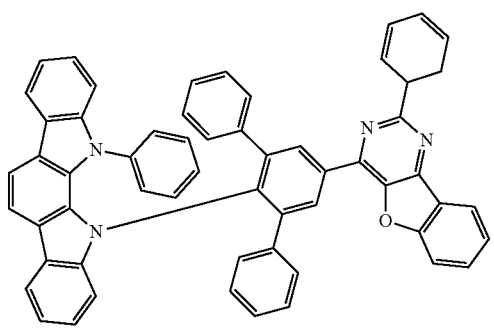
485
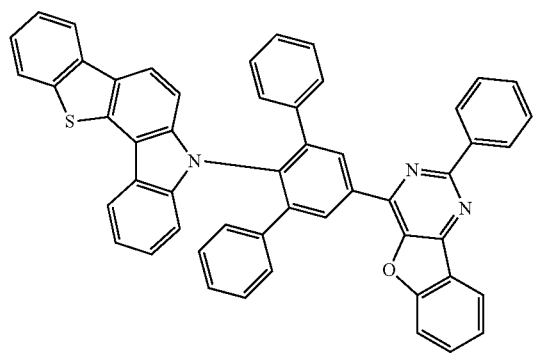
486
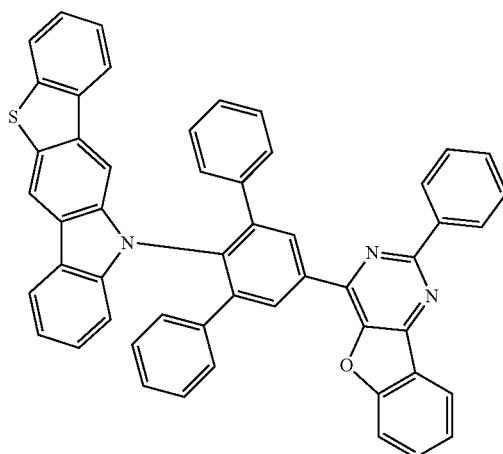

-continued
487
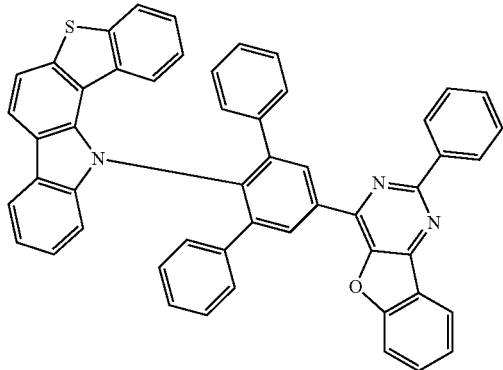
691
488
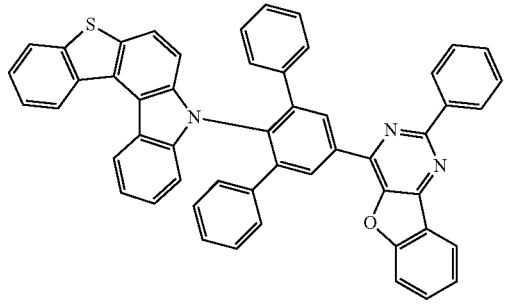
692
489
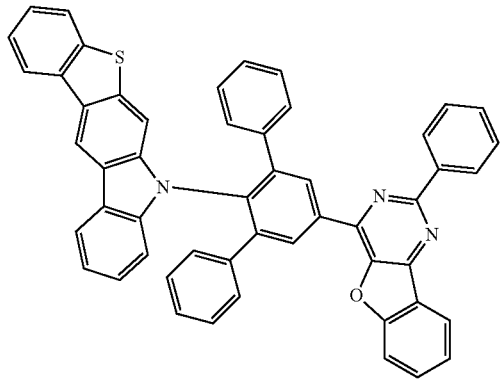
490
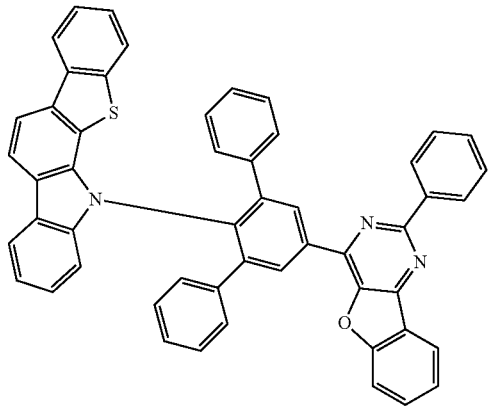
491
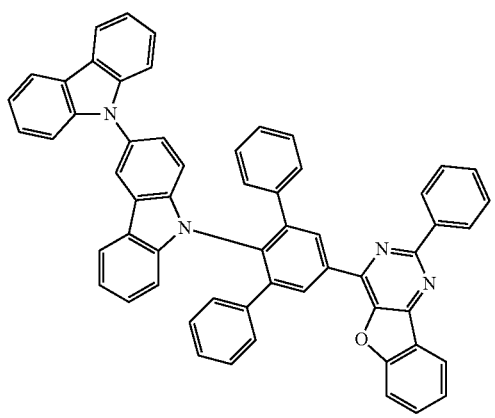
492
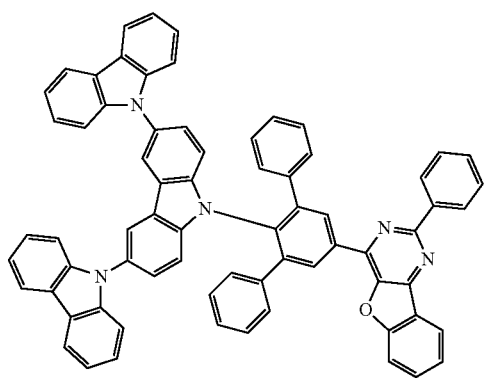

-continued
493
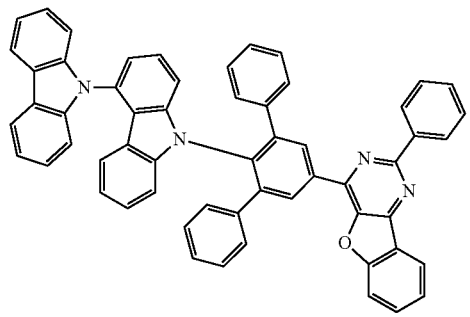
494
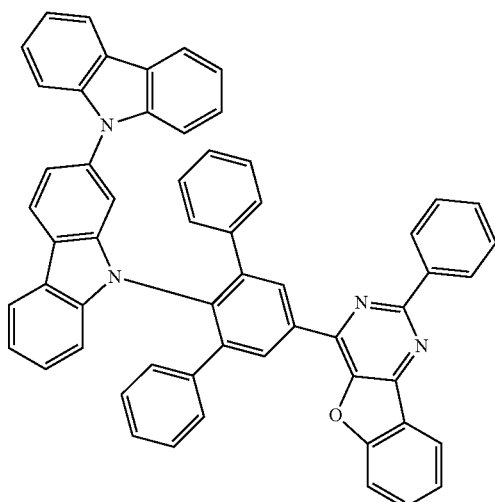
495
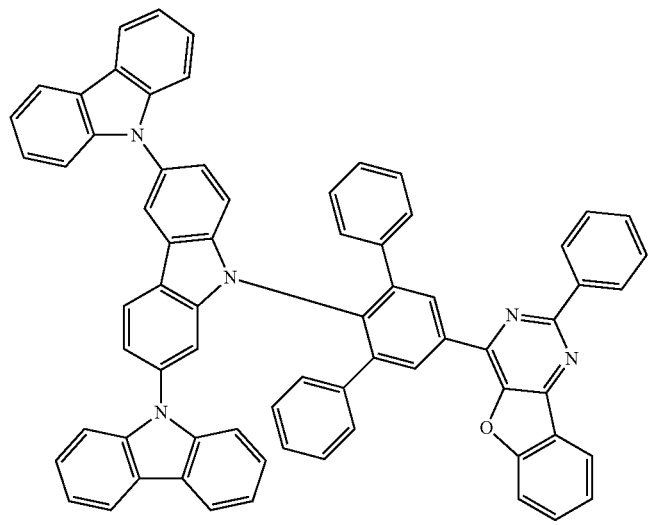
496
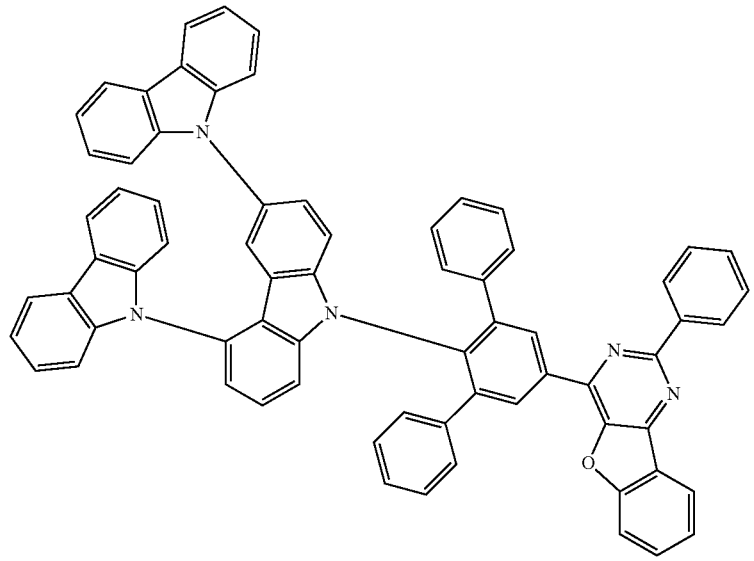

-continued
497
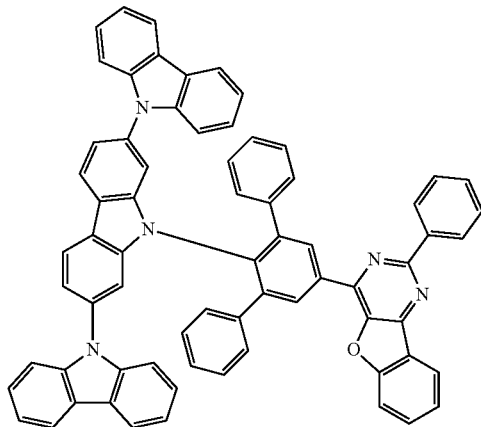
498
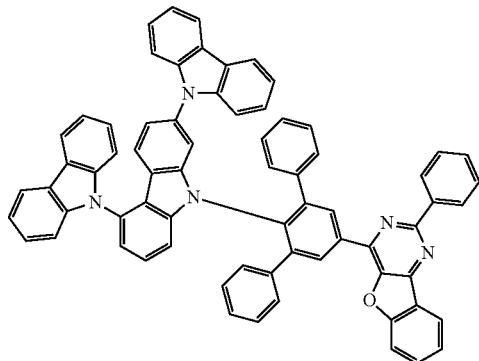
499
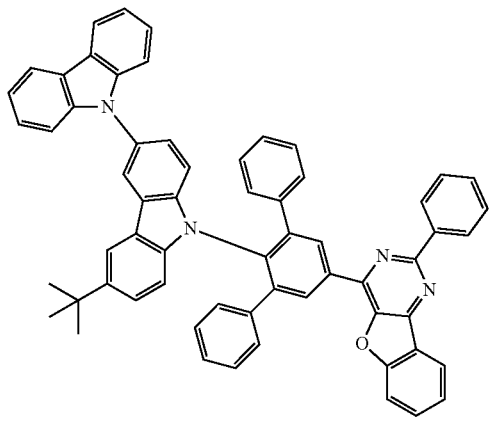
500
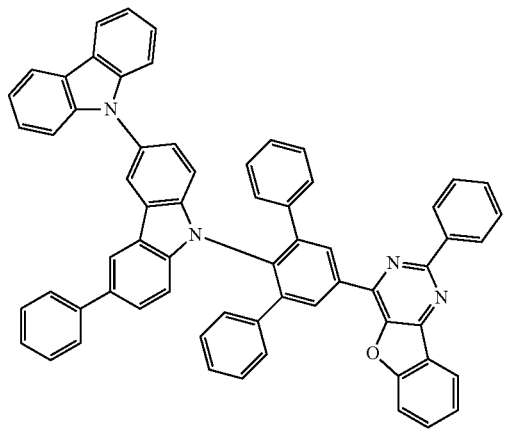
501
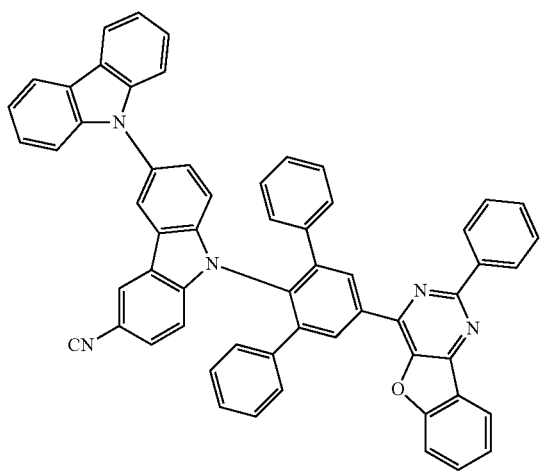
502
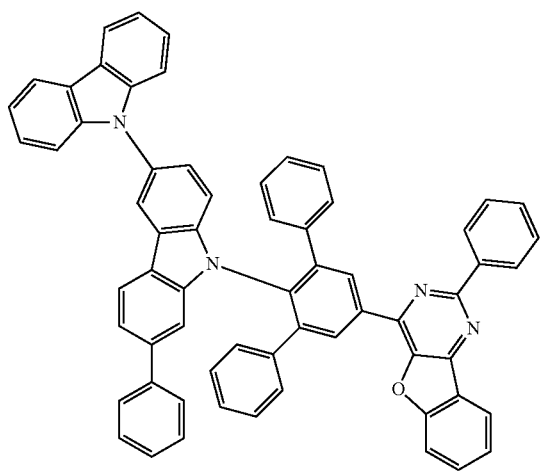

697 698
-continued
503 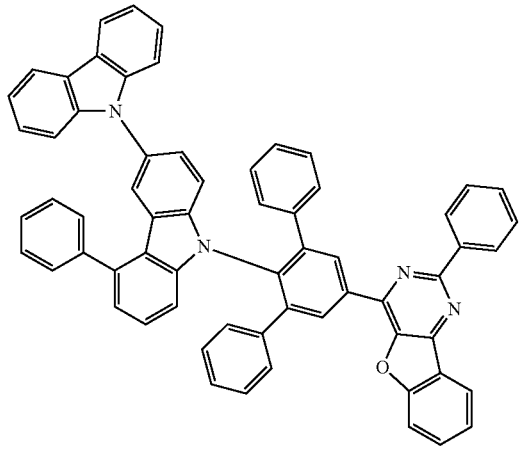 504 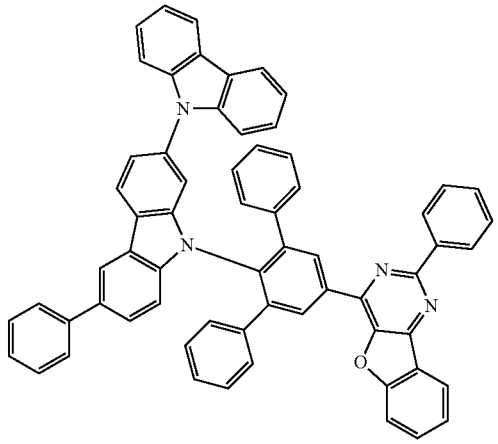
505 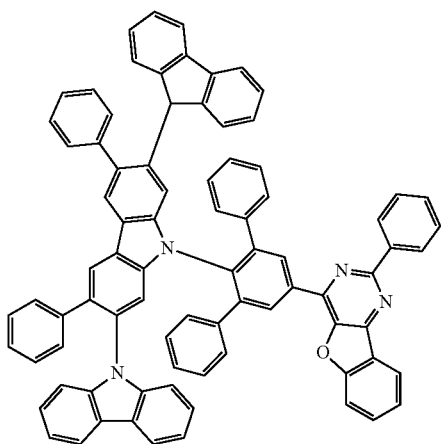 506 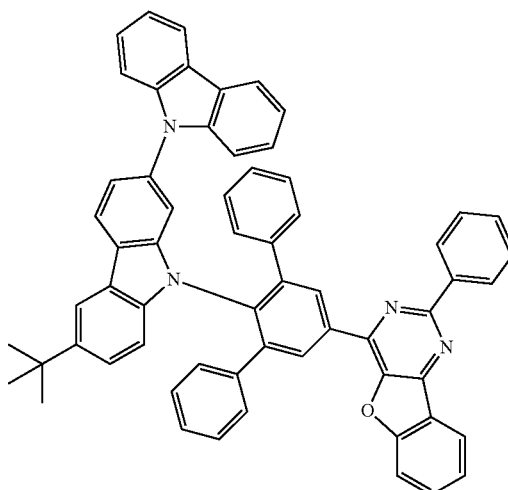
507 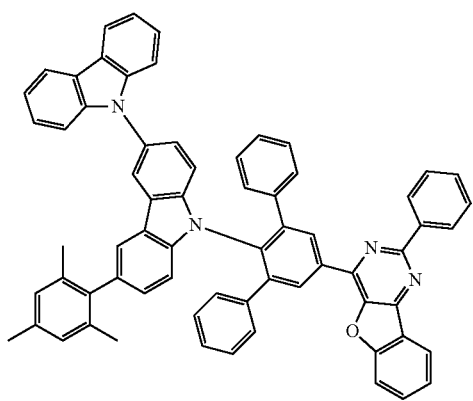 508 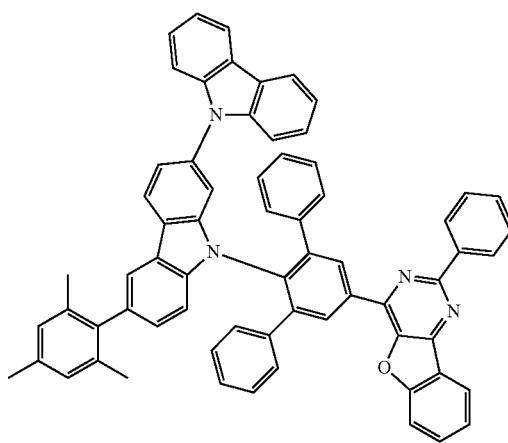

-continued
509
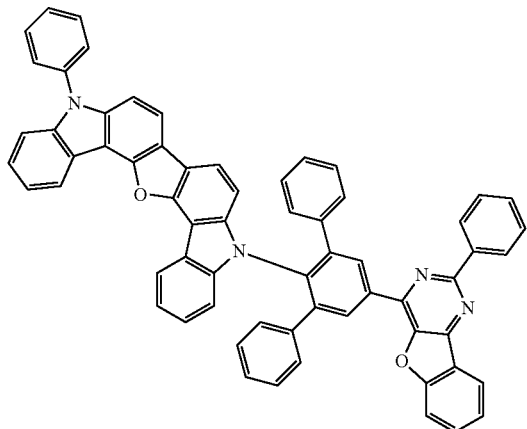
510
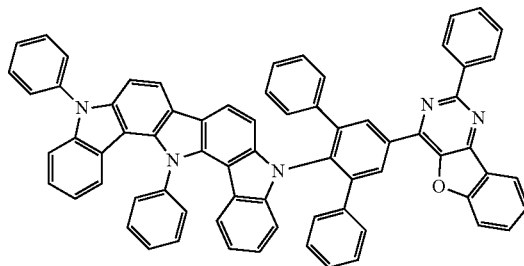
511
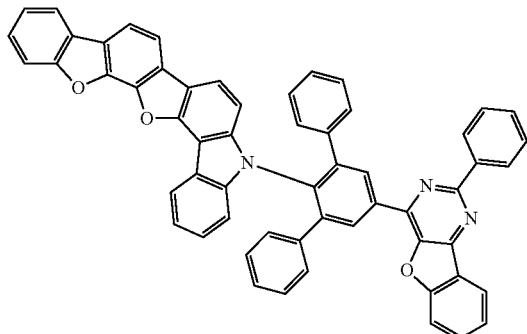
512
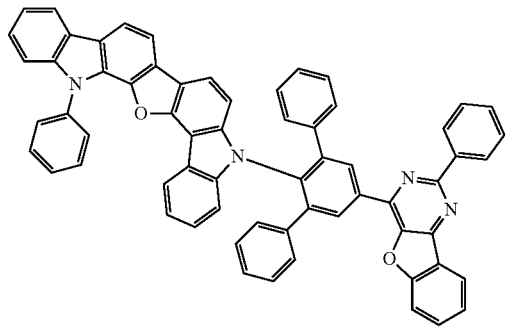
513
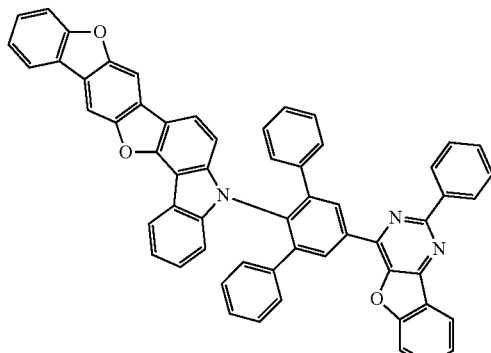
514
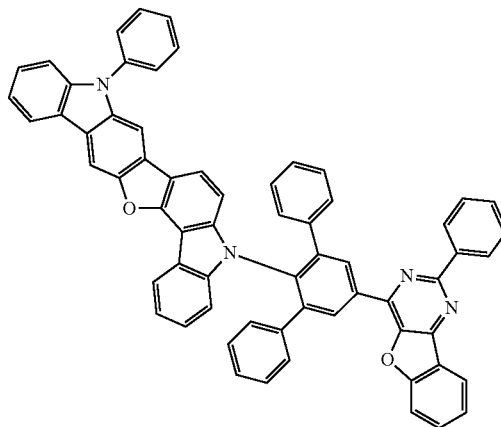

-continued
515
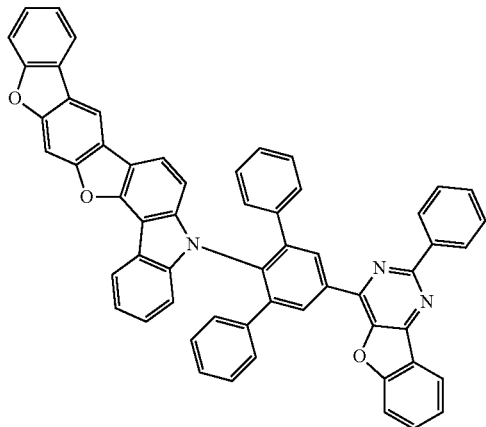
516
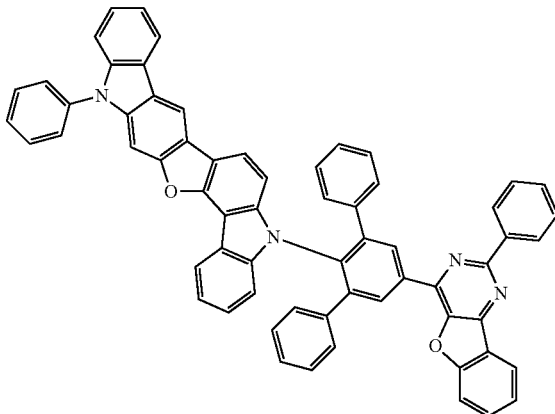
517
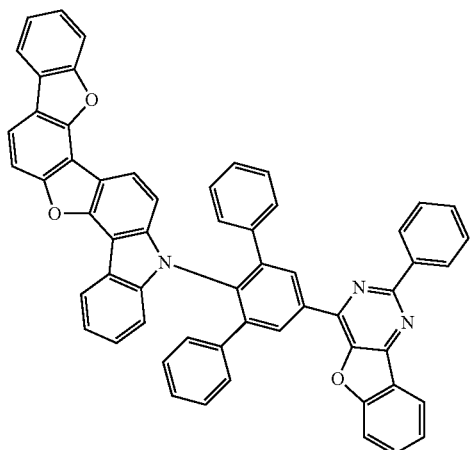
518
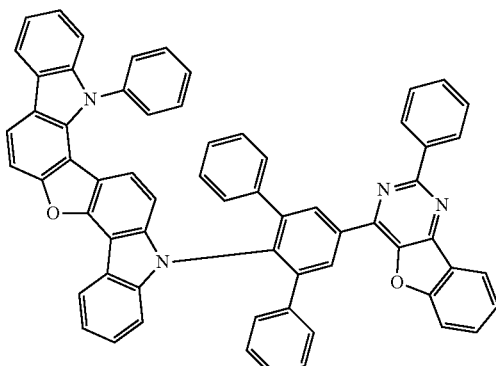
519
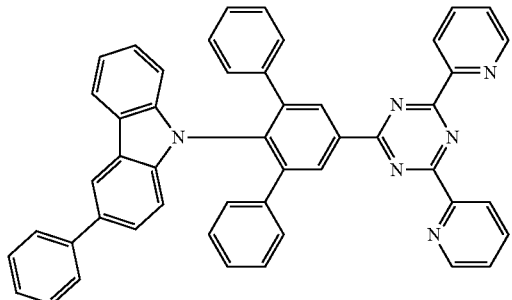
520
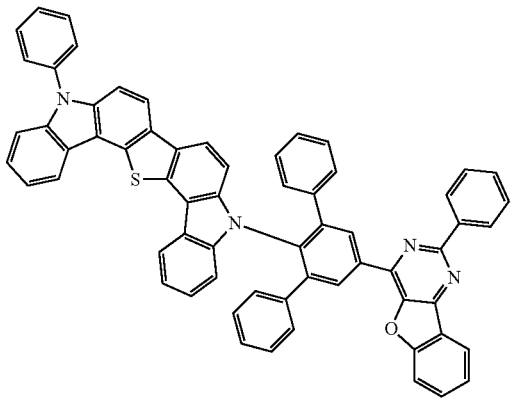
521
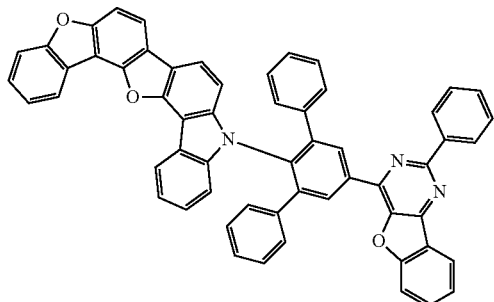
522
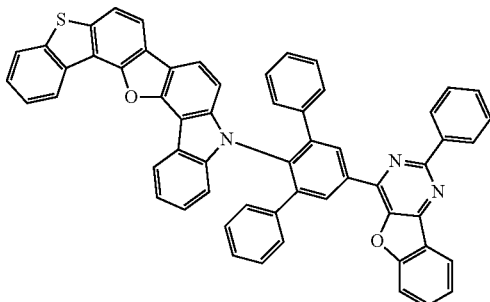

-continued
703 704
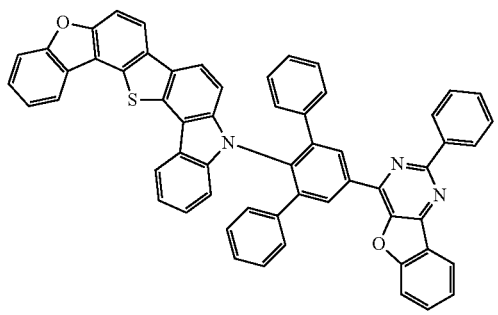
523
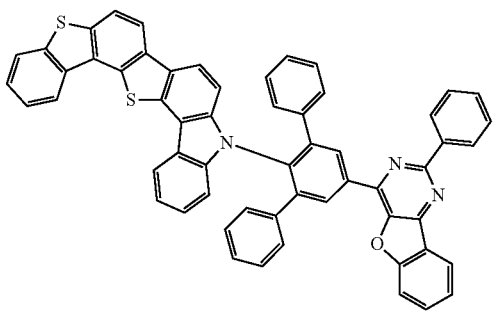
524
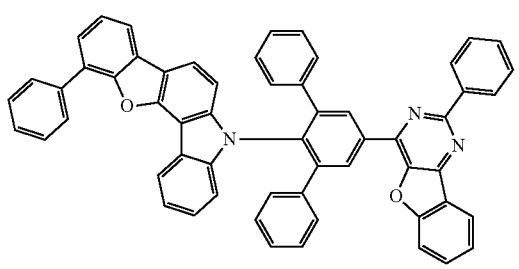
525
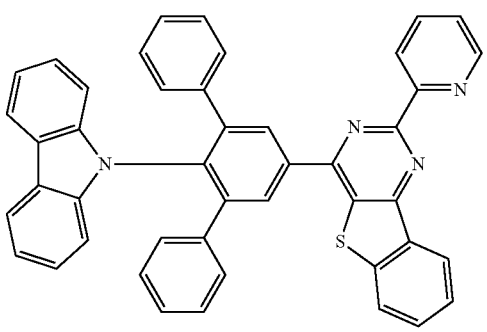
526
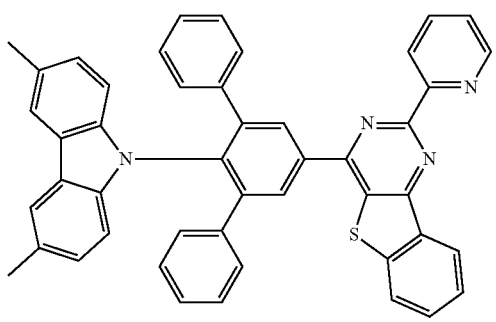
527
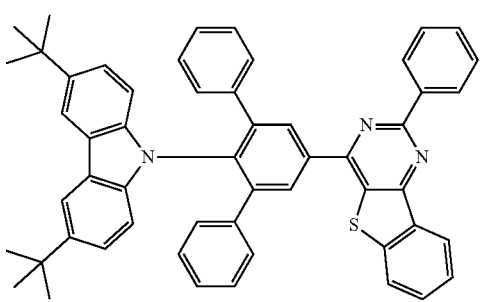
528
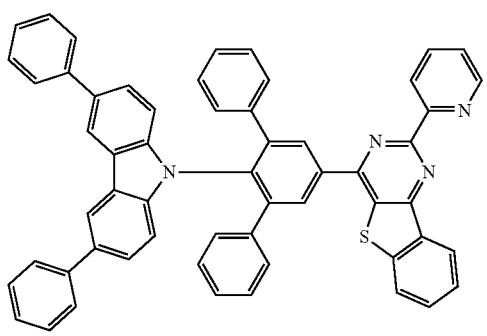
529
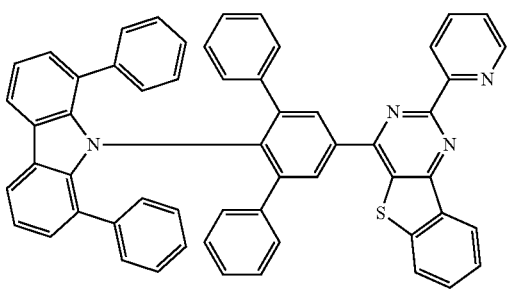
530

-continued
705
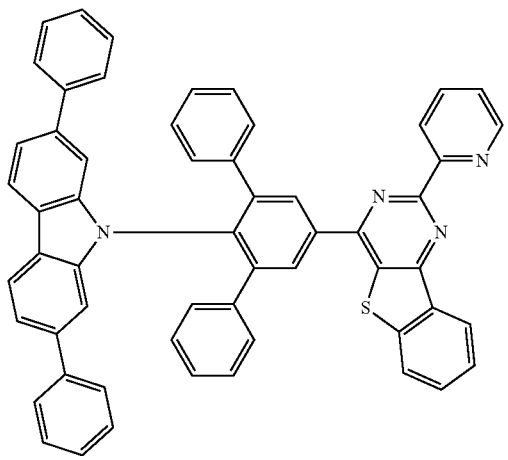
531
706
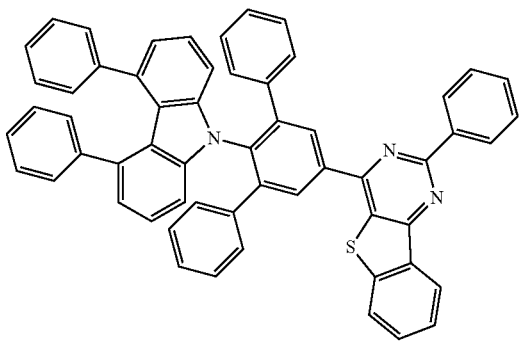
532
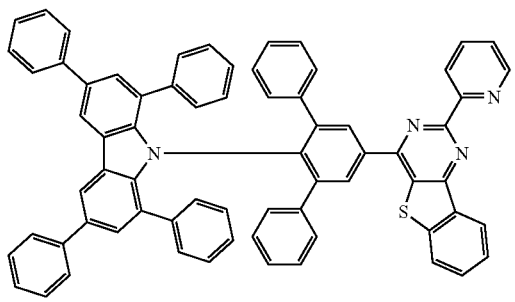
533
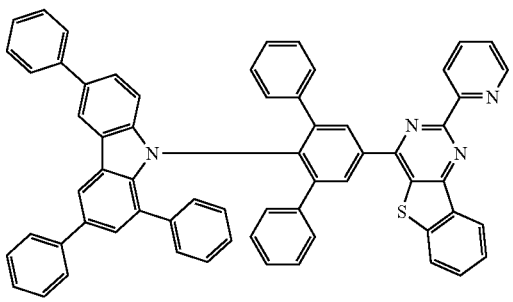
534
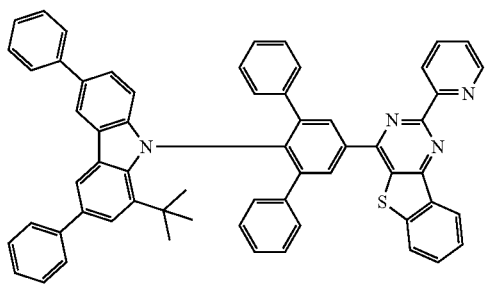
535
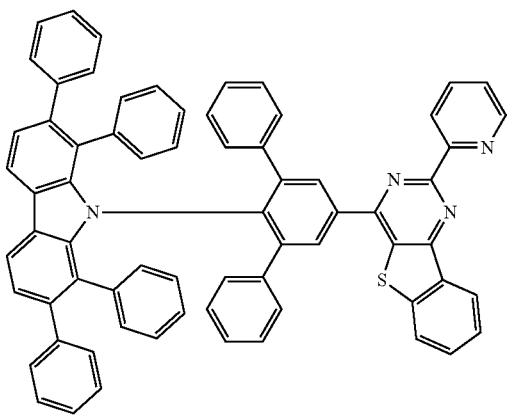
536
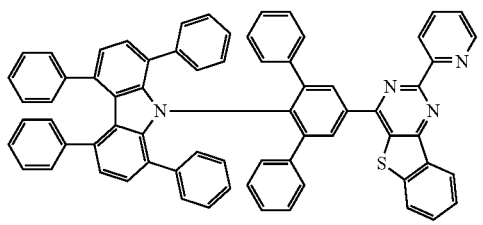
537
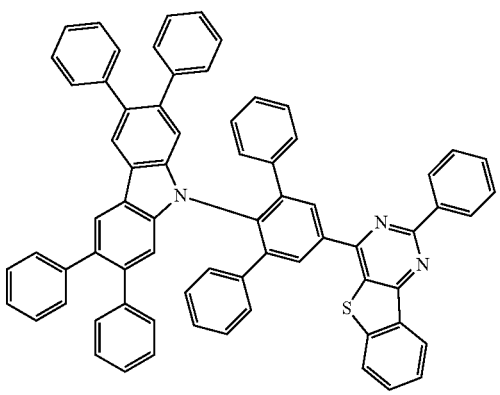
538

539
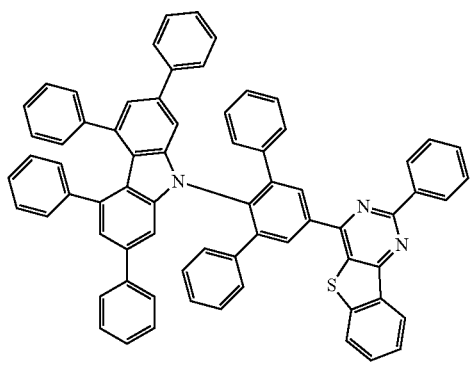
540
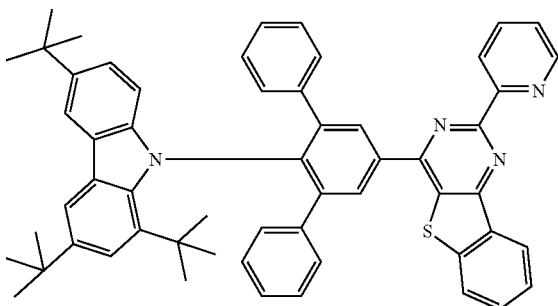
541
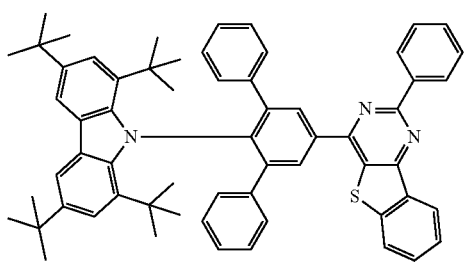
542
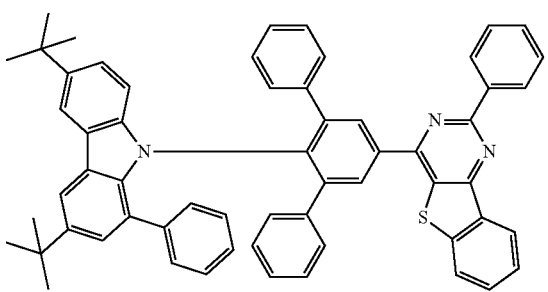
543
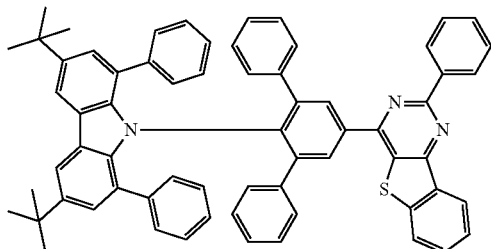
544
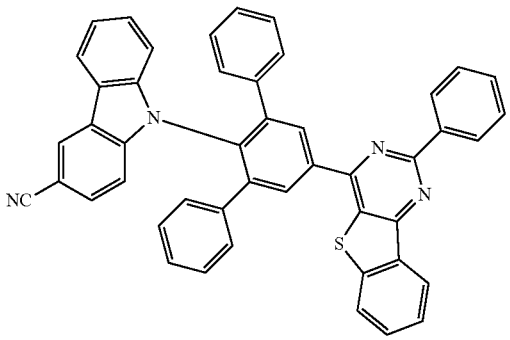
545
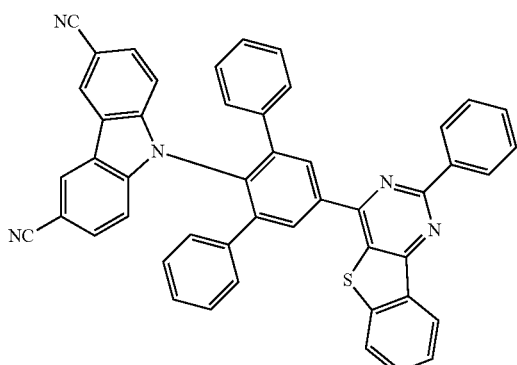
546
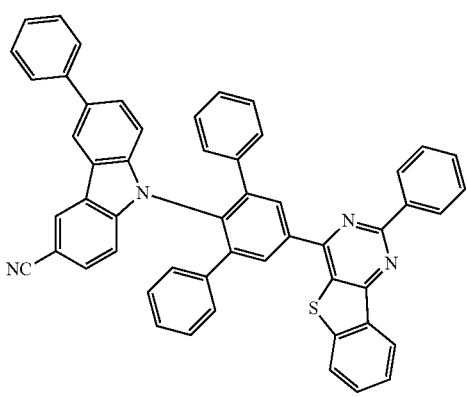

-continued
547
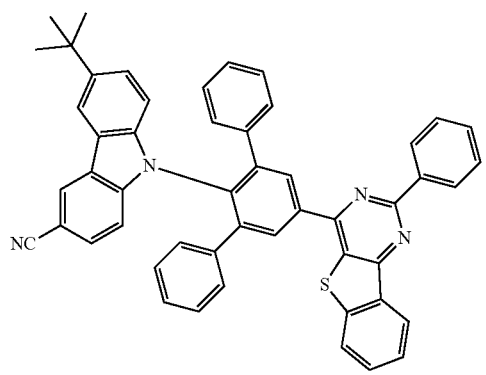
548
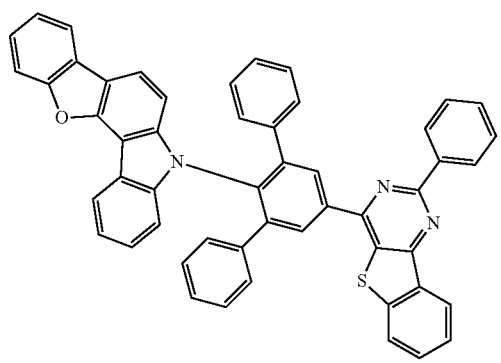
549
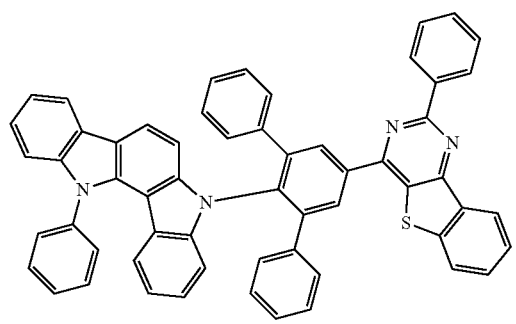
550
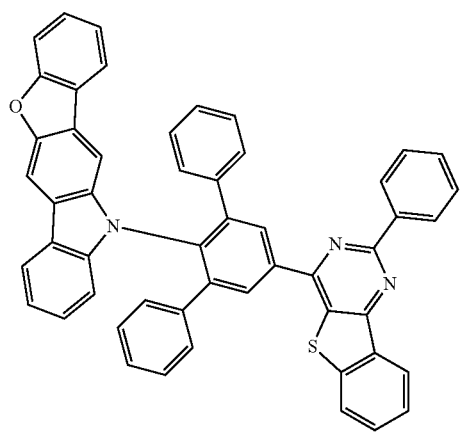
551
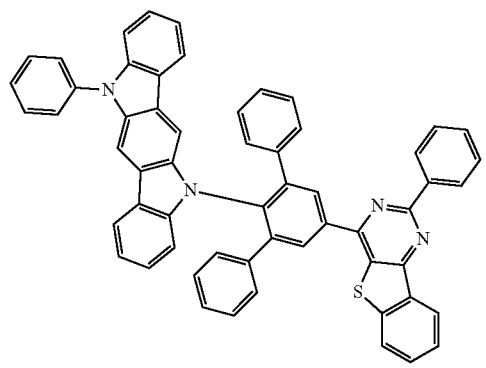
552
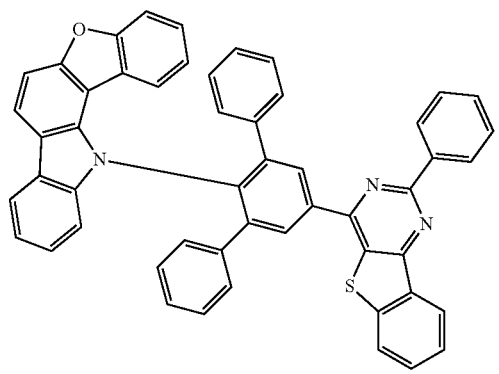
553
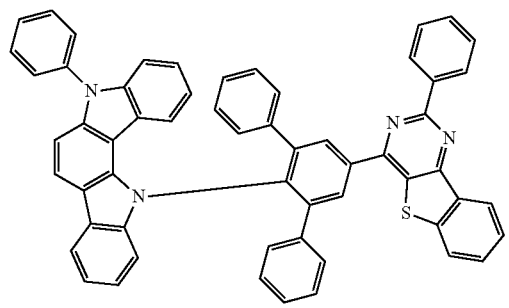
554
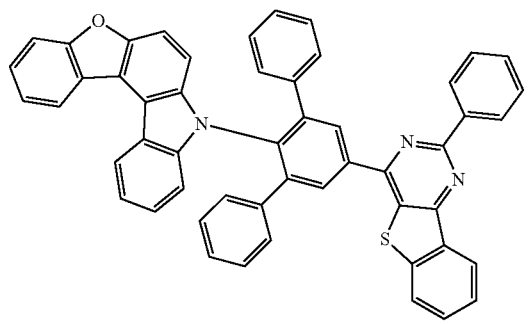

-continued
| 555 | 556 |
|---|---|
| 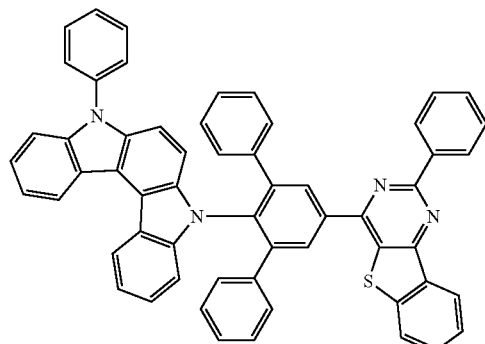 | 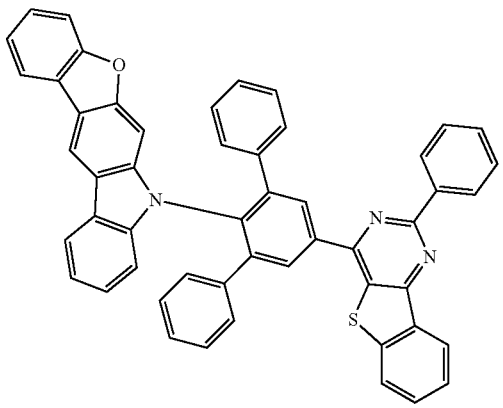 |
| 557 | 558 |
| 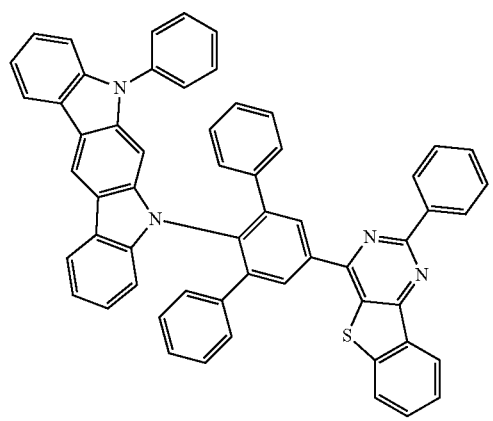 | 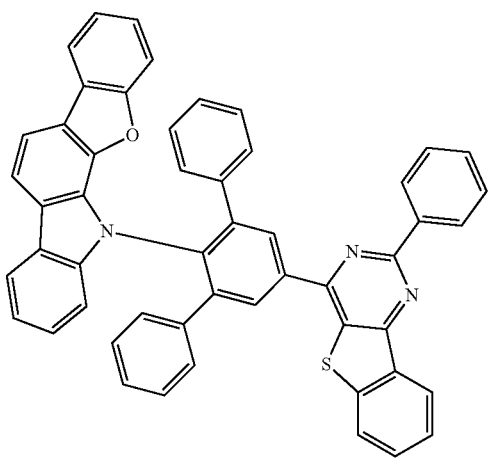 |
| 559 | 560 |
| 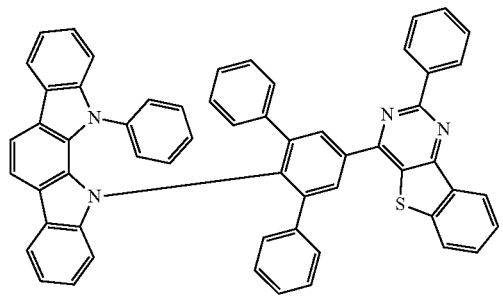 | 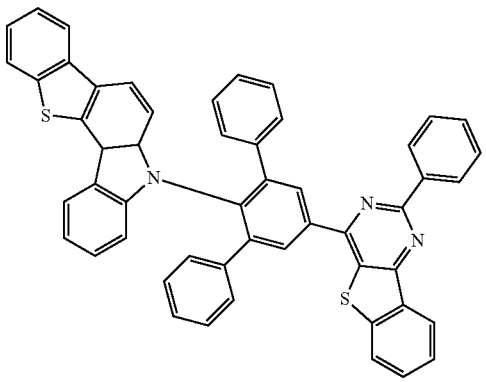 |

-continued
713
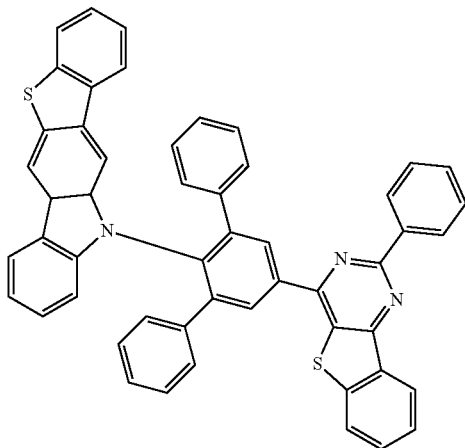
561
714
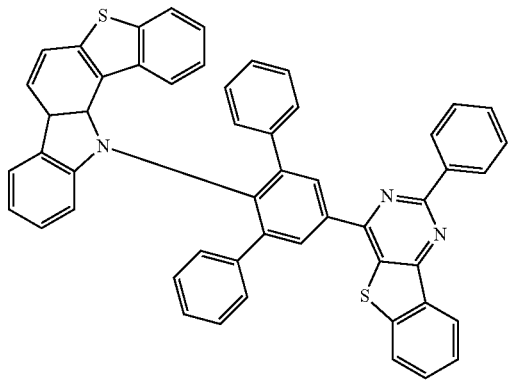
562
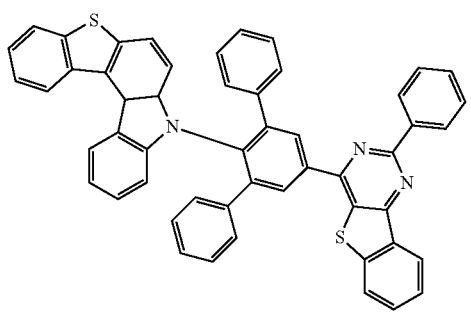
563
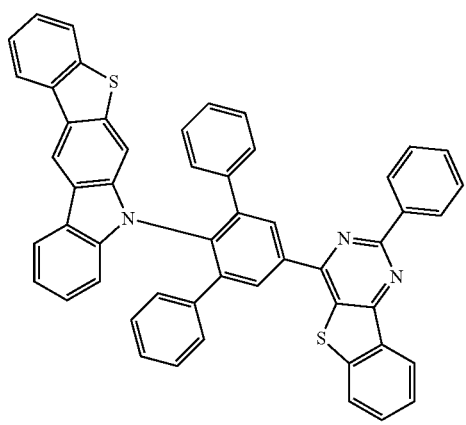
564
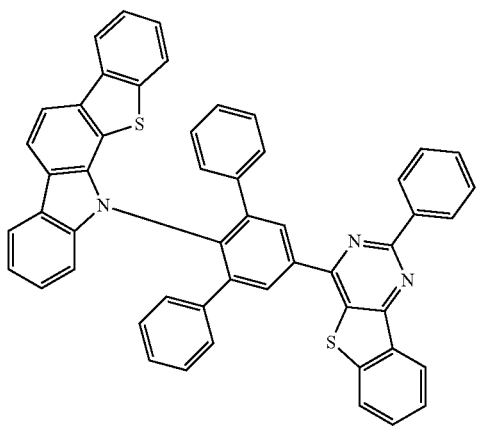
565
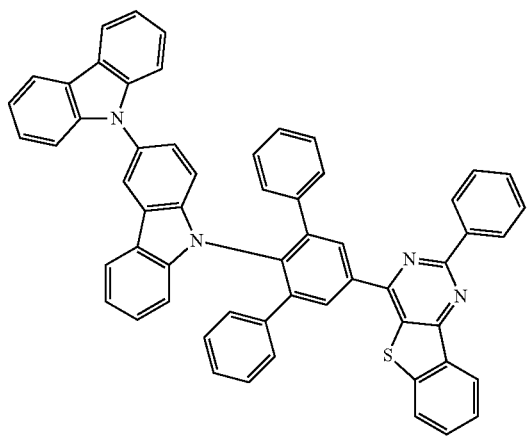
566

-continued
715
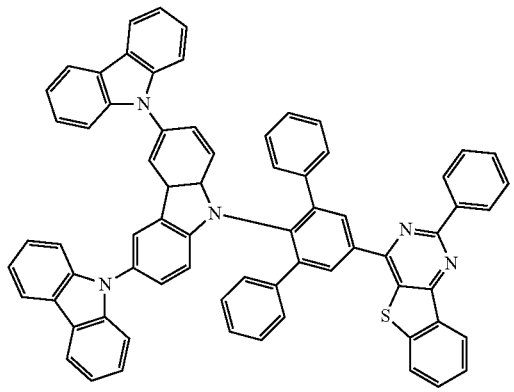
567
716
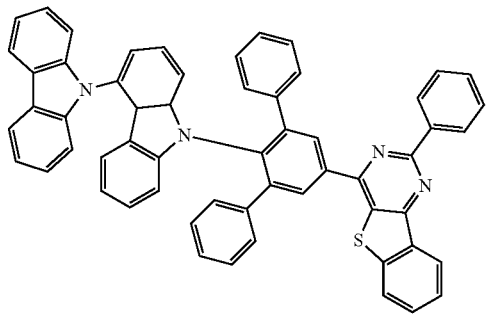
568
569
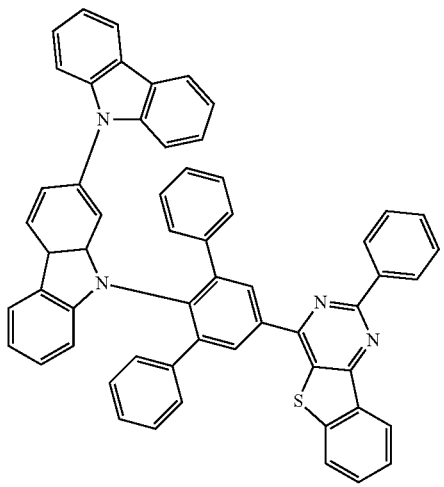
570
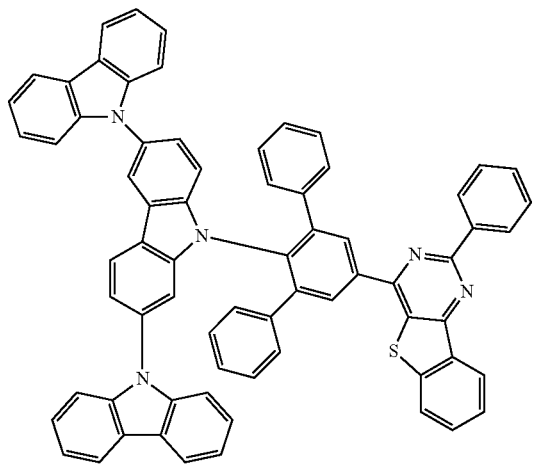
571
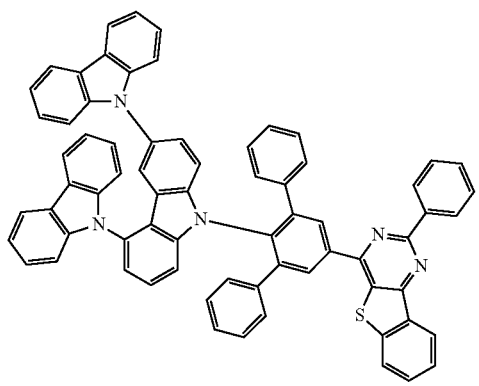
572
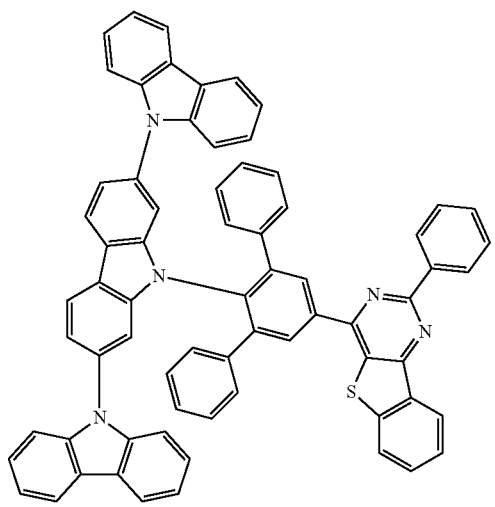

-continued
573
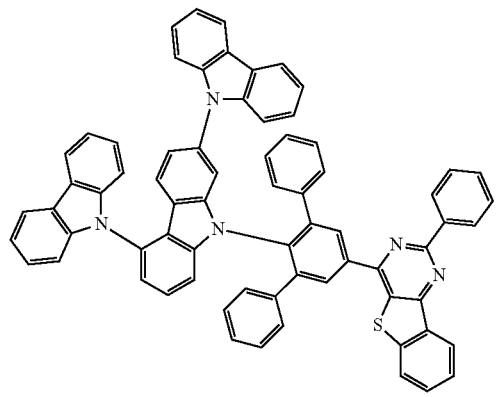
574
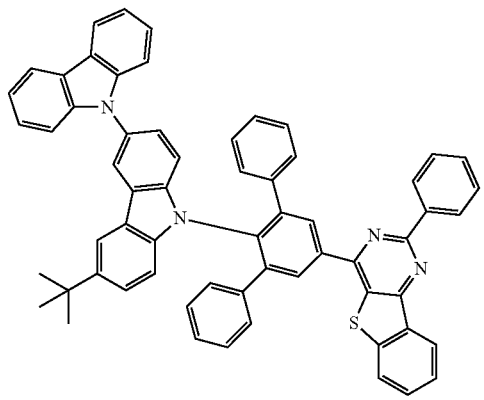
575
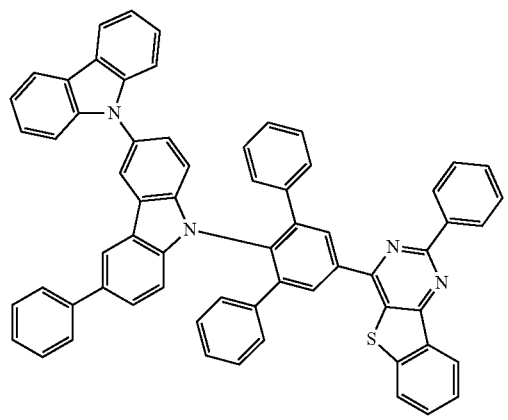
576
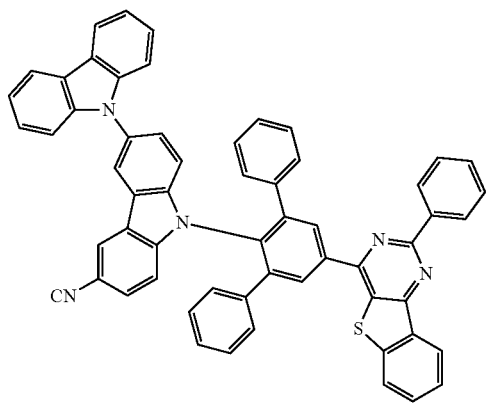
577
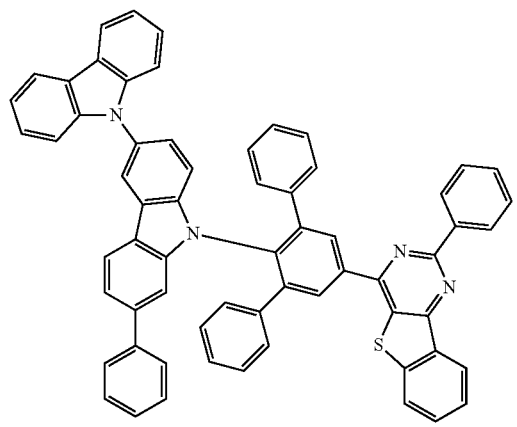
578
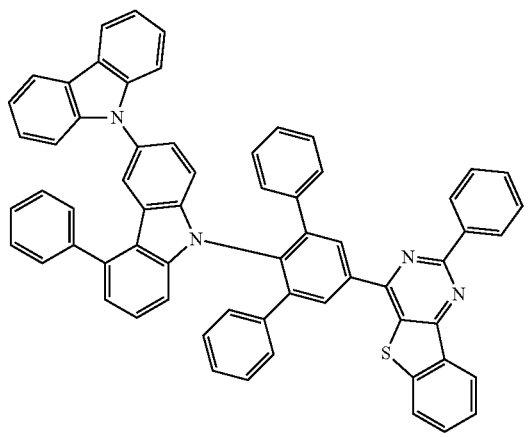

-continued
579
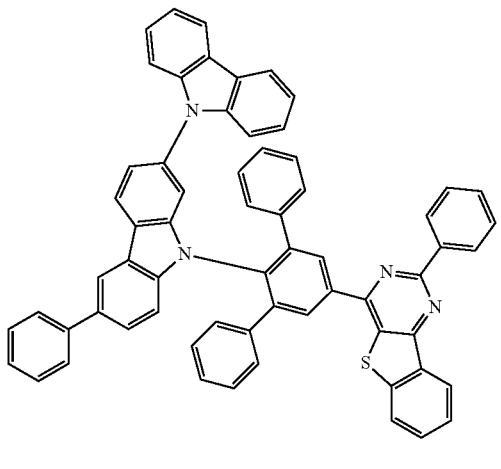
580
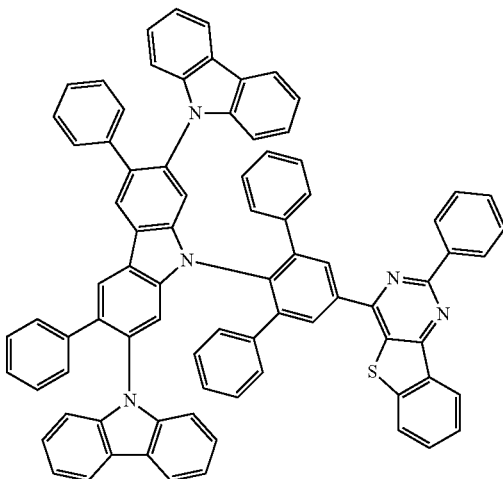
581
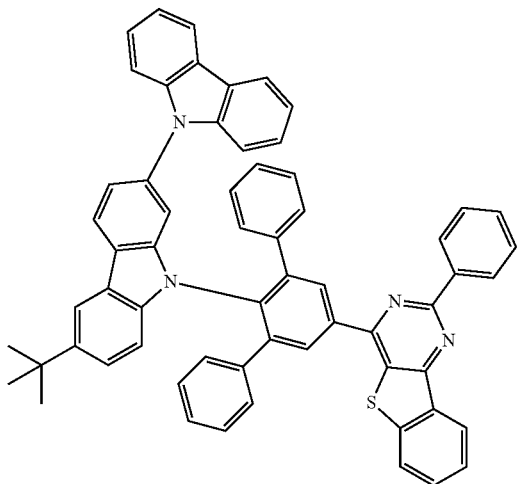
582
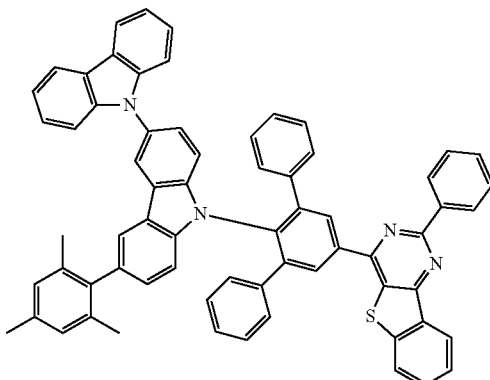
583
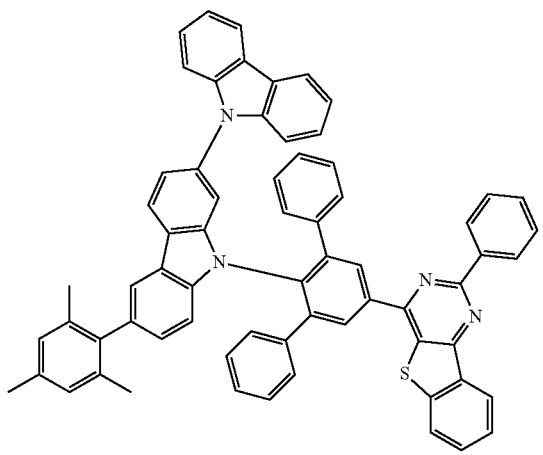
584
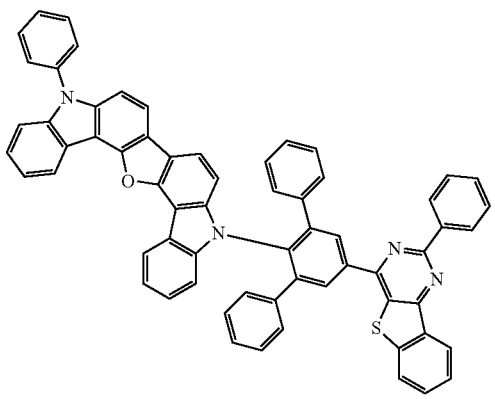

585
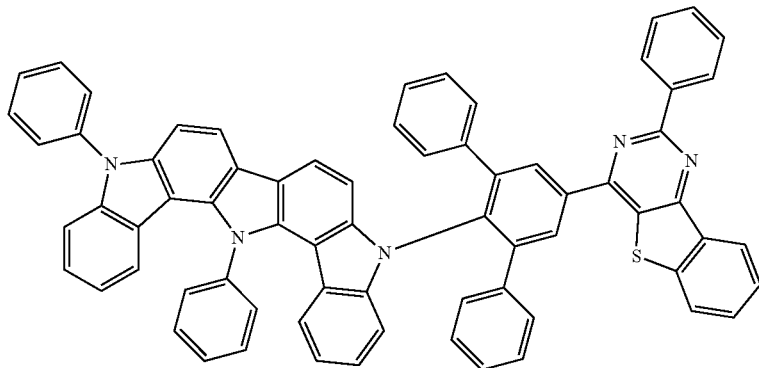
586
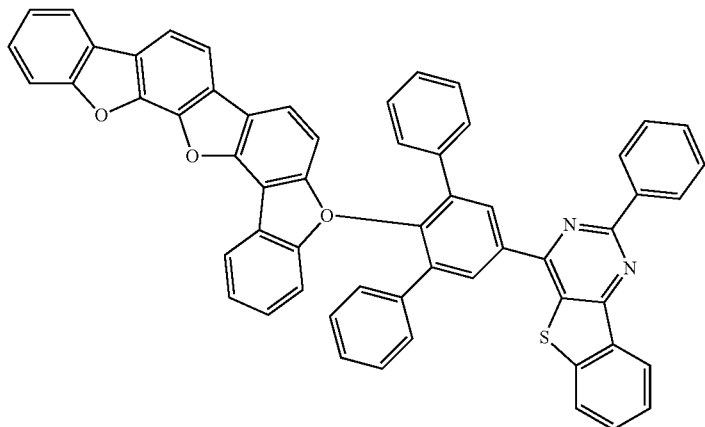
587
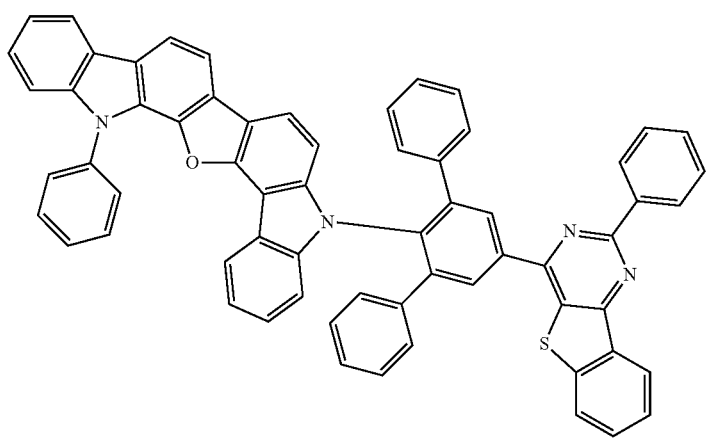

588
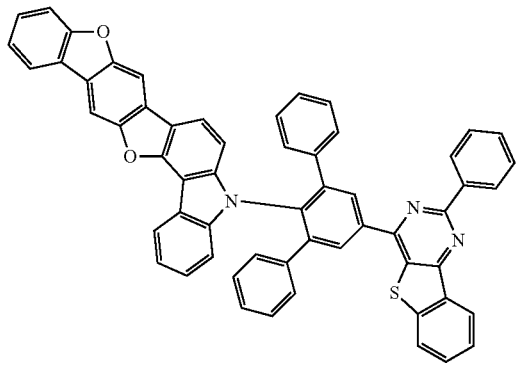
589
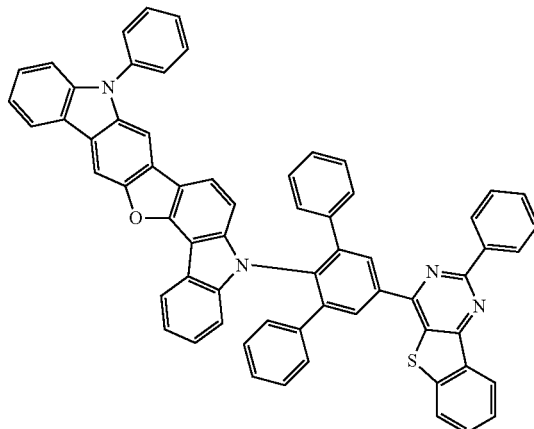
590
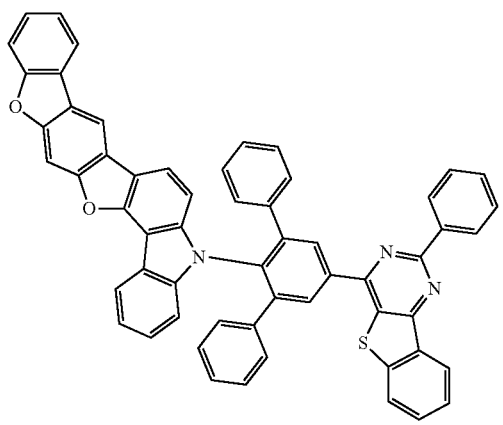
591
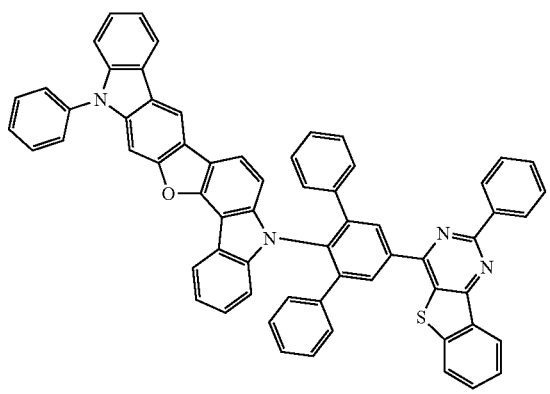
592
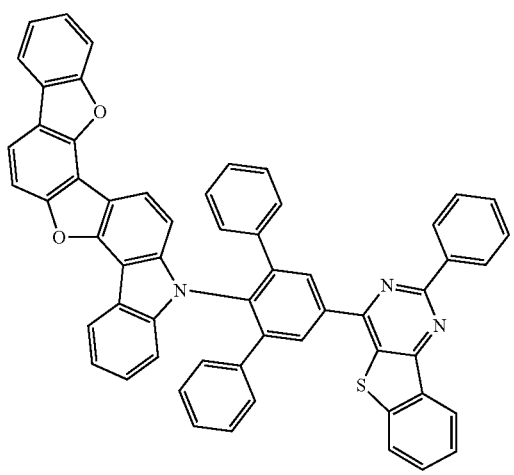
593
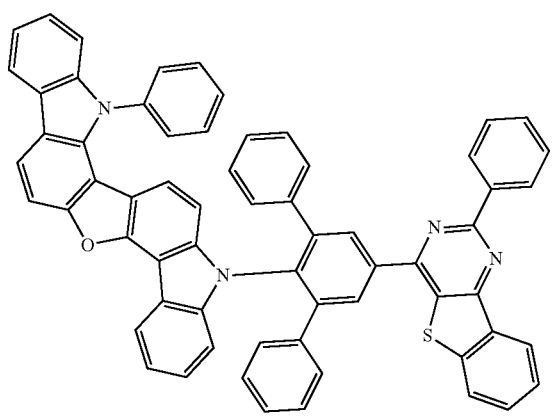

-continued
594
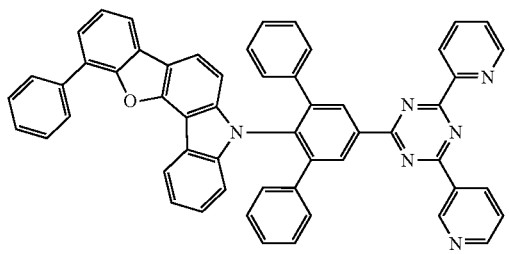
595
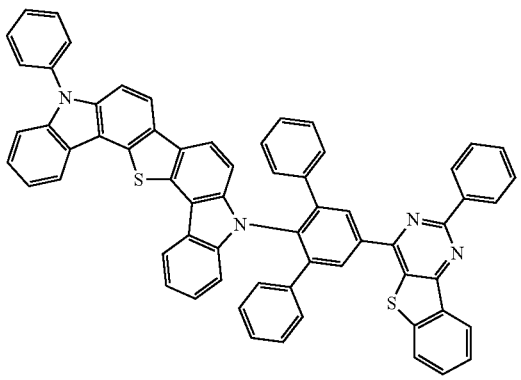
596
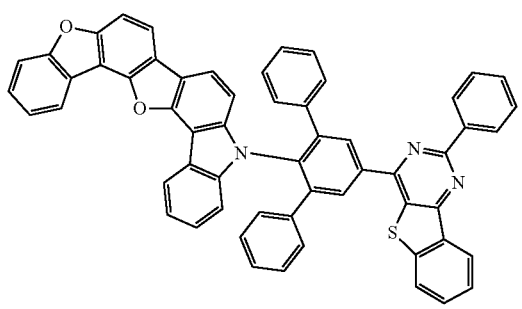
597
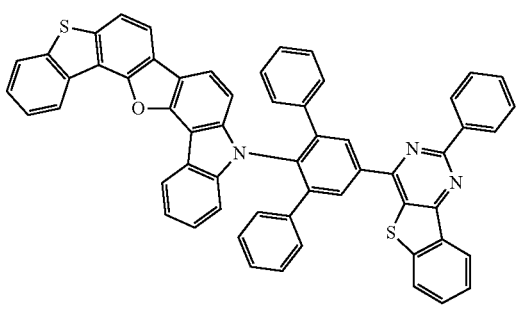
598
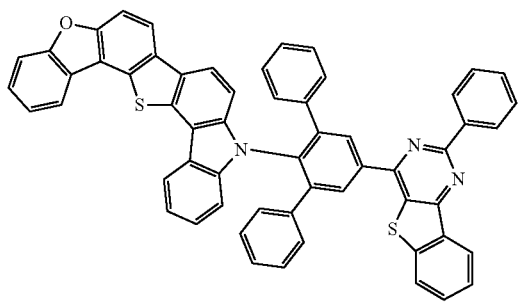
599
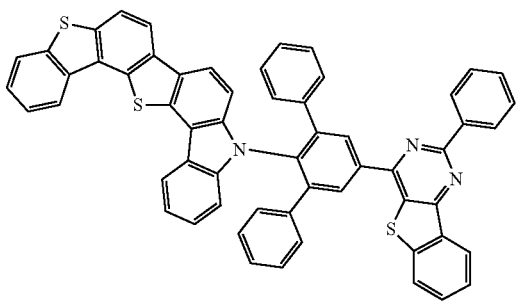
600
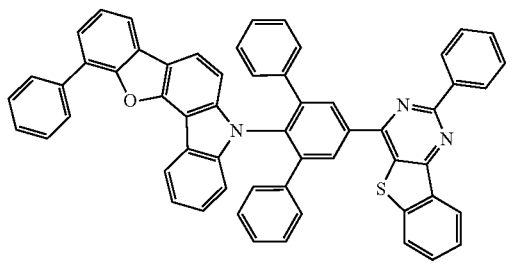
601
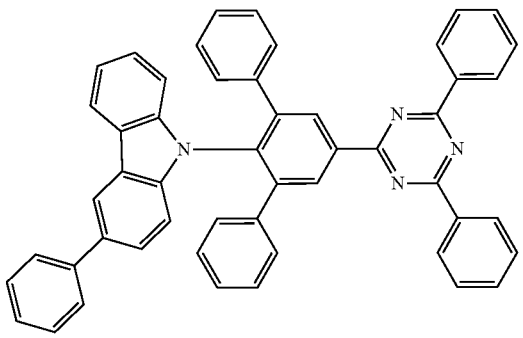
602
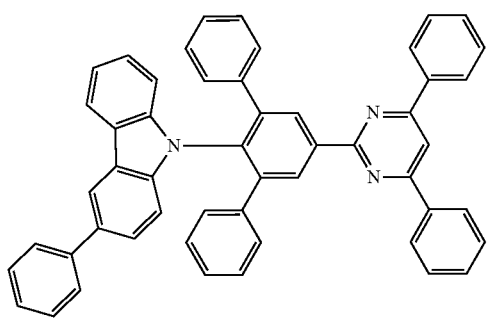
603
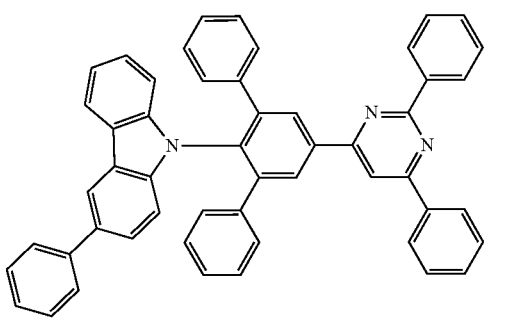

-continued
727
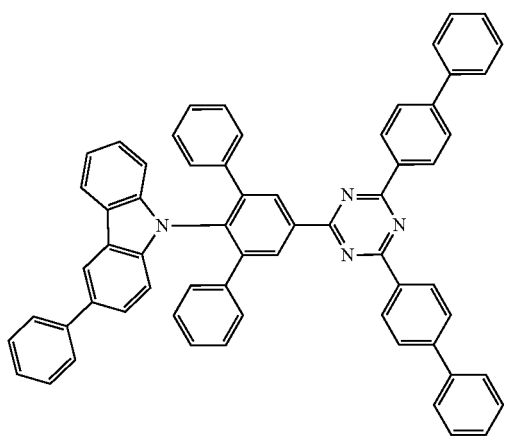
604
728
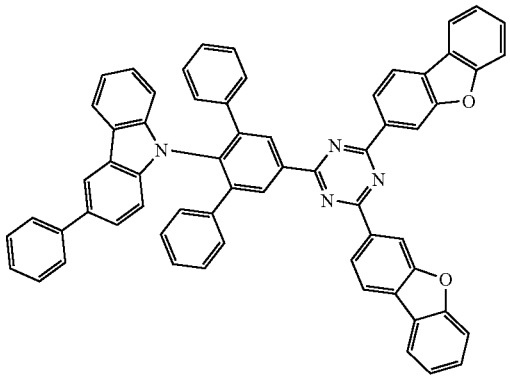
605
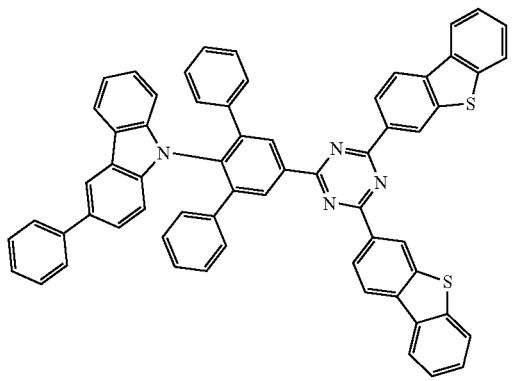
606
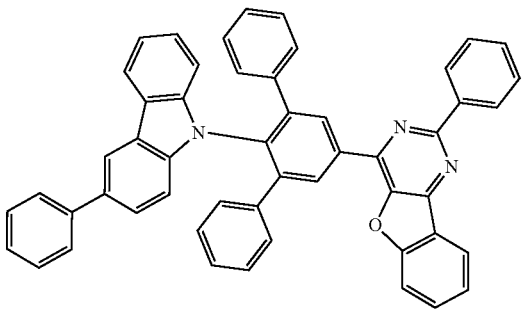
607
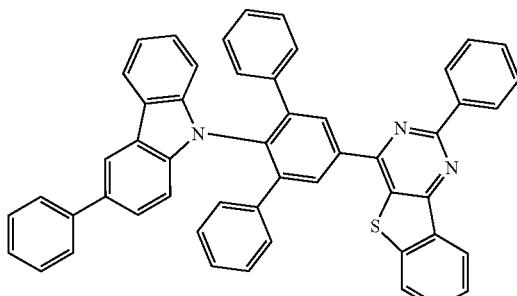
608
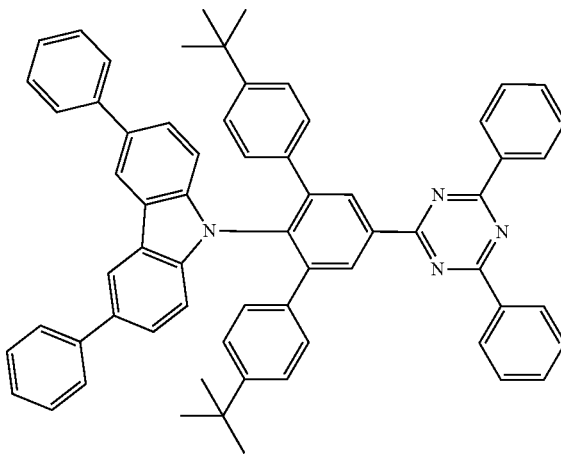
609

-continued
610
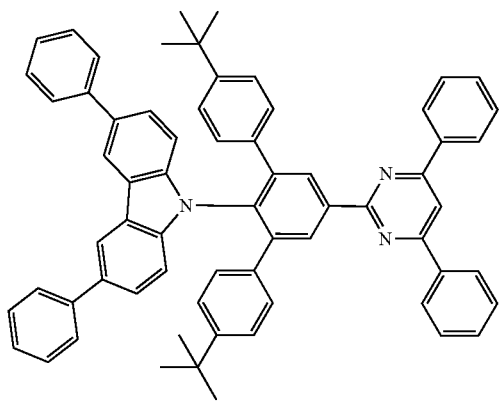
611
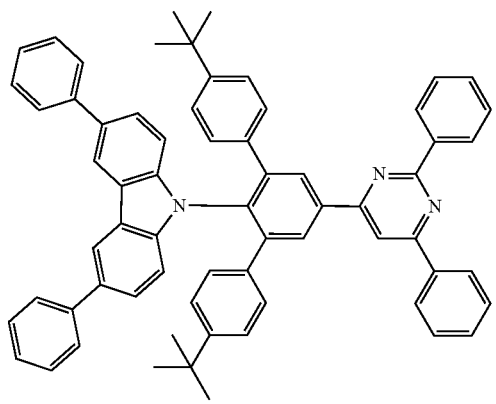
612
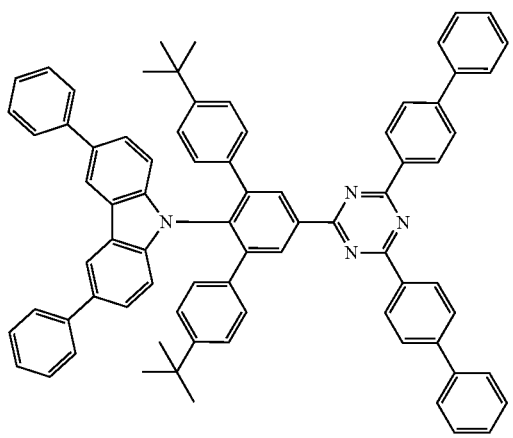
613
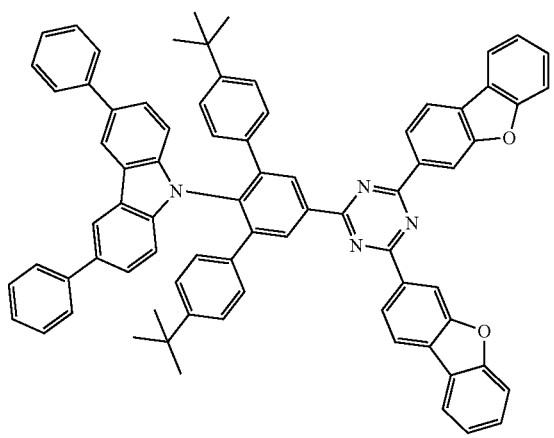
614
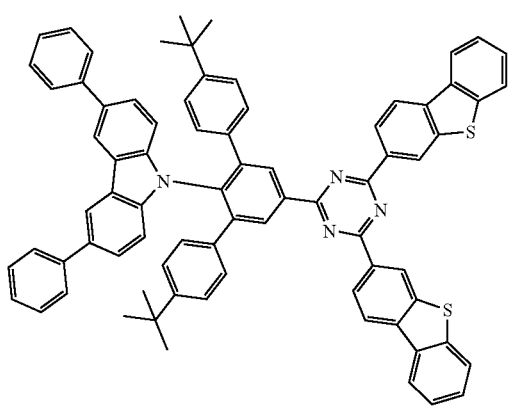
615
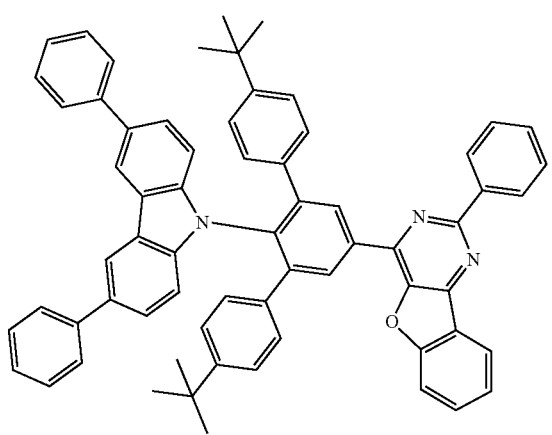

-continued
616
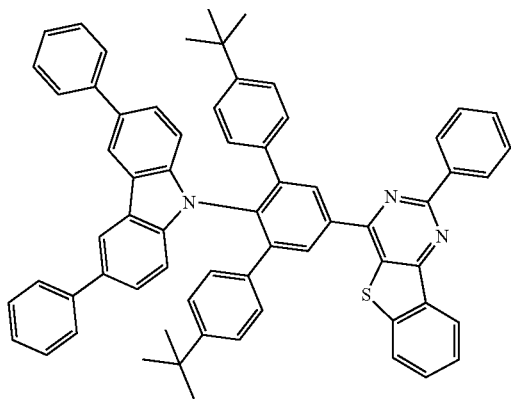
617
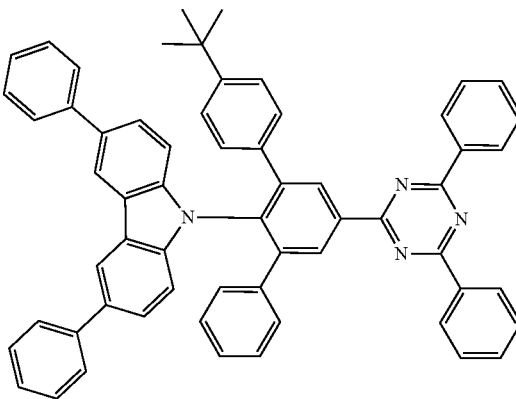
618
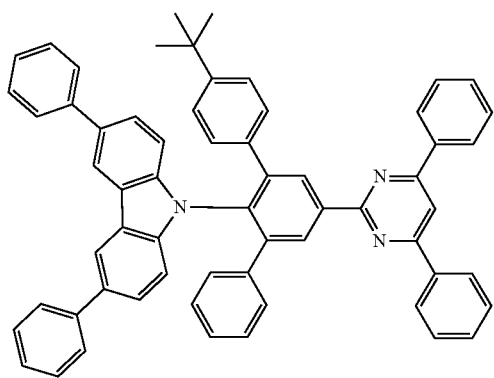
619
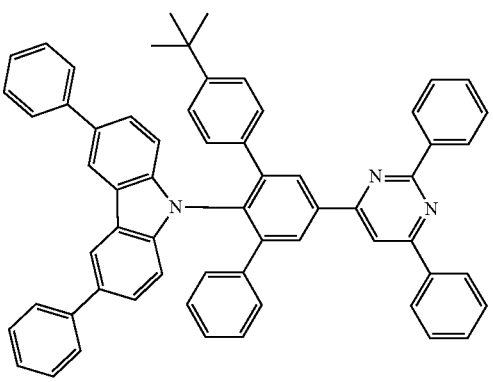
620
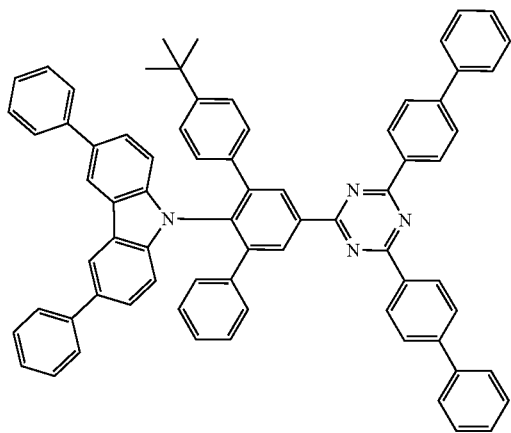
621
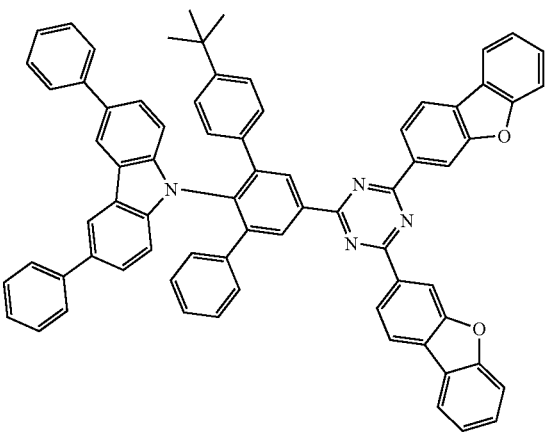

-continued
622
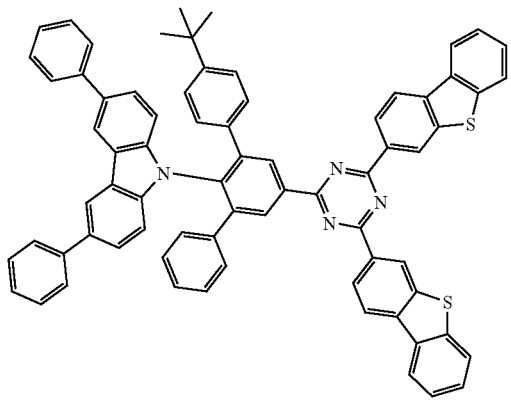
623
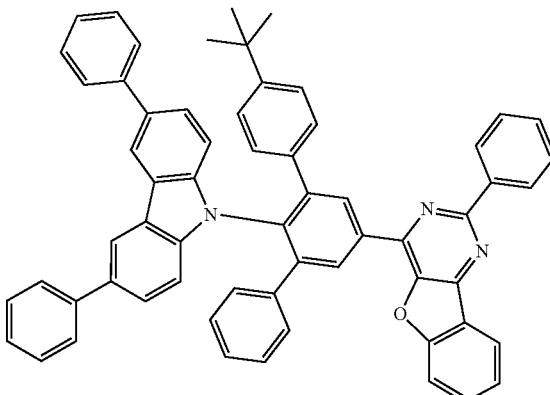
624
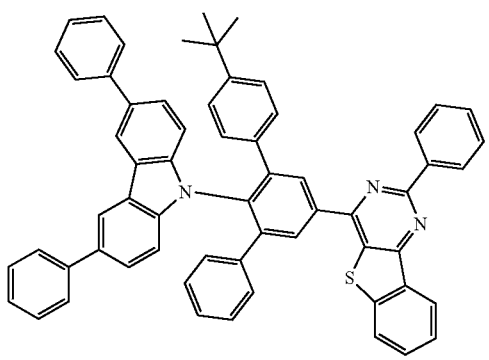
625
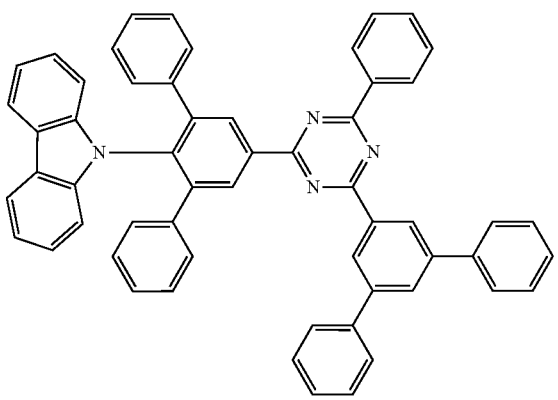
626
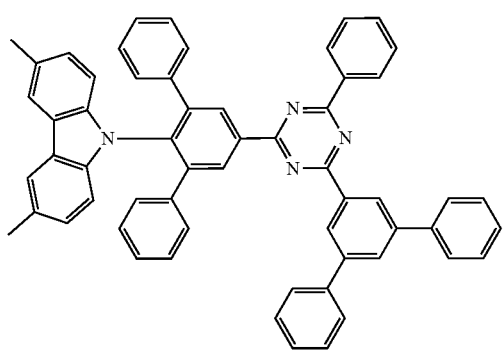
627
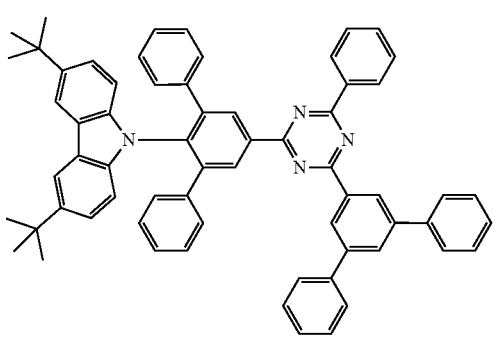
628
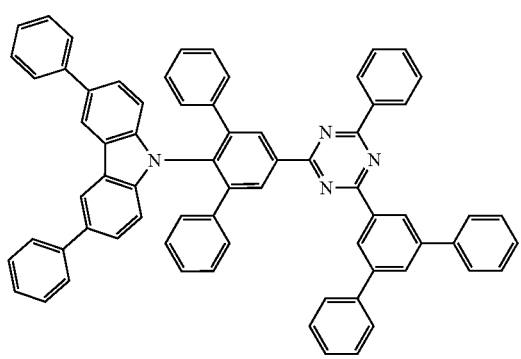
629
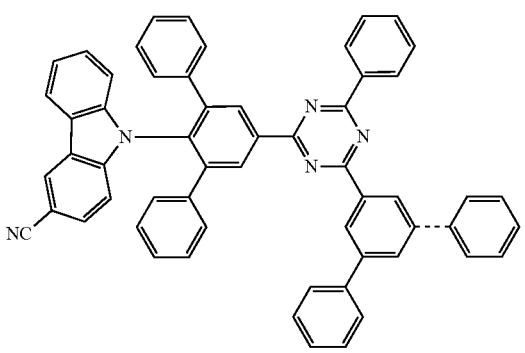

-continued
630
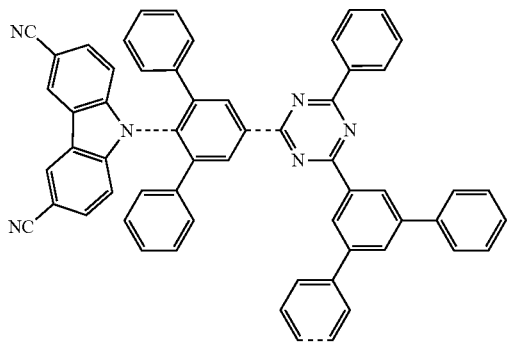
631
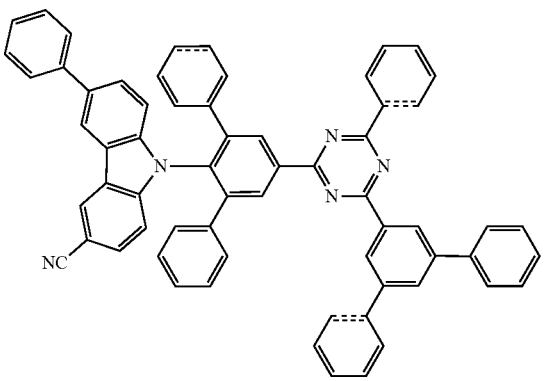
632
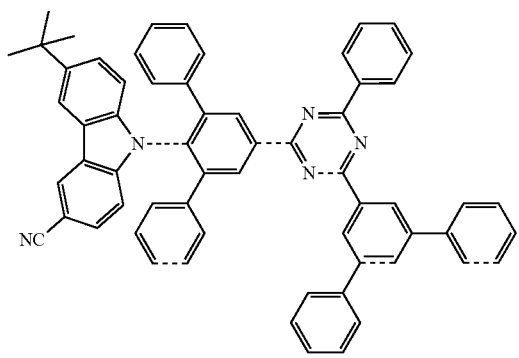
633
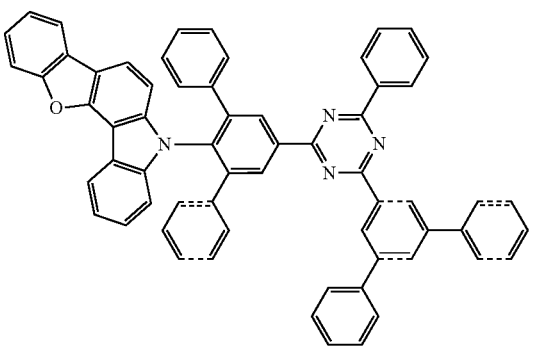
634
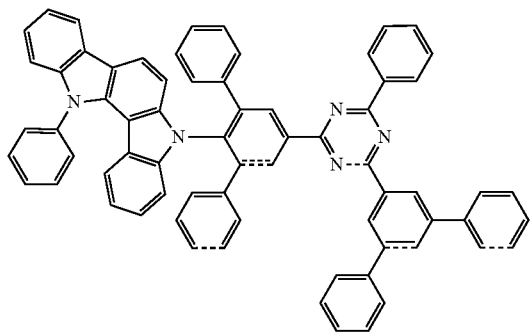
635
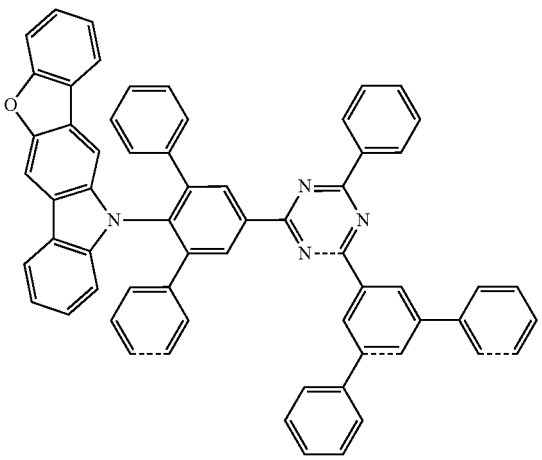

-continued
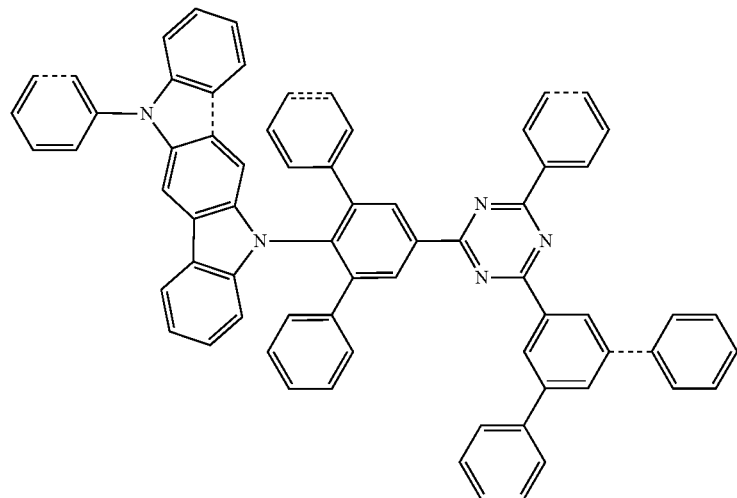
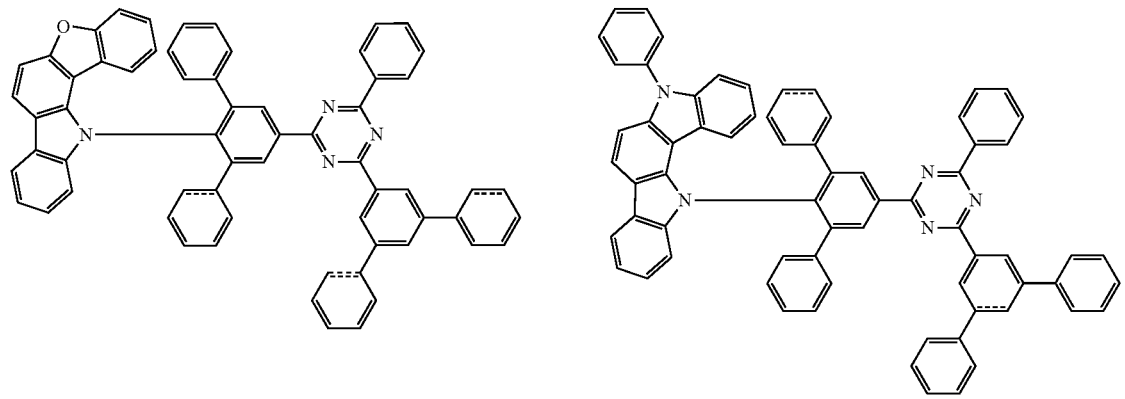
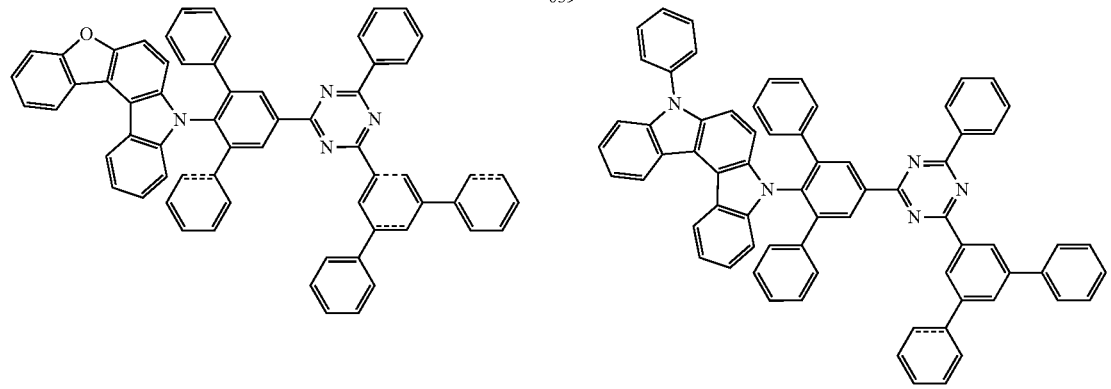

-continued
641
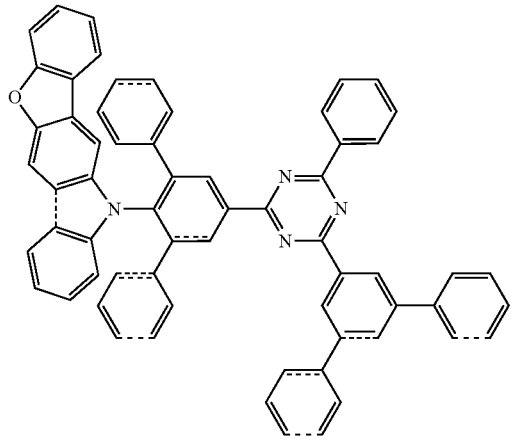
642
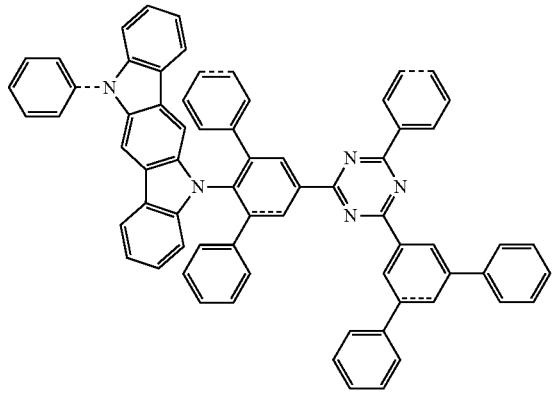
643
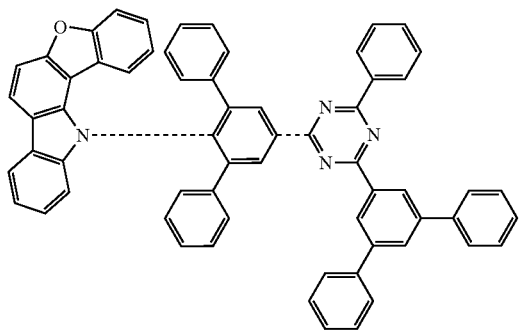
644
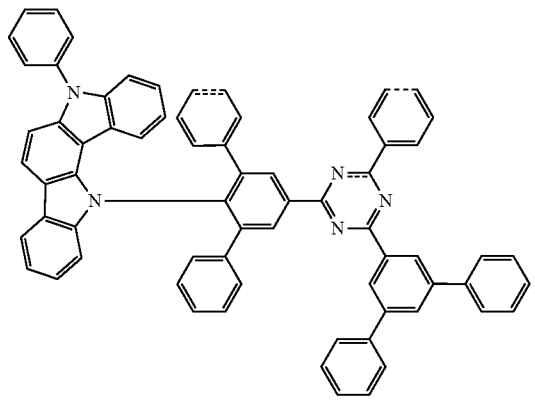
645
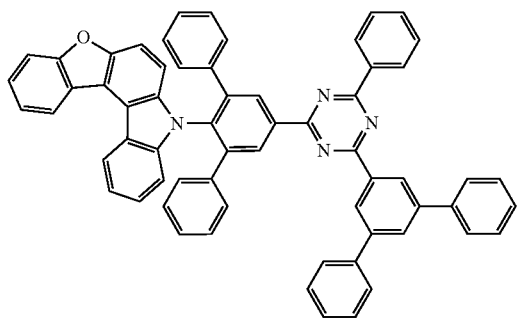
646
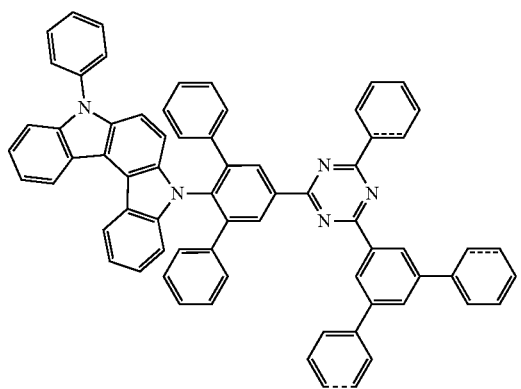
647
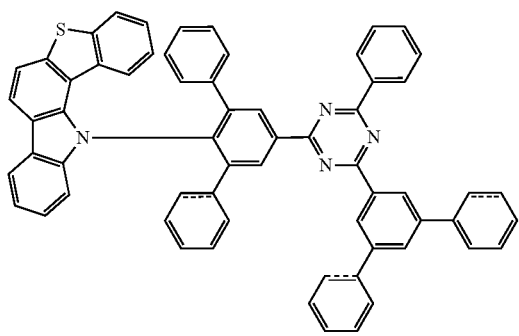
648
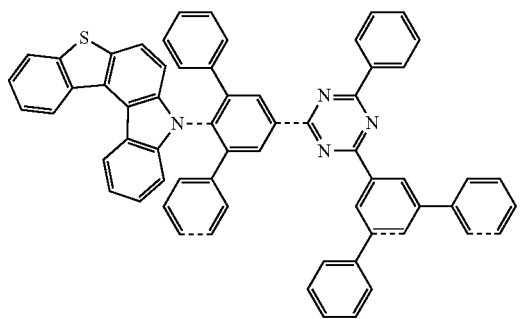

-continued
649
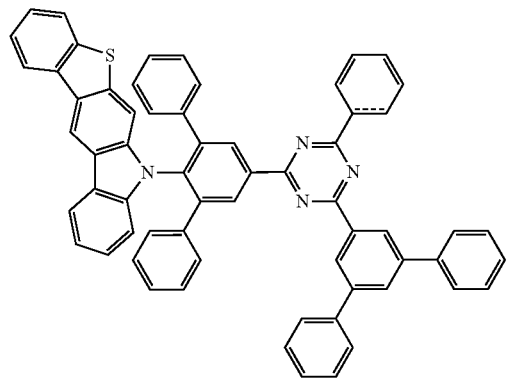
650
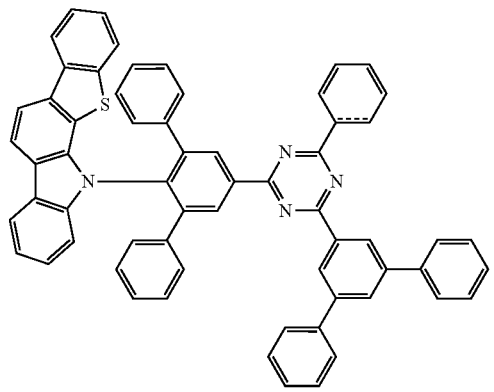
651
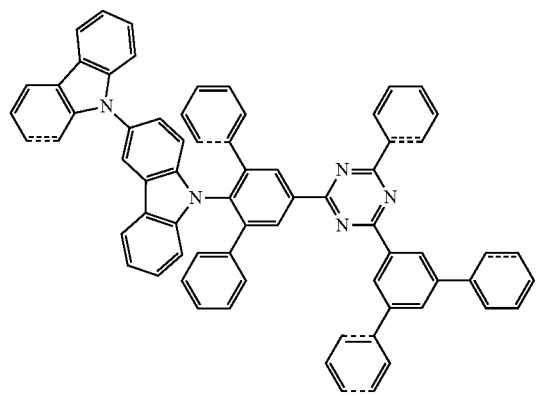
652
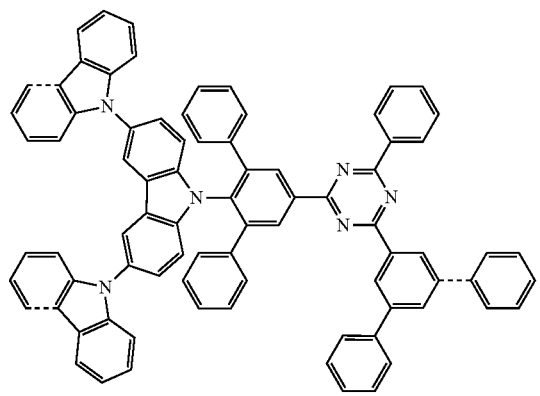
653
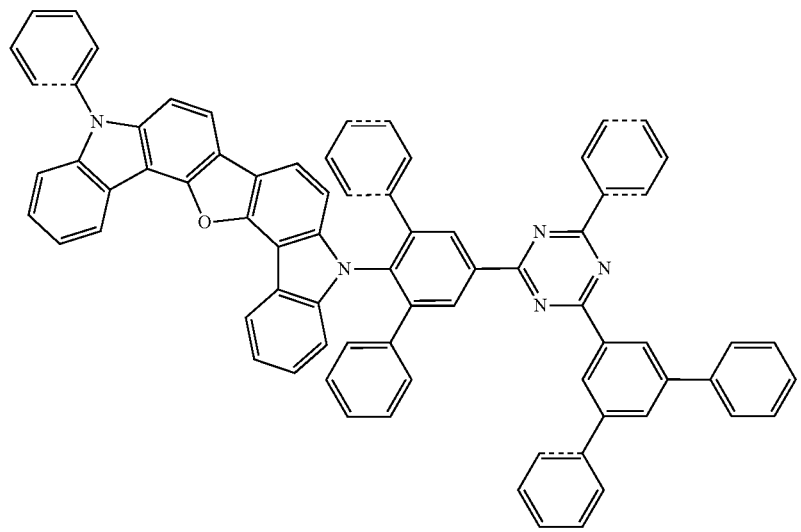

654
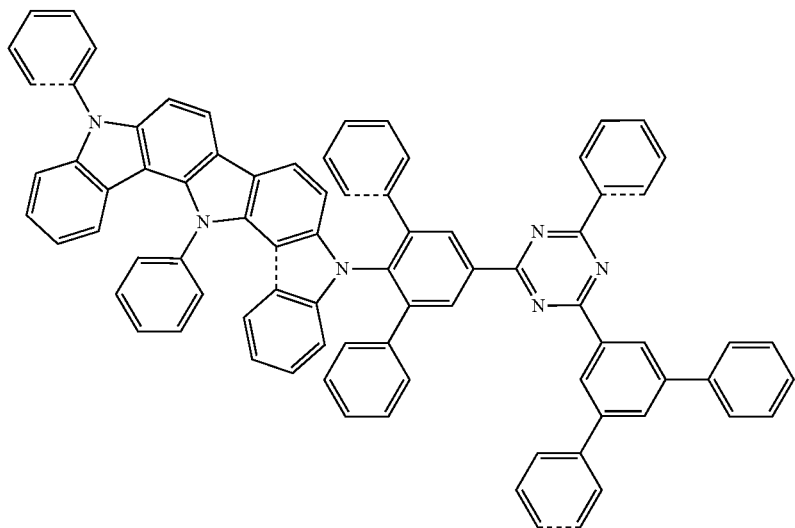
655
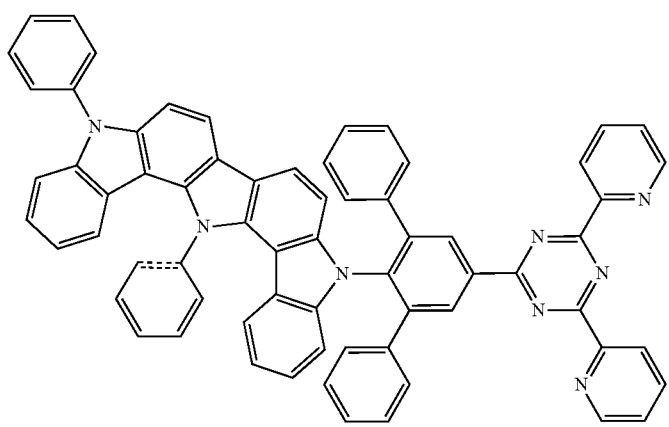
656
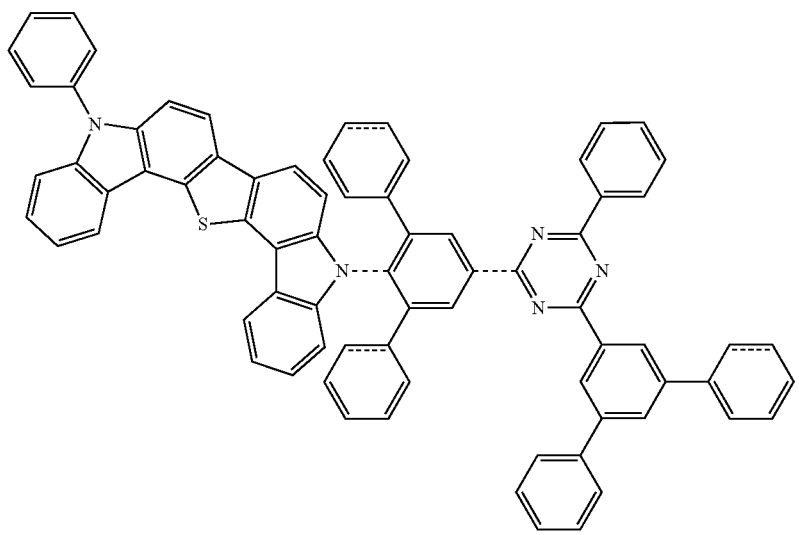

657
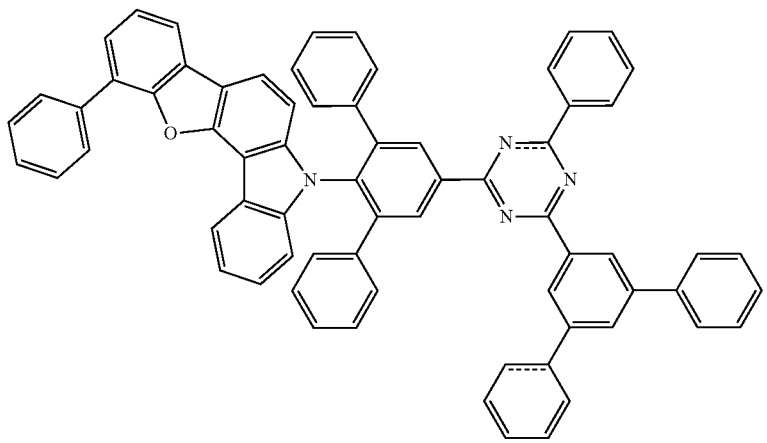
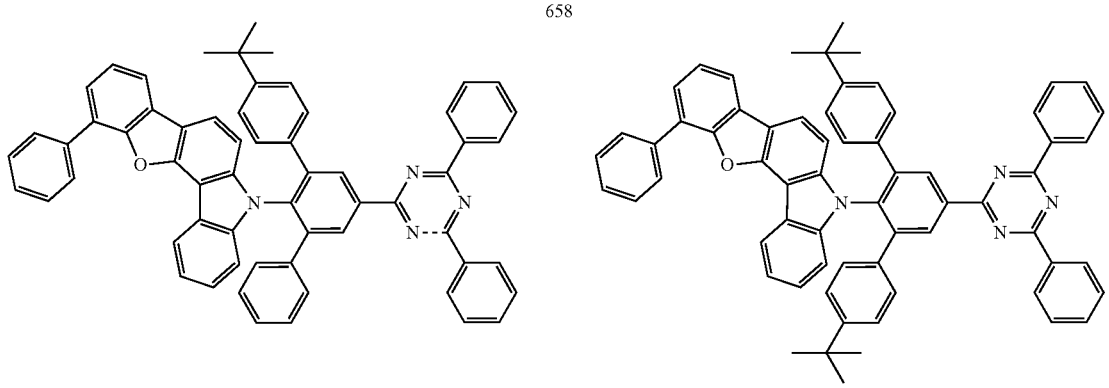
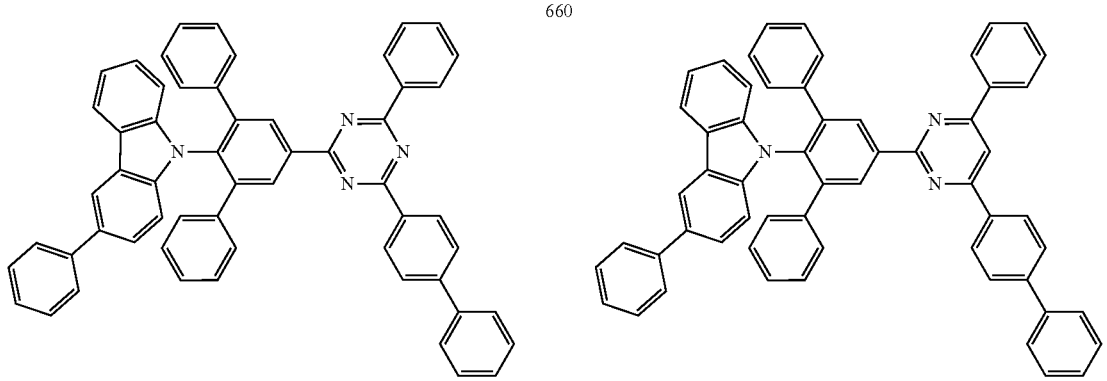
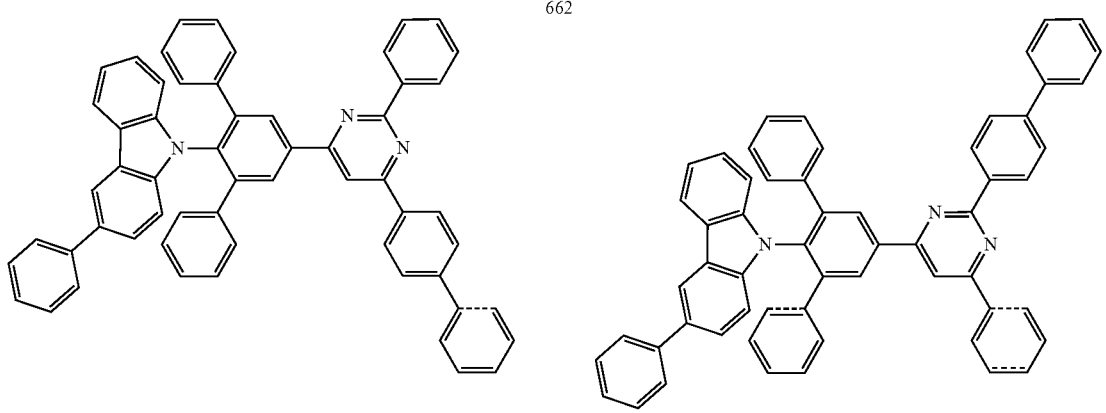

-continued
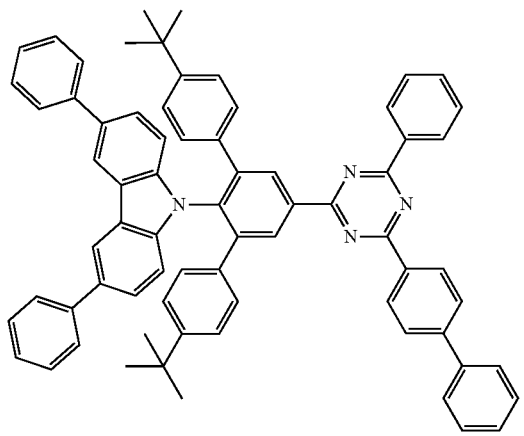
664
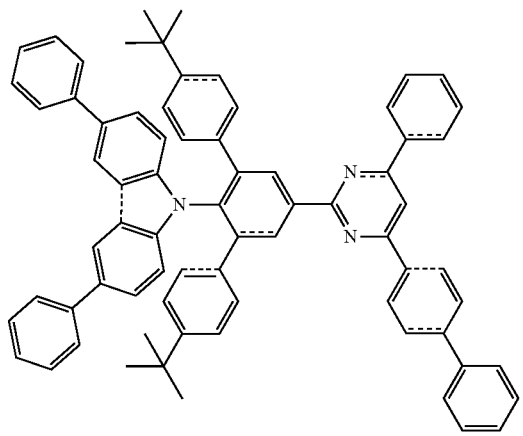
665
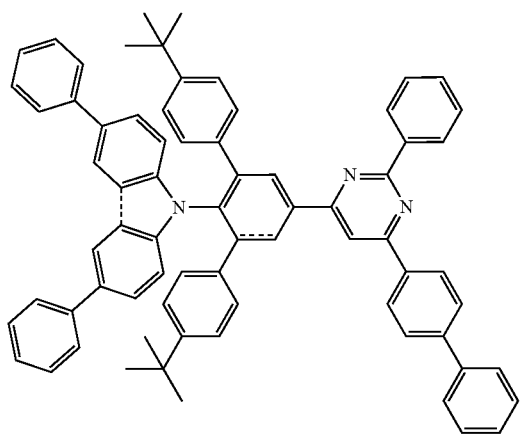
666
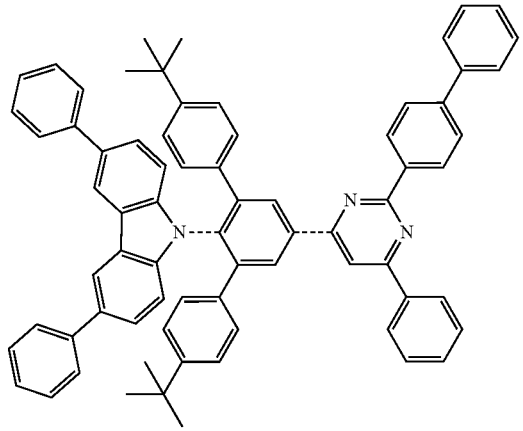
667
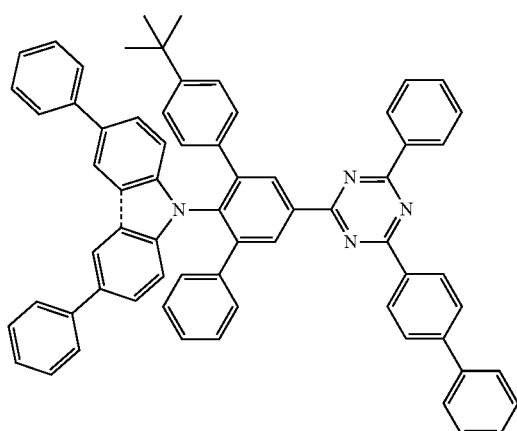
668
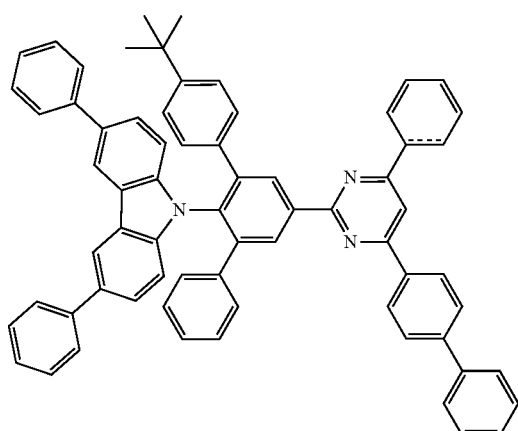
669

-continued
670 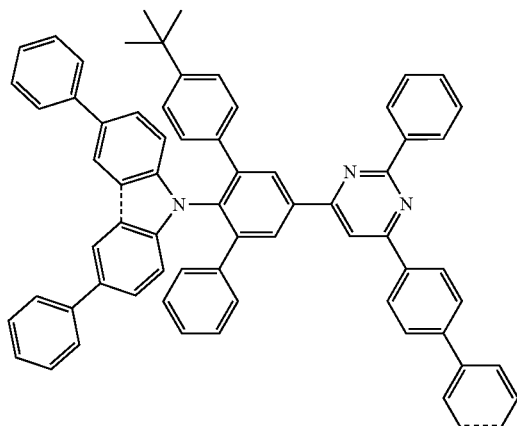
671 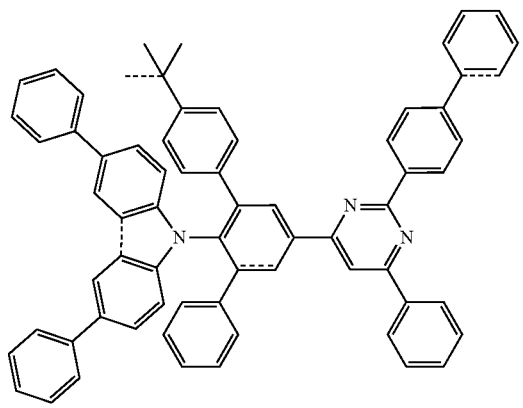
672 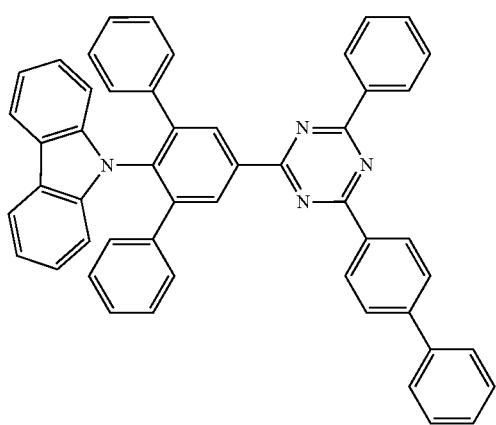
673 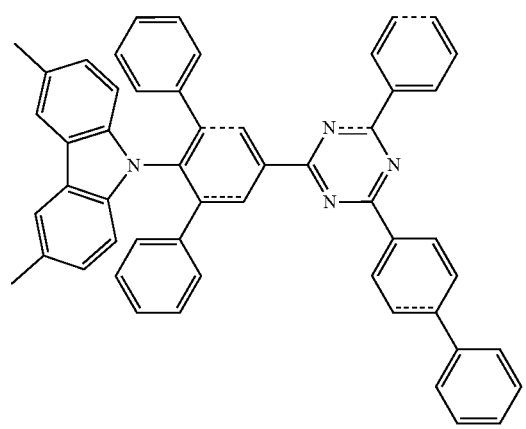
674 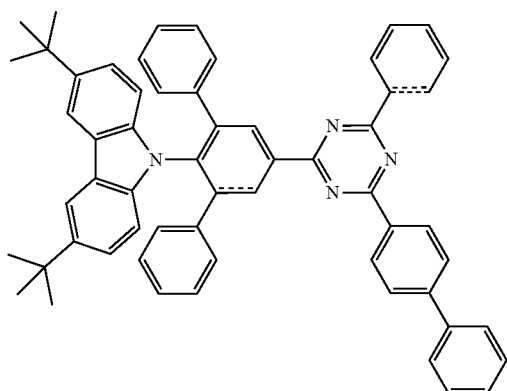
675 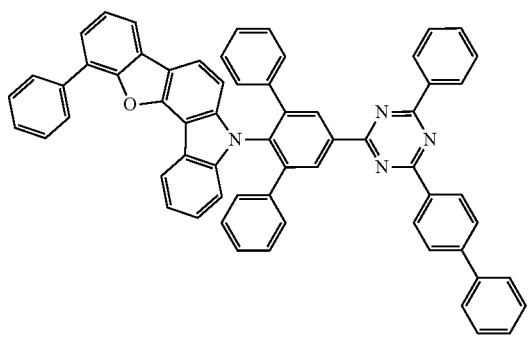
676 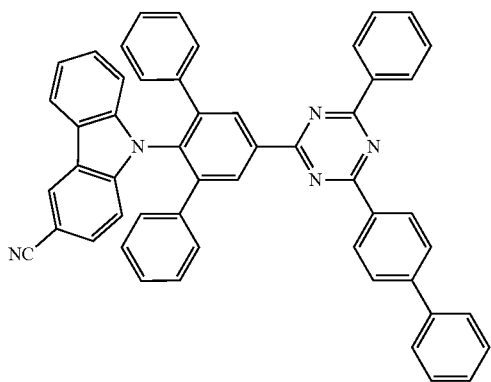
677 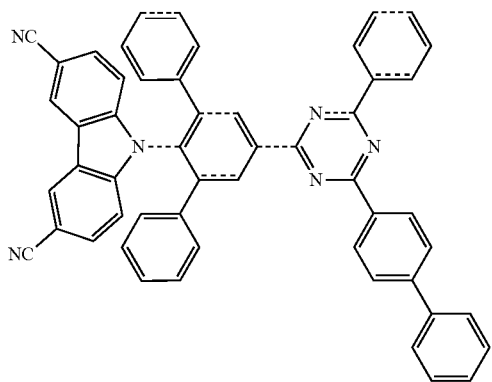

-continued
678
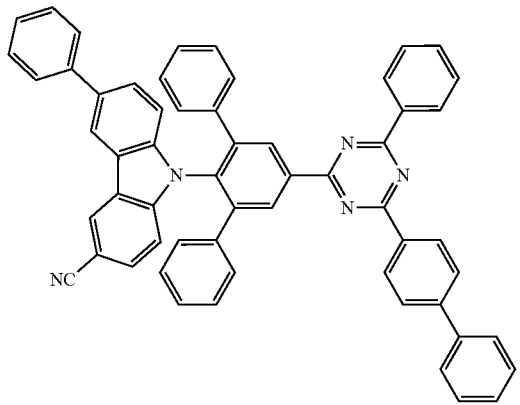
679
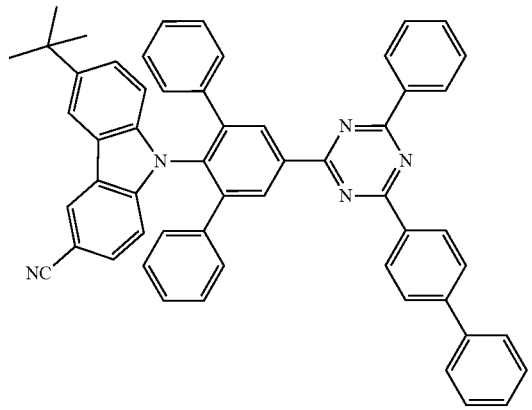
680
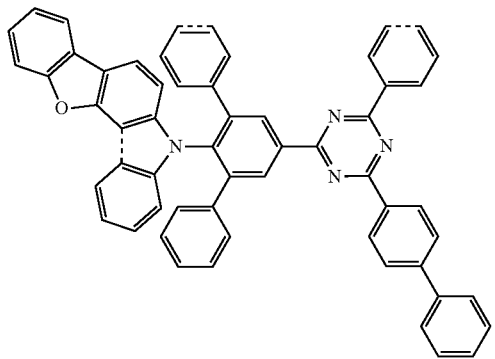
681
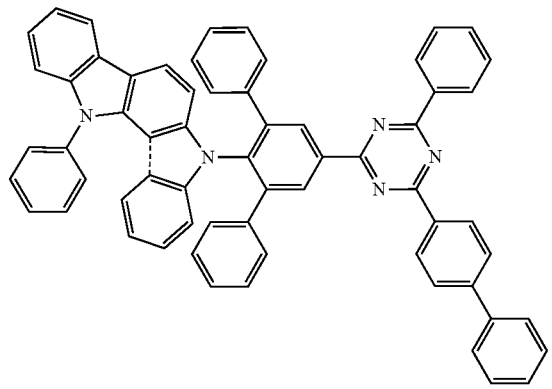
682
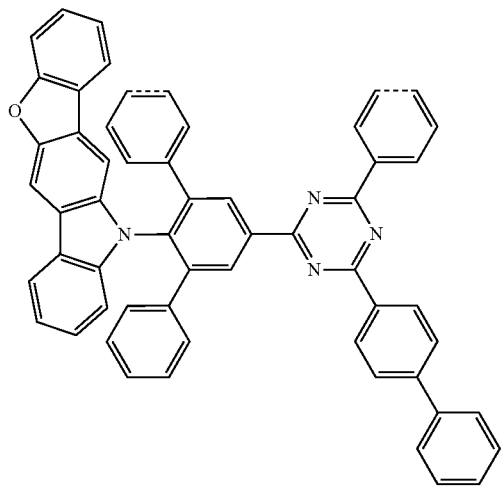
683
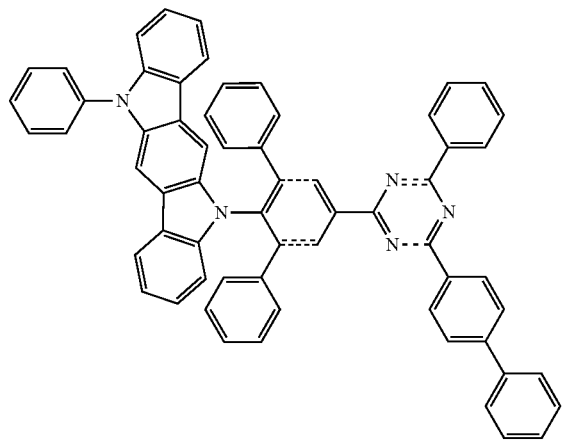

-continued
684
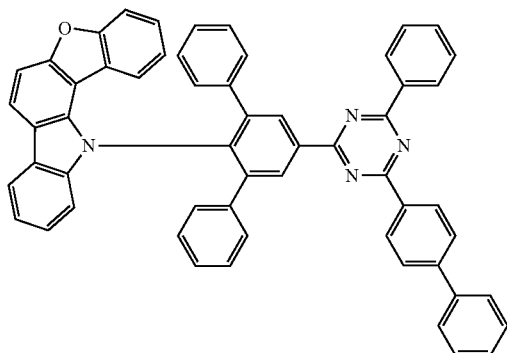
685
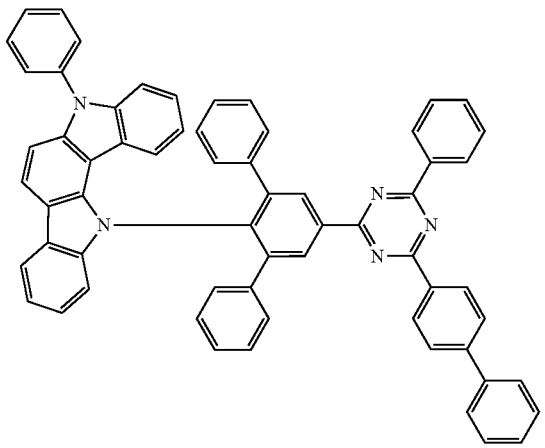
686
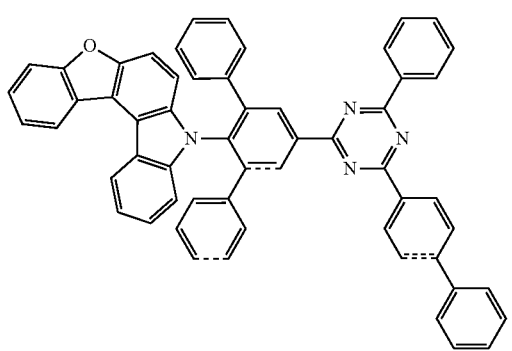
687
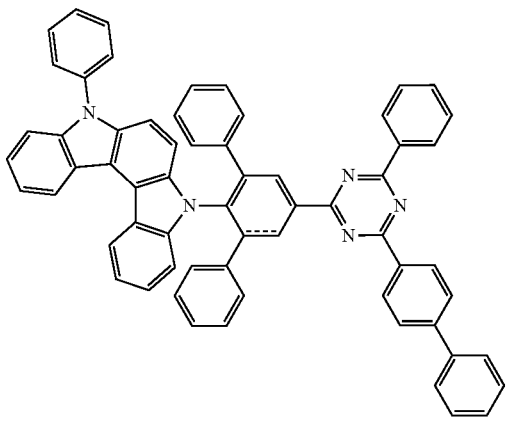
688
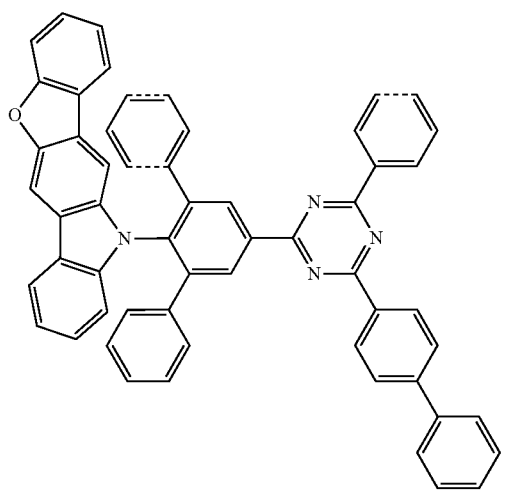
689
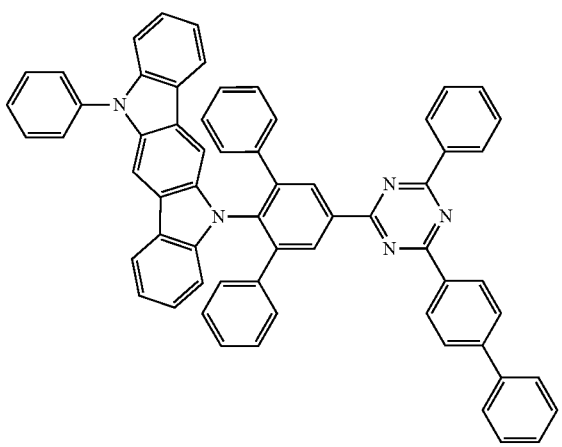

-continued
690
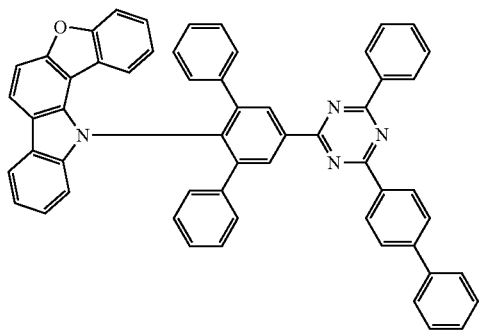
691
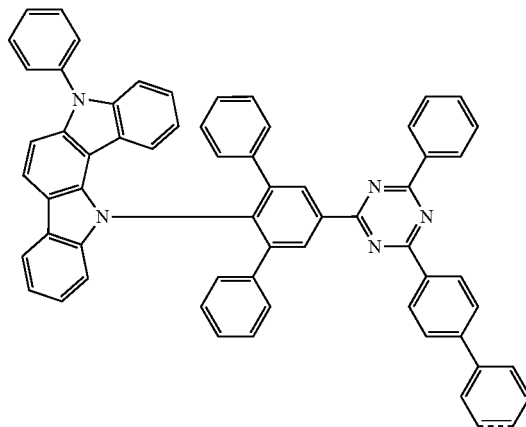
692
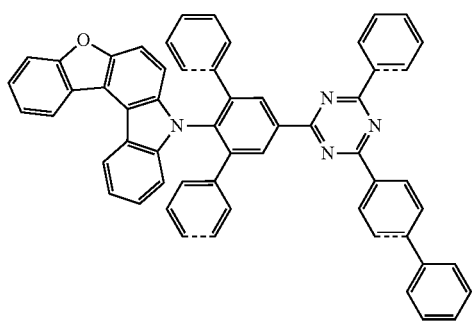
693
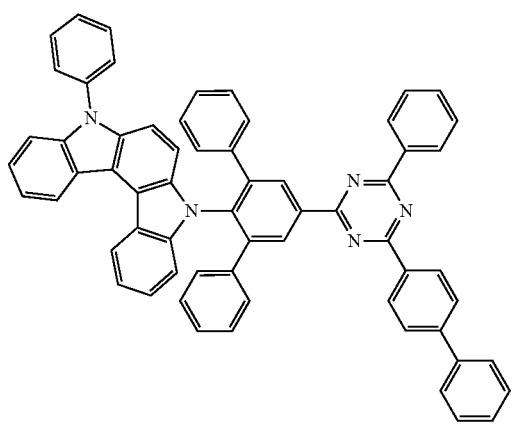
694
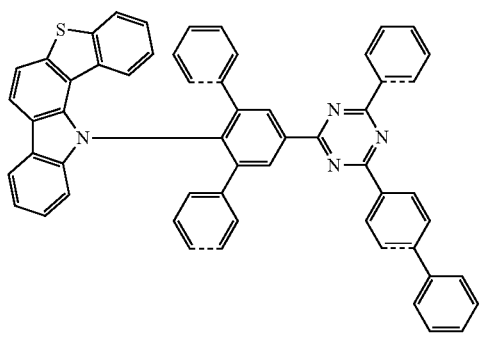
695
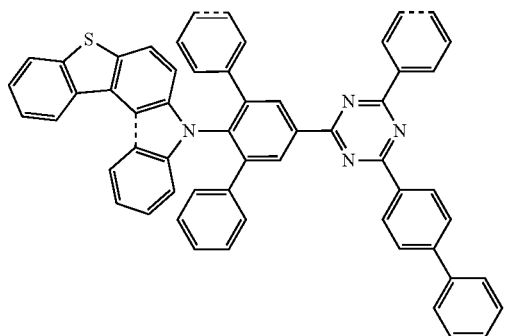

-continued
696
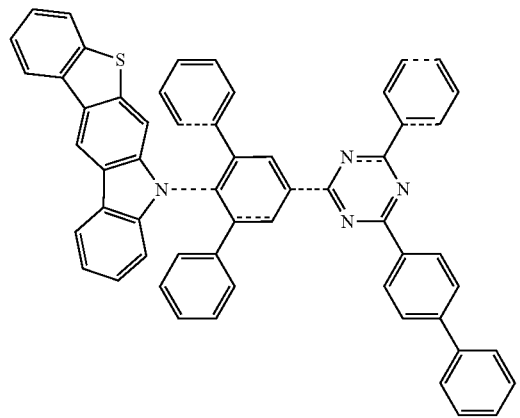
697
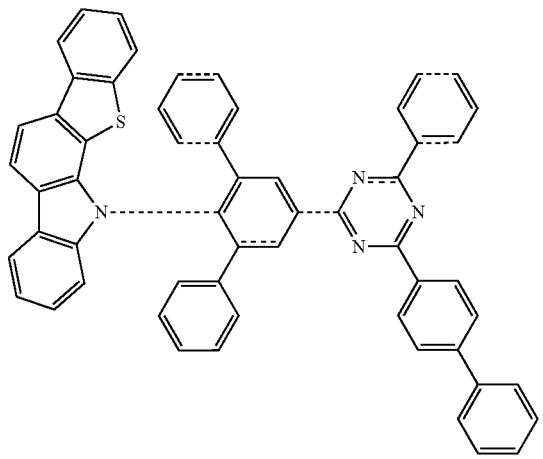
698
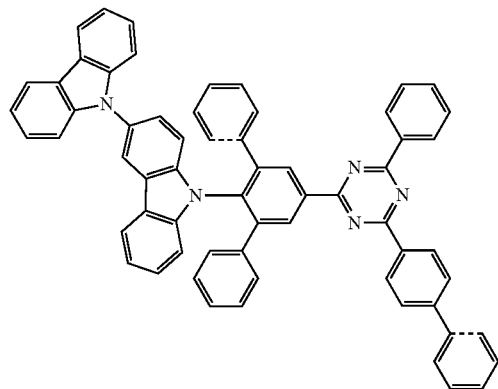
699
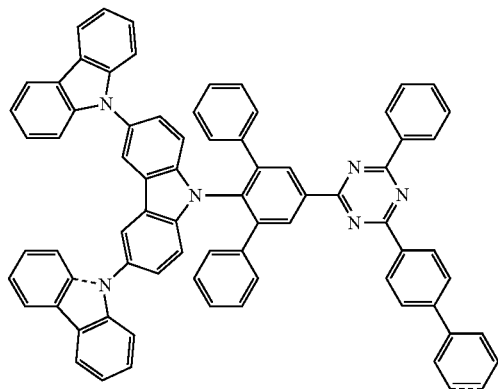
700
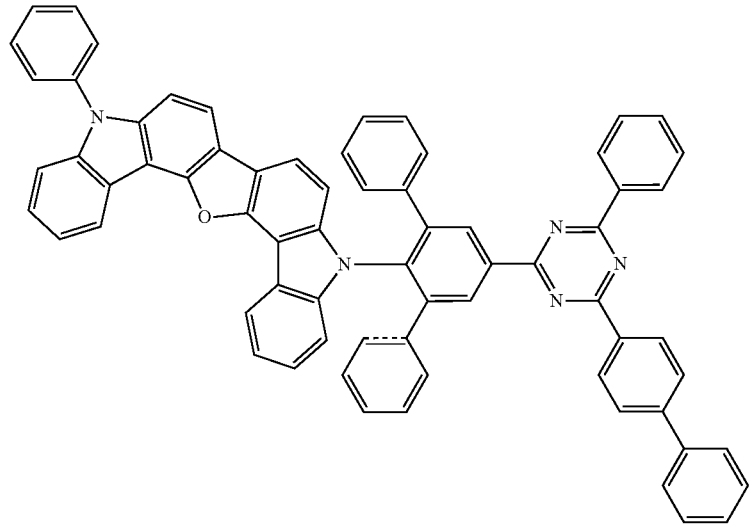

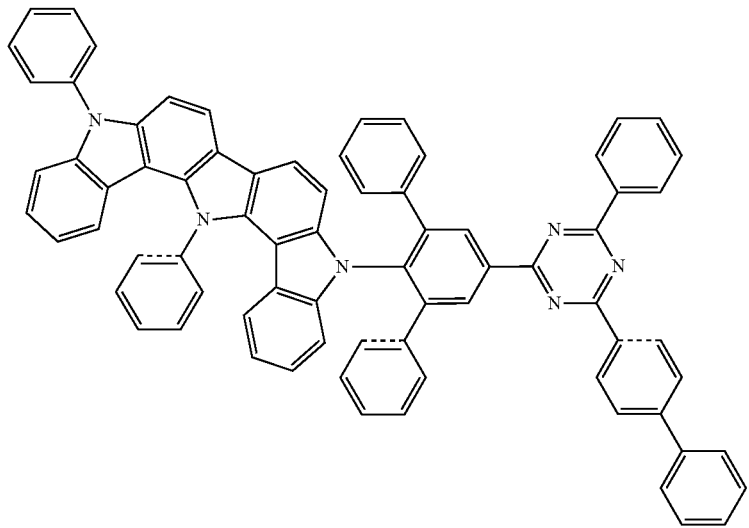
701
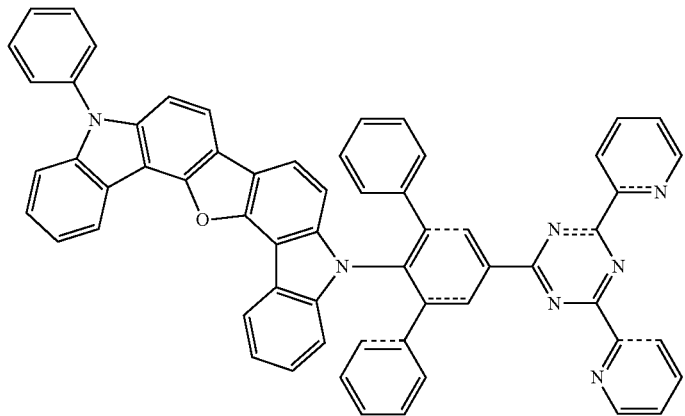
702
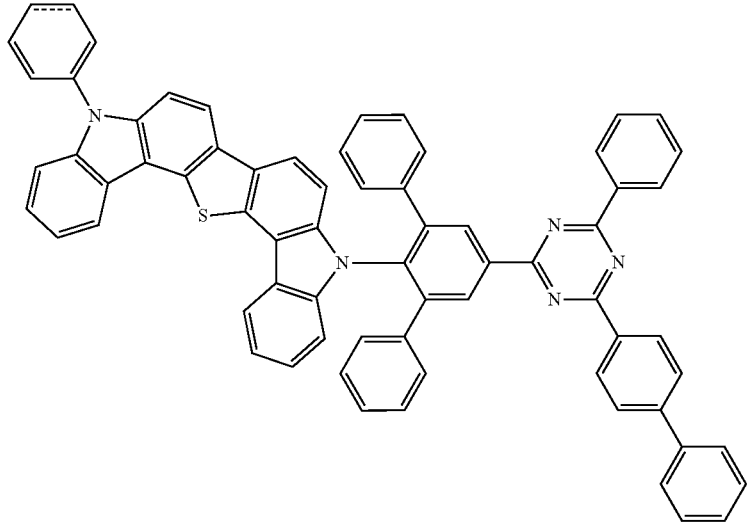
703

-continued
704
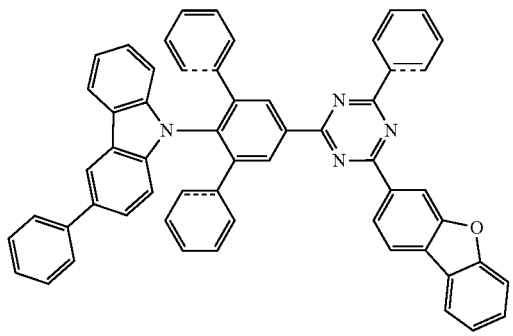
705
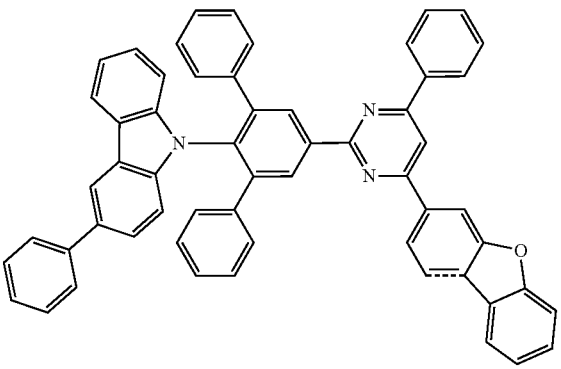
706
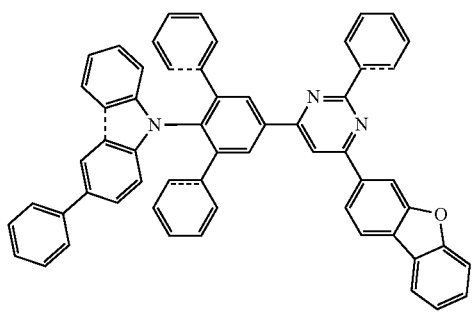
707
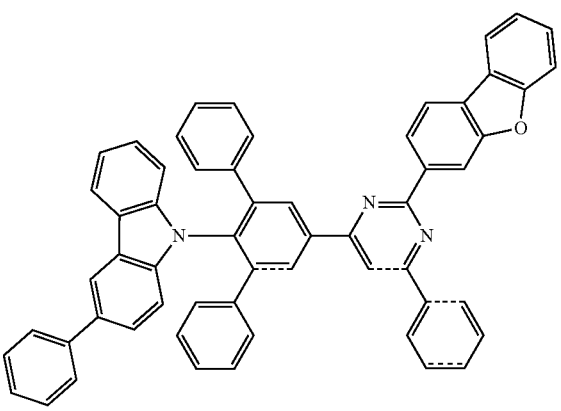
708
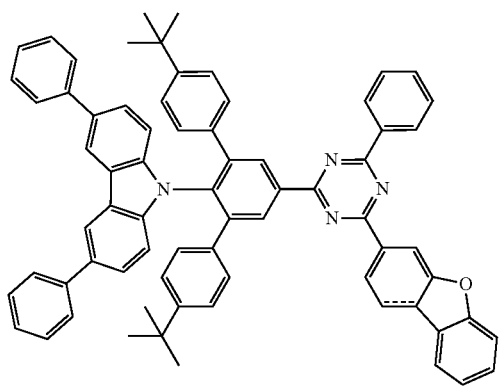
709
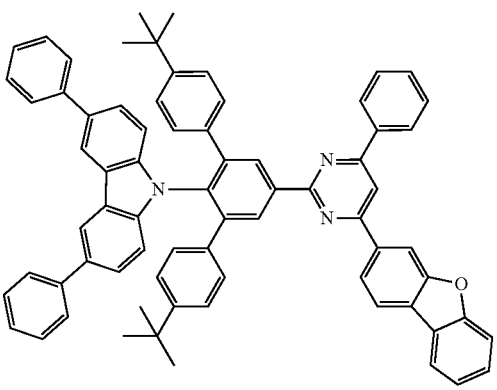
710
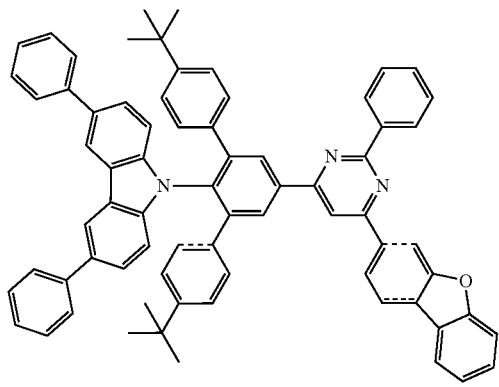
711
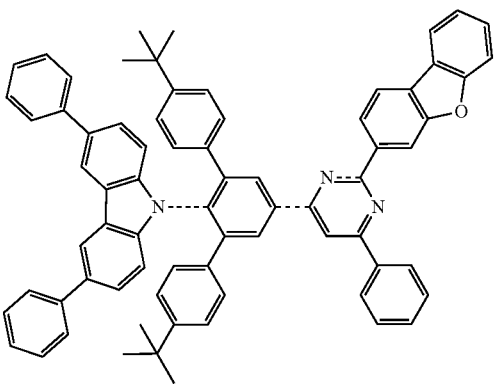

-continued
763 712 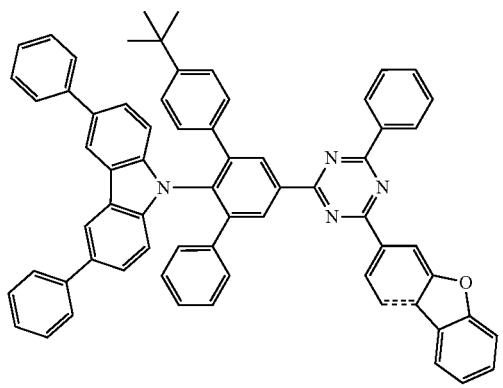
764 713 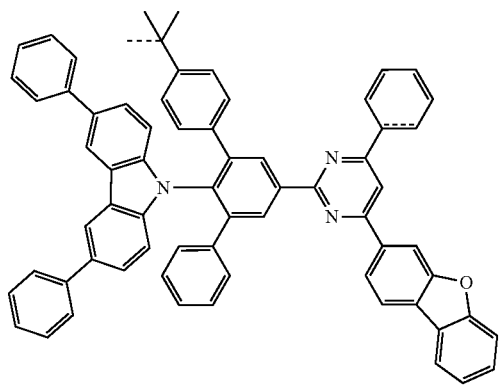
714 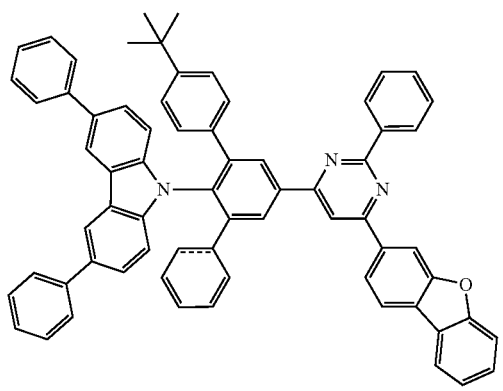
715 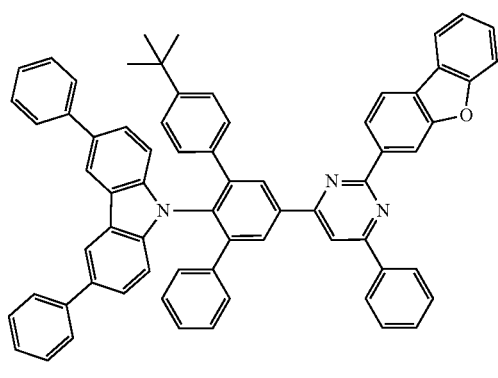
716 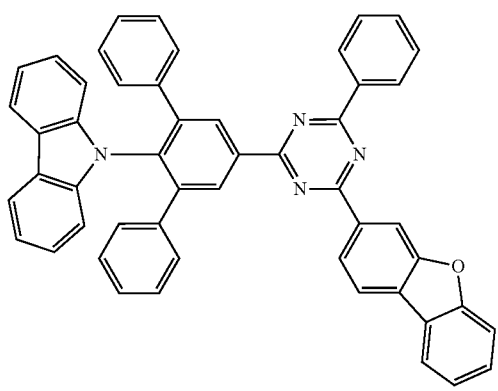
717 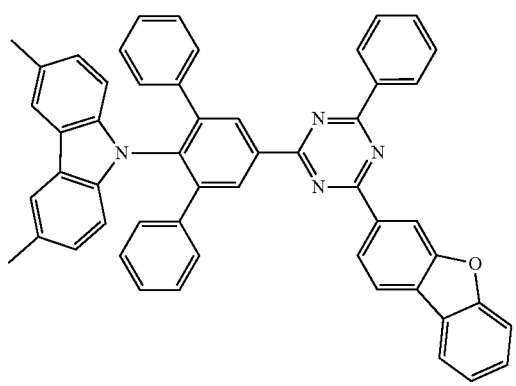
718 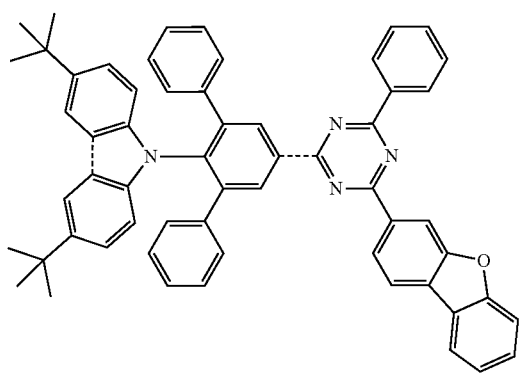
719 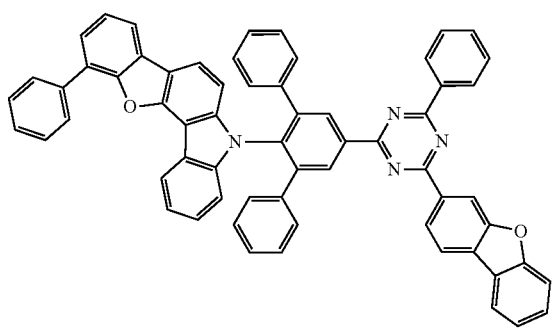

720
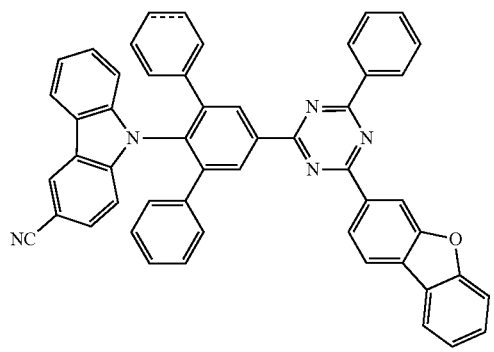
721
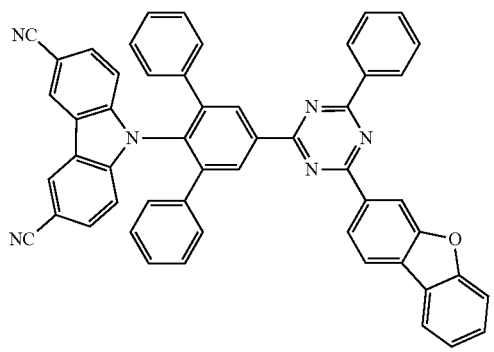
722
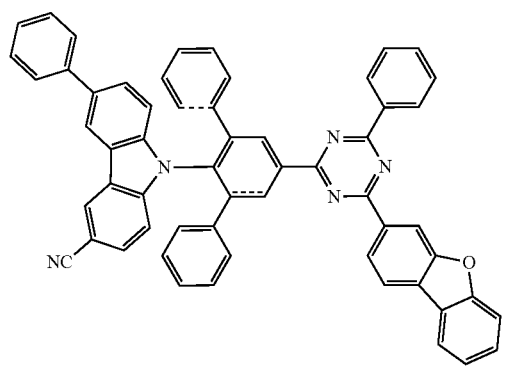
723
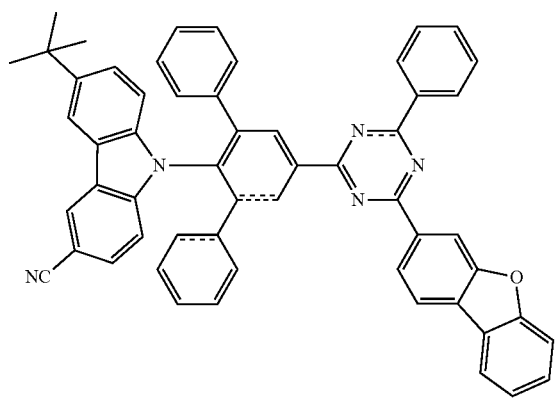
724
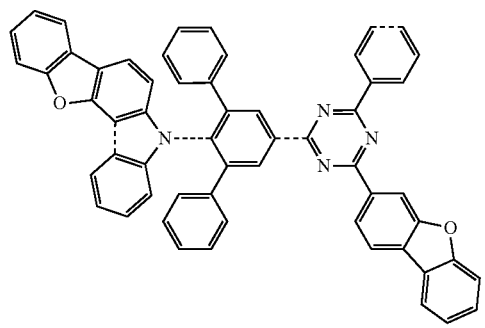
725
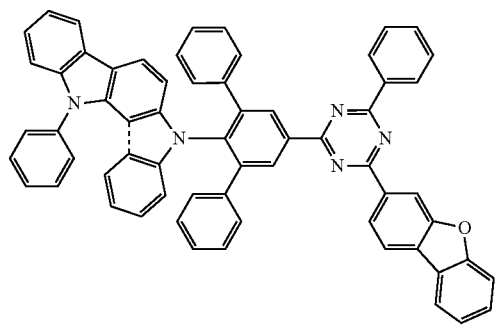
726
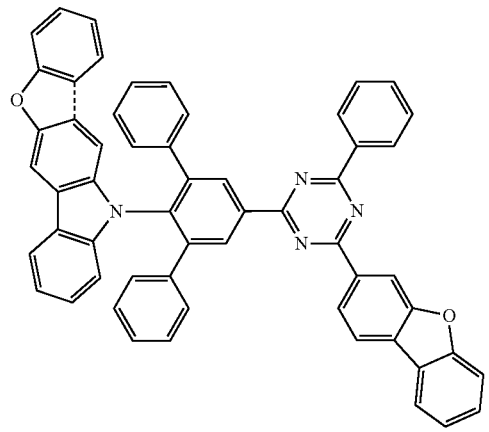
727
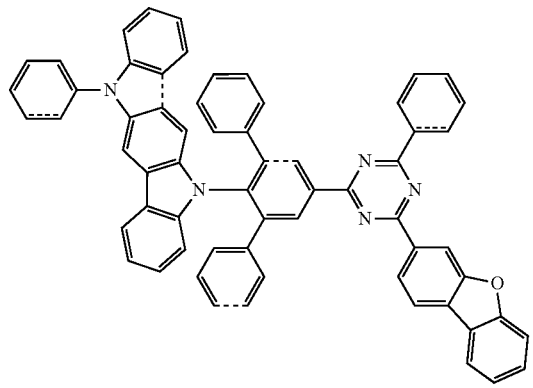

-continued
767
728
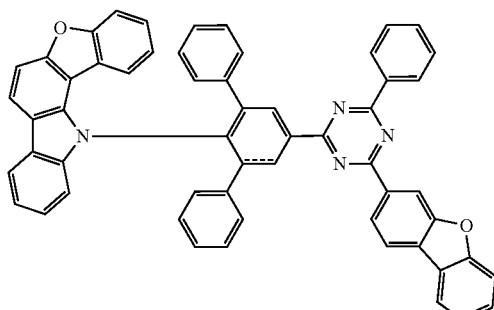
768
729
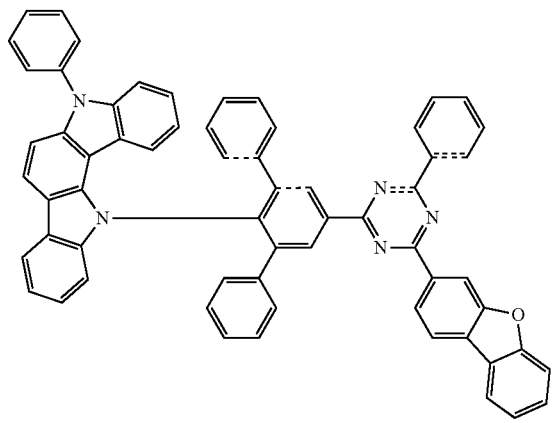
730
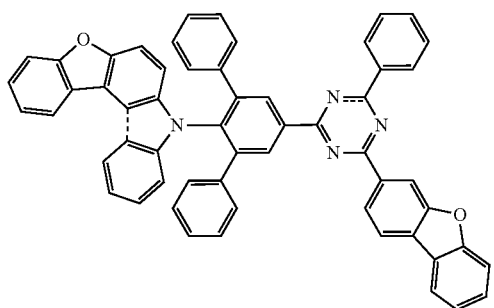
731
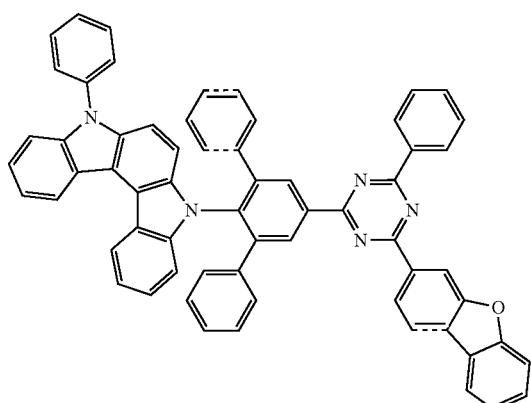
732
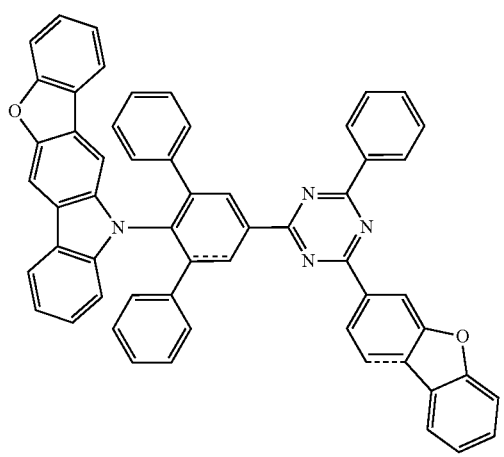
733
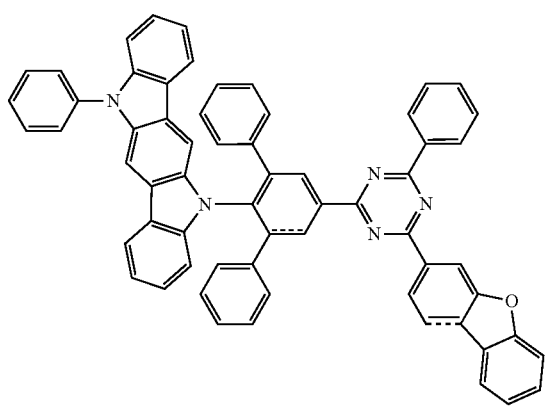

-continued
734
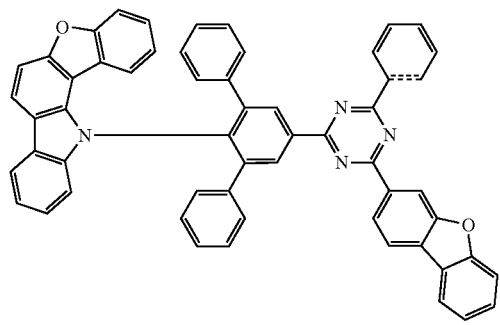
735
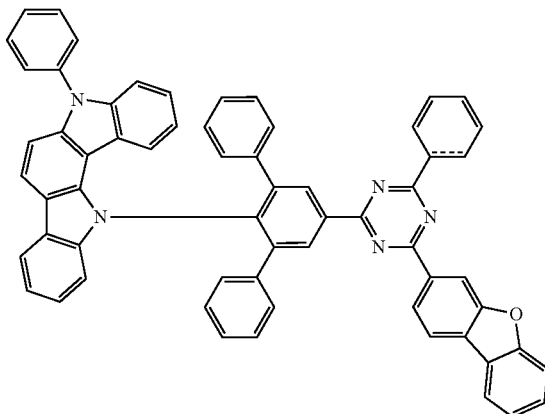
736
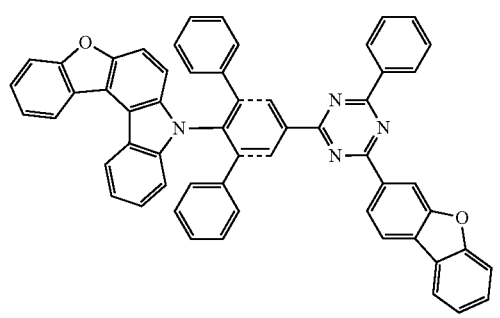
737
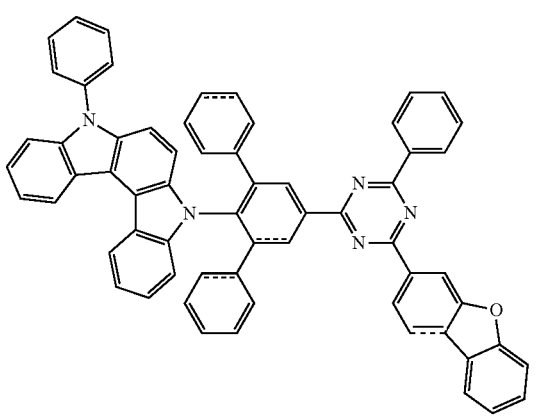
738
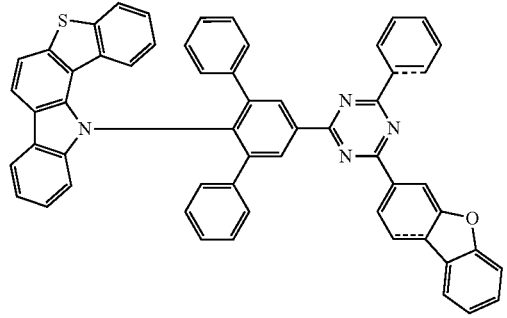
739
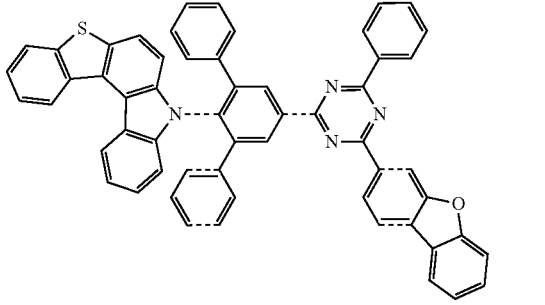
740
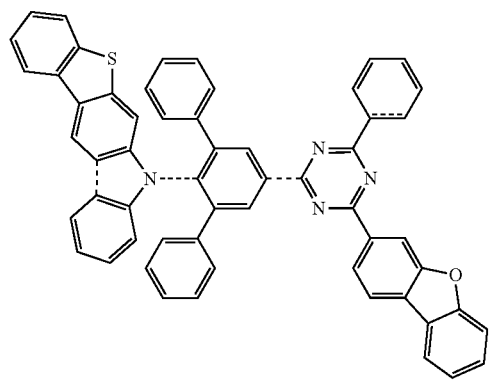
741
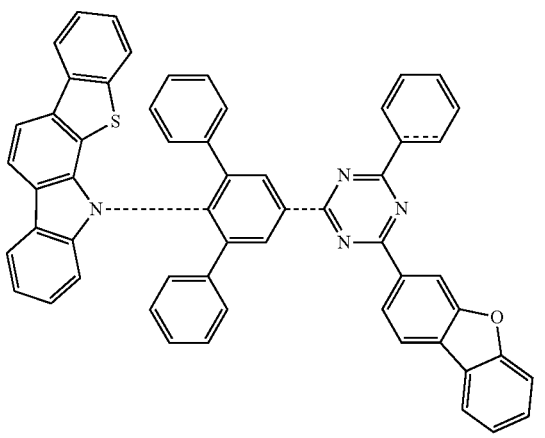

-continued
771
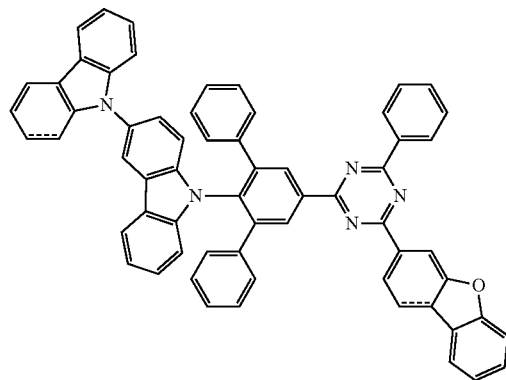
772
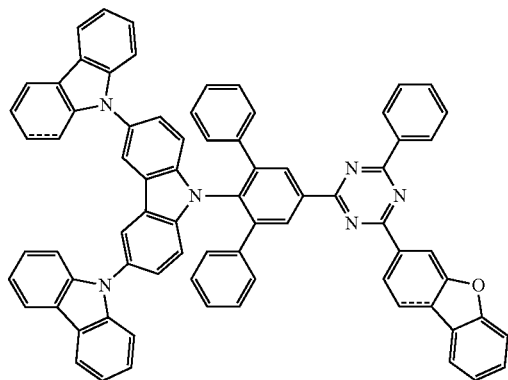
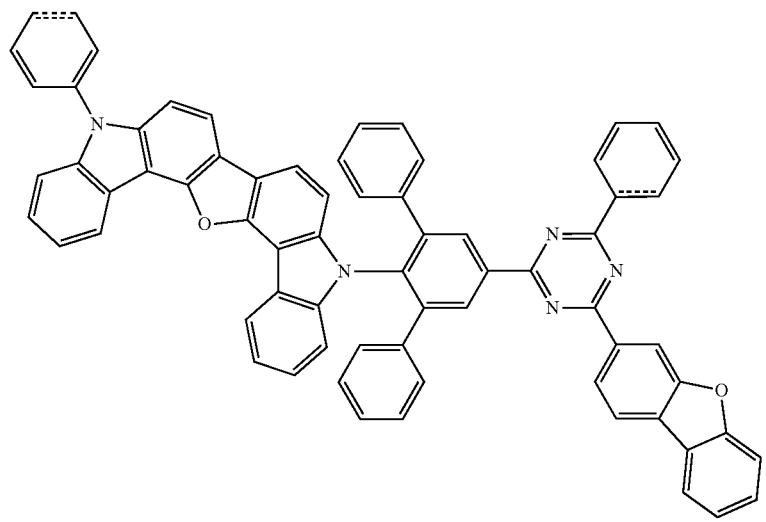
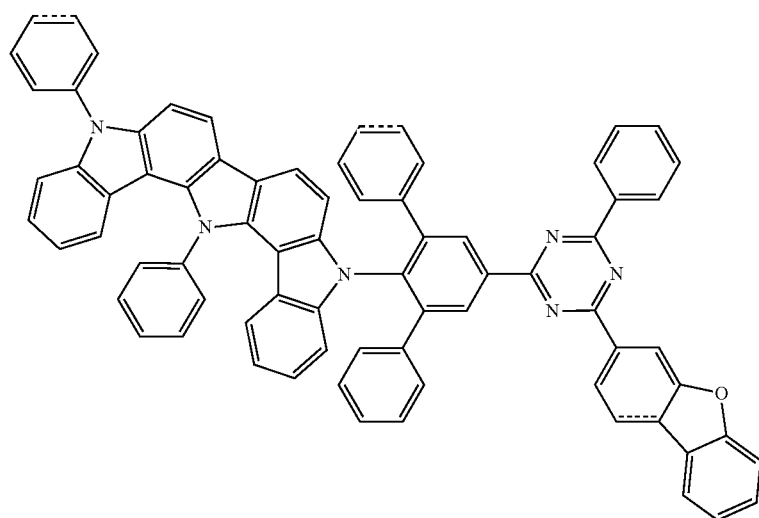

-continued
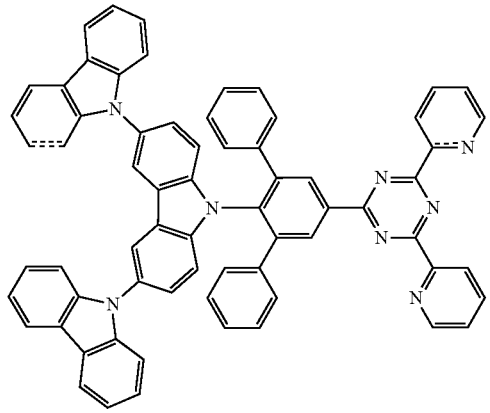
746
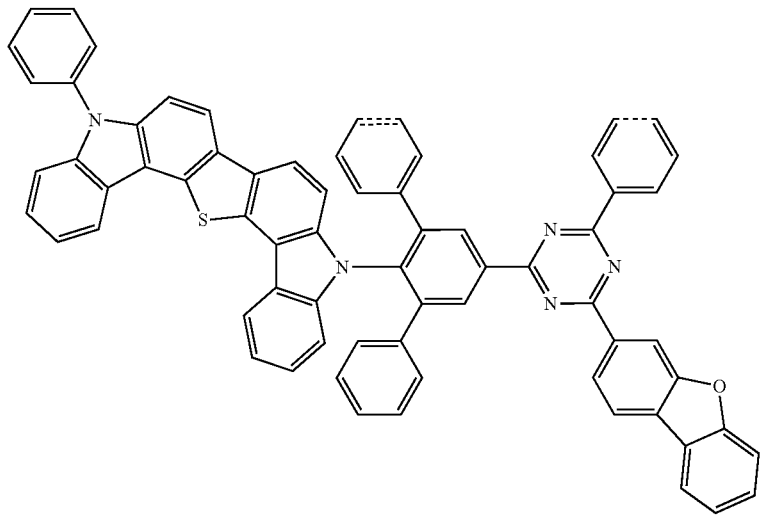
747
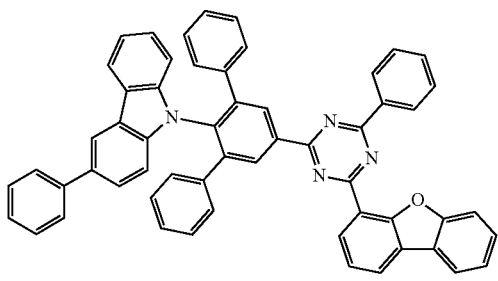
748
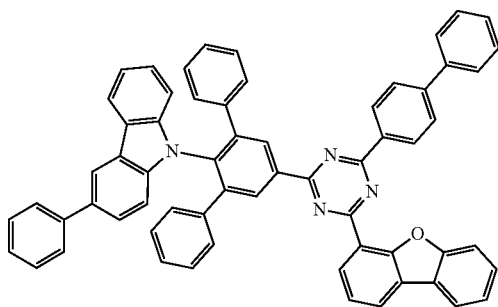
749
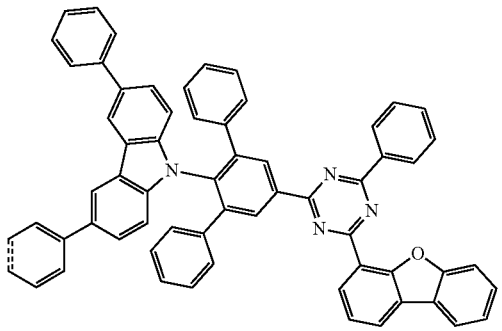
750
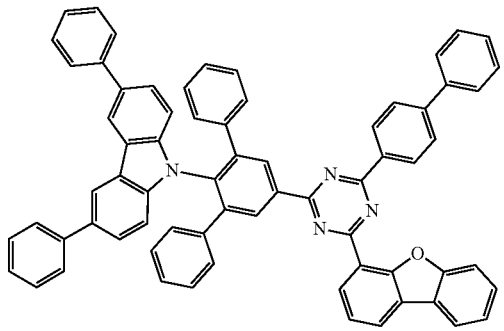
751

-continued
775
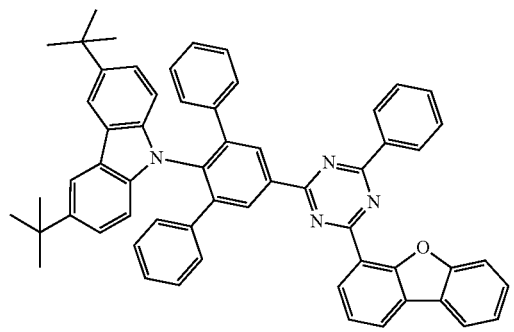
776
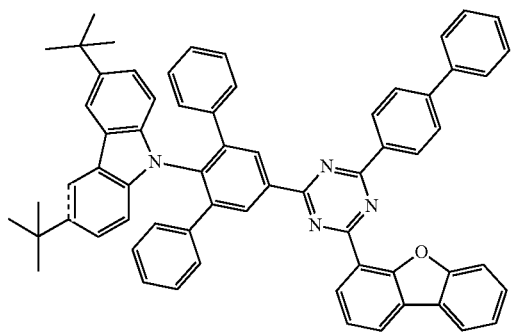
752
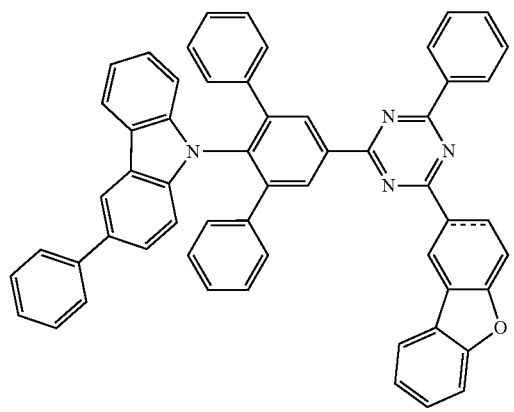
753
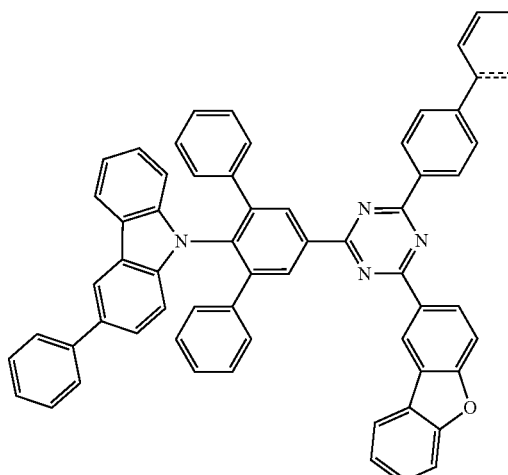
754
755
756
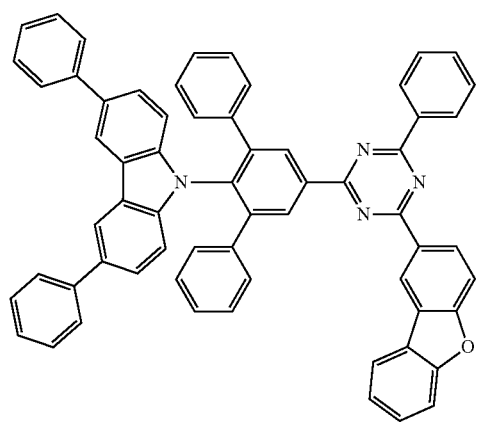
757
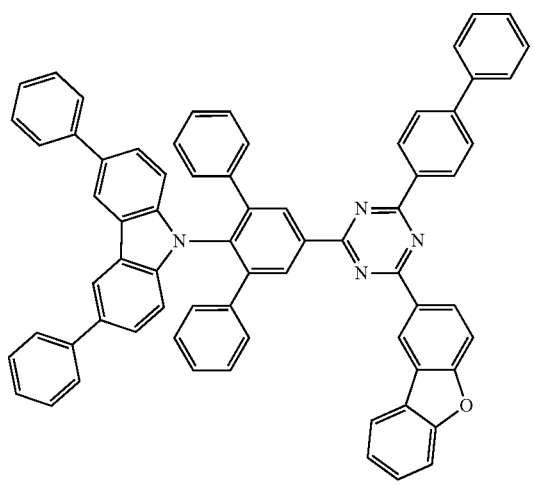

758
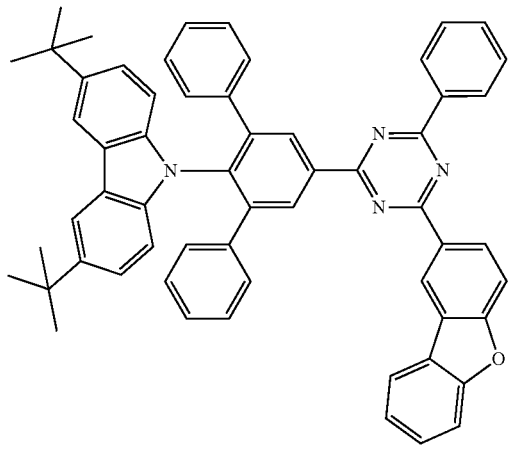
759
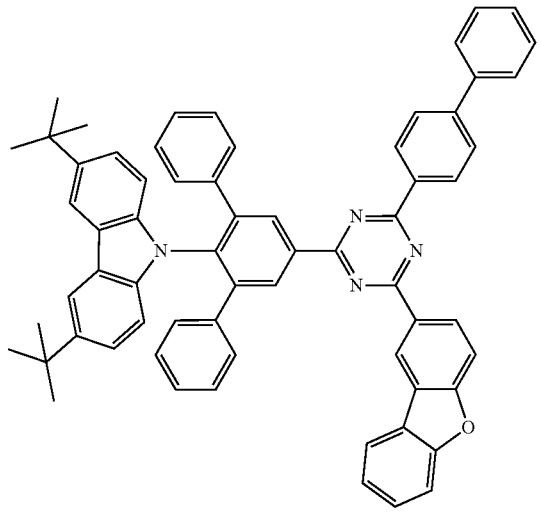
760
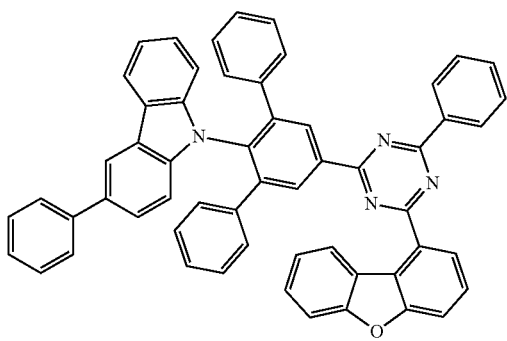
761
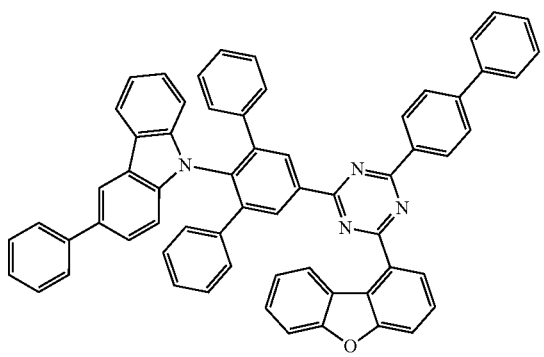
762
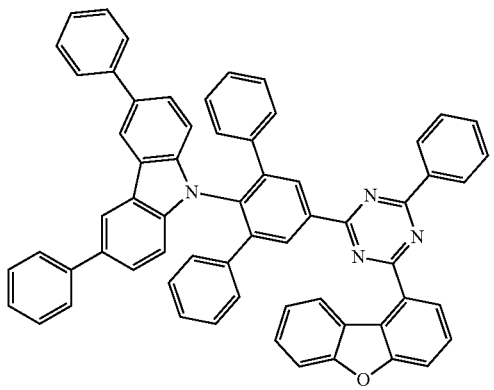
763
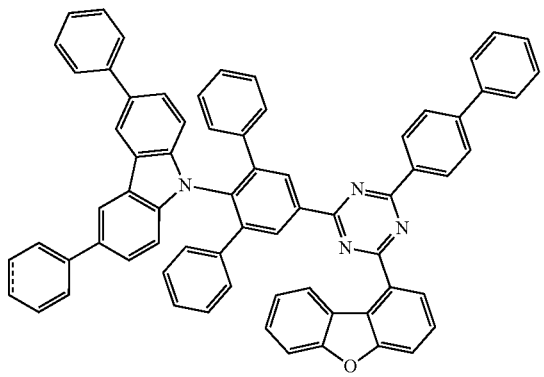

779 780
-continued
764 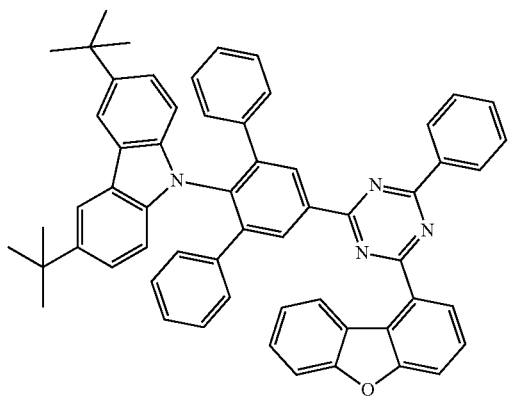 765 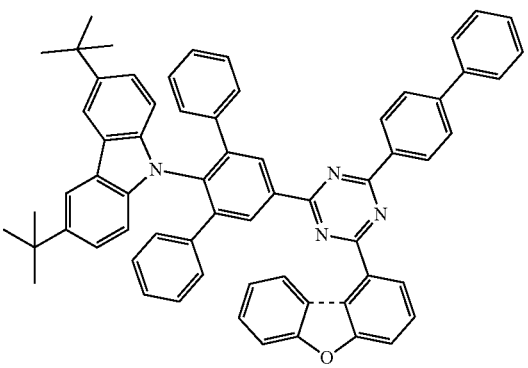
766 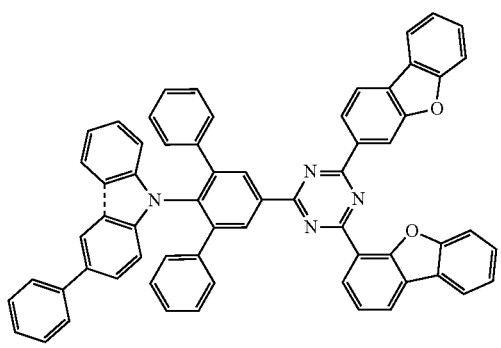 767 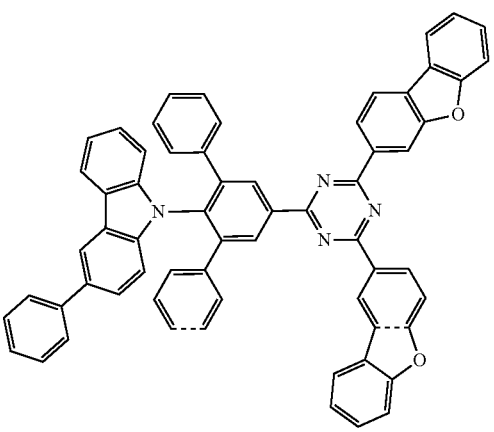
768 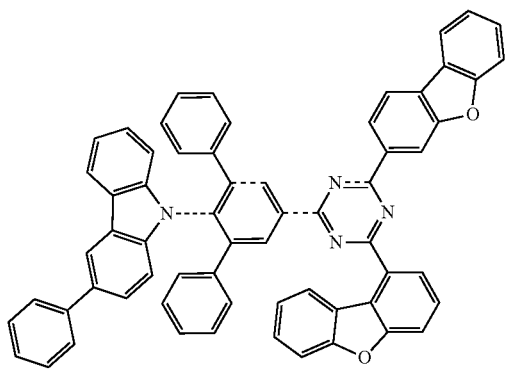 769 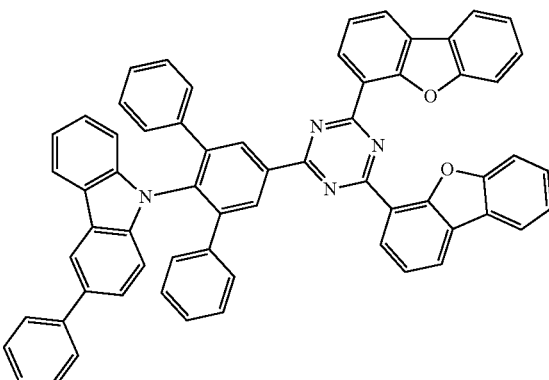
770 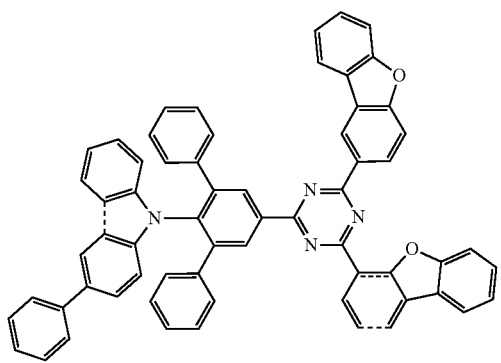 771 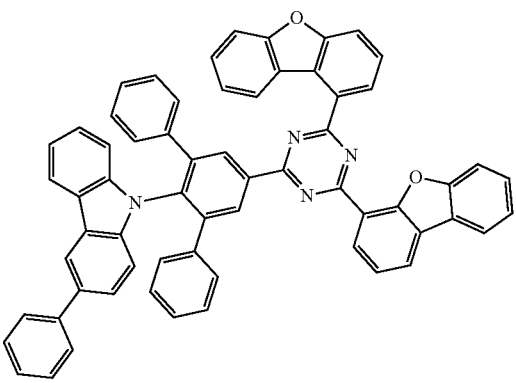

772
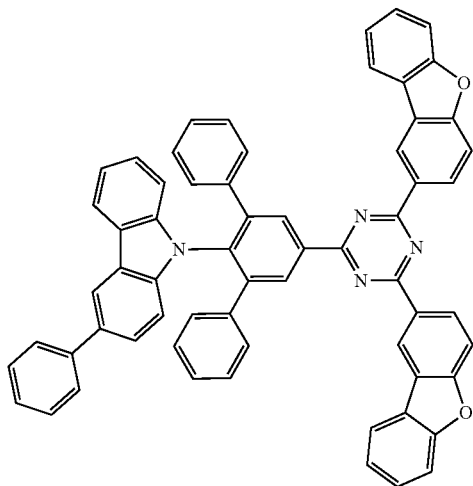
773
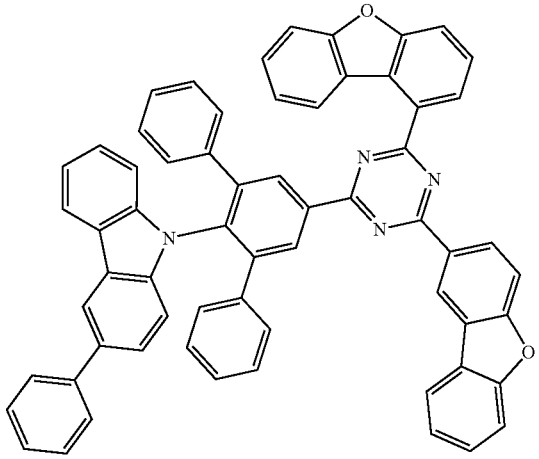
774
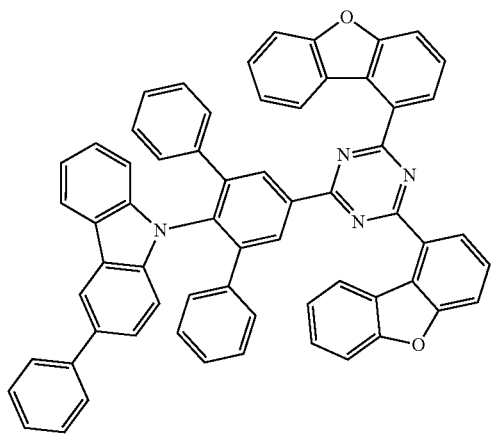
775
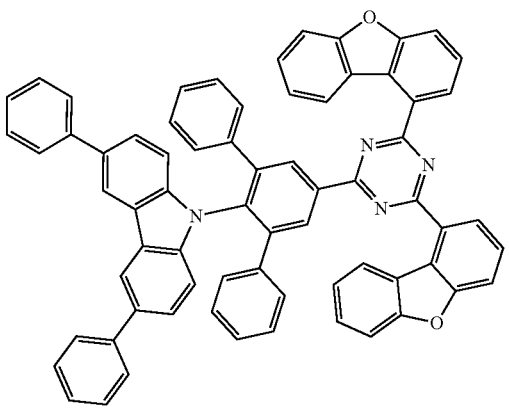
776
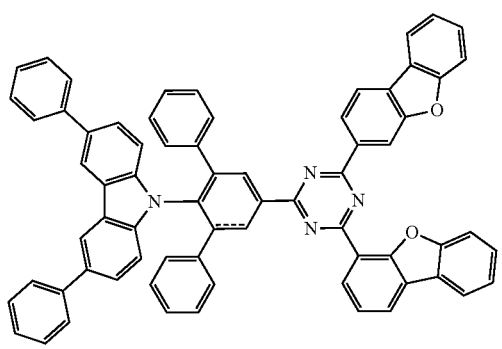
777
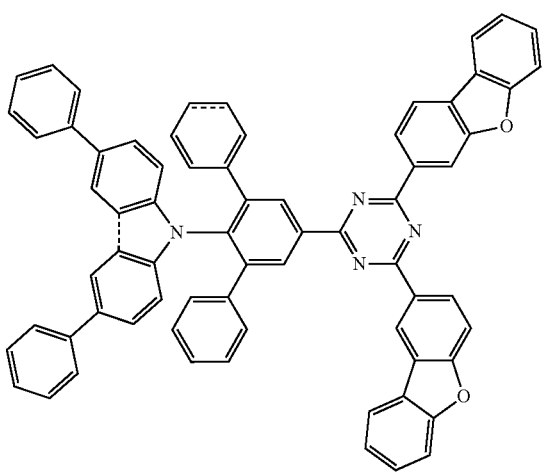

-continued
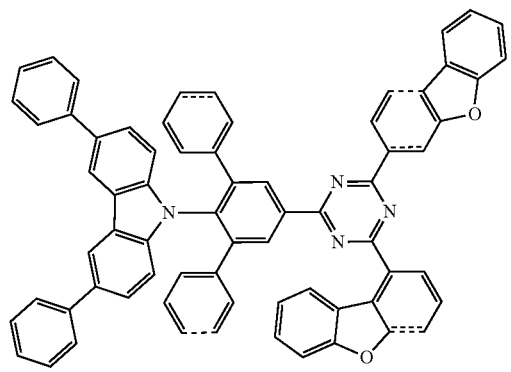
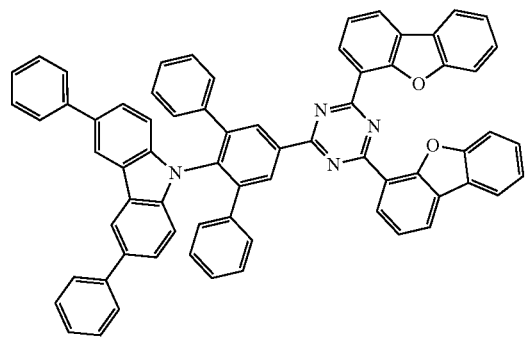
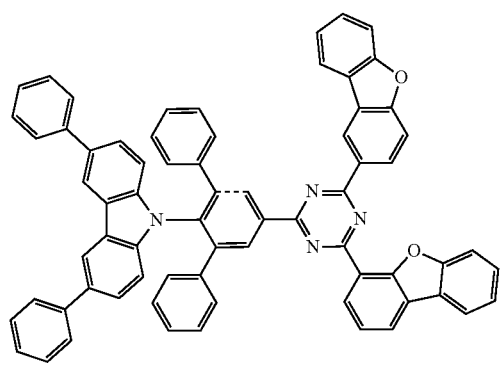
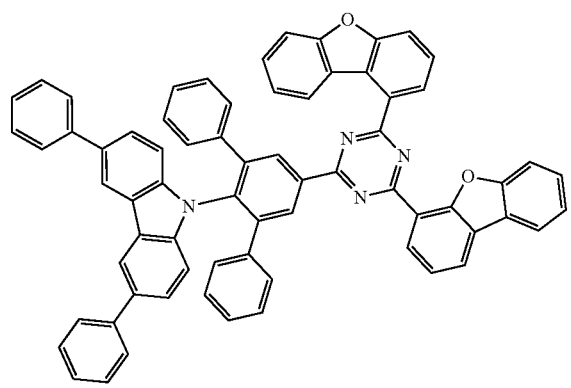
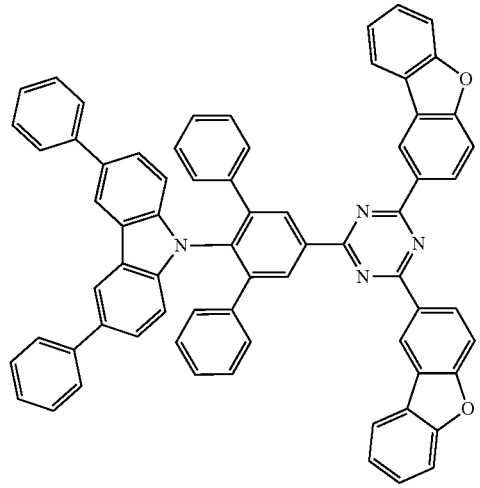
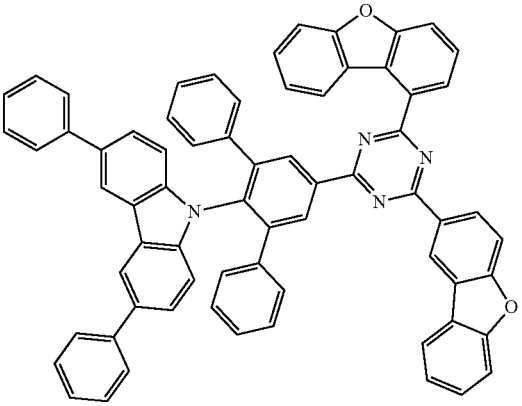

-continued
784
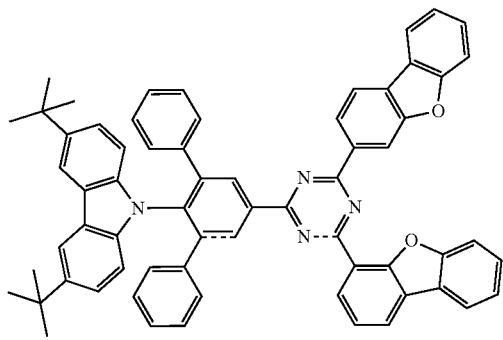
785
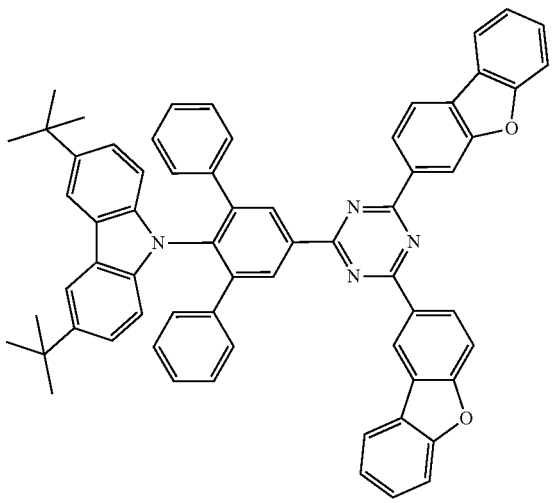
786
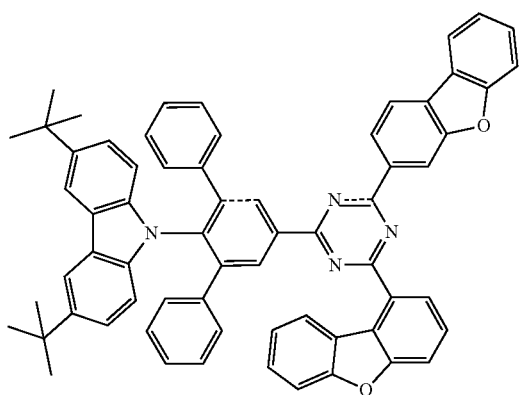
787
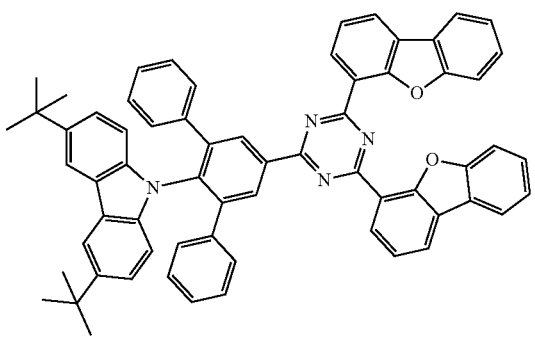
788
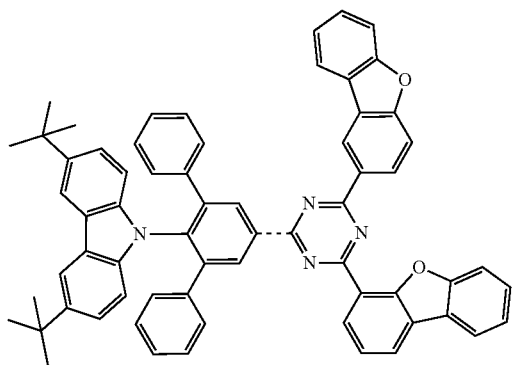
789
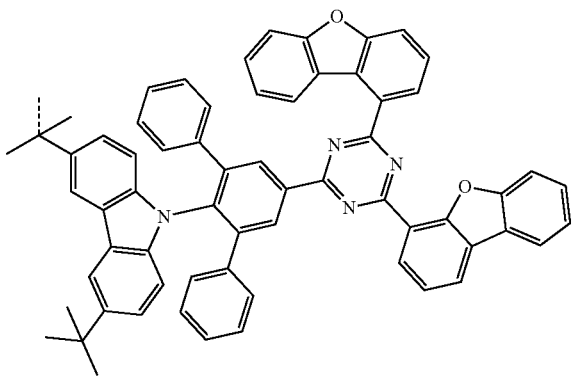

-continued
787
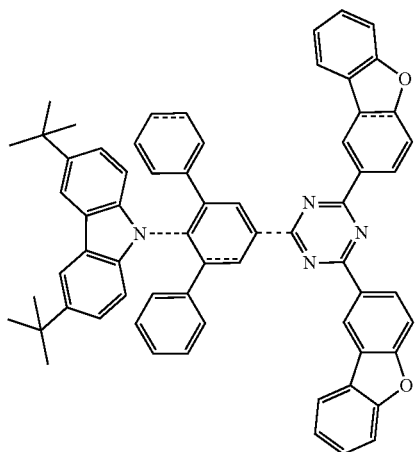
790
788
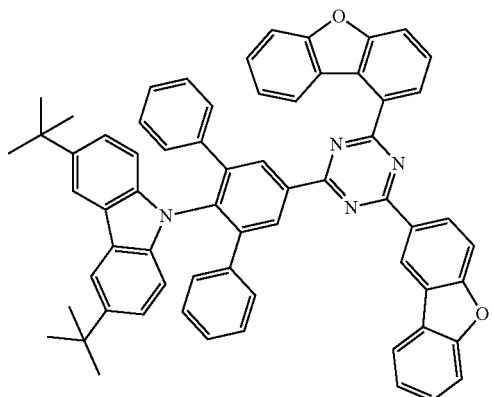
791
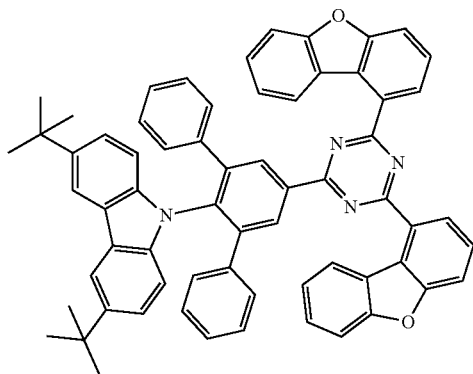
792
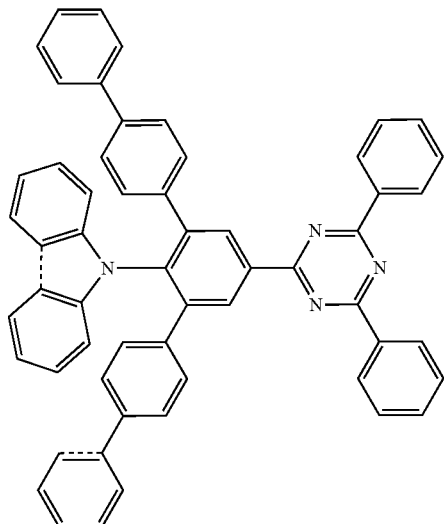
793
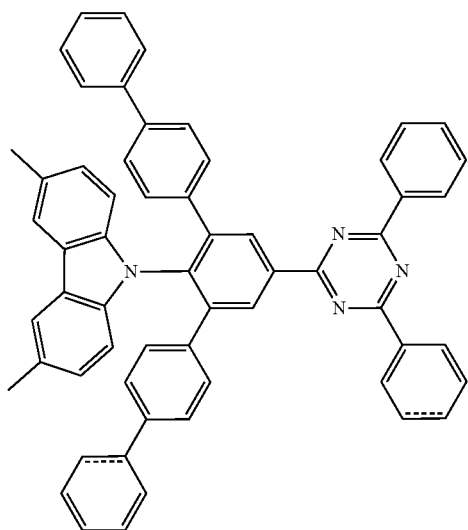
794
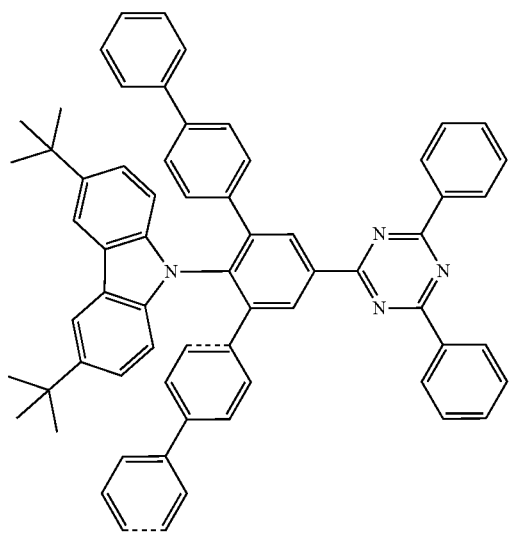
795

-continued
789
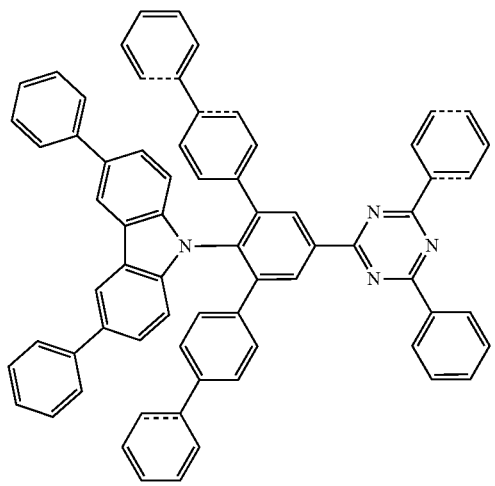
796
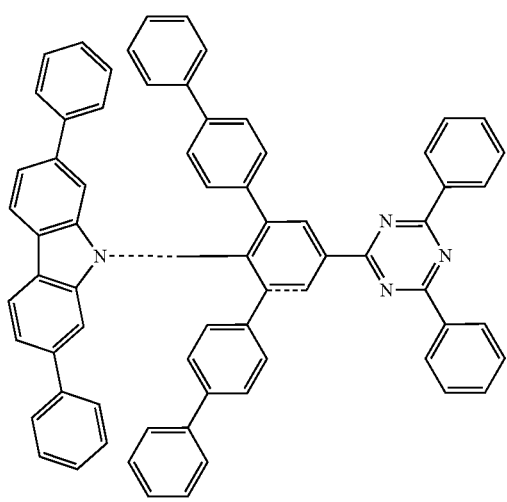
798
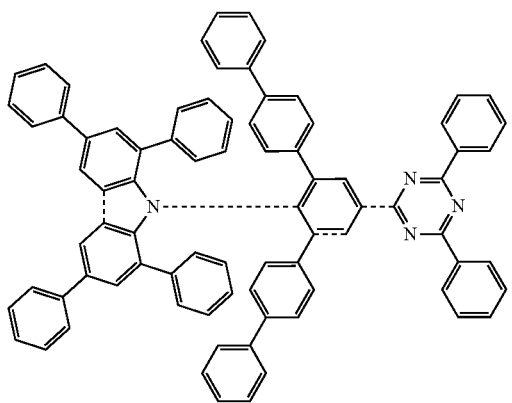
800
790
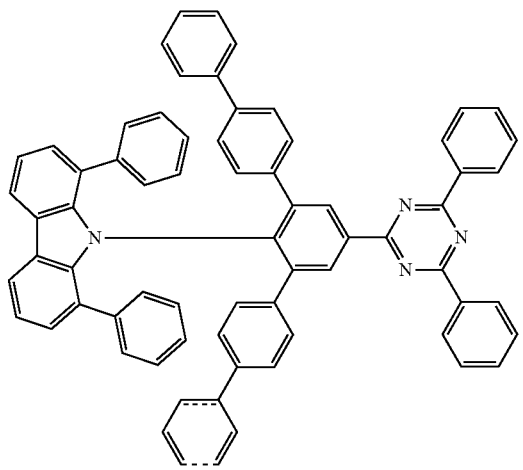
797
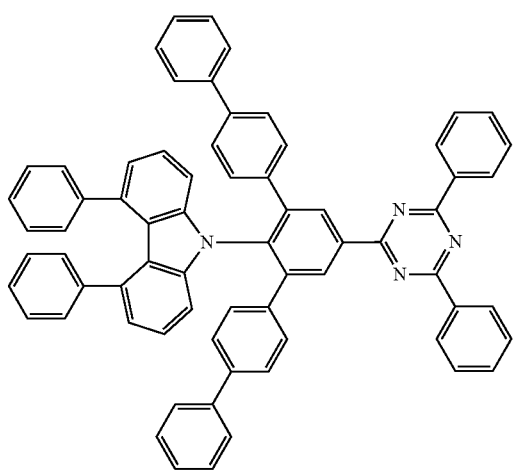
799
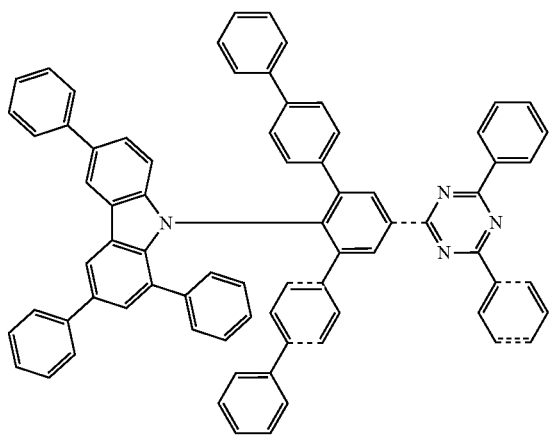
801

791
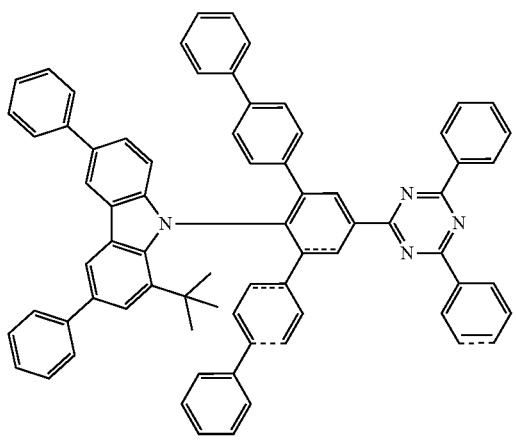
802
792
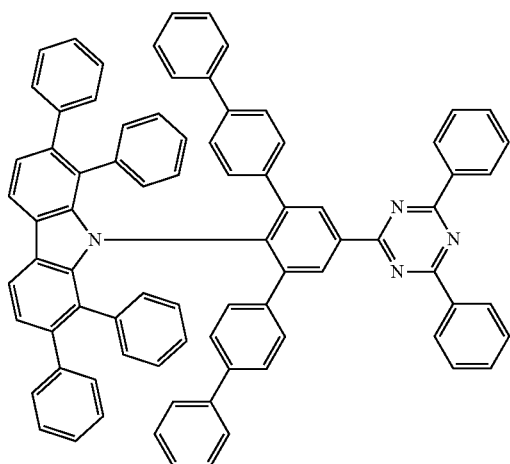
803
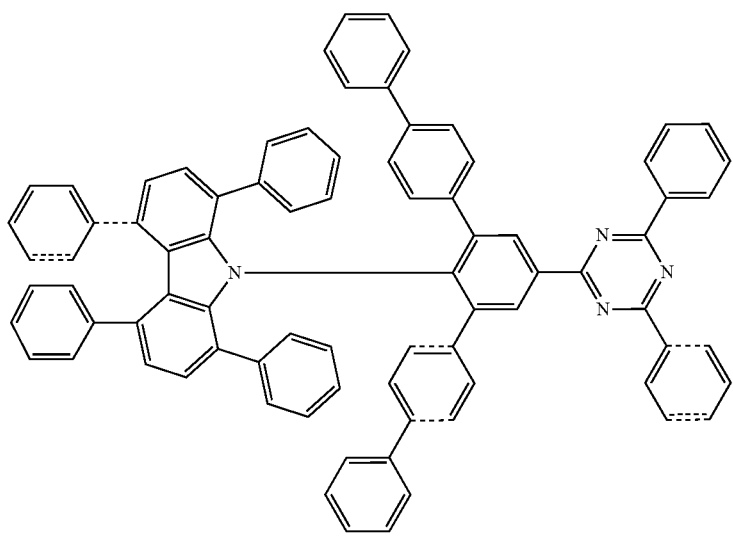
804
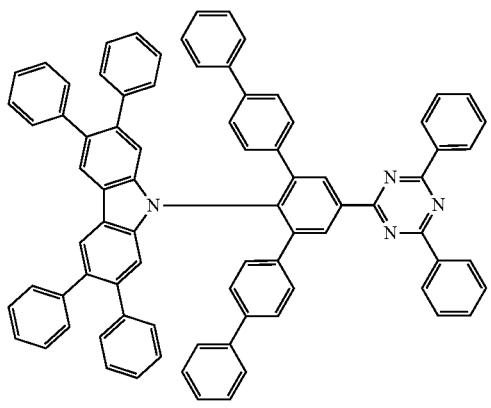
805
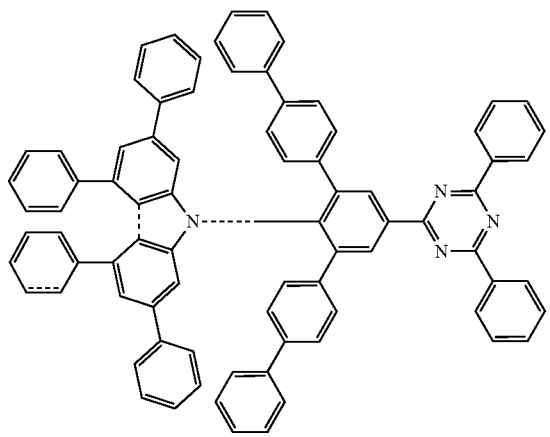
806

-continued
807
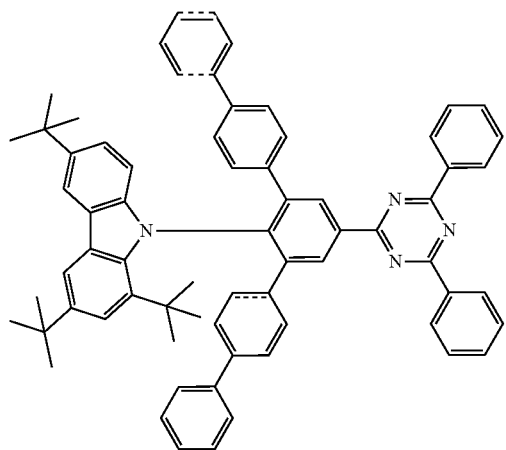
808
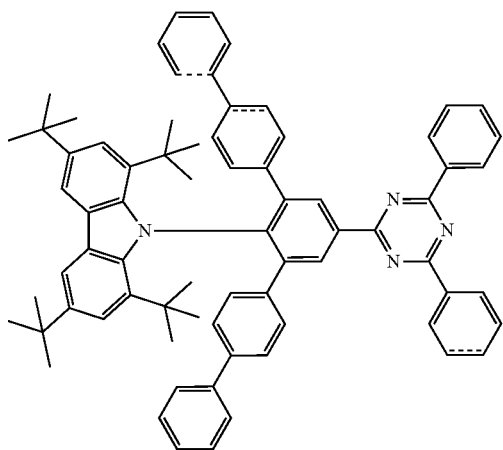
809
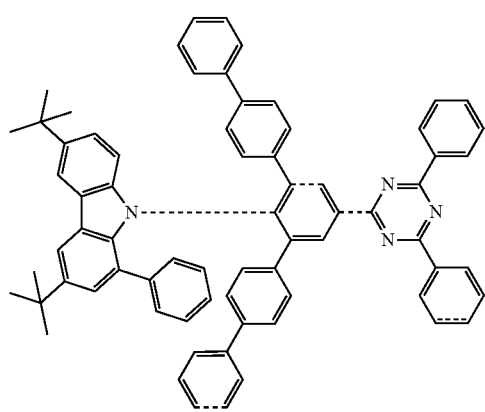
810
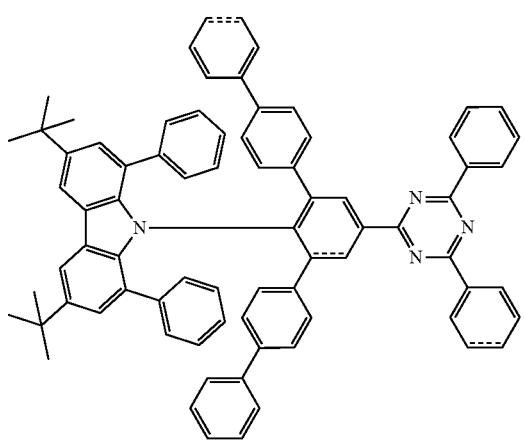
811
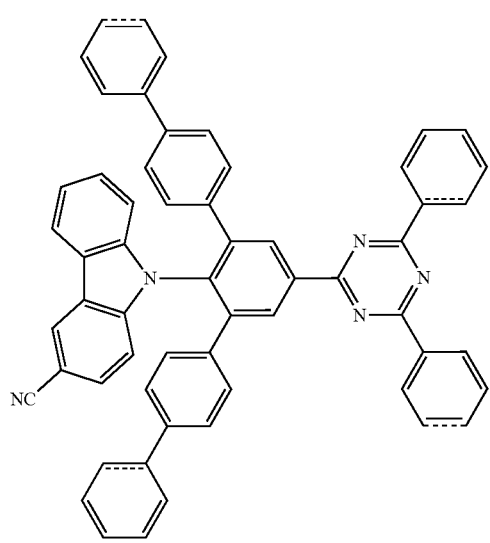
812
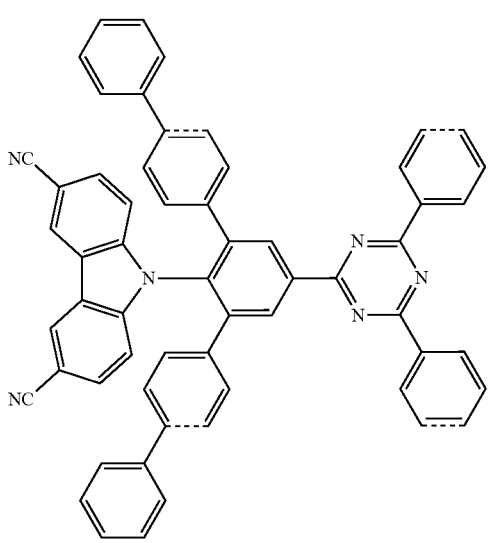

-continued
813
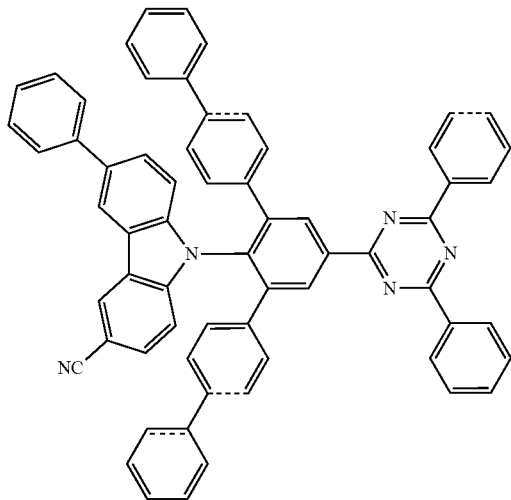
814
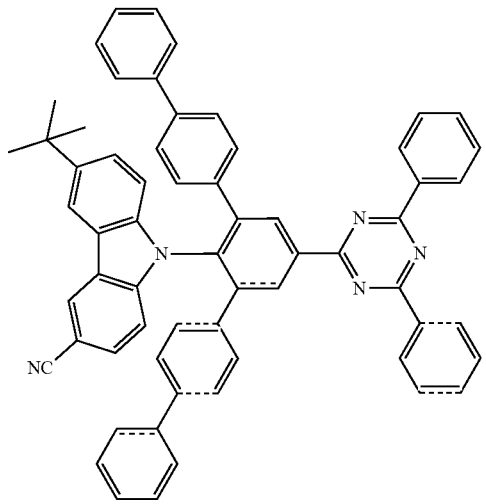
815
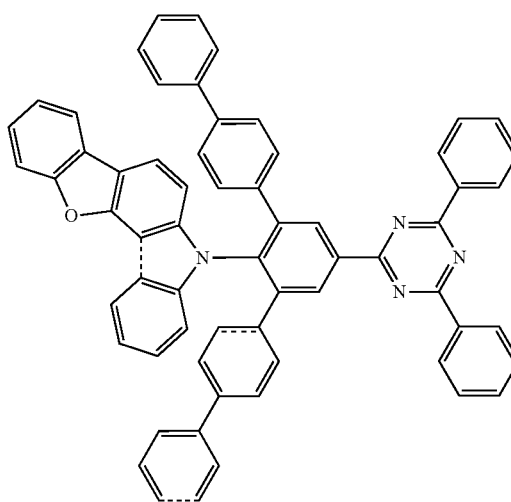
816
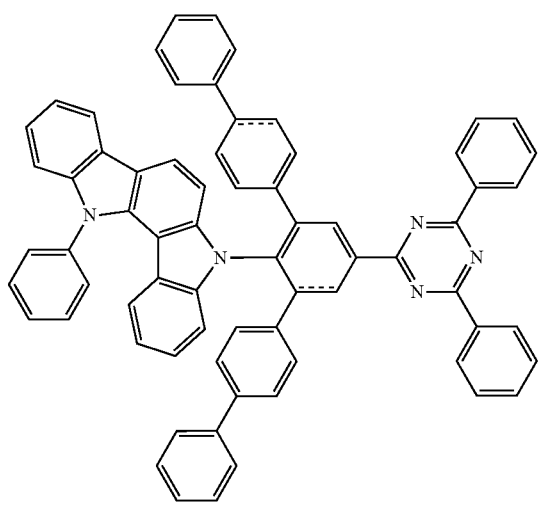
817
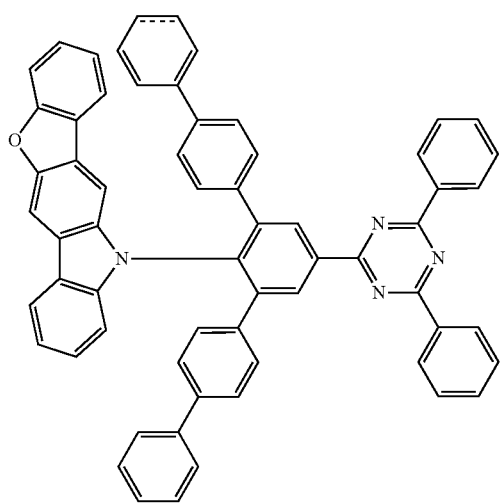
818
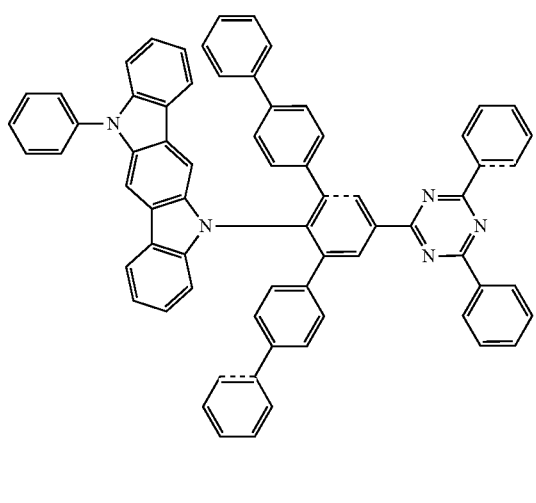

-continued
819
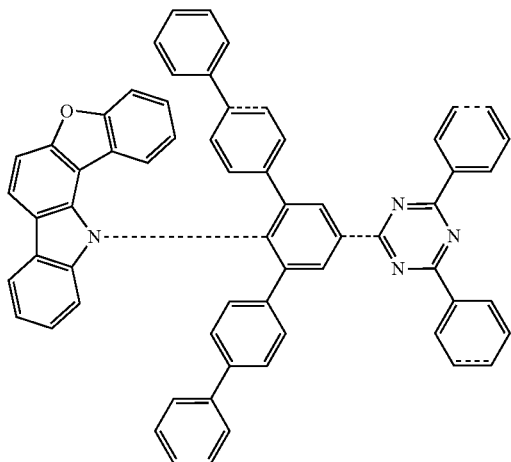
820
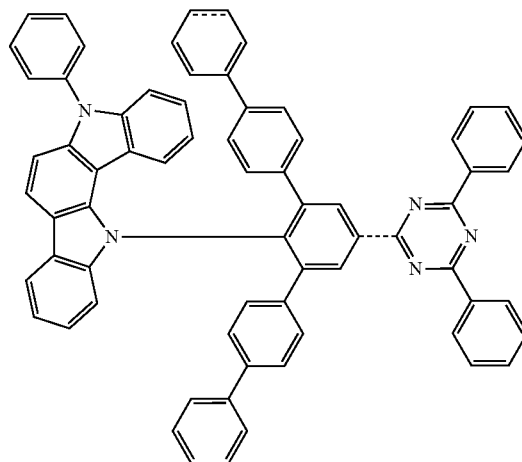
821
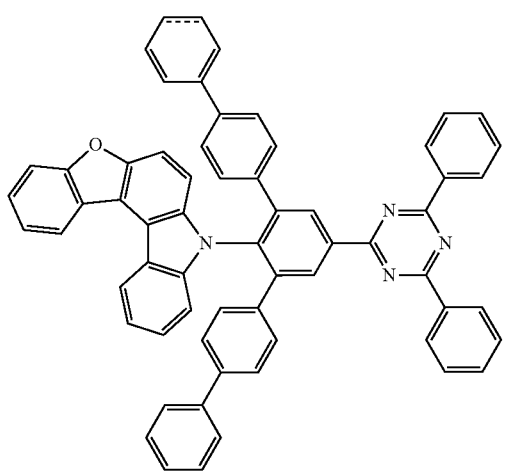
822
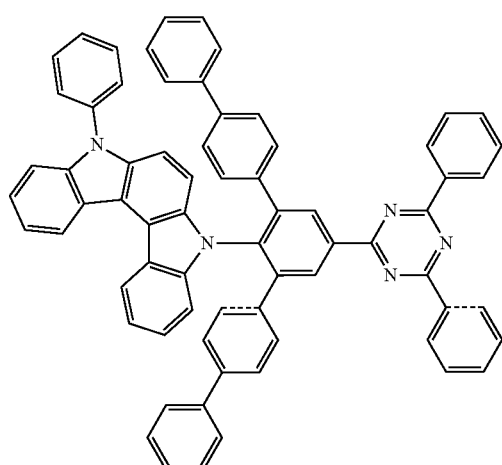
823
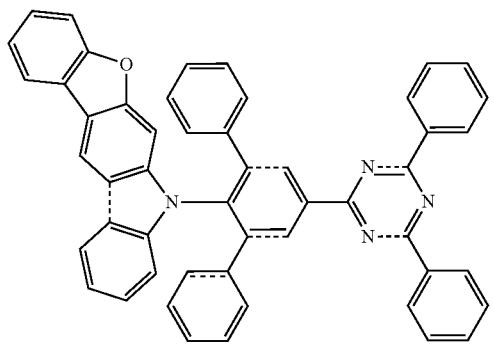
824
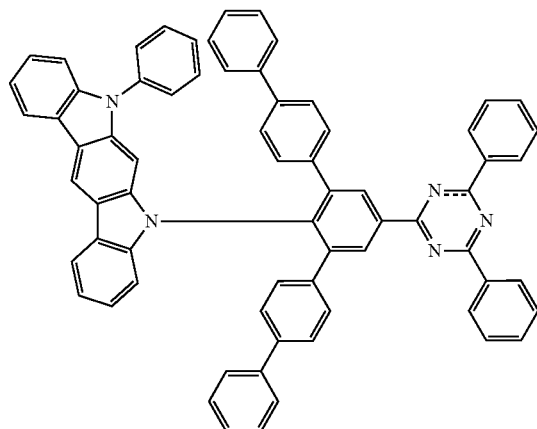

-continued
825
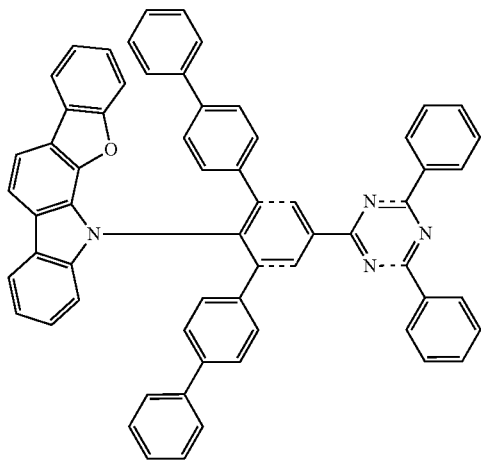
826
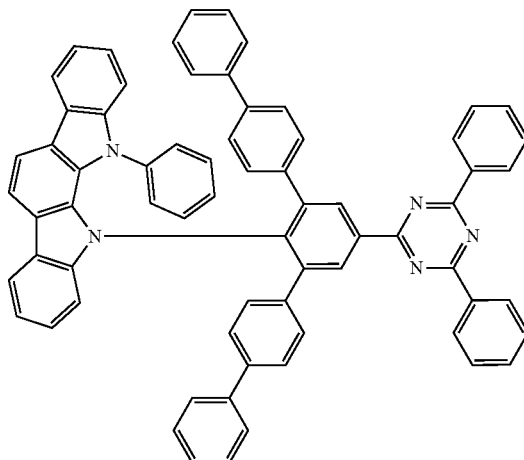
827
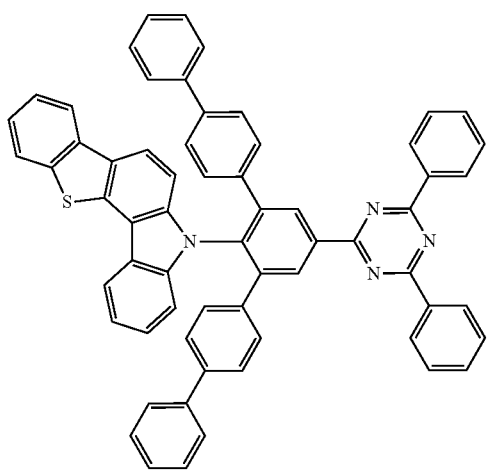
828
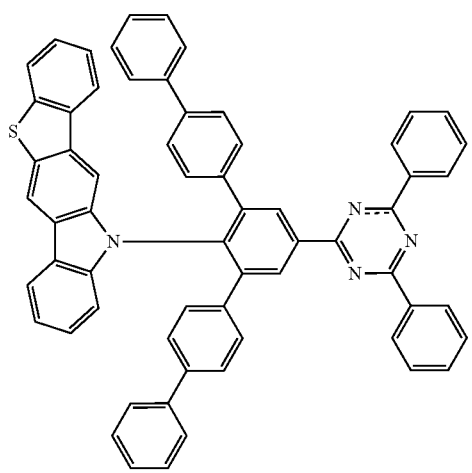
829
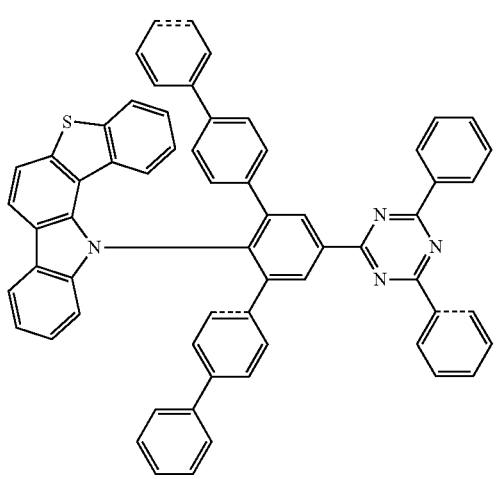
830
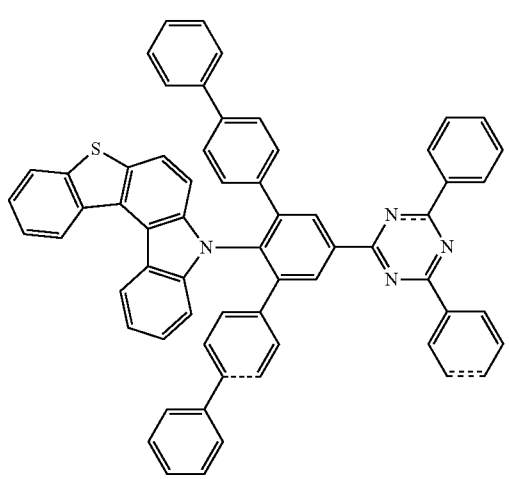

-continued
| 831 | 832 |
|---|---|
| 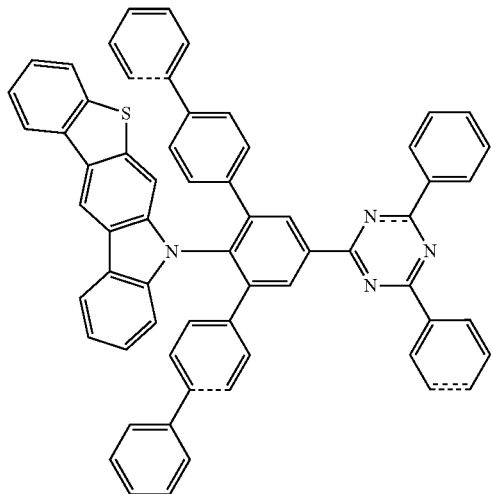 | 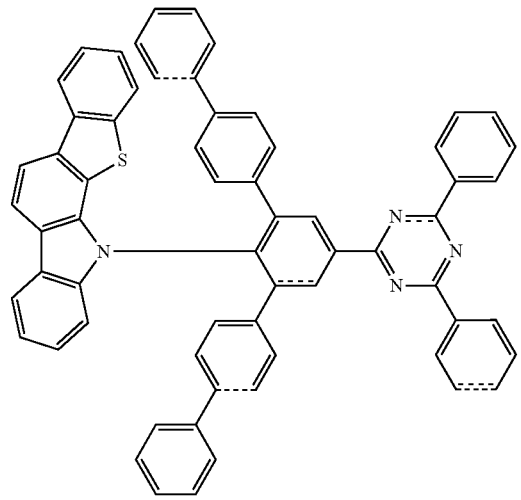 |
| 833 | 834 |
| 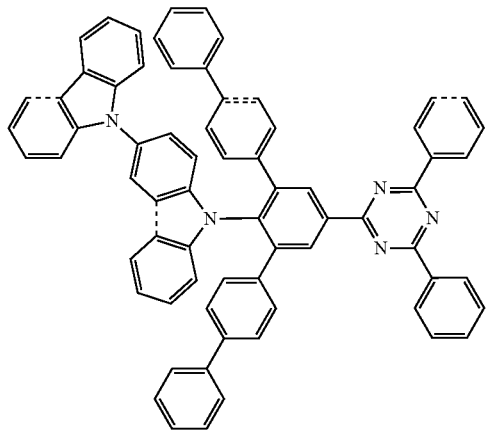 | 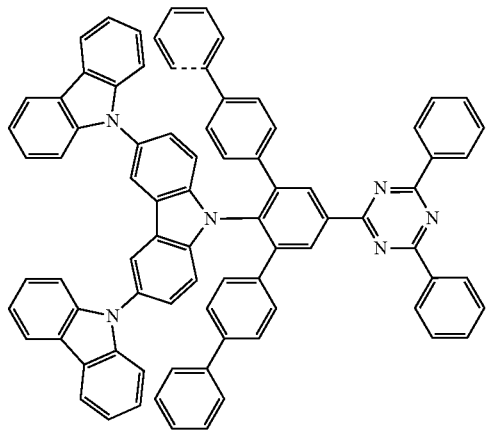 |
| 835 | 836 |
| 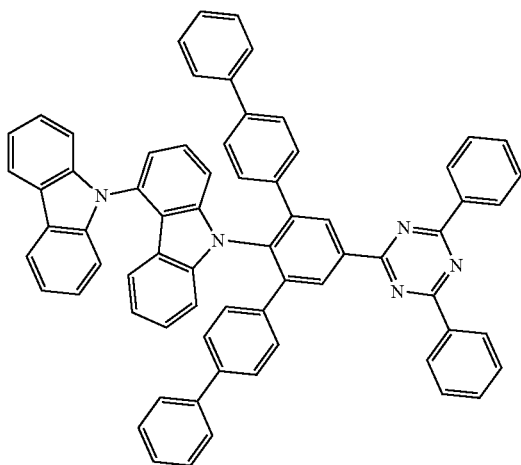 | 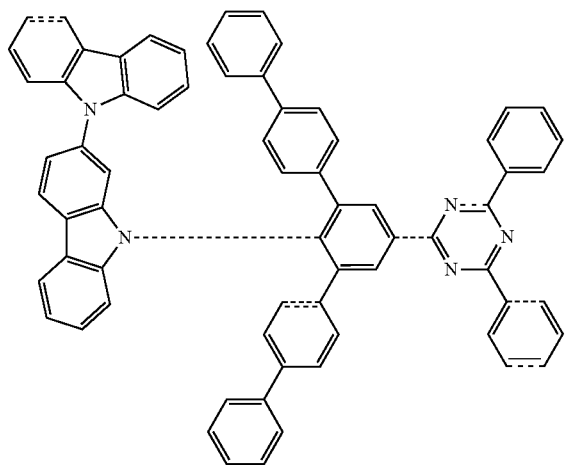 |

837
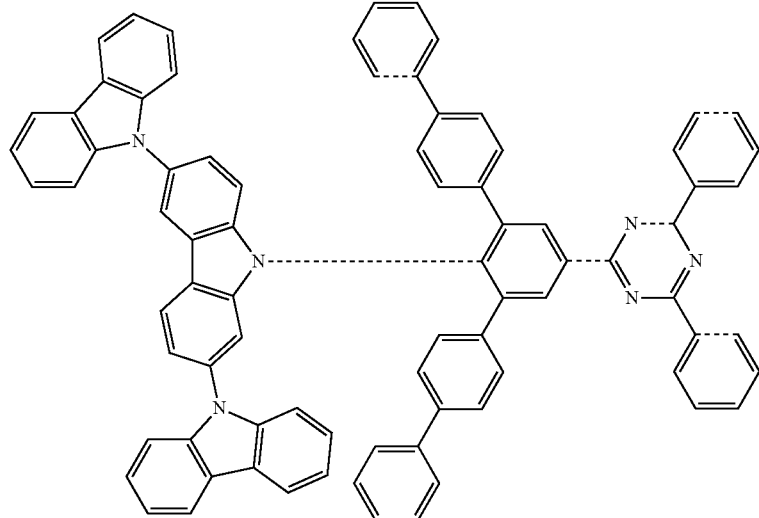
838
839
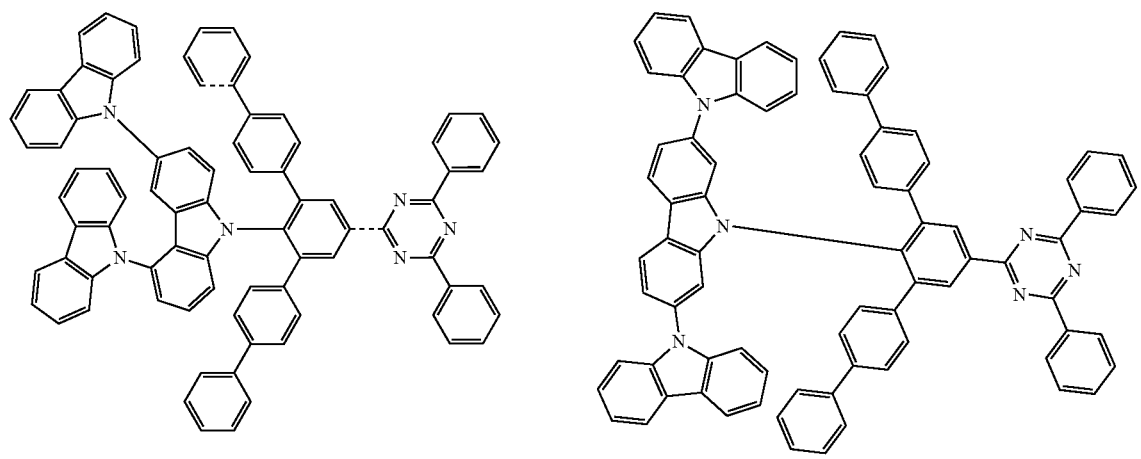
840
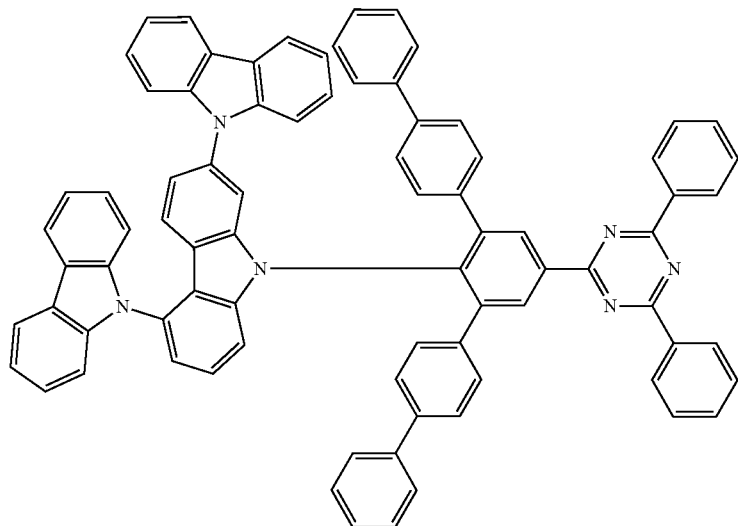

-continued
841
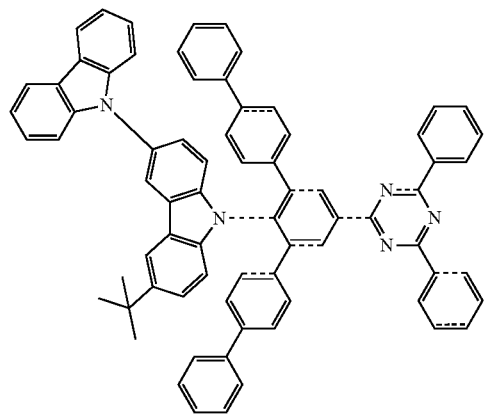
842
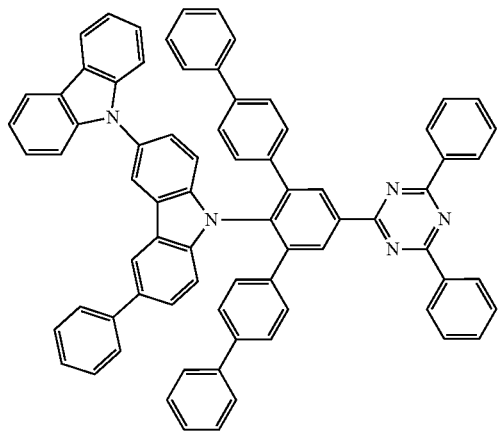
843
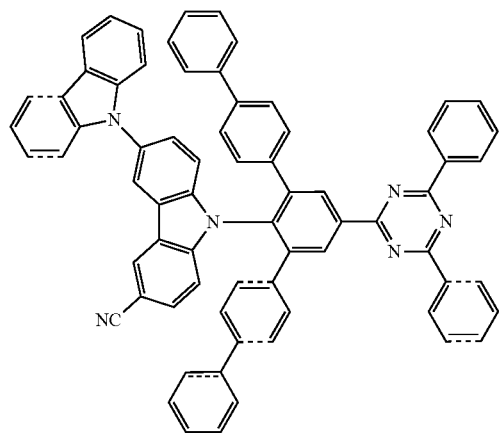
844
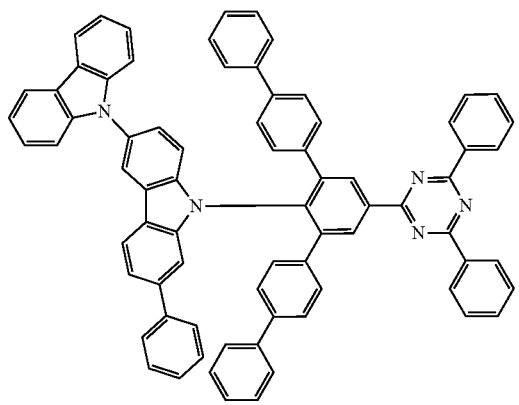
845
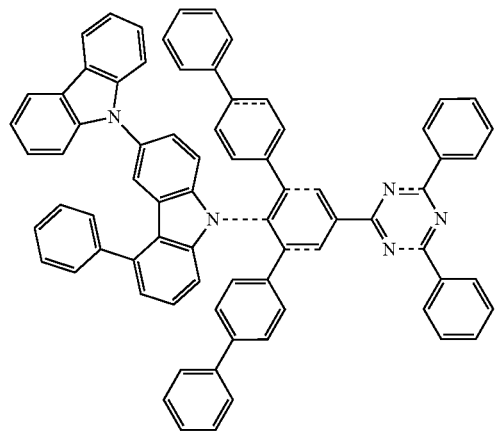
846
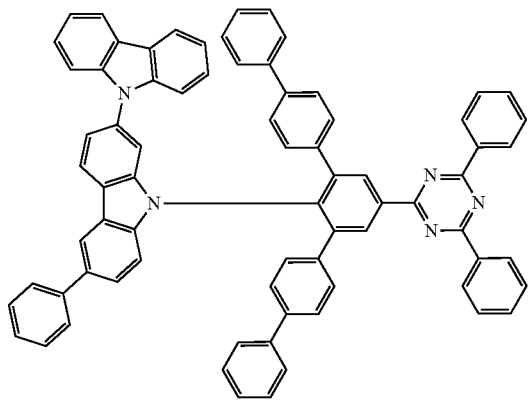

-continued
847
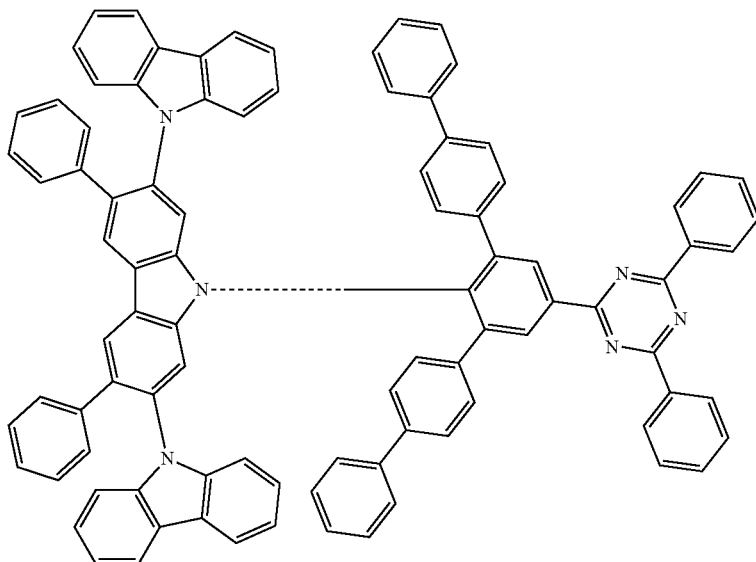
848
849
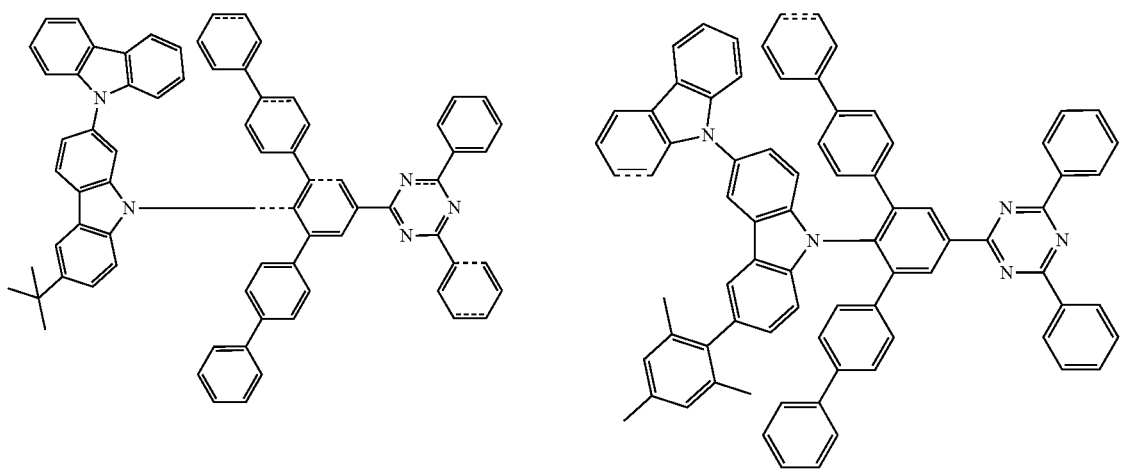
850
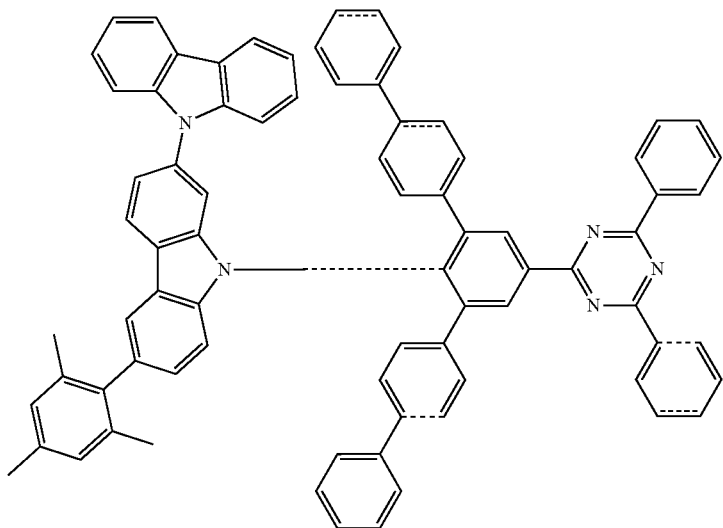

-continued
809 | 810
851
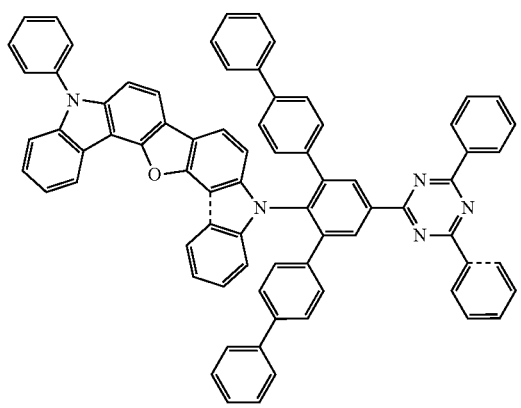
852
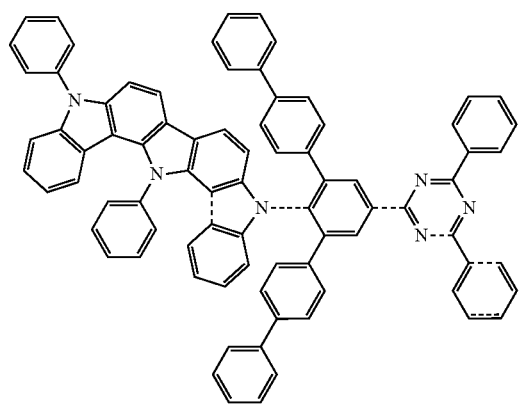
853
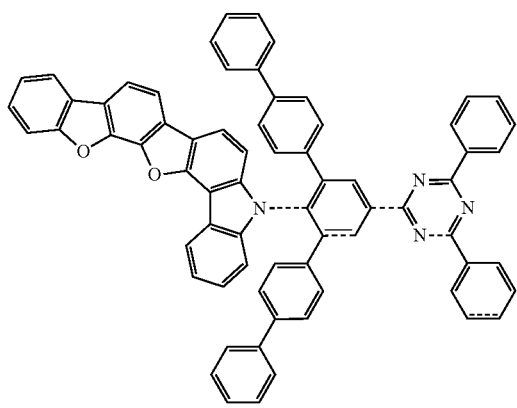
854
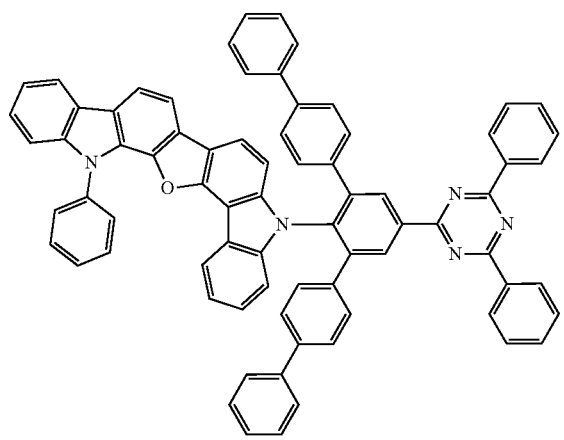
855
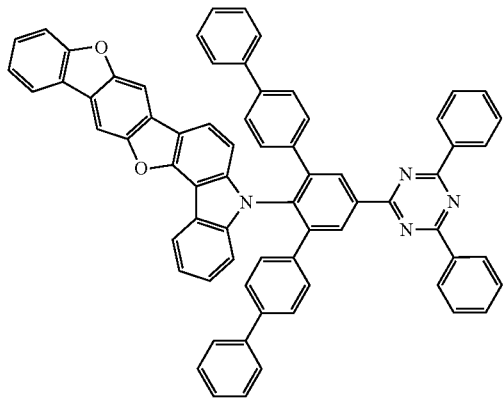
856
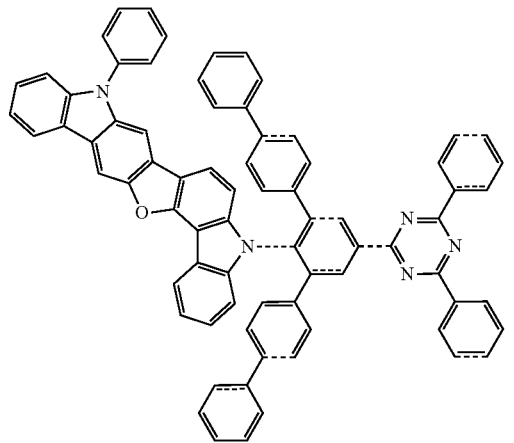

-continued
857
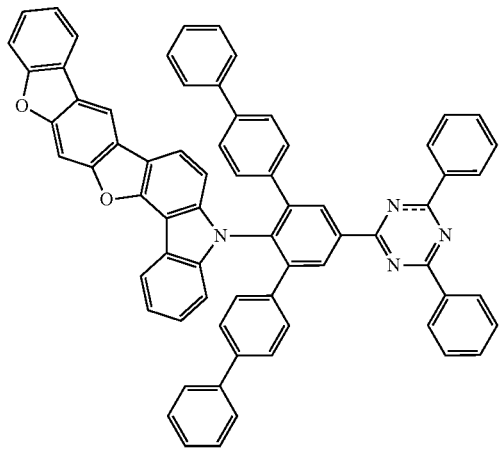
858
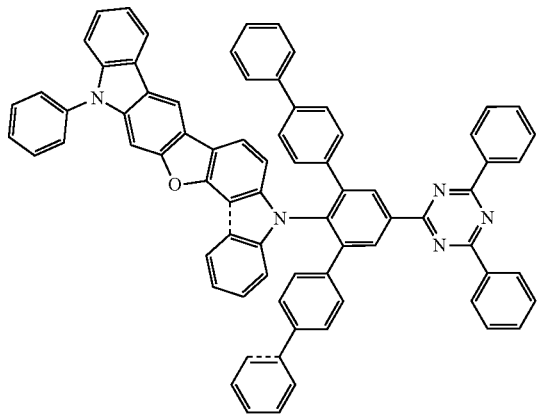
859
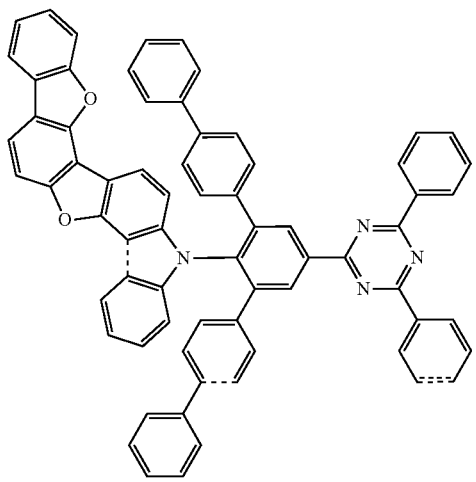
860
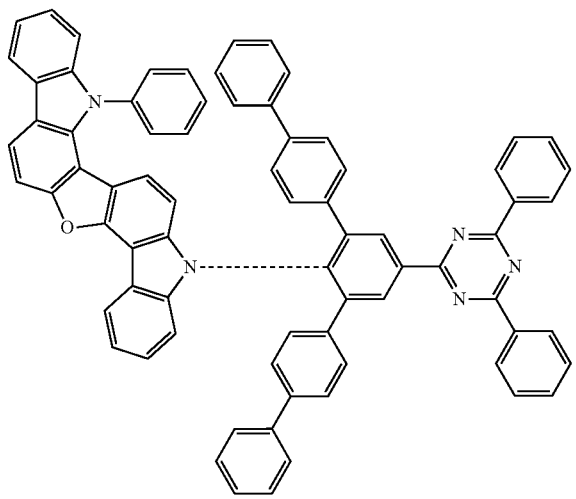
861
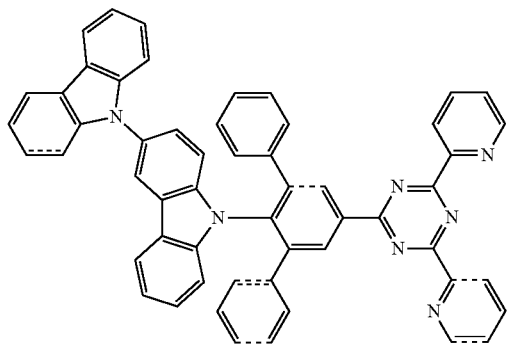
862
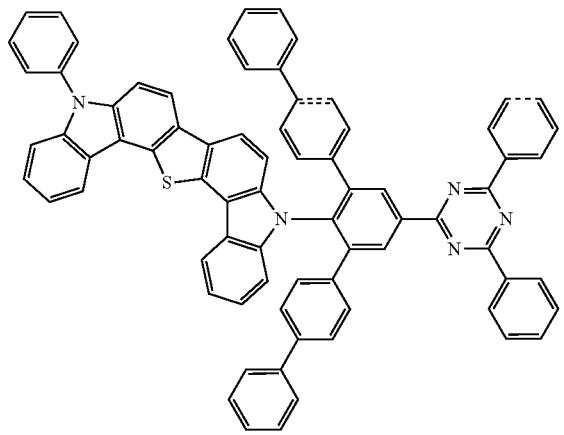

-continued
813
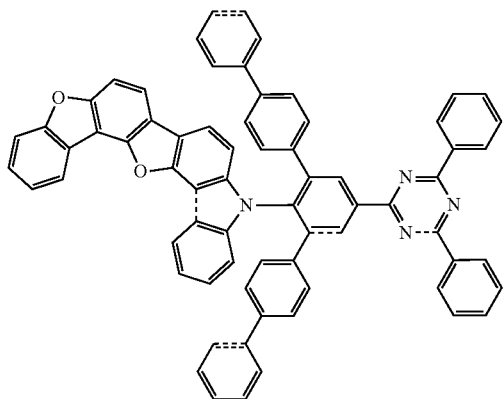
863
814
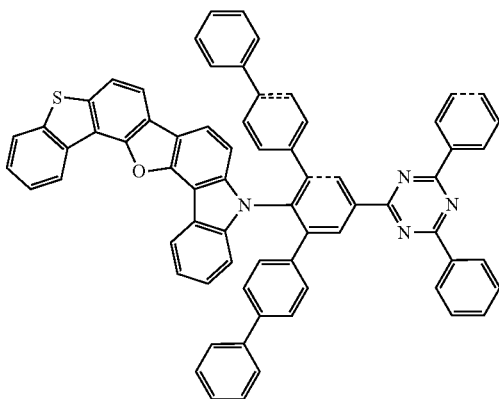
864
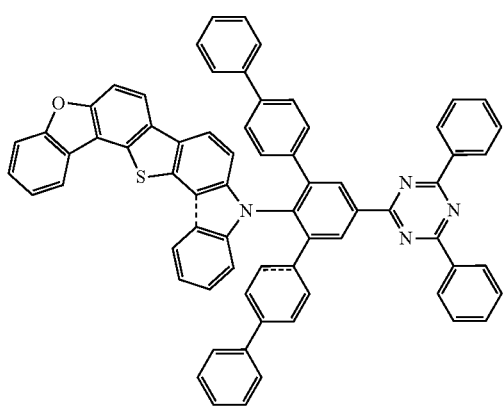
865
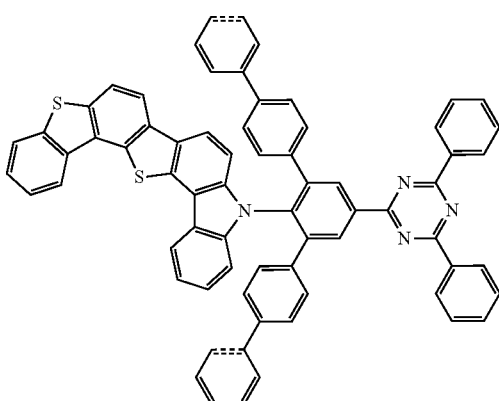
866
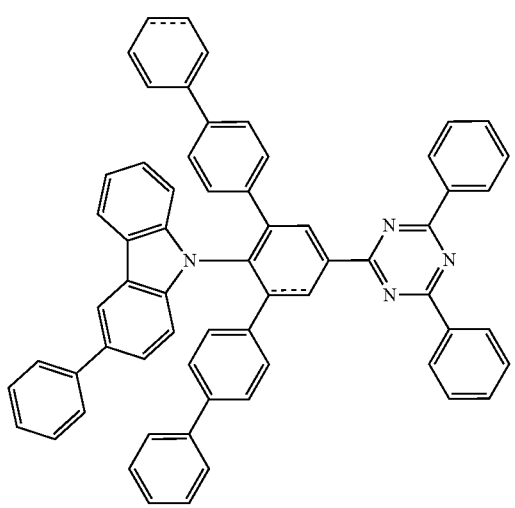
867
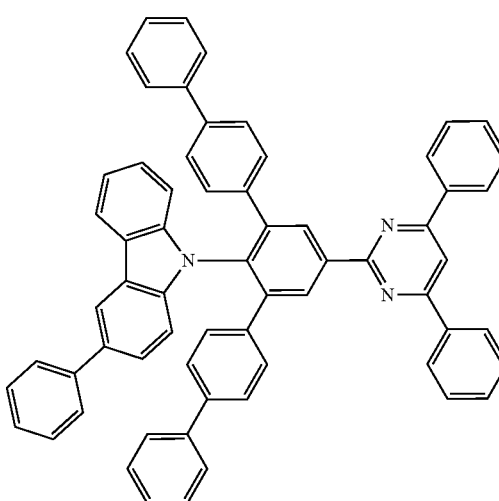
868

-continued
869
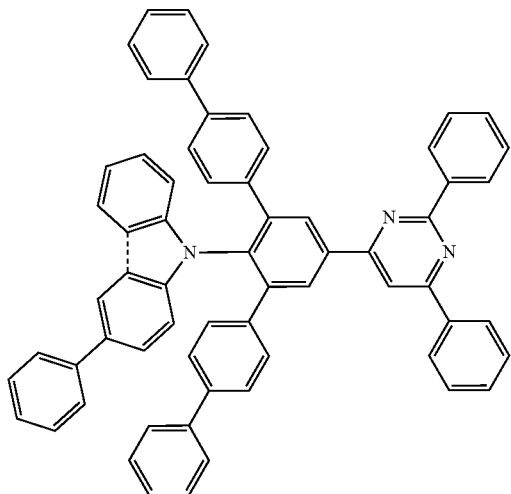
870
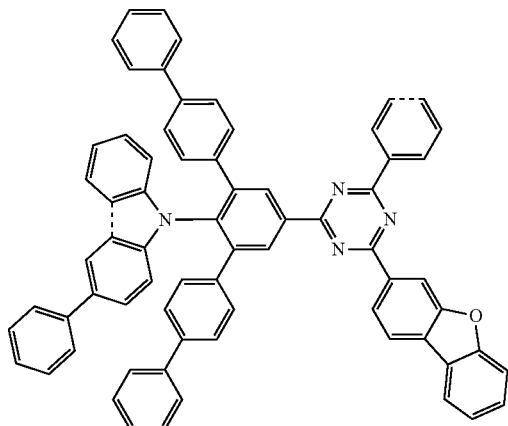
871
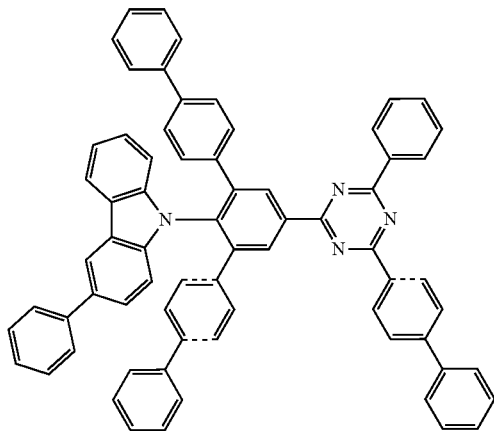
872
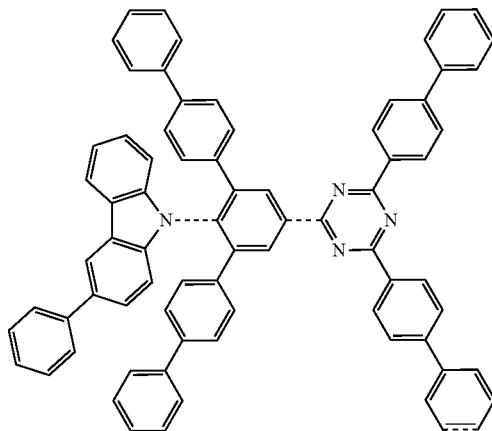
873
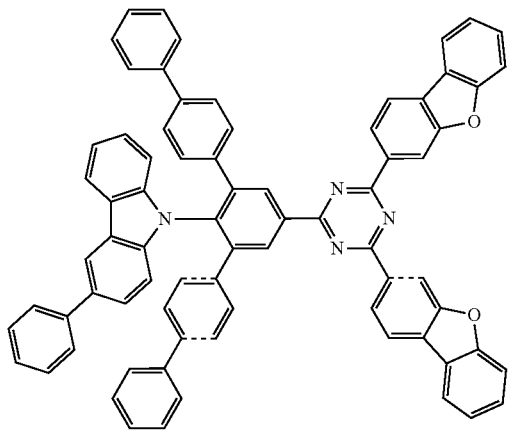
874
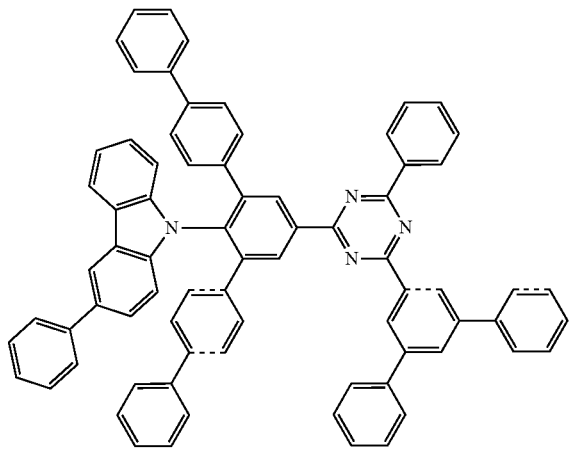

-continued
817
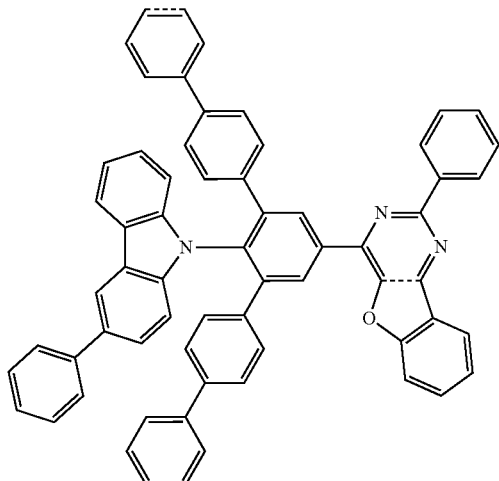
875
818
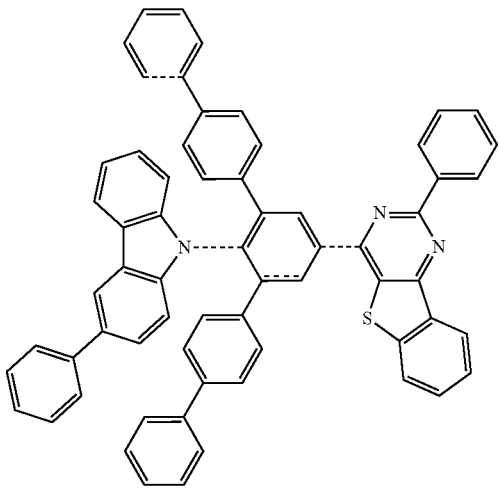
876
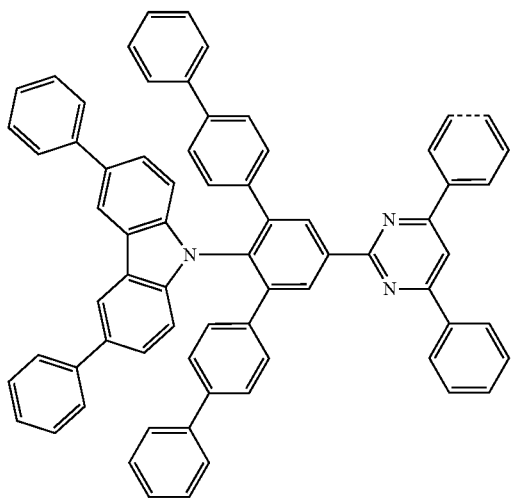
877
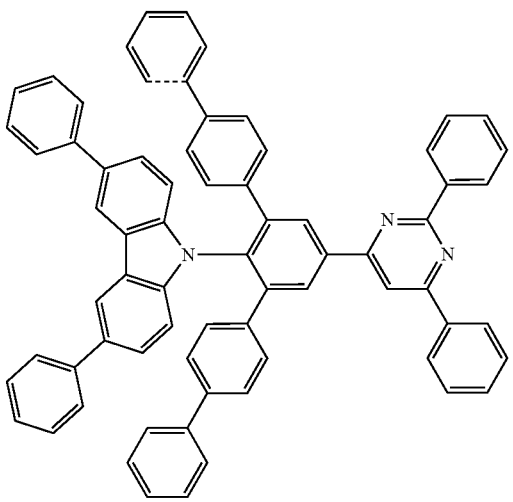
878
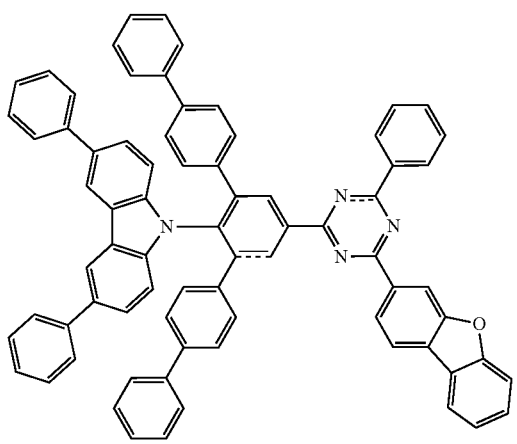
879

819 820
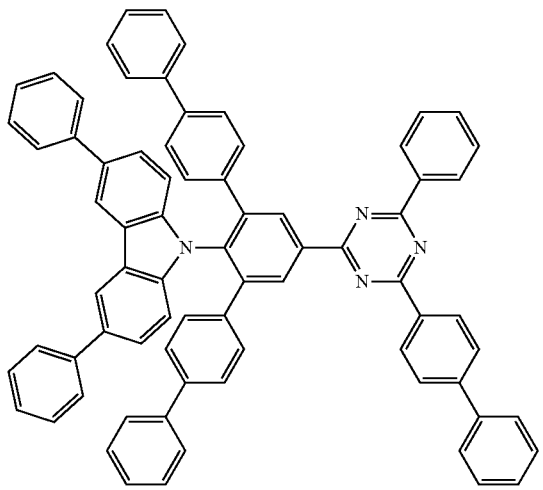
880
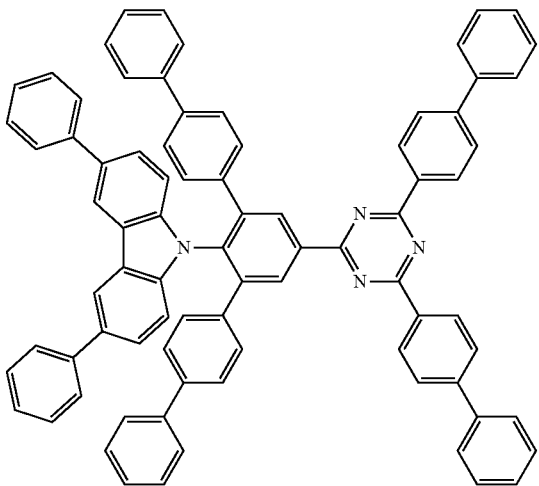
881
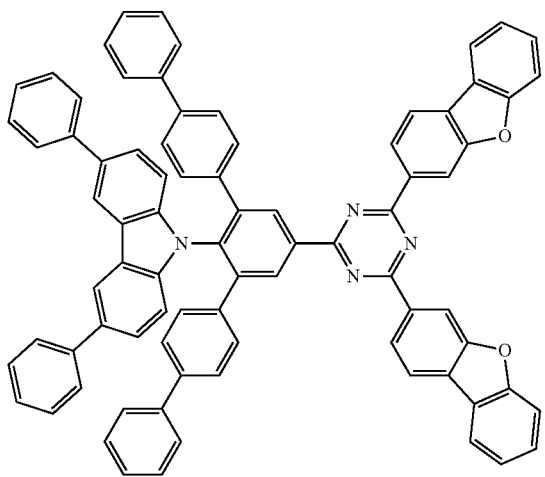
882
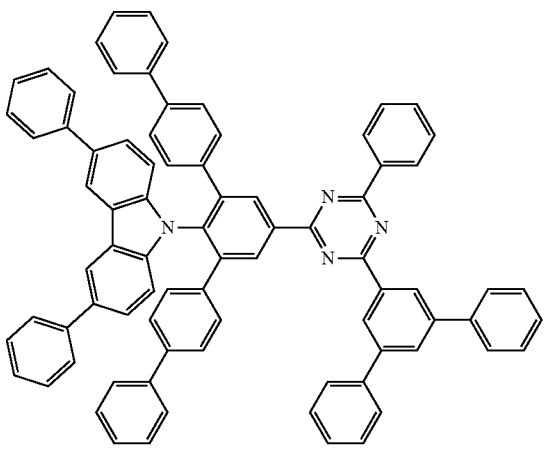
883
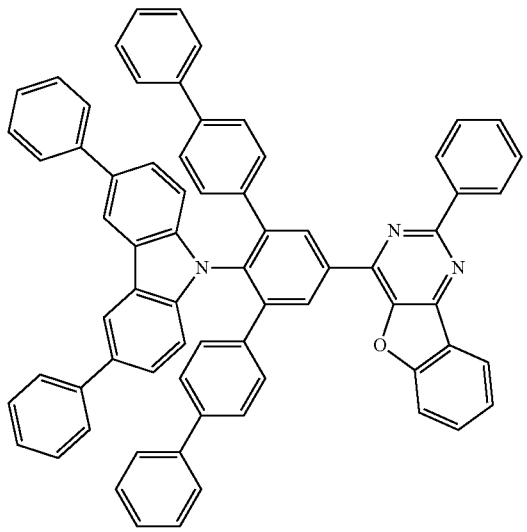
884
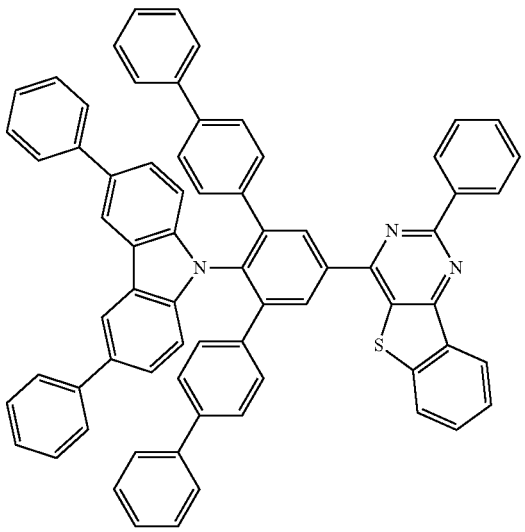
885

-continued
886
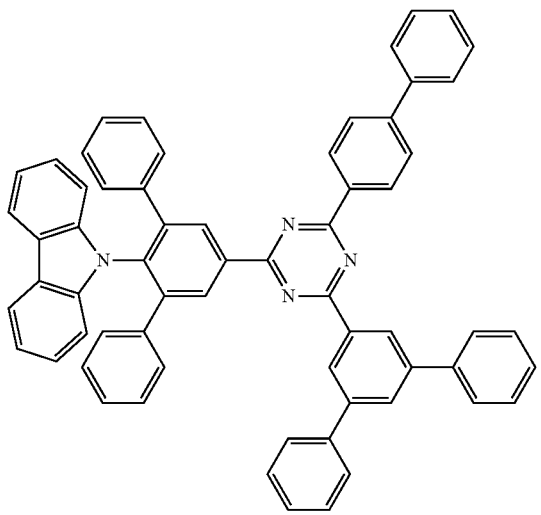
887
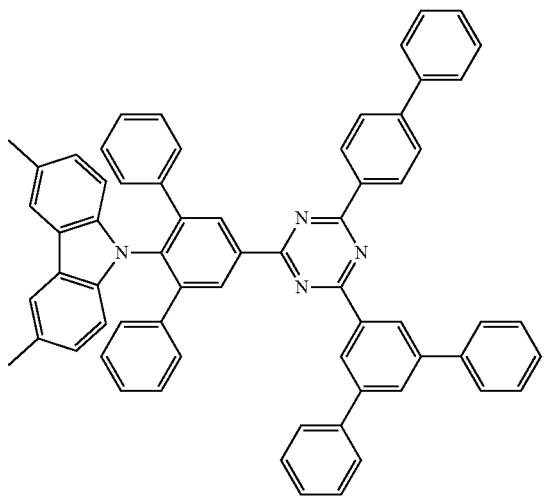
888
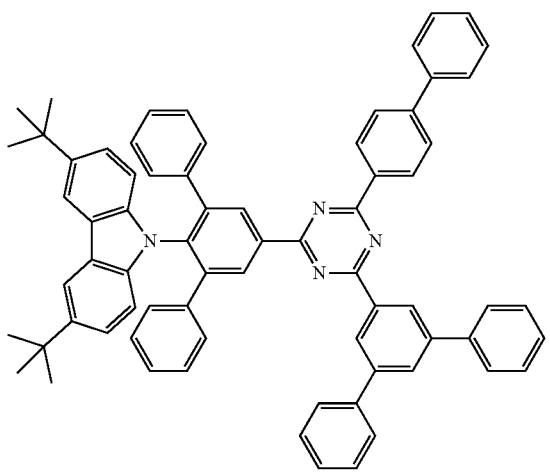
889
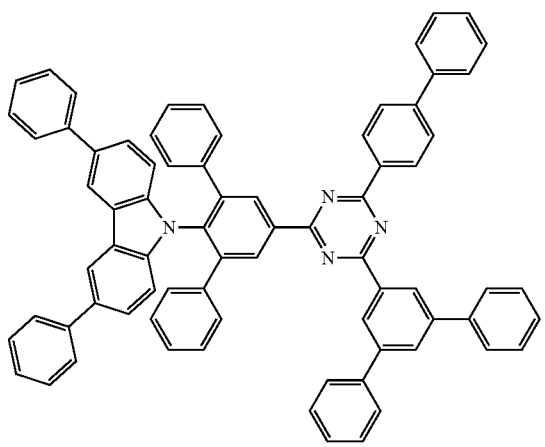
890
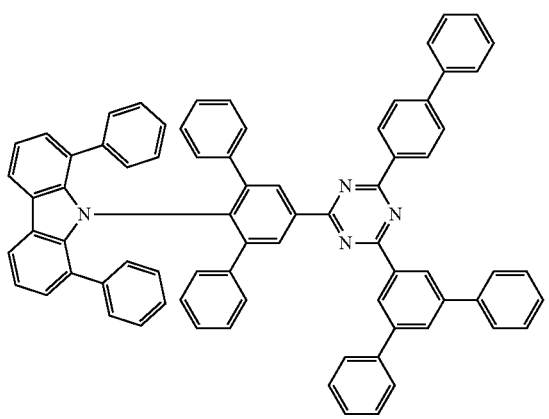
891
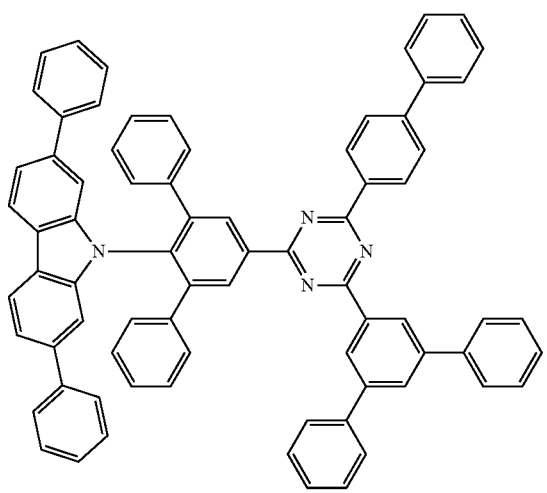

-continued
892
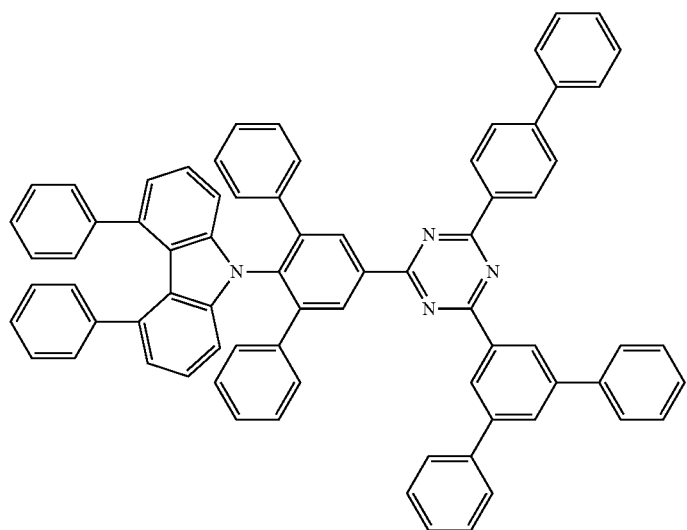
893
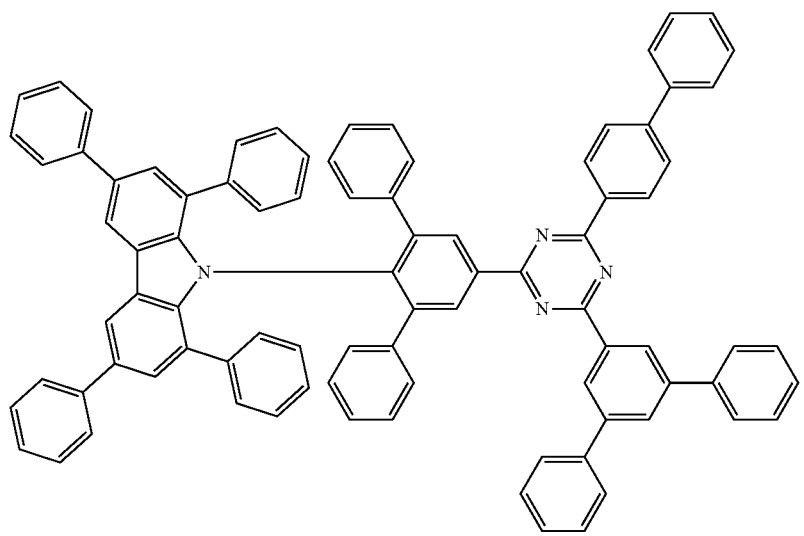
894
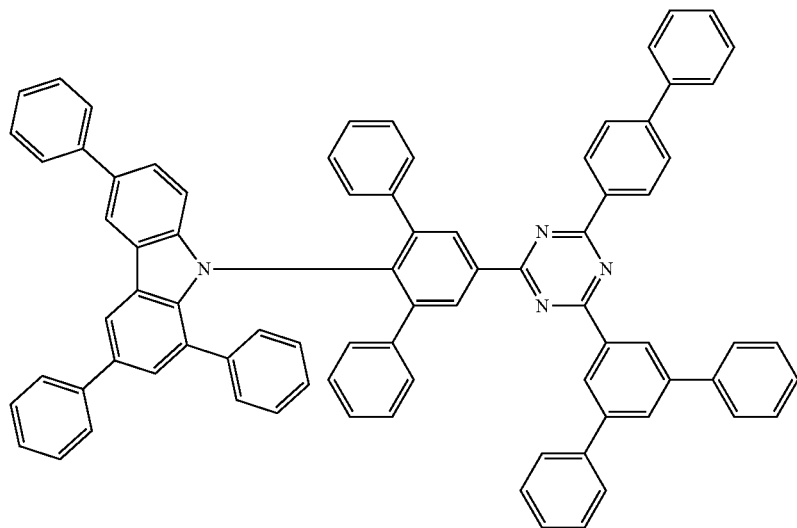

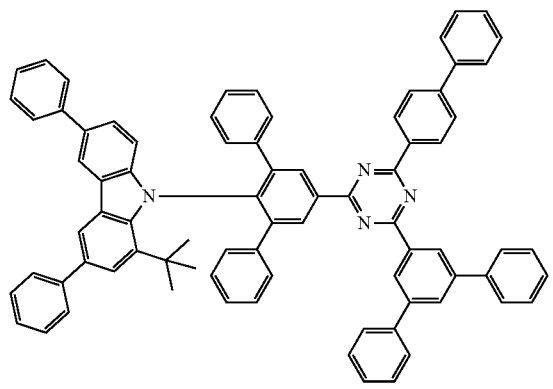

-continued
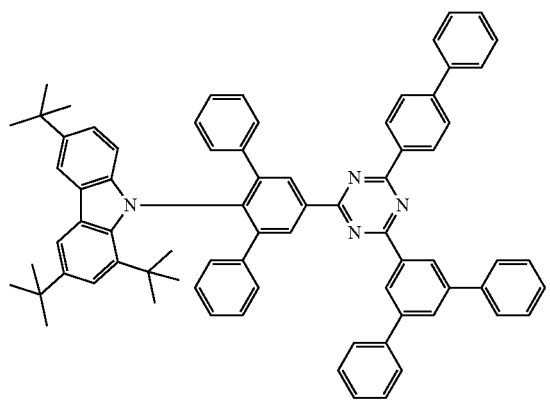
900
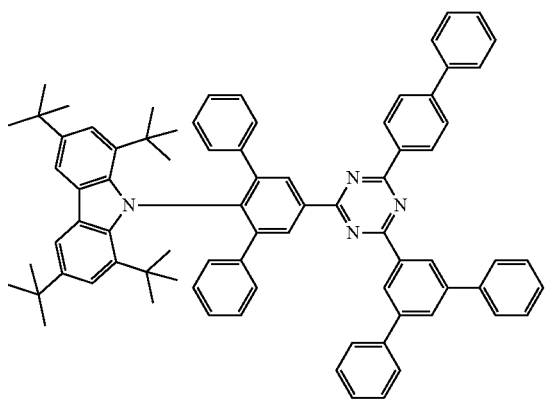
901
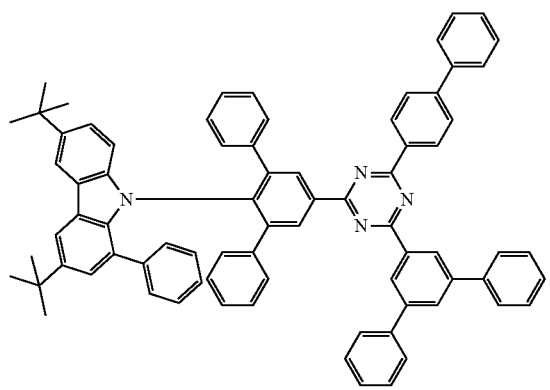
902
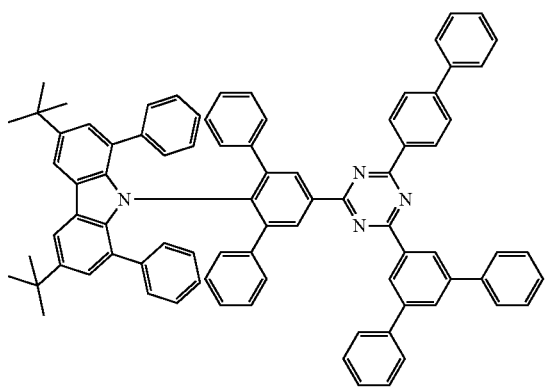
903
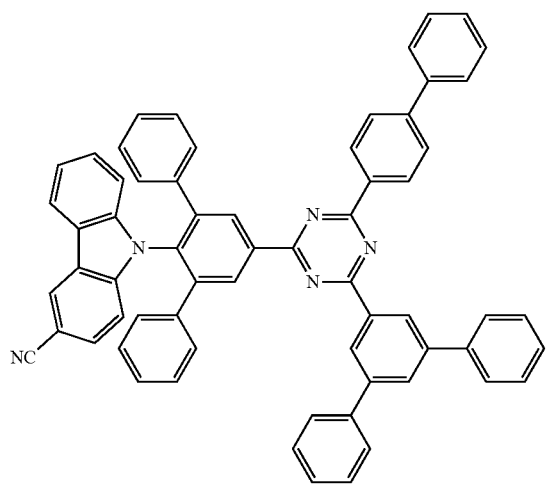
904
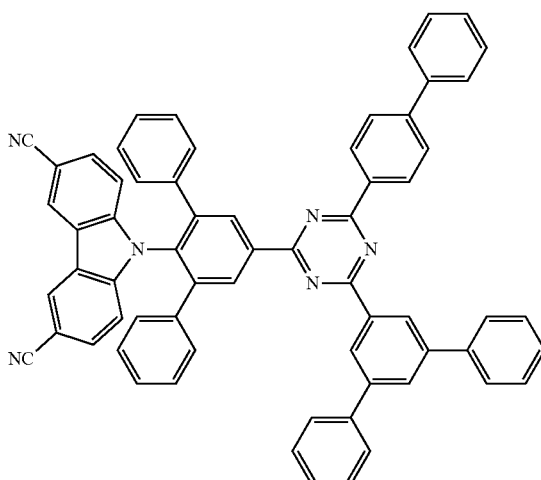
905

-continued
906
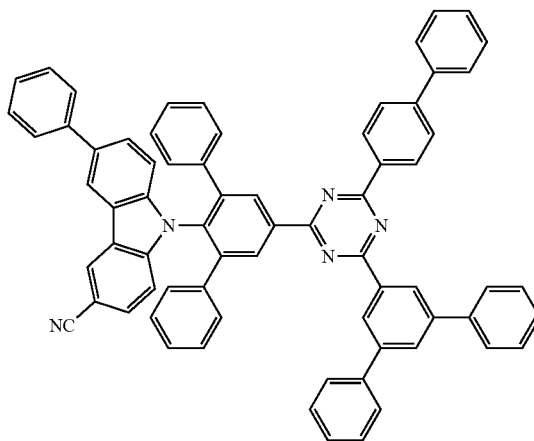
907
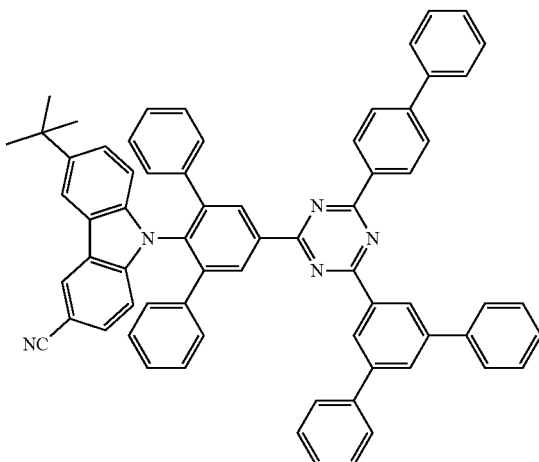
908
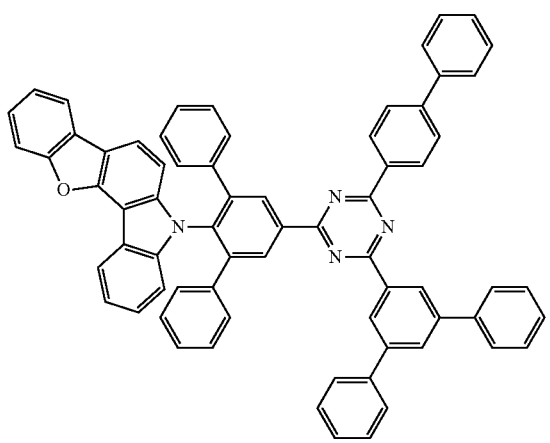
909
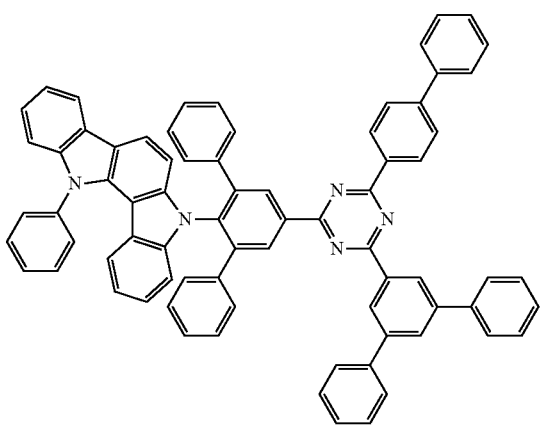
910
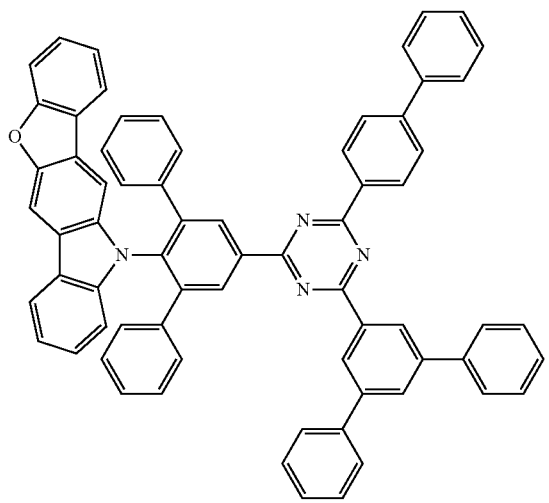
911
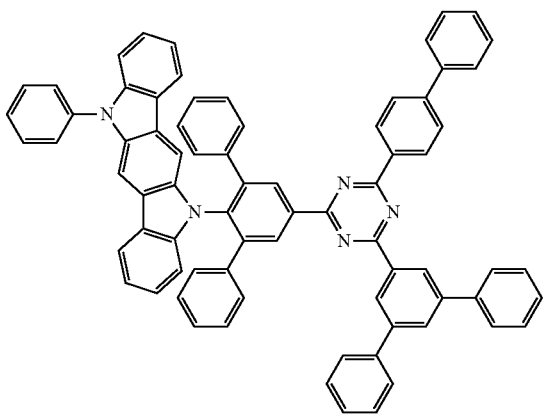

-continued
912
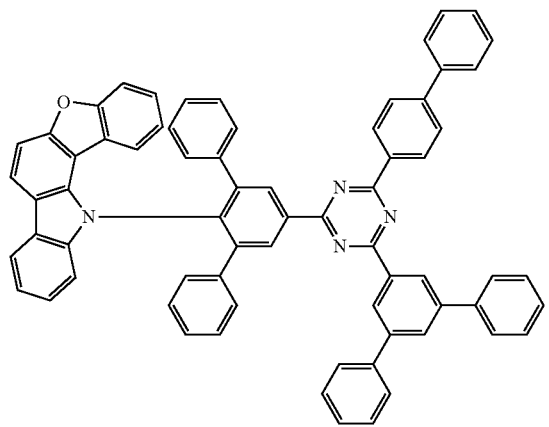
913
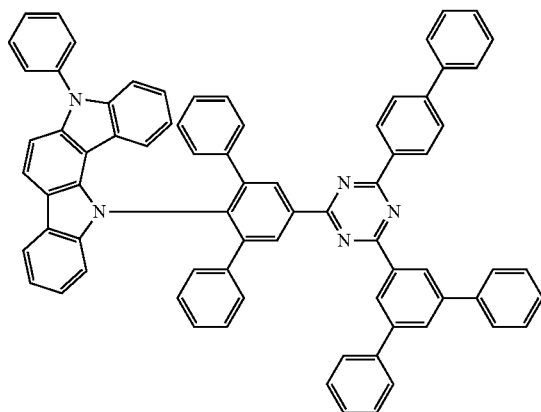
914
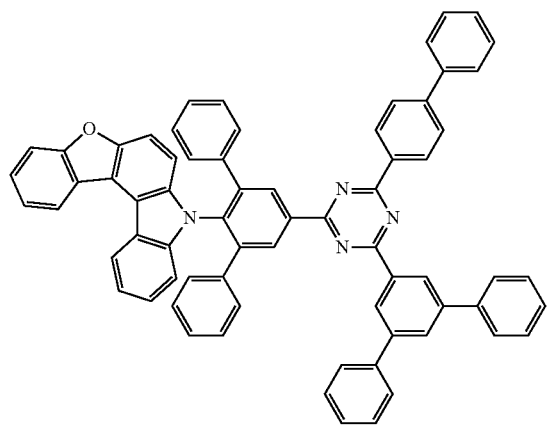
915
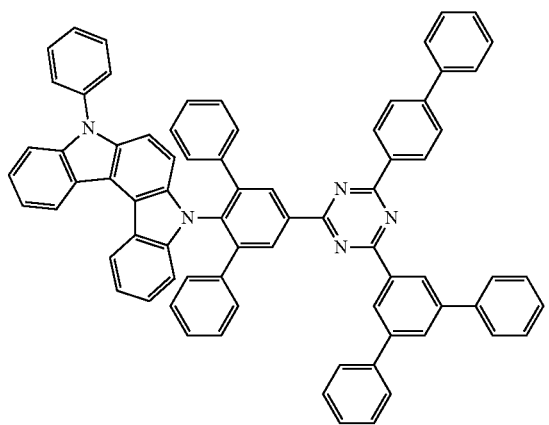
916
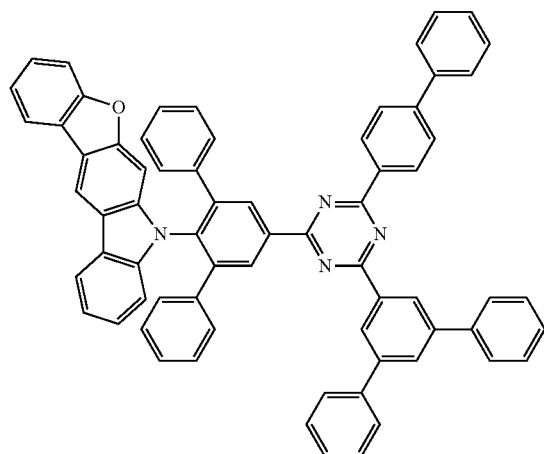
917
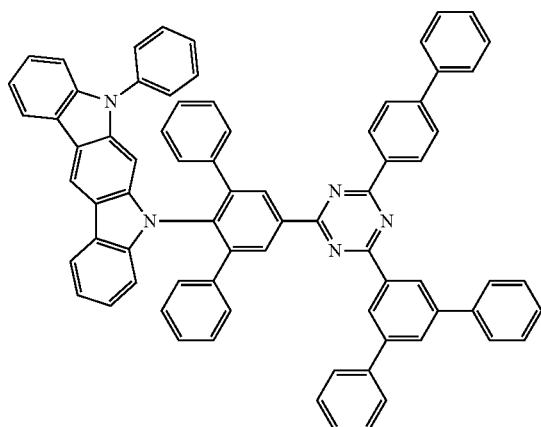

-continued
833
918
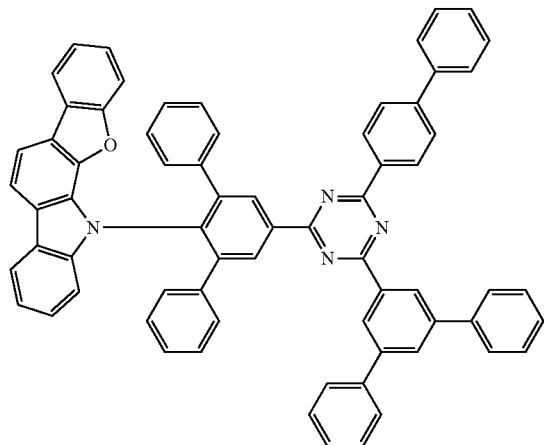
834
919
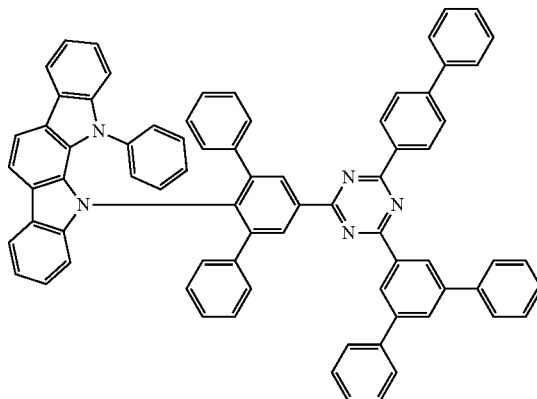
920
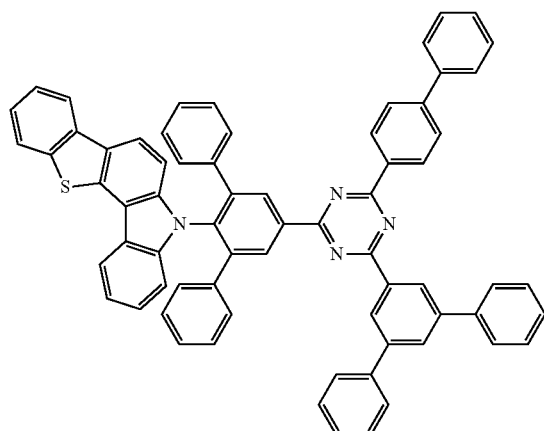
921
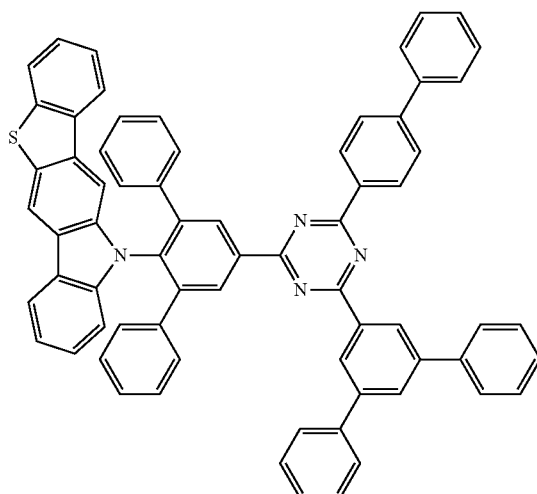
922
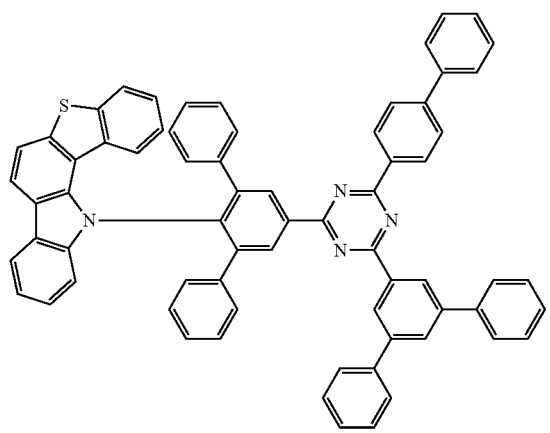
923
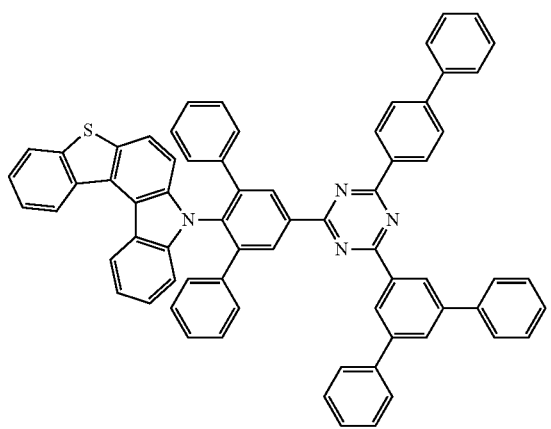

-continued
924
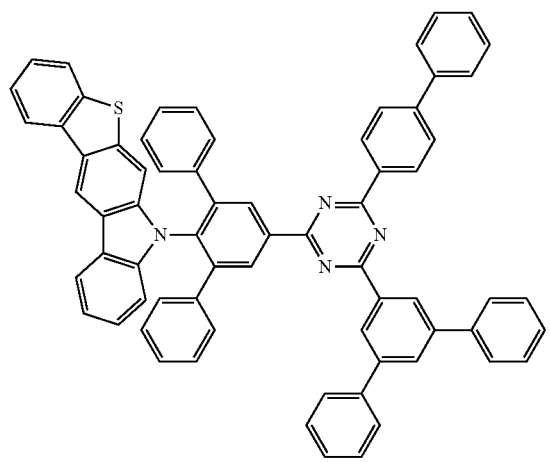
925
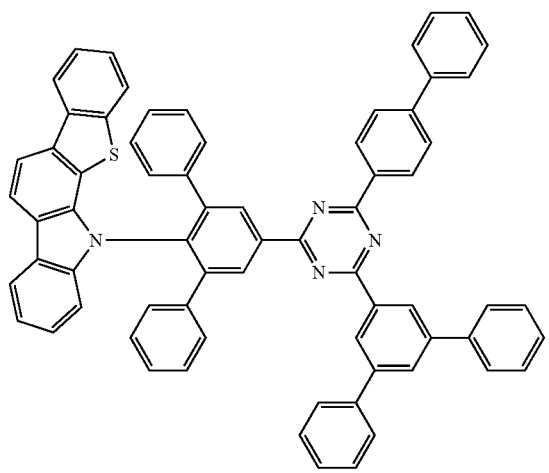
926
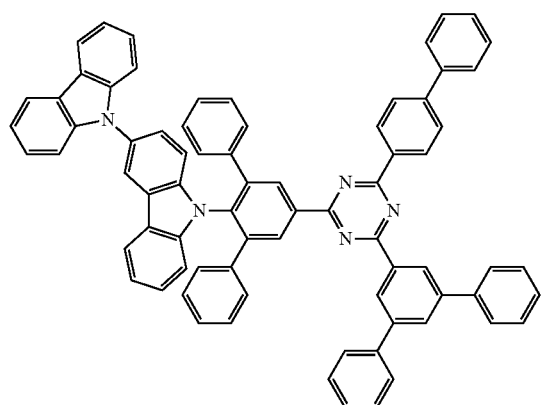
927
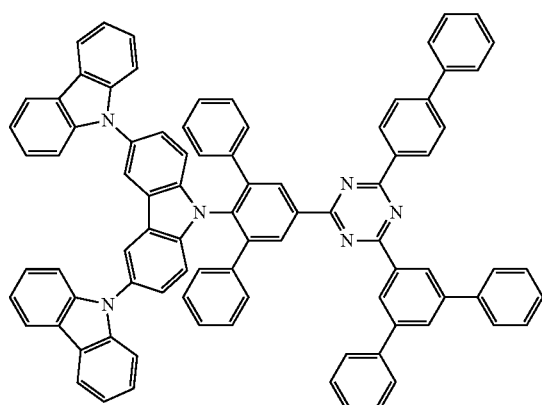
928
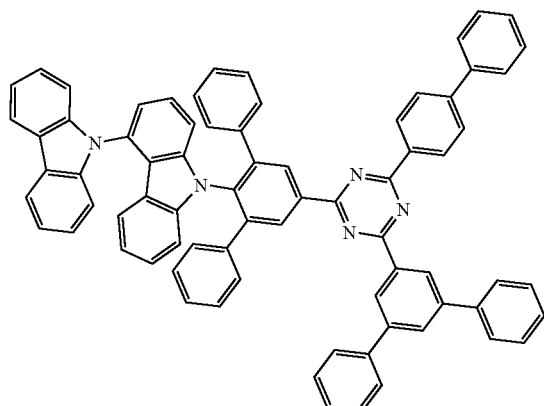
929
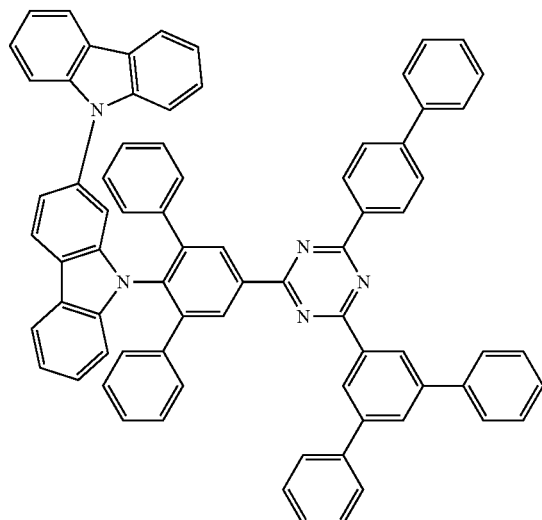

-continued
930 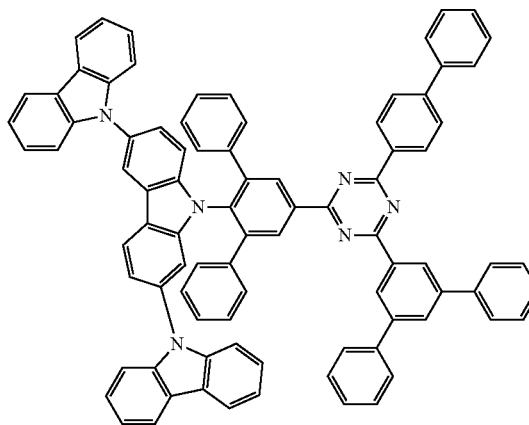 931 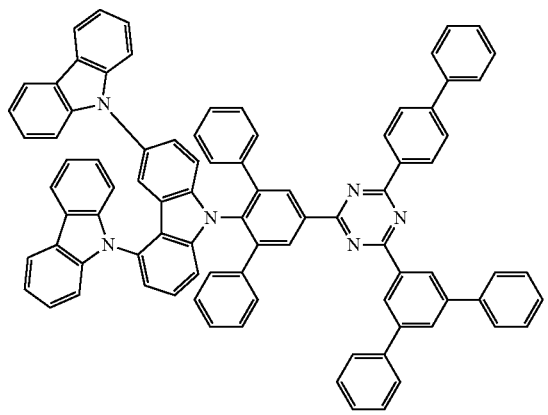
932 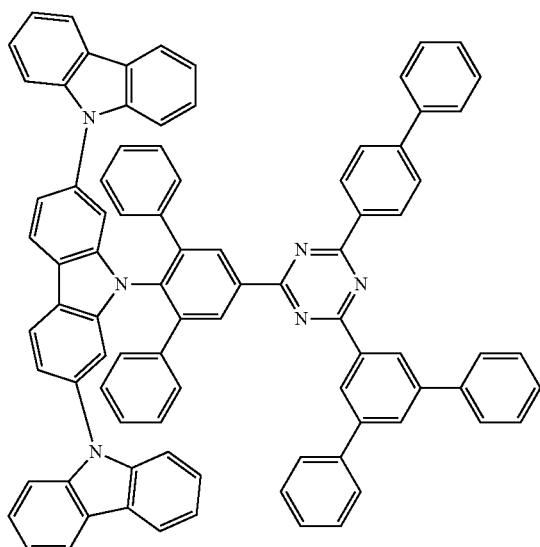 933 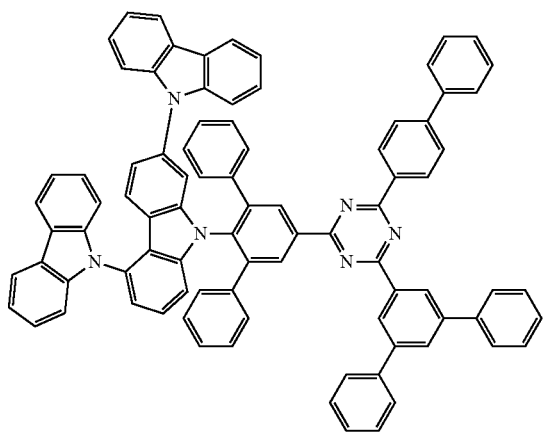
934 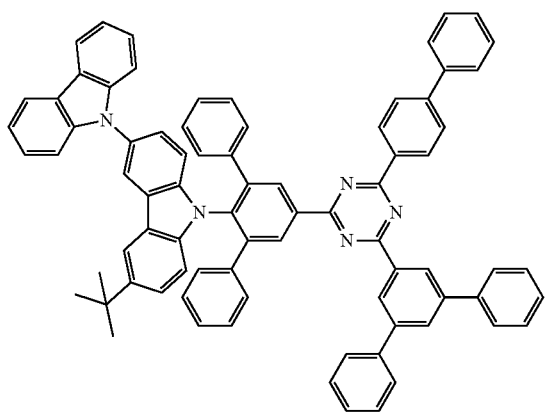 935 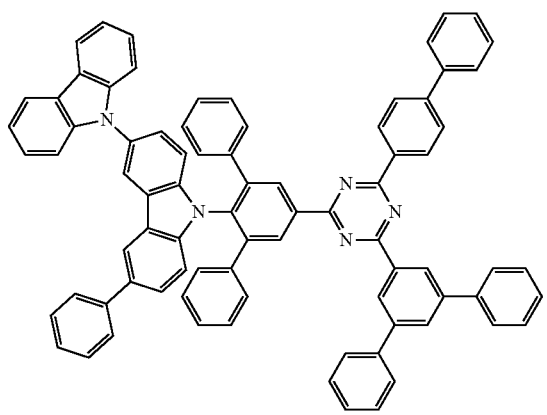

-continued
936
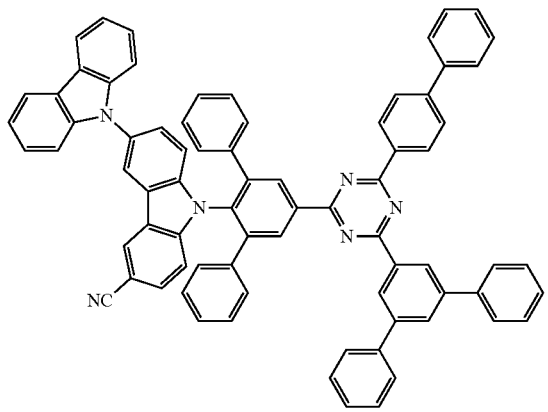
937
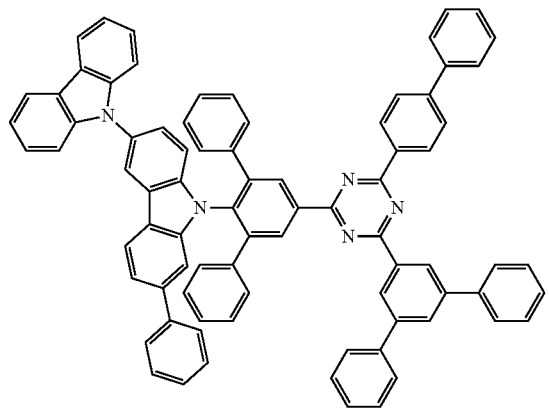
938
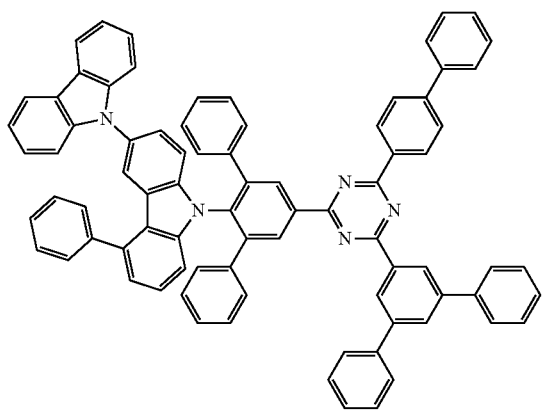
939
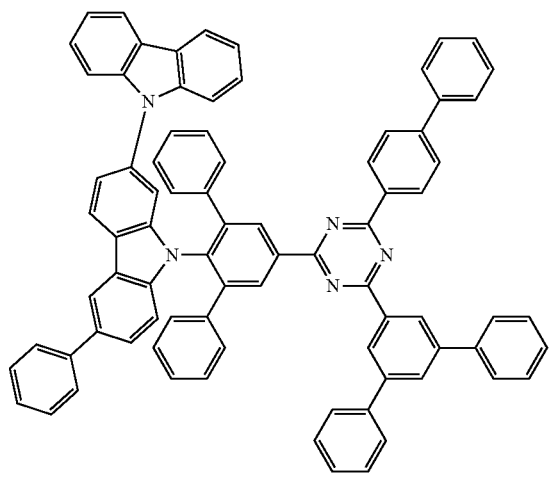
940
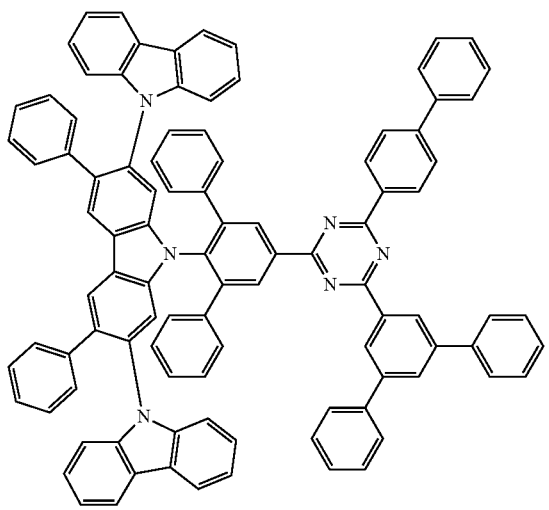
941
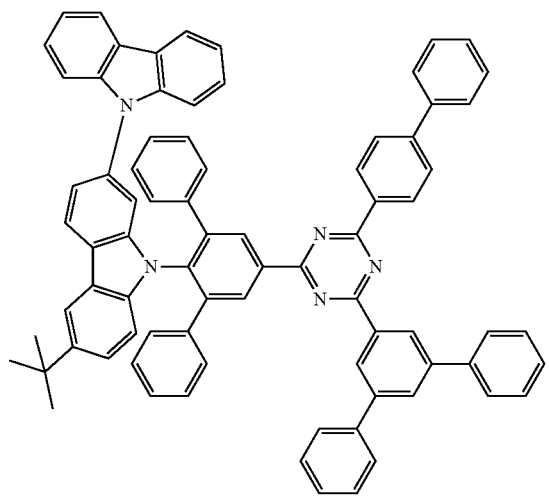

-continued
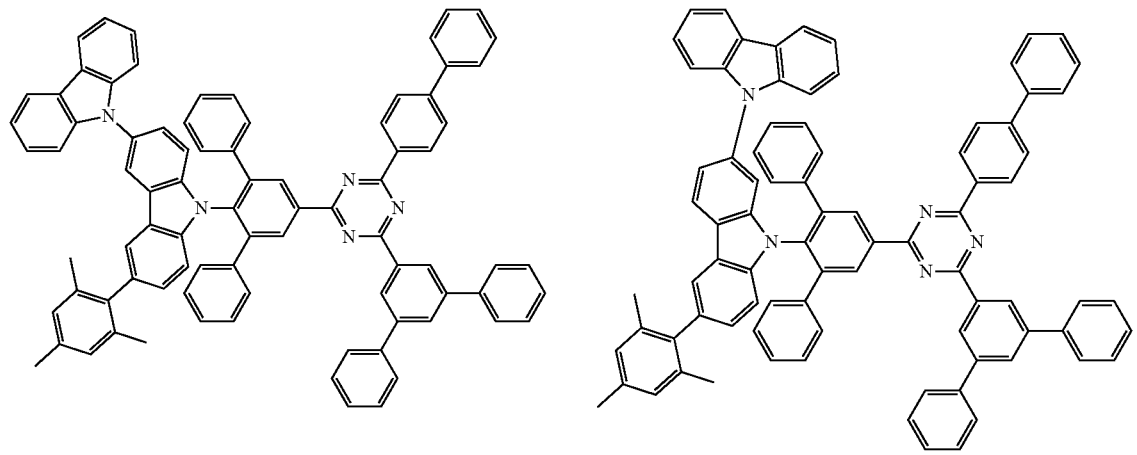
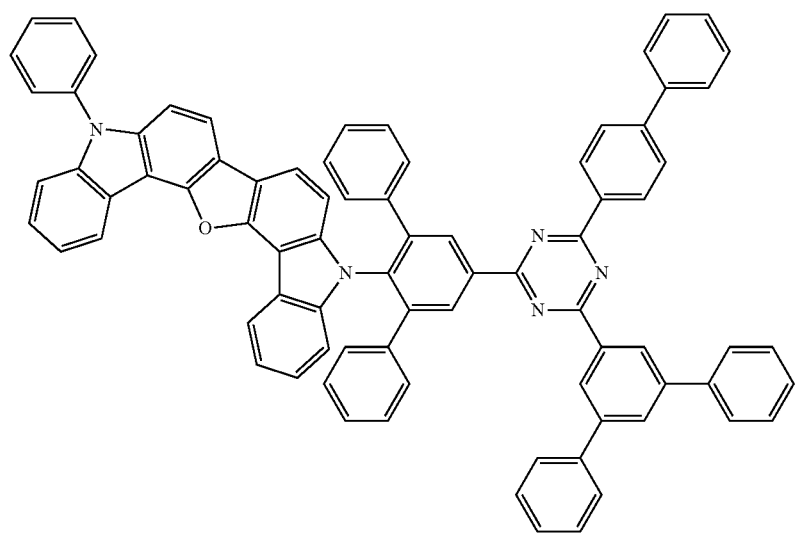
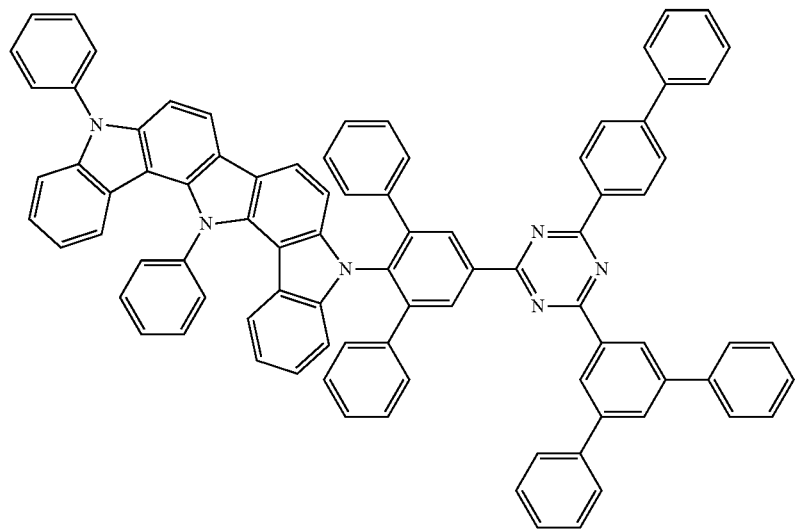

843 844
-continued
| 946 |
|---|
| 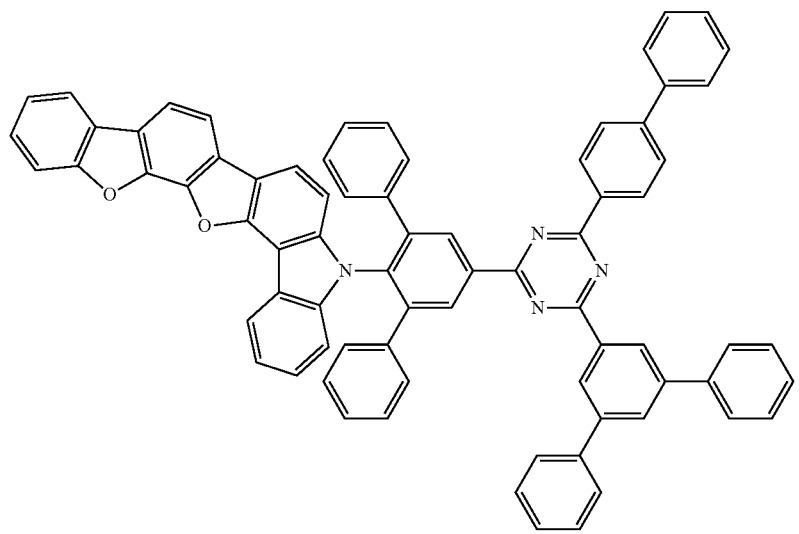 |
| 947 |
|---|
| 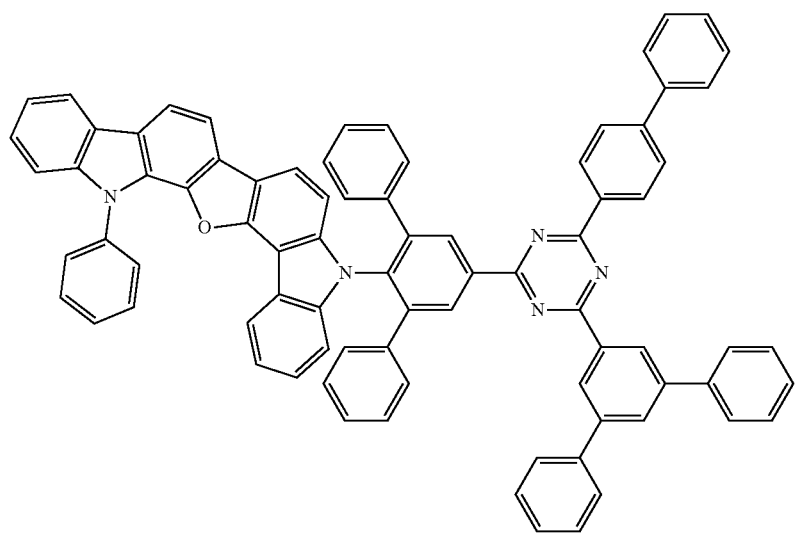 |
948 949
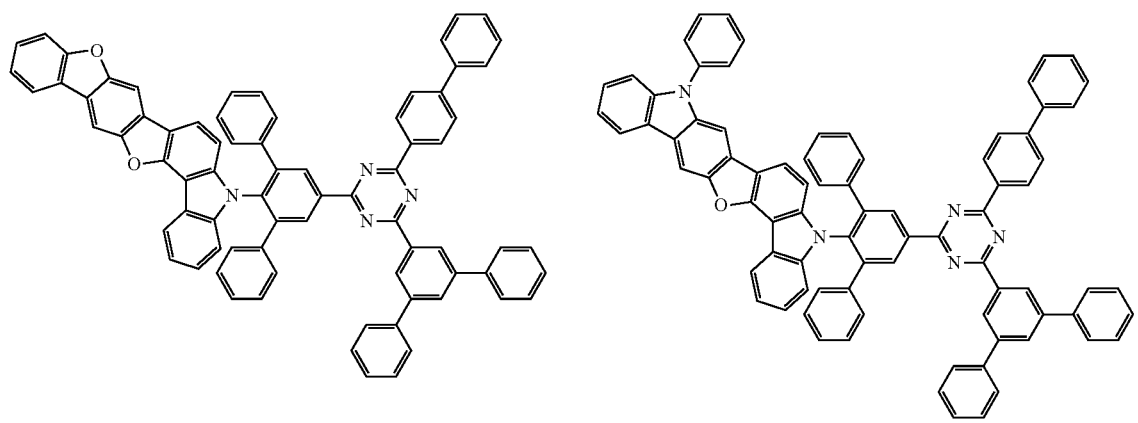

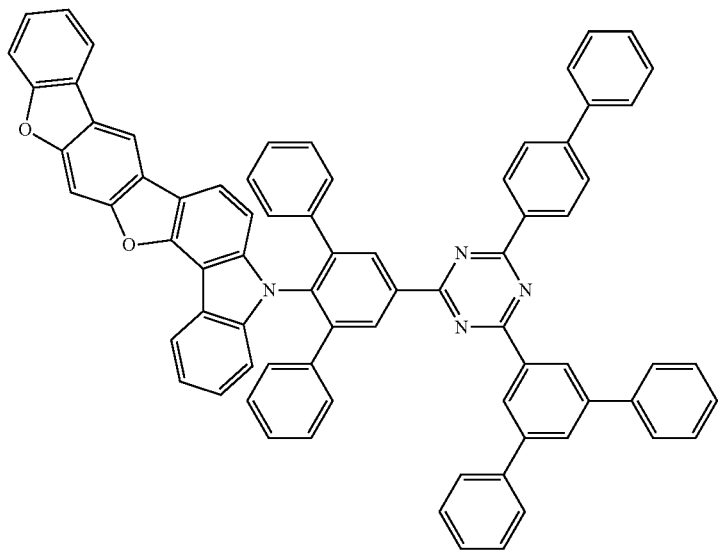
950
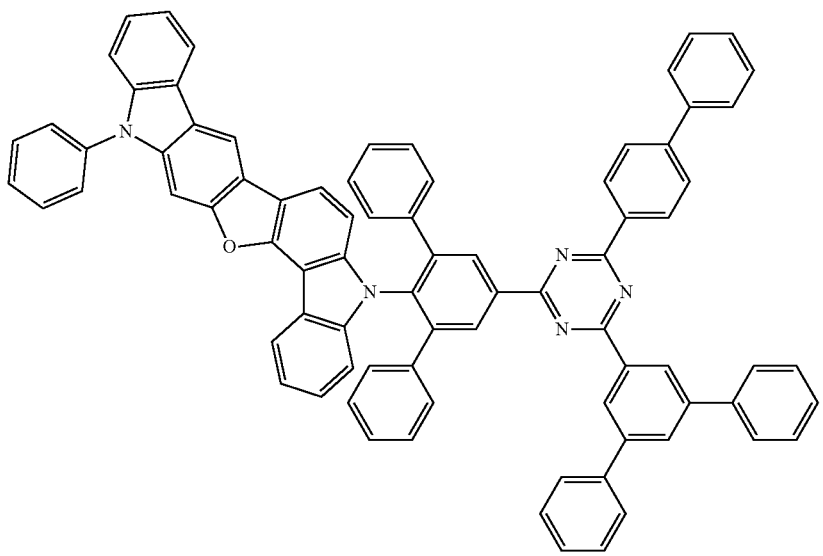
951
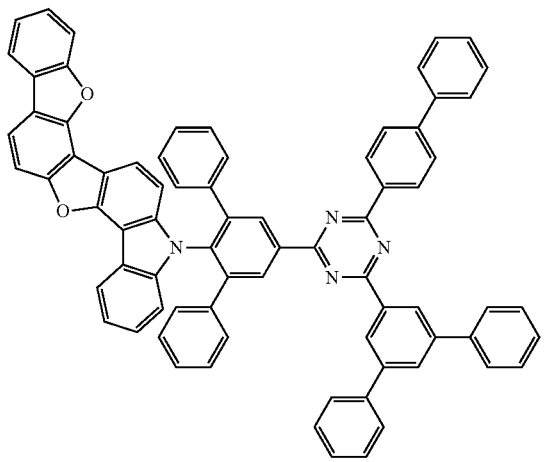
952
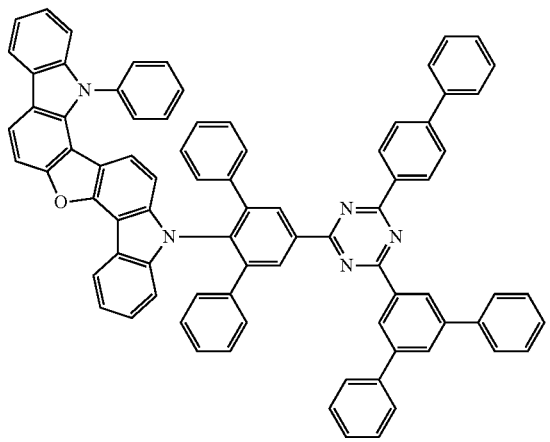
953

847  848
-continued
954
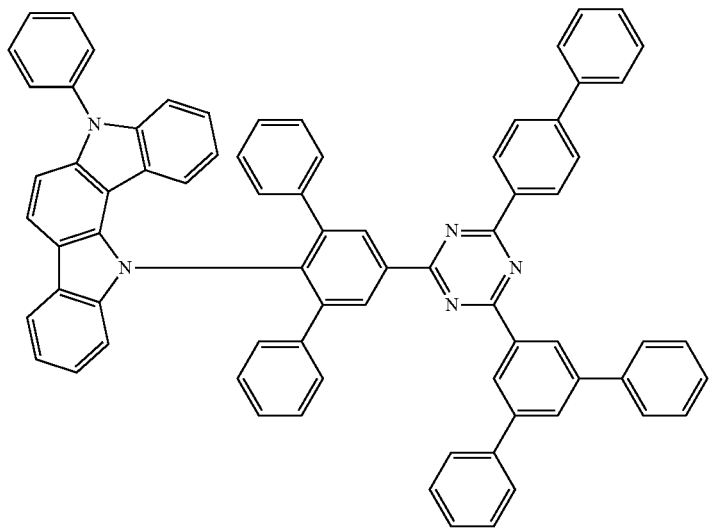
955
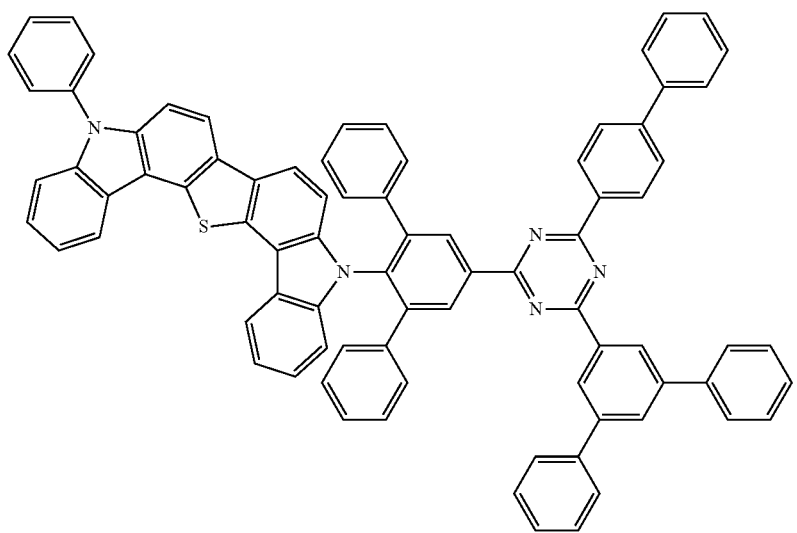
956  957
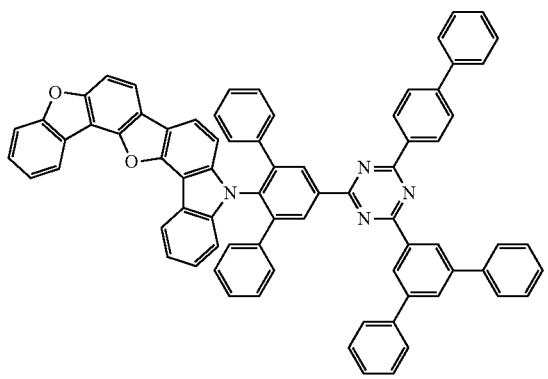 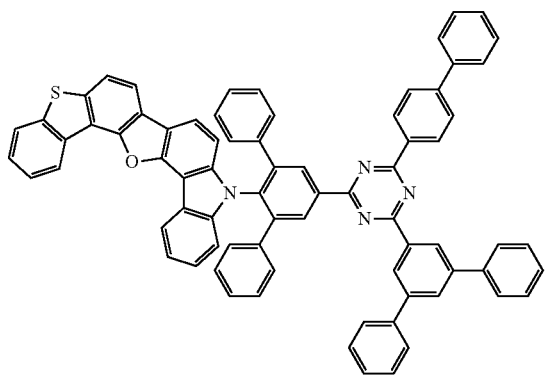

| 958 | 959 |
|---|---|
| 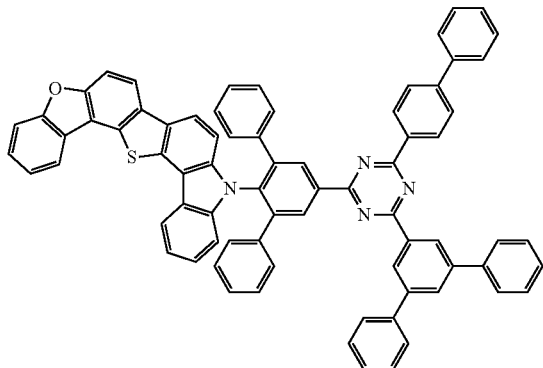 | 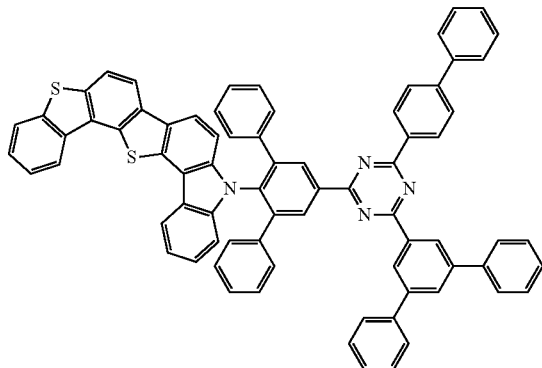 |
| 960 | 961 |
| 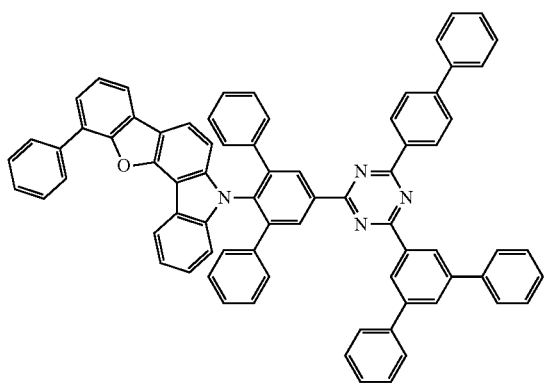 | 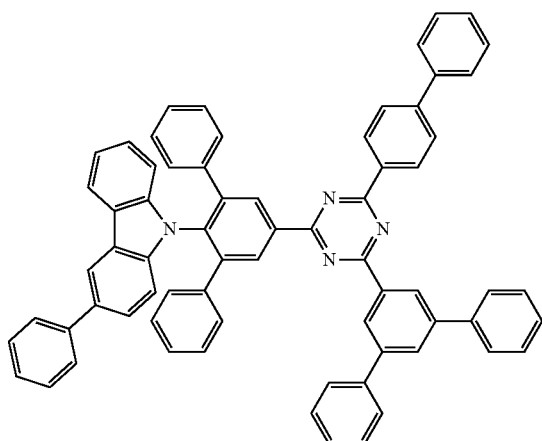 |
| 962 | 963 |
| 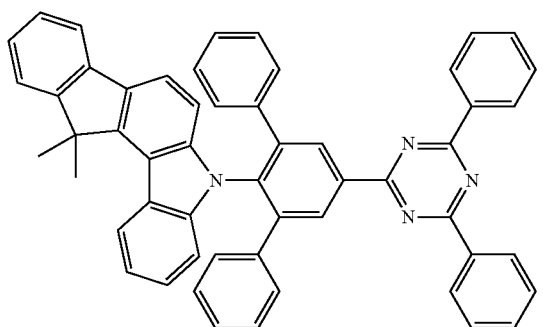 | 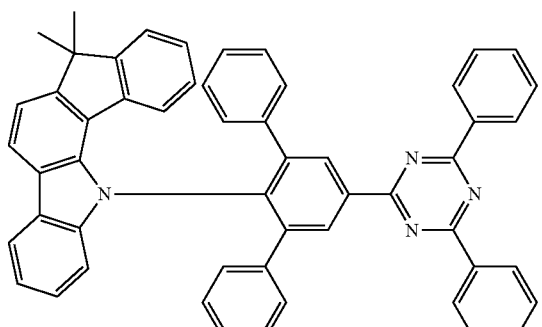 |
| 964 | 965 |
| 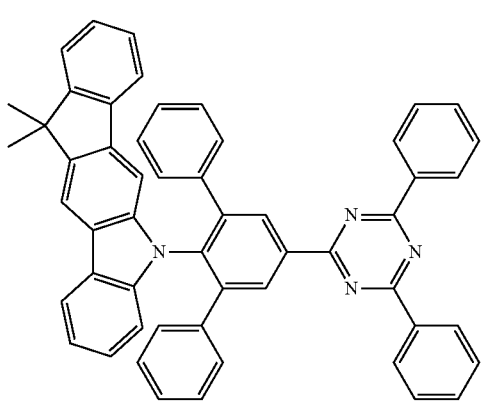 | 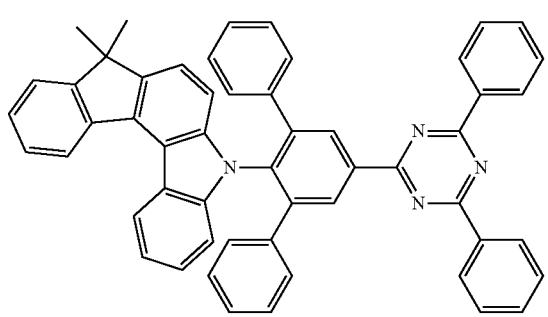 |

-continued
966
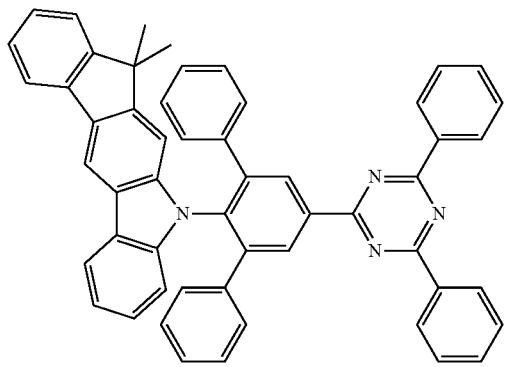
967
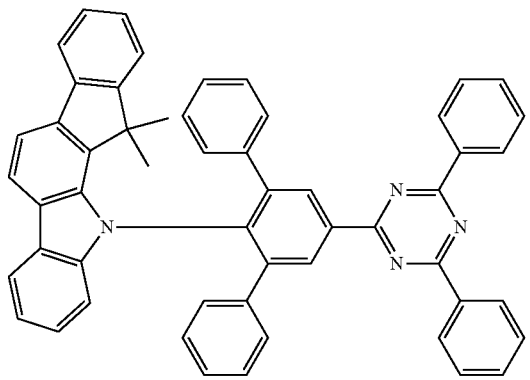
968
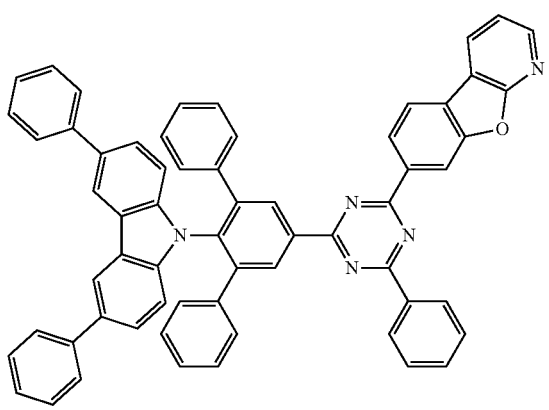
969
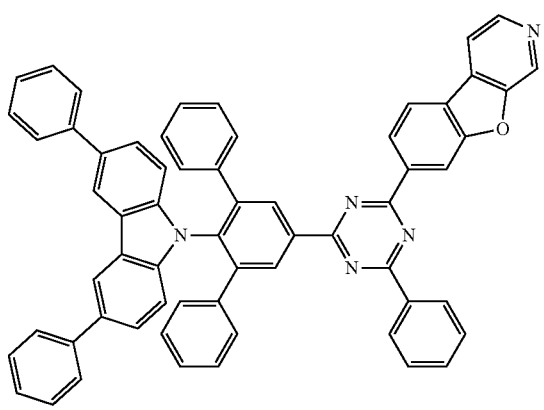
970
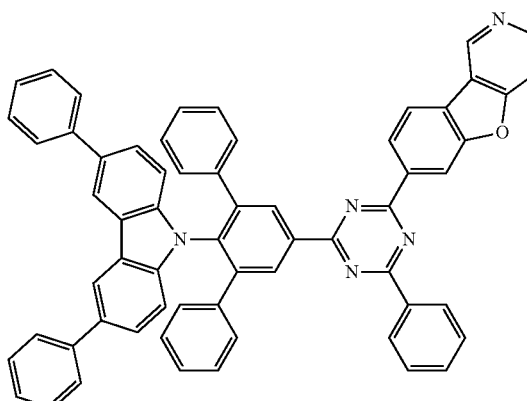
971
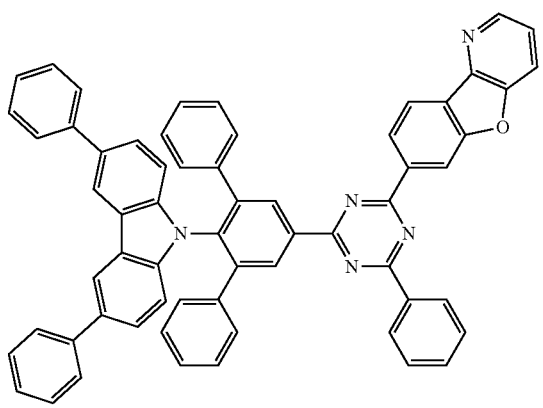
972
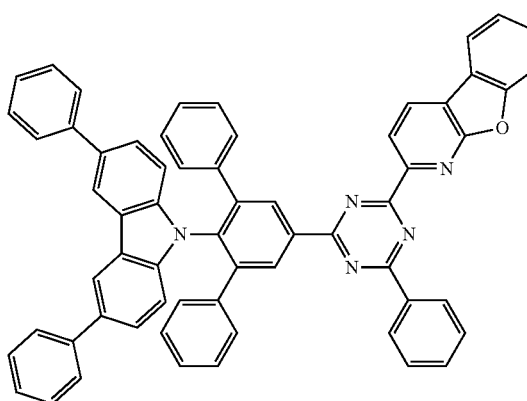
973
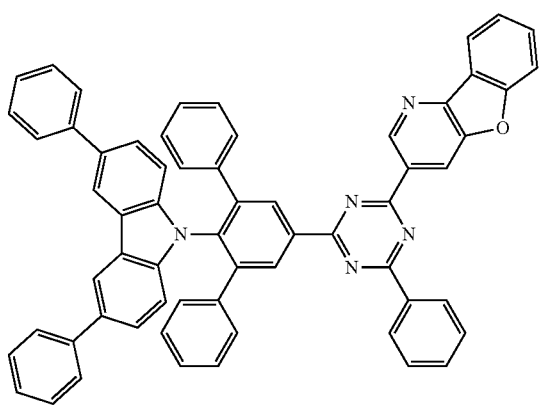

-continued
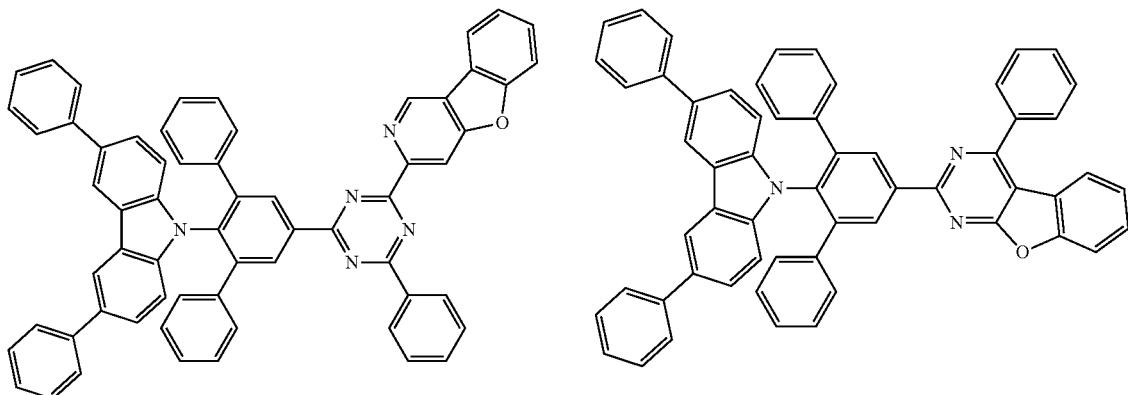
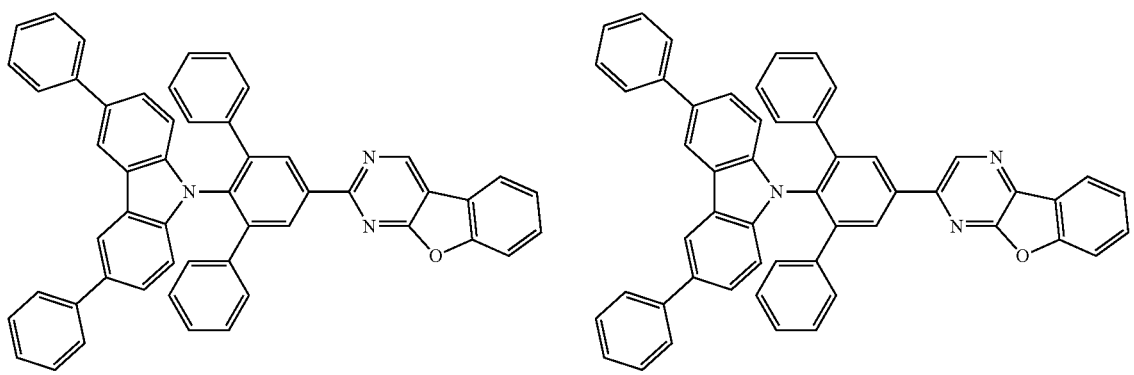
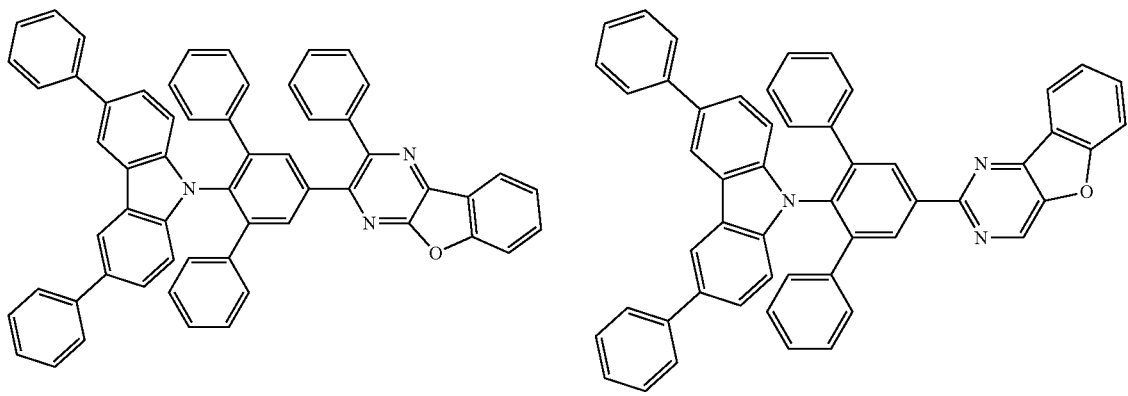
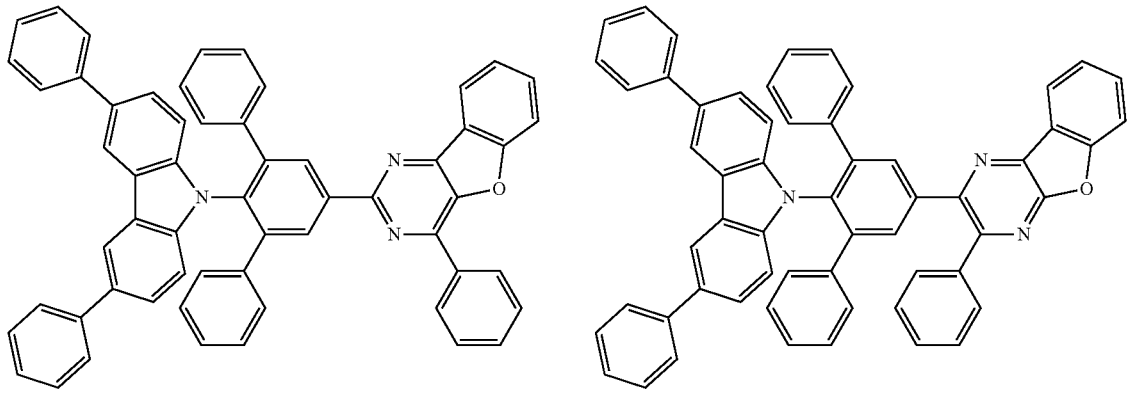

-continued
982
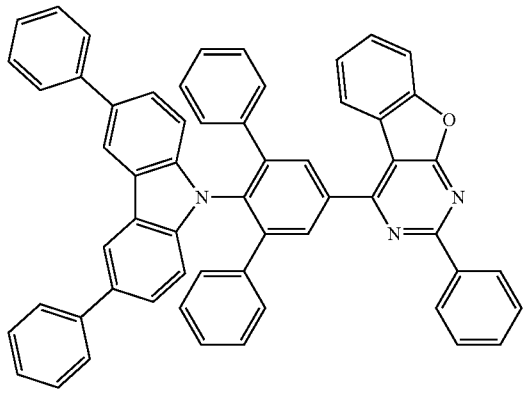
983
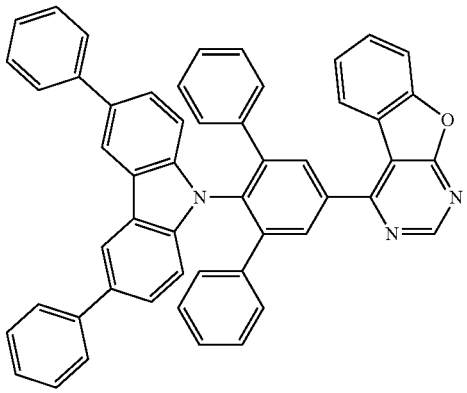
984
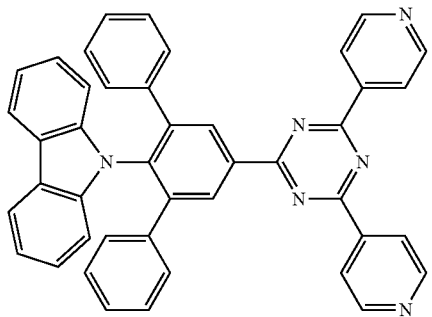
985
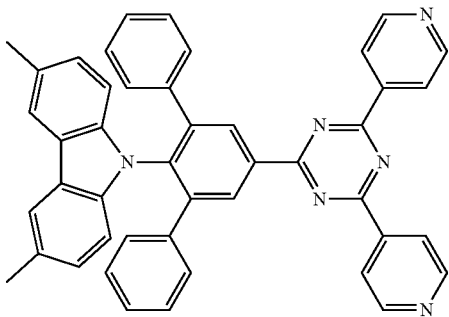
986
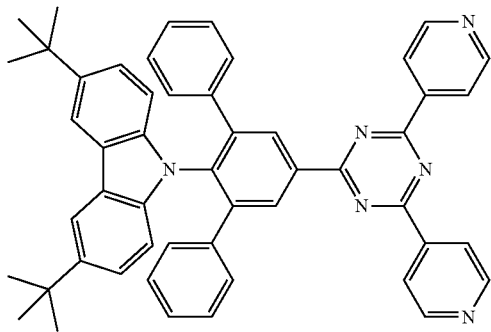
987
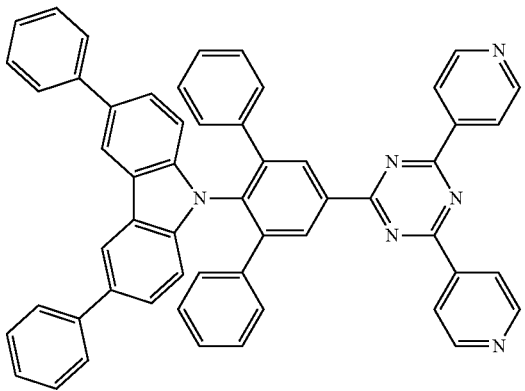
988
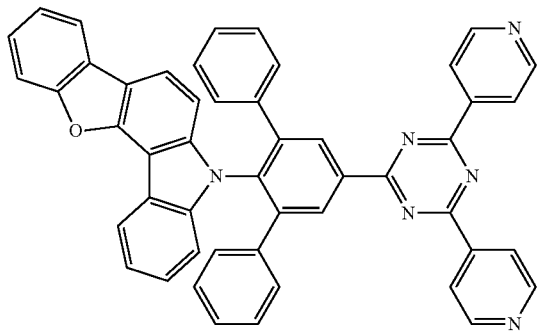
989
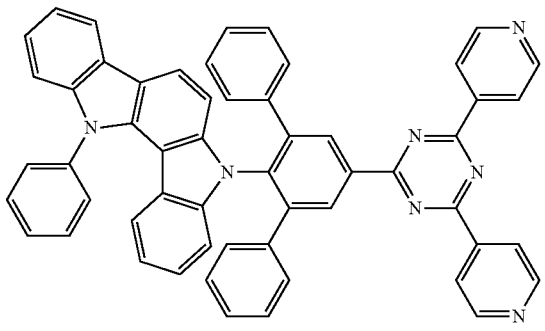

990
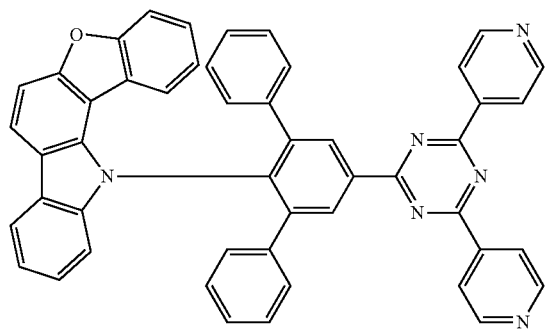
991
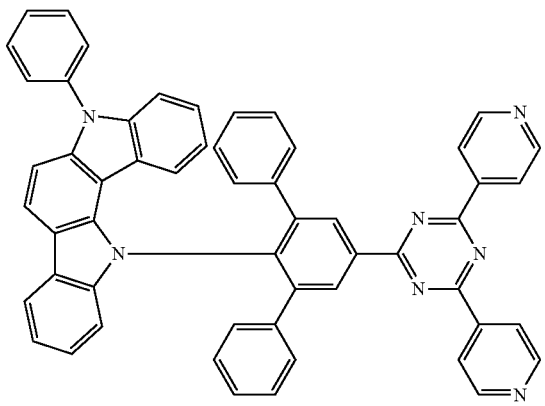
992
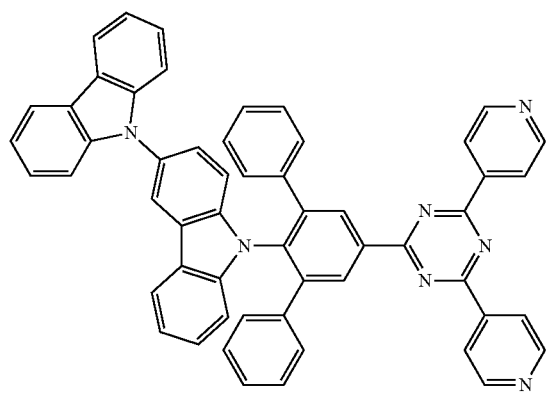
993
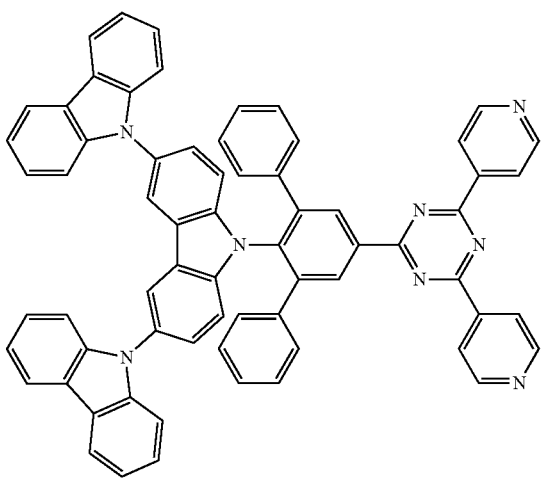
994
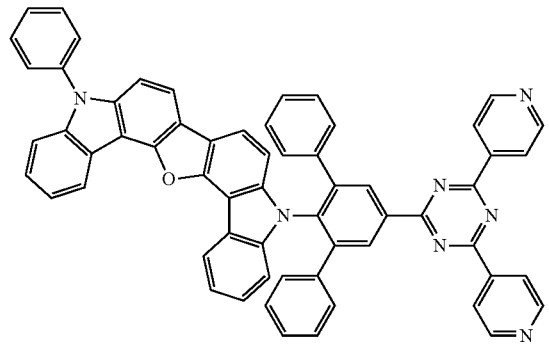
995
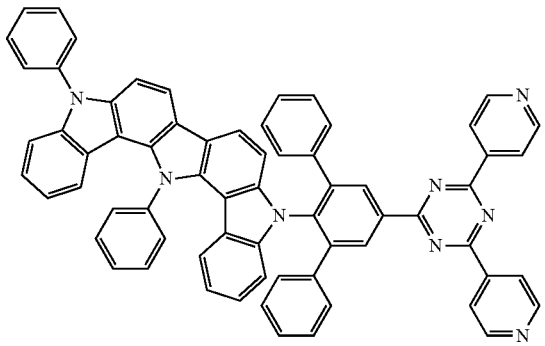

-continued
996
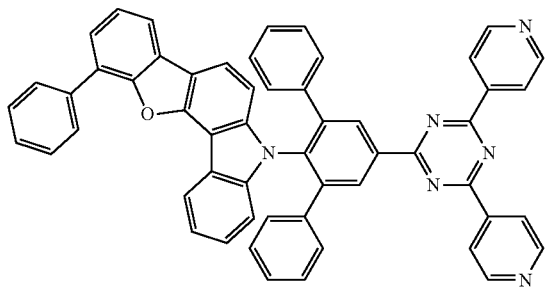
997
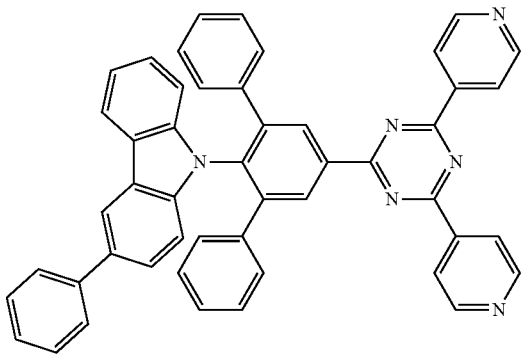
998
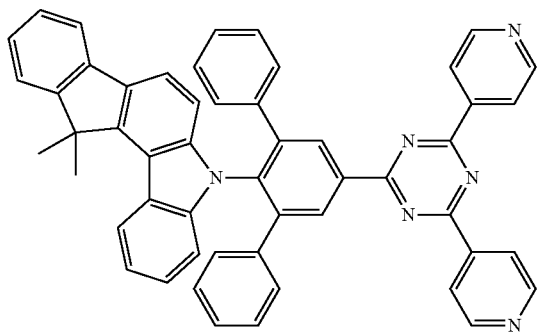
999
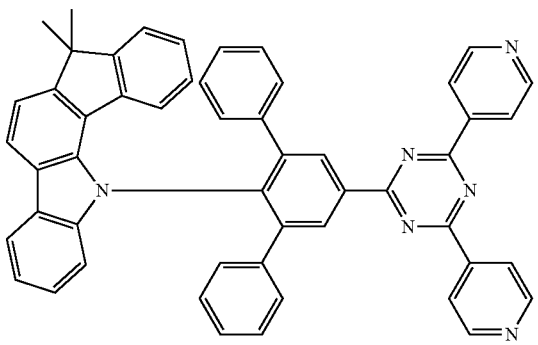
1000
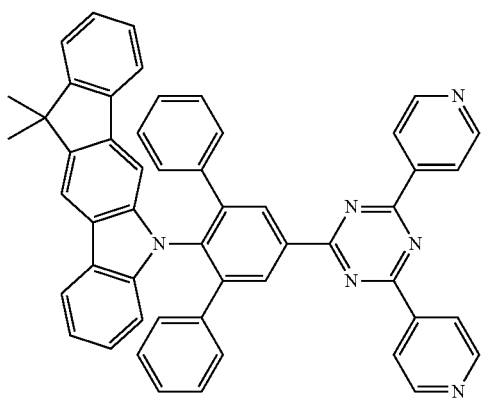
1001
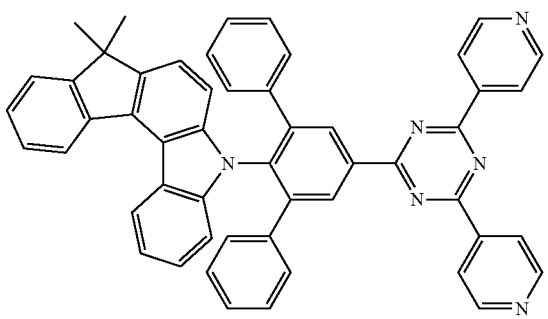
1002
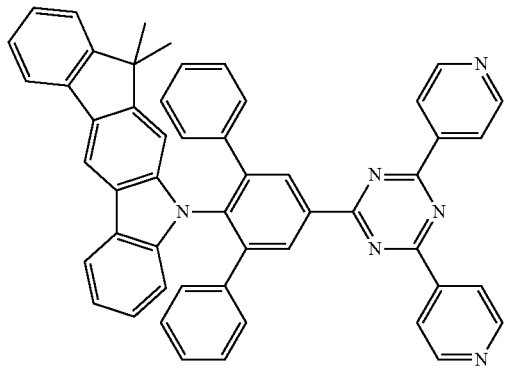
1003
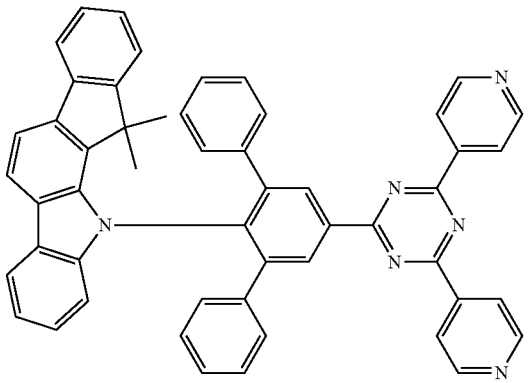

-continued
1004
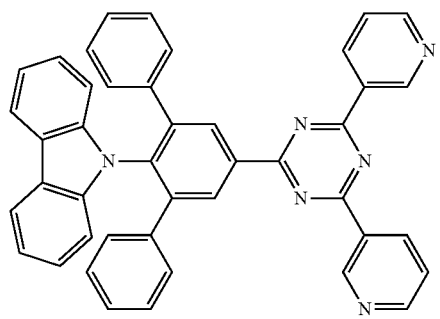
1005
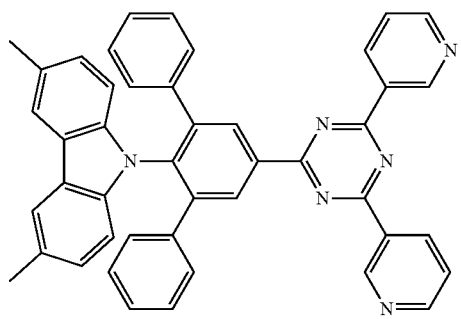
1006
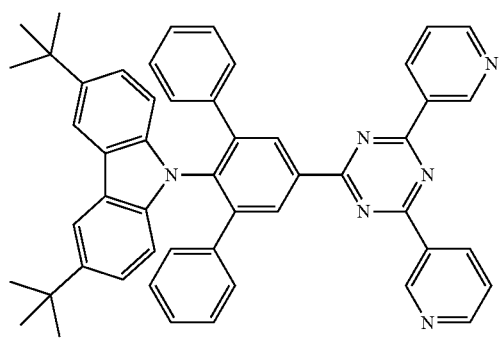
1007
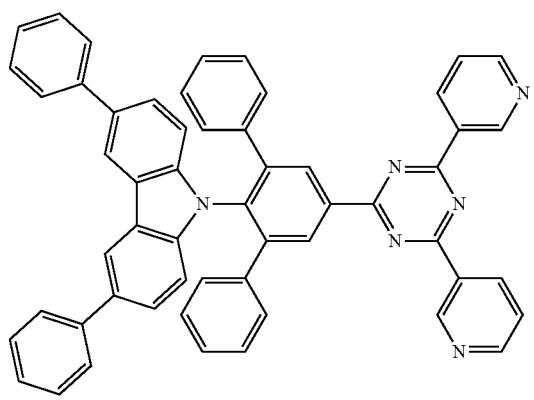
1008
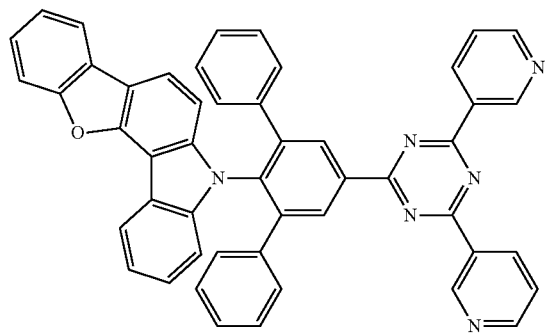
1009
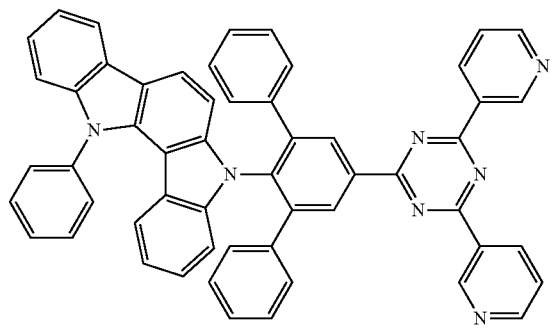
1010
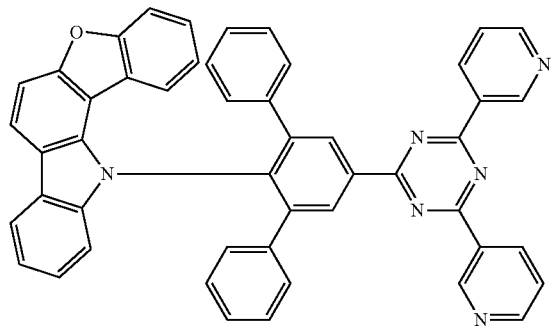
1011
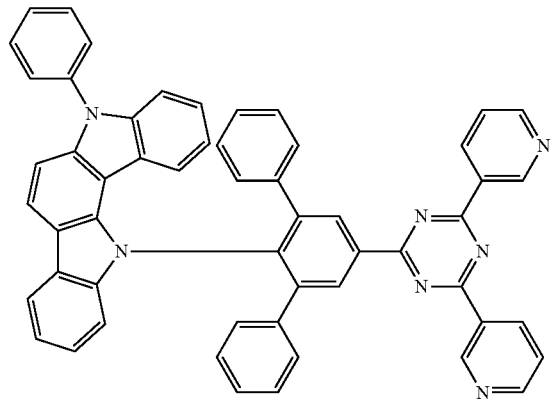

-continued
| 1012 | 1013 |
|---|---|
| 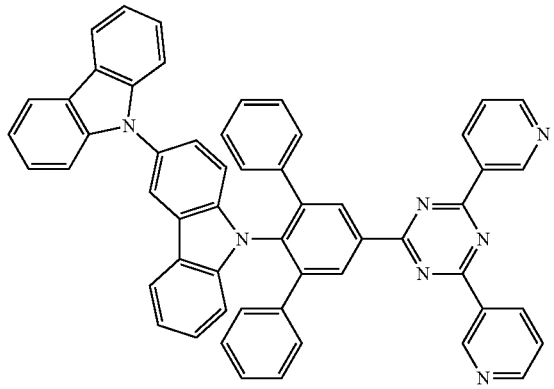 | 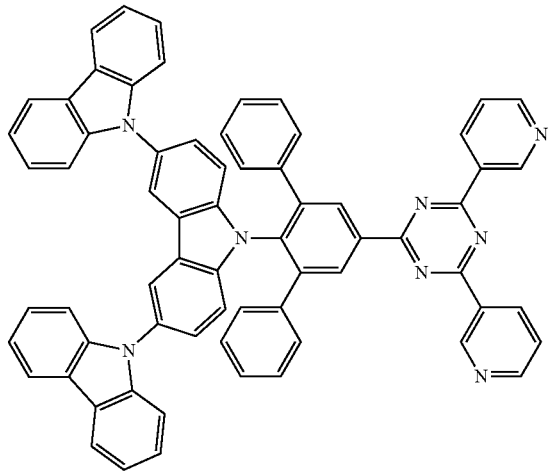 |
| 1014 | 1015 |
| 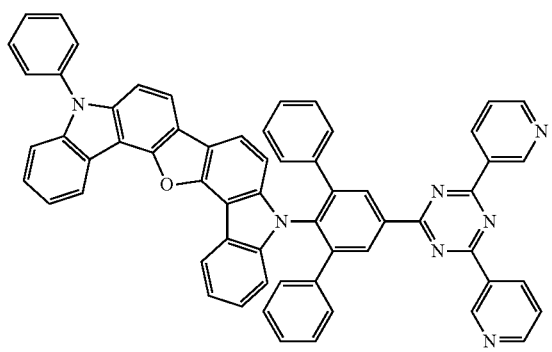 | 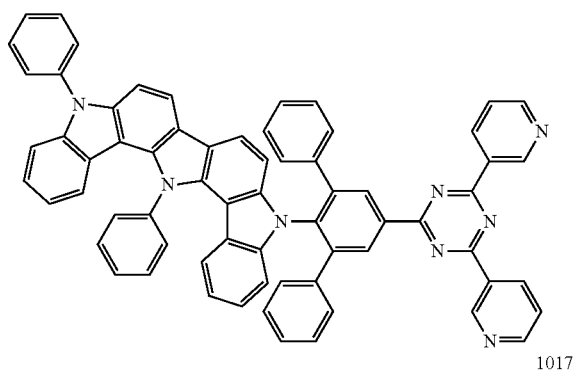 |
| 1016 | 1017 |
| 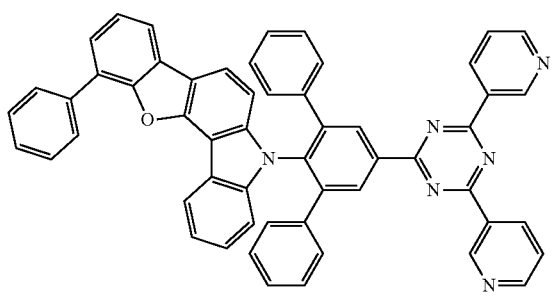 | 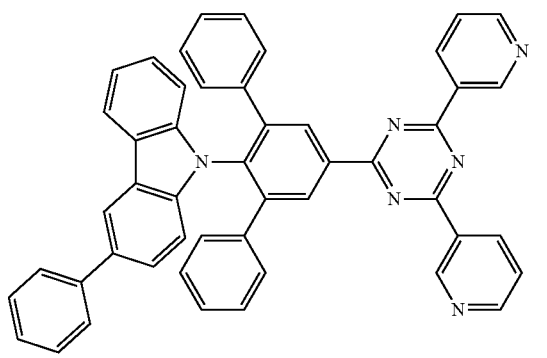 |
| 1018 | 1019 |
| 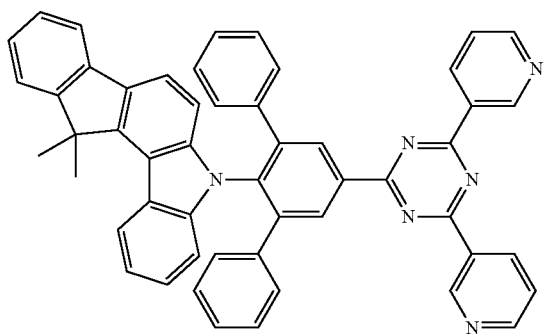 | 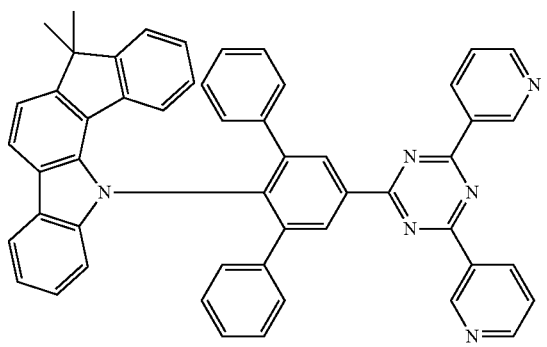 |

-continued
1020
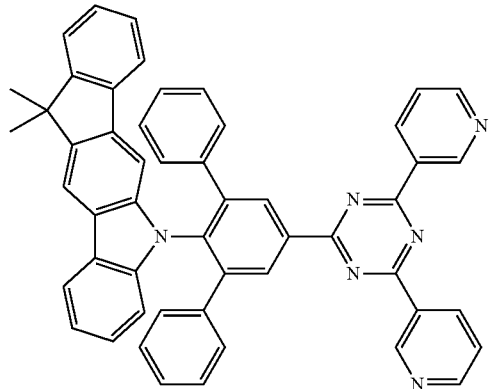
1021
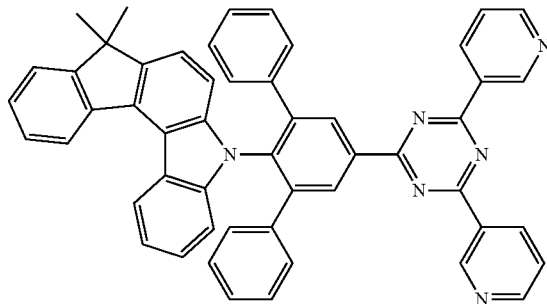
1022
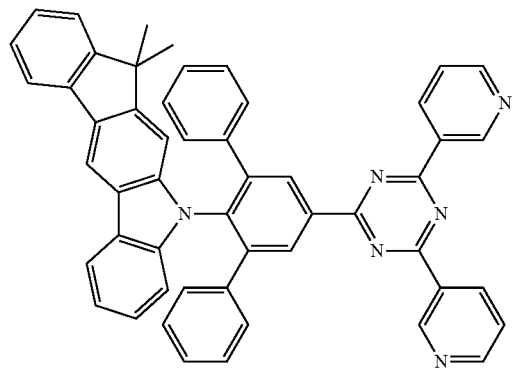
1023
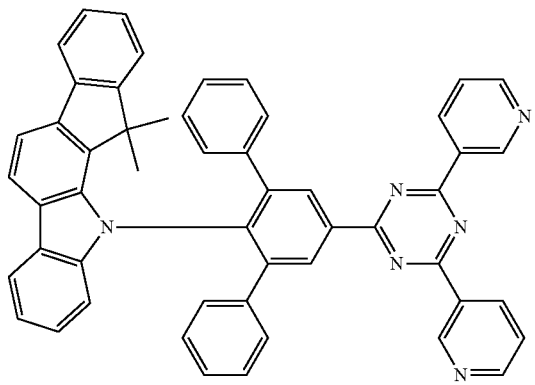
1024
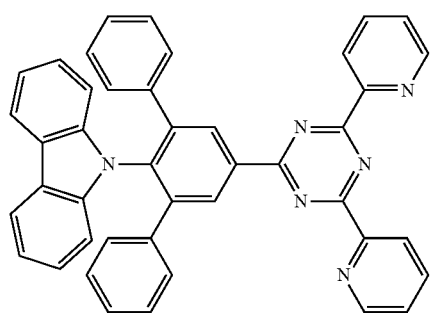
1025
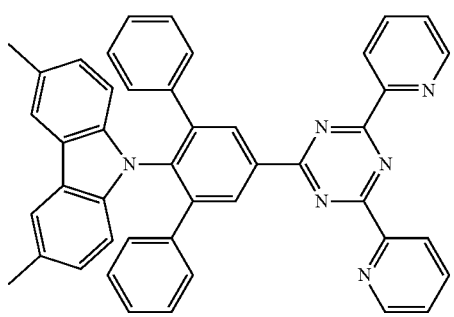
1026
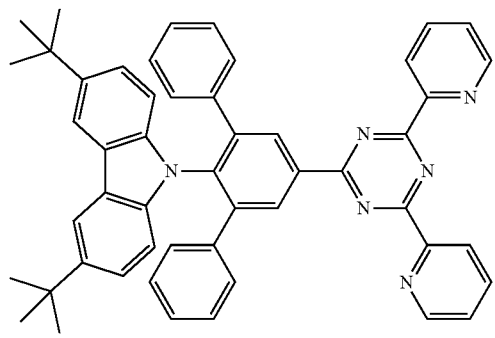
1027
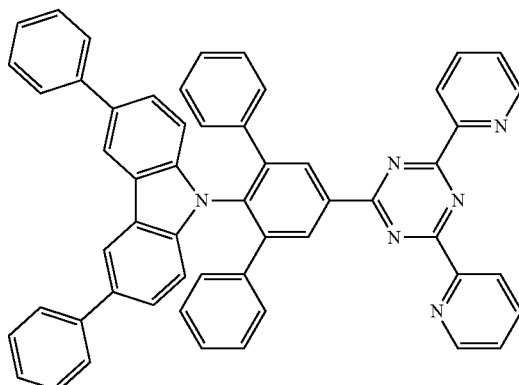

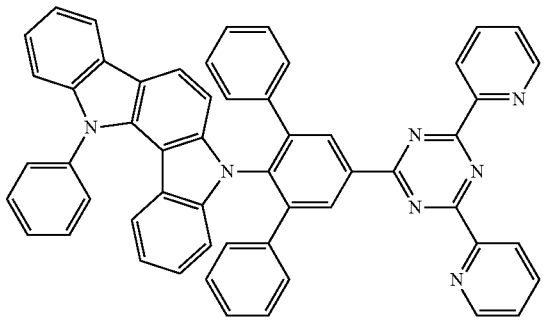

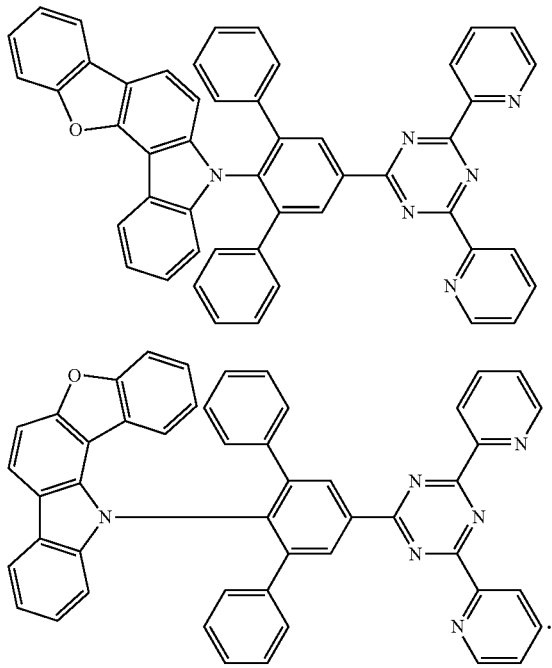

13. An organic light-emitting device comprising:
a first electrode;
a second electrode; and
an organic layer disposed between the first electrode and the second electrode,
wherein the organic layer comprises an emission layer, and
wherein the organic layer comprises at least one condensed cyclic compound of claim 1.

14. The organic light-emitting device of claim 13, wherein the first electrode is an anode,
the second electrode is a cathode,
the organic layer further comprises a hole transport region disposed between the first electrode and the emission layer and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

15. The organic light-emitting device of claim 13, wherein the emission layer comprises the condensed cyclic compound.

16. The organic light-emitting device of claim 15, wherein a ratio of a fluorescence emission component to a total emission component emitted from the emission layer is 90% or more.

17. The organic light-emitting device of claim 15, wherein the condensed cyclic compound is a fluorescence emitter, and
a ratio of an emission component emitted from the condensed cyclic compound to a total emission component emitted from the emission layer is 80% or more.

18. The organic light-emitting device of claim 17, wherein the emission layer consists of the condensed cyclic compound; or
the emission layer further comprises a host.

19. The organic light-emitting device of claim 15, wherein the emission layer comprises a host and a dopant,
the host comprises the condensed cyclic compound,
an amount of the host is larger than an amount of the dopant, and
a ratio of an emission component of the dopant to a total emission component emitted from the emission layer dopant is 80% or more.

20. The organic light-emitting device of claim 15, wherein the emission layer comprises a host, an auxiliary dopant, and a dopant,
the auxiliary dopant comprises the condensed cyclic compound, and
a ratio of an emission component of the dopant to a total emission component emitted from the emission layer is 80% or more.

* * * * *